(12) United States Patent
Wang et al.

(10) Patent No.: US 7,572,614 B2
(45) Date of Patent: Aug. 11, 2009

(54) CRYSTAL STRUCTURE OF SOLUBLE GLUTAMINYL CYCLASE

(75) Inventors: Andrew H.-J. Wang, Taipei (TW); Kai-Fa Huang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/362,051

(22) Filed: Feb. 24, 2006

(65) Prior Publication Data
US 2007/0202586 A1      Aug. 30, 2007

(51) Int. Cl.
*C12N 9/00*      (2006.01)
*C12N 9/10*      (2006.01)
*C12N 9/86*      (2006.01)
*C12P 21/06*     (2006.01)

(52) U.S. Cl. .................. 435/183; 435/193; 435/231; 435/69.1

(58) Field of Classification Search .................. None
See application file for complete search history.

(56) References Cited

U.S. PATENT DOCUMENTS

| | | | |
|---|---|---|---|
| 6,117,663 A | 9/2000 | Boriack-Sjodin et al. | |
| 2004/0224875 A1 | 11/2004 | Schilling et al. | |
| 2005/0181975 A1 | 8/2005 | Griffith et al. | |
| 2005/0202550 A1 | 9/2005 | Pandit | |

FOREIGN PATENT DOCUMENTS

| | | |
|---|---|---|
| WO | 2004098591 A2 | 11/2004 |
| WO | 2004098625 A2 | 11/2004 |

OTHER PUBLICATIONS

Branden et al., "Introduction to Protein Structure Second Edition", Garland Publishing Inc., New York, 1999.*
Drenth, "Principles of X-ray Crystallography," Springer, New York, 1995.*
Kierzek et al., Biophys Chem 91:1-20, 2001.*
Ngo et al., in The Protein Folding Problem and Tertiary Structure Prediction, 1994, Merz et al. (ed.), Birkhauser, Boston, MA, pp. 433 and 492-495.*
Azarkan et al., Crystallization and preliminary X-ray diffraction studies of the glutaminyl cyclase from Carica papaya latex, Acta Cryst., published online on Oct. 23, 2004, F61, p. 59-61.*
Witkowski et al., Biochemistry, 38, 11643-11650, 1999.*
Wishart et al., Journal of Biological Chemistry, vol. 270, No. 45, pp. 26782-26785, 1995.*
Oberg, et al., "Papaya glutamine cyclase, a plant enzyme highly resistant to proteolysis, adopts an all-b conformation", European Journal of Biochemistry, vol. 258, pp. 214-222 (1998).
Schilling, et al., "Heterologous expression and characterization of human glutaminyl cyclase: evidence for a disulfide bond with importance for catalytic activity", Biochemistry, vol. 41, pp. 10849-10857 (2002).
Van Coille, et al., "Functional comparison of two human monocyte chemotactic protein-e isoforms, role of the amino-terminal pyroglutamic acid and processing by CD26/Dipeptidyl Peptidase IV", Biochemistry, vol. 37, pp. 12672-12680 (1998).
Hinke, et al., "Dipeptidyl Peptidase IV (DPIC/DC26) Degradation of Glucagon", Journal of Biological Chemistry, vol. 275, pp. 3827-3834 (2000).
Huang, et al., "Cloning, expression, characterization, and crystallization of a glutaminyl cyclase from human bone marrow: A single zinc metalloenzyme", Protein Expression & Purification, vol. 43, pp. 65-72 (2005).
Bubsy, et al., "An enzyme(s) that converts glutaminyl-peptides into pyroglutamyl-peptides", The Journal of Biological Chemistry, vol. 262, No. 18, pp. 8532-8536 (1987).
Huang, et al., "Crystal structures of human glutaminyl cyclase, an enzyme responsible for protein N-terminal pyroglutamate formation", PNAS, vol. 102, No. 37, pp. 13117-13122 (2005).
Sykes, et al., "Evidence for tissue-specific forms of glutaminyl cyclase", FEBS Letters, vol. 455, pp. 159-161 (1999).
Shilling, et al., "Identification of human glutaminyl cyclase as a metalloenzyme", Journal of Biological Chemistry, vol. 278, pp. 29773-29779 (2003).
Fischer, et al., "Identification of a mammalian glutaminyl cyclase converting glutaminyl into pyroglutamyl peptides", Proceedings of the national academy of sciences of the United States of America, No. 84, pp. 3628-3632 (1987).
Booth, et al., "Human glytaminyl cyclase and bacterial zinc aminopeptidase share a common fold and active site", BMC Biology, vol. 2, No. 2 (2004).
Stewart, et al., "Role of genetic factors in the pathogenesis of osteoporosis", Journal of Endocrinology, vol. 166, p. 235-245 (2000).
Ezura, et al., "Association of multiple nucleotide variations in the pituitary glutaminyl cyclase gene (QPCT) with low radial BMD in adult women", Journal of Bone and Mineral Research, vol. 19, pp. 1296-1301 (2004).
Schilling, et al., "Glutaminyl cyclases unfold glutamyl cyclase activity under mild acid conditions", FEBS Letters, vol. 563, pp. 191-196 (2004).
Morgan, et al., "Structure and function of amyloid in Alzheimer's disease", Progress in Neurobiology, vol. 74, pp. 323-349 (2004).
Saido, et al., "Dominant and differential deposition of distinct beta-amyloid peptide species, A beta N3(pE), in senile plaques", Neuron, vol. 14, pp. 457-466 (1995).
Kuo, et al., "Isolation, chemical characterization, and quantitation of a beta 3-pyroglytamyl peptide from neuritic plaques and vascular amyloid deposits", Biochemical and Biophysical Research Communications, vol. 237, pp. 188-191 (1997).
Russo, et al., "Pyroglutamate-modified amyloid beta-peptides strongly affect cultured neuron and astrocyte survival", Journal of Neurochemistry, vol. 82, pp. 1480-1489 (2002).

(Continued)

*Primary Examiner*—Suzanne M. Noakes
*Assistant Examiner*—Jae W Lee
(74) *Attorney, Agent, or Firm*—Panitch Schwarze Belisario & Nadel LLP

(57) ABSTRACT

A crystalline structure of glutaminyl cyclase (QC). is described. Also described are the methods of preparing the crystalline structure of QC and the methods for identifying candidate inhibitors of QC. In addition, a structural basis for the rational design or identification of new inhibitors that may be used to treat QC-associated disorders is also described.

11 Claims, 244 Drawing Sheets
(7 of 244 Drawing Sheet(s) Filed in Color)

OTHER PUBLICATIONS

Harigaya, et al., "Amyloid beta-protein starting pyroglutamate at position 3 is a major component of the amyloid deposits in the alzheimer's disease brain", Biochemical and Biophysical Research Communications, vol. 276, pp. 422-427 (2000).

Pawlak, Joanna et al., "Snake venom glutaminyl Cyclase," Toxicon, 48:278-286 (2006).

Zerhouni, Samira et al., "Purification and characterization of papaya glutamine cyclotransferase, a plant enzyme highly resistance to chemical, acid and thermal denaturation," Biochimica et Biophysica Acta, 1387:275-290 (1998).

Schilling, Stephan et al., "Heterologous Expression and Characterization of Human Glutaminyl Cyclase: Evidence for a Disulfide Bond with Importance for Catalytic Activity," Biochemistry, 41:10849-10857 (2002).

Schilling, Stephan et al., "Substrate Specificity of Glutaminyl Cyclases from Plants and Animals," Biol. Chem, 384:1583-1592 (Dec. 2003).

Wintjens, Rene et al., "Crystal Structure of Papaya Glutaminyl Cyclase, an Archetype for Plant and Bacterial Glutaminyl Cyclases," J. Mol. Biol., 357:457-470 (2006).

Oberg, Keith A. et al., "Papaya glutamine cyclase, a plant enzyme highly resistant to proteolysis, adopts an all-beta conformation," Eur. J. Biochem, 258:214-222 (1998).

Huang, Kai-Fa et al., "Crystal structures of human glutaminyl cyclase, an enzyme responsible for protein N-terminal pyroglutamate formation," PNAS, 102(37):13117-13122 (Sep. 13, 2005).

* cited by examiner

FIGURE 1-1 (COORDINATES)

|      | ATOM | TYPE | RES | # | X | Y | Z | Occ | B |   |
|------|------|------|-----|----|---------|---------|--------|------|-------|---|
| ATOM | 1  | N   | ALA A | 33 | -6.424  | -34.116 | 36.857 | 1.00 | 43.50 | N |
| ATOM | 2  | CA  | ALA A | 33 | -6.637  | -32.639 | 36.649 | 1.00 | 41.82 | C |
| ATOM | 3  | C   | ALA A | 33 | -7.086  | -32.363 | 35.200 | 1.00 | 40.45 | C |
| ATOM | 4  | O   | ALA A | 33 | -6.245  | -32.098 | 34.341 | 1.00 | 41.89 | O |
| ATOM | 5  | CB  | ALA A | 33 | -5.327  | -31.894 | 36.952 | 1.00 | 41.01 | C |
| ATOM | 6  | N   | SER A | 34 | -8.402  | -32.395 | 34.950 | 1.00 | 37.29 | N |
| ATOM | 7  | CA  | SER A | 34 | -8.982  | -32.200 | 33.607 | 1.00 | 33.09 | C |
| ATOM | 8  | C   | SER A | 34 | -8.369  | -31.093 | 32.741 | 1.00 | 31.22 | C |
| ATOM | 9  | O   | SER A | 34 | -8.072  | -30.003 | 33.206 | 1.00 | 31.84 | O |
| ATOM | 10 | CB  | SER A | 34 | -10.489 | -31.941 | 33.710 | 1.00 | 32.22 | C |
| ATOM | 11 | OG  | SER A | 34 | -11.092 | -31.899 | 32.417 | 1.00 | 29.13 | O |
| ATOM | 12 | N   | ALA A | 35 | -8.196  | -31.401 | 31.470 | 1.00 | 28.56 | N |
| ATOM | 13 | CA  | ALA A | 35 | -7.649  | -30.450 | 30.520 | 1.00 | 26.41 | C |
| ATOM | 14 | C   | ALA A | 35 | -8.808  | -29.795 | 29.740 | 1.00 | 22.89 | C |
| ATOM | 15 | O   | ALA A | 35 | -8.594  | -29.282 | 28.640 | 1.00 | 20.68 | O |
| ATOM | 16 | CB  | ALA A | 35 | -6.755  | -31.175 | 29.551 | 1.00 | 25.99 | C |
| ATOM | 17 | N   | TRP A | 36 | -10.025 | -29.794 | 30.290 | 1.00 | 21.06 | N |
| ATOM | 18 | CA  | TRP A | 36 | -11.122 | -29.241 | 29.489 | 1.00 | 20.16 | C |
| ATOM | 19 | C   | TRP A | 36 | -10.955 | -27.763 | 29.074 | 1.00 | 17.94 | C |
| ATOM | 20 | O   | TRP A | 36 | -11.422 | -27.370 | 28.002 | 1.00 | 18.69 | O |
| ATOM | 21 | CB  | TRP A | 36 | -12.520 | -29.449 | 30.144 | 1.00 | 18.41 | C |
| ATOM | 22 | CG  | TRP A | 36 | -12.833 | -28.636 | 31.341 | 1.00 | 18.51 | C |
| ATOM | 23 | CD1 | TRP A | 36 | -12.741 | -29.036 | 32.653 | 1.00 | 18.59 | C |
| ATOM | 24 | CD2 | TRP A | 36 | -13.271 | -27.270 | 31.370 | 1.00 | 18.16 | C |
| ATOM | 25 | NE1 | TRP A | 36 | -13.090 | -28.004 | 33.494 | 1.00 | 16.41 | N |
| ATOM | 26 | CE2 | TRP A | 36 | -13.417 | -26.908 | 32.733 | 1.00 | 18.04 | C |
| ATOM | 27 | CE3 | TRP A | 36 | -13.555 | -26.317 | 30.376 | 1.00 | 17.13 | C |
| ATOM | 28 | CZ2 | TRP A | 36 | -13.832 | -25.638 | 33.136 | 1.00 | 18.56 | C |
| ATOM | 29 | CZ3 | TRP A | 36 | -13.974 | -25.040 | 30.783 | 1.00 | 17.88 | C |
| ATOM | 30 | CH2 | TRP A | 36 | -14.105 | -24.712 | 32.141 | 1.00 | 17.78 | C |
| ATOM | 31 | N   | PRO A | 37 | -10.283 | -26.948 | 29.895 | 1.00 | 18.47 | N |
| ATOM | 32 | CA  | PRO A | 37 | -10.142 | -25.541 | 29.466 | 1.00 | 17.94 | C |
| ATOM | 33 | C   | PRO A | 37 | -9.246  | -25.423 | 28.244 | 1.00 | 19.12 | C |
| ATOM | 34 | O   | PRO A | 37 | -9.124  | -24.341 | 27.660 | 1.00 | 18.10 | O |
| ATOM | 35 | CB  | PRO A | 37 | -9.543  | -24.854 | 30.689 | 1.00 | 19.04 | C |
| ATOM | 36 | CG  | PRO A | 37 | -10.043 | -25.707 | 31.852 | 1.00 | 17.87 | C |
| ATOM | 37 | CD  | PRO A | 37 | -9.825  | -27.117 | 31.288 | 1.00 | 17.60 | C |
| ATOM | 38 | N   | GLU A | 38 | -8.587  | -26.514 | 27.858 | 1.00 | 17.72 | N |
| ATOM | 39 | CA  | GLU A | 38 | -7.768  | -26.460 | 26.645 | 1.00 | 18.46 | C |
| ATOM | 40 | C   | GLU A | 38 | -8.567  | -26.831 | 25.399 | 1.00 | 17.07 | C |
| ATOM | 41 | O   | GLU A | 38 | -8.082  | -26.698 | 24.277 | 1.00 | 17.90 | O |
| ATOM | 42 | CB  | GLU A | 38 | -6.565  | -27.406 | 26.770 | 1.00 | 22.02 | C |
| ATOM | 43 | CG  | GLU A | 38 | -5.557  | -26.945 | 27.798 | 1.00 | 24.93 | C |
| ATOM | 44 | CD  | GLU A | 38 | -4.368  | -27.877 | 27.918 | 1.00 | 30.20 | C |
| ATOM | 45 | OE1 | GLU A | 38 | -3.489  | -27.836 | 27.055 | 1.00 | 32.38 | O |
| ATOM | 46 | OE2 | GLU A | 38 | -4.330  | -28.653 | 28.887 | 1.00 | 34.82 | O |
| ATOM | 47 | N   | GLU A | 39 | -9.782  | -27.345 | 25.583 | 1.00 | 17.79 | N |
| ATOM | 48 | CA  | GLU A | 39 | -10.570 | -27.760 | 24.414 | 1.00 | 17.65 | C |
| ATOM | 49 | C   | GLU A | 39 | -10.762 | -26.628 | 23.394 | 1.00 | 18.47 | C |
| ATOM | 50 | O   | GLU A | 39 | -10.767 | -26.873 | 22.187 | 1.00 | 17.74 | O |
| ATOM | 51 | CB  | GLU A | 39 | -11.937 | -28.278 | 24.864 | 1.00 | 18.26 | C |
| ATOM | 52 | CG  | GLU A | 39 | -11.808 | -29.618 | 25.619 | 1.00 | 19.41 | C |
| ATOM | 53 | CD  | GLU A | 39 | -13.114 | -30.112 | 26.202 | 1.00 | 21.71 | C |
| ATOM | 54 | OE1 | GLU A | 39 | -14.193 | -29.621 | 25.822 | 1.00 | 21.87 | O |
| ATOM | 55 | OE2 | GLU A | 39 | -13.065 | -31.038 | 27.044 | 1.00 | 23.97 | O |
| ATOM | 56 | N   | LYS A | 40 | -10.936 | -25.410 | 23.886 | 1.00 | 16.94 | N |
| ATOM | 57 | CA  | LYS A | 40 | -11.132 | -24.265 | 22.976 | 1.00 | 17.55 | C |
| ATOM | 58 | C   | LYS A | 40 | -9.974  | -24.122 | 21.983 | 1.00 | 17.47 | C |
| ATOM | 59 | O   | LYS A | 40 | -10.162 | -23.619 | 20.880 | 1.00 | 18.29 | O |
| ATOM | 60 | CB  | LYS A | 40 | -11.286 | -22.956 | 23.786 | 1.00 | 16.69 | C |
| ATOM | 61 | CG  | LYS A | 40 | -10.132 | -22.685 | 24.781 | 1.00 | 17.33 | C |
| ATOM | 62 | CD  | LYS A | 40 | -10.272 | -21.294 | 25.410 | 1.00 | 21.33 | C |
| ATOM | 63 | CE  | LYS A | 40 | -9.319  | -21.077 | 26.584 | 1.00 | 25.12 | C |
| ATOM | 64 | NZ  | LYS A | 40 | -9.925  | -21.623 | 27.911 | 1.00 | 25.17 | N |
| ATOM | 65 | N   | ASN A | 41 | -8.778  | -24.567 | 22.363 | 1.00 | 17.96 | N |
| ATOM | 66 | CA  | ASN A | 41 | -7.626  | -24.464 | 21.460 | 1.00 | 19.00 | C |
| ATOM | 67 | C   | ASN A | 41 | -7.714  | -25.371 | 20.238 | 1.00 | 20.30 | C |

FIGURE 1-2 (COORDINATES)

```
ATOM     68  O   ASN A  41      -7.115 -25.067  19.204  1.00 20.77           O
ATOM     69  CB  ASN A  41      -6.308 -24.796  22.212  1.00 21.81           C
ATOM     70  CG  ASN A  41      -6.113 -23.964  23.471  1.00 24.65           C
ATOM     71  OD1 ASN A  41      -5.445 -24.402  24.415  1.00 31.90           O
ATOM     72  ND2 ASN A  41      -6.677 -22.760  23.497  1.00 29.66           N
ATOM     73  N   TYR A  42      -8.434 -26.488  20.352  1.00 18.57           N
ATOM     74  CA  TYR A  42      -8.554 -27.454  19.256  1.00 20.18           C
ATOM     75  C   TYR A  42      -9.926 -27.465  18.616  1.00 18.68           C
ATOM     76  O   TYR A  42     -10.164 -28.178  17.646  1.00 20.49           O
ATOM     77  CB  TYR A  42      -8.252 -28.874  19.779  1.00 22.00           C
ATOM     78  CG  TYR A  42      -6.904 -28.940  20.463  1.00 24.58           C
ATOM     79  CD1 TYR A  42      -5.721 -28.884  19.722  1.00 26.68           C
ATOM     80  CD2 TYR A  42      -6.813 -28.927  21.849  1.00 22.87           C
ATOM     81  CE1 TYR A  42      -4.464 -28.795  20.350  1.00 26.90           C
ATOM     82  CE2 TYR A  42      -5.575 -28.845  22.495  1.00 25.68           C
ATOM     83  CZ  TYR A  42      -4.402 -28.772  21.743  1.00 26.95           C
ATOM     84  OH  TYR A  42      -3.177 -28.649  22.372  1.00 28.90           O
ATOM     85  N   HIS A  43     -10.842 -26.698  19.181  1.00 16.52           N
ATOM     86  CA  HIS A  43     -12.186 -26.669  18.676  1.00 16.69           C
ATOM     87  C   HIS A  43     -12.251 -26.257  17.218  1.00 18.30           C
ATOM     88  O   HIS A  43     -11.655 -25.245  16.851  1.00 18.71           O
ATOM     89  CB  HIS A  43     -13.054 -25.707  19.486  1.00 17.55           C
ATOM     90  CG  HIS A  43     -14.508 -25.859  19.193  1.00 16.63           C
ATOM     91  ND1 HIS A  43     -15.258 -24.917  18.519  1.00 21.27           N
ATOM     92  CD2 HIS A  43     -15.348 -26.881  19.469  1.00 14.46           C
ATOM     93  CE1 HIS A  43     -16.503 -25.358  18.390  1.00 14.61           C
ATOM     94  NE2 HIS A  43     -16.578 -26.550  18.962  1.00 21.87           N
ATOM     95  N   GLN A  44     -12.978 -27.029  16.408  1.00 18.41           N
ATOM     96  CA  GLN A  44     -13.141 -26.749  14.977  1.00 19.80           C
ATOM     97  C   GLN A  44     -14.599 -26.529  14.666  1.00 19.16           C
ATOM     98  O   GLN A  44     -15.481 -27.070  15.319  1.00 20.36           O
ATOM     99  CB  GLN A  44     -12.671 -27.920  14.115  1.00 22.62           C
ATOM    100  CG  GLN A  44     -11.192 -28.271  14.244  1.00 26.75           C
ATOM    101  CD  GLN A  44     -10.291 -27.101  13.923  1.00 30.25           C
ATOM    102  OE1 GLN A  44     -10.484 -26.404  12.920  1.00 32.89           O
ATOM    103  NE2 GLN A  44      -9.297 -26.878  14.764  1.00 31.18           N
ATOM    104  N   PRO A  45     -14.885 -25.735  13.632  1.00 19.57           N
ATOM    105  CA  PRO A  45     -16.301 -25.530  13.324  1.00 19.78           C
ATOM    106  C   PRO A  45     -16.849 -26.684  12.483  1.00 19.63           C
ATOM    107  O   PRO A  45     -16.076 -27.448  11.884  1.00 21.52           O
ATOM    108  CB  PRO A  45     -16.289 -24.241  12.512  1.00 19.30           C
ATOM    109  CG  PRO A  45     -14.989 -24.365  11.759  1.00 19.95           C
ATOM    110  CD  PRO A  45     -14.022 -24.864  12.821  1.00 21.33           C
ATOM    111  N   ALA A  46     -18.166 -26.811  12.473  1.00 19.31           N
ATOM    112  CA  ALA A  46     -18.852 -27.789  11.614  1.00 20.32           C
ATOM    113  C   ALA A  46     -19.437 -26.855  10.543  1.00 21.13           C
ATOM    114  O   ALA A  46     -20.458 -26.196  10.743  1.00 19.78           O
ATOM    115  CB  ALA A  46     -19.964 -28.525  12.401  1.00 22.01           C
ATOM    116  N   ILE A  47     -18.772 -26.815   9.401  1.00 21.96           N
ATOM    117  CA  ILE A  47     -19.132 -25.882   8.337  1.00 21.96           C
ATOM    118  C   ILE A  47     -20.449 -26.158   7.612  1.00 24.15           C
ATOM    119  O   ILE A  47     -20.759 -27.303   7.266  1.00 24.63           O
ATOM    120  CB  ILE A  47     -17.937 -25.775   7.361  1.00 23.19           C
ATOM    121  CG1 ILE A  47     -16.729 -25.205   8.125  1.00 22.38           C
ATOM    122  CG2 ILE A  47     -18.303 -24.910   6.161  1.00 24.72           C
ATOM    123  CD1 ILE A  47     -15.380 -25.311   7.411  1.00 23.89           C
ATOM    124  N   LEU A  48     -21.237 -25.106   7.406  1.00 22.81           N
ATOM    125  CA  LEU A  48     -22.535 -25.256   6.747  1.00 23.35           C
ATOM    126  C   LEU A  48     -22.349 -25.370   5.238  1.00 24.26           C
ATOM    127  O   LEU A  48     -21.520 -24.656   4.659  1.00 24.62           O
ATOM    128  CB  LEU A  48     -23.456 -24.047   7.036  1.00 24.15           C
ATOM    129  CG  LEU A  48     -23.763 -23.568   8.464  1.00 28.30           C
ATOM    130  CD1 LEU A  48     -25.005 -22.674   8.448  1.00 24.80           C
ATOM    131  CD2 LEU A  48     -23.962 -24.747   9.390  1.00 27.24           C
ATOM    132  N   ASN A  49     -23.109 -26.275   4.611  1.00 24.15           N
ATOM    133  CA  ASN A  49     -23.050 -26.421   3.151  1.00 23.63           C
ATOM    134  C   ASN A  49     -23.933 -25.343   2.518  1.00 22.32           C
ATOM    135  O   ASN A  49     -24.609 -24.599   3.228  1.00 23.67           O
```

FIGURE 1-3 (COORDINATES)

```
ATOM    136  CB  ASN A  49     -23.496 -27.849   2.705  1.00 24.78           C
ATOM    137  CG  ASN A  49     -24.954 -28.187   3.056  1.00 23.69           C
ATOM    138  OD1 ASN A  49     -25.794 -27.326   3.233  1.00 25.69           O
ATOM    139  ND2 ASN A  49     -25.256 -29.499   3.121  1.00 28.63           N
ATOM    140  N   SER A  50     -23.934 -25.250   1.185  1.00 22.86           N
ATOM    141  CA  SER A  50     -24.739 -24.229   0.489  1.00 22.73           C
ATOM    142  C   SER A  50     -26.207 -24.201   0.852  1.00 24.61           C
ATOM    143  O   SER A  50     -26.790 -23.135   1.046  1.00 23.64           O
ATOM    144  CB  SER A  50     -24.624 -24.408  -1.029  1.00 23.22           C
ATOM    145  OG  SER A  50     -23.278 -24.337  -1.430  1.00 25.75           O
ATOM    146  N   SER A  51     -26.853 -25.364   0.909  1.00 24.05           N
ATOM    147  CA  SER A  51     -28.257 -25.367   1.258  1.00 24.81           C
ATOM    148  C   SER A  51     -28.483 -24.755   2.654  1.00 24.23           C
ATOM    149  O   SER A  51     -29.415 -23.966   2.868  1.00 22.91           O
ATOM    150  CB  SER A  51     -28.799 -26.806   1.198  1.00 27.04           C
ATOM    151  OG  SER A  51     -30.059 -26.887   1.843  1.00 33.72           O
ATOM    152  N   ALA A  52     -27.622 -25.101   3.606  1.00 24.24           N
ATOM    153  CA  ALA A  52     -27.795 -24.565   4.950  1.00 23.35           C
ATOM    154  C   ALA A  52     -27.539 -23.054   4.973  1.00 22.71           C
ATOM    155  O   ALA A  52     -28.205 -22.328   5.702  1.00 22.01           O
ATOM    156  CB  ALA A  52     -26.862 -25.269   5.941  1.00 23.49           C
ATOM    157  N   LEU A  53     -26.583 -22.589   4.176  1.00 22.66           N
ATOM    158  CA  LEU A  53     -26.272 -21.154   4.148  1.00 21.19           C
ATOM    159  C   LEU A  53     -27.480 -20.410   3.588  1.00 22.10           C
ATOM    160  O   LEU A  53     -27.897 -19.365   4.109  1.00 21.77           O
ATOM    161  CB  LEU A  53     -25.028 -20.875   3.292  1.00 19.05           C
ATOM    162  CG  LEU A  53     -23.722 -21.347   3.918  1.00 20.85           C
ATOM    163  CD1 LEU A  53     -22.598 -21.168   2.938  1.00 19.47           C
ATOM    164  CD2 LEU A  53     -23.446 -20.524   5.167  1.00 20.22           C
ATOM    165  N   ARG A  54     -28.088 -20.959   2.539  1.00 23.64           N
ATOM    166  CA  ARG A  54     -29.263 -20.286   2.014  1.00 23.77           C
ATOM    167  C   ARG A  54     -30.339 -20.239   3.086  1.00 23.20           C
ATOM    168  O   ARG A  54     -31.046 -19.255   3.225  1.00 22.89           O
ATOM    169  CB  ARG A  54     -29.796 -21.015   0.766  1.00 24.15           C
ATOM    170  CG  ARG A  54     -28.835 -21.028  -0.380  1.00 28.99           C
ATOM    171  CD  ARG A  54     -29.502 -21.535  -1.680  1.00 33.13           C
ATOM    172  NE  ARG A  54     -28.453 -21.930  -2.614  1.00 37.88           N
ATOM    173  CZ  ARG A  54     -28.000 -23.173  -2.754  1.00 39.50           C
ATOM    174  NH1 ARG A  54     -28.513 -24.163  -2.035  1.00 40.83           N
ATOM    175  NH2 ARG A  54     -27.001 -23.419  -3.598  1.00 42.54           N
ATOM    176  N   GLN A  55     -30.469 -21.308   3.861  1.00 22.34           N
ATOM    177  CA  GLN A  55     -31.493 -21.325   4.894  1.00 22.74           C
ATOM    178  C   GLN A  55     -31.260 -20.229   5.928  1.00 21.71           C
ATOM    179  O   GLN A  55     -32.182 -19.517   6.327  1.00 20.49           O
ATOM    180  CB  GLN A  55     -31.536 -22.697   5.564  1.00 26.31           C
ATOM    181  CG  GLN A  55     -32.506 -22.785   6.714  1.00 33.31           C
ATOM    182  CD  GLN A  55     -32.440 -24.137   7.403  1.00 38.43           C
ATOM    183  OE1 GLN A  55     -32.240 -24.221   8.622  1.00 39.20           O
ATOM    184  NE2 GLN A  55     -32.603 -25.214   6.614  1.00 40.36           N
ATOM    185  N   ILE A  56     -30.009 -20.071   6.342  1.00 21.00           N
ATOM    186  CA  ILE A  56     -29.709 -19.051   7.324  1.00 21.45           C
ATOM    187  C   ILE A  56     -29.943 -17.655   6.740  1.00 19.63           C
ATOM    188  O   ILE A  56     -30.507 -16.786   7.403  1.00 20.10           O
ATOM    189  CB  ILE A  56     -28.262 -19.188   7.817  1.00 23.03           C
ATOM    190  CG1 ILE A  56     -28.043 -20.600   8.380  1.00 25.13           C
ATOM    191  CG2 ILE A  56     -27.973 -18.141   8.904  1.00 23.68           C
ATOM    192  CD1 ILE A  56     -29.162 -21.066   9.291  1.00 27.05           C
ATOM    193  N   ALA A  57     -29.539 -17.453   5.491  1.00 20.16           N
ATOM    194  CA  ALA A  57     -29.722 -16.145   4.866  1.00 20.14           C
ATOM    195  C   ALA A  57     -31.198 -15.805   4.815  1.00 21.65           C
ATOM    196  O   ALA A  57     -31.594 -14.688   5.091  1.00 22.65           O
ATOM    197  CB  ALA A  57     -29.107 -16.133   3.441  1.00 19.57           C
ATOM    198  N   GLU A  58     -32.029 -16.798   4.487  1.00 22.89           N
ATOM    199  CA  GLU A  58     -33.458 -16.567   4.397  1.00 24.62           C
ATOM    200  C   GLU A  58     -34.165 -16.481   5.750  1.00 24.51           C
ATOM    201  O   GLU A  58     -35.261 -15.904   5.848  1.00 24.96           O
ATOM    202  CB  GLU A  58     -34.103 -17.681   3.567  1.00 27.56           C
ATOM    203  CG  GLU A  58     -33.797 -17.612   2.081  1.00 36.14           C
```

FIGURE 1-4 (COORDINATES)

```
ATOM    204  CD   GLU A  58     -34.353 -16.352   1.418  1.00 41.47           C
ATOM    205  OE1  GLU A  58     -35.372 -15.804   1.913  1.00 45.17           O
ATOM    206  OE2  GLU A  58     -33.782 -15.913   0.392  1.00 44.59           O
ATOM    207  N    GLY A  59     -33.520 -16.999   6.799  1.00 23.09           N
ATOM    208  CA   GLY A  59     -34.149 -17.024   8.116  1.00 21.92           C
ATOM    209  C    GLY A  59     -34.018 -15.812   9.031  1.00 21.09           C
ATOM    210  O    GLY A  59     -34.571 -15.817  10.145  1.00 22.34           O
ATOM    211  N    THR A  60     -33.270 -14.797   8.596  1.00 20.00           N
ATOM    212  CA   THR A  60     -33.107 -13.596   9.393  1.00 18.92           C
ATOM    213  C    THR A  60     -33.815 -12.483   8.634  1.00 19.42           C
ATOM    214  O    THR A  60     -33.803 -12.471   7.390  1.00 22.65           O
ATOM    215  CB   THR A  60     -31.578 -13.252   9.600  1.00 18.42           C
ATOM    216  OG1  THR A  60     -31.462 -12.056  10.385  1.00 19.58           O
ATOM    217  CG2  THR A  60     -30.869 -13.055   8.260  1.00 19.75           C
ATOM    218  N    SER A  61     -34.431 -11.558   9.365  1.00 17.89           N
ATOM    219  CA   SER A  61     -35.209 -10.466   8.765  1.00 18.96           C
ATOM    220  C    SER A  61     -34.737  -9.132   9.275  1.00 18.62           C
ATOM    221  O    SER A  61     -35.000  -8.769  10.429  1.00 18.62           O
ATOM    222  CB   SER A  61     -36.686 -10.612   9.142  1.00 20.66           C
ATOM    223  OG   SER A  61     -37.439  -9.469   8.761  1.00 22.71           O
ATOM    224  N    ILE A  62     -34.080  -8.377   8.405  1.00 19.66           N
ATOM    225  CA   ILE A  62     -33.576  -7.080   8.826  1.00 18.77           C
ATOM    226  C    ILE A  62     -34.718  -6.114   9.144  1.00 19.86           C
ATOM    227  O    ILE A  62     -34.598  -5.296  10.058  1.00 18.41           O
ATOM    228  CB   ILE A  62     -32.586  -6.499   7.758  1.00 17.43           C
ATOM    229  CG1  ILE A  62     -31.960  -5.206   8.282  1.00 17.16           C
ATOM    230  CG2  ILE A  62     -33.315  -6.229   6.411  1.00 18.53           C
ATOM    231  CD1  ILE A  62     -30.987  -5.420   9.488  1.00 17.16           C
ATOM    232  N    SER A  63     -35.843  -6.201   8.432  1.00 21.85           N
ATOM    233  CA   SER A  63     -36.962  -5.295   8.740  1.00 22.37           C
ATOM    234  C    SER A  63     -37.609  -5.633  10.109  1.00 22.44           C
ATOM    235  O    SER A  63     -38.006  -4.732  10.844  1.00 21.69           O
ATOM    236  CB   SER A  63     -38.025  -5.354   7.634  1.00 23.80           C
ATOM    237  OG   SER A  63     -38.535  -6.674   7.534  1.00 27.62           O
ATOM    238  N    GLU A  64     -37.708  -6.910  10.447  1.00 21.50           N
ATOM    239  CA   GLU A  64     -38.255  -7.295  11.753  1.00 22.17           C
ATOM    240  C    GLU A  64     -37.290  -6.843  12.862  1.00 21.07           C
ATOM    241  O    GLU A  64     -37.717  -6.336  13.897  1.00 20.50           O
ATOM    242  CB   GLU A  64     -38.467  -8.808  11.822  1.00 24.91           C
ATOM    243  CG   GLU A  64     -39.659  -9.282  10.990  1.00 32.44           C
ATOM    244  CD   GLU A  64     -40.983  -8.896  11.621  1.00 36.82           C
ATOM    245  OE1  GLU A  64     -41.298  -9.449  12.706  1.00 40.43           O
ATOM    246  OE2  GLU A  64     -41.708  -8.046  11.044  1.00 40.57           O
ATOM    247  N    MET A  65     -35.986  -7.040  12.649  1.00 17.50           N
ATOM    248  CA   MET A  65     -35.027  -6.581  13.658  1.00 17.47           C
ATOM    249  C    MET A  65     -35.170  -5.080  13.832  1.00 15.83           C
ATOM    250  O    MET A  65     -35.196  -4.586  14.936  1.00 18.41           O
ATOM    251  CB   MET A  65     -33.571  -6.861  13.240  1.00 17.28           C
ATOM    252  CG   MET A  65     -32.579  -6.357  14.286  1.00 18.32           C
ATOM    253  SD   MET A  65     -30.901  -6.173  13.635  1.00 19.04           S
ATOM    254  CE   MET A  65     -31.073  -4.491  13.013  1.00 19.42           C
ATOM    255  N    TRP A  66     -35.252  -4.360  12.719  1.00 17.26           N
ATOM    256  CA   TRP A  66     -35.330  -2.909  12.753  1.00 17.49           C
ATOM    257  C    TRP A  66     -36.489  -2.432  13.609  1.00 18.64           C
ATOM    258  O    TRP A  66     -36.348  -1.600  14.493  1.00 17.69           O
ATOM    259  CB   TRP A  66     -35.482  -2.363  11.319  1.00 17.91           C
ATOM    260  CG   TRP A  66     -34.805  -1.042  11.133  1.00 18.54           C
ATOM    261  CD1  TRP A  66     -35.315   0.208  11.389  1.00 17.88           C
ATOM    262  CD2  TRP A  66     -33.464  -0.849  10.676  1.00 16.98           C
ATOM    263  NE1  TRP A  66     -34.359   1.177  11.118  1.00 18.33           N
ATOM    264  CE2  TRP A  66     -33.216   0.552  10.675  1.00 17.12           C
ATOM    265  CE3  TRP A  66     -32.449  -1.729  10.261  1.00 18.72           C
ATOM    266  CZ2  TRP A  66     -31.981   1.100  10.280  1.00 19.90           C
ATOM    267  CZ3  TRP A  66     -31.232  -1.198   9.868  1.00 20.38           C
ATOM    268  CH2  TRP A  66     -31.003   0.220   9.882  1.00 20.11           C
ATOM    269  N    GLN A  67     -37.659  -2.989  13.344  1.00 17.92           N
ATOM    270  CA   GLN A  67     -38.822  -2.551  14.068  1.00 19.98           C
ATOM    271  C    GLN A  67     -38.928  -3.054  15.497  1.00 18.72           C
```

FIGURE 1-5 (COORDINATES)

```
ATOM    272  O   GLN A  67     -39.230  -2.293  16.422  1.00 19.95           O
ATOM    273  CB  GLN A  67     -40.049  -2.995  13.263  1.00 21.81           C
ATOM    274  CG  GLN A  67     -41.391  -2.752  13.955  1.00 29.44           C
ATOM    275  CD  GLN A  67     -42.527  -3.358  13.153  1.00 33.73           C
ATOM    276  OE1 GLN A  67     -42.922  -2.812  12.127  1.00 37.44           O
ATOM    277  NE2 GLN A  67     -43.029  -4.520  13.598  1.00 37.00           N
ATOM    278  N   ASN A  68     -38.667  -4.337  15.678  1.00 20.61           N
ATOM    279  CA  ASN A  68     -38.862  -4.985  16.965  1.00 19.66           C
ATOM    280  C   ASN A  68     -37.738  -5.000  17.956  1.00 20.75           C
ATOM    281  O   ASN A  68     -37.983  -5.023  19.170  1.00 20.09           O
ATOM    282  CB  ASN A  68     -39.341  -6.420  16.732  1.00 21.01           C
ATOM    283  CG  ASN A  68     -40.591  -6.459  15.874  1.00 24.43           C
ATOM    284  OD1 ASN A  68     -41.475  -5.612  16.039  1.00 26.02           O
ATOM    285  ND2 ASN A  68     -40.682  -7.423  14.980  1.00 23.96           N
ATOM    286  N   ASP A  69     -36.512  -4.958  17.449  1.00 20.06           N
ATOM    287  CA  ASP A  69     -35.349  -5.002  18.328  1.00 18.83           C
ATOM    288  C   ASP A  69     -34.524  -3.721  18.381  1.00 19.77           C
ATOM    289  O   ASP A  69     -34.055  -3.324  19.457  1.00 18.84           O
ATOM    290  CB  ASP A  69     -34.477  -6.181  17.896  1.00 20.43           C
ATOM    291  CG  ASP A  69     -35.033  -7.500  18.402  1.00 23.61           C
ATOM    292  OD1 ASP A  69     -35.080  -8.472  17.655  1.00 27.68           O
ATOM    293  OD2 ASP A  69     -35.410  -7.538  19.570  1.00 24.91           O
ATOM    294  N   LEU A  70     -34.385  -3.051  17.236  1.00 17.89           N
ATOM    295  CA  LEU A  70     -33.580  -1.844  17.189  1.00 17.03           C
ATOM    296  C   LEU A  70     -34.267  -0.558  17.595  1.00 17.49           C
ATOM    297  O   LEU A  70     -33.790   0.163  18.471  1.00 17.09           O
ATOM    298  CB  LEU A  70     -33.005  -1.655  15.776  1.00 17.81           C
ATOM    299  CG  LEU A  70     -32.178  -0.399  15.544  1.00 15.89           C
ATOM    300  CD1 LEU A  70     -30.919  -0.481  16.405  1.00 15.95           C
ATOM    301  CD2 LEU A  70     -31.784  -0.290  14.048  1.00 18.87           C
ATOM    302  N   GLN A  71     -35.405  -0.251  16.978  1.00 18.47           N
ATOM    303  CA  GLN A  71     -36.030   1.026  17.298  1.00 19.55           C
ATOM    304  C   GLN A  71     -36.290   1.289  18.788  1.00 17.69           C
ATOM    305  O   GLN A  71     -36.108   2.423  19.266  1.00 18.14           O
ATOM    306  CB  GLN A  71     -37.286   1.222  16.410  1.00 18.91           C
ATOM    307  CG  GLN A  71     -36.875   1.600  14.965  1.00 22.47           C
ATOM    308  CD  GLN A  71     -38.047   1.776  14.004  1.00 26.49           C
ATOM    309  OE1 GLN A  71     -39.104   1.187  14.202  1.00 27.80           O
ATOM    310  NE2 GLN A  71     -37.846   2.559  12.935  1.00 25.23           N
ATOM    311  N   PRO A  72     -36.696   0.261  19.556  1.00 18.76           N
ATOM    312  CA  PRO A  72     -36.927   0.539  20.976  1.00 19.42           C
ATOM    313  C   PRO A  72     -35.656   0.921  21.737  1.00 20.10           C
ATOM    314  O   PRO A  72     -35.736   1.459  22.855  1.00 20.36           O
ATOM    315  CB  PRO A  72     -37.532  -0.770  21.506  1.00 20.76           C
ATOM    316  CG  PRO A  72     -38.246  -1.325  20.345  1.00 20.73           C
ATOM    317  CD  PRO A  72     -37.265  -1.055  19.177  1.00 20.13           C
ATOM    318  N   LEU A  73     -34.488   0.651  21.139  1.00 17.63           N
ATOM    319  CA  LEU A  73     -33.217   0.994  21.786  1.00 17.39           C
ATOM    320  C   LEU A  73     -32.651   2.333  21.343  1.00 17.69           C
ATOM    321  O   LEU A  73     -31.689   2.818  21.941  1.00 17.96           O
ATOM    322  CB  LEU A  73     -32.138  -0.100  21.524  1.00 16.46           C
ATOM    323  CG  LEU A  73     -32.400  -1.450  22.211  1.00 18.32           C
ATOM    324  CD1 LEU A  73     -31.414  -2.488  21.710  1.00 19.11           C
ATOM    325  CD2 LEU A  73     -32.291  -1.280  23.765  1.00 19.57           C
ATOM    326  N   LEU A  74     -33.250   2.944  20.318  1.00 18.99           N
ATOM    327  CA  LEU A  74     -32.748   4.212  19.828  1.00 18.15           C
ATOM    328  C   LEU A  74     -33.282   5.337  20.708  1.00 18.86           C
ATOM    329  O   LEU A  74     -34.044   6.212  20.267  1.00 19.80           O
ATOM    330  CB  LEU A  74     -33.136   4.391  18.360  1.00 18.92           C
ATOM    331  CG  LEU A  74     -32.403   3.403  17.429  1.00 18.60           C
ATOM    332  CD1 LEU A  74     -32.928   3.560  15.999  1.00 20.85           C
ATOM    333  CD2 LEU A  74     -30.888   3.662  17.447  1.00 19.57           C
ATOM    334  N   ILE A  75     -32.849   5.284  21.965  1.00 18.11           N
ATOM    335  CA  ILE A  75     -33.220   6.220  23.011  1.00 18.60           C
ATOM    336  C   ILE A  75     -31.997   6.534  23.877  1.00 19.21           C
ATOM    337  O   ILE A  75     -31.011   5.797  23.879  1.00 19.19           O
ATOM    338  CB  ILE A  75     -34.311   5.604  23.950  1.00 20.70           C
ATOM    339  CG1 ILE A  75     -33.796   4.300  24.594  1.00 21.62           C
```

FIGURE 1-6 (COORDINATES)

```
ATOM    340  CG2 ILE A  75     -35.608   5.335  23.161  1.00 22.12           C
ATOM    341  CD1 ILE A  75     -34.752   3.679  25.626  1.00 20.39           C
ATOM    342  N   GLU A  76     -32.057   7.638  24.598  1.00 19.29           N
ATOM    343  CA  GLU A  76     -30.992   8.032  25.504  1.00 19.39           C
ATOM    344  C   GLU A  76     -30.980   6.989  26.615  1.00 19.06           C
ATOM    345  O   GLU A  76     -32.009   6.773  27.255  1.00 19.86           O
ATOM    346  CB  GLU A  76     -31.318   9.412  26.065  1.00 22.19           C
ATOM    347  CG  GLU A  76     -30.317   9.952  26.992  1.00 24.80           C
ATOM    348  CD  GLU A  76     -30.575  11.429  27.252  1.00 29.09           C
ATOM    349  OE1 GLU A  76     -31.752  11.853  27.186  1.00 28.71           O
ATOM    350  OE2 GLU A  76     -29.618  12.156  27.529  1.00 30.15           O
ATOM    351  N   ARG A  77     -29.831   6.357  26.861  1.00 17.24           N
ATOM    352  CA  ARG A  77     -29.799   5.280  27.850  1.00 17.03           C
ATOM    353  C   ARG A  77     -28.453   5.228  28.585  1.00 17.34           C
ATOM    354  O   ARG A  77     -27.857   4.156  28.741  1.00 18.63           O
ATOM    355  CB  ARG A  77     -30.107   3.959  27.124  1.00 16.44           C
ATOM    356  CG  ARG A  77     -29.189   3.694  25.911  1.00 16.58           C
ATOM    357  CD  ARG A  77     -29.716   2.538  25.030  1.00 13.83           C
ATOM    358  NE  ARG A  77     -28.658   2.205  24.055  1.00 14.68           N
ATOM    359  CZ  ARG A  77     -28.379   2.940  22.981  1.00 16.43           C
ATOM    360  NH1 ARG A  77     -29.090   4.029  22.721  1.00 15.51           N
ATOM    361  NH2 ARG A  77     -27.338   2.625  22.201  1.00 15.81           N
ATOM    362  N   TYR A  78     -27.969   6.389  29.034  1.00 17.18           N
ATOM    363  CA  TYR A  78     -26.721   6.410  29.785  1.00 17.40           C
ATOM    364  C   TYR A  78     -26.993   5.736  31.141  1.00 18.71           C
ATOM    365  O   TYR A  78     -28.124   5.660  31.597  1.00 18.48           O
ATOM    366  CB  TYR A  78     -26.164   7.842  29.937  1.00 18.96           C
ATOM    367  CG  TYR A  78     -27.059   8.808  30.668  1.00 19.13           C
ATOM    368  CD1 TYR A  78     -27.944   9.638  29.974  1.00 22.06           C
ATOM    369  CD2 TYR A  78     -27.012   8.898  32.056  1.00 21.06           C
ATOM    370  CE1 TYR A  78     -28.758  10.537  30.654  1.00 22.45           C
ATOM    371  CE2 TYR A  78     -27.816   9.781  32.732  1.00 23.75           C
ATOM    372  CZ  TYR A  78     -28.680  10.589  32.038  1.00 24.43           C
ATOM    373  OH  TYR A  78     -29.496  11.437  32.764  1.00 27.95           O
ATOM    374  N   PRO A  79     -25.944   5.222  31.791  1.00 18.50           N
ATOM    375  CA  PRO A  79     -26.163   4.540  33.064  1.00 19.36           C
ATOM    376  C   PRO A  79     -26.975   5.301  34.103  1.00 20.68           C
ATOM    377  O   PRO A  79     -26.742   6.485  34.360  1.00 21.01           O
ATOM    378  CB  PRO A  79     -24.731   4.223  33.549  1.00 18.81           C
ATOM    379  CG  PRO A  79     -23.907   4.216  32.312  1.00 19.53           C
ATOM    380  CD  PRO A  79     -24.509   5.442  31.565  1.00 17.78           C
ATOM    381  N   GLY A  80     -27.936   4.599  34.692  1.00 21.01           N
ATOM    382  CA  GLY A  80     -28.760   5.185  35.735  1.00 23.55           C
ATOM    383  C   GLY A  80     -29.952   5.954  35.235  1.00 24.32           C
ATOM    384  O   GLY A  80     -30.809   6.343  36.040  1.00 25.59           O
ATOM    385  N   SER A  81     -30.037   6.165  33.919  1.00 22.64           N
ATOM    386  CA  SER A  81     -31.155   6.936  33.362  1.00 22.48           C
ATOM    387  C   SER A  81     -32.402   6.102  33.189  1.00 22.74           C
ATOM    388  O   SER A  81     -32.372   4.868  33.243  1.00 21.66           O
ATOM    389  CB  SER A  81     -30.779   7.503  31.983  1.00 21.78           C
ATOM    390  OG  SER A  81     -30.594   6.414  31.075  1.00 20.06           O
ATOM    391  N   PRO A  82     -33.542   6.768  32.968  1.00 24.06           N
ATOM    392  CA  PRO A  82     -34.778   6.015  32.772  1.00 22.98           C
ATOM    393  C   PRO A  82     -34.642   5.151  31.526  1.00 22.53           C
ATOM    394  O   PRO A  82     -35.225   4.061  31.429  1.00 21.63           O
ATOM    395  CB  PRO A  82     -35.822   7.118  32.560  1.00 25.09           C
ATOM    396  CG  PRO A  82     -35.292   8.250  33.357  1.00 25.93           C
ATOM    397  CD  PRO A  82     -33.804   8.215  33.073  1.00 25.36           C
ATOM    398  N   GLY A  83     -33.892   5.660  30.547  1.00 21.12           N
ATOM    399  CA  GLY A  83     -33.700   4.935  29.298  1.00 20.69           C
ATOM    400  C   GLY A  83     -32.882   3.673  29.504  1.00 19.83           C
ATOM    401  O   GLY A  83     -33.041   2.693  28.786  1.00 19.62           O
ATOM    402  N   SER A  84     -31.959   3.714  30.457  1.00 20.87           N
ATOM    403  CA  SER A  84     -31.173   2.520  30.741  1.00 20.27           C
ATOM    404  C   SER A  84     -32.131   1.446  31.227  1.00 20.24           C
ATOM    405  O   SER A  84     -32.059   0.285  30.801  1.00 18.71           O
ATOM    406  CB  SER A  84     -30.119   2.802  31.817  1.00 22.93           C
ATOM    407  OG  SER A  84     -29.419   1.609  32.134  1.00 23.71           O
```

FIGURE 1-7 (COORDINATES)

```
ATOM    408  N   TYR A  85     -33.035   1.825  32.136  1.00 20.82           N
ATOM    409  CA  TYR A  85     -34.008   0.860  32.636  1.00 22.95           C
ATOM    410  C   TYR A  85     -34.893   0.333  31.489  1.00 21.99           C
ATOM    411  O   TYR A  85     -35.157  -0.868  31.374  1.00 20.83           O
ATOM    412  CB  TYR A  85     -34.884   1.529  33.702  1.00 24.35           C
ATOM    413  CG  TYR A  85     -35.911   0.587  34.255  1.00 30.53           C
ATOM    414  CD1 TYR A  85     -35.545  -0.397  35.160  1.00 33.76           C
ATOM    415  CD2 TYR A  85     -37.246   0.665  33.861  1.00 32.79           C
ATOM    416  CE1 TYR A  85     -36.490  -1.290  35.678  1.00 36.01           C
ATOM    417  CE2 TYR A  85     -38.198  -0.232  34.370  1.00 35.31           C
ATOM    418  CZ  TYR A  85     -37.806  -1.197  35.281  1.00 36.01           C
ATOM    419  OH  TYR A  85     -38.732  -2.055  35.844  1.00 39.40           O
ATOM    420  N   ALA A  86     -35.379   1.237  30.644  1.00 20.53           N
ATOM    421  CA  ALA A  86     -36.222   0.840  29.533  1.00 19.73           C
ATOM    422  C   ALA A  86     -35.492  -0.094  28.561  1.00 19.22           C
ATOM    423  O   ALA A  86     -36.071  -1.055  28.078  1.00 18.96           O
ATOM    424  CB  ALA A  86     -36.724   2.076  28.805  1.00 19.47           C
ATOM    425  N   ALA A  87     -34.217   0.194  28.280  1.00 18.47           N
ATOM    426  CA  ALA A  87     -33.436  -0.643  27.366  1.00 17.84           C
ATOM    427  C   ALA A  87     -33.239  -2.038  27.955  1.00 17.69           C
ATOM    428  O   ALA A  87     -33.344  -3.042  27.259  1.00 18.11           O
ATOM    429  CB  ALA A  87     -32.045   0.006  27.096  1.00 17.07           C
ATOM    430  N   ARG A  88     -32.943  -2.087  29.245  1.00 17.54           N
ATOM    431  CA  ARG A  88     -32.742  -3.366  29.928  1.00 19.75           C
ATOM    432  C   ARG A  88     -34.037  -4.195  29.898  1.00 20.18           C
ATOM    433  O   ARG A  88     -34.015  -5.403  29.646  1.00 19.83           O
ATOM    434  CB  ARG A  88     -32.264  -3.077  31.363  1.00 21.29           C
ATOM    435  CG  ARG A  88     -31.891  -4.264  32.183  1.00 24.92           C
ATOM    436  CD  ARG A  88     -30.928  -3.847  33.318  1.00 25.21           C
ATOM    437  NE  ARG A  88     -31.580  -2.957  34.282  1.00 24.40           N
ATOM    438  CZ  ARG A  88     -31.304  -1.662  34.446  1.00 26.00           C
ATOM    439  NH1 ARG A  88     -30.375  -1.068  33.719  1.00 23.37           N
ATOM    440  NH2 ARG A  88     -31.985  -0.932  35.338  1.00 27.35           N
ATOM    441  N   GLN A  89     -35.174  -3.551  30.150  1.00 21.13           N
ATOM    442  CA  GLN A  89     -36.445  -4.287  30.124  1.00 22.33           C
ATOM    443  C   GLN A  89     -36.735  -4.810  28.725  1.00 20.58           C
ATOM    444  O   GLN A  89     -37.230  -5.918  28.542  1.00 21.04           O
ATOM    445  CB  GLN A  89     -37.584  -3.387  30.612  1.00 27.20           C
ATOM    446  CG  GLN A  89     -37.406  -2.955  32.069  1.00 33.59           C
ATOM    447  CD  GLN A  89     -37.298  -4.143  33.035  1.00 38.38           C
ATOM    448  OE1 GLN A  89     -38.245  -4.905  33.201  1.00 41.25           O
ATOM    449  NE2 GLN A  89     -36.132  -4.302  33.662  1.00 41.25           N
ATOM    450  N   HIS A  90     -36.430  -3.999  27.725  1.00 18.30           N
ATOM    451  CA  HIS A  90     -36.629  -4.396  26.344  1.00 18.47           C
ATOM    452  C   HIS A  90     -35.753  -5.607  25.976  1.00 17.73           C
ATOM    453  O   HIS A  90     -36.225  -6.583  25.392  1.00 18.06           O
ATOM    454  CB  HIS A  90     -36.300  -3.208  25.429  1.00 18.03           C
ATOM    455  CG  HIS A  90     -36.133  -3.584  23.988  1.00 20.66           C
ATOM    456  ND1 HIS A  90     -37.178  -4.020  23.204  1.00 21.94           N
ATOM    457  CD2 HIS A  90     -35.039  -3.569  23.184  1.00 22.83           C
ATOM    458  CE1 HIS A  90     -36.745  -4.255  21.978  1.00 21.85           C
ATOM    459  NE2 HIS A  90     -35.445  -3.991  21.939  1.00 24.04           N
ATOM    460  N   ILE A  91     -34.467  -5.543  26.317  1.00 18.66           N
ATOM    461  CA  ILE A  91     -33.571  -6.662  26.018  1.00 17.53           C
ATOM    462  C   ILE A  91     -34.062  -7.927  26.732  1.00 19.41           C
ATOM    463  O   ILE A  91     -34.166  -8.988  26.120  1.00 19.70           O
ATOM    464  CB  ILE A  91     -32.128  -6.289  26.438  1.00 17.22           C
ATOM    465  CG1 ILE A  91     -31.628  -5.206  25.460  1.00 17.55           C
ATOM    466  CG2 ILE A  91     -31.185  -7.529  26.393  1.00 17.99           C
ATOM    467  CD1 ILE A  91     -30.342  -4.471  25.908  1.00 17.90           C
ATOM    468  N   MET A  92     -34.398  -7.803  28.013  1.00 19.30           N
ATOM    469  CA  MET A  92     -34.872  -8.969  28.747  1.00 20.69           C
ATOM    470  C   MET A  92     -36.163  -9.551  28.176  1.00 22.21           C
ATOM    471  O   MET A  92     -36.293 -10.776  28.024  1.00 22.47           O
ATOM    472  CB  MET A  92     -35.043  -8.615  30.219  1.00 21.97           C
ATOM    473  CG  MET A  92     -33.715  -8.328  30.872  1.00 27.09           C
ATOM    474  SD  MET A  92     -33.894  -7.898  32.610  1.00 34.37           S
ATOM    475  CE  MET A  92     -33.907  -9.514  33.346  1.00 30.13           C
```

FIGURE 1-8 (COORDINATES)

```
ATOM    476  N   GLN A  93     -37.104  -8.682  27.833  1.00 21.74           N
ATOM    477  CA  GLN A  93     -38.387  -9.137  27.279  1.00 23.22           C
ATOM    478  C   GLN A  93     -38.244  -9.838  25.929  1.00 22.06           C
ATOM    479  O   GLN A  93     -38.897 -10.862  25.670  1.00 21.10           O
ATOM    480  CB  GLN A  93     -39.357  -7.951  27.172  1.00 24.48           C
ATOM    481  CG  GLN A  93     -39.867  -7.494  28.554  1.00 30.40           C
ATOM    482  CD  GLN A  93     -40.696  -6.205  28.537  1.00 34.25           C
ATOM    483  OE1 GLN A  93     -41.423  -5.920  29.499  1.00 38.43           O
ATOM    484  NE2 GLN A  93     -40.581  -5.418  27.468  1.00 34.55           N
ATOM    485  N   ARG A  94     -37.383  -9.297  25.060  1.00 19.71           N
ATOM    486  CA  ARG A  94     -37.175  -9.897  23.756  1.00 19.09           C
ATOM    487  C   ARG A  94     -36.518 -11.280  23.876  1.00 20.45           C
ATOM    488  O   ARG A  94     -36.781 -12.175  23.073  1.00 21.02           O
ATOM    489  CB  ARG A  94     -36.345  -8.940  22.861  1.00 17.68           C
ATOM    490  CG  ARG A  94     -37.139  -7.667  22.487  1.00 18.52           C
ATOM    491  CD  ARG A  94     -38.323  -7.954  21.512  1.00 20.06           C
ATOM    492  NE  ARG A  94     -37.847  -8.425  20.209  1.00 21.50           N
ATOM    493  CZ  ARG A  94     -38.598  -8.977  19.252  1.00 21.75           C
ATOM    494  NH1 ARG A  94     -39.917  -9.134  19.425  1.00 22.37           N
ATOM    495  NH2 ARG A  94     -38.035  -9.396  18.122  1.00 20.10           N
ATOM    496  N   ILE A  95     -35.671 -11.468  24.881  1.00 18.46           N
ATOM    497  CA  ILE A  95     -35.060 -12.768  25.054  1.00 19.44           C
ATOM    498  C   ILE A  95     -36.070 -13.730  25.701  1.00 20.01           C
ATOM    499  O   ILE A  95     -36.177 -14.886  25.283  1.00 20.08           O
ATOM    500  CB  ILE A  95     -33.797 -12.670  25.919  1.00 20.16           C
ATOM    501  CG1 ILE A  95     -32.704 -11.957  25.098  1.00 20.24           C
ATOM    502  CG2 ILE A  95     -33.341 -14.068  26.363  1.00 22.08           C
ATOM    503  CD1 ILE A  95     -31.520 -11.500  25.937  1.00 20.95           C
ATOM    504  N   GLN A  96     -36.825 -13.224  26.676  1.00 21.06           N
ATOM    505  CA  GLN A  96     -37.795 -14.053  27.402  1.00 24.45           C
ATOM    506  C   GLN A  96     -38.888 -14.663  26.538  1.00 25.21           C
ATOM    507  O   GLN A  96     -39.390 -15.754  26.852  1.00 27.25           O
ATOM    508  CB  GLN A  96     -38.414 -13.250  28.551  1.00 24.80           C
ATOM    509  CG  GLN A  96     -37.414 -12.949  29.663  1.00 30.13           C
ATOM    510  CD  GLN A  96     -37.988 -12.093  30.796  1.00 34.20           C
ATOM    511  OE1 GLN A  96     -38.800 -11.178  30.567  1.00 36.35           O
ATOM    512  NE2 GLN A  96     -37.557 -12.375  32.019  1.00 35.56           N
ATOM    513  N   ARG A  97     -39.270 -13.986  25.458  1.00 24.75           N
ATOM    514  CA  ARG A  97     -40.315 -14.523  24.579  1.00 25.55           C
ATOM    515  C   ARG A  97     -39.848 -15.684  23.689  1.00 24.41           C
ATOM    516  O   ARG A  97     -40.668 -16.362  23.056  1.00 25.96           O
ATOM    517  CB  ARG A  97     -40.907 -13.400  23.717  1.00 27.53           C
ATOM    518  CG  ARG A  97     -39.937 -12.739  22.753  1.00 27.76           C
ATOM    519  CD  ARG A  97     -40.584 -11.606  21.958  1.00 29.48           C
ATOM    520  NE  ARG A  97     -41.576 -12.104  21.003  1.00 32.23           N
ATOM    521  CZ  ARG A  97     -41.285 -12.698  19.848  1.00 33.14           C
ATOM    522  NH1 ARG A  97     -40.024 -12.872  19.455  1.00 29.83           N
ATOM    523  NH2 ARG A  97     -42.268 -13.176  19.096  1.00 34.64           N
ATOM    524  N   LEU A  98     -38.545 -15.941  23.637  1.00 21.34           N
ATOM    525  CA  LEU A  98     -38.031 -17.007  22.795  1.00 20.25           C
ATOM    526  C   LEU A  98     -38.227 -18.401  23.404  1.00 20.35           C
ATOM    527  O   LEU A  98     -38.384 -18.538  24.624  1.00 23.20           O
ATOM    528  CB  LEU A  98     -36.543 -16.748  22.497  1.00 20.05           C
ATOM    529  CG  LEU A  98     -36.357 -15.393  21.778  1.00 20.32           C
ATOM    530  CD1 LEU A  98     -34.863 -15.164  21.520  1.00 20.72           C
ATOM    531  CD2 LEU A  98     -37.096 -15.389  20.427  1.00 20.68           C
ATOM    532  N   GLN A  99     -38.247 -19.416  22.549  1.00 21.29           N
ATOM    533  CA  GLN A  99     -38.416 -20.792  22.995  1.00 23.22           C
ATOM    534  C   GLN A  99     -37.199 -21.387  23.685  1.00 23.40           C
ATOM    535  O   GLN A  99     -37.329 -22.170  24.652  1.00 22.41           O
ATOM    536  CB  GLN A  99     -38.847 -21.677  21.816  1.00 25.85           C
ATOM    537  CG  GLN A  99     -40.192 -21.227  21.235  1.00 31.52           C
ATOM    538  CD  GLN A  99     -40.602 -21.978  19.972  1.00 37.85           C
ATOM    539  OE1 GLN A  99     -41.374 -21.453  19.158  1.00 43.26           O
ATOM    540  NE2 GLN A  99     -40.107 -23.207  19.802  1.00 39.58           N
ATOM    541  N   ALA A 100     -36.002 -21.035  23.214  1.00 22.03           N
ATOM    542  CA  ALA A 100     -34.803 -21.589  23.840  1.00 20.81           C
ATOM    543  C   ALA A 100     -34.733 -21.248  25.322  1.00 20.90           C
```

FIGURE 1-9 (COORDINATES)

| | | | | | | | | | | |
|---|---|---|---|---|---|---|---|---|---|---|
| ATOM | 544 | O   | ALA | A | 100 | -35.253 | -20.235 | 25.778 | 1.00 20.11 | O |
| ATOM | 545 | CB  | ALA | A | 100 | -33.522 | -21.120 | 23.075 | 1.00 20.53 | C |
| ATOM | 546 | N   | ASP | A | 101 | -34.034 | -22.092 | 26.069 | 1.00 21.10 | N |
| ATOM | 547 | CA  | ASP | A | 101 | -33.975 | -22.001 | 27.525 | 1.00 21.82 | C |
| ATOM | 548 | C   | ASP | A | 101 | -33.006 | -20.967 | 28.095 | 1.00 21.04 | C |
| ATOM | 549 | O   | ASP | A | 101 | -32.151 | -21.298 | 28.920 | 1.00 20.38 | O |
| ATOM | 550 | CB  | ASP | A | 101 | -33.634 | -23.409 | 28.042 | 1.00 25.01 | C |
| ATOM | 551 | CG  | ASP | A | 101 | -34.006 | -23.629 | 29.510 | 1.00 27.13 | C |
| ATOM | 552 | OD1 | ASP | A | 101 | -34.771 | -22.828 | 30.102 | 1.00 28.15 | O |
| ATOM | 553 | OD2 | ASP | A | 101 | -33.524 | -24.652 | 30.073 | 1.00 29.37 | O |
| ATOM | 554 | N   | TRP | A | 102 | -33.160 | -19.707 | 27.682 | 1.00 19.49 | N |
| ATOM | 555 | CA  | TRP | A | 102 | -32.266 | -18.651 | 28.166 | 1.00 18.45 | C |
| ATOM | 556 | C   | TRP | A | 102 | -32.441 | -18.371 | 29.645 | 1.00 19.01 | C |
| ATOM | 557 | O   | TRP | A | 102 | -33.578 | -18.261 | 30.130 | 1.00 21.28 | O |
| ATOM | 558 | CB  | TRP | A | 102 | -32.537 | -17.344 | 27.397 | 1.00 16.47 | C |
| ATOM | 559 | CG  | TRP | A | 102 | -32.134 | -17.416 | 25.990 | 1.00 16.14 | C |
| ATOM | 560 | CD1 | TRP | A | 102 | -32.955 | -17.576 | 24.904 | 1.00 18.06 | C |
| ATOM | 561 | CD2 | TRP | A | 102 | -30.806 | -17.270 | 25.474 | 1.00 17.05 | C |
| ATOM | 562 | NE1 | TRP | A | 102 | -32.227 | -17.522 | 23.747 | 1.00 18.46 | N |
| ATOM | 563 | CE2 | TRP | A | 102 | -30.899 | -17.335 | 24.061 | 1.00 16.63 | C |
| ATOM | 564 | CE3 | TRP | A | 102 | -29.547 | -17.096 | 26.070 | 1.00 16.99 | C |
| ATOM | 565 | CZ2 | TRP | A | 102 | -29.775 | -17.222 | 23.224 | 1.00 16.29 | C |
| ATOM | 566 | CZ3 | TRP | A | 102 | -28.434 | -16.987 | 25.243 | 1.00 14.65 | C |
| ATOM | 567 | CH2 | TRP | A | 102 | -28.555 | -17.049 | 23.836 | 1.00 16.62 | C |
| ATOM | 568 | N   | VAL | A | 103 | -31.331 | -18.249 | 30.362 | 1.00 18.05 | N |
| ATOM | 569 | CA  | VAL | A | 103 | -31.369 | -17.924 | 31.782 | 1.00 18.69 | C |
| ATOM | 570 | C   | VAL | A | 103 | -30.840 | -16.497 | 31.874 | 1.00 20.50 | C |
| ATOM | 571 | O   | VAL | A | 103 | -29.688 | -16.231 | 31.497 | 1.00 19.39 | O |
| ATOM | 572 | CB  | VAL | A | 103 | -30.483 | -18.889 | 32.579 | 1.00 20.30 | C |
| ATOM | 573 | CG1 | VAL | A | 103 | -30.447 | -18.496 | 34.060 | 1.00 21.33 | C |
| ATOM | 574 | CG2 | VAL | A | 103 | -31.025 | -20.311 | 32.402 | 1.00 21.87 | C |
| ATOM | 575 | N   | LEU | A | 104 | -31.691 | -15.585 | 32.332 | 1.00 20.97 | N |
| ATOM | 576 | CA  | LEU | A | 104 | -31.322 | -14.177 | 32.445 | 1.00 22.60 | C |
| ATOM | 577 | C   | LEU | A | 104 | -30.856 | -13.808 | 33.834 | 1.00 23.75 | C |
| ATOM | 578 | O   | LEU | A | 104 | -31.445 | -14.215 | 34.852 | 1.00 23.56 | O |
| ATOM | 579 | CB  | LEU | A | 104 | -32.502 | -13.266 | 32.060 | 1.00 22.67 | C |
| ATOM | 580 | CG  | LEU | A | 104 | -32.797 | -13.172 | 30.568 | 1.00 24.48 | C |
| ATOM | 581 | CD1 | LEU | A | 104 | -34.145 | -12.498 | 30.375 | 1.00 27.05 | C |
| ATOM | 582 | CD2 | LEU | A | 104 | -31.685 | -12.359 | 29.855 | 1.00 24.29 | C |
| ATOM | 583 | N   | GLU | A | 105 | -29.758 | -13.074 | 33.885 | 1.00 22.48 | N |
| ATOM | 584 | CA  | GLU | A | 105 | -29.230 | -12.579 | 35.161 | 1.00 24.26 | C |
| ATOM | 585 | C   | GLU | A | 105 | -28.925 | -11.099 | 34.995 | 1.00 24.86 | C |
| ATOM | 586 | O   | GLU | A | 105 | -28.402 | -10.696 | 33.957 | 1.00 23.43 | O |
| ATOM | 587 | CB  | GLU | A | 105 | -27.912 | -13.230 | 35.502 | 1.00 26.90 | C |
| ATOM | 588 | CG  | GLU | A | 105 | -27.930 | -14.729 | 35.654 | 1.00 34.74 | C |
| ATOM | 589 | CD  | GLU | A | 105 | -26.516 | -15.244 | 35.823 | 1.00 38.44 | C |
| ATOM | 590 | OE1 | GLU | A | 105 | -25.757 | -15.263 | 34.810 | 1.00 38.98 | O |
| ATOM | 591 | OE2 | GLU | A | 105 | -26.156 | -15.604 | 36.974 | 1.00 42.23 | O |
| ATOM | 592 | N   | ILE | A | 106 | -29.247 | -10.313 | 36.017 | 1.00 24.20 | N |
| ATOM | 593 | CA  | ILE | A | 106 | -28.926 | -8.886  | 36.025 | 1.00 24.40 | C |
| ATOM | 594 | C   | ILE | A | 106 | -27.821 | -8.761  | 37.062 | 1.00 25.40 | C |
| ATOM | 595 | O   | ILE | A | 106 | -28.001 | -9.113  | 38.253 | 1.00 25.69 | O |
| ATOM | 596 | CB  | ILE | A | 106 | -30.120 | -8.015  | 36.429 | 1.00 25.33 | C |
| ATOM | 597 | CG1 | ILE | A | 106 | -31.250 | -8.189  | 35.416 | 1.00 27.69 | C |
| ATOM | 598 | CG2 | ILE | A | 106 | -29.705 | -6.550  | 36.479 | 1.00 24.20 | C |
| ATOM | 599 | CD1 | ILE | A | 106 | -30.735 | -8.207  | 33.948 | 1.00 29.61 | C |
| ATOM | 600 | N   | ASP | A | 107 | -26.666 | -8.285  | 36.612 | 1.00 22.99 | N |
| ATOM | 601 | CA  | ASP | A | 107 | -25.492 | -8.138  | 37.447 | 1.00 21.37 | C |
| ATOM | 602 | C   | ASP | A | 107 | -25.358 | -6.677  | 37.817 | 1.00 21.74 | C |
| ATOM | 603 | O   | ASP | A | 107 | -24.804 | -5.884  | 37.061 | 1.00 19.15 | O |
| ATOM | 604 | CB  | ASP | A | 107 | -24.266 | -8.659  | 36.690 | 1.00 22.52 | C |
| ATOM | 605 | CG  | ASP | A | 107 | -22.957 | -8.218  | 37.292 | 1.00 21.96 | C |
| ATOM | 606 | OD1 | ASP | A | 107 | -22.771 | -8.251  | 38.535 | 1.00 23.51 | O |
| ATOM | 607 | OD2 | ASP | A | 107 | -22.066 | -7.834  | 36.506 | 1.00 25.60 | O |
| ATOM | 608 | N   | THR | A | 108 | -25.871 | -6.346  | 38.998 | 1.00 20.90 | N |
| ATOM | 609 | CA  | THR | A | 108 | -25.900 | -4.970  | 39.490 | 1.00 20.27 | C |
| ATOM | 610 | C   | THR | A | 108 | -24.816 | -4.684  | 40.514 | 1.00 21.49 | C |
| ATOM | 611 | O   | THR | A | 108 | -24.572 | -5.482  | 41.436 | 1.00 21.20 | O |

FIGURE 1-10 (COORDINATES)

```
ATOM    612  CB  THR A 108     -27.303  -4.663  40.037  1.00 19.85           C
ATOM    613  OG1 THR A 108     -28.238  -4.782  38.969  1.00 19.94           O
ATOM    614  CG2 THR A 108     -27.387  -3.223  40.597  1.00 22.15           C
ATOM    615  N   PHE A 109     -24.156  -3.545  40.367  1.00 19.55           N
ATOM    616  CA  PHE A 109     -23.055  -3.200  41.240  1.00 19.70           C
ATOM    617  C   PHE A 109     -22.831  -1.702  41.314  1.00 19.55           C
ATOM    618  O   PHE A 109     -23.354  -0.952  40.497  1.00 18.35           O
ATOM    619  CB  PHE A 109     -21.742  -3.842  40.727  1.00 20.55           C
ATOM    620  CG  PHE A 109     -21.306  -3.341  39.347  1.00 19.01           C
ATOM    621  CD1 PHE A 109     -21.863  -3.875  38.187  1.00 19.23           C
ATOM    622  CD2 PHE A 109     -20.383  -2.300  39.232  1.00 18.63           C
ATOM    623  CE1 PHE A 109     -21.509  -3.362  36.919  1.00 18.66           C
ATOM    624  CE2 PHE A 109     -20.018  -1.774  37.959  1.00 18.03           C
ATOM    625  CZ  PHE A 109     -20.591  -2.314  36.813  1.00 19.57           C
ATOM    626  N   LEU A 110     -22.028  -1.295  42.289  1.00 19.87           N
ATOM    627  CA  LEU A 110     -21.653   0.102  42.468  1.00 19.59           C
ATOM    628  C   LEU A 110     -20.222   0.361  41.986  1.00 20.47           C
ATOM    629  O   LEU A 110     -19.339  -0.511  42.053  1.00 20.08           O
ATOM    630  CB  LEU A 110     -21.683   0.481  43.956  1.00 22.08           C
ATOM    631  CG  LEU A 110     -23.004   0.609  44.687  1.00 26.40           C
ATOM    632  CD1 LEU A 110     -22.695   0.981  46.166  1.00 25.87           C
ATOM    633  CD2 LEU A 110     -23.853   1.704  44.033  1.00 26.66           C
ATOM    634  N   SER A 111     -19.974   1.568  41.488  1.00 17.92           N
ATOM    635  CA  SER A 111     -18.633   1.952  41.150  1.00 17.09           C
ATOM    636  C   SER A 111     -18.510   3.437  41.399  1.00 18.95           C
ATOM    637  O   SER A 111     -19.509   4.143  41.317  1.00 18.28           O
ATOM    638  CB  SER A 111     -18.266   1.670  39.680  1.00 17.63           C
ATOM    639  OG  SER A 111     -16.968   2.170  39.375  1.00 21.50           O
ATOM    640  N   GLN A 112     -17.299   3.883  41.712  1.00 18.31           N
ATOM    641  CA  GLN A 112     -17.022   5.317  41.849  1.00 17.77           C
ATOM    642  C   GLN A 112     -17.008   5.814  40.396  1.00 20.05           C
ATOM    643  O   GLN A 112     -16.657   5.053  39.472  1.00 18.57           O
ATOM    644  CB  GLN A 112     -15.638   5.535  42.495  1.00 19.16           C
ATOM    645  CG  GLN A 112     -15.056   6.941  42.397  1.00 20.65           C
ATOM    646  CD  GLN A 112     -15.860   7.972  43.198  1.00 23.31           C
ATOM    647  OE1 GLN A 112     -15.308   8.698  44.068  1.00 24.93           O
ATOM    648  NE2 GLN A 112     -17.150   8.044  42.915  1.00 17.01           N
ATOM    649  N   THR A 113     -17.375   7.086  40.191  1.00 17.58           N
ATOM    650  CA  THR A 113     -17.387   7.682  38.847  1.00 18.73           C
ATOM    651  C   THR A 113     -17.053   9.172  39.030  1.00 19.63           C
ATOM    652  O   THR A 113     -16.973   9.647  40.168  1.00 20.05           O
ATOM    653  CB  THR A 113     -18.799   7.629  38.168  1.00 19.48           C
ATOM    654  OG1 THR A 113     -19.669   8.599  38.773  1.00 19.09           O
ATOM    655  CG2 THR A 113     -19.461   6.245  38.311  1.00 15.85           C
ATOM    656  N   PRO A 114     -16.877   9.918  37.925  1.00 20.37           N
ATOM    657  CA  PRO A 114     -16.565  11.351  38.085  1.00 21.57           C
ATOM    658  C   PRO A 114     -17.686  12.068  38.798  1.00 20.79           C
ATOM    659  O   PRO A 114     -17.486  13.186  39.321  1.00 21.36           O
ATOM    660  CB  PRO A 114     -16.385  11.836  36.649  1.00 20.52           C
ATOM    661  CG  PRO A 114     -15.764  10.614  35.981  1.00 22.71           C
ATOM    662  CD  PRO A 114     -16.595   9.463  36.551  1.00 20.87           C
ATOM    663  N   TYR A 115     -18.855  11.428  38.845  1.00 22.29           N
ATOM    664  CA  TYR A 115     -20.040  12.010  39.492  1.00 21.69           C
ATOM    665  C   TYR A 115     -20.395  11.350  40.821  1.00 23.69           C
ATOM    666  O   TYR A 115     -21.512  11.488  41.331  1.00 23.66           O
ATOM    667  CB  TYR A 115     -21.233  11.971  38.517  1.00 23.58           C
ATOM    668  CG  TYR A 115     -21.020  12.888  37.337  1.00 24.76           C
ATOM    669  CD1 TYR A 115     -20.858  14.267  37.531  1.00 28.77           C
ATOM    670  CD2 TYR A 115     -20.860  12.386  36.038  1.00 26.98           C
ATOM    671  CE1 TYR A 115     -20.527  15.115  36.477  1.00 29.06           C
ATOM    672  CE2 TYR A 115     -20.530  13.236  34.975  1.00 28.69           C
ATOM    673  CZ  TYR A 115     -20.362  14.598  35.206  1.00 30.72           C
ATOM    674  OH  TYR A 115     -20.006  15.444  34.170  1.00 32.20           O
ATOM    675  N   GLY A 116     -19.429  10.629  41.391  1.00 18.32           N
ATOM    676  CA  GLY A 116     -19.639   9.974  42.662  1.00 19.57           C
ATOM    677  C   GLY A 116     -20.101   8.541  42.468  1.00 19.80           C
ATOM    678  O   GLY A 116     -20.170   8.051  41.327  1.00 18.17           O
ATOM    679  N   TYR A 117     -20.439   7.869  43.564  1.00 20.68           N
```

FIGURE 1-11 (COORDINATES)

```
ATOM    680  CA  TYR A 117     -20.886   6.481  43.456  1.00 18.83           C
ATOM    681  C   TYR A 117     -22.167   6.370  42.636  1.00 21.18           C
ATOM    682  O   TYR A 117     -23.107   7.158  42.823  1.00 21.26           O
ATOM    683  CB  TYR A 117     -21.138   5.874  44.844  1.00 20.34           C
ATOM    684  CG  TYR A 117     -19.930   5.797  45.750  1.00 20.11           C
ATOM    685  CD1 TYR A 117     -20.065   5.338  47.058  1.00 23.38           C
ATOM    686  CD2 TYR A 117     -18.658   6.183  45.308  1.00 22.79           C
ATOM    687  CE1 TYR A 117     -18.972   5.265  47.899  1.00 23.19           C
ATOM    688  CE2 TYR A 117     -17.561   6.118  46.150  1.00 22.90           C
ATOM    689  CZ  TYR A 117     -17.736   5.656  47.442  1.00 23.10           C
ATOM    690  OH  TYR A 117     -16.660   5.589  48.297  1.00 27.82           O
ATOM    691  N   ARG A 118     -22.210   5.397  41.722  1.00 18.14           N
ATOM    692  CA  ARG A 118     -23.393   5.132  40.907  1.00 18.02           C
ATOM    693  C   ARG A 118     -23.576   3.628  40.749  1.00 18.65           C
ATOM    694  O   ARG A 118     -22.617   2.852  40.901  1.00 19.52           O
ATOM    695  CB  ARG A 118     -23.253   5.741  39.513  1.00 20.71           C
ATOM    696  CG  ARG A 118     -23.096   7.271  39.515  1.00 21.65           C
ATOM    697  CD  ARG A 118     -23.068   7.766  38.081  1.00 23.20           C
ATOM    698  NE  ARG A 118     -24.325   7.525  37.359  1.00 25.41           N
ATOM    699  CZ  ARG A 118     -25.302   8.425  37.238  1.00 28.88           C
ATOM    700  NH1 ARG A 118     -25.188   9.626  37.807  1.00 28.09           N
ATOM    701  NH2 ARG A 118     -26.370   8.152  36.490  1.00 28.30           N
ATOM    702  N   SER A 119     -24.793   3.237  40.393  1.00 17.42           N
ATOM    703  CA  SER A 119     -25.139   1.837  40.184  1.00 19.11           C
ATOM    704  C   SER A 119     -25.183   1.507  38.691  1.00 19.78           C
ATOM    705  O   SER A 119     -25.616   2.339  37.874  1.00 19.73           O
ATOM    706  CB  SER A 119     -26.506   1.543  40.816  1.00 21.12           C
ATOM    707  OG  SER A 119     -26.865   0.182  40.618  1.00 23.60           O
ATOM    708  N   PHE A 120     -24.749   0.293  38.348  1.00 18.50           N
ATOM    709  CA  PHE A 120     -24.723  -0.175  36.951  1.00 18.10           C
ATOM    710  C   PHE A 120     -25.323  -1.580  36.933  1.00 19.38           C
ATOM    711  O   PHE A 120     -25.249  -2.304  37.941  1.00 18.02           O
ATOM    712  CB  PHE A 120     -23.281  -0.285  36.467  1.00 19.61           C
ATOM    713  CG  PHE A 120     -22.552   1.020  36.407  1.00 17.71           C
ATOM    714  CD1 PHE A 120     -22.406   1.682  35.195  1.00 18.20           C
ATOM    715  CD2 PHE A 120     -22.007   1.595  37.557  1.00 17.28           C
ATOM    716  CE1 PHE A 120     -21.727   2.897  35.119  1.00 16.90           C
ATOM    717  CE2 PHE A 120     -21.326   2.814  37.496  1.00 16.66           C
ATOM    718  CZ  PHE A 120     -21.185   3.468  36.260  1.00 16.91           C
ATOM    719  N   SER A 121     -25.862  -1.988  35.783  1.00 18.33           N
ATOM    720  CA  SER A 121     -26.444  -3.316  35.663  1.00 18.05           C
ATOM    721  C   SER A 121     -26.101  -3.993  34.343  1.00 17.47           C
ATOM    722  O   SER A 121     -26.624  -3.617  33.304  1.00 16.54           O
ATOM    723  CB  SER A 121     -27.969  -3.258  35.766  1.00 18.10           C
ATOM    724  OG  SER A 121     -28.401  -2.880  37.091  1.00 19.11           O
ATOM    725  N   ASN A 122     -25.228  -4.990  34.384  1.00 15.69           N
ATOM    726  CA  ASN A 122     -24.936  -5.754  33.174  1.00 15.87           C
ATOM    727  C   ASN A 122     -26.075  -6.763  32.983  1.00 19.06           C
ATOM    728  O   ASN A 122     -26.678  -7.220  33.960  1.00 19.33           O
ATOM    729  CB  ASN A 122     -23.659  -6.565  33.340  1.00 16.49           C
ATOM    730  CG  ASN A 122     -22.414  -5.711  33.415  1.00 17.59           C
ATOM    731  OD1 ASN A 122     -22.248  -4.779  32.637  1.00 16.29           O
ATOM    732  ND2 ASN A 122     -21.514  -6.050  34.335  1.00 14.59           N
ATOM    733  N   ILE A 123     -26.359  -7.126  31.740  1.00 16.82           N
ATOM    734  CA  ILE A 123     -27.382  -8.129  31.452  1.00 16.62           C
ATOM    735  C   ILE A 123     -26.666  -9.365  30.908  1.00 18.37           C
ATOM    736  O   ILE A 123     -25.924  -9.264  29.927  1.00 17.55           O
ATOM    737  CB  ILE A 123     -28.356  -7.644  30.377  1.00 18.56           C
ATOM    738  CG1 ILE A 123     -29.020  -6.346  30.835  1.00 18.92           C
ATOM    739  CG2 ILE A 123     -29.456  -8.707  30.118  1.00 17.15           C
ATOM    740  CD1 ILE A 123     -29.691  -5.581  29.699  1.00 22.04           C
ATOM    741  N   ILE A 124     -26.885 -10.540  31.515  1.00 17.28           N
ATOM    742  CA  ILE A 124     -26.250 -11.752  31.005  1.00 17.81           C
ATOM    743  C   ILE A 124     -27.340 -12.756  30.678  1.00 18.95           C
ATOM    744  O   ILE A 124     -28.229 -12.992  31.489  1.00 19.05           O
ATOM    745  CB  ILE A 124     -25.261 -12.374  32.012  1.00 20.12           C
ATOM    746  CG1 ILE A 124     -24.118 -11.383  32.324  1.00 21.07           C
ATOM    747  CG2 ILE A 124     -24.601 -13.624  31.392  1.00 19.11           C
```

FIGURE 1-12 (COORDINATES)

```
ATOM    748  CD1 ILE A 124     -24.320 -10.600  33.600  1.00 25.54           C
ATOM    749  N   SER A 125     -27.283 -13.302  29.469  1.00 16.60           N
ATOM    750  CA  SER A 125     -28.286 -14.266  29.006  1.00 17.29           C
ATOM    751  C   SER A 125     -27.532 -15.534  28.649  1.00 17.88           C
ATOM    752  O   SER A 125     -26.719 -15.535  27.720  1.00 16.68           O
ATOM    753  CB  SER A 125     -29.022 -13.690  27.789  1.00 18.35           C
ATOM    754  OG  SER A 125     -30.179 -14.456  27.482  1.00 21.70           O
ATOM    755  N   THR A 126     -27.843 -16.658  29.336  1.00 15.47           N
ATOM    756  CA  THR A 126     -27.065 -17.856  29.108  1.00 17.31           C
ATOM    757  C   THR A 126     -27.858 -19.105  28.795  1.00 17.50           C
ATOM    758  O   THR A 126     -28.854 -19.364  29.458  1.00 19.15           O
ATOM    759  CB  THR A 126     -26.233 -18.167  30.396  1.00 18.07           C
ATOM    760  OG1 THR A 126     -25.541 -16.978  30.807  1.00 19.16           O
ATOM    761  CG2 THR A 126     -25.261 -19.290  30.177  1.00 19.60           C
ATOM    762  N   LEU A 127     -27.429 -19.856  27.786  1.00 16.98           N
ATOM    763  CA  LEU A 127     -28.061 -21.158  27.527  1.00 17.64           C
ATOM    764  C   LEU A 127     -27.139 -22.178  28.246  1.00 18.09           C
ATOM    765  O   LEU A 127     -25.910 -22.079  28.169  1.00 18.03           O
ATOM    766  CB  LEU A 127     -28.119 -21.461  26.017  1.00 17.18           C
ATOM    767  CG  LEU A 127     -29.118 -20.604  25.225  1.00 18.73           C
ATOM    768  CD1 LEU A 127     -29.010 -20.960  23.762  1.00 17.76           C
ATOM    769  CD2 LEU A 127     -30.559 -20.792  25.727  1.00 19.58           C
ATOM    770  N   ASN A 128     -27.728 -23.144  28.974  1.00 17.19           N
ATOM    771  CA  ASN A 128     -26.930 -24.164  29.677  1.00 18.01           C
ATOM    772  C   ASN A 128     -25.878 -23.589  30.613  1.00 18.41           C
ATOM    773  O   ASN A 128     -24.672 -23.775  30.395  1.00 17.84           O
ATOM    774  CB  ASN A 128     -26.246 -25.089  28.678  1.00 18.35           C
ATOM    775  CG  ASN A 128     -27.224 -25.677  27.674  1.00 20.61           C
ATOM    776  OD1 ASN A 128     -27.863 -26.745  27.935  1.00 25.35           O
ATOM    777  ND2 ASN A 128     -27.376 -25.012  26.534  1.00 15.53           N
ATOM    778  N   PRO A 129     -26.319 -22.927  31.697  1.00 19.63           N
ATOM    779  CA  PRO A 129     -25.439 -22.316  32.688  1.00 21.15           C
ATOM    780  C   PRO A 129     -24.384 -23.251  33.238  1.00 21.01           C
ATOM    781  O   PRO A 129     -23.295 -22.796  33.558  1.00 21.58           O
ATOM    782  CB  PRO A 129     -26.395 -21.876  33.804  1.00 22.64           C
ATOM    783  CG  PRO A 129     -27.642 -21.660  33.140  1.00 24.27           C
ATOM    784  CD  PRO A 129     -27.731 -22.721  32.074  1.00 20.63           C
ATOM    785  N   THR A 130     -24.690 -24.542  33.377  1.00 20.39           N
ATOM    786  CA  THR A 130     -23.671 -25.425  33.932  1.00 21.00           C
ATOM    787  C   THR A 130     -22.739 -26.034  32.903  1.00 22.06           C
ATOM    788  O   THR A 130     -21.788 -26.715  33.292  1.00 20.17           O
ATOM    789  CB  THR A 130     -24.278 -26.571  34.791  1.00 22.87           C
ATOM    790  OG1 THR A 130     -25.015 -27.458  33.956  1.00 25.02           O
ATOM    791  CG2 THR A 130     -25.176 -26.001  35.855  1.00 22.96           C
ATOM    792  N   ALA A 131     -23.005 -25.808  31.620  0.00 20.21           N
ATOM    793  CA  ALA A 131     -22.132 -26.329  30.575  0.00 19.36           C
ATOM    794  C   ALA A 131     -20.774 -25.714  30.885  0.00 18.49           C
ATOM    795  O   ALA A 131     -20.701 -24.550  31.280  0.00 18.50           O
ATOM    796  CB  ALA A 131     -22.620 -25.881  29.206  0.00 19.43           C
ATOM    797  N   LYS A 132     -19.699 -26.474  30.711  1.00 17.57           N
ATOM    798  CA  LYS A 132     -18.378 -25.934  31.042  1.00 15.99           C
ATOM    799  C   LYS A 132     -17.909 -24.816  30.148  1.00 16.19           C
ATOM    800  O   LYS A 132     -17.253 -23.887  30.626  1.00 15.34           O
ATOM    801  CB  LYS A 132     -17.312 -27.036  31.004  1.00 18.22           C
ATOM    802  CG  LYS A 132     -17.558 -28.071  32.117  1.00 20.99           C
ATOM    803  CD  LYS A 132     -16.417 -29.069  32.246  1.00 22.69           C
ATOM    804  CE  LYS A 132     -16.198 -29.829  30.975  1.00 26.48           C
ATOM    805  NZ  LYS A 132     -17.348 -30.758  30.724  1.00 30.36           N
ATOM    806  N   ARG A 133     -18.228 -24.914  28.861  1.00 17.95           N
ATOM    807  CA  ARG A 133     -17.731 -23.923  27.897  1.00 16.09           C
ATOM    808  C   ARG A 133     -18.846 -23.135  27.247  1.00 17.02           C
ATOM    809  O   ARG A 133     -19.918 -23.672  26.974  1.00 15.64           O
ATOM    810  CB  ARG A 133     -16.971 -24.639  26.773  1.00 15.97           C
ATOM    811  CG  ARG A 133     -15.733 -25.387  27.247  1.00 16.74           C
ATOM    812  CD  ARG A 133     -15.269 -26.436  26.221  1.00 18.50           C
ATOM    813  NE  ARG A 133     -15.018 -25.831  24.911  1.00 18.41           N
ATOM    814  CZ  ARG A 133     -15.004 -26.510  23.766  1.00 19.75           C
ATOM    815  NH1 ARG A 133     -15.228 -27.843  23.760  1.00 19.82           N
```

FIGURE 1-13 (COORDINATES)

```
ATOM    816  NH2 ARG A 133     -14.805 -25.858  22.609  1.00 17.53           N
ATOM    817  N   HIS A 134     -18.595 -21.845  27.022  1.00 15.19           N
ATOM    818  CA  HIS A 134     -19.563 -21.053  26.281  1.00 14.81           C
ATOM    819  C   HIS A 134     -18.865 -20.173  25.265  1.00 15.97           C
ATOM    820  O   HIS A 134     -17.761 -19.661  25.521  1.00 17.19           O
ATOM    821  CB  HIS A 134     -20.401 -20.115  27.179  1.00 15.04           C
ATOM    822  CG  HIS A 134     -21.422 -20.838  27.998  1.00 16.96           C
ATOM    823  ND1 HIS A 134     -21.086 -21.497  29.154  1.00 16.66           N
ATOM    824  CD2 HIS A 134     -22.746 -21.069  27.801  1.00 18.20           C
ATOM    825  CE1 HIS A 134     -22.151 -22.107  29.644  1.00 17.78           C
ATOM    826  NE2 HIS A 134     -23.173 -21.866  28.843  1.00 16.55           N
ATOM    827  N   LEU A 135     -19.490 -20.054  24.104  1.00 13.66           N
ATOM    828  CA  LEU A 135     -19.066 -19.086  23.082  1.00 15.69           C
ATOM    829  C   LEU A 135     -19.834 -17.856  23.593  1.00 15.08           C
ATOM    830  O   LEU A 135     -21.030 -17.961  23.924  1.00 15.35           O
ATOM    831  CB  LEU A 135     -19.611 -19.468  21.707  1.00 15.78           C
ATOM    832  CG  LEU A 135     -19.534 -18.332  20.669  1.00 15.02           C
ATOM    833  CD1 LEU A 135     -18.048 -17.991  20.399  1.00 15.32           C
ATOM    834  CD2 LEU A 135     -20.211 -18.813  19.366  1.00 15.08           C
ATOM    835  N   VAL A 136     -19.160 -16.696  23.680  1.00 13.81           N
ATOM    836  CA  VAL A 136     -19.821 -15.508  24.238  1.00 14.28           C
ATOM    837  C   VAL A 136     -19.888 -14.382  23.224  1.00 15.53           C
ATOM    838  O   VAL A 136     -18.874 -14.033  22.646  1.00 15.37           O
ATOM    839  CB  VAL A 136     -19.056 -14.990  25.508  1.00 15.18           C
ATOM    840  CG1 VAL A 136     -19.816 -13.809  26.147  1.00 16.59           C
ATOM    841  CG2 VAL A 136     -18.929 -16.146  26.540  1.00 15.64           C
ATOM    842  N   LEU A 137     -21.097 -13.876  22.966  1.00 14.65           N
ATOM    843  CA  LEU A 137     -21.281 -12.702  22.091  1.00 15.96           C
ATOM    844  C   LEU A 137     -21.615 -11.562  23.035  1.00 14.79           C
ATOM    845  O   LEU A 137     -22.412 -11.742  23.977  1.00 15.58           O
ATOM    846  CB  LEU A 137     -22.455 -12.849  21.126  1.00 17.02           C
ATOM    847  CG  LEU A 137     -22.567 -14.071  20.271  1.00 23.40           C
ATOM    848  CD1 LEU A 137     -23.724 -13.801  19.233  1.00 22.66           C
ATOM    849  CD2 LEU A 137     -21.259 -14.389  19.585  1.00 22.64           C
ATOM    850  N   ALA A 138     -21.070 -10.377  22.773  1.00 13.07           N
ATOM    851  CA  ALA A 138     -21.318  -9.263  23.679  1.00 11.51           C
ATOM    852  C   ALA A 138     -21.292  -7.918  22.964  1.00 12.47           C
ATOM    853  O   ALA A 138     -20.774  -7.794  21.843  1.00 12.73           O
ATOM    854  CB  ALA A 138     -20.231  -9.259  24.776  1.00 13.46           C
ATOM    855  N   CYS A 139     -21.848  -6.927  23.651  1.00 14.12           N
ATOM    856  CA  CYS A 139     -21.817  -5.537  23.209  1.00 14.57           C
ATOM    857  C   CYS A 139     -22.154  -4.696  24.443  1.00 13.83           C
ATOM    858  O   CYS A 139     -22.376  -5.245  25.522  1.00 13.47           O
ATOM    859  CB  CYS A 139     -22.815  -5.292  22.085  1.00 15.48           C
ATOM    860  SG  CYS A 139     -24.542  -5.210  22.627  1.00 17.74           S
ATOM    861  N   HIS A 140     -22.125  -3.370  24.339  1.00 12.74           N
ATOM    862  CA  HIS A 140     -22.548  -2.552  25.478  1.00 12.39           C
ATOM    863  C   HIS A 140     -23.926  -1.960  25.148  1.00 13.40           C
ATOM    864  O   HIS A 140     -24.195  -1.591  23.994  1.00 15.05           O
ATOM    865  CB  HIS A 140     -21.528  -1.415  25.801  1.00 12.72           C
ATOM    866  CG  HIS A 140     -21.490  -0.256  24.821  1.00 12.76           C
ATOM    867  ND1 HIS A 140     -22.217   0.905  25.015  1.00 14.74           N
ATOM    868  CD2 HIS A 140     -20.776  -0.062  23.686  1.00 13.17           C
ATOM    869  CE1 HIS A 140     -21.959   1.762  24.039  1.00 14.09           C
ATOM    870  NE2 HIS A 140     -21.094   1.201  23.212  1.00 14.80           N
ATOM    871  N   TYR A 141     -24.810  -1.882  26.142  1.00 13.15           N
ATOM    872  CA  TYR A 141     -26.134  -1.309  25.888  1.00 14.69           C
ATOM    873  C   TYR A 141     -26.336   0.114  26.402  1.00 14.78           C
ATOM    874  O   TYR A 141     -27.380   0.720  26.141  1.00 15.07           O
ATOM    875  CB  TYR A 141     -27.278  -2.213  26.403  1.00 13.39           C
ATOM    876  CG  TYR A 141     -27.516  -2.171  27.903  1.00 14.81           C
ATOM    877  CD1 TYR A 141     -26.720  -2.915  28.780  1.00 14.74           C
ATOM    878  CD2 TYR A 141     -28.540  -1.374  28.428  1.00 15.34           C
ATOM    879  CE1 TYR A 141     -26.948  -2.864  30.164  1.00 14.69           C
ATOM    880  CE2 TYR A 141     -28.782  -1.313  29.805  1.00 17.16           C
ATOM    881  CZ  TYR A 141     -27.990  -2.056  30.659  1.00 17.44           C
ATOM    882  OH  TYR A 141     -28.259  -2.019  32.011  1.00 18.27           O
ATOM    883  N   ASP A 142     -25.371   0.648  27.140  1.00 15.48           N
```

FIGURE 1-14 (COORDINATES)

```
ATOM    884  CA  ASP A 142     -25.477   2.032  27.590  1.00 15.71           C
ATOM    885  C   ASP A 142     -25.154   2.931  26.406  1.00 15.97           C
ATOM    886  O   ASP A 142     -24.521   2.496  25.435  1.00 16.37           O
ATOM    887  CB  ASP A 142     -24.477   2.347  28.737  1.00 16.42           C
ATOM    888  CG  ASP A 142     -23.015   2.188  28.319  1.00 16.31           C
ATOM    889  OD1 ASP A 142     -22.660   1.133  27.742  1.00 15.10           O
ATOM    890  OD2 ASP A 142     -22.212   3.102  28.590  1.00 16.59           O
ATOM    891  N   SER A 143     -25.598   4.177  26.487  1.00 15.33           N
ATOM    892  CA  SER A 143     -25.252   5.179  25.462  1.00 14.76           C
ATOM    893  C   SER A 143     -24.452   6.232  26.211  1.00 14.76           C
ATOM    894  O   SER A 143     -24.679   6.475  27.412  1.00 15.51           O
ATOM    895  CB  SER A 143     -26.500   5.830  24.808  1.00 16.40           C
ATOM    896  OG  SER A 143     -27.358   6.466  25.760  1.00 16.83           O
ATOM    897  N   LYS A 144     -23.507   6.849  25.503  1.00 15.65           N
ATOM    898  CA  LYS A 144     -22.646   7.873  26.118  1.00 16.95           C
ATOM    899  C   LYS A 144     -23.448   9.078  26.572  1.00 17.76           C
ATOM    900  O   LYS A 144     -24.309   9.575  25.844  1.00 17.53           O
ATOM    901  CB  LYS A 144     -21.562   8.306  25.124  1.00 16.36           C
ATOM    902  CG  LYS A 144     -20.509   9.273  25.697  1.00 15.50           C
ATOM    903  CD  LYS A 144     -19.335   9.393  24.742  1.00 16.35           C
ATOM    904  CE  LYS A 144     -18.319  10.437  25.228  1.00 17.18           C
ATOM    905  NZ  LYS A 144     -17.808  10.087  26.592  1.00 19.32           N
ATOM    906  N   TYR A 145     -23.153   9.556  27.780  1.00 18.41           N
ATOM    907  CA  TYR A 145     -23.855  10.715  28.307  1.00 19.66           C
ATOM    908  C   TYR A 145     -23.477  12.032  27.621  1.00 20.83           C
ATOM    909  O   TYR A 145     -22.299  12.350  27.475  1.00 19.86           O
ATOM    910  CB  TYR A 145     -23.580  10.873  29.806  1.00 22.14           C
ATOM    911  CG  TYR A 145     -24.210  12.147  30.302  1.00 26.68           C
ATOM    912  CD1 TYR A 145     -25.602  12.249  30.403  1.00 27.44           C
ATOM    913  CD2 TYR A 145     -23.451  13.301  30.473  1.00 28.55           C
ATOM    914  CE1 TYR A 145     -26.229  13.460  30.647  1.00 31.23           C
ATOM    915  CE2 TYR A 145     -24.074  14.529  30.711  1.00 31.80           C
ATOM    916  CZ  TYR A 145     -25.457  14.597  30.793  1.00 32.56           C
ATOM    917  OH  TYR A 145     -26.091  15.802  31.010  1.00 35.85           O
ATOM    918  N   PHE A 146     -24.486  12.777  27.199  1.00 21.36           N
ATOM    919  CA  PHE A 146     -24.289  14.107  26.618  1.00 23.04           C
ATOM    920  C   PHE A 146     -25.488  14.935  27.055  1.00 24.91           C
ATOM    921  O   PHE A 146     -26.622  14.465  27.012  1.00 26.14           O
ATOM    922  CB  PHE A 146     -24.296  14.078  25.097  1.00 21.65           C
ATOM    923  CG  PHE A 146     -23.058  13.517  24.498  1.00 21.24           C
ATOM    924  CD1 PHE A 146     -21.872  14.245  24.502  1.00 23.41           C
ATOM    925  CD2 PHE A 146     -23.077  12.253  23.903  1.00 20.09           C
ATOM    926  CE1 PHE A 146     -20.705  13.706  23.906  1.00 23.34           C
ATOM    927  CE2 PHE A 146     -21.935  11.707  23.310  1.00 20.83           C
ATOM    928  CZ  PHE A 146     -20.744  12.425  23.305  1.00 19.64           C
ATOM    929  N   SER A 147     -25.248  16.161  27.490  1.00 27.34           N
ATOM    930  CA  SER A 147     -26.376  17.015  27.849  1.00 29.24           C
ATOM    931  C   SER A 147     -27.062  17.303  26.472  1.00 31.11           C
ATOM    932  O   SER A 147     -26.401  17.313  25.423  1.00 31.92           O
ATOM    933  CB  SER A 147     -25.841  18.295  28.506  1.00 30.39           C
ATOM    934  OG  SER A 147     -25.406  19.183  27.502  1.00 35.18           O
ATOM    935  N   HIS A 148     -28.380  17.485  26.450  1.00 33.01           N
ATOM    936  CA  HIS A 148     -29.048  17.738  25.167  1.00 35.67           C
ATOM    937  C   HIS A 148     -28.448  18.975  24.523  1.00 36.76           C
ATOM    938  O   HIS A 148     -28.209  19.976  25.190  1.00 36.78           O
ATOM    939  CB  HIS A 148     -30.554  17.927  25.352  1.00 36.15           C
ATOM    940  CG  HIS A 148     -31.247  16.725  25.922  1.00 37.02           C
ATOM    941  ND1 HIS A 148     -30.624  15.500  26.061  1.00 37.07           N
ATOM    942  CD2 HIS A 148     -32.505  16.561  26.396  1.00 37.36           C
ATOM    943  CE1 HIS A 148     -31.465  14.636  26.603  1.00 36.88           C
ATOM    944  NE2 HIS A 148     -32.614  15.253  26.816  1.00 38.51           N
ATOM    945  N   TRP A 149     -28.200  18.907  23.224  1.00 36.84           N
ATOM    946  CA  TRP A 149     -27.584  20.034  22.548  1.00 37.42           C
ATOM    947  C   TRP A 149     -28.425  20.457  21.356  1.00 37.55           C
ATOM    948  O   TRP A 149     -28.578  19.715  20.390  1.00 36.25           O
ATOM    949  CB  TRP A 149     -26.171  19.636  22.120  1.00 38.20           C
ATOM    950  CG  TRP A 149     -25.456  20.680  21.352  1.00 40.44           C
ATOM    951  CD1 TRP A 149     -24.749  21.734  21.853  1.00 40.05           C
```

FIGURE 1-15 (COORDINATES)

```
ATOM    952  CD2 TRP A 149     -25.401  20.792  19.932  1.00 41.35           C
ATOM    953  NE1 TRP A 149     -24.253  22.499  20.827  1.00 40.32           N
ATOM    954  CE2 TRP A 149     -24.640  21.945  19.634  1.00 41.44           C
ATOM    955  CE3 TRP A 149     -25.927  20.029  18.873  1.00 43.47           C
ATOM    956  CZ2 TRP A 149     -24.387  22.360  18.322  1.00 42.16           C
ATOM    957  CZ3 TRP A 149     -25.676  20.441  17.566  1.00 44.51           C
ATOM    958  CH2 TRP A 149     -24.911  21.599  17.305  1.00 44.55           C
ATOM    959  N   ASN A 150     -28.982  21.663  21.433  1.00 38.98           N
ATOM    960  CA  ASN A 150     -29.817  22.168  20.357  1.00 38.75           C
ATOM    961  C   ASN A 150     -30.948  21.189  20.043  1.00 37.50           C
ATOM    962  O   ASN A 150     -31.249  20.896  18.884  1.00 37.51           O
ATOM    963  CB  ASN A 150     -28.956  22.460  19.117  1.00 42.78           C
ATOM    964  CG  ASN A 150     -28.012  23.659  19.330  1.00 45.31           C
ATOM    965  OD1 ASN A 150     -27.157  23.955  18.494  1.00 47.85           O
ATOM    966  ND2 ASN A 150     -28.172  24.348  20.460  1.00 47.24           N
ATOM    967  N   ASN A 151     -31.570  20.688  21.104  1.00 36.10           N
ATOM    968  CA  ASN A 151     -32.686  19.760  20.994  1.00 36.69           C
ATOM    969  C   ASN A 151     -32.330  18.399  20.434  1.00 34.21           C
ATOM    970  O   ASN A 151     -33.219  17.621  20.086  1.00 35.44           O
ATOM    971  CB  ASN A 151     -33.806  20.360  20.145  1.00 40.61           C
ATOM    972  CG  ASN A 151     -34.327  21.653  20.721  1.00 43.44           C
ATOM    973  OD1 ASN A 151     -34.721  21.703  21.881  1.00 45.87           O
ATOM    974  ND2 ASN A 151     -34.324  22.711  19.915  1.00 45.52           N
ATOM    975  N   ARG A 152     -31.042  18.110  20.323  1.00 30.76           N
ATOM    976  CA  ARG A 152     -30.637  16.793  19.826  1.00 28.07           C
ATOM    977  C   ARG A 152     -30.227  15.970  21.025  1.00 25.47           C
ATOM    978  O   ARG A 152     -29.717  16.510  22.019  1.00 23.32           O
ATOM    979  CB  ARG A 152     -29.467  16.904  18.843  1.00 29.73           C
ATOM    980  CG  ARG A 152     -29.797  17.808  17.656  1.00 32.28           C
ATOM    981  CD  ARG A 152     -28.762  17.708  16.560  1.00 33.63           C
ATOM    982  NE  ARG A 152     -28.860  16.437  15.848  1.00 33.52           N
ATOM    983  CZ  ARG A 152     -27.971  16.032  14.940  1.00 32.57           C
ATOM    984  NH1 ARG A 152     -26.931  16.799  14.650  1.00 33.71           N
ATOM    985  NH2 ARG A 152     -28.128  14.882  14.317  1.00 29.77           N
ATOM    986  N   VAL A 153     -30.465  14.667  20.923  1.00 22.86           N
ATOM    987  CA  VAL A 153     -30.139  13.729  21.992  1.00 22.59           C
ATOM    988  C   VAL A 153     -29.249  12.628  21.390  1.00 20.44           C
ATOM    989  O   VAL A 153     -29.510  12.163  20.286  1.00 21.14           O
ATOM    990  CB  VAL A 153     -31.446  13.127  22.540  1.00 24.45           C
ATOM    991  CG1 VAL A 153     -31.159  12.088  23.558  1.00 25.78           C
ATOM    992  CG2 VAL A 153     -32.288  14.242  23.188  1.00 27.34           C
ATOM    993  N   PHE A 154     -28.210  12.204  22.107  1.00 20.04           N
ATOM    994  CA  PHE A 154     -27.321  11.162  21.578  1.00 18.08           C
ATOM    995  C   PHE A 154     -27.930   9.783  21.829  1.00 18.07           C
ATOM    996  O   PHE A 154     -28.206   9.433  22.981  1.00 19.72           O
ATOM    997  CB  PHE A 154     -25.945  11.254  22.253  1.00 17.86           C
ATOM    998  CG  PHE A 154     -24.940  10.263  21.729  1.00 17.19           C
ATOM    999  CD1 PHE A 154     -24.316  10.457  20.492  1.00 16.79           C
ATOM   1000  CD2 PHE A 154     -24.652   9.093  22.454  1.00 15.91           C
ATOM   1001  CE1 PHE A 154     -23.421   9.493  19.978  1.00 19.59           C
ATOM   1002  CE2 PHE A 154     -23.755   8.124  21.936  1.00 15.67           C
ATOM   1003  CZ  PHE A 154     -23.136   8.318  20.703  1.00 16.90           C
ATOM   1004  N   VAL A 155     -28.151   9.010  20.768  1.00 15.56           N
ATOM   1005  CA  VAL A 155     -28.701   7.664  20.943  1.00 17.51           C
ATOM   1006  C   VAL A 155     -27.753   6.550  20.546  1.00 17.20           C
ATOM   1007  O   VAL A 155     -28.131   5.373  20.603  1.00 18.91           O
ATOM   1008  CB  VAL A 155     -30.059   7.464  20.199  1.00 18.22           C
ATOM   1009  CG1 VAL A 155     -31.045   8.499  20.724  1.00 21.50           C
ATOM   1010  CG2 VAL A 155     -29.906   7.593  18.660  1.00 20.01           C
ATOM   1011  N   GLY A 156     -26.535   6.900  20.147  1.00 16.73           N
ATOM   1012  CA  GLY A 156     -25.571   5.856  19.796  1.00 17.07           C
ATOM   1013  C   GLY A 156     -26.111   4.701  18.952  1.00 15.42           C
ATOM   1014  O   GLY A 156     -26.104   3.521  19.347  1.00 15.17           O
ATOM   1015  N   ALA A 157     -26.552   5.026  17.743  1.00 14.54           N
ATOM   1016  CA  ALA A 157     -27.130   3.998  16.889  1.00 14.02           C
ATOM   1017  C   ALA A 157     -26.156   2.877  16.559  1.00 15.93           C
ATOM   1018  O   ALA A 157     -26.511   1.708  16.664  1.00 15.03           O
ATOM   1019  CB  ALA A 157     -27.682   4.621  15.595  1.00 14.31           C
```

FIGURE 1-16 (COORDINATES)

```
ATOM   1020  N    THR A 158     -24.936   3.225  16.129  1.00 14.84           N
ATOM   1021  CA   THR A 158     -23.955   2.171  15.844  1.00 13.44           C
ATOM   1022  C    THR A 158     -23.253   1.781  17.147  1.00 13.70           C
ATOM   1023  O    THR A 158     -22.633   0.719  17.221  1.00 13.86           O
ATOM   1024  CB   THR A 158     -22.793   2.662  14.924  1.00 14.75           C
ATOM   1025  OG1  THR A 158     -22.072   3.724  15.591  1.00 15.81           O
ATOM   1026  CG2  THR A 158     -23.340   3.133  13.551  1.00 13.90           C
ATOM   1027  N    ASP A 159     -23.421   2.626  18.164  1.00 12.79           N
ATOM   1028  CA   ASP A 159     -22.659   2.549  19.394  1.00 13.97           C
ATOM   1029  C    ASP A 159     -23.511   2.548  20.670  1.00 14.14           C
ATOM   1030  O    ASP A 159     -23.569   3.571  21.373  1.00 13.86           O
ATOM   1031  CB   ASP A 159     -21.723   3.786  19.324  1.00 15.07           C
ATOM   1032  CG   ASP A 159     -20.739   3.911  20.470  1.00 17.82           C
ATOM   1033  OD1  ASP A 159     -20.530   2.974  21.254  1.00 16.37           O
ATOM   1034  OD2  ASP A 159     -20.129   5.003  20.556  1.00 14.49           O
ATOM   1035  N    SER A 160     -24.112   1.400  21.036  1.00 14.26           N
ATOM   1036  CA   SER A 160     -24.099   0.186  20.221  1.00 14.25           C
ATOM   1037  C    SER A 160     -25.523  -0.395  20.114  1.00 15.47           C
ATOM   1038  O    SER A 160     -25.750  -1.594  20.290  1.00 13.61           O
ATOM   1039  CB   SER A 160     -23.132  -0.871  20.810  1.00 13.11           C
ATOM   1040  OG   SER A 160     -21.800  -0.542  20.442  1.00 16.10           O
ATOM   1041  N    ALA A 161     -26.481   0.463  19.775  1.00 13.72           N
ATOM   1042  CA   ALA A 161     -27.860  -0.039  19.631  1.00 14.43           C
ATOM   1043  C    ALA A 161     -27.941  -1.122  18.547  1.00 15.20           C
ATOM   1044  O    ALA A 161     -28.638  -2.143  18.711  1.00 15.53           O
ATOM   1045  CB   ALA A 161     -28.791   1.112  19.301  1.00 13.88           C
ATOM   1046  N    VAL A 162     -27.237  -0.923  17.428  1.00 13.99           N
ATOM   1047  CA   VAL A 162     -27.272  -1.930  16.365  1.00 12.90           C
ATOM   1048  C    VAL A 162     -26.665  -3.249  16.875  1.00 14.60           C
ATOM   1049  O    VAL A 162     -27.253  -4.306  16.697  1.00 13.67           O
ATOM   1050  CB   VAL A 162     -26.604  -1.391  15.042  1.00 13.76           C
ATOM   1051  CG1  VAL A 162     -26.281  -2.532  14.105  1.00 14.28           C
ATOM   1052  CG2  VAL A 162     -27.594  -0.408  14.353  1.00 14.41           C
ATOM   1053  N    PRO A 163     -25.460  -3.228  17.461  1.00 14.55           N
ATOM   1054  CA   PRO A 163     -24.927  -4.501  17.977  1.00 12.68           C
ATOM   1055  C    PRO A 163     -25.958  -5.192  18.924  1.00 14.11           C
ATOM   1056  O    PRO A 163     -26.142  -6.418  18.845  1.00 14.46           O
ATOM   1057  CB   PRO A 163     -23.664  -4.064  18.731  1.00 12.93           C
ATOM   1058  CG   PRO A 163     -23.147  -2.972  17.828  1.00 13.03           C
ATOM   1059  CD   PRO A 163     -24.398  -2.205  17.374  1.00 14.58           C
ATOM   1060  N    CYS A 164     -26.633  -4.426  19.781  1.00 14.78           N
ATOM   1061  CA   CYS A 164     -27.623  -5.049  20.699  1.00 15.27           C
ATOM   1062  C    CYS A 164     -28.699  -5.727  19.885  1.00 15.86           C
ATOM   1063  O    CYS A 164     -29.091  -6.878  20.158  1.00 15.07           O
ATOM   1064  CB   CYS A 164     -28.303  -4.004  21.586  1.00 15.93           C
ATOM   1065  SG   CYS A 164     -27.331  -3.246  22.908  1.00 18.12           S
ATOM   1066  N    ALA A 165     -29.197  -5.004  18.889  1.00 14.69           N
ATOM   1067  CA   ALA A 165     -30.263  -5.543  18.040  1.00 14.64           C
ATOM   1068  C    ALA A 165     -29.800  -6.751  17.241  1.00 15.14           C
ATOM   1069  O    ALA A 165     -30.586  -7.669  17.008  1.00 16.60           O
ATOM   1070  CB   ALA A 165     -30.798  -4.441  17.097  1.00 14.81           C
ATOM   1071  N    MET A 166     -28.529  -6.764  16.801  1.00 14.45           N
ATOM   1072  CA   MET A 166     -28.007  -7.904  16.051  1.00 13.31           C
ATOM   1073  C    MET A 166     -27.978  -9.155  16.966  1.00 13.18           C
ATOM   1074  O    MET A 166     -28.247 -10.276  16.522  1.00 14.83           O
ATOM   1075  CB   MET A 166     -26.576  -7.607  15.537  1.00 13.47           C
ATOM   1076  CG   MET A 166     -26.605  -6.558  14.420  1.00 14.89           C
ATOM   1077  SD   MET A 166     -24.922  -6.008  14.007  1.00 15.54           S
ATOM   1078  CE   MET A 166     -24.273  -7.463  13.239  1.00 15.59           C
ATOM   1079  N    MET A 167     -27.626  -8.955  18.235  1.00 13.75           N
ATOM   1080  CA   MET A 167     -27.581 -10.083  19.145  1.00 14.07           C
ATOM   1081  C    MET A 167     -29.005 -10.596  19.386  1.00 15.31           C
ATOM   1082  O    MET A 167     -29.235 -11.804  19.395  1.00 16.55           O
ATOM   1083  CB   MET A 167     -26.917  -9.643  20.447  1.00 15.20           C
ATOM   1084  CG   MET A 167     -25.433  -9.465  20.242  1.00 13.49           C
ATOM   1085  SD   MET A 167     -24.625  -8.594  21.586  1.00 17.30           S
ATOM   1086  CE   MET A 167     -25.048  -9.641  23.064  1.00 16.22           C
ATOM   1087  N    LEU A 168     -29.954  -9.676  19.532  1.00 14.94           N
```

FIGURE 1-17 (COORDINATES)

```
ATOM   1088  CA  LEU A 168     -31.353 -10.086  19.759  1.00 15.04           C
ATOM   1089  C   LEU A 168     -31.913 -10.797  18.517  1.00 17.18           C
ATOM   1090  O   LEU A 168     -32.626 -11.794  18.637  1.00 17.81           O
ATOM   1091  CB  LEU A 168     -32.235  -8.867  20.122  1.00 15.15           C
ATOM   1092  CG  LEU A 168     -31.900  -8.222  21.470  1.00 13.60           C
ATOM   1093  CD1 LEU A 168     -32.696  -6.908  21.679  1.00 16.73           C
ATOM   1094  CD2 LEU A 168     -32.218  -9.255  22.588  1.00 17.02           C
ATOM   1095  N   GLU A 169     -31.598 -10.297  17.331  1.00 16.50           N
ATOM   1096  CA  GLU A 169     -32.079 -10.926  16.094  1.00 16.78           C
ATOM   1097  C   GLU A 169     -31.432 -12.297  15.906  1.00 16.88           C
ATOM   1098  O   GLU A 169     -32.073 -13.204  15.376  1.00 17.61           O
ATOM   1099  CB  GLU A 169     -31.796 -10.004  14.888  1.00 16.53           C
ATOM   1100  CG  GLU A 169     -31.885 -10.672  13.503  1.00 18.58           C
ATOM   1101  CD  GLU A 169     -33.288 -11.225  13.184  1.00 17.44           C
ATOM   1102  OE1 GLU A 169     -34.252 -10.897  13.919  1.00 18.49           O
ATOM   1103  OE2 GLU A 169     -33.380 -11.982  12.186  1.00 18.89           O
ATOM   1104  N   LEU A 170     -30.171 -12.458  16.334  1.00 16.54           N
ATOM   1105  CA  LEU A 170     -29.502 -13.749  16.200  1.00 15.59           C
ATOM   1106  C   LEU A 170     -30.241 -14.752  17.115  1.00 16.31           C
ATOM   1107  O   LEU A 170     -30.497 -15.893  16.710  1.00 17.79           O
ATOM   1108  CB  LEU A 170     -28.026 -13.651  16.655  1.00 15.38           C
ATOM   1109  CG  LEU A 170     -27.266 -14.991  16.619  1.00 15.13           C
ATOM   1110  CD1 LEU A 170     -25.815 -14.789  16.057  1.00 17.10           C
ATOM   1111  CD2 LEU A 170     -27.221 -15.569  18.040  1.00 15.19           C
ATOM   1112  N   ALA A 171     -30.567 -14.324  18.328  1.00 16.11           N
ATOM   1113  CA  ALA A 171     -31.253 -15.225  19.263  1.00 16.32           C
ATOM   1114  C   ALA A 171     -32.611 -15.591  18.678  1.00 17.98           C
ATOM   1115  O   ALA A 171     -33.042 -16.758  18.786  1.00 17.98           O
ATOM   1116  CB  ALA A 171     -31.410 -14.576  20.615  1.00 17.41           C
ATOM   1117  N   ARG A 172     -33.273 -14.628  18.045  1.00 18.12           N
ATOM   1118  CA  ARG A 172     -34.585 -14.928  17.456  1.00 20.19           C
ATOM   1119  C   ARG A 172     -34.454 -15.824  16.238  1.00 19.80           C
ATOM   1120  O   ARG A 172     -35.116 -16.872  16.132  1.00 19.83           O
ATOM   1121  CB  ARG A 172     -35.304 -13.651  17.029  1.00 19.16           C
ATOM   1122  CG  ARG A 172     -36.742 -13.917  16.483  1.00 22.04           C
ATOM   1123  CD  ARG A 172     -37.178 -12.764  15.577  1.00 21.03           C
ATOM   1124  NE  ARG A 172     -36.389 -12.794  14.349  1.00 22.76           N
ATOM   1125  CZ  ARG A 172     -36.592 -13.636  13.337  1.00 22.97           C
ATOM   1126  NH1 ARG A 172     -37.590 -14.517  13.392  1.00 24.05           N
ATOM   1127  NH2 ARG A 172     -35.761 -13.644  12.293  1.00 25.26           N
ATOM   1128  N   ALA A 173     -33.596 -15.437  15.289  1.00 18.07           N
ATOM   1129  CA  ALA A 173     -33.472 -16.214  14.057  1.00 18.67           C
ATOM   1130  C   ALA A 173     -33.016 -17.651  14.252  1.00 18.97           C
ATOM   1131  O   ALA A 173     -33.441 -18.566  13.510  1.00 20.69           O
ATOM   1132  CB  ALA A 173     -32.514 -15.482  13.054  1.00 15.44           C
ATOM   1133  N   LEU A 174     -32.153 -17.864  15.248  1.00 18.46           N
ATOM   1134  CA  LEU A 174     -31.622 -19.190  15.512  1.00 18.90           C
ATOM   1135  C   LEU A 174     -32.353 -19.917  16.633  1.00 17.83           C
ATOM   1136  O   LEU A 174     -31.908 -20.973  17.095  1.00 18.55           O
ATOM   1137  CB  LEU A 174     -30.137 -19.086  15.897  1.00 18.42           C
ATOM   1138  CG  LEU A 174     -29.286 -18.320  14.874  1.00 16.94           C
ATOM   1139  CD1 LEU A 174     -27.803 -18.385  15.344  1.00 18.86           C
ATOM   1140  CD2 LEU A 174     -29.430 -18.931  13.459  1.00 21.10           C
ATOM   1141  N   ASP A 175     -33.467 -19.355  17.064  1.00 17.84           N
ATOM   1142  CA  ASP A 175     -34.193 -19.925  18.198  1.00 20.63           C
ATOM   1143  C   ASP A 175     -34.482 -21.417  18.094  1.00 20.28           C
ATOM   1144  O   ASP A 175     -34.215 -22.157  19.029  1.00 19.85           O
ATOM   1145  CB  ASP A 175     -35.483 -19.150  18.417  1.00 19.89           C
ATOM   1146  CG  ASP A 175     -36.093 -19.402  19.771  1.00 22.44           C
ATOM   1147  OD1 ASP A 175     -35.329 -19.599  20.743  1.00 20.05           O
ATOM   1148  OD2 ASP A 175     -37.348 -19.355  19.852  1.00 22.49           O
ATOM   1149  N   LYS A 176     -34.986 -21.875  16.954  1.00 22.52           N
ATOM   1150  CA  LYS A 176     -35.265 -23.307  16.880  1.00 23.21           C
ATOM   1151  C   LYS A 176     -34.025 -24.162  17.040  1.00 23.68           C
ATOM   1152  O   LYS A 176     -34.050 -25.212  17.711  1.00 24.29           O
ATOM   1153  CB  LYS A 176     -35.970 -23.642  15.583  1.00 24.71           C
ATOM   1154  CG  LYS A 176     -36.328 -25.114  15.480  1.00 31.10           C
ATOM   1155  CD  LYS A 176     -37.129 -25.338  14.207  1.00 34.38           C
```

FIGURE 1-18 (COORDINATES)

```
ATOM   1156  CE  LYS A 176     -37.582 -26.781  14.073  1.00 37.45           C
ATOM   1157  NZ  LYS A 176     -38.226 -26.926  12.738  1.00 40.30           N
ATOM   1158  N   LYS A 177     -32.926 -23.736  16.425  1.00 22.10           N
ATOM   1159  CA  LYS A 177     -31.674 -24.469  16.557  1.00 22.17           C
ATOM   1160  C   LYS A 177     -31.118 -24.377  17.970  1.00 22.43           C
ATOM   1161  O   LYS A 177     -30.610 -25.380  18.510  1.00 24.58           O
ATOM   1162  CB  LYS A 177     -30.660 -23.940  15.535  1.00 22.83           C
ATOM   1163  CG  LYS A 177     -31.026 -24.421  14.135  1.00 28.22           C
ATOM   1164  CD  LYS A 177     -30.345 -23.676  13.014  1.00 32.58           C
ATOM   1165  CE  LYS A 177     -30.756 -24.290  11.663  1.00 34.78           C
ATOM   1166  NZ  LYS A 177     -30.234 -25.699  11.590  1.00 37.20           N
ATOM   1167  N   LEU A 178     -31.209 -23.200  18.593  1.00 21.54           N
ATOM   1168  CA  LEU A 178     -30.700 -23.053  19.951  1.00 20.96           C
ATOM   1169  C   LEU A 178     -31.513 -23.872  20.959  1.00 22.27           C
ATOM   1170  O   LEU A 178     -30.968 -24.363  21.956  1.00 20.59           O
ATOM   1171  CB  LEU A 178     -30.678 -21.576  20.350  1.00 20.68           C
ATOM   1172  CG  LEU A 178     -29.674 -20.796  19.471  1.00 20.44           C
ATOM   1173  CD1 LEU A 178     -29.807 -19.313  19.767  1.00 20.18           C
ATOM   1174  CD2 LEU A 178     -28.233 -21.270  19.746  1.00 22.62           C
ATOM   1175  N   LEU A 179     -32.804 -24.028  20.688  1.00 23.56           N
ATOM   1176  CA  LEU A 179     -33.679 -24.826  21.573  1.00 24.94           C
ATOM   1177  C   LEU A 179     -33.150 -26.251  21.659  1.00 25.12           C
ATOM   1178  O   LEU A 179     -33.304 -26.934  22.681  1.00 25.28           O
ATOM   1179  CB  LEU A 179     -35.101 -24.845  21.020  1.00 26.20           C
ATOM   1180  CG  LEU A 179     -36.141 -25.688  21.776  1.00 29.22           C
ATOM   1181  CD1 LEU A 179     -36.254 -25.241  23.234  1.00 29.12           C
ATOM   1182  CD2 LEU A 179     -37.470 -25.562  21.039  1.00 30.52           C
ATOM   1183  N   SER A 180     -32.512 -26.727  20.597  1.00 25.30           N
ATOM   1184  CA  SER A 180     -31.987 -28.085  20.644  1.00 26.57           C
ATOM   1185  C   SER A 180     -30.868 -28.297  21.670  1.00 28.87           C
ATOM   1186  O   SER A 180     -30.555 -29.435  22.028  1.00 28.04           O
ATOM   1187  CB  SER A 180     -31.519 -28.520  19.254  1.00 27.78           C
ATOM   1188  OG  SER A 180     -30.274 -27.940  18.907  1.00 28.62           O
ATOM   1189  N   LEU A 181     -30.238 -27.220  22.142  1.00 26.34           N
ATOM   1190  CA  LEU A 181     -29.181 -27.369  23.141  1.00 27.55           C
ATOM   1191  C   LEU A 181     -29.758 -27.671  24.536  1.00 28.38           C
ATOM   1192  O   LEU A 181     -29.005 -27.961  25.473  1.00 27.82           O
ATOM   1193  CB  LEU A 181     -28.364 -26.077  23.223  1.00 24.90           C
ATOM   1194  CG  LEU A 181     -27.512 -25.656  22.038  1.00 25.34           C
ATOM   1195  CD1 LEU A 181     -27.225 -24.151  22.149  1.00 21.04           C
ATOM   1196  CD2 LEU A 181     -26.218 -26.450  22.050  1.00 26.14           C
ATOM   1197  N   LYS A 182     -31.082 -27.571  24.678  1.00 31.22           N
ATOM   1198  CA  LYS A 182     -31.731 -27.802  25.975  1.00 35.52           C
ATOM   1199  C   LYS A 182     -31.488 -29.246  26.392  1.00 37.88           C
ATOM   1200  O   LYS A 182     -31.048 -29.466  27.540  1.00 40.06           O
ATOM   1201  CB  LYS A 182     -33.240 -27.527  25.882  1.00 34.89           C
ATOM   1202  CG  LYS A 182     -33.970 -27.423  27.234  1.00 37.88           C
ATOM   1203  CD  LYS A 182     -35.425 -26.983  27.020  1.00 39.62           C
ATOM   1204  CE  LYS A 182     -36.164 -26.684  28.327  1.00 41.15           C
ATOM   1205  NZ  LYS A 182     -37.503 -26.013  28.072  1.00 44.50           N
ATOM   1206  N   PRO A 189     -18.842 -32.370  23.444  1.00 41.61           N
ATOM   1207  CA  PRO A 189     -19.002 -30.909  23.203  1.00 38.68           C
ATOM   1208  C   PRO A 189     -19.911 -30.216  24.240  1.00 35.96           C
ATOM   1209  O   PRO A 189     -21.037 -29.818  23.903  1.00 35.22           O
ATOM   1210  CB  PRO A 189     -19.578 -30.783  21.793  1.00 39.40           C
ATOM   1211  CG  PRO A 189     -18.980 -31.982  21.126  1.00 41.62           C
ATOM   1212  CD  PRO A 189     -19.102 -33.106  22.192  1.00 41.82           C
ATOM   1213  N   ASP A 190     -19.419 -30.087  25.486  1.00 31.53           N
ATOM   1214  CA  ASP A 190     -20.151 -29.444  26.596  1.00 26.91           C
ATOM   1215  C   ASP A 190     -19.961 -27.943  26.394  1.00 22.88           C
ATOM   1216  O   ASP A 190     -19.321 -27.250  27.198  1.00 20.16           O
ATOM   1217  CB  ASP A 190     -19.540 -29.858  27.922  1.00 29.07           C
ATOM   1218  CG  ASP A 190     -20.358 -29.397  29.108  1.00 29.87           C
ATOM   1219  OD1 ASP A 190     -21.550 -29.042  28.904  1.00 32.83           O
ATOM   1220  OD2 ASP A 190     -19.834 -29.406  30.246  1.00 27.13           O
ATOM   1221  N   LEU A 191     -20.583 -27.472  25.326  1.00 19.70           N
ATOM   1222  CA  LEU A 191     -20.424 -26.110  24.857  1.00 18.62           C
ATOM   1223  C   LEU A 191     -21.756 -25.484  24.494  1.00 19.08           C
```

FIGURE 1-19 (COORDINATES)

```
ATOM   1224  O    LEU A 191     -22.548 -26.085  23.751  1.00 19.93           O
ATOM   1225  CB   LEU A 191     -19.534 -26.177  23.609  1.00 17.82           C
ATOM   1226  CG   LEU A 191     -19.466 -24.957  22.669  1.00 17.48           C
ATOM   1227  CD1  LEU A 191     -18.707 -23.849  23.411  1.00 18.94           C
ATOM   1228  CD2  LEU A 191     -18.713 -25.314  21.349  1.00 19.17           C
ATOM   1229  N    SER A 192     -21.993 -24.258  24.971  1.00 16.01           N
ATOM   1230  CA   SER A 192     -23.231 -23.585  24.634  1.00 16.75           C
ATOM   1231  C    SER A 192     -22.972 -22.097  24.351  1.00 17.74           C
ATOM   1232  O    SER A 192     -21.842 -21.729  24.070  1.00 14.92           O
ATOM   1233  CB   SER A 192     -24.276 -23.793  25.738  1.00 17.32           C
ATOM   1234  OG   SER A 192     -25.567 -23.433  25.263  1.00 17.56           O
ATOM   1235  N    LEU A 193     -24.018 -21.287  24.418  1.00 16.91           N
ATOM   1236  CA   LEU A 193     -23.955 -19.861  24.052  1.00 16.30           C
ATOM   1237  C    LEU A 193     -24.327 -18.920  25.173  1.00 16.16           C
ATOM   1238  O    LEU A 193     -25.224 -19.222  25.968  1.00 16.74           O
ATOM   1239  CB   LEU A 193     -24.918 -19.653  22.868  1.00 15.68           C
ATOM   1240  CG   LEU A 193     -24.977 -18.269  22.222  1.00 15.03           C
ATOM   1241  CD1  LEU A 193     -23.594 -17.945  21.601  1.00 17.06           C
ATOM   1242  CD2  LEU A 193     -26.066 -18.277  21.130  1.00 15.87           C
ATOM   1243  N    GLN A 194     -23.646 -17.765  25.251  1.00 14.04           N
ATOM   1244  CA   GLN A 194     -23.970 -16.763  26.252  1.00 12.96           C
ATOM   1245  C    GLN A 194     -23.912 -15.401  25.552  1.00 13.26           C
ATOM   1246  O    GLN A 194     -23.060 -15.188  24.681  1.00 14.03           O
ATOM   1247  CB   GLN A 194     -22.936 -16.768  27.393  1.00 14.65           C
ATOM   1248  CG   GLN A 194     -23.223 -15.766  28.534  1.00 16.42           C
ATOM   1249  CD   GLN A 194     -22.282 -15.977  29.676  1.00 20.09           C
ATOM   1250  OE1  GLN A 194     -22.664 -16.473  30.770  1.00 21.78           O
ATOM   1251  NE2  GLN A 194     -21.027 -15.619  29.451  1.00 17.42           N
ATOM   1252  N    LEU A 195     -24.838 -14.528  25.923  1.00 13.89           N
ATOM   1253  CA   LEU A 195     -24.863 -13.139  25.423  1.00 15.55           C
ATOM   1254  C    LEU A 195     -24.620 -12.232  26.638  1.00 16.58           C
ATOM   1255  O    LEU A 195     -25.204 -12.440  27.717  1.00 16.83           O
ATOM   1256  CB   LEU A 195     -26.251 -12.772  24.883  1.00 14.63           C
ATOM   1257  CG   LEU A 195     -26.835 -13.762  23.858  1.00 16.25           C
ATOM   1258  CD1  LEU A 195     -28.244 -13.292  23.485  1.00 17.50           C
ATOM   1259  CD2  LEU A 195     -25.966 -13.865  22.610  1.00 17.25           C
ATOM   1260  N    ILE A 196     -23.752 -11.223  26.492  1.00 14.78           N
ATOM   1261  CA   ILE A 196     -23.572 -10.272  27.579  1.00 13.83           C
ATOM   1262  C    ILE A 196     -23.821  -8.877  26.996  1.00 13.49           C
ATOM   1263  O    ILE A 196     -23.287  -8.549  25.936  1.00 13.92           O
ATOM   1264  CB   ILE A 196     -22.126 -10.287  28.128  1.00 13.33           C
ATOM   1265  CG1  ILE A 196     -21.827 -11.681  28.727  1.00 14.44           C
ATOM   1266  CG2  ILE A 196     -21.954  -9.182  29.202  1.00 14.61           C
ATOM   1267  CD1  ILE A 196     -20.327 -11.918  29.028  1.00 15.26           C
ATOM   1268  N    PHE A 197     -24.663  -8.094  27.662  1.00 14.41           N
ATOM   1269  CA   PHE A 197     -24.916  -6.689  27.276  1.00 14.97           C
ATOM   1270  C    PHE A 197     -24.319  -5.880  28.448  1.00 14.44           C
ATOM   1271  O    PHE A 197     -24.884  -5.809  29.537  1.00 16.16           O
ATOM   1272  CB   PHE A 197     -26.435  -6.403  27.126  1.00 15.19           C
ATOM   1273  CG   PHE A 197     -27.121  -7.295  26.141  1.00 15.15           C
ATOM   1274  CD1  PHE A 197     -27.347  -6.869  24.837  1.00 15.07           C
ATOM   1275  CD2  PHE A 197     -27.534  -8.582  26.526  1.00 15.27           C
ATOM   1276  CE1  PHE A 197     -27.991  -7.724  23.893  1.00 16.14           C
ATOM   1277  CE2  PHE A 197     -28.167  -9.440  25.602  1.00 16.15           C
ATOM   1278  CZ   PHE A 197     -28.399  -9.024  24.304  1.00 16.13           C
ATOM   1279  N    PHE A 198     -23.156  -5.266  28.218  1.00 13.47           N
ATOM   1280  CA   PHE A 198     -22.475  -4.508  29.271  1.00 13.43           C
ATOM   1281  C    PHE A 198     -23.060  -3.134  29.512  1.00 14.22           C
ATOM   1282  O    PHE A 198     -23.458  -2.446  28.585  1.00 13.05           O
ATOM   1283  CB   PHE A 198     -20.996  -4.288  28.906  1.00 14.70           C
ATOM   1284  CG   PHE A 198     -20.179  -5.540  28.855  1.00 14.42           C
ATOM   1285  CD1  PHE A 198     -19.813  -6.209  30.028  1.00 14.67           C
ATOM   1286  CD2  PHE A 198     -19.743  -6.030  27.637  1.00 13.38           C
ATOM   1287  CE1  PHE A 198     -19.017  -7.350  29.975  1.00 15.49           C
ATOM   1288  CE2  PHE A 198     -18.923  -7.186  27.569  1.00 14.28           C
ATOM   1289  CZ   PHE A 198     -18.566  -7.836  28.751  1.00 14.69           C
ATOM   1290  N    ASP A 199     -23.136  -2.747  30.772  1.00 13.29           N
ATOM   1291  CA   ASP A 199     -23.565  -1.392  31.082  1.00 14.71           C
```

FIGURE 1-20 (COORDINATES)

```
ATOM   1292  C    ASP A 199     -22.257   -0.600   31.266  1.00 15.07           C
ATOM   1293  O    ASP A 199     -21.168   -1.166   31.470  1.00 14.68           O
ATOM   1294  CB   ASP A 199     -24.376   -1.405   32.401  1.00 14.45           C
ATOM   1295  CG   ASP A 199     -25.083   -0.092   32.676  1.00 18.71           C
ATOM   1296  OD1  ASP A 199     -25.023    0.834   31.833  1.00 17.91           O
ATOM   1297  OD2  ASP A 199     -25.709    0.017   33.744  1.00 17.72           O
ATOM   1298  N    GLY A 200     -22.347    0.720   31.176  1.00 16.08           N
ATOM   1299  CA   GLY A 200     -21.183    1.560   31.462  1.00 16.13           C
ATOM   1300  C    GLY A 200     -19.903    1.414   30.664  1.00 15.87           C
ATOM   1301  O    GLY A 200     -18.799    1.638   31.183  1.00 15.23           O
ATOM   1302  N    GLU A 201     -20.017    1.058   29.396  1.00 14.77           N
ATOM   1303  CA   GLU A 201     -18.806    0.940   28.595  1.00 14.06           C
ATOM   1304  C    GLU A 201     -18.203    2.322   28.405  1.00 15.75           C
ATOM   1305  O    GLU A 201     -16.980    2.481   28.434  1.00 15.79           O
ATOM   1306  CB   GLU A 201     -19.135    0.372   27.232  1.00 13.49           C
ATOM   1307  CG   GLU A 201     -17.919    0.066   26.339  1.00 14.79           C
ATOM   1308  CD   GLU A 201     -17.490    1.243   25.416  1.00 19.00           C
ATOM   1309  OE1  GLU A 201     -18.239    2.230   25.258  1.00 17.31           O
ATOM   1310  OE2  GLU A 201     -16.369    1.170   24.845  1.00 25.00           O
ATOM   1311  N    GLU A 202     -19.087    3.312   28.231  1.00 14.93           N
ATOM   1312  CA   GLU A 202     -18.629    4.677   27.956  1.00 15.32           C
ATOM   1313  C    GLU A 202     -18.132    5.459   29.171  1.00 14.54           C
ATOM   1314  O    GLU A 202     -18.583    5.242   30.283  1.00 16.12           O
ATOM   1315  CB   GLU A 202     -19.758    5.492   27.337  1.00 14.67           C
ATOM   1316  CG   GLU A 202     -20.338    4.924   26.032  1.00 15.11           C
ATOM   1317  CD   GLU A 202     -19.505    5.186   24.801  1.00 15.79           C
ATOM   1318  OE1  GLU A 202     -18.315    5.608   24.899  1.00 14.67           O
ATOM   1319  OE2  GLU A 202     -20.039    4.914   23.695  1.00 16.26           O
ATOM   1320  N    ALA A 203     -17.190    6.368   28.915  1.00 16.33           N
ATOM   1321  CA   ALA A 203     -16.725    7.250   29.963  1.00 17.13           C
ATOM   1322  C    ALA A 203     -17.861    8.280   30.210  1.00 18.81           C
ATOM   1323  O    ALA A 203     -18.613    8.642   29.272  1.00 19.23           O
ATOM   1324  CB   ALA A 203     -15.489    7.977   29.472  1.00 17.63           C
ATOM   1325  N    PHE A 204     -18.025    8.742   31.458  1.00 17.65           N
ATOM   1326  CA   PHE A 204     -18.991    9.808   31.707  1.00 20.23           C
ATOM   1327  C    PHE A 204     -18.378   11.108   31.165  1.00 23.15           C
ATOM   1328  O    PHE A 204     -19.116   12.010   30.740  1.00 23.68           O
ATOM   1329  CB   PHE A 204     -19.292    9.962   33.186  1.00 21.44           C
ATOM   1330  CG   PHE A 204     -20.266    8.977   33.674  1.00 22.86           C
ATOM   1331  CD1  PHE A 204     -19.848    7.751   34.142  1.00 25.00           C
ATOM   1332  CD2  PHE A 204     -21.632    9.240   33.581  1.00 26.17           C
ATOM   1333  CE1  PHE A 204     -20.770    6.798   34.510  1.00 26.35           C
ATOM   1334  CE2  PHE A 204     -22.549    8.291   33.946  1.00 26.52           C
ATOM   1335  CZ   PHE A 204     -22.114    7.064   34.413  1.00 25.39           C
ATOM   1336  N    LEU A 205     -17.047   11.219   31.182  1.00 24.51           N
ATOM   1337  CA   LEU A 205     -16.355   12.406   30.593  1.00 25.79           C
ATOM   1338  C    LEU A 205     -15.635   11.919   29.336  1.00 27.75           C
ATOM   1339  O    LEU A 205     -16.297   11.416   28.426  1.00 28.83           O
ATOM   1340  CB   LEU A 205     -15.349   12.991   31.578  1.00 27.04           C
ATOM   1341  CG   LEU A 205     -15.961   13.426   32.914  1.00 27.26           C
ATOM   1342  CD1  LEU A 205     -14.862   14.032   33.786  1.00 28.23           C
ATOM   1343  CD2  LEU A 205     -17.072   14.462   32.703  1.00 30.16           C
ATOM   1344  N    HIS A 206     -14.312   12.108   29.219  1.00 25.95           N
ATOM   1345  CA   HIS A 206     -13.618   11.516   28.073  1.00 27.43           C
ATOM   1346  C    HIS A 206     -12.898   10.326   28.698  1.00 25.13           C
ATOM   1347  O    HIS A 206     -12.634   10.333   29.902  1.00 23.31           O
ATOM   1348  CB   HIS A 206     -12.587   12.435   27.405  1.00 29.06           C
ATOM   1349  CG   HIS A 206     -13.163   13.342   26.367  1.00 31.16           C
ATOM   1350  ND1  HIS A 206     -13.774   12.873   25.219  1.00 32.85           N
ATOM   1351  CD2  HIS A 206     -13.234   14.694   26.308  1.00 34.63           C
ATOM   1352  CE1  HIS A 206     -14.198   13.901   24.501  1.00 33.30           C
ATOM   1353  NE2  HIS A 206     -13.886   15.015   25.141  1.00 34.86           N
ATOM   1354  N    TRP A 207     -12.580    9.317   27.895  1.00 26.58           N
ATOM   1355  CA   TRP A 207     -11.907    8.125   28.420  1.00 27.20           C
ATOM   1356  C    TRP A 207     -10.733    8.345   29.358  1.00 27.29           C
ATOM   1357  O    TRP A 207      -9.854    9.183   29.117  1.00 25.95           O
ATOM   1358  CB   TRP A 207     -11.379    7.228   27.277  1.00 29.89           C
ATOM   1359  CG   TRP A 207     -10.579    5.984   27.768  1.00 31.40           C
```

FIGURE 1-21 (COORDINATES)

```
ATOM   1360  CD1 TRP A 207     -11.085   4.738  28.019  1.00 29.41           C
ATOM   1361  CD2 TRP A 207      -9.182   5.927  28.144  1.00 32.26           C
ATOM   1362  NE1 TRP A 207     -10.100   3.915  28.535  1.00 32.73           N
ATOM   1363  CE2 TRP A 207      -8.928   4.618  28.622  1.00 31.47           C
ATOM   1364  CE3 TRP A 207      -8.122   6.854  28.122  1.00 33.95           C
ATOM   1365  CZ2 TRP A 207      -7.660   4.214  29.079  1.00 33.56           C
ATOM   1366  CZ3 TRP A 207      -6.864   6.446  28.574  1.00 34.02           C
ATOM   1367  CH2 TRP A 207      -6.647   5.142  29.046  1.00 34.23           C
ATOM   1368  N   SER A 208     -10.731   7.580  30.442  1.00 24.64           N
ATOM   1369  CA  SER A 208      -9.606   7.546  31.345  1.00 25.89           C
ATOM   1370  C   SER A 208      -9.709   6.119  31.902  1.00 25.24           C
ATOM   1371  O   SER A 208     -10.763   5.477  31.811  1.00 24.88           O
ATOM   1372  CB  SER A 208      -9.701   8.584  32.455  1.00 24.91           C
ATOM   1373  OG  SER A 208     -10.636   8.203  33.427  1.00 24.60           O
ATOM   1374  N   PRO A 209      -8.615   5.594  32.454  1.00 26.16           N
ATOM   1375  CA  PRO A 209      -8.609   4.234  33.010  1.00 25.94           C
ATOM   1376  C   PRO A 209      -9.687   3.978  34.042  1.00 26.83           C
ATOM   1377  O   PRO A 209     -10.227   2.879  34.114  1.00 29.22           O
ATOM   1378  CB  PRO A 209      -7.206   4.114  33.616  1.00 26.00           C
ATOM   1379  CG  PRO A 209      -6.386   4.989  32.729  1.00 27.49           C
ATOM   1380  CD  PRO A 209      -7.284   6.217  32.583  1.00 27.15           C
ATOM   1381  N   GLN A 210     -10.006   4.992  34.853  1.00 26.50           N
ATOM   1382  CA  GLN A 210     -11.011   4.829  35.888  1.00 26.58           C
ATOM   1383  C   GLN A 210     -12.397   5.266  35.441  1.00 24.74           C
ATOM   1384  O   GLN A 210     -13.382   4.984  36.106  1.00 26.38           O
ATOM   1385  CB  GLN A 210     -10.615   5.627  37.135  1.00 30.94           C
ATOM   1386  CG  GLN A 210      -9.166   5.384  37.595  1.00 35.40           C
ATOM   1387  CD  GLN A 210      -8.126   6.194  36.802  1.00 39.06           C
ATOM   1388  OE1 GLN A 210      -8.460   6.993  35.904  1.00 39.16           O
ATOM   1389  NE2 GLN A 210      -6.852   5.990  37.138  1.00 41.02           N
ATOM   1390  N   ASP A 211     -12.490   5.980  34.329  1.00 20.70           N
ATOM   1391  CA  ASP A 211     -13.809   6.422  33.887  1.00 19.23           C
ATOM   1392  C   ASP A 211     -14.067   5.806  32.513  1.00 18.92           C
ATOM   1393  O   ASP A 211     -13.801   6.416  31.492  1.00 18.73           O
ATOM   1394  CB  ASP A 211     -13.842   7.959  33.787  1.00 19.49           C
ATOM   1395  CG  ASP A 211     -15.165   8.484  33.260  1.00 18.96           C
ATOM   1396  OD1 ASP A 211     -15.147   9.621  32.721  1.00 19.13           O
ATOM   1397  OD2 ASP A 211     -16.211   7.792  33.386  1.00 18.29           O
ATOM   1398  N   SER A 212     -14.532   4.557  32.521  1.00 18.33           N
ATOM   1399  CA  SER A 212     -14.862   3.814  31.305  1.00 17.47           C
ATOM   1400  C   SER A 212     -14.918   2.336  31.696  1.00 16.05           C
ATOM   1401  O   SER A 212     -14.449   1.949  32.765  1.00 17.08           O
ATOM   1402  CB  SER A 212     -13.791   3.994  30.212  1.00 16.69           C
ATOM   1403  OG  SER A 212     -12.546   3.481  30.647  1.00 19.66           O
ATOM   1404  N   LEU A 213     -15.513   1.536  30.826  1.00 15.80           N
ATOM   1405  CA  LEU A 213     -15.576   0.077  31.026  1.00 15.73           C
ATOM   1406  C   LEU A 213     -16.038  -0.344  32.416  1.00 15.91           C
ATOM   1407  O   LEU A 213     -15.530  -1.333  32.965  1.00 15.74           O
ATOM   1408  CB  LEU A 213     -14.195  -0.536  30.756  1.00 13.73           C
ATOM   1409  CG  LEU A 213     -13.449  -0.061  29.475  1.00 13.43           C
ATOM   1410  CD1 LEU A 213     -12.157  -0.898  29.286  1.00 15.93           C
ATOM   1411  CD2 LEU A 213     -14.399  -0.209  28.258  1.00 15.09           C
ATOM   1412  N   TYR A 214     -17.028   0.334  32.959  1.00 14.10           N
ATOM   1413  CA  TYR A 214     -17.489  -0.004  34.308  1.00 15.37           C
ATOM   1414  C   TYR A 214     -18.037  -1.425  34.396  1.00 15.95           C
ATOM   1415  O   TYR A 214     -17.642  -2.212  35.286  1.00 16.47           O
ATOM   1416  CB  TYR A 214     -18.564   0.995  34.721  1.00 14.66           C
ATOM   1417  CG  TYR A 214     -18.018   2.393  34.918  1.00 16.29           C
ATOM   1418  CD1 TYR A 214     -17.398   2.768  36.108  1.00 16.58           C
ATOM   1419  CD2 TYR A 214     -18.175   3.359  33.922  1.00 17.89           C
ATOM   1420  CE1 TYR A 214     -16.964   4.089  36.312  1.00 16.40           C
ATOM   1421  CE2 TYR A 214     -17.741   4.677  34.110  1.00 16.87           C
ATOM   1422  CZ  TYR A 214     -17.140   5.028  35.314  1.00 17.13           C
ATOM   1423  OH  TYR A 214     -16.716   6.328  35.524  1.00 18.89           O
ATOM   1424  N   GLY A 215     -18.934  -1.755  33.474  1.00 14.93           N
ATOM   1425  CA  GLY A 215     -19.571  -3.075  33.502  1.00 14.70           C
ATOM   1426  C   GLY A 215     -18.635  -4.223  33.197  1.00 16.75           C
ATOM   1427  O   GLY A 215     -18.676  -5.281  33.863  1.00 16.97           O
```

FIGURE 1-22 (COORDINATES)

```
ATOM   1428  N   SER A 216     -17.763  -4.039  32.205  1.00 13.74           N
ATOM   1429  CA  SER A 216     -16.834  -5.122  31.846  1.00 14.01           C
ATOM   1430  C   SER A 216     -15.701  -5.291  32.871  1.00 15.90           C
ATOM   1431  O   SER A 216     -15.275  -6.425  33.138  1.00 16.16           O
ATOM   1432  CB  SER A 216     -16.270  -4.902  30.431  1.00 14.11           C
ATOM   1433  OG  SER A 216     -15.761  -3.564  30.272  1.00 17.15           O
ATOM   1434  N   ARG A 217     -15.203  -4.210  33.462  1.00 15.79           N
ATOM   1435  CA  ARG A 217     -14.144  -4.407  34.462  1.00 16.45           C
ATOM   1436  C   ARG A 217     -14.761  -5.183  35.631  1.00 15.95           C
ATOM   1437  O   ARG A 217     -14.140  -6.104  36.183  1.00 17.72           O
ATOM   1438  CB  ARG A 217     -13.576  -3.050  34.923  1.00 17.58           C
ATOM   1439  CG  ARG A 217     -12.711  -2.446  33.830  1.00 19.14           C
ATOM   1440  CD  ARG A 217     -11.979  -1.177  34.266  1.00 23.50           C
ATOM   1441  NE  ARG A 217     -12.851  -0.030  34.453  1.00 24.59           N
ATOM   1442  CZ  ARG A 217     -13.279   0.434  35.631  1.00 28.28           C
ATOM   1443  NH1 ARG A 217     -12.925  -0.170  36.767  1.00 27.88           N
ATOM   1444  NH2 ARG A 217     -14.019   1.550  35.686  1.00 26.06           N
ATOM   1445  N   HIS A 218     -15.975  -4.822  36.013  1.00 15.69           N
ATOM   1446  CA  HIS A 218     -16.636  -5.510  37.099  1.00 16.80           C
ATOM   1447  C   HIS A 218     -16.929  -6.970  36.778  1.00 17.71           C
ATOM   1448  O   HIS A 218     -16.611  -7.865  37.578  1.00 17.01           O
ATOM   1449  CB  HIS A 218     -17.952  -4.840  37.428  1.00 16.38           C
ATOM   1450  CG  HIS A 218     -18.789  -5.626  38.383  1.00 19.97           C
ATOM   1451  ND1 HIS A 218     -19.789  -6.483  37.976  1.00 22.63           N
ATOM   1452  CD2 HIS A 218     -18.739  -5.711  39.730  1.00 18.79           C
ATOM   1453  CE1 HIS A 218     -20.323  -7.058  39.041  1.00 19.55           C
ATOM   1454  NE2 HIS A 218     -19.705  -6.605  40.114  1.00 22.23           N
ATOM   1455  N   LEU A 219     -17.516  -7.225  35.611  1.00 16.68           N
ATOM   1456  CA  LEU A 219     -17.904  -8.608  35.307  1.00 15.89           C
ATOM   1457  C   LEU A 219     -16.703  -9.516  35.055  1.00 16.84           C
ATOM   1458  O   LEU A 219     -16.723 -10.708  35.430  1.00 17.22           O
ATOM   1459  CB  LEU A 219     -18.877  -8.646  34.120  1.00 17.95           C
ATOM   1460  CG  LEU A 219     -19.440 -10.031  33.722  1.00 15.61           C
ATOM   1461  CD1 LEU A 219     -20.162 -10.652  34.937  1.00 17.11           C
ATOM   1462  CD2 LEU A 219     -20.414  -9.893  32.534  1.00 18.05           C
ATOM   1463  N   ALA A 220     -15.671  -8.994  34.402  1.00 15.04           N
ATOM   1464  CA  ALA A 220     -14.464  -9.820  34.185  1.00 17.09           C
ATOM   1465  C   ALA A 220     -13.880 -10.234  35.539  1.00 17.39           C
ATOM   1466  O   ALA A 220     -13.465 -11.392  35.716  1.00 16.45           O
ATOM   1467  CB  ALA A 220     -13.411  -9.039  33.353  1.00 16.95           C
ATOM   1468  N   ALA A 221     -13.873  -9.315  36.504  1.00 16.00           N
ATOM   1469  CA  ALA A 221     -13.323  -9.658  37.819  1.00 17.86           C
ATOM   1470  C   ALA A 221     -14.223 -10.684  38.531  1.00 19.17           C
ATOM   1471  O   ALA A 221     -13.718 -11.627  39.187  1.00 19.88           O
ATOM   1472  CB  ALA A 221     -13.176  -8.403  38.677  1.00 18.27           C
ATOM   1473  N   LYS A 222     -15.533 -10.513  38.386  1.00 16.62           N
ATOM   1474  CA  LYS A 222     -16.467 -11.419  39.027  1.00 17.85           C
ATOM   1475  C   LYS A 222     -16.328 -12.813  38.426  1.00 18.43           C
ATOM   1476  O   LYS A 222     -16.284 -13.817  39.156  1.00 17.43           O
ATOM   1477  CB  LYS A 222     -17.884 -10.903  38.857  1.00 19.66           C
ATOM   1478  CG  LYS A 222     -18.952 -11.698  39.603  1.00 24.82           C
ATOM   1479  CD  LYS A 222     -20.283 -11.026  39.384  1.00 29.27           C
ATOM   1480  CE  LYS A 222     -21.392 -11.686  40.175  1.00 35.55           C
ATOM   1481  NZ  LYS A 222     -22.557 -10.741  40.193  1.00 38.73           N
ATOM   1482  N   MET A 223     -16.266 -12.897  37.100  1.00 16.58           N
ATOM   1483  CA  MET A 223     -16.143 -14.203  36.450  1.00 17.87           C
ATOM   1484  C   MET A 223     -14.823 -14.869  36.781  1.00 18.07           C
ATOM   1485  O   MET A 223     -14.771 -16.109  36.939  1.00 19.47           O
ATOM   1486  CB  MET A 223     -16.294 -14.053  34.932  1.00 17.56           C
ATOM   1487  CG  MET A 223     -17.733 -13.735  34.569  1.00 17.40           C
ATOM   1488  SD  MET A 223     -17.965 -13.593  32.763  1.00 19.25           S
ATOM   1489  CE  MET A 223     -18.057 -15.283  32.237  1.00 22.78           C
ATOM   1490  N   ALA A 224     -13.763 -14.070  36.898  1.00 16.97           N
ATOM   1491  CA  ALA A 224     -12.449 -14.625  37.198  1.00 17.36           C
ATOM   1492  C   ALA A 224     -12.420 -15.247  38.593  1.00 19.49           C
ATOM   1493  O   ALA A 224     -11.579 -16.114  38.871  1.00 17.76           O
ATOM   1494  CB  ALA A 224     -11.368 -13.515  37.112  1.00 19.44           C
ATOM   1495  N   SER A 225     -13.304 -14.789  39.458  1.00 17.24           N
```

FIGURE 1-23 (COORDINATES)

```
ATOM   1496  CA  SER A 225     -13.306 -15.283  40.840  1.00 18.64           C
ATOM   1497  C   SER A 225     -14.496 -16.174  41.130  1.00 17.28           C
ATOM   1498  O   SER A 225     -14.827 -16.426  42.294  1.00 18.45           O
ATOM   1499  CB  SER A 225     -13.274 -14.082  41.798  1.00 19.04           C
ATOM   1500  OG  SER A 225     -14.466 -13.316  41.656  1.00 23.89           O
ATOM   1501  N   THR A 226     -15.151 -16.667  40.079  1.00 16.54           N
ATOM   1502  CA  THR A 226     -16.302 -17.551  40.278  1.00 17.51           C
ATOM   1503  C   THR A 226     -15.984 -18.951  39.757  1.00 17.44           C
ATOM   1504  O   THR A 226     -15.747 -19.140  38.568  1.00 17.73           O
ATOM   1505  CB  THR A 226     -17.552 -17.030  39.550  1.00 20.44           C
ATOM   1506  OG1 THR A 226     -17.882 -15.741  40.085  1.00 21.04           O
ATOM   1507  CG2 THR A 226     -18.738 -17.961  39.781  1.00 18.57           C
ATOM   1508  N   PRO A 227     -15.979 -19.960  40.653  1.00 17.75           N
ATOM   1509  CA  PRO A 227     -15.671 -21.301  40.131  1.00 16.06           C
ATOM   1510  C   PRO A 227     -16.650 -21.765  39.086  1.00 14.93           C
ATOM   1511  O   PRO A 227     -17.860 -21.505  39.196  1.00 17.00           O
ATOM   1512  CB  PRO A 227     -15.758 -22.192  41.375  1.00 18.10           C
ATOM   1513  CG  PRO A 227     -15.318 -21.269  42.487  1.00 16.06           C
ATOM   1514  CD  PRO A 227     -16.083 -19.970  42.124  1.00 17.32           C
ATOM   1515  N   HIS A 228     -16.141 -22.488  38.093  1.00 16.36           N
ATOM   1516  CA  HIS A 228     -16.983 -23.026  37.037  1.00 16.20           C
ATOM   1517  C   HIS A 228     -16.345 -24.282  36.466  1.00 17.96           C
ATOM   1518  O   HIS A 228     -15.147 -24.315  36.230  1.00 16.37           O
ATOM   1519  CB  HIS A 228     -17.136 -22.016  35.875  1.00 16.64           C
ATOM   1520  CG  HIS A 228     -18.176 -22.421  34.878  1.00 16.20           C
ATOM   1521  ND1 HIS A 228     -19.521 -22.385  35.168  1.00 18.54           N
ATOM   1522  CD2 HIS A 228     -18.075 -22.903  33.612  1.00 17.50           C
ATOM   1523  CE1 HIS A 228     -20.208 -22.828  34.123  1.00 17.85           C
ATOM   1524  NE2 HIS A 228     -19.357 -23.153  33.167  1.00 17.25           N
ATOM   1525  N   PRO A 229     -17.138 -25.349  36.257  1.00 17.74           N
ATOM   1526  CA  PRO A 229     -18.571 -25.448  36.534  1.00 19.49           C
ATOM   1527  C   PRO A 229     -18.796 -25.457  38.059  1.00 20.01           C
ATOM   1528  O   PRO A 229     -17.841 -25.517  38.816  1.00 20.28           O
ATOM   1529  CB  PRO A 229     -18.956 -26.773  35.866  1.00 20.79           C
ATOM   1530  CG  PRO A 229     -17.702 -27.581  35.913  1.00 21.30           C
ATOM   1531  CD  PRO A 229     -16.599 -26.582  35.655  1.00 20.60           C
ATOM   1532  N   PRO A 230     -20.057 -25.359  38.521  1.00 21.36           N
ATOM   1533  CA  PRO A 230     -20.356 -25.365  39.963  1.00 22.67           C
ATOM   1534  C   PRO A 230     -19.613 -26.505  40.640  1.00 21.43           C
ATOM   1535  O   PRO A 230     -19.606 -27.634  40.132  1.00 23.23           O
ATOM   1536  CB  PRO A 230     -21.875 -25.538  39.991  1.00 23.72           C
ATOM   1537  CG  PRO A 230     -22.298 -24.704  38.778  1.00 23.75           C
ATOM   1538  CD  PRO A 230     -21.287 -25.193  37.730  1.00 21.94           C
ATOM   1539  N   GLY A 231     -18.973 -26.198  41.765  1.00 20.50           N
ATOM   1540  CA  GLY A 231     -18.202 -27.181  42.498  1.00 20.45           C
ATOM   1541  C   GLY A 231     -16.742 -27.329  42.120  1.00 21.29           C
ATOM   1542  O   GLY A 231     -16.006 -28.045  42.781  1.00 21.55           O
ATOM   1543  N   ALA A 232     -16.296 -26.668  41.050  1.00 20.24           N
ATOM   1544  CA  ALA A 232     -14.925 -26.833  40.619  1.00 19.24           C
ATOM   1545  C   ALA A 232     -13.927 -26.324  41.640  1.00 19.69           C
ATOM   1546  O   ALA A 232     -14.178 -25.329  42.327  1.00 19.79           O
ATOM   1547  CB  ALA A 232     -14.692 -26.117  39.247  1.00 19.85           C
ATOM   1548  N   ARG A 233     -12.785 -26.998  41.692  1.00 20.32           N
ATOM   1549  CA  ARG A 233     -11.720 -26.647  42.617  1.00 22.90           C
ATOM   1550  C   ARG A 233     -10.779 -25.557  42.120  1.00 20.81           C
ATOM   1551  O   ARG A 233     -10.298 -24.767  42.930  1.00 21.29           O
ATOM   1552  CB  ARG A 233     -10.819 -27.871  42.914  1.00 25.57           C
ATOM   1553  CG  ARG A 233     -11.518 -29.147  43.309  1.00 34.40           C
ATOM   1554  CD  ARG A 233     -10.475 -30.238  43.581  1.00 38.92           C
ATOM   1555  NE  ARG A 233     -10.245 -31.192  42.482  1.00 45.67           N
ATOM   1556  CZ  ARG A 233      -9.471 -30.990  41.410  1.00 47.70           C
ATOM   1557  NH1 ARG A 233      -8.825 -29.846  41.239  1.00 50.21           N
ATOM   1558  NH2 ARG A 233      -9.307 -31.965  40.517  1.00 49.07           N
ATOM   1559  N   GLY A 234     -10.515 -25.501  40.806  1.00 18.75           N
ATOM   1560  CA  GLY A 234      -9.522 -24.569  40.319  1.00 18.83           C
ATOM   1561  C   GLY A 234      -9.720 -23.916  38.964  1.00 19.93           C
ATOM   1562  O   GLY A 234      -8.788 -23.334  38.398  1.00 20.87           O
ATOM   1563  N   THR A 235     -10.938 -23.981  38.458  1.00 18.49           N
```

FIGURE 1-24 (COORDINATES)

```
ATOM   1564  CA  THR A 235     -11.234 -23.356  37.180  1.00 17.90           C
ATOM   1565  C   THR A 235     -12.345 -22.332  37.390  1.00 17.45           C
ATOM   1566  O   THR A 235     -13.223 -22.507  38.229  1.00 16.81           O
ATOM   1567  CB  THR A 235     -11.667 -24.401  36.152  1.00 18.19           C
ATOM   1568  OG1 THR A 235     -12.693 -25.257  36.706  1.00 19.04           O
ATOM   1569  CG2 THR A 235     -10.449 -25.233  35.756  1.00 18.34           C
ATOM   1570  N   SER A 236     -12.314 -21.262  36.599  1.00 16.75           N
ATOM   1571  CA  SER A 236     -13.305 -20.196  36.770  1.00 15.55           C
ATOM   1572  C   SER A 236     -14.229 -20.023  35.557  1.00 15.09           C
ATOM   1573  O   SER A 236     -14.058 -20.683  34.538  1.00 15.67           O
ATOM   1574  CB  SER A 236     -12.591 -18.855  36.942  1.00 17.26           C
ATOM   1575  OG  SER A 236     -12.081 -18.423  35.678  1.00 17.68           O
ATOM   1576  N   GLN A 237     -15.188 -19.108  35.682  1.00 16.12           N
ATOM   1577  CA  GLN A 237     -16.060 -18.811  34.543  1.00 16.29           C
ATOM   1578  C   GLN A 237     -15.215 -18.252  33.394  1.00 17.38           C
ATOM   1579  O   GLN A 237     -15.594 -18.406  32.241  1.00 16.14           O
ATOM   1580  CB  GLN A 237     -17.172 -17.829  34.936  1.00 17.24           C
ATOM   1581  CG  GLN A 237     -18.199 -18.477  35.895  1.00 18.45           C
ATOM   1582  CD  GLN A 237     -19.288 -17.504  36.350  1.00 25.96           C
ATOM   1583  OE1 GLN A 237     -19.092 -16.272  36.352  1.00 25.82           O
ATOM   1584  NE2 GLN A 237     -20.431 -18.052  36.769  1.00 25.14           N
ATOM   1585  N   LEU A 238     -14.092 -17.583  33.675  1.00 17.61           N
ATOM   1586  CA  LEU A 238     -13.253 -17.114  32.559  1.00 17.07           C
ATOM   1587  C   LEU A 238     -12.615 -18.270  31.789  1.00 18.84           C
ATOM   1588  O   LEU A 238     -12.478 -18.234  30.553  1.00 19.73           O
ATOM   1589  CB  LEU A 238     -12.181 -16.133  33.053  1.00 20.48           C
ATOM   1590  CG  LEU A 238     -12.845 -14.820  33.485  1.00 22.31           C
ATOM   1591  CD1 LEU A 238     -11.791 -13.731  33.602  1.00 22.75           C
ATOM   1592  CD2 LEU A 238     -13.879 -14.372  32.412  1.00 25.46           C
ATOM   1593  N   HIS A 239     -12.205 -19.314  32.491  1.00 17.41           N
ATOM   1594  CA  HIS A 239     -11.646 -20.455  31.781  1.00 18.91           C
ATOM   1595  C   HIS A 239     -12.708 -21.065  30.863  1.00 18.29           C
ATOM   1596  O   HIS A 239     -12.380 -21.664  29.851  1.00 17.40           O
ATOM   1597  CB  HIS A 239     -11.156 -21.450  32.808  1.00 21.88           C
ATOM   1598  CG  HIS A 239     -10.089 -20.858  33.675  1.00 24.00           C
ATOM   1599  ND1 HIS A 239      -9.917 -21.187  34.996  1.00 22.74           N
ATOM   1600  CD2 HIS A 239      -9.162 -19.901  33.402  1.00 25.44           C
ATOM   1601  CE1 HIS A 239      -8.928 -20.477  35.506  1.00 25.69           C
ATOM   1602  NE2 HIS A 239      -8.452 -19.682  34.561  1.00 26.78           N
ATOM   1603  N   GLY A 240     -13.967 -20.912  31.264  1.00 17.71           N
ATOM   1604  CA  GLY A 240     -15.079 -21.443  30.475  1.00 18.81           C
ATOM   1605  C   GLY A 240     -15.400 -20.604  29.246  1.00 17.46           C
ATOM   1606  O   GLY A 240     -16.146 -21.055  28.381  1.00 16.35           O
ATOM   1607  N   MET A 241     -14.825 -19.408  29.141  1.00 16.80           N
ATOM   1608  CA  MET A 241     -15.155 -18.559  27.971  1.00 15.68           C
ATOM   1609  C   MET A 241     -14.298 -18.973  26.797  1.00 15.04           C
ATOM   1610  O   MET A 241     -13.115 -18.619  26.719  1.00 17.79           O
ATOM   1611  CB  MET A 241     -14.910 -17.068  28.277  1.00 17.25           C
ATOM   1612  CG  MET A 241     -15.718 -16.507  29.414  1.00 19.63           C
ATOM   1613  SD  MET A 241     -15.298 -14.732  29.605  1.00 27.08           S
ATOM   1614  CE  MET A 241     -15.620 -14.255  28.102  1.00 10.97           C
ATOM   1615  N   ASP A 242     -14.877 -19.715  25.861  1.00 14.52           N
ATOM   1616  CA  ASP A 242     -14.126 -20.188  24.715  1.00 15.37           C
ATOM   1617  C   ASP A 242     -13.546 -19.042  23.887  1.00 16.17           C
ATOM   1618  O   ASP A 242     -12.394 -19.055  23.456  1.00 15.95           O
ATOM   1619  CB  ASP A 242     -15.046 -20.959  23.764  1.00 16.32           C
ATOM   1620  CG  ASP A 242     -14.881 -22.464  23.852  1.00 15.60           C
ATOM   1621  OD1 ASP A 242     -14.689 -22.996  24.975  1.00 16.80           O
ATOM   1622  OD2 ASP A 242     -14.965 -23.090  22.774  1.00 17.43           O
ATOM   1623  N   LEU A 243     -14.397 -18.040  23.697  1.00 15.42           N
ATOM   1624  CA  LEU A 243     -14.064 -16.917  22.834  1.00 14.40           C
ATOM   1625  C   LEU A 243     -15.058 -15.822  23.133  1.00 14.39           C
ATOM   1626  O   LEU A 243     -16.264 -16.097  23.242  1.00 14.21           O
ATOM   1627  CB  LEU A 243     -14.255 -17.330  21.375  1.00 14.30           C
ATOM   1628  CG  LEU A 243     -13.997 -16.269  20.262  1.00 13.28           C
ATOM   1629  CD1 LEU A 243     -12.482 -15.855  20.301  1.00 16.06           C
ATOM   1630  CD2 LEU A 243     -14.340 -16.880  18.850  1.00 15.79           C
ATOM   1631  N   LEU A 244     -14.575 -14.578  23.217  1.00 13.90           N
```

FIGURE 1-25 (COORDINATES)

```
ATOM   1632  CA  LEU A 244     -15.451 -13.442  23.463  1.00 13.81           C
ATOM   1633  C   LEU A 244     -15.516 -12.695  22.139  1.00 13.77           C
ATOM   1634  O   LEU A 244     -14.504 -12.174  21.691  1.00 14.57           O
ATOM   1635  CB  LEU A 244     -14.874 -12.490  24.518  1.00 13.88           C
ATOM   1636  CG  LEU A 244     -15.647 -11.167  24.728  1.00 17.18           C
ATOM   1637  CD1 LEU A 244     -17.078 -11.427  25.281  1.00 17.64           C
ATOM   1638  CD2 LEU A 244     -14.859 -10.327  25.750  1.00 18.41           C
ATOM   1639  N   VAL A 245     -16.679 -12.724  21.497  1.00 13.15           N
ATOM   1640  CA  VAL A 245     -16.917 -12.017  20.231  1.00 12.72           C
ATOM   1641  C   VAL A 245     -17.620 -10.726  20.615  1.00 12.65           C
ATOM   1642  O   VAL A 245     -18.825 -10.715  20.974  1.00 13.33           O
ATOM   1643  CB  VAL A 245     -17.825 -12.845  19.307  1.00 13.68           C
ATOM   1644  CG1 VAL A 245     -18.022 -12.114  17.981  1.00 12.63           C
ATOM   1645  CG2 VAL A 245     -17.192 -14.234  19.083  1.00 15.77           C
ATOM   1646  N   LEU A 246     -16.887  -9.614  20.537  1.00 13.85           N
ATOM   1647  CA  LEU A 246     -17.437  -8.316  20.991  1.00 13.00           C
ATOM   1648  C   LEU A 246     -17.771  -7.430  19.809  1.00 13.20           C
ATOM   1649  O   LEU A 246     -16.901  -7.087  19.022  1.00 14.68           O
ATOM   1650  CB  LEU A 246     -16.393  -7.605  21.862  1.00 13.74           C
ATOM   1651  CG  LEU A 246     -16.724  -6.169  22.263  1.00 13.48           C
ATOM   1652  CD1 LEU A 246     -18.001  -6.217  23.154  1.00 16.06           C
ATOM   1653  CD2 LEU A 246     -15.590  -5.544  23.097  1.00 13.98           C
ATOM   1654  N   LEU A 247     -19.041  -7.095  19.680  1.00 13.68           N
ATOM   1655  CA  LEU A 247     -19.494  -6.238  18.581  1.00 13.89           C
ATOM   1656  C   LEU A 247     -19.547  -4.804  19.079  1.00 13.97           C
ATOM   1657  O   LEU A 247     -20.120  -4.547  20.118  1.00 14.75           O
ATOM   1658  CB  LEU A 247     -20.920  -6.637  18.155  1.00 15.06           C
ATOM   1659  CG  LEU A 247     -21.138  -7.996  17.451  1.00 18.37           C
ATOM   1660  CD1 LEU A 247     -20.762  -9.152  18.326  1.00 23.72           C
ATOM   1661  CD2 LEU A 247     -22.680  -8.094  17.113  1.00 20.18           C
ATOM   1662  N   ASP A 248     -19.009  -3.858  18.302  1.00 12.07           N
ATOM   1663  CA  ASP A 248     -19.098  -2.440  18.726  1.00 12.85           C
ATOM   1664  C   ASP A 248     -18.972  -1.564  17.456  1.00 12.35           C
ATOM   1665  O   ASP A 248     -18.262  -1.916  16.510  1.00 12.99           O
ATOM   1666  CB  ASP A 248     -17.938  -2.108  19.709  1.00 13.83           C
ATOM   1667  CG  ASP A 248     -18.151  -0.812  20.506  1.00 17.13           C
ATOM   1668  OD1 ASP A 248     -19.175  -0.132  20.312  1.00 16.26           O
ATOM   1669  OD2 ASP A 248     -17.259  -0.476  21.363  1.00 17.63           O
ATOM   1670  N   LEU A 249     -19.718  -0.456  17.444  1.00 13.41           N
ATOM   1671  CA  LEU A 249     -19.677   0.534  16.351  1.00 13.33           C
ATOM   1672  C   LEU A 249     -20.019  -0.038  15.003  1.00 13.84           C
ATOM   1673  O   LEU A 249     -19.352   0.236  13.992  1.00 13.95           O
ATOM   1674  CB  LEU A 249     -18.276   1.200  16.270  1.00 13.48           C
ATOM   1675  CG  LEU A 249     -17.654   1.634  17.591  1.00 14.03           C
ATOM   1676  CD1 LEU A 249     -16.314   2.324  17.315  1.00 14.82           C
ATOM   1677  CD2 LEU A 249     -18.617   2.573  18.340  1.00 15.30           C
ATOM   1678  N   ILE A 250     -21.053  -0.875  14.974  1.00 12.63           N
ATOM   1679  CA  ILE A 250     -21.460  -1.510  13.736  1.00 12.94           C
ATOM   1680  C   ILE A 250     -22.739  -0.828  13.235  1.00 14.73           C
ATOM   1681  O   ILE A 250     -23.622  -0.466  14.032  1.00 14.31           O
ATOM   1682  CB  ILE A 250     -21.730  -3.028  13.976  1.00 14.67           C
ATOM   1683  CG1 ILE A 250     -20.393  -3.736  14.303  1.00 15.31           C
ATOM   1684  CG2 ILE A 250     -22.314  -3.709  12.694  1.00 14.02           C
ATOM   1685  CD1 ILE A 250     -20.573  -5.270  14.558  1.00 18.21           C
ATOM   1686  N   GLY A 251     -22.813  -0.638  11.924  1.00 13.96           N
ATOM   1687  CA  GLY A 251     -24.008  -0.037  11.347  1.00 14.48           C
ATOM   1688  C   GLY A 251     -23.745   1.021  10.291  1.00 15.68           C
ATOM   1689  O   GLY A 251     -24.664   1.393   9.545  1.00 15.97           O
ATOM   1690  N   ALA A 252     -22.503   1.509  10.209  1.00 14.73           N
ATOM   1691  CA  ALA A 252     -22.181   2.505   9.192  1.00 15.03           C
ATOM   1692  C   ALA A 252     -21.794   1.784   7.880  1.00 15.95           C
ATOM   1693  O   ALA A 252     -21.543   0.561   7.839  1.00 16.24           O
ATOM   1694  CB  ALA A 252     -20.993   3.394   9.677  1.00 13.49           C
ATOM   1695  N   PRO A 253     -21.704   2.542   6.773  1.00 15.34           N
ATOM   1696  CA  PRO A 253     -21.335   1.955   5.475  1.00 15.73           C
ATOM   1697  C   PRO A 253     -19.850   1.563   5.428  1.00 15.66           C
ATOM   1698  O   PRO A 253     -18.996   2.173   6.077  1.00 17.32           O
ATOM   1699  CB  PRO A 253     -21.550   3.108   4.477  1.00 15.92           C
```

FIGURE 1-26 (COORDINATES)

```
ATOM   1700  CG  PRO A 253     -22.490   4.022   5.163  1.00 16.95           C
ATOM   1701  CD  PRO A 253     -22.153   3.949   6.632  1.00 17.41           C
ATOM   1702  N   ASN A 254     -19.555   0.564   4.616  1.00 15.98           N
ATOM   1703  CA  ASN A 254     -18.171   0.156   4.384  1.00 16.01           C
ATOM   1704  C   ASN A 254     -17.265  -0.089   5.566  1.00 15.17           C
ATOM   1705  O   ASN A 254     -16.119   0.357   5.585  1.00 15.71           O
ATOM   1706  CB  ASN A 254     -17.487   1.197   3.453  1.00 18.63           C
ATOM   1707  CG  ASN A 254     -18.348   1.586   2.269  1.00 19.65           C
ATOM   1708  OD1 ASN A 254     -18.778   0.735   1.477  1.00 24.45           O
ATOM   1709  ND2 ASN A 254     -18.612   2.890   2.133  1.00 17.53           N
ATOM   1710  N   PRO A 255     -17.735  -0.849   6.566  1.00 14.17           N
ATOM   1711  CA  PRO A 255     -16.849  -1.100   7.706  1.00 13.97           C
ATOM   1712  C   PRO A 255     -15.678  -2.022   7.307  1.00 14.61           C
ATOM   1713  O   PRO A 255     -15.832  -2.893   6.437  1.00 15.67           O
ATOM   1714  CB  PRO A 255     -17.770  -1.809   8.713  1.00 15.19           C
ATOM   1715  CG  PRO A 255     -18.704  -2.632   7.788  1.00 14.12           C
ATOM   1716  CD  PRO A 255     -19.018  -1.565   6.682  1.00 13.94           C
ATOM   1717  N   THR A 256     -14.524  -1.823   7.933  1.00 14.87           N
ATOM   1718  CA  THR A 256     -13.423  -2.751   7.700  1.00 15.63           C
ATOM   1719  C   THR A 256     -12.965  -3.195   9.074  1.00 15.57           C
ATOM   1720  O   THR A 256     -12.482  -2.377   9.854  1.00 15.93           O
ATOM   1721  CB  THR A 256     -12.253  -2.088   6.931  1.00 18.34           C
ATOM   1722  OG1 THR A 256     -11.913  -0.850   7.539  1.00 21.61           O
ATOM   1723  CG2 THR A 256     -12.672  -1.827   5.520  1.00 17.18           C
ATOM   1724  N   PHE A 257     -13.083  -4.500   9.352  1.00 15.48           N
ATOM   1725  CA  PHE A 257     -12.693  -5.069  10.644  1.00 16.77           C
ATOM   1726  C   PHE A 257     -11.304  -5.708  10.537  1.00 16.78           C
ATOM   1727  O   PHE A 257     -11.104  -6.615   9.747  1.00 18.81           O
ATOM   1728  CB  PHE A 257     -13.670  -6.187  11.060  1.00 14.84           C
ATOM   1729  CG  PHE A 257     -15.086  -5.725  11.222  1.00 14.33           C
ATOM   1730  CD1 PHE A 257     -15.543  -5.191  12.430  1.00 14.23           C
ATOM   1731  CD2 PHE A 257     -15.979  -5.847  10.155  1.00 16.37           C
ATOM   1732  CE1 PHE A 257     -16.885  -4.779  12.575  1.00 15.02           C
ATOM   1733  CE2 PHE A 257     -17.323  -5.445  10.289  1.00 16.49           C
ATOM   1734  CZ  PHE A 257     -17.772  -4.909  11.499  1.00 15.23           C
ATOM   1735  N   PRO A 258     -10.347  -5.231  11.332  1.00 18.16           N
ATOM   1736  CA  PRO A 258      -9.011  -5.813  11.267  1.00 18.75           C
ATOM   1737  C   PRO A 258      -8.922  -7.091  12.119  1.00 15.37           C
ATOM   1738  O   PRO A 258      -9.759  -7.334  12.990  1.00 16.16           O
ATOM   1739  CB  PRO A 258      -8.106  -4.696  11.766  1.00 21.95           C
ATOM   1740  CG  PRO A 258      -8.946  -3.833  12.612  1.00 20.86           C
ATOM   1741  CD  PRO A 258     -10.406  -4.018  12.162  1.00 18.36           C
ATOM   1742  N   ASN A 259      -7.925  -7.917  11.812  1.00 16.50           N
ATOM   1743  CA  ASN A 259      -7.692  -9.183  12.544  1.00 17.16           C
ATOM   1744  C   ASN A 259      -6.741  -8.783  13.677  1.00 15.02           C
ATOM   1745  O   ASN A 259      -5.518  -8.831  13.516  1.00 19.56           O
ATOM   1746  CB  ASN A 259      -7.021 -10.112  11.538  1.00 16.41           C
ATOM   1747  CG  ASN A 259      -6.819 -11.531  12.041  1.00 22.15           C
ATOM   1748  OD1 ASN A 259      -6.388 -12.398  11.249  1.00 23.46           O
ATOM   1749  ND2 ASN A 259      -7.107 -11.790  13.301  1.00 16.51           N
ATOM   1750  N   PHE A 260      -7.296  -8.409  14.820  1.00 15.42           N
ATOM   1751  CA  PHE A 260      -6.514  -7.895  15.921  1.00 14.70           C
ATOM   1752  C   PHE A 260      -5.579  -8.799  16.693  1.00 16.63           C
ATOM   1753  O   PHE A 260      -4.513  -8.346  17.112  1.00 18.69           O
ATOM   1754  CB  PHE A 260      -7.441  -7.267  16.990  1.00 15.60           C
ATOM   1755  CG  PHE A 260      -8.194  -6.046  16.531  1.00 15.34           C
ATOM   1756  CD1 PHE A 260      -9.539  -6.119  16.183  1.00 14.16           C
ATOM   1757  CD2 PHE A 260      -7.556  -4.796  16.524  1.00 17.48           C
ATOM   1758  CE1 PHE A 260     -10.259  -4.963  15.837  1.00 16.20           C
ATOM   1759  CE2 PHE A 260      -8.244  -3.661  16.188  1.00 17.99           C
ATOM   1760  CZ  PHE A 260      -9.601  -3.731  15.842  1.00 16.27           C
ATOM   1761  N   PHE A 261      -5.977 -10.058  16.893  1.00 16.18           N
ATOM   1762  CA  PHE A 261      -5.223 -10.929  17.811  1.00 16.28           C
ATOM   1763  C   PHE A 261      -4.834 -12.269  17.244  1.00 16.66           C
ATOM   1764  O   PHE A 261      -5.670 -12.968  16.685  1.00 16.56           O
ATOM   1765  CB  PHE A 261      -6.088 -11.177  19.062  1.00 16.98           C
ATOM   1766  CG  PHE A 261      -6.558  -9.899  19.738  1.00 17.27           C
ATOM   1767  CD1 PHE A 261      -5.636  -9.037  20.340  1.00 16.97           C
```

FIGURE 1-27 (COORDINATES)

```
ATOM   1768  CD2 PHE A 261      -7.902   -9.543  19.726  1.00 16.95           C
ATOM   1769  CE1 PHE A 261      -6.047   -7.834  20.911  1.00 20.16           C
ATOM   1770  CE2 PHE A 261      -8.323   -8.338  20.302  1.00 18.63           C
ATOM   1771  CZ  PHE A 261      -7.397   -7.478  20.892  1.00 17.40           C
ATOM   1772  N   PRO A 262      -3.569  -12.678  17.432  1.00 16.02           N
ATOM   1773  CA  PRO A 262      -3.185  -13.969  16.878  1.00 16.05           C
ATOM   1774  C   PRO A 262      -3.883  -15.148  17.472  1.00 15.38           C
ATOM   1775  O   PRO A 262      -4.070  -16.136  16.744  1.00 16.40           O
ATOM   1776  CB  PRO A 262      -1.664  -14.022  17.077  1.00 18.63           C
ATOM   1777  CG  PRO A 262      -1.406  -13.061  18.141  1.00 22.34           C
ATOM   1778  CD  PRO A 262      -2.377  -11.925  17.865  1.00 20.66           C
ATOM   1779  N   ASN A 263      -4.310  -15.057  18.732  1.00 16.04           N
ATOM   1780  CA  ASN A 263      -4.962  -16.237  19.287  1.00 18.02           C
ATOM   1781  C   ASN A 263      -6.426  -16.388  18.894  1.00 18.28           C
ATOM   1782  O   ASN A 263      -7.099  -17.368  19.287  1.00 19.08           O
ATOM   1783  CB  ASN A 263      -4.746  -16.371  20.801  1.00 18.85           C
ATOM   1784  CG  ASN A 263      -5.496  -15.361  21.593  1.00 19.96           C
ATOM   1785  OD1 ASN A 263      -6.286  -14.590  21.064  1.00 23.61           O
ATOM   1786  ND2 ASN A 263      -5.243  -15.346  22.899  1.00 22.49           N
ATOM   1787  N   SER A 264      -6.932  -15.465  18.071  1.00 16.63           N
ATOM   1788  CA  SER A 264      -8.287  -15.672  17.546  1.00 14.60           C
ATOM   1789  C   SER A 264      -8.249  -15.511  16.014  1.00 15.28           C
ATOM   1790  O   SER A 264      -9.292  -15.510  15.334  1.00 15.08           O
ATOM   1791  CB  SER A 264      -9.289  -14.685  18.147  1.00 16.17           C
ATOM   1792  OG  SER A 264      -8.998  -13.349  17.729  1.00 16.31           O
ATOM   1793  N   ALA A 265      -7.047  -15.401  15.446  1.00 16.56           N
ATOM   1794  CA  ALA A 265      -6.940  -15.212  13.994  1.00 15.48           C
ATOM   1795  C   ALA A 265      -7.636  -16.307  13.186  1.00 16.58           C
ATOM   1796  O   ALA A 265      -8.181  -16.022  12.125  1.00 16.55           O
ATOM   1797  CB  ALA A 265      -5.455  -15.132  13.575  1.00 17.36           C
ATOM   1798  N   ARG A 266      -7.610  -17.560  13.651  1.00 14.06           N
ATOM   1799  CA  ARG A 266      -8.257  -18.611  12.865  1.00 15.35           C
ATOM   1800  C   ARG A 266      -9.778  -18.408  12.813  1.00 14.72           C
ATOM   1801  O   ARG A 266     -10.437  -18.828  11.853  1.00 16.93           O
ATOM   1802  CB  ARG A 266      -7.927  -20.002  13.445  1.00 15.20           C
ATOM   1803  CG  ARG A 266      -8.478  -20.309  14.851  1.00 17.29           C
ATOM   1804  CD  ARG A 266      -7.725  -21.520  15.392  1.00 16.38           C
ATOM   1805  NE  ARG A 266      -8.326  -22.048  16.622  1.00 18.09           N
ATOM   1806  CZ  ARG A 266      -9.298  -22.965  16.646  1.00 21.96           C
ATOM   1807  NH1 ARG A 266      -9.809  -23.478  15.511  1.00 21.24           N
ATOM   1808  NH2 ARG A 266      -9.737  -23.380  17.826  1.00 21.65           N
ATOM   1809  N   TRP A 267     -10.333  -17.751  13.823  1.00 15.53           N
ATOM   1810  CA  TRP A 267     -11.776  -17.506  13.812  1.00 15.42           C
ATOM   1811  C   TRP A 267     -12.080  -16.284  12.939  1.00 16.04           C
ATOM   1812  O   TRP A 267     -13.133  -16.218  12.293  1.00 14.59           O
ATOM   1813  CB  TRP A 267     -12.301  -17.340  15.251  1.00 15.45           C
ATOM   1814  CG  TRP A 267     -12.203  -18.643  16.011  1.00 16.55           C
ATOM   1815  CD1 TRP A 267     -11.427  -18.911  17.097  1.00 16.39           C
ATOM   1816  CD2 TRP A 267     -12.891  -19.861  15.693  1.00 16.15           C
ATOM   1817  NE1 TRP A 267     -11.587  -20.236  17.488  1.00 17.51           N
ATOM   1818  CE2 TRP A 267     -12.476  -20.835  16.632  1.00 17.08           C
ATOM   1819  CE3 TRP A 267     -13.815  -20.222  14.704  1.00 15.08           C
ATOM   1820  CZ2 TRP A 267     -12.957  -22.152  16.606  1.00 17.93           C
ATOM   1821  CZ3 TRP A 267     -14.296  -21.543  14.681  1.00 17.62           C
ATOM   1822  CH2 TRP A 267     -13.864  -22.482  15.626  1.00 18.17           C
ATOM   1823  N   PHE A 268     -11.154  -15.325  12.921  1.00 14.42           N
ATOM   1824  CA  PHE A 268     -11.304  -14.180  12.032  1.00 15.85           C
ATOM   1825  C   PHE A 268     -11.321  -14.752  10.595  1.00 16.32           C
ATOM   1826  O   PHE A 268     -12.145  -14.353   9.756  1.00 15.08           O
ATOM   1827  CB  PHE A 268     -10.119  -13.192  12.206  1.00 14.57           C
ATOM   1828  CG  PHE A 268     -10.214  -11.979  11.290  1.00 15.09           C
ATOM   1829  CD1 PHE A 268     -10.842  -10.820  11.739  1.00 15.00           C
ATOM   1830  CD2 PHE A 268      -9.696  -12.025   9.984  1.00 16.23           C
ATOM   1831  CE1 PHE A 268     -10.971   -9.669  10.878  1.00 14.77           C
ATOM   1832  CE2 PHE A 268      -9.814  -10.888   9.122  1.00 17.87           C
ATOM   1833  CZ  PHE A 268     -10.456   -9.713   9.587  1.00 15.36           C
ATOM   1834  N   GLU A 269     -10.433  -15.710  10.320  1.00 15.35           N
ATOM   1835  CA  GLU A 269     -10.385  -16.315   8.979  1.00 17.50           C
```

FIGURE 1-28 (COORDINATES)

```
ATOM   1836  C    GLU A 269     -11.693 -17.004   8.616  1.00 17.53           C
ATOM   1837  O    GLU A 269     -12.082 -17.043   7.429  1.00 16.48           O
ATOM   1838  CB   GLU A 269      -9.241 -17.314   8.889  1.00 20.01           C
ATOM   1839  CG   GLU A 269      -7.892 -16.623   8.873  1.00 26.85           C
ATOM   1840  CD   GLU A 269      -6.747 -17.606   8.990  1.00 32.64           C
ATOM   1841  OE1  GLU A 269      -7.010 -18.832   8.936  1.00 36.30           O
ATOM   1842  OE2  GLU A 269      -5.590 -17.154   9.135  1.00 35.20           O
ATOM   1843  N    ARG A 270     -12.352 -17.588   9.619  1.00 16.03           N
ATOM   1844  CA   ARG A 270     -13.661 -18.211   9.373  1.00 15.62           C
ATOM   1845  C    ARG A 270     -14.666 -17.127   8.973  1.00 17.48           C
ATOM   1846  O    ARG A 270     -15.469 -17.344   8.057  1.00 16.35           O
ATOM   1847  CB   ARG A 270     -14.156 -18.949  10.601  1.00 16.06           C
ATOM   1848  CG   ARG A 270     -13.455 -20.322  10.815  1.00 18.78           C
ATOM   1849  CD   ARG A 270     -13.560 -21.241   9.565  1.00 17.24           C
ATOM   1850  NE   ARG A 270     -14.934 -21.370   9.096  1.00 17.31           N
ATOM   1851  CZ   ARG A 270     -15.303 -21.612   7.842  1.00 17.09           C
ATOM   1852  NH1  ARG A 270     -14.401 -21.784   6.875  1.00 17.86           N
ATOM   1853  NH2  ARG A 270     -16.596 -21.611   7.543  1.00 18.35           N
ATOM   1854  N    LEU A 271     -14.648 -15.965   9.646  1.00 16.34           N
ATOM   1855  CA   LEU A 271     -15.566 -14.901   9.247  1.00 15.74           C
ATOM   1856  C    LEU A 271     -15.273 -14.525   7.795  1.00 15.93           C
ATOM   1857  O    LEU A 271     -16.199 -14.254   7.030  1.00 16.63           O
ATOM   1858  CB   LEU A 271     -15.407 -13.653  10.144  1.00 15.08           C
ATOM   1859  CG   LEU A 271     -15.953 -13.829  11.580  1.00 15.86           C
ATOM   1860  CD1  LEU A 271     -15.488 -12.628  12.446  1.00 14.78           C
ATOM   1861  CD2  LEU A 271     -17.495 -13.889  11.567  1.00 14.56           C
ATOM   1862  N    GLN A 272     -13.999 -14.489   7.411  1.00 16.08           N
ATOM   1863  CA   GLN A 272     -13.659 -14.134   6.026  1.00 16.00           C
ATOM   1864  C    GLN A 272     -14.213 -15.142   5.066  1.00 17.17           C
ATOM   1865  O    GLN A 272     -14.734 -14.780   4.020  1.00 18.42           O
ATOM   1866  CB   GLN A 272     -12.140 -14.071   5.833  1.00 16.97           C
ATOM   1867  CG   GLN A 272     -11.460 -12.967   6.595  1.00 18.41           C
ATOM   1868  CD   GLN A 272     -10.020 -12.819   6.214  1.00 21.35           C
ATOM   1869  OE1  GLN A 272      -9.637 -11.876   5.492  1.00 24.44           O
ATOM   1870  NE2  GLN A 272      -9.205 -13.751   6.661  1.00 20.72           N
ATOM   1871  N    ALA A 273     -14.125 -16.417   5.431  1.00 16.05           N
ATOM   1872  CA   ALA A 273     -14.601 -17.501   4.568  1.00 16.19           C
ATOM   1873  C    ALA A 273     -16.109 -17.516   4.427  1.00 16.59           C
ATOM   1874  O    ALA A 273     -16.658 -17.822   3.358  1.00 17.76           O
ATOM   1875  CB   ALA A 273     -14.117 -18.856   5.151  1.00 16.27           C
ATOM   1876  N    ILE A 274     -16.783 -17.258   5.540  1.00 15.62           N
ATOM   1877  CA   ILE A 274     -18.235 -17.208   5.561  1.00 15.33           C
ATOM   1878  C    ILE A 274     -18.688 -16.025   4.684  1.00 16.32           C
ATOM   1879  O    ILE A 274     -19.601 -16.153   3.856  1.00 16.81           O
ATOM   1880  CB   ILE A 274     -18.701 -17.018   6.999  1.00 15.80           C
ATOM   1881  CG1  ILE A 274     -18.436 -18.323   7.779  1.00 15.63           C
ATOM   1882  CG2  ILE A 274     -20.149 -16.648   7.046  1.00 16.72           C
ATOM   1883  CD1  ILE A 274     -18.638 -18.164   9.300  1.00 15.45           C
ATOM   1884  N    GLU A 275     -18.052 -14.880   4.884  1.00 15.83           N
ATOM   1885  CA   GLU A 275     -18.411 -13.729   4.058  1.00 16.53           C
ATOM   1886  C    GLU A 275     -18.194 -14.053   2.580  1.00 17.53           C
ATOM   1887  O    GLU A 275     -19.025 -13.719   1.733  1.00 17.58           O
ATOM   1888  CB   GLU A 275     -17.569 -12.485   4.451  1.00 16.15           C
ATOM   1889  CG   GLU A 275     -17.789 -11.307   3.480  1.00 17.00           C
ATOM   1890  CD   GLU A 275     -17.049 -10.040   3.882  1.00 17.43           C
ATOM   1891  OE1  GLU A 275     -15.975 -10.154   4.489  1.00 18.80           O
ATOM   1892  OE2  GLU A 275     -17.538  -8.926   3.585  1.00 16.00           O
ATOM   1893  N    HIS A 276     -17.078 -14.695   2.263  1.00 17.33           N
ATOM   1894  CA   HIS A 276     -16.773 -14.986   0.880  1.00 18.14           C
ATOM   1895  C    HIS A 276     -17.801 -15.941   0.277  1.00 18.90           C
ATOM   1896  O    HIS A 276     -18.305 -15.717  -0.828  1.00 16.50           O
ATOM   1897  CB   HIS A 276     -15.360 -15.583   0.768  1.00 19.92           C
ATOM   1898  CG   HIS A 276     -14.974 -15.922  -0.637  1.00 24.74           C
ATOM   1899  ND1  HIS A 276     -14.219 -15.081  -1.424  1.00 25.90           N
ATOM   1900  CD2  HIS A 276     -15.256 -17.006  -1.398  1.00 25.95           C
ATOM   1901  CE1  HIS A 276     -14.051 -15.634  -2.617  1.00 26.61           C
ATOM   1902  NE2  HIS A 276     -14.672 -16.802  -2.628  1.00 26.90           N
ATOM   1903  N    GLU A 277     -18.143 -16.986   1.019  1.00 18.38           N
```

FIGURE 1-29 (COORDINATES)

```
ATOM   1904  CA  GLU A 277     -19.101 -17.957   0.486  1.00 19.20           C
ATOM   1905  C   GLU A 277     -20.512 -17.407   0.384  1.00 18.45           C
ATOM   1906  O   GLU A 277     -21.202 -17.675  -0.605  1.00 18.16           O
ATOM   1907  CB  GLU A 277     -19.103 -19.236   1.327  1.00 22.25           C
ATOM   1908  CG  GLU A 277     -19.910 -20.346   0.696  1.00 28.37           C
ATOM   1909  CD  GLU A 277     -19.298 -20.891  -0.601  1.00 32.27           C
ATOM   1910  OE1 GLU A 277     -19.966 -21.726  -1.237  1.00 34.10           O
ATOM   1911  OE2 GLU A 277     -18.173 -20.508  -0.992  1.00 34.54           O
ATOM   1912  N   LEU A 278     -20.969 -16.662   1.396  1.00 16.65           N
ATOM   1913  CA  LEU A 278     -22.294 -16.059   1.310  1.00 15.95           C
ATOM   1914  C   LEU A 278     -22.308 -15.125   0.099  1.00 17.41           C
ATOM   1915  O   LEU A 278     -23.306 -15.045  -0.616  1.00 17.66           O
ATOM   1916  CB  LEU A 278     -22.627 -15.247   2.575  1.00 16.80           C
ATOM   1917  CG  LEU A 278     -22.916 -16.122   3.808  1.00 16.51           C
ATOM   1918  CD1 LEU A 278     -23.079 -15.240   5.031  1.00 18.64           C
ATOM   1919  CD2 LEU A 278     -24.191 -16.936   3.582  1.00 19.52           C
ATOM   1920  N   HIS A 279     -21.198 -14.414  -0.109  1.00 17.77           N
ATOM   1921  CA  HIS A 279     -21.105 -13.514  -1.262  1.00 17.43           C
ATOM   1922  C   HIS A 279     -21.254 -14.309  -2.574  1.00 19.49           C
ATOM   1923  O   HIS A 279     -22.084 -13.972  -3.414  1.00 19.13           O
ATOM   1924  CB  HIS A 279     -19.748 -12.826  -1.294  1.00 17.39           C
ATOM   1925  CG  HIS A 279     -19.598 -11.900  -2.462  1.00 15.79           C
ATOM   1926  ND1 HIS A 279     -19.011 -12.280  -3.657  1.00 19.51           N
ATOM   1927. CD2 HIS A 279     -20.017 -10.624  -2.629  1.00 13.76           C
ATOM   1928  CE1 HIS A 279     -19.075 -11.267  -4.512  1.00 14.85           C
ATOM   1929  NE2 HIS A 279     -19.680 -10.256  -3.912  1.00 20.42           N
ATOM   1930  N   GLU A 280     -20.450 -15.361  -2.730  1.00 18.92           N
ATOM   1931  CA  GLU A 280     -20.458 -16.173  -3.967  1.00 20.72           C
ATOM   1932  C   GLU A 280     -21.803 -16.819  -4.249  1.00 21.02           C
ATOM   1933  O   GLU A 280     -22.154 -17.006  -5.422  1.00 21.95           O
ATOM   1934  CB  GLU A 280     -19.364 -17.241  -3.907  1.00 22.05           C
ATOM   1935  CG  GLU A 280     -17.945 -16.675  -3.978  1.00 24.02           C
ATOM   1936  CD  GLU A 280     -17.680 -15.973  -5.287  1.00 30.22           C
ATOM   1937  OE1 GLU A 280     -17.658 -16.685  -6.322  1.00 31.71           O
ATOM   1938  OE2 GLU A 280     -17.508 -14.730  -5.300  1.00 28.60           O
ATOM   1939  N   LEU A 281     -22.560 -17.142  -3.194  1.00 20.50           N
ATOM   1940  CA  LEU A 281     -23.886 -17.749  -3.338  1.00 21.32           C
ATOM   1941  C   LEU A 281     -24.979 -16.723  -3.641  1.00 21.30           C
ATOM   1942  O   LEU A 281     -26.156 -17.078  -3.803  1.00 22.02           O
ATOM   1943  CB  LEU A 281     -24.250 -18.532  -2.063  1.00 22.08           C
ATOM   1944  CG  LEU A 281     -23.404 -19.783  -1.852  1.00 22.98           C
ATOM   1945  CD1 LEU A 281     -23.744 -20.358  -0.490  1.00 22.52           C
ATOM   1946  CD2 LEU A 281     -23.711 -20.825  -2.944  1.00 24.84           C
ATOM   1947  N   GLY A 282     -24.590 -15.449  -3.717  1.00 19.97           N
ATOM   1948  CA  GLY A 282     -25.555 -14.386  -3.991  1.00 19.65           C
ATOM   1949  C   GLY A 282     -26.504 -14.113  -2.840  1.00 20.32           C
ATOM   1950  O   GLY A 282     -27.624 -13.661  -3.023  1.00 20.13           O
ATOM   1951  N   LEU A 283     -26.023 -14.370  -1.622  1.00 18.52           N
ATOM   1952  CA  LEU A 283     -26.813 -14.209  -0.423  1.00 17.80           C
ATOM   1953  C   LEU A 283     -26.582 -12.915   0.354  1.00 19.73           C
ATOM   1954  O   LEU A 283     -27.172 -12.710   1.422  1.00 19.71           O
ATOM   1955  CB  LEU A 283     -26.583 -15.439   0.479  1.00 16.98           C
ATOM   1956  CG  LEU A 283     -26.952 -16.776  -0.193  1.00 19.04           C
ATOM   1957  CD1 LEU A 283     -26.564 -17.946   0.766  1.00 19.92           C
ATOM   1958  CD2 LEU A 283     -28.448 -16.804  -0.477  1.00 19.71           C
ATOM   1959  N   LEU A 284     -25.737 -12.035  -0.177  1.00 16.82           N
ATOM   1960  CA  LEU A 284     -25.505 -10.744   0.482  1.00 17.90           C
ATOM   1961  C   LEU A 284     -26.075  -9.656  -0.444  1.00 18.03           C
ATOM   1962  O   LEU A 284     -26.284  -9.880  -1.644  1.00 19.05           O
ATOM   1963  CB  LEU A 284     -24.001 -10.491   0.739  1.00 17.26           C
ATOM   1964  CG  LEU A 284     -23.311 -11.571   1.611  1.00 17.62           C
ATOM   1965  CD1 LEU A 284     -21.842 -11.245   1.836  1.00 17.62           C
ATOM   1966  CD2 LEU A 284     -24.050 -11.680   2.963  1.00 17.50           C
ATOM   1967  N   LYS A 285     -26.304  -8.488   0.123  1.00 16.14           N
ATOM   1968  CA  LYS A 285     -26.897  -7.388  -0.609  1.00 16.24           C
ATOM   1969  C   LYS A 285     -25.947  -6.201  -0.738  1.00 17.42           C
ATOM   1970  O   LYS A 285     -25.302  -5.822   0.250  1.00 17.44           O
ATOM   1971  CB  LYS A 285     -28.163  -6.958   0.143  1.00 18.56           C
```

FIGURE 1-30 (COORDINATES)

```
ATOM   1972  CG  LYS A 285     -28.850   -5.706   -0.426  1.00 24.67           C
ATOM   1973  CD  LYS A 285     -29.632   -6.056   -1.688  1.00 27.61           C
ATOM   1974  CE  LYS A 285     -30.539   -4.906   -2.163  1.00 29.50           C
ATOM   1975  NZ  LYS A 285     -31.165   -5.236   -3.496  1.00 32.60           N
ATOM   1976  N   ASP A 286     -25.859   -5.641   -1.956  1.00 17.68           N
ATOM   1977  CA  ASP A 286     -25.011   -4.460   -2.239  1.00 18.54           C
ATOM   1978  C   ASP A 286     -23.641   -4.734   -1.642  1.00 17.11           C
ATOM   1979  O   ASP A 286     -23.128   -3.958   -0.813  1.00 19.45           O
ATOM   1980  CB  ASP A 286     -25.604   -3.189   -1.584  1.00 18.20           C
ATOM   1981  CG  ASP A 286     -26.916   -2.734   -2.220  1.00 22.61           C
ATOM   1982  OD1 ASP A 286     -27.229   -3.180   -3.345  1.00 21.73           O
ATOM   1983  OD2 ASP A 286     -27.611   -1.899   -1.576  1.00 24.78           O
ATOM   1984  N   HIS A 287     -23.022   -5.818   -2.099  1.00 15.71           N
ATOM   1985  CA  HIS A 287     -21.757   -6.250   -1.491  1.00 14.69           C
ATOM   1986  C   HIS A 287     -20.768   -6.684   -2.546  1.00 13.82           C
ATOM   1987  O   HIS A 287     -21.159   -7.341   -3.518  1.00 17.06           O
ATOM   1988  CB  HIS A 287     -22.102   -7.444   -0.547  1.00 14.37           C
ATOM   1989  CG  HIS A 287     -20.922   -8.038    0.165  1.00 15.16           C
ATOM   1990  ND1 HIS A 287     -20.105   -8.991   -0.407  1.00 14.65           N
ATOM   1991  CD2 HIS A 287     -20.408   -7.784    1.395  1.00 14.45           C
ATOM   1992  CE1 HIS A 287     -19.129   -9.290    0.431  1.00 15.27           C
ATOM   1993  NE2 HIS A 287     -19.287   -8.572    1.531  1.00 15.73           N
ATOM   1994  N   SER A 288     -19.500   -6.286   -2.406  1.00 14.14           N
ATOM   1995  CA  SER A 288     -18.478   -6.757   -3.348  1.00 16.39           C
ATOM   1996  C   SER A 288     -17.282   -7.274   -2.546  1.00 16.59           C
ATOM   1997  O   SER A 288     -17.071   -6.855   -1.412  1.00 16.50           O
ATOM   1998  CB  SER A 288     -17.977   -5.636   -4.249  1.00 17.73           C
ATOM   1999  OG  SER A 288     -17.262   -4.692   -3.480  1.00 19.33           O
ATOM   2000  N   LEU A 289     -16.489   -8.155   -3.148  1.00 16.59           N
ATOM   2001  CA  LEU A 289     -15.308   -8.673   -2.453  1.00 17.63           C
ATOM   2002  C   LEU A 289     -14.240   -7.569   -2.282  1.00 18.42           C
ATOM   2003  O   LEU A 289     -13.516   -7.532   -1.280  1.00 17.97           O
ATOM   2004  CB  LEU A 289     -14.751   -9.892   -3.203  1.00 19.23           C
ATOM   2005  CG  LEU A 289     -15.687  -11.116   -3.143  1.00 20.67           C
ATOM   2006  CD1 LEU A 289     -15.068  -12.254   -3.926  1.00 22.88           C
ATOM   2007  CD2 LEU A 289     -15.949  -11.539   -1.686  1.00 22.43           C
ATOM   2008  N   GLU A 290     -14.108   -6.659   -3.254  1.00 18.22           N
ATOM   2009  CA  GLU A 290     -13.165   -5.543   -3.077  1.00 19.91           C
ATOM   2010  C   GLU A 290     -13.559   -4.707   -1.845  1.00 19.38           C
ATOM   2011  O   GLU A 290     -12.692   -4.163   -1.147  1.00 21.60           O
ATOM   2012  CB  GLU A 290     -13.192   -4.627   -4.302  1.00 21.98           C
ATOM   2013  CG  GLU A 290     -12.493   -5.209   -5.485  1.00 27.43           C
ATOM   2014  CD  GLU A 290     -11.007   -5.273   -5.258  1.00 31.72           C
ATOM   2015  OE1 GLU A 290     -10.393   -4.223   -4.992  1.00 35.10           O
ATOM   2016  OE2 GLU A 290     -10.449   -6.377   -5.353  1.00 35.83           O
ATOM   2017  N   GLY A 291     -14.868   -4.612   -1.581  1.00 17.31           N
ATOM   2018  CA  GLY A 291     -15.369   -3.858   -0.449  1.00 16.88           C
ATOM   2019  C   GLY A 291     -15.781   -4.776    0.688  1.00 15.98           C
ATOM   2020  O   GLY A 291     -16.689   -4.448    1.450  1.00 17.48           O
ATOM   2021  N   ARG A 292     -15.093   -5.906    0.830  1.00 16.70           N
ATOM   2022  CA  ARG A 292     -15.480   -6.848    1.894  1.00 17.61           C
ATOM   2023  C   ARG A 292     -15.222   -6.258    3.264  1.00 16.58           C
ATOM   2024  O   ARG A 292     -14.407   -5.328    3.421  1.00 15.91           O
ATOM   2025  CB  ARG A 292     -14.723   -8.180    1.741  1.00 17.27           C
ATOM   2026  CG  ARG A 292     -13.247   -8.069    1.938  1.00 20.11           C
ATOM   2027  CD  ARG A 292     -12.513   -9.301    1.390  1.00 25.46           C
ATOM   2028  NE  ARG A 292     -11.054   -9.120    1.472  1.00 29.08           N
ATOM   2029  CZ  ARG A 292     -10.349   -8.144    0.881  1.00 34.26           C
ATOM   2030  NH1 ARG A 292     -10.942   -7.220    0.126  1.00 37.83           N
ATOM   2031  NH2 ARG A 292      -9.029   -8.069    1.061  1.00 37.85           N
ATOM   2032  N   TYR A 293     -15.891   -6.821    4.270  1.00 15.73           N
ATOM   2033  CA  TYR A 293     -15.752   -6.306    5.619  1.00 15.00           C
ATOM   2034  C   TYR A 293     -14.552   -6.867    6.385  1.00 16.06           C
ATOM   2035  O   TYR A 293     -13.939   -6.159    7.176  1.00 17.49           O
ATOM   2036  CB  TYR A 293     -17.020   -6.605    6.435  1.00 15.88           C
ATOM   2037  CG  TYR A 293     -18.296   -6.239    5.726  1.00 15.39           C
ATOM   2038  CD1 TYR A 293     -18.434   -5.008    5.073  1.00 15.19           C
ATOM   2039  CD2 TYR A 293     -19.368   -7.144    5.684  1.00 15.14           C
```

FIGURE 1-31 (COORDINATES)

```
ATOM   2040  CE1 TYR A 293     -19.600   -4.695    4.387  1.00 16.87           C
ATOM   2041  CE2 TYR A 293     -20.535   -6.831    5.012  1.00 17.46           C
ATOM   2042  CZ  TYR A 293     -20.649   -5.613    4.362  1.00 17.30           C
ATOM   2043  OH  TYR A 293     -21.818   -5.327    3.655  1.00 17.44           O
ATOM   2044  N   PHE A 294     -14.221   -8.132    6.142  1.00 16.74           N
ATOM   2045  CA  PHE A 294     -13.134   -8.779    6.880  1.00 18.86           C
ATOM   2046  C   PHE A 294     -11.957   -8.876    5.940  1.00 21.86           C
ATOM   2047  O   PHE A 294     -11.855   -9.776    5.121  1.00 21.61           O
ATOM   2048  CB  PHE A 294     -13.647  -10.148    7.357  1.00 17.88           C
ATOM   2049  CG  PHE A 294     -14.782  -10.020    8.334  1.00 16.71           C
ATOM   2050  CD1 PHE A 294     -14.541   -9.613    9.636  1.00 16.59           C
ATOM   2051  CD2 PHE A 294     -16.113  -10.189    7.909  1.00 17.28           C
ATOM   2052  CE1 PHE A 294     -15.605   -9.362   10.518  1.00 17.80           C
ATOM   2053  CE2 PHE A 294     -17.200   -9.940    8.794  1.00 16.18           C
ATOM   2054  CZ  PHE A 294     -16.938   -9.528   10.092  1.00 17.61           C
ATOM   2055  N   GLN A 295     -11.065   -7.905    6.040  1.00 27.76           N
ATOM   2056  CA  GLN A 295      -9.958   -7.904    5.113  1.00 32.34           C
ATOM   2057  C   GLN A 295      -8.703   -8.464    5.714  1.00 35.08           C
ATOM   2058  O   GLN A 295      -8.623   -8.671    6.903  1.00 35.36           O
ATOM   2059  CB  GLN A 295      -9.718   -6.491    4.594  1.00 33.51           C
ATOM   2060  CG  GLN A 295     -10.998   -5.767    4.248  1.00 35.83           C
ATOM   2061  CD  GLN A 295     -10.774   -4.635    3.282  1.00 36.16           C
ATOM   2062  OE1 GLN A 295      -9.704   -4.006    3.275  1.00 35.32           O
ATOM   2063  NE2 GLN A 295     -11.783   -4.352    2.466  1.00 34.48           N
ATOM   2064  N   ASN A 296      -7.717   -8.717    4.867  1.00 39.07           N
ATOM   2065  CA  ASN A 296      -6.471   -9.250    5.351  1.00 42.29           C
ATOM   2066  C   ASN A 296      -5.633   -8.088    5.830  1.00 43.76           C
ATOM   2067  O   ASN A 296      -4.967   -7.408    5.037  1.00 44.82           O
ATOM   2068  CB  ASN A 296      -5.789  -10.011    4.232  1.00 44.61           C
ATOM   2069  CG  ASN A 296      -6.771  -10.860    3.470  1.00 47.75           C
ATOM   2070  OD1 ASN A 296      -7.616  -10.337    2.731  1.00 49.22           O
ATOM   2071  ND2 ASN A 296      -6.703  -12.172    3.673  1.00 48.21           N
ATOM   2072  N   TYR A 297      -5.726   -7.824    7.129  1.00 43.96           N
ATOM   2073  CA  TYR A 297      -4.944   -6.762    7.733  1.00 44.94           C
ATOM   2074  C   TYR A 297      -5.131   -6.751    9.235  1.00 44.18           C
ATOM   2075  O   TYR A 297      -6.222   -6.992    9.758  1.00 41.97           O
ATOM   2076  CB  TYR A 297      -5.261   -5.391    7.102  1.00 46.98           C
ATOM   2077  CG  TYR A 297      -6.364   -4.557    7.731  1.00 49.66           C
ATOM   2078  CD1 TYR A 297      -7.707   -4.927    7.621  1.00 50.71           C
ATOM   2079  CD2 TYR A 297      -6.060   -3.351    8.371  1.00 49.54           C
ATOM   2080  CE1 TYR A 297      -8.727   -4.101    8.132  1.00 51.18           C
ATOM   2081  CE2 TYR A 297      -7.058   -2.527    8.880  1.00 51.35           C
ATOM   2082  CZ  TYR A 297      -8.388   -2.910    8.757  1.00 51.37           C
ATOM   2083  OH  TYR A 297      -9.361   -2.102    9.272  1.00 52.49           O
ATOM   2084  N   SER A 298      -4.024   -6.526    9.920  1.00 44.25           N
ATOM   2085  CA  SER A 298      -4.019   -6.507   11.364  1.00 43.71           C
ATOM   2086  C   SER A 298      -3.967   -5.085   11.856  1.00 41.75           C
ATOM   2087  O   SER A 298      -3.879   -4.137   11.070  1.00 40.87           O
ATOM   2088  CB  SER A 298      -2.820   -7.299   11.877  1.00 45.94           C
ATOM   2089  OG  SER A 298      -1.723   -7.120   10.997  1.00 46.50           O
ATOM   2090  N   TYR A 299      -4.023   -4.948   13.169  1.00 39.61           N
ATOM   2091  CA  TYR A 299      -4.013   -3.654   13.807  1.00 39.20           C
ATOM   2092  C   TYR A 299      -3.332   -3.931   15.137  1.00 39.34           C
ATOM   2093  O   TYR A 299      -3.917   -4.565   16.026  1.00 40.88           O
ATOM   2094  CB  TYR A 299      -5.453   -3.191   14.001  1.00 36.19           C
ATOM   2095  CG  TYR A 299      -5.615   -1.878   14.705  1.00 34.96           C
ATOM   2096  CD1 TYR A 299      -5.397   -1.769   16.084  1.00 34.77           C
ATOM   2097  CD2 TYR A 299      -6.016   -0.741   14.005  1.00 34.80           C
ATOM   2098  CE1 TYR A 299      -5.574   -0.567   16.741  1.00 33.69           C
ATOM   2099  CE2 TYR A 299      -6.193    0.465   14.648  1.00 35.62           C
ATOM   2100  CZ  TYR A 299      -5.968    0.550   16.019  1.00 35.29           C
ATOM   2101  OH  TYR A 299      -6.112    1.758   16.657  1.00 36.27           O
ATOM   2102  N   GLY A 300      -2.086   -3.479   15.243  1.00 37.94           N
ATOM   2103  CA  GLY A 300      -1.291   -3.710   16.438  1.00 36.77           C
ATOM   2104  C   GLY A 300      -1.550   -2.831   17.649  1.00 35.88           C
ATOM   2105  O   GLY A 300      -1.159   -3.203   18.764  1.00 36.86           O
ATOM   2106  N   GLY A 301      -2.190   -1.680   17.450  1.00 33.13           N
ATOM   2107  CA  GLY A 301      -2.473   -0.788   18.568  1.00 31.80           C
```

FIGURE 1-32 (COORDINATES)

```
ATOM   2108  C    GLY A 301      -3.562  -1.303  19.483  1.00 31.44           C
ATOM   2109  O    GLY A 301      -4.213  -2.313  19.201  1.00 31.71           O
ATOM   2110  N    VAL A 302      -3.779  -0.603  20.587  1.00 28.23           N
ATOM   2111  CA   VAL A 302      -4.801  -1.005  21.519  1.00 26.96           C
ATOM   2112  C    VAL A 302      -6.055  -0.157  21.325  1.00 25.00           C
ATOM   2113  O    VAL A 302      -5.972   1.057  21.164  1.00 24.43           O
ATOM   2114  CB   VAL A 302      -4.300  -0.809  22.973  1.00 28.39           C
ATOM   2115  CG1  VAL A 302      -5.459  -0.999  23.970  1.00 29.04           C
ATOM   2116  CG2  VAL A 302      -3.183  -1.788  23.262  1.00 29.99           C
ATOM   2117  N    ILE A 303      -7.217  -0.788  21.313  1.00 22.43           N
ATOM   2118  CA   ILE A 303      -8.440  -0.024  21.235  1.00 20.64           C
ATOM   2119  C    ILE A 303      -9.101  -0.295  22.588  1.00 21.38           C
ATOM   2120  O    ILE A 303      -9.228  -1.448  22.990  1.00 22.49           O
ATOM   2121  CB   ILE A 303      -9.330  -0.494  20.091  1.00 21.48           C
ATOM   2122  CG1  ILE A 303      -8.679  -0.071  18.762  1.00 20.79           C
ATOM   2123  CG2  ILE A 303     -10.721   0.159  20.228  1.00 21.85           C
ATOM   2124  CD1  ILE A 303      -9.386  -0.473  17.522  1.00 23.26           C
ATOM   2125  N    GLN A 304      -9.438   0.759  23.317  1.00 18.98           N
ATOM   2126  CA   GLN A 304     -10.105   0.601  24.607  1.00 19.43           C
ATOM   2127  C    GLN A 304     -11.563   0.222  24.356  1.00 17.85           C
ATOM   2128  O    GLN A 304     -12.309   0.935  23.671  1.00 18.10           O
ATOM   2129  CB   GLN A 304     -10.058   1.906  25.400  1.00 23.64           C
ATOM   2130  CG   GLN A 304      -8.657   2.280  25.843  1.00 26.72           C
ATOM   2131  CD   GLN A 304      -8.090   1.260  26.779  1.00 29.35           C
ATOM   2132  OE1  GLN A 304      -8.778   0.791  27.686  1.00 31.63           O
ATOM   2133  NE2  GLN A 304      -6.828   0.904  26.580  1.00 32.74           N
ATOM   2134  N    ASP A 305     -11.964  -0.917  24.919  1.00 15.63           N
ATOM   2135  CA   ASP A 305     -13.327  -1.395  24.790  1.00 13.76           C
ATOM   2136  C    ASP A 305     -13.534  -2.497  25.855  1.00 14.22           C
ATOM   2137  O    ASP A 305     -12.610  -2.861  26.589  1.00 13.44           O
ATOM   2138  CB   ASP A 305     -13.577  -1.940  23.366  1.00 13.24           C
ATOM   2139  CG   ASP A 305     -15.063  -1.895  22.948  1.00 13.40           C
ATOM   2140  OD1  ASP A 305     -15.932  -1.681  23.817  1.00 15.76           O
ATOM   2141  OD2  ASP A 305     -15.336  -2.069  21.751  1.00 15.84           O
ATOM   2142  N    ASP A 306     -14.748  -3.011  25.906  1.00 12.29           N
ATOM   2143  CA   ASP A 306     -15.157  -4.016  26.913  1.00 14.00           C
ATOM   2144  C    ASP A 306     -14.374  -5.309  26.913  1.00 15.97           C
ATOM   2145  O    ASP A 306     -14.443  -6.063  27.893  1.00 15.88           O
ATOM   2146  CB   ASP A 306     -16.646  -4.344  26.743  1.00 13.93           C
ATOM   2147  CG   ASP A 306     -17.553  -3.232  27.212  1.00 15.35           C
ATOM   2148  OD1  ASP A 306     -17.273  -2.618  28.264  1.00 16.65           O
ATOM   2149  OD2  ASP A 306     -18.576  -2.993  26.530  1.00 14.75           O
ATOM   2150  N    HIS A 307     -13.640  -5.579  25.841  1.00 13.32           N
ATOM   2151  CA   HIS A 307     -12.840  -6.809  25.816  1.00 14.90           C
ATOM   2152  C    HIS A 307     -11.576  -6.694  26.657  1.00 15.99           C
ATOM   2153  O    HIS A 307     -10.988  -7.702  27.061  1.00 15.30           O
ATOM   2154  CB   HIS A 307     -12.400  -7.147  24.389  1.00 13.44           C
ATOM   2155  CG   HIS A 307     -11.462  -6.140  23.819  1.00 15.10           C
ATOM   2156  ND1  HIS A 307     -11.817  -4.810  23.696  1.00 15.70           N
ATOM   2157  CD2  HIS A 307     -10.162  -6.227  23.437  1.00 14.14           C
ATOM   2158  CE1  HIS A 307     -10.772  -4.119  23.262  1.00 16.53           C
ATOM   2159  NE2  HIS A 307      -9.753  -4.949  23.098  1.00 15.46           N
ATOM   2160  N    ILE A 308     -11.141  -5.472  26.929  1.00 13.98           N
ATOM   2161  CA   ILE A 308      -9.873  -5.299  27.654  1.00 14.42           C
ATOM   2162  C    ILE A 308      -9.739  -6.047  28.991  1.00 15.36           C
ATOM   2163  O    ILE A 308      -8.743  -6.738  29.188  1.00 16.66           O
ATOM   2164  CB   ILE A 308      -9.562  -3.781  27.835  1.00 15.10           C
ATOM   2165  CG1  ILE A 308      -9.290  -3.161  26.449  1.00 17.54           C
ATOM   2166  CG2  ILE A 308      -8.381  -3.563  28.860  1.00 15.70           C
ATOM   2167  CD1  ILE A 308      -7.969  -3.535  25.800  1.00 19.21           C
ATOM   2168  N    PRO A 309     -10.732  -5.952  29.883  1.00 14.83           N
ATOM   2169  CA   PRO A 309     -10.576  -6.674  31.172  1.00 16.24           C
ATOM   2170  C    PRO A 309     -10.562  -8.184  31.014  1.00 16.63           C
ATOM   2171  O    PRO A 309     -10.084  -8.884  31.906  1.00 17.11           O
ATOM   2172  CB   PRO A 309     -11.745  -6.225  32.019  1.00 16.01           C
ATOM   2173  CG   PRO A 309     -12.487  -5.224  31.181  1.00 17.97           C
ATOM   2174  CD   PRO A 309     -11.908  -5.055  29.857  1.00 16.30           C
ATOM   2175  N    PHE A 310     -11.115  -8.675  29.909  1.00 15.23           N
```

FIGURE 1-33 (COORDINATES)

```
ATOM   2176  CA  PHE A 310     -11.126 -10.113  29.632  1.00 15.54           C
ATOM   2177  C   PHE A 310      -9.810 -10.537  28.979  1.00 17.53           C
ATOM   2178  O   PHE A 310      -9.140 -11.528  29.406  1.00 17.75           O
ATOM   2179  CB  PHE A 310     -12.328 -10.442  28.735  1.00 15.68           C
ATOM   2180  CG  PHE A 310     -13.643 -10.249  29.436  1.00 16.05           C
ATOM   2181  CD1 PHE A 310     -14.307  -9.021  29.397  1.00 15.10           C
ATOM   2182  CD2 PHE A 310     -14.201 -11.291  30.192  1.00 13.80           C
ATOM   2183  CE1 PHE A 310     -15.507  -8.836  30.102  1.00 15.34           C
ATOM   2184  CE2 PHE A 310     -15.392 -11.123  30.889  1.00 15.06           C
ATOM   2185  CZ  PHE A 310     -16.063  -9.881  30.852  1.00 16.90           C
ATOM   2186  N   LEU A 311      -9.395  -9.770  27.969  1.00 17.24           N
ATOM   2187  CA  LEU A 311      -8.138 -10.035  27.274  1.00 18.06           C
ATOM   2188  C   LEU A 311      -6.978 -10.026  28.278  1.00 18.15           C
ATOM   2189  O   LEU A 311      -6.098 -10.904  28.230  1.00 19.79           O
ATOM   2190  CB  LEU A 311      -7.922  -8.944  26.208  1.00 20.43           C
ATOM   2191  CG  LEU A 311      -6.644  -8.962  25.391  1.00 24.17           C
ATOM   2192  CD1 LEU A 311      -6.712 -10.084  24.374  1.00 26.48           C
ATOM   2193  CD2 LEU A 311      -6.473  -7.589  24.678  1.00 26.51           C
ATOM   2194  N   ARG A 312      -6.968  -9.084  29.215  1.00 18.84           N
ATOM   2195  CA  ARG A 312      -5.841  -9.039  30.149  1.00 20.24           C
ATOM   2196  C   ARG A 312      -5.873 -10.141  31.212  1.00 20.57           C
ATOM   2197  O   ARG A 312      -4.958 -10.256  32.024  1.00 22.21           O
ATOM   2198  CB  ARG A 312      -5.709  -7.631  30.790  1.00 21.35           C
ATOM   2199  CG  ARG A 312      -5.521  -6.555  29.719  1.00 28.09           C
ATOM   2200  CD  ARG A 312      -5.047  -5.217  30.286  1.00 32.62           C
ATOM   2201  NE  ARG A 312      -4.910  -4.124  29.300  1.00 39.58           N
ATOM   2202  CZ  ARG A 312      -4.380  -4.210  28.067  1.00 42.95           C
ATOM   2203  NH1 ARG A 312      -3.913  -5.358  27.587  1.00 44.64           N
ATOM   2204  NH2 ARG A 312      -4.289  -3.112  27.308  1.00 43.91           N
ATOM   2205  N   ARG A 313      -6.923 -10.948  31.210  1.00 17.69           N
ATOM   2206  CA  ARG A 313      -7.003 -12.084  32.117  1.00 19.64           C
ATOM   2207  C   ARG A 313      -6.900 -13.390  31.312  1.00 20.38           C
ATOM   2208  O   ARG A 313      -7.203 -14.469  31.837  1.00 23.17           O
ATOM   2209  CB  ARG A 313      -8.289 -12.039  32.906  1.00 19.94           C
ATOM   2210  CG  ARG A 313      -8.317 -10.898  33.905  1.00 20.23           C
ATOM   2211  CD  ARG A 313      -9.586 -10.984  34.714  1.00 20.12           C
ATOM   2212  NE  ARG A 313      -9.611 -10.119  35.896  1.00 24.00           N
ATOM   2213  CZ  ARG A 313      -9.842  -8.813  35.887  1.00 27.09           C
ATOM   2214  NH1 ARG A 313     -10.074  -8.167  34.739  1.00 25.16           N
ATOM   2215  NH2 ARG A 313      -9.852  -8.147  37.044  1.00 27.52           N
ATOM   2216  N   GLY A 314      -6.523 -13.265  30.037  1.00 18.71           N
ATOM   2217  CA  GLY A 314      -6.289 -14.406  29.157  1.00 19.81           C
ATOM   2218  C   GLY A 314      -7.423 -14.982  28.335  1.00 19.63           C
ATOM   2219  O   GLY A 314      -7.325 -16.088  27.808  1.00 21.34           O
ATOM   2220  N   VAL A 315      -8.504 -14.240  28.190  1.00 16.92           N
ATOM   2221  CA  VAL A 315      -9.615 -14.751  27.414  1.00 15.94           C
ATOM   2222  C   VAL A 315      -9.391 -14.415  25.936  1.00 16.29           C
ATOM   2223  O   VAL A 315      -9.007 -13.287  25.629  1.00 16.20           O
ATOM   2224  CB  VAL A 315     -10.930 -14.061  27.871  1.00 14.95           C
ATOM   2225  CG1 VAL A 315     -12.100 -14.516  26.979  1.00 15.49           C
ATOM   2226  CG2 VAL A 315     -11.206 -14.384  29.346  1.00 16.10           C
ATOM   2227  N   PRO A 316      -9.563 -15.393  25.015  1.00 15.20           N
ATOM   2228  CA  PRO A 316      -9.385 -15.120  23.581  1.00 15.26           C
ATOM   2229  C   PRO A 316     -10.514 -14.181  23.139  1.00 15.93           C
ATOM   2230  O   PRO A 316     -11.680 -14.395  23.464  1.00 14.78           O
ATOM   2231  CB  PRO A 316      -9.535 -16.481  22.908  1.00 17.46           C
ATOM   2232  CG  PRO A 316      -9.159 -17.470  24.040  1.00 17.94           C
ATOM   2233  CD  PRO A 316      -9.769 -16.833  25.281  1.00 15.65           C
ATOM   2234  N   VAL A 317     -10.163 -13.174  22.358  1.00 15.12           N
ATOM   2235  CA  VAL A 317     -11.153 -12.191  21.910  1.00 14.60           C
ATOM   2236  C   VAL A 317     -11.160 -12.049  20.401  1.00 12.90           C
ATOM   2237  O   VAL A 317     -10.092 -11.975  19.770  1.00 15.04           O
ATOM   2238  CB  VAL A 317     -10.762 -10.776  22.484  1.00 14.35           C
ATOM   2239  CG1 VAL A 317     -11.683  -9.705  21.906  1.00 14.29           C
ATOM   2240  CG2 VAL A 317     -10.804 -10.793  24.025  1.00 14.92           C
ATOM   2241  N   LEU A 318     -12.356 -11.992  19.830  1.00 13.54           N
ATOM   2242  CA  LEU A 318     -12.526 -11.691  18.417  1.00 13.94           C
ATOM   2243  C   LEU A 318     -13.261 -10.323  18.525  1.00 15.24           C
```

FIGURE 1-34 (COORDINATES)

```
ATOM   2244  O    LEU A 318     -14.442 -10.238  18.917  1.00 14.42           O
ATOM   2245  CB   LEU A 318     -13.368 -12.791  17.764  1.00 16.63           C
ATOM   2246  CG   LEU A 318     -13.584 -12.661  16.261  1.00 19.00           C
ATOM   2247  CD1  LEU A 318     -12.248 -12.607  15.495  1.00 18.90           C
ATOM   2248  CD2  LEU A 318     -14.413 -13.875  15.828  1.00 17.31           C
ATOM   2249  N    HIS A 319     -12.550  -9.228  18.219  1.00 13.46           N
ATOM   2250  CA   HIS A 319     -13.120  -7.892  18.407  1.00 15.33           C
ATOM   2251  C    HIS A 319     -13.700  -7.350  17.116  1.00 15.81           C
ATOM   2252  O    HIS A 319     -12.983  -6.923  16.224  1.00 14.74           O
ATOM   2253  CB   HIS A 319     -12.031  -6.955  18.956  1.00 14.98           C
ATOM   2254  CG   HIS A 319     -12.557  -5.679  19.541  1.00 14.98           C
ATOM   2255  ND1  HIS A 319     -11.718  -4.660  19.941  1.00 14.12           N
ATOM   2256  CD2  HIS A 319     -13.819  -5.268  19.819  1.00 13.66           C
ATOM   2257  CE1  HIS A 319     -12.443  -3.667  20.436  1.00 13.51           C
ATOM   2258  NE2  HIS A 319     -13.720  -4.007  20.369  1.00 14.53           N
ATOM   2259  N    LEU A 320     -15.024  -7.425  17.006  1.00 13.24           N
ATOM   2260  CA   LEU A 320     -15.710  -6.942  15.808  1.00 13.18           C
ATOM   2261  C    LEU A 320     -16.043  -5.480  15.950  1.00 14.12           C
ATOM   2262  O    LEU A 320     -17.192  -5.092  16.152  1.00 13.67           O
ATOM   2263  CB   LEU A 320     -16.991  -7.762  15.538  1.00 15.17           C
ATOM   2264  CG   LEU A 320     -16.693  -9.277  15.371  1.00 17.51           C
ATOM   2265  CD1  LEU A 320     -17.986  -9.971  14.824  1.00 18.95           C
ATOM   2266  CD2  LEU A 320     -15.547  -9.555  14.434  1.00 19.63           C
ATOM   2267  N    ILE A 321     -14.992  -4.669  15.848  1.00 13.87           N
ATOM   2268  CA   ILE A 321     -15.102  -3.197  15.861  1.00 14.23           C
ATOM   2269  C    ILE A 321     -14.363  -2.768  14.606  1.00 13.63           C
ATOM   2270  O    ILE A 321     -13.296  -3.302  14.275  1.00 14.48           O
ATOM   2271  CB   ILE A 321     -14.456  -2.569  17.128  1.00 12.70           C
ATOM   2272  CG1  ILE A 321     -14.800  -1.056  17.198  1.00 14.09           C
ATOM   2273  CG2  ILE A 321     -12.935  -2.771  17.142  1.00 15.04           C
ATOM   2274  CD1  ILE A 321     -14.410  -0.436  18.605  1.00 14.33           C
ATOM   2275  N    PRO A 322     -14.941  -1.847  13.844  1.00 14.93           N
ATOM   2276  CA   PRO A 322     -14.238  -1.425  12.627  1.00 15.09           C
ATOM   2277  C    PRO A 322     -13.106  -0.437  12.865  1.00 14.91           C
ATOM   2278  O    PRO A 322     -13.061   0.217  13.898  1.00 15.66           O
ATOM   2279  CB   PRO A 322     -15.354  -0.805  11.753  1.00 16.06           C
ATOM   2280  CG   PRO A 322     -16.379  -0.335  12.763  1.00 19.25           C
ATOM   2281  CD   PRO A 322     -16.280  -1.233  13.985  1.00 16.91           C
ATOM   2282  N    SER A 323     -12.188  -0.363  11.908  1.00 16.65           N
ATOM   2283  CA   SER A 323     -11.104   0.631  11.973  1.00 17.65           C
ATOM   2284  C    SER A 323     -10.917   1.091  10.531  1.00 16.57           C
ATOM   2285  O    SER A 323     -10.554   0.306   9.651  1.00 18.54           O
ATOM   2286  CB   SER A 323      -9.801   0.047  12.525  1.00 20.73           C
ATOM   2287  OG   SER A 323      -8.808   1.085  12.565  1.00 22.08           O
ATOM   2288  N    PRO A 324     -11.144   2.379  10.273  1.00 17.94           N
ATOM   2289  CA   PRO A 324     -11.550   3.428  11.215  1.00 17.07           C
ATOM   2290  C    PRO A 324     -12.970   3.316  11.762  1.00 16.54           C
ATOM   2291  O    PRO A 324     -13.808   2.583  11.243  1.00 16.84           O
ATOM   2292  CB   PRO A 324     -11.385   4.716  10.397  1.00 18.99           C
ATOM   2293  CG   PRO A 324     -11.745   4.271   9.008  1.00 19.79           C
ATOM   2294  CD   PRO A 324     -11.100   2.886   8.882  1.00 18.17           C
ATOM   2295  N    PHE A 325     -13.218   4.055  12.829  1.00 15.79           N
ATOM   2296  CA   PHE A 325     -14.564   4.084  13.400  1.00 16.52           C
ATOM   2297  C    PHE A 325     -15.526   4.835  12.438  1.00 17.40           C
ATOM   2298  O    PHE A 325     -15.098   5.576  11.536  1.00 18.06           O
ATOM   2299  CB   PHE A 325     -14.581   4.882  14.713  1.00 16.64           C
ATOM   2300  CG   PHE A 325     -13.754   4.300  15.827  1.00 16.67           C
ATOM   2301  CD1  PHE A 325     -13.286   2.972  15.785  1.00 16.37           C
ATOM   2302  CD2  PHE A 325     -13.499   5.075  16.964  1.00 16.42           C
ATOM   2303  CE1  PHE A 325     -12.583   2.456  16.877  1.00 16.84           C
ATOM   2304  CE2  PHE A 325     -12.801   4.560  18.042  1.00 19.47           C
ATOM   2305  CZ   PHE A 325     -12.342   3.239  17.995  1.00 17.29           C
ATOM   2306  N    PRO A 326     -16.848   4.625  12.593  1.00 15.46           N
ATOM   2307  CA   PRO A 326     -17.857   5.320  11.762  1.00 15.83           C
ATOM   2308  C    PRO A 326     -17.565   6.848  11.806  1.00 14.25           C
ATOM   2309  O    PRO A 326     -17.143   7.380  12.838  1.00 13.25           O
ATOM   2310  CB   PRO A 326     -19.153   5.036  12.496  1.00 15.62           C
ATOM   2311  CG   PRO A 326     -18.944   3.621  12.995  1.00 16.45           C
```

FIGURE 1-35 (COORDINATES)

```
ATOM   2312  CD  PRO A 326     -17.492   3.671  13.525  1.00 15.22           C
ATOM   2313  N   GLU A 327     -17.806   7.557  10.707  1.00 14.54           N
ATOM   2314  CA  GLU A 327     -17.549   8.991  10.705  1.00 15.86           C
ATOM   2315  C   GLU A 327     -18.397   9.715  11.761  1.00 15.32           C
ATOM   2316  O   GLU A 327     -18.000  10.753  12.281  1.00 17.13           O
ATOM   2317  CB  GLU A 327     -17.874   9.568   9.317  1.00 17.01           C
ATOM   2318  CG  GLU A 327     -17.001   9.031   8.185  1.00 17.60           C
ATOM   2319  CD  GLU A 327     -17.402   9.625   6.857  1.00 20.94           C
ATOM   2320  OE1 GLU A 327     -17.994  10.736   6.880  1.00 21.27           O
ATOM   2321  OE2 GLU A 327     -17.138   8.991   5.832  1.00 18.29           O
ATOM   2322  N   VAL A 328     -19.574   9.172  12.058  1.00 16.07           N
ATOM   2323  CA  VAL A 328     -20.465   9.798  13.051  1.00 14.89           C
ATOM   2324  C   VAL A 328     -20.111   9.484  14.498  1.00 14.76           C
ATOM   2325  O   VAL A 328     -20.817   9.922  15.403  1.00 14.50           O
ATOM   2326  CB  VAL A 328     -21.918   9.334  12.831  1.00 16.66           C
ATOM   2327  CG1 VAL A 328     -22.403   9.791  11.434  1.00 17.39           C
ATOM   2328  CG2 VAL A 328     -22.007   7.805  12.976  1.00 18.22           C
ATOM   2329  N   TRP A 329     -19.026   8.733  14.726  1.00 13.91           N
ATOM   2330  CA  TRP A 329     -18.614   8.347  16.087  1.00 14.24           C
ATOM   2331  C   TRP A 329     -18.652   9.499  17.123  1.00 14.34           C
ATOM   2332  O   TRP A 329     -18.055  10.566  16.939  1.00 14.32           O
ATOM   2333  CB  TRP A 329     -17.193   7.736  16.014  1.00 14.32           C
ATOM   2334  CG  TRP A 329     -16.618   7.283  17.349  1.00 15.76           C
ATOM   2335  CD1 TRP A 329     -16.801   6.070  17.980  1.00 16.93           C
ATOM   2336  CD2 TRP A 329     -15.694   8.014  18.154  1.00 14.49           C
ATOM   2337  NE1 TRP A 329     -16.023   6.004  19.125  1.00 14.66           N
ATOM   2338  CE2 TRP A 329     -15.337   7.185  19.254  1.00 14.62           C
ATOM   2339  CE3 TRP A 329     -15.126   9.301  18.056  1.00 15.82           C
ATOM   2340  CZ2 TRP A 329     -14.443   7.598  20.242  1.00 15.92           C
ATOM   2341  CZ3 TRP A 329     -14.254   9.707  19.030  1.00 14.57           C
ATOM   2342  CH2 TRP A 329     -13.915   8.858  20.121  1.00 17.60           C
ATOM   2343  N   HIS A 330     -19.400   9.271  18.191  1.00 13.79           N
ATOM   2344  CA  HIS A 330     -19.554  10.197  19.309  1.00 14.44           C
ATOM   2345  C   HIS A 330     -20.040  11.572  18.927  1.00 16.64           C
ATOM   2346  O   HIS A 330     -19.676  12.591  19.524  1.00 17.75           O
ATOM   2347  CB  HIS A 330     -18.255  10.254  20.118  1.00 13.65           C
ATOM   2348  CG  HIS A 330     -18.031   8.992  20.915  1.00 15.63           C
ATOM   2349  ND1 HIS A 330     -17.058   8.871  21.881  1.00 16.18           N
ATOM   2350  CD2 HIS A 330     -18.699   7.813  20.903  1.00 16.44           C
ATOM   2351  CE1 HIS A 330     -17.140   7.670  22.436  1.00 14.91           C
ATOM   2352  NE2 HIS A 330     -18.129   7.014  21.858  1.00 14.33           N
ATOM   2353  N   THR A 331     -20.916  11.555  17.951  1.00 16.47           N
ATOM   2354  CA  THR A 331     -21.526  12.726  17.406  1.00 19.52           C
ATOM   2355  C   THR A 331     -23.084  12.527  17.460  1.00 17.89           C
ATOM   2356  O   THR A 331     -23.561  11.389  17.455  1.00 16.75           O
ATOM   2357  CB  THR A 331     -20.931  12.706  16.000  1.00 22.62           C
ATOM   2358  OG1 THR A 331     -19.879  13.673  15.857  1.00 24.74           O
ATOM   2359  CG2 THR A 331     -21.927  12.610  15.012  1.00 12.87           C
ATOM   2360  N   MET A 332     -23.867  13.614  17.487  1.00 17.63           N
ATOM   2361  CA  MET A 332     -25.335  13.472  17.465  1.00 17.73           C
ATOM   2362  C   MET A 332     -25.824  12.840  16.150  1.00 17.05           C
ATOM   2363  O   MET A 332     -26.969  12.395  16.043  1.00 19.28           O
ATOM   2364  CB  MET A 332     -26.031  14.839  17.653  1.00 19.41           C
ATOM   2365  CG  MET A 332     -25.874  15.436  19.016  1.00 20.18           C
ATOM   2366  SD  MET A 332     -26.603  14.428  20.309  1.00 21.57           S
ATOM   2367  CE  MET A 332     -26.353  15.432  21.754  1.00 20.99           C
ATOM   2368  N   ASP A 333     -24.957  12.780  15.134  1.00 16.75           N
ATOM   2369  CA  ASP A 333     -25.326  12.143  13.884  1.00 15.99           C
ATOM   2370  C   ASP A 333     -25.216  10.610  13.948  1.00 16.31           C
ATOM   2371  O   ASP A 333     -25.456   9.958  12.950  1.00 15.30           O
ATOM   2372  CB  ASP A 333     -24.458  12.658  12.747  1.00 19.41           C
ATOM   2373  CG  ASP A 333     -24.756  14.117  12.410  1.00 24.27           C
ATOM   2374  OD1 ASP A 333     -25.934  14.502  12.453  1.00 24.90           O
ATOM   2375  OD2 ASP A 333     -23.801  14.846  12.083  1.00 28.43           O
ATOM   2376  N   ASP A 334     -24.873  10.032  15.105  1.00 14.97           N
ATOM   2377  CA  ASP A 334     -24.828   8.555  15.170  1.00 15.62           C
ATOM   2378  C   ASP A 334     -26.260   8.169  15.466  1.00 17.00           C
ATOM   2379  O   ASP A 334     -26.625   7.842  16.615  1.00 16.45           O
```

FIGURE 1-36 (COORDINATES)

```
ATOM   2380  CB   ASP A 334     -23.949    8.059   16.308  1.00 17.17           C
ATOM   2381  CG   ASP A 334     -23.788    6.547   16.266  1.00 16.00           C
ATOM   2382  OD1  ASP A 334     -24.387    5.921   15.363  1.00 15.67           O
ATOM   2383  OD2  ASP A 334     -23.064    6.003   17.130  1.00 17.77           O
ATOM   2384  N    ASN A 335     -27.068    8.226   14.414  1.00 16.50           N
ATOM   2385  CA   ASN A 335     -28.495    8.020   14.540  1.00 16.29           C
ATOM   2386  C    ASN A 335     -29.027    7.019   13.520  1.00 17.80           C
ATOM   2387  O    ASN A 335     -28.275    6.433   12.740  1.00 17.84           O
ATOM   2388  CB   ASN A 335     -29.186    9.396   14.359  1.00 16.97           C
ATOM   2389  CG   ASN A 335     -28.869   10.016   13.004  1.00 18.43           C
ATOM   2390  OD1  ASN A 335     -28.525    9.305   12.046  1.00 17.71           O
ATOM   2391  ND2  ASN A 335     -29.001   11.347   12.902  1.00 21.72           N
ATOM   2392  N    GLU A 336     -30.343    6.819   13.526  1.00 16.14           N
ATOM   2393  CA   GLU A 336     -30.962    5.872   12.619  1.00 16.46           C
ATOM   2394  C    GLU A 336     -30.759    6.179   11.144  1.00 16.83           C
ATOM   2395  O    GLU A 336     -30.505    5.278   10.336  1.00 17.11           O
ATOM   2396  CB   GLU A 336     -32.465    5.799   12.911  1.00 18.17           C
ATOM   2397  CG   GLU A 336     -33.141    4.619   12.234  1.00 21.32           C
ATOM   2398  CD   GLU A 336     -34.622    4.532   12.568  1.00 22.81           C
ATOM   2399  OE1  GLU A 336     -35.071    5.274   13.466  1.00 25.62           O
ATOM   2400  OE2  GLU A 336     -35.314    3.717   11.931  1.00 25.55           O
ATOM   2401  N    GLU A 337     -30.884    7.454   10.806  1.00 18.04           N
ATOM   2402  CA   GLU A 337     -30.756    7.892    9.429  1.00 19.93           C
ATOM   2403  C    GLU A 337     -29.409    7.518    8.801  1.00 19.18           C
ATOM   2404  O    GLU A 337     -29.336    7.195    7.606  1.00 20.23           O
ATOM   2405  CB   GLU A 337     -30.970    9.419    9.334  1.00 23.92           C
ATOM   2406  CG   GLU A 337     -30.521    9.957    7.963  1.00 31.60           C
ATOM   2407  CD   GLU A 337     -30.714   11.461    7.758  1.00 36.79           C
ATOM   2408  OE1  GLU A 337     -30.747   12.218    8.760  1.00 37.58           O
ATOM   2409  OE2  GLU A 337     -30.799   11.873    6.563  1.00 39.78           O
ATOM   2410  N    ASN A 338     -28.353    7.507    9.598  1.00 17.77           N
ATOM   2411  CA   ASN A 338     -27.046    7.199    9.055  1.00 17.41           C
ATOM   2412  C    ASN A 338     -26.653    5.719    9.055  1.00 16.50           C
ATOM   2413  O    ASN A 338     -25.548    5.359    8.650  1.00 16.94           O
ATOM   2414  CB   ASN A 338     -26.003    8.076    9.754  1.00 17.86           C
ATOM   2415  CG   ASN A 338     -26.129    9.544    9.331  1.00 20.48           C
ATOM   2416  OD1  ASN A 338     -26.136   10.464   10.153  1.00 21.15           O
ATOM   2417  ND2  ASN A 338     -26.273    9.756    8.030  1.00 21.29           N
ATOM   2418  N    LEU A 339     -27.569    4.856    9.480  1.00 15.97           N
ATOM   2419  CA   LEU A 339     -27.288    3.426    9.456  1.00 16.27           C
ATOM   2420  C    LEU A 339     -27.440    2.887    8.041  1.00 16.95           C
ATOM   2421  O    LEU A 339     -28.268    3.390    7.243  1.00 18.14           O
ATOM   2422  CB   LEU A 339     -28.261    2.683   10.380  1.00 13.62           C
ATOM   2423  CG   LEU A 339     -28.156    3.041   11.856  1.00 14.80           C
ATOM   2424  CD1  LEU A 339     -29.257    2.303   12.634  1.00 16.17           C
ATOM   2425  CD2  LEU A 339     -26.743    2.668   12.355  1.00 16.40           C
ATOM   2426  N    ASP A 340     -26.665    1.840    7.726  1.00 16.46           N
ATOM   2427  CA   ASP A 340     -26.674    1.202    6.408  1.00 16.25           C
ATOM   2428  C    ASP A 340     -27.355   -0.145    6.585  1.00 18.09           C
ATOM   2429  O    ASP A 340     -26.762   -1.109    7.090  1.00 15.97           O
ATOM   2430  CB   ASP A 340     -25.216    1.025    5.921  1.00 18.29           C
ATOM   2431  CG   ASP A 340     -25.106    0.425    4.523  1.00 21.64           C
ATOM   2432  OD1  ASP A 340     -25.909   -0.466    4.141  1.00 20.09           O
ATOM   2433  OD2  ASP A 340     -24.172    0.839    3.804  1.00 23.56           O
ATOM   2434  N    GLU A 341     -28.621   -0.187    6.188  1.00 17.97           N
ATOM   2435  CA   GLU A 341     -29.434   -1.389    6.356  1.00 20.15           C
ATOM   2436  C    GLU A 341     -28.880   -2.676    5.756  1.00 17.88           C
ATOM   2437  O    GLU A 341     -28.839   -3.720    6.422  1.00 17.76           O
ATOM   2438  CB   GLU A 341     -30.829   -1.123    5.784  1.00 24.08           C
ATOM   2439  CG   GLU A 341     -31.774   -2.308    5.905  1.00 29.59           C
ATOM   2440  CD   GLU A 341     -33.124   -2.042    5.258  1.00 36.44           C
ATOM   2441  OE1  GLU A 341     -33.809   -1.090    5.695  1.00 39.41           O
ATOM   2442  OE2  GLU A 341     -33.490   -2.777    4.316  1.00 38.58           O
ATOM   2443  N    SER A 342     -28.455   -2.632    4.503  1.00 16.65           N
ATOM   2444  CA   SER A 342     -27.970   -3.871    3.904  1.00 16.83           C
ATOM   2445  C    SER A 342     -26.692   -4.365    4.532  1.00 15.54           C
ATOM   2446  O    SER A 342     -26.471   -5.574    4.571  1.00 14.81           O
ATOM   2447  CB   SER A 342     -27.784   -3.737    2.382  1.00 20.21           C
```

FIGURE 1-37 (COORDINATES)

```
ATOM   2448  OG  SER A 342     -26.789  -2.790   2.038  1.00 25.65           O
ATOM   2449  N   THR A 343     -25.857  -3.449   5.014  1.00 15.43           N
ATOM   2450  CA  THR A 343     -24.589  -3.878   5.642  1.00 14.12           C
ATOM   2451  C   THR A 343     -24.890  -4.615   6.948  1.00 13.61           C
ATOM   2452  O   THR A 343     -24.260  -5.651   7.255  1.00 15.15           O
ATOM   2453  CB  THR A 343     -23.683  -2.663   5.914  1.00 17.59           C
ATOM   2454  OG1 THR A 343     -23.305  -2.095   4.648  1.00 21.11           O
ATOM   2455  CG2 THR A 343     -22.414  -3.061   6.638  1.00 16.62           C
ATOM   2456  N   ILE A 344     -25.843  -4.086   7.703  1.00 13.61           N
ATOM   2457  CA  ILE A 344     -26.234  -4.741   8.957  1.00 13.79           C
ATOM   2458  C   ILE A 344     -26.851  -6.119   8.622  1.00 15.28           C
ATOM   2459  O   ILE A 344     -26.526  -7.122   9.254  1.00 14.18           O
ATOM   2460  CB  ILE A 344     -27.204  -3.847   9.762  1.00 14.19           C
ATOM   2461  CG1 ILE A 344     -26.488  -2.511  10.082  1.00 14.94           C
ATOM   2462  CG2 ILE A 344     -27.716  -4.597  11.044  1.00 14.40           C
ATOM   2463  CD1 ILE A 344     -27.428  -1.404  10.536  1.00 14.71           C
ATOM   2464  N   ASP A 345     -27.717  -6.166   7.617  1.00 14.08           N
ATOM   2465  CA  ASP A 345     -28.324  -7.449   7.194  1.00 14.40           C
ATOM   2466  C   ASP A 345     -27.244  -8.465   6.837  1.00 14.21           C
ATOM   2467  O   ASP A 345     -27.279  -9.624   7.270  1.00 14.91           O
ATOM   2468  CB  ASP A 345     -29.245  -7.175   5.980  1.00 15.61           C
ATOM   2469  CG  ASP A 345     -30.154  -8.352   5.621  1.00 16.87           C
ATOM   2470  OD1 ASP A 345     -30.551  -9.131   6.504  1.00 18.32           O
ATOM   2471  OD2 ASP A 345     -30.500  -8.453   4.413  1.00 20.46           O
ATOM   2472  N   ASN A 346     -26.269  -8.044   6.022  1.00 14.31           N
ATOM   2473  CA  ASN A 346     -25.165  -8.916   5.620  1.00 13.89           C
ATOM   2474  C   ASN A 346     -24.393  -9.410   6.850  1.00 14.84           C
ATOM   2475  O   ASN A 346     -24.029 -10.586   6.921  1.00 14.42           O
ATOM   2476  CB  ASN A 346     -24.176  -8.152   4.711  1.00 13.58           C
ATOM   2477  CG  ASN A 346     -24.768  -7.848   3.335  1.00 16.67           C
ATOM   2478  OD1 ASN A 346     -25.746  -8.478   2.910  1.00 16.08           O
ATOM   2479  ND2 ASN A 346     -24.166  -6.870   2.624  1.00 16.31           N
ATOM   2480  N   LEU A 347     -24.096  -8.502   7.779  1.00 14.52           N
ATOM   2481  CA  LEU A 347     -23.349  -8.891   8.981  1.00 14.07           C
ATOM   2482  C   LEU A 347     -24.176  -9.841   9.858  1.00 14.83           C
ATOM   2483  O   LEU A 347     -23.604 -10.719  10.508  1.00 14.48           O
ATOM   2484  CB  LEU A 347     -22.882  -7.667   9.784  1.00 15.49           C
ATOM   2485  CG  LEU A 347     -21.703  -6.944   9.068  1.00 13.46           C
ATOM   2486  CD1 LEU A 347     -21.496  -5.556   9.732  1.00 14.94           C
ATOM   2487  CD2 LEU A 347     -20.368  -7.749   9.133  1.00 14.69           C
ATOM   2488  N   ASN A 348     -25.495  -9.676   9.881  1.00 15.21           N
ATOM   2489  CA  ASN A 348     -26.348 -10.585  10.662  1.00 16.03           C
ATOM   2490  C   ASN A 348     -26.184 -12.004  10.093  1.00 15.71           C
ATOM   2491  O   ASN A 348     -26.060 -13.002  10.835  1.00 16.29           O
ATOM   2492  CB  ASN A 348     -27.827 -10.170  10.561  1.00 14.08           C
ATOM   2493  CG  ASN A 348     -28.202  -9.118  11.557  1.00 15.45           C
ATOM   2494  OD1 ASN A 348     -27.513  -8.942  12.587  1.00 16.93           O
ATOM   2495  ND2 ASN A 348     -29.327  -8.416  11.301  1.00 14.60           N
ATOM   2496  N   LYS A 349     -26.222 -12.107   8.772  1.00 14.89           N
ATOM   2497  CA  LYS A 349     -26.074 -13.424   8.141  1.00 15.12           C
ATOM   2498  C   LYS A 349     -24.720 -14.031   8.443  1.00 16.30           C
ATOM   2499  O   LYS A 349     -24.612 -15.205   8.796  1.00 15.88           O
ATOM   2500  CB  LYS A 349     -26.268 -13.303   6.620  1.00 15.05           C
ATOM   2501  CG  LYS A 349     -27.692 -12.814   6.278  1.00 15.63           C
ATOM   2502  CD  LYS A 349     -27.854 -12.662   4.734  1.00 16.05           C
ATOM   2503  CE  LYS A 349     -29.266 -12.177   4.399  1.00 17.76           C
ATOM   2504  NZ  LYS A 349     -29.389 -11.842   2.929  1.00 17.02           N
ATOM   2505  N   ILE A 350     -23.660 -13.228   8.315  1.00 14.38           N
ATOM   2506  CA  ILE A 350     -22.328 -13.756   8.574  1.00 14.15           C
ATOM   2507  C   ILE A 350     -22.179 -14.233  10.029  1.00 13.60           C
ATOM   2508  O   ILE A 350     -21.605 -15.311  10.293  1.00 15.45           O
ATOM   2509  CB  ILE A 350     -21.281 -12.665   8.260  1.00 15.29           C
ATOM   2510  CG1 ILE A 350     -21.267 -12.435   6.734  1.00 14.50           C
ATOM   2511  CG2 ILE A 350     -19.862 -13.091   8.756  1.00 14.03           C
ATOM   2512  CD1 ILE A 350     -20.662 -11.047   6.372  1.00 16.55           C
ATOM   2513  N   LEU A 351     -22.673 -13.433  10.962  1.00 13.23           N
ATOM   2514  CA  LEU A 351     -22.537 -13.742  12.396  1.00 13.33           C
ATOM   2515  C   LEU A 351     -23.366 -14.964  12.769  1.00 14.40           C
```

FIGURE 1-38 (COORDINATES)

```
ATOM   2516  O    LEU A 351     -22.913 -15.811  13.522  1.00 13.69           O
ATOM   2517  CB   LEU A 351     -22.983 -12.536  13.244  1.00 14.19           C
ATOM   2518  CG   LEU A 351     -22.860 -12.714  14.773  1.00 15.99           C
ATOM   2519  CD1  LEU A 351     -21.382 -12.787  15.188  1.00 17.82           C
ATOM   2520  CD2  LEU A 351     -23.568 -11.518  15.473  1.00 17.32           C
ATOM   2521  N    GLN A 352     -24.571 -15.050  12.225  1.00 15.34           N
ATOM   2522  CA   GLN A 352     -25.412 -16.214  12.537  1.00 14.72           C
ATOM   2523  C    GLN A 352     -24.743 -17.500  12.001  1.00 13.89           C
ATOM   2524  O    GLN A 352     -24.701 -18.520  12.702  1.00 16.32           O
ATOM   2525  CB   GLN A 352     -26.816 -15.993  11.950  1.00 14.56           C
ATOM   2526  CG   GLN A 352     -27.593 -14.960  12.757  1.00 15.50           C
ATOM   2527  CD   GLN A 352     -28.845 -14.531  12.063  1.00 17.65           C
ATOM   2528  OE1  GLN A 352     -29.440 -15.313  11.309  1.00 18.70           O
ATOM   2529  NE2  GLN A 352     -29.265 -13.282  12.299  1.00 16.05           N
ATOM   2530  N    VAL A 353     -24.187 -17.482  10.789  1.00 14.11           N
ATOM   2531  CA   VAL A 353     -23.516 -18.663  10.300  1.00 15.35           C
ATOM   2532  C    VAL A 353     -22.327 -18.978  11.219  1.00 16.50           C
ATOM   2533  O    VAL A 353     -22.099 -20.129  11.586  1.00 14.83           O
ATOM   2534  CB   VAL A 353     -23.008 -18.452   8.874  1.00 15.91           C
ATOM   2535  CG1  VAL A 353     -22.076 -19.611   8.436  1.00 16.79           C
ATOM   2536  CG2  VAL A 353     -24.198 -18.385   7.924  1.00 16.54           C
ATOM   2537  N    PHE A 354     -21.561 -17.942  11.589  1.00 14.03           N
ATOM   2538  CA   PHE A 354     -20.404 -18.160  12.460  1.00 15.37           C
ATOM   2539  C    PHE A 354     -20.794 -18.875  13.757  1.00 15.17           C
ATOM   2540  O    PHE A 354     -20.111 -19.822  14.175  1.00 16.04           O
ATOM   2541  CB   PHE A 354     -19.747 -16.802  12.832  1.00 15.91           C
ATOM   2542  CG   PHE A 354     -18.530 -16.938  13.720  1.00 16.72           C
ATOM   2543  CD1  PHE A 354     -17.257 -17.039  13.169  1.00 16.88           C
ATOM   2544  CD2  PHE A 354     -18.675 -17.047  15.117  1.00 16.16           C
ATOM   2545  CE1  PHE A 354     -16.118 -17.256  13.992  1.00 15.15           C
ATOM   2546  CE2  PHE A 354     -17.557 -17.269  15.931  1.00 14.71           C
ATOM   2547  CZ   PHE A 354     -16.282 -17.374  15.366  1.00 14.99           C
ATOM   2548  N    VAL A 355     -21.896 -18.434  14.362  1.00 15.54           N
ATOM   2549  CA   VAL A 355     -22.323 -19.000  15.637  1.00 14.36           C
ATOM   2550  C    VAL A 355     -22.813 -20.441  15.461  1.00 16.18           C
ATOM   2551  O    VAL A 355     -22.487 -21.295  16.259  1.00 14.86           O
ATOM   2552  CB   VAL A 355     -23.427 -18.127  16.272  1.00 15.44           C
ATOM   2553  CG1  VAL A 355     -24.053 -18.853  17.481  1.00 15.57           C
ATOM   2554  CG2  VAL A 355     -22.839 -16.803  16.709  1.00 16.10           C
ATOM   2555  N    LEU A 356     -23.574 -20.705  14.403  1.00 15.74           N
ATOM   2556  CA   LEU A 356     -24.050 -22.081  14.195  1.00 17.21           C
ATOM   2557  C    LEU A 356     -22.863 -22.994  13.934  1.00 18.00           C
ATOM   2558  O    LEU A 356     -22.809 -24.093  14.479  1.00 18.25           O
ATOM   2559  CB   LEU A 356     -25.015 -22.149  12.991  1.00 18.67           C
ATOM   2560  CG   LEU A 356     -26.342 -21.423  13.196  1.00 19.48           C
ATOM   2561  CD1  LEU A 356     -27.177 -21.498  11.933  1.00 20.01           C
ATOM   2562  CD2  LEU A 356     -27.088 -22.081  14.342  1.00 20.20           C
ATOM   2563  N    GLU A 357     -21.914 -22.561  13.105  1.00 16.82           N
ATOM   2564  CA   GLU A 357     -20.758 -23.397  12.818  1.00 16.42           C
ATOM   2565  C    GLU A 357     -19.926 -23.664  14.077  1.00 16.94           C
ATOM   2566  O    GLU A 357     -19.418 -24.776  14.259  1.00 16.43           O
ATOM   2567  CB   GLU A 357     -19.889 -22.769  11.715  1.00 17.38           C
ATOM   2568  CG   GLU A 357     -20.667 -22.735  10.388  1.00 16.87           C
ATOM   2569  CD   GLU A 357     -19.825 -22.304   9.208  1.00 19.97           C
ATOM   2570  OE1  GLU A 357     -18.797 -21.649   9.434  1.00 19.05           O
ATOM   2571  OE2  GLU A 357     -20.217 -22.608   8.043  1.00 21.05           O
ATOM   2572  N    TYR A 358     -19.794 -22.663  14.942  1.00 16.16           N
ATOM   2573  CA   TYR A 358     -19.011 -22.829  16.157  1.00 16.34           C
ATOM   2574  C    TYR A 358     -19.693 -23.839  17.095  1.00 17.33           C
ATOM   2575  O    TYR A 358     -19.039 -24.700  17.658  1.00 18.65           O
ATOM   2576  CB   TYR A 358     -18.848 -21.456  16.884  1.00 16.27           C
ATOM   2577  CG   TYR A 358     -17.750 -21.433  17.933  1.00 16.61           C
ATOM   2578  CD1  TYR A 358     -16.463 -20.946  17.624  1.00 15.20           C
ATOM   2579  CD2  TYR A 358     -17.943 -22.021  19.201  1.00 15.73           C
ATOM   2580  CE1  TYR A 358     -15.401 -21.051  18.542  1.00 15.01           C
ATOM   2581  CE2  TYR A 358     -16.873 -22.135  20.102  1.00 14.94           C
ATOM   2582  CZ   TYR A 358     -15.619 -21.651  19.769  1.00 15.43           C
ATOM   2583  OH   TYR A 358     -14.598 -21.780  20.679  1.00 17.12           O
```

FIGURE 1-39 (COORDINATES)

```
ATOM   2584  N    LEU A 359     -21.011 -23.735  17.230  1.00 16.11           N
ATOM   2585  CA   LEU A 359     -21.768 -24.591  18.137  1.00 17.64           C
ATOM   2586  C    LEU A 359     -22.120 -25.959  17.550  1.00 19.28           C
ATOM   2587  O    LEU A 359     -22.653 -26.816  18.276  1.00 21.94           O
ATOM   2588  CB   LEU A 359     -23.048 -23.868  18.568  1.00 14.45           C
ATOM   2589  CG   LEU A 359     -22.851 -22.547  19.343  1.00 17.40           C
ATOM   2590  CD1  LEU A 359     -24.199 -21.907  19.602  1.00 18.87           C
ATOM   2591  CD2  LEU A 359     -22.094 -22.801  20.685  1.00 16.89           C
ATOM   2592  N    HIS A 360     -21.797 -26.174  16.276  1.00 19.81           N
ATOM   2593  CA   HIS A 360     -22.106 -27.423  15.562  1.00 21.77           C
ATOM   2594  C    HIS A 360     -23.616 -27.599  15.474  1.00 22.89           C
ATOM   2595  O    HIS A 360     -24.130 -28.694  15.768  1.00 24.63           O
ATOM   2596  CB   HIS A 360     -21.501 -28.627  16.286  1.00 24.29           C
ATOM   2597  CG   HIS A 360     -20.012 -28.733  16.158  1.00 25.21           C
ATOM   2598  ND1  HIS A 360     -19.190 -27.638  15.983  1.00 25.36           N
ATOM   2599  CD2  HIS A 360     -19.197 -29.816  16.174  1.00 26.12           C
ATOM   2600  CE1  HIS A 360     -17.935 -28.045  15.886  1.00 22.70           C
ATOM   2601  NE2  HIS A 360     -17.912 -29.361  15.999  1.00 30.64           N
ATOM   2602  N    LEU A 361     -24.327 -26.530  15.113  1.00 21.47           N
ATOM   2603  CA   LEU A 361     -25.780 -26.566  14.971  1.00 21.49           C
ATOM   2604  C    LEU A 361     -26.226 -26.317  13.534  1.00 23.06           C
ATOM   2605  O    LEU A 361     -27.432 -26.481  13.261  1.00 24.92           O
ATOM   2606  CB   LEU A 361     -26.445 -25.539  15.887  1.00 20.75           C
ATOM   2607  CG   LEU A 361     -26.238 -25.747  17.389  1.00 21.19           C
ATOM   2608  CD1  LEU A 361     -26.861 -24.593  18.128  1.00 21.80           C
ATOM   2609  CD2  LEU A 361     -26.832 -27.062  17.841  1.00 24.45           C
ATOM   2610  OXT  LEU A 361     -25.385 -25.940  12.694  1.00 23.39           O
TER    2611       LEU A 361
ATOM   2612  N    ALA B  33     -28.582  11.237  49.233  1.00 49.37           N
ATOM   2613  CA   ALA B  33     -28.103  11.783  50.547  1.00 49.34           C
ATOM   2614  C    ALA B  33     -28.813  11.065  51.681  1.00 48.48           C
ATOM   2615  O    ALA B  33     -29.478  11.697  52.505  1.00 48.42           O
ATOM   2616  CB   ALA B  33     -28.380  13.289  50.643  1.00 49.54           C
ATOM   2617  N    SER B  34     -28.670   9.743  51.714  1.00 47.34           N
ATOM   2618  CA   SER B  34     -29.300   8.940  52.752  1.00 45.76           C
ATOM   2619  C    SER B  34     -28.759   9.211  54.145  1.00 44.25           C
ATOM   2620  O    SER B  34     -27.545   9.302  54.369  1.00 43.39           O
ATOM   2621  CB   SER B  34     -29.164   7.452  52.427  1.00 46.31           C
ATOM   2622  OG   SER B  34     -30.174   7.068  51.511  1.00 46.29           O
ATOM   2623  N    ALA B  35     -29.674   9.328  55.095  1.00 41.93           N
ATOM   2624  CA   ALA B  35     -29.265   9.578  56.454  1.00 39.87           C
ATOM   2625  C    ALA B  35     -29.020   8.278  57.199  1.00 38.20           C
ATOM   2626  O    ALA B  35     -28.268   8.270  58.171  1.00 37.94           O
ATOM   2627  CB   ALA B  35     -30.321  10.404  57.181  1.00 40.50           C
ATOM   2628  N    TRP B  36     -29.619   7.174  56.742  1.00 35.60           N
ATOM   2629  CA   TRP B  36     -29.449   5.923  57.477  1.00 33.39           C
ATOM   2630  C    TRP B  36     -28.012   5.448  57.738  1.00 32.03           C
ATOM   2631  O    TRP B  36     -27.746   4.858  58.784  1.00 33.95           O
ATOM   2632  CB   TRP B  36     -30.306   4.791  56.862  1.00 32.50           C
ATOM   2633  CG   TRP B  36     -29.879   4.252  55.520  1.00 30.69           C
ATOM   2634  CD1  TRP B  36     -30.404   4.564  54.295  1.00 31.14           C
ATOM   2635  CD2  TRP B  36     -28.841   3.296  55.280  1.00 30.56           C
ATOM   2636  NE1  TRP B  36     -29.756   3.862  53.307  1.00 29.16           N
ATOM   2637  CE2  TRP B  36     -28.789   3.076  53.884  1.00 30.78           C
ATOM   2638  CE3  TRP B  36     -27.944   2.607  56.108  1.00 29.87           C
ATOM   2639  CZ2  TRP B  36     -27.866   2.187  53.295  1.00 28.66           C
ATOM   2640  CZ3  TRP B  36     -27.023   1.730  55.527  1.00 28.64           C
ATOM   2641  CH2  TRP B  36     -26.994   1.529  54.134  1.00 28.34           C
ATOM   2642  N    PRO B  37     -27.064   5.698  56.822  1.00 31.09           N
ATOM   2643  CA   PRO B  37     -25.706   5.219  57.131  1.00 30.69           C
ATOM   2644  C    PRO B  37     -25.079   5.921  58.334  1.00 30.53           C
ATOM   2645  O    PRO B  37     -24.052   5.498  58.855  1.00 28.38           O
ATOM   2646  CB   PRO B  37     -24.929   5.500  55.851  1.00 31.02           C
ATOM   2647  CG   PRO B  37     -25.991   5.389  54.774  1.00 28.83           C
ATOM   2648  CD   PRO B  37     -27.173   6.106  55.410  1.00 31.59           C
ATOM   2649  N    GLU B  38     -25.708   7.006  58.777  1.00 30.14           N
ATOM   2650  CA   GLU B  38     -25.188   7.765  59.916  1.00 30.64           C
ATOM   2651  C    GLU B  38     -25.757   7.284  61.243  1.00 29.17           C
```

FIGURE 1-40 (COORDINATES)

```
ATOM   2652  O    GLU B  38     -25.178   7.531  62.292  1.00 29.98           O
ATOM   2653  CB   GLU B  38     -25.548   9.263  59.745  1.00 30.86           C
ATOM   2654  CG   GLU B  38     -24.995   9.847  58.464  1.00 34.05           C
ATOM   2655  CD   GLU B  38     -25.542  11.240  58.167  1.00 34.41           C
ATOM   2656  OE1  GLU B  38     -26.270  11.762  59.012  1.00 34.06           O
ATOM   2657  OE2  GLU B  38     -25.237  11.792  57.082  1.00 39.95           O
ATOM   2658  N    GLU B  39     -26.894   6.612  61.198  1.00 30.41           N
ATOM   2659  CA   GLU B  39     -27.555   6.173  62.421  1.00 30.37           C
ATOM   2660  C    GLU B  39     -26.645   5.425  63.396  1.00 30.48           C
ATOM   2661  O    GLU B  39     -26.791   5.564  64.607  1.00 28.34           O
ATOM   2662  CB   GLU B  39     -28.802   5.355  62.072  1.00 32.13           C
ATOM   2663  CG   GLU B  39     -29.764   6.153  61.182  1.00 34.57           C
ATOM   2664  CD   GLU B  39     -31.026   5.419  60.792  1.00 37.50           C
ATOM   2665  OE1  GLU B  39     -31.191   4.224  61.131  1.00 38.00           O
ATOM   2666  OE2  GLU B  39     -31.878   6.051  60.116  1.00 39.53           O
ATOM   2667  N    LYS B  40     -25.674   4.678  62.885  1.00 29.31           N
ATOM   2668  CA   LYS B  40     -24.774   3.946  63.781  1.00 30.11           C
ATOM   2669  C    LYS B  40     -24.011   4.850  64.762  1.00 30.84           C
ATOM   2670  O    LYS B  40     -23.679   4.423  65.872  1.00 27.67           O
ATOM   2671  CB   LYS B  40     -23.772   3.122  62.963  1.00 30.69           C
ATOM   2672  CG   LYS B  40     -22.836   3.974  62.108  1.00 32.77           C
ATOM   2673  CD   LYS B  40     -21.640   3.149  61.643  1.00 36.86           C
ATOM   2674  CE   LYS B  40     -20.523   4.056  61.139  1.00 35.65           C
ATOM   2675  NZ   LYS B  40     -20.710   4.295  59.703  1.00 38.91           N
ATOM   2676  N    ASN B  41     -23.730   6.096  64.364  1.00 29.61           N
ATOM   2677  CA   ASN B  41     -23.014   7.013  65.241  1.00 31.91           C
ATOM   2678  C    ASN B  41     -23.850   7.385  66.455  1.00 29.93           C
ATOM   2679  O    ASN B  41     -23.290   7.683  67.509  1.00 32.26           O
ATOM   2680  CB   ASN B  41     -22.622   8.317  64.533  1.00 32.48           C
ATOM   2681  CG   ASN B  41     -21.633   8.110  63.398  1.00 35.21           C
ATOM   2682  OD1  ASN B  41     -21.993   8.201  62.217  1.00 38.15           O
ATOM   2683  ND2  ASN B  41     -20.382   7.837  63.742  1.00 36.01           N
ATOM   2684  N    TYR B  42     -25.175   7.367  66.308  1.00 30.11           N
ATOM   2685  CA   TYR B  42     -26.074   7.752  67.405  1.00 31.63           C
ATOM   2686  C    TYR B  42     -26.736   6.595  68.102  1.00 30.36           C
ATOM   2687  O    TYR B  42     -27.426   6.807  69.087  1.00 31.64           O
ATOM   2688  CB   TYR B  42     -27.224   8.647  66.901  1.00 32.77           C
ATOM   2689  CG   TYR B  42     -26.809   9.655  65.887  1.00 33.37           C
ATOM   2690  CD1  TYR B  42     -25.901  10.660  66.223  1.00 35.96           C
ATOM   2691  CD2  TYR B  42     -27.298   9.603  64.580  1.00 32.05           C
ATOM   2692  CE1  TYR B  42     -25.476  11.600  65.281  1.00 35.84           C
ATOM   2693  CE2  TYR B  42     -26.877  10.540  63.629  1.00 34.22           C
ATOM   2694  CZ   TYR B  42     -25.967  11.535  63.997  1.00 35.77           C
ATOM   2695  OH   TYR B  42     -25.557  12.481  63.096  1.00 37.33           O
ATOM   2696  N    HIS B  43     -26.558   5.380  67.590  1.00 28.99           N
ATOM   2697  CA   HIS B  43     -27.234   4.229  68.176  1.00 28.39           C
ATOM   2698  C    HIS B  43     -26.870   3.976  69.631  1.00 27.89           C
ATOM   2699  O    HIS B  43     -25.705   4.014  70.023  1.00 30.07           O
ATOM   2700  CB   HIS B  43     -26.963   2.965  67.332  1.00 27.69           C
ATOM   2701  CG   HIS B  43     -27.881   1.833  67.652  1.00 28.31           C
ATOM   2702  ND1  HIS B  43     -27.493   0.760  68.429  1.00 29.02           N
ATOM   2703  CD2  HIS B  43     -29.186   1.634  67.357  1.00 28.87           C
ATOM   2704  CE1  HIS B  43     -28.524  -0.046  68.601  1.00 26.80           C
ATOM   2705  NE2  HIS B  43     -29.562   0.460  67.963  1.00 30.73           N
ATOM   2706  N    GLN B  44     -27.894   3.720  70.433  1.00 29.89           N
ATOM   2707  CA   GLN B  44     -27.727   3.468  71.863  1.00 30.15           C
ATOM   2708  C    GLN B  44     -28.342   2.124  72.235  1.00 29.46           C
ATOM   2709  O    GLN B  44     -29.343   1.717  71.667  1.00 30.04           O
ATOM   2710  CB   GLN B  44     -28.443   4.560  72.669  1.00 33.21           C
ATOM   2711  CG   GLN B  44     -27.941   5.964  72.435  1.00 34.82           C
ATOM   2712  CD   GLN B  44     -26.486   6.099  72.760  1.00 36.85           C
ATOM   2713  OE1  GLN B  44     -26.018   5.610  73.794  1.00 40.88           O
ATOM   2714  NE2  GLN B  44     -25.745   6.773  71.887  1.00 39.11           N
ATOM   2715  N    PRO B  45     -27.758   1.428  73.221  1.00 30.36           N
ATOM   2716  CA   PRO B  45     -28.327   0.134  73.612  1.00 31.14           C
ATOM   2717  C    PRO B  45     -29.550   0.337  74.507  1.00 31.95           C
ATOM   2718  O    PRO B  45     -29.727   1.424  75.080  1.00 32.96           O
ATOM   2719  CB   PRO B  45     -27.186  -0.523  74.381  1.00 31.32           C
```

FIGURE 1-41 (COORDINATES)

```
ATOM   2720  CG  PRO B  45     -26.530   0.658  75.062  1.00 32.36           C
ATOM   2721  CD  PRO B  45     -26.499   1.698  73.927  1.00 30.16           C
ATOM   2722  N   ALA B  46     -30.382  -0.699  74.591  1.00 32.20           N
ATOM   2723  CA  ALA B  46     -31.569  -0.737  75.453  1.00 32.81           C
ATOM   2724  C   ALA B  46     -31.128  -1.772  76.493  1.00 34.62           C
ATOM   2725  O   ALA B  46     -31.273  -2.985  76.288  1.00 34.64           O
ATOM   2726  CB  ALA B  46     -32.773  -1.229  74.686  1.00 33.13           C
ATOM   2727  N   ILE B  47     -30.576  -1.272  77.596  1.00 35.36           N
ATOM   2728  CA  ILE B  47     -30.024  -2.092  78.666  1.00 37.09           C
ATOM   2729  C   ILE B  47     -31.014  -2.999  79.398  1.00 37.80           C
ATOM   2730  O   ILE B  47     -32.116  -2.581  79.752  1.00 37.90           O
ATOM   2731  CB  ILE B  47     -29.243  -1.172  79.628  1.00 37.38           C
ATOM   2732  CG1 ILE B  47     -28.143  -0.470  78.826  1.00 37.51           C
ATOM   2733  CG2 ILE B  47     -28.615  -1.967  80.774  1.00 37.68           C
ATOM   2734  CD1 ILE B  47     -27.413   0.628  79.575  1.00 40.04           C
ATOM   2735  N   LEU B  48     -30.619  -4.260  79.590  1.00 37.74           N
ATOM   2736  CA  LEU B  48     -31.472  -5.247  80.259  1.00 37.85           C
ATOM   2737  C   LEU B  48     -31.395  -5.069  81.770  1.00 37.39           C
ATOM   2738  O   LEU B  48     -30.334  -4.755  82.306  1.00 36.69           O
ATOM   2739  CB  LEU B  48     -31.035  -6.688  79.915  1.00 37.14           C
ATOM   2740  CG  LEU B  48     -30.951  -7.166  78.460  1.00 37.01           C
ATOM   2741  CD1 LEU B  48     -30.727  -8.680  78.475  1.00 37.57           C
ATOM   2742  CD2 LEU B  48     -32.216  -6.844  77.683  1.00 37.16           C
ATOM   2743  N   ASN B  49     -32.520  -5.263  82.454  1.00 39.32           N
ATOM   2744  CA  ASN B  49     -32.531  -5.139  83.914  1.00 40.46           C
ATOM   2745  C   ASN B  49     -32.107  -6.469  84.549  1.00 41.38           C
ATOM   2746  O   ASN B  49     -31.959  -7.484  83.852  1.00 39.79           O
ATOM   2747  CB  ASN B  49     -33.923  -4.718  84.438  1.00 41.09           C
ATOM   2748  CG  ASN B  49     -35.027  -5.726  84.110  1.00 42.29           C
ATOM   2749  OD1 ASN B  49     -34.771  -6.909  83.903  1.00 41.71           O
ATOM   2750  ND2 ASN B  49     -36.280  -5.247  84.087  1.00 42.49           N
ATOM   2751  N   SER B  50     -31.911  -6.449  85.870  1.00 41.51           N
ATOM   2752  CA  SER B  50     -31.495  -7.630  86.627  1.00 41.23           C
ATOM   2753  C   SER B  50     -32.264  -8.888  86.261  1.00 40.78           C
ATOM   2754  O   SER B  50     -31.671  -9.948  86.044  1.00 41.63           O
ATOM   2755  CB  SER B  50     -31.655  -7.374  88.130  1.00 42.04           C
ATOM   2756  OG  SER B  50     -30.710  -6.424  88.588  1.00 43.65           O
ATOM   2757  N   SER B  51     -33.584  -8.777  86.196  1.00 39.99           N
ATOM   2758  CA  SER B  51     -34.427  -9.923  85.876  1.00 40.31           C
ATOM   2759  C   SER B  51     -34.186 -10.482  84.477  1.00 39.82           C
ATOM   2760  O   SER B  51     -34.155 -11.705  84.278  1.00 39.76           O
ATOM   2761  CB  SER B  51     -35.900  -9.538  86.024  1.00 41.55           C
ATOM   2762  OG  SER B  51     -36.757 -10.567  85.553  1.00 45.17           O
ATOM   2763  N   ALA B  52     -34.041  -9.584  83.507  1.00 37.70           N
ATOM   2764  CA  ALA B  52     -33.810 -10.007  82.130  1.00 36.98           C
ATOM   2765  C   ALA B  52     -32.433 -10.669  82.029  1.00 35.66           C
ATOM   2766  O   ALA B  52     -32.267 -11.652  81.318  1.00 35.72           O
ATOM   2767  CB  ALA B  52     -33.899  -8.808  81.193  1.00 36.00           C
ATOM   2768  N   LEU B  53     -31.451 -10.120  82.733  1.00 35.14           N
ATOM   2769  CA  LEU B  53     -30.113 -10.697  82.717  1.00 35.69           C
ATOM   2770  C   LEU B  53     -30.177 -12.132  83.250  1.00 36.77           C
ATOM   2771  O   LEU B  53     -29.531 -13.037  82.712  1.00 35.42           O
ATOM   2772  CB  LEU B  53     -29.159  -9.853  83.566  1.00 34.23           C
ATOM   2773  CG  LEU B  53     -28.893  -8.451  83.014  1.00 33.29           C
ATOM   2774  CD1 LEU B  53     -27.967  -7.660  83.935  1.00 33.86           C
ATOM   2775  CD2 LEU B  53     -28.245  -8.611  81.622  1.00 32.79           C
ATOM   2776  N   ARG B  54     -30.956 -12.343  84.312  1.00 37.17           N
ATOM   2777  CA  ARG B  54     -31.086 -13.678  84.864  1.00 36.81           C
ATOM   2778  C   ARG B  54     -31.683 -14.602  83.817  1.00 36.37           C
ATOM   2779  O   ARG B  54     -31.262 -15.753  83.675  1.00 36.67           O
ATOM   2780  CB  ARG B  54     -31.974 -13.674  86.116  1.00 38.92           C
ATOM   2781  CG  ARG B  54     -31.227 -13.347  87.389  1.00 41.44           C
ATOM   2782  CD  ARG B  54     -32.178 -13.277  88.592  1.00 44.20           C
ATOM   2783  NE  ARG B  54     -32.176 -11.942  89.183  1.00 45.65           N
ATOM   2784  CZ  ARG B  54     -33.256 -11.179  89.322  1.00 46.58           C
ATOM   2785  NH1 ARG B  54     -34.441 -11.615  88.914  1.00 47.71           N
ATOM   2786  NH2 ARG B  54     -33.146  -9.974  89.863  1.00 46.22           N
ATOM   2787  N   GLN B  55     -32.657 -14.098  83.071  1.00 34.70           N
```

FIGURE 1-42 (COORDINATES)

```
ATOM   2788  CA  GLN B  55     -33.294 -14.898  82.044  1.00 35.67           C
ATOM   2789  C   GLN B  55     -32.275 -15.319  80.974  1.00 35.24           C
ATOM   2790  O   GLN B  55     -32.285 -16.452  80.495  1.00 34.40           O
ATOM   2791  CB  GLN B  55     -34.415 -14.122  81.356  1.00 37.88           C
ATOM   2792  CG  GLN B  55     -35.256 -15.019  80.461  1.00 41.16           C
ATOM   2793  CD  GLN B  55     -36.102 -14.271  79.446  1.00 44.51           C
ATOM   2794  OE1 GLN B  55     -35.680 -14.058  78.299  1.00 45.84           O
ATOM   2795  NE2 GLN B  55     -37.313 -13.872  79.857  1.00 45.21           N
ATOM   2796  N   ILE B  56     -31.386 -14.404  80.615  1.00 34.30           N
ATOM   2797  CA  ILE B  56     -30.405 -14.735  79.590  1.00 34.51           C
ATOM   2798  C   ILE B  56     -29.392 -15.748  80.093  1.00 33.84           C
ATOM   2799  O   ILE B  56     -29.055 -16.705  79.381  1.00 33.74           O
ATOM   2800  CB  ILE B  56     -29.681 -13.475  79.082  1.00 34.25           C
ATOM   2801  CG1 ILE B  56     -30.704 -12.500  78.480  1.00 35.12           C
ATOM   2802  CG2 ILE B  56     -28.638 -13.859  78.048  1.00 34.06           C
ATOM   2803  CD1 ILE B  56     -31.788 -13.158  77.630  1.00 34.25           C
ATOM   2804  N   ALA B  57     -28.920 -15.549  81.321  1.00 33.41           N
ATOM   2805  CA  ALA B  57     -27.945 -16.454  81.916  1.00 33.18           C
ATOM   2806  C   ALA B  57     -28.501 -17.872  81.966  1.00 33.58           C
ATOM   2807  O   ALA B  57     -27.762 -18.844  81.771  1.00 31.89           O
ATOM   2808  CB  ALA B  57     -27.572 -15.981  83.328  1.00 32.72           C
ATOM   2809  N   GLU B  58     -29.803 -17.993  82.207  1.00 34.34           N
ATOM   2810  CA  GLU B  58     -30.451 -19.301  82.287  1.00 36.14           C
ATOM   2811  C   GLU B  58     -30.878 -19.817  80.923  1.00 34.94           C
ATOM   2812  O   GLU B  58     -31.181 -20.995  80.772  1.00 35.79           O
ATOM   2813  CB  GLU B  58     -31.716 -19.240  83.159  1.00 39.35           C
ATOM   2814  CG  GLU B  58     -31.563 -18.562  84.498  1.00 44.83           C
ATOM   2815  CD  GLU B  58     -30.321 -18.999  85.243  1.00 48.64           C
ATOM   2816  OE1 GLU B  58     -30.028 -20.225  85.273  1.00 52.67           O
ATOM   2817  OE2 GLU B  58     -29.639 -18.115  85.809  1.00 50.21           O
ATOM   2818  N   GLY B  59     -30.921 -18.935  79.931  1.00 32.77           N
ATOM   2819  CA  GLY B  59     -31.360 -19.353  78.616  1.00 30.99           C
ATOM   2820  C   GLY B  59     -30.306 -20.033  77.756  1.00 29.78           C
ATOM   2821  O   GLY B  59     -30.640 -20.676  76.760  1.00 30.31           O
ATOM   2822  N   THR B  60     -29.046 -19.904  78.140  1.00 29.48           N
ATOM   2823  CA  THR B  60     -27.981 -20.520  77.352  1.00 28.57           C
ATOM   2824  C   THR B  60     -27.417 -21.777  78.027  1.00 29.12           C
ATOM   2825  O   THR B  60     -27.245 -21.833  79.263  1.00 29.82           O
ATOM   2826  CB  THR B  60     -26.851 -19.490  77.045  1.00 27.76           C
ATOM   2827  OG1 THR B  60     -25.886 -20.099  76.174  1.00 27.12           O
ATOM   2828  CG2 THR B  60     -26.154 -19.010  78.306  1.00 26.47           C
ATOM   2829  N   SER B  61     -27.122 -22.782  77.210  1.00 26.79           N
ATOM   2830  CA  SER B  61     -26.606 -24.051  77.719  1.00 25.42           C
ATOM   2831  C   SER B  61     -25.252 -24.431  77.142  1.00 24.27           C
ATOM   2832  O   SER B  61     -25.167 -24.871  75.996  1.00 26.31           O
ATOM   2833  CB  SER B  61     -27.595 -25.172  77.414  1.00 26.22           C
ATOM   2834  OG  SER B  61     -27.014 -26.423  77.742  1.00 27.19           O
ATOM   2835  N   ILE B  62     -24.207 -24.287  77.943  1.00 23.45           N
ATOM   2836  CA  ILE B  62     -22.854 -24.607  77.487  1.00 23.96           C
ATOM   2837  C   ILE B  62     -22.698 -26.094  77.143  1.00 25.28           C
ATOM   2838  O   ILE B  62     -21.951 -26.455  76.228  1.00 23.81           O
ATOM   2839  CB  ILE B  62     -21.815 -24.159  78.534  1.00 22.63           C
ATOM   2840  CG1 ILE B  62     -20.397 -24.270  77.975  1.00 22.90           C
ATOM   2841  CG2 ILE B  62     -21.943 -25.005  79.834  1.00 24.44           C
ATOM   2842  CD1 ILE B  62     -20.126 -23.280  76.755  1.00 21.65           C
ATOM   2843  N   SER B  63     -23.399 -26.982  77.856  1.00 26.17           N
ATOM   2844  CA  SER B  63     -23.254 -28.403  77.542  1.00 26.01           C
ATOM   2845  C   SER B  63     -23.926 -28.734  76.209  1.00 24.41           C
ATOM   2846  O   SER B  63     -23.449 -29.588  75.452  1.00 25.02           O
ATOM   2847  CB  SER B  63     -23.858 -29.265  78.672  1.00 27.70           C
ATOM   2848  OG  SER B  63     -25.246 -29.013  78.773  1.00 30.87           O
ATOM   2849  N   GLU B  64     -25.032 -28.056  75.909  1.00 24.11           N
ATOM   2850  CA  GLU B  64     -25.755 -28.288  74.676  1.00 24.84           C
ATOM   2851  C   GLU B  64     -24.911 -27.730  73.518  1.00 23.19           C
ATOM   2852  O   GLU B  64     -24.850 -28.327  72.450  1.00 23.40           O
ATOM   2853  CB  GLU B  64     -27.104 -27.585  74.700  1.00 28.34           C
ATOM   2854  CG  GLU B  64     -28.145 -28.283  75.587  1.00 36.30           C
ATOM   2855  CD  GLU B  64     -28.392 -29.705  75.152  1.00 39.65           C
```

FIGURE 1-43 (COORDINATES)

```
ATOM   2856  OE1 GLU B  64     -29.187 -29.916  74.202  1.00 43.89           O
ATOM   2857  OE2 GLU B  64     -27.773 -30.628  75.744  1.00 43.91           O
ATOM   2858  N   MET B  65     -24.292 -26.584  73.740  1.00 22.32           N
ATOM   2859  CA  MET B  65     -23.443 -26.009  72.681  1.00 20.83           C
ATOM   2860  C   MET B  65     -22.275 -26.980  72.432  1.00 21.68           C
ATOM   2861  O   MET B  65     -21.903 -27.272  71.281  1.00 21.43           O
ATOM   2862  CB  MET B  65     -22.867 -24.649  73.104  1.00 21.83           C
ATOM   2863  CG  MET B  65     -21.964 -23.997  72.000  1.00 20.66           C
ATOM   2864  SD  MET B  65     -20.762 -22.864  72.649  1.00 22.55           S
ATOM   2865  CE  MET B  65     -19.442 -24.054  73.248  1.00 21.83           C
ATOM   2866  N   TRP B  66     -21.693 -27.473  73.522  1.00 21.37           N
ATOM   2867  CA  TRP B  66     -20.544 -28.368  73.407  1.00 21.74           C
ATOM   2868  C   TRP B  66     -20.855 -29.568  72.543  1.00 23.68           C
ATOM   2869  O   TRP B  66     -20.141 -29.909  71.585  1.00 21.13           O
ATOM   2870  CB  TRP B  66     -20.103 -28.846  74.807  1.00 20.25           C
ATOM   2871  CG  TRP B  66     -18.636 -29.032  74.932  1.00 20.62           C
ATOM   2872  CD1 TRP B  66     -17.900 -30.122  74.567  1.00 21.31           C
ATOM   2873  CD2 TRP B  66     -17.716 -28.069  75.427  1.00 21.83           C
ATOM   2874  NE1 TRP B  66     -16.575 -29.893  74.815  1.00 21.05           N
ATOM   2875  CE2 TRP B  66     -16.434 -28.633  75.344  1.00 21.43           C
ATOM   2876  CE3 TRP B  66     -17.858 -26.773  75.933  1.00 22.14           C
ATOM   2877  CZ2 TRP B  66     -15.276 -27.941  75.754  1.00 21.40           C
ATOM   2878  CZ3 TRP B  66     -16.716 -26.083  76.339  1.00 24.25           C
ATOM   2879  CH2 TRP B  66     -15.444 -26.668  76.247  1.00 22.41           C
ATOM   2880  N   GLN B  67     -21.951 -30.225  72.868  1.00 22.89           N
ATOM   2881  CA  GLN B  67     -22.312 -31.420  72.138  1.00 24.68           C
ATOM   2882  C   GLN B  67     -22.870 -31.233  70.735  1.00 22.68           C
ATOM   2883  O   GLN B  67     -22.496 -31.939  69.792  1.00 24.08           O
ATOM   2884  CB  GLN B  67     -23.339 -32.202  72.992  1.00 25.78           C
ATOM   2885  CG  GLN B  67     -24.053 -33.316  72.253  1.00 32.20           C
ATOM   2886  CD  GLN B  67     -25.074 -34.023  73.135  1.00 37.07           C
ATOM   2887  OE1 GLN B  67     -24.717 -34.627  74.148  1.00 38.95           O
ATOM   2888  NE2 GLN B  67     -26.355 -33.934  72.762  1.00 37.82           N
ATOM   2889  N   ASN B  68     -23.746 -30.247  70.589  1.00 22.49           N
ATOM   2890  CA  ASN B  68     -24.458 -30.063  69.343  1.00 22.06           C
ATOM   2891  C   ASN B  68     -23.863 -29.077  68.348  1.00 21.95           C
ATOM   2892  O   ASN B  68     -24.065 -29.236  67.144  1.00 22.44           O
ATOM   2893  CB  ASN B  68     -25.906 -29.653  69.638  1.00 23.70           C
ATOM   2894  CG  ASN B  68     -26.622 -30.646  70.556  1.00 27.39           C
ATOM   2895  OD1 ASN B  68     -26.438 -31.875  70.436  1.00 27.29           O
ATOM   2896  ND2 ASN B  68     -27.455 -30.121  71.461  1.00 27.35           N
ATOM   2897  N   ASP B  69     -23.153 -28.073  68.857  1.00 22.97           N
ATOM   2898  CA  ASP B  69     -22.555 -27.075  67.981  1.00 21.83           C
ATOM   2899  C   ASP B  69     -21.037 -27.147  67.862  1.00 20.35           C
ATOM   2900  O   ASP B  69     -20.508 -27.006  66.748  1.00 21.05           O
ATOM   2901  CB  ASP B  69     -22.960 -25.677  68.440  1.00 21.81           C
ATOM   2902  CG  ASP B  69     -24.408 -25.373  68.125  1.00 24.40           C
ATOM   2903  OD1 ASP B  69     -25.090 -24.826  69.009  1.00 30.68           O
ATOM   2904  OD2 ASP B  69     -24.842 -25.686  67.000  1.00 28.04           O
ATOM   2905  N   LEU B  70     -20.339 -27.394  68.971  1.00 19.30           N
ATOM   2906  CA  LEU B  70     -18.876 -27.430  68.962  1.00 17.56           C
ATOM   2907  C   LEU B  70     -18.231 -28.724  68.501  1.00 20.39           C
ATOM   2908  O   LEU B  70     -17.415 -28.729  67.606  1.00 18.73           O
ATOM   2909  CB  LEU B  70     -18.330 -27.092  70.342  1.00 18.93           C
ATOM   2910  CG  LEU B  70     -16.816 -27.235  70.529  1.00 18.55           C
ATOM   2911  CD1 LEU B  70     -16.097 -26.169  69.627  1.00 19.22           C
ATOM   2912  CD2 LEU B  70     -16.440 -27.014  72.007  1.00 20.12           C
ATOM   2913  N   GLN B  71     -18.597 -29.839  69.119  1.00 19.05           N
ATOM   2914  CA  GLN B  71     -17.939 -31.063  68.731  1.00 20.39           C
ATOM   2915  C   GLN B  71     -17.889 -31.422  67.222  1.00 19.65           C
ATOM   2916  O   GLN B  71     -16.842 -31.861  66.742  1.00 17.59           O
ATOM   2917  CB  GLN B  71     -18.487 -32.207  69.616  1.00 20.24           C
ATOM   2918  CG  GLN B  71     -17.894 -32.084  71.042  1.00 25.76           C
ATOM   2919  CD  GLN B  71     -18.295 -33.208  71.976  1.00 26.53           C
ATOM   2920  OE1 GLN B  71     -19.319 -33.857  71.763  1.00 29.28           O
ATOM   2921  NE2 GLN B  71     -17.503 -33.420  73.041  1.00 26.42           N
ATOM   2922  N   PRO B  72     -18.981 -31.219  66.460  1.00 18.63           N
ATOM   2923  CA  PRO B  72     -18.925 -31.558  65.031  1.00 18.03           C
```

FIGURE 1-44 (COORDINATES)

```
ATOM   2924  C   PRO B  72     -17.904 -30.717  64.253  1.00 17.07           C
ATOM   2925  O   PRO B  72     -17.507 -31.086  63.155  1.00 18.32           O
ATOM   2926  CB  PRO B  72     -20.340 -31.269  64.538  1.00 19.90           C
ATOM   2927  CG  PRO B  72     -21.195 -31.530  65.776  1.00 20.30           C
ATOM   2928  CD  PRO B  72     -20.363 -30.858  66.859  1.00 20.14           C
ATOM   2929  N   LEU B  73     -17.539 -29.574  64.817  1.00 17.85           N
ATOM   2930  CA  LEU B  73     -16.568 -28.671  64.160  1.00 17.28           C
ATOM   2931  C   LEU B  73     -15.123 -28.984  64.515  1.00 18.14           C
ATOM   2932  O   LEU B  73     -14.199 -28.459  63.877  1.00 17.00           O
ATOM   2933  CB  LEU B  73     -16.867 -27.195  64.537  1.00 18.34           C
ATOM   2934  CG  LEU B  73     -18.118 -26.605  63.866  1.00 17.60           C
ATOM   2935  CD1 LEU B  73     -18.333 -25.180  64.424  1.00 19.25           C
ATOM   2936  CD2 LEU B  73     -17.930 -26.601  62.321  1.00 19.26           C
ATOM   2937  N   LEU B  74     -14.894 -29.822  65.536  1.00 17.47           N
ATOM   2938  CA  LEU B  74     -13.508 -30.121  65.948  1.00 16.47           C
ATOM   2939  C   LEU B  74     -12.893 -31.190  65.048  1.00 17.43           C
ATOM   2940  O   LEU B  74     -12.525 -32.315  65.475  1.00 17.33           O
ATOM   2941  CB  LEU B  74     -13.481 -30.540  67.441  1.00 18.27           C
ATOM   2942  CG  LEU B  74     -13.885 -29.402  68.393  1.00 17.83           C
ATOM   2943  CD1 LEU B  74     -14.035 -29.931  69.807  1.00 19.89           C
ATOM   2944  CD2 LEU B  74     -12.821 -28.288  68.377  1.00 18.81           C
ATOM   2945  N   ILE B  75     -12.745 -30.807  63.790  1.00 15.94           N
ATOM   2946  CA  ILE B  75     -12.232 -31.675  62.734  1.00 15.96           C
ATOM   2947  C   ILE B  75     -11.311 -30.860  61.816  1.00 16.66           C
ATOM   2948  O   ILE B  75     -11.348 -29.631  61.831  1.00 16.69           O
ATOM   2949  CB  ILE B  75     -13.416 -32.236  61.857  1.00 16.67           C
ATOM   2950  CG1 ILE B  75     -14.237 -31.070  61.266  1.00 16.36           C
ATOM   2951  CG2 ILE B  75     -14.320 -33.147  62.697  1.00 18.27           C
ATOM   2952  CD1 ILE B  75     -15.247 -31.497  60.206  1.00 18.04           C
ATOM   2953  N   GLU B  76     -10.473 -31.552  61.052  1.00 16.24           N
ATOM   2954  CA  GLU B  76      -9.574 -30.902  60.088  1.00 16.24           C
ATOM   2955  C   GLU B  76     -10.496 -30.292  59.029  1.00 16.72           C
ATOM   2956  O   GLU B  76     -11.260 -30.998  58.349  1.00 16.11           O
ATOM   2957  CB  GLU B  76      -8.624 -31.943  59.458  1.00 17.58           C
ATOM   2958  CG  GLU B  76      -7.674 -31.352  58.410  1.00 21.35           C
ATOM   2959  CD  GLU B  76      -6.497 -32.278  58.096  1.00 26.97           C
ATOM   2960  OE1 GLU B  76      -6.665 -33.503  58.185  1.00 29.44           O
ATOM   2961  OE2 GLU B  76      -5.409 -31.786  57.737  1.00 27.86           O
ATOM   2962  N   ARG B  77     -10.410 -28.971  58.862  1.00 15.81           N
ATOM   2963  CA  ARG B  77     -11.318 -28.282  57.939  1.00 14.39           C
ATOM   2964  C   ARG B  77     -10.666 -27.107  57.182  1.00 15.24           C
ATOM   2965  O   ARG B  77     -11.254 -26.018  57.048  1.00 15.61           O
ATOM   2966  CB  ARG B  77     -12.574 -27.792  58.707  1.00 14.02           C
ATOM   2967  CG  ARG B  77     -12.280 -26.875  59.894  1.00 14.35           C
ATOM   2968  CD  ARG B  77     -13.473 -26.655  60.845  1.00 14.43           C
ATOM   2969  NE  ARG B  77     -13.101 -25.624  61.826  1.00 13.07           N
ATOM   2970  CZ  ARG B  77     -12.277 -25.825  62.854  1.00 14.51           C
ATOM   2971  NH1 ARG B  77     -11.732 -27.031  63.071  1.00 14.38           N
ATOM   2972  NH2 ARG B  77     -11.911 -24.796  63.632  1.00 13.61           N
ATOM   2973  N   TYR B  78      -9.498 -27.370  56.624  1.00 14.82           N
ATOM   2974  CA  TYR B  78      -8.842 -26.317  55.842  1.00 15.42           C
ATOM   2975  C   TYR B  78      -9.623 -26.165  54.523  1.00 15.90           C
ATOM   2976  O   TYR B  78     -10.354 -27.047  54.092  1.00 14.58           O
ATOM   2977  CB  TYR B  78      -7.363 -26.642  55.686  1.00 15.60           C
ATOM   2978  CG  TYR B  78      -7.095 -27.882  54.904  1.00 16.51           C
ATOM   2979  CD1 TYR B  78      -6.817 -29.103  55.538  1.00 19.18           C
ATOM   2980  CD2 TYR B  78      -7.112 -27.835  53.501  1.00 17.11           C
ATOM   2981  CE1 TYR B  78      -6.551 -30.244  54.774  1.00 22.12           C
ATOM   2982  CE2 TYR B  78      -6.862 -28.962  52.748  1.00 21.05           C
ATOM   2983  CZ  TYR B  78      -6.580 -30.159  53.382  1.00 24.34           C
ATOM   2984  OH  TYR B  78      -6.340 -31.261  52.576  1.00 28.40           O
ATOM   2985  N   PRO B  79      -9.483 -25.011  53.847  1.00 16.30           N
ATOM   2986  CA  PRO B  79     -10.225 -24.781  52.604  1.00 16.35           C
ATOM   2987  C   PRO B  79     -10.093 -25.855  51.545  1.00 17.37           C
ATOM   2988  O   PRO B  79      -8.979 -26.297  51.248  1.00 18.33           O
ATOM   2989  CB  PRO B  79      -9.703 -23.392  52.129  1.00 17.99           C
ATOM   2990  CG  PRO B  79      -9.178 -22.775  53.379  1.00 18.09           C
ATOM   2991  CD  PRO B  79      -8.497 -23.947  54.091  1.00 16.88           C
```

FIGURE 1-45 (COORDINATES)

```
ATOM   2992  N   GLY B  80     -11.244 -26.312  51.045  1.00 16.95           N
ATOM   2993  CA  GLY B  80     -11.285 -27.330  49.995  1.00 17.62           C
ATOM   2994  C   GLY B  80     -11.275 -28.763  50.517  1.00 18.33           C
ATOM   2995  O   GLY B  80     -11.464 -29.713  49.743  1.00 17.94           O
ATOM   2996  N   SER B  81     -11.043 -28.932  51.815  1.00 17.88           N
ATOM   2997  CA  SER B  81     -11.022 -30.304  52.407  1.00 16.49           C
ATOM   2998  C   SER B  81     -12.448 -30.782  52.663  1.00 16.64           C
ATOM   2999  O   SER B  81     -13.399 -29.997  52.724  1.00 14.94           O
ATOM   3000  CB  SER B  81     -10.269 -30.287  53.749  1.00 16.79           C
ATOM   3001  OG  SER B  81     -11.058 -29.594  54.721  1.00 15.88           O
ATOM   3002  N   PRO B  82     -12.632 -32.115  52.836  1.00 15.87           N
ATOM   3003  CA  PRO B  82     -13.971 -32.614  53.104  1.00 15.34           C
ATOM   3004  C   PRO B  82     -14.490 -32.013  54.421  1.00 15.11           C
ATOM   3005  O   PRO B  82     -15.692 -31.787  54.558  1.00 17.05           O
ATOM   3006  CB  PRO B  82     -13.771 -34.153  53.188  1.00 16.49           C
ATOM   3007  CG  PRO B  82     -12.628 -34.385  52.242  1.00 12.59           C
ATOM   3008  CD  PRO B  82     -11.678 -33.207  52.595  1.00 14.41           C
ATOM   3009  N   GLY B  83     -13.587 -31.727  55.368  1.00 14.56           N
ATOM   3010  CA  GLY B  83     -13.962 -31.164  56.657  1.00 14.72           C
ATOM   3011  C   GLY B  83     -14.552 -29.767  56.483  1.00 15.81           C
ATOM   3012  O   GLY B  83     -15.457 -29.332  57.228  1.00 16.12           O
ATOM   3013  N   SER B  84     -14.038 -29.053  55.493  1.00 16.71           N
ATOM   3014  CA  SER B  84     -14.591 -27.715  55.234  1.00 16.98           C
ATOM   3015  C   SER B  84     -16.068 -27.830  54.817  1.00 15.96           C
ATOM   3016  O   SER B  84     -16.921 -27.122  55.335  1.00 15.92           O
ATOM   3017  CB  SER B  84     -13.763 -27.020  54.134  1.00 19.63           C
ATOM   3018  OG  SER B  84     -14.353 -25.758  53.785  1.00 21.03           O
ATOM   3019  N   TYR B  85     -16.370 -28.719  53.879  1.00 16.46           N
ATOM   3020  CA  TYR B  85     -17.753 -28.900  53.437  1.00 18.24           C
ATOM   3021  C   TYR B  85     -18.622 -29.428  54.585  1.00 17.65           C
ATOM   3022  O   TYR B  85     -19.770 -29.011  54.744  1.00 17.39           O
ATOM   3023  CB  TYR B  85     -17.771 -29.858  52.264  1.00 19.89           C
ATOM   3024  CG  TYR B  85     -19.140 -30.098  51.720  1.00 24.55           C
ATOM   3025  CD1 TYR B  85     -19.914 -29.048  51.246  1.00 27.95           C
ATOM   3026  CD2 TYR B  85     -19.650 -31.374  51.651  1.00 25.28           C
ATOM   3027  CE1 TYR B  85     -21.172 -29.279  50.706  1.00 29.97           C
ATOM   3028  CE2 TYR B  85     -20.908 -31.622  51.111  1.00 29.91           C
ATOM   3029  CZ  TYR B  85     -21.658 -30.572  50.642  1.00 30.71           C
ATOM   3030  OH  TYR B  85     -22.900 -30.820  50.100  1.00 33.98           O
ATOM   3031  N   ALA B  86     -18.068 -30.347  55.386  1.00 16.98           N
ATOM   3032  CA  ALA B  86     -18.814 -30.891  56.542  1.00 16.72           C
ATOM   3033  C   ALA B  86     -19.142 -29.787  57.539  1.00 16.60           C
ATOM   3034  O   ALA B  86     -20.253 -29.722  58.082  1.00 17.96           O
ATOM   3035  CB  ALA B  86     -18.001 -31.991  57.271  1.00 18.13           C
ATOM   3036  N   ALA B  87     -18.167 -28.912  57.800  1.00 16.93           N
ATOM   3037  CA  ALA B  87     -18.380 -27.825  58.748  1.00 16.16           C
ATOM   3038  C   ALA B  87     -19.442 -26.871  58.206  1.00 16.36           C
ATOM   3039  O   ALA B  87     -20.294 -26.412  58.945  1.00 16.65           O
ATOM   3040  CB  ALA B  87     -17.078 -27.076  58.994  1.00 15.19           C
ATOM   3041  N   ARG B  88     -19.365 -26.566  56.919  1.00 17.47           N
ATOM   3042  CA  ARG B  88     -20.338 -25.669  56.289  1.00 19.43           C
ATOM   3043  C   ARG B  88     -21.742 -26.274  56.386  1.00 19.59           C
ATOM   3044  O   ARG B  88     -22.719 -25.582  56.746  1.00 20.70           O
ATOM   3045  CB  ARG B  88     -19.899 -25.434  54.838  1.00 20.63           C
ATOM   3046  CG  ARG B  88     -20.677 -24.398  54.078  1.00 25.38           C
ATOM   3047  CD  ARG B  88     -19.816 -23.893  52.909  1.00 24.57           C
ATOM   3048  NE  ARG B  88     -19.470 -24.928  51.928  1.00 23.27           N
ATOM   3049  CZ  ARG B  88     -18.248 -25.428  51.742  1.00 23.93           C
ATOM   3050  NH1 ARG B  88     -17.210 -25.023  52.484  1.00 21.89           N
ATOM   3051  NH2 ARG B  88     -18.028 -26.274  50.731  1.00 25.41           N
ATOM   3052  N   GLN B  89     -21.864 -27.565  56.087  1.00 19.77           N
ATOM   3053  CA  GLN B  89     -23.172 -28.227  56.184  1.00 21.59           C
ATOM   3054  C   GLN B  89     -23.698 -28.165  57.628  1.00 20.55           C
ATOM   3055  O   GLN B  89     -24.891 -27.909  57.865  1.00 21.92           O
ATOM   3056  CB  GLN B  89     -23.073 -29.694  55.770  1.00 21.59           C
ATOM   3057  CG  GLN B  89     -22.813 -29.949  54.310  1.00 27.57           C
ATOM   3058  CD  GLN B  89     -22.922 -31.436  53.991  1.00 32.79           C
ATOM   3059  OE1 GLN B  89     -22.120 -32.243  54.477  1.00 34.07           O
```

FIGURE 1-46 (COORDINATES)

```
ATOM   3060  NE2 GLN B  89    -23.931 -31.811  53.195  1.00 33.55      N
ATOM   3061  N   HIS B  90    -22.818 -28.427  58.594  1.00 19.50      N
ATOM   3062  CA  HIS B  90    -23.191 -28.382  60.020  1.00 19.24      C
ATOM   3063  C   HIS B  90    -23.716 -27.001  60.403  1.00 19.49      C
ATOM   3064  O   HIS B  90    -24.781 -26.867  61.014  1.00 21.03      O
ATOM   3065  CB  HIS B  90    -21.961 -28.704  60.897  1.00 19.34      C
ATOM   3066  CG  HIS B  90    -22.168 -28.477  62.354  1.00 20.07      C
ATOM   3067  ND1 HIS B  90    -21.457 -27.541  63.076  1.00 21.23      N
ATOM   3068  CD2 HIS B  90    -22.987 -29.094  63.241  1.00 18.84      C
ATOM   3069  CE1 HIS B  90    -21.821 -27.594  64.344  1.00 19.06      C
ATOM   3070  NE2 HIS B  90    -22.750 -28.527  64.470  1.00 22.51      N
ATOM   3071  N   ILE B  91    -22.959 -25.964  60.038  1.00 18.93      N
ATOM   3072  CA  ILE B  91    -23.354 -24.600  60.373  1.00 18.28      C
ATOM   3073  C   ILE B  91    -24.699 -24.279  59.718  1.00 19.51      C
ATOM   3074  O   ILE B  91    -25.600 -23.744  60.393  1.00 20.28      O
ATOM   3075  CB  ILE B  91    -22.230 -23.599  59.942  1.00 18.15      C
ATOM   3076  CG1 ILE B  91    -21.021 -23.788  60.875  1.00 18.11      C
ATOM   3077  CG2 ILE B  91    -22.743 -22.145  59.997  1.00 18.32      C
ATOM   3078  CD1 ILE B  91    -19.693 -23.151  60.333  1.00 18.92      C
ATOM   3079  N   MET B  92    -24.858 -24.636  58.448  1.00 19.61      N
ATOM   3080  CA  MET B  92    -26.127 -24.370  57.751  1.00 22.17      C
ATOM   3081  C   MET B  92    -27.298 -25.116  58.378  1.00 24.04      C
ATOM   3082  O   MET B  92    -28.374 -24.536  58.588  1.00 25.48      O
ATOM   3083  CB  MET B  92    -26.015 -24.715  56.268  1.00 23.86      C
ATOM   3084  CG  MET B  92    -25.033 -23.802  55.547  1.00 26.12      C
ATOM   3085  SD  MET B  92    -24.873 -24.289  53.845  1.00 30.49      S
ATOM   3086  CE  MET B  92    -26.475 -23.713  53.207  1.00 31.96      C
ATOM   3087  N   GLN B  93    -27.088 -26.374  58.734  1.00 23.91      N
ATOM   3088  CA  GLN B  93    -28.169 -27.161  59.334  1.00 25.10      C
ATOM   3089  C   GLN B  93    -28.554 -26.677  60.724  1.00 24.78      C
ATOM   3090  O   GLN B  93    -29.737 -26.670  61.065  1.00 25.74      O
ATOM   3091  CB  GLN B  93    -27.780 -28.651  59.371  1.00 27.65      C
ATOM   3092  CG  GLN B  93    -27.639 -29.257  57.975  1.00 31.68      C
ATOM   3093  CD  GLN B  93    -26.967 -30.630  57.952  1.00 33.83      C
ATOM   3094  OE1 GLN B  93    -26.498 -31.129  58.974  1.00 36.18      O
ATOM   3095  NE2 GLN B  93    -26.905 -31.233  56.769  1.00 37.09      N
ATOM   3096  N   ARG B  94    -27.586 -26.272  61.542  1.00 22.90      N
ATOM   3097  CA  ARG B  94    -27.927 -25.801  62.874  1.00 23.83      C
ATOM   3098  C   ARG B  94    -28.707 -24.489  62.805  1.00 24.86      C
ATOM   3099  O   ARG B  94    -29.552 -24.223  63.647  1.00 26.90      O
ATOM   3100  CB  ARG B  94    -26.671 -25.642  63.734  1.00 23.40      C
ATOM   3101  CG  ARG B  94    -25.999 -26.981  64.060  1.00 24.34      C
ATOM   3102  CD  ARG B  94    -26.879 -27.811  65.014  1.00 23.51      C
ATOM   3103  NE  ARG B  94    -26.925 -27.177  66.324  1.00 26.86      N
ATOM   3104  CZ  ARG B  94    -27.748 -27.520  67.315  1.00 27.24      C
ATOM   3105  NH1 ARG B  94    -28.624 -28.506  67.155  1.00 27.33      N
ATOM   3106  NH2 ARG B  94    -27.672 -26.886  68.467  1.00 26.07      N
ATOM   3107  N   ILE B  95    -28.445 -23.679  61.789  1.00 25.31      N
ATOM   3108  CA  ILE B  95    -29.170 -22.426  61.660  1.00 26.49      C
ATOM   3109  C   ILE B  95    -30.561 -22.678  61.056  1.00 27.41      C
ATOM   3110  O   ILE B  95    -31.550 -22.088  61.514  1.00 27.53      O
ATOM   3111  CB  ILE B  95    -28.368 -21.423  60.787  1.00 25.53      C
ATOM   3112  CG1 ILE B  95    -27.203 -20.866  61.609  1.00 25.28      C
ATOM   3113  CG2 ILE B  95    -29.277 -20.317  60.263  1.00 25.61      C
ATOM   3114  CD1 ILE B  95    -26.116 -20.204  60.798  1.00 27.67      C
ATOM   3115  N   GLN B  96    -30.642 -23.542  60.048  1.00 27.75      N
ATOM   3116  CA  GLN B  96    -31.922 -23.834  59.387  1.00 30.73      C
ATOM   3117  C   GLN B  96    -32.992 -24.451  60.292  1.00 31.47      C
ATOM   3118  O   GLN B  96    -34.191 -24.309  60.022  1.00 31.88      O
ATOM   3119  CB  GLN B  96    -31.713 -24.733  58.158  1.00 31.64      C
ATOM   3120  CG  GLN B  96    -30.963 -24.050  57.002  1.00 35.47      C
ATOM   3121  CD  GLN B  96    -30.566 -25.011  55.895  1.00 36.82      C
ATOM   3122  OE1 GLN B  96    -30.101 -26.121  56.157  1.00 40.10      O
ATOM   3123  NE2 GLN B  96    -30.739 -24.587  54.650  1.00 38.43      N
ATOM   3124  N   ARG B  97    -32.583 -25.118  61.363  1.00 30.03      N
ATOM   3125  CA  ARG B  97    -33.560 -25.734  62.264  1.00 31.02      C
ATOM   3126  C   ARG B  97    -34.170 -24.730  63.247  1.00 32.03      C
ATOM   3127  O   ARG B  97    -35.101 -25.070  63.983  1.00 32.32      O
```

FIGURE 1-47 (COORDINATES)

```
ATOM   3128  CB   ARG B  97     -32.918 -26.876  63.058  1.00 32.52           C
ATOM   3129  CG   ARG B  97     -31.807 -26.424  63.986  1.00 32.48           C
ATOM   3130  CD   ARG B  97     -31.225 -27.591  64.787  1.00 34.83           C
ATOM   3131  NE   ARG B  97     -32.188 -28.032  65.793  1.00 35.60           N
ATOM   3132  CZ   ARG B  97     -32.372 -27.464  66.987  1.00 38.10           C
ATOM   3133  NH1  ARG B  97     -31.648 -26.423  67.376  1.00 33.74           N
ATOM   3134  NH2  ARG B  97     -33.339 -27.920  67.789  1.00 38.54           N
ATOM   3135  N    LEU B  98     -33.648 -23.504  63.276  1.00 29.89           N
ATOM   3136  CA   LEU B  98     -34.160 -22.496  64.186  1.00 29.63           C
ATOM   3137  C    LEU B  98     -35.451 -21.879  63.657  1.00 29.65           C
ATOM   3138  O    LEU B  98     -35.768 -21.997  62.465  1.00 30.25           O
ATOM   3139  CB   LEU B  98     -33.096 -21.412  64.436  1.00 29.17           C
ATOM   3140  CG   LEU B  98     -31.822 -21.995  65.073  1.00 28.32           C
ATOM   3141  CD1  LEU B  98     -30.783 -20.904  65.267  1.00 28.48           C
ATOM   3142  CD2  LEU B  98     -32.165 -22.664  66.420  1.00 29.52           C
ATOM   3143  N    GLN B  99     -36.199 -21.224  64.543  1.00 30.32           N
ATOM   3144  CA   GLN B  99     -37.460 -20.619  64.139  1.00 31.24           C
ATOM   3145  C    GLN B  99     -37.302 -19.256  63.472  1.00 30.04           C
ATOM   3146  O    GLN B  99     -38.056 -18.913  62.555  1.00 30.01           O
ATOM   3147  CB   GLN B  99     -38.381 -20.492  65.355  1.00 34.11           C
ATOM   3148  CG   GLN B  99     -38.860 -21.810  65.913  1.00 38.64           C
ATOM   3149  CD   GLN B  99     -39.931 -21.587  66.950  1.00 43.45           C
ATOM   3150  OE1  GLN B  99     -39.724 -20.839  67.916  1.00 47.46           O
ATOM   3151  NE2  GLN B  99     -41.092 -22.218  66.760  1.00 46.44           N
ATOM   3152  N    ALA B 100     -36.329 -18.475  63.931  1.00 29.80           N
ATOM   3153  CA   ALA B 100     -36.116 -17.158  63.346  1.00 28.70           C
ATOM   3154  C    ALA B 100     -35.940 -17.301  61.826  1.00 29.30           C
ATOM   3155  O    ALA B 100     -35.544 -18.368  61.329  1.00 29.52           O
ATOM   3156  CB   ALA B 100     -34.922 -16.493  63.995  1.00 29.86           C
ATOM   3157  N    ASP B 101     -36.244 -16.228  61.093  1.00 29.06           N
ATOM   3158  CA   ASP B 101     -36.209 -16.245  59.632  1.00 29.43           C
ATOM   3159  C    ASP B 101     -34.826 -15.994  59.025  1.00 28.41           C
ATOM   3160  O    ASP B 101     -34.625 -15.051  58.246  1.00 27.51           O
ATOM   3161  CB   ASP B 101     -37.223 -15.207  59.114  1.00 32.48           C
ATOM   3162  CG   ASP B 101     -37.548 -15.365  57.639  1.00 35.44           C
ATOM   3163  OD1  ASP B 101     -37.423 -16.477  57.083  1.00 36.70           O
ATOM   3164  OD2  ASP B 101     -37.966 -14.352  57.022  1.00 38.24           O
ATOM   3165  N    TRP B 102     -33.868 -16.858  59.351  1.00 27.06           N
ATOM   3166  CA   TRP B 102     -32.516 -16.674  58.807  1.00 25.09           C
ATOM   3167  C    TRP B 102     -32.421 -16.951  57.314  1.00 25.76           C
ATOM   3168  O    TRP B 102     -32.995 -17.932  56.818  1.00 26.10           O
ATOM   3169  CB   TRP B 102     -31.532 -17.598  59.539  1.00 23.14           C
ATOM   3170  CG   TRP B 102     -31.302 -17.259  60.966  1.00 23.44           C
ATOM   3171  CD1  TRP B 102     -31.861 -17.871  62.062  1.00 21.49           C
ATOM   3172  CD2  TRP B 102     -30.376 -16.288  61.481  1.00 23.02           C
ATOM   3173  NE1  TRP B 102     -31.327 -17.345  63.210  1.00 23.53           N
ATOM   3174  CE2  TRP B 102     -30.417 -16.373  62.886  1.00 21.84           C
ATOM   3175  CE3  TRP B 102     -29.514 -15.355  60.885  1.00 23.19           C
ATOM   3176  CZ2  TRP B 102     -29.624 -15.562  63.711  1.00 21.33           C
ATOM   3177  CZ3  TRP B 102     -28.733 -14.554  61.686  1.00 22.51           C
ATOM   3178  CH2  TRP B 102     -28.786 -14.660  63.099  1.00 23.94           C
ATOM   3179  N    VAL B 103     -31.692 -16.099  56.590  1.00 25.19           N
ATOM   3180  CA   VAL B 103     -31.502 -16.308  55.155  1.00 25.94           C
ATOM   3181  C    VAL B 103     -30.033 -16.646  54.968  1.00 25.34           C
ATOM   3182  O    VAL B 103     -29.160 -15.851  55.315  1.00 25.42           O
ATOM   3183  CB   VAL B 103     -31.814 -15.060  54.331  1.00 27.54           C
ATOM   3184  CG1  VAL B 103     -31.572 -15.343  52.843  1.00 28.53           C
ATOM   3185  CG2  VAL B 103     -33.244 -14.626  54.578  1.00 28.31           C
ATOM   3186  N    LEU B 104     -29.773 -17.830  54.428  1.00 25.96           N
ATOM   3187  CA   LEU B 104     -28.412 -18.274  54.236  1.00 27.02           C
ATOM   3188  C    LEU B 104     -27.918 -18.063  52.831  1.00 27.77           C
ATOM   3189  O    LEU B 104     -28.589 -18.433  51.867  1.00 28.11           O
ATOM   3190  CB   LEU B 104     -28.292 -19.755  54.573  1.00 26.94           C
ATOM   3191  CG   LEU B 104     -28.341 -20.089  56.057  1.00 28.64           C
ATOM   3192  CD1  LEU B 104     -28.740 -21.543  56.247  1.00 31.95           C
ATOM   3193  CD2  LEU B 104     -26.981 -19.777  56.683  1.00 28.31           C
ATOM   3194  N    GLU B 105     -26.741 -17.455  52.727  1.00 27.48           N
ATOM   3195  CA   GLU B 105     -26.107 -17.244  51.434  1.00 27.35           C
```

FIGURE 1-48 (COORDINATES)

```
ATOM   3196  C   GLU B 105     -24.705 -17.863  51.515  1.00 25.95           C
ATOM   3197  O   GLU B 105     -23.959 -17.571  52.457  1.00 26.60           O
ATOM   3198  CB  GLU B 105     -25.938 -15.758  51.103  1.00 30.03           C
ATOM   3199  CG  GLU B 105     -25.086 -15.569  49.833  1.00 36.91           C
ATOM   3200  CD  GLU B 105     -24.836 -14.113  49.438  1.00 41.33           C
ATOM   3201  OE1 GLU B 105     -25.486 -13.196  50.012  1.00 43.75           O
ATOM   3202  OE2 GLU B 105     -23.981 -13.893  48.532  1.00 43.40           O
ATOM   3203  N   ILE B 106     -24.369 -18.727  50.561  1.00 24.14           N
ATOM   3204  CA  ILE B 106     -23.028 -19.314  50.508  1.00 24.18           C
ATOM   3205  C   ILE B 106     -22.315 -18.521  49.438  1.00 22.44           C
ATOM   3206  O   ILE B 106     -22.736 -18.517  48.285  1.00 23.18           O
ATOM   3207  CB  ILE B 106     -23.052 -20.794  50.132  1.00 24.90           C
ATOM   3208  CG1 ILE B 106     -23.845 -21.567  51.191  1.00 27.49           C
ATOM   3209  CG2 ILE B 106     -21.612 -21.336  50.063  1.00 23.90           C
ATOM   3210  CD1 ILE B 106     -23.444 -21.179  52.630  1.00 30.61           C
ATOM   3211  N   ASP B 107     -21.251 -17.829  49.841  1.00 21.25           N
ATOM   3212  CA  ASP B 107     -20.456 -16.962  48.977  1.00 19.67           C
ATOM   3213  C   ASP B 107     -19.186 -17.723  48.568  1.00 18.74           C
ATOM   3214  O   ASP B 107     -18.166 -17.676  49.244  1.00 18.70           O
ATOM   3215  CB  ASP B 107     -20.157 -15.688  49.758  1.00 20.41           C
ATOM   3216  CG  ASP B 107     -19.101 -14.834  49.119  1.00 21.83           C
ATOM   3217  OD1 ASP B 107     -19.058 -14.784  47.865  1.00 22.00           O
ATOM   3218  OD2 ASP B 107     -18.322 -14.206  49.867  1.00 19.58           O
ATOM   3219  N   THR B 108     -19.281 -18.393  47.427  1.00 17.59           N
ATOM   3220  CA  THR B 108     -18.223 -19.259  46.919  1.00 18.56           C
ATOM   3221  C   THR B 108     -17.427 -18.537  45.843  1.00 17.73           C
ATOM   3222  O   THR B 108     -17.999 -18.034  44.870  1.00 20.66           O
ATOM   3223  CB  THR B 108     -18.869 -20.515  46.364  1.00 18.48           C
ATOM   3224  OG1 THR B 108     -19.534 -21.190  47.449  1.00 19.80           O
ATOM   3225  CG2 THR B 108     -17.818 -21.432  45.668  1.00 17.89           C
ATOM   3226  N   PHE B 109     -16.118 -18.505  46.017  1.00 15.29           N
ATOM   3227  CA  PHE B 109     -15.251 -17.799  45.087  1.00 15.92           C
ATOM   3228  C   PHE B 109     -13.932 -18.521  44.877  1.00 16.75           C
ATOM   3229  O   PHE B 109     -13.534 -19.407  45.635  1.00 18.11           O
ATOM   3230  CB  PHE B 109     -14.997 -16.367  45.605  1.00 16.62           C
ATOM   3231  CG  PHE B 109     -14.231 -16.323  46.912  1.00 15.72           C
ATOM   3232  CD1 PHE B 109     -14.901 -16.498  48.141  1.00 16.04           C
ATOM   3233  CD2 PHE B 109     -12.841 -16.161  46.903  1.00 15.85           C
ATOM   3234  CE1 PHE B 109     -14.178 -16.515  49.353  1.00 15.83           C
ATOM   3235  CE2 PHE B 109     -12.098 -16.179  48.123  1.00 15.93           C
ATOM   3236  CZ  PHE B 109     -12.790 -16.360  49.357  1.00 16.09           C
ATOM   3237  N   LEU B 110     -13.227 -18.108  43.846  1.00 15.88           N
ATOM   3238  CA  LEU B 110     -11.980 -18.714  43.497  1.00 16.80           C
ATOM   3239  C   LEU B 110     -10.901 -17.679  43.747  1.00 19.33           C
ATOM   3240  O   LEU B 110     -11.082 -16.504  43.432  1.00 20.07           O
ATOM   3241  CB  LEU B 110     -12.047 -19.100  42.012  1.00 17.33           C
ATOM   3242  CG  LEU B 110     -11.007 -20.118  41.571  1.00 19.73           C
ATOM   3243  CD1 LEU B 110     -11.444 -21.523  42.043  1.00 19.65           C
ATOM   3244  CD2 LEU B 110     -10.890 -20.092  40.031  1.00 18.54           C
ATOM   3245  N   SER B 111      -9.776 -18.106  44.307  1.00 16.63           N
ATOM   3246  CA  SER B 111      -8.675 -17.211  44.557  1.00 18.64           C
ATOM   3247  C   SER B 111      -7.334 -17.894  44.357  1.00 19.71           C
ATOM   3248  O   SER B 111      -7.185 -19.087  44.557  1.00 18.76           O
ATOM   3249  CB  SER B 111      -8.718 -16.653  45.978  1.00 21.21           C
ATOM   3250  OG  SER B 111      -7.497 -15.940  46.226  1.00 27.95           O
ATOM   3251  N   GLN B 112      -6.343 -17.117  43.979  1.00 19.82           N
ATOM   3252  CA  GLN B 112      -5.007 -17.642  43.809  1.00 21.05           C
ATOM   3253  C   GLN B 112      -4.394 -17.883  45.203  1.00 20.70           C
ATOM   3254  O   GLN B 112      -4.564 -17.071  46.111  1.00 22.30           O
ATOM   3255  CB  GLN B 112      -4.191 -16.598  43.056  1.00 23.87           C
ATOM   3256  CG  GLN B 112      -2.713 -16.790  43.120  1.00 29.45           C
ATOM   3257  CD  GLN B 112      -2.236 -17.840  42.150  1.00 32.82           C
ATOM   3258  OE1 GLN B 112      -1.690 -17.520  41.060  1.00 34.07           O
ATOM   3259  NE2 GLN B 112      -2.460 -19.112  42.507  1.00 30.27           N
ATOM   3260  N   THR B 113      -3.664 -18.994  45.359  1.00 19.45           N
ATOM   3261  CA  THR B 113      -2.992 -19.310  46.627  1.00 18.97           C
ATOM   3262  C   THR B 113      -1.595 -19.799  46.270  1.00 18.32           C
ATOM   3263  O   THR B 113      -1.272 -19.959  45.083  1.00 18.67           O
```

FIGURE 1-49 (COORDINATES)

```
ATOM   3264  CB   THR B 113      -3.678 -20.487  47.382  1.00 16.31           C
ATOM   3265  OG1  THR B 113      -3.348 -21.717  46.728  1.00 17.54           O
ATOM   3266  CG2  THR B 113      -5.197 -20.314  47.401  1.00 16.45           C
ATOM   3267  N    PRO B 114      -0.749 -20.058  47.282  1.00 17.91           N
ATOM   3268  CA   PRO B 114       0.595 -20.535  46.975  1.00 19.45           C
ATOM   3269  C    PRO B 114       0.550 -21.904  46.321  1.00 18.80           C
ATOM   3270  O    PRO B 114       1.569 -22.389  45.838  1.00 19.66           O
ATOM   3271  CB   PRO B 114       1.267 -20.591  48.340  1.00 19.44           C
ATOM   3272  CG   PRO B 114       0.620 -19.456  49.094  1.00 23.64           C
ATOM   3273  CD   PRO B 114      -0.850 -19.627  48.702  1.00 19.46           C
ATOM   3274  N    TYR B 115      -0.634 -22.538  46.315  1.00 19.78           N
ATOM   3275  CA   TYR B 115      -0.771 -23.869  45.712  1.00 19.74           C
ATOM   3276  C    TYR B 115      -1.615 -23.860  44.448  1.00 22.44           C
ATOM   3277  O    TYR B 115      -2.032 -24.922  43.945  1.00 24.78           O
ATOM   3278  CB   TYR B 115      -1.373 -24.851  46.741  1.00 21.84           C
ATOM   3279  CG   TYR B 115      -0.498 -25.026  47.959  1.00 21.21           C
ATOM   3280  CD1  TYR B 115       0.842 -25.356  47.817  1.00 23.68           C
ATOM   3281  CD2  TYR B 115      -0.993 -24.809  49.261  1.00 23.46           C
ATOM   3282  CE1  TYR B 115       1.686 -25.453  48.923  1.00 27.02           C
ATOM   3283  CE2  TYR B 115      -0.141 -24.921  50.384  1.00 25.07           C
ATOM   3284  CZ   TYR B 115       1.197 -25.237  50.187  1.00 26.89           C
ATOM   3285  OH   TYR B 115       2.078 -25.297  51.252  1.00 31.06           O
ATOM   3286  N    GLY B 116      -1.848 -22.665  43.915  1.00 20.89           N
ATOM   3287  CA   GLY B 116      -2.659 -22.550  42.725  1.00 21.48           C
ATOM   3288  C    GLY B 116      -4.038 -22.031  43.088  1.00 20.94           C
ATOM   3289  O    GLY B 116      -4.316 -21.673  44.247  1.00 19.43           O
ATOM   3290  N    TYR B 117      -4.919 -21.985  42.101  1.00 21.32           N
ATOM   3291  CA   TYR B 117      -6.273 -21.512  42.369  1.00 20.91           C
ATOM   3292  C    TYR B 117      -7.031 -22.509  43.253  1.00 20.42           C
ATOM   3293  O    TYR B 117      -6.937 -23.718  43.069  1.00 21.43           O
ATOM   3294  CB   TYR B 117      -7.038 -21.300  41.051  1.00 23.78           C
ATOM   3295  CG   TYR B 117      -6.320 -20.425  40.009  1.00 27.37           C
ATOM   3296  CD1  TYR B 117      -5.460 -19.386  40.381  1.00 31.18           C
ATOM   3297  CD2  TYR B 117      -6.568 -20.598  38.648  1.00 28.89           C
ATOM   3298  CE1  TYR B 117      -4.870 -18.534  39.409  1.00 31.38           C
ATOM   3299  CE2  TYR B 117      -5.995 -19.750  37.686  1.00 31.64           C
ATOM   3300  CZ   TYR B 117      -5.152 -18.725  38.069  1.00 32.91           C
ATOM   3301  OH   TYR B 117      -4.615 -17.884  37.096  1.00 35.00           O
ATOM   3302  N    ARG B 118      -7.782 -21.985  44.213  1.00 17.11           N
ATOM   3303  CA   ARG B 118      -8.598 -22.794  45.095  1.00 18.61           C
ATOM   3304  C    ARG B 118      -9.949 -22.139  45.315  1.00 17.75           C
ATOM   3305  O    ARG B 118     -10.089 -20.907  45.208  1.00 17.86           O
ATOM   3306  CB   ARG B 118      -7.930 -22.978  46.465  1.00 19.83           C
ATOM   3307  CG   ARG B 118      -6.617 -23.734  46.386  1.00 23.57           C
ATOM   3308  CD   ARG B 118      -6.074 -24.044  47.765  1.00 29.32           C
ATOM   3309  NE   ARG B 118      -6.824 -25.097  48.472  1.00 33.78           N
ATOM   3310  CZ   ARG B 118      -6.586 -26.406  48.353  1.00 35.88           C
ATOM   3311  NH1  ARG B 118      -5.620 -26.808  47.541  1.00 36.47           N
ATOM   3312  NH2  ARG B 118      -7.281 -27.310  49.081  1.00 35.96           N
ATOM   3313  N    SER B 119     -10.935 -22.970  45.635  1.00 16.27           N
ATOM   3314  CA   SER B 119     -12.280 -22.501  45.930  1.00 16.72           C
ATOM   3315  C    SER B 119     -12.480 -22.352  47.434  1.00 17.20           C
ATOM   3316  O    SER B 119     -12.022 -23.196  48.243  1.00 17.88           O
ATOM   3317  CB   SER B 119     -13.313 -23.464  45.348  1.00 17.33           C
ATOM   3318  OG   SER B 119     -14.637 -23.059  45.684  1.00 18.21           O
ATOM   3319  N    PHE B 120     -13.191 -21.297  47.811  1.00 15.40           N
ATOM   3320  CA   PHE B 120     -13.458 -20.937  49.200  1.00 16.16           C
ATOM   3321  C    PHE B 120     -14.937 -20.629  49.313  1.00 17.95           C
ATOM   3322  O    PHE B 120     -15.552 -20.167  48.337  1.00 18.03           O
ATOM   3323  CB   PHE B 120     -12.694 -19.641  49.577  1.00 15.86           C
ATOM   3324  CG   PHE B 120     -11.202 -19.769  49.573  1.00 13.98           C
ATOM   3325  CD1  PHE B 120     -10.506 -20.017  50.752  1.00 14.55           C
ATOM   3326  CD2  PHE B 120     -10.467 -19.614  48.371  1.00 15.09           C
ATOM   3327  CE1  PHE B 120      -9.087 -20.105  50.746  1.00 13.75           C
ATOM   3328  CE2  PHE B 120      -9.090 -19.704  48.354  1.00 13.78           C
ATOM   3329  CZ   PHE B 120      -8.381 -19.949  49.543  1.00 14.67           C
ATOM   3330  N    SER B 121     -15.527 -20.837  50.489  1.00 16.08           N
ATOM   3331  CA   SER B 121     -16.946 -20.538  50.633  1.00 16.88           C
```

FIGURE 1-50 (COORDINATES)

```
ATOM   3332  C   SER B 121     -17.264 -19.823  51.937  1.00 17.05           C
ATOM   3333  O   SER B 121     -17.143 -20.444  53.012  1.00 17.22           O
ATOM   3334  CB  SER B 121     -17.791 -21.833  50.558  1.00 18.29           C
ATOM   3335  OG  SER B 121     -17.806 -22.377  49.245  1.00 19.33           O
ATOM   3336  N   ASN B 122     -17.625 -18.526  51.878  1.00 16.50           N
ATOM   3337  CA  ASN B 122     -18.017 -17.847  53.120  1.00 16.64           C
ATOM   3338  C   ASN B 122     -19.472 -18.214  53.371  1.00 17.72           C
ATOM   3339  O   ASN B 122     -20.229 -18.424  52.431  1.00 19.71           O
ATOM   3340  CB  ASN B 122     -17.953 -16.313  53.030  1.00 16.70           C
ATOM   3341  CG  ASN B 122     -16.547 -15.794  52.860  1.00 16.48           C
ATOM   3342  OD1 ASN B 122     -15.634 -16.204  53.581  1.00 16.67           O
ATOM   3343  ND2 ASN B 122     -16.357 -14.860  51.907  1.00 15.41           N
ATOM   3344  N   ILE B 123     -19.855 -18.292  54.650  1.00 16.24           N
ATOM   3345  CA  ILE B 123     -21.233 -18.571  55.020  1.00 17.37           C
ATOM   3346  C   ILE B 123     -21.809 -17.302  55.636  1.00 15.48           C
ATOM   3347  O   ILE B 123     -21.271 -16.789  56.606  1.00 18.10           O
ATOM   3348  CB  ILE B 123     -21.344 -19.686  56.085  1.00 16.67           C
ATOM   3349  CG1 ILE B 123     -20.635 -20.956  55.585  1.00 19.06           C
ATOM   3350  CG2 ILE B 123     -22.841 -19.974  56.332  1.00 18.67           C
ATOM   3351  CD1 ILE B 123     -20.350 -21.989  56.727  1.00 19.21           C
ATOM   3352  N   ILE B 124     -22.898 -16.791  55.062  1.00 18.53           N
ATOM   3353  CA  ILE B 124     -23.515 -15.579  55.598  1.00 19.13           C
ATOM   3354  C   ILE B 124     -24.946 -15.907  55.974  1.00 19.54           C
ATOM   3355  O   ILE B 124     -25.696 -16.436  55.166  1.00 21.99           O
ATOM   3356  CB  ILE B 124     -23.523 -14.433  54.568  1.00 19.62           C
ATOM   3357  CG1 ILE B 124     -22.088 -14.090  54.149  1.00 20.36           C
ATOM   3358  CG2 ILE B 124     -24.107 -13.191  55.192  1.00 20.39           C
ATOM   3359  CD1 ILE B 124     -21.715 -14.635  52.828  1.00 24.34           C
ATOM   3360  N   SER B 125     -25.318 -15.596  57.207  1.00 18.91           N
ATOM   3361  CA  SER B 125     -26.668 -15.914  57.694  1.00 20.55           C
ATOM   3362  C   SER B 125     -27.265 -14.583  58.103  1.00 21.35           C
ATOM   3363  O   SER B 125     -26.757 -13.918  58.998  1.00 22.96           O
ATOM   3364  CB  SER B 125     -26.550 -16.856  58.904  1.00 20.02           C
ATOM   3365  OG  SER B 125     -27.815 -17.385  59.225  1.00 23.42           O
ATOM   3366  N   THR B 126     -28.367 -14.202  57.480  1.00 22.14           N
ATOM   3367  CA  THR B 126     -28.902 -12.875  57.745  1.00 22.99           C
ATOM   3368  C   THR B 126     -30.367 -12.843  58.105  1.00 22.51           C
ATOM   3369  O   THR B 126     -31.158 -13.546  57.502  1.00 24.03           O
ATOM   3370  CB  THR B 126     -28.734 -11.991  56.467  1.00 23.60           C
ATOM   3371  OG1 THR B 126     -27.390 -12.106  55.980  1.00 22.53           O
ATOM   3372  CG2 THR B 126     -29.025 -10.509  56.771  1.00 24.07           C
ATOM   3373  N   LEU B 127     -30.701 -12.036  59.103  1.00 23.73           N
ATOM   3374  CA  LEU B 127     -32.103 -11.809  59.468  1.00 24.42           C
ATOM   3375  C   LEU B 127     -32.459 -10.497  58.756  1.00 24.30           C
ATOM   3376  O   LEU B 127     -31.691  -9.530  58.816  1.00 23.98           O
ATOM   3377  CB  LEU B 127     -32.272 -11.627  60.975  1.00 24.82           C
ATOM   3378  CG  LEU B 127     -32.111 -12.922  61.811  1.00 24.00           C
ATOM   3379  CD1 LEU B 127     -32.165 -12.612  63.337  1.00 23.63           C
ATOM   3380  CD2 LEU B 127     -33.229 -13.906  61.386  1.00 25.89           C
ATOM   3381  N   ASN B 128     -33.598 -10.483  58.076  1.00 25.20           N
ATOM   3382  CA  ASN B 128     -34.069  -9.282  57.344  1.00 27.72           C
ATOM   3383  C   ASN B 128     -32.978  -8.768  56.411  1.00 27.14           C
ATOM   3384  O   ASN B 128     -32.412  -7.699  56.622  1.00 27.34           O
ATOM   3385  CB  ASN B 128     -34.463  -8.180  58.327  1.00 27.71           C
ATOM   3386  CG  ASN B 128     -35.413  -8.674  59.402  1.00 31.14           C
ATOM   3387  OD1 ASN B 128     -36.651  -8.734  59.206  1.00 33.20           O
ATOM   3388  ND2 ASN B 128     -34.854  -9.051  60.538  1.00 27.70           N
ATOM   3389  N   PRO B 129     -32.688  -9.526  55.346  1.00 29.59           N
ATOM   3390  CA  PRO B 129     -31.652  -9.188  54.352  1.00 30.12           C
ATOM   3391  C   PRO B 129     -31.797  -7.775  53.793  1.00 31.36           C
ATOM   3392  O   PRO B 129     -30.819  -7.099  53.474  1.00 30.24           O
ATOM   3393  CB  PRO B 129     -31.870 -10.218  53.257  1.00 29.73           C
ATOM   3394  CG  PRO B 129     -32.569 -11.367  53.951  1.00 31.93           C
ATOM   3395  CD  PRO B 129     -33.485 -10.693  54.920  1.00 28.74           C
ATOM   3396  N   THR B 130     -33.050  -7.352  53.689  1.00 31.22           N
ATOM   3397  CA  THR B 130     -33.393  -6.057  53.131  1.00 34.62           C
ATOM   3398  C   THR B 130     -33.282  -4.928  54.154  1.00 34.40           C
ATOM   3399  O   THR B 130     -33.237  -3.749  53.778  1.00 34.83           O
```

FIGURE 1-51 (COORDINATES)

```
ATOM   3400  CB  THR B 130     -34.816  -6.169  52.513  1.00 35.72           C
ATOM   3401  OG1 THR B 130     -34.689  -6.560  51.137  1.00 40.70           O
ATOM   3402  CG2 THR B 130     -35.589  -4.924  52.665  1.00 39.18           C
ATOM   3403  N   ALA B 131     -33.215  -5.287  55.433  0.00 33.89           N
ATOM   3404  CA  ALA B 131     -33.080  -4.291  56.488  0.00 33.31           C
ATOM   3405  C   ALA B 131     -31.796  -3.507  56.227  0.00 32.83           C
ATOM   3406  O   ALA B 131     -30.728  -4.092  56.048  0.00 32.88           O
ATOM   3407  CB  ALA B 131     -33.020  -4.970  57.849  0.00 33.35           C
ATOM   3408  N   LYS B 132     -31.910  -2.184  56.204  1.00 32.51           N
ATOM   3409  CA  LYS B 132     -30.767  -1.307  55.939  1.00 30.97           C
ATOM   3410  C   LYS B 132     -29.510  -1.504  56.782  1.00 29.59           C
ATOM   3411  O   LYS B 132     -28.391  -1.464  56.256  1.00 27.11           O
ATOM   3412  CB  LYS B 132     -31.200   0.156  56.035  1.00 35.26           C
ATOM   3413  CG  LYS B 132     -32.034   0.588  54.830  1.00 36.81           C
ATOM   3414  CD  LYS B 132     -32.407   2.056  54.902  1.00 41.67           C
ATOM   3415  CE  LYS B 132     -33.692   2.242  55.658  1.00 42.28           C
ATOM   3416  NZ  LYS B 132     -34.811   1.759  54.803  1.00 45.24           N
ATOM   3417  N   ARG B 133     -29.691  -1.688  58.086  1.00 26.69           N
ATOM   3418  CA  ARG B 133     -28.558  -1.855  58.989  1.00 25.59           C
ATOM   3419  C   ARG B 133     -28.518  -3.220  59.659  1.00 24.79           C
ATOM   3420  O   ARG B 133     -29.567  -3.819  59.932  1.00 24.49           O
ATOM   3421  CB  ARG B 133     -28.611  -0.781  60.088  1.00 25.72           C
ATOM   3422  CG  ARG B 133     -28.505   0.641  59.561  1.00 26.97           C
ATOM   3423  CD  ARG B 133     -29.099   1.589  60.588  1.00 28.34           C
ATOM   3424  NE  ARG B 133     -28.368   1.514  61.839  1.00 26.93           N
ATOM   3425  CZ  ARG B 133     -28.903   1.797  63.017  1.00 28.95           C
ATOM   3426  NH1 ARG B 133     -30.176   2.175  63.079  1.00 30.10           N
ATOM   3427  NH2 ARG B 133     -28.171   1.690  64.117  1.00 27.57           N
ATOM   3428  N   HIS B 134     -27.303  -3.714  59.884  1.00 23.82           N
ATOM   3429  CA  HIS B 134     -27.139  -4.968  60.612  1.00 22.94           C
ATOM   3430  C   HIS B 134     -25.976  -4.892  61.561  1.00 22.89           C
ATOM   3431  O   HIS B 134     -24.950  -4.245  61.279  1.00 22.84           O
ATOM   3432  CB  HIS B 134     -26.899  -6.178  59.680  1.00 22.09           C
ATOM   3433  CG  HIS B 134     -28.094  -6.579  58.877  1.00 22.53           C
ATOM   3434  ND1 HIS B 134     -28.413  -5.978  57.677  1.00 23.67           N
ATOM   3435  CD2 HIS B 134     -29.056  -7.503  59.099  1.00 23.62           C
ATOM   3436  CE1 HIS B 134     -29.521  -6.515  57.196  1.00 24.37           C
ATOM   3437  NE2 HIS B 134     -29.932  -7.444  58.040  1.00 24.73           N
ATOM   3438  N   LEU B 135     -26.168  -5.506  62.734  1.00 21.42           N
ATOM   3439  CA  LEU B 135     -25.088  -5.667  63.688  1.00 20.53           C
ATOM   3440  C   LEU B 135     -24.505  -6.989  63.112  1.00 19.26           C
ATOM   3441  O   LEU B 135     -25.260  -7.892  62.770  1.00 18.78           O
ATOM   3442  CB  LEU B 135     -25.655  -5.926  65.087  1.00 21.19           C
ATOM   3443  CG  LEU B 135     -24.647  -6.498  66.081  1.00 21.42           C
ATOM   3444  CD1 LEU B 135     -23.524  -5.514  66.333  1.00 21.46           C
ATOM   3445  CD2 LEU B 135     -25.395  -6.854  67.375  1.00 21.83           C
ATOM   3446  N   VAL B 136     -23.198  -7.074  62.970  1.00 18.85           N
ATOM   3447  CA  VAL B 136     -22.588  -8.271  62.373  1.00 19.45           C
ATOM   3448  C   VAL B 136     -21.671  -8.973  63.361  1.00 17.84           C
ATOM   3449  O   VAL B 136     -20.793  -8.351  63.939  1.00 19.56           O
ATOM   3450  CB  VAL B 136     -21.750  -7.900  61.092  1.00 20.66           C
ATOM   3451  CG1 VAL B 136     -21.305  -9.188  60.352  1.00 19.84           C
ATOM   3452  CG2 VAL B 136     -22.580  -7.036  60.141  1.00 20.36           C
ATOM   3453  N   LEU B 137     -21.887 -10.284  63.551  1.00 19.71           N
ATOM   3454  CA  LEU B 137     -21.025 -11.087  64.418  1.00 18.07           C
ATOM   3455  C   LEU B 137     -20.336 -12.006  63.435  1.00 17.83           C
ATOM   3456  O   LEU B 137     -20.986 -12.514  62.528  1.00 17.35           O
ATOM   3457  CB  LEU B 137     -21.844 -11.952  65.376  1.00 21.16           C
ATOM   3458  CG  LEU B 137     -22.890 -11.264  66.227  1.00 25.99           C
ATOM   3459  CD1 LEU B 137     -23.290 -12.254  67.331  1.00 25.86           C
ATOM   3460  CD2 LEU B 137     -22.357  -9.966  66.822  1.00 23.49           C
ATOM   3461  N   ALA B 138     -19.043 -12.228  63.630  1.00 16.12           N
ATOM   3462  CA  ALA B 138     -18.297 -13.053  62.690  1.00 16.32           C
ATOM   3463  C   ALA B 138     -17.145 -13.800  63.339  1.00 15.40           C
ATOM   3464  O   ALA B 138     -16.716 -13.483  64.457  1.00 16.96           O
ATOM   3465  CB  ALA B 138     -17.729 -12.164  61.579  1.00 16.90           C
ATOM   3466  N   CYS B 139     -16.657 -14.793  62.604  1.00 15.29           N
ATOM   3467  CA  CYS B 139     -15.486 -15.584  62.995  1.00 14.61           C
```

FIGURE 1-52 (COORDINATES)

```
ATOM   3468  C   CYS B 139     -15.080 -16.323  61.731  1.00 15.84           C
ATOM   3469  O   CYS B 139     -15.747 -16.171  60.684  1.00 15.77           O
ATOM   3470  CB  CYS B 139     -15.790 -16.577  64.139  1.00 16.94           C
ATOM   3471  SG  CYS B 139     -16.768 -17.963  63.636  1.00 20.18           S
ATOM   3472  N   HIS B 140     -13.976 -17.077  61.788  1.00 13.56           N
ATOM   3473  CA  HIS B 140     -13.598 -17.857  60.617  1.00 13.88           C
ATOM   3474  C   HIS B 140     -13.864 -19.344  60.940  1.00 15.08           C
ATOM   3475  O   HIS B 140     -13.648 -19.764  62.084  1.00 15.71           O
ATOM   3476  CB  HIS B 140     -12.119 -17.635  60.219  1.00 13.84           C
ATOM   3477  CG  HIS B 140     -11.092 -18.266  61.127  1.00 14.40           C
ATOM   3478  ND1 HIS B 140     -10.519 -19.495  60.863  1.00 14.85           N
ATOM   3479  CD2 HIS B 140     -10.482 -17.805  62.247  1.00 15.30           C
ATOM   3480  CE1 HIS B 140      -9.603 -19.766  61.779  1.00 15.84           C
ATOM   3481  NE2 HIS B 140      -9.558 -18.760  62.629  1.00 15.95           N
ATOM   3482  N   TYR B 141     -14.366 -20.100  59.964  1.00 14.78           N
ATOM   3483  CA  TYR B 141     -14.635 -21.525  60.214  1.00 14.28           C
ATOM   3484  C   TYR B 141     -13.605 -22.462  59.616  1.00 14.55           C
ATOM   3485  O   TYR B 141     -13.662 -23.688  59.873  1.00 14.19           O
ATOM   3486  CB  TYR B 141     -16.056 -21.929  59.776  1.00 14.51           C
ATOM   3487  CG  TYR B 141     -16.237 -22.136  58.296  1.00 13.91           C
ATOM   3488  CD1 TYR B 141     -16.495 -21.053  57.445  1.00 12.82           C
ATOM   3489  CD2 TYR B 141     -16.182 -23.419  57.732  1.00 13.92           C
ATOM   3490  CE1 TYR B 141     -16.710 -21.267  56.053  1.00 13.26           C
ATOM   3491  CE2 TYR B 141     -16.382 -23.635  56.365  1.00 15.32           C
ATOM   3492  CZ  TYR B 141     -16.644 -22.564  55.534  1.00 16.83           C
ATOM   3493  OH  TYR B 141     -16.841 -22.798  54.187  1.00 17.19           O
ATOM   3494  N   ASP B 142     -12.644 -21.952  58.831  1.00 13.27           N
ATOM   3495  CA  ASP B 142     -11.590 -22.834  58.333  1.00 13.85           C
ATOM   3496  C   ASP B 142     -10.608 -23.126  59.467  1.00 13.48           C
ATOM   3497  O   ASP B 142     -10.519 -22.365  60.436  1.00 14.29           O
ATOM   3498  CB  ASP B 142     -10.792 -22.186  57.162  1.00 13.88           C
ATOM   3499  CG  ASP B 142     -10.114 -20.869  57.544  1.00 16.45           C
ATOM   3500  OD1 ASP B 142     -10.814 -20.007  58.100  1.00 14.70           O
ATOM   3501  OD2 ASP B 142      -8.903 -20.699  57.271  1.00 15.54           O
ATOM   3502  N   SER B 143      -9.861 -24.220  59.341  1.00 13.36           N
ATOM   3503  CA  SER B 143      -8.784 -24.487  60.292  1.00 13.10           C
ATOM   3504  C   SER B 143      -7.506 -24.374  59.455  1.00 15.17           C
ATOM   3505  O   SER B 143      -7.491 -24.635  58.253  1.00 16.43           O
ATOM   3506  CB  SER B 143      -8.908 -25.888  60.953  1.00 13.99           C
ATOM   3507  OG  SER B 143      -8.838 -26.894  59.950  1.00 14.98           O
ATOM   3508  N   LYS B 144      -6.413 -23.980  60.099  1.00 15.93           N
ATOM   3509  CA  LYS B 144      -5.152 -23.804  59.385  1.00 15.73           C
ATOM   3510  C   LYS B 144      -4.627 -25.117  58.817  1.00 16.84           C
ATOM   3511  O   LYS B 144      -4.606 -26.135  59.510  1.00 16.23           O
ATOM   3512  CB  LYS B 144      -4.119 -23.182  60.341  1.00 15.94           C
ATOM   3513  CG  LYS B 144      -2.776 -22.821  59.660  1.00 17.05           C
ATOM   3514  CD  LYS B 144      -1.930 -21.914  60.574  1.00 18.16           C
ATOM   3515  CE  LYS B 144      -0.567 -21.692  59.936  1.00 18.95           C
ATOM   3516  NZ  LYS B 144      -0.703 -21.027  58.582  1.00 19.76           N
ATOM   3517  N   TYR B 145      -4.200 -25.088  57.556  1.00 15.67           N
ATOM   3518  CA  TYR B 145      -3.623 -26.248  56.905  1.00 17.93           C
ATOM   3519  C   TYR B 145      -2.259 -26.601  57.518  1.00 19.55           C
ATOM   3520  O   TYR B 145      -1.310 -25.787  57.503  1.00 19.25           O
ATOM   3521  CB  TYR B 145      -3.446 -25.958  55.412  1.00 19.20           C
ATOM   3522  CG  TYR B 145      -2.817 -27.092  54.640  1.00 21.66           C
ATOM   3523  CD1 TYR B 145      -1.644 -26.888  53.918  1.00 23.33           C
ATOM   3524  CD2 TYR B 145      -3.405 -28.343  54.612  1.00 23.29           C
ATOM   3525  CE1 TYR B 145      -1.069 -27.908  53.166  1.00 26.52           C
ATOM   3526  CE2 TYR B 145      -2.847 -29.372  53.873  1.00 25.51           C
ATOM   3527  CZ  TYR B 145      -1.678 -29.148  53.143  1.00 28.10           C
ATOM   3528  OH  TYR B 145      -1.130 -30.145  52.347  1.00 29.11           O
ATOM   3529  N   PHE B 146      -2.149 -27.806  58.077  1.00 19.56           N
ATOM   3530  CA  PHE B 146      -0.878 -28.268  58.659  1.00 18.17           C
ATOM   3531  C   PHE B 146      -0.671 -29.754  58.301  1.00 19.82           C
ATOM   3532  O   PHE B 146      -1.632 -30.489  58.066  1.00 19.05           O
ATOM   3533  CB  PHE B 146      -0.891 -28.203  60.191  1.00 17.98           C
ATOM   3534  CG  PHE B 146      -0.606 -26.824  60.786  1.00 20.76           C
ATOM   3535  CD1 PHE B 146       0.620 -26.191  60.582  1.00 23.48           C
```

FIGURE 1-53 (COORDINATES)

```
ATOM   3536  CD2 PHE B 146      -1.523  -26.233  61.631  1.00 19.57           C
ATOM   3537  CE1 PHE B 146       0.918  -24.967  61.250  1.00 25.22           C
ATOM   3538  CE2 PHE B 146      -1.266  -25.031  62.303  1.00 21.61           C
ATOM   3539  CZ  PHE B 146      -0.029  -24.392  62.113  1.00 24.38           C
ATOM   3540  N   SER B 147       0.579  -30.190  58.273  1.00 21.54           N
ATOM   3541  CA  SER B 147       0.841  -31.612  58.040  1.00 21.94           C
ATOM   3542  C   SER B 147       0.444  -32.241  59.369  1.00 21.10           C
ATOM   3543  O   SER B 147       0.233  -31.534  60.371  1.00 21.61           O
ATOM   3544  CB  SER B 147       2.329  -31.860  57.788  1.00 23.62           C
ATOM   3545  OG  SER B 147       3.027  -31.751  59.018  1.00 29.41           O
ATOM   3546  N   HIS B 148       0.328  -33.562  59.418  1.00 21.36           N
ATOM   3547  CA  HIS B 148      -0.058  -34.208  60.672  1.00 22.09           C
ATOM   3548  C   HIS B 148       1.126  -34.437  61.613  1.00 24.75           C
ATOM   3549  O   HIS B 148       1.546  -35.569  61.848  1.00 25.57           O
ATOM   3550  CB  HIS B 148      -0.752  -35.551  60.396  1.00 22.44           C
ATOM   3551  CG  HIS B 148      -2.005  -35.420  59.584  1.00 23.02           C
ATOM   3552  ND1 HIS B 148      -2.819  -34.307  59.638  1.00 26.02           N
ATOM   3553  CD2 HIS B 148      -2.605  -36.281  58.730  1.00 24.31           C
ATOM   3554  CE1 HIS B 148      -3.867  -34.486  58.853  1.00 20.32           C
ATOM   3555  NE2 HIS B 148      -3.764  -35.677  58.290  1.00 26.40           N
ATOM   3556  N   TRP B 149       1.632  -33.358  62.176  1.00 25.62           N
ATOM   3557  CA  TRP B 149       2.779  -33.423  63.068  1.00 27.92           C
ATOM   3558  C   TRP B 149       2.566  -34.402  64.241  1.00 27.79           C
ATOM   3559  O   TRP B 149       1.556  -34.342  64.952  1.00 27.07           O
ATOM   3560  CB  TRP B 149       3.054  -32.023  63.593  1.00 30.23           C
ATOM   3561  CG  TRP B 149       4.254  -31.937  64.433  1.00 34.65           C
ATOM   3562  CD1 TRP B 149       5.555  -31.956  64.013  1.00 35.44           C
ATOM   3563  CD2 TRP B 149       4.285  -31.774  65.853  1.00 36.30           C
ATOM   3564  NE1 TRP B 149       6.397  -31.804  65.093  1.00 38.68           N
ATOM   3565  CE2 TRP B 149       5.644  -31.692  66.234  1.00 36.33           C
ATOM   3566  CE3 TRP B 149       3.297  -31.685  66.844  1.00 37.43           C
ATOM   3567  CZ2 TRP B 149       6.041  -31.524  67.565  1.00 38.85           C
ATOM   3568  CZ3 TRP B 149       3.695  -31.518  68.176  1.00 39.09           C
ATOM   3569  CH2 TRP B 149       5.058  -31.439  68.520  1.00 37.23           C
ATOM   3570  N   ASN B 150       3.530  -35.301  64.450  1.00 28.25           N
ATOM   3571  CA  ASN B 150       3.433  -36.298  65.531  1.00 28.21           C
ATOM   3572  C   ASN B 150       2.152  -37.105  65.437  1.00 27.43           C
ATOM   3573  O   ASN B 150       1.611  -37.567  66.452  1.00 26.56           O
ATOM   3574  CB  ASN B 150       3.517  -35.628  66.900  1.00 31.85           C
ATOM   3575  CG  ASN B 150       4.911  -35.134  67.208  1.00 36.08           C
ATOM   3576  OD1 ASN B 150       5.878  -35.545  66.564  1.00 37.28           O
ATOM   3577  ND2 ASN B 150       5.026  -34.257  68.190  1.00 39.02           N
ATOM   3578  N   ASN B 151       1.682  -37.264  64.209  1.00 25.95           N
ATOM   3579  CA  ASN B 151       0.453  -37.997  63.910  1.00 26.11           C
ATOM   3580  C   ASN B 151      -0.778  -37.421  64.592  1.00 26.50           C
ATOM   3581  O   ASN B 151      -1.721  -38.127  64.935  1.00 26.88           O
ATOM   3582  CB  ASN B 151       0.639  -39.483  64.244  1.00 29.03           C
ATOM   3583  CG  ASN B 151       1.873  -40.049  63.578  1.00 30.68           C
ATOM   3584  OD1 ASN B 151       2.027  -39.954  62.359  1.00 30.82           O
ATOM   3585  ND2 ASN B 151       2.778  -40.610  64.378  1.00 33.10           N
ATOM   3586  N   ARG B 152      -0.765  -36.108  64.760  1.00 23.99           N
ATOM   3587  CA  ARG B 152      -1.888  -35.391  65.347  1.00 21.63           C
ATOM   3588  C   ARG B 152      -2.451  -34.524  64.233  1.00 20.32           C
ATOM   3589  O   ARG B 152      -1.781  -34.290  63.241  1.00 19.65           O
ATOM   3590  CB  ARG B 152      -1.410  -34.543  66.516  1.00 23.81           C
ATOM   3591  CG  ARG B 152      -0.911  -35.450  67.672  1.00 26.32           C
ATOM   3592  CD  ARG B 152      -0.252  -34.675  68.776  1.00 26.88           C
ATOM   3593  NE  ARG B 152      -1.211  -33.897  69.550  1.00 29.58           N
ATOM   3594  CZ  ARG B 152      -0.860  -32.985  70.455  1.00 29.17           C
ATOM   3595  NH1 ARG B 152       0.429  -32.752  70.695  1.00 30.25           N
ATOM   3596  NH2 ARG B 152      -1.793  -32.294  71.092  1.00 30.55           N
ATOM   3597  N   VAL B 153      -3.686  -34.078  64.398  1.00 19.06           N
ATOM   3598  CA  VAL B 153      -4.349  -33.256  63.394  1.00 19.24           C
ATOM   3599  C   VAL B 153      -4.739  -31.927  64.040  1.00 17.44           C
ATOM   3600  O   VAL B 153      -5.293  -31.896  65.132  1.00 17.01           O
ATOM   3601  CB  VAL B 153      -5.614  -33.980  62.895  1.00 21.91           C
ATOM   3602  CG1 VAL B 153      -6.400  -33.117  61.972  1.00 23.56           C
ATOM   3603  CG2 VAL B 153      -5.199  -35.290  62.205  1.00 21.96           C
```

FIGURE 1-54 (COORDINATES)

```
ATOM   3604  N   PHE B 154     -4.440 -30.824  63.352  1.00 16.61          N
ATOM   3605  CA  PHE B 154     -4.786 -29.511  63.880  1.00 16.47          C
ATOM   3606  C   PHE B 154     -6.259 -29.220  63.660  1.00 17.37          C
ATOM   3607  O   PHE B 154     -6.738 -29.225  62.504  1.00 17.52          O
ATOM   3608  CB  PHE B 154     -3.983 -28.417  63.169  1.00 16.10          C
ATOM   3609  CG  PHE B 154     -4.216 -27.057  63.753  1.00 16.40          C
ATOM   3610  CD1 PHE B 154     -3.641 -26.708  64.966  1.00 17.35          C
ATOM   3611  CD2 PHE B 154     -5.027 -26.144  63.085  1.00 16.19          C
ATOM   3612  CE1 PHE B 154     -3.868 -25.453  65.524  1.00 18.56          C
ATOM   3613  CE2 PHE B 154     -5.270 -24.897  63.620  1.00 13.77          C
ATOM   3614  CZ  PHE B 154     -4.699 -24.535  64.837  1.00 14.99          C
ATOM   3615  N   VAL B 155     -6.963 -28.930  64.754  1.00 16.40          N
ATOM   3616  CA  VAL B 155     -8.383 -28.652  64.656  1.00 16.51          C
ATOM   3617  C   VAL B 155     -8.746 -27.252  65.111  1.00 15.48          C
ATOM   3618  O   VAL B 155     -9.908 -26.896  65.088  1.00 16.58          O
ATOM   3619  CB  VAL B 155     -9.273 -29.714  65.431  1.00 16.98          C
ATOM   3620  CG1 VAL B 155     -9.060 -31.087  64.828  1.00 20.11          C
ATOM   3621  CG2 VAL B 155     -8.954 -29.739  66.922  1.00 19.12          C
ATOM   3622  N   GLY B 156     -7.757 -26.458  65.511  1.00 16.55          N
ATOM   3623  CA  GLY B 156     -8.063 -25.090  65.919  1.00 17.02          C
ATOM   3624  C   GLY B 156     -9.288 -24.949  66.803  1.00 16.88          C
ATOM   3625  O   GLY B 156    -10.286 -24.285  66.453  1.00 16.41          O
ATOM   3626  N   ALA B 157     -9.252 -25.558  67.986  1.00 15.74          N
ATOM   3627  CA  ALA B 157    -10.408 -25.460  68.864  1.00 15.32          C
ATOM   3628  C   ALA B 157    -10.748 -24.014  69.270  1.00 15.63          C
ATOM   3629  O   ALA B 157    -11.904 -23.618  69.204  1.00 16.50          O
ATOM   3630  CB  ALA B 157    -10.174 -26.333  70.130  1.00 16.45          C
ATOM   3631  N   THR B 158     -9.759 -23.218  69.679  1.00 16.29          N
ATOM   3632  CA  THR B 158    -10.073 -21.820  70.007  1.00 15.75          C
ATOM   3633  C   THR B 158    -10.010 -21.005  68.713  1.00 17.99          C
ATOM   3634  O   THR B 158    -10.496 -19.880  68.680  1.00 16.59          O
ATOM   3635  CB  THR B 158     -9.002 -21.131  70.895  1.00 16.45          C
ATOM   3636  OG1 THR B 158     -7.726 -21.174  70.249  1.00 17.29          O
ATOM   3637  CG2 THR B 158     -8.892 -21.824  72.271  1.00 16.18          C
ATOM   3638  N   ASP B 159     -9.447 -21.605  67.673  1.00 15.45          N
ATOM   3639  CA  ASP B 159     -9.125 -20.877  66.434  1.00 14.68          C
ATOM   3640  C   ASP B 159     -9.677 -21.540  65.165  1.00 14.91          C
ATOM   3641  O   ASP B 159     -8.919 -22.156  64.432  1.00 17.72          O
ATOM   3642  CB  ASP B 159     -7.580 -20.825  66.440  1.00 15.17          C
ATOM   3643  CG  ASP B 159     -6.960 -20.125  65.263  1.00 16.19          C
ATOM   3644  OD1 ASP B 159     -7.647 -19.399  64.517  1.00 16.71          O
ATOM   3645  OD2 ASP B 159     -5.724 -20.321  65.119  1.00 16.62          O
ATOM   3646  N   SER B 160    -10.979 -21.444  64.899  1.00 14.76          N
ATOM   3647  CA  SER B 160    -11.932 -20.730  65.734  1.00 14.85          C
ATOM   3648  C   SER B 160    -13.191 -21.557  65.894  1.00 15.83          C
ATOM   3649  O   SER B 160    -14.310 -21.082  65.720  1.00 14.84          O
ATOM   3650  CB  SER B 160    -12.258 -19.368  65.104  1.00 17.18          C
ATOM   3651  OG  SER B 160    -11.203 -18.468  65.440  1.00 18.00          O
ATOM   3652  N   ALA B 161    -13.018 -22.841  66.232  1.00 15.83          N
ATOM   3653  CA  ALA B 161    -14.202 -23.677  66.396  1.00 15.57          C
ATOM   3654  C   ALA B 161    -15.121 -23.139  67.493  1.00 15.88          C
ATOM   3655  O   ALA B 161    -16.329 -23.120  67.320  1.00 16.90          O
ATOM   3656  CB  ALA B 161    -13.774 -25.134  66.719  1.00 15.93          C
ATOM   3657  N   VAL B 162    -14.549 -22.732  68.615  1.00 16.00          N
ATOM   3658  CA  VAL B 162    -15.367 -22.211  69.700  1.00 16.92          C
ATOM   3659  C   VAL B 162    -16.141 -20.965  69.262  1.00 17.05          C
ATOM   3660  O   VAL B 162    -17.342 -20.893  69.472  1.00 17.68          O
ATOM   3661  CB  VAL B 162    -14.523 -21.977  70.975  1.00 17.33          C
ATOM   3662  CG1 VAL B 162    -15.303 -21.130  71.983  1.00 18.75          C
ATOM   3663  CG2 VAL B 162    -14.204 -23.360  71.596  1.00 19.23          C
ATOM   3664  N   PRO B 163    -15.464 -19.964  68.663  1.00 16.96          N
ATOM   3665  CA  PRO B 163    -16.223 -18.791  68.209  1.00 17.14          C
ATOM   3666  C   PRO B 163    -17.414 -19.228  67.309  1.00 16.72          C
ATOM   3667  O   PRO B 163    -18.538 -18.701  67.425  1.00 17.92          O
ATOM   3668  CB  PRO B 163    -15.176 -18.007  67.417  1.00 16.38          C
ATOM   3669  CG  PRO B 163    -13.946 -18.154  68.252  1.00 18.21          C
ATOM   3670  CD  PRO B 163    -14.015 -19.680  68.682  1.00 16.82          C
ATOM   3671  N   CYS B 164    -17.206 -20.211  66.418  1.00 16.79          N
```

FIGURE 1-55 (COORDINATES)

```
ATOM   3672  CA  CYS B 164     -18.292 -20.668  65.551  1.00 16.68           C
ATOM   3673  C   CYS B 164     -19.449 -21.183  66.388  1.00 18.93           C
ATOM   3674  O   CYS B 164     -20.607 -20.866  66.146  1.00 17.90           O
ATOM   3675  CB  CYS B 164     -17.855 -21.829  64.668  1.00 15.57           C
ATOM   3676  SG  CYS B 164     -16.756 -21.430  63.288  1.00 18.67           S
ATOM   3677  N   ALA B 165     -19.094 -22.020  67.353  1.00 17.04           N
ATOM   3678  CA  ALA B 165     -20.095 -22.628  68.250  1.00 18.60           C
ATOM   3679  C   ALA B 165     -20.805 -21.576  69.096  1.00 17.43           C
ATOM   3680  O   ALA B 165     -22.008 -21.717  69.361  1.00 18.01           O
ATOM   3681  CB  ALA B 165     -19.435 -23.712  69.160  1.00 18.53           C
ATOM   3682  N   MET B 166     -20.073 -20.551  69.515  1.00 17.17           N
ATOM   3683  CA  MET B 166     -20.666 -19.458  70.299  1.00 18.35           C
ATOM   3684  C   MET B 166     -21.704 -18.744  69.441  1.00 19.04           C
ATOM   3685  O   MET B 166     -22.799 -18.431  69.900  1.00 19.46           O
ATOM   3686  CB  MET B 166     -19.585 -18.475  70.746  1.00 18.70           C
ATOM   3687  CG  MET B 166     -18.603 -19.103  71.764  1.00 18.67           C
ATOM   3688  SD  MET B 166     -17.261 -18.029  72.206  1.00 20.85           S
ATOM   3689  CE  MET B 166     -18.201 -16.672  73.063  1.00 18.42           C
ATOM   3690  N   MET B 167     -21.370 -18.475  68.182  1.00 18.07           N
ATOM   3691  CA  MET B 167     -22.376 -17.832  67.323  1.00 17.91           C
ATOM   3692  C   MET B 167     -23.627 -18.688  67.129  1.00 19.52           C
ATOM   3693  O   MET B 167     -24.752 -18.197  67.183  1.00 20.35           O
ATOM   3694  CB  MET B 167     -21.740 -17.472  65.973  1.00 18.35           C
ATOM   3695  CG  MET B 167     -20.688 -16.429  66.204  1.00 18.98           C
ATOM   3696  SD  MET B 167     -19.552 -16.213  64.777  1.00 21.30           S
ATOM   3697  CE  MET B 167     -20.720 -15.877  63.479  1.00 19.07           C
ATOM   3698  N   LEU B 168     -23.436 -19.982  66.902  1.00 19.98           N
ATOM   3699  CA  LEU B 168     -24.558 -20.899  66.737  1.00 19.60           C
ATOM   3700  C   LEU B 168     -25.404 -20.987  68.025  1.00 19.76           C
ATOM   3701  O   LEU B 168     -26.626 -21.067  67.956  1.00 21.19           O
ATOM   3702  CB  LEU B 168     -24.037 -22.291  66.400  1.00 19.86           C
ATOM   3703  CG  LEU B 168     -23.423 -22.401  65.008  1.00 18.22           C
ATOM   3704  CD1 LEU B 168     -22.840 -23.804  64.842  1.00 20.08           C
ATOM   3705  CD2 LEU B 168     -24.500 -22.086  63.940  1.00 17.83           C
ATOM   3706  N   GLU B 169     -24.748 -21.011  69.179  1.00 21.38           N
ATOM   3707  CA  GLU B 169     -25.489 -21.096  70.445  1.00 22.10           C
ATOM   3708  C   GLU B 169     -26.229 -19.784  70.682  1.00 22.47           C
ATOM   3709  O   GLU B 169     -27.328 -19.787  71.243  1.00 22.66           O
ATOM   3710  CB  GLU B 169     -24.539 -21.432  71.588  1.00 23.29           C
ATOM   3711  CG  GLU B 169     -25.074 -21.208  73.018  1.00 25.65           C
ATOM   3712  CD  GLU B 169     -26.341 -21.996  73.364  1.00 25.77           C
ATOM   3713  OE1 GLU B 169     -26.703 -22.950  72.644  1.00 26.30           O
ATOM   3714  OE2 GLU B 169     -26.978 -21.624  74.388  1.00 28.00           O
ATOM   3715  N   LEU B 170     -25.658 -18.668  70.233  1.00 22.39           N
ATOM   3716  CA  LEU B 170     -26.333 -17.386  70.394  1.00 22.55           C
ATOM   3717  C   LEU B 170     -27.612 -17.409  69.563  1.00 24.40           C
ATOM   3718  O   LEU B 170     -28.682 -16.999  70.038  1.00 24.55           O
ATOM   3719  CB  LEU B 170     -25.432 -16.217  69.961  1.00 21.35           C
ATOM   3720  CG  LEU B 170     -26.093 -14.819  70.033  1.00 21.48           C
ATOM   3721  CD1 LEU B 170     -25.066 -13.787  70.456  1.00 21.84           C
ATOM   3722  CD2 LEU B 170     -26.741 -14.475  68.707  1.00 21.60           C
ATOM   3723  N   ALA B 171     -27.521 -17.867  68.318  1.00 22.21           N
ATOM   3724  CA  ALA B 171     -28.708 -17.942  67.474  1.00 23.01           C
ATOM   3725  C   ALA B 171     -29.764 -18.855  68.119  1.00 25.05           C
ATOM   3726  O   ALA B 171     -30.958 -18.569  68.079  1.00 26.02           O
ATOM   3727  CB  ALA B 171     -28.329 -18.473  66.068  1.00 22.79           C
ATOM   3728  N   ARG B 172     -29.316 -19.951  68.729  1.00 25.46           N
ATOM   3729  CA  ARG B 172     -30.259 -20.871  69.351  1.00 25.57           C
ATOM   3730  C   ARG B 172     -30.857 -20.285  70.630  1.00 25.70           C
ATOM   3731  O   ARG B 172     -32.099 -20.275  70.788  1.00 27.43           O
ATOM   3732  CB  ARG B 172     -29.569 -22.207  69.684  1.00 25.20           C
ATOM   3733  CG  ARG B 172     -30.539 -23.295  70.220  1.00 25.87           C
ATOM   3734  CD  ARG B 172     -29.827 -24.295  71.149  1.00 24.73           C
ATOM   3735  NE  ARG B 172     -29.347 -23.635  72.349  1.00 27.44           N
ATOM   3736  CZ  ARG B 172     -30.126 -23.283  73.371  1.00 31.00           C
ATOM   3737  NH1 ARG B 172     -31.427 -23.552  73.331  1.00 31.40           N
ATOM   3738  NH2 ARG B 172     -29.617 -22.632  74.411  1.00 32.00           N
ATOM   3739  N   ALA B 173     -30.005 -19.765  71.514  1.00 25.84           N
```

FIGURE 1-56 (COORDINATES)

```
ATOM   3740  CA  ALA B 173     -30.453 -19.235  72.812  1.00 25.96           C
ATOM   3741  C   ALA B 173     -31.407 -18.055  72.690  1.00 28.64           C
ATOM   3742  O   ALA B 173     -32.337 -17.902  73.496  1.00 29.03           O
ATOM   3743  CB  ALA B 173     -29.256 -18.836  73.656  1.00 27.03           C
ATOM   3744  N   LEU B 174     -31.175 -17.231  71.677  1.00 27.69           N
ATOM   3745  CA  LEU B 174     -31.982 -16.037  71.447  1.00 28.62           C
ATOM   3746  C   LEU B 174     -33.039 -16.191  70.361  1.00 27.79           C
ATOM   3747  O   LEU B 174     -33.670 -15.216  69.977  1.00 28.84           O
ATOM   3748  CB  LEU B 174     -31.050 -14.874  71.084  1.00 27.50           C
ATOM   3749  CG  LEU B 174     -29.895 -14.601  72.037  1.00 27.71           C
ATOM   3750  CD1 LEU B 174     -29.165 -13.319  71.618  1.00 27.77           C
ATOM   3751  CD2 LEU B 174     -30.415 -14.461  73.462  1.00 29.13           C
ATOM   3752  N   ASP B 175     -33.254 -17.416  69.891  1.00 27.63           N
ATOM   3753  CA  ASP B 175     -34.192 -17.681  68.810  1.00 28.64           C
ATOM   3754  C   ASP B 175     -35.583 -17.067  68.933  1.00 30.42           C
ATOM   3755  O   ASP B 175     -36.071 -16.435  67.999  1.00 30.94           O
ATOM   3756  CB  ASP B 175     -34.307 -19.189  68.595  1.00 28.57           C
ATOM   3757  CG  ASP B 175     -34.946 -19.535  67.287  1.00 29.16           C
ATOM   3758  OD1 ASP B 175     -34.727 -18.787  66.308  1.00 29.83           O
ATOM   3759  OD2 ASP B 175     -35.651 -20.564  67.205  1.00 30.34           O
ATOM   3760  N   LYS B 176     -36.237 -17.268  70.071  1.00 31.47           N
ATOM   3761  CA  LYS B 176     -37.571 -16.711  70.259  1.00 33.65           C
ATOM   3762  C   LYS B 176     -37.558 -15.192  70.129  1.00 33.65           C
ATOM   3763  O   LYS B 176     -38.444 -14.622  69.490  1.00 34.39           O
ATOM   3764  CB  LYS B 176     -38.116 -17.114  71.630  1.00 34.92           C
ATOM   3765  CG  LYS B 176     -39.562 -16.680  71.896  1.00 39.04           C
ATOM   3766  CD  LYS B 176     -40.024 -17.268  73.245  1.00 42.27           C
ATOM   3767  CE  LYS B 176     -41.282 -16.612  73.775  1.00 43.99           C
ATOM   3768  NZ  LYS B 176     -41.622 -17.151  75.135  1.00 46.06           N
ATOM   3769  N   LYS B 177     -36.570 -14.529  70.718  1.00 33.75           N
ATOM   3770  CA  LYS B 177     -36.488 -13.075  70.599  1.00 35.51           C
ATOM   3771  C   LYS B 177     -36.151 -12.626  69.166  1.00 35.88           C
ATOM   3772  O   LYS B 177     -36.697 -11.641  68.676  1.00 36.29           O
ATOM   3773  CB  LYS B 177     -35.463 -12.517  71.592  1.00 36.67           C
ATOM   3774  CG  LYS B 177     -35.984 -12.492  73.031  1.00 39.77           C
ATOM   3775  CD  LYS B 177     -34.878 -12.451  74.064  1.00 41.64           C
ATOM   3776  CE  LYS B 177     -35.441 -12.459  75.505  1.00 42.54           C
ATOM   3777  NZ  LYS B 177     -36.144 -11.164  75.846  1.00 45.45           N
ATOM   3778  N   LEU B 178     -35.272 -13.354  68.481  1.00 34.91           N
ATOM   3779  CA  LEU B 178     -34.902 -12.986  67.115  1.00 33.83           C
ATOM   3780  C   LEU B 178     -36.045 -13.222  66.131  1.00 35.09           C
ATOM   3781  O   LEU B 178     -36.152 -12.545  65.102  1.00 33.37           O
ATOM   3782  CB  LEU B 178     -33.660 -13.775  66.672  1.00 31.34           C
ATOM   3783  CG  LEU B 178     -32.426 -13.475  67.514  1.00 30.09           C
ATOM   3784  CD1 LEU B 178     -31.320 -14.488  67.181  1.00 28.48           C
ATOM   3785  CD2 LEU B 178     -31.951 -12.033  67.266  1.00 29.12           C
ATOM   3786  N   LEU B 179     -36.887 -14.203  66.439  1.00 35.28           N
ATOM   3787  CA  LEU B 179     -38.038 -14.504  65.597  1.00 36.51           C
ATOM   3788  C   LEU B 179     -38.944 -13.262  65.520  1.00 36.83           C
ATOM   3789  O   LEU B 179     -39.587 -13.030  64.506  1.00 36.09           O
ATOM   3790  CB  LEU B 179     -38.816 -15.689  66.175  1.00 37.01           C
ATOM   3791  CG  LEU B 179     -40.201 -15.988  65.585  1.00 38.27           C
ATOM   3792  CD1 LEU B 179     -40.089 -16.257  64.095  1.00 37.81           C
ATOM   3793  CD2 LEU B 179     -40.812 -17.181  66.306  1.00 38.51           C
ATOM   3794  N   SER B 180     -38.958 -12.455  66.579  1.00 37.30           N
ATOM   3795  CA  SER B 180     -39.786 -11.245  66.605  1.00 39.03           C
ATOM   3796  C   SER B 180     -39.342 -10.200  65.577  1.00 40.39           C
ATOM   3797  O   SER B 180     -40.055  -9.230  65.323  1.00 40.30           O
ATOM   3798  CB  SER B 180     -39.773 -10.612  68.004  1.00 38.32           C
ATOM   3799  OG  SER B 180     -38.698  -9.697  68.164  1.00 37.77           O
ATOM   3800  N   LEU B 181     -38.164 -10.400  64.989  1.00 40.98           N
ATOM   3801  CA  LEU B 181     -37.619  -9.479  63.994  1.00 41.64           C
ATOM   3802  C   LEU B 181     -38.237  -9.668  62.609  1.00 43.20           C
ATOM   3803  O   LEU B 181     -38.106  -8.803  61.739  1.00 42.69           O
ATOM   3804  CB  LEU B 181     -36.096  -9.655  63.900  1.00 40.33           C
ATOM   3805  CG  LEU B 181     -35.241  -9.076  65.031  1.00 39.04           C
ATOM   3806  CD1 LEU B 181     -33.831  -9.638  64.992  1.00 37.82           C
ATOM   3807  CD2 LEU B 181     -35.216  -7.558  64.910  1.00 40.06           C
```

FIGURE 1-57 (COORDINATES)

```
ATOM   3808  N   LYS B 182     -38.922 -10.788  62.410  1.00 44.20           N
ATOM   3809  CA  LYS B 182     -39.523 -11.087  61.119  1.00 46.85           C
ATOM   3810  C   LYS B 182     -40.537 -10.031  60.695  1.00 47.90           C
ATOM   3811  O   LYS B 182     -40.535  -9.652  59.501  1.00 49.58           O
ATOM   3812  CB  LYS B 182     -40.204 -12.453  61.141  1.00 46.71           C
ATOM   3813  CG  LYS B 182     -40.657 -12.892  59.756  1.00 48.70           C
ATOM   3814  CD  LYS B 182     -41.611 -14.068  59.795  1.00 49.41           C
ATOM   3815  CE  LYS B 182     -40.970 -15.301  60.387  1.00 51.27           C
ATOM   3816  NZ  LYS B 182     -41.912 -16.452  60.367  1.00 51.98           N
ATOM   3817  N   PRO B 189     -34.558   2.134  63.432  1.00 48.54           N
ATOM   3818  CA  PRO B 189     -34.798   0.777  63.974  1.00 47.44           C
ATOM   3819  C   PRO B 189     -34.881  -0.267  62.853  1.00 46.06           C
ATOM   3820  O   PRO B 189     -35.335  -1.387  63.080  1.00 46.46           O
ATOM   3821  CB  PRO B 189     -36.110   0.804  64.760  1.00 48.04           C
ATOM   3822  CG  PRO B 189     -36.427   2.323  64.832  1.00 49.32           C
ATOM   3823  CD  PRO B 189     -35.775   2.948  63.579  1.00 48.97           C
ATOM   3824  N   ASP B 190     -34.495   0.109  61.634  1.00 44.48           N
ATOM   3825  CA  ASP B 190     -34.483  -0.858  60.541  1.00 41.81           C
ATOM   3826  C   ASP B 190     -33.072  -1.431  60.706  1.00 39.46           C
ATOM   3827  O   ASP B 190     -32.162  -1.197  59.892  1.00 37.29           O
ATOM   3828  CB  ASP B 190     -34.637  -0.177  59.176  1.00 43.77           C
ATOM   3829  CG  ASP B 190     -34.826  -1.181  58.052  1.00 43.47           C
ATOM   3830  OD1 ASP B 190     -35.317  -2.301  58.343  1.00 46.52           O
ATOM   3831  OD2 ASP B 190     -34.504  -0.858  56.888  1.00 42.45           O
ATOM   3832  N   LEU B 191     -32.930  -2.160  61.809  1.00 36.02           N
ATOM   3833  CA  LEU B 191     -31.682  -2.775  62.232  1.00 32.82           C
ATOM   3834  C   LEU B 191     -31.911  -4.234  62.586  1.00 31.21           C
ATOM   3835  O   LEU B 191     -32.824  -4.556  63.340  1.00 31.33           O
ATOM   3836  CB  LEU B 191     -31.162  -2.039  63.471  1.00 33.36           C
ATOM   3837  CG  LEU B 191     -30.035  -2.696  64.274  1.00 31.42           C
ATOM   3838  CD1 LEU B 191     -28.774  -2.705  63.431  1.00 29.76           C
ATOM   3839  CD2 LEU B 191     -29.812  -1.932  65.585  1.00 32.15           C
ATOM   3840  N   SER B 192     -31.080  -5.122  62.054  1.00 28.72           N
ATOM   3841  CA  SER B 192     -31.237  -6.529  62.379  1.00 26.49           C
ATOM   3842  C   SER B 192     -29.867  -7.181  62.591  1.00 22.76           C
ATOM   3843  O   SER B 192     -28.877  -6.486  62.805  1.00 23.39           O
ATOM   3844  CB  SER B 192     -32.033  -7.236  61.302  1.00 26.11           C
ATOM   3845  OG  SER B 192     -32.476  -8.499  61.786  1.00 27.80           O
ATOM   3846  N   LEU B 193     -29.830  -8.507  62.536  1.00 22.98           N
ATOM   3847  CA  LEU B 193     -28.605  -9.255  62.810  1.00 21.80           C
ATOM   3848  C   LEU B 193     -28.111 -10.100  61.644  1.00 19.57           C
ATOM   3849  O   LEU B 193     -28.895 -10.652  60.875  1.00 21.03           O
ATOM   3850  CB  LEU B 193     -28.850 -10.160  64.037  1.00 21.33           C
ATOM   3851  CG  LEU B 193     -27.697 -10.997  64.610  1.00 21.62           C
ATOM   3852  CD1 LEU B 193     -26.654 -10.116  65.180  1.00 21.45           C
ATOM   3853  CD2 LEU B 193     -28.247 -11.937  65.700  1.00 21.90           C
ATOM   3854  N   GLN B 194     -26.786 -10.188  61.540  1.00 20.71           N
ATOM   3855  CA  GLN B 194     -26.132 -10.975  60.502  1.00 20.93           C
ATOM   3856  C   GLN B 194     -24.944 -11.698  61.093  1.00 19.08           C
ATOM   3857  O   GLN B 194     -24.195 -11.123  61.901  1.00 19.23           O
ATOM   3858  CB  GLN B 194     -25.626 -10.072  59.371  1.00 21.51           C
ATOM   3859  CG  GLN B 194     -24.955 -10.835  58.214  1.00 22.04           C
ATOM   3860  CD  GLN B 194     -24.678  -9.910  57.036  1.00 20.44           C
ATOM   3861  OE1 GLN B 194     -25.387  -9.928  56.023  1.00 27.04           O
ATOM   3862  NE2 GLN B 194     -23.664  -9.099  57.175  1.00 19.61           N
ATOM   3863  N   LEU B 195     -24.772 -12.965  60.706  1.00 18.81           N
ATOM   3864  CA  LEU B 195     -23.609 -13.735  61.143  1.00 18.92           C
ATOM   3865  C   LEU B 195     -22.795 -14.072  59.895  1.00 16.49           C
ATOM   3866  O   LEU B 195     -23.342 -14.445  58.862  1.00 20.12           O
ATOM   3867  CB  LEU B 195     -24.033 -15.061  61.780  1.00 19.09           C
ATOM   3868  CG  LEU B 195     -25.096 -15.006  62.872  1.00 20.92           C
ATOM   3869  CD1 LEU B 195     -25.475 -16.487  63.261  1.00 22.70           C
ATOM   3870  CD2 LEU B 195     -24.568 -14.206  64.060  1.00 21.64           C
ATOM   3871  N   ILE B 196     -21.485 -13.952  60.009  1.00 16.67           N
ATOM   3872  CA  ILE B 196     -20.623 -14.311  58.893  1.00 16.14           C
ATOM   3873  C   ILE B 196     -19.588 -15.305  59.413  1.00 15.11           C
ATOM   3874  O   ILE B 196     -18.953 -15.057  60.427  1.00 15.38           O
ATOM   3875  CB  ILE B 196     -19.826 -13.109  58.362  1.00 17.29           C
```

FIGURE 1-58 (COORDINATES)

```
ATOM   3876  CG1 ILE B 196     -20.802 -12.040  57.810  1.00 17.56           C
ATOM   3877  CG2 ILE B 196     -18.885 -13.581  57.249  1.00 17.20           C
ATOM   3878  CD1 ILE B 196     -20.126 -10.716  57.425  1.00 18.43           C
ATOM   3879  N   PHE B 197     -19.459 -16.428  58.724  1.00 16.52           N
ATOM   3880  CA  PHE B 197     -18.440 -17.413  59.072  1.00 15.11           C
ATOM   3881  C   PHE B 197     -17.520 -17.369  57.854  1.00 14.78           C
ATOM   3882  O   PHE B 197     -17.867 -17.895  56.793  1.00 13.98           O
ATOM   3883  CB  PHE B 197     -19.047 -18.810  59.203  1.00 15.82           C
ATOM   3884  CG  PHE B 197     -20.152 -18.920  60.234  1.00 17.06           C
ATOM   3885  CD1 PHE B 197     -19.894 -19.409  61.528  1.00 17.95           C
ATOM   3886  CD2 PHE B 197     -21.457 -18.547  59.905  1.00 16.64           C
ATOM   3887  CE1 PHE B 197     -20.940 -19.527  62.486  1.00 18.54           C
ATOM   3888  CE2 PHE B 197     -22.496 -18.658  60.852  1.00 17.40           C
ATOM   3889  CZ  PHE B 197     -22.231 -19.148  62.140  1.00 17.92           C
ATOM   3890  N   PHE B 198     -16.347 -16.760  58.019  1.00 15.47           N
ATOM   3891  CA  PHE B 198     -15.394 -16.624  56.908  1.00 15.01           C
ATOM   3892  C   PHE B 198     -14.620 -17.884  56.625  1.00 15.63           C
ATOM   3893  O   PHE B 198     -14.231 -18.607  57.549  1.00 15.24           O
ATOM   3894  CB  PHE B 198     -14.333 -15.560  57.227  1.00 15.59           C
ATOM   3895  CG  PHE B 198     -14.872 -14.150  57.332  1.00 15.72           C
ATOM   3896  CD1 PHE B 198     -15.310 -13.465  56.195  1.00 16.51           C
ATOM   3897  CD2 PHE B 198     -14.900 -13.510  58.571  1.00 14.85           C
ATOM   3898  CE1 PHE B 198     -15.775 -12.128  56.307  1.00 16.58           C
ATOM   3899  CE2 PHE B 198     -15.359 -12.177  58.696  1.00 15.94           C
ATOM   3900  CZ  PHE B 198     -15.796 -11.497  57.544  1.00 16.21           C
ATOM   3901  N   ASP B 199     -14.375 -18.136  55.349  1.00 13.90           N
ATOM   3902  CA  ASP B 199     -13.525 -19.271  54.977  1.00 14.35           C
ATOM   3903  C   ASP B 199     -12.131 -18.676  54.707  1.00 15.51           C
ATOM   3904  O   ASP B 199     -11.979 -17.448  54.511  1.00 14.82           O
ATOM   3905  CB  ASP B 199     -14.062 -19.940  53.694  1.00 14.00           C
ATOM   3906  CG  ASP B 199     -13.406 -21.307  53.420  1.00 14.43           C
ATOM   3907  OD1 ASP B 199     -12.537 -21.778  54.221  1.00 15.14           O
ATOM   3908  OD2 ASP B 199     -13.760 -21.887  52.384  1.00 14.55           O
ATOM   3909  N   GLY B 200     -11.092 -19.512  54.751  1.00 14.05           N
ATOM   3910  CA  GLY B 200      -9.773 -18.999  54.387  1.00 15.30           C
ATOM   3911  C   GLY B 200      -9.133 -17.865  55.170  1.00 15.89           C
ATOM   3912  O   GLY B 200      -8.341 -17.096  54.610  1.00 15.12           O
ATOM   3913  N   GLU B 201      -9.411 -17.765  56.452  1.00 13.11           N
ATOM   3914  CA  GLU B 201      -8.768 -16.719  57.225  1.00 13.87           C
ATOM   3915  C   GLU B 201      -7.289 -16.996  57.319  1.00 15.28           C
ATOM   3916  O   GLU B 201      -6.470 -16.082  57.235  1.00 15.86           O
ATOM   3917  CB  GLU B 201      -9.355 -16.668  58.621  1.00 13.93           C
ATOM   3918  CG  GLU B 201      -8.795 -15.529  59.515  1.00 18.01           C
ATOM   3919  CD  GLU B 201      -7.624 -15.907  60.436  1.00 23.69           C
ATOM   3920  OE1 GLU B 201      -7.141 -17.067  60.447  1.00 20.21           O
ATOM   3921  OE2 GLU B 201      -7.172 -14.996  61.189  1.00 26.59           O
ATOM   3922  N   GLU B 202      -6.935 -18.270  57.477  1.00 14.67           N
ATOM   3923  CA  GLU B 202      -5.545 -18.640  57.654  1.00 15.38           C
ATOM   3924  C   GLU B 202      -4.745 -18.682  56.368  1.00 15.42           C
ATOM   3925  O   GLU B 202      -5.271 -18.993  55.302  1.00 17.04           O
ATOM   3926  CB  GLU B 202      -5.449 -20.035  58.296  1.00 14.87           C
ATOM   3927  CG  GLU B 202      -6.201 -20.136  59.604  1.00 14.88           C
ATOM   3928  CD  GLU B 202      -5.405 -19.668  60.820  1.00 17.89           C
ATOM   3929  OE1 GLU B 202      -4.365 -18.965  60.682  1.00 18.09           O
ATOM   3930  OE2 GLU B 202      -5.833 -20.015  61.947  1.00 17.51           O
ATOM   3931  N   ALA B 203      -3.453 -18.398  56.493  1.00 16.78           N
ATOM   3932  CA  ALA B 203      -2.586 -18.517  55.326  1.00 18.07           C
ATOM   3933  C   ALA B 203      -2.424 -20.015  55.013  1.00 20.57           C
ATOM   3934  O   ALA B 203      -2.505 -20.857  55.917  1.00 19.65           O
ATOM   3935  CB  ALA B 203      -1.204 -17.932  55.668  1.00 19.82           C
ATOM   3936  N   PHE B 204      -2.207 -20.351  53.742  1.00 19.65           N
ATOM   3937  CA  PHE B 204      -1.947 -21.729  53.363  1.00 21.65           C
ATOM   3938  C   PHE B 204      -0.467 -22.068  53.596  1.00 25.52           C
ATOM   3939  O   PHE B 204      -0.147 -23.204  53.972  1.00 26.39           O
ATOM   3940  CB  PHE B 204      -2.276 -21.970  51.891  1.00 21.60           C
ATOM   3941  CG  PHE B 204      -3.584 -22.661  51.674  1.00 23.35           C
ATOM   3942  CD1 PHE B 204      -4.690 -21.969  51.191  1.00 25.72           C
ATOM   3943  CD2 PHE B 204      -3.721 -24.017  51.974  1.00 25.22           C
```

FIGURE 1-59 (COORDINATES)

```
ATOM   3944  CE1 PHE B 204      -5.914 -22.606  51.007  1.00 24.49           C
ATOM   3945  CE2 PHE B 204      -4.939 -24.666  51.793  1.00 23.93           C
ATOM   3946  CZ  PHE B 204      -6.042 -23.963  51.309  1.00 27.68           C
ATOM   3947  N   LEU B 205       0.424 -21.087  53.405  1.00 25.07           N
ATOM   3948  CA  LEU B 205       1.874 -21.305  53.547  1.00 25.87           C
ATOM   3949  C   LEU B 205       2.631 -20.320  54.441  1.00 28.57           C
ATOM   3950  O   LEU B 205       3.496 -20.724  55.246  1.00 30.79           O
ATOM   3951  CB  LEU B 205       2.502 -21.340  52.132  1.00 25.46           C
ATOM   3952  CG  LEU B 205       4.025 -21.512  51.966  1.00 24.98           C
ATOM   3953  CD1 LEU B 205       4.464 -22.787  52.645  1.00 26.25           C
ATOM   3954  CD2 LEU B 205       4.402 -21.540  50.484  1.00 24.32           C
ATOM   3955  N   HIS B 206       2.327 -19.035  54.334  1.00 26.72           N
ATOM   3956  CA  HIS B 206       3.001 -18.037  55.148  1.00 27.60           C
ATOM   3957  C   HIS B 206       2.165 -16.784  55.082  1.00 26.86           C
ATOM   3958  O   HIS B 206       1.883 -16.301  53.999  1.00 24.42           O
ATOM   3959  CB  HIS B 206       4.418 -17.733  54.621  1.00 29.38           C
ATOM   3960  CG  HIS B 206       5.510 -18.062  55.592  1.00 32.05           C
ATOM   3961  ND1 HIS B 206       6.458 -17.138  55.983  1.00 33.84           N
ATOM   3962  CD2 HIS B 206       5.857 -19.231  56.185  1.00 33.67           C
ATOM   3963  CE1 HIS B 206       7.346 -17.726  56.766  1.00 34.09           C
ATOM   3964  NE2 HIS B 206       7.006 -18.997  56.906  1.00 37.21           N
ATOM   3965  N   TRP B 207       1.787 -16.273  56.244  1.00 25.65           N
ATOM   3966  CA  TRP B 207       0.968 -15.085  56.362  1.00 27.01           C
ATOM   3967  C   TRP B 207       1.548 -13.887  55.623  1.00 28.72           C
ATOM   3968  O   TRP B 207       2.629 -13.381  55.953  1.00 28.77           O
ATOM   3969  CB  TRP B 207       0.771 -14.706  57.838  1.00 25.70           C
ATOM   3970  CG  TRP B 207      -0.344 -13.735  58.028  1.00 26.31           C
ATOM   3971  CD1 TRP B 207      -0.306 -12.366  57.827  1.00 27.02           C
ATOM   3972  CD2 TRP B 207      -1.693 -14.040  58.405  1.00 24.81           C
ATOM   3973  NE1 TRP B 207      -1.546 -11.820  58.061  1.00 27.47           N
ATOM   3974  CE2 TRP B 207      -2.412 -12.823  58.420  1.00 23.66           C
ATOM   3975  CE3 TRP B 207      -2.367 -15.225  58.730  1.00 23.63           C
ATOM   3976  CZ2 TRP B 207      -3.781 -12.756  58.757  1.00 26.16           C
ATOM   3977  CZ3 TRP B 207      -3.726 -15.154  59.069  1.00 23.07           C
ATOM   3978  CH2 TRP B 207      -4.416 -13.933  59.080  1.00 24.80           C
ATOM   3979  N   SER B 208       0.798 -13.413  54.646  1.00 26.95           N
ATOM   3980  CA  SER B 208       1.218 -12.276  53.851  1.00 29.48           C
ATOM   3981  C   SER B 208      -0.055 -11.739  53.213  1.00 30.10           C
ATOM   3982  O   SER B 208      -1.091 -12.391  53.267  1.00 27.39           O
ATOM   3983  CB  SER B 208       2.217 -12.741  52.796  1.00 31.48           C
ATOM   3984  OG  SER B 208       1.680 -13.784  52.012  1.00 32.89           O
ATOM   3985  N   PRO B 209       0.002 -10.545  52.602  1.00 29.95           N
ATOM   3986  CA  PRO B 209      -1.193  -9.976  51.978  1.00 28.40           C
ATOM   3987  C   PRO B 209      -1.915 -10.887  50.987  1.00 25.78           C
ATOM   3988  O   PRO B 209      -3.148 -10.875  50.939  1.00 25.72           O
ATOM   3989  CB  PRO B 209      -0.664  -8.695  51.327  1.00 29.55           C
ATOM   3990  CG  PRO B 209       0.461  -8.293  52.285  1.00 30.63           C
ATOM   3991  CD  PRO B 209       1.148  -9.614  52.487  1.00 30.77           C
ATOM   3992  N   GLN B 210      -1.171 -11.664  50.209  1.00 24.80           N
ATOM   3993  CA  GLN B 210      -1.816 -12.549  49.244  1.00 25.37           C
ATOM   3994  C   GLN B 210      -2.070 -13.975  49.728  1.00 23.67           C
ATOM   3995  O   GLN B 210      -2.674 -14.774  49.001  1.00 24.08           O
ATOM   3996  CB  GLN B 210      -1.031 -12.583  47.935  1.00 29.12           C
ATOM   3997  CG  GLN B 210      -0.924 -11.180  47.304  1.00 36.09           C
ATOM   3998  CD  GLN B 210      -2.285 -10.527  47.014  1.00 41.08           C
ATOM   3999  OE1 GLN B 210      -2.394  -9.295  47.012  1.00 45.03           O
ATOM   4000  NE2 GLN B 210      -3.320 -11.340  46.751  1.00 42.43           N
ATOM   4001  N   ASP B 211      -1.609 -14.298  50.939  1.00 21.70           N
ATOM   4002  CA  ASP B 211      -1.857 -15.643  51.478  1.00 20.06           C
ATOM   4003  C   ASP B 211      -2.340 -15.489  52.918  1.00 19.87           C
ATOM   4004  O   ASP B 211      -1.570 -15.584  53.843  1.00 21.61           O
ATOM   4005  CB  ASP B 211      -0.572 -16.484  51.431  1.00 20.07           C
ATOM   4006  CG  ASP B 211      -0.778 -17.899  51.946  1.00 22.77           C
ATOM   4007  OD1 ASP B 211       0.238 -18.527  52.320  1.00 21.53           O
ATOM   4008  OD2 ASP B 211      -1.943 -18.366  51.962  1.00 20.81           O
ATOM   4009  N   SER B 212      -3.626 -15.189  53.061  1.00 18.14           N
ATOM   4010  CA  SER B 212      -4.345 -14.997  54.317  1.00 18.59           C
ATOM   4011  C   SER B 212      -5.601 -14.207  53.995  1.00 16.10           C
```

FIGURE 1-60 (COORDINATES)

```
ATOM   4012  O    SER B 212      -5.716 -13.610  52.924  1.00 16.28           O
ATOM   4013  CB   SER B 212      -3.544 -14.202  55.375  1.00 18.04           C
ATOM   4014  OG   SER B 212      -3.229 -12.895  54.910  1.00 20.29           O
ATOM   4015  N    LEU B 213      -6.572 -14.262  54.909  1.00 15.76           N
ATOM   4016  CA   LEU B 213      -7.817 -13.495  54.806  1.00 14.88           C
ATOM   4017  C    LEU B 213      -8.496 -13.619  53.454  1.00 15.70           C
ATOM   4018  O    LEU B 213      -9.070 -12.654  52.919  1.00 15.93           O
ATOM   4019  CB   LEU B 213      -7.517 -12.000  55.123  1.00 15.35           C
ATOM   4020  CG   LEU B 213      -6.649 -11.781  56.368  1.00 15.24           C
ATOM   4021  CD1  LEU B 213      -6.555 -10.254  56.637  1.00 15.47           C
ATOM   4022  CD2  LEU B 213      -7.321 -12.418  57.616  1.00 14.27           C
ATOM   4023  N    TYR B 214      -8.469 -14.825  52.898  1.00 14.04           N
ATOM   4024  CA   TYR B 214      -9.076 -14.998  51.590  1.00 13.66           C
ATOM   4025  C    TYR B 214     -10.561 -14.638  51.562  1.00 14.75           C
ATOM   4026  O    TYR B 214     -11.036 -13.909  50.670  1.00 15.80           O
ATOM   4027  CB   TYR B 214      -8.902 -16.458  51.138  1.00 14.06           C
ATOM   4028  CG   TYR B 214      -7.469 -16.851  50.820  1.00 15.09           C
ATOM   4029  CD1  TYR B 214      -6.936 -16.614  49.542  1.00 15.77           C
ATOM   4030  CD2  TYR B 214      -6.653 -17.483  51.773  1.00 14.43           C
ATOM   4031  CE1  TYR B 214      -5.628 -17.009  49.207  1.00 16.08           C
ATOM   4032  CE2  TYR B 214      -5.334 -17.872  51.457  1.00 16.18           C
ATOM   4033  CZ   TYR B 214      -4.838 -17.642  50.176  1.00 18.08           C
ATOM   4034  OH   TYR B 214      -3.587 -18.133  49.856  1.00 19.32           O
ATOM   4035  N    GLY B 215     -11.310 -15.192  52.522  1.00 13.82           N
ATOM   4036  CA   GLY B 215     -12.737 -14.976  52.577  1.00 14.81           C
ATOM   4037  C    GLY B 215     -13.147 -13.559  52.902  1.00 15.50           C
ATOM   4038  O    GLY B 215     -14.080 -13.027  52.286  1.00 15.18           O
ATOM   4039  N    SER B 216     -12.454 -12.945  53.857  1.00 14.37           N
ATOM   4040  CA   SER B 216     -12.805 -11.571  54.267  1.00 16.29           C
ATOM   4041  C    SER B 216     -12.364 -10.530  53.224  1.00 17.55           C
ATOM   4042  O    SER B 216     -13.088  -9.568  52.977  1.00 18.04           O
ATOM   4043  CB   SER B 216     -12.218 -11.262  55.653  1.00 15.85           C
ATOM   4044  OG   SER B 216     -10.839 -11.569  55.726  1.00 16.02           O
ATOM   4045  N    ARG B 217     -11.210 -10.727  52.612  1.00 16.75           N
ATOM   4046  CA   ARG B 217     -10.814  -9.779  51.554  1.00 18.32           C
ATOM   4047  C    ARG B 217     -11.841  -9.832  50.416  1.00 18.81           C
ATOM   4048  O    ARG B 217     -12.269  -8.803  49.845  1.00 17.40           O
ATOM   4049  CB   ARG B 217      -9.421 -10.118  51.041  1.00 18.38           C
ATOM   4050  CG   ARG B 217      -8.338  -9.747  52.034  1.00 17.11           C
ATOM   4051  CD   ARG B 217      -6.900  -9.898  51.504  1.00 23.00           C
ATOM   4052  NE   ARG B 217      -6.476 -11.282  51.277  1.00 23.10           N
ATOM   4053  CZ   ARG B 217      -6.398 -11.890  50.094  1.00 27.13           C
ATOM   4054  NH1  ARG B 217      -6.726 -11.248  48.972  1.00 28.78           N
ATOM   4055  NH2  ARG B 217      -5.942 -13.142  50.022  1.00 26.01           N
ATOM   4056  N    HIS B 218     -12.254 -11.039  50.066  1.00 16.73           N
ATOM   4057  CA   HIS B 218     -13.228 -11.188  49.013  1.00 18.35           C
ATOM   4058  C    HIS B 218     -14.590 -10.587  49.403  1.00 17.88           C
ATOM   4059  O    HIS B 218     -15.190  -9.828  48.648  1.00 17.64           O
ATOM   4060  CB   HIS B 218     -13.423 -12.678  48.682  1.00 16.86           C
ATOM   4061  CG   HIS B 218     -14.602 -12.939  47.798  1.00 17.60           C
ATOM   4062  ND1  HIS B 218     -15.845 -13.277  48.276  1.00 20.29           N
ATOM   4063  CD2  HIS B 218     -14.726 -12.864  46.456  1.00 16.44           C
ATOM   4064  CE1  HIS B 218     -16.690 -13.403  47.270  1.00 17.82           C
ATOM   4065  NE2  HIS B 218     -16.036 -13.157  46.148  1.00 20.64           N
ATOM   4066  N    LEU B 219     -15.071 -10.907  50.608  1.00 16.81           N
ATOM   4067  CA   LEU B 219     -16.408 -10.481  50.993  1.00 17.13           C
ATOM   4068  C    LEU B 219     -16.508  -8.972  51.220  1.00 16.96           C
ATOM   4069  O    LEU B 219     -17.525  -8.367  50.897  1.00 19.11           O
ATOM   4070  CB   LEU B 219     -16.889 -11.265  52.238  1.00 18.72           C
ATOM   4071  CG   LEU B 219     -18.353 -10.950  52.636  1.00 16.65           C
ATOM   4072  CD1  LEU B 219     -19.292 -11.241  51.503  1.00 18.66           C
ATOM   4073  CD2  LEU B 219     -18.741 -11.778  53.894  1.00 20.17           C
ATOM   4074  N    ALA B 220     -15.467  -8.384  51.777  1.00 16.67           N
ATOM   4075  CA   ALA B 220     -15.460  -6.928  52.015  1.00 17.11           C
ATOM   4076  C    ALA B 220     -15.518  -6.231  50.637  1.00 18.96           C
ATOM   4077  O    ALA B 220     -16.280  -5.276  50.461  1.00 20.16           O
ATOM   4078  CB   ALA B 220     -14.185  -6.513  52.763  1.00 16.77           C
ATOM   4079  N    ALA B 221     -14.731  -6.709  49.669  1.00 18.79           N
```

FIGURE 1-61 (COORDINATES)

```
ATOM   4080  CA   ALA B 221     -14.770   -6.045   48.345  1.00 19.99           C
ATOM   4081  C    ALA B 221     -16.130   -6.249   47.699  1.00 22.15           C
ATOM   4082  O    ALA B 221     -16.658   -5.332   47.035  1.00 20.72           O
ATOM   4083  CB   ALA B 221     -13.677   -6.573   47.435  1.00 19.78           C
ATOM   4084  N    LYS B 222     -16.713   -7.440   47.861  1.00 21.48           N
ATOM   4085  CA   LYS B 222     -18.025   -7.711   47.301  1.00 22.06           C
ATOM   4086  C    LYS B 222     -19.120   -6.868   47.987  1.00 21.58           C
ATOM   4087  O    LYS B 222     -19.968   -6.279   47.308  1.00 23.53           O
ATOM   4088  CB   LYS B 222     -18.329   -9.210   47.407  1.00 23.39           C
ATOM   4089  CG   LYS B 222     -19.738   -9.630   47.046  1.00 26.64           C
ATOM   4090  CD   LYS B 222     -19.874  -11.166   47.177  1.00 32.33           C
ATOM   4091  CE   LYS B 222     -21.246  -11.649   46.714  1.00 35.29           C
ATOM   4092  NZ   LYS B 222     -22.333  -11.311   47.691  1.00 37.30           N
ATOM   4093  N    MET B 223     -19.110   -6.773   49.315  1.00 19.38           N
ATOM   4094  CA   MET B 223     -20.115   -5.944   49.971  1.00 19.35           C
ATOM   4095  C    MET B 223     -19.932   -4.444   49.636  1.00 21.08           C
ATOM   4096  O    MET B 223     -20.921   -3.712   49.552  1.00 19.76           O
ATOM   4097  CB   MET B 223     -20.048   -6.132   51.489  1.00 20.79           C
ATOM   4098  CG   MET B 223     -20.484   -7.537   51.895  1.00 18.89           C
ATOM   4099  SD   MET B 223     -20.351   -7.792   53.692  1.00 21.22           S
ATOM   4100  CE   MET B 223     -21.735   -6.813   54.332  1.00 21.76           C
ATOM   4101  N    ALA B 224     -18.693   -4.011   49.447  1.00 20.62           N
ATOM   4102  CA   ALA B 224     -18.410   -2.586   49.172  1.00 22.34           C
ATOM   4103  C    ALA B 224     -18.934   -2.165   47.814  1.00 24.09           C
ATOM   4104  O    ALA B 224     -19.129   -0.955   47.573  1.00 23.95           O
ATOM   4105  CB   ALA B 224     -16.942   -2.325   49.222  1.00 23.96           C
ATOM   4106  N    SER B 225     -19.170   -3.136   46.936  1.00 22.40           N
ATOM   4107  CA   SER B 225     -19.631   -2.801   45.590  1.00 23.68           C
ATOM   4108  C    SER B 225     -21.022   -3.329   45.312  1.00 22.37           C
ATOM   4109  O    SER B 225     -21.449   -3.389   44.168  1.00 24.08           O
ATOM   4110  CB   SER B 225     -18.616   -3.300   44.548  1.00 25.11           C
ATOM   4111  OG   SER B 225     -18.440   -4.706   44.642  1.00 26.53           O
ATOM   4112  N    THR B 226     -21.740   -3.725   46.363  1.00 21.11           N
ATOM   4113  CA   THR B 226     -23.085   -4.219   46.196  1.00 18.96           C
ATOM   4114  C    THR B 226     -24.066   -3.175   46.740  1.00 20.25           C
ATOM   4115  O    THR B 226     -24.028   -2.846   47.932  1.00 19.21           O
ATOM   4116  CB   THR B 226     -23.312   -5.532   46.958  1.00 21.44           C
ATOM   4117  OG1  THR B 226     -22.431   -6.536   46.424  1.00 22.81           O
ATOM   4118  CG2  THR B 226     -24.762   -6.011   46.791  1.00 20.34           C
ATOM   4119  N    PRO B 227     -24.945   -2.640   45.879  1.00 21.50           N
ATOM   4120  CA   PRO B 227     -25.909   -1.633   46.364  1.00 23.06           C
ATOM   4121  C    PRO B 227     -26.753   -2.130   47.528  1.00 24.27           C
ATOM   4122  O    PRO B 227     -27.211   -3.269   47.539  1.00 24.67           O
ATOM   4123  CB   PRO B 227     -26.786   -1.354   45.140  1.00 21.34           C
ATOM   4124  CG   PRO B 227     -25.838   -1.546   43.975  1.00 21.28           C
ATOM   4125  CD   PRO B 227     -25.041   -2.819   44.414  1.00 21.45           C
ATOM   4126  N    HIS B 228     -26.982   -1.278   48.520  1.00 23.34           N
ATOM   4127  CA   HIS B 228     -27.831   -1.671   49.637  1.00 23.95           C
ATOM   4128  C    HIS B 228     -28.494   -0.417   50.194  1.00 24.65           C
ATOM   4129  O    HIS B 228     -27.830    0.598   50.392  1.00 24.87           O
ATOM   4130  CB   HIS B 228     -27.021   -2.330   50.759  1.00 22.63           C
ATOM   4131  CG   HIS B 228     -27.866   -2.947   51.818  1.00 25.63           C
ATOM   4132  ND1  HIS B 228     -28.623   -4.074   51.594  1.00 26.86           N
ATOM   4133  CD2  HIS B 228     -28.123   -2.566   53.090  1.00 25.40           C
ATOM   4134  CE1  HIS B 228     -29.319   -4.358   52.684  1.00 26.35           C
ATOM   4135  NE2  HIS B 228     -29.032   -3.456   53.605  1.00 26.35           N
ATOM   4136  N    PRO B 229     -29.809   -0.476   50.418  1.00 25.63           N
ATOM   4137  CA   PRO B 229     -30.662   -1.645   50.161  1.00 24.84           C
ATOM   4138  C    PRO B 229     -30.831   -1.829   48.644  1.00 26.76           C
ATOM   4139  O    PRO B 229     -30.383   -0.997   47.875  1.00 26.31           O
ATOM   4140  CB   PRO B 229     -31.977   -1.264   50.840  1.00 26.06           C
ATOM   4141  CG   PRO B 229     -31.999    0.198   50.675  1.00 27.48           C
ATOM   4142  CD   PRO B 229     -30.588    0.610   51.037  1.00 26.56           C
ATOM   4143  N    PRO B 230     -31.456   -2.928   48.204  1.00 27.71           N
ATOM   4144  CA   PRO B 230     -31.633   -3.138   46.762  1.00 28.74           C
ATOM   4145  C    PRO B 230     -32.198   -1.896   46.084  1.00 28.49           C
ATOM   4146  O    PRO B 230     -33.139   -1.284   46.595  1.00 28.19           O
ATOM   4147  CB   PRO B 230     -32.602   -4.310   46.700  1.00 28.50           C
```

FIGURE 1-62 (COORDINATES)

```
ATOM   4148  CG  PRO B 230     -32.194  -5.125  47.883  1.00 29.72           C
ATOM   4149  CD  PRO B 230     -31.990  -4.073  48.964  1.00 28.68           C
ATOM   4150  N   GLY B 231     -31.613  -1.538  44.943  1.00 27.79           N
ATOM   4151  CA  GLY B 231     -32.059  -0.372  44.197  1.00 27.27           C
ATOM   4152  C   GLY B 231     -31.327   0.915  44.522  1.00 26.92           C
ATOM   4153  O   GLY B 231     -31.461   1.902  43.800  1.00 26.72           O
ATOM   4154  N   ALA B 232     -30.539   0.925  45.594  1.00 25.33           N
ATOM   4155  CA  ALA B 232     -29.801   2.127  45.986  1.00 24.98           C
ATOM   4156  C   ALA B 232     -28.786   2.535  44.937  1.00 25.38           C
ATOM   4157  O   ALA B 232     -28.182   1.678  44.278  1.00 25.71           O
ATOM   4158  CB  ALA B 232     -29.096   1.895  47.338  1.00 25.19           C
ATOM   4159  N   ARG B 233     -28.583   3.845  44.779  1.00 24.45           N
ATOM   4160  CA  ARG B 233     -27.640   4.340  43.779  1.00 26.19           C
ATOM   4161  C   ARG B 233     -26.258   4.651  44.322  1.00 24.64           C
ATOM   4162  O   ARG B 233     -25.278   4.671  43.558  1.00 25.17           O
ATOM   4163  CB  ARG B 233     -28.198   5.612  43.113  1.00 30.14           C
ATOM   4164  CG  ARG B 233     -29.567   5.436  42.397  1.00 37.00           C
ATOM   4165  CD  ARG B 233     -30.305   6.798  42.267  1.00 42.56           C
ATOM   4166  NE  ARG B 233     -31.592   6.695  41.561  1.00 47.34           N
ATOM   4167  CZ  ARG B 233     -31.736   6.525  40.240  1.00 49.59           C
ATOM   4168  NH1 ARG B 233     -30.666   6.435  39.434  1.00 49.38           N
ATOM   4169  NH2 ARG B 233     -32.961   6.431  39.716  1.00 48.75           N
ATOM   4170  N   GLY B 234     -26.145   4.882  45.630  1.00 21.53           N
ATOM   4171  CA  GLY B 234     -24.840   5.261  46.133  1.00 23.03           C
ATOM   4172  C   GLY B 234     -24.401   4.754  47.495  1.00 23.73           C
ATOM   4173  O   GLY B 234     -23.391   5.241  48.018  1.00 25.71           O
ATOM   4174  N   THR B 235     -25.159   3.824  48.058  1.00 24.41           N
ATOM   4175  CA  THR B 235     -24.867   3.226  49.373  1.00 23.71           C
ATOM   4176  C   THR B 235     -24.680   1.720  49.142  1.00 22.93           C
ATOM   4177  O   THR B 235     -25.381   1.129  48.316  1.00 22.87           O
ATOM   4178  CB  THR B 235     -26.013   3.466  50.386  1.00 25.53           C
ATOM   4179  OG1 THR B 235     -27.243   2.951  49.877  1.00 28.67           O
ATOM   4180  CG2 THR B 235     -26.160   4.980  50.678  1.00 27.38           C
ATOM   4181  N   SER B 236     -23.757   1.112  49.891  1.00 21.72           N
ATOM   4182  CA  SER B 236     -23.406  -0.316  49.710  1.00 20.03           C
ATOM   4183  C   SER B 236     -23.746  -1.165  50.929  1.00 21.77           C
ATOM   4184  O   SER B 236     -24.093  -0.642  51.991  1.00 20.66           O
ATOM   4185  CB  SER B 236     -21.900  -0.439  49.497  1.00 22.76           C
ATOM   4186  OG  SER B 236     -21.208  -0.187  50.719  1.00 21.44           O
ATOM   4187  N   GLN B 237     -23.637  -2.484  50.761  1.00 20.34           N
ATOM   4188  CA  GLN B 237     -23.875  -3.372  51.902  1.00 21.85           C
ATOM   4189  C   GLN B 237     -22.854  -3.072  52.994  1.00 19.57           C
ATOM   4190  O   GLN B 237     -23.148  -3.256  54.184  1.00 21.84           O
ATOM   4191  CB  GLN B 237     -23.736  -4.825  51.492  1.00 20.48           C
ATOM   4192  CG  GLN B 237     -24.857  -5.302  50.612  1.00 22.47           C
ATOM   4193  CD  GLN B 237     -24.636  -6.735  50.177  1.00 24.56           C
ATOM   4194  OE1 GLN B 237     -23.488  -7.177  49.999  1.00 24.98           O
ATOM   4195  NE2 GLN B 237     -25.730  -7.462  49.988  1.00 24.54           N
ATOM   4196  N   LEU B 238     -21.671  -2.607  52.643  1.00 19.36           N
ATOM   4197  CA  LEU B 238     -20.689  -2.322  53.685  1.00 21.24           C
ATOM   4198  C   LEU B 238     -21.170  -1.154  54.547  1.00 23.01           C
ATOM   4199  O   LEU B 238     -20.942  -1.132  55.761  1.00 22.61           O
ATOM   4200  CB  LEU B 238     -19.316  -2.017  53.080  1.00 22.65           C
ATOM   4201  CG  LEU B 238     -18.138  -1.759  54.009  1.00 26.52           C
ATOM   4202  CD1 LEU B 238     -16.967  -2.660  53.594  1.00 26.51           C
ATOM   4203  CD2 LEU B 238     -17.714  -0.290  53.921  1.00 28.00           C
ATOM   4204  N   HIS B 239     -21.824  -0.174  53.932  1.00 20.94           N
ATOM   4205  CA  HIS B 239     -22.338   0.959  54.716  1.00 22.71           C
ATOM   4206  C   HIS B 239     -23.412   0.432  55.687  1.00 22.15           C
ATOM   4207  O   HIS B 239     -23.680   1.023  56.731  1.00 24.80           O
ATOM   4208  CB  HIS B 239     -22.908   2.027  53.748  1.00 20.73           C
ATOM   4209  CG  HIS B 239     -21.863   2.624  52.850  1.00 21.24           C
ATOM   4210  ND1 HIS B 239     -22.111   2.970  51.538  1.00 21.30           N
ATOM   4211  CD2 HIS B 239     -20.545   2.856  53.053  1.00 21.24           C
ATOM   4212  CE1 HIS B 239     -20.990   3.376  50.973  1.00 21.40           C
ATOM   4213  NE2 HIS B 239     -20.023   3.314  51.867  1.00 22.39           N
ATOM   4214  N   GLY B 240     -24.000  -0.703  55.351  1.00 22.28           N
ATOM   4215  CA  GLY B 240     -25.029  -1.290  56.190  1.00 22.56           C
```

FIGURE 1-63 (COORDINATES)

```
ATOM   4216  C   GLY B 240     -24.514  -1.927  57.474  1.00 22.02           C
ATOM   4217  O   GLY B 240     -25.298  -2.218  58.373  1.00 23.59           O
ATOM   4218  N   MET B 241     -23.212  -2.161  57.543  1.00 22.08           N
ATOM   4219  CA  MET B 241     -22.602  -2.777  58.731  1.00 23.47           C
ATOM   4220  C   MET B 241     -22.404  -1.764  59.872  1.00 22.19           C
ATOM   4221  O   MET B 241     -21.434  -1.004  59.894  1.00 24.59           O
ATOM   4222  CB  MET B 241     -21.238  -3.385  58.368  1.00 22.73           C
ATOM   4223  CG  MET B 241     -21.312  -4.408  57.238  1.00 23.18           C
ATOM   4224  SD  MET B 241     -19.673  -5.039  56.746  1.00 23.88           S
ATOM   4225  CE  MET B 241     -19.345  -6.225  58.095  1.00 24.41           C
ATOM   4226  N   ASP B 242     -23.313  -1.808  60.842  1.00 24.33           N
ATOM   4227  CA  ASP B 242     -23.239  -0.937  62.013  1.00 24.38           C
ATOM   4228  C   ASP B 242     -21.945  -1.123  62.778  1.00 23.68           C
ATOM   4229  O   ASP B 242     -21.271  -0.163  63.184  1.00 23.18           O
ATOM   4230  CB  ASP B 242     -24.394  -1.275  62.966  1.00 25.54           C
ATOM   4231  CG  ASP B 242     -25.514  -0.246  62.934  1.00 28.47           C
ATOM   4232  OD1 ASP B 242     -25.951   0.138  61.817  1.00 27.64           O
ATOM   4233  OD2 ASP B 242     -25.957   0.139  64.042  1.00 26.76           O
ATOM   4234  N   LEU B 243     -21.585  -2.398  62.981  1.00 21.92           N
ATOM   4235  CA  LEU B 243     -20.428  -2.743  63.789  1.00 20.30           C
ATOM   4236  C   LEU B 243     -20.092  -4.197  63.482  1.00 19.31           C
ATOM   4237  O   LEU B 243     -20.999  -5.003  63.391  1.00 21.24           O
ATOM   4238  CB  LEU B 243     -20.837  -2.640  65.277  1.00 22.06           C
ATOM   4239  CG  LEU B 243     -19.825  -3.026  66.347  1.00 21.21           C
ATOM   4240  CD1 LEU B 243     -18.661  -2.068  66.330  1.00 22.42           C
ATOM   4241  CD2 LEU B 243     -20.511  -3.045  67.744  1.00 21.13           C
ATOM   4242  N   LEU B 244     -18.808  -4.498  63.314  1.00 18.72           N
ATOM   4243  CA  LEU B 244     -18.363  -5.869  63.055  1.00 18.35           C
ATOM   4244  C   LEU B 244     -17.728  -6.358  64.361  1.00 16.96           C
ATOM   4245  O   LEU B 244     -16.680  -5.852  64.800  1.00 17.51           O
ATOM   4246  CB  LEU B 244     -17.324  -5.901  61.905  1.00 18.11           C
ATOM   4247  CG  LEU B 244     -16.709  -7.285  61.634  1.00 17.80           C
ATOM   4248  CD1 LEU B 244     -17.819  -8.282  61.131  1.00 19.03           C
ATOM   4249  CD2 LEU B 244     -15.592  -7.111  60.595  1.00 18.16           C
ATOM   4250  N   VAL B 245     -18.385  -7.335  64.993  1.00 18.57           N
ATOM   4251  CA  VAL B 245     -17.901  -7.929  66.240  1.00 18.88           C
ATOM   4252  C   VAL B 245     -17.272  -9.236  65.778  1.00 16.76           C
ATOM   4253  O   VAL B 245     -17.987 -10.173  65.467  1.00 18.70           O
ATOM   4254  CB  VAL B 245     -19.070  -8.244  67.179  1.00 19.60           C
ATOM   4255  CG1 VAL B 245     -18.545  -8.757  68.516  1.00 20.59           C
ATOM   4256  CG2 VAL B 245     -19.924  -6.987  67.406  1.00 21.06           C
ATOM   4257  N   LEU B 246     -15.952  -9.260  65.753  1.00 16.98           N
ATOM   4258  CA  LEU B 246     -15.207 -10.402  65.264  1.00 17.10           C
ATOM   4259  C   LEU B 246     -14.652 -11.187  66.437  1.00 17.63           C
ATOM   4260  O   LEU B 246     -13.834 -10.665  67.209  1.00 17.56           O
ATOM   4261  CB  LEU B 246     -14.071  -9.915  64.343  1.00 18.38           C
ATOM   4262  CG  LEU B 246     -13.098 -11.009  63.856  1.00 17.89           C
ATOM   4263  CD1 LEU B 246     -13.867 -12.023  63.001  1.00 18.83           C
ATOM   4264  CD2 LEU B 246     -11.933 -10.409  63.048  1.00 17.56           C
ATOM   4265  N   LEU B 247     -15.105 -12.442  66.557  1.00 18.64           N
ATOM   4266  CA  LEU B 247     -14.641 -13.360  67.626  1.00 18.39           C
ATOM   4267  C   LEU B 247     -13.505 -14.212  67.076  1.00 18.01           C
ATOM   4268  O   LEU B 247     -13.641 -14.766  65.997  1.00 17.07           O
ATOM   4269  CB  LEU B 247     -15.772 -14.313  68.028  1.00 18.36           C
ATOM   4270  CG  LEU B 247     -16.944 -13.835  68.891  1.00 22.42           C
ATOM   4271  CD1 LEU B 247     -17.777 -12.832  68.162  1.00 23.00           C
ATOM   4272  CD2 LEU B 247     -17.797 -15.071  69.246  1.00 22.23           C
ATOM   4273  N   ASP B 248     -12.396 -14.329  67.796  1.00 17.50           N
ATOM   4274  CA  ASP B 248     -11.258 -15.123  67.344  1.00 18.82           C
ATOM   4275  C   ASP B 248     -10.403 -15.565  68.534  1.00 18.01           C
ATOM   4276  O   ASP B 248     -10.208 -14.809  69.483  1.00 17.66           O
ATOM   4277  CB  ASP B 248     -10.385 -14.297  66.364  1.00 19.23           C
ATOM   4278  CG  ASP B 248      -9.485 -15.167  65.469  1.00 21.70           C
ATOM   4279  OD1 ASP B 248      -9.433 -16.414  65.635  1.00 18.69           O
ATOM   4280  OD2 ASP B 248      -8.812 -14.590  64.572  1.00 20.52           O
ATOM   4281  N   LEU B 249      -9.918 -16.807  68.491  1.00 17.27           N
ATOM   4282  CA  LEU B 249      -9.040 -17.336  69.532  1.00 16.12           C
ATOM   4283  C   LEU B 249      -9.660 -17.303  70.918  1.00 16.17           C
```

FIGURE 1-64 (COORDINATES)

```
ATOM   4284  O    LEU B 249      -9.026  -16.911  71.913  1.00 20.37           O
ATOM   4285  CB   LEU B 249      -7.718  -16.575  69.568  1.00 16.09           C
ATOM   4286  CG   LEU B 249      -7.039  -16.322  68.206  1.00 16.64           C
ATOM   4287  CD1  LEU B 249      -5.662  -15.695  68.440  1.00 20.55           C
ATOM   4288  CD2  LEU B 249      -6.845  -17.625  67.425  1.00 16.10           C
ATOM   4289  N    ILE B 250     -10.899  -17.725  70.984  1.00 17.35           N
ATOM   4290  CA   ILE B 250     -11.619  -17.740  72.253  1.00 16.93           C
ATOM   4291  C    ILE B 250     -11.809  -19.179  72.721  1.00 19.02           C
ATOM   4292  O    ILE B 250     -12.074  -20.083  71.926  1.00 17.84           O
ATOM   4293  CB   ILE B 250     -13.002  -17.071  72.096  1.00 18.85           C
ATOM   4294  CG1  ILE B 250     -12.822  -15.562  71.840  1.00 20.30           C
ATOM   4295  CG2  ILE B 250     -13.853  -17.252  73.346  1.00 19.10           C
ATOM   4296  CD1  ILE B 250     -14.143  -14.864  71.483  1.00 21.61           C
ATOM   4297  N    GLY B 251     -11.644  -19.366  74.025  1.00 19.79           N
ATOM   4298  CA   GLY B 251     -11.837  -20.700  74.590  1.00 21.72           C
ATOM   4299  C    GLY B 251     -10.830  -21.064  75.650  1.00 22.38           C
ATOM   4300  O    GLY B 251     -11.079  -21.985  76.422  1.00 23.17           O
ATOM   4301  N    ALA B 252      -9.693  -20.374  75.683  1.00 21.65           N
ATOM   4302  CA   ALA B 252      -8.661  -20.625  76.695  1.00 23.84           C
ATOM   4303  C    ALA B 252      -9.075  -19.925  77.998  1.00 25.00           C
ATOM   4304  O    ALA B 252      -9.881  -18.997  78.000  1.00 24.08           O
ATOM   4305  CB   ALA B 252      -7.310  -20.072  76.230  1.00 24.13           C
ATOM   4306  N    PRO B 253      -8.541  -20.390  79.129  1.00 26.56           N
ATOM   4307  CA   PRO B 253      -8.912  -19.728  80.385  1.00 27.29           C
ATOM   4308  C    PRO B 253      -8.202  -18.377  80.532  1.00 28.06           C
ATOM   4309  O    PRO B 253      -7.167  -18.109  79.902  1.00 27.00           O
ATOM   4310  CB   PRO B 253      -8.457  -20.738  81.450  1.00 28.67           C
ATOM   4311  CG   PRO B 253      -7.263  -21.377  80.815  1.00 27.84           C
ATOM   4312  CD   PRO B 253      -7.745  -21.608  79.379  1.00 28.11           C
ATOM   4313  N    ASN B 254      -8.768  -17.529  81.378  1.00 28.57           N
ATOM   4314  CA   ASN B 254      -8.195  -16.217  81.683  1.00 29.66           C
ATOM   4315  C    ASN B 254      -7.849  -15.320  80.505  1.00 28.50           C
ATOM   4316  O    ASN B 254      -6.760  -14.738  80.442  1.00 29.20           O
ATOM   4317  CB   ASN B 254      -6.958  -16.394  82.564  1.00 32.35           C
ATOM   4318  CG   ASN B 254      -7.238  -17.254  83.778  1.00 35.64           C
ATOM   4319  OD1  ASN B 254      -8.165  -16.979  84.549  1.00 38.00           O
ATOM   4320  ND2  ASN B 254      -6.450  -18.317  83.945  1.00 37.38           N
ATOM   4321  N    PRO B 255      -8.774  -15.195  79.544  1.00 26.07           N
ATOM   4322  CA   PRO B 255      -8.466  -14.330  78.408  1.00 26.92           C
ATOM   4323  C    PRO B 255      -8.580  -12.875  78.826  1.00 26.99           C
ATOM   4324  O    PRO B 255      -9.325  -12.560  79.753  1.00 28.03           O
ATOM   4325  CB   PRO B 255      -9.553  -14.676  77.410  1.00 25.21           C
ATOM   4326  CG   PRO B 255     -10.738  -14.943  78.297  1.00 24.18           C
ATOM   4327  CD   PRO B 255     -10.111  -15.791  79.409  1.00 25.91           C
ATOM   4328  N    THR B 256      -7.834  -12.009  78.156  1.00 26.79           N
ATOM   4329  CA   THR B 256      -7.920  -10.572  78.409  1.00 29.01           C
ATOM   4330  C    THR B 256      -8.036   -9.915  77.045  1.00 27.58           C
ATOM   4331  O    THR B 256      -7.121  -10.010  76.235  1.00 28.53           O
ATOM   4332  CB   THR B 256      -6.685  -10.005  79.167  1.00 28.99           C
ATOM   4333  OG1  THR B 256      -5.480  -10.289  78.446  1.00 33.17           O
ATOM   4334  CG2  THR B 256      -6.598  -10.620  80.561  1.00 31.48           C
ATOM   4335  N    PHE B 257      -9.176   -9.271  76.801  1.00 28.31           N
ATOM   4336  CA   PHE B 257      -9.455   -8.596  75.527  1.00 29.39           C
ATOM   4337  C    PHE B 257      -9.219   -7.112  75.671  1.00 30.58           C
ATOM   4338  O    PHE B 257      -9.882   -6.461  76.493  1.00 32.09           O
ATOM   4339  CB   PHE B 257     -10.920   -8.756  75.120  1.00 28.49           C
ATOM   4340  CG   PHE B 257     -11.362  -10.177  74.964  1.00 27.58           C
ATOM   4341  CD1  PHE B 257     -11.247  -10.819  73.740  1.00 26.94           C
ATOM   4342  CD2  PHE B 257     -11.888  -10.877  76.046  1.00 26.73           C
ATOM   4343  CE1  PHE B 257     -11.651  -12.146  73.587  1.00 27.16           C
ATOM   4344  CE2  PHE B 257     -12.293  -12.203  75.918  1.00 24.43           C
ATOM   4345  CZ   PHE B 257     -12.179  -12.847  74.691  1.00 26.85           C
ATOM   4346  N    PRO B 258      -8.299   -6.557  74.877  1.00 30.66           N
ATOM   4347  CA   PRO B 258      -8.053   -5.115  74.976  1.00 32.45           C
ATOM   4348  C    PRO B 258      -9.062   -4.325  74.132  1.00 33.02           C
ATOM   4349  O    PRO B 258      -9.758   -4.876  73.275  1.00 32.54           O
ATOM   4350  CB   PRO B 258      -6.622   -4.974  74.464  1.00 32.60           C
ATOM   4351  CG   PRO B 258      -6.531   -6.044  73.421  1.00 32.80           C
```

FIGURE 1-65 (COORDINATES)

```
ATOM   4352  CD  PRO B 258      -7.272  -7.215  74.052  1.00 29.84           C
ATOM   4353  N   ASN B 259      -9.141  -3.024  74.398  1.00 33.84           N
ATOM   4354  CA  ASN B 259     -10.039  -2.116  73.687  1.00 33.22           C
ATOM   4355  C   ASN B 259      -9.193  -1.615  72.518  1.00 33.92           C
ATOM   4356  O   ASN B 259      -8.442  -0.648  72.652  1.00 36.05           O
ATOM   4357  CB  ASN B 259     -10.411  -0.973  74.642  1.00 34.32           C
ATOM   4358  CG  ASN B 259     -11.482  -0.056  74.100  1.00 36.10           C
ATOM   4359  OD1 ASN B 259     -11.993   0.814  74.831  1.00 39.19           O
ATOM   4360  ND2 ASN B 259     -11.827  -0.216  72.841  1.00 30.88           N
ATOM   4361  N   PHE B 260      -9.328  -2.258  71.365  1.00 30.67           N
ATOM   4362  CA  PHE B 260      -8.514  -1.920  70.209  1.00 30.24           C
ATOM   4363  C   PHE B 260      -8.697  -0.608  69.458  1.00 30.33           C
ATOM   4364  O   PHE B 260      -7.706  -0.005  69.015  1.00 30.77           O
ATOM   4365  CB  PHE B 260      -8.610  -3.045  69.157  1.00 31.38           C
ATOM   4366  CG  PHE B 260      -7.954  -4.333  69.572  1.00 30.52           C
ATOM   4367  CD1 PHE B 260      -8.715  -5.420  69.966  1.00 31.56           C
ATOM   4368  CD2 PHE B 260      -6.569  -4.447  69.564  1.00 32.04           C
ATOM   4369  CE1 PHE B 260      -8.108  -6.618  70.349  1.00 31.06           C
ATOM   4370  CE2 PHE B 260      -5.944  -5.632  69.943  1.00 32.31           C
ATOM   4371  CZ  PHE B 260      -6.718  -6.720  70.337  1.00 32.24           C
ATOM   4372  N   PHE B 261      -9.944  -0.177  69.296  1.00 28.09           N
ATOM   4373  CA  PHE B 261     -10.231   0.985  68.468  1.00 28.65           C
ATOM   4374  C   PHE B 261     -11.016   2.086  69.134  1.00 29.42           C
ATOM   4375  O   PHE B 261     -12.097   1.853  69.651  1.00 28.53           O
ATOM   4376  CB  PHE B 261     -11.008   0.514  67.228  1.00 27.68           C
ATOM   4377  CG  PHE B 261     -10.332  -0.624  66.497  1.00 27.49           C
ATOM   4378  CD1 PHE B 261      -9.148  -0.406  65.820  1.00 26.68           C
ATOM   4379  CD2 PHE B 261     -10.853  -1.910  66.541  1.00 27.86           C
ATOM   4380  CE1 PHE B 261      -8.463  -1.454  65.184  1.00 29.94           C
ATOM   4381  CE2 PHE B 261     -10.178  -2.974  65.907  1.00 25.90           C
ATOM   4382  CZ  PHE B 261      -8.990  -2.741  65.235  1.00 25.63           C
ATOM   4383  N   PRO B 262     -10.500   3.326  69.063  1.00 30.05           N
ATOM   4384  CA  PRO B 262     -11.201   4.442  69.687  1.00 31.06           C
ATOM   4385  C   PRO B 262     -12.629   4.574  69.183  1.00 30.45           C
ATOM   4386  O   PRO B 262     -13.512   4.969  69.938  1.00 31.25           O
ATOM   4387  CB  PRO B 262     -10.346   5.654  69.304  1.00 32.61           C
ATOM   4388  CG  PRO B 262      -8.983   5.074  69.060  1.00 34.95           C
ATOM   4389  CD  PRO B 262      -9.328   3.797  68.317  1.00 31.69           C
ATOM   4390  N   ASN B 263     -12.885   4.234  67.920  1.00 29.53           N
ATOM   4391  CA  ASN B 263     -14.244   4.401  67.410  1.00 30.27           C
ATOM   4392  C   ASN B 263     -15.289   3.339  67.789  1.00 31.04           C
ATOM   4393  O   ASN B 263     -16.449   3.436  67.387  1.00 33.67           O
ATOM   4394  CB  ASN B 263     -14.224   4.609  65.892  1.00 32.03           C
ATOM   4395  CG  ASN B 263     -13.963   3.336  65.146  1.00 32.98           C
ATOM   4396  OD1 ASN B 263     -13.555   2.350  65.738  1.00 33.53           O
ATOM   4397  ND2 ASN B 263     -14.194   3.347  63.837  1.00 34.26           N
ATOM   4398  N   SER B 264     -14.892   2.322  68.543  1.00 28.35           N
ATOM   4399  CA  SER B 264     -15.861   1.347  69.018  1.00 27.22           C
ATOM   4400  C   SER B 264     -15.696   1.231  70.543  1.00 27.84           C
ATOM   4401  O   SER B 264     -16.343   0.392  71.171  1.00 27.86           O
ATOM   4402  CB  SER B 264     -15.666  -0.030  68.353  1.00 27.44           C
ATOM   4403  OG  SER B 264     -14.365  -0.540  68.578  1.00 26.67           O
ATOM   4404  N   ALA B 265     -14.846   2.081  71.125  1.00 27.75           N
ATOM   4405  CA  ALA B 265     -14.602   2.052  72.580  1.00 28.99           C
ATOM   4406  C   ALA B 265     -15.856   2.046  73.433  1.00 29.19           C
ATOM   4407  O   ALA B 265     -15.888   1.363  74.462  1.00 28.24           O
ATOM   4408  CB  ALA B 265     -13.714   3.228  73.012  1.00 29.48           C
ATOM   4409  N   ARG B 266     -16.887   2.788  73.035  1.00 28.66           N
ATOM   4410  CA  ARG B 266     -18.103   2.819  73.848  1.00 29.16           C
ATOM   4411  C   ARG B 266     -18.818   1.476  73.882  1.00 29.44           C
ATOM   4412  O   ARG B 266     -19.481   1.132  74.865  1.00 27.25           O
ATOM   4413  CB  ARG B 266     -19.052   3.935  73.388  1.00 29.71           C
ATOM   4414  CG  ARG B 266     -19.736   3.715  72.041  1.00 30.51           C
ATOM   4415  CD  ARG B 266     -20.414   5.002  71.590  1.00 31.76           C
ATOM   4416  NE  ARG B 266     -21.111   4.883  70.317  1.00 30.87           N
ATOM   4417  CZ  ARG B 266     -22.396   4.581  70.176  1.00 29.11           C
ATOM   4418  NH1 ARG B 266     -23.167   4.355  71.239  1.00 31.79           N
ATOM   4419  NH2 ARG B 266     -22.925   4.524  68.965  1.00 30.66           N
```

FIGURE 1-66 (COORDINATES)

```
ATOM   4420  N    TRP B 267     -18.668   0.692  72.817  1.00 26.56           N
ATOM   4421  CA   TRP B 267     -19.298  -0.626  72.793  1.00 25.94           C
ATOM   4422  C    TRP B 267     -18.433  -1.594  73.618  1.00 24.83           C
ATOM   4423  O    TRP B 267     -18.955  -2.558  74.213  1.00 26.03           O
ATOM   4424  CB   TRP B 267     -19.467  -1.107  71.346  1.00 25.85           C
ATOM   4425  CG   TRP B 267     -20.503  -0.320  70.631  1.00 26.71           C
ATOM   4426  CD1  TRP B 267     -20.305   0.515  69.559  1.00 26.50           C
ATOM   4427  CD2  TRP B 267     -21.897  -0.221  70.969  1.00 26.29           C
ATOM   4428  NE1  TRP B 267     -21.486   1.124  69.220  1.00 26.17           N
ATOM   4429  CE2  TRP B 267     -22.480   0.696  70.065  1.00 25.64           C
ATOM   4430  CE3  TRP B 267     -22.706  -0.815  71.949  1.00 26.33           C
ATOM   4431  CZ2  TRP B 267     -23.839   1.035  70.114  1.00 26.11           C
ATOM   4432  CZ3  TRP B 267     -24.053  -0.488  72.003  1.00 25.57           C
ATOM   4433  CH2  TRP B 267     -24.614   0.438  71.083  1.00 26.34           C
ATOM   4434  N    PHE B 268     -17.132  -1.334  73.656  1.00 24.45           N
ATOM   4435  CA   PHE B 268     -16.232  -2.143  74.461  1.00 27.51           C
ATOM   4436  C    PHE B 268     -16.648  -1.883  75.908  1.00 29.34           C
ATOM   4437  O    PHE B 268     -16.747  -2.813  76.711  1.00 29.98           O
ATOM   4438  CB   PHE B 268     -14.779  -1.714  74.292  1.00 26.00           C
ATOM   4439  CG   PHE B 268     -13.807  -2.568  75.061  1.00 29.47           C
ATOM   4440  CD1  PHE B 268     -13.269  -3.722  74.491  1.00 27.70           C
ATOM   4441  CD2  PHE B 268     -13.439  -2.225  76.365  1.00 29.39           C
ATOM   4442  CE1  PHE B 268     -12.373  -4.523  75.207  1.00 30.05           C
ATOM   4443  CE2  PHE B 268     -12.543  -3.022  77.095  1.00 31.71           C
ATOM   4444  CZ   PHE B 268     -12.007  -4.173  76.516  1.00 31.40           C
ATOM   4445  N    GLU B 269     -16.920  -0.615  76.225  1.00 30.11           N
ATOM   4446  CA   GLU B 269     -17.314  -0.240  77.584  1.00 31.98           C
ATOM   4447  C    GLU B 269     -18.600  -0.939  77.990  1.00 30.96           C
ATOM   4448  O    GLU B 269     -18.793  -1.269  79.174  1.00 31.94           O
ATOM   4449  CB   GLU B 269     -17.453   1.292  77.701  1.00 33.33           C
ATOM   4450  CG   GLU B 269     -16.098   2.014  77.581  1.00 40.41           C
ATOM   4451  CD   GLU B 269     -16.196   3.559  77.555  1.00 44.61           C
ATOM   4452  OE1  GLU B 269     -16.982   4.128  76.755  1.00 47.16           O
ATOM   4453  OE2  GLU B 269     -15.465   4.209  78.334  1.00 46.61           O
ATOM   4454  N    ARG B 270     -19.479  -1.181  77.023  1.00 29.23           N
ATOM   4455  CA   ARG B 270     -20.709  -1.902  77.302  1.00 29.00           C
ATOM   4456  C    ARG B 270     -20.369  -3.366  77.665  1.00 30.79           C
ATOM   4457  O    ARG B 270     -20.949  -3.928  78.606  1.00 28.57           O
ATOM   4458  CB   ARG B 270     -21.652  -1.844  76.102  1.00 28.58           C
ATOM   4459  CG   ARG B 270     -22.404  -0.487  75.965  1.00 28.96           C
ATOM   4460  CD   ARG B 270     -23.090  -0.135  77.277  1.00 28.42           C
ATOM   4461  NE   ARG B 270     -24.026  -1.172  77.687  1.00 29.99           N
ATOM   4462  CZ   ARG B 270     -24.407  -1.386  78.946  1.00 30.83           C
ATOM   4463  NH1  ARG B 270     -23.929  -0.616  79.907  1.00 31.71           N
ATOM   4464  NH2  ARG B 270     -25.236  -2.389  79.244  1.00 29.62           N
ATOM   4465  N    LEU B 271     -19.434  -3.991  76.943  1.00 29.29           N
ATOM   4466  CA   LEU B 271     -19.059  -5.375  77.303  1.00 28.79           C
ATOM   4467  C    LEU B 271     -18.573  -5.414  78.762  1.00 30.16           C
ATOM   4468  O    LEU B 271     -18.984  -6.291  79.530  1.00 29.83           O
ATOM   4469  CB   LEU B 271     -17.953  -5.917  76.379  1.00 26.55           C
ATOM   4470  CG   LEU B 271     -18.448  -6.214  74.950  1.00 27.48           C
ATOM   4471  CD1  LEU B 271     -17.267  -6.641  74.077  1.00 25.28           C
ATOM   4472  CD2  LEU B 271     -19.508  -7.290  74.960  1.00 24.51           C
ATOM   4473  N    GLN B 272     -17.702  -4.472  79.137  1.00 30.18           N
ATOM   4474  CA   GLN B 272     -17.187  -4.371  80.503  1.00 32.74           C
ATOM   4475  C    GLN B 272     -18.325  -4.271  81.504  1.00 33.63           C
ATOM   4476  O    GLN B 272     -18.357  -5.002  82.501  1.00 33.51           O
ATOM   4477  CB   GLN B 272     -16.329  -3.125  80.673  1.00 32.07           C
ATOM   4478  CG   GLN B 272     -14.998  -3.160  80.017  1.00 34.05           C
ATOM   4479  CD   GLN B 272     -14.191  -1.939  80.369  1.00 35.09           C
ATOM   4480  OE1  GLN B 272     -13.199  -2.019  81.092  1.00 35.52           O
ATOM   4481  NE2  GLN B 272     -14.622  -0.789  79.868  1.00 34.25           N
ATOM   4482  N    ALA B 273     -19.266  -3.365  81.229  1.00 33.06           N
ATOM   4483  CA   ALA B 273     -20.400  -3.149  82.120  1.00 32.75           C
ATOM   4484  C    ALA B 273     -21.273  -4.386  82.250  1.00 32.66           C
ATOM   4485  O    ALA B 273     -21.782  -4.672  83.337  1.00 33.52           O
ATOM   4486  CB   ALA B 273     -21.240  -1.960  81.640  1.00 30.70           C
ATOM   4487  N    ILE B 274     -21.461  -5.109  81.147  1.00 30.46           N
```

FIGURE 1-67 (COORDINATES)

```
ATOM   4488  CA  ILE B 274     -22.278  -6.324  81.144  1.00 29.33           C
ATOM   4489  C   ILE B 274     -21.575  -7.416  81.952  1.00 30.04           C
ATOM   4490  O   ILE B 274     -22.220  -8.151  82.720  1.00 30.49           O
ATOM   4491  CB  ILE B 274     -22.535  -6.838  79.682  1.00 28.39           C
ATOM   4492  CG1 ILE B 274     -23.425  -5.832  78.938  1.00 28.16           C
ATOM   4493  CG2 ILE B 274     -23.247  -8.222  79.693  1.00 27.22           C
ATOM   4494  CD1 ILE B 274     -23.675  -6.157  77.458  1.00 28.37           C
ATOM   4495  N   GLU B 275     -20.261  -7.508  81.784  1.00 29.38           N
ATOM   4496  CA  GLU B 275     -19.470  -8.509  82.504  1.00 30.56           C
ATOM   4497  C   GLU B 275     -19.546  -8.209  84.010  1.00 32.45           C
ATOM   4498  O   GLU B 275     -19.747  -9.113  84.825  1.00 31.72           O
ATOM   4499  CB  GLU B 275     -18.006  -8.485  82.047  1.00 30.49           C
ATOM   4500  CG  GLU B 275     -17.114  -9.438  82.852  1.00 30.27           C
ATOM   4501  CD  GLU B 275     -15.637  -9.410  82.452  1.00 33.12           C
ATOM   4502  OE1 GLU B 275     -15.155  -8.383  81.928  1.00 32.10           O
ATOM   4503  OE2 GLU B 275     -14.934 -10.420  82.692  1.00 33.12           O
ATOM   4504  N   HIS B 276     -19.390  -6.934  84.360  1.00 32.25           N
ATOM   4505  CA  HIS B 276     -19.418  -6.514  85.762  1.00 35.05           C
ATOM   4506  C   HIS B 276     -20.743  -6.847  86.427  1.00 35.53           C
ATOM   4507  O   HIS B 276     -20.780  -7.469  87.499  1.00 36.00           O
ATOM   4508  CB  HIS B 276     -19.160  -5.007  85.875  1.00 36.23           C
ATOM   4509  CG  HIS B 276     -19.108  -4.516  87.291  1.00 39.03           C
ATOM   4510  ND1 HIS B 276     -17.954  -4.535  88.045  1.00 40.28           N
ATOM   4511  CD2 HIS B 276     -20.082  -4.051  88.107  1.00 39.80           C
ATOM   4512  CE1 HIS B 276     -18.219  -4.101  89.265  1.00 40.22           C
ATOM   4513  NE2 HIS B 276     -19.504  -3.802  89.328  1.00 39.39           N
ATOM   4514  N   GLU B 277     -21.833  -6.441  85.792  1.00 35.55           N
ATOM   4515  CA  GLU B 277     -23.157  -6.688  86.338  1.00 36.68           C
ATOM   4516  C   GLU B 277     -23.498  -8.166  86.415  1.00 37.20           C
ATOM   4517  O   GLU B 277     -24.149  -8.606  87.365  1.00 36.95           O
ATOM   4518  CB  GLU B 277     -24.222  -5.963  85.513  1.00 37.63           C
ATOM   4519  CG  GLU B 277     -25.616  -6.033  86.115  1.00 39.93           C
ATOM   4520  CD  GLU B 277     -25.718  -5.352  87.491  1.00 41.48           C
ATOM   4521  OE1 GLU B 277     -26.806  -5.432  88.110  1.00 42.14           O
ATOM   4522  OE2 GLU B 277     -24.724  -4.737  87.943  1.00 40.42           O
ATOM   4523  N   LEU B 278     -23.091  -8.946  85.413  1.00 34.30           N
ATOM   4524  CA  LEU B 278     -23.393 -10.378  85.469  1.00 33.52           C
ATOM   4525  C   LEU B 278     -22.598 -10.997  86.626  1.00 33.30           C
ATOM   4526  O   LEU B 278     -23.061 -11.930  87.280  1.00 34.45           O
ATOM   4527  CB  LEU B 278     -23.045 -11.065  84.133  1.00 30.51           C
ATOM   4528  CG  LEU B 278     -24.007 -10.751  82.972  1.00 28.53           C
ATOM   4529  CD1 LEU B 278     -23.412 -11.338  81.684  1.00 28.22           C
ATOM   4530  CD2 LEU B 278     -25.409 -11.329  83.213  1.00 27.89           C
ATOM   4531  N   HIS B 279     -21.401 -10.480  86.870  1.00 33.66           N
ATOM   4532  CA  HIS B 279     -20.591 -10.979  87.966  1.00 35.23           C
ATOM   4533  C   HIS B 279     -21.277 -10.631  89.287  1.00 36.33           C
ATOM   4534  O   HIS B 279     -21.449 -11.489  90.153  1.00 34.99           O
ATOM   4535  CB  HIS B 279     -19.215 -10.342  87.937  1.00 36.39           C
ATOM   4536  CG  HIS B 279     -18.363 -10.687  89.118  1.00 38.70           C
ATOM   4537  ND1 HIS B 279     -18.569 -10.146  90.372  1.00 41.32           N
ATOM   4538  CD2 HIS B 279     -17.278 -11.487  89.228  1.00 37.81           C
ATOM   4539  CE1 HIS B 279     -17.639 -10.596  91.200  1.00 39.61           C
ATOM   4540  NE2 HIS B 279     -16.845 -11.412  90.530  1.00 40.47           N
ATOM   4541  N   GLU B 280     -21.678  -9.369  89.425  1.00 36.79           N
ATOM   4542  CA  GLU B 280     -22.335  -8.913  90.655  1.00 37.49           C
ATOM   4543  C   GLU B 280     -23.623  -9.658  90.980  1.00 37.32           C
ATOM   4544  O   GLU B 280     -23.936  -9.878  92.161  1.00 38.58           O
ATOM   4545  CB  GLU B 280     -22.607  -7.407  90.585  1.00 37.94           C
ATOM   4546  CG  GLU B 280     -21.340  -6.562  90.588  1.00 42.28           C
ATOM   4547  CD  GLU B 280     -20.588  -6.644  91.904  1.00 44.30           C
ATOM   4548  OE1 GLU B 280     -21.114  -6.140  92.920  1.00 46.02           O
ATOM   4549  OE2 GLU B 280     -19.473  -7.205  91.935  1.00 47.02           O
ATOM   4550  N   LEU B 281     -24.386 -10.025  89.957  1.00 35.76           N
ATOM   4551  CA  LEU B 281     -25.631 -10.756  90.139  1.00 34.35           C
ATOM   4552  C   LEU B 281     -25.421 -12.264  90.332  1.00 34.98           C
ATOM   4553  O   LEU B 281     -26.394 -13.033  90.332  1.00 33.67           O
ATOM   4554  CB  LEU B 281     -26.549 -10.544  88.936  1.00 35.97           C
ATOM   4555  CG  LEU B 281     -27.118  -9.142  88.695  1.00 37.55           C
```

FIGURE 1-68 (COORDINATES)

```
ATOM   4556  CD1 LEU B 281     -27.955   -9.137  87.402  1.00 36.64           C
ATOM   4557  CD2 LEU B 281     -27.973   -8.725  89.902  1.00 37.91           C
ATOM   4558  N   GLY B 282     -24.159  -12.673  90.467  1.00 34.44           N
ATOM   4559  CA  GLY B 282     -23.819  -14.080  90.634  1.00 35.31           C
ATOM   4560  C   GLY B 282     -24.225  -14.967  89.464  1.00 36.16           C
ATOM   4561  O   GLY B 282     -24.568  -16.151  89.643  1.00 35.57           O
ATOM   4562  N   LEU B 283     -24.170  -14.413  88.249  1.00 34.54           N
ATOM   4563  CA  LEU B 283     -24.573  -15.168  87.067  1.00 34.61           C
ATOM   4564  C   LEU B 283     -23.398  -15.675  86.226  1.00 33.28           C
ATOM   4565  O   LEU B 283     -23.607  -16.252  85.173  1.00 33.17           O
ATOM   4566  CB  LEU B 283     -25.524  -14.316  86.213  1.00 34.92           C
ATOM   4567  CG  LEU B 283     -26.838  -13.905  86.904  1.00 35.66           C
ATOM   4568  CD1 LEU B 283     -27.537  -12.798  86.107  1.00 36.29           C
ATOM   4569  CD2 LEU B 283     -27.748  -15.118  87.035  1.00 35.14           C
ATOM   4570  N   LEU B 284     -22.173  -15.467  86.703  1.00 32.44           N
ATOM   4571  CA  LEU B 284     -20.970  -15.955  86.023  1.00 33.33           C
ATOM   4572  C   LEU B 284     -20.275  -17.021  86.904  1.00 34.16           C
ATOM   4573  O   LEU B 284     -20.344  -16.959  88.136  1.00 35.11           O
ATOM   4574  CB  LEU B 284     -20.018  -14.793  85.757  1.00 33.23           C
ATOM   4575  CG  LEU B 284     -20.064  -14.088  84.394  1.00 35.42           C
ATOM   4576  CD1 LEU B 284     -21.408  -14.203  83.711  1.00 34.25           C
ATOM   4577  CD2 LEU B 284     -19.632  -12.675  84.610  1.00 33.04           C
ATOM   4578  N   LYS B 285     -19.604  -17.987  86.278  1.00 33.90           N
ATOM   4579  CA  LYS B 285     -18.916  -19.058  87.017  1.00 34.53           C
ATOM   4580  C   LYS B 285     -17.391  -18.931  87.015  1.00 35.64           C
ATOM   4581  O   LYS B 285     -16.807  -18.543  86.011  1.00 35.35           O
ATOM   4582  CB  LYS B 285     -19.305  -20.409  86.424  1.00 36.27           C
ATOM   4583  CG  LYS B 285     -20.780  -20.767  86.567  1.00 38.00           C
ATOM   4584  CD  LYS B 285     -21.063  -22.089  85.875  1.00 41.28           C
ATOM   4585  CE  LYS B 285     -22.434  -22.673  86.229  1.00 41.15           C
ATOM   4586  NZ  LYS B 285     -23.559  -21.765  85.917  1.00 42.74           N
ATOM   4587  N   ASP B 286     -16.747  -19.263  88.140  1.00 35.67           N
ATOM   4588  CA  ASP B 286     -15.292  -19.201  88.252  1.00 36.36           C
ATOM   4589  C   ASP B 286     -14.776  -17.864  87.732  1.00 36.66           C
ATOM   4590  O   ASP B 286     -13.757  -17.788  87.043  1.00 35.78           O
ATOM   4591  CB  ASP B 286     -14.657  -20.346  87.448  1.00 39.67           C
ATOM   4592  CG  ASP B 286     -15.023  -21.722  87.987  1.00 42.12           C
ATOM   4593  OD1 ASP B 286     -14.611  -22.036  89.119  1.00 44.58           O
ATOM   4594  OD2 ASP B 286     -15.719  -22.496  87.286  1.00 44.54           O
ATOM   4595  N   HIS B 287     -15.477  -16.803  88.083  1.00 35.80           N
ATOM   4596  CA  HIS B 287     -15.115  -15.483  87.610  1.00 37.23           C
ATOM   4597  C   HIS B 287     -14.794  -14.494  88.722  1.00 38.70           C
ATOM   4598  O   HIS B 287     -15.534  -14.394  89.697  1.00 39.15           O
ATOM   4599  CB  HIS B 287     -16.268  -14.974  86.750  1.00 36.98           C
ATOM   4600  CG  HIS B 287     -16.024  -13.639  86.127  1.00 37.46           C
ATOM   4601  ND1 HIS B 287     -16.247  -12.456  86.795  1.00 36.25           N
ATOM   4602  CD2 HIS B 287     -15.608  -13.299  84.883  1.00 36.53           C
ATOM   4603  CE1 HIS B 287     -15.981  -11.441  85.990  1.00 37.54           C
ATOM   4604  NE2 HIS B 287     -15.593  -11.926  84.823  1.00 36.52           N
ATOM   4605  N   SER B 288     -13.689  -13.771  88.573  1.00 40.10           N
ATOM   4606  CA  SER B 288     -13.288  -12.776  89.567  1.00 42.42           C
ATOM   4607  C   SER B 288     -13.082  -11.432  88.872  1.00 44.13           C
ATOM   4608  O   SER B 288     -12.659  -11.380  87.710  1.00 43.57           O
ATOM   4609  CB  SER B 288     -11.995  -13.195  90.274  1.00 42.24           C
ATOM   4610  OG  SER B 288     -10.850  -12.845  89.517  1.00 44.48           O
ATOM   4611  N   LEU B 289     -13.390  -10.343  89.570  1.00 44.65           N
ATOM   4612  CA  LEU B 289     -13.218   -9.028  88.977  1.00 45.48           C
ATOM   4613  C   LEU B 289     -11.740   -8.709  88.756  1.00 46.41           C
ATOM   4614  O   LEU B 289     -11.399   -7.902  87.881  1.00 47.47           O
ATOM   4615  CB  LEU B 289     -13.906   -7.959  89.838  1.00 46.64           C
ATOM   4616  CG  LEU B 289     -15.437   -8.126  89.885  1.00 47.74           C
ATOM   4617  CD1 LEU B 289     -16.079   -6.977  90.649  1.00 47.79           C
ATOM   4618  CD2 LEU B 289     -15.995   -8.175  88.473  1.00 48.68           C
ATOM   4619  N   GLU B 290     -10.860   -9.357  89.519  1.00 45.46           N
ATOM   4620  CA  GLU B 290      -9.421   -9.148  89.364  1.00 46.22           C
ATOM   4621  C   GLU B 290      -8.948   -9.822  88.070  1.00 45.29           C
ATOM   4622  O   GLU B 290      -7.885   -9.495  87.528  1.00 45.70           O
```

FIGURE 1-69 (COORDINATES)

```
ATOM   4623  CB  GLU B 290      -8.659  -9.746  90.550  1.00 48.49           C
ATOM   4624  CG  GLU B 290      -7.132  -9.695  90.428  1.00 51.95           C
ATOM   4625  CD  GLU B 290      -6.526  -8.321  90.739  1.00 54.34           C
ATOM   4626  OE1 GLU B 290      -6.745  -7.361  89.964  1.00 56.08           O
ATOM   4627  OE2 GLU B 290      -5.818  -8.200  91.767  1.00 55.57           O
ATOM   4628  N   GLY B 291      -9.735 -10.774  87.587  1.00 42.43           N
ATOM   4629  CA  GLY B 291      -9.369 -11.466  86.366  1.00 40.52           C
ATOM   4630  C   GLY B 291     -10.418 -11.275  85.285  1.00 38.73           C
ATOM   4631  O   GLY B 291     -10.643 -12.176  84.476  1.00 37.69           O
ATOM   4632  N   ARG B 292     -11.063 -10.111  85.275  1.00 36.69           N
ATOM   4633  CA  ARG B 292     -12.087  -9.827  84.279  1.00 36.39           C
ATOM   4634  C   ARG B 292     -11.532  -9.941  82.868  1.00 34.25           C
ATOM   4635  O   ARG B 292     -10.344  -9.739  82.631  1.00 34.43           O
ATOM   4636  CB  ARG B 292     -12.706  -8.433  84.488  1.00 37.78           C
ATOM   4637  CG  ARG B 292     -11.739  -7.248  84.444  1.00 40.58           C
ATOM   4638  CD  ARG B 292     -12.430  -5.936  84.898  1.00 43.47           C
ATOM   4639  NE  ARG B 292     -11.526  -4.786  84.839  1.00 46.52           N
ATOM   4640  CZ  ARG B 292     -10.421  -4.661  85.577  1.00 48.81           C
ATOM   4641  NH1 ARG B 292     -10.086  -5.621  86.442  1.00 49.68           N
ATOM   4642  NH2 ARG B 292      -9.631  -3.592  85.440  1.00 48.13           N
ATOM   4643  N   TYR B 293     -12.406 -10.271  81.930  1.00 33.04           N
ATOM   4644  CA  TYR B 293     -11.987 -10.423  80.542  1.00 31.82           C
ATOM   4645  C   TYR B 293     -11.813  -9.087  79.816  1.00 32.03           C
ATOM   4646  O   TYR B 293     -10.893  -8.923  79.026  1.00 31.71           O
ATOM   4647  CB  TYR B 293     -13.004 -11.281  79.793  1.00 29.99           C
ATOM   4648  CG  TYR B 293     -13.420 -12.543  80.521  1.00 27.40           C
ATOM   4649  CD1 TYR B 293     -12.480 -13.352  81.159  1.00 28.03           C
ATOM   4650  CD2 TYR B 293     -14.762 -12.934  80.556  1.00 27.65           C
ATOM   4651  CE1 TYR B 293     -12.860 -14.524  81.820  1.00 26.79           C
ATOM   4652  CE2 TYR B 293     -15.155 -14.115  81.216  1.00 28.06           C
ATOM   4653  CZ  TYR B 293     -14.187 -14.897  81.844  1.00 28.25           C
ATOM   4654  OH  TYR B 293     -14.558 -16.052  82.480  1.00 29.27           O
ATOM   4655  N   PHE B 294     -12.681  -8.124  80.093  1.00 32.75           N
ATOM   4656  CA  PHE B 294     -12.595  -6.841  79.412  1.00 35.35           C
ATOM   4657  C   PHE B 294     -11.923  -5.793  80.282  1.00 38.74           C
ATOM   4658  O   PHE B 294     -12.543  -5.153  81.131  1.00 37.74           O
ATOM   4659  CB  PHE B 294     -13.999  -6.454  78.956  1.00 32.28           C
ATOM   4660  CG  PHE B 294     -14.590  -7.460  78.006  1.00 31.71           C
ATOM   4661  CD1 PHE B 294     -14.131  -7.537  76.685  1.00 30.42           C
ATOM   4662  CD2 PHE B 294     -15.506  -8.407  78.449  1.00 30.63           C
ATOM   4663  CE1 PHE B 294     -14.568  -8.539  75.835  1.00 28.54           C
ATOM   4664  CE2 PHE B 294     -15.951  -9.424  77.597  1.00 28.37           C
ATOM   4665  CZ  PHE B 294     -15.475  -9.487  76.286  1.00 29.04           C
ATOM   4666  N   GLN B 295     -10.626  -5.640  80.042  1.00 43.06           N
ATOM   4667  CA  GLN B 295      -9.770  -4.732  80.795  1.00 48.62           C
ATOM   4668  C   GLN B 295      -9.620  -3.325  80.243  1.00 51.37           C
ATOM   4669  O   GLN B 295      -9.533  -3.122  79.035  1.00 52.12           O
ATOM   4670  CB  GLN B 295      -8.382  -5.348  80.920  1.00 49.89           C
ATOM   4671  CG  GLN B 295      -8.375  -6.696  81.600  1.00 52.61           C
ATOM   4672  CD  GLN B 295      -7.754  -6.625  82.967  1.00 55.23           C
ATOM   4673  OE1 GLN B 295      -8.229  -5.891  83.846  1.00 56.97           O
ATOM   4674  NE2 GLN B 295      -6.679  -7.379  83.163  1.00 56.15           N
ATOM   4675  N   ASN B 296      -9.554  -2.369  81.163  1.00 54.73           N
ATOM   4676  CA  ASN B 296      -9.392  -0.958  80.845  1.00 57.83           C
ATOM   4677  C   ASN B 296      -8.012  -0.767  80.210  1.00 59.56           C
ATOM   4678  O   ASN B 296      -7.132  -0.170  80.831  1.00 60.36           O
ATOM   4679  CB  ASN B 296      -9.457  -0.103  82.125  1.00 58.39           C
ATOM   4680  CG  ASN B 296     -10.361  -0.699  83.216  1.00 59.54           C
ATOM   4681  OD1 ASN B 296     -10.926   0.039  84.026  1.00 60.65           O
ATOM   4682  ND2 ASN B 296     -10.474  -2.022  83.262  1.00 59.50           N
ATOM   4683  N   TYR B 297      -7.816  -1.251  78.984  1.00 60.87           N
ATOM   4684  CA  TYR B 297      -6.504  -1.125  78.349  1.00 62.32           C
ATOM   4685  C   TYR B 297      -6.519  -1.097  76.815  1.00 62.67           C
ATOM   4686  O   TYR B 297      -7.251  -1.844  76.166  1.00 62.17           O
ATOM   4687  CB  TYR B 297      -5.593  -2.235  78.907  1.00 63.46           C
ATOM   4688  CG  TYR B 297      -4.958  -3.201  77.924  1.00 65.15           C
ATOM   4689  CD1 TYR B 297      -3.897  -2.809  77.105  1.00 65.33           C
ATOM   4690  CD2 TYR B 297      -5.347  -4.545  77.897  1.00 65.68           C
```

FIGURE 1-70 (COORDINATES)

```
ATOM   4691  CE1 TYR B 297      -3.227  -3.735  76.289  1.00 65.53           C
ATOM   4692  CE2 TYR B 297      -4.686  -5.479  77.086  1.00 66.01           C
ATOM   4693  CZ  TYR B 297      -3.624  -5.068  76.289  1.00 66.08           C
ATOM   4694  OH  TYR B 297      -2.942  -5.996  75.523  1.00 65.66           O
ATOM   4695  N   SER B 298      -5.699  -0.211  76.250  1.00 62.71           N
ATOM   4696  CA  SER B 298      -5.614  -0.035  74.807  1.00 62.91           C
ATOM   4697  C   SER B 298      -4.441  -0.760  74.158  1.00 62.63           C
ATOM   4698  O   SER B 298      -3.466  -1.123  74.814  1.00 63.08           O
ATOM   4699  CB  SER B 298      -5.538   1.459  74.465  1.00 63.35           C
ATOM   4700  OG  SER B 298      -4.355   2.056  74.980  1.00 62.92           O
ATOM   4701  N   TYR B 299      -4.554  -0.948  72.848  1.00 62.05           N
ATOM   4702  CA  TYR B 299      -3.545  -1.627  72.044  1.00 60.95           C
ATOM   4703  C   TYR B 299      -3.359  -0.753  70.797  1.00 60.23           C
ATOM   4704  O   TYR B 299      -4.217  -0.723  69.910  1.00 60.36           O
ATOM   4705  CB  TYR B 299      -4.072  -3.021  71.685  1.00 60.80           C
ATOM   4706  CG  TYR B 299      -3.060  -3.985  71.112  1.00 61.03           C
ATOM   4707  CD1 TYR B 299      -2.624  -3.873  69.787  1.00 61.34           C
ATOM   4708  CD2 TYR B 299      -2.564  -5.037  71.885  1.00 60.90           C
ATOM   4709  CE1 TYR B 299      -1.716  -4.796  69.246  1.00 61.37           C
ATOM   4710  CE2 TYR B 299      -1.661  -5.961  71.359  1.00 60.98           C
ATOM   4711  CZ  TYR B 299      -1.240  -5.837  70.041  1.00 61.05           C
ATOM   4712  OH  TYR B 299      -0.340  -6.744  69.532  1.00 60.06           O
ATOM   4713  N   GLY B 300      -2.238  -0.035  70.758  1.00 59.53           N
ATOM   4714  CA  GLY B 300      -1.928   0.878  69.667  1.00 57.56           C
ATOM   4715  C   GLY B 300      -2.171   0.443  68.236  1.00 56.12           C
ATOM   4716  O   GLY B 300      -2.937   1.073  67.507  1.00 55.62           O
ATOM   4717  N   GLY B 301      -1.488  -0.619  67.822  1.00 55.26           N
ATOM   4718  CA  GLY B 301      -1.640  -1.119  66.469  1.00 52.66           C
ATOM   4719  C   GLY B 301      -2.803  -2.083  66.320  1.00 50.87           C
ATOM   4720  O   GLY B 301      -3.791  -2.045  67.068  1.00 51.04           O
ATOM   4721  N   VAL B 302      -2.694  -2.966  65.339  1.00 48.57           N
ATOM   4722  CA  VAL B 302      -3.761  -3.921  65.117  1.00 43.76           C
ATOM   4723  C   VAL B 302      -3.132  -5.300  65.023  1.00 39.86           C
ATOM   4724  O   VAL B 302      -1.918  -5.454  64.905  1.00 38.79           O
ATOM   4725  CB  VAL B 302      -4.545  -3.611  63.789  1.00 44.87           C
ATOM   4726  CG1 VAL B 302      -5.805  -4.486  63.688  1.00 42.32           C
ATOM   4727  CG2 VAL B 302      -4.947  -2.134  63.734  1.00 45.52           C
ATOM   4728  N   ILE B 303      -3.980  -6.303  65.114  1.00 35.81           N
ATOM   4729  CA  ILE B 303      -3.548  -7.670  64.978  1.00 31.38           C
ATOM   4730  C   ILE B 303      -4.200  -7.983  63.651  1.00 30.20           C
ATOM   4731  O   ILE B 303      -5.368  -7.657  63.469  1.00 32.79           O
ATOM   4732  CB  ILE B 303      -4.134  -8.499  66.114  1.00 31.81           C
ATOM   4733  CG1 ILE B 303      -3.345  -8.188  67.397  1.00 30.01           C
ATOM   4734  CG2 ILE B 303      -4.074  -9.980  65.775  1.00 31.09           C
ATOM   4735  CD1 ILE B 303      -3.917  -8.780  68.651  1.00 33.24           C
ATOM   4736  N   GLN B 304      -3.468  -8.571  62.710  1.00 27.10           N
ATOM   4737  CA  GLN B 304      -4.065  -8.885  61.413  1.00 25.60           C
ATOM   4738  C   GLN B 304      -5.125  -9.975  61.589  1.00 23.67           C
ATOM   4739  O   GLN B 304      -4.853 -10.988  62.199  1.00 22.68           O
ATOM   4740  CB  GLN B 304      -2.986  -9.382  60.451  1.00 27.23           C
ATOM   4741  CG  GLN B 304      -1.911  -8.334  60.146  1.00 31.86           C
ATOM   4742  CD  GLN B 304      -2.508  -7.074  59.536  1.00 35.98           C
ATOM   4743  OE1 GLN B 304      -3.161  -7.119  58.482  1.00 36.24           O
ATOM   4744  NE2 GLN B 304      -2.294  -5.929  60.208  1.00 39.27           N
ATOM   4745  N   ASP B 305      -6.321  -9.755  61.056  1.00 20.51           N
ATOM   4746  CA  ASP B 305      -7.407 -10.730  61.166  1.00 19.77           C
ATOM   4747  C   ASP B 305      -8.465 -10.365  60.122  1.00 19.29           C
ATOM   4748  O   ASP B 305      -8.276  -9.417  59.341  1.00 19.36           O
ATOM   4749  CB  ASP B 305      -7.985 -10.713  62.604  1.00 18.17           C
ATOM   4750  CG  ASP B 305      -8.699 -12.009  62.980  1.00 21.97           C
ATOM   4751  OD1 ASP B 305      -8.962 -12.848  62.087  1.00 18.65           O
ATOM   4752  OD2 ASP B 305      -9.004 -12.187  64.192  1.00 20.77           O
ATOM   4753  N   ASP B 306      -9.586 -11.095  60.123  1.00 17.20           N
ATOM   4754  CA  ASP B 306     -10.645 -10.918  59.124  1.00 16.72           C
ATOM   4755  C   ASP B 306     -11.296  -9.521  59.115  1.00 16.08           C
ATOM   4756  O   ASP B 306     -11.970  -9.168  58.170  1.00 18.09           O
ATOM   4757  CB  ASP B 306     -11.756 -11.962  59.344  1.00 16.17           C
ATOM   4758  CG  ASP B 306     -11.371 -13.351  58.835  1.00 18.77           C
```

FIGURE 1-71 (COORDINATES)

```
ATOM   4759  OD1 ASP B 306     -10.781 -13.442  57.737  1.00 16.53           O
ATOM   4760  OD2 ASP B 306     -11.712 -14.354  59.523  1.00 16.97           O
ATOM   4761  N   HIS B 307     -11.123  -8.762  60.188  1.00 16.29           N
ATOM   4762  CA  HIS B 307     -11.744  -7.445  60.230  1.00 17.67           C
ATOM   4763  C   HIS B 307     -10.989  -6.426  59.365  1.00 18.55           C
ATOM   4764  O   HIS B 307     -11.562  -5.388  58.995  1.00 20.10           O
ATOM   4765  CB  HIS B 307     -11.773  -6.921  61.677  1.00 17.87           C
ATOM   4766  CG  HIS B 307     -10.417  -6.682  62.234  1.00 19.19           C
ATOM   4767  ND1 HIS B 307      -9.442  -7.653  62.262  1.00 18.96           N
ATOM   4768  CD2 HIS B 307      -9.842  -5.555  62.720  1.00 19.82           C
ATOM   4769  CE1 HIS B 307      -8.324  -7.138  62.740  1.00 20.35           C
ATOM   4770  NE2 HIS B 307      -8.541  -5.862  63.026  1.00 20.22           N
ATOM   4771  N   ILE B 308      -9.736  -6.717  59.043  1.00 17.60           N
ATOM   4772  CA  ILE B 308      -8.880  -5.756  58.311  1.00 20.48           C
ATOM   4773  C   ILE B 308      -9.480  -5.182  57.016  1.00 20.68           C
ATOM   4774  O   ILE B 308      -9.542  -3.947  56.849  1.00 21.58           O
ATOM   4775  CB  ILE B 308      -7.471  -6.355  58.080  1.00 21.35           C
ATOM   4776  CG1 ILE B 308      -6.709  -6.456  59.417  1.00 23.65           C
ATOM   4777  CG2 ILE B 308      -6.655  -5.486  57.106  1.00 24.29           C
ATOM   4778  CD1 ILE B 308      -6.270  -5.095  60.069  1.00 24.41           C
ATOM   4779  N   PRO B 309      -9.963  -6.040  56.102  1.00 20.72           N
ATOM   4780  CA  PRO B 309     -10.561  -5.547  54.848  1.00 19.69           C
ATOM   4781  C   PRO B 309     -11.795  -4.679  55.091  1.00 21.55           C
ATOM   4782  O   PRO B 309     -12.195  -3.870  54.225  1.00 22.56           O
ATOM   4783  CB  PRO B 309     -10.918  -6.838  54.082  1.00 21.61           C
ATOM   4784  CG  PRO B 309     -10.037  -7.881  54.707  1.00 22.40           C
ATOM   4785  CD  PRO B 309      -9.947  -7.521  56.152  1.00 20.82           C
ATOM   4786  N   PHE B 310     -12.429  -4.832  56.251  1.00 19.52           N
ATOM   4787  CA  PHE B 310     -13.596  -4.025  56.579  1.00 21.00           C
ATOM   4788  C   PHE B 310     -13.162  -2.743  57.276  1.00 21.96           C
ATOM   4789  O   PHE B 310     -13.667  -1.647  56.961  1.00 22.67           O
ATOM   4790  CB  PHE B 310     -14.541  -4.822  57.469  1.00 18.09           C
ATOM   4791  CG  PHE B 310     -15.105  -6.035  56.782  1.00 19.97           C
ATOM   4792  CD1 PHE B 310     -14.441  -7.260  56.849  1.00 18.97           C
ATOM   4793  CD2 PHE B 310     -16.271  -5.940  56.027  1.00 19.22           C
ATOM   4794  CE1 PHE B 310     -14.957  -8.392  56.156  1.00 16.09           C
ATOM   4795  CE2 PHE B 310     -16.770  -7.036  55.353  1.00 19.04           C
ATOM   4796  CZ  PHE B 310     -16.097  -8.280  55.425  1.00 16.69           C
ATOM   4797  N   LEU B 311     -12.208  -2.886  58.191  1.00 23.24           N
ATOM   4798  CA  LEU B 311     -11.664  -1.763  58.952  1.00 23.95           C
ATOM   4799  C   LEU B 311     -11.130  -0.716  57.978  1.00 25.85           C
ATOM   4800  O   LEU B 311     -11.425   0.481  58.106  1.00 23.46           O
ATOM   4801  CB  LEU B 311     -10.507  -2.247  59.841  1.00 25.17           C
ATOM   4802  CG  LEU B 311      -9.827  -1.214  60.749  1.00 26.20           C
ATOM   4803  CD1 LEU B 311     -10.820  -0.839  61.832  1.00 28.88           C
ATOM   4804  CD2 LEU B 311      -8.552  -1.806  61.376  1.00 26.29           C
ATOM   4805  N   ARG B 312     -10.363  -1.176  56.991  1.00 26.45           N
ATOM   4806  CA  ARG B 312      -9.755  -0.262  56.040  1.00 26.78           C
ATOM   4807  C   ARG B 312     -10.743   0.467  55.146  1.00 26.21           C
ATOM   4808  O   ARG B 312     -10.348   1.409  54.460  1.00 26.62           O
ATOM   4809  CB  ARG B 312      -8.681  -0.978  55.203  1.00 28.72           C
ATOM   4810  CG  ARG B 312      -9.176  -1.891  54.095  1.00 32.33           C
ATOM   4811  CD  ARG B 312      -7.944  -2.466  53.374  1.00 34.48           C
ATOM   4812  NE  ARG B 312      -8.220  -3.416  52.283  1.00 36.91           N
ATOM   4813  CZ  ARG B 312      -8.638  -3.083  51.062  1.00 37.78           C
ATOM   4814  NH1 ARG B 312      -8.859  -1.805  50.743  1.00 37.33           N
ATOM   4815  NH2 ARG B 312      -8.790  -4.025  50.134  1.00 36.85           N
ATOM   4816  N   ARG B 313     -12.007   0.058  55.172  1.00 23.14           N
ATOM   4817  CA  ARG B 313     -13.053   0.695  54.398  1.00 24.23           C
ATOM   4818  C   ARG B 313     -14.023   1.459  55.285  1.00 23.95           C
ATOM   4819  O   ARG B 313     -15.090   1.884  54.835  1.00 25.48           O
ATOM   4820  CB  ARG B 313     -13.802  -0.323  53.551  1.00 23.02           C
ATOM   4821  CG  ARG B 313     -12.919  -0.999  52.491  1.00 22.36           C
ATOM   4822  CD  ARG B 313     -13.769  -1.983  51.705  1.00 24.62           C
ATOM   4823  NE  ARG B 313     -13.185  -2.414  50.437  1.00 26.71           N
ATOM   4824  CZ  ARG B 313     -12.288  -3.383  50.304  1.00 28.71           C
ATOM   4825  NH1 ARG B 313     -11.839  -4.035  51.380  1.00 25.90           N
ATOM   4826  NH2 ARG B 313     -11.876  -3.740  49.081  1.00 27.09           N
```

FIGURE 1-72 (COORDINATES)

```
ATOM   4827  N   GLY B 314     -13.648   1.607  56.554  1.00 25.79           N
ATOM   4828  CA  GLY B 314     -14.457   2.394  57.482  1.00 25.70           C
ATOM   4829  C   GLY B 314     -15.483   1.714  58.372  1.00 25.44           C
ATOM   4830  O   GLY B 314     -16.180   2.392  59.118  1.00 25.01           O
ATOM   4831  N   VAL B 315     -15.597   0.388  58.305  1.00 25.52           N
ATOM   4832  CA  VAL B 315     -16.569  -0.319  59.144  1.00 21.94           C
ATOM   4833  C   VAL B 315     -16.050  -0.322  60.602  1.00 20.32           C
ATOM   4834  O   VAL B 315     -14.872  -0.594  60.853  1.00 22.22           O
ATOM   4835  CB  VAL B 315     -16.732  -1.804  58.682  1.00 20.62           C
ATOM   4836  CG1 VAL B 315     -17.677  -2.548  59.639  1.00 21.53           C
ATOM   4837  CG2 VAL B 315     -17.282  -1.872  57.252  1.00 21.04           C
ATOM   4838  N   PRO B 316     -16.914   0.015  61.570  1.00 20.92           N
ATOM   4839  CA  PRO B 316     -16.473   0.020  62.969  1.00 20.84           C
ATOM   4840  C   PRO B 316     -16.302  -1.445  63.374  1.00 19.40           C
ATOM   4841  O   PRO B 316     -17.144  -2.278  63.035  1.00 21.93           O
ATOM   4842  CB  PRO B 316     -17.641   0.673  63.718  1.00 21.14           C
ATOM   4843  CG  PRO B 316     -18.271   1.592  62.651  1.00 21.99           C
ATOM   4844  CD  PRO B 316     -18.242   0.640  61.419  1.00 22.29           C
ATOM   4845  N   VAL B 317     -15.243  -1.706  64.113  1.00 19.79           N
ATOM   4846  CA  VAL B 317     -14.926  -3.083  64.523  1.00 19.99           C
ATOM   4847  C   VAL B 317     -14.748  -3.206  66.028  1.00 20.48           C
ATOM   4848  O   VAL B 317     -14.109  -2.365  66.658  1.00 21.11           O
ATOM   4849  CB  VAL B 317     -13.610  -3.536  63.891  1.00 19.15           C
ATOM   4850  CG1 VAL B 317     -13.228  -4.978  64.398  1.00 18.74           C
ATOM   4851  CG2 VAL B 317     -13.735  -3.549  62.344  1.00 19.37           C
ATOM   4852  N   LEU B 318     -15.319  -4.267  66.591  1.00 19.77           N
ATOM   4853  CA  LEU B 318     -15.123  -4.587  68.004  1.00 21.17           C
ATOM   4854  C   LEU B 318     -14.402  -5.946  67.842  1.00 21.25           C
ATOM   4855  O   LEU B 318     -15.037  -6.937  67.513  1.00 22.86           O
ATOM   4856  CB  LEU B 318     -16.489  -4.728  68.670  1.00 24.94           C
ATOM   4857  CG  LEU B 318     -16.524  -4.857  70.192  1.00 27.81           C
ATOM   4858  CD1 LEU B 318     -15.701  -3.743  70.855  1.00 28.49           C
ATOM   4859  CD2 LEU B 318     -17.977  -4.827  70.626  1.00 25.13           C
ATOM   4860  N   HIS B 319     -13.083  -5.974  68.037  1.00 21.45           N
ATOM   4861  CA  HIS B 319     -12.288  -7.192  67.818  1.00 20.89           C
ATOM   4862  C   HIS B 319     -12.118  -7.994  69.081  1.00 20.80           C
ATOM   4863  O   HIS B 319     -11.246  -7.695  69.905  1.00 23.26           O
ATOM   4864  CB  HIS B 319     -10.920  -6.804  67.271  1.00 21.25           C
ATOM   4865  CG  HIS B 319     -10.168  -7.920  66.609  1.00 19.32           C
ATOM   4866  ND1 HIS B 319      -8.884  -7.749  66.139  1.00 19.09           N
ATOM   4867  CD2 HIS B 319     -10.514  -9.199  66.307  1.00 19.18           C
ATOM   4868  CE1 HIS B 319      -8.466  -8.866  65.572  1.00 21.03           C
ATOM   4869  NE2 HIS B 319      -9.436  -9.764  65.659  1.00 17.94           N
ATOM   4870  N   LEU B 320     -12.942  -9.026  69.214  1.00 21.14           N
ATOM   4871  CA  LEU B 320     -12.892  -9.876  70.404  1.00 19.67           C
ATOM   4872  C   LEU B 320     -11.858 -10.998  70.218  1.00 20.94           C
ATOM   4873  O   LEU B 320     -12.195 -12.170  69.987  1.00 19.88           O
ATOM   4874  CB  LEU B 320     -14.292 -10.427  70.711  1.00 22.77           C
ATOM   4875  CG  LEU B 320     -15.394  -9.354  70.936  1.00 25.88           C
ATOM   4876  CD1 LEU B 320     -16.693 -10.004  71.467  1.00 25.99           C
ATOM   4877  CD2 LEU B 320     -14.901  -8.287  71.896  1.00 27.06           C
ATOM   4878  N   ILE B 321     -10.596 -10.594  70.277  1.00 18.99           N
ATOM   4879  CA  ILE B 321      -9.457 -11.496  70.179  1.00 20.40           C
ATOM   4880  C   ILE B 321      -8.604 -11.155  71.398  1.00 22.76           C
ATOM   4881  O   ILE B 321      -8.348  -9.974  71.694  1.00 23.32           O
ATOM   4882  CB  ILE B 321      -8.644 -11.294  68.850  1.00 18.84           C
ATOM   4883  CG1 ILE B 321      -7.551 -12.358  68.754  1.00 21.08           C
ATOM   4884  CG2 ILE B 321      -7.951  -9.899  68.787  1.00 20.67           C
ATOM   4885  CD1 ILE B 321      -6.835 -12.324  67.405  1.00 20.34           C
ATOM   4886  N   PRO B 322      -8.161 -12.176  72.139  1.00 21.96           N
ATOM   4887  CA  PRO B 322      -7.344 -11.882  73.329  1.00 22.53           C
ATOM   4888  C   PRO B 322      -5.893 -11.523  73.072  1.00 24.66           C
ATOM   4889  O   PRO B 322      -5.298 -11.896  72.060  1.00 23.94           O
ATOM   4890  CB  PRO B 322      -7.408 -13.185  74.153  1.00 22.86           C
ATOM   4891  CG  PRO B 322      -8.370 -14.113  73.398  1.00 23.99           C
ATOM   4892  CD  PRO B 322      -8.393 -13.622  71.977  1.00 22.68           C
ATOM   4893  N   SER B 323      -5.308 -10.797  74.020  1.00 24.83           N
ATOM   4894  CA  SER B 323      -3.890 -10.502  73.927  1.00 29.59           C
```

FIGURE 1-73 (COORDINATES)

```
ATOM   4895  C   SER B 323      -3.456 -10.621  75.368  1.00 29.68           C
ATOM   4896  O   SER B 323      -3.954  -9.889  76.227  1.00 30.61           O
ATOM   4897  CB  SER B 323      -3.599  -9.095  73.414  1.00 32.00           C
ATOM   4898  OG  SER B 323      -2.215  -9.026  73.088  1.00 36.44           O
ATOM   4899  N   PRO B 324      -2.546 -11.564  75.661  1.00 28.35           N
ATOM   4900  CA  PRO B 324      -1.912 -12.502  74.721  1.00 26.21           C
ATOM   4901  C   PRO B 324      -2.858 -13.539  74.112  1.00 24.19           C
ATOM   4902  O   PRO B 324      -3.981 -13.738  74.584  1.00 23.33           O
ATOM   4903  CB  PRO B 324      -0.827 -13.165  75.575  1.00 27.27           C
ATOM   4904  CG  PRO B 324      -1.464 -13.185  76.939  1.00 28.68           C
ATOM   4905  CD  PRO B 324      -2.124 -11.830  77.050  1.00 29.16           C
ATOM   4906  N   PHE B 325      -2.384 -14.168  73.050  1.00 21.62           N
ATOM   4907  CA  PHE B 325      -3.129 -15.224  72.375  1.00 22.00           C
ATOM   4908  C   PHE B 325      -3.031 -16.421  73.316  1.00 21.33           C
ATOM   4909  O   PHE B 325      -2.169 -16.469  74.197  1.00 20.02           O
ATOM   4910  CB  PHE B 325      -2.422 -15.645  71.084  1.00 20.96           C
ATOM   4911  CG  PHE B 325      -2.537 -14.652  69.942  1.00 21.65           C
ATOM   4912  CD1 PHE B 325      -3.323 -13.532  70.038  1.00 22.42           C
ATOM   4913  CD2 PHE B 325      -1.872 -14.898  68.752  1.00 21.85           C
ATOM   4914  CE1 PHE B 325      -3.456 -12.650  68.948  1.00 23.09           C
ATOM   4915  CE2 PHE B 325      -2.001 -14.021  67.654  1.00 23.87           C
ATOM   4916  CZ  PHE B 325      -2.798 -12.902  67.764  1.00 21.57           C
ATOM   4917  N   PRO B 326      -3.919 -17.408  73.137  1.00 20.39           N
ATOM   4918  CA  PRO B 326      -3.900 -18.621  73.969  1.00 20.58           C
ATOM   4919  C   PRO B 326      -2.504 -19.260  73.893  1.00 21.70           C
ATOM   4920  O   PRO B 326      -1.840 -19.236  72.848  1.00 21.16           O
ATOM   4921  CB  PRO B 326      -4.950 -19.513  73.290  1.00 21.38           C
ATOM   4922  CG  PRO B 326      -5.961 -18.528  72.805  1.00 21.59           C
ATOM   4923  CD  PRO B 326      -5.092 -17.383  72.249  1.00 20.33           C
ATOM   4924  N   GLU B 327      -2.032 -19.843  74.989  1.00 21.95           N
ATOM   4925  CA  GLU B 327      -0.718 -20.480  74.977  1.00 23.03           C
ATOM   4926  C   GLU B 327      -0.604 -21.547  73.902  1.00 22.17           C
ATOM   4927  O   GLU B 327       0.481 -21.771  73.368  1.00 23.10           O
ATOM   4928  CB  GLU B 327      -0.410 -21.140  76.328  1.00 26.16           C
ATOM   4929  CG  GLU B 327      -0.273 -20.171  77.489  1.00 35.85           C
ATOM   4930  CD  GLU B 327      -0.052 -20.898  78.813  1.00 39.61           C
ATOM   4931  OE1 GLU B 327      -0.155 -22.153  78.838  1.00 40.01           O
ATOM   4932  OE2 GLU B 327       0.215 -20.205  79.822  1.00 44.30           O
ATOM   4933  N   VAL B 328      -1.728 -22.198  73.571  1.00 21.69           N
ATOM   4934  CA  VAL B 328      -1.702 -23.262  72.561  1.00 21.15           C
ATOM   4935  C   VAL B 328      -1.842 -22.794  71.115  1.00 20.95           C
ATOM   4936  O   VAL B 328      -1.891 -23.634  70.236  1.00 19.19           O
ATOM   4937  CB  VAL B 328      -2.812 -24.302  72.804  1.00 21.49           C
ATOM   4938  CG1 VAL B 328      -2.582 -24.995  74.175  1.00 23.04           C
ATOM   4939  CG2 VAL B 328      -4.203 -23.630  72.725  1.00 20.87           C
ATOM   4940  N   TRP B 329      -1.870 -21.470  70.884  1.00 20.13           N
ATOM   4941  CA  TRP B 329      -2.029 -20.923  69.524  1.00 19.49           C
ATOM   4942  C   TRP B 329      -1.099 -21.568  68.482  1.00 19.15           C
ATOM   4943  O   TRP B 329       0.128 -21.633  68.643  1.00 19.58           O
ATOM   4944  CB  TRP B 329      -1.823 -19.392  69.565  1.00 19.83           C
ATOM   4945  CG  TRP B 329      -1.975 -18.694  68.220  1.00 20.15           C
ATOM   4946  CD1 TRP B 329      -3.134 -18.287  67.635  1.00 22.66           C
ATOM   4947  CD2 TRP B 329      -0.913 -18.274  67.351  1.00 21.44           C
ATOM   4948  NE1 TRP B 329      -2.859 -17.619  66.453  1.00 21.35           N
ATOM   4949  CE2 TRP B 329      -1.504 -17.599  66.263  1.00 21.56           C
ATOM   4950  CE3 TRP B 329       0.486 -18.405  67.389  1.00 22.05           C
ATOM   4951  CZ2 TRP B 329      -0.752 -17.045  65.219  1.00 22.98           C
ATOM   4952  CZ3 TRP B 329       1.236 -17.855  66.339  1.00 24.00           C
ATOM   4953  CH2 TRP B 329       0.612 -17.184  65.274  1.00 23.67           C
ATOM   4954  N   HIS B 330      -1.709 -22.036  67.393  1.00 19.32           N
ATOM   4955  CA  HIS B 330      -1.029 -22.678  66.290  1.00 18.57           C
ATOM   4956  C   HIS B 330      -0.152 -23.849  66.644  1.00 20.49           C
ATOM   4957  O   HIS B 330       0.892 -24.074  66.036  1.00 22.41           O
ATOM   4958  CB  HIS B 330      -0.299 -21.659  65.400  1.00 18.85           C
ATOM   4959  CG  HIS B 330      -1.252 -20.818  64.608  1.00 19.84           C
ATOM   4960  ND1 HIS B 330      -0.845 -19.934  63.627  1.00 19.41           N
ATOM   4961  CD2 HIS B 330      -2.604 -20.730  64.663  1.00 17.01           C
ATOM   4962  CE1 HIS B 330      -1.912 -19.335  63.111  1.00 18.05           C
```

FIGURE 1-74 (COORDINATES)

```
ATOM   4963  NE2 HIS B 330      -2.993  -19.801  63.724  1.00 19.07           N
ATOM   4964  N   THR B 331      -0.637  -24.619  67.620  1.00 20.45           N
ATOM   4965  CA  THR B 331       0.011  -25.887  67.972  1.00 20.73           C
ATOM   4966  C   THR B 331      -1.087  -26.966  67.993  1.00 19.87           C
ATOM   4967  O   THR B 331      -2.280  -26.655  68.034  1.00 18.51           O
ATOM   4968  CB  THR B 331       0.655  -25.894  69.367  1.00 21.71           C
ATOM   4969  OG1 THR B 331      -0.361  -25.935  70.366  1.00 21.67           O
ATOM   4970  CG2 THR B 331       1.559  -24.672  69.543  1.00 23.23           C
ATOM   4971  N   MET B 332      -0.668  -28.231  67.986  1.00 21.23           N
ATOM   4972  CA  MET B 332      -1.609  -29.351  68.037  1.00 20.42           C
ATOM   4973  C   MET B 332      -2.352  -29.393  69.375  1.00 21.20           C
ATOM   4974  O   MET B 332      -3.332  -30.116  69.514  1.00 21.02           O
ATOM   4975  CB  MET B 332      -0.873  -30.678  67.811  1.00 19.99           C
ATOM   4976  CG  MET B 332      -0.388  -30.851  66.417  1.00 18.77           C
ATOM   4977  SD  MET B 332      -1.721  -30.732  65.175  1.00 21.22           S
ATOM   4978  CE  MET B 332      -0.773  -30.912  63.674  1.00 21.75           C
ATOM   4979  N   ASP B 333      -1.899  -28.619  70.358  1.00 20.25           N
ATOM   4980  CA  ASP B 333      -2.579  -28.583  71.641  1.00 21.40           C
ATOM   4981  C   ASP B 333      -3.766  -27.630  71.644  1.00 20.72           C
ATOM   4982  O   ASP B 333      -4.439  -27.473  72.660  1.00 20.18           O
ATOM   4983  CB  ASP B 333      -1.607  -28.235  72.773  1.00 23.09           C
ATOM   4984  CG  ASP B .333     -0.565  -29.335  72.993  1.00 26.62           C
ATOM   4985  OD1 ASP B 333      -0.938  -30.532  72.948  1.00 24.87           O
ATOM   4986  OD2 ASP B 333       0.617  -29.005  73.222  1.00 30.48           O
ATOM   4987  N   ASP B 334      -4.041  -26.977  70.507  1.00 18.92           N
ATOM   4988  CA  ASP B 334      -5.217  -26.113  70.495  1.00 17.71           C
ATOM   4989  C   ASP B 334      -6.358  -27.078  70.174  1.00 18.78           C
ATOM   4990  O   ASP B 334      -6.868  -27.171  69.058  1.00 17.27           O
ATOM   4991  CB  ASP B 334      -5.099  -25.011  69.441  1.00 19.36           C
ATOM   4992  CG  ASP B 334      -6.339  -24.119  69.425  1.00 18.33           C
ATOM   4993  OD1 ASP B 334      -7.218  -24.258  70.314  1.00 18.29           O
ATOM   4994  OD2 ASP B 334      -6.459  -23.308  68.492  1.00 20.02           O
ATOM   4995  N   ASN B 335      -6.737  -27.816  71.213  1.00 19.65           N
ATOM   4996  CA  ASN B 335      -7.735  -28.864  71.110  1.00 19.72           C
ATOM   4997  C   ASN B 335      -8.830  -28.763  72.170  1.00 19.71           C
ATOM   4998  O   ASN B 335      -8.853  -27.848  72.992  1.00 18.95           O
ATOM   4999  CB  ASN B 335      -7.008  -30.225  71.225  1.00 19.87           C
ATOM   5000  CG  ASN B 335      -6.212  -30.332  72.519  1.00 21.39           C
ATOM   5001  OD1 ASN B 335      -6.515  -29.640  73.486  1.00 21.70           O
ATOM   5002  ND2 ASN B 335      -5.192  -31.207  72.545  1.00 22.02           N
ATOM   5003  N   GLU B 336      -9.742  -29.719  72.138  1.00 19.78           N
ATOM   5004  CA  GLU B 336     -10.853  -29.709  73.055  1.00 20.55           C
ATOM   5005  C   GLU B 336     -10.433  -29.773  74.529  1.00 20.18           C
ATOM   5006  O   GLU B 336     -10.983  -29.041  75.358  1.00 19.40           O
ATOM   5007  CB  GLU B 336     -11.829  -30.844  72.715  1.00 19.80           C
ATOM   5008  CG  GLU B 336     -13.104  -30.815  73.523  1.00 20.56           C
ATOM   5009  CD  GLU B 336     -14.061  -31.950  73.188  1.00 24.46           C
ATOM   5010  OE1 GLU B 336     -13.784  -32.734  72.255  1.00 26.51           O
ATOM   5011  OE2 GLU B 336     -15.108  -32.063  73.864  1.00 24.86           O
ATOM   5012  N   GLU B 337      -9.438  -30.601  74.840  1.00 21.02           N
ATOM   5013  CA  GLU B 337      -8.989  -30.758  76.234  1.00 24.71           C
ATOM   5014  C   GLU B 337      -8.472  -29.462  76.851  1.00 24.67           C
ATOM   5015  O   GLU B 337      -8.580  -29.235  78.074  1.00 25.34           O
ATOM   5016  CB  GLU B 337      -7.908  -31.847  76.271  1.00 29.00           C
ATOM   5017  CG  GLU B 337      -7.310  -32.142  77.614  1.00 37.91           C
ATOM   5018  CD  GLU B 337      -6.398  -33.358  77.556  1.00 42.48           C
ATOM   5019  OE1 GLU B 337      -6.928  -34.499  77.543  1.00 45.48           O
ATOM   5020  OE2 GLU B 337      -5.154  -33.179  77.501  1.00 44.22           O
ATOM   5021  N   ASN B 338      -7.925  -28.581  76.019  1.00 23.08           N
ATOM   5022  CA  ASN B 338      -7.414  -27.335  76.577  1.00 22.27           C
ATOM   5023  C   ASN B 338      -8.391  -26.173  76.653  1.00 21.73           C
ATOM   5024  O   ASN B 338      -8.030  -25.083  77.097  1.00 22.97           O
ATOM   5025  CB  ASN B 338      -6.120  -26.960  75.867  1.00 23.29           C
ATOM   5026  CG  ASN B 338      -5.008  -27.915  76.233  1.00 27.15           C
ATOM   5027  OD1 ASN B 338      -4.341  -28.506  75.387  1.00 27.90           O
ATOM   5028  ND2 ASN B 338      -4.831  -28.097  77.533  1.00 30.54           N
ATOM   5029  N   LEU B 339      -9.634  -26.414  76.264  1.00 22.28           N
ATOM   5030  CA  LEU B 339     -10.661  -25.372  76.359  1.00 21.90           C
```

FIGURE 1-75 (COORDINATES)

```
ATOM   5031  C    LEU B 339     -11.148 -25.291  77.790  1.00 23.93           C
ATOM   5032  O    LEU B 339     -11.009 -26.258  78.559  1.00 23.19           O
ATOM   5033  CB   LEU B 339     -11.861 -25.691  75.487  1.00 20.92           C
ATOM   5034  CG   LEU B 339     -11.590 -25.753  73.992  1.00 20.59           C
ATOM   5035  CD1  LEU B 339     -12.817 -26.219  73.276  1.00 19.30           C
ATOM   5036  CD2  LEU B 339     -11.137 -24.358  73.500  1.00 19.17           C
ATOM   5037  N    ASP B 340     -11.715 -24.138  78.146  1.00 22.58           N
ATOM   5038  CA   ASP B 340     -12.235 -23.945  79.484  1.00 24.94           C
ATOM   5039  C    ASP B 340     -13.714 -23.659  79.414  1.00 26.30           C
ATOM   5040  O    ASP B 340     -14.155 -22.568  78.994  1.00 24.51           O
ATOM   5041  CB   ASP B 340     -11.514 -22.813  80.191  1.00 25.24           C
ATOM   5042  CG   ASP B 340     -11.946 -22.691  81.639  1.00 31.45           C
ATOM   5043  OD1  ASP B 340     -12.536 -21.660  82.016  1.00 29.00           O
ATOM   5044  OD2  ASP B 340     -11.708 -23.658  82.398  1.00 31.72           O
ATOM   5045  N    GLU B 341     -14.487 -24.657  79.821  1.00 25.45           N
ATOM   5046  CA   GLU B 341     -15.943 -24.591  79.806  1.00 27.28           C
ATOM   5047  C    GLU B 341     -16.540 -23.319  80.439  1.00 27.43           C
ATOM   5048  O    GLU B 341     -17.376 -22.649  79.831  1.00 25.60           O
ATOM   5049  CB   GLU B 341     -16.507 -25.832  80.526  1.00 29.69           C
ATOM   5050  CG   GLU B 341     -18.011 -25.905  80.517  1.00 36.71           C
ATOM   5051  CD   GLU B 341     -18.556 -27.028  81.393  1.00 39.70           C
ATOM   5052  OE1  GLU B 341     -18.142 -27.128  82.566  1.00 42.99           O
ATOM   5053  OE2  GLU B 341     -19.408 -27.798  80.912  1.00 42.10           O
ATOM   5054  N    SER B 342     -16.122 -22.996  81.662  1.00 27.80           N
ATOM   5055  CA   SER B 342     -16.677 -21.831  82.351  1.00 28.96           C
ATOM   5056  C    SER B 342     -16.430 -20.514  81.625  1.00 27.16           C
ATOM   5057  O    SER B 342     -17.332 -19.685  81.501  1.00 27.53           O
ATOM   5058  CB   SER B 342     -16.127 -21.742  83.767  1.00 30.37           C
ATOM   5059  OG   SER B 342     -16.793 -22.707  84.554  1.00 35.39           O
ATOM   5060  N    THR B 343     -15.211 -20.338  81.147  1.00 24.78           N
ATOM   5061  CA   THR B 343     -14.874 -19.111  80.430  1.00 25.37           C
ATOM   5062  C    THR B 343     -15.792 -18.905  79.232  1.00 24.59           C
ATOM   5063  O    THR B 343     -16.320 -17.796  79.019  1.00 24.02           O
ATOM   5064  CB   THR B 343     -13.424 -19.155  79.945  1.00 26.13           C
ATOM   5065  OG1  THR B 343     -12.558 -19.335  81.081  1.00 27.32           O
ATOM   5066  CG2  THR B 343     -13.053 -17.841  79.223  1.00 25.47           C
ATOM   5067  N    ILE B 344     -16.008 -19.974  78.465  1.00 23.52           N
ATOM   5068  CA   ILE B 344     -16.860 -19.895  77.269  1.00 22.42           C
ATOM   5069  C    ILE B 344     -18.309 -19.643  77.650  1.00 23.46           C
ATOM   5070  O    ILE B 344     -19.010 -18.856  77.028  1.00 22.31           O
ATOM   5071  CB   ILE B 344     -16.741 -21.196  76.416  1.00 19.55           C
ATOM   5072  CG1  ILE B 344     -15.282 -21.389  75.991  1.00 21.82           C
ATOM   5073  CG2  ILE B 344     -17.620 -21.115  75.155  1.00 21.55           C
ATOM   5074  CD1  ILE B 344     -14.996 -22.785  75.409  1.00 20.39           C
ATOM   5075  N    ASP B 345     -18.763 -20.294  78.720  1.00 22.10           N
ATOM   5076  CA   ASP B 345     -20.136 -20.114  79.141  1.00 21.44           C
ATOM   5077  C    ASP B 345     -20.322 -18.650  79.578  1.00 21.71           C
ATOM   5078  O    ASP B 345     -21.342 -18.041  79.248  1.00 24.21           O
ATOM   5079  CB   ASP B 345     -20.408 -21.105  80.290  1.00 22.03           C
ATOM   5080  CG   ASP B 345     -21.839 -21.107  80.767  1.00 25.25           C
ATOM   5081  OD1  ASP B 345     -22.791 -21.011  79.962  1.00 25.25           O
ATOM   5082  OD2  ASP B 345     -22.010 -21.260  82.009  1.00 28.60           O
ATOM   5083  N    ASN B 346     -19.339 -18.093  80.293  1.00 23.04           N
ATOM   5084  CA   ASN B 346     -19.418 -16.694  80.748  1.00 23.28           C
ATOM   5085  C    ASN B 346     -19.468 -15.746  79.524  1.00 23.00           C
ATOM   5086  O    ASN B 346     -20.291 -14.832  79.479  1.00 22.61           O
ATOM   5087  CB   ASN B 346     -18.211 -16.324  81.599  1.00 22.86           C
ATOM   5088  CG   ASN B 346     -18.220 -17.031  82.982  1.00 24.36           C
ATOM   5089  OD1  ASN B 346     -19.265 -17.525  83.438  1.00 27.00           O
ATOM   5090  ND2  ASN B 346     -17.072 -17.058  83.627  1.00 25.23           N
ATOM   5091  N    LEU B 347     -18.595 -15.986  78.541  1.00 22.69           N
ATOM   5092  CA   LEU B 347     -18.583 -15.130  77.345  1.00 21.55           C
ATOM   5093  C    LEU B 347     -19.868 -15.266  76.536  1.00 23.12           C
ATOM   5094  O    LEU B 347     -20.317 -14.279  75.940  1.00 22.14           O
ATOM   5095  CB   LEU B 347     -17.323 -15.383  76.490  1.00 21.97           C
ATOM   5096  CG   LEU B 347     -15.976 -14.977  77.121  1.00 20.91           C
ATOM   5097  CD1  LEU B 347     -14.802 -15.492  76.314  1.00 20.84           C
ATOM   5098  CD2  LEU B 347     -15.868 -13.450  77.231  1.00 23.82           C
```

FIGURE 1-76 (COORDINATES)

```
ATOM   5099  N    ASN B 348     -20.468 -16.467  76.482  1.00 20.38           N
ATOM   5100  CA   ASN B 348     -21.744 -16.635  75.799  1.00 20.75           C
ATOM   5101  C    ASN B 348     -22.782 -15.716  76.442  1.00 22.17           C
ATOM   5102  O    ASN B 348     -23.544 -15.014  75.767  1.00 20.91           O
ATOM   5103  CB   ASN B 348     -22.244 -18.077  75.875  1.00 21.13           C
ATOM   5104  CG   ASN B 348     -21.539 -18.986  74.879  1.00 24.03           C
ATOM   5105  OD1  ASN B 348     -20.952 -18.501  73.917  1.00 23.89           O
ATOM   5106  ND2  ASN B 348     -21.606 -20.306  75.102  1.00 23.16           N
ATOM   5107  N    LYS B 349     -22.823 -15.720  77.763  1.00 22.34           N
ATOM   5108  CA   LYS B 349     -23.784 -14.858  78.443  1.00 23.25           C
ATOM   5109  C    LYS B 349     -23.549 -13.383  78.130  1.00 22.86           C
ATOM   5110  O    LYS B 349     -24.496 -12.647  77.804  1.00 24.76           O
ATOM   5111  CB   LYS B 349     -23.706 -15.120  79.956  1.00 23.90           C
ATOM   5112  CG   LYS B 349     -24.248 -16.499  80.288  1.00 24.79           C
ATOM   5113  CD   LYS B 349     -24.017 -16.852  81.752  1.00 26.17           C
ATOM   5114  CE   LYS B 349     -24.560 -18.246  82.071  1.00 27.90           C
ATOM   5115  NZ   LYS B 349     -24.280 -18.542  83.533  1.00 29.87           N
ATOM   5116  N    ILE B 350     -22.297 -12.959  78.236  1.00 23.64           N
ATOM   5117  CA   ILE B 350     -21.928 -11.566  77.988  1.00 24.10           C
ATOM   5118  C    ILE B 350     -22.261 -11.135  76.556  1.00 25.52           C
ATOM   5119  O    ILE B 350     -22.800 -10.055  76.336  1.00 25.14           O
ATOM   5120  CB   ILE B 350     -20.432 -11.346  78.231  1.00 23.89           C
ATOM   5121  CG1  ILE B 350     -20.095 -11.497  79.732  1.00 24.63           C
ATOM   5122  CG2  ILE B 350     -20.035  -9.937  77.775  1.00 24.15           C
ATOM   5123  CD1  ILE B 350     -18.633 -11.720  80.028  1.00 24.17           C
ATOM   5124  N    LEU B 351     -21.918 -11.974  75.582  1.00 23.97           N
ATOM   5125  CA   LEU B 351     -22.194 -11.654  74.166  1.00 23.09           C
ATOM   5126  C    LEU B 351     -23.678 -11.601  73.879  1.00 22.52           C
ATOM   5127  O    LEU B 351     -24.168 -10.719  73.173  1.00 23.41           O
ATOM   5128  CB   LEU B 351     -21.562 -12.722  73.263  1.00 20.20           C
ATOM   5129  CG   LEU B 351     -21.721 -12.536  71.750  1.00 19.99           C
ATOM   5130  CD1  LEU B 351     -20.990 -11.236  71.344  1.00 25.06           C
ATOM   5131  CD2  LEU B 351     -21.127 -13.762  71.018  1.00 20.41           C
ATOM   5132  N    GLN B 352     -24.405 -12.585  74.391  1.00 23.23           N
ATOM   5133  CA   GLN B 352     -25.832 -12.645  74.170  1.00 23.45           C
ATOM   5134  C    GLN B 352     -26.509 -11.399  74.735  1.00 24.58           C
ATOM   5135  O    GLN B 352     -27.387 -10.834  74.087  1.00 25.73           O
ATOM   5136  CB   GLN B 352     -26.408 -13.918  74.781  1.00 23.46           C
ATOM   5137  CG   GLN B 352     -26.140 -15.156  73.918  1.00 23.65           C
ATOM   5138  CD   GLN B 352     -26.448 -16.448  74.645  1.00 27.55           C
ATOM   5139  OE1  GLN B 352     -27.365 -16.501  75.468  1.00 28.23           O
ATOM   5140  NE2  GLN B 352     -25.706 -17.507  74.327  1.00 25.33           N
ATOM   5141  N    VAL B 353     -26.130 -10.981  75.935  1.00 25.12           N
ATOM   5142  CA   VAL B 353     -26.730  -9.764  76.479  1.00 25.56           C
ATOM   5143  C    VAL B 353     -26.383  -8.590  75.555  1.00 26.35           C
ATOM   5144  O    VAL B 353     -27.271  -7.821  75.169  1.00 27.13           O
ATOM   5145  CB   VAL B 353     -26.217  -9.442  77.900  1.00 27.98           C
ATOM   5146  CG1  VAL B 353     -26.690  -8.025  78.308  1.00 26.33           C
ATOM   5147  CG2  VAL B 353     -26.768 -10.483  78.884  1.00 27.01           C
ATOM   5148  N    PHE B 354     -25.106  -8.481  75.185  1.00 26.06           N
ATOM   5149  CA   PHE B 354     -24.651  -7.398  74.317  1.00 25.26           C
ATOM   5150  C    PHE B 354     -25.485  -7.335  73.053  1.00 25.13           C
ATOM   5151  O    PHE B 354     -25.877  -6.250  72.626  1.00 25.13           O
ATOM   5152  CB   PHE B 354     -23.175  -7.566  73.936  1.00 24.90           C
ATOM   5153  CG   PHE B 354     -22.658  -6.486  73.006  1.00 23.92           C
ATOM   5154  CD1  PHE B 354     -21.981  -5.376  73.517  1.00 23.72           C
ATOM   5155  CD2  PHE B 354     -22.890  -6.560  71.630  1.00 24.06           C
ATOM   5156  CE1  PHE B 354     -21.534  -4.348  72.682  1.00 22.95           C
ATOM   5157  CE2  PHE B 354     -22.444  -5.524  70.770  1.00 23.32           C
ATOM   5158  CZ   PHE B 354     -21.770  -4.430  71.295  1.00 23.63           C
ATOM   5159  N    VAL B 355     -25.763  -8.480  72.439  1.00 25.00           N
ATOM   5160  CA   VAL B 355     -26.541  -8.485  71.213  1.00 25.06           C
ATOM   5161  C    VAL B 355     -28.000  -8.043  71.399  1.00 27.41           C
ATOM   5162  O    VAL B 355     -28.548  -7.265  70.596  1.00 27.15           O
ATOM   5163  CB   VAL B 355     -26.481  -9.878  70.520  1.00 25.83           C
ATOM   5164  CG1  VAL B 355     -27.489  -9.948  69.411  1.00 24.08           C
ATOM   5165  CG2  VAL B 355     -25.066 -10.126  69.977  1.00 26.89           C
ATOM   5166  N    LEU B 356     -28.641  -8.523  72.458  1.00 27.04           N
```

FIGURE 1-77 (COORDINATES)

```
ATOM   5167  CA   LEU B 356     -30.022   -8.137   72.707  1.00 27.98           C
ATOM   5168  C    LEU B 356     -30.092   -6.619   72.969  1.00 27.44           C
ATOM   5169  O    LEU B 356     -30.975   -5.934   72.436  1.00 30.09           O
ATOM   5170  CB   LEU B 356     -30.583   -8.895   73.924  1.00 27.81           C
ATOM   5171  CG   LEU B 356     -30.829  -10.395   73.708  1.00 28.75           C
ATOM   5172  CD1  LEU B 356     -31.189  -11.025   75.061  1.00 32.08           C
ATOM   5173  CD2  LEU B 356     -31.918  -10.643   72.669  1.00 29.77           C
ATOM   5174  N    GLU B 357     -29.163   -6.101   73.759  1.00 27.48           N
ATOM   5175  CA   GLU B 357     -29.169   -4.667   74.073  1.00 28.31           C
ATOM   5176  C    GLU B 357     -28.935   -3.812   72.833  1.00 29.04           C
ATOM   5177  O    GLU B 357     -29.514   -2.734   72.689  1.00 28.02           O
ATOM   5178  CB   GLU B 357     -28.124   -4.323   75.125  1.00 28.14           C
ATOM   5179  CG   GLU B 357     -28.386   -5.060   76.463  1.00 29.72           C
ATOM   5180  CD   GLU B 357     -27.478   -4.637   77.590  1.00 28.97           C
ATOM   5181  OE1  GLU B 357     -26.355   -4.126   77.349  1.00 31.28           O
ATOM   5182  OE2  GLU B 357     -27.888   -4.835   78.762  1.00 31.72           O
ATOM   5183  N    TYR B 358     -28.097   -4.296   71.929  1.00 28.49           N
ATOM   5184  CA   TYR B 358     -27.823   -3.546   70.702  1.00 28.21           C
ATOM   5185  C    TYR B 358     -29.078   -3.507   69.815  1.00 28.44           C
ATOM   5186  O    TYR B 358     -29.437   -2.462   69.237  1.00 29.59           O
ATOM   5187  CB   TYR B 358     -26.671   -4.218   69.938  1.00 26.92           C
ATOM   5188  CG   TYR B 358     -26.082   -3.338   68.873  1.00 22.94           C
ATOM   5189  CD1  TYR B 358     -24.940   -2.612   69.120  1.00 23.76           C
ATOM   5190  CD2  TYR B 358     -26.740   -3.149   67.657  1.00 26.25           C
ATOM   5191  CE1  TYR B 358     -24.451   -1.687   68.188  1.00 25.21           C
ATOM   5192  CE2  TYR B 358     -26.270   -2.223   66.714  1.00 24.11           C
ATOM   5193  CZ   TYR B 358     -25.131   -1.491   66.998  1.00 23.59           C
ATOM   5194  OH   TYR B 358     -24.693   -0.473   66.166  1.00 25.37           O
ATOM   5195  N    LEU B 359     -29.748   -4.644   69.706  1.00 27.80           N
ATOM   5196  CA   LEU B 359     -30.932   -4.779   68.879  1.00 29.25           C
ATOM   5197  C    LEU B 359     -32.228   -4.337   69.542  1.00 31.13           C
ATOM   5198  O    LEU B 359     -33.279   -4.383   68.912  1.00 32.14           O
ATOM   5199  CB   LEU B 359     -31.097   -6.237   68.456  1.00 29.65           C
ATOM   5200  CG   LEU B 359     -29.992   -6.807   67.565  1.00 28.83           C
ATOM   5201  CD1  LEU B 359     -30.264   -8.284   67.363  1.00 29.10           C
ATOM   5202  CD2  LEU B 359     -29.938   -6.059   66.209  1.00 29.28           C
ATOM   5203  N    HIS B 360     -32.143   -3.937   70.808  1.00 32.63           N
ATOM   5204  CA   HIS B 360     -33.309   -3.529   71.586  1.00 35.06           C
ATOM   5205  C    HIS B 360     -34.323   -4.655   71.698  1.00 35.86           C
ATOM   5206  O    HIS B 360     -35.523   -4.450   71.500  1.00 36.16           O
ATOM   5207  CB   HIS B 360     -33.968   -2.281   70.975  1.00 35.38           C
ATOM   5208  CG   HIS B 360     -33.101   -1.068   71.041  1.00 36.56           C
ATOM   5209  ND1  HIS B 360     -33.608    0.211   71.072  1.00 37.52           N
ATOM   5210  CD2  HIS B 360     -31.754   -0.943   71.102  1.00 36.86           C
ATOM   5211  CE1  HIS B 360     -32.612    1.074   71.156  1.00 39.19           C
ATOM   5212  NE2  HIS B 360     -31.475    0.401   71.175  1.00 38.08           N
ATOM   5213  N    LEU B 361     -33.833   -5.850   72.027  1.00 35.29           N
ATOM   5214  CA   LEU B 361     -34.692   -7.021   72.182  1.00 35.44           C
ATOM   5215  C    LEU B 361     -34.635   -7.512   73.626  1.00 35.01           C
ATOM   5216  O    LEU B 361     -35.434   -8.406   73.964  1.00 36.61           O
ATOM   5217  CB   LEU B 361     -34.249   -8.154   71.242  1.00 34.64           C
ATOM   5218  CG   LEU B 361     -34.436   -7.921   69.738  1.00 36.17           C
ATOM   5219  CD1  LEU B 361     -33.920   -9.143   68.953  1.00 34.77           C
ATOM   5220  CD2  LEU B 361     -35.901   -7.685   69.435  1.00 36.40           C
ATOM   5221  OXT  LEU B 361     -33.776   -7.022   74.387  1.00 35.39           O
TER    5222       LEU B 361
```

FIGURE 1-78 (REMARKS)

```
HEADER      ----                                     xx-xxx-xx    xxxx
TITLE       ---
REMARK   3
REMARK   3 REFINEMENT.
REMARK   3   PROGRAM     : CNS 1.1
REMARK   3   AUTHORS     : BRUNGER,ADAMS,CLORE,DELANO,GROS,GROSSE-
REMARK   3               : KUNSTLEVE,JIANG,KUSZEWSKI,NILGES, PANNU,
REMARK   3               : READ,RICE,SIMONSON,WARREN
REMARK   3
REMARK   3  REFINEMENT TARGET : ENGH & HUBER
REMARK   3
REMARK   3  DATA USED IN REFINEMENT.
REMARK   3   RESOLUTION RANGE HIGH (ANGSTROMS) : 1.66
REMARK   3   RESOLUTION RANGE LOW  (ANGSTROMS) : 50.00
REMARK   3   DATA CUTOFF            (SIGMA(F)) : 0.000
REMARK   3   DATA CUTOFF HIGH         (ABS(F)) : NULL
REMARK   3   DATA CUTOFF LOW          (ABS(F)) : NULL
REMARK   3   COMPLETENESS (WORKING+TEST)   (%) : NULL
REMARK   3   NUMBER OF REFLECTIONS             : 96578
REMARK   3
REMARK   3  FIT TO DATA USED IN REFINEMENT.
REMARK   3   CROSS-VALIDATION METHOD          : NULL
REMARK   3   FREE R VALUE TEST SET SELECTION  : RANDOM
REMARK   3   R VALUE            (WORKING SET) : 0.182
REMARK   3   FREE R VALUE                     : 0.204
REMARK   3   FREE R VALUE TEST SET SIZE   (%) : NULL
REMARK   3   FREE R VALUE TEST SET COUNT      : 5097
REMARK   3   ESTIMATED ERROR OF FREE R VALUE  : NULL
REMARK   3
REMARK   3  FIT IN THE HIGHEST RESOLUTION BIN.
REMARK   3   TOTAL NUMBER OF BINS USED            : NULL
REMARK   3   BIN RESOLUTION RANGE HIGH       (A)  : NULL
REMARK   3   BIN RESOLUTION RANGE LOW        (A)  : NULL
REMARK   3   BIN COMPLETENESS (WORKING+TEST) (%)  : NULL
REMARK   3   REFLECTIONS IN BIN    (WORKING SET)  : NULL
REMARK   3   BIN R VALUE           (WORKING SET)  : NULL
REMARK   3   BIN FREE R VALUE                     : NULL
REMARK   3   BIN FREE R VALUE TEST SET SIZE  (%)  : NULL
REMARK   3   BIN FREE R VALUE TEST SET COUNT      : NULL
REMARK   3   ESTIMATED ERROR OF BIN FREE R VALUE  : NULL
REMARK   3
REMARK   3  NUMBER OF NON-HYDROGEN ATOMS USED IN REFINEMENT.
REMARK   3   PROTEIN ATOMS            : 5220
REMARK   3   NUCLEIC ACID ATOMS       : 0
REMARK   3   HETEROGEN ATOMS          : 12
REMARK   3   SOLVENT ATOMS            : 602
REMARK   3
REMARK   3  B VALUES.
REMARK   3   FROM WILSON PLOT           (A**2) : NULL
REMARK   3   MEAN B VALUE      (OVERALL, A**2) : NULL
REMARK   3   OVERALL ANISOTROPIC B VALUE.
REMARK   3    B11 (A**2) : NULL
REMARK   3    B22 (A**2) : NULL
REMARK   3    B33 (A**2) : NULL
REMARK   3    B12 (A**2) : NULL
REMARK   3    B13 (A**2) : NULL
REMARK   3    B23 (A**2) : NULL
REMARK   3
REMARK   3  ESTIMATED COORDINATE ERROR.
REMARK   3   ESD FROM LUZZATI PLOT        (A) : NULL
REMARK   3   ESD FROM SIGMAA              (A) : NULL
REMARK   3   LOW RESOLUTION CUTOFF        (A) : NULL
REMARK   3
REMARK   3  CROSS-VALIDATED ESTIMATED COORDINATE ERROR.
REMARK   3   ESD FROM C-V LUZZATI PLOT    (A) : NULL
REMARK   3   ESD FROM C-V SIGMAA          (A) : NULL
REMARK   3
REMARK   3  RMS DEVIATIONS FROM IDEAL VALUES.
```

FIGURE 1-79 (REMARKS)

```
REMARK   3   BOND LENGTHS                    (A) : 0.013
REMARK   3   BOND ANGLES               (DEGREES) : 1.65
REMARK   3   DIHEDRAL ANGLES           (DEGREES) : NULL
REMARK   3   IMPROPER ANGLES           (DEGREES) : NULL
REMARK   3
REMARK   3   ISOTROPIC THERMAL MODEL : NULL
REMARK   3
REMARK   3   ISOTROPIC THERMAL FACTOR RESTRAINTS.    RMS     SIGMA
REMARK   3    MAIN-CHAIN BOND                (A**2) : NULL ; NULL
REMARK   3    MAIN-CHAIN ANGLE               (A**2) : NULL ; NULL
REMARK   3    SIDE-CHAIN BOND                (A**2) : NULL ; NULL
REMARK   3    SIDE-CHAIN ANGLE               (A**2) : NULL ; NULL
REMARK   3
REMARK   3   BULK SOLVENT MODELING.
REMARK   3    METHOD USED : NULL
REMARK   3    KSOL        : NULL
REMARK   3    BSOL        : NULL
REMARK   3
REMARK   3   NCS MODEL : NULL
REMARK   3
REMARK   3   NCS RESTRAINTS.                         RMS    SIGMA/WEIGHT
REMARK   3    GROUP  1  POSITIONAL            (A) : NULL ; NULL
REMARK   3    GROUP  1  B-FACTOR           (A**2) : NULL ; NULL
REMARK   3
REMARK   3   PARAMETER FILE  1  : NULL
REMARK   3   TOPOLOGY FILE   1  : NULL
REMARK   3
REMARK   3   OTHER REFINEMENT REMARKS: NULL
CRYST1  119.029  119.029  332.938  90.00  90.00 120.00 H 3 2        36
SCALE1    0.008401  0.004851  0.000000       0.00000
SCALE2    0.000000  0.009701  0.000000       0.00000
SCALE3    0.000000  0.000000  0.003004       0.00000
```

FIGURE 2-1 (COORDINATES)

| | ATOM | TYPE | RES | | # | X | Y | Z | Occ | B | |
|---|---|---|---|---|---|---|---|---|---|---|---|
| ATOM | 1 | N | ALA | A | 33 | -6.215 | -33.667 | 37.097 | 1.00 | 56.33 | N |
| ATOM | 2 | CA | ALA | A | 33 | -6.794 | -32.329 | 36.756 | 1.00 | 56.28 | C |
| ATOM | 3 | C | ALA | A | 33 | -7.218 | -32.264 | 35.285 | 1.00 | 55.30 | C |
| ATOM | 4 | O | ALA | A | 33 | -6.366 | -32.154 | 34.396 | 1.00 | 55.68 | O |
| ATOM | 5 | CB | ALA | A | 33 | -5.768 | -31.226 | 37.052 | 1.00 | 56.59 | C |
| ATOM | 6 | N | SER | A | 34 | -8.530 | -32.316 | 35.039 | 1.00 | 52.84 | N |
| ATOM | 7 | CA | SER | A | 34 | -9.077 | -32.275 | 33.683 | 1.00 | 49.42 | C |
| ATOM | 8 | C | SER | A | 34 | -8.497 | -31.154 | 32.828 | 1.00 | 47.40 | C |
| ATOM | 9 | O | SER | A | 34 | -8.260 | -30.040 | 33.302 | 1.00 | 47.23 | O |
| ATOM | 10 | CB | SER | A | 34 | -10.602 | -32.130 | 33.717 | 1.00 | 49.63 | C |
| ATOM | 11 | OG | SER | A | 34 | -11.142 | -32.145 | 32.402 | 1.00 | 49.03 | O |
| ATOM | 12 | N | ALA | A | 35 | -8.281 | -31.461 | 31.556 | 1.00 | 44.06 | N |
| ATOM | 13 | CA | ALA | A | 35 | -7.735 | -30.496 | 30.626 | 1.00 | 41.04 | C |
| ATOM | 14 | C | ALA | A | 35 | -8.840 | -29.863 | 29.780 | 1.00 | 39.57 | C |
| ATOM | 15 | O | ALA | A | 35 | -8.566 | -29.366 | 28.685 | 1.00 | 39.31 | O |
| ATOM | 16 | CB | ALA | A | 35 | -6.728 | -31.180 | 29.729 | 1.00 | 40.24 | C |
| ATOM | 17 | N | TRP | A | 36 | -10.079 | -29.860 | 30.280 | 1.00 | 36.84 | N |
| ATOM | 18 | CA | TRP | A | 36 | -11.175 | -29.306 | 29.491 | 1.00 | 34.81 | C |
| ATOM | 19 | C | TRP | A | 36 | -10.999 | -27.843 | 29.077 | 1.00 | 33.36 | C |
| ATOM | 20 | O | TRP | A | 36 | -11.422 | -27.460 | 27.991 | 1.00 | 32.13 | O |
| ATOM | 21 | CB | TRP | A | 36 | -12.539 | -29.512 | 30.186 | 1.00 | 33.78 | C |
| ATOM | 22 | CG | TRP | A | 36 | -12.812 | -28.674 | 31.393 | 1.00 | 32.71 | C |
| ATOM | 23 | CD1 | TRP | A | 36 | -12.692 | -29.050 | 32.701 | 1.00 | 32.77 | C |
| ATOM | 24 | CD2 | TRP | A | 36 | -13.296 | -27.325 | 31.406 | 1.00 | 32.42 | C |
| ATOM | 25 | NE1 | TRP | A | 36 | -13.077 | -28.022 | 33.529 | 1.00 | 31.67 | N |
| ATOM | 26 | CE2 | TRP | A | 36 | -13.453 | -26.950 | 32.761 | 1.00 | 32.42 | C |
| ATOM | 27 | CE3 | TRP | A | 36 | -13.615 | -26.398 | 30.404 | 1.00 | 31.00 | C |
| ATOM | 28 | CZ2 | TRP | A | 36 | -13.916 | -25.680 | 33.141 | 1.00 | 31.25 | C |
| ATOM | 29 | CZ3 | TRP | A | 36 | -14.074 | -25.140 | 30.777 | 1.00 | 31.38 | C |
| ATOM | 30 | CH2 | TRP | A | 36 | -14.221 | -24.792 | 32.141 | 1.00 | 31.23 | C |
| ATOM | 31 | N | PRO | A | 37 | -10.364 | -27.011 | 29.927 | 1.00 | 32.64 | N |
| ATOM | 32 | CA | PRO | A | 37 | -10.189 | -25.611 | 29.532 | 1.00 | 32.08 | C |
| ATOM | 33 | C | PRO | A | 37 | -9.321 | -25.473 | 28.283 | 1.00 | 32.05 | C |
| ATOM | 34 | O | PRO | A | 37 | -9.247 | -24.397 | 27.695 | 1.00 | 31.08 | O |
| ATOM | 35 | CB | PRO | A | 37 | -9.540 | -24.985 | 30.764 | 1.00 | 32.23 | C |
| ATOM | 36 | CG | PRO | A | 37 | -10.086 | -25.806 | 31.887 | 1.00 | 30.94 | C |
| ATOM | 37 | CD | PRO | A | 37 | -9.969 | -27.201 | 31.335 | 1.00 | 31.68 | C |
| ATOM | 38 | N | GLU | A | 38 | -8.674 | -26.564 | 27.872 | 1.00 | 32.21 | N |
| ATOM | 39 | CA | GLU | A | 38 | -7.820 | -26.540 | 26.681 | 1.00 | 32.21 | C |
| ATOM | 40 | C | GLU | A | 38 | -8.570 | -26.940 | 25.425 | 1.00 | 31.23 | C |
| ATOM | 41 | O | GLU | A | 38 | -8.079 | -26.753 | 24.308 | 1.00 | 30.38 | O |
| ATOM | 42 | CB | GLU | A | 38 | -6.617 | -27.465 | 26.857 | 1.00 | 33.24 | C |
| ATOM | 43 | CG | GLU | A | 38 | -5.665 | -27.001 | 27.929 | 1.00 | 36.55 | C |
| ATOM | 44 | CD | GLU | A | 38 | -4.521 | -27.963 | 28.136 | 1.00 | 37.73 | C |
| ATOM | 45 | OE1 | GLU | A | 38 | -3.638 | -28.043 | 27.256 | 1.00 | 36.89 | O |
| ATOM | 46 | OE2 | GLU | A | 38 | -4.520 | -28.642 | 29.187 | 1.00 | 40.77 | O |
| ATOM | 47 | N | GLU | A | 39 | -9.759 | -27.493 | 25.612 | 1.00 | 31.02 | N |
| ATOM | 48 | CA | GLU | A | 39 | -10.582 | -27.922 | 24.490 | 1.00 | 32.34 | C |
| ATOM | 49 | C | GLU | A | 39 | -10.793 | -26.832 | 23.429 | 1.00 | 32.38 | C |
| ATOM | 50 | O | GLU | A | 39 | -10.872 | -27.130 | 22.242 | 1.00 | 32.55 | O |
| ATOM | 51 | CB | GLU | A | 39 | -11.932 | -28.433 | 25.008 | 1.00 | 32.55 | C |
| ATOM | 52 | CG | GLU | A | 39 | -11.844 | -29.812 | 25.668 | 1.00 | 34.28 | C |
| ATOM | 53 | CD | GLU | A | 39 | -13.161 | -30.280 | 26.274 | 1.00 | 35.16 | C |
| ATOM | 54 | OE1 | GLU | A | 39 | -14.233 | -29.819 | 25.832 | 1.00 | 35.84 | O |
| ATOM | 55 | OE2 | GLU | A | 39 | -13.125 | -31.128 | 27.186 | 1.00 | 36.41 | O |
| ATOM | 56 | N | LYS | A | 40 | -10.874 | -25.576 | 23.858 | 1.00 | 32.10 | N |
| ATOM | 57 | CA | LYS | A | 40 | -11.079 | -24.461 | 22.936 | 1.00 | 32.75 | C |
| ATOM | 58 | C | LYS | A | 40 | -9.946 | -24.283 | 21.916 | 1.00 | 33.13 | C |
| ATOM | 59 | O | LYS | A | 40 | -10.179 | -23.824 | 20.796 | 1.00 | 33.75 | O |
| ATOM | 60 | CB | LYS | A | 40 | -11.287 | -23.153 | 23.723 | 1.00 | 31.98 | C |
| ATOM | 61 | CG | LYS | A | 40 | -10.214 | -22.862 | 24.770 | 1.00 | 31.48 | C |
| ATOM | 62 | CD | LYS | A | 40 | -10.322 | -21.431 | 25.287 | 1.00 | 31.53 | C |
| ATOM | 63 | CE | LYS | A | 40 | -9.334 | -21.142 | 26.422 | 1.00 | 32.33 | C |
| ATOM | 64 | NZ | LYS | A | 40 | -9.797 | -21.663 | 27.758 | 1.00 | 31.32 | N |
| ATOM | 65 | N | ASN | A | 41 | -8.726 | -24.646 | 22.293 | 1.00 | 33.26 | N |
| ATOM | 66 | CA | ASN | A | 41 | -7.585 | -24.510 | 21.392 | 1.00 | 33.29 | C |
| ATOM | 67 | C | ASN | A | 41 | -7.741 | -25.414 | 20.172 | 1.00 | 33.18 | C |

FIGURE 2-2 (COORDINATES)

```
ATOM     68  O   ASN A  41      -7.150 -25.158  19.122  1.00 33.18           O
ATOM     69  CB  ASN A  41      -6.282 -24.906  22.097  1.00 35.00           C
ATOM     70  CG  ASN A  41      -6.018 -24.114  23.364  1.00 37.26           C
ATOM     71  OD1 ASN A  41      -5.257 -24.559  24.219  1.00 39.68           O
ATOM     72  ND2 ASN A  41      -6.625 -22.937  23.487  1.00 38.12           N
ATOM     73  N   TYR A  42      -8.534 -26.472  20.305  1.00 32.42           N
ATOM     74  CA  TYR A  42      -8.697 -27.426  19.207  1.00 32.10           C
ATOM     75  C   TYR A  42     -10.091 -27.482  18.625  1.00 30.88           C
ATOM     76  O   TYR A  42     -10.329 -28.202  17.665  1.00 31.16           O
ATOM     77  CB  TYR A  42      -8.304 -28.834  19.678  1.00 31.59           C
ATOM     78  CG  TYR A  42      -6.977 -28.875  20.390  1.00 32.85           C
ATOM     79  CD1 TYR A  42      -5.777 -28.862  19.673  1.00 33.24           C
ATOM     80  CD2 TYR A  42      -6.916 -28.877  21.785  1.00 32.81           C
ATOM     81  CE1 TYR A  42      -4.551 -28.847  20.327  1.00 33.04           C
ATOM     82  CE2 TYR A  42      -5.699 -28.863  22.446  1.00 33.24           C
ATOM     83  CZ  TYR A  42      -4.520 -28.846  21.711  1.00 33.92           C
ATOM     84  OH  TYR A  42      -3.310 -28.817  22.365  1.00 35.44           O
ATOM     85  N   HIS A  43     -11.018 -26.742  19.211  1.00 29.59           N
ATOM     86  CA  HIS A  43     -12.369 -26.761  18.704  1.00 29.35           C
ATOM     87  C   HIS A  43     -12.406 -26.357  17.236  1.00 29.46           C
ATOM     88  O   HIS A  43     -11.808 -25.365  16.834  1.00 30.19           O
ATOM     89  CB  HIS A  43     -13.254 -25.836  19.528  1.00 29.04           C
ATOM     90  CG  HIS A  43     -14.705 -25.945  19.188  1.00 29.09           C
ATOM     91  ND1 HIS A  43     -15.375 -24.981  18.464  1.00 31.01           N
ATOM     92  CD2 HIS A  43     -15.604 -26.926  19.432  1.00 28.64           C
ATOM     93  CE1 HIS A  43     -16.625 -25.365  18.278  1.00 29.56           C
ATOM     94  NE2 HIS A  43     -16.790 -26.542  18.856  1.00 29.31           N
ATOM     95  N   GLN A  44     -13.101 -27.152  16.435  1.00 30.26           N
ATOM     96  CA  GLN A  44     -13.230 -26.890  15.009  1.00 30.54           C
ATOM     97  C   GLN A  44     -14.693 -26.596  14.707  1.00 30.49           C
ATOM     98  O   GLN A  44     -15.588 -27.063  15.404  1.00 29.82           O
ATOM     99  CB  GLN A  44     -12.790 -28.110  14.194  1.00 30.91           C
ATOM    100  CG  GLN A  44     -11.312 -28.448  14.275  1.00 32.97           C
ATOM    101  CD  GLN A  44     -10.421 -27.281  13.879  1.00 36.19           C
ATOM    102  OE1 GLN A  44     -10.686 -26.577  12.900  1.00 36.71           O
ATOM    103  NE2 GLN A  44      -9.349 -27.076  14.637  1.00 37.68           N
ATOM    104  N   PRO A  45     -14.957 -25.808  13.661  1.00 30.69           N
ATOM    105  CA  PRO A  45     -16.356 -25.523  13.355  1.00 30.95           C
ATOM    106  C   PRO A  45     -16.944 -26.655  12.516  1.00 31.36           C
ATOM    107  O   PRO A  45     -16.214 -27.460  11.936  1.00 31.96           O
ATOM    108  CB  PRO A  45     -16.266 -24.229  12.569  1.00 30.62           C
ATOM    109  CG  PRO A  45     -15.024 -24.462  11.753  1.00 30.70           C
ATOM    110  CD  PRO A  45     -14.056 -25.082  12.748  1.00 29.68           C
ATOM    111  N   ALA A  46     -18.264 -26.719  12.479  1.00 31.46           N
ATOM    112  CA  ALA A  46     -18.962 -27.705  11.675  1.00 32.86           C
ATOM    113  C   ALA A  46     -19.537 -26.848  10.554  1.00 33.06           C
ATOM    114  O   ALA A  46     -20.586 -26.227  10.705  1.00 32.42           O
ATOM    115  CB  ALA A  46     -20.075 -28.367  12.487  1.00 32.64           C
ATOM    116  N   ILE A  47     -18.812 -26.800   9.445  1.00 34.47           N
ATOM    117  CA  ILE A  47     -19.181 -25.989   8.290  1.00 36.40           C
ATOM    118  C   ILE A  47     -20.510 -26.353   7.618  1.00 37.17           C
ATOM    119  O   ILE A  47     -20.756 -27.512   7.282  1.00 38.21           O
ATOM    120  CB  ILE A  47     -18.041 -26.026   7.242  1.00 37.05           C
ATOM    121  CG1 ILE A  47     -16.728 -25.602   7.908  1.00 37.98           C
ATOM    122  CG2 ILE A  47     -18.342 -25.082   6.084  1.00 37.05           C
ATOM    123  CD1 ILE A  47     -15.496 -25.802   7.035  1.00 39.20           C
ATOM    124  N   LEU A  48     -21.364 -25.351   7.429  1.00 37.31           N
ATOM    125  CA  LEU A  48     -22.655 -25.554   6.782  1.00 37.59           C
ATOM    126  C   LEU A  48     -22.470 -25.602   5.269  1.00 37.47           C
ATOM    127  O   LEU A  48     -21.597 -24.924   4.732  1.00 38.01           O
ATOM    128  CB  LEU A  48     -23.611 -24.402   7.110  1.00 37.23           C
ATOM    129  CG  LEU A  48     -23.861 -24.015   8.564  1.00 37.63           C
ATOM    130  CD1 LEU A  48     -24.924 -22.927   8.597  1.00 37.46           C
ATOM    131  CD2 LEU A  48     -24.301 -25.218   9.364  1.00 36.86           C
ATOM    132  N   ASN A  49     -23.292 -26.387   4.577  1.00 37.37           N
ATOM    133  CA  ASN A  49     -23.196 -26.457   3.121  1.00 36.87           C
ATOM    134  C   ASN A  49     -24.063 -25.372   2.483  1.00 36.60           C
ATOM    135  O   ASN A  49     -24.806 -24.675   3.178  1.00 36.18           O
```

FIGURE 2-3 (COORDINATES)

```
ATOM    136  CB  ASN A  49     -23.623 -27.838   2.598  1.00 37.76           C
ATOM    137  CG  ASN A  49     -25.021 -28.253   3.054  1.00 38.10           C
ATOM    138  OD1 ASN A  49     -25.904 -27.422   3.276  1.00 39.02           O
ATOM    139  ND2 ASN A  49     -25.229 -29.559   3.169  1.00 38.92           N
ATOM    140  N   SER A  50     -23.967 -25.236   1.162  1.00 36.76           N
ATOM    141  CA  SER A  50     -24.742 -24.236   0.421  1.00 37.63           C
ATOM    142  C   SER A  50     -26.207 -24.174   0.835  1.00 38.01           C
ATOM    143  O   SER A  50     -26.751 -23.102   1.105  1.00 38.76           O
ATOM    144  CB  SER A  50     -24.678 -24.519  -1.081  1.00 37.16           C
ATOM    145  OG  SER A  50     -23.350 -24.445  -1.560  1.00 38.54           O
ATOM    146  N   SER A  51     -26.844 -25.335   0.877  1.00 38.21           N
ATOM    147  CA  SER A  51     -28.247 -25.425   1.236  1.00 38.00           C
ATOM    148  C   SER A  51     -28.529 -24.812   2.607  1.00 37.11           C
ATOM    149  O   SER A  51     -29.464 -24.027   2.776  1.00 37.17           O
ATOM    150  CB  SER A  51     -28.680 -26.893   1.211  1.00 39.58           C
ATOM    151  OG  SER A  51     -30.085 -27.010   1.305  1.00 41.15           O
ATOM    152  N   ALA A  52     -27.724 -25.166   3.597  1.00 36.00           N
ATOM    153  CA  ALA A  52     -27.937 -24.616   4.931  1.00 34.69           C
ATOM    154  C   ALA A  52     -27.699 -23.102   4.919  1.00 33.92           C
ATOM    155  O   ALA A  52     -28.421 -22.345   5.575  1.00 33.54           O
ATOM    156  CB  ALA A  52     -27.011 -25.295   5.931  1.00 33.41           C
ATOM    157  N   LEU A  53     -26.701 -22.662   4.158  1.00 33.04           N
ATOM    158  CA  LEU A  53     -26.382 -21.239   4.089  1.00 33.59           C
ATOM    159  C   LEU A  53     -27.548 -20.424   3.554  1.00 34.30           C
ATOM    160  O   LEU A  53     -27.818 -19.328   4.048  1.00 34.47           O
ATOM    161  CB  LEU A  53     -25.129 -21.005   3.240  1.00 30.73           C
ATOM    162  CG  LEU A  53     -23.845 -21.491   3.910  1.00 31.04           C
ATOM    163  CD1 LEU A  53     -22.672 -21.392   2.949  1.00 30.49           C
ATOM    164  CD2 LEU A  53     -23.594 -20.671   5.171  1.00 29.57           C
ATOM    165  N   ARG A  54     -28.248 -20.953   2.554  1.00 34.83           N
ATOM    166  CA  ARG A  54     -29.392 -20.236   2.014  1.00 35.73           C
ATOM    167  C   ARG A  54     -30.466 -20.147   3.085  1.00 34.85           C
ATOM    168  O   ARG A  54     -31.149 -19.134   3.205  1.00 34.81           O
ATOM    169  CB  ARG A  54     -29.964 -20.945   0.786  1.00 37.62           C
ATOM    170  CG  ARG A  54     -28.988 -21.093  -0.368  1.00 40.60           C
ATOM    171  CD  ARG A  54     -29.683 -21.610  -1.623  1.00 42.21           C
ATOM    172  NE  ARG A  54     -28.706 -22.017  -2.625  1.00 44.08           N
ATOM    173  CZ  ARG A  54     -28.156 -23.226  -2.688  1.00 45.19           C
ATOM    174  NH1 ARG A  54     -28.489 -24.165  -1.814  1.00 45.78           N
ATOM    175  NH2 ARG A  54     -27.254 -23.492  -3.622  1.00 46.67           N
ATOM    176  N   GLN A  55     -30.608 -21.207   3.872  1.00 35.26           N
ATOM    177  CA  GLN A  55     -31.611 -21.231   4.928  1.00 36.04           C
ATOM    178  C   GLN A  55     -31.359 -20.138   5.960  1.00 35.16           C
ATOM    179  O   GLN A  55     -32.269 -19.393   6.322  1.00 34.70           O
ATOM    180  CB  GLN A  55     -31.627 -22.587   5.635  1.00 38.31           C
ATOM    181  CG  GLN A  55     -32.772 -22.718   6.635  1.00 43.50           C
ATOM    182  CD  GLN A  55     -32.587 -23.854   7.640  1.00 46.68           C
ATOM    183  OE1 GLN A  55     -31.783 -23.754   8.575  1.00 47.21           O
ATOM    184  NE2 GLN A  55     -33.337 -24.942   7.449  1.00 48.07           N
ATOM    185  N   ILE A  56     -30.120 -20.045   6.433  1.00 34.33           N
ATOM    186  CA  ILE A  56     -29.783 -19.040   7.428  1.00 34.22           C
ATOM    187  C   ILE A  56     -30.020 -17.640   6.859  1.00 34.26           C
ATOM    188  O   ILE A  56     -30.572 -16.773   7.541  1.00 33.16           O
ATOM    189  CB  ILE A  56     -28.313 -19.185   7.892  1.00 34.22           C
ATOM    190  CG1 ILE A  56     -28.019 -20.652   8.236  1.00 33.84           C
ATOM    191  CG2 ILE A  56     -28.055 -18.291   9.103  1.00 33.49           C
ATOM    192  CD1 ILE A  56     -29.029 -21.284   9.181  1.00 33.87           C
ATOM    193  N   ALA A  57     -29.615 -17.433   5.607  1.00 33.87           N
ATOM    194  CA  ALA A  57     -29.799 -16.146   4.941  1.00 35.42           C
ATOM    195  C   ALA A  57     -31.275 -15.752   4.897  1.00 36.26           C
ATOM    196  O   ALA A  57     -31.633 -14.621   5.207  1.00 36.48           O
ATOM    197  CB  ALA A  57     -29.237 -16.199   3.525  1.00 35.12           C
ATOM    198  N   GLU A  58     -32.131 -16.689   4.508  1.00 37.55           N
ATOM    199  CA  GLU A  58     -33.559 -16.424   4.435  1.00 38.49           C
ATOM    200  C   GLU A  58     -34.229 -16.371   5.806  1.00 37.04           C
ATOM    201  O   GLU A  58     -35.275 -15.746   5.960  1.00 36.47           O
ATOM    202  CB  GLU A  58     -34.251 -17.488   3.578  1.00 42.10           C
ATOM    203  CG  GLU A  58     -33.859 -17.454   2.107  1.00 47.73           C
```

FIGURE 2-4 (COORDINATES)

```
ATOM    204  CD  GLU A  58     -34.008 -16.063   1.502  1.00 51.63       C
ATOM    205  OE1 GLU A  58     -35.088 -15.446   1.675  1.00 53.69       O
ATOM    206  OE2 GLU A  58     -33.049 -15.586   0.854  1.00 53.85       O
ATOM    207  N   GLY A  59     -33.625 -17.014   6.801  1.00 35.63       N
ATOM    208  CA  GLY A  59     -34.212 -17.040   8.134  1.00 33.85       C
ATOM    209  C   GLY A  59     -34.138 -15.784   8.988  1.00 33.15       C
ATOM    210  O   GLY A  59     -34.833 -15.682   9.996  1.00 33.82       O
ATOM    211  N   THR A  60     -33.308 -14.825   8.599  1.00 32.18       N
ATOM    212  CA  THR A  60     -33.166 -13.592   9.364  1.00 31.62       C
ATOM    213  C   THR A  60     -33.901 -12.460   8.639  1.00 31.82       C
ATOM    214  O   THR A  60     -33.929 -12.418   7.414  1.00 33.47       O
ATOM    215  CB  THR A  60     -31.651 -13.256   9.563  1.00 31.51       C
ATOM    216  OG1 THR A  60     -31.512 -12.042  10.309  1.00 31.41       O
ATOM    217  CG2 THR A  60     -30.948 -13.123   8.228  1.00 29.56       C
ATOM    218  N   SER A  61     -34.512 -11.556   9.393  1.00 31.15       N
ATOM    219  CA  SER A  61     -35.264 -10.450   8.803  1.00 31.56       C
ATOM    220  C   SER A  61     -34.768  -9.093   9.297  1.00 31.35       C
ATOM    221  O   SER A  61     -35.008  -8.716  10.444  1.00 30.68       O
ATOM    222  CB  SER A  61     -36.755 -10.604   9.137  1.00 32.24       C
ATOM    223  OG  SER A  61     -37.501  -9.449   8.782  1.00 32.61       O
ATOM    224  N   ILE A  62     -34.098  -8.348   8.426  1.00 31.35       N
ATOM    225  CA  ILE A  62     -33.574  -7.051   8.824  1.00 31.61       C
ATOM    226  C   ILE A  62     -34.700  -6.082   9.189  1.00 32.44       C
ATOM    227  O   ILE A  62     -34.558  -5.278  10.110  1.00 31.82       O
ATOM    228  CB  ILE A  62     -32.661  -6.441   7.713  1.00 30.36       C
ATOM    229  CG1 ILE A  62     -31.912  -5.222   8.263  1.00 30.43       C
ATOM    230  CG2 ILE A  62     -33.477  -6.042   6.512  1.00 30.55       C
ATOM    231  CD1 ILE A  62     -31.004  -5.537   9.453  1.00 28.95       C
ATOM    232  N   SER A  63     -35.826  -6.176   8.489  1.00 34.25       N
ATOM    233  CA  SER A  63     -36.956  -5.289   8.771  1.00 36.78       C
ATOM    234  C   SER A  63     -37.598  -5.610  10.122  1.00 36.96       C
ATOM    235  O   SER A  63     -38.001  -4.703  10.849  1.00 37.81       O
ATOM    236  CB  SER A  63     -38.008  -5.378   7.660  1.00 37.00       C
ATOM    237  OG  SER A  63     -38.587  -6.668   7.621  1.00 40.67       O
ATOM    238  N   GLU A  64     -37.700  -6.891  10.457  1.00 37.74       N
ATOM    239  CA  GLU A  64     -38.271  -7.284  11.743  1.00 38.87       C
ATOM    240  C   GLU A  64     -37.356  -6.832  12.888  1.00 38.31       C
ATOM    241  O   GLU A  64     -37.828  -6.346  13.927  1.00 37.01       O
ATOM    242  CB  GLU A  64     -38.468  -8.801  11.796  1.00 42.72       C
ATOM    243  CG  GLU A  64     -39.672  -9.278  11.001  1.00 48.86       C
ATOM    244  CD  GLU A  64     -40.962  -8.660  11.523  1.00 52.89       C
ATOM    245  OE1 GLU A  64     -41.410  -9.063  12.628  1.00 55.11       O
ATOM    246  OE2 GLU A  64     -41.515  -7.760  10.842  1.00 54.57       O
ATOM    247  N   MET A  65     -36.047  -6.996  12.696  1.00 36.25       N
ATOM    248  CA  MET A  65     -35.089  -6.584  13.707  1.00 35.09       C
ATOM    249  C   MET A  65     -35.191  -5.076  13.888  1.00 34.79       C
ATOM    250  O   MET A  65     -35.233  -4.569  15.014  1.00 35.07       O
ATOM    251  CB  MET A  65     -33.663  -6.933  13.284  1.00 34.26       C
ATOM    252  CG  MET A  65     -32.619  -6.463  14.291  1.00 35.12       C
ATOM    253  SD  MET A  65     -30.972  -6.149  13.614  1.00 33.26       S
ATOM    254  CE  MET A  65     -31.153  -4.457  13.107  1.00 33.91       C
ATOM    255  N   TRP A  66     -35.245  -4.367  12.766  1.00 33.94       N
ATOM    256  CA  TRP A  66     -35.318  -2.911  12.761  1.00 34.23       C
ATOM    257  C   TRP A  66     -36.481  -2.339  13.564  1.00 35.53       C
ATOM    258  O   TRP A  66     -36.331  -1.365  14.304  1.00 36.15       O
ATOM    259  CB  TRP A  66     -35.418  -2.416  11.323  1.00 33.07       C
ATOM    260  CG  TRP A  66     -34.808  -1.087  11.129  1.00 32.17       C
ATOM    261  CD1 TRP A  66     -35.358   0.126  11.430  1.00 32.10       C
ATOM    262  CD2 TRP A  66     -33.494  -0.824  10.636  1.00 31.55       C
ATOM    263  NE1 TRP A  66     -34.465   1.132  11.155  1.00 31.70       N
ATOM    264  CE2 TRP A  66     -33.310   0.579  10.668  1.00 31.43       C
ATOM    265  CE3 TRP A  66     -32.449  -1.637  10.172  1.00 31.24       C
ATOM    266  CZ2 TRP A  66     -32.120   1.190  10.253  1.00 30.83       C
ATOM    267  CZ3 TRP A  66     -31.266  -1.032   9.758  1.00 31.57       C
ATOM    268  CH2 TRP A  66     -31.112   0.373   9.803  1.00 31.56       C
ATOM    269  N   GLN A  67     -37.645  -2.950  13.417  1.00 36.17       N
ATOM    270  CA  GLN A  67     -38.829  -2.483  14.104  1.00 36.24       C
ATOM    271  C   GLN A  67     -38.980  -3.036  15.514  1.00 35.72       C
```

FIGURE 2-5 (COORDINATES)

```
ATOM    272  O    GLN A  67     -39.323   -2.305   16.443  1.00 36.09           O
ATOM    273  CB   GLN A  67     -40.055   -2.850   13.267  1.00 38.39           C
ATOM    274  CG   GLN A  67     -41.405   -2.465   13.866  1.00 41.77           C
ATOM    275  CD   GLN A  67     -42.560   -3.153   13.144  1.00 43.96           C
ATOM    276  OE1  GLN A  67     -42.868   -2.837   11.993  1.00 44.52           O
ATOM    277  NE2  GLN A  67     -43.188   -4.117   13.815  1.00 44.43           N
ATOM    278  N    ASN A  68     -38.693   -4.319   15.682  1.00 35.46           N
ATOM    279  CA   ASN A  68     -38.878   -4.971   16.975  1.00 35.21           C
ATOM    280  C    ASN A  68     -37.737   -5.008   17.982  1.00 34.78           C
ATOM    281  O    ASN A  68     -37.981   -5.147   19.181  1.00 34.55           O
ATOM    282  CB   ASN A  68     -39.393   -6.388   16.736  1.00 34.63           C
ATOM    283  CG   ASN A  68     -40.587   -6.405   15.817  1.00 34.02           C
ATOM    284  OD1  ASN A  68     -41.405   -5.483   15.841  1.00 34.74           O
ATOM    285  ND2  ASN A  68     -40.701   -7.445   15.002  1.00 33.31           N
ATOM    286  N    ASP A  69     -36.503   -4.884   17.512  1.00 34.26           N
ATOM    287  CA   ASP A  69     -35.357   -4.915   18.414  1.00 33.42           C
ATOM    288  C    ASP A  69     -34.559   -3.619   18.443  1.00 32.75           C
ATOM    289  O    ASP A  69     -34.123   -3.183   19.505  1.00 32.67           O
ATOM    290  CB   ASP A  69     -34.424   -6.062   18.031  1.00 33.81           C
ATOM    291  CG   ASP A  69     -35.011   -7.410   18.342  1.00 34.35           C
ATOM    292  OD1  ASP A  69     -35.025   -8.282   17.454  1.00 35.93           O
ATOM    293  OD2  ASP A  69     -35.459   -7.601   19.483  1.00 35.92           O
ATOM    294  N    LEU A  70     -34.381   -3.004   17.276  1.00 31.85           N
ATOM    295  CA   LEU A  70     -33.592   -1.787   17.171  1.00 30.84           C
ATOM    296  C    LEU A  70     -34.253   -0.481   17.592  1.00 31.18           C
ATOM    297  O    LEU A  70     -33.746    0.219   18.475  1.00 31.69           O
ATOM    298  CB   LEU A  70     -33.058   -1.643   15.743  1.00 29.58           C
ATOM    299  CG   LEU A  70     -32.251   -0.370   15.457  1.00 27.81           C
ATOM    300  CD1  LEU A  70     -31.011   -0.320   16.339  1.00 24.49           C
ATOM    301  CD2  LEU A  70     -31.874   -0.338   13.987  1.00 26.78           C
ATOM    302  N    GLN A  71     -35.375   -0.139   16.975  1.00 31.10           N
ATOM    303  CA   GLN A  71     -36.021    1.121   17.311  1.00 32.06           C
ATOM    304  C    GLN A  71     -36.306    1.352   18.797  1.00 31.71           C
ATOM    305  O    GLN A  71     -36.148    2.470   19.283  1.00 31.89           O
ATOM    306  CB   GLN A  71     -37.277    1.317   16.448  1.00 33.30           C
ATOM    307  CG   GLN A  71     -36.921    1.548   14.981  1.00 35.60           C
ATOM    308  CD   GLN A  71     -38.124    1.760   14.073  1.00 37.98           C
ATOM    309  OE1  GLN A  71     -39.193    1.188   14.293  1.00 39.40           O
ATOM    310  NE2  GLN A  71     -37.943    2.568   13.026  1.00 36.92           N
ATOM    311  N    PRO A  72     -36.727    0.313   19.543  1.00 31.76           N
ATOM    312  CA   PRO A  72     -36.976    0.592   20.966  1.00 31.99           C
ATOM    313  C    PRO A  72     -35.695    0.967   21.703  1.00 32.52           C
ATOM    314  O    PRO A  72     -35.743    1.578   22.767  1.00 33.47           O
ATOM    315  CB   PRO A  72     -37.580   -0.712   21.483  1.00 31.38           C
ATOM    316  CG   PRO A  72     -38.326   -1.226   20.271  1.00 31.35           C
ATOM    317  CD   PRO A  72     -37.334   -0.971   19.143  1.00 31.67           C
ATOM    318  N    LEU A  73     -34.548    0.613   21.131  1.00 32.02           N
ATOM    319  CA   LEU A  73     -33.267    0.925   21.759  1.00 31.64           C
ATOM    320  C    LEU A  73     -32.683    2.286   21.371  1.00 31.75           C
ATOM    321  O    LEU A  73     -31.706    2.726   21.974  1.00 31.73           O
ATOM    322  CB   LEU A  73     -32.239   -0.169   21.448  1.00 31.89           C
ATOM    323  CG   LEU A  73     -32.372   -1.486   22.213  1.00 32.63           C
ATOM    324  CD1  LEU A  73     -31.350   -2.479   21.707  1.00 32.10           C
ATOM    325  CD2  LEU A  73     -32.164   -1.230   23.700  1.00 33.53           C
ATOM    326  N    LEU A  74     -33.266    2.946   20.370  1.00 31.17           N
ATOM    327  CA   LEU A  74     -32.766    4.246   19.942  1.00 30.85           C
ATOM    328  C    LEU A  74     -33.313    5.340   20.843  1.00 31.22           C
ATOM    329  O    LEU A  74     -34.129    6.165   20.444  1.00 31.44           O
ATOM    330  CB   LEU A  74     -33.134    4.511   18.481  1.00 29.36           C
ATOM    331  CG   LEU A  74     -32.442    3.569   17.486  1.00 30.16           C
ATOM    332  CD1  LEU A  74     -32.946    3.843   16.066  1.00 30.18           C
ATOM    333  CD2  LEU A  74     -30.923    3.750   17.568  1.00 27.76           C
ATOM    334  N    ILE A  75     -32.835    5.326   22.078  1.00 31.55           N
ATOM    335  CA   ILE A  75     -33.249    6.280   23.089  1.00 31.51           C
ATOM    336  C    ILE A  75     -32.047    6.580   23.974  1.00 32.18           C
ATOM    337  O    ILE A  75     -31.095    5.802   24.029  1.00 31.82           O
ATOM    338  CB   ILE A  75     -34.360    5.687   23.979  1.00 31.72           C
ATOM    339  CG1  ILE A  75     -33.855    4.387   24.632  1.00 29.61           C
```

FIGURE 2-6 (COORDINATES)

```
ATOM    340  CG2 ILE A   75     -35.619   5.441  23.154  1.00 30.25           C
ATOM    341  CD1 ILE A   75     -34.833   3.734  25.581  1.00 26.15           C
ATOM    342  N   GLU A   76     -32.095   7.715  24.658  1.00 32.83           N
ATOM    343  CA  GLU A   76     -31.028   8.112  25.562  1.00 33.77           C
ATOM    344  C   GLU A   76     -31.009   7.072  26.683  1.00 33.04           C
ATOM    345  O   GLU A   76     -32.011   6.855  27.355  1.00 32.88           O
ATOM    346  CB  GLU A   76     -31.334   9.507  26.087  1.00 35.29           C
ATOM    347  CG  GLU A   76     -30.357  10.062  27.058  1.00 39.04           C
ATOM    348  CD  GLU A   76     -30.493  11.560  27.167  1.00 41.90           C
ATOM    349  OE1 GLU A   76     -31.640  12.049  27.229  1.00 44.46           O
ATOM    350  OE2 GLU A   76     -29.459  12.253  27.192  1.00 43.46           O
ATOM    351  N   ARG A   77     -29.875   6.412  26.874  1.00 32.70           N
ATOM    352  CA  ARG A   77     -29.794   5.372  27.888  1.00 32.01           C
ATOM    353  C   ARG A   77     -28.447   5.300  28.614  1.00 33.03           C
ATOM    354  O   ARG A   77     -27.825   4.226  28.688  1.00 32.79           O
ATOM    355  CB  ARG A   77     -30.124   4.019  27.242  1.00 30.24           C
ATOM    356  CG  ARG A   77     -29.271   3.721  26.016  1.00 29.88           C
ATOM    357  CD  ARG A   77     -29.748   2.515  25.215  1.00 27.60           C
ATOM    358  NE  ARG A   77     -28.789   2.196  24.161  1.00 27.64           N
ATOM    359  CZ  ARG A   77     -28.530   2.967  23.105  1.00 29.21           C
ATOM    360  NH1 ARG A   77     -29.166   4.115  22.928  1.00 28.73           N
ATOM    361  NH2 ARG A   77     -27.592   2.614  22.238  1.00 30.82           N
ATOM    362  N   TYR A   78     -27.986   6.438  29.136  1.00 32.95           N
ATOM    363  CA  TYR A   78     -26.738   6.450  29.883  1.00 33.51           C
ATOM    364  C   TYR A   78     -27.058   5.810  31.238  1.00 33.59           C
ATOM    365  O   TYR A   78     -28.203   5.824  31.677  1.00 32.90           O
ATOM    366  CB  TYR A   78     -26.186   7.881  30.038  1.00 33.97           C
ATOM    367  CG  TYR A   78     -27.114   8.876  30.698  1.00 34.88           C
ATOM    368  CD1 TYR A   78     -28.028   9.617  29.946  1.00 34.18           C
ATOM    369  CD2 TYR A   78     -27.091   9.064  32.083  1.00 34.68           C
ATOM    370  CE1 TYR A   78     -28.896  10.519  30.555  1.00 35.07           C
ATOM    371  CE2 TYR A   78     -27.953   9.955  32.701  1.00 35.13           C
ATOM    372  CZ  TYR A   78     -28.855  10.682  31.936  1.00 35.80           C
ATOM    373  OH  TYR A   78     -29.720  11.557  32.557  1.00 36.40           O
ATOM    374  N   PRO A   79     -26.050   5.236  31.913  1.00 34.60           N
ATOM    375  CA  PRO A   79     -26.218   4.574  33.217  1.00 35.13           C
ATOM    376  C   PRO A   79     -27.024   5.352  34.260  1.00 35.65           C
ATOM    377  O   PRO A   79     -26.765   6.528  34.505  1.00 36.25           O
ATOM    378  CB  PRO A   79     -24.780   4.337  33.677  1.00 34.64           C
ATOM    379  CG  PRO A   79     -24.009   4.282  32.394  1.00 34.61           C
ATOM    380  CD  PRO A   79     -24.621   5.398  31.599  1.00 34.13           C
ATOM    381  N   GLY A   80     -27.992   4.673  34.873  1.00 35.70           N
ATOM    382  CA  GLY A   80     -28.820   5.289  35.890  1.00 35.46           C
ATOM    383  C   GLY A   80     -29.984   6.100  35.357  1.00 36.04           C
ATOM    384  O   GLY A   80     -30.797   6.599  36.134  1.00 36.77           O
ATOM    385  N   SER A   81     -30.081   6.230  34.038  1.00 35.77           N
ATOM    386  CA  SER A   81     -31.159   7.009  33.439  1.00 35.22           C
ATOM    387  C   SER A   81     -32.408   6.168  33.206  1.00 35.23           C
ATOM    388  O   SER A   81     -32.346   4.941  33.164  1.00 35.74           O
ATOM    389  CB  SER A   81     -30.695   7.629  32.111  1.00 36.00           C
ATOM    390  OG  SER A   81     -30.608   6.664  31.068  1.00 35.46           O
ATOM    391  N   PRO A   82     -33.568   6.821  33.051  1.00 35.60           N
ATOM    392  CA  PRO A   82     -34.799   6.059  32.821  1.00 35.34           C
ATOM    393  C   PRO A   82     -34.637   5.206  31.566  1.00 35.03           C
ATOM    394  O   PRO A   82     -35.137   4.083  31.495  1.00 34.97           O
ATOM    395  CB  PRO A   82     -35.857   7.150  32.647  1.00 35.60           C
ATOM    396  CG  PRO A   82     -35.298   8.306  33.428  1.00 35.42           C
ATOM    397  CD  PRO A   82     -33.838   8.268  33.050  1.00 35.62           C
ATOM    398  N   GLY A   83     -33.930   5.756  30.581  1.00 34.72           N
ATOM    399  CA  GLY A   83     -33.690   5.042  29.335  1.00 34.28           C
ATOM    400  C   GLY A   83     -32.914   3.753  29.544  1.00 34.00           C
ATOM    401  O   GLY A   83     -33.173   2.744  28.886  1.00 33.12           O
ATOM    402  N   SER A   84     -31.953   3.791  30.460  1.00 33.67           N
ATOM    403  CA  SER A   84     -31.153   2.617  30.776  1.00 34.10           C
ATOM    404  C   SER A   84     -32.095   1.516  31.247  1.00 34.83           C
ATOM    405  O   SER A   84     -31.971   0.355  30.844  1.00 34.80           O
ATOM    406  CB  SER A   84     -30.142   2.942  31.884  1.00 33.74           C
ATOM    407  OG  SER A   84     -29.460   1.778  32.330  1.00 33.44           O
```

FIGURE 2-7 (COORDINATES)

```
ATOM    408  N    TYR A  85     -33.046   1.889  32.097  1.00 35.29           N
ATOM    409  CA   TYR A  85     -34.009   0.929  32.621  1.00 36.20           C
ATOM    410  C    TYR A  85     -34.897   0.348  31.502  1.00 35.80           C
ATOM    411  O    TYR A  85     -35.062  -0.874  31.390  1.00 35.03           O
ATOM    412  CB   TYR A  85     -34.876   1.592  33.694  1.00 37.67           C
ATOM    413  CG   TYR A  85     -35.933   0.674  34.249  1.00 41.30           C
ATOM    414  CD1  TYR A  85     -35.590  -0.378  35.095  1.00 43.18           C
ATOM    415  CD2  TYR A  85     -37.274   0.820  33.887  1.00 42.02           C
ATOM    416  CE1  TYR A  85     -36.554  -1.264  35.565  1.00 43.91           C
ATOM    417  CE2  TYR A  85     -38.243  -0.058  34.351  1.00 43.29           C
ATOM    418  CZ   TYR A  85     -37.877  -1.098  35.189  1.00 44.32           C
ATOM    419  OH   TYR A  85     -38.829  -1.975  35.657  1.00 46.35           O
ATOM    420  N    ALA A  86     -35.457   1.228  30.675  1.00 34.85           N
ATOM    421  CA   ALA A  86     -36.323   0.812  29.573  1.00 34.26           C
ATOM    422  C    ALA A  86     -35.594  -0.090  28.591  1.00 34.00           C
ATOM    423  O    ALA A  86     -36.153  -1.077  28.112  1.00 34.55           O
ATOM    424  CB   ALA A  86     -36.871   2.039  28.839  1.00 33.60           C
ATOM    425  N    ALA A  87     -34.345   0.256  28.288  1.00 33.57           N
ATOM    426  CA   ALA A  87     -33.541  -0.530  27.357  1.00 33.24           C
ATOM    427  C    ALA A  87     -33.355  -1.928  27.920  1.00 33.09           C
ATOM    428  O    ALA A  87     -33.472  -2.921  27.206  1.00 32.84           O
ATOM    429  CB   ALA A  87     -32.174   0.135  27.144  1.00 32.84           C
ATOM    430  N    ARG A  88     -33.059  -1.985  29.215  1.00 33.02           N
ATOM    431  CA   ARG A  88     -32.840  -3.238  29.923  1.00 33.58           C
ATOM    432  C    ARG A  88     -34.109  -4.102  29.902  1.00 33.42           C
ATOM    433  O    ARG A  88     -34.028  -5.319  29.733  1.00 33.79           O
ATOM    434  CB   ARG A  88     -32.394  -2.922  31.361  1.00 33.54           C
ATOM    435  CG   ARG A  88     -31.910  -4.103  32.178  1.00 33.51           C
ATOM    436  CD   ARG A  88     -30.959  -3.682  33.310  1.00 33.11           C
ATOM    437  NE   ARG A  88     -31.544  -2.716  34.239  1.00 33.39           N
ATOM    438  CZ   ARG A  88     -31.177  -1.436  34.316  1.00 33.86           C
ATOM    439  NH1  ARG A  88     -30.224  -0.972  33.521  1.00 33.80           N
ATOM    440  NH2  ARG A  88     -31.764  -0.614  35.179  1.00 33.04           N
ATOM    441  N    GLN A  89     -35.276  -3.469  30.054  1.00 35.76           N
ATOM    442  CA   GLN A  89     -36.550  -4.189  30.043  1.00 36.92           C
ATOM    443  C    GLN A  89     -36.814  -4.754  28.658  1.00 35.78           C
ATOM    444  O    GLN A  89     -37.233  -5.902  28.505  1.00 35.15           O
ATOM    445  CB   GLN A  89     -37.704  -3.262  30.431  1.00 39.81           C
ATOM    446  CG   GLN A  89     -37.547  -2.610  31.797  1.00 45.40           C
ATOM    447  CD   GLN A  89     -37.386  -3.619  32.930  1.00 48.66           C
ATOM    448  OE1  GLN A  89     -38.272  -4.447  33.181  1.00 49.97           O
ATOM    449  NE2  GLN A  89     -36.250  -3.549  33.625  1.00 50.74           N
ATOM    450  N    HIS A  90     -36.563  -3.933  27.649  1.00 34.50           N
ATOM    451  CA   HIS A  90     -36.762  -4.331  26.270  1.00 33.57           C
ATOM    452  C    HIS A  90     -35.931  -5.562  25.934  1.00 34.19           C
ATOM    453  O    HIS A  90     -36.444  -6.532  25.372  1.00 34.70           O
ATOM    454  CB   HIS A  90     -36.382  -3.175  25.345  1.00 33.00           C
ATOM    455  CG   HIS A  90     -36.241  -3.570  23.910  1.00 33.33           C
ATOM    456  ND1  HIS A  90     -37.313  -3.934  23.129  1.00 33.70           N
ATOM    457  CD2  HIS A  90     -35.148  -3.657  23.115  1.00 33.75           C
ATOM    458  CE1  HIS A  90     -36.889  -4.225  21.912  1.00 33.66           C
ATOM    459  NE2  HIS A  90     -35.579  -4.065  21.877  1.00 33.33           N
ATOM    460  N    ILE A  91     -34.649  -5.520  26.283  1.00 34.39           N
ATOM    461  CA   ILE A  91     -33.747  -6.631  26.006  1.00 34.30           C
ATOM    462  C    ILE A  91     -34.182  -7.920  26.693  1.00 34.63           C
ATOM    463  O    ILE A  91     -34.223  -8.976  26.064  1.00 34.78           O
ATOM    464  CB   ILE A  91     -32.296  -6.287  26.429  1.00 33.83           C
ATOM    465  CG1  ILE A  91     -31.744  -5.181  25.520  1.00 33.98           C
ATOM    466  CG2  ILE A  91     -31.411  -7.535  26.356  1.00 33.14           C
ATOM    467  CD1  ILE A  91     -30.428  -4.556  26.001  1.00 32.43           C
ATOM    468  N    MET A  92     -34.501  -7.841  27.980  1.00 35.54           N
ATOM    469  CA   MET A  92     -34.936  -9.024  28.710  1.00 36.81           C
ATOM    470  C    MET A  92     -36.231  -9.577  28.121  1.00 36.62           C
ATOM    471  O    MET A  92     -36.378 -10.785  27.944  1.00 36.65           O
ATOM    472  CB   MET A  92     -35.126  -8.698  30.189  1.00 38.17           C
ATOM    473  CG   MET A  92     -33.831  -8.381  30.907  1.00 41.40           C
ATOM    474  SD   MET A  92     -34.110  -7.983  32.639  1.00 46.04           S
ATOM    475  CE   MET A  92     -34.278  -9.614  33.306  1.00 46.28           C
```

FIGURE 2-8 (COORDINATES)

```
ATOM    476  N   GLN A  93     -37.162  -8.688  27.798  1.00 36.78           N
ATOM    477  CA  GLN A  93     -38.438  -9.103  27.228  1.00 37.13           C
ATOM    478  C   GLN A  93     -38.287  -9.832  25.894  1.00 36.01           C
ATOM    479  O   GLN A  93     -38.882 -10.890  25.692  1.00 36.17           O
ATOM    480  CB  GLN A  93     -39.360  -7.888  27.079  1.00 37.74           C
ATOM    481  CG  GLN A  93     -39.903  -7.405  28.421  1.00 41.12           C
ATOM    482  CD  GLN A  93     -40.680  -6.094  28.330  1.00 43.77           C
ATOM    483  OE1 GLN A  93     -41.289  -5.652  29.312  1.00 43.28           O
ATOM    484  NE2 GLN A  93     -40.656  -5.463  27.156  1.00 44.58           N
ATOM    485  N   ARG A  94     -37.485  -9.275  24.992  1.00 35.02           N
ATOM    486  CA  ARG A  94     -37.264  -9.894  23.690  1.00 33.88           C
ATOM    487  C   ARG A  94     -36.621 -11.285  23.825  1.00 33.43           C
ATOM    488  O   ARG A  94     -36.849 -12.167  22.998  1.00 33.09           O
ATOM    489  CB  ARG A  94     -36.394  -8.979  22.824  1.00 33.57           C
ATOM    490  CG  ARG A  94     -37.066  -7.656  22.479  1.00 33.32           C
ATOM    491  CD  ARG A  94     -38.263  -7.866  21.563  1.00 34.18           C
ATOM    492  NE  ARG A  94     -37.856  -8.274  20.218  1.00 35.16           N
ATOM    493  CZ  ARG A  94     -38.670  -8.809  19.310  1.00 36.39           C
ATOM    494  NH1 ARG A  94     -39.948  -9.011  19.601  1.00 35.96           N
ATOM    495  NH2 ARG A  94     -38.209  -9.142  18.106  1.00 36.19           N
ATOM    496  N   ILE A  95     -35.825 -11.486  24.868  1.00 32.76           N
ATOM    497  CA  ILE A  95     -35.197 -12.777  25.075  1.00 32.71           C
ATOM    498  C   ILE A  95     -36.180 -13.764  25.705  1.00 34.10           C
ATOM    499  O   ILE A  95     -36.268 -14.920  25.291  1.00 32.78           O
ATOM    500  CB  ILE A  95     -33.951 -12.656  25.981  1.00 32.08           C
ATOM    501  CG1 ILE A  95     -32.842 -11.916  25.224  1.00 31.87           C
ATOM    502  CG2 ILE A  95     -33.496 -14.053  26.449  1.00 29.59           C
ATOM    503  CD1 ILE A  95     -31.551 -11.730  26.006  1.00 31.38           C
ATOM    504  N   GLN A  96     -36.925 -13.297  26.701  1.00 35.89           N
ATOM    505  CA  GLN A  96     -37.885 -14.145  27.401  1.00 37.55           C
ATOM    506  C   GLN A  96     -38.976 -14.728  26.516  1.00 37.62           C
ATOM    507  O   GLN A  96     -39.446 -15.830  26.778  1.00 37.61           O
ATOM    508  CB  GLN A  96     -38.519 -13.381  28.565  1.00 37.90           C
ATOM    509  CG  GLN A  96     -37.503 -12.946  29.602  1.00 41.52           C
ATOM    510  CD  GLN A  96     -38.122 -12.253  30.801  1.00 42.71           C
ATOM    511  OE1 GLN A  96     -38.975 -11.374  30.657  1.00 44.96           O
ATOM    512  NE2 GLN A  96     -37.680 -12.636  31.993  1.00 42.43           N
ATOM    513  N   ARG A  97     -39.374 -14.005  25.471  1.00 37.74           N
ATOM    514  CA  ARG A  97     -40.423 -14.494  24.578  1.00 38.06           C
ATOM    515  C   ARG A  97     -39.971 -15.637  23.669  1.00 38.02           C
ATOM    516  O   ARG A  97     -40.795 -16.278  23.018  1.00 38.84           O
ATOM    517  CB  ARG A  97     -40.974 -13.352  23.717  1.00 38.26           C
ATOM    518  CG  ARG A  97     -39.957 -12.693  22.812  1.00 38.73           C
ATOM    519  CD  ARG A  97     -40.578 -11.521  22.066  1.00 40.92           C
ATOM    520  NE  ARG A  97     -41.557 -11.964  21.079  1.00 41.88           N
ATOM    521  CZ  ARG A  97     -41.249 -12.582  19.943  1.00 42.25           C
ATOM    522  NH1 ARG A  97     -39.983 -12.830  19.634  1.00 42.17           N
ATOM    523  NH2 ARG A  97     -42.210 -12.976  19.121  1.00 43.59           N
ATOM    524  N   LEU A  98     -38.668 -15.892  23.623  1.00 37.19           N
ATOM    525  CA  LEU A  98     -38.138 -16.953  22.779  1.00 36.74           C
ATOM    526  C   LEU A  98     -38.309 -18.329  23.421  1.00 37.28           C
ATOM    527  O   LEU A  98     -38.425 -18.451  24.640  1.00 36.35           O
ATOM    528  CB  LEU A  98     -36.657 -16.696  22.474  1.00 35.79           C
ATOM    529  CG  LEU A  98     -36.316 -15.383  21.759  1.00 34.45           C
ATOM    530  CD1 LEU A  98     -34.830 -15.358  21.457  1.00 34.07           C
ATOM    531  CD2 LEU A  98     -37.116 -15.250  20.466  1.00 33.71           C
ATOM    532  N   GLN A  99     -38.316 -19.364  22.588  1.00 37.77           N
ATOM    533  CA  GLN A  99     -38.489 -20.729  23.058  1.00 39.18           C
ATOM    534  C   GLN A  99     -37.278 -21.329  23.759  1.00 38.45           C
ATOM    535  O   GLN A  99     -37.435 -22.103  24.701  1.00 38.48           O
ATOM    536  CB  GLN A  99     -38.917 -21.619  21.892  1.00 41.42           C
ATOM    537  CG  GLN A  99     -40.305 -21.281  21.382  1.00 45.32           C
ATOM    538  CD  GLN A  99     -40.626 -21.956  20.066  1.00 48.63           C
ATOM    539  OE1 GLN A  99     -41.164 -21.323  19.154  1.00 52.19           O
ATOM    540  NE2 GLN A  99     -40.308 -23.244  19.956  1.00 49.28           N
ATOM    541  N   ALA A 100     -36.076 -20.982  23.308  1.00 37.75           N
ATOM    542  CA  ALA A 100     -34.859 -21.502  23.927  1.00 37.18           C
ATOM    543  C   ALA A 100     -34.875 -21.217  25.431  1.00 36.40           C
```

FIGURE 2-9 (COORDINATES)

```
ATOM    544  O   ALA A 100     -35.458 -20.233  25.880  1.00 35.82           O
ATOM    545  CB  ALA A 100     -33.622 -20.879  23.278  1.00 37.91           C
ATOM    546  N   ASP A 101     -34.224 -22.081  26.200  1.00 36.13           N
ATOM    547  CA  ASP A 101     -34.202 -21.960  27.650  1.00 35.95           C
ATOM    548  C   ASP A 101     -33.155 -20.968  28.147  1.00 35.38           C
ATOM    549  O   ASP A 101     -32.212 -21.346  28.843  1.00 35.31           O
ATOM    550  CB  ASP A 101     -33.970 -23.352  28.258  1.00 37.88           C
ATOM    551  CG  ASP A 101     -34.270 -23.411  29.751  1.00 40.12           C
ATOM    552  OD1 ASP A 101     -35.044 -22.563  30.254  1.00 41.62           O
ATOM    553  OD2 ASP A 101     -33.739 -24.327  30.420  1.00 41.79           O
ATOM    554  N   TRP A 102     -33.334 -19.697  27.792  1.00 34.72           N
ATOM    555  CA  TRP A 102     -32.410 -18.640  28.195  1.00 33.81           C
ATOM    556  C   TRP A 102     -32.551 -18.298  29.665  1.00 33.59           C
ATOM    557  O   TRP A 102     -33.655 -18.063  30.147  1.00 34.74           O
ATOM    558  CB  TRP A 102     -32.656 -17.351  27.396  1.00 32.65           C
ATOM    559  CG  TRP A 102     -32.248 -17.402  25.970  1.00 33.17           C
ATOM    560  CD1 TRP A 102     -33.066 -17.556  24.890  1.00 32.75           C
ATOM    561  CD2 TRP A 102     -30.914 -17.271  25.451  1.00 33.31           C
ATOM    562  NE1 TRP A 102     -32.328 -17.526  23.727  1.00 33.72           N
ATOM    563  CE2 TRP A 102     -31.004 -17.352  24.042  1.00 33.64           C
ATOM    564  CE3 TRP A 102     -29.653 -17.093  26.041  1.00 32.25           C
ATOM    565  CZ2 TRP A 102     -29.881 -17.260  23.211  1.00 33.13           C
ATOM    566  CZ3 TRP A 102     -28.536 -17.003  25.214  1.00 32.75           C
ATOM    567  CH2 TRP A 102     -28.661 -17.086  23.812  1.00 33.30           C
ATOM    568  N   VAL A 103     -31.435 -18.255  30.377  1.00 33.16           N
ATOM    569  CA  VAL A 103     -31.470 -17.885  31.785  1.00 32.80           C
ATOM    570  C   VAL A 103     -30.920 -16.466  31.879  1.00 33.78           C
ATOM    571  O   VAL A 103     -29.761 -16.221  31.547  1.00 33.67           O
ATOM    572  CB  VAL A 103     -30.604 -18.820  32.660  1.00 31.80           C
ATOM    573  CG1 VAL A 103     -30.652 -18.354  34.106  1.00 29.47           C
ATOM    574  CG2 VAL A 103     -31.105 -20.250  32.555  1.00 30.69           C
ATOM    575  N   LEU A 104     -31.753 -15.534  32.326  1.00 34.88           N
ATOM    576  CA  LEU A 104     -31.339 -14.143  32.439  1.00 36.49           C
ATOM    577  C   LEU A 104     -30.897 -13.749  33.838  1.00 37.80           C
ATOM    578  O   LEU A 104     -31.561 -14.066  34.815  1.00 38.42           O
ATOM    579  CB  LEU A 104     -32.477 -13.223  31.993  1.00 35.86           C
ATOM    580  CG  LEU A 104     -32.747 -13.167  30.492  1.00 35.88           C
ATOM    581  CD1 LEU A 104     -34.114 -12.573  30.253  1.00 35.67           C
ATOM    582  CD2 LEU A 104     -31.658 -12.343  29.799  1.00 35.68           C
ATOM    583  N   GLU A 105     -29.770 -13.051  33.914  1.00 39.28           N
ATOM    584  CA  GLU A 105     -29.221 -12.570  35.174  1.00 40.86           C
ATOM    585  C   GLU A 105     -28.852 -11.097  35.033  1.00 40.61           C
ATOM    586  O   GLU A 105     -28.253 -10.690  34.035  1.00 39.34           O
ATOM    587  CB  GLU A 105     -27.955 -13.332  35.543  1.00 43.96           C
ATOM    588  CG  GLU A 105     -28.133 -14.798  35.841  1.00 49.53           C
ATOM    589  CD  GLU A 105     -26.793 -15.502  35.951  1.00 52.67           C
ATOM    590  OE1 GLU A 105     -26.085 -15.571  34.917  1.00 54.11           O
ATOM    591  OE2 GLU A 105     -26.442 -15.972  37.061  1.00 54.39           O
ATOM    592  N   ILE A 106     -29.209 -10.304  36.035  1.00 39.82           N
ATOM    593  CA  ILE A 106     -28.875  -8.890  36.031  1.00 38.58           C
ATOM    594  C   ILE A 106     -27.771  -8.684  37.062  1.00 37.55           C
ATOM    595  O   ILE A 106     -28.003  -8.802  38.261  1.00 37.70           O
ATOM    596  CB  ILE A 106     -30.092  -8.018  36.406  1.00 39.28           C
ATOM    597  CG1 ILE A 106     -31.202  -8.198  35.372  1.00 40.15           C
ATOM    598  CG2 ILE A 106     -29.689  -6.556  36.475  1.00 37.95           C
ATOM    599  CD1 ILE A 106     -30.782  -7.839  33.957  1.00 42.48           C
ATOM    600  N   ASP A 107     -26.565  -8.400  36.586  1.00 36.33           N
ATOM    601  CA  ASP A 107     -25.421  -8.167  37.463  1.00 34.98           C
ATOM    602  C   ASP A 107     -25.332  -6.675  37.803  1.00 34.46           C
ATOM    603  O   ASP A 107     -24.816  -5.873  37.022  1.00 34.00           O
ATOM    604  CB  ASP A 107     -24.146  -8.653  36.770  1.00 35.40           C
ATOM    605  CG  ASP A 107     -22.895  -8.128  37.413  1.00 35.73           C
ATOM    606  OD1 ASP A 107     -22.801  -8.162  38.657  1.00 37.66           O
ATOM    607  OD2 ASP A 107     -21.994  -7.689  36.669  1.00 36.89           O
ATOM    608  N   THR A 108     -25.853  -6.319  38.975  1.00 33.36           N
ATOM    609  CA  THR A 108     -25.882  -4.937  39.439  1.00 33.03           C
ATOM    610  C   THR A 108     -24.799  -4.628  40.471  1.00 32.65           C
ATOM    611  O   THR A 108     -24.533  -5.422  41.370  1.00 32.50           O
```

FIGURE 2-10 (COORDINATES)

```
ATOM    612  CB  THR A 108     -27.274  -4.601  40.020  1.00 33.00           C
ATOM    613  OG1 THR A 108     -28.256  -4.744  38.988  1.00 33.82           O
ATOM    614  CG2 THR A 108     -27.320  -3.174  40.557  1.00 32.89           C
ATOM    615  N   PHE A 109     -24.179  -3.461  40.342  1.00 31.22           N
ATOM    616  CA  PHE A 109     -23.113  -3.083  41.250  1.00 30.29           C
ATOM    617  C   PHE A 109     -22.918  -1.581  41.302  1.00 29.73           C
ATOM    618  O   PHE A 109     -23.385  -0.857  40.423  1.00 28.83           O
ATOM    619  CB  PHE A 109     -21.796  -3.733  40.804  1.00 29.97           C
ATOM    620  CG  PHE A 109     -21.352  -3.305  39.429  1.00 30.26           C
ATOM    621  CD1 PHE A 109     -22.025  -3.754  38.295  1.00 29.27           C
ATOM    622  CD2 PHE A 109     -20.287  -2.423  39.270  1.00 30.01           C
ATOM    623  CE1 PHE A 109     -21.650  -3.332  37.025  1.00 29.38           C
ATOM    624  CE2 PHE A 109     -19.906  -1.995  37.997  1.00 30.97           C
ATOM    625  CZ  PHE A 109     -20.591  -2.452  36.874  1.00 30.18           C
ATOM    626  N   LEU A 110     -22.222  -1.128  42.343  1.00 30.17           N
ATOM    627  CA  LEU A 110     -21.905   0.280  42.525  1.00 32.22           C
ATOM    628  C   LEU A 110     -20.465   0.502  42.109  1.00 32.80           C
ATOM    629  O   LEU A 110     -19.650  -0.413  42.165  1.00 34.23           O
ATOM    630  CB  LEU A 110     -22.020   0.698  43.989  1.00 33.45           C
ATOM    631  CG  LEU A 110     -23.383   0.941  44.623  1.00 35.25           C
ATOM    632  CD1 LEU A 110     -23.173   1.358  46.074  1.00 36.36           C
ATOM    633  CD2 LEU A 110     -24.127   2.027  43.867  1.00 35.66           C
ATOM    634  N   SER A 111     -20.149   1.724  41.703  1.00 32.62           N
ATOM    635  CA  SER A 111     -18.792   2.058  41.324  1.00 31.63           C
ATOM    636  C   SER A 111     -18.589   3.558  41.393  1.00 32.17           C
ATOM    637  O   SER A 111     -19.510   4.321  41.149  1.00 33.25           O
ATOM    638  CB  SER A 111     -18.484   1.561  39.908  1.00 31.00           C
ATOM    639  OG  SER A 111     -17.207   2.015  39.482  1.00 30.43           O
ATOM    640  N   GLN A 112     -17.378   3.973  41.736  1.00 32.23           N
ATOM    641  CA  GLN A 112     -17.042   5.381  41.791  1.00 32.77           C
ATOM    642  C   GLN A 112     -16.961   5.906  40.351  1.00 32.79           C
ATOM    643  O   GLN A 112     -16.548   5.187  39.440  1.00 32.62           O
ATOM    644  CB  GLN A 112     -15.696   5.567  42.505  1.00 32.79           C
ATOM    645  CG  GLN A 112     -15.134   6.986  42.499  1.00 34.67           C
ATOM    646  CD  GLN A 112     -16.024   8.016  43.203  1.00 36.61           C
ATOM    647  OE1 GLN A 112     -15.526   8.880  43.927  1.00 37.83           O
ATOM    648  NE2 GLN A 112     -17.335   7.939  42.977  1.00 35.78           N
ATOM    649  N   THR A 113     -17.380   7.152  40.152  1.00 32.97           N
ATOM    650  CA  THR A 113     -17.351   7.786  38.838  1.00 33.21           C
ATOM    651  C   THR A 113     -17.014   9.251  39.072  1.00 34.01           C
ATOM    652  O   THR A 113     -16.985   9.708  40.218  1.00 34.12           O
ATOM    653  CB  THR A 113     -18.730   7.728  38.134  1.00 33.83           C
ATOM    654  OG1 THR A 113     -19.621   8.662  38.759  1.00 34.69           O
ATOM    655  CG2 THR A 113     -19.335   6.327  38.218  1.00 32.19           C
ATOM    656  N   PRO A 114     -16.754  10.010  37.995  1.00 34.31           N
ATOM    657  CA  PRO A 114     -16.426  11.430  38.152  1.00 34.72           C
ATOM    658  C   PRO A 114     -17.545  12.203  38.846  1.00 35.29           C
ATOM    659  O   PRO A 114     -17.328  13.309  39.335  1.00 36.07           O
ATOM    660  CB  PRO A 114     -16.210  11.896  36.716  1.00 34.77           C
ATOM    661  CG  PRO A 114     -15.703  10.651  36.028  1.00 33.88           C
ATOM    662  CD  PRO A 114     -16.608   9.587  36.590  1.00 33.96           C
ATOM    663  N   TYR A 115     -18.736  11.611  38.887  1.00 35.75           N
ATOM    664  CA  TYR A 115     -19.898  12.232  39.518  1.00 35.84           C
ATOM    665  C   TYR A 115     -20.273  11.543  40.823  1.00 36.39           C
ATOM    666  O   TYR A 115     -21.385  11.709  41.324  1.00 36.88           O
ATOM    667  CB  TYR A 115     -21.095  12.200  38.559  1.00 36.52           C
ATOM    668  CG  TYR A 115     -20.894  13.056  37.326  1.00 37.76           C
ATOM    669  CD1 TYR A 115     -20.711  14.436  37.440  1.00 38.15           C
ATOM    670  CD2 TYR A 115     -20.839  12.484  36.052  1.00 37.91           C
ATOM    671  CE1 TYR A 115     -20.472  15.227  36.320  1.00 38.99           C
ATOM    672  CE2 TYR A 115     -20.600  13.262  34.922  1.00 38.24           C
ATOM    673  CZ  TYR A 115     -20.415  14.637  35.064  1.00 39.48           C
ATOM    674  OH  TYR A 115     -20.162  15.423  33.959  1.00 39.75           O
ATOM    675  N   GLY A 116     -19.339  10.776  41.377  1.00 36.43           N
ATOM    676  CA  GLY A 116     -19.598  10.064  42.618  1.00 35.85           C
ATOM    677  C   GLY A 116     -20.087   8.648  42.369  1.00 35.41           C
ATOM    678  O   GLY A 116     -20.186   8.209  41.218  1.00 34.68           O
ATOM    679  N   TYR A 117     -20.394   7.931  43.446  1.00 35.15           N
```

FIGURE 2-11 (COORDINATES)

```
ATOM    680  CA  TYR A 117     -20.877   6.556  43.345  1.00 35.23           C
ATOM    681  C   TYR A 117     -22.145   6.427  42.513  1.00 35.63           C
ATOM    682  O   TYR A 117     -23.075   7.220  42.659  1.00 36.14           O
ATOM    683  CB  TYR A 117     -21.166   5.986  44.733  1.00 36.24           C
ATOM    684  CG  TYR A 117     -19.967   5.866  45.640  1.00 37.22           C
ATOM    685  CD1 TYR A 117     -20.123   5.488  46.974  1.00 37.55           C
ATOM    686  CD2 TYR A 117     -18.676   6.124  45.171  1.00 38.28           C
ATOM    687  CE1 TYR A 117     -19.029   5.371  47.820  1.00 38.17           C
ATOM    688  CE2 TYR A 117     -17.569   6.008  46.013  1.00 38.61           C
ATOM    689  CZ  TYR A 117     -17.758   5.633  47.334  1.00 38.64           C
ATOM    690  OH  TYR A 117     -16.679   5.536  48.177  1.00 41.41           O
ATOM    691  N   ARG A 118     -22.178   5.422  41.644  1.00 35.04           N
ATOM    692  CA  ARG A 118     -23.347   5.167  40.813  1.00 35.58           C
ATOM    693  C   ARG A 118     -23.604   3.670  40.677  1.00 35.16           C
ATOM    694  O   ARG A 118     -22.711   2.847  40.904  1.00 35.28           O
ATOM    695  CB  ARG A 118     -23.176   5.783  39.422  1.00 37.96           C
ATOM    696  CG  ARG A 118     -23.211   7.298  39.395  1.00 41.57           C
ATOM    697  CD  ARG A 118     -23.001   7.802  37.978  1.00 45.45           C
ATOM    698  NE  ARG A 118     -24.229   7.780  37.185  1.00 47.69           N
ATOM    699  CZ  ARG A 118     -25.147   8.743  37.207  1.00 48.84           C
ATOM    700  NH1 ARG A 118     -24.978   9.814  37.985  1.00 49.43           N
ATOM    701  NH2 ARG A 118     -26.232   8.640  36.451  1.00 49.24           N
ATOM    702  N   SER A 119     -24.828   3.329  40.294  1.00 33.51           N
ATOM    703  CA  SER A 119     -25.232   1.941  40.127  1.00 32.95           C
ATOM    704  C   SER A 119     -25.217   1.529  38.654  1.00 31.80           C
ATOM    705  O   SER A 119     -25.595   2.301  37.785  1.00 31.57           O
ATOM    706  CB  SER A 119     -26.633   1.743  40.709  1.00 32.78           C
ATOM    707  OG  SER A 119     -27.020   0.387  40.628  1.00 34.98           O
ATOM    708  N   PHE A 120     -24.781   0.303  38.383  1.00 31.06           N
ATOM    709  CA  PHE A 120     -24.708  -0.210  37.017  1.00 29.25           C
ATOM    710  C   PHE A 120     -25.333  -1.601  36.932  1.00 29.13           C
ATOM    711  O   PHE A 120     -25.325  -2.353  37.905  1.00 28.14           O
ATOM    712  CB  PHE A 120     -23.250  -0.310  36.571  1.00 28.58           C
ATOM    713  CG  PHE A 120     -22.549   1.007  36.449  1.00 28.30           C
ATOM    714  CD1 PHE A 120     -22.302   1.560  35.197  1.00 27.18           C
ATOM    715  CD2 PHE A 120     -22.083   1.671  37.580  1.00 28.32           C
ATOM    716  CE1 PHE A 120     -21.597   2.747  35.072  1.00 26.79           C
ATOM    717  CE2 PHE A 120     -21.376   2.861  37.464  1.00 27.79           C
ATOM    718  CZ  PHE A 120     -21.131   3.398  36.206  1.00 27.46           C
ATOM    719  N   SER A 121     -25.843  -1.955  35.757  1.00 28.74           N
ATOM    720  CA  SER A 121     -26.450  -3.264  35.581  1.00 29.59           C
ATOM    721  C   SER A 121     -26.104  -3.974  34.275  1.00 29.40           C
ATOM    722  O   SER A 121     -26.550  -3.582  33.199  1.00 28.85           O
ATOM    723  CB  SER A 121     -27.971  -3.156  35.712  1.00 30.32           C
ATOM    724  OG  SER A 121     -28.339  -2.819  37.037  1.00 31.30           O
ATOM    725  N   ASN A 122     -25.294  -5.018  34.376  1.00 29.73           N
ATOM    726  CA  ASN A 122     -24.942  -5.803  33.205  1.00 29.61           C
ATOM    727  C   ASN A 122     -26.068  -6.799  32.999  1.00 30.02           C
ATOM    728  O   ASN A 122     -26.700  -7.238  33.963  1.00 30.83           O
ATOM    729  CB  ASN A 122     -23.648  -6.581  33.426  1.00 29.42           C
ATOM    730  CG  ASN A 122     -22.436  -5.693  33.470  1.00 29.16           C
ATOM    731  OD1 ASN A 122     -22.287  -4.791  32.647  1.00 29.60           O
ATOM    732  ND2 ASN A 122     -21.552  -5.948  34.423  1.00 28.36           N
ATOM    733  N   ILE A 123     -26.331  -7.143  31.747  1.00 29.23           N
ATOM    734  CA  ILE A 123     -27.365  -8.118  31.444  1.00 29.29           C
ATOM    735  C   ILE A 123     -26.685  -9.358  30.877  1.00 29.74           C
ATOM    736  O   ILE A 123     -25.929  -9.266  29.910  1.00 30.44           O
ATOM    737  CB  ILE A 123     -28.365  -7.580  30.390  1.00 30.30           C
ATOM    738  CG1 ILE A 123     -29.020  -6.293  30.905  1.00 29.31           C
ATOM    739  CG2 ILE A 123     -29.410  -8.647  30.073  1.00 27.45           C
ATOM    740  CD1 ILE A 123     -29.794  -5.538  29.855  1.00 30.88           C
ATOM    741  N   ILE A 124     -26.923 -10.515  31.483  1.00 29.54           N
ATOM    742  CA  ILE A 124     -26.321 -11.735  30.969  1.00 29.71           C
ATOM    743  C   ILE A 124     -27.403 -12.753  30.636  1.00 30.40           C
ATOM    744  O   ILE A 124     -28.205 -13.115  31.487  1.00 31.01           O
ATOM    745  CB  ILE A 124     -25.329 -12.381  31.977  1.00 29.70           C
ATOM    746  CG1 ILE A 124     -24.182 -11.414  32.298  1.00 29.46           C
ATOM    747  CG2 ILE A 124     -24.775 -13.686  31.393  1.00 27.18           C
```

FIGURE 2-12 (COORDINATES)

```
ATOM    748  CD1 ILE A 124     -24.208 -10.861  33.714  1.00 30.05           C
ATOM    749  N   SER A 125     -27.420 -13.205  29.388  1.00 30.46           N
ATOM    750  CA  SER A 125     -28.387 -14.191  28.937  1.00 30.93           C
ATOM    751  C   SER A 125     -27.609 -15.460  28.593  1.00 31.20           C
ATOM    752  O   SER A 125     -26.802 -15.458  27.672  1.00 31.27           O
ATOM    753  CB  SER A 125     -29.125 -13.665  27.713  1.00 31.70           C
ATOM    754  OG  SER A 125     -30.212 -14.505  27.387  1.00 34.17           O
ATOM    755  N   THR A 126     -27.865 -16.542  29.326  1.00 31.35           N
ATOM    756  CA  THR A 126     -27.142 -17.793  29.126  1.00 31.49           C
ATOM    757  C   THR A 126     -27.978 -19.034  28.809  1.00 32.24           C
ATOM    758  O   THR A 126     -29.056 -19.231  29.370  1.00 33.30           O
ATOM    759  CB  THR A 126     -26.324 -18.147  30.388  1.00 31.57           C
ATOM    760  OG1 THR A 126     -25.671 -16.972  30.886  1.00 31.76           O
ATOM    761  CG2 THR A 126     -25.282 -19.225  30.077  1.00 30.41           C
ATOM    762  N   LEU A 127     -27.465 -19.871  27.910  1.00 31.91           N
ATOM    763  CA  LEU A 127     -28.109 -21.142  27.582  1.00 31.13           C
ATOM    764  C   LEU A 127     -27.230 -22.196  28.253  1.00 30.93           C
ATOM    765  O   LEU A 127     -26.009 -22.174  28.113  1.00 30.40           O
ATOM    766  CB  LEU A 127     -28.153 -21.388  26.071  1.00 30.27           C
ATOM    767  CG  LEU A 127     -29.179 -20.583  25.260  1.00 30.15           C
ATOM    768  CD1 LEU A 127     -29.079 -20.980  23.796  1.00 28.45           C
ATOM    769  CD2 LEU A 127     -30.596 -20.831  25.786  1.00 29.15           C
ATOM    770  N   ASN A 128     -27.843 -23.099  29.009  1.00 31.39           N
ATOM    771  CA  ASN A 128     -27.086 -24.146  29.694  1.00 30.93           C
ATOM    772  C   ASN A 128     -26.059 -23.557  30.661  1.00 30.90           C
ATOM    773  O   ASN A 128     -24.856 -23.705  30.472  1.00 31.37           O
ATOM    774  CB  ASN A 128     -26.388 -25.019  28.661  1.00 30.28           C
ATOM    775  CG  ASN A 128     -27.349 -25.546  27.618  1.00 32.02           C
ATOM    776  OD1 ASN A 128     -27.995 -26.582  27.815  1.00 34.14           O
ATOM    777  ND2 ASN A 128     -27.470 -24.827  26.508  1.00 30.44           N
ATOM    778  N   PRO A 129     -26.531 -22.884  31.720  1.00 30.82           N
ATOM    779  CA  PRO A 129     -25.689 -22.257  32.742  1.00 30.78           C
ATOM    780  C   PRO A 129     -24.560 -23.143  33.271  1.00 31.23           C
ATOM    781  O   PRO A 129     -23.448 -22.672  33.486  1.00 31.82           O
ATOM    782  CB  PRO A 129     -26.688 -21.916  33.841  1.00 30.28           C
ATOM    783  CG  PRO A 129     -27.917 -21.620  33.085  1.00 31.40           C
ATOM    784  CD  PRO A 129     -27.956 -22.722  32.055  1.00 30.65           C
ATOM    785  N   THR A 130     -24.842 -24.423  33.492  1.00 31.63           N
ATOM    786  CA  THR A 130     -23.815 -25.312  34.024  1.00 31.47           C
ATOM    787  C   THR A 130     -22.900 -25.887  32.956  1.00 31.89           C
ATOM    788  O   THR A 130     -21.977 -26.640  33.275  1.00 32.60           O
ATOM    789  CB  THR A 130     -24.425 -26.471  34.883  1.00 29.99           C
ATOM    790  OG1 THR A 130     -25.227 -27.328  34.065  1.00 29.97           O
ATOM    791  CG2 THR A 130     -25.281 -25.905  35.992  1.00 27.70           C
ATOM    792  N   ALA A 131     -23.136 -25.516  31.701  0.00 32.06           N
ATOM    793  CA  ALA A 131     -22.296 -25.983  30.607  0.00 32.13           C
ATOM    794  C   ALA A 131     -20.899 -25.420  30.845  0.00 32.21           C
ATOM    795  O   ALA A 131     -20.734 -24.223  31.080  0.00 32.21           O
ATOM    796  CB  ALA A 131     -22.843 -25.495  29.273  0.00 32.15           C
ATOM    797  N   LYS A 132     -19.900 -26.290  30.790  1.00 32.32           N
ATOM    798  CA  LYS A 132     -18.511 -25.894  31.024  1.00 32.53           C
ATOM    799  C   LYS A 132     -18.013 -24.812  30.076  1.00 31.96           C
ATOM    800  O   LYS A 132     -17.421 -23.832  30.512  1.00 31.80           O
ATOM    801  CB  LYS A 132     -17.565 -27.108  30.949  1.00 31.87           C
ATOM    802  CG  LYS A 132     -17.887 -28.200  31.962  1.00 35.13           C
ATOM    803  CD  LYS A 132     -16.671 -29.047  32.385  1.00 36.89           C
ATOM    804  CE  LYS A 132     -16.022 -29.810  31.236  1.00 38.30           C
ATOM    805  NZ  LYS A 132     -16.877 -30.874  30.634  1.00 39.74           N
ATOM    806  N   ARG A 133     -18.252 -24.991  28.783  1.00 31.40           N
ATOM    807  CA  ARG A 133     -17.807 -24.016  27.796  1.00 30.73           C
ATOM    808  C   ARG A 133     -18.964 -23.254  27.178  1.00 30.31           C
ATOM    809  O   ARG A 133     -20.057 -23.789  27.003  1.00 30.38           O
ATOM    810  CB  ARG A 133     -17.031 -24.704  26.670  1.00 30.20           C
ATOM    811  CG  ARG A 133     -15.799 -25.457  27.109  1.00 30.54           C
ATOM    812  CD  ARG A 133     -15.419 -26.514  26.082  1.00 30.86           C
ATOM    813  NE  ARG A 133     -15.148 -25.944  24.767  1.00 30.86           N
ATOM    814  CZ  ARG A 133     -15.053 -26.661  23.650  1.00 32.09           C
ATOM    815  NH1 ARG A 133     -15.212 -27.980  23.698  1.00 30.83           N
```

FIGURE 2-13 (COORDINATES)

```
ATOM    816  NH2 ARG A 133     -14.800 -26.062  22.488  1.00 30.46           N
ATOM    817  N   HIS A 134     -18.708 -21.990  26.860  1.00 29.70           N
ATOM    818  CA  HIS A 134     -19.693 -21.138  26.209  1.00 29.17           C
ATOM    819  C   HIS A 134     -19.031 -20.217  25.198  1.00 28.50           C
ATOM    820  O   HIS A 134     -17.942 -19.692  25.438  1.00 29.10           O
ATOM    821  CB  HIS A 134     -20.444 -20.257  27.211  1.00 28.18           C
ATOM    822  CG  HIS A 134     -21.492 -20.980  27.993  1.00 29.17           C
ATOM    823  ND1 HIS A 134     -21.214 -21.680  29.146  1.00 28.04           N
ATOM    824  CD2 HIS A 134     -22.823 -21.112  27.784  1.00 29.14           C
ATOM    825  CE1 HIS A 134     -22.327 -22.212  29.615  1.00 28.08           C
ATOM    826  NE2 HIS A 134     -23.319 -21.882  28.808  1.00 29.16           N
ATOM    827  N   LEU A 135     -19.685 -20.058  24.056  1.00 27.20           N
ATOM    828  CA  LEU A 135     -19.232 -19.123  23.045  1.00 26.27           C
ATOM    829  C   LEU A 135     -19.941 -17.864  23.543  1.00 25.21           C
ATOM    830  O   LEU A 135     -21.126 -17.922  23.866  1.00 24.96           O
ATOM    831  CB  LEU A 135     -19.769 -19.505  21.663  1.00 26.43           C
ATOM    832  CG  LEU A 135     -19.659 -18.422  20.581  1.00 27.15           C
ATOM    833  CD1 LEU A 135     -18.205 -18.102  20.311  1.00 24.70           C
ATOM    834  CD2 LEU A 135     -20.347 -18.903  19.303  1.00 27.32           C
ATOM    835  N   VAL A 136     -19.239 -16.741  23.628  1.00 24.36           N
ATOM    836  CA  VAL A 136     -19.873 -15.519  24.123  1.00 25.53           C
ATOM    837  C   VAL A 136     -19.924 -14.362  23.126  1.00 25.76           C
ATOM    838  O   VAL A 136     -18.914 -13.999  22.531  1.00 27.10           O
ATOM    839  CB  VAL A 136     -19.171 -14.998  25.429  1.00 24.90           C
ATOM    840  CG1 VAL A 136     -19.975 -13.867  26.037  1.00 24.10           C
ATOM    841  CG2 VAL A 136     -19.009 -16.131  26.437  1.00 24.01           C
ATOM    842  N   LEU A 137     -21.110 -13.801  22.927  1.00 26.52           N
ATOM    843  CA  LEU A 137     -21.259 -12.643  22.046  1.00 27.11           C
ATOM    844  C   LEU A 137     -21.584 -11.509  23.006  1.00 26.41           C
ATOM    845  O   LEU A 137     -22.356 -11.702  23.943  1.00 26.10           O
ATOM    846  CB  LEU A 137     -22.414 -12.815  21.054  1.00 28.23           C
ATOM    847  CG  LEU A 137     -22.457 -14.054  20.157  1.00 29.58           C
ATOM    848  CD1 LEU A 137     -23.636 -13.907  19.183  1.00 30.20           C
ATOM    849  CD2 LEU A 137     -21.146 -14.226  19.401  1.00 30.11           C
ATOM    850  N   ALA A 138     -21.005 -10.336  22.778  1.00 25.76           N
ATOM    851  CA  ALA A 138     -21.238  -9.210  23.668  1.00 24.79           C
ATOM    852  C   ALA A 138     -21.221  -7.842  22.999  1.00 24.80           C
ATOM    853  O   ALA A 138     -20.755  -7.682  21.868  1.00 25.06           O
ATOM    854  CB  ALA A 138     -20.206  -9.238  24.792  1.00 23.41           C
ATOM    855  N   CYS A 139     -21.743  -6.860  23.725  1.00 24.64           N
ATOM    856  CA  CYS A 139     -21.774  -5.463  23.292  1.00 25.85           C
ATOM    857  C   CYS A 139     -22.230  -4.670  24.508  1.00 25.56           C
ATOM    858  O   CYS A 139     -22.636  -5.256  25.515  1.00 26.20           O
ATOM    859  CB  CYS A 139     -22.756  -5.256  22.128  1.00 26.55           C
ATOM    860  SG  CYS A 139     -24.496  -5.144  22.597  1.00 28.46           S
ATOM    861  N   HIS A 140     -22.145  -3.349  24.441  1.00 25.38           N
ATOM    862  CA  HIS A 140     -22.592  -2.541  25.566  1.00 25.77           C
ATOM    863  C   HIS A 140     -23.951  -1.946  25.200  1.00 25.56           C
ATOM    864  O   HIS A 140     -24.177  -1.583  24.043  1.00 25.44           O
ATOM    865  CB  HIS A 140     -21.565  -1.447  25.882  1.00 25.78           C
ATOM    866  CG  HIS A 140     -21.508  -0.346  24.869  1.00 26.19           C
ATOM    867  ND1 HIS A 140     -22.234   0.819  24.996  1.00 25.82           N
ATOM    868  CD2 HIS A 140     -20.816  -0.234  23.711  1.00 26.75           C
ATOM    869  CE1 HIS A 140     -21.988   1.602  23.961  1.00 27.01           C
ATOM    870  NE2 HIS A 140     -21.132   0.986  23.166  1.00 26.51           N
ATOM    871  N   TYR A 141     -24.868  -1.870  26.164  1.00 25.39           N
ATOM    872  CA  TYR A 141     -26.188  -1.324  25.863  1.00 26.06           C
ATOM    873  C   TYR A 141     -26.399   0.095  26.375  1.00 26.24           C
ATOM    874  O   TYR A 141     -27.447   0.683  26.144  1.00 28.48           O
ATOM    875  CB  TYR A 141     -27.313  -2.243  26.381  1.00 24.77           C
ATOM    876  CG  TYR A 141     -27.573  -2.172  27.876  1.00 26.86           C
ATOM    877  CD1 TYR A 141     -26.761  -2.857  28.783  1.00 25.20           C
ATOM    878  CD2 TYR A 141     -28.628  -1.408  28.382  1.00 26.93           C
ATOM    879  CE1 TYR A 141     -26.988  -2.788  30.141  1.00 25.81           C
ATOM    880  CE2 TYR A 141     -28.866  -1.330  29.754  1.00 26.96           C
ATOM    881  CZ  TYR A 141     -28.043  -2.025  30.631  1.00 27.05           C
ATOM    882  OH  TYR A 141     -28.281  -1.979  31.990  1.00 24.72           O
ATOM    883  N   ASP A 142     -25.414   0.646  27.072  1.00 26.24           N
```

FIGURE 2-14 (COORDINATES)

```
ATOM    884  CA   ASP A 142     -25.527   2.017  27.552  1.00 26.41           C
ATOM    885  C    ASP A 142     -25.171   2.951  26.399  1.00 26.30           C
ATOM    886  O    ASP A 142     -24.535   2.537  25.433  1.00 26.53           O
ATOM    887  CB   ASP A 142     -24.568   2.271  28.724  1.00 25.43           C
ATOM    888  CG   ASP A 142     -23.105   2.123  28.332  1.00 26.83           C
ATOM    889  OD1  ASP A 142     -22.750   1.088  27.733  1.00 26.27           O
ATOM    890  OD2  ASP A 142     -22.306   3.038  28.631  1.00 27.47           O
ATOM    891  N    SER A 143     -25.593   4.204  26.501  1.00 26.03           N
ATOM    892  CA   SER A 143     -25.282   5.200  25.488  1.00 26.81           C
ATOM    893  C    SER A 143     -24.459   6.256  26.213  1.00 27.37           C
ATOM    894  O    SER A 143     -24.720   6.560  27.379  1.00 26.91           O
ATOM    895  CB   SER A 143     -26.565   5.823  24.908  1.00 26.68           C
ATOM    896  OG   SER A 143     -27.303   6.531  25.892  1.00 25.46           O
ATOM    897  N    LYS A 144     -23.460   6.803  25.532  1.00 27.96           N
ATOM    898  CA   LYS A 144     -22.593   7.815  26.132  1.00 29.84           C
ATOM    899  C    LYS A 144     -23.381   9.037  26.616  1.00 30.94           C
ATOM    900  O    LYS A 144     -24.243   9.561  25.906  1.00 30.35           O
ATOM    901  CB   LYS A 144     -21.526   8.242  25.121  1.00 28.31           C
ATOM    902  CG   LYS A 144     -20.477   9.176  25.677  1.00 28.11           C
ATOM    903  CD   LYS A 144     -19.369   9.397  24.660  1.00 28.69           C
ATOM    904  CE   LYS A 144     -18.318  10.350  25.176  1.00 27.72           C
ATOM    905  NZ   LYS A 144     -17.776   9.896  26.477  1.00 28.42           N
ATOM    906  N    TYR A 145     -23.089   9.488  27.831  1.00 32.70           N
ATOM    907  CA   TYR A 145     -23.782  10.649  28.379  1.00 34.64           C
ATOM    908  C    TYR A 145     -23.413  11.966  27.702  1.00 35.44           C
ATOM    909  O    TYR A 145     -22.242  12.327  27.607  1.00 35.88           O
ATOM    910  CB   TYR A 145     -23.508  10.820  29.874  1.00 36.22           C
ATOM    911  CG   TYR A 145     -24.124  12.109  30.377  1.00 39.11           C
ATOM    912  CD1  TYR A 145     -25.515  12.245  30.468  1.00 39.49           C
ATOM    913  CD2  TYR A 145     -23.337  13.232  30.631  1.00 39.82           C
ATOM    914  CE1  TYR A 145     -26.101  13.458  30.786  1.00 40.84           C
ATOM    915  CE2  TYR A 145     -23.918  14.459  30.950  1.00 41.03           C
ATOM    916  CZ   TYR A 145     -25.298  14.563  31.022  1.00 41.97           C
ATOM    917  OH   TYR A 145     -25.885  15.777  31.299  1.00 44.66           O
ATOM    918  N    PHE A 146     -24.430  12.690  27.265  1.00 36.32           N
ATOM    919  CA   PHE A 146     -24.255  13.983  26.621  1.00 38.01           C
ATOM    920  C    PHE A 146     -25.459  14.814  27.010  1.00 39.67           C
ATOM    921  O    PHE A 146     -26.588  14.339  26.931  1.00 40.32           O
ATOM    922  CB   PHE A 146     -24.261  13.847  25.097  1.00 36.87           C
ATOM    923  CG   PHE A 146     -22.966  13.381  24.511  1.00 36.23           C
ATOM    924  CD1  PHE A 146     -21.846  14.211  24.508  1.00 35.97           C
ATOM    925  CD2  PHE A 146     -22.879  12.137  23.892  1.00 35.29           C
ATOM    926  CE1  PHE A 146     -20.657  13.813  23.886  1.00 34.97           C
ATOM    927  CE2  PHE A 146     -21.693  11.728  23.266  1.00 35.50           C
ATOM    928  CZ   PHE A 146     -20.581  12.571  23.262  1.00 34.68           C
ATOM    929  N    SER A 147     -25.240  16.044  27.443  1.00 41.75           N
ATOM    930  CA   SER A 147     -26.378  16.891  27.772  1.00 44.80           C
ATOM    931  C    SER A 147     -27.039  17.225  26.424  1.00 45.98           C
ATOM    932  O    SER A 147     -26.395  17.150  25.372  1.00 46.04           O
ATOM    933  CB   SER A 147     -25.910  18.172  28.465  1.00 44.80           C
ATOM    934  OG   SER A 147     -25.173  18.978  27.567  1.00 46.57           O
ATOM    935  N    HIS A 148     -28.318  17.581  26.436  1.00 47.65           N
ATOM    936  CA   HIS A 148     -28.981  17.906  25.179  1.00 48.67           C
ATOM    937  C    HIS A 148     -28.346  19.140  24.542  1.00 49.72           C
ATOM    938  O    HIS A 148     -27.991  20.102  25.224  1.00 49.30           O
ATOM    939  CB   HIS A 148     -30.479  18.129  25.395  1.00 48.27           C
ATOM    940  CG   HIS A 148     -31.195  16.928  25.931  1.00 48.48           C
ATOM    941  ND1  HIS A 148     -30.689  15.650  25.821  1.00 48.49           N
ATOM    942  CD2  HIS A 148     -32.383  16.809  26.572  1.00 48.40           C
ATOM    943  CE1  HIS A 148     -31.533  14.796  26.373  1.00 48.60           C
ATOM    944  NE2  HIS A 148     -32.569  15.473  26.835  1.00 48.59           N
ATOM    945  N    TRP A 149     -28.197  19.099  23.225  1.00 51.09           N
ATOM    946  CA   TRP A 149     -27.594  20.198  22.492  1.00 52.69           C
ATOM    947  C    TRP A 149     -28.484  20.574  21.313  1.00 53.28           C
ATOM    948  O    TRP A 149     -28.633  19.801  20.370  1.00 53.13           O
ATOM    949  CB   TRP A 149     -26.217  19.774  21.991  1.00 53.96           C
ATOM    950  CG   TRP A 149     -25.455  20.864  21.309  1.00 55.95           C
ATOM    951  CD1  TRP A 149     -24.725  21.858  21.904  1.00 55.67           C
```

FIGURE 2-15 (COORDINATES)

```
ATOM    952  CD2 TRP A 149     -25.333  21.064  19.893  1.00 56.75           C
ATOM    953  NE1 TRP A 149     -24.152  22.659  20.944  1.00 56.24           N
ATOM    954  CE2 TRP A 149     -24.509  22.196  19.702  1.00 56.63           C
ATOM    955  CE3 TRP A 149     -25.840  20.396  18.766  1.00 57.12           C
ATOM    956  CZ2 TRP A 149     -24.177  22.677  18.425  1.00 57.07           C
ATOM    957  CZ3 TRP A 149     -25.509  20.875  17.496  1.00 57.57           C
ATOM    958  CH2 TRP A 149     -24.685  22.005  17.340  1.00 57.07           C
ATOM    959  N   ASN A 150     -29.069  21.766  21.370  1.00 54.27           N
ATOM    960  CA  ASN A 150     -29.956  22.233  20.309  1.00 55.08           C
ATOM    961  C   ASN A 150     -31.111  21.256  20.092  1.00 54.60           C
ATOM    962  O   ASN A 150     -31.478  20.944  18.956  1.00 54.19           O
ATOM    963  CB  ASN A 150     -29.173  22.425  19.007  1.00 57.05           C
ATOM    964  CG  ASN A 150     -28.178  23.572  19.090  1.00 59.07           C
ATOM    965  OD1 ASN A 150     -27.372  23.774  18.182  1.00 60.52           O
ATOM    966  ND2 ASN A 150     -28.233  24.331  20.184  1.00 59.41           N
ATOM    967  N   ASN A 151     -31.673  20.781  21.200  1.00 53.84           N
ATOM    968  CA  ASN A 151     -32.793  19.848  21.177  1.00 53.26           C
ATOM    969  C   ASN A 151     -32.448  18.501  20.557  1.00 51.34           C
ATOM    970  O   ASN A 151     -33.340  17.726  20.212  1.00 51.71           O
ATOM    971  CB  ASN A 151     -33.982  20.469  20.437  1.00 55.00           C
ATOM    972  CG  ASN A 151     -34.449  21.760  21.080  1.00 56.92           C
ATOM    973  OD1 ASN A 151     -34.828  21.778  22.254  1.00 58.84           O
ATOM    974  ND2 ASN A 151     -34.419  22.851  20.318  1.00 57.36           N
ATOM    975  N   ARG A 152     -31.156  18.225  20.407  1.00 48.60           N
ATOM    976  CA  ARG A 152     -30.719  16.949  19.853  1.00 46.06           C
ATOM    977  C   ARG A 152     -30.238  16.049  20.990  1.00 43.31           C
ATOM    978  O   ARG A 152     -29.609  16.515  21.946  1.00 42.97           O
ATOM    979  CB  ARG A 152     -29.604  17.154  18.818  1.00 47.34           C
ATOM    980  CG  ARG A 152     -30.067  17.885  17.563  1.00 48.42           C
ATOM    981  CD  ARG A 152     -29.049  17.782  16.441  1.00 49.10           C
ATOM    982  NE  ARG A 152     -29.004  16.435  15.878  1.00 50.45           N
ATOM    983  CZ  ARG A 152     -28.100  16.023  14.992  1.00 50.32           C
ATOM    984  NH1 ARG A 152     -27.160  16.856  14.568  1.00 51.17           N
ATOM    985  NH2 ARG A 152     -28.135  14.780  14.528  1.00 49.91           N
ATOM    986  N   VAL A 153     -30.553  14.763  20.886  1.00 40.24           N
ATOM    987  CA  VAL A 153     -30.180  13.791  21.907  1.00 37.42           C
ATOM    988  C   VAL A 153     -29.267  12.715  21.326  1.00 35.96           C
ATOM    989  O   VAL A 153     -29.473  12.270  20.204  1.00 34.83           O
ATOM    990  CB  VAL A 153     -31.452  13.136  22.501  1.00 36.84           C
ATOM    991  CG1 VAL A 153     -31.080  12.033  23.476  1.00 36.21           C
ATOM    992  CG2 VAL A 153     -32.300  14.203  23.197  1.00 35.93           C
ATOM    993  N   PHE A 154     -28.249  12.306  22.080  1.00 34.05           N
ATOM    994  CA  PHE A 154     -27.339  11.270  21.596  1.00 31.93           C
ATOM    995  C   PHE A 154     -27.945   9.890  21.858  1.00 31.43           C
ATOM    996  O   PHE A 154     -28.305   9.565  22.992  1.00 30.06           O
ATOM    997  CB  PHE A 154     -25.981  11.379  22.296  1.00 31.59           C
ATOM    998  CG  PHE A 154     -24.961  10.383  21.802  1.00 31.76           C
ATOM    999  CD1 PHE A 154     -24.353  10.547  20.560  1.00 30.69           C
ATOM   1000  CD2 PHE A 154     -24.637   9.265  22.564  1.00 31.24           C
ATOM   1001  CE1 PHE A 154     -23.436   9.611  20.078  1.00 30.96           C
ATOM   1002  CE2 PHE A 154     -23.725   8.323  22.096  1.00 32.20           C
ATOM   1003  CZ  PHE A 154     -23.121   8.497  20.845  1.00 31.38           C
ATOM   1004  N   VAL A 155     -28.071   9.080  20.812  1.00 30.76           N
ATOM   1005  CA  VAL A 155     -28.635   7.744  20.987  1.00 31.67           C
ATOM   1006  C   VAL A 155     -27.696   6.611  20.568  1.00 31.25           C
ATOM   1007  O   VAL A 155     -28.062   5.441  20.667  1.00 31.60           O
ATOM   1008  CB  VAL A 155     -29.991   7.584  20.225  1.00 31.64           C
ATOM   1009  CG1 VAL A 155     -30.989   8.622  20.717  1.00 31.78           C
ATOM   1010  CG2 VAL A 155     -29.782   7.714  18.720  1.00 32.45           C
ATOM   1011  N   GLY A 156     -26.495   6.961  20.106  1.00 30.86           N
ATOM   1012  CA  GLY A 156     -25.521   5.958  19.681  1.00 29.65           C
ATOM   1013  C   GLY A 156     -26.092   4.798  18.876  1.00 28.32           C
ATOM   1014  O   GLY A 156     -26.074   3.655  19.319  1.00 28.27           O
ATOM   1015  N   ALA A 157     -26.593   5.083  17.682  1.00 28.06           N
ATOM   1016  CA  ALA A 157     -27.175   4.043  16.846  1.00 27.68           C
ATOM   1017  C   ALA A 157     -26.195   2.898  16.552  1.00 27.72           C
ATOM   1018  O   ALA A 157     -26.544   1.725  16.706  1.00 28.98           O
ATOM   1019  CB  ALA A 157     -27.707   4.657  15.546  1.00 26.81           C
```

FIGURE 2-16 (COORDINATES)

```
ATOM   1020  N    THR A 158     -24.977   3.221  16.127  1.00 26.95           N
ATOM   1021  CA   THR A 158     -23.990   2.179  15.857  1.00 26.97           C
ATOM   1022  C    THR A 158     -23.247   1.861  17.150  1.00 27.39           C
ATOM   1023  O    THR A 158     -22.595   0.816  17.259  1.00 28.28           O
ATOM   1024  CB   THR A 158     -22.874   2.620  14.848  1.00 26.24           C
ATOM   1025  OG1  THR A 158     -22.057   3.627  15.459  1.00 25.10           O
ATOM   1026  CG2  THR A 158     -23.457   3.156  13.559  1.00 24.21           C
ATOM   1027  N    ASP A 159     -23.373   2.756  18.127  1.00 26.10           N
ATOM   1028  CA   ASP A 159     -22.636   2.655  19.384  1.00 26.39           C
ATOM   1029  C    ASP A 159     -23.458   2.599  20.692  1.00 26.64           C
ATOM   1030  O    ASP A 159     -23.501   3.588  21.429  1.00 26.82           O
ATOM   1031  CB   ASP A 159     -21.669   3.855  19.403  1.00 26.27           C
ATOM   1032  CG   ASP A 159     -20.653   3.803  20.528  1.00 28.50           C
ATOM   1033  OD1  ASP A 159     -20.447   2.714  21.112  1.00 27.42           O
ATOM   1034  OD2  ASP A 159     -20.041   4.869  20.811  1.00 28.54           O
ATOM   1035  N    SER A 160     -24.077   1.463  21.017  1.00 25.90           N
ATOM   1036  CA   SER A 160     -24.089   0.261  20.197  1.00 26.41           C
ATOM   1037  C    SER A 160     -25.501  -0.330  20.103  1.00 25.96           C
ATOM   1038  O    SER A 160     -25.714  -1.521  20.354  1.00 25.74           O
ATOM   1039  CB   SER A 160     -23.128  -0.781  20.774  1.00 26.28           C
ATOM   1040  OG   SER A 160     -21.787  -0.433  20.504  1.00 26.90           O
ATOM   1041  N    ALA A 161     -26.463   0.508  19.732  1.00 25.68           N
ATOM   1042  CA   ALA A 161     -27.846   0.070  19.596  1.00 25.66           C
ATOM   1043  C    ALA A 161     -27.969  -1.047  18.542  1.00 26.23           C
ATOM   1044  O    ALA A 161     -28.654  -2.050  18.766  1.00 26.08           O
ATOM   1045  CB   ALA A 161     -28.731   1.257  19.228  1.00 24.91           C
ATOM   1046  N    VAL A 162     -27.312  -0.875  17.398  1.00 26.04           N
ATOM   1047  CA   VAL A 162     -27.352  -1.898  16.350  1.00 26.61           C
ATOM   1048  C    VAL A 162     -26.732  -3.223  16.851  1.00 27.00           C
ATOM   1049  O    VAL A 162     -27.332  -4.287  16.698  1.00 27.76           O
ATOM   1050  CB   VAL A 162     -26.649  -1.399  15.058  1.00 26.05           C
ATOM   1051  CG1  VAL A 162     -26.425  -2.545  14.097  1.00 24.66           C
ATOM   1052  CG2  VAL A 162     -27.509  -0.315  14.396  1.00 23.91           C
ATOM   1053  N    PRO A 163     -25.523  -3.182  17.443  1.00 26.78           N
ATOM   1054  CA   PRO A 163     -24.984  -4.465  17.920  1.00 26.47           C
ATOM   1055  C    PRO A 163     -25.991  -5.189  18.850  1.00 26.85           C
ATOM   1056  O    PRO A 163     -26.185  -6.408  18.748  1.00 26.72           O
ATOM   1057  CB   PRO A 163     -23.701  -4.046  18.633  1.00 25.23           C
ATOM   1058  CG   PRO A 163     -23.206  -2.945  17.755  1.00 24.97           C
ATOM   1059  CD   PRO A 163     -24.480  -2.137  17.466  1.00 25.74           C
ATOM   1060  N    CYS A 164     -26.634  -4.435  19.741  1.00 27.07           N
ATOM   1061  CA   CYS A 164     -27.631  -5.013  20.646  1.00 27.91           C
ATOM   1062  C    CYS A 164     -28.720  -5.730  19.836  1.00 27.74           C
ATOM   1063  O    CYS A 164     -29.030  -6.893  20.086  1.00 28.40           O
ATOM   1064  CB   CYS A 164     -28.285  -3.921  21.510  1.00 27.79           C
ATOM   1065  SG   CYS A 164     -27.274  -3.242  22.863  1.00 29.50           S
ATOM   1066  N    ALA A 165     -29.285  -5.027  18.859  1.00 27.31           N
ATOM   1067  CA   ALA A 165     -30.335  -5.570  18.004  1.00 26.70           C
ATOM   1068  C    ALA A 165     -29.872  -6.796  17.230  1.00 27.23           C
ATOM   1069  O    ALA A 165     -30.637  -7.741  17.058  1.00 28.07           O
ATOM   1070  CB   ALA A 165     -30.828  -4.497  17.036  1.00 26.10           C
ATOM   1071  N    MET A 166     -28.628  -6.779  16.756  1.00 27.30           N
ATOM   1072  CA   MET A 166     -28.083  -7.916  16.015  1.00 27.69           C
ATOM   1073  C    MET A 166     -28.063  -9.164  16.903  1.00 27.55           C
ATOM   1074  O    MET A 166     -28.378 -10.265  16.452  1.00 27.03           O
ATOM   1075  CB   MET A 166     -26.659  -7.607  15.530  1.00 27.73           C
ATOM   1076  CG   MET A 166     -26.578  -6.466  14.517  1.00 28.11           C
ATOM   1077  SD   MET A 166     -24.874  -6.040  14.043  1.00 28.54           S
ATOM   1078  CE   MET A 166     -24.405  -7.479  13.108  1.00 24.79           C
ATOM   1079  N    MET A 167     -27.683  -8.983  18.165  1.00 27.32           N
ATOM   1080  CA   MET A 167     -27.633 -10.087  19.106  1.00 27.75           C
ATOM   1081  C    MET A 167     -29.048 -10.598  19.366  1.00 28.51           C
ATOM   1082  O    MET A 167     -29.271 -11.807  19.473  1.00 28.48           O
ATOM   1083  CB   MET A 167     -26.962  -9.635  20.404  1.00 28.34           C
ATOM   1084  CG   MET A 167     -25.446  -9.532  20.285  1.00 28.62           C
ATOM   1085  SD   MET A 167     -24.639  -8.607  21.610  1.00 30.42           S
ATOM   1086  CE   MET A 167     -24.970  -9.664  23.047  1.00 27.73           C
ATOM   1087  N    LEU A 168     -30.004  -9.677  19.454  1.00 28.28           N
```

FIGURE 2-17 (COORDINATES)

```
ATOM   1088  CA  LEU A 168     -31.396 -10.062  19.674  1.00 29.33           C
ATOM   1089  C   LEU A 168     -31.944 -10.774  18.435  1.00 29.57           C
ATOM   1090  O   LEU A 168     -32.633 -11.788  18.548  1.00 29.54           O
ATOM   1091  CB  LEU A 168     -32.262  -8.839  19.986  1.00 28.41           C
ATOM   1092  CG  LEU A 168     -32.038  -8.216  21.358  1.00 29.31           C
ATOM   1093  CD1 LEU A 168     -32.916  -6.982  21.510  1.00 30.38           C
ATOM   1094  CD2 LEU A 168     -32.354  -9.244  22.442  1.00 29.55           C
ATOM   1095  N   GLU A 169     -31.629 -10.243  17.259  1.00 29.03           N
ATOM   1096  CA  GLU A 169     -32.089 -10.842  16.015  1.00 29.10           C
ATOM   1097  C   GLU A 169     -31.498 -12.239  15.864  1.00 29.18           C
ATOM   1098  O   GLU A 169     -32.180 -13.155  15.404  1.00 29.43           O
ATOM   1099  CB  GLU A 169     -31.698  -9.957  14.822  1.00 29.54           C
ATOM   1100  CG  GLU A 169     -31.910 -10.576  13.434  1.00 29.75           C
ATOM   1101  CD  GLU A 169     -33.324 -11.114  13.208  1.00 31.05           C
ATOM   1102  OE1 GLU A 169     -34.266 -10.681  13.916  1.00 30.63           O
ATOM   1103  OE2 GLU A 169     -33.490 -11.968  12.305  1.00 30.36           O
ATOM   1104  N   LEU A 170     -30.235 -12.407  16.253  1.00 28.53           N
ATOM   1105  CA  LEU A 170     -29.599 -13.717  16.159  1.00 28.18           C
ATOM   1106  C   LEU A 170     -30.322 -14.704  17.082  1.00 28.73           C
ATOM   1107  O   LEU A 170     -30.591 -15.846  16.701  1.00 29.29           O
ATOM   1108  CB  LEU A 170     -28.118 -13.629  16.535  1.00 26.13           C
ATOM   1109  CG  LEU A 170     -27.400 -14.976  16.633  1.00 25.29           C
ATOM   1110  CD1 LEU A 170     -25.963 -14.841  16.148  1.00 22.60           C
ATOM   1111  CD2 LEU A 170     -27.473 -15.490  18.078  1.00 23.22           C
ATOM   1112  N   ALA A 171     -30.637 -14.254  18.291  1.00 28.90           N
ATOM   1113  CA  ALA A 171     -31.340 -15.088  19.248  1.00 29.45           C
ATOM   1114  C   ALA A 171     -32.694 -15.493  18.663  1.00 30.98           C
ATOM   1115  O   ALA A 171     -33.120 -16.647  18.791  1.00 31.16           O
ATOM   1116  CB  ALA A 171     -31.540 -14.330  20.554  1.00 28.59           C
ATOM   1117  N   ARG A 172     -33.369 -14.548  18.012  1.00 31.11           N
ATOM   1118  CA  ARG A 172     -34.670 -14.837  17.430  1.00 31.47           C
ATOM   1119  C   ARG A 172     -34.581 -15.746  16.212  1.00 31.56           C
ATOM   1120  O   ARG A 172     -35.325 -16.713  16.117  1.00 32.98           O
ATOM   1121  CB  ARG A 172     -35.394 -13.550  17.028  1.00 31.99           C
ATOM   1122  CG  ARG A 172     -36.827 -13.786  16.548  1.00 32.26           C
ATOM   1123  CD  ARG A 172     -37.346 -12.649  15.674  1.00 32.83           C
ATOM   1124  NE  ARG A 172     -36.679 -12.618  14.373  1.00 35.01           N
ATOM   1125  CZ  ARG A 172     -36.744 -13.590  13.463  1.00 35.16           C
ATOM   1126  NH1 ARG A 172     -37.449 -14.686  13.693  1.00 35.75           N
ATOM   1127  NH2 ARG A 172     -36.085 -13.472  12.320  1.00 36.20           N
ATOM   1128  N   ALA A 173     -33.671 -15.442  15.290  1.00 30.65           N
ATOM   1129  CA  ALA A 173     -33.519 -16.225  14.063  1.00 29.50           C
ATOM   1130  C   ALA A 173     -33.059 -17.667  14.259  1.00 30.24           C
ATOM   1131  O   ALA A 173     -33.468 -18.573  13.516  1.00 28.68           O
ATOM   1132  CB  ALA A 173     -32.559 -15.508  13.100  1.00 28.91           C
ATOM   1133  N   LEU A 174     -32.195 -17.876  15.246  1.00 31.17           N
ATOM   1134  CA  LEU A 174     -31.660 -19.202  15.516  1.00 32.00           C
ATOM   1135  C   LEU A 174     -32.378 -19.873  16.667  1.00 32.27           C
ATOM   1136  O   LEU A 174     -31.972 -20.947  17.110  1.00 31.92           O
ATOM   1137  CB  LEU A 174     -30.163 -19.110  15.841  1.00 32.05           C
ATOM   1138  CG  LEU A 174     -29.290 -18.391  14.813  1.00 31.90           C
ATOM   1139  CD1 LEU A 174     -27.841 -18.452  15.260  1.00 32.90           C
ATOM   1140  CD2 LEU A 174     -29.457 -19.032  13.442  1.00 31.93           C
ATOM   1141  N   ASP A 175     -33.446 -19.241  17.140  1.00 33.30           N
ATOM   1142  CA  ASP A 175     -34.204 -19.759  18.274  1.00 35.47           C
ATOM   1143  C   ASP A 175     -34.529 -21.253  18.212  1.00 36.77           C
ATOM   1144  O   ASP A 175     -34.271 -21.987  19.169  1.00 36.74           O
ATOM   1145  CB  ASP A 175     -35.489 -18.948  18.457  1.00 35.43           C
ATOM   1146  CG  ASP A 175     -36.214 -19.293  19.744  1.00 36.24           C
ATOM   1147  OD1 ASP A 175     -35.540 -19.516  20.774  1.00 35.82           O
ATOM   1148  OD2 ASP A 175     -37.460 -19.329  19.728  1.00 37.71           O
ATOM   1149  N   LYS A 176     -35.073 -21.709  17.090  1.00 38.05           N
ATOM   1150  CA  LYS A 176     -35.416 -23.114  16.955  1.00 40.01           C
ATOM   1151  C   LYS A 176     -34.189 -24.013  17.095  1.00 39.69           C
ATOM   1152  O   LYS A 176     -34.223 -25.007  17.821  1.00 39.68           O
ATOM   1153  CB  LYS A 176     -36.102 -23.366  15.610  1.00 42.69           C
ATOM   1154  CG  LYS A 176     -36.680 -24.764  15.458  1.00 47.02           C
ATOM   1155  CD  LYS A 176     -37.319 -24.947  14.077  1.00 50.65           C
```

FIGURE 2-18 (COORDINATES)

```
ATOM   1156  CE   LYS A 176     -37.973 -26.320  13.919  1.00 52.13           C
ATOM   1157  NZ   LYS A 176     -38.628 -26.463  12.578  1.00 54.37           N
ATOM   1158  N    LYS A 177     -33.106 -23.670  16.407  1.00 39.25           N
ATOM   1159  CA   LYS A 177     -31.885 -24.472  16.486  1.00 38.77           C
ATOM   1160  C    LYS A 177     -31.216 -24.419  17.862  1.00 38.25           C
ATOM   1161  O    LYS A 177     -30.594 -25.388  18.288  1.00 37.41           O
ATOM   1162  CB   LYS A 177     -30.895 -24.026  15.410  1.00 39.87           C
ATOM   1163  CG   LYS A 177     -31.334 -24.403  14.008  1.00 41.79           C
ATOM   1164  CD   LYS A 177     -30.601 -23.612  12.950  1.00 43.81           C
ATOM   1165  CE   LYS A 177     -31.131 -23.946  11.563  1.00 44.63           C
ATOM   1166  NZ   LYS A 177     -30.889 -25.378  11.232  1.00 46.83           N
ATOM   1167  N    LEU A 178     -31.345 -23.289  18.553  1.00 37.49           N
ATOM   1168  CA   LEU A 178     -30.744 -23.138  19.873  1.00 37.38           C
ATOM   1169  C    LEU A 178     -31.535 -23.930  20.916  1.00 38.04           C
ATOM   1170  O    LEU A 178     -31.008 -24.311  21.964  1.00 36.61           O
ATOM   1171  CB   LEU A 178     -30.684 -21.655  20.261  1.00 35.86           C
ATOM   1172  CG   LEU A 178     -29.731 -20.785  19.425  1.00 35.65           C
ATOM   1173  CD1  LEU A 178     -29.891 -19.317  19.820  1.00 32.95           C
ATOM   1174  CD2  LEU A 178     -28.285 -21.254  19.631  1.00 32.51           C
ATOM   1175  N    LEU A 179     -32.800 -24.188  20.604  1.00 39.14           N
ATOM   1176  CA   LEU A 179     -33.684 -24.938  21.491  1.00 39.60           C
ATOM   1177  C    LEU A 179     -33.186 -26.371  21.683  1.00 39.58           C
ATOM   1178  O    LEU A 179     -33.474 -27.006  22.694  1.00 40.05           O
ATOM   1179  CB   LEU A 179     -35.099 -24.950  20.912  1.00 40.24           C
ATOM   1180  CG   LEU A 179     -36.223 -25.612  21.704  1.00 41.53           C
ATOM   1181  CD1  LEU A 179     -36.368 -24.953  23.068  1.00 41.91           C
ATOM   1182  CD2  LEU A 179     -37.514 -25.490  20.906  1.00 42.41           C
ATOM   1183  N    SER A 180     -32.426 -26.873  20.719  1.00 39.57           N
ATOM   1184  CA   SER A 180     -31.898 -28.226  20.800  1.00 40.16           C
ATOM   1185  C    SER A 180     -30.673 -28.389  21.717  1.00 41.62           C
ATOM   1186  O    SER A 180     -30.173 -29.500  21.896  1.00 42.63           O
ATOM   1187  CB   SER A 180     -31.549 -28.725  19.394  1.00 39.99           C
ATOM   1188  OG   SER A 180     -30.449 -28.022  18.845  1.00 39.86           O
ATOM   1189  N    LEU A 181     -30.185 -27.302  22.304  1.00 41.78           N
ATOM   1190  CA   LEU A 181     -29.013 -27.399  23.169  1.00 42.34           C
ATOM   1191  C    LEU A 181     -29.289 -28.009  24.549  1.00 42.81           C
ATOM   1192  O    LEU A 181     -30.963 -27.641  24.938  1.00 42.83           O
ATOM   1193  CB   LEU A 181     -28.366 -26.021  23.321  1.00 42.10           C
ATOM   1194  CG   LEU A 181     -27.619 -25.488  22.092  1.00 42.00           C
ATOM   1195  CD1  LEU A 181     -27.216 -24.035  22.321  1.00 40.23           C
ATOM   1196  CD2  LEU A 181     -26.398 -26.355  21.826  1.00 40.39           C
ATOM   1197  N    ASP A 190     -21.222 -30.011  25.607  1.00 43.01           N
ATOM   1198  CA   ASP A 190     -20.910 -29.242  26.842  1.00 41.02           C
ATOM   1199  C    ASP A 190     -20.330 -27.886  26.453  1.00 38.61           C
ATOM   1200  O    ASP A 190     -19.462 -27.326  27.126  1.00 38.14           O
ATOM   1201  CB   ASP A 190     -19.929 -30.022  27.713  1.00 41.77           C
ATOM   1202  CG   ASP A 190     -20.023 -29.628  29.171  1.00 43.57           C
ATOM   1203  OD1  ASP A 190     -21.127 -29.261  29.619  1.00 43.67           O
ATOM   1204  OD2  ASP A 190     -19.000 -29.693  29.875  1.00 45.35           O
ATOM   1205  N    LEU A 191     -20.855 -27.379  25.347  1.00 35.50           N
ATOM   1206  CA   LEU A 191     -20.490 -26.101  24.781  1.00 33.85           C
ATOM   1207  C    LEU A 191     -21.806 -25.442  24.407  1.00 32.91           C
ATOM   1208  O    LEU A 191     -22.554 -25.967  23.585  1.00 32.87           O
ATOM   1209  CB   LEU A 191     -19.636 -26.297  23.524  1.00 33.31           C
ATOM   1210  CG   LEU A 191     -19.465 -25.088  22.593  1.00 34.05           C
ATOM   1211  CD1  LEU A 191     -18.815 -23.927  23.351  1.00 32.91           C
ATOM   1212  CD2  LEU A 191     -18.620 -25.479  21.390  1.00 32.80           C
ATOM   1213  N    SER A 192     -22.111 -24.305  25.017  1.00 31.42           N
ATOM   1214  CA   SER A 192     -23.351 -23.626  24.688  1.00 30.37           C
ATOM   1215  C    SER A 192     -23.130 -22.147  24.363  1.00 29.37           C
ATOM   1216  O    SER A 192     -22.003 -21.723  24.108  1.00 27.76           O
ATOM   1217  CB   SER A 192     -24.360 -23.782  25.824  1.00 29.68           C
ATOM   1218  OG   SER A 192     -25.651 -23.439  25.360  1.00 31.62           O
ATOM   1219  N    LEU A 193     -24.210 -21.369  24.377  1.00 28.98           N
ATOM   1220  CA   LEU A 193     -24.128 -19.955  24.042  1.00 28.90           C
ATOM   1221  C    LEU A 193     -24.499 -19.012  25.174  1.00 28.90           C
ATOM   1222  O    LEU A 193     -25.341 -19.331  26.019  1.00 29.29           O
ATOM   1223  CB   LEU A 193     -25.023 -19.664  22.837  1.00 29.00           C
```

FIGURE 2-19 (COORDINATES)

```
ATOM   1224  CG   LEU A 193     -24.991  -18.269   22.203  1.00  28.87       C
ATOM   1225  CD1  LEU A 193     -23.623  -18.023   21.571  1.00  29.08       C
ATOM   1226  CD2  LEU A 193     -26.090  -18.168   21.141  1.00  29.11       C
ATOM   1227  N    GLN A 194     -23.862  -17.843   25.176  1.00  27.78       N
ATOM   1228  CA   GLN A 194     -24.125  -16.816   26.178  1.00  27.05       C
ATOM   1229  C    GLN A 194     -24.041  -15.429   25.544  1.00  26.43       C
ATOM   1230  O    GLN A 194     -23.223  -15.185   24.652  1.00  25.32       O
ATOM   1231  CB   GLN A 194     -23.123  -16.920   27.337  1.00  27.70       C
ATOM   1232  CG   GLN A 194     -23.291  -15.856   28.424  1.00  27.95       C
ATOM   1233  CD   GLN A 194     -22.408  -16.120   29.634  1.00  29.28       C
ATOM   1234  OE1  GLN A 194     -22.891  -16.511   30.701  1.00  29.41       O
ATOM   1235  NE2  GLN A 194     -21.105  -15.928   29.469  1.00  29.50       N
ATOM   1236  N    LEU A 195     -24.907  -14.533   26.000  1.00  26.05       N
ATOM   1237  CA   LEU A 195     -24.935  -13.165   25.506  1.00  26.56       C
ATOM   1238  C    LEU A 195     -24.699  -12.206   26.666  1.00  27.36       C
ATOM   1239  O    LEU A 195     -25.340  -12.316   27.713  1.00  27.99       O
ATOM   1240  CB   LEU A 195     -26.292  -12.837   24.880  1.00  25.62       C
ATOM   1241  CG   LEU A 195     -26.841  -13.701   23.745  1.00  26.80       C
ATOM   1242  CD1  LEU A 195     -28.255  -13.239   23.406  1.00  26.09       C
ATOM   1243  CD2  LEU A 195     -25.936  -13.609   22.533  1.00  25.69       C
ATOM   1244  N    ILE A 196     -23.774  -11.268   26.496  1.00  27.20       N
ATOM   1245  CA   ILE A 196     -23.540  -10.284   27.545  1.00  26.90       C
ATOM   1246  C    ILE A 196     -23.792   -8.880   27.000  1.00  27.26       C
ATOM   1247  O    ILE A 196     -23.262   -8.505   25.951  1.00  28.05       O
ATOM   1248  CB   ILE A 196     -22.100  -10.337   28.090  1.00  26.75       C
ATOM   1249  CG1  ILE A 196     -21.825  -11.701   28.724  1.00  25.82       C
ATOM   1250  CG2  ILE A 196     -21.895   -9.221   29.116  1.00  25.86       C
ATOM   1251  CD1  ILE A 196     -20.369  -11.906   29.116  1.00  24.14       C
ATOM   1252  N    PHE A 197     -24.624   -8.124   27.704  1.00  26.82       N
ATOM   1253  CA   PHE A 197     -24.926   -6.739   27.338  1.00  26.78       C
ATOM   1254  C    PHE A 197     -24.316   -5.911   28.468  1.00  26.55       C
ATOM   1255  O    PHE A 197     -24.880   -5.845   29.559  1.00  26.70       O
ATOM   1256  CB   PHE A 197     -26.448   -6.505   27.277  1.00  25.93       C
ATOM   1257  CG   PHE A 197     -27.148   -7.297   26.201  1.00  24.89       C
ATOM   1258  CD1  PHE A 197     -27.354   -6.751   24.939  1.00  24.60       C
ATOM   1259  CD2  PHE A 197     -27.575   -8.603   26.443  1.00  24.89       C
ATOM   1260  CE1  PHE A 197     -27.978   -7.491   23.920  1.00  24.81       C
ATOM   1261  CE2  PHE A 197     -28.202   -9.359   25.431  1.00  24.77       C
ATOM   1262  CZ   PHE A 197     -28.401   -8.801   24.170  1.00  24.45       C
ATOM   1263  N    PHE A 198     -23.158   -5.307   28.212  1.00  26.25       N
ATOM   1264  CA   PHE A 198     -22.464   -4.498   29.221  1.00  26.04       C
ATOM   1265  C    PHE A 198     -23.072   -3.114   29.454  1.00  25.74       C
ATOM   1266  O    PHE A 198     -23.596   -2.481   28.542  1.00  25.04       O
ATOM   1267  CB   PHE A 198     -20.988   -4.300   28.839  1.00  25.24       C
ATOM   1268  CG   PHE A 198     -20.173   -5.567   28.833  1.00  26.03       C
ATOM   1269  CD1  PHE A 198     -19.834   -6.204   30.023  1.00  25.59       C
ATOM   1270  CD2  PHE A 198     -19.714   -6.111   27.634  1.00  25.28       C
ATOM   1271  CE1  PHE A 198     -19.046   -7.363   30.016  1.00  25.05       C
ATOM   1272  CE2  PHE A 198     -18.923   -7.274   27.622  1.00  25.10       C
ATOM   1273  CZ   PHE A 198     -18.593   -7.895   28.811  1.00  24.09       C
ATOM   1274  N    ASP A 199     -22.986   -2.657   30.697  1.00  26.92       N
ATOM   1275  CA   ASP A 199     -23.462   -1.335   31.071  1.00  26.66       C
ATOM   1276  C    ASP A 199     -22.190   -0.524   31.312  1.00  26.51       C
ATOM   1277  O    ASP A 199     -21.119   -1.096   31.518  1.00  25.42       O
ATOM   1278  CB   ASP A 199     -24.283   -1.405   32.361  1.00  26.78       C
ATOM   1279  CG   ASP A 199     -25.065   -0.116   32.637  1.00  28.55       C
ATOM   1280  OD1  ASP A 199     -25.010    0.821   31.806  1.00  28.29       O
ATOM   1281  OD2  ASP A 199     -25.739   -0.042   33.687  1.00  27.73       O
ATOM   1282  N    GLY A 200     -22.304    0.800   31.251  1.00  26.75       N
ATOM   1283  CA   GLY A 200     -21.161    1.663   31.506  1.00  27.37       C
ATOM   1284  C    GLY A 200     -19.877    1.448   30.724  1.00  27.92       C
ATOM   1285  O    GLY A 200     -18.786    1.591   31.273  1.00  29.38       O
ATOM   1286  N    GLU A 201     -19.982    1.098   29.450  1.00  28.01       N
ATOM   1287  CA   GLU A 201     -18.786    0.923   28.644  1.00  27.48       C
ATOM   1288  C    GLU A 201     -18.186    2.312   28.414  1.00  27.65       C
ATOM   1289  O    GLU A 201     -16.969    2.493   28.478  1.00  26.42       O
ATOM   1290  CB   GLU A 201     -19.138    0.292   27.297  1.00  27.60       C
ATOM   1291  CG   GLU A 201     -17.956    0.106   26.346  1.00  29.00       C
```

FIGURE 2-20 (COORDINATES)

```
ATOM   1292  CD   GLU A 201     -17.683   1.318  25.445  1.00 31.43           C
ATOM   1293  OE1  GLU A 201     -18.352   2.358  25.578  1.00 30.35           O
ATOM   1294  OE2  GLU A 201     -16.782   1.227  24.589  1.00 32.75           O
ATOM   1295  N    GLU A 202     -19.059   3.289  28.160  1.00 27.08           N
ATOM   1296  CA   GLU A 202     -18.640   4.662  27.891  1.00 27.30           C
ATOM   1297  C    GLU A 202     -18.170   5.433  29.120  1.00 27.79           C
ATOM   1298  O    GLU A 202     -18.612   5.176  30.244  1.00 28.56           O
ATOM   1299  CB   GLU A 202     -19.786   5.441  27.243  1.00 25.64           C
ATOM   1300  CG   GLU A 202     -20.292   4.840  25.942  1.00 26.32           C
ATOM   1301  CD   GLU A 202     -19.409   5.145  24.752  1.00 26.14           C
ATOM   1302  OE1  GLU A 202     -18.211   5.442  24.945  1.00 26.52           O
ATOM   1303  OE2  GLU A 202     -19.916   5.074  23.616  1.00 26.76           O
ATOM   1304  N    ALA A 203     -17.266   6.380  28.893  1.00 27.83           N
ATOM   1305  CA   ALA A 203     -16.763   7.235  29.959  1.00 28.57           C
ATOM   1306  C    ALA A 203     -17.806   8.332  30.175  1.00 29.50           C
ATOM   1307  O    ALA A 203     -18.540   8.686  29.245  1.00 29.36           O
ATOM   1308  CB   ALA A 203     -15.444   7.858  29.549  1.00 26.71           C
ATOM   1309  N    PHE A 204     -17.893   8.856  31.394  1.00 30.91           N
ATOM   1310  CA   PHE A 204     -18.835   9.933  31.662  1.00 32.87           C
ATOM   1311  C    PHE A 204     -18.271  11.235  31.103  1.00 33.92           C
ATOM   1312  O    PHE A 204     -19.019  12.083  30.613  1.00 33.76           O
ATOM   1313  CB   PHE A 204     -19.122  10.054  33.156  1.00 33.71           C
ATOM   1314  CG   PHE A 204     -20.093   9.030  33.659  1.00 36.00           C
ATOM   1315  CD1  PHE A 204     -19.646   7.837  34.216  1.00 36.69           C
ATOM   1316  CD2  PHE A 204     -21.463   9.241  33.538  1.00 36.51           C
ATOM   1317  CE1  PHE A 204     -20.548   6.871  34.648  1.00 37.53           C
ATOM   1318  CE2  PHE A 204     -22.375   8.279  33.968  1.00 37.65           C
ATOM   1319  CZ   PHE A 204     -21.916   7.090  34.525  1.00 38.08           C
ATOM   1320  N    LEU A 205     -16.950  11.380  31.170  1.00 34.19           N
ATOM   1321  CA   LEU A 205     -16.260  12.549  30.620  1.00 36.24           C
ATOM   1322  C    LEU A 205     -15.561  11.979  29.392  1.00 37.94           C
ATOM   1323  O    LEU A 205     -16.207  11.362  28.546  1.00 39.89           O
ATOM   1324  CB   LEU A 205     -15.233  13.082  31.623  1.00 35.06           C
ATOM   1325  CG   LEU A 205     -15.810  13.489  32.986  1.00 35.07           C
ATOM   1326  CD1  LEU A 205     -14.702  13.951  33.894  1.00 34.58           C
ATOM   1327  CD2  LEU A 205     -16.842  14.592  32.810  1.00 35.02           C
ATOM   1328  N    HIS A 206     -14.256  12.179  29.273  1.00 39.44           N
ATOM   1329  CA   HIS A 206     -13.531  11.574  28.160  1.00 40.44           C
ATOM   1330  C    HIS A 206     -12.803  10.364  28.744  1.00 40.30           C
ATOM   1331  O    HIS A 206     -12.517  10.330  29.940  1.00 39.48           O
ATOM   1332  CB   HIS A 206     -12.550  12.558  27.532  1.00 41.73           C
ATOM   1333  CG   HIS A 206     -13.146  13.366  26.421  1.00 43.12           C
ATOM   1334  ND1  HIS A 206     -13.654  12.791  25.275  1.00 42.90           N
ATOM   1335  CD2  HIS A 206     -13.316  14.702  26.280  1.00 43.47           C
ATOM   1336  CE1  HIS A 206     -14.112  13.739  24.476  1.00 43.13           C
ATOM   1337  NE2  HIS A 206     -13.918  14.907  25.061  1.00 43.85           N
ATOM   1338  N    TRP A 207     -12.514   9.371  27.912  1.00 40.47           N
ATOM   1339  CA   TRP A 207     -11.861   8.156  28.394  1.00 41.62           C
ATOM   1340  C    TRP A 207     -10.697   8.346  29.361  1.00 41.26           C
ATOM   1341  O    TRP A 207      -9.838   9.208  29.174  1.00 40.77           O
ATOM   1342  CB   TRP A 207     -11.358   7.297  27.228  1.00 42.88           C
ATOM   1343  CG   TRP A 207     -10.654   6.042  27.708  1.00 45.15           C
ATOM   1344  CD1  TRP A 207     -11.223   4.818  27.943  1.00 45.54           C
ATOM   1345  CD2  TRP A 207      -9.276   5.924  28.103  1.00 45.84           C
ATOM   1346  NE1  TRP A 207     -10.289   3.952  28.462  1.00 46.26           N
ATOM   1347  CE2  TRP A 207      -9.087   4.602  28.572  1.00 46.80           C
ATOM   1348  CE3  TRP A 207      -8.185   6.808  28.109  1.00 46.81           C
ATOM   1349  CZ2  TRP A 207      -7.847   4.140  29.044  1.00 47.35           C
ATOM   1350  CZ3  TRP A 207      -6.952   6.351  28.577  1.00 47.53           C
ATOM   1351  CH2  TRP A 207      -6.795   5.026  29.039  1.00 47.43           C
ATOM   1352  N    SER A 208     -10.681   7.514  30.396  1.00 40.86           N
ATOM   1353  CA   SER A 208      -9.604   7.511  31.375  1.00 40.62           C
ATOM   1354  C    SER A 208      -9.633   6.110  31.968  1.00 40.64           C
ATOM   1355  O    SER A 208     -10.665   5.438  31.936  1.00 40.19           O
ATOM   1356  CB   SER A 208      -9.815   8.583  32.461  1.00 39.96           C
ATOM   1357  OG   SER A 208     -10.745   8.187  33.447  1.00 40.23           O
ATOM   1358  N    PRO A 209      -8.497   5.636  32.492  1.00 40.98           N
ATOM   1359  CA   PRO A 209      -8.431   4.298  33.084  1.00 41.24           C
```

FIGURE 2-21 (COORDINATES)

```
ATOM   1360  C    PRO A 209      -9.552   4.016  34.082  1.00 41.12           C
ATOM   1361  O    PRO A 209     -10.116   2.924  34.096  1.00 41.20           O
ATOM   1362  CB   PRO A 209      -7.058   4.288  33.753  1.00 40.60           C
ATOM   1363  CG   PRO A 209      -6.253   5.148  32.849  1.00 41.38           C
ATOM   1364  CD   PRO A 209      -7.192   6.312  32.592  1.00 41.85           C
ATOM   1365  N    GLN A 210      -9.880   5.009  34.902  1.00 40.98           N
ATOM   1366  CA   GLN A 210     -10.911   4.848  35.919  1.00 40.93           C
ATOM   1367  C    GLN A 210     -12.312   5.277  35.488  1.00 39.12           C
ATOM   1368  O    GLN A 210     -13.280   5.047  36.210  1.00 40.61           O
ATOM   1369  CB   GLN A 210     -10.524   5.623  37.185  1.00 43.39           C
ATOM   1370  CG   GLN A 210      -9.035   5.598  37.549  1.00 46.87           C
ATOM   1371  CD   GLN A 210      -8.159   6.353  36.543  1.00 49.60           C
ATOM   1372  OE1  GLN A 210      -8.651   7.177  35.757  1.00 50.00           O
ATOM   1373  NE2  GLN A 210      -6.852   6.082  36.575  1.00 50.27           N
ATOM   1374  N    ASP A 211     -12.431   5.914  34.332  1.00 36.45           N
ATOM   1375  CA   ASP A 211     -13.744   6.356  33.862  1.00 33.58           C
ATOM   1376  C    ASP A 211     -14.077   5.760  32.498  1.00 31.92           C
ATOM   1377  O    ASP A 211     -13.888   6.403  31.466  1.00 30.60           O
ATOM   1378  CB   ASP A 211     -13.792   7.882  33.773  1.00 32.74           C
ATOM   1379  CG   ASP A 211     -15.128   8.393  33.285  1.00 32.15           C
ATOM   1380  OD1  ASP A 211     -15.173   9.531  32.783  1.00 31.31           O
ATOM   1381  OD2  ASP A 211     -16.137   7.666  33.407  1.00 32.56           O
ATOM   1382  N    SER A 212     -14.570   4.525  32.520  1.00 31.11           N
ATOM   1383  CA   SER A 212     -14.961   3.767  31.327  1.00 29.14           C
ATOM   1384  C    SER A 212     -14.890   2.293  31.682  1.00 27.62           C
ATOM   1385  O    SER A 212     -14.295   1.927  32.691  1.00 27.32           O
ATOM   1386  CB   SER A 212     -14.009   4.034  30.152  1.00 29.03           C
ATOM   1387  OG   SER A 212     -12.702   3.571  30.448  1.00 28.82           O
ATOM   1388  N    LEU A 213     -15.498   1.452  30.855  1.00 26.32           N
ATOM   1389  CA   LEU A 213     -15.470   0.007  31.068  1.00 26.04           C
ATOM   1390  C    LEU A 213     -15.940  -0.409  32.452  1.00 26.14           C
ATOM   1391  O    LEU A 213     -15.420  -1.350  33.032  1.00 26.36           O
ATOM   1392  CB   LEU A 213     -14.050  -0.522  30.848  1.00 24.35           C
ATOM   1393  CG   LEU A 213     -13.328  -0.036  29.591  1.00 24.15           C
ATOM   1394  CD1  LEU A 213     -12.070  -0.862  29.389  1.00 23.85           C
ATOM   1395  CD2  LEU A 213     -14.236  -0.162  28.373  1.00 21.73           C
ATOM   1396  N    TYR A 214     -16.931   0.287  32.985  1.00 26.70           N
ATOM   1397  CA   TYR A 214     -17.425  -0.036  34.315  1.00 26.37           C
ATOM   1398  C    TYR A 214     -17.986  -1.449  34.390  1.00 25.85           C
ATOM   1399  O    TYR A 214     -17.541  -2.257  35.201  1.00 25.51           O
ATOM   1400  CB   TYR A 214     -18.506   0.961  34.722  1.00 26.29           C
ATOM   1401  CG   TYR A 214     -17.991   2.353  34.950  1.00 27.84           C
ATOM   1402  CD1  TYR A 214     -17.398   2.711  36.165  1.00 27.37           C
ATOM   1403  CD2  TYR A 214     -18.104   3.327  33.955  1.00 27.88           C
ATOM   1404  CE1  TYR A 214     -16.938   4.009  36.386  1.00 28.36           C
ATOM   1405  CE2  TYR A 214     -17.643   4.623  34.162  1.00 28.62           C
ATOM   1406  CZ   TYR A 214     -17.065   4.962  35.376  1.00 29.56           C
ATOM   1407  OH   TYR A 214     -16.628   6.256  35.575  1.00 30.06           O
ATOM   1408  N    GLY A 215     -18.959  -1.738  33.533  1.00 25.79           N
ATOM   1409  CA   GLY A 215     -19.591  -3.046  33.536  1.00 26.37           C
ATOM   1410  C    GLY A 215     -18.675  -4.212  33.227  1.00 27.19           C
ATOM   1411  O    GLY A 215     -18.742  -5.241  33.896  1.00 26.97           O
ATOM   1412  N    SER A 216     -17.820  -4.054  32.217  1.00 27.58           N
ATOM   1413  CA   SER A 216     -16.901  -5.113  31.831  1.00 27.87           C
ATOM   1414  C    SER A 216     -15.766  -5.323  32.838  1.00 28.82           C
ATOM   1415  O    SER A 216     -15.401  -6.463  33.136  1.00 28.93           O
ATOM   1416  CB   SER A 216     -16.336  -4.846  30.425  1.00 27.29           C
ATOM   1417  OG   SER A 216     -15.670  -3.594  30.337  1.00 27.43           O
ATOM   1418  N    ARG A 217     -15.204  -4.246  33.374  1.00 29.27           N
ATOM   1419  CA   ARG A 217     -14.130  -4.418  34.343  1.00 31.06           C
ATOM   1420  C    ARG A 217     -14.701  -5.166  35.548  1.00 31.08           C
ATOM   1421  O    ARG A 217     -14.038  -6.009  36.151  1.00 32.15           O
ATOM   1422  CB   ARG A 217     -13.544  -3.062  34.776  1.00 32.40           C
ATOM   1423  CG   ARG A 217     -12.698  -2.369  33.696  1.00 34.89           C
ATOM   1424  CD   ARG A 217     -11.947  -1.150  34.237  1.00 36.96           C
ATOM   1425  NE   ARG A 217     -12.826  -0.011  34.514  1.00 41.51           N
ATOM   1426  CZ   ARG A 217     -13.016   0.533  35.717  1.00 42.68           C
ATOM   1427  NH1  ARG A 217     -12.393   0.045  36.782  1.00 44.69           N
```

FIGURE 2-22 (COORDINATES)

```
ATOM   1428  NH2 ARG A 217     -13.812   1.585  35.855  1.00 43.19           N
ATOM   1429  N   HIS A 218     -15.952  -4.876  35.879  1.00 30.64           N
ATOM   1430  CA  HIS A 218     -16.589  -5.528  37.006  1.00 29.60           C
ATOM   1431  C   HIS A 218     -16.970  -6.984  36.737  1.00 29.77           C
ATOM   1432  O   HIS A 218     -16.747  -7.853  37.583  1.00 30.07           O
ATOM   1433  CB  HIS A 218     -17.839  -4.755  37.432  1.00 29.49           C
ATOM   1434  CG  HIS A 218     -18.702  -5.509  38.394  1.00 29.82           C
ATOM   1435  ND1 HIS A 218     -19.702  -6.366  37.984  1.00 30.23           N
ATOM   1436  CD2 HIS A 218     -18.676  -5.582  39.746  1.00 29.14           C
ATOM   1437  CE1 HIS A 218     -20.256  -6.930  39.042  1.00 29.67           C
ATOM   1438  NE2 HIS A 218     -19.651  -6.472  40.123  1.00 29.87           N
ATOM   1439  N   LEU A 219     -17.550  -7.255  35.570  1.00 28.98           N
ATOM   1440  CA  LEU A 219     -17.967  -8.613  35.251  1.00 28.65           C
ATOM   1441  C   LEU A 219     -16.783  -9.549  35.016  1.00 28.77           C
ATOM   1442  O   LEU A 219     -16.839 -10.724  35.365  1.00 28.84           O
ATOM   1443  CB  LEU A 219     -18.899  -8.622  34.034  1.00 27.17           C
ATOM   1444  CG  LEU A 219     -19.557  -9.979  33.763  1.00 26.96           C
ATOM   1445  CD1 LEU A 219     -20.389 -10.392  34.970  1.00 25.47           C
ATOM   1446  CD2 LEU A 219     -20.428  -9.899  32.518  1.00 26.67           C
ATOM   1447  N   ALA A 220     -15.709  -9.030  34.431  1.00 29.24           N
ATOM   1448  CA  ALA A 220     -14.525  -9.852  34.180  1.00 29.59           C
ATOM   1449  C   ALA A 220     -13.958 -10.348  35.506  1.00 29.25           C
ATOM   1450  O   ALA A 220     -13.662 -11.536  35.656  1.00 29.81           O
ATOM   1451  CB  ALA A 220     -13.452  -9.047  33.416  1.00 29.91           C
ATOM   1452  N   ALA A 221     -13.814  -9.438  36.464  1.00 27.38           N
ATOM   1453  CA  ALA A 221     -13.273  -9.787  37.772  1.00 27.35           C
ATOM   1454  C   ALA A 221     -14.193 -10.753  38.521  1.00 27.28           C
ATOM   1455  O   ALA A 221     -13.730 -11.644  39.240  1.00 26.98           O
ATOM   1456  CB  ALA A 221     -13.057  -8.524  38.603  1.00 25.25           C
ATOM   1457  N   LYS A 222     -15.496 -10.574  38.344  1.00 27.36           N
ATOM   1458  CA  LYS A 222     -16.467 -11.420  39.013  1.00 29.00           C
ATOM   1459  C   LYS A 222     -16.406 -12.839  38.444  1.00 29.21           C
ATOM   1460  O   LYS A 222     -16.297 -13.816  39.188  1.00 28.87           O
ATOM   1461  CB  LYS A 222     -17.872 -10.831  38.850  1.00 29.90           C
ATOM   1462  CG  LYS A 222     -18.970 -11.656  39.496  1.00 31.64           C
ATOM   1463  CD  LYS A 222     -20.331 -11.002  39.319  1.00 34.39           C
ATOM   1464  CE  LYS A 222     -21.419 -11.824  39.997  1.00 35.97           C
ATOM   1465  NZ  LYS A 222     -22.755 -11.166  39.927  1.00 38.75           N
ATOM   1466  N   MET A 223     -16.457 -12.949  37.122  1.00 28.99           N
ATOM   1467  CA  MET A 223     -16.399 -14.254  36.485  1.00 29.58           C
ATOM   1468  C   MET A 223     -15.075 -14.972  36.779  1.00 29.80           C
ATOM   1469  O   MET A 223     -15.036 -16.196  36.879  1.00 31.24           O
ATOM   1470  CB  MET A 223     -16.601 -14.112  34.973  1.00 29.02           C
ATOM   1471  CG  MET A 223     -18.011 -13.720  34.576  1.00 29.61           C
ATOM   1472  SD  MET A 223     -18.222 -13.587  32.782  1.00 30.56           S
ATOM   1473  CE  MET A 223     -18.843 -15.216  32.355  1.00 32.77           C
ATOM   1474  N   ALA A 224     -13.999 -14.206  36.917  1.00 29.25           N
ATOM   1475  CA  ALA A 224     -12.683 -14.762  37.194  1.00 27.74           C
ATOM   1476  C   ALA A 224     -12.588 -15.325  38.613  1.00 27.65           C
ATOM   1477  O   ALA A 224     -11.740 -16.162  38.902  1.00 26.46           O
ATOM   1478  CB  ALA A 224     -11.620 -13.694  36.987  1.00 27.27           C
ATOM   1479  N   SER A 225     -13.449 -14.857  39.506  1.00 27.74           N
ATOM   1480  CA  SER A 225     -13.417 -15.345  40.875  1.00 28.63           C
ATOM   1481  C   SER A 225     -14.626 -16.225  41.170  1.00 28.39           C
ATOM   1482  O   SER A 225     -14.986 -16.428  42.328  1.00 27.92           O
ATOM   1483  CB  SER A 225     -13.374 -14.171  41.851  1.00 28.12           C
ATOM   1484  OG  SER A 225     -14.504 -13.347  41.675  1.00 31.36           O
ATOM   1485  N   THR A 226     -15.245 -16.746  40.115  1.00 28.40           N
ATOM   1486  CA  THR A 226     -16.412 -17.611  40.258  1.00 28.61           C
ATOM   1487  C   THR A 226     -16.077 -19.004  39.727  1.00 29.21           C
ATOM   1488  O   THR A 226     -15.821 -19.181  38.530  1.00 29.13           O
ATOM   1489  CB  THR A 226     -17.615 -17.043  39.480  1.00 29.34           C
ATOM   1490  OG1 THR A 226     -17.925 -15.734  39.979  1.00 29.37           O
ATOM   1491  CG2 THR A 226     -18.836 -17.949  39.637  1.00 29.04           C
ATOM   1492  N   PRO A 227     -16.050 -20.011  40.620  1.00 29.16           N
ATOM   1493  CA  PRO A 227     -15.737 -21.387  40.218  1.00 28.89           C
ATOM   1494  C   PRO A 227     -16.695 -21.875  39.144  1.00 28.81           C
ATOM   1495  O   PRO A 227     -17.896 -21.627  39.218  1.00 29.69           O
```

FIGURE 2-23 (COORDINATES)

```
ATOM   1496  CB   PRO A 227     -15.891 -22.170  41.524  1.00 28.61           C
ATOM   1497  CG   PRO A 227     -15.502 -21.167  42.561  1.00 27.48           C
ATOM   1498  CD   PRO A 227     -16.215 -19.923  42.084  1.00 28.66           C
ATOM   1499  N    HIS A 228     -16.164 -22.558  38.141  1.00 28.54           N
ATOM   1500  CA   HIS A 228     -17.003 -23.079  37.072  1.00 28.36           C
ATOM   1501  C    HIS A 228     -16.395 -24.340  36.485  1.00 28.70           C
ATOM   1502  O    HIS A 228     -15.191 -24.403  36.253  1.00 28.89           O
ATOM   1503  CB   HIS A 228     -17.178 -22.052  35.958  1.00 27.57           C
ATOM   1504  CG   HIS A 228     -18.215 -22.438  34.950  1.00 27.15           C
ATOM   1505  ND1  HIS A 228     -19.566 -22.286  35.178  1.00 26.90           N
ATOM   1506  CD2  HIS A 228     -18.102 -23.005  33.725  1.00 27.35           C
ATOM   1507  CE1  HIS A 228     -20.239 -22.741  34.136  1.00 26.74           C
ATOM   1508  NE2  HIS A 228     -19.375 -23.183  33.241  1.00 26.90           N
ATOM   1509  N    PRO A 229     -17.223 -25.373  36.261  1.00 28.74           N
ATOM   1510  CA   PRO A 229     -18.660 -25.366  36.549  1.00 28.84           C
ATOM   1511  C    PRO A 229     -18.887 -25.459  38.059  1.00 29.64           C
ATOM   1512  O    PRO A 229     -17.944 -25.706  38.814  1.00 31.18           O
ATOM   1513  CB   PRO A 229     -19.153 -26.598  35.800  1.00 28.12           C
ATOM   1514  CG   PRO A 229     -18.012 -27.540  35.964  1.00 27.87           C
ATOM   1515  CD   PRO A 229     -16.814 -26.666  35.682  1.00 28.76           C
ATOM   1516  N    PRO A 230     -20.137 -25.270  38.521  1.00 30.06           N
ATOM   1517  CA   PRO A 230     -20.443 -25.340  39.957  1.00 29.97           C
ATOM   1518  C    PRO A 230     -19.722 -26.479  40.668  1.00 29.80           C
ATOM   1519  O    PRO A 230     -19.806 -27.628  40.244  1.00 31.45           O
ATOM   1520  CB   PRO A 230     -21.956 -25.519  39.975  1.00 29.18           C
ATOM   1521  CG   PRO A 230     -22.389 -24.708  38.811  1.00 29.59           C
ATOM   1522  CD   PRO A 230     -21.374 -25.092  37.738  1.00 30.40           C
ATOM   1523  N    GLY A 231     -19.009 -26.151  41.740  1.00 29.83           N
ATOM   1524  CA   GLY A 231     -18.290 -27.160  42.495  1.00 28.76           C
ATOM   1525  C    GLY A 231     -16.841 -27.370  42.086  1.00 29.63           C
ATOM   1526  O    GLY A 231     -16.117 -28.122  42.730  1.00 28.76           O
ATOM   1527  N    ALA A 232     -16.409 -26.715  41.017  1.00 29.56           N
ATOM   1528  CA   ALA A 232     -15.038 -26.866  40.556  1.00 30.63           C
ATOM   1529  C    ALA A 232     -14.022 -26.434  41.615  1.00 31.71           C
ATOM   1530  O    ALA A 232     -14.293 -25.551  42.431  1.00 31.70           O
ATOM   1531  CB   ALA A 232     -14.832 -26.070  39.275  1.00 30.16           C
ATOM   1532  N    ARG A 233     -12.851 -27.063  41.586  1.00 33.18           N
ATOM   1533  CA   ARG A 233     -11.779 -26.769  42.527  1.00 35.69           C
ATOM   1534  C    ARG A 233     -10.874 -25.617  42.086  1.00 35.27           C
ATOM   1535  O    ARG A 233     -10.527 -24.757  42.896  1.00 35.98           O
ATOM   1536  CB   ARG A 233     -10.903 -28.013  42.754  1.00 38.99           C
ATOM   1537  CG   ARG A 233     -11.632 -29.226  43.314  1.00 45.74           C
ATOM   1538  CD   ARG A 233     -10.659 -30.327  43.773  1.00 50.36           C
ATOM   1539  NE   ARG A 233     -10.378 -31.364  42.772  1.00 55.06           N
ATOM   1540  CZ   ARG A 233      -9.765 -31.158  41.606  1.00 57.61           C
ATOM   1541  NH1  ARG A 233      -9.360 -29.939  41.263  1.00 59.50           N
ATOM   1542  NH2  ARG A 233      -9.541 -32.177  40.783  1.00 58.12           N
ATOM   1543  N    GLY A 234     -10.491 -25.593  40.812  1.00 33.68           N
ATOM   1544  CA   GLY A 234      -9.594 -24.546  40.365  1.00 33.64           C
ATOM   1545  C    GLY A 234      -9.818 -23.888  39.018  1.00 33.66           C
ATOM   1546  O    GLY A 234      -8.882 -23.307  38.461  1.00 34.34           O
ATOM   1547  N    THR A 235     -11.035 -23.977  38.485  1.00 32.53           N
ATOM   1548  CA   THR A 235     -11.350 -23.347  37.208  1.00 30.73           C
ATOM   1549  C    THR A 235     -12.455 -22.326  37.424  1.00 30.73           C
ATOM   1550  O    THR A 235     -13.337 -22.515  38.262  1.00 30.55           O
ATOM   1551  CB   THR A 235     -11.815 -24.370  36.150  1.00 30.73           C
ATOM   1552  OG1  THR A 235     -12.864 -25.181  36.692  1.00 29.02           O
ATOM   1553  CG2  THR A 235     -10.653 -25.248  35.702  1.00 29.84           C
ATOM   1554  N    SER A 236     -12.405 -21.244  36.658  1.00 30.52           N
ATOM   1555  CA   SER A 236     -13.389 -20.179  36.778  1.00 30.90           C
ATOM   1556  C    SER A 236     -14.274 -20.079  35.545  1.00 30.87           C
ATOM   1557  O    SER A 236     -14.089 -20.804  34.570  1.00 29.93           O
ATOM   1558  CB   SER A 236     -12.674 -18.848  36.951  1.00 30.87           C
ATOM   1559  OG   SER A 236     -12.169 -18.413  35.698  1.00 30.55           O
ATOM   1560  N    GLN A 237     -15.229 -19.156  35.598  1.00 31.39           N
ATOM   1561  CA   GLN A 237     -16.120 -18.913  34.478  1.00 32.31           C
ATOM   1562  C    GLN A 237     -15.310 -18.412  33.284  1.00 32.50           C
ATOM   1563  O    GLN A 237     -15.691 -18.635  32.145  1.00 33.55           O
```

FIGURE 2-24 (COORDINATES)

```
ATOM   1564  CB   GLN A 237     -17.191 -17.884  34.854  1.00 32.55           C
ATOM   1565  CG   GLN A 237     -18.119 -18.352  35.967  1.00 33.68           C
ATOM   1566  CD   GLN A 237     -19.302 -17.424  36.187  1.00 34.27           C
ATOM   1567  OE1  GLN A 237     -19.167 -16.201  36.152  1.00 34.61           O
ATOM   1568  NE2  GLN A 237     -20.466 -18.006  36.438  1.00 34.08           N
ATOM   1569  N    LEU A 238     -14.191 -17.735  33.540  1.00 33.25           N
ATOM   1570  CA   LEU A 238     -13.350 -17.246  32.452  1.00 32.99           C
ATOM   1571  C    LEU A 238     -12.671 -18.402  31.733  1.00 33.11           C
ATOM   1572  O    LEU A 238     -12.464 -18.358  30.522  1.00 33.58           O
ATOM   1573  CB   LEU A 238     -12.304 -16.257  32.967  1.00 32.94           C
ATOM   1574  CG   LEU A 238     -12.855 -14.890  33.393  1.00 34.28           C
ATOM   1575  CD1  LEU A 238     -11.694 -13.910  33.541  1.00 33.91           C
ATOM   1576  CD2  LEU A 238     -13.846 -14.364  32.340  1.00 34.15           C
ATOM   1577  N    HIS A 239     -12.319 -19.443  32.475  1.00 33.72           N
ATOM   1578  CA   HIS A 239     -11.702 -20.609  31.857  1.00 34.47           C
ATOM   1579  C    HIS A 239     -12.729 -21.230  30.919  1.00 33.23           C
ATOM   1580  O    HIS A 239     -12.375 -21.892  29.949  1.00 32.04           O
ATOM   1581  CB   HIS A 239     -11.299 -21.624  32.925  1.00 37.20           C
ATOM   1582  CG   HIS A 239     -10.234 -21.129  33.855  1.00 40.65           C
ATOM   1583  ND1  HIS A 239     -10.058 -21.637  35.122  1.00 41.95           N
ATOM   1584  CD2  HIS A 239      -9.287 -20.174  33.698  1.00 43.06           C
ATOM   1585  CE1  HIS A 239      -9.050 -21.018  35.708  1.00 43.26           C
ATOM   1586  NE2  HIS A 239      -8.564 -20.126  34.865  1.00 44.33           N
ATOM   1587  N    GLY A 240     -14.005 -20.989  31.216  1.00 32.72           N
ATOM   1588  CA   GLY A 240     -15.088 -21.527  30.408  1.00 32.57           C
ATOM   1589  C    GLY A 240     -15.405 -20.723  29.161  1.00 32.37           C
ATOM   1590  O    GLY A 240     -16.116 -21.203  28.278  1.00 31.65           O
ATOM   1591  N    MET A 241     -14.887 -19.497  29.091  1.00 32.38           N
ATOM   1592  CA   MET A 241     -15.117 -18.623  27.938  1.00 32.57           C
ATOM   1593  C    MET A 241     -14.253 -19.025  26.756  1.00 31.30           C
ATOM   1594  O    MET A 241     -13.090 -18.639  26.660  1.00 32.29           O
ATOM   1595  CB   MET A 241     -14.828 -17.157  28.290  1.00 34.20           C
ATOM   1596  CG   MET A 241     -16.018 -16.395  28.845  1.00 37.75           C
ATOM   1597  SD   MET A 241     -15.699 -14.620  29.118  1.00 40.11           S
ATOM   1598  CE   MET A 241     -15.860 -13.994  27.499  1.00 37.76           C
ATOM   1599  N    ASP A 242     -14.830 -19.807  25.859  1.00 29.43           N
ATOM   1600  CA   ASP A 242     -14.136 -20.269  24.675  1.00 28.62           C
ATOM   1601  C    ASP A 242     -13.601 -19.097  23.863  1.00 29.07           C
ATOM   1602  O    ASP A 242     -12.440 -19.074  23.443  1.00 27.95           O
ATOM   1603  CB   ASP A 242     -15.107 -21.054  23.804  1.00 29.34           C
ATOM   1604  CG   ASP A 242     -14.880 -22.540  23.870  1.00 29.26           C
ATOM   1605  OD1  ASP A 242     -14.674 -23.071  24.988  1.00 28.34           O
ATOM   1606  OD2  ASP A 242     -14.920 -23.166  22.787  1.00 29.03           O
ATOM   1607  N    LEU A 243     -14.469 -18.121  23.649  1.00 28.54           N
ATOM   1608  CA   LEU A 243     -14.120 -16.966  22.856  1.00 28.30           C
ATOM   1609  C    LEU A 243     -15.117 -15.862  23.113  1.00 28.69           C
ATOM   1610  O    LEU A 243     -16.322 -16.113  23.239  1.00 27.96           O
ATOM   1611  CB   LEU A 243     -14.162 -17.342  21.371  1.00 27.60           C
ATOM   1612  CG   LEU A 243     -13.928 -16.263  20.311  1.00 27.90           C
ATOM   1613  CD1  LEU A 243     -12.465 -15.790  20.329  1.00 25.48           C
ATOM   1614  CD2  LEU A 243     -14.293 -16.856  18.941  1.00 26.15           C
ATOM   1615  N    LEU A 244     -14.605 -14.638  23.195  1.00 28.68           N
ATOM   1616  CA   LEU A 244     -15.439 -13.466  23.405  1.00 27.21           C
ATOM   1617  C    LEU A 244     -15.527 -12.699  22.096  1.00 27.06           C
ATOM   1618  O    LEU A 244     -14.540 -12.113  21.656  1.00 27.01           O
ATOM   1619  CB   LEU A 244     -14.844 -12.561  24.476  1.00 27.64           C
ATOM   1620  CG   LEU A 244     -15.560 -11.212  24.612  1.00 29.26           C
ATOM   1621  CD1  LEU A 244     -17.012 -11.440  25.057  1.00 28.05           C
ATOM   1622  CD2  LEU A 244     -14.817 -10.327  25.612  1.00 27.27           C
ATOM   1623  N    VAL A 245     -16.704 -12.737  21.472  1.00 26.57           N
ATOM   1624  CA   VAL A 245     -16.964 -12.033  20.226  1.00 26.06           C
ATOM   1625  C    VAL A 245     -17.643 -10.716  20.600  1.00 26.44           C
ATOM   1626  O    VAL A 245     -18.845 -10.689  20.881  1.00 26.58           O
ATOM   1627  CB   VAL A 245     -17.908 -12.847  19.298  1.00 26.86           C
ATOM   1628  CG1  VAL A 245     -18.101 -12.118  17.965  1.00 25.91           C
ATOM   1629  CG2  VAL A 245     -17.332 -14.232  19.048  1.00 26.65           C
ATOM   1630  N    LEU A 246     -16.868  -9.631  20.612  1.00 26.18           N
ATOM   1631  CA   LEU A 246     -17.380  -8.308  20.970  1.00 25.71           C
```

FIGURE 2-25 (COORDINATES)

```
ATOM   1632  C    LEU A 246     -17.743  -7.455  19.754  1.00 25.85           C
ATOM   1633  O    LEU A 246     -16.887  -7.117  18.937  1.00 25.92           O
ATOM   1634  CB   LEU A 246     -16.347  -7.560  21.819  1.00 26.21           C
ATOM   1635  CG   LEU A 246     -16.729  -6.156  22.308  1.00 26.44           C
ATOM   1636  CD1  LEU A 246     -17.986  -6.244  23.173  1.00 25.61           C
ATOM   1637  CD2  LEU A 246     -15.576  -5.542  23.087  1.00 24.88           C
ATOM   1638  N    LEU A 247     -19.025  -7.122  19.643  1.00 25.45           N
ATOM   1639  CA   LEU A 247     -19.537  -6.292  18.553  1.00 24.88           C
ATOM   1640  C    LEU A 247     -19.588  -4.850  19.037  1.00 24.03           C
ATOM   1641  O    LEU A 247     -20.093  -4.578  20.127  1.00 23.15           O
ATOM   1642  CB   LEU A 247     -20.956  -6.732  18.153  1.00 26.08           C
ATOM   1643  CG   LEU A 247     -21.129  -7.966  17.258  1.00 28.52           C
ATOM   1644  CD1  LEU A 247     -20.523  -9.171  17.929  1.00 29.37           C
ATOM   1645  CD2  LEU A 247     -22.620  -8.203  16.978  1.00 28.79           C
ATOM   1646  N    ASP A 248     -19.078  -3.926  18.232  1.00 23.80           N
ATOM   1647  CA   ASP A 248     -19.090  -2.515  18.613  1.00 23.74           C
ATOM   1648  C    ASP A 248     -18.982  -1.595  17.384  1.00 23.90           C
ATOM   1649  O    ASP A 248     -18.308  -1.924  16.404  1.00 22.95           O
ATOM   1650  CB   ASP A 248     -17.936  -2.234  19.600  1.00 23.22           C
ATOM   1651  CG   ASP A 248     -18.162  -0.972  20.427  1.00 24.18           C
ATOM   1652  OD1  ASP A 248     -19.187  -0.291  20.214  1.00 23.37           O
ATOM   1653  OD2  ASP A 248     -17.316  -0.654  21.290  1.00 22.95           O
ATOM   1654  N    LEU A 249     -19.676  -0.458  17.436  1.00 23.99           N
ATOM   1655  CA   LEU A 249     -19.654   0.536  16.351  1.00 24.60           C
ATOM   1656  C    LEU A 249     -20.014  -0.046  14.981  1.00 25.23           C
ATOM   1657  O    LEU A 249     -19.381   0.264  13.970  1.00 25.46           O
ATOM   1658  CB   LEU A 249     -18.269   1.212  16.276  1.00 23.91           C
ATOM   1659  CG   LEU A 249     -17.644   1.667  17.613  1.00 24.67           C
ATOM   1660  CD1  LEU A 249     -16.322   2.377  17.342  1.00 24.13           C
ATOM   1661  CD2  LEU A 249     -18.598   2.592  18.375  1.00 21.62           C
ATOM   1662  N    ILE A 250     -21.043  -0.884  14.955  1.00 25.35           N
ATOM   1663  CA   ILE A 250     -21.498  -1.498  13.722  1.00 24.92           C
ATOM   1664  C    ILE A 250     -22.769  -0.799  13.217  1.00 24.96           C
ATOM   1665  O    ILE A 250     -23.624  -0.394  14.016  1.00 24.17           O
ATOM   1666  CB   ILE A 250     -21.752  -3.002  13.955  1.00 25.83           C
ATOM   1667  CG1  ILE A 250     -20.431  -3.658  14.385  1.00 25.17           C
ATOM   1668  CG2  ILE A 250     -22.344  -3.650  12.702  1.00 24.53           C
ATOM   1669  CD1  ILE A 250     -20.520  -5.124  14.696  1.00 25.57           C
ATOM   1670  N    GLY A 251     -22.875  -0.636  11.898  1.00 23.85           N
ATOM   1671  CA   GLY A 251     -24.042   0.011  11.332  1.00 24.00           C
ATOM   1672  C    GLY A 251     -23.751   1.064  10.280  1.00 25.01           C
ATOM   1673  O    GLY A 251     -24.650   1.465   9.539  1.00 25.86           O
ATOM   1674  N    ALA A 252     -22.511   1.537  10.221  1.00 25.02           N
ATOM   1675  CA   ALA A 252     -22.137   2.532   9.225  1.00 25.78           C
ATOM   1676  C    ALA A 252     -21.749   1.798   7.936  1.00 26.18           C
ATOM   1677  O    ALA A 252     -21.548   0.583   7.937  1.00 25.58           O
ATOM   1678  CB   ALA A 252     -20.969   3.384   9.729  1.00 24.41           C
ATOM   1679  N    PRO A 253     -21.643   2.529   6.818  1.00 26.89           N
ATOM   1680  CA   PRO A 253     -21.278   1.915   5.536  1.00 26.91           C
ATOM   1681  C    PRO A 253     -19.802   1.541   5.450  1.00 26.89           C
ATOM   1682  O    PRO A 253     -18.965   2.124   6.130  1.00 26.63           O
ATOM   1683  CB   PRO A 253     -21.619   3.003   4.513  1.00 26.48           C
ATOM   1684  CG   PRO A 253     -22.591   3.886   5.231  1.00 27.66           C
ATOM   1685  CD   PRO A 253     -22.038   3.933   6.623  1.00 26.29           C
ATOM   1686  N    ASN A 254     -19.507   0.569   4.592  1.00 27.28           N
ATOM   1687  CA   ASN A 254     -18.147   0.100   4.331  1.00 27.11           C
ATOM   1688  C    ASN A 254     -17.266  -0.144   5.556  1.00 26.96           C
ATOM   1689  O    ASN A 254     -16.188   0.427   5.684  1.00 25.85           O
ATOM   1690  CB   ASN A 254     -17.440   1.082   3.392  1.00 27.49           C
ATOM   1691  CG   ASN A 254     -18.306   1.483   2.215  1.00 29.72           C
ATOM   1692  OD1  ASN A 254     -18.755   0.628   1.445  1.00 31.70           O
ATOM   1693  ND2  ASN A 254     -18.548   2.787   2.064  1.00 28.13           N
ATOM   1694  N    PRO A 255     -17.717  -0.994   6.483  1.00 27.26           N
ATOM   1695  CA   PRO A 255     -16.838  -1.209   7.631  1.00 27.47           C
ATOM   1696  C    PRO A 255     -15.693  -2.165   7.243  1.00 28.39           C
ATOM   1697  O    PRO A 255     -15.846  -3.036   6.380  1.00 27.60           O
ATOM   1698  CB   PRO A 255     -17.778  -1.816   8.668  1.00 26.98           C
ATOM   1699  CG   PRO A 255     -18.703  -2.630   7.817  1.00 26.90           C
```

FIGURE 2-26 (COORDINATES)

```
ATOM   1700  CD  PRO A 255     -19.003  -1.688   6.662  1.00 26.52           C
ATOM   1701  N   THR A 256     -14.541  -1.970   7.869  1.00 28.21           N
ATOM   1702  CA  THR A 256     -13.392  -2.819   7.628  1.00 27.81           C
ATOM   1703  C   THR A 256     -12.918  -3.271   9.004  1.00 27.03           C
ATOM   1704  O   THR A 256     -12.398  -2.474   9.787  1.00 26.79           O
ATOM   1705  CB  THR A 256     -12.259  -2.051   6.896  1.00 28.51           C
ATOM   1706  OG1 THR A 256     -12.040  -0.795   7.548  1.00 30.45           O
ATOM   1707  CG2 THR A 256     -12.626  -1.799   5.454  1.00 27.28           C
ATOM   1708  N   PHE A 257     -13.128  -4.551   9.291  1.00 26.41           N
ATOM   1709  CA  PHE A 257     -12.748  -5.152  10.559  1.00 25.81           C
ATOM   1710  C   PHE A 257     -11.364  -5.792  10.460  1.00 26.39           C
ATOM   1711  O   PHE A 257     -11.159  -6.713   9.676  1.00 26.52           O
ATOM   1712  CB  PHE A 257     -13.764  -6.227  10.938  1.00 26.91           C
ATOM   1713  CG  PHE A 257     -15.165  -5.707  11.149  1.00 26.13           C
ATOM   1714  CD1 PHE A 257     -15.533  -5.129  12.363  1.00 25.71           C
ATOM   1715  CD2 PHE A 257     -16.120  -5.821  10.140  1.00 25.58           C
ATOM   1716  CE1 PHE A 257     -16.837  -4.673  12.572  1.00 25.76           C
ATOM   1717  CE2 PHE A 257     -17.427  -5.369  10.332  1.00 26.74           C
ATOM   1718  CZ  PHE A 257     -17.789  -4.793  11.552  1.00 25.87           C
ATOM   1719  N   PRO A 258     -10.391  -5.306  11.247  1.00 27.20           N
ATOM   1720  CA  PRO A 258      -9.058  -5.911  11.167  1.00 28.17           C
ATOM   1721  C   PRO A 258      -8.904  -7.135  12.084  1.00 28.52           C
ATOM   1722  O   PRO A 258      -9.677  -7.327  13.023  1.00 28.66           O
ATOM   1723  CB  PRO A 258      -8.138  -4.756  11.556  1.00 27.23           C
ATOM   1724  CG  PRO A 258      -8.947  -4.026  12.572  1.00 27.48           C
ATOM   1725  CD  PRO A 258     -10.345  -4.026  11.980  1.00 27.46           C
ATOM   1726  N   ASN A 259      -7.900  -7.957  11.792  1.00 28.52           N
ATOM   1727  CA  ASN A 259      -7.604  -9.170  12.559  1.00 27.63           C
ATOM   1728  C   ASN A 259      -6.680  -8.770  13.717  1.00 27.13           C
ATOM   1729  O   ASN A 259      -5.464  -8.826  13.588  1.00 28.37           O
ATOM   1730  CB  ASN A 259      -6.922 -10.162  11.611  1.00 27.66           C
ATOM   1731  CG  ASN A 259      -6.765 -11.555  12.197  1.00 28.70           C
ATOM   1732  OD1 ASN A 259      -6.440 -12.487  11.466  1.00 29.28           O
ATOM   1733  ND2 ASN A 259      -6.987 -11.707  13.500  1.00 26.14           N
ATOM   1734  N   PHE A 260      -7.265  -8.372  14.843  1.00 26.90           N
ATOM   1735  CA  PHE A 260      -6.508  -7.907  16.010  1.00 27.45           C
ATOM   1736  C   PHE A 260      -5.617  -8.875  16.794  1.00 28.25           C
ATOM   1737  O   PHE A 260      -4.518  -8.509  17.200  1.00 28.94           O
ATOM   1738  CB  PHE A 260      -7.445  -7.266  17.046  1.00 27.42           C
ATOM   1739  CG  PHE A 260      -8.203  -6.068  16.548  1.00 27.40           C
ATOM   1740  CD1 PHE A 260      -9.502  -6.203  16.061  1.00 26.32           C
ATOM   1741  CD2 PHE A 260      -7.641  -4.794  16.614  1.00 27.66           C
ATOM   1742  CE1 PHE A 260     -10.236  -5.084  15.652  1.00 27.41           C
ATOM   1743  CE2 PHE A 260      -8.366  -3.665  16.206  1.00 27.08           C
ATOM   1744  CZ  PHE A 260      -9.665  -3.811  15.726  1.00 26.77           C
ATOM   1745  N   PHE A 261      -6.085 -10.097  17.017  1.00 28.08           N
ATOM   1746  CA  PHE A 261      -5.334 -11.032  17.845  1.00 28.59           C
ATOM   1747  C   PHE A 261      -4.954 -12.366  17.229  1.00 29.07           C
ATOM   1748  O   PHE A 261      -5.787 -13.052  16.641  1.00 29.12           O
ATOM   1749  CB  PHE A 261      -6.122 -11.282  19.132  1.00 27.06           C
ATOM   1750  CG  PHE A 261      -6.579 -10.022  19.806  1.00 26.05           C
ATOM   1751  CD1 PHE A 261      -5.658  -9.164  20.401  1.00 24.71           C
ATOM   1752  CD2 PHE A 261      -7.922  -9.650  19.781  1.00 24.37           C
ATOM   1753  CE1 PHE A 261      -6.066  -7.953  20.954  1.00 24.25           C
ATOM   1754  CE2 PHE A 261      -8.338  -8.439  20.335  1.00 24.01           C
ATOM   1755  CZ  PHE A 261      -7.405  -7.589  20.920  1.00 23.34           C
ATOM   1756  N   PRO A 262      -3.676 -12.755  17.367  1.00 29.57           N
ATOM   1757  CA  PRO A 262      -3.215 -14.025  16.815  1.00 29.46           C
ATOM   1758  C   PRO A 262      -3.879 -15.247  17.433  1.00 29.71           C
ATOM   1759  O   PRO A 262      -4.072 -16.242  16.746  1.00 30.41           O
ATOM   1760  CB  PRO A 262      -1.703 -13.986  17.053  1.00 28.95           C
ATOM   1761  CG  PRO A 262      -1.547 -13.058  18.201  1.00 30.58           C
ATOM   1762  CD  PRO A 262      -2.538 -11.972  17.876  1.00 30.11           C
ATOM   1763  N   ASN A 263      -4.251 -15.191  18.709  1.00 30.02           N
ATOM   1764  CA  ASN A 263      -4.874 -16.369  19.296  1.00 31.42           C
ATOM   1765  C   ASN A 263      -6.368 -16.509  18.966  1.00 31.82           C
ATOM   1766  O   ASN A 263      -7.069 -17.333  19.555  1.00 33.28           O
ATOM   1767  CB  ASN A 263      -4.642 -16.429  20.812  1.00 32.19           C
```

FIGURE 2-27 (COORDINATES)

```
ATOM   1768  CG   ASN A 263      -5.495  -15.456  21.569  1.00 33.86           C
ATOM   1769  OD1  ASN A 263      -6.367  -14.798  21.001  1.00 35.24           O
ATOM   1770  ND2  ASN A 263      -5.259  -15.363  22.868  1.00 34.93           N
ATOM   1771  N    SER A 264      -6.853  -15.711  18.020  1.00 31.00           N
ATOM   1772  CA   SER A 264      -8.245  -15.803  17.589  1.00 30.61           C
ATOM   1773  C    SER A 264      -8.271  -15.623  16.078  1.00 29.56           C
ATOM   1774  O    SER A 264      -9.332  -15.607  15.457  1.00 29.34           O
ATOM   1775  CB   SER A 264      -9.113  -14.734  18.262  1.00 30.35           C
ATOM   1776  OG   SER A 264      -8.856  -13.439  17.751  1.00 32.06           O
ATOM   1777  N    ALA A 265      -7.081  -15.506  15.497  1.00 28.87           N
ATOM   1778  CA   ALA A 265      -6.928  -15.314  14.061  1.00 28.74           C
ATOM   1779  C    ALA A 265      -7.601  -16.396  13.216  1.00 28.82           C
ATOM   1780  O    ALA A 265      -8.149  -16.096  12.155  1.00 29.56           O
ATOM   1781  CB   ALA A 265      -5.445  -15.221  13.705  1.00 27.61           C
ATOM   1782  N    ARG A 266      -7.565  -17.651  13.662  1.00 28.06           N
ATOM   1783  CA   ARG A 266      -8.199  -18.698  12.872  1.00 28.32           C
ATOM   1784  C    ARG A 266      -9.712  -18.486  12.806  1.00 28.31           C
ATOM   1785  O    ARG A 266     -10.342  -18.833  11.812  1.00 28.61           O
ATOM   1786  CB   ARG A 266      -7.857  -20.098  13.411  1.00 28.87           C
ATOM   1787  CG   ARG A 266      -8.389  -20.454  14.789  1.00 30.33           C
ATOM   1788  CD   ARG A 266      -7.797  -21.791  15.229  1.00 29.99           C
ATOM   1789  NE   ARG A 266      -8.300  -22.256  16.523  1.00 32.14           N
ATOM   1790  CZ   ARG A 266      -9.300  -23.124  16.678  1.00 32.05           C
ATOM   1791  NH1  ARG A 266      -9.916  -23.627  15.616  1.00 31.56           N
ATOM   1792  NH2  ARG A 266      -9.672  -23.508  17.897  1.00 32.14           N
ATOM   1793  N    TRP A 267     -10.292  -17.902  13.850  1.00 27.66           N
ATOM   1794  CA   TRP A 267     -11.721  -17.637  13.837  1.00 27.84           C
ATOM   1795  C    TRP A 267     -12.013  -16.410  12.968  1.00 28.19           C
ATOM   1796  O    TRP A 267     -13.082  -16.309  12.370  1.00 28.29           O
ATOM   1797  CB   TRP A 267     -12.254  -17.457  15.266  1.00 26.25           C
ATOM   1798  CG   TRP A 267     -12.253  -18.757  16.034  1.00 27.42           C
ATOM   1799  CD1  TRP A 267     -11.531  -19.048  17.156  1.00 27.43           C
ATOM   1800  CD2  TRP A 267     -12.945  -19.968  15.681  1.00 27.10           C
ATOM   1801  NE1  TRP A 267     -11.721  -20.359  17.518  1.00 27.06           N
ATOM   1802  CE2  TRP A 267     -12.584  -20.947  16.633  1.00 27.18           C
ATOM   1803  CE3  TRP A 267     -13.828  -20.318  14.650  1.00 27.32           C
ATOM   1804  CZ2  TRP A 267     -13.077  -22.260  16.587  1.00 27.15           C
ATOM   1805  CZ3  TRP A 267     -14.317  -21.628  14.602  1.00 27.51           C
ATOM   1806  CH2  TRP A 267     -13.938  -22.578  15.567  1.00 27.46           C
ATOM   1807  N    PHE A 268     -11.066  -15.479  12.890  1.00 28.81           N
ATOM   1808  CA   PHE A 268     -11.258  -14.303  12.042  1.00 29.03           C
ATOM   1809  C    PHE A 268     -11.295  -14.838  10.607  1.00 29.34           C
ATOM   1810  O    PHE A 268     -12.097  -14.401   9.790  1.00 28.47           O
ATOM   1811  CB   PHE A 268     -10.093  -13.309  12.193  1.00 27.65           C
ATOM   1812  CG   PHE A 268     -10.200  -12.103  11.284  1.00 26.74           C
ATOM   1813  CD1  PHE A 268     -10.876  -10.951  11.701  1.00 25.46           C
ATOM   1814  CD2  PHE A 268      -9.665  -12.139   9.992  1.00 25.36           C
ATOM   1815  CE1  PHE A 268     -11.024   -9.852  10.845  1.00 26.64           C
ATOM   1816  CE2  PHE A 268      -9.804  -11.049   9.122  1.00 25.55           C
ATOM   1817  CZ   PHE A 268     -10.488   -9.899   9.548  1.00 25.85           C
ATOM   1818  N    GLU A 269     -10.417  -15.794  10.314  1.00 30.25           N
ATOM   1819  CA   GLU A 269     -10.373  -16.398   8.986  1.00 31.67           C
ATOM   1820  C    GLU A 269     -11.702  -17.061   8.638  1.00 31.21           C
ATOM   1821  O    GLU A 269     -12.126  -17.047   7.477  1.00 31.16           O
ATOM   1822  CB   GLU A 269      -9.239  -17.424   8.898  1.00 33.10           C
ATOM   1823  CG   GLU A 269      -7.901  -16.835   8.481  1.00 36.79           C
ATOM   1824  CD   GLU A 269      -6.718  -17.547   9.126  1.00 40.40           C
ATOM   1825  OE1  GLU A 269      -6.689  -18.800   9.110  1.00 41.61           O
ATOM   1826  OE2  GLU A 269      -5.814  -16.850   9.646  1.00 41.85           O
ATOM   1827  N    ARG A 270     -12.354  -17.648   9.640  1.00 30.80           N
ATOM   1828  CA   ARG A 270     -13.645  -18.290   9.423  1.00 30.45           C
ATOM   1829  C    ARG A 270     -14.683  -17.264   8.975  1.00 30.54           C
ATOM   1830  O    ARG A 270     -15.477  -17.539   8.081  1.00 30.64           O
ATOM   1831  CB   ARG A 270     -14.114  -18.998  10.693  1.00 30.23           C
ATOM   1832  CG   ARG A 270     -13.430  -20.346  10.925  1.00 31.29           C
ATOM   1833  CD   ARG A 270     -13.529  -21.247   9.686  1.00 30.23           C
ATOM   1834  NE   ARG A 270     -14.896  -21.333   9.190  1.00 29.98           N
ATOM   1835  CZ   ARG A 270     -15.218  -21.699   7.954  1.00 31.49           C
```

FIGURE 2-28 (COORDINATES)

```
ATOM   1836  NH1 ARG A 270     -14.264 -22.016   7.084  1.00 31.21           N
ATOM   1837  NH2 ARG A 270     -16.492 -21.735   7.581  1.00 31.30           N
ATOM   1838  N   LEU A 271     -14.672 -16.083   9.594  1.00 30.14           N
ATOM   1839  CA  LEU A 271     -15.598 -15.022   9.219  1.00 30.06           C
ATOM   1840  C   LEU A 271     -15.340 -14.591   7.772  1.00 30.49           C
ATOM   1841  O   LEU A 271     -16.274 -14.237   7.051  1.00 30.64           O
ATOM   1842  CB  LEU A 271     -15.442 -13.806  10.142  1.00 29.02           C
ATOM   1843  CG  LEU A 271     -15.991 -13.918  11.563  1.00 29.56           C
ATOM   1844  CD1 LEU A 271     -15.480 -12.740  12.399  1.00 28.76           C
ATOM   1845  CD2 LEU A 271     -17.516 -13.954  11.532  1.00 27.03           C
ATOM   1846  N   GLN A 272     -14.076 -14.618   7.349  1.00 29.97           N
ATOM   1847  CA  GLN A 272     -13.734 -14.235   5.984  1.00 29.13           C
ATOM   1848  C   GLN A 272     -14.303 -15.267   5.043  1.00 29.18           C
ATOM   1849  O   GLN A 272     -14.924 -14.923   4.035  1.00 31.26           O
ATOM   1850  CB  GLN A 272     -12.216 -14.168   5.772  1.00 28.92           C
ATOM   1851  CG  GLN A 272     -11.477 -13.195   6.661  1.00 30.19           C
ATOM   1852  CD  GLN A 272     -10.028 -12.989   6.225  1.00 31.95           C
ATOM   1853  OE1 GLN A 272      -9.714 -12.069   5.456  1.00 30.73           O
ATOM   1854  NE2 GLN A 272      -9.139 -13.856   6.710  1.00 31.36           N
ATOM   1855  N   ALA A 273     -14.090 -16.536   5.375  1.00 27.68           N
ATOM   1856  CA  ALA A 273     -14.573 -17.637   4.554  1.00 25.84           C
ATOM   1857  C   ALA A 273     -16.084 -17.558   4.393  1.00 25.58           C
ATOM   1858  O   ALA A 273     -16.613 -17.732   3.299  1.00 26.44           O
ATOM   1859  CB  ALA A 273     -14.183 -18.973   5.186  1.00 24.02           C
ATOM   1860  N   ILE A 274     -16.768 -17.297   5.501  1.00 25.35           N
ATOM   1861  CA  ILE A 274     -18.214 -17.198   5.522  1.00 25.16           C
ATOM   1862  C   ILE A 274     -18.685 -16.051   4.643  1.00 26.24           C
ATOM   1863  O   ILE A 274     -19.575 -16.224   3.806  1.00 26.46           O
ATOM   1864  CB  ILE A 274     -18.708 -17.003   6.968  1.00 25.23           C
ATOM   1865  CG1 ILE A 274     -18.335 -18.240   7.789  1.00 25.61           C
ATOM   1866  CG2 ILE A 274     -20.215 -16.776   6.993  1.00 25.08           C
ATOM   1867  CD1 ILE A 274     -18.609 -18.120   9.263  1.00 26.41           C
ATOM   1868  N   GLU A 275     -18.089 -14.878   4.830  1.00 26.33           N
ATOM   1869  CA  GLU A 275     -18.463 -13.723   4.027  1.00 27.36           C
ATOM   1870  C   GLU A 275     -18.264 -14.040   2.543  1.00 27.85           C
ATOM   1871  O   GLU A 275     -19.104 -13.714   1.705  1.00 27.88           O
ATOM   1872  CB  GLU A 275     -17.622 -12.495   4.404  1.00 25.93           C
ATOM   1873  CG  GLU A 275     -17.783 -11.335   3.416  1.00 26.97           C
ATOM   1874  CD  GLU A 275     -17.055 -10.066   3.838  1.00 27.34           C
ATOM   1875  OE1 GLU A 275     -15.882 -10.149   4.269  1.00 26.14           O
ATOM   1876  OE2 GLU A 275     -17.661  -8.980   3.725  1.00 26.85           O
ATOM   1877  N   HIS A 276     -17.150 -14.690   2.236  1.00 27.45           N
ATOM   1878  CA  HIS A 276     -16.817 -15.044   0.870  1.00 28.93           C
ATOM   1879  C   HIS A 276     -17.826 -16.003   0.231  1.00 30.11           C
ATOM   1880  O   HIS A 276     -18.223 -15.827  -0.928  1.00 29.32           O
ATOM   1881  CB  HIS A 276     -15.414 -15.660   0.835  1.00 29.99           C
ATOM   1882  CG  HIS A 276     -14.946 -16.001  -0.541  1.00 31.94           C
ATOM   1883  ND1 HIS A 276     -14.176 -15.144  -1.298  1.00 33.23           N
ATOM   1884  CD2 HIS A 276     -15.202 -17.074  -1.327  1.00 32.55           C
ATOM   1885  CE1 HIS A 276     -13.981 -15.672  -2.493  1.00 33.20           C
ATOM   1886  NE2 HIS A 276     -14.594 -16.842  -2.537  1.00 34.05           N
ATOM   1887  N   GLU A 277     -18.241 -17.017   0.983  1.00 30.87           N
ATOM   1888  CA  GLU A 277     -19.188 -17.990   0.464  1.00 32.14           C
ATOM   1889  C   GLU A 277     -20.620 -17.450   0.380  1.00 31.82           C
ATOM   1890  O   GLU A 277     -21.328 -17.731  -0.581  1.00 32.57           O
ATOM   1891  CB  GLU A 277     -19.149 -19.261   1.312  1.00 34.39           C
ATOM   1892  CG  GLU A 277     -19.891 -20.414   0.681  1.00 38.60           C
ATOM   1893  CD  GLU A 277     -19.260 -20.874  -0.626  1.00 41.15           C
ATOM   1894  OE1 GLU A 277     -19.922 -21.635  -1.365  1.00 43.42           O
ATOM   1895  OE2 GLU A 277     -18.101 -20.489  -0.913  1.00 42.93           O
ATOM   1896  N   LEU A 278     -21.058 -16.685   1.378  1.00 30.96           N
ATOM   1897  CA  LEU A 278     -22.403 -16.114   1.329  1.00 31.05           C
ATOM   1898  C   LEU A 278     -22.471 -15.176   0.120  1.00 31.74           C
ATOM   1899  O   LEU A 278     -23.500 -15.064  -0.552  1.00 31.45           O
ATOM   1900  CB  LEU A 278     -22.719 -15.344   2.616  1.00 29.86           C
ATOM   1901  CG  LEU A 278     -23.004 -16.194   3.865  1.00 30.76           C
ATOM   1902  CD1 LEU A 278     -23.190 -15.307   5.087  1.00 28.52           C
ATOM   1903  CD2 LEU A 278     -24.257 -17.036   3.638  1.00 30.07           C
```

FIGURE 2-29 (COORDINATES)

```
ATOM   1904  N   HIS A 279     -21.349 -14.521  -0.159  1.00 32.02           N
ATOM   1905  CA  HIS A 279     -21.255 -13.606  -1.282  1.00 32.52           C
ATOM   1906  C   HIS A 279     -21.296 -14.348  -2.619  1.00 33.28           C
ATOM   1907  O   HIS A 279     -22.057 -13.975  -3.509  1.00 33.29           O
ATOM   1908  CB  HIS A 279     -19.968 -12.791  -1.186  1.00 32.27           C
ATOM   1909  CG  HIS A 279     -19.753 -11.880  -2.348  1.00 32.46           C
ATOM   1910  ND1 HIS A 279     -19.224 -12.313  -3.544  1.00 33.38           N
ATOM   1911  CD2 HIS A 279     -20.030 -10.565  -2.511  1.00 31.47           C
ATOM   1912  CE1 HIS A 279     -19.184 -11.303  -4.395  1.00 32.43           C
ATOM   1913  NE2 HIS A 279     -19.668 -10.231  -3.792  1.00 33.46           N
ATOM   1914  N   GLU A 280     -20.477 -15.390  -2.757  1.00 33.30           N
ATOM   1915  CA  GLU A 280     -20.443 -16.169  -3.992  1.00 34.22           C
ATOM   1916  C   GLU A 280     -21.786 -16.825  -4.299  1.00 34.32           C
ATOM   1917  O   GLU A 280     -22.131 -17.010  -5.463  1.00 35.16           O
ATOM   1918  CB  GLU A 280     -19.351 -17.238  -3.928  1.00 34.40           C
ATOM   1919  CG  GLU A 280     -17.950 -16.678  -4.068  1.00 37.60           C
ATOM   1920  CD  GLU A 280     -17.746 -15.964  -5.392  1.00 39.95           C
ATOM   1921  OE1 GLU A 280     -17.886 -16.616  -6.455  1.00 42.35           O
ATOM   1922  OE2 GLU A 280     -17.453 -14.750  -5.371  1.00 40.00           O
ATOM   1923  N   LEU A 281     -22.530 -17.177  -3.251  1.00 33.75           N
ATOM   1924  CA  LEU A 281     -23.844 -17.793  -3.388  1.00 32.74           C
ATOM   1925  C   LEU A 281     -24.906 -16.720  -3.626  1.00 32.65           C
ATOM   1926  O   LEU A 281     -26.103 -17.020  -3.681  1.00 33.29           O
ATOM   1927  CB  LEU A 281     -24.216 -18.568  -2.118  1.00 32.30           C
ATOM   1928  CG  LEU A 281     -23.418 -19.806  -1.712  1.00 32.00           C
ATOM   1929  CD1 LEU A 281     -24.034 -20.383  -0.455  1.00 30.85           C
ATOM   1930  CD2 LEU A 281     -23.428 -20.833  -2.830  1.00 30.23           C
ATOM   1931  N   GLY A 282     -24.469 -15.472  -3.747  1.00 31.68           N
ATOM   1932  CA  GLY A 282     -25.404 -14.385  -3.970  1.00 31.10           C
ATOM   1933  C   GLY A 282     -26.374 -14.206  -2.820  1.00 30.85           C
ATOM   1934  O   GLY A 282     -27.538 -13.894  -3.031  1.00 30.85           O
ATOM   1935  N   LEU A 283     -25.901 -14.394  -1.593  1.00 31.17           N
ATOM   1936  CA  LEU A 283     -26.769 -14.253  -0.431  1.00 30.11           C
ATOM   1937  C   LEU A 283     -26.589 -12.940   0.336  1.00 29.65           C
ATOM   1938  O   LEU A 283     -27.205 -12.741   1.389  1.00 29.89           O
ATOM   1939  CB  LEU A 283     -26.574 -15.446   0.508  1.00 29.40           C
ATOM   1940  CG  LEU A 283     -27.001 -16.797  -0.074  1.00 30.34           C
ATOM   1941  CD1 LEU A 283     -26.778 -17.894   0.969  1.00 31.77           C
ATOM   1942  CD2 LEU A 283     -28.475 -16.746  -0.486  1.00 29.94           C
ATOM   1943  N   LEU A 284     -25.754 -12.048  -0.190  1.00 28.41           N
ATOM   1944  CA  LEU A 284     -25.527 -10.748   0.447  1.00 28.55           C
ATOM   1945  C   LEU A 284     -26.098  -9.643  -0.446  1.00 28.72           C
ATOM   1946  O   LEU A 284     -26.279  -9.837  -1.641  1.00 29.25           O
ATOM   1947  CB  LEU A 284     -24.023 -10.521   0.690  1.00 27.08           C
ATOM   1948  CG  LEU A 284     -23.274 -11.556   1.546  1.00 25.93           C
ATOM   1949  CD1 LEU A 284     -21.820 -11.125   1.721  1.00 25.76           C
ATOM   1950  CD2 LEU A 284     -23.945 -11.707   2.902  1.00 25.22           C
ATOM   1951  N   LYS A 285     -26.373  -8.484   0.134  1.00 30.09           N
ATOM   1952  CA  LYS A 285     -26.950  -7.360  -0.606  1.00 31.40           C
ATOM   1953  C   LYS A 285     -25.942  -6.210  -0.756  1.00 31.03           C
ATOM   1954  O   LYS A 285     -25.253  -5.851   0.206  1.00 30.86           O
ATOM   1955  CB  LYS A 285     -28.213  -6.886   0.133  1.00 33.40           C
ATOM   1956  CG  LYS A 285     -28.873  -5.627  -0.421  1.00 36.94           C
ATOM   1957  CD  LYS A 285     -29.615  -5.888  -1.727  1.00 39.71           C
ATOM   1958  CE  LYS A 285     -30.290  -4.612  -2.241  1.00 40.61           C
ATOM   1959  NZ  LYS A 285     -31.014  -4.821  -3.534  1.00 41.36           N
ATOM   1960  N   ASP A 286     -25.870  -5.633  -1.957  1.00 30.43           N
ATOM   1961  CA  ASP A 286     -24.938  -4.531  -2.254  1.00 30.94           C
ATOM   1962  C   ASP A 286     -23.591  -4.841  -1.614  1.00 29.73           C
ATOM   1963  O   ASP A 286     -23.108  -4.117  -0.744  1.00 28.74           O
ATOM   1964  CB  ASP A 286     -25.461  -3.196  -1.712  1.00 31.91           C
ATOM   1965  CG  ASP A 286     -26.812  -2.814  -2.289  1.00 34.92           C
ATOM   1966  OD1 ASP A 286     -27.114  -3.191  -3.446  1.00 34.24           O
ATOM   1967  OD2 ASP A 286     -27.571  -2.113  -1.583  1.00 37.21           O
ATOM   1968  N   HIS A 287     -22.979  -5.920  -2.072  1.00 29.00           N
ATOM   1969  CA  HIS A 287     -21.725  -6.361  -1.501  1.00 27.99           C
ATOM   1970  C   HIS A 287     -20.733  -6.810  -2.572  1.00 27.76           C
ATOM   1971  O   HIS A 287     -21.098  -7.493  -3.526  1.00 27.70           O
```

FIGURE 2-30 (COORDINATES)

```
ATOM   1972  CB  HIS A 287     -22.039  -7.505  -0.525  1.00 25.84           C
ATOM   1973  CG  HIS A 287     -20.848  -8.035   0.205  1.00 24.68           C
ATOM   1974  ND1 HIS A 287     -19.973  -8.939  -0.356  1.00 23.07           N
ATOM   1975  CD2 HIS A 287     -20.375  -7.772   1.447  1.00 23.41           C
ATOM   1976  CE1 HIS A 287     -19.010  -9.208   0.506  1.00 23.46           C
ATOM   1977  NE2 HIS A 287     -19.230  -8.513   1.608  1.00 24.09           N
ATOM   1978  N   SER A 288     -19.479  -6.410  -2.410. 1.00 27.54           N
ATOM   1979  CA  SER A 288     -18.430  -6.800  -3.339  1.00 28.86           C
ATOM   1980  C   SER A 288     -17.225  -7.313  -2.554  1.00 28.91           C
ATOM   1981  O   SER A 288     -17.005  -6.917  -1.412  1.00 28.88           O
ATOM   1982  CB  SER A 288     -18.006  -5.610  -4.200  1.00 28.46           C
ATOM   1983  OG  SER A 288     -17.288  -4.664  -3.432  1.00 30.20           O
ATOM   1984  N   LEU A 289     -16.446  -8.201  -3.158  1.00 29.37           N
ATOM   1985  CA  LEU A 289     -15.269  -8.712  -2.476  1.00 30.69           C
ATOM   1986  C   LEU A 289     -14.219  -7.607  -2.298  1.00 31.47           C
ATOM   1987  O   LEU A 289     -13.486  -7.600  -1.306  1.00 31.40           O
ATOM   1988  CB  LEU A 289     -14.693  -9.914  -3.232  1.00 30.31           C
ATOM   1989  CG  LEU A 289     -15.622 -11.140  -3.213  1.00 30.65           C
ATOM   1990  CD1 LEU A 289     -14.980 -12.308  -3.950  1.00 29.92           C
ATOM   1991  CD2 LEU A 289     -15.923 -11.528  -1.769  1.00 30.22           C
ATOM   1992  N   GLU A 290     -14.142  -6.669  -3.242  1.00 32.49           N
ATOM   1993  CA  GLU A 290     -13.188  -5.562  -3.105  1.00 33.08           C
ATOM   1994  C   GLU A 290     -13.545  -4.795  -1.843  1.00 33.06           C
ATOM   1995  O   GLU A 290     -12.667  -4.356  -1.105  1.00 32.52           O
ATOM   1996  CB  GLU A 290     -13.259  -4.606  -4.290  1.00 33.72           C
ATOM   1997  CG  GLU A 290     -12.493  -5.062  -5.493  1.00 37.08           C
ATOM   1998  CD  GLU A 290     -11.022  -5.203  -5.198  1.00 39.04           C
ATOM   1999  OE1 GLU A 290     -10.409  -4.213  -4.746  1.00 41.22           O
ATOM   2000  OE2 GLU A 290     -10.477  -6.303  -5.414  1.00 40.92           O
ATOM   2001  N   GLY A 291     -14.844  -4.649  -1.595  1.00 33.19           N
ATOM   2002  CA  GLY A 291     -15.291  -3.938  -0.412  1.00 33.03           C
ATOM   2003  C   GLY A 291     -15.675  -4.862   0.730  1.00 33.09           C
ATOM   2004  O   GLY A 291     -16.560  -4.528   1.513  1.00 34.01           O
ATOM   2005  N   ARG A 292     -15.016  -6.015   0.844  1.00 33.00           N
ATOM   2006  CA  ARG A 292     -15.329  -6.965   1.917  1.00 33.31           C
ATOM   2007  C   ARG A 292     -15.140  -6.333   3.306  1.00 32.17           C
ATOM   2008  O   ARG A 292     -14.389  -5.370   3.466  1.00 31.32           O
ATOM   2009  CB  ARG A 292     -14.473  -8.231   1.770  1.00 34.23           C
ATOM   2010  CG  ARG A 292     -12.973  -7.999   1.794  1.00 36.04           C
ATOM   2011  CD  ARG A 292     -12.219  -9.258   1.385  1.00 38.44           C
ATOM   2012  NE  ARG A 292     -10.764  -9.081   1.402  1.00 42.02           N
ATOM   2013  CZ  ARG A 292     -10.097  -8.156   0.710  1.00 43.51           C
ATOM   2014  NH1 ARG A 292     -10.742  -7.301  -0.072  1.00 45.26           N
ATOM   2015  NH2 ARG A 292      -8.773  -8.078   0.804  1.00 44.24           N
ATOM   2016  N   TYR A 293     -15.835  -6.862   4.305  1.00 31.10           N
ATOM   2017  CA  TYR A 293     -15.733  -6.310   5.650  1.00 30.76           C
ATOM   2018  C   TYR A 293     -14.560  -6.879   6.454  1.00 31.79           C
ATOM   2019  O   TYR A 293     -13.938  -6.170   7.245  1.00 31.72           O
ATOM   2020  CB  TYR A 293     -17.026  -6.555   6.433  1.00 29.20           C
ATOM.  2021  CG  TYR A 293     -18.298  -6.221   5.689  1.00 29.54           C
ATOM   2022  CD1 TYR A 293     -18.429  -5.030   4.969  1.00 28.86           C
ATOM   2023  CD2 TYR A 293     -19.380  -7.105   5.704  1.00 28.65           C
ATOM   2024  CE1 TYR A 293     -19.603  -4.735   4.279  1.00 28.52           C
ATOM   2025  CE2 TYR A 293     -20.555  -6.819   5.025  1.00 28.50           C
ATOM   2026  CZ  TYR A 293     -20.663  -5.638   4.310  1.00 29.12           C
ATOM   2027  OH  TYR A 293     -21.815  -5.391   3.598  1.00 27.91           O
ATOM   2028  N   PHE A 294     -14.268  -8.158   6.251  1.00 32.17           N
ATOM   2029  CA  PHE A 294     -13.195  -8.819   6.975  1.00 34.52           C
ATOM   2030  C   PHE A 294     -11.981  -8.929   6.084  1.00 38.00           C
ATOM   2031  O   PHE A 294     -11.856  -9.842   5.261  1.00 38.24           O
ATOM   2032  CB  PHE A 294     -13.683 -10.187   7.449  1.00 33.00           C
ATOM   2033  CG  PHE A 294     -14.834 -10.097   8.412  1.00 33.02           C
ATOM   2034  CD1 PHE A 294     -14.626  -9.668   9.725  1.00 32.00           C
ATOM   2035  CD2 PHE A 294     -16.138 -10.359   7.987  1.00 31.90           C
ATOM   2036  CE1 PHE A 294     -15.699  -9.497  10.598  1.00 31.96           C
ATOM   2037  CE2 PHE A 294     -17.214 -10.192   8.849  1.00 31.74           C
ATOM   2038  CZ  PHE A 294     -16.997  -9.759  10.159  1.00 32.36           C
ATOM   2039  N   GLN A 295     -11.073  -7.979   6.257  1.00 41.87           N
```

FIGURE 2-31 (COORDINATES)

```
ATOM   2040  CA   GLN A 295      -9.900  -7.939   5.419  1.00 46.11           C
ATOM   2041  C    GLN A 295      -8.641  -8.492   6.039  1.00 48.76           C
ATOM   2042  O    GLN A 295      -8.458  -8.489   7.253  1.00 48.95           O
ATOM   2043  CB   GLN A 295      -9.669  -6.511   4.929  1.00 46.38           C
ATOM   2044  CG   GLN A 295     -10.921  -5.872   4.360  1.00 46.53           C
ATOM   2045  CD   GLN A 295     -10.619  -4.661   3.508  1.00 46.55           C
ATOM   2046  OE1  GLN A 295      -9.813  -3.812   3.881  1.00 47.20           O
ATOM   2047  NE2  GLN A 295     -11.272  -4.572   2.359  1.00 46.50           N
ATOM   2048  N    ASN A 296      -7.775  -8.962   5.153  1.00 52.61           N
ATOM   2049  CA   ASN A 296      -6.502  -9.569   5.497  1.00 55.92           C
ATOM   2050  C    ASN A 296      -5.504  -8.538   6.020  1.00 58.23           C
ATOM   2051  O    ASN A 296      -4.648  -8.073   5.264  1.00 60.10           O
ATOM   2052  CB   ASN A 296      -5.921 -10.242   4.244  1.00 55.17           C
ATOM   2053  CG   ASN A 296      -7.001 -10.698   3.257  1.00 54.63           C
ATOM   2054  OD1  ASN A 296      -7.855  -9.913   2.830  1.00 52.22           O
ATOM   2055  ND2  ASN A 296      -6.952 -11.971   2.883  1.00 55.01           N
ATOM   2056  N    TYR A 297      -5.613  -8.158   7.290  1.00 59.64           N
ATOM   2057  CA   TYR A 297      -4.666  -7.199   7.849  1.00 61.18           C
ATOM   2058  C    TYR A 297      -4.770  -7.047   9.355  1.00 61.39           C
ATOM   2059  O    TYR A 297      -5.865  -6.980   9.921  1.00 60.96           O
ATOM   2060  CB   TYR A 297      -4.791  -5.821   7.172  1.00 63.28           C
ATOM   2061  CG   TYR A 297      -5.920  -4.927   7.651  1.00 65.54           C
ATOM   2062  CD1  TYR A 297      -7.255  -5.275   7.445  1.00 66.73           C
ATOM   2063  CD2  TYR A 297      -5.648  -3.707   8.276  1.00 66.16           C
ATOM   2064  CE1  TYR A 297      -8.295  -4.425   7.847  1.00 68.08           C
ATOM   2065  CE2  TYR A 297      -6.675  -2.850   8.681  1.00 67.14           C
ATOM   2066  CZ   TYR A 297      -7.995  -3.214   8.463  1.00 68.16           C
ATOM   2067  OH   TYR A 297      -9.011  -2.370   8.856  1.00 68.47           O
ATOM   2068  N    SER A 298      -3.607  -7.005   9.996  1.00 61.22           N
ATOM   2069  CA   SER A 298      -3.535  -6.870  11.439  1.00 61.27           C
ATOM   2070  C    SER A 298      -3.620  -5.407  11.858  1.00 60.43           C
ATOM   2071  O    SER A 298      -3.740  -4.504  11.022  1.00 59.97           O
ATOM   2072  CB   SER A 298      -2.230  -7.483  11.960  1.00 62.20           C
ATOM   2073  OG   SER A 298      -1.102  -6.760  11.498  1.00 62.72           O
ATOM   2074  N    TYR A 299      -3.556  -5.187  13.164  1.00 58.80           N
ATOM   2075  CA   TYR A 299      -3.629  -3.850  13.725  1.00 58.09           C
ATOM   2076  C    TYR A 299      -2.882  -3.898  15.050  1.00 58.03           C
ATOM   2077  O    TYR A 299      -3.367  -4.477  16.022  1.00 59.76           O
ATOM   2078  CB   TYR A 299      -5.099  -3.465  13.921  1.00 56.87           C
ATOM   2079  CG   TYR A 299      -5.343  -2.157  14.638  1.00 55.64           C
ATOM   2080  CD1  TYR A 299      -5.134  -2.044  16.013  1.00 55.22           C
ATOM   2081  CD2  TYR A 299      -5.821  -1.044  13.952  1.00 55.13           C
ATOM   2082  CE1  TYR A 299      -5.400  -0.863  16.687  1.00 54.85           C
ATOM   2083  CE2  TYR A 299      -6.089   0.149  14.619  1.00 54.75           C
ATOM   2084  CZ   TYR A 299      -5.877   0.229  15.987  1.00 54.77           C
ATOM   2085  OH   TYR A 299      -6.146   1.393  16.665  1.00 55.11           O
ATOM   2086  N    GLY A 300      -1.696  -3.298  15.075  1.00 57.07           N
ATOM   2087  CA   GLY A 300      -0.877  -3.302  16.274  1.00 55.96           C
ATOM   2088  C    GLY A 300      -1.466  -2.692  17.537  1.00 55.13           C
ATOM   2089  O    GLY A 300      -1.661  -3.393  18.534  1.00 55.21           O
ATOM   2090  N    GLY A 301      -1.745  -1.390  17.495  1.00 53.87           N
ATOM   2091  CA   GLY A 301      -2.282  -0.677  18.647  1.00 51.27           C
ATOM   2092  C    GLY A 301      -3.366  -1.330  19.495  1.00 49.62           C
ATOM   2093  O    GLY A 301      -3.862  -2.423  19.204  1.00 49.99           O
ATOM   2094  N    VAL A 302      -3.741  -0.637  20.563  1.00 46.96           N
ATOM   2095  CA   VAL A 302      -4.769  -1.121  21.467  1.00 44.13           C
ATOM   2096  C    VAL A 302      -6.017  -0.253  21.379  1.00 42.12           C
ATOM   2097  O    VAL A 302      -5.930   0.968  21.382  1.00 41.83           O
ATOM   2098  CB   VAL A 302      -4.287  -1.080  22.931  1.00 44.33           C
ATOM   2099  CG1  VAL A 302      -5.375  -1.636  23.850  1.00 44.24           C
ATOM   2100  CG2  VAL A 302      -2.987  -1.857  23.081  1.00 44.57           C
ATOM   2101  N    ILE A 303      -7.183  -0.881  21.304  1.00 39.74           N
ATOM   2102  CA   ILE A 303      -8.420  -0.118  21.273  1.00 36.82           C
ATOM   2103  C    ILE A 303      -9.186  -0.368  22.567  1.00 35.99           C
ATOM   2104  O    ILE A 303      -9.538  -1.503  22.876  1.00 37.00           O
ATOM   2105  CB   ILE A 303      -9.298  -0.501  20.071  1.00 35.22           C
ATOM   2106  CG1  ILE A 303      -8.568  -0.132  18.774  1.00 32.98           C
ATOM   2107  CG2  ILE A 303     -10.654   0.201  20.172  1.00 33.69           C
```

FIGURE 2-32 (COORDINATES)

```
ATOM   2108  CD1 ILE A 303      -9.401   -0.271   17.526  1.00 32.69           C
ATOM   2109  N   GLN A 304      -9.421    0.693   23.331  1.00 34.48           N
ATOM   2110  CA  GLN A 304     -10.149    0.578   24.589  1.00 33.32           C
ATOM   2111  C   GLN A 304     -11.593    0.155   24.341  1.00 31.47           C
ATOM   2112  O   GLN A 304     -12.320    0.808   23.600  1.00 30.48           O
ATOM   2113  CB  GLN A 304     -10.137    1.912   25.335  1.00 34.65           C
ATOM   2114  CG  GLN A 304      -8.773    2.336   25.811  1.00 37.96           C
ATOM   2115  CD  GLN A 304      -8.194    1.356   26.803  1.00 40.37           C
ATOM   2116  OE1 GLN A 304      -8.790    1.091   27.854  1.00 42.57           O
ATOM   2117  NE2 GLN A 304      -7.030    0.804   26.477  1.00 40.60           N
ATOM   2118  N   ASP A 305     -12.000   -0.945   24.960  1.00 29.69           N
ATOM   2119  CA  ASP A 305     -13.363   -1.433   24.811  1.00 28.20           C
ATOM   2120  C   ASP A 305     -13.627   -2.507   25.864  1.00 27.72           C
ATOM   2121  O   ASP A 305     -12.728   -2.875   26.613  1.00 27.56           O
ATOM   2122  CB  ASP A 305     -13.579   -2.003   23.404  1.00 27.52           C
ATOM   2123  CG  ASP A 305     -15.027   -1.900   22.950  1.00 26.95           C
ATOM   2124  OD1 ASP A 305     -15.919   -1.805   23.818  1.00 26.56           O
ATOM   2125  OD2 ASP A 305     -15.274   -1.926   21.728  1.00 25.35           O
ATOM   2126  N   ASP A 306     -14.857   -3.010   25.909  1.00 27.47           N
ATOM   2127  CA  ASP A 306     -15.237   -4.033   26.881  1.00 27.73           C
ATOM   2128  C   ASP A 306     -14.424   -5.333   26.905  1.00 27.42           C
ATOM   2129  O   ASP A 306     -14.504   -6.084   27.873  1.00 26.89           O
ATOM   2130  CB  ASP A 306     -16.715   -4.386   26.718  1.00 27.77           C
ATOM   2131  CG  ASP A 306     -17.620   -3.275   27.154  1.00 27.88           C
ATOM   2132  OD1 ASP A 306     -17.347   -2.665   28.211  1.00 28.71           O
ATOM   2133  OD2 ASP A 306     -18.608   -3.019   26.447  1.00 28.35           O
ATOM   2134  N   HIS A 307     -13.652   -5.602   25.856  1.00 27.64           N
ATOM   2135  CA  HIS A 307     -12.853   -6.824   25.797  1.00 27.59           C
ATOM   2136  C   HIS A 307     -11.587   -6.754   26.648  1.00 28.00           C
ATOM   2137  O   HIS A 307     -11.057   -7.783   27.063  1.00 29.32           O
ATOM   2138  CB  HIS A 307     -12.450   -7.122   24.352  1.00 27.43           C
ATOM   2139  CG  HIS A 307     -11.478   -6.131   23.787  1.00 27.83           C
ATOM   2140  ND1 HIS A 307     -11.777   -4.792   23.647  1.00 26.26           N
ATOM   2141  CD2 HIS A 307     -10.194   -6.275   23.380  1.00 26.85           C
ATOM   2142  CE1 HIS A 307     -10.718   -4.155   23.182  1.00 26.53           C
ATOM   2143  NE2 HIS A 307      -9.744   -5.031   23.011  1.00 26.48           N
ATOM   2144  N   ILE A 308     -11.096   -5.544   26.899  1.00 28.17           N
ATOM   2145  CA  ILE A 308      -9.865   -5.358   27.674  1.00 27.34           C
ATOM   2146  C   ILE A 308      -9.787   -6.143   28.988  1.00 27.41           C
ATOM   2147  O   ILE A 308      -8.858   -6.931   29.185  1.00 27.38           O
ATOM   2148  CB  ILE A 308      -9.601   -3.840   27.967  1.00 27.71           C
ATOM   2149  CG1 ILE A 308      -9.333   -3.095   26.649  1.00 26.33           C
ATOM   2150  CG2 ILE A 308      -8.438   -3.676   28.947  1.00 24.41           C
ATOM   2151  CD1 ILE A 308      -8.200   -3.675   25.827  1.00 24.82           C
ATOM   2152  N   PRO A 309     -10.761   -5.951   29.894  1.00 27.17           N
ATOM   2153  CA  PRO A 309     -10.731   -6.675   31.171  1.00 27.75           C
ATOM   2154  C   PRO A 309     -10.657   -8.198   30.979  1.00 28.27           C
ATOM   2155  O   PRO A 309     -10.097   -8.907   31.807  1.00 29.56           O
ATOM   2156  CB  PRO A 309     -12.032   -6.250   31.850  1.00 27.04           C
ATOM   2157  CG  PRO A 309     -12.418   -4.974   31.147  1.00 26.83           C
ATOM   2158  CD  PRO A 309     -12.038   -5.237   29.733  1.00 27.22           C
ATOM   2159  N   PHE A 310     -11.220   -8.698   29.885  1.00 28.09           N
ATOM   2160  CA  PHE A 310     -11.199  -10.129   29.632  1.00 28.12           C
ATOM   2161  C   PHE A 310      -9.884  -10.582   29.027  1.00 28.85           C
ATOM   2162  O   PHE A 310      -9.287  -11.561   29.482  1.00 28.19           O
ATOM   2163  CB  PHE A 310     -12.374  -10.517   28.736  1.00 26.92           C
ATOM   2164  CG  PHE A 310     -13.709  -10.324   29.396  1.00 26.05           C
ATOM   2165  CD1 PHE A 310     -14.363   -9.088   29.331  1.00 23.66           C
ATOM   2166  CD2 PHE A 310     -14.278  -11.351   30.153  1.00 23.60           C
ATOM   2167  CE1 PHE A 310     -15.560   -8.874   30.013  1.00 22.69           C
ATOM   2168  CE2 PHE A 310     -15.472  -11.149   30.837  1.00 23.62           C
ATOM   2169  CZ  PHE A 310     -16.117   -9.900   30.767  1.00 24.12           C
ATOM   2170  N   LEU A 311      -9.436   -9.852   28.012  1.00 29.70           N
ATOM   2171  CA  LEU A 311      -8.180  -10.127   27.328  1.00 30.81           C
ATOM   2172  C   LEU A 311      -6.999  -10.139   28.306  1.00 32.33           C
ATOM   2173  O   LEU A 311      -6.140  -11.019   28.245  1.00 33.79           O
ATOM   2174  CB  LEU A 311      -7.952   -9.060   26.260  1.00 30.87           C
ATOM   2175  CG  LEU A 311      -6.649   -9.081   25.464  1.00 32.15           C
```

FIGURE 2-33 (COORDINATES)

```
ATOM   2176  CD1 LEU A 311      -6.705 -10.163  24.402  1.00 31.62           C
ATOM   2177  CD2 LEU A 311      -6.447  -7.714  24.811  1.00 31.70           C
ATOM   2178  N   ARG A 312      -6.955  -9.164  29.208  1.00 33.14           N
ATOM   2179  CA  ARG A 312      -5.870  -9.089  30.183  1.00 35.10           C
ATOM   2180  C   ARG A 312      -5.941 -10.184  31.254  1.00 34.68           C
ATOM   2181  O   ARG A 312      -5.112 -10.237  32.164  1.00 34.98           O
ATOM   2182  CB  ARG A 312      -5.835  -7.704  30.843  1.00 36.98           C
ATOM   2183  CG  ARG A 312      -5.606  -6.577  29.843  1.00 41.22           C
ATOM   2184  CD  ARG A 312      -4.986  -5.345  30.483  1.00 44.28           C
ATOM   2185  NE  ARG A 312      -4.897  -4.223  29.541  1.00 49.17           N
ATOM   2186  CZ  ARG A 312      -4.255  -4.237  28.367  1.00 50.97           C
ATOM   2187  NH1 ARG A 312      -3.616  -5.325  27.950  1.00 51.63           N
ATOM   2188  NH2 ARG A 312      -4.265  -3.153  27.592  1.00 50.93           N
ATOM   2189  N   ARG A 313      -6.937 -11.053  31.144  1.00 33.45           N
ATOM   2190  CA  ARG A 313      -7.078 -12.158  32.077  1.00 32.31           C
ATOM   2191  C   ARG A 313      -6.979 -13.491  31.328  1.00 31.74           C
ATOM   2192  O   ARG A 313      -7.359 -14.537  31.845  1.00 30.83           O
ATOM   2193  CB  ARG A 313      -8.402 -12.064  32.829  1.00 32.18           C
ATOM   2194  CG  ARG A 313      -8.434 -10.980  33.883  1.00 32.10           C
ATOM   2195  CD  ARG A 313      -9.662 -11.136  34.752  1.00 33.61           C
ATOM   2196  NE  ARG A 313      -9.638 -10.282  35.935  1.00 35.44           N
ATOM   2197  CZ  ARG A 313      -9.857  -8.969  35.931  1.00 36.18           C
ATOM   2198  NH1 ARG A 313     -10.123  -8.329  34.792  1.00 34.39           N
ATOM   2199  NH2 ARG A 313      -9.825  -8.295  37.078  1.00 35.19           N
ATOM   2200  N   GLY A 314      -6.475 -13.435  30.097  1.00 31.25           N
ATOM   2201  CA  GLY A 314      -6.305 -14.643  29.309  1.00 30.95           C
ATOM   2202  C   GLY A 314      -7.444 -15.116  28.420  1.00 30.74           C
ATOM   2203  O   GLY A 314      -7.341 -16.195  27.830  1.00 32.11           O
ATOM   2204  N   VAL A 315      -8.527 -14.349  28.315  1.00 28.70           N
ATOM   2205  CA  VAL A 315      -9.640 -14.754  27.466  1.00 26.84           C
ATOM   2206  C   VAL A 315      -9.378 -14.417  26.000  1.00 26.68           C
ATOM   2207  O   VAL A 315      -8.941 -13.308  25.681  1.00 27.05           O
ATOM   2208  CB  VAL A 315     -10.961 -14.058  27.849  1.00 27.24           C
ATOM   2209  CG1 VAL A 315     -12.069 -14.528  26.902  1.00 26.98           C
ATOM   2210  CG2 VAL A 315     -11.333 -14.360  29.296  1.00 26.13           C
ATOM   2211  N   PRO A 316      -9.629 -15.379  25.092  1.00 25.88           N
ATOM   2212  CA  PRO A 316      -9.436 -15.197  23.646  1.00 26.05           C
ATOM   2213  C   PRO A 316     -10.522 -14.246  23.152  1.00 26.50           C
ATOM   2214  O   PRO A 316     -11.708 -14.444  23.446  1.00 26.57           O
ATOM   2215  CB  PRO A 316      -9.633 -16.609  23.083  1.00 25.29           C
ATOM   2216  CG  PRO A 316      -9.265 -17.489  24.232  1.00 26.15           C
ATOM   2217  CD  PRO A 316      -9.917 -16.792  25.391  1.00 25.61           C
ATOM   2218  N   VAL A 317     -10.126 -13.227  22.398  1.00 25.92           N
ATOM   2219  CA  VAL A 317     -11.083 -12.251  21.905  1.00 24.80           C
ATOM   2220  C   VAL A 317     -11.125 -12.077  20.395  1.00 25.12           C
ATOM   2221  O   VAL A 317     -10.093 -12.043  19.732  1.00 25.41           O
ATOM   2222  CB  VAL A 317     -10.813 -10.843  22.512  1.00 23.76           C
ATOM   2223  CG1 VAL A 317     -11.808  -9.833  21.937  1.00 21.51           C
ATOM   2224  CG2 VAL A 317     -10.905 -10.891  24.034  1.00 22.07           C
ATOM   2225  N   LEU A 318     -12.339 -11.976  19.866  1.00 25.46           N
ATOM   2226  CA  LEU A 318     -12.565 -11.713  18.448  1.00 26.36           C
ATOM   2227  C   LEU A 318     -13.306 -10.363  18.533  1.00 27.20           C
ATOM   2228  O   LEU A 318     -14.505 -10.313  18.822  1.00 27.30           O
ATOM   2229  CB  LEU A 318     -13.445 -12.800  17.831  1.00 26.44           C
ATOM   2230  CG  LEU A 318     -13.635 -12.780  16.306  1.00 26.65           C
ATOM   2231  CD1 LEU A 318     -12.290 -12.686  15.592  1.00 25.35           C
ATOM   2232  CD2 LEU A 318     -14.380 -14.042  15.885  1.00 25.93           C
ATOM   2233  N   HIS A 319     -12.569  -9.273  18.331  1.00 26.75           N
ATOM   2234  CA  HIS A 319     -13.129  -7.926  18.457  1.00 27.42           C
ATOM   2235  C   HIS A 319     -13.721  -7.381  17.167  1.00 28.16           C
ATOM   2236  O   HIS A 319     -12.987  -6.919  16.293  1.00 28.04           O
ATOM   2237  CB  HIS A 319     -12.045  -6.966  18.965  1.00 27.07           C
ATOM   2238  CG  HIS A 319     -12.584  -5.697  19.552  1.00 28.13           C
ATOM   2239  ND1 HIS A 319     -11.771  -4.665  19.972  1.00 27.81           N
ATOM   2240  CD2 HIS A 319     -13.854  -5.303  19.814  1.00 27.51           C
ATOM   2241  CE1 HIS A 319     -12.517  -3.693  20.468  1.00 27.40           C
ATOM   2242  NE2 HIS A 319     -13.784  -4.056  20.384  1.00 26.89           N
ATOM   2243  N   LEU A 320     -15.046  -7.424  17.050  1.00 28.18           N
```

FIGURE 2-34 (COORDINATES)

```
ATOM   2244  CA  LEU A 320     -15.692  -6.923  15.846  1.00 28.15           C
ATOM   2245  C   LEU A 320     -16.041  -5.442  15.951  1.00 27.95           C
ATOM   2246  O   LEU A 320     -17.185  -5.050  16.183  1.00 28.01           O
ATOM   2247  CB  LEU A 320     -16.941  -7.745  15.514  1.00 28.59           C
ATOM   2248  CG  LEU A 320     -16.722  -9.256  15.345  1.00 30.04           C
ATOM   2249  CD1 LEU A 320     -18.006  -9.922  14.827  1.00 29.35           C
ATOM   2250  CD2 LEU A 320     -15.568  -9.506  14.385  1.00 29.13           C
ATOM   2251  N   ILE A 321     -15.011  -4.623  15.812  1.00 27.55           N
ATOM   2252  CA  ILE A 321     -15.158  -3.183  15.827  1.00 26.68           C
ATOM   2253  C   ILE A 321     -14.430  -2.748  14.566  1.00 26.93           C
ATOM   2254  O   ILE A 321     -13.382  -3.292  14.230  1.00 26.62           O
ATOM   2255  CB  ILE A 321     -14.514  -2.543  17.082  1.00 25.02           C
ATOM   2256  CG1 ILE A 321     -14.730  -1.026  17.047  1.00 24.98           C
ATOM   2257  CG2 ILE A 321     -13.035  -2.889  17.158  1.00 24.56           C
ATOM   2258  CD1 ILE A 321     -14.432  -0.330  18.369  1.00 21.91           C
ATOM   2259  N   PRO A 322     -14.995  -1.786  13.827  1.00 27.54           N
ATOM   2260  CA  PRO A 322     -14.322  -1.342  12.601  1.00 27.87           C
ATOM   2261  C   PRO A 322     -13.200  -0.335  12.832  1.00 28.83           C
ATOM   2262  O   PRO A 322     -13.202   0.414  13.819  1.00 29.47           O
ATOM   2263  CB  PRO A 322     -15.463  -0.747  11.788  1.00 27.09           C
ATOM   2264  CG  PRO A 322     -16.335  -0.147  12.865  1.00 27.07           C
ATOM   2265  CD  PRO A 322     -16.357  -1.224  13.918  1.00 27.81           C
ATOM   2266  N   SER A 323     -12.239  -0.335  11.915  1.00 28.75           N
ATOM   2267  CA  SER A 323     -11.114   0.588  11.962  1.00 28.93           C
ATOM   2268  C   SER A 323     -10.876   1.044  10.533  1.00 29.62           C
ATOM   2269  O   SER A 323     -10.496   0.248   9.672  1.00 29.41           O
ATOM   2270  CB  SER A 323      -9.863  -0.098  12.501  1.00 29.19           C
ATOM   2271  OG  SER A 323      -8.797   0.829  12.613  1.00 31.15           O
ATOM   2272  N   PRO A 324     -11.088   2.340  10.257  1.00 29.29           N
ATOM   2273  CA  PRO A 324     -11.522   3.399  11.176  1.00 29.09           C
ATOM   2274  C   PRO A 324     -12.945   3.279  11.736  1.00 29.14           C
ATOM   2275  O   PRO A 324     -13.759   2.485  11.257  1.00 29.27           O
ATOM   2276  CB  PRO A 324     -11.369   4.656  10.327  1.00 30.02           C
ATOM   2277  CG  PRO A 324     -11.806   4.159   8.966  1.00 29.48           C
ATOM   2278  CD  PRO A 324     -11.062   2.835   8.866  1.00 28.91           C
ATOM   2279  N   PHE A 325     -13.223   4.092  12.752  1.00 27.31           N
ATOM   2280  CA  PHE A 325     -14.531   4.143  13.388  1.00 26.40           C
ATOM   2281  C   PHE A 325     -15.518   4.834  12.454  1.00 26.35           C
ATOM   2282  O   PHE A 325     -15.126   5.509  11.510  1.00 26.50           O
ATOM   2283  CB  PHE A 325     -14.480   4.967  14.682  1.00 25.40           C
ATOM   2284  CG  PHE A 325     -13.711   4.327  15.803  1.00 25.29           C
ATOM   2285  CD1 PHE A 325     -13.258   3.008  15.712  1.00 25.39           C
ATOM   2286  CD2 PHE A 325     -13.472   5.039  16.974  1.00 24.66           C
ATOM   2287  CE1 PHE A 325     -12.581   2.411  16.773  1.00 25.63           C
ATOM   2288  CE2 PHE A 325     -12.792   4.450  18.049  1.00 24.99           C
ATOM   2289  CZ  PHE A 325     -12.346   3.130  17.946  1.00 24.45           C
ATOM   2290  N   PRO A 326     -16.819   4.657  12.698  1.00 26.41           N
ATOM   2291  CA  PRO A 326     -17.807   5.320  11.840  1.00 25.71           C
ATOM   2292  C   PRO A 326     -17.566   6.841  11.889  1.00 25.28           C
ATOM   2293  O   PRO A 326     -17.205   7.382  12.925  1.00 25.12           O
ATOM   2294  CB  PRO A 326     -19.130   4.930  12.490  1.00 24.82           C
ATOM   2295  CG  PRO A 326     -18.846   3.548  12.993  1.00 25.51           C
ATOM   2296  CD  PRO A 326     -17.466   3.694  13.607  1.00 25.35           C
ATOM   2297  N   GLU A 327     -17.759   7.530  10.775  1.00 26.15           N
ATOM   2298  CA  GLU A 327     -17.553   8.970  10.754  1.00 26.75           C
ATOM   2299  C   GLU A 327     -18.369   9.690  11.823  1.00 26.77           C
ATOM   2300  O   GLU A 327     -17.915  10.679  12.403  1.00 27.02           O
ATOM   2301  CB  GLU A 327     -17.921   9.528   9.386  1.00 28.30           C
ATOM   2302  CG  GLU A 327     -16.887   9.275   8.309  1.00 29.97           C
ATOM   2303  CD  GLU A 327     -17.391   9.684   6.938  1.00 31.27           C
ATOM   2304  OE1 GLU A 327     -17.987  10.780   6.834  1.00 31.23           O
ATOM   2305  OE2 GLU A 327     -17.190   8.915   5.975  1.00 30.38           O
ATOM   2306  N   VAL A 328     -19.572   9.187  12.084  1.00 26.27           N
ATOM   2307  CA  VAL A 328     -20.469   9.786  13.068  1.00 24.96           C
ATOM   2308  C   VAL A 328     -20.121   9.470  14.524  1.00 25.51           C
ATOM   2309  O   VAL A 328     -20.838   9.874  15.433  1.00 25.96           O
ATOM   2310  CB  VAL A 328     -21.930   9.344  12.820  1.00 24.71           C
ATOM   2311  CG1 VAL A 328     -22.362   9.762  11.426  1.00 24.22           C
```

FIGURE 2-35 (COORDINATES)

```
ATOM   2312  CG2 VAL A 328     -22.069   7.832  12.992  1.00 23.72           C
ATOM   2313  N   TRP A 329     -19.022   8.754  14.737  1.00 25.87           N
ATOM   2314  CA  TRP A 329     -18.592   8.357  16.073  1.00 26.41           C
ATOM   2315  C   TRP A 329     -18.665   9.454  17.136  1.00 27.97           C
ATOM   2316  O   TRP A 329     -18.051  10.516  16.993  1.00 28.60           O
ATOM   2317  CB  TRP A 329     -17.165   7.816  16.008  1.00 24.99           C
ATOM   2318  CG  TRP A 329     -16.619   7.378  17.327  1.00 23.64           C
ATOM   2319  CD1 TRP A 329     -16.875   6.200  17.976  1.00 22.97           C
ATOM   2320  CD2 TRP A 329     -15.668   8.081  18.133  1.00 23.51           C
ATOM   2321  NE1 TRP A 329     -16.132   6.121  19.129  1.00 22.35           N
ATOM   2322  CE2 TRP A 329     -15.381   7.260  19.252  1.00 22.68           C
ATOM   2323  CE3 TRP A 329     -15.030   9.324  18.021  1.00 21.88           C
ATOM   2324  CZ2 TRP A 329     -14.481   7.640  20.251  1.00 22.37           C
ATOM   2325  CZ3 TRP A 329     -14.140   9.706  19.014  1.00 22.15           C
ATOM   2326  CH2 TRP A 329     -13.872   8.862  20.119  1.00 23.49           C
ATOM   2327  N   HIS A 330     -19.413   9.175  18.206  1.00 29.20           N
ATOM   2328  CA  HIS A 330     -19.588  10.091  19.338  1.00 29.90           C
ATOM   2329  C   HIS A 330     -20.060  11.463  18.912  1.00 30.68           C
ATOM   2330  O   HIS A 330     -19.632  12.494  19.443  1.00 31.35           O
ATOM   2331  CB  HIS A 330     -18.291  10.194  20.136  1.00 29.30           C
ATOM   2332  CG  HIS A 330     -17.988   8.959  20.921  1.00 31.29           C
ATOM   2333  ND1 HIS A 330     -16.969   8.890  21.846  1.00 31.94           N
ATOM   2334  CD2 HIS A 330     -18.598   7.752  20.942  1.00 30.52           C
ATOM   2335  CE1 HIS A 330     -16.968   7.693  22.406  1.00 30.86           C
ATOM   2336  NE2 HIS A 330     -17.947   6.985  21.876  1.00 30.67           N
ATOM   2337  N   THR A 331     -20.992  11.434  17.972  1.00 29.60           N
ATOM   2338  CA  THR A 331     -21.585  12.612  17.375  1.00 29.68           C
ATOM   2339  C   THR A 331     -23.119  12.485  17.431  1.00 29.42           C
ATOM   2340  O   THR A 331     -23.649  11.376  17.470  1.00 28.87           O
ATOM   2341  CB  THR A 331     -21.072  12.691  15.911  1.00 29.68           C
ATOM   2342  OG1 THR A 331     -19.988  13.621  15.841  1.00 30.67           O
ATOM   2343  CG2 THR A 331     -22.160  13.057  14.951  1.00 28.07           C
ATOM   2344  N   MET A 332     -23.833  13.607  17.438  1.00 29.91           N
ATOM   2345  CA  MET A 332     -25.301  13.550  17.475  1.00 31.27           C
ATOM   2346  C   MET A 332     -25.849  12.913  16.198  1.00 31.64           C
ATOM   2347  O   MET A 332     -27.009  12.509  16.143  1.00 31.10           O
ATOM   2348  CB  MET A 332     -25.912  14.949  17.646  1.00 31.83           C
ATOM   2349  CG  MET A 332     -25.763  15.555  19.043  1.00 32.40           C
ATOM   2350  SD  MET A 332     -26.623  14.631  20.341  1.00 33.04           S
ATOM   2351  CE  MET A 332     -26.333  15.681  21.748  1.00 29.76           C
ATOM   2352  N   ASP A 333     -25.007  12.824  15.171  1.00 31.50           N
ATOM   2353  CA  ASP A 333     -25.409  12.223  13.909  1.00 31.59           C
ATOM   2354  C   ASP A 333     -25.314  10.702  13.920  1.00 30.97           C
ATOM   2355  O   ASP A 333     -25.581  10.061  12.907  1.00 30.42           O
ATOM   2356  CB  ASP A 333     -24.577  12.785  12.757  1.00 33.40           C
ATOM   2357  CG  ASP A 333     -24.873  14.253  12.490  1.00 35.07           C
ATOM   2358  OD1 ASP A 333     -26.060  14.615  12.363  1.00 36.70           O
ATOM   2359  OD2 ASP A 333     -23.922  15.048  12.399  1.00 36.94           O
ATOM   2360  N   ASP A 334     -24.914  10.116  15.046  1.00 29.98           N
ATOM   2361  CA  ASP A 334     -24.872   8.662  15.108  1.00 29.91           C
ATOM   2362  C   ASP A 334     -26.300   8.243  15.417  1.00 29.61           C
ATOM   2363  O   ASP A 334     -26.621   7.831  16.534  1.00 29.72           O
ATOM   2364  CB  ASP A 334     -23.937   8.147  16.205  1.00 28.71           C
ATOM   2365  CG  ASP A 334     -23.874   6.618  16.231  1.00 28.91           C
ATOM   2366  OD1 ASP A 334     -24.499   5.985  15.339  1.00 26.62           O
ATOM   2367  OD2 ASP A 334     -23.208   6.049  17.126  1.00 27.96           O
ATOM   2368  N   ASN A 335     -27.153   8.372  14.409  1.00 30.10           N
ATOM   2369  CA  ASN A 335     -28.569   8.061  14.528  1.00 30.70           C
ATOM   2370  C   ASN A 335     -29.037   7.019  13.517  1.00 30.89           C
ATOM   2371  O   ASN A 335     -28.249   6.492  12.730  1.00 30.47           O
ATOM   2372  CB  ASN A 335     -29.392   9.336  14.338  1.00 31.27           C
ATOM   2373  CG  ASN A 335     -29.053  10.057  13.047  1.00 32.62           C
ATOM   2374  OD1 ASN A 335     -28.655   9.434  12.055  1.00 33.48           O
ATOM   2375  ND2 ASN A 335     -29.217  11.374  13.046  1.00 34.04           N
ATOM   2376  N   GLU A 336     -30.339   6.749  13.545  1.00 31.29           N
ATOM   2377  CA  GLU A 336     -30.968   5.779  12.664  1.00 31.73           C
ATOM   2378  C   GLU A 336     -30.789   6.127  11.201  1.00 31.81           C
ATOM   2379  O   GLU A 336     -30.507   5.270  10.371  1.00 31.55           O
```

FIGURE 2-36 (COORDINATES)

```
ATOM   2380  CB   GLU A 336     -32.454   5.704  12.966  1.00 31.42           C
ATOM   2381  CG   GLU A 336     -33.188   4.638  12.176  1.00 32.25           C
ATOM   2382  CD   GLU A 336     -34.638   4.542  12.585  1.00 33.21           C
ATOM   2383  OE1  GLU A 336     -35.037   5.264  13.531  1.00 33.54           O
ATOM   2384  OE2  GLU A 336     -35.378   3.749  11.972  1.00 33.46           O
ATOM   2385  N    GLU A 337     -30.969   7.400  10.895  1.00 32.94           N
ATOM   2386  CA   GLU A 337     -30.854   7.881   9.536  1.00 34.16           C
ATOM   2387  C    GLU A 337     -29.507   7.578   8.871  1.00 32.67           C
ATOM   2388  O    GLU A 337     -29.443   7.378   7.664  1.00 32.13           O
ATOM   2389  CB   GLU A 337     -31.140   9.379   9.520  1.00 37.80           C
ATOM   2390  CG   GLU A 337     -30.763  10.067   8.235  1.00 45.13           C
ATOM   2391  CD   GLU A 337     -31.026  11.553   8.288  1.00 48.78           C
ATOM   2392  OE1  GLU A 337     -30.817  12.150   9.372  1.00 50.33           O
ATOM   2393  OE2  GLU A 337     -31.430  12.120   7.243  1.00 51.42           O
ATOM   2394  N    ASN A 338     -28.431   7.531   9.645  1.00 31.17           N
ATOM   2395  CA   ASN A 338     -27.129   7.255   9.046  1.00 30.20           C
ATOM   2396  C    ASN A 338     -26.704   5.790   9.062  1.00 29.15           C
ATOM   2397  O    ASN A 338     -25.560   5.472   8.768  1.00 28.71           O
ATOM   2398  CB   ASN A 338     -26.063   8.127   9.703  1.00 30.48           C
ATOM   2399  CG   ASN A 338     -26.196   9.585   9.308  1.00 31.71           C
ATOM   2400  OD1  ASN A 338     -26.199  10.474  10.158  1.00 32.39           O
ATOM   2401  ND2  ASN A 338     -26.312   9.836   8.007  1.00 31.08           N
ATOM   2402  N    LEU A 339     -27.631   4.898   9.390  1.00 28.03           N
ATOM   2403  CA   LEU A 339     -27.328   3.479   9.414  1.00 27.82           C
ATOM   2404  C    LEU A 339     -27.458   2.897   8.013  1.00 28.69           C
ATOM   2405  O    LEU A 339     -28.267   3.356   7.210  1.00 29.16           O
ATOM   2406  CB   LEU A 339     -28.271   2.743  10.380  1.00 26.72           C
ATOM   2407  CG   LEU A 339     -28.128   3.078  11.867  1.00 25.84           C
ATOM   2408  CD1  LEU A 339     -29.189   2.356  12.671  1.00 25.09           C
ATOM   2409  CD2  LEU A 339     -26.734   2.697  12.343  1.00 24.17           C
ATOM   2410  N    ASP A 340     -26.643   1.888   7.724  1.00 30.03           N
ATOM   2411  CA   ASP A 340     -26.666   1.224   6.433  1.00 30.10           C
ATOM   2412  C    ASP A 340     -27.379  -0.114   6.619  1.00 31.57           C
ATOM   2413  O    ASP A 340     -26.785  -1.074   7.116  1.00 31.27           O
ATOM   2414  CB   ASP A 340     -25.239   0.991   5.954  1.00 30.36           C
ATOM   2415  CG   ASP A 340     -25.183   0.388   4.570  1.00 29.80           C
ATOM   2416  OD1  ASP A 340     -25.954  -0.559   4.299  1.00 30.46           O
ATOM   2417  OD2  ASP A 340     -24.359   0.854   3.760  1.00 29.72           O
ATOM   2418  N    GLU A 341     -28.645  -0.174   6.209  1.00 32.91           N
ATOM   2419  CA   GLU A 341     -29.466  -1.377   6.356  1.00 34.15           C
ATOM   2420  C    GLU A 341     -28.946  -2.687   5.757  1.00 33.36           C
ATOM   2421  O    GLU A 341     -28.915  -3.712   6.443  1.00 34.38           O
ATOM   2422  CB   GLU A 341     -30.877  -1.128   5.807  1.00 36.60           C
ATOM   2423  CG   GLU A 341     -31.776  -2.362   5.892  1.00 41.75           C
ATOM   2424  CD   GLU A 341     -33.162  -2.148   5.299  1.00 45.39           C
ATOM   2425  OE1  GLU A 341     -33.853  -1.196   5.734  1.00 47.74           O
ATOM   2426  OE2  GLU A 341     -33.563  -2.939   4.409  1.00 46.76           O
ATOM   2427  N    SER A 342     -28.560  -2.673   4.487  1.00 31.96           N
ATOM   2428  CA   SER A 342     -28.092  -3.899   3.856  1.00 31.32           C
ATOM   2429  C    SER A 342     -26.791  -4.397   4.468  1.00 30.01           C
ATOM   2430  O    SER A 342     -26.555  -5.608   4.528  1.00 30.33           O
ATOM   2431  CB   SER A 342     -27.944  -3.711   2.338  1.00 31.47           C
ATOM   2432  OG   SER A 342     -27.027  -2.679   2.019  1.00 35.22           O
ATOM   2433  N    THR A 343     -25.958  -3.470   4.932  1.00 28.04           N
ATOM   2434  CA   THR A 343     -24.695  -3.835   5.561  1.00 27.41           C
ATOM   2435  C    THR A 343     -24.959  -4.576   6.875  1.00 26.98           C
ATOM   2436  O    THR A 343     -24.282  -5.560   7.199  1.00 26.26           O
ATOM   2437  CB   THR A 343     -23.830  -2.588   5.855  1.00 27.61           C
ATOM   2438  OG1  THR A 343     -23.441  -1.981   4.617  1.00 27.73           O
ATOM   2439  CG2  THR A 343     -22.581  -2.967   6.653  1.00 25.16           C
ATOM   2440  N    ILE A 344     -25.945  -4.101   7.629  1.00 25.59           N
ATOM   2441  CA   ILE A 344     -26.289  -4.738   8.893  1.00 25.86           C
ATOM   2442  C    ILE A 344     -26.896  -6.107   8.591  1.00 26.63           C
ATOM   2443  O    ILE A 344     -26.604  -7.101   9.263  1.00 27.09           O
ATOM   2444  CB   ILE A 344     -27.277  -3.859   9.699  1.00 25.81           C
ATOM   2445  CG1  ILE A 344     -26.623  -2.494   9.978  1.00 24.87           C
ATOM   2446  CG2  ILE A 344     -27.663  -4.557  11.005  1.00 25.07           C
ATOM   2447  CD1  ILE A 344     -27.564  -1.447  10.515  1.00 22.88           C
```

FIGURE 2-37 (COORDINATES)

```
ATOM   2448  N   ASP A 345     -27.728  -6.154   7.558  1.00 26.20           N
ATOM   2449  CA  ASP A 345     -28.357  -7.395   7.137  1.00 26.22           C
ATOM   2450  C   ASP A 345     -27.274  -8.411   6.757  1.00 26.19           C
ATOM   2451  O   ASP A 345     -27.317  -9.572   7.180  1.00 25.86           O
ATOM   2452  CB  ASP A 345     -29.282  -7.108   5.950  1.00 27.19           C
ATOM   2453  CG  ASP A 345     -30.159  -8.280   5.592  1.00 27.27           C
ATOM   2454  OD1 ASP A 345     -30.552  -9.045   6.495  1.00 28.05           O
ATOM   2455  OD2 ASP A 345     -30.476  -8.423   4.399  1.00 28.72           O
ATOM   2456  N   ASN A 346     -26.298  -7.974   5.963  1.00 26.18           N
ATOM   2457  CA  ASN A 346     -25.207  -8.862   5.571  1.00 26.53           C
ATOM   2458  C   ASN A 346     -24.454  -9.398   6.804  1.00 26.81           C
ATOM   2459  O   ASN A 346     -24.137 -10.584   6.870  1.00 26.45           O
ATOM   2460  CB  ASN A 346     -24.200  -8.146   4.648  1.00 26.47           C
ATOM   2461  CG  ASN A 346     -24.762  -7.841   3.262  1.00 27.74           C
ATOM   2462  OD1 ASN A 346     -25.684  -8.504   2.779  1.00 28.36           O
ATOM   2463  ND2 ASN A 346     -24.182  -6.842   2.602  1.00 27.32           N
ATOM   2464  N   LEU A 347     -24.165  -8.525   7.769  1.00 26.42           N
ATOM   2465  CA  LEU A 347     -23.448  -8.938   8.973  1.00 27.03           C
ATOM   2466  C   LEU A 347     -24.241  -9.915   9.840  1.00 27.48           C
ATOM   2467  O   LEU A 347     -23.658 -10.831  10.419  1.00 26.67           O
ATOM   2468  CB  LEU A 347     -23.019  -7.718   9.801  1.00 26.73           C
ATOM   2469  CG  LEU A 347     -21.911  -6.888   9.141  1.00 28.07           C
ATOM   2470  CD1 LEU A 347     -21.634  -5.636   9.962  1.00 28.12           C
ATOM   2471  CD2 LEU A 347     -20.652  -7.733   8.994  1.00 26.97           C
ATOM   2472  N   ASN A 348     -25.558  -9.727   9.938  1.00 27.29           N
ATOM   2473  CA  ASN A 348     -26.385 -10.657  10.714  1.00 26.90           C
ATOM   2474  C   ASN A 348     -26.232 -12.051  10.110  1.00 26.42           C
ATOM   2475  O   ASN A 348     -26.109 -13.040  10.818  1.00 26.29           O
ATOM   2476  CB  ASN A 348     -27.870 -10.275  10.666  1.00 25.70           C
ATOM   2477  CG  ASN A 348     -28.204  -9.108  11.562  1.00 26.31           C
ATOM   2478  OD1 ASN A 348     -27.585  -8.918  12.614  1.00 26.44           O
ATOM   2479  ND2 ASN A 348     -29.204  -8.328  11.167  1.00 25.57           N
ATOM   2480  N   LYS A 349     -26.248 -12.123   8.788  1.00 26.54           N
ATOM   2481  CA  LYS A 349     -26.118 -13.404   8.125  1.00 27.19           C
ATOM   2482  C   LYS A 349     -24.761 -14.009   8.416  1.00 27.35           C
ATOM   2483  O   LYS A 349     -24.664 -15.191   8.748  1.00 27.85           O
ATOM   2484  CB  LYS A 349     -26.319 -13.250   6.614  1.00 26.68           C
ATOM   2485  CG  LYS A 349     -27.711 -12.756   6.245  1.00 27.25           C
ATOM   2486  CD  LYS A 349     -27.866 -12.597   4.746  1.00 27.08           C
ATOM   2487  CE  LYS A 349     -29.274 -12.159   4.375  1.00 26.43           C
ATOM   2488  NZ  LYS A 349     -29.370 -11.909   2.915  1.00 25.69           N
ATOM   2489  N   ILE A 350     -23.715 -13.196   8.301  1.00 26.16           N
ATOM   2490  CA  ILE A 350     -22.359 -13.667   8.548  1.00 24.88           C
ATOM   2491  C   ILE A 350     -22.202 -14.168   9.985  1.00 25.33           C
ATOM   2492  O   ILE A 350     -21.672 -15.252  10.207  1.00 25.50           O
ATOM   2493  CB  ILE A 350     -21.311 -12.541   8.230  1.00 25.14           C
ATOM   2494  CG1 ILE A 350     -21.315 -12.247   6.716  1.00 24.31           C
ATOM   2495  CG2 ILE A 350     -19.900 -12.967   8.660  1.00 22.43           C
ATOM   2496  CD1 ILE A 350     -20.479 -11.061   6.306  1.00 23.58           C
ATOM   2497  N   LEU A 351     -22.689 -13.391  10.950  1.00 25.53           N
ATOM   2498  CA  LEU A 351     -22.595 -13.745  12.365  1.00 25.68           C
ATOM   2499  C   LEU A 351     -23.400 -14.997  12.752  1.00 26.71           C
ATOM   2500  O   LEU A 351     -22.896 -15.868  13.469  1.00 26.45           O
ATOM   2501  CB  LEU A 351     -23.030 -12.558  13.225  1.00 24.59           C
ATOM   2502  CG  LEU A 351     -22.944 -12.698  14.752  1.00 25.63           C
ATOM   2503  CD1 LEU A 351     -21.495 -12.848  15.194  1.00 24.55           C
ATOM   2504  CD2 LEU A 351     -23.566 -11.470  15.399  1.00 25.60           C
ATOM   2505  N   GLN A 352     -24.645 -15.083  12.292  1.00 26.26           N
ATOM   2506  CA  GLN A 352     -25.482 -16.240  12.589  1.00 26.97           C
ATOM   2507  C   GLN A 352     -24.837 -17.523  12.046  1.00 27.09           C
ATOM   2508  O   GLN A 352     -24.810 -18.550  12.726  1.00 27.40           O
ATOM   2509  CB  GLN A 352     -26.883 -16.032  12.006  1.00 27.84           C
ATOM   2510  CG  GLN A 352     -27.700 -14.990  12.774  1.00 28.72           C
ATOM   2511  CD  GLN A 352     -28.914 -14.518  12.014  1.00 29.20           C
ATOM   2512  OE1 GLN A 352     -29.492 -15.265  11.228  1.00 30.76           O
ATOM   2513  NE2 GLN A 352     -29.320 -13.275  12.253  1.00 28.56           N
ATOM   2514  N   VAL A 353     -24.310 -17.473  10.829  1.00 26.32           N
ATOM   2515  CA  VAL A 353     -23.643 -18.644  10.295  1.00 26.71           C
```

FIGURE 2-38 (COORDINATES)

```
ATOM   2516  C   VAL A 353     -22.428 -18.986  11.179  1.00 27.42           C
ATOM   2517  O   VAL A 353     -22.190 -20.150  11.483  1.00 27.58           O
ATOM   2518  CB  VAL A 353     -23.166 -18.424   8.849  1.00 26.83           C
ATOM   2519  CG1 VAL A 353     -22.296 -19.603   8.398  1.00 26.57           C
ATOM   2520  CG2 VAL A 353     -24.359 -18.280   7.933  1.00 26.36           C
ATOM   2521  N   PHE A 354     -21.674 -17.968  11.597  1.00 26.46           N
ATOM   2522  CA  PHE A 354     -20.500 -18.180  12.440  1.00 25.92           C
ATOM   2523  C   PHE A 354     -20.859 -18.904  13.742  1.00 27.03           C
ATOM   2524  O   PHE A 354     -20.166 -19.848  14.150  1.00 26.51           O
ATOM   2525  CB  PHE A 354     -19.836 -16.844  12.790  1.00 24.07           C
ATOM   2526  CG  PHE A 354     -18.627 -16.979  13.671  1.00 22.99           C
ATOM   2527  CD1 PHE A 354     -17.367 -17.214  13.121  1.00 23.45           C
ATOM   2528  CD2 PHE A 354     -18.753 -16.921  15.060  1.00 23.58           C
ATOM   2529  CE1 PHE A 354     -16.245 -17.394  13.945  1.00 22.80           C
ATOM   2530  CE2 PHE A 354     -17.646 -17.100  15.894  1.00 22.69           C
ATOM   2531  CZ  PHE A 354     -16.389 -17.339  15.335  1.00 23.32           C
ATOM   2532  N   VAL A 355     -21.928 -18.443  14.391  1.00 26.63           N
ATOM   2533  CA  VAL A 355     -22.374 -19.027  15.646  1.00 27.56           C
ATOM   2534  C   VAL A 355     -22.834 -20.476  15.474  1.00 28.01           C
ATOM   2535  O   VAL A 355     -22.413 -21.354  16.226  1.00 28.23           O
ATOM   2536  CB  VAL A 355     -23.501 -18.178  16.279  1.00 27.87           C
ATOM   2537  CG1 VAL A 355     -24.049 -18.870  17.524  1.00 27.29           C
ATOM   2538  CG2 VAL A 355     -22.958 -16.800  16.645  1.00 26.57           C
ATOM   2539  N   LEU A 356     -23.683 -20.731  14.485  1.00 28.29           N
ATOM   2540  CA  LEU A 356     -24.148 -22.092  14.237  1.00 28.73           C
ATOM   2541  C   LEU A 356     -22.970 -23.040  13.990  1.00 29.15           C
ATOM   2542  O   LEU A 356     -22.923 -24.130  14.559  1.00 29.19           O
ATOM   2543  CB  LEU A 356     -25.089 -22.136  13.028  1.00 27.76           C
ATOM   2544  CG  LEU A 356     -26.474 -21.516  13.187  1.00 28.54           C
ATOM   2545  CD1 LEU A 356     -27.188 -21.562  11.844  1.00 27.13           C
ATOM   2546  CD2 LEU A 356     -27.274 -22.259  14.256  1.00 27.09           C
ATOM   2547  N   GLU A 357     -22.023 -22.626  13.148  1.00 28.50           N
ATOM   2548  CA  GLU A 357     -20.865 -23.465  12.847  1.00 29.27           C
ATOM   2549  C   GLU A 357     -20.004 -23.720  14.083  1.00 29.58           C
ATOM   2550  O   GLU A 357     -19.476 -24.819  14.266  1.00 30.15           O
ATOM   2551  CB  GLU A 357     -20.016 -22.843  11.733  1.00 29.19           C
ATOM   2552  CG  GLU A 357     -20.783 -22.640  10.423  1.00 30.94           C
ATOM   2553  CD  GLU A 357     -19.886 -22.325   9.234  1.00 32.69           C
ATOM   2554  OE1 GLU A 357     -18.782 -21.785   9.439  1.00 32.61           O
ATOM   2555  OE2 GLU A 357     -20.296 -22.605   8.085  1.00 34.17           O
ATOM   2556  N   TYR A 358     -19.871 -22.715  14.938  1.00 29.08           N
ATOM   2557  CA  TYR A 358     -19.074 -22.871  16.147  1.00 29.15           C
ATOM   2558  C   TYR A 358     -19.777 -23.864  17.068  1.00 30.04           C
ATOM   2559  O   TYR A 358     -19.148 -24.751  17.637  1.00 29.45           O
ATOM   2560  CB  TYR A 358     -18.924 -21.529  16.880  1.00 28.25           C
ATOM   2561  CG  TYR A 358     -17.803 -21.522  17.898  1.00 27.68           C
ATOM   2562  CD1 TYR A 358     -16.542 -21.024  17.568  1.00 27.22           C
ATOM   2563  CD2 TYR A 358     -17.975 -22.088  19.165  1.00 28.06           C
ATOM   2564  CE1 TYR A 358     -15.480 -21.096  18.466  1.00 27.22           C
ATOM   2565  CE2 TYR A 358     -16.917 -22.166  20.072  1.00 27.82           C
ATOM   2566  CZ  TYR A 358     -15.671 -21.671  19.715  1.00 28.25           C
ATOM   2567  OH  TYR A 358     -14.613 -21.758  20.594  1.00 28.35           O
ATOM   2568  N   LEU A 359     -21.094 -23.715  17.194  1.00 31.08           N
ATOM   2569  CA  LEU A 359     -21.879 -24.574  18.067  1.00 32.26           C
ATOM   2570  C   LEU A 359     -22.266 -25.933  17.481  1.00 33.99           C
ATOM   2571  O   LEU A 359     -22.849 -26.767  18.173  1.00 35.10           O
ATOM   2572  CB  LEU A 359     -23.132 -23.824  18.530  1.00 30.33           C
ATOM   2573  CG  LEU A 359     -22.889 -22.617  19.451  1.00 31.15           C
ATOM   2574  CD1 LEU A 359     -24.212 -21.933  19.774  1.00 29.78           C
ATOM   2575  CD2 LEU A 359     -22.206 -23.069  20.743  1.00 29.31           C
ATOM   2576  N   HIS A 360     -21.932 -26.170  16.217  1.00 35.65           N
ATOM   2577  CA  HIS A 360     -22.274 -27.442  15.586  1.00 36.37           C
ATOM   2578  C   HIS A 360     -23.788 -27.608  15.539  1.00 36.30           C
ATOM   2579  O   HIS A 360     -24.308 -28.701  15.760  1.00 37.30           O
ATOM   2580  CB  HIS A 360     -21.659 -28.614  16.361  1.00 36.93           C
ATOM   2581  CG  HIS A 360     -20.179 -28.749  16.181  1.00 38.69           C
ATOM   2582  ND1 HIS A 360     -19.333 -27.661  16.134  1.00 38.96           N
ATOM   2583  CD2 HIS A 360     -19.394 -29.844  16.047  1.00 39.00           C
```

FIGURE 2-39 (COORDINATES)

```
ATOM   2584  CE1 HIS A 360     -18.090 -28.081  15.977  1.00 38.68           C
ATOM   2585  NE2 HIS A 360     -18.099 -29.401  15.922  1.00 39.36           N
ATOM   2586  N   LEU A 361     -24.494 -26.514  15.285  1.00 35.39           N
ATOM   2587  CA  LEU A 361     -25.944 -26.554  15.177  1.00 34.65           C
ATOM   2588  C   LEU A 361     -26.303 -26.385  13.702  1.00 34.78           C
ATOM   2589  O   LEU A 361     -27.506 -26.307  13.389  1.00 35.91           O
ATOM   2590  CB  LEU A 361     -26.579 -25.431  15.999  1.00 33.34           C
ATOM   2591  CG  LEU A 361     -26.398 -25.509  17.516  1.00 32.82           C
ATOM   2592  CD1 LEU A 361     -27.126 -24.345  18.175  1.00 31.44           C
ATOM   2593  CD2 LEU A 361     -26.937 -26.835  18.031  1.00 31.99           C
ATOM   2594  OXT LEU A 361     -25.371 -26.333  12.872  1.00 34.30           O
TER    2595      LEU A 361
ATOM   2596  N   ALA B  33     -28.394  11.963  49.201  1.00 68.63           N
ATOM   2597  CA  ALA B  33     -27.726  12.079  50.529  1.00 67.81           C
ATOM   2598  C   ALA B  33     -28.519  11.324  51.589  1.00 67.14           C
ATOM   2599  O   ALA B  33     -29.127  11.943  52.471  1.00 67.77           O
ATOM   2600  CB  ALA B  33     -27.595  13.554  50.926  1.00 67.80           C
ATOM   2601  N   SER B  34     -28.519   9.992  51.497  1.00 65.40           N
ATOM   2602  CA  SER B  34     -29.237   9.164  52.465  1.00 63.21           C
ATOM   2603  C   SER B  34     -28.618   9.333  53.844  1.00 61.42           C
ATOM   2604  O   SER B  34     -27.395   9.283  54.005  1.00 61.39           O
ATOM   2605  CB  SER B  34     -29.200   7.688  52.058  1.00 63.99           C
ATOM   2606  OG  SER B  34     -30.021   7.448  50.927  1.00 64.89           O
ATOM   2607  N   ALA B  35     -29.471   9.531  54.840  1.00 58.62           N
ATOM   2608  CA  ALA B  35     -29.003   9.731  56.198  1.00 55.75           C
ATOM   2609  C   ALA B  35     -28.880   8.447  57.004  1.00 53.75           C
ATOM   2610  O   ALA B  35     -28.148   8.416  57.995  1.00 53.63           O
ATOM   2611  CB  ALA B  35     -29.926  10.703  56.920  1.00 55.93           C
ATOM   2612  N   TRP B  36     -29.571   7.383  56.592  1.00 51.02           N
ATOM   2613  CA  TRP B  36     -29.508   6.149  57.369  1.00 48.04           C
ATOM   2614  C   TRP B  36     -28.096   5.621  57.674  1.00 46.27           C
ATOM   2615  O   TRP B  36     -27.896   4.925  58.664  1.00 45.72           O
ATOM   2616  CB  TRP B  36     -30.386   5.046  56.743  1.00 46.99           C
ATOM   2617  CG  TRP B  36     -29.927   4.478  55.436  1.00 45.86           C
ATOM   2618  CD1 TRP B  36     -30.394   4.796  54.194  1.00 45.40           C
ATOM   2619  CD2 TRP B  36     -28.929   3.473  55.245  1.00 44.66           C
ATOM   2620  NE1 TRP B  36     -29.750   4.049  53.242  1.00 44.66           N
ATOM   2621  CE2 TRP B  36     -28.843   3.229  53.860  1.00 44.69           C
ATOM   2622  CE3 TRP B  36     -28.098   2.755  56.111  1.00 44.28           C
ATOM   2623  CZ2 TRP B  36     -27.956   2.294  53.317  1.00 44.39           C
ATOM   2624  CZ3 TRP B  36     -27.214   1.826  55.573  1.00 44.35           C
ATOM   2625  CH2 TRP B  36     -27.152   1.605  54.186  1.00 44.41           C
ATOM   2626  N   PRO B  37     -27.100   5.940  56.834  1.00 45.30           N
ATOM   2627  CA  PRO B  37     -25.762   5.430  57.155  1.00 44.97           C
ATOM   2628  C   PRO B  37     -25.136   6.117  58.372  1.00 45.19           C
ATOM   2629  O   PRO B  37     -24.141   5.643  58.922  1.00 44.95           O
ATOM   2630  CB  PRO B  37     -24.977   5.706  55.877  1.00 43.71           C
ATOM   2631  CG  PRO B  37     -26.017   5.571  54.822  1.00 44.26           C
ATOM   2632  CD  PRO B  37     -27.171   6.334  55.416  1.00 44.83           C
ATOM   2633  N   GLU B  38     -25.725   7.232  58.792  1.00 46.18           N
ATOM   2634  CA  GLU B  38     -25.208   7.989  59.933  1.00 46.80           C
ATOM   2635  C   GLU B  38     -25.824   7.509  61.236  1.00 46.19           C
ATOM   2636  O   GLU B  38     -25.256   7.699  62.308  1.00 46.33           O
ATOM   2637  CB  GLU B  38     -25.518   9.480  59.774  1.00 47.06           C
ATOM   2638  CG  GLU B  38     -25.547   9.952  58.344  1.00 49.13           C
ATOM   2639  CD  GLU B  38     -25.843  11.426  58.232  1.00 50.57           C
ATOM   2640  OE1 GLU B  38     -26.766  11.897  58.933  1.00 50.51           O
ATOM   2641  OE2 GLU B  38     -25.158  12.107  57.436  1.00 51.70           O
ATOM   2642  N   GLU B  39     -26.996   6.898  61.137  1.00 46.09           N
ATOM   2643  CA  GLU B  39     -27.698   6.409  62.313  1.00 46.22           C
ATOM   2644  C   GLU B  39     -26.807   5.685  63.324  1.00 46.25           C
ATOM   2645  O   GLU B  39     -26.966   5.865  64.531  1.00 45.58           O
ATOM   2646  CB  GLU B  39     -28.869   5.523  61.879  1.00 46.45           C
ATOM   2647  CG  GLU B  39     -30.077   6.342  61.438  1.00 48.10           C
ATOM   2648  CD  GLU B  39     -31.185   5.519  60.803  1.00 49.93           C
ATOM   2649  OE1 GLU B  39     -31.380   4.346  61.204  1.00 50.22           O
ATOM   2650  OE2 GLU B  39     -31.879   6.063  59.909  1.00 50.23           O
ATOM   2651  N   LYS B  40     -25.850   4.902  62.839  1.00 46.21           N
```

FIGURE 2-40 (COORDINATES)

```
ATOM   2652  CA   LYS B  40     -24.964   4.158  63.728  1.00 46.24           C
ATOM   2653  C    LYS B  40     -24.211   5.034  64.733  1.00 45.99           C
ATOM   2654  O    LYS B  40     -23.803   4.554  65.796  1.00 45.11           O
ATOM   2655  CB   LYS B  40     -23.963   3.322  62.911  1.00 46.82           C
ATOM   2656  CG   LYS B  40     -22.836   4.101  62.255  1.00 47.12           C
ATOM   2657  CD   LYS B  40     -21.924   3.153  61.496  1.00 47.70           C
ATOM   2658  CE   LYS B  40     -20.537   3.748  61.274  1.00 48.33           C
ATOM   2659  NZ   LYS B  40     -20.500   4.873  60.319  1.00 49.16           N
ATOM   2660  N    ASN B  41     -24.031   6.313  64.408  1.00 46.03           N
ATOM   2661  CA   ASN B  41     -23.322   7.229  65.303  1.00 45.93           C
ATOM   2662  C    ASN B  41     -24.102   7.612  66.555  1.00 45.81           C
ATOM   2663  O    ASN B  41     -23.507   7.872  67.599  1.00 45.26           O
ATOM   2664  CB   ASN B  41     -22.930   8.516  64.572  1.00 46.33           C
ATOM   2665  CG   ASN B  41     -21.786   8.312  63.603  1.00 47.27           C
ATOM   2666  OD1  ASN B  41     -21.991   8.162  62.397  1.00 48.01           O
ATOM   2667  ND2  ASN B  41     -20.569   8.296  64.129  1.00 46.58           N
ATOM   2668  N    TYR B  42     -25.427   7.646  66.451  1.00 46.03           N
ATOM   2669  CA   TYR B  42     -26.267   8.034  67.582  1.00 46.93           C
ATOM   2670  C    TYR B  42     -26.952   6.852  68.249  1.00 46.30           C
ATOM   2671  O    TYR B  42     -27.611   7.019  69.272  1.00 47.16           O
ATOM   2672  CB   TYR B  42     -27.359   9.016  67.131  1.00 47.68           C
ATOM   2673  CG   TYR B  42     -26.945   9.956  66.027  1.00 49.14           C
ATOM   2674  CD1  TYR B  42     -25.977  10.945  66.241  1.00 50.44           C
ATOM   2675  CD2  TYR B  42     -27.514   9.852  64.759  1.00 49.31           C
ATOM   2676  CE1  TYR B  42     -25.584  11.815  65.208  1.00 50.52           C
ATOM   2677  CE2  TYR B  42     -27.131  10.707  63.724  1.00 51.00           C
ATOM   2678  CZ   TYR B  42     -26.168  11.688  63.953  1.00 50.93           C
ATOM   2679  OH   TYR B  42     -25.809  12.533  62.923  1.00 51.36           O
ATOM   2680  N    HIS B  43     -26.813   5.664  67.673  1.00 45.19           N
ATOM   2681  CA   HIS B  43     -27.468   4.495  68.237  1.00 44.29           C
ATOM   2682  C    HIS B  43     -27.019   4.203  69.664  1.00 44.18           C
ATOM   2683  O    HIS B  43     -25.829   4.205  69.984  1.00 43.63           O
ATOM   2684  CB   HIS B  43     -27.248   3.270  67.343  1.00 44.61           C
ATOM   2685  CG   HIS B  43     -28.040   2.071  67.764  1.00 43.96           C
ATOM   2686  ND1  HIS B  43     -27.486   1.019  68.461  1.00 43.89           N
ATOM   2687  CD2  HIS B  43     -29.356   1.780  67.628  1.00 43.17           C
ATOM   2688  CE1  HIS B  43     -28.425   0.133  68.738  1.00 42.91           C
ATOM   2689  NE2  HIS B  43     -29.569   0.571  68.245  1.00 42.30           N
ATOM   2690  N    GLN B  44     -28.001   3.964  70.523  1.00 44.52           N
ATOM   2691  CA   GLN B  44     -27.752   3.676  71.925  1.00 44.61           C
ATOM   2692  C    GLN B  44     -28.371   2.331  72.280  1.00 44.87           C
ATOM   2693  O    GLN B  44     -29.367   1.919  71.681  1.00 44.13           O
ATOM   2694  CB   GLN B  44     -28.374   4.771  72.798  1.00 44.72           C
ATOM   2695  CG   GLN B  44     -27.815   6.164  72.566  1.00 44.62           C
ATOM   2696  CD   GLN B  44     -26.359   6.274  72.957  1.00 45.65           C
ATOM   2697  OE1  GLN B  44     -25.935   5.731  73.979  1.00 46.51           O
ATOM   2698  NE2  GLN B  44     -25.585   6.991  72.156  1.00 46.22           N
ATOM   2699  N    PRO B  45     -27.792   1.629  73.267  1.00 45.68           N
ATOM   2700  CA   PRO B  45     -28.322   0.327  73.676  1.00 46.34           C
ATOM   2701  C    PRO B  45     -29.533   0.480  74.583  1.00 47.17           C
ATOM   2702  O    PRO B  45     -29.709   1.518  75.227  1.00 47.58           O
ATOM   2703  CB   PRO B  45     -27.150  -0.295  74.418  1.00 45.78           C
ATOM   2704  CG   PRO B  45     -26.585   0.886  75.132  1.00 45.82           C
ATOM   2705  CD   PRO B  45     -26.572   1.951  74.031  1.00 45.72           C
ATOM   2706  N    ALA B  46     -30.361  -0.559  74.616  1.00 47.87           N
ATOM   2707  CA   ALA B  46     -31.542  -0.600  75.465  1.00 49.23           C
ATOM   2708  C    ALA B  46     -31.185  -1.590  76.569  1.00 50.59           C
ATOM   2709  O    ALA B  46     -31.539  -2.771  76.500  1.00 50.67           O
ATOM   2710  CB   ALA B  46     -32.742  -1.100  74.677  1.00 48.97           C
ATOM   2711  N    ILE B  47     -30.470  -1.098  77.578  1.00 52.11           N
ATOM   2712  CA   ILE B  47     -30.011  -1.919  78.695  1.00 53.90           C
ATOM   2713  C    ILE B  47     -31.087  -2.739  79.401  1.00 54.60           C
ATOM   2714  O    ILE B  47     -32.202  -2.273  79.621  1.00 54.35           O
ATOM   2715  CB   ILE B  47     -29.280  -1.057  79.733  1.00 53.90           C
ATOM   2716  CG1  ILE B  47     -28.193  -0.239  79.033  1.00 54.56           C
ATOM   2717  CG2  ILE B  47     -28.646  -1.948  80.793  1.00 54.29           C
ATOM   2718  CD1  ILE B  47     -27.392   0.658  79.958  1.00 55.43           C
ATOM   2719  N    LEU B  48     -30.730  -3.972  79.750  1.00 55.70           N
```

FIGURE 2-41 (COORDINATES)

```
ATOM   2720  CA  LEU B  48     -31.639   -4.892  80.424  1.00 56.75           C
ATOM   2721  C   LEU B  48     -31.541   -4.746  81.947  1.00 57.06           C
ATOM   2722  O   LEU B  48     -30.489   -4.392  82.476  1.00 57.08           O
ATOM   2723  CB  LEU B  48     -31.303   -6.333  80.023  1.00 56.97           C
ATOM   2724  CG  LEU B  48     -31.229   -6.676  78.528  1.00 57.31           C
ATOM   2725  CD1 LEU B  48     -30.763   -8.110  78.360  1.00 57.33           C
ATOM   2726  CD2 LEU B  48     -32.583   -6.493  77.875  1.00 57.43           C
ATOM   2727  N   ASN B  49     -32.638   -5.017  82.650  1.00 57.93           N
ATOM   2728  CA  ASN B  49     -32.641   -4.917  84.110  1.00 58.40           C
ATOM   2729  C   ASN B  49     -32.160   -6.225  84.738  1.00 58.90           C
ATOM   2730  O   ASN B  49     -31.941   -7.217  84.034  1.00 58.88           O
ATOM   2731  CB  ASN B  49     -34.044   -4.578  84.639  1.00 57.82           C
ATOM   2732  CG  ASN B  49     -35.086   -5.630  84.276  1.00 58.30           C
ATOM   2733  OD1 ASN B  49     -34.786   -6.823  84.195  1.00 58.33           O
ATOM   2734  ND2 ASN B  49     -36.323   -5.189  84.074  1.00 58.02           N
ATOM   2735  N   SER B  50     -32.001   -6.218  86.062  1.00 59.18           N
ATOM   2736  CA  SER B  50     -31.545   -7.393  86.802  1.00 59.26           C
ATOM   2737  C   SER B  50     -32.347   -8.648  86.489  1.00 58.99           C
ATOM   2738  O   SER B  50     -31.782   -9.728  86.321  1.00 59.25           O
ATOM   2739  CB  SER B  50     -31.599   -7.126  88.308  1.00 59.41           C
ATOM   2740  OG  SER B  50     -30.569   -6.236  88.701  1.00 60.69           O
ATOM   2741  N   SER B  51     -33.664   -8.507  86.415  1.00 58.71           N
ATOM   2742  CA  SER B  51     -34.528   -9.643  86.127  1.00 58.90           C
ATOM   2743  C   SER B  51     -34.239  -10.200  84.732  1.00 58.80           C
ATOM   2744  O   SER B  51     -34.115  -11.413  84.549  1.00 58.49           O
ATOM   2745  CB  SER B  51     -35.996   -9.216  86.233  1.00 59.47           C
ATOM   2746  OG  SER B  51     -36.872  -10.324  86.099  1.00 60.83           O
ATOM   2747  N   ALA B  52     -34.129   -9.305  83.753  1.00 58.89           N
ATOM   2748  CA  ALA B  52     -33.857   -9.696  82.371  1.00 58.55           C
ATOM   2749  C   ALA B  52     -32.502  -10.389  82.261  1.00 58.29           C
ATOM   2750  O   ALA B  52     -32.379  -11.431  81.611  1.00 58.02           O
ATOM   2751  CB  ALA B  52     -33.899   -8.465  81.458  1.00 57.89           C
ATOM   2752  N   LEU B  53     -31.490   -9.805  82.897  1.00 57.89           N
ATOM   2753  CA  LEU B  53     -30.150  -10.375  82.878  1.00 58.29           C
ATOM   2754  C   LEU B  53     -30.135  -11.822  83.376  1.00 58.80           C
ATOM   2755  O   LEU B  53     -29.382  -12.656  82.858  1.00 58.59           O
ATOM   2756  CB  LEU B  53     -29.197   -9.527  83.725  1.00 57.61           C
ATOM   2757  CG  LEU B  53     -28.787   -8.180  83.125  1.00 57.66           C
ATOM   2758  CD1 LEU B  53     -27.850   -7.451  84.072  1.00 57.30           C
ATOM   2759  CD2 LEU B  53     -28.100   -8.409  81.786  1.00 57.10           C
ATOM   2760  N   ARG B  54     -30.965  -12.124  84.373  1.00 58.90           N
ATOM   2761  CA  ARG B  54     -31.025  -13.480  84.907  1.00 58.88           C
ATOM   2762  C   ARG B  54     -31.674  -14.398  83.880  1.00 58.14           C
ATOM   2763  O   ARG B  54     -31.225  -15.528  83.679  1.00 57.63           O
ATOM   2764  CB  ARG B  54     -31.827  -13.535  86.216  1.00 59.96           C
ATOM   2765  CG  ARG B  54     -31.384  -12.545  87.284  1.00 61.66           C
ATOM   2766  CD  ARG B  54     -31.963  -12.907  88.655  1.00 62.56           C
ATOM   2767  NE  ARG B  54     -31.909  -11.783  89.586  1.00 63.54           N
ATOM   2768  CZ  ARG B  54     -32.863  -10.862  89.700  1.00 64.19           C
ATOM   2769  NH1 ARG B  54     -33.952  -10.934  88.946  1.00 64.35           N
ATOM   2770  NH2 ARG B  54     -32.723   -9.858  90.556  1.00 64.54           N
ATOM   2771  N   GLN B  55     -32.728  -13.916  83.227  1.00 57.05           N
ATOM   2772  CA  GLN B  55     -33.401  -14.732  82.226  1.00 57.06           C
ATOM   2773  C   GLN B  55     -32.376  -15.164  81.179  1.00 56.22           C
ATOM   2774  O   GLN B  55     -32.320  -16.333  80.784  1.00 55.98           O
ATOM   2775  CB  GLN B  55     -34.520  -13.949  81.536  1.00 58.08           C
ATOM   2776  CG  GLN B  55     -35.462  -14.846  80.743  1.00 60.58           C
ATOM   2777  CD  GLN B  55     -36.174  -14.127  79.609  1.00 62.19           C
ATOM   2778  OE1 GLN B  55     -35.571  -13.822  78.575  1.00 63.50           O
ATOM   2779  NE2 GLN B  55     -37.463  -13.852  79.796  1.00 62.17           N
ATOM   2780  N   ILE B  56     -31.556  -14.210  80.747  1.00 54.63           N
ATOM   2781  CA  ILE B  56     -30.536  -14.470  79.738  1.00 53.38           C
ATOM   2782  C   ILE B  56     -29.521  -15.511  80.184  1.00 52.75           C
ATOM   2783  O   ILE B  56     -29.258  -16.474  79.466  1.00 51.99           O
ATOM   2784  CB  ILE B  56     -29.801  -13.166  79.350  1.00 52.10           C
ATOM   2785  CG1 ILE B  56     -30.824  -12.132  78.874  1.00 51.63           C
ATOM   2786  CG2 ILE B  56     -28.789  -13.437  78.251  1.00 51.00           C
ATOM   2787  CD1 ILE B  56     -31.811  -12.675  77.853  1.00 50.85           C
```

FIGURE 2-42 (COORDINATES)

```
ATOM   2788  N    ALA B  57     -28.954 -15.319  81.369  1.00 52.76           N
ATOM   2789  CA   ALA B  57     -27.969 -16.256  81.893  1.00 52.74           C
ATOM   2790  C    ALA B  57     -28.560 -17.656  82.029  1.00 53.12           C
ATOM   2791  O    ALA B  57     -27.841 -18.649  81.922  1.00 53.65           O
ATOM   2792  CB   ALA B  57     -27.449 -15.772  83.241  1.00 51.70           C
ATOM   2793  N    GLU B  58     -29.869 -17.738  82.249  1.00 53.56           N
ATOM   2794  CA   GLU B  58     -30.523 -19.035  82.401  1.00 53.98           C
ATOM   2795  C    GLU B  58     -30.928 -19.639  81.053  1.00 52.49           C
ATOM   2796  O    GLU B  58     -31.129 -20.848  80.947  1.00 52.40           O
ATOM   2797  CB   GLU B  58     -31.782 -18.916  83.277  1.00 56.84           C
ATOM   2798  CG   GLU B  58     -31.631 -18.185  84.622  1.00 61.51           C
ATOM   2799  CD   GLU B  58     -30.522 -18.736  85.509  1.00 64.27           C
ATOM   2800  OE1  GLU B  58     -30.307 -19.971  85.505  1.00 66.46           O
ATOM   2801  OE2  GLU B  58     -29.876 -17.931  86.225  1.00 65.40           O
ATOM   2802  N    GLY B  59     -31.044 -18.802  80.026  1.00 50.49           N
ATOM   2803  CA   GLY B  59     -31.458 -19.289  78.721  1.00 48.19           C
ATOM   2804  C    GLY B  59     -30.408 -19.909  77.811  1.00 47.38           C
ATOM   2805  O    GLY B  59     -30.741 -20.386  76.719  1.00 46.79           O
ATOM   2806  N    THR B  60     -29.149 -19.918  78.237  1.00 45.95           N
ATOM   2807  CA   THR B  60     -28.097 -20.489  77.405  1.00 45.68           C
ATOM   2808  C    THR B  60     -27.465 -21.739  78.036  1.00 45.67           C
ATOM   2809  O    THR B  60     -27.112 -21.741  79.214  1.00 46.73           O
ATOM   2810  CB   THR B  60     -26.997 -19.420  77.104  1.00 44.86           C
ATOM   2811  OG1  THR B  60     -26.061 -19.941  76.149  1.00 43.17           O
ATOM   2812  CG2  THR B  60     -26.266 -19.027  78.384  1.00 43.15           C
ATOM   2813  N    SER B  61     -27.324 -22.799  77.246  1.00 44.62           N
ATOM   2814  CA   SER B  61     -26.743 -24.045  77.742  1.00 44.85           C
ATOM   2815  C    SER B  61     -25.366 -24.353  77.163  1.00 44.21           C
ATOM   2816  O    SER B  61     -25.243 -24.777  76.011  1.00 43.95           O
ATOM   2817  CB   SER B  61     -27.673 -25.222  77.447  1.00 44.62           C
ATOM   2818  OG   SER B  61     -27.040 -26.441  77.794  1.00 45.42           O
ATOM   2819  N    ILE B  62     -24.334 -24.171  77.977  1.00 43.82           N
ATOM   2820  CA   ILE B  62     -22.975 -24.422  77.527  1.00 44.29           C
ATOM   2821  C    ILE B  62     -22.756 -25.882  77.121  1.00 44.84           C
ATOM   2822  O    ILE B  62     -21.933 -26.168  76.250  1.00 44.82           O
ATOM   2823  CB   ILE B  62     -21.955 -24.018  78.616  1.00 44.09           C
ATOM   2824  CG1  ILE B  62     -20.526 -24.233  78.111  1.00 44.15           C
ATOM   2825  CG2  ILE B  62     -22.215 -24.798  79.880  1.00 44.18           C
ATOM   2826  CD1  ILE B  62     -20.150 -23.347  76.933  1.00 43.91           C
ATOM   2827  N    SER B  63     -23.500 -26.804  77.732  1.00 45.51           N
ATOM   2828  CA   SER B  63     -23.346 -28.219  77.404  1.00 45.79           C
ATOM   2829  C    SER B  63     -24.076 -28.540  76.114  1.00 45.68           C
ATOM   2830  O    SER B  63     -23.626 -29.378  75.341  1.00 45.96           O
ATOM   2831  CB   SER B  63     -23.870 -29.113  78.537  1.00 46.23           C
ATOM   2832  OG   SER B  63     -25.283 -29.225  78.506  1.00 47.85           O
ATOM   2833  N    GLU B  64     -25.210 -27.885  75.883  1.00 46.10           N
ATOM   2834  CA   GLU B  64     -25.956 -28.107  74.650  1.00 46.54           C
ATOM   2835  C    GLU B  64     -25.119 -27.582  73.486  1.00 45.14           C
ATOM   2836  O    GLU B  64     -25.087 -28.179  72.407  1.00 44.85           O
ATOM   2837  CB   GLU B  64     -27.295 -27.373  74.688  1.00 49.82           C
ATOM   2838  CG   GLU B  64     -28.283 -27.952  75.674  1.00 54.70           C
ATOM   2839  CD   GLU B  64     -28.524 -29.416  75.419  1.00 57.60           C
ATOM   2840  OE1  GLU B  64     -28.963 -29.753  74.295  1.00 59.63           O
ATOM   2841  OE2  GLU B  64     -28.269 -30.230  76.335  1.00 60.01           O
ATOM   2842  N    MET B  65     -24.444 -26.457  73.711  1.00 43.03           N
ATOM   2843  CA   MET B  65     -23.597 -25.880  72.680  1.00 41.93           C
ATOM   2844  C    MET B  65     -22.421 -26.812  72.418  1.00 41.58           C
ATOM   2845  O    MET B  65     -22.053 -27.071  71.267  1.00 40.69           O
ATOM   2846  CB   MET B  65     -23.038 -24.521  73.106  1.00 40.53           C
ATOM   2847  CG   MET B  65     -22.074 -23.950  72.066  1.00 39.07           C
ATOM   2848  SD   MET B  65     -20.967 -22.703  72.698  1.00 37.48           S
ATOM   2849  CE   MET B  65     -19.581 -23.708  73.253  1.00 37.03           C
ATOM   2850  N    TRP B  66     -21.834 -27.304  73.503  1.00 40.42           N
ATOM   2851  CA   TRP B  66     -20.690 -28.197  73.415  1.00 40.09           C
ATOM   2852  C    TRP B  66     -21.004 -29.414  72.555  1.00 41.46           C
ATOM   2853  O    TRP B  66     -20.295 -29.711  71.589  1.00 42.00           O
ATOM   2854  CB   TRP B  66     -20.279 -28.644  74.819  1.00 36.77           C
ATOM   2855  CG   TRP B  66     -18.815 -28.868  74.971  1.00 33.54           C
```

FIGURE 2-43 (COORDINATES)

```
ATOM   2856  CD1 TRP B  66     -18.113 -29.974  74.606  1.00 32.11           C
ATOM   2857  CD2 TRP B  66     -17.860 -27.938  75.500  1.00 32.60           C
ATOM   2858  NE1 TRP B  66     -16.773 -29.795  74.875  1.00 32.52           N
ATOM   2859  CE2 TRP B  66     -16.592 -28.552  75.423  1.00 32.25           C
ATOM   2860  CE3 TRP B  66     -17.953 -26.642  76.030  1.00 32.42           C
ATOM   2861  CZ2 TRP B  66     -15.420 -27.916  75.858  1.00 32.79           C
ATOM   2862  CZ3 TRP B  66     -16.787 -26.008  76.464  1.00 32.51           C
ATOM   2863  CH2 TRP B  66     -15.537 -26.648  76.374  1.00 32.41           C
ATOM   2864  N   GLN B  67     -22.090 -30.099  72.894  1.00 42.05           N
ATOM   2865  CA  GLN B  67     -22.488 -31.303  72.179  1.00 42.76           C
ATOM   2866  C   GLN B  67     -23.063 -31.108  70.779  1.00 42.37           C
ATOM   2867  O   GLN B  67     -22.636 -31.768  69.830  1.00 42.04           O
ATOM   2868  CB  GLN B  67     -23.493 -32.100  73.023  1.00 43.43           C
ATOM   2869  CG  GLN B  67     -24.218 -33.194  72.237  1.00 46.61           C
ATOM   2870  CD  GLN B  67     -24.991 -34.157  73.123  1.00 48.23           C
ATOM   2871  OE1 GLN B  67     -24.402 -34.891  73.919  1.00 49.64           O
ATOM   2872  NE2 GLN B  67     -26.316 -34.162  72.986  1.00 48.17           N
ATOM   2873  N   ASN B  68     -24.030 -30.206  70.652  1.00 42.19           N
ATOM   2874  CA  ASN B  68     -24.690 -29.987  69.373  1.00 42.05           C
ATOM   2875  C   ASN B  68     -24.055 -28.975  68.415  1.00 41.75           C
ATOM   2876  O   ASN B  68     -24.216 -29.089  67.195  1.00 40.87           O
ATOM   2877  CB  ASN B  68     -26.157 -29.623  69.624  1.00 42.86           C
ATOM   2878  CG  ASN B  68     -26.856 -30.626  70.541  1.00 43.91           C
ATOM   2879  OD1 ASN B  68     -26.704 -31.840  70.381  1.00 44.12           O
ATOM   2880  ND2 ASN B  68     -27.628 -30.119  71.499  1.00 43.17           N
ATOM   2881  N   ASP B  69     -23.329 -27.998  68.952  1.00 40.52           N
ATOM   2882  CA  ASP B  69     -22.706 -26.988  68.103  1.00 39.77           C
ATOM   2883  C   ASP B  69     -21.196 -27.121  67.951  1.00 38.44           C
ATOM   2884  O   ASP B  69     -20.678 -27.055  66.839  1.00 38.53           O
ATOM   2885  CB  ASP B  69     -23.025 -25.586  68.631  1.00 41.00           C
ATOM   2886  CG  ASP B  69     -24.481 -25.206  68.449  1.00 42.98           C
ATOM   2887  OD1 ASP B  69     -25.016 -24.510  69.335  1.00 45.18           O
ATOM   2888  OD2 ASP B  69     -25.088 -25.588  67.424  1.00 42.53           O
ATOM   2889  N   LEU B  70     -20.500 -27.324  69.064  1.00 36.19           N
ATOM   2890  CA  LEU B  70     -19.046 -27.405  69.061  1.00 34.98           C
ATOM   2891  C   LEU B  70     -18.381 -28.669  68.526  1.00 34.98           C
ATOM   2892  O   LEU B  70     -17.651 -28.621  67.542  1.00 35.37           O
ATOM   2893  CB  LEU B  70     -18.522 -27.129  70.475  1.00 34.01           C
ATOM   2894  CG  LEU B  70     -17.001 -27.152  70.647  1.00 33.59           C
ATOM   2895  CD1 LEU B  70     -16.353 -26.105  69.741  1.00 31.51           C
ATOM   2896  CD2 LEU B  70     -16.653 -26.896  72.111  1.00 32.25           C
ATOM   2897  N   GLN B  71     -18.631 -29.798  69.171  1.00 34.56           N
ATOM   2898  CA  GLN B  71     -17.996 -31.045  68.775  1.00 34.34           C
ATOM   2899  C   GLN B  71     -17.973 -31.393  67.290  1.00 33.50           C
ATOM   2900  O   GLN B  71     -16.965 -31.886  66.791  1.00 32.57           O
ATOM   2901  CB  GLN B  71     -18.581 -32.194  69.605  1.00 34.88           C
ATOM   2902  CG  GLN B  71     -18.361 -31.943  71.095  1.00 37.23           C
ATOM   2903  CD  GLN B  71     -18.639 -33.135  71.965  1.00 38.05           C
ATOM   2904  OE1 GLN B  71     -19.675 -33.775  71.833  1.00 40.72           O
ATOM   2905  NE2 GLN B  71     -17.722 -33.431  72.879  1.00 37.02           N
ATOM   2906  N   PRO B  72     -19.071 -31.137  66.560  1.00 32.93           N
ATOM   2907  CA  PRO B  72     -19.059 -31.467  65.128  1.00 32.04           C
ATOM   2908  C   PRO B  72     -18.036 -30.653  64.336  1.00 32.20           C
ATOM   2909  O   PRO B  72     -17.580 -31.084  63.276  1.00 32.06           O
ATOM   2910  CB  PRO B  72     -20.491 -31.166  64.690  1.00 32.72           C
ATOM   2911  CG  PRO B  72     -21.291 -31.442  65.944  1.00 32.66           C
ATOM   2912  CD  PRO B  72     -20.431 -30.792  67.012  1.00 32.81           C
ATOM   2913  N   LEU B  73     -17.669 -29.485  64.863  1.00 31.72           N
ATOM   2914  CA  LEU B  73     -16.712 -28.593  64.205  1.00 31.62           C
ATOM   2915  C   LEU B  73     -15.238 -28.901  64.483  1.00 31.57           C
ATOM   2916  O   LEU B  73     -14.355 -28.431  63.764  1.00 31.13           O
ATOM   2917  CB  LEU B  73     -17.005 -27.134  64.591  1.00 30.61           C
ATOM   2918  CG  LEU B  73     -18.334 -26.545  64.100  1.00 30.30           C
ATOM   2919  CD1 LEU B  73     -18.424 -25.068  64.505  1.00 30.51           C
ATOM   2920  CD2 LEU B  73     -18.429 -26.676  62.590  1.00 27.72           C
ATOM   2921  N   LEU B  74     -14.974 -29.688  65.521  1.00 31.45           N
ATOM   2922  CA  LEU B  74     -13.608 -30.039  65.887  1.00 31.16           C
ATOM   2923  C   LEU B  74     -13.034 -31.090  64.950  1.00 31.16           C
```

FIGURE 2-44 (COORDINATES)

```
ATOM   2924  O    LEU B  74     -12.707 -32.196  65.359  1.00 32.25           O
ATOM   2925  CB   LEU B  74     -13.580 -30.534  67.335  1.00 31.18           C
ATOM   2926  CG   LEU B  74     -14.087 -29.470  68.318  1.00 31.70           C
ATOM   2927  CD1  LEU B  74     -14.218 -30.054  69.710  1.00 31.16           C
ATOM   2928  CD2  LEU B  74     -13.129 -28.284  68.318  1.00 30.70           C
ATOM   2929  N    ILE B  75     -12.909 -30.719  63.682  1.00 31.18           N
ATOM   2930  CA   ILE B  75     -12.390 -31.598  62.647  1.00 30.03           C
ATOM   2931  C    ILE B  75     -11.446 -30.837  61.708  1.00 30.88           C
ATOM   2932  O    ILE B  75     -11.450 -29.604  61.678  1.00 29.66           O
ATOM   2933  CB   ILE B  75     -13.549 -32.159  61.811  1.00 30.35           C
ATOM   2934  CG1  ILE B  75     -14.342 -31.006  61.188  1.00 29.33           C
ATOM   2935  CG2  ILE B  75     -14.468 -33.001  62.687  1.00 29.96           C
ATOM   2936  CD1  ILE B  75     -15.464 -31.453  60.268  1.00 28.63           C
ATOM   2937  N    GLU B  76     -10.630 -31.564  60.948  1.00 31.10           N
ATOM   2938  CA   GLU B  76      -9.729 -30.918  59.989  1.00 31.60           C
ATOM   2939  C    GLU B  76     -10.642 -30.303  58.919  1.00 30.74           C
ATOM   2940  O    GLU B  76     -11.366 -31.018  58.223  1.00 30.73           O
ATOM   2941  CB   GLU B  76      -8.778 -31.952  59.368  1.00 33.09           C
ATOM   2942  CG   GLU B  76      -7.954 -31.422  58.204  1.00 36.95           C
ATOM   2943  CD   GLU B  76      -6.768 -32.311  57.860  1.00 39.53           C
ATOM   2944  OE1  GLU B  76      -6.944 -33.543  57.787  1.00 42.38           O
ATOM   2945  OE2  GLU B  76      -5.655 -31.781  57.649  1.00 40.98           O
ATOM   2946  N    ARG B  77     -10.605 -28.980  58.788  1.00 29.79           N
ATOM   2947  CA   ARG B  77     -11.478 -28.287  57.844  1.00 28.74           C
ATOM   2948  C    ARG B  77     -10.842 -27.129  57.070  1.00 29.54           C
ATOM   2949  O    ARG B  77     -11.429 -26.053  56.964  1.00 28.53           O
ATOM   2950  CB   ARG B  77     -12.712 -27.772  58.596  1.00 26.65           C
ATOM   2951  CG   ARG B  77     -12.359 -26.904  59.805  1.00 24.63           C
ATOM   2952  CD   ARG B  77     -13.549 -26.615  60.692  1.00 23.59           C
ATOM   2953  NE   ARG B  77     -13.224 -25.620  61.715  1.00 24.92           N
ATOM   2954  CZ   ARG B  77     -12.420 -25.833  62.753  1.00 24.46           C
ATOM   2955  NH1  ARG B  77     -11.851 -27.014  62.926  1.00 25.61           N
ATOM   2956  NH2  ARG B  77     -12.165 -24.858  63.608  1.00 24.52           N
ATOM   2957  N    TYR B  78      -9.648 -27.333  56.529  1.00 30.13           N
ATOM   2958  CA   TYR B  78      -9.030 -26.263  55.759  1.00 30.24           C
ATOM   2959  C    TYR B  78      -9.822 -26.102  54.457  1.00 29.55           C
ATOM   2960  O    TYR B  78     -10.505 -27.030  54.018  1.00 27.91           O
ATOM   2961  CB   TYR B  78      -7.566 -26.585  55.464  1.00 30.29           C
ATOM   2962  CG   TYR B  78      -7.356 -27.872  54.709  1.00 32.16           C
ATOM   2963  CD1  TYR B  78      -7.030 -29.056  55.380  1.00 31.53           C
ATOM   2964  CD2  TYR B  78      -7.434 -27.902  53.315  1.00 31.70           C
ATOM   2965  CE1  TYR B  78      -6.778 -30.228  54.681  1.00 31.62           C
ATOM   2966  CE2  TYR B  78      -7.187 -29.070  52.608  1.00 31.85           C
ATOM   2967  CZ   TYR B  78      -6.854 -30.227  53.292  1.00 32.65           C
ATOM   2968  OH   TYR B  78      -6.566 -31.367  52.582  1.00 33.01           O
ATOM   2969  N    PRO B  79      -9.736 -24.922  53.818  1.00 29.26           N
ATOM   2970  CA   PRO B  79     -10.456 -24.650  52.567  1.00 28.74           C
ATOM   2971  C    PRO B  79     -10.363 -25.752  51.516  1.00 28.35           C
ATOM   2972  O    PRO B  79      -9.274 -26.247  51.213  1.00 29.45           O
ATOM   2973  CB   PRO B  79      -9.826 -23.342  52.081  1.00 28.00           C
ATOM   2974  CG   PRO B  79      -9.435 -22.670  53.350  1.00 27.90           C
ATOM   2975  CD   PRO B  79      -8.822 -23.811  54.132  1.00 28.75           C
ATOM   2976  N    GLY B  80     -11.519 -26.135  50.976  1.00 27.77           N
ATOM   2977  CA   GLY B  80     -11.569 -27.155  49.943  1.00 27.66           C
ATOM   2978  C    GLY B  80     -11.566 -28.604  50.398  1.00 28.64           C
ATOM   2979  O    GLY B  80     -11.732 -29.508  49.577  1.00 28.46           O
ATOM   2980  N    SER B  81     -11.373 -28.839  51.692  1.00 28.63           N
ATOM   2981  CA   SER B  81     -11.349 -30.202  52.210  1.00 28.67           C
ATOM   2982  C    SER B  81     -12.758 -30.663  52.571  1.00 29.11           C
ATOM   2983  O    SER B  81     -13.669 -29.847  52.708  1.00 29.19           O
ATOM   2984  CB   SER B  81     -10.471 -30.289  53.454  1.00 27.31           C
ATOM   2985  OG   SER B  81     -11.163 -29.766  54.570  1.00 26.72           O
ATOM   2986  N    PRO B  82     -12.950 -31.985  52.742  1.00 28.80           N
ATOM   2987  CA   PRO B  82     -14.280 -32.488  53.091  1.00 28.17           C
ATOM   2988  C    PRO B  82     -14.772 -31.891  54.408  1.00 29.08           C
ATOM   2989  O    PRO B  82     -15.967 -31.632  54.579  1.00 30.11           O
ATOM   2990  CB   PRO B  82     -14.065 -33.999  53.174  1.00 28.78           C
ATOM   2991  CG   PRO B  82     -12.947 -34.244  52.168  1.00 27.25           C
```

FIGURE 2-45 (COORDINATES)

```
ATOM   2992  CD   PRO B  82     -12.008 -33.096  52.492  1.00 27.23           C
ATOM   2993  N    GLY B  83     -13.850 -31.673  55.341  1.00 29.13           N
ATOM   2994  CA   GLY B  83     -14.222 -31.096  56.621  1.00 28.91           C
ATOM   2995  C    GLY B  83     -14.808 -29.699  56.471  1.00 30.08           C
ATOM   2996  O    GLY B  83     -15.678 -29.279  57.252  1.00 29.62           O
ATOM   2997  N    SER B  84     -14.324 -28.967  55.470  1.00 30.07           N
ATOM   2998  CA   SER B  84     -14.812 -27.614  55.215  1.00 30.12           C
ATOM   2999  C    SER B  84     -16.282 -27.708  54.811  1.00 29.16           C
ATOM   3000  O    SER B  84     -17.128 -26.958  55.295  1.00 28.51           O
ATOM   3001  CB   SER B  84     -13.989 -26.965  54.089  1.00 30.65           C
ATOM   3002  OG   SER B  84     -14.468 -25.674  53.752  1.00 30.42           O
ATOM   3003  N    TYR B  85     -16.579 -28.647  53.925  1.00 29.80           N
ATOM   3004  CA   TYR B  85     -17.941 -28.838  53.454  1.00 31.41           C
ATOM   3005  C    TYR B  85     -18.853 -29.367  54.567  1.00 30.56           C
ATOM   3006  O    TYR B  85     -20.003 -28.942  54.697  1.00 29.98           O
ATOM   3007  CB   TYR B  85     -17.939 -29.799  52.266  1.00 33.99           C
ATOM   3008  CG   TYR B  85     -19.293 -30.010  51.647  1.00 36.38           C
ATOM   3009  CD1  TYR B  85     -19.956 -28.969  51.011  1.00 38.17           C
ATOM   3010  CD2  TYR B  85     -19.917 -31.250  51.705  1.00 37.86           C
ATOM   3011  CE1  TYR B  85     -21.218 -29.160  50.442  1.00 40.02           C
ATOM   3012  CE2  TYR B  85     -21.172 -31.452  51.142  1.00 40.06           C
ATOM   3013  CZ   TYR B  85     -21.818 -30.405  50.512  1.00 40.31           C
ATOM   3014  OH   TYR B  85     -23.062 -30.605  49.958  1.00 41.46           O
ATOM   3015  N    ALA B  86     -18.335 -30.292  55.371  1.00 30.20           N
ATOM   3016  CA   ALA B  86     -19.106 -30.861  56.473  1.00 30.00           C
ATOM   3017  C    ALA B  86     -19.437 -29.765  57.487  1.00 29.40           C
ATOM   3018  O    ALA B  86     -20.557 -29.691  57.998  1.00 28.56           O
ATOM   3019  CB   ALA B  86     -18.314 -31.983  57.144  1.00 29.22           C
ATOM   3020  N    ALA B  87     -18.453 -28.915  57.769  1.00 29.63           N
ATOM   3021  CA   ALA B  87     -18.633 -27.808  58.711  1.00 29.64           C
ATOM   3022  C    ALA B  87     -19.676 -26.827  58.186  1.00 29.64           C
ATOM   3023  O    ALA B  87     -20.512 -26.341  58.932  1.00 29.27           O
ATOM   3024  CB   ALA B  87     -17.315 -27.089  58.935  1.00 28.99           C
ATOM   3025  N    ARG B  88     -19.622 -26.545  56.892  1.00 31.31           N
ATOM   3026  CA   ARG B  88     -20.564 -25.628  56.278  1.00 32.38           C
ATOM   3027  C    ARG B  88     -21.990 -26.182  56.404  1.00 33.24           C
ATOM   3028  O    ARG B  88     -22.917 -25.450  56.754  1.00 33.09           O
ATOM   3029  CB   ARG B  88     -20.174 -25.400  54.814  1.00 33.20           C
ATOM   3030  CG   ARG B  88     -20.978 -24.321  54.109  1.00 35.57           C
ATOM   3031  CD   ARG B  88     -20.264 -23.770  52.872  1.00 37.29           C
ATOM   3032  NE   ARG B  88     -19.849 -24.794  51.912  1.00 38.78           N
ATOM   3033  CZ   ARG B  88     -18.594 -25.218  51.765  1.00 40.01           C
ATOM   3034  NH1  ARG B  88     -17.625 -24.707  52.516  1.00 40.17           N
ATOM   3035  NH2  ARG B  88     -18.304 -26.152  50.865  1.00 40.06           N
ATOM   3036  N    GLN B  89     -22.162 -27.476  56.144  1.00 34.08           N
ATOM   3037  CA   GLN B  89     -23.481 -28.100  56.259  1.00 34.80           C
ATOM   3038  C    GLN B  89     -23.991 -28.093  57.697  1.00 34.46           C
ATOM   3039  O    GLN B  89     -25.175 -27.891  57.940  1.00 34.43           O
ATOM   3040  CB   GLN B  89     -23.446 -29.545  55.764  1.00 35.91           C
ATOM   3041  CG   GLN B  89     -23.313 -29.708  54.268  1.00 40.47           C
ATOM   3042  CD   GLN B  89     -23.348 -31.171  53.859  1.00 44.37           C
ATOM   3043  OE1  GLN B  89     -22.522 -31.972  54.308  1.00 46.27           O
ATOM   3044  NE2  GLN B  89     -24.307 -31.529  53.008  1.00 44.98           N
ATOM   3045  N    HIS B  90     -23.097 -28.340  58.647  1.00 33.98           N
ATOM   3046  CA   HIS B  90     -23.471 -28.358  60.056  1.00 34.38           C
ATOM   3047  C    HIS B  90     -23.994 -26.995  60.498  1.00 35.50           C
ATOM   3048  O    HIS B  90     -25.051 -26.888  61.129  1.00 35.84           O
ATOM   3049  CB   HIS B  90     -22.265 -28.742  60.916  1.00 33.82           C
ATOM   3050  CG   HIS B  90     -22.491 -28.565  62.384  1.00 33.43           C
ATOM   3051  ND1  HIS B  90     -21.849 -27.594  63.123  1.00 33.51           N
ATOM   3052  CD2  HIS B  90     -23.301 -29.224  63.247  1.00 32.65           C
ATOM   3053  CE1  HIS B  90     -22.253 -27.662  64.379  1.00 32.61           C
ATOM   3054  NE2  HIS B  90     -23.133 -28.642  64.481  1.00 33.00           N
ATOM   3055  N    ILE B  91     -23.235 -25.958  60.163  1.00 35.90           N
ATOM   3056  CA   ILE B  91     -23.582 -24.587  60.498  1.00 36.37           C
ATOM   3057  C    ILE B  91     -24.927 -24.189  59.884  1.00 36.94           C
ATOM   3058  O    ILE B  91     -25.734 -23.519  60.527  1.00 36.13           O
ATOM   3059  CB   ILE B  91     -22.459 -23.635  60.020  1.00 36.02           C
```

FIGURE 2-46 (COORDINATES)

```
ATOM   3060  CG1 ILE B  91     -21.188 -23.933  60.818  1.00 35.55           C
ATOM   3061  CG2 ILE B  91     -22.875 -22.178  60.177  1.00 34.94           C
ATOM   3062  CD1 ILE B  91     -19.949 -23.211  60.323  1.00 35.96           C
ATOM   3063  N   MET B  92     -25.168 -24.622  58.650  1.00 37.45           N
ATOM   3064  CA  MET B  92     -26.413 -24.312  57.962  1.00 38.99           C
ATOM   3065  C   MET B  92     -27.616 -25.038  58.561  1.00 39.58           C
ATOM   3066  O   MET B  92     -28.675 -24.444  58.744  1.00 39.49           O
ATOM   3067  CB  MET B  92     -26.302 -24.657  56.474  1.00 39.59           C
ATOM   3068  CG  MET B  92     -25.396 -23.723  55.684  1.00 41.65           C
ATOM   3069  SD  MET B  92     -25.320 -24.177  53.942  1.00 44.26           S
ATOM   3070  CE  MET B  92     -26.805 -23.367  53.339  1.00 42.74           C
ATOM   3071  N   GLN B  93     -27.454 -26.319  58.868  1.00 40.00           N
ATOM   3072  CA  GLN B  93     -28.550 -27.093  59.439  1.00 40.72           C
ATOM   3073  C   GLN B  93     -28.915 -26.593  60.834  1.00 40.05           C
ATOM   3074  O   GLN B  93     -30.087 -26.578  61.197  1.00 40.64           O
ATOM   3075  CB  GLN B  93     -28.185 -28.585  59.485  1.00 42.37           C
ATOM   3076  CG  GLN B  93     -27.849 -29.165  58.107  1.00 46.05           C
ATOM   3077  CD  GLN B  93     -27.276 -30.580  58.153  1.00 48.43           C
ATOM   3078  OE1 GLN B  93     -26.518 -30.936  59.068  1.00 51.20           O
ATOM   3079  NE2 GLN B  93     -27.614 -31.386  57.148  1.00 47.94           N
ATOM   3080  N   ARG B  94     -27.924 -26.168  61.610  1.00 38.91           N
ATOM   3081  CA  ARG B  94     -28.204 -25.682  62.954  1.00 39.26           C
ATOM   3082  C   ARG B  94     -28.974 -24.363  62.935  1.00 39.95           C
ATOM   3083  O   ARG B  94     -29.785 -24.096  63.819  1.00 41.16           O
ATOM   3084  CB  ARG B  94     -26.903 -25.534  63.744  1.00 38.00           C
ATOM   3085  CG  ARG B  94     -26.243 -26.872  64.059  1.00 38.46           C
ATOM   3086  CD  ARG B  94     -27.052 -27.656  65.087  1.00 37.64           C
ATOM   3087  NE  ARG B  94     -26.986 -27.013  66.396  1.00 38.61           N
ATOM   3088  CZ  ARG B  94     -27.702 -27.370  67.458  1.00 38.50           C
ATOM   3089  NH1 ARG B  94     -28.560 -28.377  67.380  1.00 37.04           N
ATOM   3090  NH2 ARG B  94     -27.546 -26.722  68.604  1.00 38.14           N
ATOM   3091  N   ILE B  95     -28.727 -23.541  61.924  1.00 39.87           N
ATOM   3092  CA  ILE B  95     -29.418 -22.271  61.808  1.00 39.77           C
ATOM   3093  C   ILE B  95     -30.798 -22.488  61.186  1.00 40.90           C
ATOM   3094  O   ILE B  95     -31.778 -21.883  61.618  1.00 40.43           O
ATOM   3095  CB  ILE B  95     -28.598 -21.269  60.954  1.00 38.64           C
ATOM   3096  CG1 ILE B  95     -27.408 -20.765  61.768  1.00 37.70           C
ATOM   3097  CG2 ILE B  95     -29.469 -20.106  60.506  1.00 36.73           C
ATOM   3098  CD1 ILE B  95     -26.408 -19.958  60.970  1.00 37.46           C
ATOM   3099  N   GLN B  96     -30.873 -23.362  60.185  1.00 41.75           N
ATOM   3100  CA  GLN B  96     -32.138 -23.645  59.512  1.00 43.88           C
ATOM   3101  C   GLN B  96     -33.204 -24.282  60.402  1.00 44.77           C
ATOM   3102  O   GLN B  96     -34.389 -24.225  60.082  1.00 45.05           O
ATOM   3103  CB  GLN B  96     -31.906 -24.536  58.291  1.00 44.24           C
ATOM   3104  CG  GLN B  96     -31.108 -23.863  57.197  1.00 46.50           C
ATOM   3105  CD  GLN B  96     -30.821 -24.779  56.025  1.00 47.73           C
ATOM   3106  OE1 GLN B  96     -30.336 -25.900  56.197  1.00 49.11           O
ATOM   3107  NE2 GLN B  96     -31.112 -24.302  54.824  1.00 48.12           N
ATOM   3108  N   ARG B  97     -32.790 -24.883  61.513  1.00 46.00           N
ATOM   3109  CA  ARG B  97     -33.735 -25.525  62.425  1.00 47.04           C
ATOM   3110  C   ARG B  97     -34.338 -24.540  63.424  1.00 47.53           C
ATOM   3111  O   ARG B  97     -35.276 -24.879  64.151  1.00 47.65           O
ATOM   3112  CB  ARG B  97     -33.050 -26.654  63.198  1.00 48.03           C
ATOM   3113  CG  ARG B  97     -31.948 -26.180  64.138  1.00 49.76           C
ATOM   3114  CD  ARG B  97     -31.414 -27.330  64.982  1.00 51.02           C
ATOM   3115  NE  ARG B  97     -32.345 -27.710  66.041  1.00 52.02           N
ATOM   3116  CZ  ARG B  97     -32.557 -27.001  67.147  1.00 52.87           C
ATOM   3117  NH1 ARG B  97     -31.897 -25.868  67.349  1.00 52.80           N
ATOM   3118  NH2 ARG B  97     -33.436 -27.420  68.052  1.00 53.67           N
ATOM   3119  N   LEU B  98     -33.792 -23.327  63.468  1.00 47.45           N
ATOM   3120  CA  LEU B  98     -34.277 -22.298  64.381  1.00 47.19           C
ATOM   3121  C   LEU B  98     -35.562 -21.679  63.853  1.00 47.46           C
ATOM   3122  O   LEU B  98     -35.892 -21.824  62.675  1.00 47.86           O
ATOM   3123  CB  LEU B  98     -33.216 -21.208  64.573  1.00 46.91           C
ATOM   3124  CG  LEU B  98     -31.912 -21.654  65.246  1.00 46.12           C
ATOM   3125  CD1 LEU B  98     -30.951 -20.480  65.316  1.00 45.85           C
ATOM   3126  CD2 LEU B  98     -32.205 -22.194  66.642  1.00 45.37           C
ATOM   3127  N   GLN B  99     -36.286 -20.979  64.720  1.00 47.55           N
```

FIGURE 2-47 (COORDINATES)

```
ATOM   3128  CA  GLN B  99     -37.541 -20.371  64.305  1.00 47.53           C
ATOM   3129  C   GLN B  99     -37.429 -19.035  63.585  1.00 45.73           C
ATOM   3130  O   GLN B  99     -38.219 -18.758  62.685  1.00 44.72           O
ATOM   3131  CB  GLN B  99     -38.482 -20.240  65.502  1.00 49.94           C
ATOM   3132  CG  GLN B  99     -39.027 -21.578  65.972  1.00 54.00           C
ATOM   3133  CD  GLN B  99     -40.331 -21.434  66.725  1.00 57.26           C
ATOM   3134  OE1 GLN B  99     -40.403 -20.739  67.744  1.00 59.07           O
ATOM   3135  NE2 GLN B  99     -41.376 -22.091  66.227  1.00 59.25           N
ATOM   3136  N   ALA B 100     -36.457 -18.210  63.969  1.00 44.18           N
ATOM   3137  CA  ALA B 100     -36.282 -16.912  63.324  1.00 43.19           C
ATOM   3138  C   ALA B 100     -36.187 -17.072  61.803  1.00 42.90           C
ATOM   3139  O   ALA B 100     -35.877 -18.156  61.296  1.00 41.83           O
ATOM   3140  CB  ALA B 100     -35.038 -16.212  63.866  1.00 43.39           C
ATOM   3141  N   ASP B 101     -36.458 -15.990  61.079  1.00 42.29           N
ATOM   3142  CA  ASP B 101     -36.431 -16.026  59.622  1.00 42.87           C
ATOM   3143  C   ASP B 101     -35.037 -15.765  59.038  1.00 41.73           C
ATOM   3144  O   ASP B 101     -34.827 -14.807  58.293  1.00 41.16           O
ATOM   3145  CB  ASP B 101     -37.444 -15.014  59.069  1.00 45.22           C
ATOM   3146  CG  ASP B 101     -37.745 -15.233  57.600  1.00 47.91           C
ATOM   3147  OD1 ASP B 101     -37.786 -16.410  57.173  1.00 49.02           O
ATOM   3148  OD2 ASP B 101     -37.954 -14.232  56.874  1.00 50.22           O
ATOM   3149  N   TRP B 102     -34.087 -16.630  59.380  1.00 40.04           N
ATOM   3150  CA  TRP B 102     -32.726 -16.489  58.887  1.00 39.24           C
ATOM   3151  C   TRP B 102     -32.630 -16.823  57.408  1.00 38.95           C
ATOM   3152  O   TRP B 102     -33.208 -17.806  56.947  1.00 39.75           O
ATOM   3153  CB  TRP B 102     -31.773 -17.410  59.645  1.00 37.91           C
ATOM   3154  CG  TRP B 102     -31.530 -17.044  61.073  1.00 36.80           C
ATOM   3155  CD1 TRP B 102     -32.140 -17.574  62.171  1.00 36.16           C
ATOM   3156  CD2 TRP B 102     -30.548 -16.124  61.563  1.00 35.72           C
ATOM   3157  NE1 TRP B 102     -31.591 -17.051  63.316  1.00 35.21           N
ATOM   3158  CE2 TRP B 102     -30.612 -16.157  62.971  1.00 35.29           C
ATOM   3159  CE3 TRP B 102     -29.617 -15.275  60.947  1.00 34.71           C
ATOM   3160  CZ2 TRP B 102     -29.777 -15.375  63.778  1.00 35.06           C
ATOM   3161  CZ3 TRP B 102     -28.790 -14.500  61.745  1.00 34.22           C
ATOM   3162  CH2 TRP B 102     -28.875 -14.556  63.147  1.00 34.65           C
ATOM   3163  N   VAL B 103     -31.903 -15.997  56.664  1.00 38.29           N
ATOM   3164  CA  VAL B 103     -31.703 -16.238  55.243  1.00 37.74           C
ATOM   3165  C   VAL B 103     -30.225 -16.567  55.053  1.00 37.95           C
ATOM   3166  O   VAL B 103     -29.348 -15.788  55.424  1.00 36.58           O
ATOM   3167  CB  VAL B 103     -32.077 -15.012  54.392  1.00 37.30           C
ATOM   3168  CG1 VAL B 103     -31.738 -15.282  52.937  1.00 35.67           C
ATOM   3169  CG2 VAL B 103     -33.561 -14.708  54.545  1.00 35.39           C
ATOM   3170  N   LEU B 104     -29.959 -17.735  54.485  1.00 39.13           N
ATOM   3171  CA  LEU B 104     -28.595 -18.186  54.282  1.00 40.21           C
ATOM   3172  C   LEU B 104     -28.097 -17.993  52.869  1.00 40.75           C
ATOM   3173  O   LEU B 104     -28.790 -18.295  51.902  1.00 41.08           O
ATOM   3174  CB  LEU B 104     -28.473 -19.659  54.677  1.00 40.99           C
ATOM   3175  CG  LEU B 104     -28.557 -19.921  56.186  1.00 42.41           C
ATOM   3176  CD1 LEU B 104     -28.925 -21.377  56.455  1.00 43.55           C
ATOM   3177  CD2 LEU B 104     -27.231 -19.567  56.830  1.00 42.38           C
ATOM   3178  N   GLU B 105     -26.877 -17.485  52.765  1.00 41.71           N
ATOM   3179  CA  GLU B 105     -26.246 -17.251  51.479  1.00 42.90           C
ATOM   3180  C   GLU B 105     -24.831 -17.819  51.530  1.00 41.46           C
ATOM   3181  O   GLU B 105     -24.067 -17.521  52.450  1.00 40.73           O
ATOM   3182  CB  GLU B 105     -26.181 -15.744  51.190  1.00 46.58           C
ATOM   3183  CG  GLU B 105     -25.489 -15.378  49.872  1.00 52.43           C
ATOM   3184  CD  GLU B 105     -25.140 -13.890  49.771  1.00 56.72           C
ATOM   3185  OE1 GLU B 105     -25.942 -13.055  50.260  1.00 58.92           O
ATOM   3186  OE2 GLU B 105     -24.070 -13.556  49.193  1.00 58.34           O
ATOM   3187  N   ILE B 106     -24.491 -18.650  50.552  1.00 39.77           N
ATOM   3188  CA  ILE B 106     -23.154 -19.213  50.483  1.00 38.07           C
ATOM   3189  C   ILE B 106     -22.393 -18.382  49.458  1.00 37.00           C
ATOM   3190  O   ILE B 106     -22.714 -18.402  48.274  1.00 36.85           O
ATOM   3191  CB  ILE B 106     -23.163 -20.684  50.008  1.00 38.46           C
ATOM   3192  CG1 ILE B 106     -24.076 -21.525  50.904  1.00 38.22           C
ATOM   3193  CG2 ILE B 106     -21.738 -21.239  50.014  1.00 36.75           C
ATOM   3194  CD1 ILE B 106     -23.664 -21.543  52.362  1.00 39.98           C
ATOM   3195  N   ASP B 107     -21.400 -17.637  49.928  1.00 35.44           N
```

FIGURE 2-48 (COORDINATES)

```
ATOM   3196  CA  ASP B 107     -20.576 -16.801  49.070  1.00 33.87           C
ATOM   3197  C   ASP B 107     -19.359 -17.634  48.645  1.00 34.05           C
ATOM   3198  O   ASP B 107     -18.369 -17.729  49.367  1.00 33.78           O
ATOM   3199  CB  ASP B 107     -20.165 -15.553  49.849  1.00 33.47           C
ATOM   3200  CG  ASP B 107     -19.133 -14.725  49.129  1.00 33.76           C
ATOM   3201  OD1 ASP B 107     -19.255 -14.548  47.895  1.00 34.88           O
ATOM   3202  OD2 ASP B 107     -18.201 -14.243  49.805  1.00 32.93           O
ATOM   3203  N   THR B 108     -19.458 -18.247  47.469  1.00 33.14           N
ATOM   3204  CA  THR B 108     -18.416 -19.117  46.935  1.00 31.68           C
ATOM   3205  C   THR B 108     -17.605 -18.439  45.842  1.00 31.53           C
ATOM   3206  O   THR B 108     -18.151 -18.039  44.821  1.00 31.90           O
ATOM   3207  CB  THR B 108     -19.045 -20.397  46.354  1.00 31.38           C
ATOM   3208  OG1 THR B 108     -19.749 -21.081  47.394  1.00 31.46           O
ATOM   3209  CG2 THR B 108     -17.983 -21.314  45.753  1.00 29.72           C
ATOM   3210  N   PHE B 109     -16.297 -18.336  46.052  1.00 30.07           N
ATOM   3211  CA  PHE B 109     -15.427 -17.699  45.086  1.00 29.38           C
ATOM   3212  C   PHE B 109     -14.143 -18.480  44.856  1.00 29.93           C
ATOM   3213  O   PHE B 109     -13.789 -19.379  45.618  1.00 28.96           O
ATOM   3214  CB  PHE B 109     -15.066 -16.289  45.553  1.00 28.02           C
ATOM   3215  CG  PHE B 109     -14.349 -16.260  46.873  1.00 26.78           C
ATOM   3216  CD1 PHE B 109     -15.061 -16.345  48.070  1.00 25.31           C
ATOM   3217  CD2 PHE B 109     -12.957 -16.164  46.922  1.00 25.13           C
ATOM   3218  CE1 PHE B 109     -14.391 -16.332  49.309  1.00 25.55           C
ATOM   3219  CE2 PHE B 109     -12.279 -16.151  48.148  1.00 25.19           C
ATOM   3220  CZ  PHE B 109     -12.996 -16.235  49.343  1.00 24.51           C
ATOM   3221  N   LEU B 110     -13.444 -18.112  43.792  1.00 30.69           N
ATOM   3222  CA  LEU B 110     -12.197 -18.747  43.443  1.00 31.48           C
ATOM   3223  C   LEU B 110     -11.112 -17.723  43.708  1.00 33.06           C
ATOM   3224  O   LEU B 110     -11.301 -16.529  43.456  1.00 34.31           O
ATOM   3225  CB  LEU B 110     -12.197 -19.120  41.969  1.00 31.40           C
ATOM   3226  CG  LEU B 110     -11.078 -20.059  41.530  1.00 31.13           C
ATOM   3227  CD1 LEU B 110     -11.353 -21.450  42.097  1.00 30.45           C
ATOM   3228  CD2 LEU B 110     -11.004 -20.098  39.994  1.00 30.70           C
ATOM   3229  N   SER B 111      -9.979 -18.182  44.223  1.00 33.03           N
ATOM   3230  CA  SER B 111      -8.882 -17.284  44.504  1.00 33.37           C
ATOM   3231  C   SER B 111      -7.526 -17.971  44.364  1.00 33.25           C
ATOM   3232  O   SER B 111      -7.396 -19.169  44.588  1.00 32.72           O
ATOM   3233  CB  SER B 111      -9.042 -16.695  45.905  1.00 34.02           C
ATOM   3234  OG  SER B 111      -7.971 -15.819  46.201  1.00 38.28           O
ATOM   3235  N   GLN B 112      -6.527 -17.190  43.975  1.00 34.02           N
ATOM   3236  CA  GLN B 112      -5.161 -17.660  43.781  1.00 35.25           C
ATOM   3237  C   GLN B 112      -4.500 -17.938  45.130  1.00 34.70           C
ATOM   3238  O   GLN B 112      -4.667 -17.166  46.068  1.00 35.75           O
ATOM   3239  CB  GLN B 112      -4.376 -16.582  43.031  1.00 37.22           C
ATOM   3240  CG  GLN B 112      -2.891 -16.813  42.954  1.00 42.81           C
ATOM   3241  CD  GLN B 112      -2.503 -17.749  41.828  1.00 45.52           C
ATOM   3242  OE1 GLN B 112      -2.151 -17.305  40.723  1.00 46.85           O
ATOM   3243  NE2 GLN B 112      -2.574 -19.054  42.093  1.00 45.70           N
ATOM   3244  N   THR B 113      -3.760 -19.037  45.235  1.00 33.76           N
ATOM   3245  CA  THR B 113      -3.072 -19.369  46.483  1.00 33.46           C
ATOM   3246  C   THR B 113      -1.660 -19.844  46.163  1.00 33.43           C
ATOM   3247  O   THR B 113      -1.309 -20.017  44.994  1.00 32.72           O
ATOM   3248  CB  THR B 113      -3.777 -20.519  47.266  1.00 33.46           C
ATOM   3249  OG1 THR B 113      -3.551 -21.763  46.591  1.00 33.58           O
ATOM   3250  CG2 THR B 113      -5.276 -20.266  47.385  1.00 31.60           C
ATOM   3251  N   PRO B 114      -0.826 -20.054  47.198  1.00 33.65           N
ATOM   3252  CA  PRO B 114       0.544 -20.523  46.951  1.00 33.34           C
ATOM   3253  C   PRO B 114       0.550 -21.910  46.305  1.00 33.62           C
ATOM   3254  O   PRO B 114       1.605 -22.389  45.875  1.00 34.60           O
ATOM   3255  CB  PRO B 114       1.167 -20.540  48.345  1.00 32.51           C
ATOM   3256  CG  PRO B 114       0.464 -19.411  49.036  1.00 33.64           C
ATOM   3257  CD  PRO B 114      -0.980 -19.608  48.597  1.00 33.42           C
ATOM   3258  N   TYR B 115      -0.623 -22.542  46.228  1.00 33.22           N
ATOM   3259  CA  TYR B 115      -0.743 -23.875  45.632  1.00 34.34           C
ATOM   3260  C   TYR B 115      -1.594 -23.918  44.368  1.00 34.96           C
ATOM   3261  O   TYR B 115      -1.844 -24.993  43.831  1.00 35.07           O
ATOM   3262  CB  TYR B 115      -1.325 -24.870  46.640  1.00 35.17           C
ATOM   3263  CG  TYR B 115      -0.552 -24.960  47.936  1.00 37.06           C
```

FIGURE 2-49 (COORDINATES)

```
ATOM   3264  CD1 TYR B 115       0.818 -25.223  47.938  1.00 37.71           C
ATOM   3265  CD2 TYR B 115      -1.186 -24.767  49.162  1.00 37.65           C
ATOM   3266  CE1 TYR B 115       1.534 -25.286  49.128  1.00 39.11           C
ATOM   3267  CE2 TYR B 115      -0.477 -24.830  50.357  1.00 38.81           C
ATOM   3268  CZ  TYR B 115       0.882 -25.087  50.331  1.00 39.73           C
ATOM   3269  OH  TYR B 115       1.595 -25.120  51.512  1.00 42.70           O
ATOM   3270  N   GLY B 116      -2.031 -22.755  43.893  1.00 35.48           N
ATOM   3271  CA  GLY B 116      -2.858 -22.699  42.702  1.00 34.53           C
ATOM   3272  C   GLY B 116      -4.221 -22.150  43.068  1.00 35.26           C
ATOM   3273  O   GLY B 116      -4.453 -21.772  44.219  1.00 35.21           O
ATOM   3274  N   TYR B 117      -5.128 -22.103  42.100  1.00 36.17           N
ATOM   3275  CA  TYR B 117      -6.466 -21.593  42.353  1.00 37.45           C
ATOM   3276  C   TYR B 117      -7.213 -22.559  43.254  1.00 37.11           C
ATOM   3277  O   TYR B 117      -7.054 -23.774  43.144  1.00 36.29           O
ATOM   3278  CB  TYR B 117      -7.251 -21.433  41.046  1.00 40.28           C
ATOM   3279  CG  TYR B 117      -6.696 -20.401  40.095  1.00 43.63           C
ATOM   3280  CD1 TYR B 117      -6.455 -19.091  40.513  1.00 45.20           C
ATOM   3281  CD2 TYR B 117      -6.406 -20.735  38.773  1.00 45.15           C
ATOM   3282  CE1 TYR B 117      -5.933 -18.141  39.637  1.00 47.34           C
ATOM   3283  CE2 TYR B 117      -5.887 -19.795  37.889  1.00 46.72           C
ATOM   3284  CZ  TYR B 117      -5.649 -18.502  38.327  1.00 47.39           C
ATOM   3285  OH  TYR B 117      -5.104 -17.585  37.457  1.00 49.12           O
ATOM   3286  N   ARG B 118      -8.038 -22.010  44.137  1.00 36.49           N
ATOM   3287  CA  ARG B 118      -8.817 -22.822  45.050  1.00 36.28           C
ATOM   3288  C   ARG B 118     -10.146 -22.169  45.386  1.00 34.49           C
ATOM   3289  O   ARG B 118     -10.282 -20.947  45.348  1.00 34.34           O
ATOM   3290  CB  ARG B 118      -8.008 -23.103  46.315  1.00 38.49           C
ATOM   3291  CG  ARG B 118      -6.791 -23.944  46.016  1.00 43.41           C
ATOM   3292  CD  ARG B 118      -6.114 -24.469  47.249  1.00 47.84           C
ATOM   3293  NE  ARG B 118      -6.942 -25.427  47.977  1.00 51.90           N
ATOM   3294  CZ  ARG B 118      -6.528 -26.635  48.355  1.00 53.32           C
ATOM   3295  NH1 ARG B 118      -5.294 -27.029  48.061  1.00 53.33           N
ATOM   3296  NH2 ARG B 118      -7.339 -27.437  49.046  1.00 53.10           N
ATOM   3297  N   SER B 119     -11.127 -23.003  45.700  1.00 32.68           N
ATOM   3298  CA  SER B 119     -12.458 -22.540  46.023  1.00 31.27           C
ATOM   3299  C   SER B 119     -12.632 -22.315  47.523  1.00 31.26           C
ATOM   3300  O   SER B 119     -12.142 -23.090  48.346  1.00 32.64           O
ATOM   3301  CB  SER B 119     -13.485 -23.551  45.514  1.00 30.79           C
ATOM   3302  OG  SER B 119     -14.810 -23.092  45.729  1.00 30.97           O
ATOM   3303  N   PHE B 120     -13.332 -21.238  47.860  1.00 29.04           N
ATOM   3304  CA  PHE B 120     -13.607 -20.856  49.234  1.00 27.48           C
ATOM   3305  C   PHE B 120     -15.103 -20.576  49.326  1.00 27.83           C
ATOM   3306  O   PHE B 120     -15.735 -20.202  48.330  1.00 28.26           O
ATOM   3307  CB  PHE B 120     -12.842 -19.577  49.585  1.00 25.81           C
ATOM   3308  CG  PHE B 120     -11.350 -19.736  49.597  1.00 23.78           C
ATOM   3309  CD1 PHE B 120     -10.674 -19.982  50.791  1.00 21.64           C
ATOM   3310  CD2 PHE B 120     -10.610 -19.612  48.418  1.00 23.13           C
ATOM   3311  CE1 PHE B 120      -9.277 -20.102  50.816  1.00 21.30           C
ATOM   3312  CE2 PHE B 120      -9.214 -19.728  48.433  1.00 22.31           C
ATOM   3313  CZ  PHE B 120      -8.547 -19.974  49.641  1.00 21.75           C
ATOM   3314  N   SER B 121     -15.676 -20.743  50.510  1.00 26.82           N
ATOM   3315  CA  SER B 121     -17.099 -20.482  50.672  1.00 27.15           C
ATOM   3316  C   SER B 121     -17.428 -19.777  51.970  1.00 27.48           C
ATOM   3317  O   SER B 121     -17.327 -20.377  53.034  1.00 27.02           O
ATOM   3318  CB  SER B 121     -17.901 -21.785  50.613  1.00 27.10           C
ATOM   3319  OG  SER B 121     -17.880 -22.347  49.315  1.00 29.72           O
ATOM   3320  N   ASN B 122     -17.803 -18.499  51.893  1.00 27.52           N
ATOM   3321  CA  ASN B 122     -18.196 -17.781  53.095  1.00 27.45           C
ATOM   3322  C   ASN B 122     -19.653 -18.144  53.360  1.00 28.28           C
ATOM   3323  O   ASN B 122     -20.425 -18.410  52.435  1.00 26.60           O
ATOM   3324  CB  ASN B 122     -18.090 -16.263  52.919  1.00 28.66           C
ATOM   3325  CG  ASN B 122     -16.653 -15.767  52.883  1.00 29.78           C
ATOM   3326  OD1 ASN B 122     -15.803 -16.196  53.682  1.00 29.73           O
ATOM   3327  ND2 ASN B 122     -16.375 -14.840  51.966  1.00 27.94           N
ATOM   3328  N   ILE B 123     -20.021 -18.175  54.632  1.00 29.40           N
ATOM   3329  CA  ILE B 123     -21.385 -18.480  55.021  1.00 30.06           C
ATOM   3330  C   ILE B 123     -21.976 -17.215  55.635  1.00 31.12           C
ATOM   3331  O   ILE B 123     -21.439 -16.694  56.611  1.00 31.71           O
```

FIGURE 2-50 (COORDINATES)

```
ATOM   3332  CB  ILE B 123     -21.431 -19.603  56.083  1.00 30.30           C
ATOM   3333  CG1 ILE B 123     -20.727 -20.854  55.553  1.00 29.97           C
ATOM   3334  CG2 ILE B 123     -22.882 -19.908  56.451  1.00 28.20           C
ATOM   3335  CD1 ILE B 123     -20.407 -21.874  56.630  1.00 30.15           C
ATOM   3336  N   ILE B 124     -23.064 -16.711  55.062  1.00 31.61           N
ATOM   3337  CA  ILE B 124     -23.702 -15.519  55.611  1.00 32.22           C
ATOM   3338  C   ILE B 124     -25.138 -15.846  55.979  1.00 32.29           C
ATOM   3339  O   ILE B 124     -25.915 -16.331  55.154  1.00 32.63           O
ATOM   3340  CB  ILE B 124     -23.700 -14.321  54.623  1.00 31.79           C
ATOM   3341  CG1 ILE B 124     -22.268 -13.930  54.253  1.00 31.47           C
ATOM   3342  CG2 ILE B 124     -24.391 -13.127  55.265  1.00 31.38           C
ATOM   3343  CD1 ILE B 124     -21.811 -14.493  52.923  1.00 32.09           C
ATOM   3344  N   SER B 125     -25.476 -15.583  57.232  1.00 32.77           N
ATOM   3345  CA  SER B 125     -26.801 -15.853  57.756  1.00 33.53           C
ATOM   3346  C   SER B 125     -27.373 -14.497  58.137  1.00 34.04           C
ATOM   3347  O   SER B 125     -26.872 -13.840  59.046  1.00 35.39           O
ATOM   3348  CB  SER B 125     -26.682 -16.767  58.982  1.00 33.03           C
ATOM   3349  OG  SER B 125     -27.951 -17.221  59.411  1.00 35.38           O
ATOM   3350  N   THR B 126     -28.420 -14.069  57.445  1.00 34.28           N
ATOM   3351  CA  THR B 126     -28.987 -12.758  57.727  1.00 34.90           C
ATOM   3352  C   THR B 126     -30.472 -12.732  58.084  1.00 35.61           C
ATOM   3353  O   THR B 126     -31.281 -13.470  57.517  1.00 35.80           O
ATOM   3354  CB  THR B 126     -28.760 -11.809  56.526  1.00 34.33           C
ATOM   3355  OG1 THR B 126     -27.408 -11.934  56.067  1.00 32.65           O
ATOM   3356  CG2 THR B 126     -29.009 -10.364  56.928  1.00 33.25           C
ATOM   3357  N   LEU B 127     -30.809 -11.889  59.056  1.00 36.61           N
ATOM   3358  CA  LEU B 127     -32.197 -11.692  59.469  1.00 37.88           C
ATOM   3359  C   LEU B 127     -32.574 -10.381  58.803  1.00 38.01           C
ATOM   3360  O   LEU B 127     -31.859  -9.392  58.946  1.00 36.90           O
ATOM   3361  CB  LEU B 127     -32.323 -11.536  60.993  1.00 37.99           C
ATOM   3362  CG  LEU B 127     -32.334 -12.802  61.862  1.00 39.13           C
ATOM   3363  CD1 LEU B 127     -32.489 -12.414  63.338  1.00 38.74           C
ATOM   3364  CD2 LEU B 127     -33.479 -13.719  61.425  1.00 37.51           C
ATOM   3365  N   ASN B 128     -33.672 -10.375  58.056  1.00 38.93           N
ATOM   3366  CA  ASN B 128     -34.105  -9.150  57.391  1.00 40.18           C
ATOM   3367  C   ASN B 128     -33.014  -8.690  56.422  1.00 40.63           C
ATOM   3368  O   ASN B 128     -32.392  -7.654  56.630  1.00 40.49           O
ATOM   3369  CB  ASN B 128     -34.358  -8.061  58.441  1.00 40.16           C
ATOM   3370  CG  ASN B 128     -35.371  -8.484  59.489  1.00 40.93           C
ATOM   3371  OD1 ASN B 128     -36.576  -8.417  59.259  1.00 42.36           O
ATOM   3372  ND2 ASN B 128     -34.886  -8.936  60.642  1.00 39.93           N
ATOM   3373  N   PRO B 129     -32.776  -9.458  55.346  1.00 41.56           N
ATOM   3374  CA  PRO B 129     -31.749  -9.119  54.352  1.00 42.36           C
ATOM   3375  C   PRO B 129     -31.887  -7.670  53.898  1.00 43.46           C
ATOM   3376  O   PRO B 129     -30.897  -6.976  53.661  1.00 43.40           O
ATOM   3377  CB  PRO B 129     -32.030 -10.093  53.212  1.00 41.51           C
ATOM   3378  CG  PRO B 129     -32.690 -11.241  53.888  1.00 42.03           C
ATOM   3379  CD  PRO B 129     -33.602 -10.582  54.878  1.00 41.32           C
ATOM   3380  N   THR B 130     -33.137  -7.237  53.787  1.00 44.89           N
ATOM   3381  CA  THR B 130     -33.488  -5.885  53.369  1.00 46.68           C
ATOM   3382  C   THR B 130     -33.249  -4.858  54.484  1.00 46.23           C
ATOM   3383  O   THR B 130     -33.227  -3.659  54.225  1.00 46.82           O
ATOM   3384  CB  THR B 130     -34.978  -5.850  52.905  1.00 47.58           C
ATOM   3385  OG1 THR B 130     -35.080  -6.477  51.622  1.00 49.44           O
ATOM   3386  CG2 THR B 130     -35.508  -4.433  52.812  1.00 49.47           C
ATOM   3387  N   ALA B 131     -33.060  -5.324  55.713  0.00 45.68           N
ATOM   3388  CA  ALA B 131     -32.814  -4.404  56.818  0.00 44.89           C
ATOM   3389  C   ALA B 131     -31.598  -3.548  56.477  0.00 44.37           C
ATOM   3390  O   ALA B 131     -30.478  -4.046  56.393  0.00 44.28           O
ATOM   3391  CB  ALA B 131     -32.575  -5.174  58.109  0.00 45.00           C
ATOM   3392  N   LYS B 132     -31.833  -2.258  56.271  1.00 43.44           N
ATOM   3393  CA  LYS B 132     -30.769  -1.317  55.925  1.00 43.41           C
ATOM   3394  C   LYS B 132     -29.554  -1.394  56.842  1.00 42.45           C
ATOM   3395  O   LYS B 132     -28.416  -1.279  56.390  1.00 41.84           O
ATOM   3396  CB  LYS B 132     -31.305   0.119  55.910  1.00 44.06           C
ATOM   3397  CG  LYS B 132     -32.320   0.373  54.790  1.00 47.61           C
ATOM   3398  CD  LYS B 132     -32.458   1.860  54.446  1.00 48.89           C
ATOM   3399  CE  LYS B 132     -33.205   2.636  55.509  1.00 50.08           C
```

FIGURE 2-51 (COORDINATES)

```
ATOM   3400  NZ   LYS B 132     -34.618    2.177   55.620  1.00 52.48           N
ATOM   3401  N    ARG B 133     -29.803   -1.589   58.133  1.00 40.82           N
ATOM   3402  CA   ARG B 133     -28.731   -1.687   59.113  1.00 38.53           C
ATOM   3403  C    ARG B 133     -28.687   -3.054   59.781  1.00 37.21           C
ATOM   3404  O    ARG B 133     -29.721   -3.668   60.044  1.00 36.62           O
ATOM   3405  CB   ARG B 133     -28.904   -0.611   60.181  1.00 38.16           C
ATOM   3406  CG   ARG B 133     -28.622    0.794   59.686  1.00 38.56           C
ATOM   3407  CD   ARG B 133     -29.090    1.806   60.702  1.00 38.56           C
ATOM   3408  NE   ARG B 133     -28.492    1.578   62.011  1.00 37.51           N
ATOM   3409  CZ   ARG B 133     -29.047    1.973   63.149  1.00 36.81           C
ATOM   3410  NH1  ARG B 133     -30.207    2.611   63.126  1.00 37.20           N
ATOM   3411  NH2  ARG B 133     -28.451    1.722   64.303  1.00 36.31           N
ATOM   3412  N    HIS B 134     -27.478   -3.535   60.041  1.00 35.49           N
ATOM   3413  CA   HIS B 134     -27.312   -4.814   60.714  1.00 34.20           C
ATOM   3414  C    HIS B 134     -26.131   -4.801   61.664  1.00 33.46           C
ATOM   3415  O    HIS B 134     -25.101   -4.196   61.384  1.00 34.26           O
ATOM   3416  CB   HIS B 134     -27.088   -5.962   59.720  1.00 33.62           C
ATOM   3417  CG   HIS B 134     -28.318   -6.404   58.993  1.00 34.00           C
ATOM   3418  ND1  HIS B 134     -28.636   -5.958   57.726  1.00 34.79           N
ATOM   3419  CD2  HIS B 134     -29.281   -7.294   59.332  1.00 33.82           C
ATOM   3420  CE1  HIS B 134     -29.739   -6.559   57.314  1.00 33.71           C
ATOM   3421  NE2  HIS B 134     -30.151   -7.374   58.270  1.00 34.60           N
ATOM   3422  N    LEU B 135     -26.303   -5.459   62.803  1.00 32.66           N
ATOM   3423  CA   LEU B 135     -25.228   -5.622   63.766  1.00 31.62           C
ATOM   3424  C    LEU B 135     -24.614   -6.906   63.218  1.00 31.11           C
ATOM   3425  O    LEU B 135     -25.337   -7.865   62.936  1.00 30.70           O
ATOM   3426  CB   LEU B 135     -25.791   -5.869   65.169  1.00 32.22           C
ATOM   3427  CG   LEU B 135     -24.802   -6.359   66.225  1.00 32.03           C
ATOM   3428  CD1  LEU B 135     -23.714   -5.324   66.439  1.00 32.78           C
ATOM   3429  CD2  LEU B 135     -25.543   -6.629   67.519  1.00 33.21           C
ATOM   3430  N    VAL B 136     -23.301   -6.934   63.042  1.00 30.96           N
ATOM   3431  CA   VAL B 136     -22.670   -8.126   62.484  1.00 30.80           C
ATOM   3432  C    VAL B 136     -21.722   -8.856   63.429  1.00 30.59           C
ATOM   3433  O    VAL B 136     -20.820   -8.254   64.010  1.00 31.10           O
ATOM   3434  CB   VAL B 136     -21.887   -7.785   61.178  1.00 31.01           C
ATOM   3435  CG1  VAL B 136     -21.425   -9.068   60.496  1.00 30.11           C
ATOM   3436  CG2  VAL B 136     -22.763   -6.960   60.240  1.00 29.12           C
ATOM   3437  N    LEU B 137     -21.945  -10.161   63.577  1.00 30.76           N
ATOM   3438  CA   LEU B 137     -21.098  -11.013   64.405  1.00 29.52           C
ATOM   3439  C    LEU B 137     -20.400  -11.940   63.430  1.00 28.51           C
ATOM   3440  O    LEU B 137     -21.029  -12.475   62.525  1.00 27.53           O
ATOM   3441  CB   LEU B 137     -21.934  -11.836   65.386  1.00 29.96           C
ATOM   3442  CG   LEU B 137     -22.832  -11.040   66.329  1.00 31.53           C
ATOM   3443  CD1  LEU B 137     -23.545  -11.994   67.286  1.00 30.94           C
ATOM   3444  CD2  LEU B 137     -21.998  -10.022   67.089  1.00 31.75           C
ATOM   3445  N    ALA B 138     -19.100  -12.131   63.606  1.00 28.75           N
ATOM   3446  CA   ALA B 138     -18.357  -12.984   62.691  1.00 28.66           C
ATOM   3447  C    ALA B 138     -17.165  -13.724   63.302  1.00 28.88           C
ATOM   3448  O    ALA B 138     -16.721  -13.419   64.409  1.00 27.93           O
ATOM   3449  CB   ALA B 138     -17.889  -12.150   61.504  1.00 27.61           C
ATOM   3450  N    CYS B 139     -16.655  -14.693   62.546  1.00 29.12           N
ATOM   3451  CA   CYS B 139     -15.491  -15.493   62.932  1.00 30.19           C
ATOM   3452  C    CYS B 139     -15.143  -16.298   61.687  1.00 29.99           C
ATOM   3453  O    CYS B 139     -15.880  -16.246   60.701  1.00 31.83           O
ATOM   3454  CB   CYS B 139     -15.834  -16.460   64.079  1.00 30.77           C
ATOM   3455  SG   CYS B 139     -16.867  -17.864   63.579  1.00 30.86           S
ATOM   3456  N    HIS B 140     -14.035  -17.026   61.707  1.00 28.36           N
ATOM   3457  CA   HIS B 140     -13.685  -17.838   60.549  1.00 28.89           C
ATOM   3458  C    HIS B 140     -13.949  -19.310   60.899  1.00 29.75           C
ATOM   3459  O    HIS B 140     -13.671  -19.750   62.027  1.00 30.32           O
ATOM   3460  CB   HIS B 140     -12.223  -17.599   60.139  1.00 26.98           C
ATOM   3461  CG   HIS B 140     -11.210  -18.264   61.022  1.00 28.13           C
ATOM   3462  ND1  HIS B 140     -10.632  -19.477   60.710  1.00 28.06           N
ATOM   3463  CD2  HIS B 140     -10.657  -17.877   62.197  1.00 27.76           C
ATOM   3464  CE1  HIS B 140      -9.768  -19.807   61.653  1.00 28.05           C
ATOM   3465  NE2  HIS B 140      -9.765  -18.853   62.567  1.00 28.02           N
ATOM   3466  N    TYR B 141     -14.508  -20.068   59.958  1.00 29.25           N
ATOM   3467  CA   TYR B 141     -14.806  -21.466   60.242  1.00 28.74           C
```

FIGURE 2-52 (COORDINATES)

```
ATOM   3468  C    TYR B 141     -13.803 -22.448  59.664  1.00 28.73           C
ATOM   3469  O    TYR B 141     -13.901 -23.644  59.917  1.00 28.44           O
ATOM   3470  CB   TYR B 141     -16.229 -21.833  59.792  1.00 28.44           C
ATOM   3471  CG   TYR B 141     -16.413 -22.057  58.309  1.00 27.83           C
ATOM   3472  CD1  TYR B 141     -16.546 -20.988  57.425  1.00 27.81           C
ATOM   3473  CD2  TYR B 141     -16.471 -23.349  57.793  1.00 28.76           C
ATOM   3474  CE1  TYR B 141     -16.737 -21.209  56.063  1.00 27.85           C
ATOM   3475  CE2  TYR B 141     -16.658 -23.583  56.446  1.00 28.60           C
ATOM   3476  CZ   TYR B 141     -16.792 -22.516  55.584  1.00 29.42           C
ATOM   3477  OH   TYR B 141     -16.987 -22.772  54.245  1.00 30.89           O
ATOM   3478  N    ASP B 142     -12.836 -21.949  58.898  1.00 28.80           N
ATOM   3479  CA   ASP B 142     -11.804 -22.818  58.337  1.00 28.48           C
ATOM   3480  C    ASP B 142     -10.786 -23.081  59.428  1.00 27.71           C
ATOM   3481  O    ASP B 142     -10.710 -22.330  60.396  1.00 26.71           O
ATOM   3482  CB   ASP B 142     -11.092 -22.158  57.139  1.00 28.49           C
ATOM   3483  CG   ASP B 142     -10.296 -20.910  57.526  1.00 29.27           C
ATOM   3484  OD1  ASP B 142     -10.882 -19.969  58.101  1.00 29.07           O
ATOM   3485  OD2  ASP B 142      -9.078 -20.860  57.242  1.00 29.55           O
ATOM   3486  N    SER B 143     -10.024 -24.158  59.284  1.00 27.70           N
ATOM   3487  CA   SER B 143      -8.976 -24.477  60.253  1.00 27.97           C
ATOM   3488  C    SER B 143      -7.676 -24.395  59.474  1.00 27.56           C
ATOM   3489  O    SER B 143      -7.643 -24.757  58.299  1.00 26.16           O
ATOM   3490  CB   SER B 143      -9.161 -25.885  60.843  1.00 27.79           C
ATOM   3491  OG   SER B 143      -9.103 -26.883  59.843  1.00 28.11           O
ATOM   3492  N    LYS B 144      -6.614 -23.922  60.118  1.00 28.26           N
ATOM   3493  CA   LYS B 144      -5.333 -23.770  59.444  1.00 28.39           C
ATOM   3494  C    LYS B 144      -4.821 -25.084  58.895  1.00 29.87           C
ATOM   3495  O    LYS B 144      -4.825 -26.101  59.582  1.00 29.97           O
ATOM   3496  CB   LYS B 144      -4.297 -23.155  60.386  1.00 28.24           C
ATOM   3497  CG   LYS B 144      -2.922 -22.904  59.740  1.00 27.74           C
ATOM   3498  CD   LYS B 144      -2.074 -21.948  60.583  1.00 26.71           C
ATOM   3499  CE   LYS B 144      -0.714 -21.706  59.963  1.00 26.70           C
ATOM   3500  NZ   LYS B 144      -0.816 -21.167  58.580  1.00 26.87           N
ATOM   3501  N    TYR B 145      -4.381 -25.044  57.644  1.00 30.95           N
ATOM   3502  CA   TYR B 145      -3.858 -26.210  56.962  1.00 33.25           C
ATOM   3503  C    TYR B 145      -2.483 -26.640  57.483  1.00 33.83           C
ATOM   3504  O    TYR B 145      -1.512 -25.892  57.387  1.00 33.72           O
ATOM   3505  CB   TYR B 145      -3.764 -25.921  55.468  1.00 35.79           C
ATOM   3506  CG   TYR B 145      -3.073 -27.020  54.720  1.00 39.59           C
ATOM   3507  CD1  TYR B 145      -1.900 -26.775  54.008  1.00 40.93           C
ATOM   3508  CD2  TYR B 145      -3.557 -28.324  54.774  1.00 40.76           C
ATOM   3509  CE1  TYR B 145      -1.221 -27.805  53.373  1.00 42.94           C
ATOM   3510  CE2  TYR B 145      -2.890 -29.361  54.146  1.00 43.48           C
ATOM   3511  CZ   TYR B 145      -1.722 -29.101  53.450  1.00 44.40           C
ATOM   3512  OH   TYR B 145      -1.041 -30.142  52.857  1.00 46.70           O
ATOM   3513  N    PHE B 146      -2.405 -27.853  58.021  1.00 34.12           N
ATOM   3514  CA   PHE B 146      -1.154 -28.393  58.561  1.00 34.25           C
ATOM   3515  C    PHE B 146      -0.992 -29.853  58.163  1.00 35.70           C
ATOM   3516  O    PHE B 146      -1.968 -30.542  57.853  1.00 35.66           O
ATOM   3517  CB   PHE B 146      -1.148 -28.353  60.097  1.00 32.70           C
ATOM   3518  CG   PHE B 146      -0.826 -27.010  60.700  1.00 32.22           C
ATOM   3519  CD1  PHE B 146       0.423 -26.419  60.513  1.00 33.51           C
ATOM   3520  CD2  PHE B 146      -1.743 -26.376  61.539  1.00 31.51           C
ATOM   3521  CE1  PHE B 146       0.753 -25.215  61.166  1.00 33.31           C
ATOM   3522  CE2  PHE B 146      -1.424 -25.177  62.193  1.00 30.83           C
ATOM   3523  CZ   PHE B 146      -0.177 -24.597  62.009  1.00 31.60           C
ATOM   3524  N    SER B 147       0.247 -30.332  58.180  1.00 37.44           N
ATOM   3525  CA   SER B 147       0.497 -31.739  57.900  1.00 39.09           C
ATOM   3526  C    SER B 147       0.176 -32.386  59.250  1.00 39.95           C
ATOM   3527  O    SER B 147       0.040 -31.683  60.253  1.00 38.83           O
ATOM   3528  CB   SER B 147       1.964 -31.968  57.538  1.00 39.24           C
ATOM   3529  OG   SER B 147       2.799 -31.682  58.644  1.00 41.69           O
ATOM   3530  N    HIS B 148       0.056 -33.708  59.296  1.00 42.19           N
ATOM   3531  CA   HIS B 148      -0.271 -34.372  60.559  1.00 44.42           C
ATOM   3532  C    HIS B 148       0.940 -34.603  61.463  1.00 45.49           C
ATOM   3533  O    HIS B 148       1.474 -35.703  61.543  1.00 46.17           O
ATOM   3534  CB   HIS B 148      -0.985 -35.695  60.284  1.00 43.80           C
ATOM   3535  CG   HIS B 148      -2.214 -35.547  59.444  1.00 43.66           C
```

FIGURE 2-53 (COORDINATES)

```
ATOM   3536  ND1  HIS B 148      -3.100  -34.503  59.602  1.00 43.68          N
ATOM   3537  CD2  HIS B 148      -2.717  -36.320  58.453  1.00 43.34          C
ATOM   3538  CE1  HIS B 148      -4.095  -34.640  58.744  1.00 43.63          C
ATOM   3539  NE2  HIS B 148      -3.886  -35.735  58.036  1.00 43.44          N
ATOM   3540  N    TRP B 149       1.352  -33.545  62.149  1.00 47.09          N
ATOM   3541  CA   TRP B 149       2.494  -33.585  63.049  1.00 48.71          C
ATOM   3542  C    TRP B 149       2.251  -34.563  64.196  1.00 48.48          C
ATOM   3543  O    TRP B 149       1.270  -34.438  64.932  1.00 48.52          O
ATOM   3544  CB   TRP B 149       2.752  -32.185  63.606  1.00 50.54          C
ATOM   3545  CG   TRP B 149       3.966  -32.091  64.478  1.00 54.65          C
ATOM   3546  CD1  TRP B 149       5.278  -32.130  64.076  1.00 55.36          C
ATOM   3547  CD2  TRP B 149       3.988  -31.920  65.905  1.00 56.04          C
ATOM   3548  NE1  TRP B 149       6.111  -31.989  65.167  1.00 56.26          N
ATOM   3549  CE2  TRP B 149       5.347  -31.859  66.299  1.00 56.27          C
ATOM   3550  CE3  TRP B 149       2.992  -31.812  66.888  1.00 56.84          C
ATOM   3551  CZ2  TRP B 149       5.736  -31.693  67.638  1.00 57.26          C
ATOM   3552  CZ3  TRP B 149       3.378  -31.647  68.224  1.00 57.14          C
ATOM   3553  CH2  TRP B 149       4.741  -31.589  68.583  1.00 57.61          C
ATOM   3554  N    ASN B 150       3.156  -35.526  64.348  1.00 48.04          N
ATOM   3555  CA   ASN B 150       3.048  -36.543  65.391  1.00 47.50          C
ATOM   3556  C    ASN B 150       1.758  -37.322  65.239  1.00 46.63          C
ATOM   3557  O    ASN B 150       1.204  -37.824  66.216  1.00 46.26          O
ATOM   3558  CB   ASN B 150       3.099  -35.916  66.789  1.00 49.22          C
ATOM   3559  CG   ASN B 150       4.496  -35.461  67.181  1.00 50.46          C
ATOM   3560  OD1  ASN B 150       5.492  -36.098  66.833  1.00 52.22          O
ATOM   3561  ND2  ASN B 150       4.574  -34.369  67.926  1.00 50.35          N
ATOM   3562  N    ASN B 151       1.284  -37.416  64.002  1.00 45.89          N
ATOM   3563  CA   ASN B 151       0.053  -38.129  63.701  1.00 45.64          C
ATOM   3564  C    ASN B 151      -1.170  -37.480  64.351  1.00 44.35          C
ATOM   3565  O    ASN B 151      -2.210  -38.107  64.530  1.00 44.80          O
ATOM   3566  CB   ASN B 151       0.194  -39.592  64.123  1.00 46.26          C
ATOM   3567  CG   ASN B 151       1.337  -40.283  63.405  1.00 47.72          C
ATOM   3568  OD1  ASN B 151       1.324  -40.414  62.182  1.00 48.11          O
ATOM   3569  ND2  ASN B 151       2.342  -40.714  64.162  1.00 49.21          N
ATOM   3570  N    ARG B 152      -1.034  -36.210  64.705  1.00 42.76          N
ATOM   3571  CA   ARG B 152      -2.137  -35.469  65.291  1.00 40.95          C
ATOM   3572  C    ARG B 152      -2.730  -34.596  64.177  1.00 38.88          C
ATOM   3573  O    ARG B 152      -2.104  -34.376  63.142  1.00 38.17          O
ATOM   3574  CB   ARG B 152      -1.637  -34.623  66.466  1.00 41.61          C
ATOM   3575  CG   ARG B 152      -0.990  -35.464  67.565  1.00 42.28          C
ATOM   3576  CD   ARG B 152      -0.462  -34.614  68.704  1.00 43.10          C
ATOM   3577  NE   ARG B 152      -1.541  -33.954  69.433  1.00 45.15          N
ATOM   3578  CZ   ARG B 152      -1.363  -33.025  70.369  1.00 44.91          C
ATOM   3579  NH1  ARG B 152      -0.139  -32.632  70.702  1.00 45.39          N
ATOM   3580  NH2  ARG B 152      -2.414  -32.486  70.971  1.00 45.06          N
ATOM   3581  N    VAL B 153      -3.946  -34.117  64.383  1.00 37.21          N
ATOM   3582  CA   VAL B 153      -4.618  -33.295  63.385  1.00 35.09          C
ATOM   3583  C    VAL B 153      -4.986  -31.959  63.998  1.00 33.97          C
ATOM   3584  O    VAL B 153      -5.596  -31.916  65.068  1.00 33.74          O
ATOM   3585  CB   VAL B 153      -5.906  -33.996  62.887  1.00 34.78          C
ATOM   3586  CG1  VAL B 153      -6.630  -33.129  61.880  1.00 34.30          C
ATOM   3587  CG2  VAL B 153      -5.550  -35.345  62.280  1.00 34.89          C
ATOM   3588  N    PHE B 154      -4.610  -30.871  63.329  1.00 32.07          N
ATOM   3589  CA   PHE B 154      -4.942  -29.540  63.831  1.00 30.61          C
ATOM   3590  C    PHE B 154      -6.428  -29.275  63.594  1.00 30.19          C
ATOM   3591  O    PHE B 154      -6.910  -29.367  62.462  1.00 29.09          O
ATOM   3592  CB   PHE B 154      -4.123  -28.464  63.119  1.00 31.07          C
ATOM   3593  CG   PHE B 154      -4.371  -27.081  63.649  1.00 31.06          C
ATOM   3594  CD1  PHE B 154      -3.831  -26.685  64.870  1.00 31.05          C
ATOM   3595  CD2  PHE B 154      -5.197  -26.198  62.962  1.00 30.16          C
ATOM   3596  CE1  PHE B 154      -4.114  -25.430  65.403  1.00 31.45          C
ATOM   3597  CE2  PHE B 154      -5.487  -24.949  63.483  1.00 31.13          C
ATOM   3598  CZ   PHE B 154      -4.945  -24.559  64.711  1.00 31.26          C
ATOM   3599  N    VAL B 155      -7.151  -28.938  64.656  1.00 28.82          N
ATOM   3600  CA   VAL B 155      -8.581  -28.686  64.535  1.00 28.81          C
ATOM   3601  C    VAL B 155      -8.980  -27.307  65.050  1.00 28.96          C
ATOM   3602  O    VAL B 155     -10.169  -26.972  65.083  1.00 28.75          O
ATOM   3603  CB   VAL B 155      -9.419  -29.775  65.292  1.00 29.10          C
```

FIGURE 2-54 (COORDINATES)

```
ATOM   3604  CG1  VAL B 155      -9.250  -31.123  64.622  1.00 28.64           C
ATOM   3605  CG2  VAL B 155      -8.987  -29.861  66.749  1.00 27.68           C
ATOM   3606  N    GLY B 156      -7.981  -26.524  65.450  1.00 28.74           N
ATOM   3607  CA   GLY B 156      -8.211  -25.181  65.956  1.00 28.96           C
ATOM   3608  C    GLY B 156      -9.465  -25.017  66.788  1.00 30.20           C
ATOM   3609  O    GLY B 156     -10.437  -24.399  66.348  1.00 30.58           O
ATOM   3610  N    ALA B 157      -9.441  -25.564  68.001  1.00 30.73           N
ATOM   3611  CA   ALA B 157     -10.583  -25.486  68.903  1.00 30.89           C
ATOM   3612  C    ALA B 157     -10.958  -24.035  69.221  1.00 30.83           C
ATOM   3613  O    ALA B 157     -12.120  -23.650  69.111  1.00 32.00           O
ATOM   3614  CB   ALA B 157     -10.278  -26.251  70.189  1.00 30.85           C
ATOM   3615  N    THR B 158      -9.980  -23.233  69.623  1.00 30.65           N
ATOM   3616  CA   THR B 158     -10.240  -21.826  69.934  1.00 30.82           C
ATOM   3617  C    THR B 158     -10.145  -20.989  68.656  1.00 31.56           C
ATOM   3618  O    THR B 158     -10.679  -19.876  68.580  1.00 30.98           O
ATOM   3619  CB   THR B 158      -9.180  -21.242  70.875  1.00 31.29           C
ATOM   3620  OG1  THR B 158      -7.918  -21.236  70.191  1.00 29.19           O
ATOM   3621  CG2  THR B 158      -9.068  -22.060  72.181  1.00 29.89           C
ATOM   3622  N    ASP B 159      -9.483  -21.566  67.653  1.00 31.27           N
ATOM   3623  CA   ASP B 159      -9.192  -20.898  66.396  1.00 31.12           C
ATOM   3624  C    ASP B 159      -9.711  -21.600  65.123  1.00 30.77           C
ATOM   3625  O    ASP B 159      -8.932  -22.204  64.380  1.00 30.52           O
ATOM   3626  CB   ASP B 159      -7.663  -20.719  66.368  1.00 30.50           C
ATOM   3627  CG   ASP B 159      -7.152  -20.036  65.129  1.00 31.24           C
ATOM   3628  OD1  ASP B 159      -7.926  -19.317  64.463  1.00 32.65           O
ATOM   3629  OD2  ASP B 159      -5.950  -20.207  64.839  1.00 30.19           O
ATOM   3630  N    SER B 160     -11.010  -21.495  64.853  1.00 29.89           N
ATOM   3631  CA   SER B 160     -11.966  -20.801  65.722  1.00 30.84           C
ATOM   3632  C    SER B 160     -13.287  -21.566  65.859  1.00 30.94           C
ATOM   3633  O    SER B 160     -14.367  -21.009  65.643  1.00 30.22           O
ATOM   3634  CB   SER B 160     -12.249  -19.397  65.189  1.00 30.23           C
ATOM   3635  OG   SER B 160     -11.207  -18.510  65.547  1.00 31.63           O
ATOM   3636  N    ALA B 161     -13.195  -22.843  66.225  1.00 31.04           N
ATOM   3637  CA   ALA B 161     -14.385  -23.672  66.384  1.00 30.60           C
ATOM   3638  C    ALA B 161     -15.317  -23.113  67.460  1.00 30.72           C
ATOM   3639  O    ALA B 161     -16.530  -23.038  67.254  1.00 31.20           O
ATOM   3640  CB   ALA B 161     -13.981  -25.109  66.718  1.00 30.50           C
ATOM   3641  N    VAL B 162     -14.756  -22.718  68.601  1.00 30.15           N
ATOM   3642  CA   VAL B 162     -15.561  -22.156  69.686  1.00 30.76           C
ATOM   3643  C    VAL B 162     -16.321  -20.907  69.218  1.00 30.96           C
ATOM   3644  O    VAL B 162     -17.540  -20.835  69.368  1.00 31.55           O
ATOM   3645  CB   VAL B 162     -14.687  -21.821  70.930  1.00 31.59           C
ATOM   3646  CG1  VAL B 162     -15.509  -21.054  71.960  1.00 30.98           C
ATOM   3647  CG2  VAL B 162     -14.152  -23.115  71.551  1.00 31.70           C
ATOM   3648  N    PRO B 163     -15.615  -19.901  68.665  1.00 30.82           N
ATOM   3649  CA   PRO B 163     -16.333  -18.711  68.200  1.00 31.09           C
ATOM   3650  C    PRO B 163     -17.514  -19.103  67.295  1.00 31.93           C
ATOM   3651  O    PRO B 163     -18.575  -18.483  67.342  1.00 31.89           O
ATOM   3652  CB   PRO B 163     -15.250  -17.934  67.464  1.00 31.22           C
ATOM   3653  CG   PRO B 163     -14.041  -18.194  68.330  1.00 30.12           C
ATOM   3654  CD   PRO B 163     -14.155  -19.686  68.609  1.00 29.96           C
ATOM   3655  N    CYS B 164     -17.330  -20.137  66.476  1.00 32.13           N
ATOM   3656  CA   CYS B 164     -18.411  -20.606  65.611  1.00 31.98           C
ATOM   3657  C    CYS B 164     -19.563  -21.109  66.484  1.00 32.27           C
ATOM   3658  O    CYS B 164     -20.720  -20.735  66.281  1.00 32.79           O
ATOM   3659  CB   CYS B 164     -17.949  -21.765  64.721  1.00 31.52           C
ATOM   3660  SG   CYS B 164     -16.866  -21.385  63.327  1.00 30.72           S
ATOM   3661  N    ALA B 165     -19.234  -21.968  67.448  1.00 31.88           N
ATOM   3662  CA   ALA B 165     -20.230  -22.550  68.351  1.00 31.89           C
ATOM   3663  C    ALA B 165     -20.958  -21.483  69.146  1.00 31.79           C
ATOM   3664  O    ALA B 165     -22.174  -21.556  69.325  1.00 31.09           O
ATOM   3665  CB   ALA B 165     -19.563  -23.552  69.305  1.00 31.41           C
ATOM   3666  N    MET B 166     -20.209  -20.499  69.633  1.00 32.57           N
ATOM   3667  CA   MET B 166     -20.793  -19.400  70.398  1.00 33.65           C
ATOM   3668  C    MET B 166     -21.850  -18.668  69.566  1.00 33.58           C
ATOM   3669  O    MET B 166     -22.924  -18.339  70.065  1.00 33.93           O
ATOM   3670  CB   MET B 166     -19.697  -18.423  70.834  1.00 34.66           C
ATOM   3671  CG   MET B 166     -18.679  -19.045  71.778  1.00 36.04           C
```

FIGURE 2-55 (COORDINATES)

```
ATOM   3672  SD  MET B 166     -17.314 -17.939  72.198  1.00 38.60           S
ATOM   3673  CE  MET B 166     -18.192 -16.629  73.128  1.00 36.18           C
ATOM   3674  N   MET B 167     -21.549 -18.429  68.294  1.00 33.49           N
ATOM   3675  CA  MET B 167     -22.490 -17.743  67.412  1.00 33.76           C
ATOM   3676  C   MET B 167     -23.738 -18.595  67.201  1.00 34.15           C
ATOM   3677  O   MET B 167     -24.859 -18.080  67.216  1.00 32.81           O
ATOM   3678  CB  MET B 167     -21.820 -17.416  66.077  1.00 33.21           C
ATOM   3679  CG  MET B 167     -20.882 -16.222  66.162  1.00 33.03           C
ATOM   3680  SD  MET B 167     -19.663 -16.136  64.838  1.00 35.74           S
ATOM   3681  CE  MET B 167     -20.726 -15.860  63.408  1.00 32.34           C
ATOM   3682  N   LEU B 168     -23.539 -19.898  67.011  1.00 34.33           N
ATOM   3683  CA  LEU B 168     -24.658 -20.815  66.828  1.00 34.77           C
ATOM   3684  C   LEU B 168     -25.492 -20.878  68.113  1.00 35.41           C
ATOM   3685  O   LEU B 168     -26.723 -20.902  68.066  1.00 35.35           O
ATOM   3686  CB  LEU B 168     -24.154 -22.212  66.462  1.00 34.19           C
ATOM   3687  CG  LEU B 168     -23.551 -22.350  65.065  1.00 33.61           C
ATOM   3688  CD1 LEU B 168     -23.034 -23.762  64.853  1.00 32.11           C
ATOM   3689  CD2 LEU B 168     -24.608 -22.009  64.034  1.00 33.30           C
ATOM   3690  N   GLU B 169     -24.821 -20.895  69.260  1.00 35.50           N
ATOM   3691  CA  GLU B 169     -25.527 -20.938  70.532  1.00 35.84           C
ATOM   3692  C   GLU B 169     -26.317 -19.644  70.752  1.00 36.17           C
ATOM   3693  O   GLU B 169     -27.417 -19.664  71.304  1.00 35.14           O
ATOM   3694  CB  GLU B 169     -24.539 -21.155  71.682  1.00 35.50           C
ATOM   3695  CG  GLU B 169     -25.107 -20.914  73.086  1.00 35.85           C
ATOM   3696  CD  GLU B 169     -26.354 -21.743  73.403  1.00 36.99           C
ATOM   3697  OE1 GLU B 169     -26.642 -22.727  72.682  1.00 35.70           O
ATOM   3698  OE2 GLU B 169     -27.045 -21.405  74.391  1.00 37.69           O
ATOM   3699  N   LEU B 170     -25.753 -18.519  70.323  1.00 36.89           N
ATOM   3700  CA  LEU B 170     -26.427 -17.236  70.486  1.00 37.06           C
ATOM   3701  C   LEU B 170     -27.721 -17.224  69.668  1.00 37.62           C
ATOM   3702  O   LEU B 170     -28.768 -16.766  70.140  1.00 37.35           O
ATOM   3703  CB  LEU B 170     -25.502 -16.086  70.066  1.00 36.14           C
ATOM   3704  CG  LEU B 170     -26.097 -14.672  70.158  1.00 36.69           C
ATOM   3705  CD1 LEU B 170     -25.022 -13.665  70.567  1.00 36.57           C
ATOM   3706  CD2 LEU B 170     -26.727 -14.297  68.816  1.00 35.89           C
ATOM   3707  N   ALA B 171     -27.646 -17.743  68.449  1.00 37.62           N
ATOM   3708  CA  ALA B 171     -28.806 -17.807  67.580  1.00 38.36           C
ATOM   3709  C   ALA B 171     -29.891 -18.710  68.172  1.00 39.91           C
ATOM   3710  O   ALA B 171     -31.080 -18.438  68.031  1.00 40.26           O
ATOM   3711  CB  ALA B 171     -28.397 -18.318  66.211  1.00 37.52           C
ATOM   3712  N   ARG B 172     -29.484 -19.789  68.829  1.00 41.08           N
ATOM   3713  CA  ARG B 172     -30.447 -20.711  69.422  1.00 42.43           C
ATOM   3714  C   ARG B 172     -31.067 -20.145  70.703  1.00 42.74           C
ATOM   3715  O   ARG B 172     -32.288 -20.163  70.871  1.00 43.28           O
ATOM   3716  CB  ARG B 172     -29.775 -22.051  69.728  1.00 42.41           C
ATOM   3717  CG  ARG B 172     -30.730 -23.132  70.226  1.00 42.98           C
ATOM   3718  CD  ARG B 172     -29.985 -24.183  71.046  1.00 42.40           C
ATOM   3719  NE  ARG B 172     -29.432 -23.601  72.267  1.00 43.67           N
ATOM   3720  CZ  ARG B 172     -30.170 -23.127  73.269  1.00 44.08           C
ATOM   3721  NH1 ARG B 172     -31.495 -23.171  73.198  1.00 44.21           N
ATOM   3722  NH2 ARG B 172     -29.586 -22.597  74.337  1.00 43.23           N
ATOM   3723  N   ALA B 173     -30.223 -19.635  71.595  1.00 42.52           N
ATOM   3724  CA  ALA B 173     -30.672 -19.074  72.869  1.00 42.55           C
ATOM   3725  C   ALA B 173     -31.576 -17.848  72.732  1.00 42.89           C
ATOM   3726  O   ALA B 173     -32.478 -17.644  73.547  1.00 43.59           O
ATOM   3727  CB  ALA B 173     -29.464 -18.730  73.737  1.00 41.57           C
ATOM   3728  N   LEU B 174     -31.339 -17.029  71.711  1.00 42.80           N
ATOM   3729  CA  LEU B 174     -32.153 -15.834  71.506  1.00 42.64           C
ATOM   3730  C   LEU B 174     -33.175 -16.031  70.394  1.00 42.93           C
ATOM   3731  O   LEU B 174     -33.850 -15.083  69.996  1.00 43.18           O
ATOM   3732  CB  LEU B 174     -31.263 -14.638  71.157  1.00 41.11           C
ATOM   3733  CG  LEU B 174     -30.113 -14.337  72.117  1.00 40.20           C
ATOM   3734  CD1 LEU B 174     -29.333 -13.132  71.614  1.00 39.69           C
ATOM   3735  CD2 LEU B 174     -30.655 -14.090  73.511  1.00 38.98           C
ATOM   3736  N   ASP B 175     -33.296 -17.260  69.903  1.00 43.69           N
ATOM   3737  CA  ASP B 175     -34.216 -17.566  68.809  1.00 45.22           C
ATOM   3738  C   ASP B 175     -35.594 -16.914  68.939  1.00 46.58           C
ATOM   3739  O   ASP B 175     -36.025 -16.191  68.041  1.00 46.49           O
```

FIGURE 2-56 (COORDINATES)

```
ATOM   3740  CB   ASP B 175     -34.357 -19.086  68.653  1.00 44.63           C
ATOM   3741  CG   ASP B 175     -35.138 -19.479  67.408  1.00 45.63           C
ATOM   3742  OD1  ASP B 175     -34.988 -18.793  66.374  1.00 46.57           O
ATOM   3743  OD2  ASP B 175     -35.888 -20.481  67.454  1.00 45.88           O
ATOM   3744  N    LYS B 176     -36.276 -17.165  70.055  1.00 48.17           N
ATOM   3745  CA   LYS B 176     -37.603 -16.605  70.291  1.00 49.73           C
ATOM   3746  C    LYS B 176     -37.620 -15.078  70.179  1.00 49.73           C
ATOM   3747  O    LYS B 176     -38.492 -14.514  69.524  1.00 49.37           O
ATOM   3748  CB   LYS B 176     -38.114 -17.024  71.673  1.00 51.18           C
ATOM   3749  CG   LYS B 176     -39.553 -16.622  71.959  1.00 53.79           C
ATOM   3750  CD   LYS B 176     -39.955 -16.996  73.388  1.00 56.87           C
ATOM   3751  CE   LYS B 176     -41.431 -16.711  73.661  1.00 57.92           C
ATOM   3752  NZ   LYS B 176     -41.828 -17.126  75.043  1.00 59.71           N
ATOM   3753  N    LYS B 177     -36.663 -14.412  70.818  1.00 50.01           N
ATOM   3754  CA   LYS B 177     -36.598 -12.954  70.758  1.00 51.04           C
ATOM   3755  C    LYS B 177     -36.241 -12.432  69.363  1.00 51.41           C
ATOM   3756  O    LYS B 177     -36.732 -11.384  68.951  1.00 51.84           O
ATOM   3757  CB   LYS B 177     -35.595 -12.417  71.787  1.00 51.04           C
ATOM   3758  CG   LYS B 177     -36.057 -12.584  73.223  1.00 51.72           C
ATOM   3759  CD   LYS B 177     -34.988 -12.176  74.217  1.00 52.18           C
ATOM   3760  CE   LYS B 177     -35.436 -12.433  75.659  1.00 52.71           C
ATOM   3761  NZ   LYS B 177     -36.601 -11.592  76.060  1.00 53.49           N
ATOM   3762  N    LEU B 178     -35.393 -13.156  68.638  1.00 51.35           N
ATOM   3763  CA   LEU B 178     -34.999 -12.736  67.294  1.00 51.44           C
ATOM   3764  C    LEU B 178     -36.169 -12.900  66.323  1.00 52.23           C
ATOM   3765  O    LEU B 178     -36.259 -12.206  65.300  1.00 51.91           O
ATOM   3766  CB   LEU B 178     -33.803 -13.562  66.808  1.00 50.17           C
ATOM   3767  CG   LEU B 178     -32.469 -13.370  67.539  1.00 49.95           C
ATOM   3768  CD1  LEU B 178     -31.460 -14.403  67.042  1.00 48.49           C
ATOM   3769  CD2  LEU B 178     -31.952 -11.950  67.317  1.00 47.82           C
ATOM   3770  N    LEU B 179     -37.069 -13.818  66.661  1.00 52.68           N
ATOM   3771  CA   LEU B 179     -38.244 -14.107  65.847  1.00 53.21           C
ATOM   3772  C    LEU B 179     -39.157 -12.893  65.679  1.00 53.44           C
ATOM   3773  O    LEU B 179     -39.891 -12.798  64.697  1.00 53.31           O
ATOM   3774  CB   LEU B 179     -39.035 -15.265  66.471  1.00 52.96           C
ATOM   3775  CG   LEU B 179     -40.354 -15.668  65.811  1.00 52.50           C
ATOM   3776  CD1  LEU B 179     -40.092 -16.080  64.381  1.00 52.43           C
ATOM   3777  CD2  LEU B 179     -40.994 -16.804  66.587  1.00 51.89           C
ATOM   3778  N    SER B 180     -39.111 -11.969  66.634  1.00 53.50           N
ATOM   3779  CA   SER B 180     -39.946 -10.771  66.577  1.00 54.41           C
ATOM   3780  C    SER B 180     -39.505  -9.768  65.500  1.00 55.01           C
ATOM   3781  O    SER B 180     -40.286  -8.911  65.088  1.00 56.03           O
ATOM   3782  CB   SER B 180     -39.962 -10.079  67.940  1.00 54.22           C
ATOM   3783  OG   SER B 180     -38.689  -9.549  68.259  1.00 54.76           O
ATOM   3784  N    LEU B 181     -38.260  -9.875  65.047  1.00 55.23           N
ATOM   3785  CA   LEU B 181     -37.735  -8.978  64.020  1.00 54.80           C
ATOM   3786  C    LEU B 181     -38.514  -9.055  62.703  1.00 54.98           C
ATOM   3787  O    LEU B 181     -39.378 -10.621  62.284  1.00 51.92           O
ATOM   3788  CB   LEU B 181     -36.254  -9.278  63.773  1.00 54.28           C
ATOM   3789  CG   LEU B 181     -35.314  -8.919  64.930  1.00 53.91           C
ATOM   3790  CD1  LEU B 181     -33.934  -9.517  64.700  1.00 53.58           C
ATOM   3791  CD2  LEU B 181     -35.234  -7.406  65.063  1.00 53.52           C
ATOM   3792  N    ASP B 190     -35.327  -0.620  61.674  1.00 52.48           N
ATOM   3793  CA   ASP B 190     -34.722  -1.122  60.404  1.00 51.95           C
ATOM   3794  C    ASP B 190     -33.255  -1.448  60.665  1.00 50.22           C
ATOM   3795  O    ASP B 190     -32.348  -1.008  59.953  1.00 48.84           O
ATOM   3796  CB   ASP B 190     -34.852  -0.066  59.308  1.00 53.94           C
ATOM   3797  CG   ASP B 190     -34.741  -0.656  57.919  1.00 55.84           C
ATOM   3798  OD1  ASP B 190     -35.379  -1.696  57.656  1.00 57.12           O
ATOM   3799  OD2  ASP B 190     -34.022  -0.077  57.083  1.00 56.92           O
ATOM   3800  N    LEU B 191     -33.060  -2.227  61.720  1.00 47.72           N
ATOM   3801  CA   LEU B 191     -31.758  -2.680  62.171  1.00 45.55           C
ATOM   3802  C    LEU B 191     -31.957  -4.126  62.605  1.00 43.85           C
ATOM   3803  O    LEU B 191     -32.801  -4.404  63.449  1.00 43.94           O
ATOM   3804  CB   LEU B 191     -31.305  -1.838  63.364  1.00 45.08           C
ATOM   3805  CG   LEU B 191     -30.171  -2.422  64.205  1.00 44.41           C
ATOM   3806  CD1  LEU B 191     -28.889  -2.423  63.390  1.00 43.88           C
ATOM   3807  CD2  LEU B 191     -30.002  -1.612  65.482  1.00 43.57           C
```

FIGURE 2-57 (COORDINATES)

```
ATOM   3808  N    SER B 192     -31.198   -5.049  62.025  1.00 42.21           N
ATOM   3809  CA   SER B 192     -31.339   -6.452  62.389  1.00 40.09           C
ATOM   3810  C    SER B 192     -29.989   -7.125  62.655  1.00 38.65           C
ATOM   3811  O    SER B 192     -28.987   -6.449  62.890  1.00 37.66           O
ATOM   3812  CB   SER B 192     -32.110   -7.198  61.297  1.00 40.35           C
ATOM   3813  OG   SER B 192     -32.645   -8.411  61.795  1.00 40.87           O
ATOM   3814  N    LEU B 193     -29.965   -8.454  62.606  1.00 37.11           N
ATOM   3815  CA   LEU B 193     -28.750   -9.210  62.889  1.00 35.59           C
ATOM   3816  C    LEU B 193     -28.218  -10.041  61.726  1.00 34.99           C
ATOM   3817  O    LEU B 193     -28.979  -10.613  60.934  1.00 34.26           O
ATOM   3818  CB   LEU B 193     -28.991  -10.120  64.097  1.00 36.51           C
ATOM   3819  CG   LEU B 193     -27.843  -10.968  64.655  1.00 37.14           C
ATOM   3820  CD1  LEU B 193     -26.692  -10.070  65.100  1.00 36.71           C
ATOM   3821  CD2  LEU B 193     -28.354  -11.791  65.831  1.00 35.30           C
ATOM   3822  N    GLN B 194     -26.892  -10.094  61.636  1.00 33.24           N
ATOM   3823  CA   GLN B 194     -26.221  -10.853  60.596  1.00 31.45           C
ATOM   3824  C    GLN B 194     -25.026  -11.615  61.155  1.00 31.41           C
ATOM   3825  O    GLN B 194     -24.254  -11.101  61.975  1.00 31.15           O
ATOM   3826  CB   GLN B 194     -25.771   -9.927  59.467  1.00 30.65           C
ATOM   3827  CG   GLN B 194     -24.991  -10.618  58.366  1.00 31.34           C
ATOM   3828  CD   GLN B 194     -24.803   -9.742  57.133  1.00 32.06           C
ATOM   3829  OE1  GLN B 194     -25.490   -9.915  56.128  1.00 33.02           O
ATOM   3830  NE2  GLN B 194     -23.877   -8.796  57.210  1.00 29.85           N
ATOM   3831  N    LEU B 195     -24.897  -12.862  60.720  1.00 30.57           N
ATOM   3832  CA   LEU B 195     -23.797  -13.711  61.144  1.00 29.55           C
ATOM   3833  C    LEU B 195     -22.946  -14.024  59.923  1.00 29.44           C
ATOM   3834  O    LEU B 195     -23.468  -14.336  58.842  1.00 29.80           O
ATOM   3835  CB   LEU B 195     -24.322  -15.021  61.731  1.00 28.35           C
ATOM   3836  CG   LEU B 195     -25.354  -14.944  62.856  1.00 28.49           C
ATOM   3837  CD1  LEU B 195     -25.753  -16.362  63.263  1.00 27.67           C
ATOM   3838  CD2  LEU B 195     -24.769  -14.178  64.046  1.00 28.18           C
ATOM   3839  N    ILE B 196     -21.637  -13.924  60.083  1.00 27.94           N
ATOM   3840  CA   ILE B 196     -20.747  -14.248  58.989  1.00 27.46           C
ATOM   3841  C    ILE B 196     -19.691  -15.233  59.462  1.00 27.47           C
ATOM   3842  O    ILE B 196     -19.015  -15.014  60.471  1.00 26.29           O
ATOM   3843  CB   ILE B 196     -20.031  -13.004  58.421  1.00 27.31           C
ATOM   3844  CG1  ILE B 196     -21.050  -12.046  57.793  1.00 27.12           C
ATOM   3845  CG2  ILE B 196     -18.987  -13.439  57.386  1.00 26.49           C
ATOM   3846  CD1  ILE B 196     -20.426  -10.774  57.221  1.00 24.61           C
ATOM   3847  N    PHE B 197     -19.568  -16.328  58.725  1.00 27.94           N
ATOM   3848  CA   PHE B 197     -18.578  -17.348  59.024  1.00 27.90           C
ATOM   3849  C    PHE B 197     -17.597  -17.285  57.854  1.00 28.20           C
ATOM   3850  O    PHE B 197     -17.886  -17.774  56.761  1.00 28.02           O
ATOM   3851  CB   PHE B 197     -19.247  -18.725  59.106  1.00 28.06           C
ATOM   3852  CG   PHE B 197     -20.294  -18.830  60.190  1.00 28.69           C
ATOM   3853  CD1  PHE B 197     -19.971  -19.345  61.445  1.00 29.05           C
ATOM   3854  CD2  PHE B 197     -21.604  -18.398  59.959  1.00 29.34           C
ATOM   3855  CE1  PHE B 197     -20.935  -19.432  62.460  1.00 29.17           C
ATOM   3856  CE2  PHE B 197     -22.579  -18.479  60.965  1.00 29.39           C
ATOM   3857  CZ   PHE B 197     -22.240  -18.997  62.219  1.00 29.13           C
ATOM   3858  N    PHE B 198     -16.446  -16.657  58.080  1.00 27.49           N
ATOM   3859  CA   PHE B 198     -15.445  -16.535  57.035  1.00 26.84           C
ATOM   3860  C    PHE B 198     -14.721  -17.843  56.754  1.00 26.41           C
ATOM   3861  O    PHE B 198     -14.457  -18.634  57.654  1.00 26.52           O
ATOM   3862  CB   PHE B 198     -14.398  -15.470  57.402  1.00 27.04           C
ATOM   3863  CG   PHE B 198     -14.936  -14.063  57.446  1.00 26.23           C
ATOM   3864  CD1  PHE B 198     -15.411  -13.446  56.291  1.00 26.19           C
ATOM   3865  CD2  PHE B 198     -14.954  -13.350  58.643  1.00 25.92           C
ATOM   3866  CE1  PHE B 198     -15.897  -12.132  56.326  1.00 25.52           C
ATOM   3867  CE2  PHE B 198     -15.434  -12.043  58.689  1.00 26.11           C
ATOM   3868  CZ   PHE B 198     -15.907  -11.431  57.524  1.00 25.64           C
ATOM   3869  N    ASP B 199     -14.418  -18.063  55.483  1.00 26.28           N
ATOM   3870  CA   ASP B 199     -13.665  -19.230  55.066  1.00 26.03           C
ATOM   3871  C    ASP B 199     -12.278  -18.664  54.737  1.00 26.20           C
ATOM   3872  O    ASP B 199     -12.131  -17.455  54.556  1.00 25.94           O
ATOM   3873  CB   ASP B 199     -14.304  -19.862  53.821  1.00 26.01           C
ATOM   3874  CG   ASP B 199     -13.643  -21.178  53.427  1.00 26.19           C
ATOM   3875  OD1  ASP B 199     -12.843  -21.696  54.226  1.00 25.83           O
```

FIGURE 2-58 (COORDINATES)

```
ATOM   3876  OD2 ASP B 199     -13.925 -21.698  52.328  1.00 24.25           O
ATOM   3877  N   GLY B 200     -11.262 -19.519  54.702  1.00 26.30           N
ATOM   3878  CA  GLY B 200      -9.919 -19.070  54.372  1.00 26.67           C
ATOM   3879  C   GLY B 200      -9.261 -17.932  55.146  1.00 27.21           C
ATOM   3880  O   GLY B 200      -8.497 -17.149  54.579  1.00 27.61           O
ATOM   3881  N   GLU B 201      -9.522 -17.822  56.439  1.00 27.43           N
ATOM   3882  CA  GLU B 201      -8.876 -16.766  57.202  1.00 27.18           C
ATOM   3883  C   GLU B 201      -7.368 -17.064  57.303  1.00 27.50           C
ATOM   3884  O   GLU B 201      -6.540 -16.167  57.173  1.00 28.13           O
ATOM   3885  CB  GLU B 201      -9.497 -16.674  58.595  1.00 26.67           C
ATOM   3886  CG  GLU B 201      -8.961 -15.544  59.477  1.00 29.10           C
ATOM   3887  CD  GLU B 201      -7.715 -15.922  60.293  1.00 31.79           C
ATOM   3888  OE1 GLU B 201      -7.224 -17.071  60.186  1.00 31.09           O
ATOM   3889  OE2 GLU B 201      -7.225 -15.054  61.053  1.00 33.70           O
ATOM   3890  N   GLU B 202      -7.031 -18.332  57.526  1.00 27.20           N
ATOM   3891  CA  GLU B 202      -5.648 -18.778  57.674  1.00 27.14           C
ATOM   3892  C   GLU B 202      -4.865 -18.823  56.361  1.00 28.04           C
ATOM   3893  O   GLU B 202      -5.409 -19.130  55.297  1.00 27.70           O
ATOM   3894  CB  GLU B 202      -5.608 -20.180  58.313  1.00 26.45           C
ATOM   3895  CG  GLU B 202      -6.247 -20.293  59.700  1.00 26.25           C
ATOM   3896  CD  GLU B 202      -5.406 -19.672  60.807  1.00 27.06           C
ATOM   3897  OE1 GLU B 202      -4.405 -18.984  60.496  1.00 28.39           O
ATOM   3898  OE2 GLU B 202      -5.747 -19.869  61.995  1.00 25.88           O
ATOM   3899  N   ALA B 203      -3.576 -18.522  56.455  1.00 27.94           N
ATOM   3900  CA  ALA B 203      -2.704 -18.556  55.299  1.00 29.43           C
ATOM   3901  C   ALA B 203      -2.495 -20.026  54.978  1.00 30.48           C
ATOM   3902  O   ALA B 203      -2.536 -20.868  55.868  1.00 31.50           O
ATOM   3903  CB  ALA B 203      -1.373 -17.895  55.628  1.00 28.34           C
ATOM   3904  N   PHE B 204      -2.286 -20.337  53.706  1.00 32.23           N
ATOM   3905  CA  PHE B 204      -2.063 -21.714  53.296  1.00 34.23           C
ATOM   3906  C   PHE B 204      -0.607 -22.122  53.488  1.00 35.76           C
ATOM   3907  O   PHE B 204      -0.314 -23.254  53.886  1.00 36.14           O
ATOM   3908  CB  PHE B 204      -2.440 -21.898  51.829  1.00 34.41           C
ATOM   3909  CG  PHE B 204      -3.774 -22.539  51.626  1.00 36.07           C
ATOM   3910  CD1 PHE B 204      -4.820 -21.836  51.038  1.00 36.32           C
ATOM   3911  CD2 PHE B 204      -3.991 -23.853  52.030  1.00 36.82           C
ATOM   3912  CE1 PHE B 204      -6.061 -22.432  50.854  1.00 36.03           C
ATOM   3913  CE2 PHE B 204      -5.229 -24.458  51.850  1.00 36.51           C
ATOM   3914  CZ  PHE B 204      -6.264 -23.746  51.262  1.00 37.16           C
ATOM   3915  N   LEU B 205       0.300 -21.191  53.204  1.00 36.42           N
ATOM   3916  CA  LEU B 205       1.725 -21.454  53.311  1.00 36.78           C
ATOM   3917  C   LEU B 205       2.466 -20.521  54.259  1.00 37.40           C
ATOM   3918  O   LEU B 205       3.295 -20.972  55.044  1.00 38.01           O
ATOM   3919  CB  LEU B 205       2.361 -21.381  51.923  1.00 35.72           C
ATOM   3920  CG  LEU B 205       3.882 -21.502  51.846  1.00 35.84           C
ATOM   3921  CD1 LEU B 205       4.348 -22.808  52.482  1.00 35.01           C
ATOM   3922  CD2 LEU B 205       4.297 -21.433  50.391  1.00 35.86           C
ATOM   3923  N   HIS B 206       2.176 -19.227  54.183  1.00 37.43           N
ATOM   3924  CA  HIS B 206       2.838 -18.247  55.032  1.00 38.64           C
ATOM   3925  C   HIS B 206       2.031 -16.965  55.025  1.00 38.80           C
ATOM   3926  O   HIS B 206       1.725 -16.424  53.966  1.00 38.54           O
ATOM   3927  CB  HIS B 206       4.245 -17.962  54.515  1.00 39.81           C
ATOM   3928  CG  HIS B 206       5.313 -18.150  55.542  1.00 42.24           C
ATOM   3929  ND1 HIS B 206       6.228 -17.167  55.851  1.00 43.18           N
ATOM   3930  CD2 HIS B 206       5.635 -19.220  56.308  1.00 43.58           C
ATOM   3931  CE1 HIS B 206       7.070 -17.625  56.762  1.00 43.85           C
ATOM   3932  NE2 HIS B 206       6.733 -18.868  57.056  1.00 44.05           N
ATOM   3933  N   TRP B 207       1.697 -16.468  56.208  1.00 38.92           N
ATOM   3934  CA  TRP B 207       0.895 -15.261  56.292  1.00 40.53           C
ATOM   3935  C   TRP B 207       1.497 -14.112  55.496  1.00 42.19           C
ATOM   3936  O   TRP B 207       2.705 -13.857  55.551  1.00 43.48           O
ATOM   3937  CB  TRP B 207       0.705 -14.852  57.751  1.00 39.07           C
ATOM   3938  CG  TRP B 207      -0.356 -13.819  57.936  1.00 39.17           C
ATOM   3939  CD1 TRP B 207      -0.230 -12.471  57.752  1.00 39.27           C
ATOM   3940  CD2 TRP B 207      -1.714 -14.045  58.339  1.00 38.57           C
ATOM   3941  NE1 TRP B 207      -1.425 -11.841  58.020  1.00 39.86           N
ATOM   3942  CE2 TRP B 207      -2.353 -12.783  58.382  1.00 39.18           C
ATOM   3943  CE3 TRP B 207      -2.453 -15.190  58.665  1.00 38.07           C
```

FIGURE 2-59 (COORDINATES)

```
ATOM   3944  CZ2 TRP B 207      -3.704 -12.634  58.745  1.00 38.85           C
ATOM   3945  CZ3 TRP B 207      -3.800 -15.041  59.024  1.00 38.30           C
ATOM   3946  CH2 TRP B 207      -4.407 -13.771  59.061  1.00 38.38           C
ATOM   3947  N   SER B 208       0.642 -13.432  54.743  1.00 42.40           N
ATOM   3948  CA  SER B 208       1.057 -12.298  53.927  1.00 42.08           C
ATOM   3949  C   SER B 208      -0.190 -11.730  53.251  1.00 42.00           C
ATOM   3950  O   SER B 208      -1.242 -12.376  53.236  1.00 42.14           O
ATOM   3951  CB  SER B 208       2.085 -12.748  52.887  1.00 42.15           C
ATOM   3952  OG  SER B 208       1.570 -13.785  52.075  1.00 42.84           O
ATOM   3953  N   PRO B 209      -0.092 -10.518  52.679  1.00 41.96           N
ATOM   3954  CA  PRO B 209      -1.236  -9.886  52.012  1.00 41.29           C
ATOM   3955  C   PRO B 209      -2.030 -10.786  51.060  1.00 40.87           C
ATOM   3956  O   PRO B 209      -3.254 -10.774  51.077  1.00 40.19           O
ATOM   3957  CB  PRO B 209      -0.597  -8.702  51.291  1.00 41.63           C
ATOM   3958  CG  PRO B 209       0.532  -8.334  52.202  1.00 41.41           C
ATOM   3959  CD  PRO B 209       1.117  -9.682  52.537  1.00 41.50           C
ATOM   3960  N   GLN B 210      -1.335 -11.567  50.237  1.00 41.17           N
ATOM   3961  CA  GLN B 210      -2.008 -12.437  49.276  1.00 41.39           C
ATOM   3962  C   GLN B 210      -2.214 -13.889  49.732  1.00 40.07           C
ATOM   3963  O   GLN B 210      -2.765 -14.706  48.995  1.00 39.45           O
ATOM   3964  CB  GLN B 210      -1.259 -12.403  47.942  1.00 43.38           C
ATOM   3965  CG  GLN B 210      -1.193 -11.001  47.316  1.00 47.95           C
ATOM   3966  CD  GLN B 210      -2.569 -10.429  46.925  1.00 49.83           C
ATOM   3967  OE1 GLN B 210      -2.728  -9.212  46.796  1.00 51.15           O
ATOM   3968  NE2 GLN B 210      -3.553 -11.304  46.724  1.00 49.62           N
ATOM   3969  N   ASP B 211      -1.759 -14.211  50.937  1.00 38.46           N
ATOM   3970  CA  ASP B 211      -1.937 -15.550  51.485  1.00 36.63           C
ATOM   3971  C   ASP B 211      -2.469 -15.421  52.911  1.00 35.48           C
ATOM   3972  O   ASP B 211      -1.721 -15.517  53.881  1.00 35.39           O
ATOM   3973  CB  ASP B 211      -0.625 -16.331  51.497  1.00 36.44           C
ATOM   3974  CG  ASP B 211      -0.830 -17.806  51.836  1.00 37.06           C
ATOM   3975  OD1 ASP B 211       0.172 -18.531  52.013  1.00 37.25           O
ATOM   3976  OD2 ASP B 211      -1.996 -18.241  51.920  1.00 35.68           O
ATOM   3977  N   SER B 212      -3.770 -15.173  53.003  1.00 33.67           N
ATOM   3978  CA  SER B 212      -4.493 -15.020  54.260  1.00 32.69           C
ATOM   3979  C   SER B 212      -5.726 -14.177  53.959  1.00 31.12           C
ATOM   3980  O   SER B 212      -5.804 -13.537  52.912  1.00 29.59           O
ATOM   3981  CB  SER B 212      -3.636 -14.314  55.327  1.00 32.83           C
ATOM   3982  OG  SER B 212      -3.341 -12.976  54.969  1.00 32.11           O
ATOM   3983  N   LEU B 213      -6.681 -14.194  54.878  1.00 30.31           N
ATOM   3984  CA  LEU B 213      -7.910 -13.418  54.747  1.00 29.96           C
ATOM   3985  C   LEU B 213      -8.592 -13.550  53.382  1.00 29.81           C
ATOM   3986  O   LEU B 213      -9.223 -12.609  52.898  1.00 30.29           O
ATOM   3987  CB  LEU B 213      -7.617 -11.945  55.035  1.00 27.73           C
ATOM   3988  CG  LEU B 213      -6.732 -11.697  56.259  1.00 26.68           C
ATOM   3989  CD1 LEU B 213      -6.516 -10.204  56.437  1.00 26.88           C
ATOM   3990  CD2 LEU B 213      -7.383 -12.291  57.495  1.00 26.15           C
ATOM   3991  N   TYR B 214      -8.470 -14.716  52.768  1.00 29.14           N
ATOM   3992  CA  TYR B 214      -9.087 -14.962  51.470  1.00 30.11           C
ATOM   3993  C   TYR B 214     -10.573 -14.592  51.471  1.00 30.22           C
ATOM   3994  O   TYR B 214     -11.037 -13.819  50.622  1.00 29.87           O
ATOM   3995  CB  TYR B 214      -8.930 -16.440  51.094  1.00 30.93           C
ATOM   3996  CG  TYR B 214      -7.509 -16.855  50.769  1.00 31.47           C
ATOM   3997  CD1 TYR B 214      -6.959 -16.604  49.508  1.00 31.93           C
ATOM   3998  CD2 TYR B 214      -6.714 -17.502  51.721  1.00 31.53           C
ATOM   3999  CE1 TYR B 214      -5.659 -16.989  49.200  1.00 31.87           C
ATOM   4000  CE2 TYR B 214      -5.411 -17.892  51.429  1.00 31.70           C
ATOM   4001  CZ  TYR B 214      -4.889 -17.634  50.165  1.00 32.97           C
ATOM   4002  OH  TYR B 214      -3.606 -18.028  49.860  1.00 33.88           O
ATOM   4003  N   GLY B 215     -11.306 -15.145  52.439  1.00 29.82           N
ATOM   4004  CA  GLY B 215     -12.734 -14.903  52.544  1.00 28.91           C
ATOM   4005  C   GLY B 215     -13.161 -13.484  52.860  1.00 29.07           C
ATOM   4006  O   GLY B 215     -14.047 -12.939  52.201  1.00 28.55           O
ATOM   4007  N   SER B 216     -12.542 -12.881  53.869  1.00 28.75           N
ATOM   4008  CA  SER B 216     -12.897 -11.523  54.270  1.00 28.98           C
ATOM   4009  C   SER B 216     -12.461 -10.462  53.244  1.00 29.01           C
ATOM   4010  O   SER B 216     -13.161  -9.469  53.044  1.00 28.93           O
ATOM   4011  CB  SER B 216     -12.320 -11.219  55.665  1.00 27.95           C
```

FIGURE 2-60 (COORDINATES)

```
ATOM   4012  OG  SER B 216     -10.923 -11.455  55.696  1.00 27.86           O
ATOM   4013  N   ARG B 217     -11.318 -10.662  52.595  1.00 29.02           N
ATOM   4014  CA  ARG B 217     -10.880  -9.706  51.577  1.00 29.84           C
ATOM   4015  C   ARG B 217     -11.898  -9.746  50.435  1.00 29.20           C
ATOM   4016  O   ARG B 217     -12.302  -8.722  49.894  1.00 28.34           O
ATOM   4017  CB  ARG B 217      -9.477 -10.056  51.044  1.00 30.41           C
ATOM   4018  CG  ARG B 217      -8.333  -9.617  51.967  1.00 31.23           C
ATOM   4019  CD  ARG B 217      -6.948  -9.749  51.312  1.00 33.18           C
ATOM   4020  NE  ARG B 217      -6.485 -11.132  51.201  1.00 35.95           N
ATOM   4021  CZ  ARG B 217      -6.360 -11.803  50.054  1.00 37.90           C
ATOM   4022  NH1 ARG B 217      -6.663 -11.221  48.902  1.00 39.68           N
ATOM   4023  NH2 ARG B 217      -5.924 -13.059  50.052  1.00 36.92           N
ATOM   4024  N   HIS B 218     -12.334 -10.946  50.094  1.00 29.35           N
ATOM   4025  CA  HIS B 218     -13.298 -11.096  49.026  1.00 29.88           C
ATOM   4026  C   HIS B 218     -14.696 -10.565  49.360  1.00 30.18           C
ATOM   4027  O   HIS B 218     -15.323  -9.911  48.527  1.00 30.29           O
ATOM   4028  CB  HIS B 218     -13.383 -12.566  48.606  1.00 29.01           C
ATOM   4029  CG  HIS B 218     -14.585 -12.881  47.779  1.00 28.33           C
ATOM   4030  ND1 HIS B 218     -15.833 -13.078  48.328  1.00 29.76           N
ATOM   4031  CD2 HIS B 218     -14.743 -12.982  46.439  1.00 27.93           C
ATOM   4032  CE1 HIS B 218     -16.709 -13.290  47.361  1.00 28.64           C
ATOM   4033  NE2 HIS B 218     -16.073 -13.237  46.206  1.00 28.52           N
ATOM   4034  N   LEU B 219     -15.180 -10.834  50.569  1.00 30.06           N
ATOM   4035  CA  LEU B 219     -16.520 -10.402  50.961  1.00 30.86           C
ATOM   4036  C   LEU B 219     -16.626  -8.893  51.212  1.00 30.42           C
ATOM   4037  O   LEU B 219     -17.653  -8.281  50.919  1.00 30.70           O
ATOM   4038  CB  LEU B 219     -17.001 -11.185  52.201  1.00 29.37           C
ATOM   4039  CG  LEU B 219     -18.444 -10.891  52.652  1.00 29.40           C
ATOM   4040  CD1 LEU B 219     -19.411 -11.175  51.511  1.00 27.55           C
ATOM   4041  CD2 LEU B 219     -18.803 -11.734  53.876  1.00 29.43           C
ATOM   4042  N   ALA B 220     -15.575  -8.296  51.760  1.00 31.26           N
ATOM   4043  CA  ALA B 220     -15.581  -6.858  52.010  1.00 31.44           C
ATOM   4044  C   ALA B 220     -15.646  -6.102  50.666  1.00 31.63           C
ATOM   4045  O   ALA B 220     -16.356  -5.105  50.538  1.00 31.98           O
ATOM   4046  CB  ALA B 220     -14.328  -6.451  52.805  1.00 30.54           C
ATOM   4047  N   ALA B 221     -14.923  -6.588  49.661  1.00 30.83           N
ATOM   4048  CA  ALA B 221     -14.929  -5.937  48.353  1.00 31.68           C
ATOM   4049  C   ALA B 221     -16.276  -6.131  47.668  1.00 32.90           C
ATOM   4050  O   ALA B 221     -16.763  -5.238  46.968  1.00 32.86           O
ATOM   4051  CB  ALA B 221     -13.818  -6.498  47.476  1.00 30.37           C
ATOM   4052  N   LYS B 222     -16.873  -7.302  47.874  1.00 32.95           N
ATOM   4053  CA  LYS B 222     -18.161  -7.615  47.279  1.00 32.90           C
ATOM   4054  C   LYS B 222     -19.285  -6.803  47.926  1.00 33.19           C
ATOM   4055  O   LYS B 222     -20.196  -6.335  47.234  1.00 32.82           O
ATOM   4056  CB  LYS B 222     -18.431  -9.114  47.404  1.00 34.67           C
ATOM   4057  CG  LYS B 222     -19.811  -9.579  46.962  1.00 36.37           C
ATOM   4058  CD  LYS B 222     -19.834 -11.108  46.887  1.00 39.36           C
ATOM   4059  CE  LYS B 222     -21.215 -11.672  46.558  1.00 40.31           C
ATOM   4060  NZ  LYS B 222     -22.143 -11.577  47.736  1.00 42.93           N
ATOM   4061  N   MET B 223     -19.229  -6.628  49.243  1.00 32.32           N
ATOM   4062  CA  MET B 223     -20.260  -5.852  49.916  1.00 32.75           C
ATOM   4063  C   MET B 223     -20.114  -4.359  49.604  1.00 33.53           C
ATOM   4064  O   MET B 223     -21.111  -3.645  49.488  1.00 34.04           O
ATOM   4065  CB  MET B 223     -20.213  -6.089  51.425  1.00 32.45           C
ATOM   4066  CG  MET B 223     -20.624  -7.497  51.839  1.00 30.99           C
ATOM   4067  SD  MET B 223     -20.492  -7.745  53.618  1.00 33.16           S
ATOM   4068  CE  MET B 223     -22.148  -7.260  54.194  1.00 32.09           C
ATOM   4069  N   ALA B 224     -18.873  -3.894  49.454  1.00 33.38           N
ATOM   4070  CA  ALA B 224     -18.613  -2.488  49.135  1.00 33.94           C
ATOM   4071  C   ALA B 224     -19.121  -2.116  47.744  1.00 34.96           C
ATOM   4072  O   ALA B 224     -19.422  -0.945  47.486  1.00 36.27           O
ATOM   4073  CB  ALA B 224     -17.124  -2.194  49.223  1.00 32.98           C
ATOM   4074  N   SER B 225     -19.222  -3.100  46.850  1.00 33.94           N
ATOM   4075  CA  SER B 225     -19.683  -2.828  45.497  1.00 33.98           C
ATOM   4076  C   SER B 225     -21.094  -3.340  45.240  1.00 34.13           C
ATOM   4077  O   SER B 225     -21.535  -3.437  44.090  1.00 33.14           O
ATOM   4078  CB  SER B 225     -18.710  -3.420  44.469  1.00 33.82           C
ATOM   4079  OG  SER B 225     -18.704  -4.840  44.494  1.00 35.58           O
```

FIGURE 2-61 (COORDINATES)

```
ATOM   4080  N    THR B 226     -21.807  -3.665  46.312  1.00 34.39      N
ATOM   4081  CA   THR B 226     -23.180  -4.149  46.178  1.00 35.30      C
ATOM   4082  C    THR B 226     -24.149  -3.105  46.713  1.00 35.73      C
ATOM   4083  O    THR B 226     -24.072  -2.717  47.877  1.00 36.32      O
ATOM   4084  CB   THR B 226     -23.395  -5.470  46.947  1.00 34.80      C
ATOM   4085  OG1  THR B 226     -22.568  -6.492  46.373  1.00 36.26      O
ATOM   4086  CG2  THR B 226     -24.850  -5.904  46.872  1.00 33.81      C
ATOM   4087  N    PRO B 227     -25.074  -2.627  45.866  1.00 36.43      N
ATOM   4088  CA   PRO B 227     -26.029  -1.622  46.338  1.00 36.29      C
ATOM   4089  C    PRO B 227     -26.869  -2.146  47.491  1.00 36.57      C
ATOM   4090  O    PRO B 227     -27.315  -3.293  47.471  1.00 36.60      O
ATOM   4091  CB   PRO B 227     -26.883  -1.338  45.101  1.00 34.74      C
ATOM   4092  CG   PRO B 227     -25.948  -1.594  43.979  1.00 35.90      C
ATOM   4093  CD   PRO B 227     -25.225  -2.850  44.417  1.00 36.51      C
ATOM   4094  N    HIS B 228     -27.068  -1.299  48.497  1.00 37.34      N
ATOM   4095  CA   HIS B 228     -27.889  -1.642  49.649  1.00 37.96      C
ATOM   4096  C    HIS B 228     -28.484  -0.373  50.240  1.00 38.61      C
ATOM   4097  O    HIS B 228     -27.776   0.609  50.474  1.00 38.21      O
ATOM   4098  CB   HIS B 228     -27.083  -2.352  50.731  1.00 37.67      C
ATOM   4099  CG   HIS B 228     -27.932  -2.914  51.830  1.00 37.81      C
ATOM   4100  ND1  HIS B 228     -28.719  -4.033  51.662  1.00 38.28      N
ATOM   4101  CD2  HIS B 228     -28.143  -2.495  53.101  1.00 38.38      C
ATOM   4102  CE1  HIS B 228     -29.378  -4.279  52.781  1.00 37.85      C
ATOM   4103  NE2  HIS B 228     -29.046  -3.360  53.670  1.00 38.22      N
ATOM   4104  N    PRO B 229     -29.807  -0.368  50.460  1.00 38.87      N
ATOM   4105  CA   PRO B 229     -30.702  -1.496  50.167  1.00 38.89      C
ATOM   4106  C    PRO B 229     -30.888  -1.671  48.659  1.00 39.10      C
ATOM   4107  O    PRO B 229     -30.405  -0.860  47.871  1.00 38.52      O
ATOM   4108  CB   PRO B 229     -31.991  -1.098  50.874  1.00 39.25      C
ATOM   4109  CG   PRO B 229     -31.970   0.395  50.758  1.00 39.86      C
ATOM   4110  CD   PRO B 229     -30.540   0.742  51.087  1.00 37.99      C
ATOM   4111  N    PRO B 230     -31.581  -2.739  48.234  1.00 39.77      N
ATOM   4112  CA   PRO B 230     -31.789  -2.956  46.800  1.00 39.90      C
ATOM   4113  C    PRO B 230     -32.356  -1.719  46.117  1.00 40.14      C
ATOM   4114  O    PRO B 230     -33.329  -1.138  46.589  1.00 40.69      O
ATOM   4115  CB   PRO B 230     -32.755  -4.127  46.769  1.00 39.59      C
ATOM   4116  CG   PRO B 230     -32.337  -4.913  47.952  1.00 39.91      C
ATOM   4117  CD   PRO B 230     -32.157  -3.847  49.013  1.00 40.13      C
ATOM   4118  N    GLY B 231     -31.725  -1.312  45.018  1.00 40.46      N
ATOM   4119  CA   GLY B 231     -32.180  -0.144  44.288  1.00 40.01      C
ATOM   4120  C    GLY B 231     -31.422   1.133  44.597  1.00 40.27      C
ATOM   4121  O    GLY B 231     -31.543   2.106  43.863  1.00 40.55      O
ATOM   4122  N    ALA B 232     -30.643   1.146  45.673  1.00 40.56      N
ATOM   4123  CA   ALA B 232     -29.888   2.340  46.045  1.00 41.41      C
ATOM   4124  C    ALA B 232     -28.880   2.726  44.965  1.00 42.46      C
ATOM   4125  O    ALA B 232     -28.329   1.864  44.284  1.00 43.29      O
ATOM   4126  CB   ALA B 232     -29.175   2.113  47.367  1.00 40.73      C
ATOM   4127  N    ARG B 233     -28.637   4.025  44.823  1.00 43.68      N
ATOM   4128  CA   ARG B 233     -27.707   4.537  43.823  1.00 44.81      C
ATOM   4129  C    ARG B 233     -26.309   4.838  44.356  1.00 44.21      C
ATOM   4130  O    ARG B 233     -25.336   4.805  43.600  1.00 44.35      O
ATOM   4131  CB   ARG B 233     -28.279   5.809  43.190  1.00 48.09      C
ATOM   4132  CG   ARG B 233     -29.596   5.599  42.453  1.00 53.28      C
ATOM   4133  CD   ARG B 233     -30.314   6.920  42.183  1.00 56.79      C
ATOM   4134  NE   ARG B 233     -31.555   6.704  41.442  1.00 60.37      N
ATOM   4135  CZ   ARG B 233     -31.615   6.354  40.157  1.00 62.18      C
ATOM   4136  NH1  ARG B 233     -30.495   6.186  39.453  1.00 61.53      N
ATOM   4137  NH2  ARG B 233     -32.798   6.150  39.579  1.00 62.65      N
ATOM   4138  N    GLY B 234     -26.198   5.134  45.647  1.00 42.83      N
ATOM   4139  CA   GLY B 234     -24.890   5.451  46.192  1.00 42.36      C
ATOM   4140  C    GLY B 234     -24.518   4.869  47.545  1.00 41.47      C
ATOM   4141  O    GLY B 234     -23.550   5.321  48.159  1.00 40.86      O
ATOM   4142  N    THR B 235     -25.273   3.881  48.018  1.00 40.63      N
ATOM   4143  CA   THR B 235     -24.975   3.259  49.303  1.00 40.40      C
ATOM   4144  C    THR B 235     -24.825   1.754  49.123  1.00 39.83      C
ATOM   4145  O    THR B 235     -25.551   1.135  48.343  1.00 39.69      O
ATOM   4146  CB   THR B 235     -26.072   3.553  50.343  1.00 40.10      C
ATOM   4147  OG1  THR B 235     -27.333   3.086  49.855  1.00 41.22      O
```

FIGURE 2-62 (COORDINATES)

```
ATOM   4148  CG2 THR B 235     -26.161    5.045   50.609  1.00 39.65           C
ATOM   4149  N   SER B 236     -23.869    1.173   49.842  1.00 39.11           N
ATOM   4150  CA  SER B 236     -23.598   -0.257   49.737  1.00 38.02           C
ATOM   4151  C   SER B 236     -23.918   -1.042   51.000  1.00 37.60           C
ATOM   4152  O   SER B 236     -24.223   -0.468   52.059  1.00 36.72           O
ATOM   4153  CB  SER B 236     -22.128   -0.477   49.388  1.00 38.42           C
ATOM   4154  OG  SER B 236     -21.288    0.013   50.420  1.00 38.58           O
ATOM   4155  N   GLN B 237     -23.835   -2.365   50.876  1.00 36.20           N
ATOM   4156  CA  GLN B 237     -24.080   -3.254   52.002  1.00 35.09           C
ATOM   4157  C   GLN B 237     -23.055   -2.977   53.100  1.00 34.84           C
ATOM   4158  O   GLN B 237     -23.331   -3.154   54.281  1.00 34.88           O
ATOM   4159  CB  GLN B 237     -23.968   -4.713   51.566  1.00 33.84           C
ATOM   4160  CG  GLN B 237     -24.942   -5.112   50.493  1.00 33.37           C
ATOM   4161  CD  GLN B 237     -24.921   -6.601   50.232  1.00 34.00           C
ATOM   4162  OE1 GLN B 237     -23.855   -7.220   50.176  1.00 32.27           O
ATOM   4163  NE2 GLN B 237     -26.102   -7.184   50.053  1.00 32.41           N
ATOM   4164  N   LEU B 238     -21.867   -2.542   52.706  1.00 34.84           N
ATOM   4165  CA  LEU B 238     -20.823   -2.258   53.674  1.00 35.79           C
ATOM   4166  C   LEU B 238     -21.204   -1.046   54.530  1.00 36.34           C
ATOM   4167  O   LEU B 238     -20.815   -0.949   55.694  1.00 36.20           O
ATOM   4168  CB  LEU B 238     -19.498   -2.029   52.948  1.00 36.21           C
ATOM   4169  CG  LEU B 238     -18.270   -2.054   53.846  1.00 38.05           C
ATOM   4170  CD1 LEU B 238     -17.106   -2.648   53.081  1.00 38.47           C
ATOM   4171  CD2 LEU B 238     -17.957   -0.639   54.344  1.00 39.15           C
ATOM   4172  N   HIS B 239     -21.970   -0.125   53.952  1.00 36.04           N
ATOM   4173  CA  HIS B 239     -22.417    1.055   54.685  1.00 36.28           C
ATOM   4174  C   HIS B 239     -23.510    0.639   55.670  1.00 36.83           C
ATOM   4175  O   HIS B 239     -23.804    1.353   56.627  1.00 37.70           O
ATOM   4176  CB  HIS B 239     -22.966    2.112   53.715  1.00 34.95           C
ATOM   4177  CG  HIS B 239     -21.923    2.710   52.823  1.00 34.63           C
ATOM   4178  ND1 HIS B 239     -22.195    3.138   51.542  1.00 34.54           N
ATOM   4179  CD2 HIS B 239     -20.599    2.924   53.019  1.00 34.25           C
ATOM   4180  CE1 HIS B 239     -21.082    3.583   50.984  1.00 34.46           C
ATOM   4181  NE2 HIS B 239     -20.100    3.463   51.859  1.00 33.88           N
ATOM   4182  N   GLY B 240     -24.106   -0.526   55.433  1.00 36.54           N
ATOM   4183  CA  GLY B 240     -25.165   -1.002   56.304  1.00 36.64           C
ATOM   4184  C   GLY B 240     -24.694   -1.717   57.557  1.00 36.34           C
ATOM   4185  O   GLY B 240     -25.504   -2.071   58.413  1.00 37.16           O
ATOM   4186  N   MET B 241     -23.390   -1.940   57.665  1.00 36.52           N
ATOM   4187  CA  MET B 241     -22.817   -2.611   58.828  1.00 36.31           C
ATOM   4188  C   MET B 241     -22.564   -1.625   59.967  1.00 36.74           C
ATOM   4189  O   MET B 241     -21.570   -0.895   59.968  1.00 36.98           O
ATOM   4190  CB  MET B 241     -21.500   -3.299   58.456  1.00 36.49           C
ATOM   4191  CG  MET B 241     -21.640   -4.399   57.413  1.00 36.84           C
ATOM   4192  SD  MET B 241     -20.047   -5.056   56.868  1.00 37.87           S
ATOM   4193  CE  MET B 241     -19.630   -6.110   58.255  1.00 36.09           C
ATOM   4194  N   ASP B 242     -23.476   -1.614   60.932  1.00 36.35           N
ATOM   4195  CA  ASP B 242     -23.379   -0.746   62.099  1.00 35.76           C
ATOM   4196  C   ASP B 242     -22.069   -0.978   62.831  1.00 35.10           C
ATOM   4197  O   ASP B 242     -21.375   -0.034   63.213  1.00 34.92           O
ATOM   4198  CB  ASP B 242     -24.530   -1.049   63.063  1.00 37.37           C
ATOM   4199  CG  ASP B 242     -25.659   -0.041   62.978  1.00 38.91           C
ATOM   4200  OD1 ASP B 242     -26.131    0.281   61.862  1.00 40.34           O
ATOM   4201  OD2 ASP B 242     -26.089    0.420   64.050  1.00 39.09           O
ATOM   4202  N   LEU B 243     -21.744   -2.253   63.021  1.00 34.47           N
ATOM   4203  CA  LEU B 243     -20.549   -2.653   63.752  1.00 32.88           C
ATOM   4204  C   LEU B 243     -20.224   -4.116   63.480  1.00 31.96           C
ATOM   4205  O   LEU B 243     -21.121   -4.957   63.381  1.00 31.53           O
ATOM   4206  CB  LEU B 243     -20.785   -2.460   65.257  1.00 32.16           C
ATOM   4207  CG  LEU B 243     -19.726   -2.956   66.240  1.00 31.39           C
ATOM   4208  CD1 LEU B 243     -18.517   -2.066   66.157  1.00 31.75           C
ATOM   4209  CD2 LEU B 243     -20.283   -2.953   67.659  1.00 32.02           C
ATOM   4210  N   LEU B 244     -18.934   -4.405   63.364  1.00 31.01           N
ATOM   4211  CA  LEU B 244     -18.460   -5.757   63.116  1.00 30.33           C
ATOM   4212  C   LEU B 244     -17.826   -6.302   64.389  1.00 30.41           C
ATOM   4213  O   LEU B 244     -16.745   -5.871   64.784  1.00 30.19           O
ATOM   4214  CB  LEU B 244     -17.426   -5.764   61.990  1.00 29.39           C
ATOM   4215  CG  LEU B 244     -16.760   -7.117   61.719  1.00 29.64           C
```

FIGURE 2-63 (COORDINATES)

```
ATOM   4216  CD1 LEU B 244     -17.828  -8.131  61.301  1.00 29.22           C
ATOM   4217  CD2 LEU B 244     -15.696  -6.970  60.633  1.00 28.86           C
ATOM   4218  N   VAL B 245     -18.512  -7.239  65.034  1.00 30.68           N
ATOM   4219  CA  VAL B 245     -18.014  -7.856  66.259  1.00 30.05           C
ATOM   4220  C   VAL B 245     -17.361  -9.163  65.840  1.00 30.27           C
ATOM   4221  O   VAL B 245     -18.038 -10.151  65.568  1.00 30.75           O
ATOM   4222  CB  VAL B 245     -19.170  -8.129  67.248  1.00 29.56           C
ATOM   4223  CG1 VAL B 245     -18.616  -8.619  68.581  1.00 29.09           C
ATOM   4224  CG2 VAL B 245     -19.985  -6.860  67.447  1.00 27.56           C
ATOM   4225  N   LEU B 246     -16.036  -9.153  65.767  1.00 30.58           N
ATOM   4226  CA  LEU B 246     -15.287 -10.324  65.340  1.00 30.98           C
ATOM   4227  C   LEU B 246     -14.709 -11.141  66.491  1.00 31.85           C
ATOM   4228  O   LEU B 246     -13.879 -10.636  67.255  1.00 32.16           O
ATOM   4229  CB  LEU B 246     -14.150  -9.890  64.406  1.00 30.41           C
ATOM   4230  CG  LEU B 246     -13.231 -11.003  63.891  1.00 30.15           C
ATOM   4231  CD1 LEU B 246     -14.037 -11.986  63.038  1.00 29.59           C
ATOM   4232  CD2 LEU B 246     -12.097 -10.393  63.080  1.00 30.31           C
ATOM   4233  N   LEU B 247     -15.143 -12.399  66.602  1.00 32.00           N
ATOM   4234  CA  LEU B 247     -14.654 -13.316  67.645  1.00 32.14           C
ATOM   4235  C   LEU B 247     -13.556 -14.214  67.083  1.00 31.28           C
ATOM   4236  O   LEU B 247     -13.700 -14.786  66.001  1.00 30.21           O
ATOM   4237  CB  LEU B 247     -15.784 -14.203  68.179  1.00 33.11           C
ATOM   4238  CG  LEU B 247     -16.944 -13.551  68.926  1.00 33.76           C
ATOM   4239  CD1 LEU B 247     -17.784 -12.757  67.968  1.00 34.73           C
ATOM   4240  CD2 LEU B 247     -17.792 -14.623  69.570  1.00 34.84           C
ATOM   4241  N   ASP B 248     -12.466 -14.352  67.826  1.00 31.49           N
ATOM   4242  CA  ASP B 248     -11.349 -15.167  67.366  1.00 31.52           C
ATOM   4243  C   ASP B 248     -10.460 -15.617  68.528  1.00 32.04           C
ATOM   4244  O   ASP B 248     -10.236 -14.866  69.477  1.00 31.18           O
ATOM   4245  CB  ASP B 248     -10.513 -14.359  66.360  1.00 30.77           C
ATOM   4246  CG  ASP B 248      -9.581 -15.229  65.532  1.00 31.73           C
ATOM   4247  OD1 ASP B 248      -9.495 -16.442  65.794  1.00 31.85           O
ATOM   4248  OD2 ASP B 248      -8.931 -14.696  64.612  1.00 32.72           O
ATOM   4249  N   LEU B 249      -9.961 -16.847  68.443  1.00 32.56           N
ATOM   4250  CA  LEU B 249      -9.068 -17.394  69.464  1.00 33.54           C
ATOM   4251  C   LEU B 249      -9.680 -17.367  70.859  1.00 34.30           C
ATOM   4252  O   LEU B 249      -9.003 -17.041  71.838  1.00 35.56           O
ATOM   4253  CB  LEU B 249      -7.751 -16.613  69.460  1.00 32.76           C
ATOM   4254  CG  LEU B 249      -7.158 -16.411  68.056  1.00 33.42           C
ATOM   4255  CD1 LEU B 249      -5.814 -15.698  68.157  1.00 33.34           C
ATOM   4256  CD2 LEU B 249      -6.984 -17.754  67.369  1.00 30.89           C
ATOM   4257  N   ILE B 250     -10.961 -17.717  70.941  1.00 34.75           N
ATOM   4258  CA  ILE B 250     -11.688 -17.734  72.204  1.00 34.79           C
ATOM   4259  C   ILE B 250     -11.936 -19.166  72.683  1.00 36.08           C
ATOM   4260  O   ILE B 250     -12.240 -20.053  71.886  1.00 35.49           O
ATOM   4261  CB  ILE B 250     -13.047 -17.020  72.057  1.00 34.51           C
ATOM   4262  CG1 ILE B 250     -12.819 -15.535  71.739  1.00 34.76           C
ATOM   4263  CG2 ILE B 250     -13.875 -17.192  73.329  1.00 33.53           C
ATOM   4264  CD1 ILE B 250     -14.103 -14.726  71.542  1.00 33.46           C
ATOM   4265  N   GLY B 251     -11.808 -19.384  73.988  1.00 36.57           N
ATOM   4266  CA  GLY B 251     -12.038 -20.710  74.525  1.00 38.00           C
ATOM   4267  C   GLY B 251     -11.028 -21.080  75.588  1.00 39.03           C
ATOM   4268  O   GLY B 251     -11.242 -22.011  76.365  1.00 39.19           O
ATOM   4269  N   ALA B 252      -9.918 -20.353  75.618  1.00 39.45           N
ATOM   4270  CA  ALA B 252      -8.881 -20.600  76.606  1.00 40.54           C
ATOM   4271  C   ALA B 252      -9.237 -19.861  77.904  1.00 41.53           C
ATOM   4272  O   ALA B 252      -9.997 -18.891  77.893  1.00 41.08           O
ATOM   4273  CB  ALA B 252      -7.534 -20.132  76.072  1.00 39.22           C
ATOM   4274  N   PRO B 253      -8.705 -20.323  79.044  1.00 42.80           N
ATOM   4275  CA  PRO B 253      -9.015 -19.650  80.308  1.00 43.99           C
ATOM   4276  C   PRO B 253      -8.268 -18.331  80.498  1.00 45.12           C
ATOM   4277  O   PRO B 253      -7.211 -18.105  79.904  1.00 45.07           O
ATOM   4278  CB  PRO B 253      -8.634 -20.695  81.354  1.00 43.67           C
ATOM   4279  CG  PRO B 253      -7.472 -21.387  80.713  1.00 43.28           C
ATOM   4280  CD  PRO B 253      -7.952 -21.569  79.283  1.00 43.32           C
ATOM   4281  N   ASN B 254      -8.838 -17.464  81.327  1.00 46.37           N
ATOM   4282  CA  ASN B 254      -8.247 -16.165  81.629  1.00 47.17           C
ATOM   4283  C   ASN B 254      -7.897 -15.310  80.416  1.00 47.01           C
```

FIGURE 2-64 (COORDINATES)

```
ATOM   4284  O   ASN B 254      -6.758 -14.859  80.265  1.00 46.80           O
ATOM   4285  CB  ASN B 254      -7.004 -16.348  82.502  1.00 48.10           C
ATOM   4286  CG  ASN B 254      -7.332 -16.954  83.845  1.00 50.31           C
ATOM   4287  OD1 ASN B 254      -8.198 -16.451  84.570  1.00 51.39           O
ATOM   4288  ND2 ASN B 254      -6.647 -18.041  84.190  1.00 51.21           N
ATOM   4289  N   PRO B 255      -8.871 -15.082  79.523  1.00 46.75           N
ATOM   4290  CA  PRO B 255      -8.560 -14.255  78.358  1.00 46.63           C
ATOM   4291  C   PRO B 255      -8.641 -12.779  78.746  1.00 46.73           C
ATOM   4292  O   PRO B 255      -9.361 -12.411  79.674  1.00 46.50           O
ATOM   4293  CB  PRO B 255      -9.643 -14.653  77.364  1.00 46.18           C
ATOM   4294  CG  PRO B 255     -10.813 -14.912  78.255  1.00 45.40           C
ATOM   4295  CD  PRO B 255     -10.191 -15.722  79.371  1.00 46.11           C
ATOM   4296  N   THR B 256      -7.880 -11.942  78.055  1.00 46.44           N
ATOM   4297  CA  THR B 256      -7.908 -10.514  78.316  1.00 46.88           C
ATOM   4298  C   THR B 256      -8.055  -9.820  76.966  1.00 46.52           C
ATOM   4299  O   THR B 256      -7.153  -9.857  76.126  1.00 46.40           O
ATOM   4300  CB  THR B 256      -6.624 -10.035  79.058  1.00 47.46           C
ATOM   4301  OG1 THR B 256      -5.464 -10.323  78.271  1.00 49.48           O
ATOM   4302  CG2 THR B 256      -6.493 -10.743  80.401  1.00 47.43           C
ATOM   4303  N   PHE B 257      -9.223  -9.219  76.758  1.00 46.64           N
ATOM   4304  CA  PHE B 257      -9.545  -8.522  75.517  1.00 46.27           C
ATOM   4305  C   PHE B 257      -9.264  -7.036  75.632  1.00 46.88           C
ATOM   4306  O   PHE B 257      -9.857  -6.353  76.466  1.00 48.42           O
ATOM   4307  CB  PHE B 257     -11.026  -8.698  75.181  1.00 45.27           C
ATOM   4308  CG  PHE B 257     -11.449 -10.124  75.006  1.00 44.02           C
ATOM   4309  CD1 PHE B 257     -11.139 -10.817  73.839  1.00 43.23           C
ATOM   4310  CD2 PHE B 257     -12.168 -10.772  76.005  1.00 42.98           C
ATOM   4311  CE1 PHE B 257     -11.539 -12.131  73.668  1.00 43.52           C
ATOM   4312  CE2 PHE B 257     -12.575 -12.088  75.848  1.00 42.95           C
ATOM   4313  CZ  PHE B 257     -12.261 -12.772  74.676  1.00 43.58           C
ATOM   4314  N   PRO B 258      -8.356  -6.511  74.799  1.00 47.08           N
ATOM   4315  CA  PRO B 258      -8.046  -5.081  74.853  1.00 47.25           C
ATOM   4316  C   PRO B 258      -9.004  -4.277  73.977  1.00 46.96           C
ATOM   4317  O   PRO B 258      -9.661  -4.827  73.094  1.00 46.28           O
ATOM   4318  CB  PRO B 258      -6.613  -5.028  74.339  1.00 47.42           C
ATOM   4319  CG  PRO B 258      -6.623  -6.087  73.293  1.00 47.26           C
ATOM   4320  CD  PRO B 258      -7.374  -7.225  73.963  1.00 47.43           C
ATOM   4321  N   ASN B 259      -9.088  -2.979  74.239  1.00 47.33           N
ATOM   4322  CA  ASN B 259      -9.945  -2.086  73.469  1.00 47.61           C
ATOM   4323  C   ASN B 259      -9.075  -1.529  72.351  1.00 47.18           C
ATOM   4324  O   ASN B 259      -8.348  -0.560  72.543  1.00 47.42           O
ATOM   4325  CB  ASN B 259     -10.455  -0.949  74.356  1.00 48.48           C
ATOM   4326  CG  ASN B 259     -11.375  -0.003  73.617  1.00 49.60           C
ATOM   4327  OD1 ASN B 259     -11.916   0.929  74.200  1.00 51.10           O
ATOM   4328  ND2 ASN B 259     -11.556  -0.238  72.329  1.00 49.73           N
ATOM   4329  N   PHE B 260      -9.163  -2.147  71.181  1.00 46.46           N
ATOM   4330  CA  PHE B 260      -8.353  -1.751  70.040  1.00 45.76           C
ATOM   4331  C   PHE B 260      -8.671  -0.435  69.337  1.00 45.27           C
ATOM   4332  O   PHE B 260      -7.754   0.256  68.897  1.00 45.34           O
ATOM   4333  CB  PHE B 260      -8.371  -2.850  68.971  1.00 45.86           C
ATOM   4334  CG  PHE B 260      -7.807  -4.164  69.422  1.00 45.84           C
ATOM   4335  CD1 PHE B 260      -8.639  -5.150  69.938  1.00 45.56           C
ATOM   4336  CD2 PHE B 260      -6.448  -4.437  69.281  1.00 45.63           C
ATOM   4337  CE1 PHE B 260      -8.127  -6.401  70.302  1.00 46.64           C
ATOM   4338  CE2 PHE B 260      -5.924  -5.683  69.641  1.00 45.96           C
ATOM   4339  CZ  PHE B 260      -6.766  -6.668  70.150  1.00 46.44           C
ATOM   4340  N   PHE B 261      -9.950  -0.084  69.225  1.00 44.46           N
ATOM   4341  CA  PHE B 261     -10.323   1.112  68.474  1.00 44.03           C
ATOM   4342  C   PHE B 261     -11.096   2.205  69.193  1.00 45.05           C
ATOM   4343  O   PHE B 261     -12.086   1.944  69.876  1.00 45.28           O
ATOM   4344  CB  PHE B 261     -11.106   0.684  67.231  1.00 42.61           C
ATOM   4345  CG  PHE B 261     -10.456  -0.427  66.473  1.00 41.15           C
ATOM   4346  CD1 PHE B 261      -9.302  -0.198  65.734  1.00 40.27           C
ATOM   4347  CD2 PHE B 261     -10.964  -1.719  66.543  1.00 39.70           C
ATOM   4348  CE1 PHE B 261      -8.656  -1.247  65.074  1.00 40.53           C
ATOM   4349  CE2 PHE B 261     -10.328  -2.773  65.890  1.00 39.80           C
ATOM   4350  CZ  PHE B 261      -9.172  -2.539  65.154  1.00 39.48           C
ATOM   4351  N   PRO B 262     -10.661   3.464  69.018  1.00 45.70           N
```

FIGURE 2-65 (COORDINATES)

```
ATOM   4352  CA  PRO B 262     -11.295   4.627  69.638  1.00 45.41           C
ATOM   4353  C   PRO B 262     -12.738   4.780  69.193  1.00 45.27           C
ATOM   4354  O   PRO B 262     -13.608   5.110  69.994  1.00 45.82           O
ATOM   4355  CB  PRO B 262     -10.432   5.792  69.153  1.00 45.78           C
ATOM   4356  CG  PRO B 262      -9.096   5.175  68.968  1.00 46.29           C
ATOM   4357  CD  PRO B 262      -9.450   3.871  68.287  1.00 46.31           C
ATOM   4358  N   ASN B 263     -12.987   4.526  67.912  1.00 45.15           N
ATOM   4359  CA  ASN B 263     -14.326   4.675  67.360  1.00 45.33           C
ATOM   4360  C   ASN B 263     -15.337   3.595  67.749  1.00 45.01           C
ATOM   4361  O   ASN B 263     -16.495   3.662  67.343  1.00 46.58           O
ATOM   4362  CB  ASN B 263     -14.253   4.825  65.827  1.00 46.06           C
ATOM   4363  CG  ASN B 263     -13.936   3.526  65.111  1.00 47.00           C
ATOM   4364  OD1 ASN B 263     -13.261   2.647  65.645  1.00 48.58           O
ATOM   4365  ND2 ASN B 263     -14.411   3.409  63.877  1.00 47.61           N
ATOM   4366  N   SER B 264     -14.917   2.600  68.523  1.00 43.58           N
ATOM   4367  CA  SER B 264     -15.851   1.570  68.964  1.00 42.31           C
ATOM   4368  C   SER B 264     -15.699   1.384  70.474  1.00 42.52           C
ATOM   4369  O   SER B 264     -16.338   0.519  71.080  1.00 42.18           O
ATOM   4370  CB  SER B 264     -15.611   0.245  68.220  1.00 41.70           C
ATOM   4371  OG  SER B 264     -14.316  -0.281  68.454  1.00 40.45           O
ATOM   4372  N   ALA B 265     -14.863   2.228  71.074  1.00 41.96           N
ATOM   4373  CA  ALA B 265     -14.602   2.177  72.508  1.00 42.27           C
ATOM   4374  C   ALA B 265     -15.865   2.211  73.360  1.00 42.49           C
ATOM   4375  O   ALA B 265     -15.936   1.531  74.379  1.00 42.50           O
ATOM   4376  CB  ALA B 265     -13.676   3.315  72.916  1.00 40.96           C
ATOM   4377  N   ARG B 266     -16.868   2.984  72.955  1.00 42.54           N
ATOM   4378  CA  ARG B 266     -18.087   3.048  73.756  1.00 42.88           C
ATOM   4379  C   ARG B 266     -18.816   1.706  73.828  1.00 42.61           C
ATOM   4380  O   ARG B 266     -19.502   1.425  74.803  1.00 43.03           O
ATOM   4381  CB  ARG B 266     -19.034   4.151  73.248  1.00 41.64           C
ATOM   4382  CG  ARG B 266     -19.886   3.822  72.031  1.00 41.96           C
ATOM   4383  CD  ARG B 266     -20.675   5.074  71.616  1.00 41.60           C
ATOM   4384  NE  ARG B 266     -21.342   4.956  70.321  1.00 41.20           N
ATOM   4385  CZ  ARG B 266     -22.621   4.632  70.159  1.00 41.67           C
ATOM   4386  NH1 ARG B 266     -23.388   4.388  71.213  1.00 42.14           N
ATOM   4387  NH2 ARG B 266     -23.136   4.562  68.939  1.00 41.60           N
ATOM   4388  N   TRP B 267     -18.667   0.875  72.803  1.00 42.99           N
ATOM   4389  CA  TRP B 267     -19.320  -0.428  72.809  1.00 42.98           C
ATOM   4390  C   TRP B 267     -18.462  -1.410  73.595  1.00 43.51           C
ATOM   4391  O   TRP B 267     -18.967  -2.376  74.166  1.00 43.69           O
ATOM   4392  CB  TRP B 267     -19.546  -0.925  71.383  1.00 42.12           C
ATOM   4393  CG  TRP B 267     -20.582  -0.127  70.680  1.00 41.83           C
ATOM   4394  CD1 TRP B 267     -20.397   0.693  69.607  1.00 41.65           C
ATOM   4395  CD2 TRP B 267     -21.970  -0.034  71.024  1.00 41.54           C
ATOM   4396  NE1 TRP B 267     -21.585   1.297  69.259  1.00 41.78           N
ATOM   4397  CE2 TRP B 267     -22.567   0.869  70.111  1.00 41.36           C
ATOM   4398  CE3 TRP B 267     -22.768  -0.624  72.016  1.00 41.77           C
ATOM   4399  CZ2 TRP B 267     -23.925   1.196  70.157  1.00 41.24           C
ATOM   4400  CZ3 TRP B 267     -24.122  -0.302  72.065  1.00 41.98           C
ATOM   4401  CH2 TRP B 267     -24.687   0.603  71.137  1.00 42.46           C
ATOM   4402  N   PHE B 268     -17.160  -1.158  73.629  1.00 43.76           N
ATOM   4403  CA  PHE B 268     -16.269  -2.013  74.389  1.00 45.17           C
ATOM   4404  C   PHE B 268     -16.641  -1.813  75.859  1.00 46.59           C
ATOM   4405  O   PHE B 268     -16.788  -2.774  76.617  1.00 46.69           O
ATOM   4406  CB  PHE B 268     -14.815  -1.601  74.172  1.00 44.25           C
ATOM   4407  CG  PHE B 268     -13.837  -2.425  74.949  1.00 44.84           C
ATOM   4408  CD1 PHE B 268     -13.320  -3.604  74.416  1.00 44.28           C
ATOM   4409  CD2 PHE B 268     -13.451  -2.038  76.232  1.00 44.74           C
ATOM   4410  CE1 PHE B 268     -12.430  -4.388  75.147  1.00 44.58           C
ATOM   4411  CE2 PHE B 268     -12.563  -2.813  76.974  1.00 45.24           C
ATOM   4412  CZ  PHE B 268     -12.049  -3.992  76.431  1.00 44.83           C
ATOM   4413  N   GLU B 269     -16.800  -0.550  76.242  1.00 47.57           N
ATOM   4414  CA  GLU B 269     -17.151  -0.189  77.606  1.00 49.38           C
ATOM   4415  C   GLU B 269     -18.472  -0.841  78.012  1.00 49.49           C
ATOM   4416  O   GLU B 269     -18.684  -1.145  79.188  1.00 48.94           O
ATOM   4417  CB  GLU B 269     -17.214   1.344  77.740  1.00 51.33           C
ATOM   4418  CG  GLU B 269     -15.870   2.021  77.401  1.00 55.05           C
ATOM   4419  CD  GLU B 269     -15.905   3.553  77.427  1.00 57.59           C
```

FIGURE 2-66 (COORDINATES)

```
ATOM   4420  OE1 GLU B 269     -16.832   4.160  76.836  1.00 59.16           O
ATOM   4421  OE2 GLU B 269     -14.984   4.154  78.027  1.00 58.66           O
ATOM   4422  N   ARG B 270     -19.356  -1.071  77.042  1.00 49.19           N
ATOM   4423  CA  ARG B 270     -20.629  -1.720  77.336  1.00 49.00           C
ATOM   4424  C   ARG B 270     -20.406  -3.176  77.741  1.00 48.44           C
ATOM   4425  O   ARG B 270     -21.097  -3.695  78.617  1.00 47.89           O
ATOM   4426  CB  ARG B 270     -21.569  -1.654  76.129  1.00 49.72           C
ATOM   4427  CG  ARG B 270     -22.316  -0.337  75.996  1.00 50.99           C
ATOM   4428  CD  ARG B 270     -23.044  -0.005  77.289  1.00 52.20           C
ATOM   4429  NE  ARG B 270     -23.917  -1.101  77.713  1.00 53.28           N
ATOM   4430  CZ  ARG B 270     -24.495  -1.183  78.909  1.00 53.49           C
ATOM   4431  NH1 ARG B 270     -24.294  -0.230  79.811  1.00 53.48           N
ATOM   4432  NH2 ARG B 270     -25.272  -2.218  79.205  1.00 52.45           N
ATOM   4433  N   LEU B 271     -19.444  -3.837  77.101  1.00 47.53           N
ATOM   4434  CA  LEU B 271     -19.144  -5.227  77.439  1.00 46.81           C
ATOM   4435  C   LEU B 271     -18.616  -5.300  78.869  1.00 46.87           C
ATOM   4436  O   LEU B 271     -18.946  -6.223  79.606  1.00 47.07           O
ATOM   4437  CB  LEU B 271     -18.106  -5.820  76.477  1.00 45.20           C
ATOM   4438  CG  LEU B 271     -18.597  -6.178  75.073  1.00 44.22           C
ATOM   4439  CD1 LEU B 271     -17.438  -6.700  74.243  1.00 43.35           C
ATOM   4440  CD2 LEU B 271     -19.699  -7.217  75.166  1.00 42.81           C
ATOM   4441  N   GLN B 272     -17.793  -4.325  79.253  1.00 47.08           N
ATOM   4442  CA  GLN B 272     -17.242  -4.284  80.603  1.00 47.07           C
ATOM   4443  C   GLN B 272     -18.404  -4.183  81.579  1.00 46.80           C
ATOM   4444  O   GLN B 272     -18.531  -4.994  82.497  1.00 46.92           O
ATOM   4445  CB  GLN B 272     -16.336  -3.068  80.788  1.00 47.45           C
ATOM   4446  CG  GLN B 272     -15.163  -2.996  79.836  1.00 48.81           C
ATOM   4447  CD  GLN B 272     -14.168  -1.919  80.229  1.00 49.68           C
ATOM   4448  OE1 GLN B 272     -13.224  -2.169  80.979  1.00 49.77           O
ATOM   4449  NE2 GLN B 272     -14.386  -0.705  79.732  1.00 49.91           N
ATOM   4450  N   ALA B 273     -19.249  -3.181  81.355  1.00 45.87           N
ATOM   4451  CA  ALA B 273     -20.415  -2.937  82.190  1.00 45.11           C
ATOM   4452  C   ALA B 273     -21.222  -4.215  82.342  1.00 45.07           C
ATOM   4453  O   ALA B 273     -21.600  -4.587  83.452  1.00 44.88           O
ATOM   4454  CB  ALA B 273     -21.285  -1.832  81.576  1.00 43.64           C
ATOM   4455  N   ILE B 274     -21.485  -4.878  81.218  1.00 45.56           N
ATOM   4456  CA  ILE B 274     -22.237  -6.126  81.211  1.00 45.83           C
ATOM   4457  C   ILE B 274     -21.509  -7.208  82.016  1.00 46.69           C
ATOM   4458  O   ILE B 274     -22.122  -7.923  82.802  1.00 46.24           O
ATOM   4459  CB  ILE B 274     -22.459  -6.622  79.763  1.00 45.34           C
ATOM   4460  CG1 ILE B 274     -23.354  -5.632  79.020  1.00 44.93           C
ATOM   4461  CG2 ILE B 274     -23.100  -8.006  79.761  1.00 45.36           C
ATOM   4462  CD1 ILE B 274     -23.608  -5.998  77.586  1.00 44.18           C
ATOM   4463  N   GLU B 275     -20.200  -7.323  81.820  1.00 48.25           N
ATOM   4464  CA  GLU B 275     -19.419  -8.321  82.544  1.00 50.10           C
ATOM   4465  C   GLU B 275     -19.493  -8.044  84.047  1.00 51.26           C
ATOM   4466  O   GLU B 275     -19.809  -8.932  84.836  1.00 51.17           O
ATOM   4467  CB  GLU B 275     -17.960  -8.302  82.072  1.00 49.22           C
ATOM   4468  CG  GLU B 275     -17.034  -9.195  82.882  1.00 48.96           C
ATOM   4469  CD  GLU B 275     -15.598  -9.181  82.371  1.00 49.99           C
ATOM   4470  OE1 GLU B 275     -15.117  -8.105  81.946  1.00 49.65           O
ATOM   4471  OE2 GLU B 275     -14.944 -10.245  82.412  1.00 49.87           O
ATOM   4472  N   HIS B 276     -19.219  -6.800  84.427  1.00 52.46           N
ATOM   4473  CA  HIS B 276     -19.248  -6.385  85.824  1.00 53.43           C
ATOM   4474  C   HIS B 276     -20.584  -6.706  86.484  1.00 53.63           C
ATOM   4475  O   HIS B 276     -20.627  -7.308  87.556  1.00 53.63           O
ATOM   4476  CB  HIS B 276     -18.991  -4.879  85.928  1.00 54.09           C
ATOM   4477  CG  HIS B 276     -18.884  -4.381  87.337  1.00 54.83           C
ATOM   4478  ND1 HIS B 276     -17.731  -4.500  88.083  1.00 54.88           N
ATOM   4479  CD2 HIS B 276     -19.796  -3.791  88.146  1.00 54.75           C
ATOM   4480  CE1 HIS B 276     -17.937  -4.004  89.290  1.00 55.23           C
ATOM   4481  NE2 HIS B 276     -19.182  -3.568  89.354  1.00 55.40           N
ATOM   4482  N   GLU B 277     -21.671  -6.303  85.833  1.00 53.80           N
ATOM   4483  CA  GLU B 277     -23.012  -6.523  86.361  1.00 54.03           C
ATOM   4484  C   GLU B 277     -23.413  -7.991  86.484  1.00 54.27           C
ATOM   4485  O   GLU B 277     -24.006  -8.387  87.486  1.00 54.52           O
ATOM   4486  CB  GLU B 277     -24.042  -5.776  85.508  1.00 54.06           C
ATOM   4487  CG  GLU B 277     -25.468  -5.861  86.043  1.00 55.80           C
```

FIGURE 2-67 (COORDINATES)

```
ATOM   4488  CD  GLU B 277     -25.627  -5.266  87.445  1.00 56.77           C
ATOM   4489  OE1 GLU B 277     -26.755  -5.310  87.987  1.00 56.97           O
ATOM   4490  OE2 GLU B 277     -24.631  -4.753  88.005  1.00 57.34           O
ATOM   4491  N   LEU B 278     -23.108  -8.796  85.471  1.00 54.23           N
ATOM   4492  CA  LEU B 278     -23.450 -10.216  85.517  1.00 54.13           C
ATOM   4493  C   LEU B 278     -22.683 -10.898  86.653  1.00 54.57           C
ATOM   4494  O   LEU B 278     -23.165 -11.855  87.262  1.00 54.10           O
ATOM   4495  CB  LEU B 278     -23.112 -10.897  84.188  1.00 53.20           C
ATOM   4496  CG  LEU B 278     -23.951 -10.575  82.951  1.00 52.70           C
ATOM   4497  CD1 LEU B 278     -23.359 -11.303  81.761  1.00 51.62           C
ATOM   4498  CD2 LEU B 278     -25.410 -10.988  83.167  1.00 51.69           C
ATOM   4499  N   HIS B 279     -21.481 -10.399  86.919  1.00 55.04           N
ATOM   4500  CA  HIS B 279     -20.636 -10.926  87.980  1.00 56.18           C
ATOM   4501  C   HIS B 279     -21.268 -10.587  89.330  1.00 56.73           C
ATOM   4502  O   HIS B 279     -21.512 -11.470  90.153  1.00 56.47           O
ATOM   4503  CB  HIS B 279     -19.243 -10.303  87.876  1.00 56.90           C
ATOM   4504  CG  HIS B 279     -18.356 -10.580  89.050  1.00 58.83           C
ATOM   4505  ND1 HIS B 279     -18.698 -10.236  90.341  1.00 59.35           N
ATOM   4506  CD2 HIS B 279     -17.111 -11.110  89.120  1.00 58.87           C
ATOM   4507  CE1 HIS B 279     -17.701 -10.538  91.153  1.00 59.16           C
ATOM   4508  NE2 HIS B 279     -16.726 -11.069  90.438  1.00 59.40           N
ATOM   4509  N   GLU B 280     -21.536  -9.300  89.536  1.00 57.23           N
ATOM   4510  CA  GLU B 280     -22.136  -8.804  90.772  1.00 57.69           C
ATOM   4511  C   GLU B 280     -23.441  -9.507  91.118  1.00 57.45           C
ATOM   4512  O   GLU B 280     -23.785  -9.644  92.289  1.00 58.50           O
ATOM   4513  CB  GLU B 280     -22.380  -7.295  90.669  1.00 57.98           C
ATOM   4514  CG  GLU B 280     -21.107  -6.466  90.609  1.00 59.48           C
ATOM   4515  CD  GLU B 280     -20.397  -6.383  91.949  1.00 60.61           C
ATOM   4516  OE1 GLU B 280     -20.941  -5.730  92.865  1.00 62.16           O
ATOM   4517  OE2 GLU B 280     -19.300  -6.969  92.092  1.00 60.63           O
ATOM   4518  N   LEU B 281     -24.172  -9.947  90.101  1.00 56.64           N
ATOM   4519  CA  LEU B 281     -25.433 -10.642  90.321  1.00 55.66           C
ATOM   4520  C   LEU B 281     -25.179 -12.139  90.466  1.00 55.18           C
ATOM   4521  O   LEU B 281     -26.116 -12.936  90.504  1.00 54.72           O
ATOM   4522  CB  LEU B 281     -26.380 -10.396  89.148  1.00 55.61           C
ATOM   4523  CG  LEU B 281     -26.733  -8.940  88.831  1.00 56.71           C
ATOM   4524  CD1 LEU B 281     -27.502  -8.876  87.513  1.00 56.83           C
ATOM   4525  CD2 LEU B 281     -27.560  -8.347  89.961  1.00 56.12           C
ATOM   4526  N   GLY B 282     -23.906 -12.513  90.545  1.00 55.22           N
ATOM   4527  CA  GLY B 282     -23.547 -13.915  90.674  1.00 56.08           C
ATOM   4528  C   GLY B 282     -24.079 -14.774  89.537  1.00 56.38           C
ATOM   4529  O   GLY B 282     -24.567 -15.885  89.756  1.00 56.62           O
ATOM   4530  N   LEU B 283     -23.987 -14.262  88.314  1.00 56.36           N
ATOM   4531  CA  LEU B 283     -24.471 -14.993  87.151  1.00 56.06           C
ATOM   4532  C   LEU B 283     -23.316 -15.502  86.293  1.00 56.12           C
ATOM   4533  O   LEU B 283     -23.510 -15.894  85.145  1.00 56.31           O
ATOM   4534  CB  LEU B 283     -25.396 -14.098  86.329  1.00 55.15           C
ATOM   4535  CG  LEU B 283     -26.681 -13.689  87.051  1.00 54.34           C
ATOM   4536  CD1 LEU B 283     -27.352 -12.528  86.334  1.00 53.96           C
ATOM   4537  CD2 LEU B 283     -27.606 -14.886  87.131  1.00 53.84           C
ATOM   4538  N   LEU B 284     -22.119 -15.496  86.874  1.00 56.61           N
ATOM   4539  CA  LEU B 284     -20.901 -15.958  86.209  1.00 57.17           C
ATOM   4540  C   LEU B 284     -20.171 -16.986  87.084  1.00 57.70           C
ATOM   4541  O   LEU B 284     -20.107 -16.834  88.309  1.00 57.12           O
ATOM   4542  CB  LEU B 284     -19.963 -14.774  85.936  1.00 57.36           C
ATOM   4543  CG  LEU B 284     -20.097 -13.983  84.631  1.00 57.73           C
ATOM   4544  CD1 LEU B 284     -21.546 -13.646  84.369  1.00 57.71           C
ATOM   4545  CD2 LEU B 284     -19.242 -12.717  84.714  1.00 56.89           C
ATOM   4546  N   LYS B 285     -19.610 -18.014  86.448  1.00 57.85           N
ATOM   4547  CA  LYS B 285     -18.885 -19.067  87.157  1.00 57.96           C
ATOM   4548  C   LYS B 285     -17.367 -18.897  87.064  1.00 58.31           C
ATOM   4549  O   LYS B 285     -16.841 -18.548  86.008  1.00 58.44           O
ATOM   4550  CB  LYS B 285     -19.273 -20.437  86.593  1.00 57.84           C
ATOM   4551  CG  LYS B 285     -20.744 -20.799  86.753  1.00 57.97           C
ATOM   4552  CD  LYS B 285     -21.041 -22.138  86.084  1.00 58.51           C
ATOM   4553  CE  LYS B 285     -22.419 -22.685  86.453  1.00 58.80           C
ATOM   4554  NZ  LYS B 285     -23.534 -21.792  86.034  1.00 58.61           N
ATOM   4555  N   ASP B 286     -16.672 -19.155  88.172  1.00 58.40           N
```

FIGURE 2-68 (COORDINATES)

```
ATOM   4556  CA  ASP B 286     -15.214 -19.046  88.236  1.00 58.47           C
ATOM   4557  C   ASP B 286     -14.723 -17.714  87.693  1.00 58.40           C
ATOM   4558  O   ASP B 286     -13.717 -17.662  86.989  1.00 58.68           O
ATOM   4559  CB  ASP B 286     -14.567 -20.180  87.434  1.00 59.52           C
ATOM   4560  CG  ASP B 286     -14.917 -21.556  87.975  1.00 61.18           C
ATOM   4561  OD1 ASP B 286     -14.467 -21.886  89.094  1.00 62.38           O
ATOM   4562  OD2 ASP B 286     -15.643 -22.308  87.286  1.00 61.43           O
ATOM   4563  N   HIS B 287     -15.422 -16.638  88.032  1.00 58.60           N
ATOM   4564  CA  HIS B 287     -15.072 -15.311  87.538  1.00 59.10           C
ATOM   4565  C   HIS B 287     -14.784 -14.311  88.658  1.00 59.75           C
ATOM   4566  O   HIS B 287     -15.574 -14.173  89.594  1.00 59.97           O
ATOM   4567  CB  HIS B 287     -16.217 -14.804  86.651  1.00 59.12           C
ATOM   4568  CG  HIS B 287     -15.956 -13.479  86.006  1.00 59.19           C
ATOM   4569  ND1 HIS B 287     -15.864 -12.305  86.722  1.00 59.10           N
ATOM   4570  CD2 HIS B 287     -15.788 -13.140  84.706  1.00 59.33           C
ATOM   4571  CE1 HIS B 287     -15.650 -11.300  85.892  1.00 59.96           C
ATOM   4572  NE2 HIS B 287     -15.600 -11.780  84.662  1.00 59.91           N
ATOM   4573  N   SER B 288     -13.652 -13.616  88.556  1.00 60.12           N
ATOM   4574  CA  SER B 288     -13.265 -12.615  89.553  1.00 60.87           C
ATOM   4575  C   SER B 288     -12.943 -11.286  88.870  1.00 61.88           C
ATOM   4576  O   SER B 288     -12.294 -11.258  87.820  1.00 62.17           O
ATOM   4577  CB  SER B 288     -12.038 -13.077  90.343  1.00 60.27           C
ATOM   4578  OG  SER B 288     -10.858 -12.946  89.574  1.00 59.09           O
ATOM   4579  N   LEU B 289     -13.390 -10.185  89.466  1.00 62.41           N
ATOM   4580  CA  LEU B 289     -13.139  -8.872  88.893  1.00 62.98           C
ATOM   4581  C   LEU B 289     -11.648  -8.594  88.723  1.00 63.48           C
ATOM   4582  O   LEU B 289     -11.252  -7.795  87.868  1.00 63.91           O
ATOM   4583  CB  LEU B 289     -13.782  -7.783  89.754  1.00 62.79           C
ATOM   4584  CG  LEU B 289     -15.312  -7.822  89.823  1.00 63.25           C
ATOM   4585  CD1 LEU B 289     -15.821  -6.587  90.550  1.00 62.75           C
ATOM   4586  CD2 LEU B 289     -15.890  -7.878  88.417  1.00 63.38           C
ATOM   4587  N   GLU B 290     -10.819  -9.252  89.529  1.00 63.73           N
ATOM   4588  CA  GLU B 290      -9.377  -9.059  89.432  1.00 63.98           C
ATOM   4589  C   GLU B 290      -8.909  -9.536  88.064  1.00 63.40           C
ATOM   4590  O   GLU B 290      -8.027  -8.935  87.451  1.00 63.70           O
ATOM   4591  CB  GLU B 290      -8.651  -9.838  90.535  1.00 65.12           C
ATOM   4592  CG  GLU B 290      -7.125  -9.755  90.466  1.00 67.04           C
ATOM   4593  CD  GLU B 290      -6.595  -8.332  90.603  1.00 68.83           C
ATOM   4594  OE1 GLU B 290      -6.991  -7.458  89.798  1.00 69.71           O
ATOM   4595  OE2 GLU B 290      -5.774  -8.087  91.516  1.00 69.35           O
ATOM   4596  N   GLY B 291      -9.516 -10.617  87.587  1.00 62.40           N
ATOM   4597  CA  GLY B 291      -9.155 -11.152  86.289  1.00 61.38           C
ATOM   4598  C   GLY B 291     -10.273 -11.002  85.277  1.00 60.71           C
ATOM   4599  O   GLY B 291     -10.527 -11.919  84.495  1.00 60.98           O
ATOM   4600  N   ARG B 292     -10.948  -9.855  85.290  1.00 59.76           N
ATOM   4601  CA  ARG B 292     -12.039  -9.617  84.354  1.00 59.14           C
ATOM   4602  C   ARG B 292     -11.508  -9.789  82.938  1.00 58.24           C
ATOM   4603  O   ARG B 292     -10.315  -9.617  82.691  1.00 57.80           O
ATOM   4604  CB  ARG B 292     -12.641  -8.211  84.553  1.00 60.11           C
ATOM   4605  CG  ARG B 292     -11.668  -7.037  84.440  1.00 61.28           C
ATOM   4606  CD  ARG B 292     -12.357  -5.698  84.772  1.00 62.68           C
ATOM   4607  NE  ARG B 292     -11.456  -4.548  84.655  1.00 64.32           N
ATOM   4608  CZ  ARG B 292     -10.381  -4.344  85.421  1.00 65.96           C
ATOM   4609  NH1 ARG B 292     -10.060  -5.213  86.378  1.00 66.23           N
ATOM   4610  NH2 ARG B 292      -9.615  -3.273  85.227  1.00 65.71           N
ATOM   4611  N   TYR B 293     -12.390 -10.140  82.011  1.00 57.24           N
ATOM   4612  CA  TYR B 293     -11.983 -10.360  80.630  1.00 56.57           C
ATOM   4613  C   TYR B 293     -11.730  -9.078  79.830  1.00 57.07           C
ATOM   4614  O   TYR B 293     -10.798  -9.009  79.032  1.00 57.06           O
ATOM   4615  CB  TYR B 293     -13.029 -11.218  79.917  1.00 54.36           C
ATOM   4616  CG  TYR B 293     -13.370 -12.505  80.635  1.00 52.39           C
ATOM   4617  CD1 TYR B 293     -12.367 -13.341  81.135  1.00 51.17           C
ATOM   4618  CD2 TYR B 293     -14.696 -12.913  80.774  1.00 51.26           C
ATOM   4619  CE1 TYR B 293     -12.678 -14.551  81.751  1.00 49.93           C
ATOM   4620  CE2 TYR B 293     -15.018 -14.122  81.387  1.00 50.70           C
ATOM   4621  CZ  TYR B 293     -14.005 -14.937  81.871  1.00 50.00           C
ATOM   4622  OH  TYR B 293     -14.324 -16.143  82.452  1.00 49.00           O
ATOM   4623  N   PHE B 294     -12.552  -8.061  80.045  1.00 57.91           N
```

FIGURE 2-69 (COORDINATES)

```
ATOM   4624  CA  PHE B 294     -12.392   -6.810   79.319  1.00  59.77           C
ATOM   4625  C   PHE B 294     -11.669   -5.750   80.142  1.00  62.01           C
ATOM   4626  O   PHE B 294     -12.285   -4.950   80.845  1.00  61.86           O
ATOM   4627  CB  PHE B 294     -13.765   -6.319   78.863  1.00  58.05           C
ATOM   4628  CG  PHE B 294     -14.484   -7.308   77.996  1.00  56.42           C
ATOM   4629  CD1 PHE B 294     -14.049   -7.553   76.695  1.00  55.47           C
ATOM   4630  CD2 PHE B 294     -15.553   -8.047   78.498  1.00  55.67           C
ATOM   4631  CE1 PHE B 294     -14.665   -8.522   75.908  1.00  54.78           C
ATOM   4632  CE2 PHE B 294     -16.177   -9.018   77.718  1.00  55.03           C
ATOM   4633  CZ  PHE B 294     -15.731   -9.256   76.421  1.00  54.48           C
ATOM   4634  N   GLN B 295     -10.345   -5.760   80.034  1.00  65.43           N
ATOM   4635  CA  GLN B 295      -9.488   -4.829   80.760  1.00  68.72           C
ATOM   4636  C   GLN B 295      -9.591   -3.407   80.230  1.00  70.41           C
ATOM   4637  O   GLN B 295      -9.898   -3.189   79.059  1.00  70.36           O
ATOM   4638  CB  GLN B 295      -8.034   -5.296   80.675  1.00  69.46           C
ATOM   4639  CG  GLN B 295      -7.803   -6.678   81.254  1.00  71.00           C
ATOM   4640  CD  GLN B 295      -7.906   -6.698   82.763  1.00  72.04           C
ATOM   4641  OE1 GLN B 295      -8.858   -6.170   83.341  1.00  72.88           O
ATOM   4642  NE2 GLN B 295      -6.924   -7.316   83.414  1.00  72.11           N
ATOM   4643  N   ASN B 296      -9.318   -2.443   81.105  1.00  72.76           N
ATOM   4644  CA  ASN B 296      -9.373   -1.031   80.745  1.00  75.04           C
ATOM   4645  C   ASN B 296      -8.029   -0.647   80.126  1.00  75.98           C
ATOM   4646  O   ASN B 296      -7.364    0.271   80.609  1.00  76.51           O
ATOM   4647  CB  ASN B 296      -9.608   -0.143   81.983  1.00  75.81           C
ATOM   4648  CG  ASN B 296     -10.471   -0.809   83.060  1.00  76.89           C
ATOM   4649  OD1 ASN B 296     -10.912   -0.146   84.000  1.00  77.52           O
ATOM   4650  ND2 ASN B 296     -10.697   -2.112   82.940  1.00  77.38           N
ATOM   4651  N   TYR B 297      -7.623   -1.344   79.068  1.00  76.74           N
ATOM   4652  CA  TYR B 297      -6.342   -1.045   78.438  1.00  77.37           C
ATOM   4653  C   TYR B 297      -6.396   -1.072   76.905  1.00  77.26           C
ATOM   4654  O   TYR B 297      -7.084   -1.900   76.308  1.00  77.53           O
ATOM   4655  CB  TYR B 297      -5.271   -1.997   79.008  1.00  78.36           C
ATOM   4656  CG  TYR B 297      -4.792   -3.121   78.115  1.00  79.49           C
ATOM   4657  CD1 TYR B 297      -3.859   -2.883   77.103  1.00  79.97           C
ATOM   4658  CD2 TYR B 297      -5.223   -4.435   78.319  1.00  79.77           C
ATOM   4659  CE1 TYR B 297      -3.361   -3.923   76.319  1.00  80.57           C
ATOM   4660  CE2 TYR B 297      -4.732   -5.486   77.539  1.00  80.17           C
ATOM   4661  CZ  TYR B 297      -3.799   -5.222   76.543  1.00  80.73           C
ATOM   4662  OH  TYR B 297      -3.293   -6.253   75.781  1.00  80.92           O
ATOM   4663  N   SER B 298      -5.673   -0.143   76.280  1.00  76.58           N
ATOM   4664  CA  SER B 298      -5.645   -0.018   74.825  1.00  75.80           C
ATOM   4665  C   SER B 298      -4.488   -0.736   74.135  1.00  75.29           C
ATOM   4666  O   SER B 298      -3.497   -1.105   74.764  1.00  75.15           O
ATOM   4667  CB  SER B 298      -5.623    1.464   74.435  1.00  76.17           C
ATOM   4668  OG  SER B 298      -4.502    2.126   74.999  1.00  75.72           O
ATOM   4669  N   TYR B 299      -4.627   -0.911   72.824  1.00  74.63           N
ATOM   4670  CA  TYR B 299      -3.629   -1.587   72.002  1.00  73.78           C
ATOM   4671  C   TYR B 299      -3.334   -0.703   70.783  1.00  73.02           C
ATOM   4672  O   TYR B 299      -4.090   -0.682   69.809  1.00  72.80           O
ATOM   4673  CB  TYR B 299      -4.182   -2.953   71.575  1.00  74.12           C
ATOM   4674  CG  TYR B 299      -3.154   -3.951   71.087  1.00  74.62           C
ATOM   4675  CD1 TYR B 299      -2.643   -3.883   69.790  1.00  74.85           C
ATOM   4676  CD2 TYR B 299      -2.710   -4.983   71.919  1.00  74.47           C
ATOM   4677  CE1 TYR B 299      -1.716   -4.821   69.331  1.00  75.35           C
ATOM   4678  CE2 TYR B 299      -1.783   -5.924   71.471  1.00  74.69           C
ATOM   4679  CZ  TYR B 299      -1.291   -5.837   70.176  1.00  75.07           C
ATOM   4680  OH  TYR B 299      -0.378   -6.762   69.723  1.00  75.20           O
ATOM   4681  N   GLY B 300      -2.223    0.027   70.863  1.00  72.31           N
ATOM   4682  CA  GLY B 300      -1.805    0.945   69.813  1.00  70.24           C
ATOM   4683  C   GLY B 300      -2.080    0.615   68.356  1.00  68.82           C
ATOM   4684  O   GLY B 300      -2.539    1.471   67.594  1.00  68.71           O
ATOM   4685  N   GLY B 301      -1.785   -0.615   67.956  1.00  67.33           N
ATOM   4686  CA  GLY B 301      -2.003   -1.004   66.576  1.00  64.80           C
ATOM   4687  C   GLY B 301      -3.152   -1.971   66.362  1.00  62.73           C
ATOM   4688  O   GLY B 301      -4.194   -1.894   67.019  1.00  62.61           O
ATOM   4689  N   VAL B 302      -2.954   -2.889   65.425  1.00  60.31           N
ATOM   4690  CA  VAL B 302      -3.967   -3.876   65.101  1.00  57.12           C
ATOM   4691  C   VAL B 302      -3.330   -5.253   64.968  1.00  54.31           C
```

FIGURE 2-70 (COORDINATES)

```
ATOM   4692  O   VAL B 302      -2.124  -5.382  64.745  1.00 53.22           O
ATOM   4693  CB  VAL B 302      -4.682  -3.526  63.765  1.00 57.68           C
ATOM   4694  CG1 VAL B 302      -5.847  -4.481  63.521  1.00 57.59           C
ATOM   4695  CG2 VAL B 302      -5.177  -2.088  63.799  1.00 57.56           C
ATOM   4696  N   ILE B 303      -4.157  -6.274  65.132  1.00 50.87           N
ATOM   4697  CA  ILE B 303      -3.726  -7.650  64.999  1.00 47.59           C
ATOM   4698  C   ILE B 303      -4.377  -8.097  63.705  1.00 45.56           C
ATOM   4699  O   ILE B 303      -5.589  -7.987  63.556  1.00 45.66           O
ATOM   4700  CB  ILE B 303      -4.232  -8.503  66.182  1.00 47.32           C
ATOM   4701  CG1 ILE B 303      -3.504  -8.076  67.463  1.00 47.44           C
ATOM   4702  CG2 ILE B 303      -4.015  -9.976  65.902  1.00 46.45           C
ATOM   4703  CD1 ILE B 303      -3.962  -8.797  68.720  1.00 47.89           C
ATOM   4704  N   GLN B 304      -3.575  -8.567  62.757  1.00 43.29           N
ATOM   4705  CA  GLN B 304      -4.113  -9.011  61.476  1.00 41.12           C
ATOM   4706  C   GLN B 304      -5.228 -10.028  61.687  1.00 38.92           C
ATOM   4707  O   GLN B 304      -5.067 -10.983  62.430  1.00 39.03           O
ATOM   4708  CB  GLN B 304      -3.011  -9.631  60.621  1.00 41.59           C
ATOM   4709  CG  GLN B 304      -1.895  -8.680  60.278  1.00 43.70           C
ATOM   4710  CD  GLN B 304      -2.391  -7.448  59.547  1.00 46.85           C
ATOM   4711  OE1 GLN B 304      -2.874  -7.526  58.408  1.00 47.78           O
ATOM   4712  NE2 GLN B 304      -2.281  -6.295  60.203  1.00 48.15           N
ATOM   4713  N   ASP B 305      -6.364  -9.806  61.039  1.00 36.69           N
ATOM   4714  CA  ASP B 305      -7.491 -10.714  61.158  1.00 35.36           C
ATOM   4715  C   ASP B 305      -8.553 -10.345  60.119  1.00 34.94           C
ATOM   4716  O   ASP B 305      -8.373  -9.390  59.370  1.00 34.37           O
ATOM   4717  CB  ASP B 305      -8.073 -10.647  62.572  1.00 34.44           C
ATOM   4718  CG  ASP B 305      -8.768 -11.934  62.979  1.00 33.19           C
ATOM   4719  OD1 ASP B 305      -8.985 -12.803  62.112  1.00 31.81           O
ATOM   4720  OD2 ASP B 305      -9.102 -12.074  64.170  1.00 33.05           O
ATOM   4721  N   ASP B 306      -9.653 -11.098  60.084  1.00 34.31           N
ATOM   4722  CA  ASP B 306     -10.728 -10.871  59.118  1.00 33.54           C
ATOM   4723  C   ASP B 306     -11.348  -9.473  59.108  1.00 33.42           C
ATOM   4724  O   ASP B 306     -11.998  -9.094  58.140  1.00 33.73           O
ATOM   4725  CB  ASP B 306     -11.855 -11.899  59.311  1.00 33.48           C
ATOM   4726  CG  ASP B 306     -11.481 -13.292  58.819  1.00 34.40           C
ATOM   4727  OD1 ASP B 306     -10.859 -13.403  57.739  1.00 33.53           O
ATOM   4728  OD2 ASP B 306     -11.829 -14.279  59.508  1.00 33.56           O
ATOM   4729  N   HIS B 307     -11.163  -8.707  60.173  1.00 33.00           N
ATOM   4730  CA  HIS B 307     -11.744  -7.372  60.234  1.00 32.56           C
ATOM   4731  C   HIS B 307     -11.017  -6.344  59.362  1.00 32.86           C
ATOM   4732  O   HIS B 307     -11.618  -5.362  58.930  1.00 32.31           O
ATOM   4733  CB  HIS B 307     -11.754  -6.876  61.679  1.00 31.51           C
ATOM   4734  CG  HIS B 307     -10.387  -6.675  62.250  1.00 30.15           C
ATOM   4735  ND1 HIS B 307      -9.433  -7.669  62.262  1.00 29.98           N
ATOM   4736  CD2 HIS B 307      -9.807  -5.588  62.814  1.00 30.02           C
ATOM   4737  CE1 HIS B 307      -8.323  -7.202  62.806  1.00 31.34           C
ATOM   4738  NE2 HIS B 307      -8.523  -5.942  63.150  1.00 30.28           N
ATOM   4739  N   ILE B 308      -9.734  -6.573  59.101  1.00 33.32           N
ATOM   4740  CA  ILE B 308      -8.935  -5.640  58.316  1.00 34.27           C
ATOM   4741  C   ILE B 308      -9.579  -5.108  57.023  1.00 35.00           C
ATOM   4742  O   ILE B 308      -9.688  -3.895  56.837  1.00 35.45           O
ATOM   4743  CB  ILE B 308      -7.552  -6.243  57.990  1.00 34.86           C
ATOM   4744  CG1 ILE B 308      -6.762  -6.468  59.290  1.00 35.76           C
ATOM   4745  CG2 ILE B 308      -6.779  -5.312  57.052  1.00 35.70           C
ATOM   4746  CD1 ILE B 308      -6.482  -5.195  60.091  1.00 34.77           C
ATOM   4747  N   PRO B 309     -10.025  -5.998  56.122  1.00 34.79           N
ATOM   4748  CA  PRO B 309     -10.640  -5.534  54.877  1.00 33.99           C
ATOM   4749  C   PRO B 309     -11.844  -4.619  55.097  1.00 33.93           C
ATOM   4750  O   PRO B 309     -12.149  -3.782  54.253  1.00 34.13           O
ATOM   4751  CB  PRO B 309     -11.033  -6.835  54.176  1.00 34.68           C
ATOM   4752  CG  PRO B 309     -10.076  -7.831  54.735  1.00 34.49           C
ATOM   4753  CD  PRO B 309     -10.039  -7.468  56.189  1.00 34.28           C
ATOM   4754  N   PHE B 310     -12.538  -4.782  56.220  1.00 33.59           N
ATOM   4755  CA  PHE B 310     -13.700  -3.943  56.503  1.00 33.16           C
ATOM   4756  C   PHE B 310     -13.267  -2.667  57.227  1.00 34.16           C
ATOM   4757  O   PHE B 310     -13.784  -1.578  56.973  1.00 33.98           O
ATOM   4758  CB  PHE B 310     -14.718  -4.712  57.346  1.00 32.04           C
ATOM   4759  CG  PHE B 310     -15.210  -5.978  56.695  1.00 31.53           C
```

FIGURE 2-71 (COORDINATES)

```
ATOM   4760  CD1 PHE B 310     -14.403   -7.120   56.657  1.00 29.73           C
ATOM   4761  CD2 PHE B 310     -16.467   -6.025   56.097  1.00 29.82           C
ATOM   4762  CE1 PHE B 310     -14.840   -8.287   56.033  1.00 28.57           C
ATOM   4763  CE2 PHE B 310     -16.917   -7.190   55.467  1.00 30.50           C
ATOM   4764  CZ  PHE B 310     -16.100   -8.326   55.435  1.00 29.40           C
ATOM   4765  N   LEU B 311     -12.306   -2.818   58.126  1.00 35.01           N
ATOM   4766  CA  LEU B 311     -11.775   -1.703   58.883  1.00 36.21           C
ATOM   4767  C   LEU B 311     -11.246   -0.633   57.924  1.00 37.56           C
ATOM   4768  O   LEU B 311     -11.604    0.541   58.026  1.00 37.33           O
ATOM   4769  CB  LEU B 311     -10.631   -2.189   59.780  1.00 36.56           C
ATOM   4770  CG  LEU B 311      -9.915   -1.114   60.599  1.00 36.98           C
ATOM   4771  CD1 LEU B 311     -10.857   -0.593   61.671  1.00 38.52           C
ATOM   4772  CD2 LEU B 311      -8.665   -1.689   61.233  1.00 37.41           C
ATOM   4773  N   ARG B 312     -10.398   -1.042   56.986  1.00 38.31           N
ATOM   4774  CA  ARG B 312      -9.824   -0.089   56.062  1.00 40.14           C
ATOM   4775  C   ARG B 312     -10.848    0.548   55.128  1.00 39.92           C
ATOM   4776  O   ARG B 312     -10.500    1.397   54.312  1.00 41.26           O
ATOM   4777  CB  ARG B 312      -8.676   -0.729   55.265  1.00 41.90           C
ATOM   4778  CG  ARG B 312      -9.082   -1.764   54.249  1.00 46.15           C
ATOM   4779  CD  ARG B 312      -7.842   -2.370   53.605  1.00 49.43           C
ATOM   4780  NE  ARG B 312      -8.150   -3.375   52.583  1.00 52.85           N
ATOM   4781  CZ  ARG B 312      -8.742   -3.120   51.414  1.00 54.07           C
ATOM   4782  NH1 ARG B 312      -9.115   -1.882   51.092  1.00 54.20           N
ATOM   4783  NH2 ARG B 312      -8.933   -4.107   50.547  1.00 54.74           N
ATOM   4784  N   ARG B 313     -12.111    0.153   55.253  1.00 38.87           N
ATOM   4785  CA  ARG B 313     -13.158    0.731   54.425  1.00 37.89           C
ATOM   4786  C   ARG B 313     -14.134    1.504   55.296  1.00 38.13           C
ATOM   4787  O   ARG B 313     -15.189    1.949   54.830  1.00 38.10           O
ATOM   4788  CB  ARG B 313     -13.899   -0.349   53.636  1.00 38.24           C
ATOM   4789  CG  ARG B 313     -13.106   -0.962   52.488  1.00 36.86           C
ATOM   4790  CD  ARG B 313     -14.006   -1.895   51.693  1.00 38.73           C
ATOM   4791  NE  ARG B 313     -13.397   -2.382   50.460  1.00 39.42           N
ATOM   4792  CZ  ARG B 313     -12.399   -3.260   50.403  1.00 40.55           C
ATOM   4793  NH1 ARG B 313     -11.878   -3.762   51.520  1.00 39.81           N
ATOM   4794  NH2 ARG B 313     -11.929   -3.650   49.222  1.00 40.08           N
ATOM   4795  N   GLY B 314     -13.791    1.638   56.574  1.00 37.89           N
ATOM   4796  CA  GLY B 314     -14.631    2.403   57.477  1.00 37.73           C
ATOM   4797  C   GLY B 314     -15.673    1.709   58.332  1.00 37.82           C
ATOM   4798  O   GLY B 314     -16.489    2.381   58.960  1.00 38.45           O
ATOM   4799  N   VAL B 315     -15.681    0.384   58.370  1.00 37.34           N
ATOM   4800  CA  VAL B 315     -16.660   -0.297   59.209  1.00 36.02           C
ATOM   4801  C   VAL B 315     -16.182   -0.264   60.662  1.00 35.45           C
ATOM   4802  O   VAL B 315     -15.033   -0.596   60.956  1.00 34.64           O
ATOM   4803  CB  VAL B 315     -16.852   -1.764   58.786  1.00 35.62           C
ATOM   4804  CG1 VAL B 315     -17.818   -2.456   59.740  1.00 34.60           C
ATOM   4805  CG2 VAL B 315     -17.379   -1.827   57.361  1.00 35.25           C
ATOM   4806  N   PRO B 316     -17.047    0.176   61.586  1.00 35.15           N
ATOM   4807  CA  PRO B 316     -16.605    0.205   62.986  1.00 35.06           C
ATOM   4808  C   PRO B 316     -16.384   -1.243   63.436  1.00 34.77           C
ATOM   4809  O   PRO B 316     -17.225   -2.115   63.192  1.00 34.61           O
ATOM   4810  CB  PRO B 316     -17.779    0.878   63.709  1.00 34.48           C
ATOM   4811  CG  PRO B 316     -18.357    1.781   62.645  1.00 35.11           C
ATOM   4812  CD  PRO B 316     -18.323    0.898   61.413  1.00 35.35           C
ATOM   4813  N   VAL B 317     -15.265   -1.502   64.097  1.00 34.15           N
ATOM   4814  CA  VAL B 317     -14.964   -2.861   64.517  1.00 34.14           C
ATOM   4815  C   VAL B 317     -14.743   -3.065   65.998  1.00 34.13           C
ATOM   4816  O   VAL B 317     -14.024   -2.311   66.641  1.00 35.31           O
ATOM   4817  CB  VAL B 317     -13.703   -3.400   63.805  1.00 33.72           C
ATOM   4818  CG1 VAL B 317     -13.377   -4.792   64.315  1.00 34.07           C
ATOM   4819  CG2 VAL B 317     -13.912   -3.417   62.312  1.00 33.49           C
ATOM   4820  N   LEU B 318     -15.364   -4.112   66.522  1.00 34.14           N
ATOM   4821  CA  LEU B 318     -15.211   -4.499   67.916  1.00 34.13           C
ATOM   4822  C   LEU B 318     -14.499   -5.857   67.796  1.00 33.88           C
ATOM   4823  O   LEU B 318     -15.135   -6.876   67.528  1.00 34.57           O
ATOM   4824  CB  LEU B 318     -16.592   -4.639   68.558  1.00 34.42           C
ATOM   4825  CG  LEU B 318     -16.695   -4.741   70.079  1.00 34.86           C
ATOM   4826  CD1 LEU B 318     -15.872   -3.648   70.737  1.00 34.09           C
ATOM   4827  CD2 LEU B 318     -18.169   -4.629   70.487  1.00 34.94           C
```

FIGURE 2-72 (COORDINATES)

```
ATOM   4828  N    HIS B 319     -13.179   -5.855   67.972  1.00 33.46           N
ATOM   4829  CA   HIS B 319     -12.366   -7.061   67.823  1.00 33.17           C
ATOM   4830  C    HIS B 319     -12.163   -7.899   69.083  1.00 34.32           C
ATOM   4831  O    HIS B 319     -11.264   -7.631   69.882  1.00 35.15           O
ATOM   4832  CB   HIS B 319     -10.999   -6.678   67.244  1.00 31.56           C
ATOM   4833  CG   HIS B 319     -10.265   -7.817   66.598  1.00 30.98           C
ATOM   4834  ND1  HIS B 319      -8.988   -7.687   66.093  1.00 29.97           N
ATOM   4835  CD2  HIS B 319     -10.621   -9.108   66.389  1.00 30.66           C
ATOM   4836  CE1  HIS B 319      -8.588   -8.849   65.606  1.00 30.44           C
ATOM   4837  NE2  HIS B 319      -9.560   -9.728   65.773  1.00 29.74           N
ATOM   4838  N    LEU B 320     -12.979   -8.935   69.240  1.00 34.84           N
ATOM   4839  CA   LEU B 320     -12.888   -9.807   70.402  1.00 35.74           C
ATOM   4840  C    LEU B 320     -11.871  -10.934   70.211  1.00 36.47           C
ATOM   4841  O    LEU B 320     -12.232  -12.100   70.036  1.00 36.15           O
ATOM   4842  CB   LEU B 320     -14.269  -10.384   70.739  1.00 35.94           C
ATOM   4843  CG   LEU B 320     -15.397   -9.348   70.892  1.00 37.33           C
ATOM   4844  CD1  LEU B 320     -16.606   -9.987   71.564  1.00 36.76           C
ATOM   4845  CD2  LEU B 320     -14.914   -8.161   71.722  1.00 37.36           C
ATOM   4846  N    ILE B 321     -10.594  -10.561   70.234  1.00 36.85           N
ATOM   4847  CA   ILE B 321      -9.483  -11.499   70.097  1.00 37.53           C
ATOM   4848  C    ILE B 321      -8.600  -11.231   71.323  1.00 38.65           C
ATOM   4849  O    ILE B 321      -8.306  -10.083   71.647  1.00 38.27           O
ATOM   4850  CB   ILE B 321      -8.694  -11.256   68.773  1.00 36.18           C
ATOM   4851  CG1  ILE B 321      -7.617  -12.325   68.601  1.00 36.03           C
ATOM   4852  CG2  ILE B 321      -8.062   -9.878   68.775  1.00 35.09           C
ATOM   4853  CD1  ILE B 321      -6.933  -12.294   67.244  1.00 35.14           C
ATOM   4854  N    PRO B 322      -8.174  -12.287   72.028  1.00 39.68           N
ATOM   4855  CA   PRO B 322      -7.341  -12.092   73.217  1.00 40.54           C
ATOM   4856  C    PRO B 322      -5.891  -11.703   72.974  1.00 40.94           C
ATOM   4857  O    PRO B 322      -5.290  -12.052   71.959  1.00 40.49           O
ATOM   4858  CB   PRO B 322      -7.431  -13.442   73.942  1.00 40.52           C
ATOM   4859  CG   PRO B 322      -8.599  -14.158   73.291  1.00 41.40           C
ATOM   4860  CD   PRO B 322      -8.513  -13.708   71.862  1.00 40.84           C
ATOM   4861  N    SER B 323      -5.339  -10.980   73.938  1.00 41.70           N
ATOM   4862  CA   SER B 323      -3.943  -10.576   73.901  1.00 42.45           C
ATOM   4863  C    SER B 323      -3.466  -10.720   75.340  1.00 42.32           C
ATOM   4864  O    SER B 323      -3.961  -10.033   76.238  1.00 42.65           O
ATOM   4865  CB   SER B 323      -3.799   -9.129   73.438  1.00 43.27           C
ATOM   4866  OG   SER B 323      -2.474   -8.892   72.991  1.00 45.54           O
ATOM   4867  N    PRO B 324      -2.511  -11.631   75.584  1.00 41.62           N
ATOM   4868  CA   PRO B 324      -1.864  -12.514   74.605  1.00 40.91           C
ATOM   4869  C    PRO B 324      -2.786  -13.580   74.013  1.00 40.57           C
ATOM   4870  O    PRO B 324      -3.903  -13.796   74.491  1.00 39.80           O
ATOM   4871  CB   PRO B 324      -0.739  -13.140   75.417  1.00 40.87           C
ATOM   4872  CG   PRO B 324      -1.409  -13.334   76.751  1.00 40.52           C
ATOM   4873  CD   PRO B 324      -2.127  -12.009   76.959  1.00 40.56           C
ATOM   4874  N    PHE B 325      -2.301  -14.241   72.965  1.00 40.12           N
ATOM   4875  CA   PHE B 325      -3.051  -15.307   72.311  1.00 40.59           C
ATOM   4876  C    PHE B 325      -2.986  -16.527   73.223  1.00 40.92           C
ATOM   4877  O    PHE B 325      -2.134  -16.598   74.111  1.00 42.20           O
ATOM   4878  CB   PHE B 325      -2.408  -15.680   70.971  1.00 39.97           C
ATOM   4879  CG   PHE B 325      -2.579  -14.648   69.884  1.00 40.74           C
ATOM   4880  CD1  PHE B 325      -3.398  -13.539   70.062  1.00 40.80           C
ATOM   4881  CD2  PHE B 325      -1.949  -14.820   68.656  1.00 40.21           C
ATOM   4882  CE1  PHE B 325      -3.592  -12.619   69.030  1.00 41.13           C
ATOM   4883  CE2  PHE B 325      -2.138  -13.909   67.623  1.00 40.87           C
ATOM   4884  CZ   PHE B 325      -2.961  -12.809   67.808  1.00 40.79           C
ATOM   4885  N    PRO B 326      -3.879  -17.505   73.020  1.00 40.32           N
ATOM   4886  CA   PRO B 326      -3.854  -18.707   73.862  1.00 39.94           C
ATOM   4887  C    PRO B 326      -2.492  -19.389   73.734  1.00 40.22           C
ATOM   4888  O    PRO B 326      -1.871  -19.337   72.675  1.00 40.58           O
ATOM   4889  CB   PRO B 326      -4.973  -19.555   73.276  1.00 39.05           C
ATOM   4890  CG   PRO B 326      -5.932  -18.526   72.768  1.00 40.02           C
ATOM   4891  CD   PRO B 326      -5.024  -17.533   72.099  1.00 39.35           C
ATOM   4892  N    GLU B 327      -2.030  -20.028   74.804  1.00 40.98           N
ATOM   4893  CA   GLU B 327      -0.731  -20.701   74.785  1.00 41.27           C
ATOM   4894  C    GLU B 327      -0.630  -21.783   73.714  1.00 39.85           C
ATOM   4895  O    GLU B 327       0.451  -22.025   73.176  1.00 39.34           O
```

FIGURE 2-73 (COORDINATES)

```
ATOM   4896  CB   GLU B 327      -0.423 -21.322  76.151  1.00 43.43           C
ATOM   4897  CG   GLU B 327      -0.436 -20.325  77.295  1.00 49.12           C
ATOM   4898  CD   GLU B 327      -0.033 -20.945  78.628  1.00 51.81           C
ATOM   4899  OE1  GLU B 327      -0.607 -21.994  79.005  1.00 52.97           O
ATOM   4900  OE2  GLU B 327       0.855 -20.374  79.299  1.00 53.43           O
ATOM   4901  N    VAL B 328      -1.749 -22.433  73.407  1.00 38.40           N
ATOM   4902  CA   VAL B 328      -1.756 -23.490  72.398  1.00 37.64           C
ATOM   4903  C    VAL B 328      -1.844 -22.959  70.961  1.00 37.38           C
ATOM   4904  O    VAL B 328      -1.899 -23.744  70.015  1.00 37.64           O
ATOM   4905  CB   VAL B 328      -2.932 -24.475  72.625  1.00 37.60           C
ATOM   4906  CG1  VAL B 328      -2.742 -25.233  73.937  1.00 37.48           C
ATOM   4907  CG2  VAL B 328      -4.255 -23.716  72.642  1.00 37.21           C
ATOM   4908  N    TRP B 329      -1.837 -21.639  70.798  1.00 36.20           N
ATOM   4909  CA   TRP B 329      -1.946 -21.035  69.473  1.00 35.81           C
ATOM   4910  C    TRP B 329      -1.142 -21.736  68.385  1.00 35.90           C
ATOM   4911  O    TRP B 329       0.088 -21.830  68.439  1.00 36.00           O
ATOM   4912  CB   TRP B 329      -1.552 -19.556  69.515  1.00 35.07           C
ATOM   4913  CG   TRP B 329      -1.824 -18.821  68.225  1.00 34.51           C
ATOM   4914  CD1  TRP B 329      -3.048 -18.458  67.723  1.00 34.22           C
ATOM   4915  CD2  TRP B 329      -0.852 -18.347  67.283  1.00 33.62           C
ATOM   4916  NE1  TRP B 329      -2.893 -17.786  66.533  1.00 32.85           N
ATOM   4917  CE2  TRP B 329      -1.558 -17.703  66.240  1.00 32.83           C
ATOM   4918  CE3  TRP B 329       0.547 -18.402  67.218  1.00 33.66           C
ATOM   4919  CZ2  TRP B 329      -0.910 -17.118  65.146  1.00 32.66           C
ATOM   4920  CZ3  TRP B 329       1.190 -17.820  66.126  1.00 34.07           C
ATOM   4921  CH2  TRP B 329       0.458 -17.186  65.106  1.00 32.81           C
ATOM   4922  N    HIS B 330      -1.863 -22.231  67.391  1.00 35.86           N
ATOM   4923  CA   HIS B 330      -1.259 -22.916  66.263  1.00 36.30           C
ATOM   4924  C    HIS B 330      -0.398 -24.119  66.635  1.00 36.64           C
ATOM   4925  O    HIS B 330       0.693 -24.316  66.094  1.00 37.34           O
ATOM   4926  CB   HIS B 330      -0.463 -21.919  65.401  1.00 34.41           C
ATOM   4927  CG   HIS B 330      -1.330 -20.994  64.597  1.00 33.73           C
ATOM   4928  ND1  HIS B 330      -0.858 -20.269  63.524  1.00 33.88           N
ATOM   4929  CD2  HIS B 330      -2.643 -20.680  64.711  1.00 32.64           C
ATOM   4930  CE1  HIS B 330      -1.840 -19.549  63.012  1.00 32.48           C
ATOM   4931  NE2  HIS B 330      -2.934 -19.779  63.713  1.00 31.79           N
ATOM   4932  N    THR B 331      -0.900 -24.923  67.569  1.00 36.33           N
ATOM   4933  CA   THR B 331      -0.220 -26.146  67.973  1.00 36.00           C
ATOM   4934  C    THR B 331      -1.300 -27.213  67.993  1.00 35.78           C
ATOM   4935  O    THR B 331      -2.489 -26.896  68.064  1.00 35.33           O
ATOM   4936  CB   THR B 331       0.386 -26.064  69.390  1.00 35.94           C
ATOM   4937  OG1  THR B 331      -0.665 -26.083  70.364  1.00 35.52           O
ATOM   4938  CG2  THR B 331       1.213 -24.797  69.544  1.00 36.93           C
ATOM   4939  N    MET B 332      -0.894 -28.473  67.922  1.00 35.78           N
ATOM   4940  CA   MET B 332      -1.860 -29.555  67.960  1.00 36.48           C
ATOM   4941  C    MET B 332      -2.592 -29.557  69.304  1.00 36.76           C
ATOM   4942  O    MET B 332      -3.562 -30.286  69.482  1.00 37.16           O
ATOM   4943  CB   MET B 332      -1.159 -30.891  67.734  1.00 36.04           C
ATOM   4944  CG   MET B 332      -0.553 -31.001  66.358  1.00 34.79           C
ATOM   4945  SD   MET B 332      -1.802 -30.803  65.061  1.00 34.99           S
ATOM   4946  CE   MET B 332      -0.845 -31.229  63.642  1.00 33.92           C
ATOM   4947  N    ASP B 333      -2.144 -28.720  70.237  1.00 37.02           N
ATOM   4948  CA   ASP B 333      -2.785 -28.655  71.541  1.00 37.87           C
ATOM   4949  C    ASP B 333      -3.972 -27.706  71.580  1.00 37.86           C
ATOM   4950  O    ASP B 333      -4.634 -27.589  72.615  1.00 37.20           O
ATOM   4951  CB   ASP B 333      -1.775 -28.282  72.633  1.00 39.42           C
ATOM   4952  CG   ASP B 333      -0.693 -29.346  72.813  1.00 40.96           C
ATOM   4953  OD1  ASP B 333      -1.039 -30.547  72.879  1.00 40.69           O
ATOM   4954  OD2  ASP B 333       0.502 -28.984  72.887  1.00 42.70           O
ATOM   4955  N    ASP B 334      -4.242 -27.012  70.473  1.00 37.19           N
ATOM   4956  CA   ASP B 334      -5.407 -26.133  70.446  1.00 36.51           C
ATOM   4957  C    ASP B 334      -6.551 -27.080  70.124  1.00 36.33           C
ATOM   4958  O    ASP B 334      -7.109 -27.070  69.028  1.00 35.47           O
ATOM   4959  CB   ASP B 334      -5.299 -25.046  69.370  1.00 35.82           C
ATOM   4960  CG   ASP B 334      -6.534 -24.134  69.335  1.00 35.90           C
ATOM   4961  OD1  ASP B 334      -7.444 -24.301  70.177  1.00 35.06           O
ATOM   4962  OD2  ASP B 334      -6.603 -23.249  68.459  1.00 36.29           O
ATOM   4963  N    ASN B 335      -6.869 -27.915  71.107  1.00 37.03           N
```

FIGURE 2-74 (COORDINATES)

```
ATOM   4964  CA  ASN B 335      -7.914 -28.921  70.991  1.00 37.39           C
ATOM   4965  C   ASN B 335      -9.013 -28.741  72.036  1.00 36.93           C
ATOM   4966  O   ASN B 335      -9.025 -27.777  72.797  1.00 36.85           O
ATOM   4967  CB  ASN B 335      -7.301 -30.316  71.135  1.00 36.90           C
ATOM   4968  CG  ASN B 335      -6.488 -30.458  72.410  1.00 37.51           C
ATOM   4969  OD1 ASN B 335      -6.733 -29.759  73.397  1.00 38.02           O
ATOM   4970  ND2 ASN B 335      -5.523 -31.371  72.401  1.00 38.04           N
ATOM   4971  N   GLU B 336      -9.934 -29.692  72.059  1.00 37.47           N
ATOM   4972  CA  GLU B 336     -11.056 -29.659  72.982  1.00 39.62           C
ATOM   4973  C   GLU B 336     -10.619 -29.739  74.440  1.00 40.57           C
ATOM   4974  O   GLU B 336     -11.131 -29.007  75.289  1.00 40.17           O
ATOM   4975  CB  GLU B 336     -12.017 -30.807  72.659  1.00 38.29           C
ATOM   4976  CG  GLU B 336     -13.182 -30.945  73.615  1.00 38.17           C
ATOM   4977  CD  GLU B 336     -14.189 -31.980  73.153  1.00 37.31           C
ATOM   4978  OE1 GLU B 336     -13.905 -32.697  72.172  1.00 38.74           O
ATOM   4979  OE2 GLU B 336     -15.264 -32.081  73.768  1.00 37.61           O
ATOM   4980  N   GLU B 337      -9.664 -30.616  74.722  1.00 42.12           N
ATOM   4981  CA  GLU B 337      -9.176 -30.796  76.084  1.00 44.59           C
ATOM   4982  C   GLU B 337      -8.706 -29.522  76.781  1.00 43.74           C
ATOM   4983  O   GLU B 337      -8.893 -29.370  77.991  1.00 44.14           O
ATOM   4984  CB  GLU B 337      -8.040 -31.827  76.113  1.00 47.92           C
ATOM   4985  CG  GLU B 337      -7.447 -32.018  77.502  1.00 54.04           C
ATOM   4986  CD  GLU B 337      -6.513 -33.221  77.607  1.00 58.39           C
ATOM   4987  OE1 GLU B 337      -6.951 -34.347  77.275  1.00 59.91           O
ATOM   4988  OE2 GLU B 337      -5.347 -33.039  78.036  1.00 60.26           O
ATOM   4989  N   ASN B 338      -8.107 -28.604  76.028  1.00 42.47           N
ATOM   4990  CA  ASN B 338      -7.593 -27.377  76.618  1.00 40.68           C
ATOM   4991  C   ASN B 338      -8.568 -26.214  76.699  1.00 39.77           C
ATOM   4992  O   ASN B 338      -8.202 -25.125  77.127  1.00 39.49           O
ATOM   4993  CB  ASN B 338      -6.304 -26.969  75.896  1.00 41.03           C
ATOM   4994  CG  ASN B 338      -5.150 -27.919  76.203  1.00 41.40           C
ATOM   4995  OD1 ASN B 338      -4.191 -28.032  75.443  1.00 41.55           O
ATOM   4996  ND2 ASN B 338      -5.242 -28.602  77.334  1.00 42.62           N
ATOM   4997  N   LEU B 339      -9.815 -26.442  76.304  1.00 39.86           N
ATOM   4998  CA  LEU B 339     -10.828 -25.389  76.384  1.00 40.03           C
ATOM   4999  C   LEU B 339     -11.307 -25.258  77.829  1.00 41.44           C
ATOM   5000  O   LEU B 339     -11.161 -26.185  78.625  1.00 41.60           O
ATOM   5001  CB  LEU B 339     -12.021 -25.720  75.488  1.00 37.50           C
ATOM   5002  CG  LEU B 339     -11.764 -25.728  73.983  1.00 37.48           C
ATOM   5003  CD1 LEU B 339     -13.008 -26.230  73.266  1.00 36.73           C
ATOM   5004  CD2 LEU B 339     -11.383 -24.327  73.511  1.00 35.85           C
ATOM   5005  N   ASP B 340     -11.875 -24.104  78.166  1.00 42.67           N
ATOM   5006  CA  ASP B 340     -12.377 -23.867  79.509  1.00 43.02           C
ATOM   5007  C   ASP B 340     -13.877 -23.592  79.467  1.00 44.12           C
ATOM   5008  O   ASP B 340     -14.316 -22.514  79.066  1.00 43.78           O
ATOM   5009  CB  ASP B 340     -11.638 -22.692  80.155  1.00 44.04           C
ATOM   5010  CG  ASP B 340     -12.042 -22.478  81.610  1.00 44.94           C
ATOM   5011  OD1 ASP B 340     -13.021 -21.745  81.869  1.00 44.57           O
ATOM   5012  OD2 ASP B 340     -11.385 -23.060  82.496  1.00 45.99           O
ATOM   5013  N   GLU B 341     -14.654 -24.582  79.894  1.00 45.03           N
ATOM   5014  CA  GLU B 341     -16.111 -24.494  79.910  1.00 46.11           C
ATOM   5015  C   GLU B 341     -16.673 -23.196  80.496  1.00 45.73           C
ATOM   5016  O   GLU B 341     -17.517 -22.551  79.879  1.00 45.83           O
ATOM   5017  CB  GLU B 341     -16.695 -25.683  80.682  1.00 47.26           C
ATOM   5018  CG  GLU B 341     -18.198 -25.843  80.518  1.00 51.07           C
ATOM   5019  CD  GLU B 341     -18.797 -26.866  81.477  1.00 53.29           C
ATOM   5020  OE1 GLU B 341     -18.842 -26.589  82.696  1.00 54.97           O
ATOM   5021  OE2 GLU B 341     -19.220 -27.947  81.012  1.00 54.27           O
ATOM   5022  N   SER B 342     -16.210 -22.816  81.684  1.00 45.33           N
ATOM   5023  CA  SER B 342     -16.704 -21.607  82.335  1.00 45.46           C
ATOM   5024  C   SER B 342     -16.404 -20.311  81.587  1.00 44.89           C
ATOM   5025  O   SER B 342     -17.291 -19.474  81.412  1.00 44.58           O
ATOM   5026  CB  SER B 342     -16.162 -21.518  83.764  1.00 45.77           C
ATOM   5027  OG  SER B 342     -16.808 -22.464  84.596  1.00 46.75           O
ATOM   5028  N   THR B 343     -15.157 -20.142  81.158  1.00 43.93           N
ATOM   5029  CA  THR B 343     -14.769 -18.941  80.431  1.00 43.84           C
ATOM   5030  C   THR B 343     -15.707 -18.756  79.242  1.00 43.44           C
ATOM   5031  O   THR B 343     -16.260 -17.670  79.029  1.00 43.68           O
```

FIGURE 2-75 (COORDINATES)

```
ATOM   5032  CB  THR B 343     -13.322 -19.042  79.889  1.00 44.79           C
ATOM   5033  OG1 THR B 343     -12.417 -19.339  80.962  1.00 44.05           O
ATOM   5034  CG2 THR B 343     -12.913 -17.723  79.229  1.00 43.73           C
ATOM   5035  N   ILE B 344     -15.891 -19.834  78.483  1.00 41.97           N
ATOM   5036  CA  ILE B 344     -16.749 -19.817  77.305  1.00 41.17           C
ATOM   5037  C   ILE B 344     -18.217 -19.579  77.650  1.00 41.24           C
ATOM   5038  O   ILE B 344     -18.922 -18.877  76.926  1.00 40.86           O
ATOM   5039  CB  ILE B 344     -16.630 -21.147  76.513  1.00 40.00           C
ATOM   5040  CG1 ILE B 344     -15.193 -21.334  76.020  1.00 38.44           C
ATOM   5041  CG2 ILE B 344     -17.601 -21.148  75.335  1.00 39.09           C
ATOM   5042  CD1 ILE B 344     -14.908 -22.716  75.429  1.00 37.33           C
ATOM   5043  N   ASP B 345     -18.673 -20.162  78.755  1.00 41.65           N
ATOM   5044  CA  ASP B 345     -20.063 -20.018  79.175  1.00 41.24           C
ATOM   5045  C   ASP B 345     -20.355 -18.583  79.603  1.00 40.69           C
ATOM   5046  O   ASP B 345     -21.444 -18.065  79.354  1.00 40.18           O
ATOM   5047  CB  ASP B 345     -20.369 -20.999  80.316  1.00 42.20           C
ATOM   5048  CG  ASP B 345     -21.830 -20.951  80.767  1.00 43.29           C
ATOM   5049  OD1 ASP B 345     -22.732 -21.032  79.906  1.00 43.23           O
ATOM   5050  OD2 ASP B 345     -22.078 -20.848  81.990  1.00 43.99           O
ATOM   5051  N   ASN B 346     -19.381 -17.936  80.238  1.00 40.57           N
ATOM   5052  CA  ASN B 346     -19.556 -16.552  80.682  1.00 40.37           C
ATOM   5053  C   ASN B 346     -19.612 -15.598  79.492  1.00 39.88           C
ATOM   5054  O   ASN B 346     -20.454 -14.696  79.447  1.00 39.44           O
ATOM   5055  CB  ASN B 346     -18.414 -16.114  81.604  1.00 40.95           C
ATOM   5056  CG  ASN B 346     -18.379 -16.888  82.911  1.00 41.74           C
ATOM   5057  OD1 ASN B 346     -19.422 -17.246  83.466  1.00 41.06           O
ATOM   5058  ND2 ASN B 346     -17.172 -17.132  83.421  1.00 41.12           N
ATOM   5059  N   LEU B 347     -18.704 -15.794  78.537  1.00 38.77           N
ATOM   5060  CA  LEU B 347     -18.665 -14.942  77.355  1.00 38.16           C
ATOM   5061  C   LEU B 347     -19.968 -15.048  76.579  1.00 38.13           C
ATOM   5062  O   LEU B 347     -20.480 -14.047  76.087  1.00 38.12           O
ATOM   5063  CB  LEU B 347     -17.476 -15.312  76.471  1.00 36.12           C
ATOM   5064  CG  LEU B 347     -16.139 -14.951  77.119  1.00 35.15           C
ATOM   5065  CD1 LEU B 347     -14.997 -15.525  76.310  1.00 34.36           C
ATOM   5066  CD2 LEU B 347     -16.021 -13.439  77.229  1.00 34.22           C
ATOM   5067  N   ASN B 348     -20.513 -16.259  76.478  1.00 38.22           N
ATOM   5068  CA  ASN B 348     -21.776 -16.445  75.778  1.00 38.44           C
ATOM   5069  C   ASN B 348     -22.824 -15.541  76.413  1.00 39.13           C
ATOM   5070  O   ASN B 348     -23.644 -14.944  75.719  1.00 39.31           O
ATOM   5071  CB  ASN B 348     -22.254 -17.897  75.864  1.00 37.91           C
ATOM   5072  CG  ASN B 348     -21.593 -18.802  74.840  1.00 38.31           C
ATOM   5073  OD1 ASN B 348     -20.998 -18.338  73.867  1.00 37.94           O
ATOM   5074  ND2 ASN B 348     -21.714 -20.108  75.046  1.00 37.74           N
ATOM   5075  N   LYS B 349     -22.791 -15.444  77.739  1.00 40.22           N
ATOM   5076  CA  LYS B 349     -23.746 -14.614  78.467  1.00 40.82           C
ATOM   5077  C   LYS B 349     -23.544 -13.135  78.185  1.00 40.82           C
ATOM   5078  O   LYS B 349     -24.499 -12.418  77.884  1.00 40.86           O
ATOM   5079  CB  LYS B 349     -23.644 -14.889  79.973  1.00 41.41           C
ATOM   5080  CG  LYS B 349     -24.335 -16.186  80.384  1.00 42.21           C
ATOM   5081  CD  LYS B 349     -23.954 -16.638  81.788  1.00 42.90           C
ATOM   5082  CE  LYS B 349     -24.783 -17.853  82.210  1.00 43.09           C
ATOM   5083  NZ  LYS B 349     -24.298 -18.479  83.473  1.00 41.83           N
ATOM   5084  N   ILE B 350     -22.301 -12.680  78.280  1.00 40.90           N
ATOM   5085  CA  ILE B 350     -21.988 -11.283  78.023  1.00 41.79           C
ATOM   5086  C   ILE B 350     -22.398 -10.922  76.595  1.00 42.18           C
ATOM   5087  O   ILE B 350     -23.132  -9.959  76.370  1.00 42.14           O
ATOM   5088  CB  ILE B 350     -20.478 -11.020  78.208  1.00 42.30           C
ATOM   5089  CG1 ILE B 350     -20.077 -11.321  79.659  1.00 42.00           C
ATOM   5090  CG2 ILE B 350     -20.150  -9.578  77.839  1.00 42.51           C
ATOM   5091  CD1 ILE B 350     -18.575 -11.353  79.906  1.00 40.68           C
ATOM   5092  N   LEU B 351     -21.934 -11.720  75.638  1.00 42.63           N
ATOM   5093  CA  LEU B 351     -22.234 -11.505  74.224  1.00 42.93           C
ATOM   5094  C   LEU B 351     -23.734 -11.466  73.939  1.00 42.56           C
ATOM   5095  O   LEU B 351     -24.214 -10.598  73.220  1.00 42.33           O
ATOM   5096  CB  LEU B 351     -21.577 -12.603  73.373  1.00 42.00           C
ATOM   5097  CG  LEU B 351     -21.878 -12.554  71.871  1.00 42.02           C
ATOM   5098  CD1 LEU B 351     -21.269 -11.296  71.277  1.00 41.49           C
ATOM   5099  CD2 LEU B 351     -21.322 -13.789  71.184  1.00 41.40           C
```

FIGURE 2-76 (COORDINATES)

```
ATOM   5100  N    GLN B 352     -24.471 -12.415  74.498  1.00 43.21           N
ATOM   5101  CA   GLN B 352     -25.911 -12.473  74.284  1.00 43.59           C
ATOM   5102  C    GLN B 352     -26.636 -11.245  74.832  1.00 43.36           C
ATOM   5103  O    GLN B 352     -27.605 -10.777  74.240  1.00 43.67           O
ATOM   5104  CB   GLN B 352     -26.471 -13.761  74.892  1.00 44.23           C
ATOM   5105  CG   GLN B 352     -26.125 -14.995  74.059  1.00 45.36           C
ATOM   5106  CD   GLN B 352     -26.471 -16.299  74.747  1.00 46.08           C
ATOM   5107  OE1  GLN B 352     -27.572 -16.465  75.271  1.00 47.44           O
ATOM   5108  NE2  GLN B 352     -25.535 -17.240  74.736  1.00 45.83           N
ATOM   5109  N    VAL B 353     -26.158 -10.718  75.954  1.00 43.20           N
ATOM   5110  CA   VAL B 353     -26.757  -9.528  76.545  1.00 42.98           C
ATOM   5111  C    VAL B 353     -26.407  -8.318  75.675  1.00 43.07           C
ATOM   5112  O    VAL B 353     -27.235  -7.431  75.467  1.00 43.77           O
ATOM   5113  CB   VAL B 353     -26.242  -9.295  77.993  1.00 43.42           C
ATOM   5114  CG1  VAL B 353     -26.635  -7.902  78.482  1.00 42.22           C
ATOM   5115  CG2  VAL B 353     -26.812 -10.362  78.920  1.00 42.25           C
ATOM   5116  N    PHE B 354     -25.178  -8.290  75.168  1.00 42.22           N
ATOM   5117  CA   PHE B 354     -24.739  -7.200  74.307  1.00 41.55           C
ATOM   5118  C    PHE B 354     -25.584  -7.134  73.036  1.00 41.72           C
ATOM   5119  O    PHE B 354     -26.001  -6.057  72.618  1.00 42.44           O
ATOM   5120  CB   PHE B 354     -23.277  -7.383  73.910  1.00 40.86           C
ATOM   5121  CG   PHE B 354     -22.740  -6.268  73.054  1.00 40.69           C
ATOM   5122  CD1  PHE B 354     -22.071  -5.191  73.630  1.00 40.82           C
ATOM   5123  CD2  PHE B 354     -22.908  -6.291  71.668  1.00 40.25           C
ATOM   5124  CE1  PHE B 354     -21.574  -4.154  72.840  1.00 40.71           C
ATOM   5125  CE2  PHE B 354     -22.419  -5.263  70.867  1.00 38.90           C
ATOM   5126  CZ   PHE B 354     -21.750  -4.192  71.452  1.00 41.32           C
ATOM   5127  N    VAL B 355     -25.821  -8.283  72.412  1.00 41.45           N
ATOM   5128  CA   VAL B 355     -26.605  -8.319  71.186  1.00 41.76           C
ATOM   5129  C    VAL B 355     -28.035  -7.843  71.425  1.00 42.80           C
ATOM   5130  O    VAL B 355     -28.552  -7.024  70.667  1.00 42.34           O
ATOM   5131  CB   VAL B 355     -26.617  -9.743  70.571  1.00 41.21           C
ATOM   5132  CG1  VAL B 355     -27.609  -9.822  69.409  1.00 39.27           C
ATOM   5133  CG2  VAL B 355     -25.224 -10.096  70.086  1.00 40.52           C
ATOM   5134  N    LEU B 356     -28.668  -8.347  72.481  1.00 43.77           N
ATOM   5135  CA   LEU B 356     -30.040  -7.960  72.807  1.00 44.91           C
ATOM   5136  C    LEU B 356     -30.211  -6.462  73.087  1.00 45.45           C
ATOM   5137  O    LEU B 356     -31.180  -5.847  72.633  1.00 45.02           O
ATOM   5138  CB   LEU B 356     -30.545  -8.766  74.005  1.00 44.73           C
ATOM   5139  CG   LEU B 356     -30.881 -10.221  73.674  1.00 44.90           C
ATOM   5140  CD1  LEU B 356     -31.223 -10.960  74.956  1.00 45.69           C
ATOM   5141  CD2  LEU B 356     -32.043 -10.277  72.689  1.00 43.10           C
ATOM   5142  N    GLU B 357     -29.280  -5.877  73.833  1.00 45.46           N
ATOM   5143  CA   GLU B 357     -29.371  -4.460  74.141  1.00 46.82           C
ATOM   5144  C    GLU B 357     -29.198  -3.624  72.874  1.00 47.18           C
ATOM   5145  O    GLU B 357     -29.953  -2.680  72.635  1.00 47.20           O
ATOM   5146  CB   GLU B 357     -28.323  -4.077  75.184  1.00 48.02           C
ATOM   5147  CG   GLU B 357     -28.433  -4.899  76.458  1.00 50.11           C
ATOM   5148  CD   GLU B 357     -27.565  -4.369  77.579  1.00 51.63           C
ATOM   5149  OE1  GLU B 357     -26.421  -3.959  77.294  1.00 52.99           O
ATOM   5150  OE2  GLU B 357     -28.021  -4.372  78.747  1.00 52.51           O
ATOM   5151  N    TYR B 358     -28.209  -3.980  72.058  1.00 46.70           N
ATOM   5152  CA   TYR B 358     -27.957  -3.264  70.814  1.00 45.79           C
ATOM   5153  C    TYR B 358     -29.205  -3.284  69.919  1.00 45.85           C
ATOM   5154  O    TYR B 358     -29.601  -2.258  69.375  1.00 46.36           O
ATOM   5155  CB   TYR B 358     -26.782  -3.898  70.062  1.00 45.02           C
ATOM   5156  CG   TYR B 358     -26.227  -3.014  68.974  1.00 43.79           C
ATOM   5157  CD1  TYR B 358     -25.082  -2.261  69.190  1.00 43.37           C
ATOM   5158  CD2  TYR B 358     -26.894  -2.867  67.758  1.00 44.01           C
ATOM   5159  CE1  TYR B 358     -24.612  -1.378  68.230  1.00 44.38           C
ATOM   5160  CE2  TYR B 358     -26.436  -1.979  66.784  1.00 43.56           C
ATOM   5161  CZ   TYR B 358     -25.294  -1.237  67.028  1.00 44.30           C
ATOM   5162  OH   TYR B 358     -24.831  -0.342  66.089  1.00 43.69           O
ATOM   5163  N    LEU B 359     -29.823  -4.452  69.773  1.00 45.69           N
ATOM   5164  CA   LEU B 359     -31.013  -4.596  68.934  1.00 45.86           C
ATOM   5165  C    LEU B 359     -32.301  -4.154  69.622  1.00 47.13           C
ATOM   5166  O    LEU B 359     -33.376  -4.175  69.013  1.00 46.98           O
ATOM   5167  CB   LEU B 359     -31.173  -6.052  68.494  1.00 44.54           C
```

FIGURE 2-77 (COORDINATES)

```
ATOM   5168  CG   LEU B 359     -30.059   -6.618   67.617  1.00 44.79           C
ATOM   5169  CD1  LEU B 359     -30.369   -8.070   67.301  1.00 44.33           C
ATOM   5170  CD2  LEU B 359     -29.929   -5.791   66.331  1.00 44.17           C
ATOM   5171  N    HIS B 360     -32.195   -3.756   70.886  1.00 48.05           N
ATOM   5172  CA   HIS B 360     -33.363   -3.337   71.650  1.00 48.87           C
ATOM   5173  C    HIS B 360     -34.380   -4.475   71.712  1.00 49.70           C
ATOM   5174  O    HIS B 360     -35.557   -4.302   71.398  1.00 49.37           O
ATOM   5175  CB   HIS B 360     -34.003   -2.089   71.030  1.00 48.66           C
ATOM   5176  CG   HIS B 360     -33.129   -0.875   71.079  1.00 49.40           C
ATOM   5177  ND1  HIS B 360     -33.627    0.406   70.982  1.00 50.13           N
ATOM   5178  CD2  HIS B 360     -31.788   -0.747   71.218  1.00 49.84           C
ATOM   5179  CE1  HIS B 360     -32.631    1.271   71.061  1.00 50.23           C
ATOM   5180  NE2  HIS B 360     -31.504    0.597   71.205  1.00 49.78           N
ATOM   5181  N    LEU B 361     -33.904   -5.649   72.109  1.00 50.88           N
ATOM   5182  CA   LEU B 361     -34.757   -6.822   72.234  1.00 51.81           C
ATOM   5183  C    LEU B 361     -34.775   -7.258   73.690  1.00 51.90           C
ATOM   5184  O    LEU B 361     -35.697   -8.013   74.060  1.00 52.64           O
ATOM   5185  CB   LEU B 361     -34.244   -7.965   71.353  1.00 51.71           C
ATOM   5186  CG   LEU B 361     -34.429   -7.788   69.844  1.00 52.23           C
ATOM   5187  CD1  LEU B 361     -33.887   -9.011   69.111  1.00 51.71           C
ATOM   5188  CD2  LEU B 361     -35.908   -7.586   69.534  1.00 52.12           C
ATOM   5189  OXT  LEU B 361     -33.857   -6.848   74.433  1.00 51.21           O
TER    5190       LEU B 361
```

FIGURE 2-78 (REMARKS)

```
HEADER     ----                                       xx-xxx-xx   xxxx
TITLE      ---
REMARK   3
REMARK   3 REFINEMENT.
REMARK   3   PROGRAM       : CNS 1.1
REMARK   3   AUTHORS       : BRUNGER,ADAMS,CLORE,DELANO,GROS,GROSSE-
REMARK   3                 : KUNSTLEVE,JIANG,KUSZEWSKI,NILGES, PANNU,
REMARK   3                 : READ,RICE,SIMONSON,WARREN
REMARK   3
REMARK   3   REFINEMENT TARGET : ENGH & HUBER
REMARK   3
REMARK   3  DATA USED IN REFINEMENT.
REMARK   3   RESOLUTION RANGE HIGH (ANGSTROMS) : 2.35
REMARK   3   RESOLUTION RANGE LOW  (ANGSTROMS) : 30.00
REMARK   3   DATA CUTOFF            (SIGMA(F)) : 0.000
REMARK   3   DATA CUTOFF HIGH         (ABS(F)) : NULL
REMARK   3   DATA CUTOFF LOW          (ABS(F)) : NULL
REMARK   3   COMPLETENESS (WORKING+TEST)   (%) : NULL
REMARK   3   NUMBER OF REFLECTIONS             : 33673
REMARK   3
REMARK   3  FIT TO DATA USED IN REFINEMENT.
REMARK   3   CROSS-VALIDATION METHOD           : NULL
REMARK   3   FREE R VALUE TEST SET SELECTION   : RANDOM
REMARK   3   R VALUE            (WORKING SET)  : 0.185
REMARK   3   FREE R VALUE                      : 0.216
REMARK   3   FREE R VALUE TEST SET SIZE   (%)  : NULL
REMARK   3   FREE R VALUE TEST SET COUNT       : 1769
REMARK   3   ESTIMATED ERROR OF FREE R VALUE   : NULL
REMARK   3
REMARK   3  FIT IN THE HIGHEST RESOLUTION BIN.
REMARK   3   TOTAL NUMBER OF BINS USED             : NULL
REMARK   3   BIN RESOLUTION RANGE HIGH       (A)   : NULL
REMARK   3   BIN RESOLUTION RANGE LOW        (A)   : NULL
REMARK   3   BIN COMPLETENESS (WORKING+TEST) (%)   : NULL
REMARK   3   REFLECTIONS IN BIN    (WORKING SET)   : NULL
REMARK   3   BIN R VALUE           (WORKING SET)   : NULL
REMARK   3   BIN FREE R VALUE                      : NULL
REMARK   3   BIN FREE R VALUE TEST SET SIZE  (%)   : NULL
REMARK   3   BIN FREE R VALUE TEST SET COUNT       : NULL
REMARK   3   ESTIMATED ERROR OF BIN FREE R VALUE   : NULL
REMARK   3
REMARK   3  NUMBER OF NON-HYDROGEN ATOMS USED IN REFINEMENT.
REMARK   3   PROTEIN ATOMS            : 5188
REMARK   3   NUCLEIC ACID ATOMS       : 0
REMARK   3   HETEROGEN ATOMS          : 12
REMARK   3   SOLVENT ATOMS            : 460
REMARK   3
REMARK   3  B VALUES.
REMARK   3   FROM WILSON PLOT           (A**2) : NULL
REMARK   3   MEAN B VALUE      (OVERALL, A**2) : NULL
REMARK   3   OVERALL ANISOTROPIC B VALUE.
REMARK   3    B11 (A**2) : NULL
REMARK   3    B22 (A**2) : NULL
REMARK   3    B33 (A**2) : NULL
REMARK   3    B12 (A**2) : NULL
REMARK   3    B13 (A**2) : NULL
REMARK   3    B23 (A**2) : NULL
REMARK   3
REMARK   3  ESTIMATED COORDINATE ERROR.
REMARK   3   ESD FROM LUZZATI PLOT        (A) : NULL
REMARK   3   ESD FROM SIGMAA              (A) : NULL
REMARK   3   LOW RESOLUTION CUTOFF        (A) : NULL
REMARK   3
REMARK   3  CROSS-VALIDATED ESTIMATED COORDINATE ERROR.
REMARK   3   ESD FROM C-V LUZZATI PLOT    (A) : NULL
REMARK   3   ESD FROM C-V SIGMAA          (A) : NULL
REMARK   3
REMARK   3  RMS DEVIATIONS FROM IDEAL VALUES.
```

FIGURE 2-79 (REMARKS)

```
REMARK   3    BOND LENGTHS                   (A) : 0.006
REMARK   3    BOND ANGLES              (DEGREES) : 1.30
REMARK   3    DIHEDRAL ANGLES          (DEGREES) : NULL
REMARK   3    IMPROPER ANGLES          (DEGREES) : NULL
REMARK   3
REMARK   3  ISOTROPIC THERMAL MODEL : NULL
REMARK   3
REMARK   3  ISOTROPIC THERMAL FACTOR RESTRAINTS.    RMS      SIGMA
REMARK   3    MAIN-CHAIN BOND              (A**2) : NULL  ; NULL
REMARK   3    MAIN-CHAIN ANGLE             (A**2) : NULL  ; NULL
REMARK   3    SIDE-CHAIN BOND              (A**2) : NULL  ; NULL
REMARK   3    SIDE-CHAIN ANGLE             (A**2) : NULL  ; NULL
REMARK   3
REMARK   3  BULK SOLVENT MODELING.
REMARK   3    METHOD USED : NULL
REMARK   3    KSOL        : NULL
REMARK   3    BSOL        : NULL
REMARK   3
REMARK   3  NCS MODEL : NULL
REMARK   3
REMARK   3  NCS RESTRAINTS.                         RMS    SIGMA/WEIGHT
REMARK   3    GROUP  1  POSITIONAL            (A) : NULL  ; NULL
REMARK   3    GROUP  1  B-FACTOR           (A**2) : NULL  ; NULL
REMARK   3
REMARK   3  PARAMETER FILE  1  : NULL
REMARK   3  TOPOLOGY FILE   1  : NULL
REMARK   3
REMARK   3  OTHER REFINEMENT REMARKS: NULL
CRYST1  118.988  118.988  332.258  90.00  90.00 120.00 H 3 2         36
SCALE1      0.008404  0.004852  0.000000        0.00000
SCALE2      0.000000  0.009704  0.000000        0.00000
SCALE3      0.000000  0.000000  0.003010        0.00000
```

FIGURE 4-1 (COORDINATES)

| | ATOM | TYPE | RES | # | X | Y | Z | Occ | B | |
|---|---|---|---|---|---|---|---|---|---|---|
| ATOM | 1 | N | ALA A | 33 | -6.061 | -33.757 | 36.946 | 1.00 | 50.95 | N |
| ATOM | 2 | CA | ALA A | 33 | -6.866 | -32.538 | 36.620 | 1.00 | 50.05 | C |
| ATOM | 3 | C | ALA A | 33 | -7.338 | -32.560 | 35.166 | 1.00 | 49.27 | C |
| ATOM | 4 | O | ALA A | 33 | -6.560 | -32.848 | 34.252 | 1.00 | 48.66 | O |
| ATOM | 5 | CB | ALA A | 33 | -6.038 | -31.276 | 36.881 | 1.00 | 50.21 | C |
| ATOM | 6 | N | SER A | 34 | -8.619 | -32.259 | 34.960 | 1.00 | 47.63 | N |
| ATOM | 7 | CA | SER A | 34 | -9.190 | -32.237 | 33.620 | 1.00 | 45.06 | C |
| ATOM | 8 | C | SER A | 34 | -8.633 | -31.063 | 32.819 | 1.00 | 43.36 | C |
| ATOM | 9 | O | SER A | 34 | -8.458 | -29.959 | 33.342 | 1.00 | 42.71 | O |
| ATOM | 10 | CB | SER A | 34 | -10.715 | -32.129 | 33.686 | 1.00 | 45.58 | C |
| ATOM | 11 | OG | SER A | 34 | -11.265 | -32.085 | 32.378 | 1.00 | 45.77 | O |
| ATOM | 12 | N | ALA A | 35 | -8.360 | -31.317 | 31.546 | 1.00 | 40.91 | N |
| ATOM | 13 | CA | ALA A | 35 | -7.819 | -30.304 | 30.655 | 1.00 | 38.62 | C |
| ATOM | 14 | C | ALA A | 35 | -8.910 | -29.730 | 29.759 | 1.00 | 36.61 | C |
| ATOM | 15 | O | ALA A | 35 | -8.625 | -29.249 | 28.667 | 1.00 | 34.87 | O |
| ATOM | 16 | CB | ALA A | 35 | -6.726 | -30.914 | 29.803 | 1.00 | 38.82 | C |
| ATOM | 17 | N | TRP A | 36 | -10.158 | -29.774 | 30.218 | 1.00 | 35.13 | N |
| ATOM | 18 | CA | TRP A | 36 | -11.248 | -29.266 | 29.398 | 1.00 | 33.66 | C |
| ATOM | 19 | C | TRP A | 36 | -11.067 | -27.797 | 28.991 | 1.00 | 31.87 | C |
| ATOM | 20 | O | TRP A | 36 | -11.473 | -27.404 | 27.898 | 1.00 | 31.00 | O |
| ATOM | 21 | CB | TRP A | 36 | -12.612 | -29.487 | 30.083 | 1.00 | 32.45 | C |
| ATOM | 22 | CG | TRP A | 36 | -12.882 | -28.649 | 31.289 | 1.00 | 32.79 | C |
| ATOM | 23 | CD1 | TRP A | 36 | -12.713 | -29.007 | 32.597 | 1.00 | 32.98 | C |
| ATOM | 24 | CD2 | TRP A | 36 | -13.376 | -27.304 | 31.301 | 1.00 | 32.08 | C |
| ATOM | 25 | NE1 | TRP A | 36 | -13.075 | -27.968 | 33.423 | 1.00 | 31.70 | N |
| ATOM | 26 | CE2 | TRP A | 36 | -13.482 | -26.910 | 32.654 | 1.00 | 31.93 | C |
| ATOM | 27 | CE3 | TRP A | 36 | -13.738 | -26.392 | 30.298 | 1.00 | 31.49 | C |
| ATOM | 28 | CZ2 | TRP A | 36 | -13.936 | -25.641 | 33.031 | 1.00 | 31.47 | C |
| ATOM | 29 | CZ3 | TRP A | 36 | -14.190 | -25.130 | 30.671 | 1.00 | 31.15 | C |
| ATOM | 30 | CH2 | TRP A | 36 | -14.285 | -24.767 | 32.029 | 1.00 | 31.21 | C |
| ATOM | 31 | N | PRO A | 37 | -10.449 | -26.970 | 29.857 | 1.00 | 31.17 | N |
| ATOM | 32 | CA | PRO A | 37 | -10.262 | -25.566 | 29.483 | 1.00 | 30.07 | C |
| ATOM | 33 | C | PRO A | 37 | -9.413 | -25.433 | 28.217 | 1.00 | 30.85 | C |
| ATOM | 34 | O | PRO A | 37 | -9.377 | -24.372 | 27.600 | 1.00 | 31.52 | O |
| ATOM | 35 | CB | PRO A | 37 | -9.570 | -24.974 | 30.707 | 1.00 | 29.47 | C |
| ATOM | 36 | CG | PRO A | 37 | -10.104 | -25.805 | 31.827 | 1.00 | 28.91 | C |
| ATOM | 37 | CD | PRO A | 37 | -10.034 | -27.192 | 31.255 | 1.00 | 29.59 | C |
| ATOM | 38 | N | GLU A | 38 | -8.737 | -26.515 | 27.830 | 1.00 | 31.01 | N |
| ATOM | 39 | CA | GLU A | 38 | -7.901 | -26.509 | 26.634 | 1.00 | 30.89 | C |
| ATOM | 40 | C | GLU A | 38 | -8.652 | -26.912 | 25.376 | 1.00 | 30.83 | C |
| ATOM | 41 | O | GLU A | 38 | -8.141 | -26.761 | 24.263 | 1.00 | 29.69 | O |
| ATOM | 42 | CB | GLU A | 38 | -6.704 | -27.438 | 26.822 | 1.00 | 31.75 | C |
| ATOM | 43 | CG | GLU A | 38 | -5.649 | -26.861 | 27.735 | 1.00 | 34.64 | C |
| ATOM | 44 | CD | GLU A | 38 | -4.466 | -27.785 | 27.919 | 1.00 | 35.39 | C |
| ATOM | 45 | OE1 | GLU A | 38 | -3.839 | -28.160 | 26.913 | 1.00 | 35.05 | O |
| ATOM | 46 | OE2 | GLU A | 38 | -4.165 | -28.134 | 29.079 | 1.00 | 39.00 | O |
| ATOM | 47 | N | GLU A | 39 | -9.863 | -27.428 | 25.555 | 1.00 | 31.23 | N |
| ATOM | 48 | CA | GLU A | 39 | -10.690 | -27.859 | 24.433 | 1.00 | 31.53 | C |
| ATOM | 49 | C | GLU A | 39 | -10.868 | -26.755 | 23.388 | 1.00 | 32.06 | C |
| ATOM | 50 | O | GLU A | 39 | -10.846 | -27.023 | 22.183 | 1.00 | 32.01 | O |
| ATOM | 51 | CB | GLU A | 39 | -12.064 | -28.336 | 24.937 | 1.00 | 31.17 | C |
| ATOM | 52 | CG | GLU A | 39 | -12.082 | -29.783 | 25.436 | 1.00 | 31.46 | C |
| ATOM | 53 | CD | GLU A | 39 | -13.399 | -30.179 | 26.101 | 1.00 | 32.41 | C |
| ATOM | 54 | OE1 | GLU A | 39 | -14.485 | -29.858 | 25.570 | 1.00 | 32.30 | O |
| ATOM | 55 | OE2 | GLU A | 39 | -13.348 | -30.827 | 27.163 | 1.00 | 33.98 | O |
| ATOM | 56 | N | LYS A | 40 | -11.033 | -25.517 | 23.844 | 1.00 | 31.89 | N |
| ATOM | 57 | CA | LYS A | 40 | -11.221 | -24.397 | 22.927 | 1.00 | 31.81 | C |
| ATOM | 58 | C | LYS A | 40 | -10.088 | -24.280 | 21.911 | 1.00 | 31.72 | C |
| ATOM | 59 | O | LYS A | 40 | -10.304 | -23.861 | 20.772 | 1.00 | 31.50 | O |
| ATOM | 60 | CB | LYS A | 40 | -11.358 | -23.078 | 23.705 | 1.00 | 31.67 | C |
| ATOM | 61 | CG | LYS A | 40 | -10.229 | -22.789 | 24.692 | 1.00 | 31.91 | C |
| ATOM | 62 | CD | LYS A | 40 | -10.337 | -21.367 | 25.243 | 1.00 | 31.98 | C |
| ATOM | 63 | CE | LYS A | 40 | -9.313 | -21.093 | 26.343 | 1.00 | 33.32 | C |
| ATOM | 64 | NZ | LYS A | 40 | -9.749 | -21.588 | 27.694 | 1.00 | 34.48 | N |
| ATOM | 65 | N | ASN A | 41 | -8.883 | -24.662 | 22.314 | 1.00 | 31.26 | N |
| ATOM | 66 | CA | ASN A | 41 | -7.739 | -24.569 | 21.416 | 1.00 | 31.64 | C |

FIGURE 4-2 (COORDINATES)

```
ATOM     67  C   ASN A  41      -7.855 -25.497  20.216  1.00 31.17           C
ATOM     68  O   ASN A  41      -7.274 -25.221  19.177  1.00 30.73           O
ATOM     69  CB  ASN A  41      -6.438 -24.894  22.161  1.00 32.61           C
ATOM     70  CG  ASN A  41      -6.194 -23.982  23.346  1.00 34.31           C
ATOM     71  OD1 ASN A  41      -5.550 -24.377  24.315  1.00 36.12           O
ATOM     72  ND2 ASN A  41      -6.697 -22.755  23.273  1.00 35.01           N
ATOM     73  N   TYR A  42      -8.607 -26.587  20.353  1.00 30.69           N
ATOM     74  CA  TYR A  42      -8.732 -27.558  19.261  1.00 31.22           C
ATOM     75  C   TYR A  42     -10.093 -27.589  18.595  1.00 30.31           C
ATOM     76  O   TYR A  42     -10.290 -28.276  17.593  1.00 30.17           O
ATOM     77  CB  TYR A  42      -8.398 -28.963  19.779  1.00 32.41           C
ATOM     78  CG  TYR A  42      -7.024 -29.041  20.390  1.00 34.76           C
ATOM     79  CD1 TYR A  42      -5.884 -29.081  19.584  1.00 36.24           C
ATOM     80  CD2 TYR A  42      -6.852 -28.979  21.771  1.00 34.57           C
ATOM     81  CE1 TYR A  42      -4.607 -29.048  20.139  1.00 36.98           C
ATOM     82  CE2 TYR A  42      -5.583 -28.945  22.335  1.00 36.54           C
ATOM     83  CZ  TYR A  42      -4.463 -28.976  21.515  1.00 37.80           C
ATOM     84  OH  TYR A  42      -3.198 -28.919  22.067  1.00 39.69           O
ATOM     85  N   HIS A  43     -11.029 -26.840  19.153  1.00 29.19           N
ATOM     86  CA  HIS A  43     -12.373 -26.811  18.623  1.00 28.51           C
ATOM     87  C   HIS A  43     -12.412 -26.410  17.157  1.00 29.05           C
ATOM     88  O   HIS A  43     -11.822 -25.403  16.763  1.00 29.10           O
ATOM     89  CB  HIS A  43     -13.233 -25.855  19.441  1.00 27.42           C
ATOM     90  CG  HIS A  43     -14.689 -25.940  19.118  1.00 26.85           C
ATOM     91  ND1 HIS A  43     -15.382 -24.903  18.530  1.00 27.38           N
ATOM     92  CD2 HIS A  43     -15.581 -26.943  19.286  1.00 25.49           C
ATOM     93  CE1 HIS A  43     -16.640 -25.266  18.351  1.00 26.81           C
ATOM     94  NE2 HIS A  43     -16.787 -26.499  18.802  1.00 26.34           N
ATOM     95  N   GLN A  44     -13.112 -27.211  16.357  1.00 29.38           N
ATOM     96  CA  GLN A  44     -13.263 -26.961  14.929  1.00 29.53           C
ATOM     97  C   GLN A  44     -14.733 -26.676  14.657  1.00 28.74           C
ATOM     98  O   GLN A  44     -15.607 -27.151  15.379  1.00 28.71           O
ATOM     99  CB  GLN A  44     -12.839 -28.190  14.118  1.00 30.68           C
ATOM    100  CG  GLN A  44     -11.376 -28.572  14.233  1.00 34.67           C
ATOM    101  CD  GLN A  44     -10.448 -27.427  13.868  1.00 38.05           C
ATOM    102  OE1 GLN A  44     -10.655 -26.746  12.864  1.00 39.62           O
ATOM    103  NE2 GLN A  44      -9.414 -27.212  14.681  1.00 39.99           N
ATOM    104  N   PRO A  45     -15.030 -25.895  13.611  1.00 28.09           N
ATOM    105  CA  PRO A  45     -16.431 -25.607  13.321  1.00 28.20           C
ATOM    106  C   PRO A  45     -17.062 -26.716  12.485  1.00 28.54           C
ATOM    107  O   PRO A  45     -16.365 -27.535  11.889  1.00 28.17           O
ATOM    108  CB  PRO A  45     -16.347 -24.303  12.547  1.00 27.74           C
ATOM    109  CG  PRO A  45     -15.125 -24.521  11.726  1.00 26.63           C
ATOM    110  CD  PRO A  45     -14.148 -25.092  12.744  1.00 27.96           C
ATOM    111  N   ALA A  46     -18.388 -26.736  12.468  1.00 29.05           N
ATOM    112  CA  ALA A  46     -19.147 -27.693  11.676  1.00 30.56           C
ATOM    113  C   ALA A  46     -19.728 -26.810  10.577  1.00 30.80           C
ATOM    114  O   ALA A  46     -20.761 -26.172  10.756  1.00 30.42           O
ATOM    115  CB  ALA A  46     -20.259 -28.319  12.513  1.00 30.19           C
ATOM    116  N   ILE A  47     -19.032 -26.763   9.451  1.00 32.33           N
ATOM    117  CA  ILE A  47     -19.419 -25.930   8.317  1.00 34.24           C
ATOM    118  C   ILE A  47     -20.742 -26.284   7.632  1.00 35.02           C
ATOM    119  O   ILE A  47     -21.003 -27.441   7.319  1.00 35.58           O
ATOM    120  CB  ILE A  47     -18.284 -25.928   7.277  1.00 34.56           C
ATOM    121  CG1 ILE A  47     -16.995 -25.428   7.947  1.00 35.24           C
ATOM    122  CG2 ILE A  47     -18.653 -25.052   6.092  1.00 35.01           C
ATOM    123  CD1 ILE A  47     -15.761 -25.490   7.064  1.00 36.38           C
ATOM    124  N   LEU A  48     -21.572 -25.268   7.406  1.00 36.07           N
ATOM    125  CA  LEU A  48     -22.865 -25.449   6.749  1.00 37.23           C
ATOM    126  C   LEU A  48     -22.691 -25.522   5.231  1.00 38.11           C
ATOM    127  O   LEU A  48     -21.866 -24.809   4.662  1.00 38.49           O
ATOM    128  CB  LEU A  48     -23.798 -24.276   7.068  1.00 36.74           C
ATOM    129  CG  LEU A  48     -24.080 -23.888   8.518  1.00 36.71           C
ATOM    130  CD1 LEU A  48     -25.121 -22.775   8.526  1.00 36.26           C
ATOM    131  CD2 LEU A  48     -24.582 -25.082   9.304  1.00 35.91           C
ATOM    132  N   ASN A  49     -23.470 -26.378   4.575  1.00 38.68           N
ATOM    133  CA  ASN A  49     -23.388 -26.493   3.126  1.00 38.70           C
```

FIGURE 4-3 (COORDINATES)

```
ATOM    134  C    ASN A  49     -24.273 -25.431   2.470  1.00 39.24           C
ATOM    135  O    ASN A  49     -25.063 -24.763   3.147  1.00 39.31           O
ATOM    136  CB   ASN A  49     -23.812 -27.896   2.660  1.00 38.58           C
ATOM    137  CG   ASN A  49     -25.218 -28.276   3.111  1.00 38.76           C
ATOM    138  OD1  ASN A  49     -26.117 -27.438   3.175  1.00 38.98           O
ATOM    139  ND2  ASN A  49     -25.416 -29.556   3.405  1.00 38.89           N
ATOM    140  N    SER A  50     -24.134 -25.280   1.154  1.00 38.92           N
ATOM    141  CA   SER A  50     -24.910 -24.304   0.386  1.00 38.94           C
ATOM    142  C    SER A  50     -26.386 -24.237   0.780  1.00 39.28           C
ATOM    143  O    SER A  50     -26.939 -23.157   1.003  1.00 39.60           O
ATOM    144  CB   SER A  50     -24.816 -24.623  -1.105  1.00 37.87           C
ATOM    145  OG   SER A  50     -23.471 -24.630  -1.537  1.00 38.47           O
ATOM    146  N    SER A  51     -27.023 -25.397   0.852  1.00 38.69           N
ATOM    147  CA   SER A  51     -28.434 -25.470   1.200  1.00 38.95           C
ATOM    148  C    SER A  51     -28.710 -24.823   2.561  1.00 38.51           C
ATOM    149  O    SER A  51     -29.635 -24.015   2.709  1.00 37.64           O
ATOM    150  CB   SER A  51     -28.875 -26.939   1.201  1.00 40.76           C
ATOM    151  OG   SER A  51     -30.249 -27.078   1.515  1.00 42.34           O
ATOM    152  N    ALA A  52     -27.897 -25.175   3.551  1.00 37.81           N
ATOM    153  CA   ALA A  52     -28.056 -24.638   4.898  1.00 37.18           C
ATOM    154  C    ALA A  52     -27.829 -23.127   4.941  1.00 36.81           C
ATOM    155  O    ALA A  52     -28.476 -22.418   5.710  1.00 36.58           O
ATOM    156  CB   ALA A  52     -27.096 -25.333   5.848  1.00 36.59           C
ATOM    157  N    LEU A  53     -26.910 -22.639   4.116  1.00 36.31           N
ATOM    158  CA   LEU A  53     -26.610 -21.213   4.082  1.00 36.94           C
ATOM    159  C    LEU A  53     -27.777 -20.380   3.552  1.00 38.22           C
ATOM    160  O    LEU A  53     -28.111 -19.345   4.127  1.00 38.11           O
ATOM    161  CB   LEU A  53     -25.350 -20.958   3.247  1.00 35.12           C
ATOM    162  CG   LEU A  53     -24.044 -21.463   3.866  1.00 34.69           C
ATOM    163  CD1  LEU A  53     -22.897 -21.319   2.885  1.00 33.12           C
ATOM    164  CD2  LEU A  53     -23.764 -20.683   5.138  1.00 34.61           C
ATOM    165  N    ARG A  54     -28.400 -20.821   2.461  1.00 39.62           N
ATOM    166  CA   ARG A  54     -29.529 -20.080   1.909  1.00 41.42           C
ATOM    167  C    ARG A  54     -30.616 -20.024   2.964  1.00 41.07           C
ATOM    168  O    ARG A  54     -31.325 -19.033   3.094  1.00 41.84           O
ATOM    169  CB   ARG A  54     -30.092 -20.767   0.662  1.00 42.87           C
ATOM    170  CG   ARG A  54     -29.074 -21.055  -0.424  1.00 46.03           C
ATOM    171  CD   ARG A  54     -29.754 -21.520  -1.709  1.00 47.82           C
ATOM    172  NE   ARG A  54     -28.775 -21.839  -2.746  1.00 50.11           N
ATOM    173  CZ   ARG A  54     -28.088 -22.977  -2.812  1.00 51.18           C
ATOM    174  NH1  ARG A  54     -28.271 -23.926  -1.899  1.00 51.66           N
ATOM    175  NH2  ARG A  54     -27.210 -23.164  -3.791  1.00 51.37           N
ATOM    176  N    GLN A  55     -30.735 -21.104   3.719  1.00 41.35           N
ATOM    177  CA   GLN A  55     -31.740 -21.209   4.763  1.00 41.99           C
ATOM    178  C    GLN A  55     -31.521 -20.187   5.872  1.00 40.45           C
ATOM    179  O    GLN A  55     -32.474 -19.582   6.367  1.00 39.50           O
ATOM    180  CB   GLN A  55     -31.730 -22.633   5.323  1.00 44.69           C
ATOM    181  CG   GLN A  55     -32.753 -22.911   6.404  1.00 48.23           C
ATOM    182  CD   GLN A  55     -32.960 -24.403   6.614  1.00 51.44           C
ATOM    183  OE1  GLN A  55     -33.427 -24.838   7.672  1.00 52.35           O
ATOM    184  NE2  GLN A  55     -32.624 -25.199   5.592  1.00 51.44           N
ATOM    185  N    ILE A  56     -30.266 -19.992   6.260  1.00 39.29           N
ATOM    186  CA   ILE A  56     -29.957 -19.022   7.299  1.00 38.49           C
ATOM    187  C    ILE A  56     -30.224 -17.624   6.751  1.00 38.10           C
ATOM    188  O    ILE A  56     -30.838 -16.792   7.420  1.00 37.31           O
ATOM    189  CB   ILE A  56     -28.484 -19.123   7.752  1.00 38.22           C
ATOM    190  CG1  ILE A  56     -28.168 -20.559   8.184  1.00 38.96           C
ATOM    191  CG2  ILE A  56     -28.229 -18.168   8.908  1.00 36.60           C
ATOM    192  CD1  ILE A  56     -29.123 -21.110   9.240  1.00 39.71           C
ATOM    193  N    ALA A  57     -29.769 -17.379   5.526  1.00 38.13           N
ATOM    194  CA   ALA A  57     -29.963 -16.088   4.876  1.00 38.82           C
ATOM    195  C    ALA A  57     -31.446 -15.739   4.825  1.00 39.14           C
ATOM    196  O    ALA A  57     -31.825 -14.581   4.977  1.00 39.36           O
ATOM    197  CB   ALA A  57     -29.385 -16.121   3.461  1.00 38.63           C
ATOM    198  N    GLU A  58     -32.281 -16.751   4.615  1.00 39.95           N
ATOM    199  CA   GLU A  58     -33.726 -16.562   4.538  1.00 40.80           C
ATOM    200  C    GLU A  58     -34.375 -16.489   5.921  1.00 39.45           C
```

FIGURE 4-4 (COORDINATES)

```
ATOM    201  O   GLU A  58     -35.468 -15.944   6.073  1.00 39.13           O
ATOM    202  CB  GLU A  58     -34.362 -17.718   3.763  1.00 43.50           C
ATOM    203  CG  GLU A  58     -33.916 -17.857   2.314  1.00 48.73           C
ATOM    204  CD  GLU A  58     -34.365 -16.693   1.446  1.00 51.91           C
ATOM    205  OE1 GLU A  58     -35.532 -16.258   1.593  1.00 53.34           O
ATOM    206  OE2 GLU A  58     -33.556 -16.223   0.610  1.00 53.31           O
ATOM    207  N   GLY A  59     -33.694 -17.033   6.926  1.00 37.90           N
ATOM    208  CA  GLY A  59     -34.241 -17.054   8.272  1.00 36.63           C
ATOM    209  C   GLY A  59     -34.204 -15.775   9.084  1.00 35.79           C
ATOM    210  O   GLY A  59     -34.909 -15.662  10.090  1.00 34.84           O
ATOM    211  N   THR A  60     -33.389 -14.812   8.667  1.00 34.53           N
ATOM    212  CA  THR A  60     -33.287 -13.559   9.397  1.00 33.70           C
ATOM    213  C   THR A  60     -34.038 -12.469   8.643  1.00 33.44           C
ATOM    214  O   THR A  60     -34.064 -12.456   7.417  1.00 34.80           O
ATOM    215  CB  THR A  60     -31.795 -13.158   9.602  1.00 34.01           C
ATOM    216  OG1 THR A  60     -31.713 -11.969  10.399  1.00 33.65           O
ATOM    217  CG2 THR A  60     -31.114 -12.919   8.268  1.00 32.77           C
ATOM    218  N   SER A  61     -34.670 -11.569   9.380  1.00 33.22           N
ATOM    219  CA  SER A  61     -35.422 -10.484   8.771  1.00 33.41           C
ATOM    220  C   SER A  61     -34.902  -9.152   9.272  1.00 33.74           C
ATOM    221  O   SER A  61     -35.093  -8.809  10.437  1.00 34.37           O
ATOM    222  CB  SER A  61     -36.908 -10.606   9.117  1.00 33.84           C
ATOM    223  OG  SER A  61     -37.614  -9.420   8.774  1.00 33.91           O
ATOM    224  N   ILE A  62     -34.255  -8.396   8.392  1.00 33.68           N
ATOM    225  CA  ILE A  62     -33.721  -7.100   8.775  1.00 33.90           C
ATOM    226  C   ILE A  62     -34.819  -6.127   9.204  1.00 34.14           C
ATOM    227  O   ILE A  62     -34.649  -5.386  10.169  1.00 33.78           O
ATOM    228  CB  ILE A  62     -32.896  -6.463   7.624  1.00 33.27           C
ATOM    229  CG1 ILE A  62     -32.211  -5.190   8.125  1.00 33.11           C
ATOM    230  CG2 ILE A  62     -33.786  -6.147   6.436  1.00 33.16           C
ATOM    231  CD1 ILE A  62     -31.130  -5.451   9.166  1.00 32.74           C
ATOM    232  N   SER A  63     -35.946  -6.127   8.498  1.00 35.29           N
ATOM    233  CA  SER A  63     -37.034  -5.213   8.844  1.00 36.85           C
ATOM    234  C   SER A  63     -37.673  -5.600  10.174  1.00 37.33           C
ATOM    235  O   SER A  63     -38.093  -4.735  10.943  1.00 36.52           O
ATOM    236  CB  SER A  63     -38.089  -5.170   7.727  1.00 37.58           C
ATOM    237  OG  SER A  63     -38.616  -6.454   7.455  1.00 40.05           O
ATOM    238  N   GLU A  64     -37.741  -6.900  10.450  1.00 38.64           N
ATOM    239  CA  GLU A  64     -38.300  -7.374  11.714  1.00 39.55           C
ATOM    240  C   GLU A  64     -37.400  -6.912  12.863  1.00 38.50           C
ATOM    241  O   GLU A  64     -37.883  -6.427  13.891  1.00 37.88           O
ATOM    242  CB  GLU A  64     -38.387  -8.905  11.725  1.00 43.00           C
ATOM    243  CG  GLU A  64     -39.530  -9.484  10.912  1.00 47.70           C
ATOM    244  CD  GLU A  64     -40.880  -9.194  11.535  1.00 51.09           C
ATOM    245  OE1 GLU A  64     -41.114  -9.652  12.679  1.00 52.92           O
ATOM    246  OE2 GLU A  64     -41.703  -8.506  10.885  1.00 52.99           O
ATOM    247  N   MET A  65     -36.091  -7.069  12.684  1.00 36.18           N
ATOM    248  CA  MET A  65     -35.136  -6.660  13.704  1.00 35.11           C
ATOM    249  C   MET A  65     -35.265  -5.164  13.946  1.00 34.52           C
ATOM    250  O   MET A  65     -35.341  -4.704  15.083  1.00 34.93           O
ATOM    251  CB  MET A  65     -33.704  -6.960  13.260  1.00 34.53           C
ATOM    252  CG  MET A  65     -32.670  -6.593  14.321  1.00 34.79           C
ATOM    253  SD  MET A  65     -31.046  -6.168  13.669  1.00 33.80           S
ATOM    254  CE  MET A  65     -31.331  -4.467  13.218  1.00 33.99           C
ATOM    255  N   TRP A  66     -35.290  -4.416  12.852  1.00 33.76           N
ATOM    256  CA  TRP A  66     -35.387  -2.965  12.878  1.00 33.07           C
ATOM    257  C   TRP A  66     -36.550  -2.429  13.712  1.00 33.77           C
ATOM    258  O   TRP A  66     -36.383  -1.536  14.548  1.00 33.79           O
ATOM    259  CB  TRP A  66     -35.510  -2.453  11.445  1.00 31.05           C
ATOM    260  CG  TRP A  66     -34.912  -1.107  11.253  1.00 30.46           C
ATOM    261  CD1 TRP A  66     -35.493   0.096  11.517  1.00 29.58           C
ATOM    262  CD2 TRP A  66     -33.598  -0.822  10.773  1.00 29.10           C
ATOM    263  NE1 TRP A  66     -34.626   1.116  11.226  1.00 28.63           N
ATOM    264  CE2 TRP A  66     -33.452   0.583  10.768  1.00 28.94           C
ATOM    265  CE3 TRP A  66     -32.529  -1.617  10.344  1.00 28.80           C
ATOM    266  CZ2 TRP A  66     -32.278   1.215  10.350  1.00 28.86           C
ATOM    267  CZ3 TRP A  66     -31.361  -0.992   9.928  1.00 30.17           C
ATOM    268  CH2 TRP A  66     -31.246   0.415   9.934  1.00 29.32           C
```

FIGURE 4-5 (COORDINATES)

```
ATOM    269  N    GLN A  67     -37.731   -2.981   13.488  1.00 34.02           N
ATOM    270  CA   GLN A  67     -38.907   -2.535   14.200  1.00 34.38           C
ATOM    271  C    GLN A  67     -39.031   -3.086   15.612  1.00 33.52           C
ATOM    272  O    GLN A  67     -39.323   -2.344   16.549  1.00 32.91           O
ATOM    273  CB   GLN A  67     -40.151   -2.918   13.409  1.00 37.21           C
ATOM    274  CG   GLN A  67     -41.450   -2.441   14.037  1.00 42.00           C
ATOM    275  CD   GLN A  67     -42.658   -3.105   13.414  1.00 44.54           C
ATOM    276  OE1  GLN A  67     -42.831   -3.087   12.194  1.00 45.98           O
ATOM    277  NE2  GLN A  67     -43.503   -3.701   14.251  1.00 46.93           N
ATOM    278  N    ASN A  68     -38.792   -4.382   15.767  1.00 33.14           N
ATOM    279  CA   ASN A  68     -38.954   -5.023   17.067  1.00 32.93           C
ATOM    280  C    ASN A  68     -37.778   -5.070   18.029  1.00 32.56           C
ATOM    281  O    ASN A  68     -37.982   -5.210   19.235  1.00 32.21           O
ATOM    282  CB   ASN A  68     -39.490   -6.443   16.868  1.00 33.05           C
ATOM    283  CG   ASN A  68     -40.738   -6.468   16.014  1.00 32.40           C
ATOM    284  OD1  ASN A  68     -41.641   -5.651   16.197  1.00 32.23           O
ATOM    285  ND2  ASN A  68     -40.797   -7.405   15.073  1.00 32.04           N
ATOM    286  N    ASP A  69     -36.559   -4.942   17.520  1.00 32.22           N
ATOM    287  CA   ASP A  69     -35.388   -5.007   18.389  1.00 31.96           C
ATOM    288  C    ASP A  69     -34.558   -3.736   18.486  1.00 31.89           C
ATOM    289  O    ASP A  69     -34.079   -3.385   19.564  1.00 31.69           O
ATOM    290  CB   ASP A  69     -34.490   -6.163   17.946  1.00 31.48           C
ATOM    291  CG   ASP A  69     -35.083   -7.506   18.284  1.00 32.49           C
ATOM    292  OD1  ASP A  69     -35.039   -8.419   17.435  1.00 34.16           O
ATOM    293  OD2  ASP A  69     -35.593   -7.647   19.411  1.00 32.13           O
ATOM    294  N    LEU A  70     -34.400   -3.045   17.362  1.00 30.81           N
ATOM    295  CA   LEU A  70     -33.594   -1.837   17.318  1.00 30.16           C
ATOM    296  C    LEU A  70     -34.272   -0.538   17.754  1.00 30.38           C
ATOM    297  O    LEU A  70     -33.806    0.130   18.682  1.00 30.33           O
ATOM    298  CB   LEU A  70     -33.023   -1.675   15.908  1.00 28.76           C
ATOM    299  CG   LEU A  70     -32.183   -0.436   15.607  1.00 27.77           C
ATOM    300  CD1  LEU A  70     -30.941   -0.408   16.486  1.00 26.55           C
ATOM    301  CD2  LEU A  70     -31.796   -0.458   14.139  1.00 26.08           C
ATOM    302  N    GLN A  71     -35.368   -0.175   17.098  1.00 31.13           N
ATOM    303  CA   GLN A  71     -36.044    1.076   17.418  1.00 31.79           C
ATOM    304  C    GLN A  71     -36.345    1.314   18.893  1.00 31.66           C
ATOM    305  O    GLN A  71     -36.156    2.423   19.389  1.00 32.23           O
ATOM    306  CB   GLN A  71     -37.310    1.228   16.566  1.00 33.52           C
ATOM    307  CG   GLN A  71     -36.985    1.427   15.082  1.00 35.47           C
ATOM    308  CD   GLN A  71     -38.203    1.717   14.219  1.00 37.61           C
ATOM    309  OE1  GLN A  71     -39.235    1.052   14.331  1.00 38.81           O
ATOM    310  NE2  GLN A  71     -38.078    2.702   13.335  1.00 36.86           N
ATOM    311  N    PRO A  72     -36.827    0.292   19.618  1.00 31.50           N
ATOM    312  CA   PRO A  72     -37.096    0.560   21.037  1.00 30.72           C
ATOM    313  C    PRO A  72     -35.811    0.926   21.778  1.00 30.97           C
ATOM    314  O    PRO A  72     -35.858    1.481   22.874  1.00 31.76           O
ATOM    315  CB   PRO A  72     -37.701   -0.754   21.530  1.00 29.64           C
ATOM    316  CG   PRO A  72     -38.440   -1.242   20.326  1.00 29.95           C
ATOM    317  CD   PRO A  72     -37.447   -0.978   19.198  1.00 31.16           C
ATOM    318  N    LEU A  73     -34.665    0.622   21.168  1.00 30.60           N
ATOM    319  CA   LEU A  73     -33.365    0.917   21.776  1.00 30.34           C
ATOM    320  C    LEU A  73     -32.759    2.262   21.390  1.00 30.30           C
ATOM    321  O    LEU A  73     -31.755    2.676   21.968  1.00 30.34           O
ATOM    322  CB   LEU A  73     -32.354   -0.181   21.435  1.00 29.77           C
ATOM    323  CG   LEU A  73     -32.477   -1.486   22.214  1.00 30.75           C
ATOM    324  CD1  LEU A  73     -31.344   -2.417   21.818  1.00 30.67           C
ATOM    325  CD2  LEU A  73     -32.429   -1.186   23.715  1.00 30.68           C
ATOM    326  N    LEU A  74     -33.357    2.935   20.410  1.00 30.13           N
ATOM    327  CA   LEU A  74     -32.853    4.223   19.960  1.00 29.05           C
ATOM    328  C    LEU A  74     -33.363    5.341   20.848  1.00 29.11           C
ATOM    329  O    LEU A  74     -34.090    6.233   20.414  1.00 29.38           O
ATOM    330  CB   LEU A  74     -33.255    4.461   18.508  1.00 28.69           C
ATOM    331  CG   LEU A  74     -32.544    3.527   17.531  1.00 28.73           C
ATOM    332  CD1  LEU A  74     -33.067    3.768   16.130  1.00 29.88           C
ATOM    333  CD2  LEU A  74     -31.032    3.765   17.598  1.00 28.31           C
ATOM    334  N    ILE A  75     -32.949    5.281   22.105  1.00 29.68           N
ATOM    335  CA   ILE A  75     -33.348    6.245   23.111  1.00 29.02           C
ATOM    336  C    ILE A  75     -32.141    6.593   23.972  1.00 29.76           C
```

FIGURE 4-6 (COORDINATES)

```
ATOM    337  O    ILE A   75     -31.170   5.833  24.030  1.00 28.99           O
ATOM    338  CB   ILE A   75     -34.417   5.637  24.034  1.00 29.34           C
ATOM    339  CG1  ILE A   75     -33.835   4.399  24.736  1.00 27.79           C
ATOM    340  CG2  ILE A   75     -35.651   5.258  23.228  1.00 28.23           C
ATOM    341  CD1  ILE A   75     -34.783   3.720  25.704  1.00 25.43           C
ATOM    342  N    GLU A   76     -32.205   7.739  24.639  1.00 29.50           N
ATOM    343  CA   GLU A   76     -31.128   8.149  25.525  1.00 30.75           C
ATOM    344  C    GLU A   76     -31.115   7.075  26.613  1.00 30.33           C
ATOM    345  O    GLU A   76     -32.143   6.794  27.226  1.00 30.76           O
ATOM    346  CB   GLU A   76     -31.444   9.533  26.099  1.00 31.70           C
ATOM    347  CG   GLU A   76     -30.439  10.092  27.074  1.00 34.37           C
ATOM    348  CD   GLU A   76     -30.582  11.605  27.240  1.00 37.23           C
ATOM    349  OE1  GLU A   76     -31.709  12.123  27.088  1.00 38.60           O
ATOM    350  OE2  GLU A   76     -29.573  12.280  27.532  1.00 37.27           O
ATOM    351  N    ARG A   77     -29.965   6.451  26.841  1.00 30.06           N
ATOM    352  CA   ARG A   77     -29.899   5.392  27.839  1.00 29.81           C
ATOM    353  C    ARG A   77     -28.587   5.308  28.621  1.00 30.42           C
ATOM    354  O    ARG A   77     -28.040   4.218  28.807  1.00 30.52           O
ATOM    355  CB   ARG A   77     -30.194   4.043  27.162  1.00 28.65           C
ATOM    356  CG   ARG A   77     -29.301   3.759  25.961  1.00 28.13           C
ATOM    357  CD   ARG A   77     -29.748   2.539  25.159  1.00 27.49           C
ATOM    358  NE   ARG A   77     -28.750   2.198  24.148  1.00 27.71           N
ATOM    359  CZ   ARG A   77     -28.500   2.922  23.057  1.00 28.26           C
ATOM    360  NH1  ARG A   77     -29.184   4.031  22.813  1.00 28.24           N
ATOM    361  NH2  ARG A   77     -27.532   2.559  22.226  1.00 27.00           N
ATOM    362  N    TYR A   78     -28.075   6.448  29.080  1.00 30.38           N
ATOM    363  CA   TYR A   78     -26.845   6.421  29.862  1.00 29.88           C
ATOM    364  C    TYR A   78     -27.163   5.756  31.199  1.00 29.23           C
ATOM    365  O    TYR A   78     -28.310   5.707  31.619  1.00 28.64           O
ATOM    366  CB   TYR A   78     -26.283   7.835  30.081  1.00 30.26           C
ATOM    367  CG   TYR A   78     -27.225   8.801  30.758  1.00 30.68           C
ATOM    368  CD1  TYR A   78     -28.136   9.558  30.018  1.00 31.26           C
ATOM    369  CD2  TYR A   78     -27.205   8.964  32.142  1.00 30.96           C
ATOM    370  CE1  TYR A   78     -29.003  10.456  30.645  1.00 30.47           C
ATOM    371  CE2  TYR A   78     -28.065   9.853  32.775  1.00 31.00           C
ATOM    372  CZ   TYR A   78     -28.959  10.594  32.025  1.00 30.71           C
ATOM    373  OH   TYR A   78     -29.811  11.459  32.663  1.00 31.43           O
ATOM    374  N    PRO A   79     -26.143   5.234  31.885  1.00 30.29           N
ATOM    375  CA   PRO A   79     -26.321   4.562  33.175  1.00 30.74           C
ATOM    376  C    PRO A   79     -27.143   5.322  34.212  1.00 31.19           C
ATOM    377  O    PRO A   79     -26.917   6.507  34.457  1.00 30.91           O
ATOM    378  CB   PRO A   79     -24.888   4.329  33.636  1.00 30.78           C
ATOM    379  CG   PRO A   79     -24.146   4.158  32.331  1.00 30.27           C
ATOM    380  CD   PRO A   79     -24.718   5.279  31.513  1.00 30.30           C
ATOM    381  N    GLY A   80     -28.091   4.617  34.824  1.00 31.11           N
ATOM    382  CA   GLY A   80     -28.931   5.216  35.843  1.00 31.00           C
ATOM    383  C    GLY A   80     -30.129   5.980  35.315  1.00 31.45           C
ATOM    384  O    GLY A   80     -31.017   6.324  36.083  1.00 32.98           O
ATOM    385  N    SER A   81     -30.180   6.244  34.015  1.00 31.02           N
ATOM    386  CA   SER A   81     -31.303   6.999  33.467  1.00 31.45           C
ATOM    387  C    SER A   81     -32.547   6.143  33.255  1.00 32.03           C
ATOM    388  O    SER A   81     -32.494   4.918  33.328  1.00 32.44           O
ATOM    389  CB   SER A   81     -30.906   7.645  32.141  1.00 31.24           C
ATOM    390  OG   SER A   81     -30.824   6.680  31.108  1.00 30.54           O
ATOM    391  N    PRO A   82     -33.695   6.784  32.990  1.00 32.92           N
ATOM    392  CA   PRO A   82     -34.929   6.025  32.767  1.00 32.78           C
ATOM    393  C    PRO A   82     -34.758   5.152  31.533  1.00 32.66           C
ATOM    394  O    PRO A   82     -35.291   4.047  31.459  1.00 32.56           O
ATOM    395  CB   PRO A   82     -35.971   7.116  32.549  1.00 33.81           C
ATOM    396  CG   PRO A   82     -35.418   8.279  33.328  1.00 34.07           C
ATOM    397  CD   PRO A   82     -33.961   8.232  32.963  1.00 33.23           C
ATOM    398  N    GLY A   83     -34.004   5.664  30.564  1.00 32.09           N
ATOM    399  CA   GLY A   83     -33.761   4.922  29.341  1.00 31.91           C
ATOM    400  C    GLY A   83     -33.001   3.631  29.594  1.00 32.09           C
ATOM    401  O    GLY A   83     -33.308   2.594  29.003  1.00 32.26           O
ATOM    402  N    SER A   84     -32.003   3.693  30.471  1.00 31.79           N
ATOM    403  CA   SER A   84     -31.205   2.523  30.804  1.00 32.34           C
ATOM    404  C    SER A   84     -32.147   1.423  31.282  1.00 32.96           C
```

FIGURE 4-7 (COORDINATES)

```
ATOM    405  O    SER A   84     -32.037   0.265  30.876  1.00 33.29           O
ATOM    406  CB   SER A   84     -30.195   2.871  31.904  1.00 32.43           C
ATOM    407  OG   SER A   84     -29.504   1.719  32.367  1.00 31.88           O
ATOM    408  N    TYR A   85     -33.085   1.802  32.140  1.00 33.21           N
ATOM    409  CA   TYR A   85     -34.053   0.857  32.667  1.00 33.96           C
ATOM    410  C    TYR A   85     -34.947   0.313  31.550  1.00 32.91           C
ATOM    411  O    TYR A   85     -35.207  -0.894  31.477  1.00 32.95           O
ATOM    412  CB   TYR A   85     -34.916   1.532  33.735  1.00 36.72           C
ATOM    413  CG   TYR A   85     -35.986   0.627  34.287  1.00 41.42           C
ATOM    414  CD1  TYR A   85     -35.653  -0.467  35.088  1.00 43.41           C
ATOM    415  CD2  TYR A   85     -37.333   0.840  33.987  1.00 42.67           C
ATOM    416  CE1  TYR A   85     -36.635  -1.327  35.575  1.00 44.26           C
ATOM    417  CE2  TYR A   85     -38.321  -0.013  34.469  1.00 43.91           C
ATOM    418  CZ   TYR A   85     -37.965  -1.091  35.263  1.00 44.58           C
ATOM    419  OH   TYR A   85     -38.937  -1.932  35.757  1.00 46.60           O
ATOM    420  N    ALA A   86     -35.410   1.202  30.677  1.00 30.84           N
ATOM    421  CA   ALA A   86     -36.285   0.800  29.576  1.00 30.22           C
ATOM    422  C    ALA A   86     -35.574  -0.125  28.600  1.00 29.29           C
ATOM    423  O    ALA A   86     -36.160  -1.084  28.100  1.00 29.56           O
ATOM    424  CB   ALA A   86     -36.809   2.034  28.842  1.00 29.06           C
ATOM    425  N    ALA A   87     -34.306   0.170  28.336  1.00 28.66           N
ATOM    426  CA   ALA A   87     -33.504  -0.628  27.420  1.00 28.15           C
ATOM    427  C    ALA A   87     -33.342  -2.033  27.972  1.00 28.07           C
ATOM    428  O    ALA A   87     -33.511  -3.028  27.265  1.00 26.23           O
ATOM    429  CB   ALA A   87     -32.141   0.015  27.246  1.00 27.25           C
ATOM    430  N    ARG A   88     -32.998  -2.087  29.253  1.00 29.02           N
ATOM    431  CA   ARG A   88     -32.782  -3.337  29.968  1.00 30.49           C
ATOM    432  C    ARG A   88     -34.049  -4.212  29.976  1.00 30.78           C
ATOM    433  O    ARG A   88     -33.962  -5.431  29.848  1.00 30.94           O
ATOM    434  CB   ARG A   88     -32.314  -2.999  31.393  1.00 30.14           C
ATOM    435  CG   ARG A   88     -31.672  -4.128  32.169  1.00 30.70           C
ATOM    436  CD   ARG A   88     -30.816  -3.586  33.319  1.00 30.49           C
ATOM    437  NE   ARG A   88     -31.562  -2.679  34.189  1.00 30.44           N
ATOM    438  CZ   ARG A   88     -31.244  -1.404  34.398  1.00 31.37           C
ATOM    439  NH1  ARG A   88     -30.186  -0.877  33.801  1.00 30.62           N
ATOM    440  NH2  ARG A   88     -31.991  -0.650  35.198  1.00 31.88           N
ATOM    441  N    GLN A   89     -35.218  -3.589  30.108  1.00 31.40           N
ATOM    442  CA   GLN A   89     -36.484  -4.326  30.123  1.00 33.06           C
ATOM    443  C    GLN A   89     -36.806  -4.835  28.729  1.00 32.97           C
ATOM    444  O    GLN A   89     -37.353  -5.927  28.559  1.00 33.15           O
ATOM    445  CB   GLN A   89     -37.631  -3.433  30.596  1.00 34.72           C
ATOM    446  CG   GLN A   89     -37.450  -2.872  31.994  1.00 40.64           C
ATOM    447  CD   GLN A   89     -37.337  -3.955  33.059  1.00 43.82           C
ATOM    448  OE1  GLN A   89     -38.245  -4.775  33.228  1.00 44.96           O
ATOM    449  NE2  GLN A   89     -36.217  -3.959  33.787  1.00 45.58           N
ATOM    450  N    HIS A   90     -36.477  -4.028  27.728  1.00 31.72           N
ATOM    451  CA   HIS A   90     -36.722  -4.403  26.347  1.00 31.27           C
ATOM    452  C    HIS A   90     -35.902  -5.651  26.019  1.00 31.52           C
ATOM    453  O    HIS A   90     -36.433  -6.647  25.522  1.00 31.74           O
ATOM    454  CB   HIS A   90     -36.329  -3.241  25.426  1.00 30.72           C
ATOM    455  CG   HIS A   90     -36.229  -3.615  23.982  1.00 30.29           C
ATOM    456  ND1  HIS A   90     -37.309  -4.058  23.250  1.00 30.24           N
ATOM    457  CD2  HIS A   90     -35.174  -3.611  23.133  1.00 30.88           C
ATOM    458  CE1  HIS A   90     -36.925  -4.309  22.012  1.00 29.84           C
ATOM    459  NE2  HIS A   90     -35.633  -4.046  21.915  1.00 30.14           N
ATOM    460  N    ILE A   91     -34.606  -5.590  26.308  1.00 31.54           N
ATOM    461  CA   ILE A   91     -33.704  -6.704  26.049  1.00 31.14           C
ATOM    462  C    ILE A   91     -34.157  -7.975  26.756  1.00 31.57           C
ATOM    463  O    ILE A   91     -34.108  -9.062  26.182  1.00 31.75           O
ATOM    464  CB   ILE A   91     -32.264  -6.355  26.490  1.00 30.66           C
ATOM    465  CG1  ILE A   91     -31.686  -5.291  25.549  1.00 29.37           C
ATOM    466  CG2  ILE A   91     -31.400  -7.610  26.509  1.00 28.16           C
ATOM    467  CD1  ILE A   91     -30.342  -4.723  25.991  1.00 29.37           C
ATOM    468  N    MET A   92     -34.596  -7.843  28.001  1.00 32.63           N
ATOM    469  CA   MET A   92     -35.060  -9.002  28.749  1.00 34.44           C
ATOM    470  C    MET A   92     -36.369  -9.527  28.163  1.00 34.76           C
ATOM    471  O    MET A   92     -36.521 -10.725  27.932  1.00 35.73           O
ATOM    472  CB   MET A   92     -35.254  -8.645  30.220  1.00 35.50           C
```

FIGURE 4-8 (COORDINATES)

```
ATOM   473  CG  MET A  92     -33.977  -8.255  30.926  1.00 37.67           C
ATOM   474  SD  MET A  92     -34.263  -7.926  32.673  1.00 41.28           S
ATOM   475  CE  MET A  92     -33.846  -9.523  33.355  1.00 40.66           C
ATOM   476  N   GLN A  93     -37.312  -8.628  27.913  1.00 34.79           N
ATOM   477  CA  GLN A  93     -38.591  -9.023  27.345  1.00 34.75           C
ATOM   478  C   GLN A  93     -38.398  -9.774  26.031  1.00 34.16           C
ATOM   479  O   GLN A  93     -38.981 -10.835  25.826  1.00 33.45           O
ATOM   480  CB  GLN A  93     -39.476  -7.788  27.131  1.00 35.78           C
ATOM   481  CG  GLN A  93     -40.090  -7.250  28.428  1.00 39.60           C
ATOM   482  CD  GLN A  93     -40.841  -5.925  28.258  1.00 41.79           C
ATOM   483  OE1 GLN A  93     -41.502  -5.457  29.189  1.00 42.51           O
ATOM   484  NE2 GLN A  93     -40.732  -5.313  27.078  1.00 42.22           N
ATOM   485  N   ARG A  94     -37.562  -9.228  25.152  1.00 33.79           N
ATOM   486  CA  ARG A  94     -37.308  -9.842  23.851  1.00 34.00           C
ATOM   487  C   ARG A  94     -36.685 -11.235  23.935  1.00 33.97           C
ATOM   488  O   ARG A  94     -36.912 -12.077  23.063  1.00 33.78           O
ATOM   489  CB  ARG A  94     -36.432  -8.918  22.997  1.00 34.20           C
ATOM   490  CG  ARG A  94     -37.120  -7.619  22.603  1.00 34.31           C
ATOM   491  CD  ARG A  94     -38.306  -7.867  21.676  1.00 35.71           C
ATOM   492  NE  ARG A  94     -37.886  -8.406  20.385  1.00 36.89           N
ATOM   493  CZ  ARG A  94     -38.717  -8.800  19.425  1.00 37.72           C
ATOM   494  NH1 ARG A  94     -40.028  -8.719  19.603  1.00 38.69           N
ATOM   495  NH2 ARG A  94     -38.236  -9.279  18.284  1.00 37.76           N
ATOM   496  N   ILE A  95     -35.903 -11.484  24.979  1.00 33.68           N
ATOM   497  CA  ILE A  95     -35.292 -12.792  25.145  1.00 34.14           C
ATOM   498  C   ILE A  95     -36.277 -13.790  25.751  1.00 35.29           C
ATOM   499  O   ILE A  95     -36.327 -14.947  25.334  1.00 34.76           O
ATOM   500  CB  ILE A  95     -34.045 -12.717  26.048  1.00 34.29           C
ATOM   501  CG1 ILE A  95     -32.917 -12.009  25.294  1.00 34.65           C
ATOM   502  CG2 ILE A  95     -33.624 -14.121  26.484  1.00 32.89           C
ATOM   503  CD1 ILE A  95     -31.663 -11.813  26.102  1.00 34.34           C
ATOM   504  N   GLN A  96     -37.059 -13.335  26.729  1.00 36.15           N
ATOM   505  CA  GLN A  96     -38.024 -14.195  27.411  1.00 37.79           C
ATOM   506  C   GLN A  96     -39.131 -14.753  26.525  1.00 37.65           C
ATOM   507  O   GLN A  96     -39.668 -15.824  26.806  1.00 38.15           O
ATOM   508  CB  GLN A  96     -38.653 -13.455  28.593  1.00 38.55           C
ATOM   509  CG  GLN A  96     -37.653 -13.074  29.666  1.00 42.96           C
ATOM   510  CD  GLN A  96     -38.303 -12.473  30.906  1.00 44.94           C
ATOM   511  OE1 GLN A  96     -39.078 -11.511  30.818  1.00 46.21           O
ATOM   512  NE2 GLN A  96     -37.984 -13.034  32.071  1.00 44.76           N
ATOM   513  N   ARG A  97     -39.475 -14.040  25.460  1.00 37.51           N
ATOM   514  CA  ARG A  97     -40.530 -14.513  24.573  1.00 37.68           C
ATOM   515  C   ARG A  97     -40.078 -15.671  23.692  1.00 37.40           C
ATOM   516  O   ARG A  97     -40.906 -16.361  23.098  1.00 38.05           O
ATOM   517  CB  ARG A  97     -41.054 -13.372  23.692  1.00 38.24           C
ATOM   518  CG  ARG A  97     -40.048 -12.766  22.737  1.00 39.39           C
ATOM   519  CD  ARG A  97     -40.714 -11.701  21.875  1.00 41.82           C
ATOM   520  NE  ARG A  97     -41.596 -12.289  20.874  1.00 43.27           N
ATOM   521  CZ  ARG A  97     -41.184 -12.772  19.705  1.00 44.61           C
ATOM   522  NH1 ARG A  97     -39.898 -12.729  19.380  1.00 44.02           N
ATOM   523  NH2 ARG A  97     -42.057 -13.319  18.865  1.00 45.41           N
ATOM   524  N   LEU A  98     -38.770 -15.891  23.615  1.00 36.69           N
ATOM   525  CA  LEU A  98     -38.225 -16.961  22.789  1.00 36.35           C
ATOM   526  C   LEU A  98     -38.401 -18.333  23.422  1.00 36.57           C
ATOM   527  O   LEU A  98     -38.517 -18.457  24.640  1.00 36.89           O
ATOM   528  CB  LEU A  98     -36.741 -16.706  22.514  1.00 36.33           C
ATOM   529  CG  LEU A  98     -36.422 -15.398  21.784  1.00 35.95           C
ATOM   530  CD1 LEU A  98     -34.916 -15.241  21.650  1.00 35.96           C
ATOM   531  CD2 LEU A  98     -37.091 -15.402  20.417  1.00 35.79           C
ATOM   532  N   GLN A  99     -38.419 -19.366  22.587  1.00 36.78           N
ATOM   533  CA  GLN A  99     -38.586 -20.726  23.075  1.00 37.36           C
ATOM   534  C   GLN A  99     -37.347 -21.264  23.790  1.00 36.80           C
ATOM   535  O   GLN A  99     -37.468 -21.967  24.792  1.00 37.43           O
ATOM   536  CB  GLN A  99     -38.955 -21.665  21.926  1.00 38.98           C
ATOM   537  CG  GLN A  99     -40.256 -21.323  21.211  1.00 42.28           C
ATOM   538  CD  GLN A  99     -40.657 -22.387  20.191  1.00 45.05           C
ATOM   539  OE1 GLN A  99     -41.291 -22.086  19.179  1.00 47.42           O
ATOM   540  NE2 GLN A  99     -40.298 -23.639  20.464  1.00 46.14           N
```

FIGURE 4-9 (COORDINATES)

```
ATOM    541  N   ALA A 100     -36.160 -20.944  23.280  1.00 35.45           N
ATOM    542  CA  ALA A 100     -34.923 -21.416  23.899  1.00 33.93           C
ATOM    543  C   ALA A 100     -34.932 -21.144  25.404  1.00 32.65           C
ATOM    544  O   ALA A 100     -35.436 -20.123  25.861  1.00 31.99           O
ATOM    545  CB  ALA A 100     -33.716 -20.749  23.243  1.00 34.47           C
ATOM    546  N   ASP A 101     -34.358 -22.069  26.162  1.00 32.33           N
ATOM    547  CA  ASP A 101     -34.324 -21.984  27.614  1.00 32.57           C
ATOM    548  C   ASP A 101     -33.269 -21.008  28.121  1.00 31.74           C
ATOM    549  O   ASP A 101     -32.281 -21.407  28.738  1.00 32.07           O
ATOM    550  CB  ASP A 101     -34.092 -23.392  28.182  1.00 34.09           C
ATOM    551  CG  ASP A 101     -34.323 -23.475  29.677  1.00 35.98           C
ATOM    552  OD1 ASP A 101     -35.068 -22.627  30.217  1.00 37.92           O
ATOM    553  OD2 ASP A 101     -33.772 -24.406  30.311  1.00 37.18           O
ATOM    554  N   TRP A 102     -33.491 -19.722  27.863  1.00 31.20           N
ATOM    555  CA  TRP A 102     -32.560 -18.678  28.285  1.00 30.47           C
ATOM    556  C   TRP A 102     -32.683 -18.344  29.768  1.00 30.44           C
ATOM    557  O   TRP A 102     -33.784 -18.193  30.296  1.00 30.71           O
ATOM    558  CB  TRP A 102     -32.784 -17.385  27.485  1.00 29.10           C
ATOM    559  CG  TRP A 102     -32.404 -17.450  26.049  1.00 28.63           C
ATOM    560  CD1 TRP A 102     -33.240 -17.625  24.985  1.00 28.79           C
ATOM    561  CD2 TRP A 102     -31.087 -17.303  25.504  1.00 29.55           C
ATOM    562  NE1 TRP A 102     -32.529 -17.593  23.806  1.00 28.53           N
ATOM    563  CE2 TRP A 102     -31.205 -17.396  24.093  1.00 29.13           C
ATOM    564  CE3 TRP A 102     -29.816 -17.101  26.068  1.00 28.54           C
ATOM    565  CZ2 TRP A 102     -30.103 -17.294  23.239  1.00 28.08           C
ATOM    566  CZ3 TRP A 102     -28.716 -17.001  25.216  1.00 29.29           C
ATOM    567  CH2 TRP A 102     -28.870 -17.097  23.815  1.00 28.91           C
ATOM    568  N   VAL A 103     -31.543 -18.216  30.437  1.00 30.72           N
ATOM    569  CA  VAL A 103     -31.536 -17.859  31.846  1.00 29.91           C
ATOM    570  C   VAL A 103     -30.982 -16.446  31.923  1.00 30.63           C
ATOM    571  O   VAL A 103     -29.820 -16.205  31.600  1.00 30.24           O
ATOM    572  CB  VAL A 103     -30.653 -18.817  32.677  1.00 29.92           C
ATOM    573  CG1 VAL A 103     -30.726 -18.442  34.152  1.00 27.30           C
ATOM    574  CG2 VAL A 103     -31.115 -20.256  32.478  1.00 29.27           C
ATOM    575  N   LEU A 104     -31.827 -15.511  32.339  1.00 32.43           N
ATOM    576  CA  LEU A 104     -31.438 -14.113  32.445  1.00 34.56           C
ATOM    577  C   LEU A 104     -30.986 -13.717  33.842  1.00 36.56           C
ATOM    578  O   LEU A 104     -31.627 -14.067  34.832  1.00 37.86           O
ATOM    579  CB  LEU A 104     -32.605 -13.220  32.022  1.00 34.17           C
ATOM    580  CG  LEU A 104     -32.928 -13.180  30.529  1.00 34.88           C
ATOM    581  CD1 LEU A 104     -34.326 -12.621  30.322  1.00 34.70           C
ATOM    582  CD2 LEU A 104     -31.884 -12.336  29.800  1.00 34.16           C
ATOM    583  N   GLU A 105     -29.877 -12.984  33.913  1.00 38.14           N
ATOM    584  CA  GLU A 105     -29.334 -12.496  35.180  1.00 39.60           C
ATOM    585  C   GLU A 105     -29.012 -11.009  35.053  1.00 39.10           C
ATOM    586  O   GLU A 105     -28.439 -10.577  34.052  1.00 38.54           O
ATOM    587  CB  GLU A 105     -28.037 -13.220  35.543  1.00 42.43           C
ATOM    588  CG  GLU A 105     -28.142 -14.720  35.678  1.00 47.54           C
ATOM    589  CD  GLU A 105     -26.784 -15.360  35.913  1.00 50.40           C
ATOM    590  OE1 GLU A 105     -25.911 -15.245  35.017  1.00 51.27           O
ATOM    591  OE2 GLU A 105     -26.591 -15.969  36.992  1.00 51.63           O
ATOM    592  N   ILE A 106     -29.390 -10.227  36.058  1.00 37.88           N
ATOM    593  CA  ILE A 106     -29.086  -8.808  36.050  1.00 36.63           C
ATOM    594  C   ILE A 106     -27.956  -8.652  37.057  1.00 36.48           C
ATOM    595  O   ILE A 106     -28.142  -8.860  38.257  1.00 36.66           O
ATOM    596  CB  ILE A 106     -30.299  -7.952  36.483  1.00 37.22           C
ATOM    597  CG1 ILE A 106     -31.461  -8.155  35.508  1.00 37.00           C
ATOM    598  CG2 ILE A 106     -29.918  -6.481  36.516  1.00 36.39           C
ATOM    599  CD1 ILE A 106     -31.146  -7.755  34.079  1.00 38.33           C
ATOM    600  N   ASP A 107     -26.774  -8.320  36.555  1.00 35.14           N
ATOM    601  CA  ASP A 107     -25.598  -8.150  37.395  1.00 33.87           C
ATOM    602  C   ASP A 107     -25.486  -6.681  37.781  1.00 33.35           C
ATOM    603  O   ASP A 107     -24.932  -5.868  37.034  1.00 32.51           O
ATOM    604  CB  ASP A 107     -24.359  -8.613  36.622  1.00 34.84           C
ATOM    605  CG  ASP A 107     -23.065  -8.259  37.316  1.00 35.59           C
ATOM    606  OD1 ASP A 107     -22.938  -8.537  38.527  1.00 37.56           O
ATOM    607  OD2 ASP A 107     -22.169  -7.711  36.643  1.00 36.17           O
ATOM    608  N   THR A 108     -26.025  -6.349  38.950  1.00 32.13           N
```

FIGURE 4-10 (COORDINATES)

| ATOM | 609 | CA  | THR | A | 108 | -26.020 | -4.977 | 39.444 | 1.00 | 31.70 | C |
|------|-----|-----|-----|---|-----|---------|--------|--------|------|-------|---|
| ATOM | 610 | C   | THR | A | 108 | -24.924 | -4.731 | 40.473 | 1.00 | 31.65 | C |
| ATOM | 611 | O   | THR | A | 108 | -24.707 | -5.541 | 41.375 | 1.00 | 31.91 | O |
| ATOM | 612 | CB  | THR | A | 108 | -27.386 | -4.619 | 40.064 | 1.00 | 31.14 | C |
| ATOM | 613 | OG1 | THR | A | 108 | -28.405 | -4.774 | 39.072 | 1.00 | 32.42 | O |
| ATOM | 614 | CG2 | THR | A | 108 | -27.398 | -3.179 | 40.565 | 1.00 | 29.84 | C |
| ATOM | 615 | N   | PHE | A | 109 | -24.239 | -3.601 | 40.335 | 1.00 | 30.27 | N |
| ATOM | 616 | CA  | PHE | A | 109 | -23.160 | -3.254 | 41.247 | 1.00 | 29.16 | C |
| ATOM | 617 | C   | PHE | A | 109 | -22.976 | -1.743 | 41.341 | 1.00 | 28.48 | C |
| ATOM | 618 | O   | PHE | A | 109 | -23.531 | -0.986 | 40.547 | 1.00 | 27.03 | O |
| ATOM | 619 | CB  | PHE | A | 109 | -21.846 | -3.873 | 40.762 | 1.00 | 28.20 | C |
| ATOM | 620 | CG  | PHE | A | 109 | -21.427 | -3.389 | 39.402 | 1.00 | 27.68 | C |
| ATOM | 621 | CD1 | PHE | A | 109 | -22.037 | -3.884 | 38.256 | 1.00 | 27.28 | C |
| ATOM | 622 | CD2 | PHE | A | 109 | -20.454 | -2.405 | 39.270 | 1.00 | 27.92 | C |
| ATOM | 623 | CE1 | PHE | A | 109 | -21.690 | -3.410 | 37.001 | 1.00 | 27.53 | C |
| ATOM | 624 | CE2 | PHE | A | 109 | -20.097 | -1.919 | 38.014 | 1.00 | 28.17 | C |
| ATOM | 625 | CZ  | PHE | A | 109 | -20.718 | -2.423 | 36.876 | 1.00 | 28.20 | C |
| ATOM | 626 | N   | LEU | A | 110 | -22.182 | -1.328 | 42.324 | 1.00 | 27.88 | N |
| ATOM | 627 | CA  | LEU | A | 110 | -21.859 |  0.072 | 42.538 | 1.00 | 28.27 | C |
| ATOM | 628 | C   | LEU | A | 110 | -20.415 |  0.301 | 42.141 | 1.00 | 28.25 | C |
| ATOM | 629 | O   | LEU | A | 110 | -19.575 | -0.594 | 42.266 | 1.00 | 29.42 | O |
| ATOM | 630 | CB  | LEU | A | 110 | -21.987 |  0.452 | 44.010 | 1.00 | 29.32 | C |
| ATOM | 631 | CG  | LEU | A | 110 | -23.335 |  0.797 | 44.629 | 1.00 | 31.41 | C |
| ATOM | 632 | CD1 | LEU | A | 110 | -23.105 |  1.139 | 46.097 | 1.00 | 31.76 | C |
| ATOM | 633 | CD2 | LEU | A | 110 | -23.969 |  1.976 | 43.900 | 1.00 | 31.03 | C |
| ATOM | 634 | N   | SER | A | 111 | -20.122 |  1.506 | 41.681 | 1.00 | 27.00 | N |
| ATOM | 635 | CA  | SER | A | 111 | -18.765 |  1.855 | 41.315 | 1.00 | 27.20 | C |
| ATOM | 636 | C   | SER | A | 111 | -18.595 |  3.355 | 41.454 | 1.00 | 27.61 | C |
| ATOM | 637 | O   | SER | A | 111 | -19.569 |  4.102 | 41.348 | 1.00 | 27.82 | O |
| ATOM | 638 | CB  | SER | A | 111 | -18.464 |  1.434 | 39.878 | 1.00 | 26.63 | C |
| ATOM | 639 | OG  | SER | A | 111 | -17.201 |  1.925 | 39.480 | 1.00 | 28.26 | O |
| ATOM | 640 | N   | GLN | A | 112 | -17.361 |  3.780 | 41.712 | 1.00 | 27.60 | N |
| ATOM | 641 | CA  | GLN | A | 112 | -17.025 |  5.190 | 41.840 | 1.00 | 28.16 | C |
| ATOM | 642 | C   | GLN | A | 112 | -16.934 |  5.756 | 40.431 | 1.00 | 28.56 | C |
| ATOM | 643 | O   | GLN | A | 112 | -16.477 |  5.079 | 39.514 | 1.00 | 29.37 | O |
| ATOM | 644 | CB  | GLN | A | 112 | -15.679 |  5.358 | 42.557 | 1.00 | 28.82 | C |
| ATOM | 645 | CG  | GLN | A | 112 | -15.114 |  6.781 | 42.580 | 1.00 | 30.48 | C |
| ATOM | 646 | CD  | GLN | A | 112 | -16.010 |  7.794 | 43.298 | 1.00 | 33.49 | C |
| ATOM | 647 | OE1 | GLN | A | 112 | -15.543 |  8.553 | 44.157 | 1.00 | 33.49 | O |
| ATOM | 648 | NE2 | GLN | A | 112 | -17.295 |  7.820 | 42.939 | 1.00 | 33.21 | N |
| ATOM | 649 | N   | THR | A | 113 | -17.385 |  6.993 | 40.262 | 1.00 | 28.58 | N |
| ATOM | 650 | CA  | THR | A | 113 | -17.358 |  7.654 | 38.969 | 1.00 | 27.96 | C |
| ATOM | 651 | C   | THR | A | 113 | -16.989 |  9.114 | 39.192 | 1.00 | 28.51 | C |
| ATOM | 652 | O   | THR | A | 113 | -16.901 |  9.574 | 40.333 | 1.00 | 27.94 | O |
| ATOM | 653 | CB  | THR | A | 113 | -18.741 |  7.628 | 38.283 | 1.00 | 28.93 | C |
| ATOM | 654 | OG1 | THR | A | 113 | -19.609 |  8.579 | 38.922 | 1.00 | 28.12 | O |
| ATOM | 655 | CG2 | THR | A | 113 | -19.358 |  6.235 | 38.363 | 1.00 | 27.34 | C |
| ATOM | 656 | N   | PRO | A | 114 | -16.763 |  9.863 | 38.102 | 1.00 | 28.66 | N |
| ATOM | 657 | CA  | PRO | A | 114 | -16.409 | 11.276 | 38.249 | 1.00 | 28.91 | C |
| ATOM | 658 | C   | PRO | A | 114 | -17.530 | 12.053 | 38.934 | 1.00 | 29.05 | C |
| ATOM | 659 | O   | PRO | A | 114 | -17.316 | 13.162 | 39.420 | 1.00 | 29.43 | O |
| ATOM | 660 | CB  | PRO | A | 114 | -16.181 | 11.726 | 36.806 | 1.00 | 28.25 | C |
| ATOM | 661 | CG  | PRO | A | 114 | -15.641 | 10.484 | 36.161 | 1.00 | 27.92 | C |
| ATOM | 662 | CD  | PRO | A | 114 | -16.567 |  9.415 | 36.710 | 1.00 | 27.62 | C |
| ATOM | 663 | N   | TYR | A | 115 | -18.720 | 11.459 | 38.971 | 1.00 | 28.60 | N |
| ATOM | 664 | CA  | TYR | A | 115 | -19.880 | 12.086 | 39.602 | 1.00 | 29.28 | C |
| ATOM | 665 | C   | TYR | A | 115 | -20.283 | 11.362 | 40.885 | 1.00 | 29.58 | C |
| ATOM | 666 | O   | TYR | A | 115 | -21.418 | 11.482 | 41.346 | 1.00 | 28.95 | O |
| ATOM | 667 | CB  | TYR | A | 115 | -21.065 | 12.110 | 38.630 | 1.00 | 29.69 | C |
| ATOM | 668 | CG  | TYR | A | 115 | -20.824 | 12.990 | 37.429 | 1.00 | 30.95 | C |
| ATOM | 669 | CD1 | TYR | A | 115 | -20.716 | 14.374 | 37.567 | 1.00 | 31.78 | C |
| ATOM | 670 | CD2 | TYR | A | 115 | -20.626 | 12.435 | 36.162 | 1.00 | 31.68 | C |
| ATOM | 671 | CE1 | TYR | A | 115 | -20.408 | 15.184 | 36.474 | 1.00 | 32.53 | C |
| ATOM | 672 | CE2 | TYR | A | 115 | -20.318 | 13.234 | 35.063 | 1.00 | 32.25 | C |
| ATOM | 673 | CZ  | TYR | A | 115 | -20.209 | 14.606 | 35.226 | 1.00 | 32.75 | C |
| ATOM | 674 | OH  | TYR | A | 115 | -19.903 | 15.402 | 34.144 | 1.00 | 33.19 | O |
| ATOM | 675 | N   | GLY | A | 116 | -19.347 | 10.608 | 41.455 | 1.00 | 29.71 | N |
| ATOM | 676 | CA  | GLY | A | 116 | -19.629 |  9.884 | 42.680 | 1.00 | 30.20 | C |

FIGURE 4-11 (COORDINATES)

```
ATOM    677  C   GLY A 116     -20.158   8.486  42.443  1.00 30.20           C
ATOM    678  O   GLY A 116     -20.265   8.041  41.300  1.00 30.07           O
ATOM    679  N   TYR A 117     -20.491   7.794  43.528  1.00 29.90           N
ATOM    680  CA  TYR A 117     -21.005   6.432  43.448  1.00 29.94           C
ATOM    681  C   TYR A 117     -22.271   6.331  42.606  1.00 30.55           C
ATOM    682  O   TYR A 117     -23.187   7.143  42.740  1.00 30.73           O
ATOM    683  CB  TYR A 117     -21.302   5.883  44.849  1.00 30.60           C
ATOM    684  CG  TYR A 117     -20.100   5.761  45.772  1.00 31.34           C
ATOM    685  CD1 TYR A 117     -20.253   5.296  47.076  1.00 31.38           C
ATOM    686  CD2 TYR A 117     -18.816   6.119  45.348  1.00 31.84           C
ATOM    687  CE1 TYR A 117     -19.159   5.190  47.938  1.00 32.70           C
ATOM    688  CE2 TYR A 117     -17.719   6.019  46.197  1.00 31.73           C
ATOM    689  CZ  TYR A 117     -17.900   5.554  47.491  1.00 32.87           C
ATOM    690  OH  TYR A 117     -16.827   5.464  48.346  1.00 35.13           O
ATOM    691  N   ARG A 118     -22.311   5.324  41.738  1.00 29.60           N
ATOM    692  CA  ARG A 118     -23.466   5.079  40.890  1.00 28.90           C
ATOM    693  C   ARG A 118     -23.699   3.576  40.758  1.00 28.31           C
ATOM    694  O   ARG A 118     -22.812   2.761  41.047  1.00 26.94           O
ATOM    695  CB  ARG A 118     -23.273   5.704  39.504  1.00 30.22           C
ATOM    696  CG  ARG A 118     -23.376   7.229  39.489  1.00 32.48           C
ATOM    697  CD  ARG A 118     -23.260   7.791  38.075  1.00 34.63           C
ATOM    698  NE  ARG A 118     -24.472   7.622  37.272  1.00 35.50           N
ATOM    699  CZ  ARG A 118     -25.559   8.385  37.377  1.00 37.92           C
ATOM    700  NH1 ARG A 118     -25.601   9.384  38.256  1.00 38.74           N
ATOM    701  NH2 ARG A 118     -26.609   8.151  36.602  1.00 37.77           N
ATOM    702  N   SER A 119     -24.903   3.218  40.329  1.00 26.35           N
ATOM    703  CA  SER A 119     -25.269   1.824  40.162  1.00 25.75           C
ATOM    704  C   SER A 119     -25.265   1.433  38.691  1.00 25.10           C
ATOM    705  O   SER A 119     -25.674   2.210  37.833  1.00 25.27           O
ATOM    706  CB  SER A 119     -26.652   1.580  40.752  1.00 25.81           C
ATOM    707  OG  SER A 119     -27.014   0.225  40.607  1.00 28.23           O
ATOM    708  N   PHE A 120     -24.798   0.225  38.402  1.00 24.24           N
ATOM    709  CA  PHE A 120     -24.747  -0.261  37.034  1.00 23.92           C
ATOM    710  C   PHE A 120     -25.398  -1.631  36.990  1.00 24.61           C
ATOM    711  O   PHE A 120     -25.441  -2.327  38.000  1.00 24.76           O
ATOM    712  CB  PHE A 120     -23.297  -0.379  36.571  1.00 22.89           C
ATOM    713  CG  PHE A 120     -22.579   0.933  36.476  1.00 23.87           C
ATOM    714  CD1 PHE A 120     -22.498   1.609  35.264  1.00 23.81           C
ATOM    715  CD2 PHE A 120     -21.972   1.493  37.599  1.00 23.35           C
ATOM    716  CE1 PHE A 120     -21.822   2.818  35.167  1.00 22.83           C
ATOM    717  CE2 PHE A 120     -21.295   2.700  37.514  1.00 22.58           C
ATOM    718  CZ  PHE A 120     -21.218   3.364  36.298  1.00 23.20           C
ATOM    719  N   SER A 121     -25.888  -2.021  35.817  1.00 25.09           N
ATOM    720  CA  SER A 121     -26.522  -3.321  35.656  1.00 25.74           C
ATOM    721  C   SER A 121     -26.189  -4.018  34.338  1.00 25.56           C
ATOM    722  O   SER A 121     -26.674  -3.627  33.275  1.00 24.42           O
ATOM    723  CB  SER A 121     -28.042  -3.182  35.786  1.00 26.35           C
ATOM    724  OG  SER A 121     -28.400  -2.781  37.095  1.00 28.34           O
ATOM    725  N   ASN A 122     -25.352  -5.048  34.409  1.00 25.96           N
ATOM    726  CA  ASN A 122     -25.006  -5.807  33.215  1.00 26.75           C
ATOM    727  C   ASN A 122     -26.139  -6.800  33.006  1.00 27.99           C
ATOM    728  O   ASN A 122     -26.777  -7.231  33.969  1.00 29.13           O
ATOM    729  CB  ASN A 122     -23.705  -6.593  33.404  1.00 26.29           C
ATOM    730  CG  ASN A 122     -22.490  -5.704  33.527  1.00 25.64           C
ATOM    731  OD1 ASN A 122     -22.307  -4.771  32.753  1.00 26.24           O
ATOM    732  ND2 ASN A 122     -21.639  -6.005  34.494  1.00 26.56           N
ATOM    733  N   ILE A 123     -26.403  -7.151  31.754  1.00 27.73           N
ATOM    734  CA  ILE A 123     -27.441  -8.127  31.456  1.00 28.27           C
ATOM    735  C   ILE A 123     -26.756  -9.359  30.868  1.00 28.48           C
ATOM    736  O   ILE A 123     -26.022  -9.254  29.887  1.00 29.98           O
ATOM    737  CB  ILE A 123     -28.462  -7.586  30.426  1.00 28.53           C
ATOM    738  CG1 ILE A 123     -29.095  -6.291  30.942  1.00 28.12           C
ATOM    739  CG2 ILE A 123     -29.548  -8.630  30.173  1.00 26.30           C
ATOM    740  CD1 ILE A 123     -29.838  -5.513  29.873  1.00 28.51           C
ATOM    741  N   ILE A 124     -26.970 -10.519  31.477  1.00 28.08           N
ATOM    742  CA  ILE A 124     -26.369 -11.746  30.971  1.00 28.12           C
ATOM    743  C   ILE A 124     -27.464 -12.745  30.632  1.00 28.39           C
ATOM    744  O   ILE A 124     -28.334 -13.007  31.449  1.00 29.41           O
```

FIGURE 4-12 (COORDINATES)

```
ATOM    745  CB   ILE A 124     -25.406 -12.419  32.000  1.00 27.74           C
ATOM    746  CG1  ILE A 124     -24.238 -11.487  32.358  1.00 28.43           C
ATOM    747  CG2  ILE A 124     -24.828 -13.701  31.401  1.00 26.59           C
ATOM    748  CD1  ILE A 124     -24.538 -10.471  33.444  1.00 29.26           C
ATOM    749  N    SER A 125     -27.422 -13.290  29.420  1.00 28.71           N
ATOM    750  CA   SER A 125     -28.400 -14.275  28.981  1.00 28.98           C
ATOM    751  C    SER A 125     -27.624 -15.549  28.641  1.00 28.95           C
ATOM    752  O    SER A 125     -26.815 -15.566  27.711  1.00 28.56           O
ATOM    753  CB   SER A 125     -29.154 -13.759  27.757  1.00 29.26           C
ATOM    754  OG   SER A 125     -30.266 -14.584  27.469  1.00 30.17           O
ATOM    755  N    THR A 126     -27.893 -16.617  29.386  1.00 28.41           N
ATOM    756  CA   THR A 126     -27.180 -17.874  29.212  1.00 28.29           C
ATOM    757  C    THR A 126     -28.009 -19.122  28.935  1.00 28.83           C
ATOM    758  O    THR A 126     -28.990 -19.393  29.633  1.00 29.65           O
ATOM    759  CB   THR A 126     -26.362 -18.192  30.474  1.00 28.12           C
ATOM    760  OG1  THR A 126     -25.621 -17.033  30.874  1.00 28.42           O
ATOM    761  CG2  THR A 126     -25.407 -19.352  30.216  1.00 27.97           C
ATOM    762  N    LEU A 127     -27.605 -19.886  27.924  1.00 28.24           N
ATOM    763  CA   LEU A 127     -28.259 -21.159  27.617  1.00 27.92           C
ATOM    764  C    LEU A 127     -27.336 -22.207  28.246  1.00 27.93           C
ATOM    765  O    LEU A 127     -26.120 -22.139  28.070  1.00 26.55           O
ATOM    766  CB   LEU A 127     -28.352 -21.399  26.106  1.00 26.88           C
ATOM    767  CG   LEU A 127     -29.388 -20.618  25.285  1.00 27.03           C
ATOM    768  CD1  LEU A 127     -29.277 -21.049  23.822  1.00 23.87           C
ATOM    769  CD2  LEU A 127     -30.804 -20.873  25.815  1.00 25.35           C
ATOM    770  N    ASN A 128     -27.904 -23.150  28.998  1.00 28.02           N
ATOM    771  CA   ASN A 128     -27.117 -24.199  29.656  1.00 28.05           C
ATOM    772  C    ASN A 128     -26.086 -23.628  30.642  1.00 28.32           C
ATOM    773  O    ASN A 128     -24.884 -23.822  30.483  1.00 28.33           O
ATOM    774  CB   ASN A 128     -26.418 -25.048  28.594  1.00 29.10           C
ATOM    775  CG   ASN A 128     -27.398 -25.655  27.593  1.00 30.54           C
ATOM    776  OD1  ASN A 128     -28.012 -26.696  27.853  1.00 31.40           O
ATOM    777  ND2  ASN A 128     -27.563 -24.995  26.452  1.00 29.59           N
ATOM    778  N    PRO A 129     -26.555 -22.937  31.696  1.00 28.41           N
ATOM    779  CA   PRO A 129     -25.705 -22.322  32.722  1.00 29.04           C
ATOM    780  C    PRO A 129     -24.554 -23.189  33.222  1.00 29.80           C
ATOM    781  O    PRO A 129     -23.480 -22.683  33.529  1.00 30.27           O
ATOM    782  CB   PRO A 129     -26.693 -21.998  33.838  1.00 28.14           C
ATOM    783  CG   PRO A 129     -27.935 -21.697  33.095  1.00 29.12           C
ATOM    784  CD   PRO A 129     -27.976 -22.795  32.056  1.00 28.65           C
ATOM    785  N    THR A 130     -24.779 -24.493  33.315  1.00 30.82           N
ATOM    786  CA   THR A 130     -23.733 -25.378  33.802  1.00 30.77           C
ATOM    787  C    THR A 130     -22.894 -25.970  32.677  1.00 30.83           C
ATOM    788  O    THR A 130     -22.010 -26.785  32.932  1.00 31.66           O
ATOM    789  CB   THR A 130     -24.322 -26.514  34.694  1.00 30.20           C
ATOM    790  OG1  THR A 130     -25.136 -27.391  33.910  1.00 30.02           O
ATOM    791  CG2  THR A 130     -25.175 -25.915  35.801  1.00 29.62           C
ATOM    792  N    ALA A 131     -23.160 -25.547  31.444  0.00 30.26           N
ATOM    793  CA   ALA A 131     -22.400 -26.026  30.295  0.00 29.54           C
ATOM    794  C    ALA A 131     -20.984 -25.475  30.420  0.00 29.10           C
ATOM    795  O    ALA A 131     -20.736 -24.301  30.153  0.00 28.96           O
ATOM    796  CB   ALA A 131     -23.039 -25.546  29.000  0.00 29.62           C
ATOM    797  N    LYS A 132     -20.061 -26.335  30.832  1.00 28.11           N
ATOM    798  CA   LYS A 132     -18.659 -25.958  31.031  1.00 28.69           C
ATOM    799  C    LYS A 132     -18.134 -24.866  30.116  1.00 28.27           C
ATOM    800  O    LYS A 132     -17.502 -23.920  30.574  1.00 28.04           O
ATOM    801  CB   LYS A 132     -17.732 -27.172  30.900  1.00 28.00           C
ATOM    802  CG   LYS A 132     -17.790 -28.138  32.063  1.00 29.38           C
ATOM    803  CD   LYS A 132     -16.581 -29.085  32.093  1.00 31.30           C
ATOM    804  CE   LYS A 132     -16.472 -29.927  30.828  1.00 32.59           C
ATOM    805  NZ   LYS A 132     -17.725 -30.703  30.576  1.00 34.22           N
ATOM    806  N    ARG A 133     -18.391 -25.002  28.822  1.00 28.69           N
ATOM    807  CA   ARG A 133     -17.915 -24.030  27.852  1.00 27.40           C
ATOM    808  C    ARG A 133     -19.049 -23.257  27.205  1.00 27.74           C
ATOM    809  O    ARG A 133     -20.141 -23.782  26.992  1.00 27.33           O
ATOM    810  CB   ARG A 133     -17.122 -24.735  26.755  1.00 27.22           C
ATOM    811  CG   ARG A 133     -15.968 -25.574  27.255  1.00 27.49           C
ATOM    812  CD   ARG A 133     -15.525 -26.557  26.186  1.00 27.77           C
```

FIGURE 4-13 (COORDINATES)

```
ATOM    813  NE   ARG A 133     -15.290 -25.897  24.906  1.00 28.38           N
ATOM    814  CZ   ARG A 133     -15.212 -26.535  23.743  1.00 29.19           C
ATOM    815  NH1  ARG A 133     -15.353 -27.855  23.700  1.00 29.11           N
ATOM    816  NH2  ARG A 133     -14.989 -25.857  22.624  1.00 28.39           N
ATOM    817  N    HIS A 134     -18.777 -21.998  26.894  1.00 27.27           N
ATOM    818  CA   HIS A 134     -19.762 -21.155  26.236  1.00 27.13           C
ATOM    819  C    HIS A 134     -19.121 -20.238  25.218  1.00 26.32           C
ATOM    820  O    HIS A 134     -18.035 -19.698  25.447  1.00 27.08           O
ATOM    821  CB   HIS A 134     -20.502 -20.263  27.235  1.00 27.42           C
ATOM    822  CG   HIS A 134     -21.555 -20.966  28.023  1.00 27.62           C
ATOM    823  ND1  HIS A 134     -21.278 -21.667  29.174  1.00 28.12           N
ATOM    824  CD2  HIS A 134     -22.889 -21.075  27.824  1.00 28.26           C
ATOM    825  CE1  HIS A 134     -22.399 -22.178  29.653  1.00 29.27           C
ATOM    826  NE2  HIS A 134     -23.391 -21.833  28.852  1.00 29.23           N
ATOM    827  N    LEU A 135     -19.789 -20.090  24.083  1.00 25.24           N
ATOM    828  CA   LEU A 135     -19.348 -19.149  23.070  1.00 24.57           C
ATOM    829  C    LEU A 135     -20.077 -17.901  23.573  1.00 24.18           C
ATOM    830  O    LEU A 135     -21.275 -17.967  23.880  1.00 22.46           O
ATOM    831  CB   LEU A 135     -19.883 -19.534  21.690  1.00 23.58           C
ATOM    832  CG   LEU A 135     -19.808 -18.407  20.654  1.00 22.66           C
ATOM    833  CD1  LEU A 135     -18.351 -18.050  20.392  1.00 21.15           C
ATOM    834  CD2  LEU A 135     -20.500 -18.847  19.366  1.00 22.72           C
ATOM    835  N    VAL A 136     -19.378 -16.775  23.664  1.00 24.56           N
ATOM    836  CA   VAL A 136     -20.005 -15.557  24.168  1.00 25.48           C
ATOM    837  C    VAL A 136     -20.037 -14.402  23.172  1.00 26.55           C
ATOM    838  O    VAL A 136     -19.008 -14.041  22.600  1.00 27.48           O
ATOM    839  CB   VAL A 136     -19.286 -15.060  25.453  1.00 25.76           C
ATOM    840  CG1  VAL A 136     -20.030 -13.872  26.049  1.00 25.00           C
ATOM    841  CG2  VAL A 136     -19.174 -16.196  26.470  1.00 26.03           C
ATOM    842  N    LEU A 137     -21.223 -13.834  22.960  1.00 26.71           N
ATOM    843  CA   LEU A 137     -21.378 -12.680  22.073  1.00 27.15           C
ATOM    844  C    LEU A 137     -21.705 -11.524  23.001  1.00 26.46           C
ATOM    845  O    LEU A 137     -22.465 -11.696  23.957  1.00 26.10           O
ATOM    846  CB   LEU A 137     -22.534 -12.862  21.079  1.00 27.43           C
ATOM    847  CG   LEU A 137     -22.539 -14.076  20.147  1.00 29.39           C
ATOM    848  CD1  LEU A 137     -23.675 -13.908  19.138  1.00 29.76           C
ATOM    849  CD2  LEU A 137     -21.210 -14.215  19.429  1.00 30.00           C
ATOM    850  N    ALA A 138     -21.150 -10.347  22.728  1.00 26.06           N
ATOM    851  CA   ALA A 138     -21.404  -9.211  23.600  1.00 24.91           C
ATOM    852  C    ALA A 138     -21.341  -7.844  22.936  1.00 25.26           C
ATOM    853  O    ALA A 138     -20.893  -7.694  21.797  1.00 25.23           O
ATOM    854  CB   ALA A 138     -20.424  -9.249  24.773  1.00 23.83           C
ATOM    855  N    CYS A 139     -21.812  -6.850  23.681  1.00 25.05           N
ATOM    856  CA   CYS A 139     -21.801  -5.449  23.263  1.00 24.72           C
ATOM    857  C    CYS A 139     -22.202  -4.676  24.505  1.00 24.16           C
ATOM    858  O    CYS A 139     -22.432  -5.278  25.556  1.00 24.00           O
ATOM    859  CB   CYS A 139     -22.801  -5.184  22.126  1.00 24.50           C
ATOM    860  SG   CYS A 139     -24.559  -5.199  22.558  1.00 26.88           S
ATOM    861  N    HIS A 140     -22.262  -3.353  24.406  1.00 24.21           N
ATOM    862  CA   HIS A 140     -22.668  -2.545  25.549  1.00 24.33           C
ATOM    863  C    HIS A 140     -24.017  -1.932  25.183  1.00 24.92           C
ATOM    864  O    HIS A 140     -24.214  -1.523  24.033  1.00 25.38           O
ATOM    865  CB   HIS A 140     -21.620  -1.459  25.833  1.00 24.97           C
ATOM    866  CG   HIS A 140     -21.679  -0.286  24.903  1.00 24.63           C
ATOM    867  ND1  HIS A 140     -22.369   0.871  25.205  1.00 24.41           N
ATOM    868  CD2  HIS A 140     -21.145  -0.094  23.674  1.00 24.35           C
ATOM    869  CE1  HIS A 140     -22.257   1.723  24.202  1.00 24.55           C
ATOM    870  NE2  HIS A 140     -21.521   1.162  23.260  1.00 25.34           N
ATOM    871  N    TYR A 141     -24.955  -1.891  26.128  1.00 24.17           N
ATOM    872  CA   TYR A 141     -26.267  -1.318  25.822  1.00 24.62           C
ATOM    873  C    TYR A 141     -26.468   0.112  26.328  1.00 24.61           C
ATOM    874  O    TYR A 141     -27.457   0.757  25.991  1.00 25.47           O
ATOM    875  CB   TYR A 141     -27.408  -2.215  26.333  1.00 23.74           C
ATOM    876  CG   TYR A 141     -27.644  -2.179  27.826  1.00 25.38           C
ATOM    877  CD1  TYR A 141     -26.893  -2.969  28.693  1.00 23.74           C
ATOM    878  CD2  TYR A 141     -28.621  -1.342  28.372  1.00 25.55           C
ATOM    879  CE1  TYR A 141     -27.103  -2.928  30.061  1.00 25.55           C
ATOM    880  CE2  TYR A 141     -28.841  -1.291  29.744  1.00 25.73           C
```

FIGURE 4-14 (COORDINATES)

```
ATOM    881  CZ   TYR A 141     -28.078  -2.084  30.588  1.00 26.89           C
ATOM    882  OH   TYR A 141     -28.276  -2.021  31.959  1.00 24.55           O
ATOM    883  N    ASP A 142     -25.540   0.613  27.134  1.00 23.80           N
ATOM    884  CA   ASP A 142     -25.667   1.977  27.615  1.00 23.19           C
ATOM    885  C    ASP A 142     -25.321   2.898  26.452  1.00 23.38           C
ATOM    886  O    ASP A 142     -24.756   2.454  25.454  1.00 21.69           O
ATOM    887  CB   ASP A 142     -24.712   2.239  28.785  1.00 22.50           C
ATOM    888  CG   ASP A 142     -23.253   2.134  28.387  1.00 23.00           C
ATOM    889  OD1  ASP A 142     -22.864   1.097  27.814  1.00 23.50           O
ATOM    890  OD2  ASP A 142     -22.490   3.085  28.653  1.00 23.54           O
ATOM    891  N    SER A 143     -25.688   4.170  26.576  1.00 23.72           N
ATOM    892  CA   SER A 143     -25.388   5.166  25.555  1.00 24.90           C
ATOM    893  C    SER A 143     -24.602   6.270  26.255  1.00 24.88           C
ATOM    894  O    SER A 143     -24.917   6.629  27.389  1.00 23.92           O
ATOM    895  CB   SER A 143     -26.674   5.738  24.956  1.00 25.44           C
ATOM    896  OG   SER A 143     -27.423   6.439  25.931  1.00 27.58           O
ATOM    897  N    LYS A 144     -23.582   6.799  25.584  1.00 25.24           N
ATOM    898  CA   LYS A 144     -22.743   7.844  26.166  1.00 25.82           C
ATOM    899  C    LYS A 144     -23.536   9.078  26.586  1.00 26.28           C
ATOM    900  O    LYS A 144     -24.371   9.573  25.834  1.00 25.86           O
ATOM    901  CB   LYS A 144     -21.645   8.256  25.177  1.00 24.86           C
ATOM    902  CG   LYS A 144     -20.674   9.306  25.729  1.00 22.88           C
ATOM    903  CD   LYS A 144     -19.515   9.554  24.760  1.00 21.93           C
ATOM    904  CE   LYS A 144     -18.499  10.507  25.350  1.00 20.76           C
ATOM    905  NZ   LYS A 144     -17.968  10.021  26.655  1.00 21.00           N
ATOM    906  N    TYR A 145     -23.271   9.572  27.790  1.00 27.36           N
ATOM    907  CA   TYR A 145     -23.965  10.755  28.283  1.00 29.36           C
ATOM    908  C    TYR A 145     -23.557  12.057  27.590  1.00 30.86           C
ATOM    909  O    TYR A 145     -22.370  12.353  27.422  1.00 30.41           O
ATOM    910  CB   TYR A 145     -23.755  10.950  29.788  1.00 29.78           C
ATOM    911  CG   TYR A 145     -24.374  12.253  30.254  1.00 31.46           C
ATOM    912  CD1  TYR A 145     -25.757  12.379  30.384  1.00 31.62           C
ATOM    913  CD2  TYR A 145     -23.591  13.393  30.444  1.00 33.10           C
ATOM    914  CE1  TYR A 145     -26.346  13.598  30.680  1.00 33.13           C
ATOM    915  CE2  TYR A 145     -24.174  14.630  30.743  1.00 33.60           C
ATOM    916  CZ   TYR A 145     -25.552  14.721  30.856  1.00 33.99           C
ATOM    917  OH   TYR A 145     -26.144  15.933  31.131  1.00 35.84           O
ATOM    918  N    PHE A 146     -24.565  12.837  27.219  1.00 32.08           N
ATOM    919  CA   PHE A 146     -24.379  14.133  26.576  1.00 35.11           C
ATOM    920  C    PHE A 146     -25.546  15.015  27.004  1.00 37.42           C
ATOM    921  O    PHE A 146     -26.695  14.580  26.970  1.00 37.37           O
ATOM    922  CB   PHE A 146     -24.410  13.998  25.048  1.00 34.15           C
ATOM    923  CG   PHE A 146     -23.132  13.498  24.449  1.00 32.48           C
ATOM    924  CD1  PHE A 146     -21.981  14.279  24.481  1.00 32.77           C
ATOM    925  CD2  PHE A 146     -23.080  12.255  23.827  1.00 32.20           C
ATOM    926  CE1  PHE A 146     -20.794  13.829  23.897  1.00 31.78           C
ATOM    927  CE2  PHE A 146     -21.897  11.795  23.241  1.00 31.75           C
ATOM    928  CZ   PHE A 146     -20.753  12.584  23.275  1.00 30.88           C
ATOM    929  N    SER A 147     -25.271  16.242  27.427  1.00 40.73           N
ATOM    930  CA   SER A 147     -26.369  17.128  27.796  1.00 44.39           C
ATOM    931  C    SER A 147     -27.019  17.543  26.469  1.00 46.25           C
ATOM    932  O    SER A 147     -26.328  17.725  25.462  1.00 46.08           O
ATOM    933  CB   SER A 147     -25.846  18.347  28.558  1.00 44.85           C
ATOM    934  OG   SER A 147     -24.993  19.128  27.748  1.00 47.96           O
ATOM    935  N    HIS A 148     -28.341  17.669  26.454  1.00 49.43           N
ATOM    936  CA   HIS A 148     -29.043  18.032  25.222  1.00 52.47           C
ATOM    937  C    HIS A 148     -28.439  19.245  24.521  1.00 53.36           C
ATOM    938  O    HIS A 148     -28.131  20.264  25.147  1.00 53.24           O
ATOM    939  CB   HIS A 148     -30.534  18.270  25.496  1.00 54.24           C
ATOM    940  CG   HIS A 148     -31.256  17.059  26.005  1.00 56.46           C
ATOM    941  ND1  HIS A 148     -30.979  15.784  25.557  1.00 57.20           N
ATOM    942  CD2  HIS A 148     -32.253  16.930  26.914  1.00 57.36           C
ATOM    943  CE1  HIS A 148     -31.773  14.923  26.170  1.00 57.45           C
ATOM    944  NE2  HIS A 148     -32.556  15.592  26.997  1.00 57.55           N
ATOM    945  N    TRP A 149     -28.281  19.116  23.208  1.00 54.41           N
ATOM    946  CA   TRP A 149     -27.699  20.165  22.388  1.00 55.82           C
ATOM    947  C    TRP A 149     -28.599  20.475  21.194  1.00 56.05           C
ATOM    948  O    TRP A 149     -28.765  19.642  20.301  1.00 55.75           O
```

FIGURE 4-15 (COORDINATES)

```
ATOM    949  CB   TRP A 149     -26.326  19.712  21.892  1.00 57.33           C
ATOM    950  CG   TRP A 149     -25.590  20.753  21.121  1.00 58.95           C
ATOM    951  CD1  TRP A 149     -24.887  21.807  21.629  1.00 59.10           C
ATOM    952  CD2  TRP A 149     -25.505  20.860  19.695  1.00 59.88           C
ATOM    953  NE1  TRP A 149     -24.369  22.566  20.607  1.00 59.68           N
ATOM    954  CE2  TRP A 149     -24.733  22.009  19.409  1.00 59.93           C
ATOM    955  CE3  TRP A 149     -26.009  20.097  18.630  1.00 60.18           C
ATOM    956  CZ2  TRP A 149     -24.451  22.418  18.098  1.00 59.95           C
ATOM    957  CZ3  TRP A 149     -25.728  20.502  17.326  1.00 60.47           C
ATOM    958  CH2  TRP A 149     -24.955  21.655  17.075  1.00 60.37           C
ATOM    959  N    ASN A 150     -29.167  21.677  21.178  1.00 56.38           N
ATOM    960  CA   ASN A 150     -30.053  22.093  20.095  1.00 56.56           C
ATOM    961  C    ASN A 150     -31.201  21.106  19.922  1.00 56.00           C
ATOM    962  O    ASN A 150     -31.570  20.746  18.803  1.00 55.90           O
ATOM    963  CB   ASN A 150     -29.269  22.215  18.787  1.00 57.85           C
ATOM    964  CG   ASN A 150     -28.289  23.371  18.804  1.00 59.53           C
ATOM    965  OD1  ASN A 150     -27.455  23.505  17.908  1.00 60.51           O
ATOM    966  ND2  ASN A 150     -28.389  24.220  19.825  1.00 59.61           N
ATOM    967  N    ASN A 151     -31.760  20.675  21.048  1.00 55.19           N
ATOM    968  CA   ASN A 151     -32.869  19.732  21.059  1.00 54.31           C
ATOM    969  C    ASN A 151     -32.542  18.380  20.447  1.00 52.24           C
ATOM    970  O    ASN A 151     -33.437  17.668  19.988  1.00 52.91           O
ATOM    971  CB   ASN A 151     -34.085  20.334  20.355  1.00 56.15           C
ATOM    972  CG   ASN A 151     -34.725  21.440  21.162  1.00 57.79           C
ATOM    973  OD1  ASN A 151     -35.047  21.255  22.340  1.00 59.43           O
ATOM    974  ND2  ASN A 151     -34.915  22.598  20.538  1.00 58.12           N
ATOM    975  N    ARG A 152     -31.262  18.026  20.436  1.00 48.90           N
ATOM    976  CA   ARG A 152     -30.855  16.734  19.901  1.00 45.72           C
ATOM    977  C    ARG A 152     -30.322  15.868  21.033  1.00 43.23           C
ATOM    978  O    ARG A 152     -29.615  16.346  21.923  1.00 42.52           O
ATOM    979  CB   ARG A 152     -29.795  16.901  18.805  1.00 45.21           C
ATOM    980  CG   ARG A 152     -30.316  17.610  17.560  1.00 44.00           C
ATOM    981  CD   ARG A 152     -29.284  17.633  16.440  1.00 42.51           C
ATOM    982  NE   ARG A 152     -29.122  16.328  15.805  1.00 41.65           N
ATOM    983  CZ   ARG A 152     -28.163  16.038  14.931  1.00 40.80           C
ATOM    984  NH1  ARG A 152     -27.277  16.962  14.589  1.00 41.09           N
ATOM    985  NH2  ARG A 152     -28.088  14.828  14.398  1.00 40.03           N
ATOM    986  N    VAL A 153     -30.684  14.593  20.999  1.00 40.75           N
ATOM    987  CA   VAL A 153     -30.262  13.645  22.017  1.00 38.49           C
ATOM    988  C    VAL A 153     -29.353  12.593  21.386  1.00 36.36           C
ATOM    989  O    VAL A 153     -29.570  12.190  20.247  1.00 35.66           O
ATOM    990  CB   VAL A 153     -31.492  12.956  22.637  1.00 39.14           C
ATOM    991  CG1  VAL A 153     -31.070  12.044  23.765  1.00 40.39           C
ATOM    992  CG2  VAL A 153     -32.470  14.006  23.136  1.00 39.23           C
ATOM    993  N    PHE A 154     -28.332  12.153  22.113  1.00 33.85           N
ATOM    994  CA   PHE A 154     -27.425  11.143  21.574  1.00 31.70           C
ATOM    995  C    PHE A 154     -27.972   9.743  21.846  1.00 30.64           C
ATOM    996  O    PHE A 154     -28.194   9.370  22.997  1.00 30.15           O
ATOM    997  CB   PHE A 154     -26.039  11.280  22.203  1.00 31.44           C
ATOM    998  CG   PHE A 154     -25.039  10.274  21.693  1.00 31.95           C
ATOM    999  CD1  PHE A 154     -24.395  10.466  20.475  1.00 30.80           C
ATOM   1000  CD2  PHE A 154     -24.752   9.125  22.430  1.00 30.80           C
ATOM   1001  CE1  PHE A 154     -23.477   9.527  19.999  1.00 32.20           C
ATOM   1002  CE2  PHE A 154     -23.840   8.186  21.965  1.00 31.32           C
ATOM   1003  CZ   PHE A 154     -23.200   8.385  20.747  1.00 30.35           C
ATOM   1004  N    VAL A 155     -28.184   8.963  20.791  1.00 28.85           N
ATOM   1005  CA   VAL A 155     -28.710   7.614  20.965  1.00 27.64           C
ATOM   1006  C    VAL A 155     -27.760   6.490  20.560  1.00 27.09           C
ATOM   1007  O    VAL A 155     -28.140   5.325  20.606  1.00 27.17           O
ATOM   1008  CB   VAL A 155     -30.053   7.433  20.200  1.00 27.41           C
ATOM   1009  CG1  VAL A 155     -31.094   8.394  20.753  1.00 27.36           C
ATOM   1010  CG2  VAL A 155     -29.857   7.668  18.710  1.00 25.75           C
ATOM   1011  N    GLY A 156     -26.534   6.839  20.168  1.00 26.86           N
ATOM   1012  CA   GLY A 156     -25.554   5.839  19.764  1.00 26.09           C
ATOM   1013  C    GLY A 156     -26.130   4.709  18.925  1.00 25.99           C
ATOM   1014  O    GLY A 156     -26.158   3.550  19.346  1.00 25.75           O
ATOM   1015  N    ALA A 157     -26.593   5.045  17.728  1.00 24.75           N
ATOM   1016  CA   ALA A 157     -27.183   4.058  16.839  1.00 24.79           C
```

FIGURE 4-16 (COORDINATES)

```
ATOM   1017  C    ALA A 157     -26.234   2.874  16.586  1.00 24.91           C
ATOM   1018  O    ALA A 157     -26.604   1.716  16.794  1.00 25.66           O
ATOM   1019  CB   ALA A 157     -27.586   4.729  15.522  1.00 23.12           C
ATOM   1020  N    THR A 158     -25.017   3.164  16.136  1.00 24.58           N
ATOM   1021  CA   THR A 158     -24.032   2.117  15.884  1.00 25.18           C
ATOM   1022  C    THR A 158     -23.263   1.837  17.169  1.00 25.91           C
ATOM   1023  O    THR A 158     -22.537   0.848  17.266  1.00 26.81           O
ATOM   1024  CB   THR A 158     -22.954   2.550  14.854  1.00 24.81           C
ATOM   1025  OG1  THR A 158     -22.125   3.556  15.446  1.00 24.08           O
ATOM   1026  CG2  THR A 158     -23.577   3.098  13.578  1.00 22.91           C
ATOM   1027  N    ASP A 159     -23.435   2.707  18.157  1.00 25.69           N
ATOM   1028  CA   ASP A 159     -22.677   2.601  19.391  1.00 26.24           C
ATOM   1029  C    ASP A 159     -23.505   2.596  20.688  1.00 26.37           C
ATOM   1030  O    ASP A 159     -23.528   3.598  21.414  1.00 26.38           O
ATOM   1031  CB   ASP A 159     -21.665   3.761  19.369  1.00 27.18           C
ATOM   1032  CG   ASP A 159     -20.750   3.796  20.575  1.00 28.60           C
ATOM   1033  OD1  ASP A 159     -20.606   2.764  21.262  1.00 29.05           O
ATOM   1034  OD2  ASP A 159     -20.155   4.873  20.818  1.00 28.73           O
ATOM   1035  N    SER A 160     -24.158   1.474  21.007  1.00 24.78           N
ATOM   1036  CA   SER A 160     -24.174   0.268  20.178  1.00 24.89           C
ATOM   1037  C    SER A 160     -25.581  -0.333  20.097  1.00 24.70           C
ATOM   1038  O    SER A 160     -25.775  -1.532  20.337  1.00 25.27           O
ATOM   1039  CB   SER A 160     -23.213  -0.788  20.734  1.00 23.34           C
ATOM   1040  OG   SER A 160     -21.868  -0.406  20.527  1.00 24.23           O
ATOM   1041  N    ALA A 161     -26.562   0.498  19.758  1.00 23.91           N
ATOM   1042  CA   ALA A 161     -27.939   0.028  19.640  1.00 23.79           C
ATOM   1043  C    ALA A 161     -28.039  -1.103  18.603  1.00 24.07           C
ATOM   1044  O    ALA A 161     -28.704  -2.114  18.839  1.00 22.35           O
ATOM   1045  CB   ALA A 161     -28.853   1.184  19.246  1.00 23.92           C
ATOM   1046  N    VAL A 162     -27.375  -0.922  17.462  1.00 23.85           N
ATOM   1047  CA   VAL A 162     -27.385  -1.921  16.397  1.00 24.77           C
ATOM   1048  C    VAL A 162     -26.800  -3.248  16.904  1.00 25.69           C
ATOM   1049  O    VAL A 162     -27.425  -4.297  16.766  1.00 26.67           O
ATOM   1050  CB   VAL A 162     -26.619  -1.386  15.137  1.00 25.09           C
ATOM   1051  CG1  VAL A 162     -26.289  -2.513  14.168  1.00 22.75           C
ATOM   1052  CG2  VAL A 162     -27.480  -0.332  14.435  1.00 23.16           C
ATOM   1053  N    PRO A 163     -25.591  -3.227  17.484  1.00 26.20           N
ATOM   1054  CA   PRO A 163     -25.059  -4.503  17.975  1.00 25.68           C
ATOM   1055  C    PRO A 163     -26.064  -5.214  18.904  1.00 25.88           C
ATOM   1056  O    PRO A 163     -26.234  -6.439  18.836  1.00 24.46           O
ATOM   1057  CB   PRO A 163     -23.784  -4.077  18.697  1.00 25.21           C
ATOM   1058  CG   PRO A 163     -23.277  -2.981  17.800  1.00 24.45           C
ATOM   1059  CD   PRO A 163     -24.545  -2.184  17.481  1.00 25.47           C
ATOM   1060  N    CYS A 164     -26.730  -4.445  19.765  1.00 25.60           N
ATOM   1061  CA   CYS A 164     -27.714  -5.020  20.678  1.00 26.37           C
ATOM   1062  C    CYS A 164     -28.800  -5.733  19.882  1.00 27.15           C
ATOM   1063  O    CYS A 164     -29.103  -6.902  20.130  1.00 28.21           O
ATOM   1064  CB   CYS A 164     -28.365  -3.937  21.549  1.00 26.11           C
ATOM   1065  SG   CYS A 164     -27.368  -3.284  22.913  1.00 25.83           S
ATOM   1066  N    ALA A 165     -29.379  -5.019  18.921  1.00 26.90           N
ATOM   1067  CA   ALA A 165     -30.442  -5.558  18.079  1.00 26.22           C
ATOM   1068  C    ALA A 165     -29.987  -6.794  17.315  1.00 27.15           C
ATOM   1069  O    ALA A 165     -30.753  -7.746  17.154  1.00 28.47           O
ATOM   1070  CB   ALA A 165     -30.921  -4.490  17.109  1.00 24.33           C
ATOM   1071  N    MET A 166     -28.744  -6.774  16.839  1.00 27.26           N
ATOM   1072  CA   MET A 166     -28.182  -7.901  16.095  1.00 27.57           C
ATOM   1073  C    MET A 166     -28.129  -9.157  16.963  1.00 28.02           C
ATOM   1074  O    MET A 166     -28.383 -10.265  16.490  1.00 27.00           O
ATOM   1075  CB   MET A 166     -26.773  -7.561  15.605  1.00 27.35           C
ATOM   1076  CG   MET A 166     -26.738  -6.509  14.508  1.00 27.25           C
ATOM   1077  SD   MET A 166     -25.053  -6.033  14.059  1.00 28.67           S
ATOM   1078  CE   MET A 166     -24.509  -7.499  13.193  1.00 25.92           C
ATOM   1079  N    MET A 167     -27.783  -8.981  18.234  1.00 28.32           N
ATOM   1080  CA   MET A 167     -27.719 -10.109  19.145  1.00 28.32           C
ATOM   1081  C    MET A 167     -29.130 -10.636  19.387  1.00 28.57           C
ATOM   1082  O    MET A 167     -29.348 -11.846  19.430  1.00 28.25           O
ATOM   1083  CB   MET A 167     -27.055  -9.683  20.456  1.00 29.01           C
ATOM   1084  CG   MET A 167     -25.541  -9.560  20.329  1.00 29.06           C
```

FIGURE 4-17 (COORDINATES)

```
ATOM   1085  SD  MET A 167     -24.727  -8.675  21.665  1.00 31.42           S
ATOM   1086  CE  MET A 167     -25.052  -9.742  23.082  1.00 28.98           C
ATOM   1087  N   LEU A 168     -30.092  -9.724  19.524  1.00 28.26           N
ATOM   1088  CA  LEU A 168     -31.482 -10.115  19.744  1.00 27.27           C
ATOM   1089  C   LEU A 168     -32.057 -10.823  18.510  1.00 27.33           C
ATOM   1090  O   LEU A 168     -32.753 -11.833  18.633  1.00 26.61           O
ATOM   1091  CB  LEU A 168     -32.331  -8.889  20.094  1.00 26.58           C
ATOM   1092  CG  LEU A 168     -32.043  -8.226  21.443  1.00 26.49           C
ATOM   1093  CD1 LEU A 168     -32.867  -6.960  21.562  1.00 26.71           C
ATOM   1094  CD2 LEU A 168     -32.366  -9.189  22.589  1.00 25.03           C
ATOM   1095  N   GLU A 169     -31.764 -10.292  17.325  1.00 27.44           N
ATOM   1096  CA  GLU A 169     -32.239 -10.892  16.081  1.00 27.51           C
ATOM   1097  C   GLU A 169     -31.631 -12.280  15.913  1.00 27.66           C
ATOM   1098  O   GLU A 169     -32.293 -13.204  15.428  1.00 27.74           O
ATOM   1099  CB  GLU A 169     -31.871 -10.003  14.881  1.00 27.66           C
ATOM   1100  CG  GLU A 169     -32.032 -10.648  13.493  1.00 28.15           C
ATOM   1101  CD  GLU A 169     -33.437 -11.181  13.208  1.00 28.91           C
ATOM   1102  OE1 GLU A 169     -34.402 -10.770  13.891  1.00 28.58           O
ATOM   1103  OE2 GLU A 169     -33.572 -12.010  12.283  1.00 28.84           O
ATOM   1104  N   LEU A 170     -30.371 -12.430  16.312  1.00 26.88           N
ATOM   1105  CA  LEU A 170     -29.713 -13.724  16.203  1.00 26.32           C
ATOM   1106  C   LEU A 170     -30.420 -14.728  17.124  1.00 27.52           C
ATOM   1107  O   LEU A 170     -30.671 -15.875  16.742  1.00 28.05           O
ATOM   1108  CB  LEU A 170     -28.233 -13.602  16.570  1.00 24.13           C
ATOM   1109  CG  LEU A 170     -27.416 -14.895  16.475  1.00 23.68           C
ATOM   1110  CD1 LEU A 170     -25.996 -14.592  15.986  1.00 22.03           C
ATOM   1111  CD2 LEU A 170     -27.401 -15.584  17.831  1.00 20.59           C
ATOM   1112  N   ALA A 171     -30.747 -14.290  18.335  1.00 27.81           N
ATOM   1113  CA  ALA A 171     -31.433 -15.153  19.284  1.00 28.37           C
ATOM   1114  C   ALA A 171     -32.785 -15.580  18.704  1.00 29.94           C
ATOM   1115  O   ALA A 171     -33.191 -16.742  18.826  1.00 30.18           O
ATOM   1116  CB  ALA A 171     -31.631 -14.424  20.596  1.00 27.60           C
ATOM   1117  N   ARG A 172     -33.474 -14.641  18.062  1.00 30.19           N
ATOM   1118  CA  ARG A 172     -34.771 -14.931  17.470  1.00 30.58           C
ATOM   1119  C   ARG A 172     -34.648 -15.842  16.251  1.00 31.29           C
ATOM   1120  O   ARG A 172     -35.343 -16.855  16.158  1.00 32.11           O
ATOM   1121  CB  ARG A 172     -35.473 -13.637  17.054  1.00 30.25           C
ATOM   1122  CG  ARG A 172     -36.885 -13.860  16.527  1.00 31.92           C
ATOM   1123  CD  ARG A 172     -37.326 -12.751  15.587  1.00 31.88           C
ATOM   1124  NE  ARG A 172     -36.579 -12.768  14.333  1.00 34.19           N
ATOM   1125  CZ  ARG A 172     -36.671 -13.728  13.413  1.00 35.60           C
ATOM   1126  NH1 ARG A 172     -37.482 -14.760  13.599  1.00 35.64           N
ATOM   1127  NH2 ARG A 172     -35.948 -13.657  12.299  1.00 35.05           N
ATOM   1128  N   ALA A 173     -33.756 -15.485  15.328  1.00 30.72           N
ATOM   1129  CA  ALA A 173     -33.561 -16.245  14.095  1.00 30.14           C
ATOM   1130  C   ALA A 173     -33.078 -17.683  14.264  1.00 30.61           C
ATOM   1131  O   ALA A 173     -33.411 -18.553  13.457  1.00 30.89           O
ATOM   1132  CB  ALA A 173     -32.605 -15.492  13.165  1.00 30.34           C
ATOM   1133  N   LEU A 174     -32.290 -17.939  15.301  1.00 30.50           N
ATOM   1134  CA  LEU A 174     -31.767 -19.281  15.522  1.00 30.10           C
ATOM   1135  C   LEU A 174     -32.474 -19.956  16.681  1.00 30.74           C
ATOM   1136  O   LEU A 174     -32.069 -21.029  17.120  1.00 30.61           O
ATOM   1137  CB  LEU A 174     -30.266 -19.224  15.821  1.00 28.98           C
ATOM   1138  CG  LEU A 174     -29.389 -18.392  14.883  1.00 28.16           C
ATOM   1139  CD1 LEU A 174     -27.929 -18.557  15.301  1.00 28.10           C
ATOM   1140  CD2 LEU A 174     -29.596 -18.829  13.432  1.00 26.33           C
ATOM   1141  N   ASP A 175     -33.538 -19.331  17.168  1.00 31.74           N
ATOM   1142  CA  ASP A 175     -34.274 -19.865  18.303  1.00 33.68           C
ATOM   1143  C   ASP A 175     -34.569 -21.362  18.231  1.00 35.17           C
ATOM   1144  O   ASP A 175     -34.336 -22.090  19.199  1.00 35.18           O
ATOM   1145  CB  ASP A 175     -35.574 -19.083  18.498  1.00 33.55           C
ATOM   1146  CG  ASP A 175     -36.240 -19.392  19.820  1.00 34.00           C
ATOM   1147  OD1 ASP A 175     -35.512 -19.577  20.817  1.00 33.60           O
ATOM   1148  OD2 ASP A 175     -37.487 -19.439  19.867  1.00 34.72           O
ATOM   1149  N   LYS A 176     -35.065 -21.832  17.093  1.00 36.59           N
ATOM   1150  CA  LYS A 176     -35.377 -23.247  16.965  1.00 38.25           C
ATOM   1151  C   LYS A 176     -34.135 -24.113  17.111  1.00 38.42           C
ATOM   1152  O   LYS A 176     -34.150 -25.107  17.834  1.00 38.94           O
```

FIGURE 4-18 (COORDINATES)

```
ATOM   1153  CB   LYS A 176     -36.051 -23.534  15.624  1.00 40.42           C
ATOM   1154  CG   LYS A 176     -36.528 -24.973  15.487  1.00 44.14           C
ATOM   1155  CD   LYS A 176     -37.235 -25.199  14.158  1.00 47.10           C
ATOM   1156  CE   LYS A 176     -37.723 -26.633  14.011  1.00 47.79           C
ATOM   1157  NZ   LYS A 176     -38.506 -26.791  12.745  1.00 49.89           N
ATOM   1158  N    LYS A 177     -33.056 -23.742  16.430  1.00 38.42           N
ATOM   1159  CA   LYS A 177     -31.822 -24.514  16.517  1.00 38.93           C
ATOM   1160  C    LYS A 177     -31.181 -24.447  17.905  1.00 38.65           C
ATOM   1161  O    LYS A 177     -30.608 -25.429  18.375  1.00 38.72           O
ATOM   1162  CB   LYS A 177     -30.832 -24.046  15.448  1.00 39.74           C
ATOM   1163  CG   LYS A 177     -31.232 -24.474  14.040  1.00 41.85           C
ATOM   1164  CD   LYS A 177     -30.533 -23.655  12.966  1.00 43.27           C
ATOM   1165  CE   LYS A 177     -30.977 -24.082  11.568  1.00 43.87           C
ATOM   1166  NZ   LYS A 177     -30.643 -25.510  11.299  1.00 44.14           N
ATOM   1167  N    LEU A 178     -31.287 -23.298  18.565  1.00 38.06           N
ATOM   1168  CA   LEU A 178     -30.710 -23.140  19.895  1.00 38.41           C
ATOM   1169  C    LEU A 178     -31.492 -23.940  20.935  1.00 39.42           C
ATOM   1170  O    LEU A 178     -30.957 -24.304  21.983  1.00 38.73           O
ATOM   1171  CB   LEU A 178     -30.681 -21.658  20.286  1.00 37.85           C
ATOM   1172  CG   LEU A 178     -29.749 -20.787  19.437  1.00 37.18           C
ATOM   1173  CD1  LEU A 178     -29.935 -19.329  19.804  1.00 36.38           C
ATOM   1174  CD2  LEU A 178     -28.304 -21.231  19.648  1.00 36.98           C
ATOM   1175  N    LEU A 179     -32.759 -24.211  20.630  1.00 39.93           N
ATOM   1176  CA   LEU A 179     -33.639 -24.974  21.514  1.00 40.80           C
ATOM   1177  C    LEU A 179     -33.171 -26.418  21.699  1.00 40.59           C
ATOM   1178  O    LEU A 179     -33.453 -27.040  22.720  1.00 41.10           O
ATOM   1179  CB   LEU A 179     -35.068 -24.971  20.955  1.00 41.31           C
ATOM   1180  CG   LEU A 179     -36.144 -25.793  21.675  1.00 42.30           C
ATOM   1181  CD1  LEU A 179     -36.278 -25.344  23.125  1.00 41.68           C
ATOM   1182  CD2  LEU A 179     -37.465 -25.623  20.943  1.00 42.19           C
ATOM   1183  N    SER A 180     -32.454 -26.945  20.714  1.00 40.94           N
ATOM   1184  CA   SER A 180     -31.966 -28.315  20.776  1.00 41.86           C
ATOM   1185  C    SER A 180     -30.792 -28.492  21.739  1.00 42.90           C
ATOM   1186  O    SER A 180     -30.292 -29.602  21.914  1.00 42.84           O
ATOM   1187  CB   SER A 180     -31.557 -28.786  19.380  1.00 41.71           C
ATOM   1188  OG   SER A 180     -30.443 -28.051  18.903  1.00 42.30           O
ATOM   1189  N    LEU A 181     -30.351 -27.402  22.360  1.00 43.84           N
ATOM   1190  CA   LEU A 181     -29.232 -27.461  23.299  1.00 44.71           C
ATOM   1191  C    LEU A 181     -29.676 -27.852  24.719  1.00 45.14           C
ATOM   1192  O    LEU A 181     -30.900 -27.932  24.964  1.00 45.54           O
ATOM   1193  CB   LEU A 181     -28.512 -26.107  23.333  1.00 44.90           C
ATOM   1194  CG   LEU A 181     -27.690 -25.697  22.104  1.00 45.03           C
ATOM   1195  CD1  LEU A 181     -27.379 -24.207  22.153  1.00 44.22           C
ATOM   1196  CD2  LEU A 181     -26.408 -26.510  22.056  1.00 44.69           C
ATOM   1197  N    ASP A 190     -19.807 -30.221  25.495  1.00 35.07           N
ATOM   1198  CA   ASP A 190     -20.398 -29.436  26.615  1.00 35.41           C
ATOM   1199  C    ASP A 190     -20.141 -27.961  26.337  1.00 34.12           C
ATOM   1200  O    ASP A 190     -19.470 -27.261  27.100  1.00 34.11           O
ATOM   1201  CB   ASP A 190     -19.767 -29.862  27.946  1.00 36.97           C
ATOM   1202  CG   ASP A 190     -20.575 -29.403  29.142  1.00 38.42           C
ATOM   1203  OD1  ASP A 190     -21.815 -29.302  29.013  1.00 40.77           O
ATOM   1204  OD2  ASP A 190     -19.983 -29.157  30.212  1.00 39.87           O
ATOM   1205  N    LEU A 191     -20.704 -27.511  25.223  1.00 32.48           N
ATOM   1206  CA   LEU A 191     -20.564 -26.152  24.744  1.00 30.82           C
ATOM   1207  C    LEU A 191     -21.928 -25.548  24.420  1.00 30.48           C
ATOM   1208  O    LEU A 191     -22.741 -26.167  23.736  1.00 30.36           O
ATOM   1209  CB   LEU A 191     -19.693 -26.163  23.482  1.00 30.03           C
ATOM   1210  CG   LEU A 191     -19.592 -24.904  22.620  1.00 29.98           C
ATOM   1211  CD1  LEU A 191     -18.856 -23.799  23.373  1.00 29.91           C
ATOM   1212  CD2  LEU A 191     -18.868 -25.247  21.337  1.00 28.73           C
ATOM   1213  N    SER A 192     -22.176 -24.337  24.910  1.00 29.16           N
ATOM   1214  CA   SER A 192     -23.438 -23.664  24.640  1.00 27.93           C
ATOM   1215  C    SER A 192     -23.217 -22.171  24.378  1.00 27.34           C
ATOM   1216  O    SER A 192     -22.081 -21.725  24.214  1.00 26.09           O
ATOM   1217  CB   SER A 192     -24.412 -23.868  25.803  1.00 28.35           C
ATOM   1218  OG   SER A 192     -25.732 -23.545  25.399  1.00 28.50           O
ATOM   1219  N    LEU A 193     -24.300 -21.400  24.360  1.00 26.48           N
ATOM   1220  CA   LEU A 193     -24.217 -19.978  24.052  1.00 25.37           C
```

FIGURE 4-19 (COORDINATES)

```
ATOM   1221  C    LEU A 193     -24.589 -19.030  25.184  1.00 24.99           C
ATOM   1222  O    LEU A 193     -25.459 -19.330  26.000  1.00 25.02           O
ATOM   1223  CB   LEU A 193     -25.103 -19.682  22.838  1.00 25.87           C
ATOM   1224  CG   LEU A 193     -25.038 -18.296  22.183  1.00 25.97           C
ATOM   1225  CD1  LEU A 193     -23.659 -18.097  21.567  1.00 24.48           C
ATOM   1226  CD2  LEU A 193     -26.124 -18.173  21.105  1.00 26.41           C
ATOM   1227  N    GLN A 194     -23.925 -17.876  25.210  1.00 23.94           N
ATOM   1228  CA   GLN A 194     -24.180 -16.846  26.210  1.00 23.50           C
ATOM   1229  C    GLN A 194     -24.094 -15.454  25.586  1.00 23.93           C
ATOM   1230  O    GLN A 194     -23.257 -15.195  24.721  1.00 24.05           O
ATOM   1231  CB   GLN A 194     -23.179 -16.953  27.365  1.00 22.83           C
ATOM   1232  CG   GLN A 194     -23.249 -15.808  28.376  1.00 22.39           C
ATOM   1233  CD   GLN A 194     -22.338 -16.031  29.583  1.00 22.54           C
ATOM   1234  OE1  GLN A 194     -22.792 -16.447  30.657  1.00 22.09           O
ATOM   1235  NE2  GLN A 194     -21.048 -15.768  29.407  1.00 20.28           N
ATOM   1236  N    LEU A 195     -24.972 -14.565  26.029  1.00 23.72           N
ATOM   1237  CA   LEU A 195     -24.995 -13.197  25.538  1.00 23.87           C
ATOM   1238  C    LEU A 195     -24.751 -12.256  26.701  1.00 24.72           C
ATOM   1239  O    LEU A 195     -25.289 -12.456  27.790  1.00 23.78           O
ATOM   1240  CB   LEU A 195     -26.351 -12.858  24.927  1.00 21.93           C
ATOM   1241  CG   LEU A 195     -26.873 -13.729  23.790  1.00 23.71           C
ATOM   1242  CD1  LEU A 195     -28.308 -13.317  23.467  1.00 24.01           C
ATOM   1243  CD2  LEU A 195     -25.975 -13.592  22.573  1.00 23.08           C
ATOM   1244  N    ILE A 196     -23.935 -11.232  26.472  1.00 25.19           N
ATOM   1245  CA   ILE A 196     -23.674 -10.251  27.512  1.00 24.50           C
ATOM   1246  C    ILE A 196     -23.888  -8.847  26.974  1.00 23.48           C
ATOM   1247  O    ILE A 196     -23.337  -8.469  25.945  1.00 23.80           O
ATOM   1248  CB   ILE A 196     -22.235 -10.341  28.058  1.00 24.82           C
ATOM   1249  CG1  ILE A 196     -21.989 -11.719  28.676  1.00 23.37           C
ATOM   1250  CG2  ILE A 196     -22.013  -9.237  29.115  1.00 24.35           C
ATOM   1251  CD1  ILE A 196     -20.577 -11.888  29.243  1.00 21.98           C
ATOM   1252  N    PHE A 197     -24.711  -8.085  27.674  1.00 23.26           N
ATOM   1253  CA   PHE A 197     -24.992  -6.706  27.299  1.00 23.56           C
ATOM   1254  C    PHE A 197     -24.374  -5.888  28.429  1.00 23.68           C
ATOM   1255  O    PHE A 197     -24.939  -5.814  29.517  1.00 24.74           O
ATOM   1256  CB   PHE A 197     -26.506  -6.467  27.234  1.00 21.95           C
ATOM   1257  CG   PHE A 197     -27.210  -7.274  26.171  1.00 21.09           C
ATOM   1258  CD1  PHE A 197     -27.395  -6.758  24.888  1.00 20.49           C
ATOM   1259  CD2  PHE A 197     -27.691  -8.552  26.451  1.00 21.58           C
ATOM   1260  CE1  PHE A 197     -28.047  -7.496  23.896  1.00 19.33           C
ATOM   1261  CE2  PHE A 197     -28.349  -9.308  25.461  1.00 21.78           C
ATOM   1262  CZ   PHE A 197     -28.526  -8.773  24.180  1.00 20.18           C
ATOM   1263  N    PHE A 198     -23.206  -5.300  28.185  1.00 23.40           N
ATOM   1264  CA   PHE A 198     -22.525  -4.518  29.221  1.00 23.79           C
ATOM   1265  C    PHE A 198     -23.137  -3.154  29.485  1.00 24.47           C
ATOM   1266  O    PHE A 198     -23.580  -2.467  28.568  1.00 25.98           O
ATOM   1267  CB   PHE A 198     -21.057  -4.285  28.856  1.00 22.65           C
ATOM   1268  CG   PHE A 198     -20.246  -5.534  28.755  1.00 21.81           C
ATOM   1269  CD1  PHE A 198     -19.905  -6.252  29.891  1.00 21.68           C
ATOM   1270  CD2  PHE A 198     -19.809  -5.990  27.518  1.00 22.23           C
ATOM   1271  CE1  PHE A 198     -19.133  -7.413  29.795  1.00 22.09           C
ATOM   1272  CE2  PHE A 198     -19.032  -7.156  27.415  1.00 22.24           C
ATOM   1273  CZ   PHE A 198     -18.697  -7.862  28.552  1.00 21.26           C
ATOM   1274  N    ASP A 199     -23.154  -2.758  30.750  1.00 25.00           N
ATOM   1275  CA   ASP A 199     -23.645  -1.438  31.099  1.00 24.84           C
ATOM   1276  C    ASP A 199     -22.385  -0.616  31.360  1.00 25.01           C
ATOM   1277  O    ASP A 199     -21.294  -1.175  31.539  1.00 24.67           O
ATOM   1278  CB   ASP A 199     -24.507  -1.477  32.363  1.00 24.71           C
ATOM   1279  CG   ASP A 199     -25.186  -0.140  32.643  1.00 25.25           C
ATOM   1280  OD1  ASP A 199     -25.131   0.748  31.767  1.00 23.50           O
ATOM   1281  OD2  ASP A 199     -25.780   0.023  33.730  1.00 24.62           O
ATOM   1282  N    GLY A 200     -22.530   0.703  31.349  1.00 24.72           N
ATOM   1283  CA   GLY A 200     -21.403   1.576  31.616  1.00 24.55           C
ATOM   1284  C    GLY A 200     -20.139   1.416  30.790  1.00 24.56           C
ATOM   1285  O    GLY A 200     -19.039   1.553  31.314  1.00 24.64           O
ATOM   1286  N    GLN A 201     -20.256   1.133  29.502  1.00 24.13           N
ATOM   1287  CA   GLN A 201     -19.038   1.022  28.733  1.00 24.13           C
ATOM   1288  C    GLN A 201     -18.422   2.415  28.573  1.00 23.73           C
```

FIGURE 4-20 (COORDINATES)

```
ATOM   1289  O    GLN A 201     -17.220   2.597  28.754  1.00 20.70           O
ATOM   1290  CB   GLN A 201     -19.307   0.440  27.353  1.00 24.52           C
ATOM   1291  CG   GLN A 201     -18.050   0.356  26.514  1.00 25.91           C
ATOM   1292  CD   GLN A 201     -18.195   1.056  25.179  1.00 29.01           C
ATOM   1293  OE1  GLN A 201     -18.592   2.224  25.115  1.00 29.58           O
ATOM   1294  NE2  GLN A 201     -17.867   0.347  24.102  1.00 26.96           N
ATOM   1295  N    GLU A 202     -19.271   3.389  28.250  1.00 23.79           N
ATOM   1296  CA   GLU A 202     -18.835   4.760  28.011  1.00 24.76           C
ATOM   1297  C    GLU A 202     -18.329   5.507  29.233  1.00 26.33           C
ATOM   1298  O    GLU A 202     -18.715   5.227  30.366  1.00 25.40           O
ATOM   1299  CB   GLU A 202     -19.972   5.570  27.384  1.00 24.78           C
ATOM   1300  CG   GLU A 202     -20.510   5.015  26.067  1.00 24.61           C
ATOM   1301  CD   GLU A 202     -19.608   5.284  24.872  1.00 24.91           C
ATOM   1302  OE1  GLU A 202     -18.469   5.764  25.050  1.00 24.43           O
ATOM   1303  OE2  GLU A 202     -20.047   5.005  23.739  1.00 26.23           O
ATOM   1304  N    ALA A 203     -17.451   6.469  28.990  1.00 27.44           N
ATOM   1305  CA   ALA A 203     -16.924   7.284  30.065  1.00 28.62           C
ATOM   1306  C    ALA A 203     -17.952   8.390  30.272  1.00 29.95           C
ATOM   1307  O    ALA A 203     -18.599   8.819  29.312  1.00 28.68           O
ATOM   1308  CB   ALA A 203     -15.587   7.876  29.659  1.00 27.81           C
ATOM   1309  N    PHE A 204     -18.123   8.838  31.514  1.00 32.12           N
ATOM   1310  CA   PHE A 204     -19.069   9.910  31.786  1.00 34.47           C
ATOM   1311  C    PHE A 204     -18.484  11.219  31.278  1.00 35.79           C
ATOM   1312  O    PHE A 204     -19.214  12.092  30.819  1.00 36.46           O
ATOM   1313  CB   PHE A 204     -19.389  10.002  33.280  1.00 35.84           C
ATOM   1314  CG   PHE A 204     -20.290   8.903  33.772  1.00 37.07           C
ATOM   1315  CD1  PHE A 204     -19.766   7.694  34.200  1.00 37.61           C
ATOM   1316  CD2  PHE A 204     -21.670   9.072  33.782  1.00 38.25           C
ATOM   1317  CE1  PHE A 204     -20.602   6.666  34.631  1.00 38.51           C
ATOM   1318  CE2  PHE A 204     -22.513   8.048  34.213  1.00 39.15           C
ATOM   1319  CZ   PHE A 204     -21.976   6.842  34.639  1.00 37.84           C
ATOM   1320  N    LEU A 205     -17.164  11.347  31.353  1.00 37.78           N
ATOM   1321  CA   LEU A 205     -16.477  12.537  30.852  1.00 41.16           C
ATOM   1322  C    LEU A 205     -15.811  12.133  29.540  1.00 43.25           C
ATOM   1323  O    LEU A 205     -16.485  11.905  28.532  1.00 44.07           O
ATOM   1324  CB   LEU A 205     -15.417  13.011  31.852  1.00 40.46           C
ATOM   1325  CG   LEU A 205     -15.959  13.524  33.188  1.00 39.91           C
ATOM   1326  CD1  LEU A 205     -14.808  13.980  34.068  1.00 38.88           C
ATOM   1327  CD2  LEU A 205     -16.934  14.676  32.932  1.00 39.47           C
ATOM   1328  N    HIS A 206     -14.487  12.052  29.555  1.00 45.74           N
ATOM   1329  CA   HIS A 206     -13.731  11.617  28.383  1.00 48.57           C
ATOM   1330  C    HIS A 206     -12.991  10.358  28.836  1.00 48.41           C
ATOM   1331  O    HIS A 206     -12.656  10.233  30.016  1.00 48.29           O
ATOM   1332  CB   HIS A 206     -12.752  12.708  27.927  1.00 50.65           C
ATOM   1333  CG   HIS A 206     -13.374  13.742  27.037  1.00 52.73           C
ATOM   1334  ND1  HIS A 206     -13.524  13.561  25.678  1.00 53.13           N
ATOM   1335  CD2  HIS A 206     -13.920  14.951  27.319  1.00 52.90           C
ATOM   1336  CE1  HIS A 206     -14.136  14.612  25.160  1.00 53.04           C
ATOM   1337  NE2  HIS A 206     -14.387  15.469  26.134  1.00 53.47           N
ATOM   1338  N    TRP A 207     -12.746   9.428  27.914  1.00 48.78           N
ATOM   1339  CA   TRP A 207     -12.088   8.180  28.282  1.00 49.28           C
ATOM   1340  C    TRP A 207     -10.988   8.344  29.313  1.00 49.23           C
ATOM   1341  O    TRP A 207     -10.170   9.267  29.246  1.00 49.02           O
ATOM   1342  CB   TRP A 207     -11.495   7.458  27.074  1.00 50.08           C
ATOM   1343  CG   TRP A 207     -10.784   6.195  27.504  1.00 51.30           C
ATOM   1344  CD1  TRP A 207     -11.355   4.983  27.767  1.00 51.29           C
ATOM   1345  CD2  TRP A 207      -9.392   6.062  27.845  1.00 51.87           C
ATOM   1346  NE1  TRP A 207     -10.413   4.106  28.255  1.00 51.93           N
ATOM   1347  CE2  TRP A 207      -9.200   4.742  28.313  1.00 52.04           C
ATOM   1348  CE3  TRP A 207      -8.291   6.934  27.804  1.00 52.00           C
ATOM   1349  CZ2  TRP A 207      -7.948   4.269  28.739  1.00 52.38           C
ATOM   1350  CZ3  TRP A 207      -7.046   6.464  28.227  1.00 52.02           C
ATOM   1351  CH2  TRP A 207      -6.888   5.142  28.688  1.00 51.93           C
ATOM   1352  N    SER A 208     -10.975   7.414  30.258  1.00 48.36           N
ATOM   1353  CA   SER A 208      -9.992   7.396  31.326  1.00 47.93           C
ATOM   1354  C    SER A 208     -10.000   5.995  31.909  1.00 47.46           C
ATOM   1355  O    SER A 208     -11.050   5.368  32.009  1.00 47.63           O
ATOM   1356  CB   SER A 208     -10.366   8.419  32.404  1.00 47.76           C
```

FIGURE 4-21 (COORDINATES)

```
ATOM   1357  OG   SER A 208      -9.976   7.973  33.691  1.00 47.66           O
ATOM   1358  N    PRO A 209      -8.826   5.478  32.288  1.00 47.21           N
ATOM   1359  CA   PRO A 209      -8.752   4.134  32.863  1.00 46.80           C
ATOM   1360  C    PRO A 209      -9.805   3.886  33.944  1.00 45.98           C
ATOM   1361  O    PRO A 209     -10.390   2.808  34.011  1.00 46.60           O
ATOM   1362  CB   PRO A 209      -7.329   4.083  33.410  1.00 46.65           C
ATOM   1363  CG   PRO A 209      -6.577   4.864  32.382  1.00 47.07           C
ATOM   1364  CD   PRO A 209      -7.481   6.069  32.158  1.00 47.36           C
ATOM   1365  N    GLN A 210     -10.050   4.889  34.781  1.00 45.26           N
ATOM   1366  CA   GLN A 210     -11.025   4.760  35.859  1.00 44.26           C
ATOM   1367  C    GLN A 210     -12.440   5.108  35.394  1.00 41.87           C
ATOM   1368  O    GLN A 210     -13.427   4.649  35.972  1.00 42.14           O
ATOM   1369  CB   GLN A 210     -10.643   5.671  37.034  1.00 46.60           C
ATOM   1370  CG   GLN A 210      -9.202   5.535  37.537  1.00 50.29           C
ATOM   1371  CD   GLN A 210      -8.163   6.003  36.517  1.00 53.33           C
ATOM   1372  OE1  GLN A 210      -8.312   7.063  35.894  1.00 53.38           O
ATOM   1373  NE2  GLN A 210      -7.097   5.217  36.353  1.00 54.56           N
ATOM   1374  N    ASP A 211     -12.535   5.916  34.344  1.00 38.85           N
ATOM   1375  CA   ASP A 211     -13.830   6.334  33.818  1.00 35.21           C
ATOM   1376  C    ASP A 211     -14.158   5.678  32.479  1.00 33.78           C
ATOM   1377  O    ASP A 211     -13.912   6.265  31.431  1.00 33.65           O
ATOM   1378  CB   ASP A 211     -13.847   7.854  33.649  1.00 34.32           C
ATOM   1379  CG   ASP A 211     -15.216   8.390  33.261  1.00 33.12           C
ATOM   1380  OD1  ASP A 211     -15.277   9.551  32.817  1.00 32.20           O
ATOM   1381  OD2  ASP A 211     -16.225   7.667  33.406  1.00 32.69           O
ATOM   1382  N    SER A 212     -14.710   4.467  32.527  1.00 32.18           N
ATOM   1383  CA   SER A 212     -15.112   3.704  31.338  1.00 30.05           C
ATOM   1384  C    SER A 212     -15.048   2.218  31.646  1.00 28.42           C
ATOM   1385  O    SER A 212     -14.454   1.814  32.641  1.00 29.21           O
ATOM   1386  CB   SER A 212     -14.205   3.999  30.130  1.00 29.83           C
ATOM   1387  OG   SER A 212     -12.919   3.429  30.290  1.00 29.78           O
ATOM   1388  N    LEU A 213     -15.669   1.409  30.797  1.00 27.20           N
ATOM   1389  CA   LEU A 213     -15.657  -0.038  30.970  1.00 26.67           C
ATOM   1390  C    LEU A 213     -16.072  -0.468  32.372  1.00 27.44           C
ATOM   1391  O    LEU A 213     -15.527  -1.424  32.915  1.00 28.37           O
ATOM   1392  CB   LEU A 213     -14.258  -0.579  30.678  1.00 24.53           C
ATOM   1393  CG   LEU A 213     -13.615  -0.058  29.386  1.00 25.24           C
ATOM   1394  CD1  LEU A 213     -12.293  -0.773  29.152  1.00 23.17           C
ATOM   1395  CD2  LEU A 213     -14.570  -0.278  28.205  1.00 22.23           C
ATOM   1396  N    TYR A 214     -17.040   0.227  32.953  1.00 27.42           N
ATOM   1397  CA   TYR A 214     -17.500  -0.100  34.298  1.00 27.10           C
ATOM   1398  C    TYR A 214     -18.063  -1.507  34.367  1.00 27.22           C
ATOM   1399  O    TYR A 214     -17.647  -2.315  35.202  1.00 26.23           O
ATOM   1400  CB   TYR A 214     -18.578   0.889  34.736  1.00 26.83           C
ATOM   1401  CG   TYR A 214     -18.075   2.297  34.952  1.00 27.90           C
ATOM   1402  CD1  TYR A 214     -17.478   2.668  36.161  1.00 26.72           C
ATOM   1403  CD2  TYR A 214     -18.207   3.265  33.955  1.00 27.84           C
ATOM   1404  CE1  TYR A 214     -17.031   3.966  36.374  1.00 28.09           C
ATOM   1405  CE2  TYR A 214     -17.759   4.574  34.158  1.00 28.86           C
ATOM   1406  CZ   TYR A 214     -17.173   4.918  35.370  1.00 29.16           C
ATOM   1407  OH   TYR A 214     -16.725   6.209  35.576  1.00 29.62           O
ATOM   1408  N    GLY A 215     -19.010  -1.790  33.476  1.00 27.21           N
ATOM   1409  CA   GLY A 215     -19.651  -3.092  33.449  1.00 26.93           C
ATOM   1410  C    GLY A 215     -18.741  -4.273  33.174  1.00 26.91           C
ATOM   1411  O    GLY A 215     -18.791  -5.274  33.885  1.00 27.71           O
ATOM   1412  N    SER A 216     -17.914  -4.169  32.140  1.00 26.67           N
ATOM   1413  CA   SER A 216     -17.006  -5.251  31.785  1.00 25.87           C
ATOM   1414  C    SER A 216     -15.885  -5.452  32.810  1.00 26.25           C
ATOM   1415  O    SER A 216     -15.516  -6.586  33.113  1.00 26.54           O
ATOM   1416  CB   SER A 216     -16.420  -5.001  30.392  1.00 25.11           C
ATOM   1417  OG   SER A 216     -15.896  -3.688  30.282  1.00 25.43           O
ATOM   1418  N    ARG A 217     -15.340  -4.366  33.346  1.00 26.26           N
ATOM   1419  CA   ARG A 217     -14.282  -4.507  34.335  1.00 27.75           C
ATOM   1420  C    ARG A 217     -14.848  -5.244  35.544  1.00 27.54           C
ATOM   1421  O    ARG A 217     -14.187  -6.095  36.137  1.00 28.10           O
ATOM   1422  CB   ARG A 217     -13.724  -3.135  34.757  1.00 28.40           C
ATOM   1423  CG   ARG A 217     -12.783  -2.507  33.726  1.00 30.83           C
ATOM   1424  CD   ARG A 217     -12.070  -1.253  34.239  1.00 31.92           C
```

FIGURE 4-22 (COORDINATES)

```
ATOM   1425  NE  ARG A 217     -12.963   -0.107   34.408  1.00 35.00           N
ATOM   1426  CZ  ARG A 217     -13.350    0.387   35.585  1.00 35.99           C
ATOM   1427  NH1 ARG A 217     -12.925   -0.163   36.713  1.00 37.01           N
ATOM   1428  NH2 ARG A 217     -14.150    1.446   35.637  1.00 34.91           N
ATOM   1429  N   HIS A 218     -16.086   -4.928   35.898  1.00 27.04           N
ATOM   1430  CA  HIS A 218     -16.713   -5.579   37.034  1.00 27.07           C
ATOM   1431  C   HIS A 218     -17.086   -7.039   36.764  1.00 27.11           C
ATOM   1432  O   HIS A 218     -16.826   -7.910   37.595  1.00 26.51           O
ATOM   1433  CB  HIS A 218     -17.964   -4.816   37.463  1.00 26.93           C
ATOM   1434  CG  HIS A 218     -18.801   -5.560   38.453  1.00 26.55           C
ATOM   1435  ND1 HIS A 218     -19.765   -6.468   38.075  1.00 27.73           N
ATOM   1436  CD2 HIS A 218     -18.776   -5.577   39.805  1.00 26.17           C
ATOM   1437  CE1 HIS A 218     -20.300   -7.012   39.153  1.00 26.68           C
ATOM   1438  NE2 HIS A 218     -19.717   -6.488   40.216  1.00 27.03           N
ATOM   1439  N   LEU A 219     -17.691   -7.307   35.611  1.00 25.98           N
ATOM   1440  CA  LEU A 219     -18.096   -8.671   35.293  1.00 25.96           C
ATOM   1441  C   LEU A 219     -16.911   -9.612   35.064  1.00 25.90           C
ATOM   1442  O   LEU A 219     -16.971  -10.789   35.420  1.00 26.46           O
ATOM   1443  CB  LEU A 219     -19.027   -8.683   34.075  1.00 24.73           C
ATOM   1444  CG  LEU A 219     -19.724  -10.025   33.788  1.00 24.69           C
ATOM   1445  CD1 LEU A 219     -20.411  -10.552   35.037  1.00 22.16           C
ATOM   1446  CD2 LEU A 219     -20.737   -9.840   32.680  1.00 23.32           C
ATOM   1447  N   ALA A 220     -15.837   -9.095   34.480  1.00 25.71           N
ATOM   1448  CA  ALA A 220     -14.654   -9.909   34.222  1.00 25.75           C
ATOM   1449  C   ALA A 220     -14.063  -10.368   35.556  1.00 25.95           C
ATOM   1450  O   ALA A 220     -13.803  -11.559   35.761  1.00 25.57           O
ATOM   1451  CB  ALA A 220     -13.623   -9.103   33.436  1.00 25.90           C
ATOM   1452  N   ALA A 221     -13.868   -9.415   36.461  1.00 24.45           N
ATOM   1453  CA  ALA A 221     -13.321   -9.708   37.775  1.00 24.84           C
ATOM   1454  C   ALA A 221     -14.212  -10.719   38.494  1.00 25.51           C
ATOM   1455  O   ALA A 221     -13.723  -11.642   39.151  1.00 26.67           O
ATOM   1456  CB  ALA A 221     -13.223   -8.424   38.591  1.00 22.96           C
ATOM   1457  N   LYS A 222     -15.522  -10.541   38.354  1.00 25.11           N
ATOM   1458  CA  LYS A 222     -16.497  -11.416   38.994  1.00 26.93           C
ATOM   1459  C   LYS A 222     -16.420  -12.842   38.433  1.00 27.50           C
ATOM   1460  O   LYS A 222     -16.329  -13.813   39.190  1.00 27.29           O
ATOM   1461  CB  LYS A 222     -17.905  -10.839   38.806  1.00 28.36           C
ATOM   1462  CG  LYS A 222     -18.985  -11.568   39.586  1.00 32.08           C
ATOM   1463  CD  LYS A 222     -20.372  -11.100   39.185  1.00 33.96           C
ATOM   1464  CE  LYS A 222     -21.449  -11.930   39.864  1.00 36.49           C
ATOM   1465  NZ  LYS A 222     -22.776  -11.745   39.196  1.00 39.78           N
ATOM   1466  N   MET A 223     -16.450  -12.966   37.108  1.00 27.02           N
ATOM   1467  CA  MET A 223     -16.363  -14.275   36.467  1.00 27.11           C
ATOM   1468  C   MET A 223     -15.013  -14.954   36.747  1.00 27.05           C
ATOM   1469  O   MET A 223     -14.936  -16.178   36.866  1.00 26.82           O
ATOM   1470  CB  MET A 223     -16.568  -14.140   34.954  1.00 27.16           C
ATOM   1471  CG  MET A 223     -17.975  -13.731   34.558  1.00 27.75           C
ATOM   1472  SD  MET A 223     -18.220  -13.660   32.772  1.00 29.57           S
ATOM   1473  CE  MET A 223     -18.579  -15.392   32.394  1.00 30.42           C
ATOM   1474  N   ALA A 224     -13.955  -14.155   36.848  1.00 26.53           N
ATOM   1475  CA  ALA A 224     -12.624  -14.682   37.114  1.00 26.60           C
ATOM   1476  C   ALA A 224     -12.538  -15.314   38.501  1.00 27.35           C
ATOM   1477  O   ALA A 224     -11.709  -16.191   38.740  1.00 27.01           O
ATOM   1478  CB  ALA A 224     -11.574  -13.568   36.979  1.00 24.85           C
ATOM   1479  N   SER A 225     -13.400  -14.877   39.413  1.00 28.14           N
ATOM   1480  CA  SER A 225     -13.381  -15.416   40.765  1.00 28.95           C
ATOM   1481  C   SER A 225     -14.612  -16.242   41.097  1.00 29.47           C
ATOM   1482  O   SER A 225     -14.921  -16.448   42.266  1.00 29.35           O
ATOM   1483  CB  SER A 225     -13.234  -14.287   41.784  1.00 29.18           C
ATOM   1484  OG  SER A 225     -14.265  -13.334   41.629  1.00 31.33           O
ATOM   1485  N   THR A 226     -15.317  -16.710   40.071  1.00 29.62           N
ATOM   1486  CA  THR A 226     -16.502  -17.538   40.278  1.00 29.23           C
ATOM   1487  C   THR A 226     -16.184  -18.930   39.752  1.00 29.53           C
ATOM   1488  O   THR A 226     -15.979  -19.112   38.551  1.00 29.13           O
ATOM   1489  CB  THR A 226     -17.733  -16.986   39.518  1.00 29.79           C
ATOM   1490  OG1 THR A 226     -18.159  -15.757   40.122  1.00 29.72           O
ATOM   1491  CG2 THR A 226     -18.879  -17.989   39.550  1.00 28.67           C
ATOM   1492  N   PRO A 227     -16.130  -19.934   40.646  1.00 29.52           N
```

FIGURE 4-23 (COORDINATES)

```
ATOM   1493  CA  PRO A 227     -15.827 -21.306  40.224  1.00 29.00           C
ATOM   1494  C   PRO A 227     -16.796 -21.813  39.160  1.00 28.91           C
ATOM   1495  O   PRO A 227     -18.004 -21.590  39.248  1.00 29.63           O
ATOM   1496  CB  PRO A 227     -15.934 -22.096  41.525  1.00 29.10           C
ATOM   1497  CG  PRO A 227     -15.532 -21.087  42.558  1.00 29.39           C
ATOM   1498  CD  PRO A 227     -16.281 -19.863  42.110  1.00 28.97           C
ATOM   1499  N   HIS A 228     -16.258 -22.495  38.156  1.00 28.45           N
ATOM   1500  CA  HIS A 228     -17.068 -23.044  37.080  1.00 28.11           C
ATOM   1501  C   HIS A 228     -16.389 -24.267  36.489  1.00 28.77           C
ATOM   1502  O   HIS A 228     -15.175 -24.264  36.258  1.00 29.02           O
ATOM   1503  CB  HIS A 228     -17.275 -22.018  35.968  1.00 27.85           C
ATOM   1504  CG  HIS A 228     -18.290 -22.438  34.953  1.00 27.93           C
ATOM   1505  ND1 HIS A 228     -19.643 -22.453  35.218  1.00 27.89           N
ATOM   1506  CD2 HIS A 228     -18.149 -22.904  33.689  1.00 27.79           C
ATOM   1507  CE1 HIS A 228     -20.291 -22.912  34.162  1.00 27.24           C
ATOM   1508  NE2 HIS A 228     -19.408 -23.194  33.221  1.00 27.49           N
ATOM   1509  N   PRO A 229     -17.159 -25.341  36.258  1.00 28.42           N
ATOM   1510  CA  PRO A 229     -18.596 -25.418  36.537  1.00 28.97           C
ATOM   1511  C   PRO A 229     -18.836 -25.491  38.048  1.00 29.24           C
ATOM   1512  O   PRO A 229     -17.894 -25.640  38.818  1.00 30.43           O
ATOM   1513  CB  PRO A 229     -19.007 -26.694  35.815  1.00 28.48           C
ATOM   1514  CG  PRO A 229     -17.804 -27.556  35.974  1.00 28.29           C
ATOM   1515  CD  PRO A 229     -16.674 -26.600  35.665  1.00 29.06           C
ATOM   1516  N   PRO A 230     -20.098 -25.381  38.490  1.00 29.52           N
ATOM   1517  CA  PRO A 230     -20.399 -25.443  39.926  1.00 29.29           C
ATOM   1518  C   PRO A 230     -19.662 -26.559  40.653  1.00 28.50           C
ATOM   1519  O   PRO A 230     -19.682 -27.704  40.218  1.00 29.97           O
ATOM   1520  CB  PRO A 230     -21.907 -25.641  39.945  1.00 28.98           C
ATOM   1521  CG  PRO A 230     -22.339 -24.794  38.790  1.00 29.58           C
ATOM   1522  CD  PRO A 230     -21.331 -25.178  37.709  1.00 30.02           C
ATOM   1523  N   GLY A 231     -19.006 -26.216  41.756  1.00 27.91           N
ATOM   1524  CA  GLY A 231     -18.283 -27.211  42.527  1.00 27.50           C
ATOM   1525  C   GLY A 231     -16.833 -27.387  42.121  1.00 27.86           C
ATOM   1526  O   GLY A 231     -16.078 -28.081  42.796  1.00 26.90           O
ATOM   1527  N   ALA A 232     -16.442 -26.764  41.015  1.00 28.36           N
ATOM   1528  CA  ALA A 232     -15.074 -26.868  40.529  1.00 29.95           C
ATOM   1529  C   ALA A 232     -14.098 -26.344  41.571  1.00 30.95           C
ATOM   1530  O   ALA A 232     -14.402 -25.407  42.300  1.00 32.05           O
ATOM   1531  CB  ALA A 232     -14.921 -26.091  39.229  1.00 29.35           C
ATOM   1532  N   ARG A 233     -12.920 -26.953  41.627  1.00 33.08           N
ATOM   1533  CA  ARG A 233     -11.888 -26.564  42.580  1.00 34.62           C
ATOM   1534  C   ARG A 233     -10.954 -25.456  42.094  1.00 33.61           C
ATOM   1535  O   ARG A 233     -10.632 -24.543  42.854  1.00 34.38           O
ATOM   1536  CB  ARG A 233     -11.050 -27.789  42.960  1.00 38.14           C
ATOM   1537  CG  ARG A 233     -11.807 -28.825  43.777  1.00 44.48           C
ATOM   1538  CD  ARG A 233     -11.085 -30.174  43.797  1.00 50.14           C
ATOM   1539  NE  ARG A 233     -10.964 -30.749  42.454  1.00 55.40           N
ATOM   1540  CZ  ARG A 233     -10.500 -31.971  42.193  1.00 57.47           C
ATOM   1541  NH1 ARG A 233     -10.109 -32.765  43.187  1.00 57.73           N
ATOM   1542  NH2 ARG A 233     -10.424 -32.400  40.935  1.00 58.10           N
ATOM   1543  N   GLY A 234     -10.520 -25.526  40.837  1.00 31.80           N
ATOM   1544  CA  GLY A 234      -9.592 -24.522  40.348  1.00 30.44           C
ATOM   1545  C   GLY A 234      -9.831 -23.877  38.991  1.00 29.95           C
ATOM   1546  O   GLY A 234      -8.900 -23.318  38.408  1.00 30.24           O
ATOM   1547  N   THR A 235     -11.057 -23.943  38.481  1.00 28.31           N
ATOM   1548  CA  THR A 235     -11.370 -23.326  37.199  1.00 27.76           C
ATOM   1549  C   THR A 235     -12.493 -22.299  37.348  1.00 27.73           C
ATOM   1550  O   THR A 235     -13.445 -22.511  38.091  1.00 27.49           O
ATOM   1551  CB  THR A 235     -11.765 -24.386  36.155  1.00 27.70           C
ATOM   1552  OG1 THR A 235     -12.776 -25.248  36.697  1.00 27.12           O
ATOM   1553  CG2 THR A 235     -10.543 -25.205  35.751  1.00 26.49           C
ATOM   1554  N   SER A 236     -12.379 -21.185  36.634  1.00 27.41           N
ATOM   1555  CA  SER A 236     -13.373 -20.119  36.717  1.00 27.89           C
ATOM   1556  C   SER A 236     -14.289 -20.069  35.505  1.00 28.29           C
ATOM   1557  O   SER A 236     -14.128 -20.836  34.550  1.00 28.37           O
ATOM   1558  CB  SER A 236     -12.677 -18.772  36.822  1.00 27.53           C
ATOM   1559  OG  SER A 236     -12.180 -18.392  35.546  1.00 27.23           O
ATOM   1560  N   GLN A 237     -15.252 -19.153  35.553  1.00 28.43           N
```

FIGURE 4-24 (COORDINATES)

```
ATOM   1561  CA  GLN A 237     -16.180 -18.960  34.448  1.00 29.47           C
ATOM   1562  C   GLN A 237     -15.376 -18.431  33.261  1.00 29.28           C
ATOM   1563  O   GLN A 237     -15.747 -18.631  32.111  1.00 29.28           O
ATOM   1564  CB  GLN A 237     -17.284 -17.969  34.839  1.00 30.75           C
ATOM   1565  CG  GLN A 237     -18.167 -18.469  35.973  1.00 33.14           C
ATOM   1566  CD  GLN A 237     -19.319 -17.530  36.295  1.00 35.48           C
ATOM   1567  OE1 GLN A 237     -19.126 -16.330  36.494  1.00 36.36           O
ATOM   1568  NE2 GLN A 237     -20.525 -18.081  36.364  1.00 35.35           N
ATOM   1569  N   LEU A 238     -14.264 -17.756  33.538  1.00 29.91           N
ATOM   1570  CA  LEU A 238     -13.434 -17.251  32.457  1.00 29.34           C
ATOM   1571  C   LEU A 238     -12.776 -18.426  31.740  1.00 30.25           C
ATOM   1572  O   LEU A 238     -12.598 -18.393  30.523  1.00 30.20           O
ATOM   1573  CB  LEU A 238     -12.394 -16.268  32.989  1.00 29.71           C
ATOM   1574  CG  LEU A 238     -12.993 -14.910  33.373  1.00 30.51           C
ATOM   1575  CD1 LEU A 238     -11.891 -13.881  33.528  1.00 30.99           C
ATOM   1576  CD2 LEU A 238     -13.964 -14.453  32.285  1.00 31.80           C
ATOM   1577  N   HIS A 239     -12.423 -19.473  32.485  1.00 30.94           N
ATOM   1578  CA  HIS A 239     -11.837 -20.656  31.857  1.00 31.62           C
ATOM   1579  C   HIS A 239     -12.904 -21.188  30.901  1.00 30.84           C
ATOM   1580  O   HIS A 239     -12.600 -21.789  29.876  1.00 30.10           O
ATOM   1581  CB  HIS A 239     -11.532 -21.738  32.896  1.00 33.58           C
ATOM   1582  CG  HIS A 239     -10.349 -21.444  33.769  1.00 36.24           C
ATOM   1583  ND1 HIS A 239      -9.131 -22.074  33.609  1.00 37.30           N
ATOM   1584  CD2 HIS A 239     -10.209 -20.620  34.835  1.00 36.24           C
ATOM   1585  CE1 HIS A 239      -8.296 -21.652  34.542  1.00 38.24           C
ATOM   1586  NE2 HIS A 239      -8.925 -20.769  35.299  1.00 37.31           N
ATOM   1587  N   GLY A 240     -14.163 -20.949  31.255  1.00 30.45           N
ATOM   1588  CA  GLY A 240     -15.271 -21.412  30.440  1.00 30.63           C
ATOM   1589  C   GLY A 240     -15.533 -20.613  29.179  1.00 30.65           C
ATOM   1590  O   GLY A 240     -16.214 -21.097  28.275  1.00 30.70           O
ATOM   1591  N   MET A 241     -15.010 -19.391  29.110  1.00 31.27           N
ATOM   1592  CA  MET A 241     -15.208 -18.553  27.930  1.00 31.28           C
ATOM   1593  C   MET A 241     -14.356 -19.007  26.761  1.00 30.23           C
ATOM   1594  O   MET A 241     -13.188 -18.653  26.659  1.00 30.72           O
ATOM   1595  CB  MET A 241     -14.879 -17.092  28.227  1.00 33.94           C
ATOM   1596  CG  MET A 241     -15.916 -16.371  29.053  1.00 38.23           C
ATOM   1597  SD  MET A 241     -15.739 -14.582  28.892  1.00 41.31           S
ATOM   1598  CE  MET A 241     -16.036 -14.399  27.180  1.00 41.11           C
ATOM   1599  N   ASP A 242     -14.955 -19.792  25.878  1.00 29.55           N
ATOM   1600  CA  ASP A 242     -14.275 -20.296  24.697  1.00 28.87           C
ATOM   1601  C   ASP A 242     -13.712 -19.153  23.870  1.00 28.98           C
ATOM   1602  O   ASP A 242     -12.542 -19.147  23.486  1.00 28.24           O
ATOM   1603  CB  ASP A 242     -15.266 -21.078  23.835  1.00 29.07           C
ATOM   1604  CG  ASP A 242     -14.984 -22.557  23.824  1.00 29.08           C
ATOM   1605  OD1 ASP A 242     -14.747 -23.123  24.912  1.00 27.63           O
ATOM   1606  OD2 ASP A 242     -15.012 -23.151  22.725  1.00 29.96           O
ATOM   1607  N   LEU A 243     -14.575 -18.182  23.602  1.00 28.30           N
ATOM   1608  CA  LEU A 243     -14.218 -17.042  22.789  1.00 27.06           C
ATOM   1609  C   LEU A 243     -15.220 -15.937  23.052  1.00 26.87           C
ATOM   1610  O   LEU A 243     -16.422 -16.193  23.162  1.00 26.80           O
ATOM   1611  CB  LEU A 243     -14.281 -17.440  21.312  1.00 26.41           C
ATOM   1612  CG  LEU A 243     -14.029 -16.374  20.244  1.00 26.63           C
ATOM   1613  CD1 LEU A 243     -12.541 -15.980  20.240  1.00 24.39           C
ATOM   1614  CD2 LEU A 243     -14.457 -16.932  18.875  1.00 25.12           C
ATOM   1615  N   LEU A 244     -14.722 -14.711  23.157  1.00 25.97           N
ATOM   1616  CA  LEU A 244     -15.584 -13.560  23.378  1.00 24.72           C
ATOM   1617  C   LEU A 244     -15.685 -12.788  22.070  1.00 23.36           C
ATOM   1618  O   LEU A 244     -14.706 -12.217  21.601  1.00 22.57           O
ATOM   1619  CB  LEU A 244     -15.008 -12.658  24.468  1.00 24.97           C
ATOM   1620  CG  LEU A 244     -15.770 -11.355  24.718  1.00 25.65           C
ATOM   1621  CD1 LEU A 244     -17.213 -11.657  25.119  1.00 24.51           C
ATOM   1622  CD2 LEU A 244     -15.064 -10.563  25.805  1.00 24.72           C
ATOM   1623  N   VAL A 245     -16.869 -12.802  21.471  1.00 23.78           N
ATOM   1624  CA  VAL A 245     -17.108 -12.085  20.224  1.00 24.17           C
ATOM   1625  C   VAL A 245     -17.795 -10.775  20.614  1.00 24.66           C
ATOM   1626  O   VAL A 245     -18.975 -10.760  20.976  1.00 25.08           O
ATOM   1627  CB  VAL A 245     -18.004 -12.921  19.277  1.00 23.96           C
ATOM   1628  CG1 VAL A 245     -18.184 -12.209  17.940  1.00 23.01           C
```

FIGURE 4-25 (COORDINATES)

```
ATOM   1629  CG2 VAL A 245     -17.373  -14.292  19.056  1.00 23.44           C
ATOM   1630  N   LEU A 246     -17.037   -9.683  20.562  1.00 25.00           N
ATOM   1631  CA  LEU A 246     -17.542   -8.365  20.937  1.00 24.98           C
ATOM   1632  C   LEU A 246     -17.874   -7.492  19.738  1.00 25.58           C
ATOM   1633  O   LEU A 246     -17.008   -7.187  18.922  1.00 25.53           O
ATOM   1634  CB  LEU A 246     -16.515   -7.636  21.799  1.00 24.14           C
ATOM   1635  CG  LEU A 246     -16.987   -6.323  22.430  1.00 25.30           C
ATOM   1636  CD1 LEU A 246     -17.996   -6.634  23.544  1.00 25.06           C
ATOM   1637  CD2 LEU A 246     -15.793   -5.557  22.992  1.00 23.39           C
ATOM   1638  N   LEU A 247     -19.136   -7.092  19.642  1.00 25.63           N
ATOM   1639  CA  LEU A 247     -19.590   -6.232  18.557  1.00 25.49           C
ATOM   1640  C   LEU A 247     -19.644   -4.788  19.060  1.00 25.41           C
ATOM   1641  O   LEU A 247     -20.154   -4.523  20.155  1.00 24.39           O
ATOM   1642  CB  LEU A 247     -20.988   -6.651  18.097  1.00 25.92           C
ATOM   1643  CG  LEU A 247     -21.142   -7.915  17.249  1.00 28.03           C
ATOM   1644  CD1 LEU A 247     -20.454   -9.087  17.906  1.00 27.98           C
ATOM   1645  CD2 LEU A 247     -22.628   -8.203  17.062  1.00 30.12           C
ATOM   1646  N   ASP A 248     -19.119   -3.857  18.270  1.00 24.78           N
ATOM   1647  CA  ASP A 248     -19.142   -2.447  18.656  1.00 25.18           C
ATOM   1648  C   ASP A 248     -19.028   -1.562  17.417  1.00 24.85           C
ATOM   1649  O   ASP A 248     -18.367   -1.922  16.444  1.00 25.56           O
ATOM   1650  CB  ASP A 248     -17.998   -2.153  19.639  1.00 24.20           C
ATOM   1651  CG  ASP A 248     -18.200   -0.853  20.415  1.00 24.99           C
ATOM   1652  OD1 ASP A 248     -19.259   -0.209  20.270  1.00 23.88           O
ATOM   1653  OD2 ASP A 248     -17.295   -0.475  21.186  1.00 24.42           O
ATOM   1654  N   LEU A 249     -19.700   -0.416  17.449  1.00 25.52           N
ATOM   1655  CA  LEU A 249     -19.669    0.542  16.344  1.00 26.11           C
ATOM   1656  C   LEU A 249     -20.024   -0.087  14.997  1.00 26.32           C
ATOM   1657  O   LEU A 249     -19.318    0.093  14.006  1.00 27.35           O
ATOM   1658  CB  LEU A 249     -18.283    1.199  16.257  1.00 25.71           C
ATOM   1659  CG  LEU A 249     -17.704    1.709  17.584  1.00 26.51           C
ATOM   1660  CD1 LEU A 249     -16.400    2.465  17.326  1.00 26.49           C
ATOM   1661  CD2 LEU A 249     -18.718    2.610  18.280  1.00 25.39           C
ATOM   1662  N   ILE A 250     -21.125   -0.823  14.967  1.00 25.45           N
ATOM   1663  CA  ILE A 250     -21.570   -1.470  13.747  1.00 25.46           C
ATOM   1664  C   ILE A 250     -22.870   -0.822  13.255  1.00 24.73           C
ATOM   1665  O   ILE A 250     -23.728   -0.442  14.050  1.00 23.85           O
ATOM   1666  CB  ILE A 250     -21.784   -2.979  13.994  1.00 25.28           C
ATOM   1667  CG1 ILE A 250     -20.443   -3.623  14.349  1.00 26.20           C
ATOM   1668  CG2 ILE A 250     -22.394   -3.641  12.765  1.00 24.85           C
ATOM   1669  CD1 ILE A 250     -20.529   -5.102  14.680  1.00 26.18           C
ATOM   1670  N   GLY A 251     -23.002   -0.687  11.941  1.00 23.96           N
ATOM   1671  CA  GLY A 251     -24.197   -0.079  11.388  1.00 24.12           C
ATOM   1672  C   GLY A 251     -23.907    1.014  10.377  1.00 24.23           C
ATOM   1673  O   GLY A 251     -24.811    1.485   9.696  1.00 25.24           O
ATOM   1674  N   ALA A 252     -22.650    1.432  10.280  1.00 24.92           N
ATOM   1675  CA  ALA A 252     -22.280    2.463   9.318  1.00 25.04           C
ATOM   1676  C   ALA A 252     -21.918    1.787   7.990  1.00 26.07           C
ATOM   1677  O   ALA A 252     -21.740    0.566   7.928  1.00 24.91           O
ATOM   1678  CB  ALA A 252     -21.098    3.279   9.840  1.00 24.57           C
ATOM   1679  N   PRO A 253     -21.816    2.573   6.908  1.00 26.61           N
ATOM   1680  CA  PRO A 253     -21.471    1.993   5.606  1.00 27.34           C
ATOM   1681  C   PRO A 253     -20.016    1.535   5.505  1.00 27.38           C
ATOM   1682  O   PRO A 253     -19.143    2.022   6.225  1.00 27.49           O
ATOM   1683  CB  PRO A 253     -21.770    3.130   4.624  1.00 26.32           C
ATOM   1684  CG  PRO A 253     -22.808    3.940   5.335  1.00 26.88           C
ATOM   1685  CD  PRO A 253     -22.285    3.959   6.749  1.00 26.19           C
ATOM   1686  N   ASN A 254     -19.783    0.588   4.602  1.00 27.93           N
ATOM   1687  CA  ASN A 254     -18.457    0.048   4.318  1.00 27.40           C
ATOM   1688  C   ASN A 254     -17.549   -0.213   5.504  1.00 26.54           C
ATOM   1689  O   ASN A 254     -16.442    0.314   5.566  1.00 25.94           O
ATOM   1690  CB  ASN A 254     -17.725    0.971   3.347  1.00 28.34           C
ATOM   1691  CG  ASN A 254     -18.600    1.415   2.197  1.00 29.83           C
ATOM   1692  OD1 ASN A 254     -19.165    0.594   1.473  1.00 32.28           O
ATOM   1693  ND2 ASN A 254     -18.719    2.723   2.021  1.00 30.77           N
ATOM   1694  N   PRO A 255     -17.996   -1.026   6.467  1.00 26.32           N
ATOM   1695  CA  PRO A 255     -17.097   -1.271   7.594  1.00 26.81           C
ATOM   1696  C   PRO A 255     -15.937   -2.184   7.168  1.00 26.92           C
```

FIGURE 4-26 (COORDINATES)

```
ATOM   1697  O    PRO A 255     -16.090   -3.027    6.288  1.00 26.57           O
ATOM   1698  CB   PRO A 255     -18.011   -1.943    8.612  1.00 26.24           C
ATOM   1699  CG   PRO A 255     -18.948   -2.716    7.731  1.00 25.22           C
ATOM   1700  CD   PRO A 255     -19.288   -1.700    6.672  1.00 25.54           C
ATOM   1701  N    THR A 256     -14.776   -1.990    7.779  1.00 26.60           N
ATOM   1702  CA   THR A 256     -13.617   -2.820    7.497  1.00 25.91           C
ATOM   1703  C    THR A 256     -13.116   -3.273    8.855  1.00 26.34           C
ATOM   1704  O    THR A 256     -12.606   -2.472    9.640  1.00 26.13           O
ATOM   1705  CB   THR A 256     -12.504   -2.042    6.752  1.00 26.05           C
ATOM   1706  OG1  THR A 256     -12.249   -0.803    7.422  1.00 28.07           O
ATOM   1707  CG2  THR A 256     -12.919   -1.752    5.323  1.00 25.85           C
ATOM   1708  N    PHE A 257     -13.299   -4.560    9.130  1.00 26.46           N
ATOM   1709  CA   PHE A 257     -12.893   -5.168   10.386  1.00 26.70           C
ATOM   1710  C    PHE A 257     -11.517   -5.813   10.279  1.00 27.42           C
ATOM   1711  O    PHE A 257     -11.303   -6.708    9.461  1.00 27.94           O
ATOM   1712  CB   PHE A 257     -13.878   -6.266   10.794  1.00 26.30           C
ATOM   1713  CG   PHE A 257     -15.277   -5.786   11.038  1.00 25.71           C
ATOM   1714  CD1  PHE A 257     -15.649   -5.293   12.286  1.00 25.22           C
ATOM   1715  CD2  PHE A 257     -16.234   -5.866   10.032  1.00 25.14           C
ATOM   1716  CE1  PHE A 257     -16.954   -4.890   12.530  1.00 25.39           C
ATOM   1717  CE2  PHE A 257     -17.547   -5.465   10.263  1.00 25.60           C
ATOM   1718  CZ   PHE A 257     -17.910   -4.977   11.513  1.00 25.79           C
ATOM   1719  N    PRO A 258     -10.560   -5.355   11.093  1.00 27.79           N
ATOM   1720  CA   PRO A 258      -9.229   -5.957   11.036  1.00 28.33           C
ATOM   1721  C    PRO A 258      -9.123   -7.116   12.036  1.00 28.84           C
ATOM   1722  O    PRO A 258      -9.909   -7.221   12.978  1.00 28.16           O
ATOM   1723  CB   PRO A 258      -8.316   -4.795   11.415  1.00 28.46           C
ATOM   1724  CG   PRO A 258      -9.143   -4.060   12.434  1.00 28.05           C
ATOM   1725  CD   PRO A 258     -10.518   -4.048   11.782  1.00 27.70           C
ATOM   1726  N    ASN A 259      -8.145   -7.982   11.813  1.00 30.43           N
ATOM   1727  CA   ASN A 259      -7.881   -9.117   12.686  1.00 31.10           C
ATOM   1728  C    ASN A 259      -6.989   -8.536   13.786  1.00 30.56           C
ATOM   1729  O    ASN A 259      -5.961   -7.942   13.494  1.00 32.46           O
ATOM   1730  CB   ASN A 259      -7.145  -10.189   11.885  1.00 33.10           C
ATOM   1731  CG   ASN A 259      -6.981  -11.482   12.642  1.00 35.66           C
ATOM   1732  OD1  ASN A 259      -6.577  -12.490   12.069  1.00 40.12           O
ATOM   1733  ND2  ASN A 259      -7.292  -11.468   13.925  1.00 35.49           N
ATOM   1734  N    PHE A 260      -7.381   -8.680   15.044  1.00 29.40           N
ATOM   1735  CA   PHE A 260      -6.590   -8.107   16.122  1.00 28.79           C
ATOM   1736  C    PHE A 260      -5.673   -9.059   16.861  1.00 28.94           C
ATOM   1737  O    PHE A 260      -4.584   -8.674   17.274  1.00 28.89           O
ATOM   1738  CB   PHE A 260      -7.489   -7.451   17.177  1.00 27.59           C
ATOM   1739  CG   PHE A 260      -8.250   -6.251   16.687  1.00 27.74           C
ATOM   1740  CD1  PHE A 260      -9.504   -6.396   16.106  1.00 27.01           C
ATOM   1741  CD2  PHE A 260      -7.726   -4.970   16.842  1.00 27.52           C
ATOM   1742  CE1  PHE A 260     -10.230   -5.284   15.692  1.00 28.32           C
ATOM   1743  CE2  PHE A 260      -8.442   -3.848   16.430  1.00 27.31           C
ATOM   1744  CZ   PHE A 260      -9.697   -4.003   15.854  1.00 28.09           C
ATOM   1745  N    PHE A 261      -6.103  -10.298   17.039  1.00 28.07           N
ATOM   1746  CA   PHE A 261      -5.298  -11.217   17.821  1.00 28.45           C
ATOM   1747  C    PHE A 261      -4.947  -12.521   17.153  1.00 28.56           C
ATOM   1748  O    PHE A 261      -5.772  -13.124   16.463  1.00 28.32           O
ATOM   1749  CB   PHE A 261      -6.009  -11.499   19.147  1.00 27.72           C
ATOM   1750  CG   PHE A 261      -6.500  -10.262   19.834  1.00 27.46           C
ATOM   1751  CD1  PHE A 261      -5.603   -9.365   20.405  1.00 27.29           C
ATOM   1752  CD2  PHE A 261      -7.858   -9.960   19.860  1.00 26.90           C
ATOM   1753  CE1  PHE A 261      -6.049   -8.179   20.989  1.00 26.85           C
ATOM   1754  CE2  PHE A 261      -8.316   -8.778   20.440  1.00 26.47           C
ATOM   1755  CZ   PHE A 261      -7.410   -7.884   21.005  1.00 26.92           C
ATOM   1756  N    PRO A 262      -3.701  -12.976   17.355  1.00 28.99           N
ATOM   1757  CA   PRO A 262      -3.220  -14.223   16.776  1.00 28.04           C
ATOM   1758  C    PRO A 262      -3.919  -15.445   17.356  1.00 27.92           C
ATOM   1759  O    PRO A 262      -4.070  -16.445   16.666  1.00 28.75           O
ATOM   1760  CB   PRO A 262      -1.723  -14.187   17.080  1.00 28.53           C
ATOM   1761  CG   PRO A 262      -1.649  -13.402   18.342  1.00 28.76           C
ATOM   1762  CD   PRO A 262      -2.615  -12.283   18.072  1.00 29.52           C
ATOM   1763  N    ASN A 263      -4.367  -15.374   18.607  1.00 27.89           N
ATOM   1764  CA   ASN A 263      -5.035  -16.538   19.190  1.00 29.22           C
```

FIGURE 4-27 (COORDINATES)

```
ATOM   1765  C    ASN A 263      -6.509 -16.706  18.788  1.00 29.30           C
ATOM   1766  O    ASN A 263      -7.187 -17.605  19.274  1.00 31.34           O
ATOM   1767  CB   ASN A 263      -4.880 -16.555  20.724  1.00 29.70           C
ATOM   1768  CG   ASN A 263      -5.808 -15.588  21.433  1.00 30.06           C
ATOM   1769  OD1  ASN A 263      -6.492 -14.782  20.809  1.00 30.78           O
ATOM   1770  ND2  ASN A 263      -5.830 -15.667  22.757  1.00 30.91           N
ATOM   1771  N    SER A 264      -7.000 -15.856  17.892  1.00 28.91           N
ATOM   1772  CA   SER A 264      -8.380 -15.962  17.423  1.00 27.85           C
ATOM   1773  C    SER A 264      -8.431 -15.691  15.924  1.00 27.36           C
ATOM   1774  O    SER A 264      -9.507 -15.607  15.322  1.00 27.58           O
ATOM   1775  CB   SER A 264      -9.290 -14.984  18.168  1.00 27.87           C
ATOM   1776  OG   SER A 264      -8.925 -13.648  17.909  1.00 28.39           O
ATOM   1777  N    ALA A 265      -7.250 -15.572  15.327  1.00 27.36           N
ATOM   1778  CA   ALA A 265      -7.127 -15.314  13.896  1.00 27.53           C
ATOM   1779  C    ALA A 265      -7.798 -16.395  13.048  1.00 27.46           C
ATOM   1780  O    ALA A 265      -8.420 -16.083  12.033  1.00 28.03           O
ATOM   1781  CB   ALA A 265      -5.654 -15.183  13.516  1.00 26.46           C
ATOM   1782  N    ARG A 266      -7.682 -17.659  13.452  1.00 27.56           N
ATOM   1783  CA   ARG A 266      -8.311 -18.731  12.680  1.00 28.21           C
ATOM   1784  C    ARG A 266      -9.825 -18.526  12.650  1.00 27.83           C
ATOM   1785  O    ARG A 266     -10.501 -18.944  11.714  1.00 28.64           O
ATOM   1786  CB   ARG A 266      -7.964 -20.114  13.259  1.00 28.40           C
ATOM   1787  CG   ARG A 266      -8.618 -20.488  14.589  1.00 29.92           C
ATOM   1788  CD   ARG A 266      -7.865 -21.657  15.207  1.00 30.52           C
ATOM   1789  NE   ARG A 266      -8.450 -22.183  16.441  1.00 32.36           N
ATOM   1790  CZ   ARG A 266      -9.416 -23.104  16.490  1.00 33.49           C
ATOM   1791  NH1  ARG A 266      -9.924 -23.609  15.370  1.00 31.89           N
ATOM   1792  NH2  ARG A 266      -9.857 -23.543  17.662  1.00 32.43           N
ATOM   1793  N    TRP A 267     -10.356 -17.873  13.675  1.00 27.60           N
ATOM   1794  CA   TRP A 267     -11.783 -17.603  13.721  1.00 27.83           C
ATOM   1795  C    TRP A 267     -12.118 -16.388  12.862  1.00 28.15           C
ATOM   1796  O    TRP A 267     -13.211 -16.289  12.309  1.00 29.17           O
ATOM   1797  CB   TRP A 267     -12.235 -17.416  15.174  1.00 27.24           C
ATOM   1798  CG   TRP A 267     -12.253 -18.725  15.899  1.00 26.43           C
ATOM   1799  CD1  TRP A 267     -11.478 -19.092  16.965  1.00 26.44           C
ATOM   1800  CD2  TRP A 267     -13.021 -19.884  15.543  1.00 26.03           C
ATOM   1801  NE1  TRP A 267     -11.711 -20.409  17.288  1.00 26.66           N
ATOM   1802  CE2  TRP A 267     -12.653 -20.918  16.432  1.00 26.55           C
ATOM   1803  CE3  TRP A 267     -13.981 -20.149  14.556  1.00 25.65           C
ATOM   1804  CZ2  TRP A 267     -13.213 -22.200  16.362  1.00 26.56           C
ATOM   1805  CZ3  TRP A 267     -14.537 -21.422  14.486  1.00 25.75           C
ATOM   1806  CH2  TRP A 267     -14.150 -22.431  15.385  1.00 26.32           C
ATOM   1807  N    PHE A 268     -11.173 -15.463  12.743  1.00 28.39           N
ATOM   1808  CA   PHE A 268     -11.386 -14.291  11.909  1.00 28.39           C
ATOM   1809  C    PHE A 268     -11.463 -14.810  10.480  1.00 28.80           C
ATOM   1810  O    PHE A 268     -12.253 -14.325   9.673  1.00 28.68           O
ATOM   1811  CB   PHE A 268     -10.212 -13.309  12.020  1.00 27.01           C
ATOM   1812  CG   PHE A 268     -10.381 -12.066  11.178  1.00 26.87           C
ATOM   1813  CD1  PHE A 268     -11.077 -10.963  11.670  1.00 25.48           C
ATOM   1814  CD2  PHE A 268      -9.861 -12.006   9.882  1.00 25.54           C
ATOM   1815  CE1  PHE A 268     -11.252  -9.819  10.884  1.00 24.27           C
ATOM   1816  CE2  PHE A 268     -10.031 -10.868   9.090  1.00 24.28           C
ATOM   1817  CZ   PHE A 268     -10.728  -9.772   9.592  1.00 23.95           C
ATOM   1818  N    GLU A 269     -10.635 -15.806  10.176  1.00 29.30           N
ATOM   1819  CA   GLU A 269     -10.618 -16.383   8.840  1.00 30.41           C
ATOM   1820  C    GLU A 269     -11.934 -17.073   8.522  1.00 29.98           C
ATOM   1821  O    GLU A 269     -12.360 -17.099   7.362  1.00 30.16           O
ATOM   1822  CB   GLU A 269      -9.464 -17.370   8.690  1.00 32.29           C
ATOM   1823  CG   GLU A 269      -8.101 -16.711   8.694  1.00 37.02           C
ATOM   1824  CD   GLU A 269      -6.981 -17.701   8.449  1.00 39.64           C
ATOM   1825  OE1  GLU A 269      -6.926 -18.266   7.337  1.00 42.48           O
ATOM   1826  OE2  GLU A 269      -6.160 -17.920   9.367  1.00 42.86           O
ATOM   1827  N    ARG A 270     -12.573 -17.642   9.542  1.00 28.94           N
ATOM   1828  CA   ARG A 270     -13.845 -18.301   9.326  1.00 28.51           C
ATOM   1829  C    ARG A 270     -14.862 -17.256   8.888  1.00 28.96           C
ATOM   1830  O    ARG A 270     -15.647 -17.493   7.970  1.00 29.16           O
ATOM   1831  CB   ARG A 270     -14.313 -19.025  10.594  1.00 28.36           C
ATOM   1832  CG   ARG A 270     -13.651 -20.398  10.789  1.00 28.03           C
```

FIGURE 4-28 (COORDINATES)

```
ATOM   1833  CD  ARG A 270     -13.767 -21.243   9.513  1.00 26.38           C
ATOM   1834  NE  ARG A 270     -15.159 -21.429   9.120  1.00 25.80           N
ATOM   1835  CZ  ARG A 270     -15.561 -21.696   7.881  1.00 26.93           C
ATOM   1836  NH1 ARG A 270     -14.676 -21.814   6.900  1.00 26.20           N
ATOM   1837  NH2 ARG A 270     -16.857 -21.824   7.617  1.00 27.39           N
ATOM   1838  N   LEU A 271     -14.837 -16.090   9.530  1.00 28.79           N
ATOM   1839  CA  LEU A 271     -15.752 -15.022   9.158  1.00 28.33           C
ATOM   1840  C   LEU A 271     -15.500 -14.628   7.706  1.00 28.58           C
ATOM   1841  O   LEU A 271     -16.446 -14.343   6.971  1.00 28.92           O
ATOM   1842  CB  LEU A 271     -15.573 -13.800  10.069  1.00 27.91           C
ATOM   1843  CG  LEU A 271     -16.087 -13.921  11.509  1.00 27.91           C
ATOM   1844  CD1 LEU A 271     -15.655 -12.702  12.322  1.00 26.97           C
ATOM   1845  CD2 LEU A 271     -17.601 -14.051  11.498  1.00 26.26           C
ATOM   1846  N   GLN A 272     -14.233 -14.613   7.290  1.00 28.45           N
ATOM   1847  CA  GLN A 272     -13.903 -14.267   5.910  1.00 29.53           C
ATOM   1848  C   GLN A 272     -14.491 -15.315   4.985  1.00 29.64           C
ATOM   1849  O   GLN A 272     -15.132 -14.991   3.984  1.00 30.80           O
ATOM   1850  CB  GLN A 272     -12.392 -14.231   5.675  1.00 30.53           C
ATOM   1851  CG  GLN A 272     -11.621 -13.217   6.493  1.00 32.15           C
ATOM   1852  CD  GLN A 272     -10.231 -12.968   5.920  1.00 32.64           C
ATOM   1853  OE1 GLN A 272      -9.993 -11.963   5.250  1.00 32.67           O
ATOM   1854  NE2 GLN A 272      -9.314 -13.892   6.170  1.00 33.15           N
ATOM   1855  N   ALA A 273     -14.259 -16.577   5.325  1.00 29.06           N
ATOM   1856  CA  ALA A 273     -14.757 -17.688   4.527  1.00 28.73           C
ATOM   1857  C   ALA A 273     -16.276 -17.627   4.409  1.00 28.84           C
ATOM   1858  O   ALA A 273     -16.828 -17.829   3.330  1.00 29.99           O
ATOM   1859  CB  ALA A 273     -14.325 -19.017   5.152  1.00 26.84           C
ATOM   1860  N   ILE A 274     -16.948 -17.337   5.518  1.00 28.33           N
ATOM   1861  CA  ILE A 274     -18.400 -17.262   5.519  1.00 28.41           C
ATOM   1862  C   ILE A 274     -18.887 -16.120   4.645  1.00 29.28           C
ATOM   1863  O   ILE A 274     -19.823 -16.281   3.856  1.00 29.82           O
ATOM   1864  CB  ILE A 274     -18.952 -17.062   6.944  1.00 27.97           C
ATOM   1865  CG1 ILE A 274     -18.686 -18.314   7.781  1.00 28.71           C
ATOM   1866  CG2 ILE A 274     -20.449 -16.772   6.888  1.00 27.42           C
ATOM   1867  CD1 ILE A 274     -19.003 -18.156   9.251  1.00 28.40           C
ATOM   1868  N   GLU A 275     -18.264 -14.958   4.793  1.00 29.29           N
ATOM   1869  CA  GLU A 275     -18.661 -13.808   3.996  1.00 30.41           C
ATOM   1870  C   GLU A 275     -18.460 -14.111   2.512  1.00 30.85           C
ATOM   1871  O   GLU A 275     -19.292 -13.757   1.676  1.00 30.25           O
ATOM   1872  CB  GLU A 275     -17.847 -12.569   4.390  1.00 28.63           C
ATOM   1873  CG  GLU A 275     -17.943 -11.435   3.374  1.00 27.28           C
ATOM   1874  CD  GLU A 275     -17.154 -10.207   3.779  1.00 25.31           C
ATOM   1875  OE1 GLU A 275     -16.010 -10.352   4.242  1.00 25.14           O
ATOM   1876  OE2 GLU A 275     -17.675  -9.092   3.619  1.00 25.81           O
ATOM   1877  N   HIS A 276     -17.352 -14.770   2.195  1.00 31.79           N
ATOM   1878  CA  HIS A 276     -17.044 -15.110   0.817  1.00 34.12           C
ATOM   1879  C   HIS A 276     -18.082 -16.058   0.220  1.00 34.51           C
ATOM   1880  O   HIS A 276     -18.569 -15.841  -0.893  1.00 34.07           O
ATOM   1881  CB  HIS A 276     -15.660 -15.758   0.725  1.00 36.37           C
ATOM   1882  CG  HIS A 276     -15.241 -16.068  -0.677  1.00 39.58           C
ATOM   1883  ND1 HIS A 276     -14.753 -15.107  -1.538  1.00 40.86           N
ATOM   1884  CD2 HIS A 276     -15.290 -17.221  -1.388  1.00 40.19           C
ATOM   1885  CE1 HIS A 276     -14.522 -15.654  -2.719  1.00 40.86           C
ATOM   1886  NE2 HIS A 276     -14.840 -16.935  -2.655  1.00 40.85           N
ATOM   1887  N   GLU A 277     -18.423 -17.108   0.961  1.00 34.13           N
ATOM   1888  CA  GLU A 277     -19.389 -18.078   0.471  1.00 33.88           C
ATOM   1889  C   GLU A 277     -20.793 -17.496   0.376  1.00 32.91           C
ATOM   1890  O   GLU A 277     -21.499 -17.727  -0.601  1.00 32.90           O
ATOM   1891  CB  GLU A 277     -19.392 -19.319   1.360  1.00 35.74           C
ATOM   1892  CG  GLU A 277     -20.257 -20.435   0.818  1.00 38.50           C
ATOM   1893  CD  GLU A 277     -19.785 -20.926  -0.538  1.00 39.78           C
ATOM   1894  OE1 GLU A 277     -20.547 -21.671  -1.191  1.00 41.24           O
ATOM   1895  OE2 GLU A 277     -18.653 -20.575  -0.947  1.00 40.55           O
ATOM   1896  N   LEU A 278     -21.204 -16.743   1.388  1.00 32.19           N
ATOM   1897  CA  LEU A 278     -22.526 -16.129   1.358  1.00 32.30           C
ATOM   1898  C   LEU A 278     -22.618 -15.170   0.169  1.00 32.62           C
ATOM   1899  O   LEU A 278     -23.687 -14.979  -0.420  1.00 31.97           O
ATOM   1900  CB  LEU A 278     -22.796 -15.368   2.657  1.00 32.02           C
```

FIGURE 4-29 (COORDINATES)

```
ATOM   1901  CG  LEU A 278     -23.215 -16.181   3.888  1.00 32.17           C
ATOM   1902  CD1 LEU A 278     -23.442 -15.236   5.057  1.00 31.20           C
ATOM   1903  CD2 LEU A 278     -24.492 -16.967   3.591  1.00 30.71           C
ATOM   1904  N   HIS A 279     -21.482 -14.572  -0.178  1.00 32.64           N
ATOM   1905  CA  HIS A 279     -21.411 -13.641  -1.289  1.00 32.23           C
ATOM   1906  C   HIS A 279     -21.512 -14.373  -2.632  1.00 33.23           C
ATOM   1907  O   HIS A 279     -22.330 -14.003  -3.481  1.00 32.17           O
ATOM   1908  CB  HIS A 279     -20.109 -12.839  -1.218  1.00 31.93           C
ATOM   1909  CG  HIS A 279     -19.929 -11.891  -2.360  1.00 32.53           C
ATOM   1910  ND1 HIS A 279     -19.403 -12.280  -3.574  1.00 33.17           N
ATOM   1911  CD2 HIS A 279     -20.271 -10.590  -2.497  1.00 31.83           C
ATOM   1912  CE1 HIS A 279     -19.431 -11.257  -4.409  1.00 32.20           C
ATOM   1913  NE2 HIS A 279     -19.953 -10.220  -3.780  1.00 32.97           N
ATOM   1914  N   GLU A 280     -20.685 -15.403  -2.817  1.00 33.61           N
ATOM   1915  CA  GLU A 280     -20.692 -16.192  -4.051  1.00 35.55           C
ATOM   1916  C   GLU A 280     -22.061 -16.819  -4.336  1.00 35.94           C
ATOM   1917  O   GLU A 280     -22.444 -16.978  -5.491  1.00 37.62           O
ATOM   1918  CB  GLU A 280     -19.639 -17.303  -3.991  1.00 36.14           C
ATOM   1919  CG  GLU A 280     -18.206 -16.832  -4.110  1.00 37.77           C
ATOM   1920  CD  GLU A 280     -17.911 -16.201  -5.458  1.00 40.24           C
ATOM   1921  OE1 GLU A 280     -18.098 -16.875  -6.497  1.00 42.14           O
ATOM   1922  OE2 GLU A 280     -17.490 -15.027  -5.481  1.00 41.55           O
ATOM   1923  N   LEU A 281     -22.789 -17.184  -3.286  1.00 35.88           N
ATOM   1924  CA  LEU A 281     -24.111 -17.778  -3.443  1.00 34.66           C
ATOM   1925  C   LEU A 281     -25.148 -16.679  -3.669  1.00 34.84           C
ATOM   1926  O   LEU A 281     -26.349 -16.947  -3.756  1.00 34.11           O
ATOM   1927  CB  LEU A 281     -24.484 -18.582  -2.193  1.00 34.83           C
ATOM   1928  CG  LEU A 281     -23.616 -19.789  -1.823  1.00 34.25           C
ATOM   1929  CD1 LEU A 281     -24.090 -20.366  -0.502  1.00 33.91           C
ATOM   1930  CD2 LEU A 281     -23.688 -20.836  -2.918  1.00 33.94           C
ATOM   1931  N   GLY A 282     -24.672 -15.439  -3.758  1.00 34.56           N
ATOM   1932  CA  GLY A 282     -25.561 -14.311  -3.976  1.00 34.12           C
ATOM   1933  C   GLY A 282     -26.566 -14.101  -2.859  1.00 34.23           C
ATOM   1934  O   GLY A 282     -27.715 -13.740  -3.112  1.00 34.01           O
ATOM   1935  N   LEU A 283     -26.129 -14.310  -1.618  1.00 33.59           N
ATOM   1936  CA  LEU A 283     -27.006 -14.158  -0.464  1.00 32.31           C
ATOM   1937  C   LEU A 283     -26.801 -12.844   0.292  1.00 31.62           C
ATOM   1938  O   LEU A 283     -27.417 -12.622   1.333  1.00 31.64           O
ATOM   1939  CB  LEU A 283     -26.822 -15.352   0.486  1.00 31.52           C
ATOM   1940  CG  LEU A 283     -27.176 -16.730  -0.097  1.00 31.59           C
ATOM   1941  CD1 LEU A 283     -26.856 -17.836   0.912  1.00 30.82           C
ATOM   1942  CD2 LEU A 283     -28.663 -16.759  -0.467  1.00 30.78           C
ATOM   1943  N   LEU A 284     -25.940 -11.977  -0.229  1.00 30.52           N
ATOM   1944  CA  LEU A 284     -25.688 -10.685   0.411  1.00 30.55           C
ATOM   1945  C   LEU A 284     -26.228  -9.561  -0.469  1.00 30.60           C
ATOM   1946  O   LEU A 284     -26.289  -9.699  -1.687  1.00 31.67           O
ATOM   1947  CB  LEU A 284     -24.183 -10.489   0.661  1.00 28.96           C
ATOM   1948  CG  LEU A 284     -23.506 -11.558   1.530  1.00 27.94           C
ATOM   1949  CD1 LEU A 284     -22.050 -11.203   1.758  1.00 26.82           C
ATOM   1950  CD2 LEU A 284     -24.238 -11.683   2.857  1.00 27.61           C
ATOM   1951  N   LYS A 285     -26.622  -8.453   0.145  1.00 31.04           N
ATOM   1952  CA  LYS A 285     -27.167  -7.317  -0.595  1.00 31.85           C
ATOM   1953  C   LYS A 285     -26.116  -6.229  -0.843  1.00 31.74           C
ATOM   1954  O   LYS A 285     -25.380  -5.848   0.067  1.00 31.69           O
ATOM   1955  CB  LYS A 285     -28.345  -6.723   0.182  1.00 34.04           C
ATOM   1956  CG  LYS A 285     -29.071  -5.576  -0.515  1.00 36.12           C
ATOM   1957  CD  LYS A 285     -29.840  -6.064  -1.741  1.00 38.39           C
ATOM   1958  CE  LYS A 285     -30.771  -4.978  -2.277  1.00 39.01           C
ATOM   1959  NZ  LYS A 285     -31.538  -5.438  -3.468  1.00 39.62           N
ATOM   1960  N   ASP A 286     -26.063  -5.724  -2.072  1.00 31.37           N
ATOM   1961  CA  ASP A 286     -25.112  -4.679  -2.446  1.00 32.05           C
ATOM   1962  C   ASP A 286     -23.767  -4.917  -1.776  1.00 31.15           C
ATOM   1963  O   ASP A 286     -23.264  -4.067  -1.051  1.00 30.90           O
ATOM   1964  CB  ASP A 286     -25.649  -3.303  -2.041  1.00 34.36           C
ATOM   1965  CG  ASP A 286     -27.059  -3.058  -2.544  1.00 37.14           C
ATOM   1966  OD1 ASP A 286     -27.362  -3.457  -3.690  1.00 37.86           O
ATOM   1967  OD2 ASP A 286     -27.861  -2.460  -1.794  1.00 39.43           O
ATOM   1968  N   HIS A 287     -23.184  -6.078  -2.040  1.00 31.27           N
```

FIGURE 4-30 (COORDINATES)

```
ATOM   1969  CA  HIS A 287     -21.915  -6.456  -1.436  1.00 31.08           C
ATOM   1970  C   HIS A 287     -20.912  -6.869  -2.504  1.00 31.28           C
ATOM   1971  O   HIS A 287     -21.248  -7.599  -3.430  1.00 31.77           O
ATOM   1972  CB  HIS A 287     -22.176  -7.606  -0.452  1.00 29.62           C
ATOM   1973  CG  HIS A 287     -20.958  -8.100   0.267  1.00 30.19           C
ATOM   1974  ND1 HIS A 287     -20.010  -8.900  -0.333  1.00 28.11           N
ATOM   1975  CD2 HIS A 287     -20.556  -7.938   1.551  1.00 28.84           C
ATOM   1976  CE1 HIS A 287     -19.077  -9.212   0.549  1.00 28.33           C
ATOM   1977  NE2 HIS A 287     -19.385  -8.642   1.700  1.00 28.29           N
ATOM   1978  N   SER A 288     -19.681  -6.383  -2.383  1.00 32.22           N
ATOM   1979  CA  SER A 288     -18.634  -6.731  -3.336  1.00 32.16           C
ATOM   1980  C   SER A 288     -17.420  -7.223  -2.564  1.00 32.39           C
ATOM   1981  O   SER A 288     -17.180  -6.790  -1.441  1.00 32.19           O
ATOM   1982  CB  SER A 288     -18.250  -5.520  -4.198  1.00 32.28           C
ATOM   1983  OG  SER A 288     -17.473  -4.582  -3.476  1.00 31.72           O
ATOM   1984  N   LEU A 289     -16.665  -8.139  -3.159  1.00 32.67           N
ATOM   1985  CA  LEU A 289     -15.484  -8.675  -2.503  1.00 33.85           C
ATOM   1986  C   LEU A 289     -14.429  -7.597  -2.311  1.00 34.07           C
ATOM   1987  O   LEU A 289     -13.754  -7.561  -1.283  1.00 34.99           O
ATOM   1988  CB  LEU A 289     -14.913  -9.842  -3.310  1.00 34.52           C
ATOM   1989  CG  LEU A 289     -15.848 -11.057  -3.352  1.00 36.03           C
ATOM   1990  CD1 LEU A 289     -15.339 -12.087  -4.339  1.00 36.83           C
ATOM   1991  CD2 LEU A 289     -15.958 -11.654  -1.956  1.00 37.59           C
ATOM   1992  N   GLU A 290     -14.281  -6.718  -3.297  1.00 34.54           N
ATOM   1993  CA  GLU A 290     -13.306  -5.640  -3.182  1.00 34.17           C
ATOM   1994  C   GLU A 290     -13.607  -4.802  -1.947  1.00 33.13           C
ATOM   1995  O   GLU A 290     -12.695  -4.365  -1.250  1.00 32.26           O
ATOM   1996  CB  GLU A 290     -13.326  -4.760  -4.426  1.00 34.57           C
ATOM   1997  CG  GLU A 290     -12.545  -5.341  -5.579  1.00 37.40           C
ATOM   1998  CD  GLU A 290     -11.068  -5.499  -5.256  1.00 38.17           C
ATOM   1999  OE1 GLU A 290     -10.419  -4.492  -4.895  1.00 37.86           O
ATOM   2000  OE2 GLU A 290     -10.559  -6.632  -5.368  1.00 38.85           O
ATOM   2001  N   GLY A 291     -14.891  -4.593  -1.674  1.00 32.10           N
ATOM   2002  CA  GLY A 291     -15.273  -3.817  -0.512  1.00 31.90           C
ATOM   2003  C   GLY A 291     -15.850  -4.706   0.577  1.00 32.52           C
ATOM   2004  O   GLY A 291     -16.871  -4.376   1.181  1.00 32.68           O
ATOM   2005  N   ARG A 292     -15.205  -5.842   0.830  1.00 32.02           N
ATOM   2006  CA  ARG A 292     -15.691  -6.760   1.855  1.00 32.24           C
ATOM   2007  C   ARG A 292     -15.375  -6.237   3.258  1.00 31.13           C
ATOM   2008  O   ARG A 292     -14.472  -5.418   3.436  1.00 29.67           O
ATOM   2009  CB  ARG A 292     -15.085  -8.148   1.656  1.00 32.86           C
ATOM   2010  CG  ARG A 292     -13.581  -8.181   1.709  1.00 34.18           C
ATOM   2011  CD  ARG A 292     -13.106  -9.604   1.609  1.00 37.00           C
ATOM   2012  NE  ARG A 292     -11.657  -9.703   1.723  1.00 40.37           N
ATOM   2013  CZ  ARG A 292     -11.011 -10.833   1.987  1.00 42.53           C
ATOM   2014  NH1 ARG A 292     -11.695 -11.959   2.166  1.00 43.25           N
ATOM   2015  NH2 ARG A 292      -9.684 -10.840   2.076  1.00 42.46           N
ATOM   2016  N   TYR A 293     -16.123  -6.724   4.243  1.00 30.16           N
ATOM   2017  CA  TYR A 293     -15.967  -6.287   5.624  1.00 30.11           C
ATOM   2018  C   TYR A 293     -14.750  -6.848   6.339  1.00 31.59           C
ATOM   2019  O   TYR A 293     -14.077  -6.132   7.081  1.00 31.47           O
ATOM   2020  CB  TYR A 293     -17.224  -6.633   6.419  1.00 29.21           C
ATOM   2021  CG  TYR A 293     -18.515  -6.292   5.700  1.00 29.50           C
ATOM   2022  CD1 TYR A 293     -18.678  -5.065   5.048  1.00 27.89           C
ATOM   2023  CD2 TYR A 293     -19.574  -7.204   5.660  1.00 29.10           C
ATOM   2024  CE1 TYR A 293     -19.857  -4.760   4.375  1.00 27.66           C
ATOM   2025  CE2 TYR A 293     -20.760  -6.907   4.989  1.00 27.57           C
ATOM   2026  CZ  TYR A 293     -20.895  -5.689   4.347  1.00 28.22           C
ATOM   2027  OH  TYR A 293     -22.054  -5.415   3.658  1.00 27.65           O
ATOM   2028  N   PHE A 294     -14.465  -8.125   6.116  1.00 32.94           N
ATOM   2029  CA  PHE A 294     -13.333  -8.773   6.762  1.00 34.76           C
ATOM   2030  C   PHE A 294     -12.170  -8.894   5.799  1.00 37.76           C
ATOM   2031  O   PHE A 294     -12.069  -9.852   5.034  1.00 38.22           O
ATOM   2032  CB  PHE A 294     -13.771 -10.140   7.273  1.00 33.45           C
ATOM   2033  CG  PHE A 294     -14.917 -10.068   8.236  1.00 32.75           C
ATOM   2034  CD1 PHE A 294     -14.706  -9.689   9.559  1.00 31.56           C
ATOM   2035  CD2 PHE A 294     -16.222 -10.292   7.800  1.00 31.84           C
ATOM   2036  CE1 PHE A 294     -15.775  -9.527  10.434  1.00 32.00           C
```

FIGURE 4-31 (COORDINATES)

```
ATOM   2037  CE2 PHE A 294     -17.301 -10.133   8.666  1.00 31.67           C
ATOM   2038  CZ  PHE A 294     -17.080  -9.748   9.987  1.00 31.69           C
ATOM   2039  N   GLN A 295     -11.282  -7.910   5.852  1.00 41.77           N
ATOM   2040  CA  GLN A 295     -10.139  -7.877   4.961  1.00 45.40           C
ATOM   2041  C   GLN A 295      -8.895  -8.553   5.519  1.00 46.87           C
ATOM   2042  O   GLN A 295      -8.833  -8.894   6.694  1.00 46.58           O
ATOM   2043  CB  GLN A 295      -9.840  -6.428   4.579  1.00 47.57           C
ATOM   2044  CG  GLN A 295     -11.078  -5.678   4.121  1.00 50.22           C
ATOM   2045  CD  GLN A 295     -10.768  -4.606   3.099  1.00 52.88           C
ATOM   2046  OE1 GLN A 295      -9.995  -3.681   3.366  1.00 54.37           O
ATOM   2047  NE2 GLN A 295     -11.372  -4.723   1.915  1.00 53.13           N
ATOM   2048  N   ASN A 296      -7.908  -8.736   4.648  1.00 49.63           N
ATOM   2049  CA  ASN A 296      -6.650  -9.393   4.989  1.00 51.65           C
ATOM   2050  C   ASN A 296      -5.634  -8.542   5.734  1.00 52.84           C
ATOM   2051  O   ASN A 296      -4.517  -8.358   5.251  1.00 53.92           O
ATOM   2052  CB  ASN A 296      -5.980  -9.926   3.719  1.00 51.71           C
ATOM   2053  CG  ASN A 296      -6.696 -11.117   3.136  1.00 51.86           C
ATOM   2054  OD1 ASN A 296      -6.367 -11.579   2.041  1.00 52.44           O
ATOM   2055  ND2 ASN A 296      -7.676 -11.630   3.864  1.00 52.07           N
ATOM   2056  N   TYR A 297      -5.989  -8.019   6.899  1.00 53.52           N
ATOM   2057  CA  TYR A 297      -5.009  -7.230   7.627  1.00 54.33           C
ATOM   2058  C   TYR A 297      -5.273  -7.163   9.117  1.00 53.88           C
ATOM   2059  O   TYR A 297      -6.422  -7.079   9.563  1.00 53.43           O
ATOM   2060  CB  TYR A 297      -4.894  -5.809   7.044  1.00 55.67           C
ATOM   2061  CG  TYR A 297      -5.929  -4.811   7.524  1.00 56.43           C
ATOM   2062  CD1 TYR A 297      -7.245  -4.851   7.059  1.00 56.96           C
ATOM   2063  CD2 TYR A 297      -5.583  -3.817   8.439  1.00 56.49           C
ATOM   2064  CE1 TYR A 297      -8.192  -3.919   7.496  1.00 57.61           C
ATOM   2065  CE2 TYR A 297      -6.518  -2.885   8.883  1.00 56.97           C
ATOM   2066  CZ  TYR A 297      -7.819  -2.939   8.410  1.00 57.84           C
ATOM   2067  OH  TYR A 297      -8.742  -2.018   8.860  1.00 57.30           O
ATOM   2068  N   SER A 298      -4.190  -7.226   9.882  1.00 52.97           N
ATOM   2069  CA  SER A 298      -4.282  -7.162  11.325  1.00 52.98           C
ATOM   2070  C   SER A 298      -4.033  -5.722  11.742  1.00 52.02           C
ATOM   2071  O   SER A 298      -3.562  -4.903  10.953  1.00 52.06           O
ATOM   2072  CB  SER A 298      -3.252  -8.091  11.976  1.00 53.19           C
ATOM   2073  OG  SER A 298      -1.935  -7.682  11.660  1.00 54.87           O
ATOM   2074  N   TYR A 299      -4.362  -5.417  12.986  1.00 50.74           N
ATOM   2075  CA  TYR A 299      -4.193  -4.078  13.510  1.00 49.94           C
ATOM   2076  C   TYR A 299      -3.052  -4.130  14.514  1.00 50.59           C
ATOM   2077  O   TYR A 299      -3.019  -5.004  15.379  1.00 51.31           O
ATOM   2078  CB  TYR A 299      -5.508  -3.643  14.159  1.00 48.63           C
ATOM   2079  CG  TYR A 299      -5.530  -2.262  14.763  1.00 46.82           C
ATOM   2080  CD1 TYR A 299      -5.028  -2.033  16.042  1.00 46.39           C
ATOM   2081  CD2 TYR A 299      -6.091  -1.190  14.073  1.00 45.89           C
ATOM   2082  CE1 TYR A 299      -5.087  -0.775  16.622  1.00 45.69           C
ATOM   2083  CE2 TYR A 299      -6.153   0.074  14.642  1.00 45.42           C
ATOM   2084  CZ  TYR A 299      -5.649   0.273  15.917  1.00 44.80           C
ATOM   2085  OH  TYR A 299      -5.691   1.518  16.485  1.00 44.79           O
ATOM   2086  N   GLY A 300      -2.106  -3.207  14.379  1.00 50.91           N
ATOM   2087  CA  GLY A 300      -0.969  -3.176  15.279  1.00 51.22           C
ATOM   2088  C   GLY A 300      -1.345  -3.250  16.745  1.00 51.45           C
ATOM   2089  O   GLY A 300      -1.375  -4.332  17.329  1.00 52.53           O
ATOM   2090  N   GLY A 301      -1.648  -2.100  17.338  1.00 51.55           N
ATOM   2091  CA  GLY A 301      -2.001  -2.052  18.748  1.00 50.86           C
ATOM   2092  C   GLY A 301      -3.346  -2.632  19.157  1.00 49.73           C
ATOM   2093  O   GLY A 301      -3.765  -3.684  18.674  1.00 49.50           O
ATOM   2094  N   VAL A 302      -4.015  -1.945  20.077  1.00 48.43           N
ATOM   2095  CA  VAL A 302      -5.319  -2.378  20.566  1.00 46.81           C
ATOM   2096  C   VAL A 302      -6.245  -1.192  20.770  1.00 44.62           C
ATOM   2097  O   VAL A 302      -5.801  -0.067  21.017  1.00 43.88           O
ATOM   2098  CB  VAL A 302      -5.216  -3.122  21.918  1.00 47.96           C
ATOM   2099  CG1 VAL A 302      -4.799  -4.570  21.695  1.00 48.38           C
ATOM   2100  CG2 VAL A 302      -4.218  -2.399  22.823  1.00 47.84           C
ATOM   2101  N   ILE A 303      -7.539  -1.467  20.680  1.00 41.49           N
ATOM   2102  CA  ILE A 303      -8.555  -0.449  20.851  1.00 38.48           C
ATOM   2103  C   ILE A 303      -9.300  -0.703  22.158  1.00 37.16           C
ATOM   2104  O   ILE A 303      -9.805  -1.799  22.385  1.00 37.74           O
```

FIGURE 4-32 (COORDINATES)

```
ATOM   2105  CB  ILE A 303      -9.526  -0.482  19.661  1.00 37.64           C
ATOM   2106  CG1 ILE A 303      -8.734  -0.251  18.365  1.00 36.62           C
ATOM   2107  CG2 ILE A 303     -10.619   0.559  19.845  1.00 36.58           C
ATOM   2108  CD1 ILE A 303      -9.532  -0.404  17.090  1.00 35.52           C
ATOM   2109  N   GLN A 304      -9.351   0.304  23.024  1.00 34.81           N
ATOM   2110  CA  GLN A 304     -10.042   0.171  24.300  1.00 33.00           C
ATOM   2111  C   GLN A 304     -11.511  -0.170  24.109  1.00 30.25           C
ATOM   2112  O   GLN A 304     -12.233   0.531  23.413  1.00 30.14           O
ATOM   2113  CB  GLN A 304      -9.932   1.466  25.105  1.00 34.81           C
ATOM   2114  CG  GLN A 304      -8.573   1.701  25.721  1.00 37.92           C
ATOM   2115  CD  GLN A 304      -8.209   0.627  26.724  1.00 40.01           C
ATOM   2116  OE1 GLN A 304      -8.934   0.395  27.694  1.00 42.13           O
ATOM   2117  NE2 GLN A 304      -7.083  -0.036  26.498  1.00 39.94           N
ATOM   2118  N   ASP A 305     -11.946  -1.259  24.726  1.00 28.43           N
ATOM   2119  CA  ASP A 305     -13.340  -1.677  24.643  1.00 27.11           C
ATOM   2120  C   ASP A 305     -13.613  -2.665  25.772  1.00 26.59           C
ATOM   2121  O   ASP A 305     -12.712  -2.974  26.557  1.00 26.17           O
ATOM   2122  CB  ASP A 305     -13.636  -2.329  23.288  1.00 25.25           C
ATOM   2123  CG  ASP A 305     -15.061  -2.067  22.818  1.00 24.62           C
ATOM   2124  OD1 ASP A 305     -15.958  -2.004  23.681  1.00 23.31           O
ATOM   2125  OD2 ASP A 305     -15.291  -1.938  21.593  1.00 21.87           O
ATOM   2126  N   ASP A 306     -14.846  -3.161  25.842  1.00 25.66           N
ATOM   2127  CA  ASP A 306     -15.261  -4.105  26.879  1.00 25.65           C
ATOM   2128  C   ASP A 306     -14.508  -5.433  26.921  1.00 25.83           C
ATOM   2129  O   ASP A 306     -14.641  -6.187  27.883  1.00 25.80           O
ATOM   2130  CB  ASP A 306     -16.760  -4.402  26.752  1.00 25.34           C
ATOM   2131  CG  ASP A 306     -17.623  -3.231  27.163  1.00 25.98           C
ATOM   2132  OD1 ASP A 306     -17.379  -2.670  28.255  1.00 23.04           O
ATOM   2133  OD2 ASP A 306     -18.551  -2.878  26.399  1.00 27.35           O
ATOM   2134  N   HIS A 307     -13.731  -5.723  25.884  1.00 25.98           N
ATOM   2135  CA  HIS A 307     -12.977  -6.974  25.810  1.00 26.40           C
ATOM   2136  C   HIS A 307     -11.683  -6.914  26.623  1.00 26.72           C
ATOM   2137  O   HIS A 307     -11.157  -7.944  27.042  1.00 27.50           O
ATOM   2138  CB  HIS A 307     -12.632  -7.292  24.348  1.00 26.41           C
ATOM   2139  CG  HIS A 307     -11.639  -6.346  23.746  1.00 26.59           C
ATOM   2140  ND1 HIS A 307     -11.885  -4.997  23.609  1.00 26.03           N
ATOM   2141  CD2 HIS A 307     -10.374  -6.544  23.304  1.00 27.20           C
ATOM   2142  CE1 HIS A 307     -10.814  -4.404  23.114  1.00 26.09           C
ATOM   2143  NE2 HIS A 307      -9.882  -5.319  22.920  1.00 26.13           N
ATOM   2144  N   ILE A 308     -11.175  -5.705  26.838  1.00 26.64           N
ATOM   2145  CA  ILE A 308      -9.933  -5.509  27.580  1.00 26.85           C
ATOM   2146  C   ILE A 308      -9.868  -6.243  28.919  1.00 27.33           C
ATOM   2147  O   ILE A 308      -8.937  -7.017  29.161  1.00 26.93           O
ATOM   2148  CB  ILE A 308      -9.651  -3.995  27.815  1.00 26.26           C
ATOM   2149  CG1 ILE A 308      -9.377  -3.304  26.476  1.00 25.34           C
ATOM   2150  CG2 ILE A 308      -8.474  -3.814  28.764  1.00 25.43           C
ATOM   2151  CD1 ILE A 308      -8.209  -3.875  25.714  1.00 24.31           C
ATOM   2152  N   PRO A 309     -10.854  -6.019  29.803  1.00 27.62           N
ATOM   2153  CA  PRO A 309     -10.845  -6.694  31.109  1.00 28.09           C
ATOM   2154  C   PRO A 309     -10.799  -8.224  30.981  1.00 28.68           C
ATOM   2155  O   PRO A 309     -10.337  -8.905  31.890  1.00 30.40           O
ATOM   2156  CB  PRO A 309     -12.143  -6.216  31.762  1.00 26.56           C
ATOM   2157  CG  PRO A 309     -12.439  -4.927  31.063  1.00 27.92           C
ATOM   2158  CD  PRO A 309     -12.080  -5.222  29.640  1.00 27.90           C
ATOM   2159  N   PHE A 310     -11.288  -8.759  29.864  1.00 28.04           N
ATOM   2160  CA  PHE A 310     -11.280 -10.203  29.659  1.00 28.25           C
ATOM   2161  C   PHE A 310      -9.968 -10.646  29.030  1.00 29.66           C
ATOM   2162  O   PHE A 310      -9.327 -11.596  29.495  1.00 28.58           O
ATOM   2163  CB  PHE A 310     -12.451 -10.630  28.773  1.00 26.88           C
ATOM   2164  CG  PHE A 310     -13.790 -10.445  29.419  1.00 26.82           C
ATOM   2165  CD1 PHE A 310     -14.444  -9.217  29.358  1.00 26.64           C
ATOM   2166  CD2 PHE A 310     -14.370 -11.480  30.150  1.00 26.47           C
ATOM   2167  CE1 PHE A 310     -15.662  -9.015  30.023  1.00 27.28           C
ATOM   2168  CE2 PHE A 310     -15.586 -11.293  30.818  1.00 27.53           C
ATOM   2169  CZ  PHE A 310     -16.233 -10.052  30.755  1.00 26.53           C
ATOM   2170  N   LEU A 311      -9.578  -9.946  27.969  1.00 30.66           N
ATOM   2171  CA  LEU A 311      -8.337 -10.229  27.263  1.00 31.01           C
ATOM   2172  C   LEU A 311      -7.177 -10.257  28.262  1.00 32.47           C
```

FIGURE 4-33 (COORDINATES)

```
ATOM   2173  O   LEU A 311      -6.401 -11.212  28.291  1.00 33.57           O
ATOM   2174  CB  LEU A 311      -8.095  -9.149  26.205  1.00 30.03           C
ATOM   2175  CG  LEU A 311      -6.908  -9.275  25.249  1.00 30.67           C
ATOM   2176  CD1 LEU A 311      -7.180 -10.362  24.226  1.00 29.29           C
ATOM   2177  CD2 LEU A 311      -6.685  -7.943  24.545  1.00 30.69           C
ATOM   2178  N   ARG A 312      -7.071  -9.218  29.090  1.00 33.83           N
ATOM   2179  CA  ARG A 312      -5.995  -9.134  30.082  1.00 36.07           C
ATOM   2180  C   ARG A 312      -6.024 -10.260  31.114  1.00 35.50           C
ATOM   2181  O   ARG A 312      -5.116 -10.388  31.931  1.00 36.10           O
ATOM   2182  CB  ARG A 312      -6.024  -7.774  30.794  1.00 38.22           C
ATOM   2183  CG  ARG A 312      -5.813  -6.601  29.843  1.00 42.57           C
ATOM   2184  CD  ARG A 312      -5.023  -5.461  30.483  1.00 46.14           C
ATOM   2185  NE  ARG A 312      -4.841  -4.336  29.562  1.00 50.28           N
ATOM   2186  CZ  ARG A 312      -4.204  -4.400  28.389  1.00 52.43           C
ATOM   2187  NH1 ARG A 312      -3.669  -5.544  27.971  1.00 52.69           N
ATOM   2188  NH2 ARG A 312      -4.116  -3.317  27.619  1.00 52.94           N
ATOM   2189  N   ARG A 313      -7.074 -11.071  31.079  1.00 34.87           N
ATOM   2190  CA  ARG A 313      -7.193 -12.193  31.991  1.00 33.79           C
ATOM   2191  C   ARG A 313      -7.112 -13.518  31.230  1.00 33.69           C
ATOM   2192  O   ARG A 313      -7.502 -14.565  31.749  1.00 33.72           O
ATOM   2193  CB  ARG A 313      -8.505 -12.117  32.780  1.00 33.67           C
ATOM   2194  CG  ARG A 313      -8.521 -11.058  33.873  1.00 31.49           C
ATOM   2195  CD  ARG A 313      -9.729 -11.247  34.767  1.00 31.97           C
ATOM   2196  NE  ARG A 313      -9.739 -10.374  35.939  1.00 32.38           N
ATOM   2197  CZ  ARG A 313      -9.945  -9.058  35.911  1.00 33.93           C
ATOM   2198  NH1 ARG A 313     -10.164  -8.427  34.759  1.00 33.48           N
ATOM   2199  NH2 ARG A 313      -9.944  -8.372  37.047  1.00 33.13           N
ATOM   2200  N   GLY A 314      -6.628 -13.462  29.991  1.00 32.75           N
ATOM   2201  CA  GLY A 314      -6.466 -14.674  29.199  1.00 32.49           C
ATOM   2202  C   GLY A 314      -7.596 -15.175  28.314  1.00 32.54           C
ATOM   2203  O   GLY A 314      -7.466 -16.236  27.693  1.00 33.52           O
ATOM   2204  N   VAL A 315      -8.700 -14.441  28.237  1.00 30.79           N
ATOM   2205  CA  VAL A 315      -9.808 -14.881  27.410  1.00 28.90           C
ATOM   2206  C   VAL A 315      -9.561 -14.537  25.945  1.00 28.94           C
ATOM   2207  O   VAL A 315      -9.182 -13.408  25.625  1.00 29.33           O
ATOM   2208  CB  VAL A 315     -11.129 -14.215  27.830  1.00 28.70           C
ATOM   2209  CG1 VAL A 315     -12.259 -14.742  26.970  1.00 28.64           C
ATOM   2210  CG2 VAL A 315     -11.410 -14.480  29.299  1.00 28.55           C
ATOM   2211  N   PRO A 316      -9.752 -15.515  25.039  1.00 27.32           N
ATOM   2212  CA  PRO A 316      -9.561 -15.314  23.599  1.00 26.26           C
ATOM   2213  C   PRO A 316     -10.652 -14.366  23.110  1.00 25.80           C
ATOM   2214  O   PRO A 316     -11.836 -14.542  23.429  1.00 24.68           O
ATOM   2215  CB  PRO A 316      -9.732 -16.720  23.024  1.00 27.17           C
ATOM   2216  CG  PRO A 316      -9.279 -17.600  24.147  1.00 27.63           C
ATOM   2217  CD  PRO A 316      -9.943 -16.942  25.337  1.00 27.16           C
ATOM   2218  N   VAL A 317     -10.264 -13.378  22.318  1.00 24.05           N
ATOM   2219  CA  VAL A 317     -11.232 -12.408  21.848  1.00 23.64           C
ATOM   2220  C   VAL A 317     -11.277 -12.221  20.351  1.00 23.96           C
ATOM   2221  O   VAL A 317     -10.246 -12.203  19.684  1.00 24.73           O
ATOM   2222  CB  VAL A 317     -10.966 -11.005  22.474  1.00 23.02           C
ATOM   2223  CG1 VAL A 317     -12.046 -10.029  22.042  1.00 21.63           C
ATOM   2224  CG2 VAL A 317     -10.905 -11.102  23.987  1.00 20.96           C
ATOM   2225  N   LEU A 318     -12.491 -12.082  19.836  1.00 24.05           N
ATOM   2226  CA  LEU A 318     -12.711 -11.804  18.429  1.00 24.79           C
ATOM   2227  C   LEU A 318     -13.423 -10.442  18.503  1.00 25.62           C
ATOM   2228  O   LEU A 318     -14.634 -10.370  18.724  1.00 25.40           O
ATOM   2229  CB  LEU A 318     -13.604 -12.873  17.807  1.00 25.23           C
ATOM   2230  CG  LEU A 318     -13.769 -12.797  16.288  1.00 25.73           C
ATOM   2231  CD1 LEU A 318     -12.409 -12.733  15.607  1.00 24.36           C
ATOM   2232  CD2 LEU A 318     -14.562 -14.007  15.820  1.00 25.55           C
ATOM   2233  N   HIS A 319     -12.648  -9.368  18.346  1.00 25.37           N
ATOM   2234  CA  HIS A 319     -13.160  -8.000  18.457  1.00 25.66           C
ATOM   2235  C   HIS A 319     -13.750  -7.435  17.167  1.00 26.42           C
ATOM   2236  O   HIS A 319     -13.024  -6.934  16.302  1.00 26.54           O
ATOM   2237  CB  HIS A 319     -12.037  -7.082  18.953  1.00 24.18           C
ATOM   2238  CG  HIS A 319     -12.516  -5.755  19.452  1.00 25.36           C
ATOM   2239  ND1 HIS A 319     -11.655  -4.730  19.784  1.00 25.33           N
ATOM   2240  CD2 HIS A 319     -13.764  -5.300  19.716  1.00 23.91           C
```

FIGURE 4-34 (COORDINATES)

```
ATOM   2241  CE1 HIS A 319     -12.353  -3.701  20.233  1.00 24.93           C
ATOM   2242  NE2 HIS A 319     -13.635  -4.022  20.204  1.00 24.49           N
ATOM   2243  N   LEU A 320     -15.072  -7.495  17.046  1.00 26.41           N
ATOM   2244  CA  LEU A 320     -15.722  -6.995  15.850  1.00 25.90           C
ATOM   2245  C   LEU A 320     -16.064  -5.512  15.914  1.00 25.60           C
ATOM   2246  O   LEU A 320     -17.216  -5.122  16.092  1.00 24.53           O
ATOM   2247  CB  LEU A 320     -16.977  -7.820  15.541  1.00 28.12           C
ATOM   2248  CG  LEU A 320     -16.734  -9.329  15.353  1.00 30.06           C
ATOM   2249  CD1 LEU A 320     -18.019 -10.015  14.896  1.00 30.15           C
ATOM   2250  CD2 LEU A 320     -15.624  -9.552  14.328  1.00 29.17           C
ATOM   2251  N   ILE A 321     -15.034  -4.687  15.779  1.00 25.80           N
ATOM   2252  CA  ILE A 321     -15.189  -3.240  15.760  1.00 25.20           C
ATOM   2253  C   ILE A 321     -14.476  -2.823  14.477  1.00 25.46           C
ATOM   2254  O   ILE A 321     -13.404  -3.336  14.152  1.00 26.11           O
ATOM   2255  CB  ILE A 321     -14.537  -2.569  17.001  1.00 24.50           C
ATOM   2256  CG1 ILE A 321     -14.817  -1.065  16.992  1.00 25.03           C
ATOM   2257  CG2 ILE A 321     -13.040  -2.839  17.029  1.00 24.52           C
ATOM   2258  CD1 ILE A 321     -14.322  -0.339  18.252  1.00 24.15           C
ATOM   2259  N   PRO A 322     -15.074  -1.913  13.710  1.00 25.17           N
ATOM   2260  CA  PRO A 322     -14.394  -1.516  12.478  1.00 26.22           C
ATOM   2261  C   PRO A 322     -13.299  -0.474  12.687  1.00 27.53           C
ATOM   2262  O   PRO A 322     -13.320   0.293  13.660  1.00 28.03           O
ATOM   2263  CB  PRO A 322     -15.538  -0.996  11.617  1.00 24.97           C
ATOM   2264  CG  PRO A 322     -16.448  -0.378  12.632  1.00 25.94           C
ATOM   2265  CD  PRO A 322     -16.446  -1.377  13.763  1.00 25.69           C
ATOM   2266  N   SER A 323     -12.334  -0.469  11.775  1.00 27.81           N
ATOM   2267  CA  SER A 323     -11.241   0.493  11.817  1.00 28.80           C
ATOM   2268  C   SER A 323     -11.006   0.968  10.391  1.00 28.58           C
ATOM   2269  O   SER A 323     -10.687   0.173   9.511  1.00 28.93           O
ATOM   2270  CB  SER A 323      -9.968  -0.146  12.364  1.00 29.77           C
ATOM   2271  OG  SER A 323      -8.963   0.839  12.531  1.00 32.63           O
ATOM   2272  N   PRO A 324     -11.175   2.272  10.137  1.00 28.40           N
ATOM   2273  CA  PRO A 324     -11.564   3.332  11.073  1.00 28.38           C
ATOM   2274  C   PRO A 324     -13.004   3.244  11.576  1.00 28.34           C
ATOM   2275  O   PRO A 324     -13.832   2.534  11.004  1.00 28.62           O
ATOM   2276  CB  PRO A 324     -11.336   4.597  10.257  1.00 28.92           C
ATOM   2277  CG  PRO A 324     -11.720   4.150   8.871  1.00 28.67           C
ATOM   2278  CD  PRO A 324     -11.022   2.813   8.774  1.00 28.04           C
ATOM   2279  N   PHE A 325     -13.284   3.981  12.648  1.00 27.73           N
ATOM   2280  CA  PHE A 325     -14.612   4.032  13.245  1.00 26.87           C
ATOM   2281  C   PHE A 325     -15.580   4.766  12.322  1.00 27.12           C
ATOM   2282  O   PHE A 325     -15.165   5.469  11.407  1.00 27.88           O
ATOM   2283  CB  PHE A 325     -14.599   4.821  14.560  1.00 26.60           C
ATOM   2284  CG  PHE A 325     -13.739   4.234  15.641  1.00 26.86           C
ATOM   2285  CD1 PHE A 325     -13.348   2.898  15.613  1.00 26.84           C
ATOM   2286  CD2 PHE A 325     -13.386   5.013  16.740  1.00 27.35           C
ATOM   2287  CE1 PHE A 325     -12.623   2.347  16.663  1.00 26.67           C
ATOM   2288  CE2 PHE A 325     -12.662   4.473  17.801  1.00 27.21           C
ATOM   2289  CZ  PHE A 325     -12.280   3.136  17.763  1.00 27.78           C
ATOM   2290  N   PRO A 326     -16.890   4.606  12.556  1.00 26.50           N
ATOM   2291  CA  PRO A 326     -17.900   5.286  11.743  1.00 26.68           C
ATOM   2292  C   PRO A 326     -17.674   6.802  11.855  1.00 27.19           C
ATOM   2293  O   PRO A 326     -17.335   7.308  12.925  1.00 27.42           O
ATOM   2294  CB  PRO A 326     -19.206   4.865  12.405  1.00 25.90           C
ATOM   2295  CG  PRO A 326     -18.905   3.488  12.872  1.00 25.99           C
ATOM   2296  CD  PRO A 326     -17.515   3.615  13.446  1.00 25.82           C
ATOM   2297  N   GLU A 327     -17.861   7.524  10.759  1.00 27.75           N
ATOM   2298  CA  GLU A 327     -17.668   8.970  10.769  1.00 27.90           C
ATOM   2299  C   GLU A 327     -18.454   9.661  11.869  1.00 27.38           C
ATOM   2300  O   GLU A 327     -18.008  10.661  12.434  1.00 27.51           O
ATOM   2301  CB  GLU A 327     -18.086   9.567   9.426  1.00 29.25           C
ATOM   2302  CG  GLU A 327     -17.111   9.301   8.297  1.00 31.63           C
ATOM   2303  CD  GLU A 327     -17.638   9.775   6.953  1.00 33.10           C
ATOM   2304  OE1 GLU A 327     -18.208  10.891   6.890  1.00 33.06           O
ATOM   2305  OE2 GLU A 327     -17.472   9.033   5.964  1.00 32.75           O
ATOM   2306  N   VAL A 328     -19.627   9.120  12.171  1.00 26.73           N
ATOM   2307  CA  VAL A 328     -20.509   9.702  13.167  1.00 25.88           C
ATOM   2308  C   VAL A 328     -20.141   9.415  14.614  1.00 25.83           C
```

FIGURE 4-35 (COORDINATES)

```
ATOM   2309  O    VAL A 328     -20.853   9.826  15.528  1.00 25.59           O
ATOM   2310  CB   VAL A 328     -21.951   9.240  12.926  1.00 26.44           C
ATOM   2311  CG1  VAL A 328     -22.418   9.721  11.562  1.00 26.17           C
ATOM   2312  CG2  VAL A 328     -22.032   7.718  13.006  1.00 26.19           C
ATOM   2313  N    TRP A 329     -19.027   8.718  14.815  1.00 25.94           N
ATOM   2314  CA   TRP A 329     -18.564   8.345  16.147  1.00 25.00           C
ATOM   2315  C    TRP A 329     -18.717   9.458  17.194  1.00 25.87           C
ATOM   2316  O    TRP A 329     -18.133  10.535  17.062  1.00 26.95           O
ATOM   2317  CB   TRP A 329     -17.099   7.904  16.061  1.00 24.02           C
ATOM   2318  CG   TRP A 329     -16.506   7.442  17.362  1.00 24.19           C
ATOM   2319  CD1  TRP A 329     -16.662   6.219  17.954  1.00 23.81           C
ATOM   2320  CD2  TRP A 329     -15.660   8.201  18.228  1.00 24.60           C
ATOM   2321  NE1  TRP A 329     -15.958   6.169  19.139  1.00 22.93           N
ATOM   2322  CE2  TRP A 329     -15.336   7.375  19.329  1.00 24.21           C
ATOM   2323  CE3  TRP A 329     -15.142   9.502  18.183  1.00 25.21           C
ATOM   2324  CZ2  TRP A 329     -14.518   7.811  20.376  1.00 23.83           C
ATOM   2325  CZ3  TRP A 329     -14.329   9.934  19.227  1.00 24.26           C
ATOM   2326  CH2  TRP A 329     -14.028   9.088  20.308  1.00 24.01           C
ATOM   2327  N    HIS A 330     -19.505   9.186  18.230  1.00 26.04           N
ATOM   2328  CA   HIS A 330     -19.736  10.124  19.328  1.00 26.85           C
ATOM   2329  C    HIS A 330     -20.249  11.495  18.900  1.00 28.21           C
ATOM   2330  O    HIS A 330     -19.899  12.528  19.477  1.00 28.08           O
ATOM   2331  CB   HIS A 330     -18.461  10.270  20.161  1.00 26.41           C
ATOM   2332  CG   HIS A 330     -18.125   9.045  20.956  1.00 26.66           C
ATOM   2333  ND1  HIS A 330     -17.109   9.014  21.887  1.00 27.13           N
ATOM   2334  CD2  HIS A 330     -18.679   7.811  20.966  1.00 25.67           C
ATOM   2335  CE1  HIS A 330     -17.052   7.815  22.437  1.00 24.06           C
ATOM   2336  NE2  HIS A 330     -17.994   7.066  21.895  1.00 26.14           N
ATOM   2337  N    THR A 331     -21.110  11.469  17.896  1.00 27.72           N
ATOM   2338  CA   THR A 331     -21.721  12.653  17.320  1.00 28.54           C
ATOM   2339  C    THR A 331     -23.230  12.450  17.403  1.00 28.46           C
ATOM   2340  O    THR A 331     -23.696  11.313  17.481  1.00 27.94           O
ATOM   2341  CB   THR A 331     -21.276  12.779  15.838  1.00 28.87           C
ATOM   2342  OG1  THR A 331     -20.050  13.515  15.772  1.00 30.67           O
ATOM   2343  CG2  THR A 331     -22.324  13.433  15.000  1.00 29.70           C
ATOM   2344  N    MET A 332     -23.993  13.540  17.395  1.00 29.04           N
ATOM   2345  CA   MET A 332     -25.450  13.436  17.449  1.00 29.42           C
ATOM   2346  C    MET A 332     -25.969  12.800  16.161  1.00 30.00           C
ATOM   2347  O    MET A 332     -27.142  12.448  16.056  1.00 30.34           O
ATOM   2348  CB   MET A 332     -26.082  14.818  17.630  1.00 29.36           C
ATOM   2349  CG   MET A 332     -25.835  15.447  18.996  1.00 29.96           C
ATOM   2350  SD   MET A 332     -26.653  14.562  20.332  1.00 30.67           S
ATOM   2351  CE   MET A 332     -26.199  15.562  21.751  1.00 28.59           C
ATOM   2352  N    ASP A 333     -25.090  12.661  15.175  1.00 29.97           N
ATOM   2353  CA   ASP A 333     -25.472  12.061  13.909  1.00 30.16           C
ATOM   2354  C    ASP A 333     -25.378  10.542  13.937  1.00 29.35           C
ATOM   2355  O    ASP A 333     -25.685   9.888  12.943  1.00 28.57           O
ATOM   2356  CB   ASP A 333     -24.622  12.616  12.767  1.00 31.68           C
ATOM   2357  CG   ASP A 333     -24.941  14.068  12.463  1.00 33.47           C
ATOM   2358  OD1  ASP A 333     -26.138  14.404  12.390  1.00 34.87           O
ATOM   2359  OD2  ASP A 333     -24.004  14.872  12.287  1.00 34.67           O
ATOM   2360  N    ASP A 334     -24.935   9.976  15.057  1.00 27.92           N
ATOM   2361  CA   ASP A 334     -24.885   8.521  15.159  1.00 28.04           C
ATOM   2362  C    ASP A 334     -26.318   8.118  15.488  1.00 28.32           C
ATOM   2363  O    ASP A 334     -26.622   7.693  16.606  1.00 28.42           O
ATOM   2364  CB   ASP A 334     -23.952   8.066  16.276  1.00 27.12           C
ATOM   2365  CG   ASP A 334     -23.824   6.552  16.340  1.00 27.53           C
ATOM   2366  OD1  ASP A 334     -24.422   5.870  15.481  1.00 27.38           O
ATOM   2367  OD2  ASP A 334     -23.123   6.040  17.240  1.00 27.42           O
ATOM   2368  N    ASN A 335     -27.194   8.289  14.500  1.00 28.44           N
ATOM   2369  CA   ASN A 335     -28.616   7.993  14.627  1.00 28.95           C
ATOM   2370  C    ASN A 335     -29.111   6.961  13.598  1.00 29.60           C
ATOM   2371  O    ASN A 335     -28.330   6.418  12.811  1.00 29.11           O
ATOM   2372  CB   ASN A 335     -29.416   9.291  14.475  1.00 28.30           C
ATOM   2373  CG   ASN A 335     -29.106  10.014  13.167  1.00 29.32           C
ATOM   2374  OD1  ASN A 335     -28.787   9.380  12.161  1.00 29.11           O
ATOM   2375  ND2  ASN A 335     -29.214  11.340  13.175  1.00 28.59           N
ATOM   2376  N    GLU A 336     -30.420   6.711  13.608  1.00 30.27           N
```

FIGURE 4-36 (COORDINATES)

```
ATOM   2377  CA   GLU A 336     -31.046    5.737   12.719  1.00 31.25           C
ATOM   2378  C    GLU A 336     -30.897    6.082   11.247  1.00 31.54           C
ATOM   2379  O    GLU A 336     -30.653    5.209   10.415  1.00 30.19           O
ATOM   2380  CB   GLU A 336     -32.529    5.610   13.056  1.00 31.58           C
ATOM   2381  CG   GLU A 336     -33.298    4.631   12.176  1.00 32.01           C
ATOM   2382  CD   GLU A 336     -34.745    4.487   12.613  1.00 32.62           C
ATOM   2383  OE1  GLU A 336     -35.144    5.183   13.573  1.00 33.01           O
ATOM   2384  OE2  GLU A 336     -35.484    3.686   12.004  1.00 32.68           O
ATOM   2385  N    GLU A 337     -31.050    7.364   10.939  1.00 33.29           N
ATOM   2386  CA   GLU A 337     -30.952    7.856    9.571  1.00 33.95           C
ATOM   2387  C    GLU A 337     -29.621    7.508    8.902  1.00 33.24           C
ATOM   2388  O    GLU A 337     -29.569    7.272    7.694  1.00 33.39           O
ATOM   2389  CB   GLU A 337     -31.175    9.373    9.566  1.00 36.55           C
ATOM   2390  CG   GLU A 337     -30.590   10.101    8.370  1.00 41.68           C
ATOM   2391  CD   GLU A 337     -30.786   11.610    8.445  1.00 45.03           C
ATOM   2392  OE1  GLU A 337     -30.685   12.175    9.561  1.00 45.73           O
ATOM   2393  OE2  GLU A 337     -31.026   12.229    7.382  1.00 46.90           O
ATOM   2394  N    ASN A 338     -28.548    7.456    9.683  1.00 31.88           N
ATOM   2395  CA   ASN A 338     -27.242    7.149    9.116  1.00 30.51           C
ATOM   2396  C    ASN A 338     -26.828    5.684    9.144  1.00 29.33           C
ATOM   2397  O    ASN A 338     -25.668    5.356    8.900  1.00 29.22           O
ATOM   2398  CB   ASN A 338     -26.185    8.015    9.792  1.00 30.71           C
ATOM   2399  CG   ASN A 338     -26.294    9.466    9.378  1.00 31.45           C
ATOM   2400  OD1  ASN A 338     -26.273   10.375   10.211  1.00 31.34           O
ATOM   2401  ND2  ASN A 338     -26.415    9.691    8.077  1.00 30.26           N
ATOM   2402  N    LEU A 339     -27.778    4.801    9.423  1.00 27.87           N
ATOM   2403  CA   LEU A 339     -27.489    3.374    9.453  1.00 27.46           C
ATOM   2404  C    LEU A 339     -27.603    2.775    8.050  1.00 28.16           C
ATOM   2405  O    LEU A 339     -28.421    3.211    7.240  1.00 27.36           O
ATOM   2406  CB   LEU A 339     -28.452    2.664   10.410  1.00 24.91           C
ATOM   2407  CG   LEU A 339     -28.264    3.042   11.880  1.00 24.21           C
ATOM   2408  CD1  LEU A 339     -29.309    2.362   12.738  1.00 23.76           C
ATOM   2409  CD2  LEU A 339     -26.866    2.642   12.325  1.00 24.02           C
ATOM   2410  N    ASP A 340     -26.769    1.783    7.761  1.00 29.33           N
ATOM   2411  CA   ASP A 340     -26.794    1.125    6.460  1.00 30.47           C
ATOM   2412  C    ASP A 340     -27.499   -0.216    6.633  1.00 30.78           C
ATOM   2413  O    ASP A 340     -26.886   -1.202    7.049  1.00 29.35           O
ATOM   2414  CB   ASP A 340     -25.368    0.901    5.955  1.00 31.69           C
ATOM   2415  CG   ASP A 340     -25.326    0.339    4.545  1.00 32.20           C
ATOM   2416  OD1  ASP A 340     -26.215   -0.464    4.179  1.00 31.42           O
ATOM   2417  OD2  ASP A 340     -24.384    0.696    3.807  1.00 34.12           O
ATOM   2418  N    GLU A 341     -28.789   -0.238    6.313  1.00 32.34           N
ATOM   2419  CA   GLU A 341     -29.623   -1.434    6.434  1.00 34.16           C
ATOM   2420  C    GLU A 341     -29.046   -2.722    5.851  1.00 33.47           C
ATOM   2421  O    GLU A 341     -28.958   -3.739    6.539  1.00 34.07           O
ATOM   2422  CB   GLU A 341     -30.994   -1.187    5.788  1.00 37.32           C
ATOM   2423  CG   GLU A 341     -31.863   -2.443    5.691  1.00 41.84           C
ATOM   2424  CD   GLU A 341     -33.198   -2.191    5.012  1.00 45.16           C
ATOM   2425  OE1  GLU A 341     -33.957   -1.326    5.509  1.00 47.09           O
ATOM   2426  OE2  GLU A 341     -33.488   -2.857    3.987  1.00 45.95           O
ATOM   2427  N    SER A 342     -28.667   -2.683    4.582  1.00 32.38           N
ATOM   2428  CA   SER A 342     -28.150   -3.871    3.929  1.00 32.49           C
ATOM   2429  C    SER A 342     -26.847   -4.353    4.546  1.00 30.86           C
ATOM   2430  O    SER A 342     -26.585   -5.556    4.593  1.00 30.10           O
ATOM   2431  CB   SER A 342     -27.976   -3.618    2.426  1.00 34.41           C
ATOM   2432  OG   SER A 342     -26.970   -2.648    2.176  1.00 39.13           O
ATOM   2433  N    THR A 343     -26.026   -3.423    5.021  1.00 29.21           N
ATOM   2434  CA   THR A 343     -24.771   -3.817    5.649  1.00 28.11           C
ATOM   2435  C    THR A 343     -25.070   -4.583    6.931  1.00 26.45           C
ATOM   2436  O    THR A 343     -24.431   -5.597    7.220  1.00 26.18           O
ATOM   2437  CB   THR A 343     -23.885   -2.598    5.993  1.00 27.97           C
ATOM   2438  OG1  THR A 343     -23.416   -2.000    4.782  1.00 28.69           O
ATOM   2439  CG2  THR A 343     -22.690   -3.020    6.833  1.00 26.10           C
ATOM   2440  N    ILE A 344     -26.041   -4.099    7.697  1.00 25.16           N
ATOM   2441  CA   ILE A 344     -26.408   -4.756    8.946  1.00 25.18           C
ATOM   2442  C    ILE A 344     -27.021   -6.118    8.643  1.00 26.70           C
ATOM   2443  O    ILE A 344     -26.775   -7.100    9.347  1.00 26.99           O
ATOM   2444  CB   ILE A 344     -27.419   -3.905    9.758  1.00 23.83           C
```

FIGURE 4-37 (COORDINATES)

```
ATOM   2445  CG1 ILE A 344     -26.806   -2.533  10.064  1.00 22.40           C
ATOM   2446  CG2 ILE A 344     -27.785   -4.619  11.063  1.00 21.98           C
ATOM   2447  CD1 ILE A 344     -27.749   -1.569  10.733  1.00 21.58           C
ATOM   2448  N   ASP A 345     -27.812   -6.169   7.579  1.00 27.11           N
ATOM   2449  CA  ASP A 345     -28.464   -7.399   7.161  1.00 27.50           C
ATOM   2450  C   ASP A 345     -27.401   -8.435   6.810  1.00 27.71           C
ATOM   2451  O   ASP A 345     -27.447   -9.575   7.286  1.00 27.27           O
ATOM   2452  CB  ASP A 345     -29.366   -7.101   5.961  1.00 28.05           C
ATOM   2453  CG  ASP A 345     -30.258   -8.259   5.590  1.00 27.77           C
ATOM   2454  OD1 ASP A 345     -30.755   -8.944   6.502  1.00 27.40           O
ATOM   2455  OD2 ASP A 345     -30.477   -8.468   4.379  1.00 28.05           O
ATOM   2456  N   ASN A 346     -26.438   -8.030   5.986  1.00 27.23           N
ATOM   2457  CA  ASN A 346     -25.350   -8.919   5.591  1.00 27.02           C
ATOM   2458  C   ASN A 346     -24.595   -9.429   6.817  1.00 27.47           C
ATOM   2459  O   ASN A 346     -24.283  -10.617   6.914  1.00 27.94           O
ATOM   2460  CB  ASN A 346     -24.361   -8.204   4.655  1.00 26.14           C
ATOM   2461  CG  ASN A 346     -24.958   -7.894   3.280  1.00 26.75           C
ATOM   2462  OD1 ASN A 346     -25.879   -8.568   2.819  1.00 26.26           O
ATOM   2463  ND2 ASN A 346     -24.412   -6.881   2.614  1.00 24.56           N
ATOM   2464  N   LEU A 347     -24.298   -8.530   7.753  1.00 27.53           N
ATOM   2465  CA  LEU A 347     -23.575   -8.919   8.957  1.00 26.58           C
ATOM   2466  C   LEU A 347     -24.383   -9.890   9.811  1.00 26.40           C
ATOM   2467  O   LEU A 347     -23.815  -10.783  10.441  1.00 25.99           O
ATOM   2468  CB  LEU A 347     -23.175   -7.678   9.765  1.00 24.39           C
ATOM   2469  CG  LEU A 347     -22.068   -6.853   9.088  1.00 24.71           C
ATOM   2470  CD1 LEU A 347     -21.825   -5.549   9.850  1.00 24.52           C
ATOM   2471  CD2 LEU A 347     -20.790   -7.674   9.021  1.00 22.36           C
ATOM   2472  N   ASN A 348     -25.703   -9.722   9.835  1.00 25.24           N
ATOM   2473  CA  ASN A 348     -26.545  -10.626  10.607  1.00 25.16           C
ATOM   2474  C   ASN A 348     -26.410  -12.047  10.073  1.00 25.18           C
ATOM   2475  O   ASN A 348     -26.277  -13.000  10.829  1.00 25.73           O
ATOM   2476  CB  ASN A 348     -28.018  -10.202  10.545  1.00 23.77           C
ATOM   2477  CG  ASN A 348     -28.353   -9.123  11.551  1.00 23.67           C
ATOM   2478  OD1 ASN A 348     -27.715   -9.023  12.604  1.00 23.19           O
ATOM   2479  ND2 ASN A 348     -29.369   -8.319  11.247  1.00 22.46           N
ATOM   2480  N   LYS A 349     -26.439  -12.183   8.758  1.00 25.48           N
ATOM   2481  CA  LYS A 349     -26.328  -13.491   8.147  1.00 26.17           C
ATOM   2482  C   LYS A 349     -24.971  -14.121   8.438  1.00 25.86           C
ATOM   2483  O   LYS A 349     -24.869  -15.320   8.709  1.00 25.42           O
ATOM   2484  CB  LYS A 349     -26.547  -13.372   6.633  1.00 26.44           C
ATOM   2485  CG  LYS A 349     -27.918  -12.824   6.264  1.00 26.65           C
ATOM   2486  CD  LYS A 349     -28.049  -12.632   4.765  1.00 26.57           C
ATOM   2487  CE  LYS A 349     -29.447  -12.184   4.400  1.00 26.85           C
ATOM   2488  NZ  LYS A 349     -29.541  -11.905   2.952  1.00 27.09           N
ATOM   2489  N   ILE A 350     -23.928  -13.305   8.381  1.00 25.38           N
ATOM   2490  CA  ILE A 350     -22.584  -13.790   8.626  1.00 24.52           C
ATOM   2491  C   ILE A 350     -22.421  -14.257  10.074  1.00 26.10           C
ATOM   2492  O   ILE A 350     -21.959  -15.373  10.326  1.00 27.12           O
ATOM   2493  CB  ILE A 350     -21.548  -12.689   8.293  1.00 23.84           C
ATOM   2494  CG1 ILE A 350     -21.602  -12.371   6.789  1.00 22.59           C
ATOM   2495  CG2 ILE A 350     -20.145  -13.143   8.681  1.00 23.86           C
ATOM   2496  CD1 ILE A 350     -20.709  -11.218   6.353  1.00 20.96           C
ATOM   2497  N   LEU A 351     -22.813  -13.408  11.017  1.00 25.33           N
ATOM   2498  CA  LEU A 351     -22.696  -13.728  12.431  1.00 26.23           C
ATOM   2499  C   LEU A 351     -23.498  -14.979  12.790  1.00 27.04           C
ATOM   2500  O   LEU A 351     -23.014  -15.848  13.519  1.00 27.02           O
ATOM   2501  CB  LEU A 351     -23.168  -12.542  13.278  1.00 25.58           C
ATOM   2502  CG  LEU A 351     -23.052  -12.680  14.800  1.00 25.60           C
ATOM   2503  CD1 LEU A 351     -21.592  -12.866  15.210  1.00 24.82           C
ATOM   2504  CD2 LEU A 351     -23.635  -11.441  15.450  1.00 24.83           C
ATOM   2505  N   GLN A 352     -24.721  -15.065  12.273  1.00 27.52           N
ATOM   2506  CA  GLN A 352     -25.583  -16.211  12.534  1.00 28.04           C
ATOM   2507  C   GLN A 352     -24.970  -17.519  12.043  1.00 28.23           C
ATOM   2508  O   GLN A 352     -25.046  -18.535  12.727  1.00 29.89           O
ATOM   2509  CB  GLN A 352     -26.957  -15.980  11.907  1.00 28.24           C
ATOM   2510  CG  GLN A 352     -27.870  -15.130  12.786  1.00 27.84           C
ATOM   2511  CD  GLN A 352     -29.072  -14.595  12.043  1.00 28.56           C
ATOM   2512  OE1 GLN A 352     -29.740  -15.325  11.316  1.00 29.16           O
```

FIGURE 4-38 (COORDINATES)

```
ATOM   2513  NE2 GLN A 352     -29.359 -13.312  12.226  1.00 27.77           N
ATOM   2514  N   VAL A 353     -24.353 -17.496  10.869  1.00 28.02           N
ATOM   2515  CA  VAL A 353     -23.708 -18.689  10.342  1.00 28.15           C
ATOM   2516  C   VAL A 353     -22.523 -19.059  11.237  1.00 28.27           C
ATOM   2517  O   VAL A 353     -22.361 -20.218  11.620  1.00 28.87           O
ATOM   2518  CB  VAL A 353     -23.196 -18.462   8.906  1.00 28.82           C
ATOM   2519  CG1 VAL A 353     -22.367 -19.656   8.452  1.00 29.39           C
ATOM   2520  CG2 VAL A 353     -24.373 -18.250   7.966  1.00 29.50           C
ATOM   2521  N   PHE A 354     -21.700 -18.067  11.567  1.00 27.37           N
ATOM   2522  CA  PHE A 354     -20.536 -18.279  12.425  1.00 26.93           C
ATOM   2523  C   PHE A 354     -20.946 -18.990  13.719  1.00 27.40           C
ATOM   2524  O   PHE A 354     -20.334 -19.984  14.122  1.00 28.04           O
ATOM   2525  CB  PHE A 354     -19.880 -16.935  12.773  1.00 23.85           C
ATOM   2526  CG  PHE A 354     -18.698 -17.059  13.687  1.00 21.85           C
ATOM   2527  CD1 PHE A 354     -17.426 -17.300  13.175  1.00 19.67           C
ATOM   2528  CD2 PHE A 354     -18.863 -16.993  15.072  1.00 21.13           C
ATOM   2529  CE1 PHE A 354     -16.339 -17.477  14.022  1.00 19.78           C
ATOM   2530  CE2 PHE A 354     -17.784 -17.169  15.930  1.00 18.37           C
ATOM   2531  CZ  PHE A 354     -16.521 -17.413  15.412  1.00 18.13           C
ATOM   2532  N   VAL A 355     -21.986 -18.473  14.362  1.00 28.16           N
ATOM   2533  CA  VAL A 355     -22.474 -19.047  15.613  1.00 29.16           C
ATOM   2534  C   VAL A 355     -22.974 -20.479  15.441  1.00 28.89           C
ATOM   2535  O   VAL A 355     -22.627 -21.356  16.233  1.00 29.23           O
ATOM   2536  CB  VAL A 355     -23.605 -18.190  16.223  1.00 29.57           C
ATOM   2537  CG1 VAL A 355     -24.135 -18.853  17.496  1.00 29.34           C
ATOM   2538  CG2 VAL A 355     -23.081 -16.791  16.536  1.00 29.35           C
ATOM   2539  N   LEU A 356     -23.783 -20.721  14.415  1.00 28.61           N
ATOM   2540  CA  LEU A 356     -24.289 -22.070  14.187  1.00 27.79           C
ATOM   2541  C   LEU A 356     -23.138 -23.038  13.930  1.00 27.38           C
ATOM   2542  O   LEU A 356     -23.124 -24.141  14.472  1.00 26.91           O
ATOM   2543  CB  LEU A 356     -25.266 -22.103  13.008  1.00 27.57           C
ATOM   2544  CG  LEU A 356     -26.665 -21.518  13.222  1.00 27.66           C
ATOM   2545  CD1 LEU A 356     -27.457 -21.626  11.930  1.00 26.30           C
ATOM   2546  CD2 LEU A 356     -27.382 -22.258  14.339  1.00 26.12           C
ATOM   2547  N   GLU A 357     -22.168 -22.622  13.119  1.00 26.77           N
ATOM   2548  CA  GLU A 357     -21.026 -23.480  12.812  1.00 27.03           C
ATOM   2549  C   GLU A 357     -20.168 -23.746  14.049  1.00 27.16           C
ATOM   2550  O   GLU A 357     -19.676 -24.858  14.242  1.00 27.32           O
ATOM   2551  CB  GLU A 357     -20.163 -22.860  11.706  1.00 27.28           C
ATOM   2552  CG  GLU A 357     -20.925 -22.610  10.407  1.00 28.64           C
ATOM   2553  CD  GLU A 357     -20.020 -22.284   9.228  1.00 29.67           C
ATOM   2554  OE1 GLU A 357     -18.938 -21.694   9.437  1.00 29.95           O
ATOM   2555  OE2 GLU A 357     -20.405 -22.605   8.081  1.00 31.50           O
ATOM   2556  N   TYR A 358     -19.991 -22.725  14.885  1.00 26.89           N
ATOM   2557  CA  TYR A 358     -19.191 -22.872  16.096  1.00 26.51           C
ATOM   2558  C   TYR A 358     -19.877 -23.845  17.053  1.00 27.49           C
ATOM   2559  O   TYR A 358     -19.220 -24.658  17.694  1.00 27.11           O
ATOM   2560  CB  TYR A 358     -19.011 -21.517  16.800  1.00 25.35           C
ATOM   2561  CG  TYR A 358     -17.910 -21.521  17.837  1.00 23.67           C
ATOM   2562  CD1 TYR A 358     -16.635 -21.048  17.527  1.00 23.20           C
ATOM   2563  CD2 TYR A 358     -18.111 -22.083  19.096  1.00 22.96           C
ATOM   2564  CE1 TYR A 358     -15.592 -21.145  18.432  1.00 22.96           C
ATOM   2565  CE2 TYR A 358     -17.066 -22.187  20.015  1.00 23.79           C
ATOM   2566  CZ  TYR A 358     -15.808 -21.719  19.670  1.00 23.83           C
ATOM   2567  OH  TYR A 358     -14.756 -21.852  20.543  1.00 24.48           O
ATOM   2568  N   LEU A 359     -21.202 -23.765  17.137  1.00 27.92           N
ATOM   2569  CA  LEU A 359     -21.956 -24.625  18.038  1.00 29.23           C
ATOM   2570  C   LEU A 359     -22.393 -25.964  17.450  1.00 31.13           C
ATOM   2571  O   LEU A 359     -23.079 -26.736  18.119  1.00 32.46           O
ATOM   2572  CB  LEU A 359     -23.189 -23.882  18.553  1.00 28.22           C
ATOM   2573  CG  LEU A 359     -22.983 -22.625  19.403  1.00 27.64           C
ATOM   2574  CD1 LEU A 359     -24.334 -21.975  19.683  1.00 27.29           C
ATOM   2575  CD2 LEU A 359     -22.285 -22.987  20.711  1.00 26.37           C
ATOM   2576  N   HIS A 360     -22.008 -26.245  16.209  1.00 32.50           N
ATOM   2577  CA  HIS A 360     -22.388 -27.500  15.565  1.00 32.95           C
ATOM   2578  C   HIS A 360     -23.903 -27.662  15.489  1.00 32.90           C
ATOM   2579  O   HIS A 360     -24.438 -28.739  15.750  1.00 33.08           O
ATOM   2580  CB  HIS A 360     -21.788 -28.684  16.326  1.00 33.97           C
```

FIGURE 4-39 (COORDINATES)

```
ATOM   2581  CG   HIS A 360     -20.313 -28.834  16.135  1.00 36.60           C
ATOM   2582  ND1  HIS A 360     -19.462 -27.755  16.044  1.00 37.19           N
ATOM   2583  CD2  HIS A 360     -19.536 -29.938  16.019  1.00 37.85           C
ATOM   2584  CE1  HIS A 360     -18.224 -28.186  15.877  1.00 37.76           C
ATOM   2585  NE2  HIS A 360     -18.241 -29.506  15.858  1.00 38.59           N
ATOM   2586  N    LEU A 361     -24.595 -26.584  15.140  1.00 33.07           N
ATOM   2587  CA   LEU A 361     -26.046 -26.613  15.016  1.00 32.22           C
ATOM   2588  C    LEU A 361     -26.429 -26.406  13.555  1.00 32.74           C
ATOM   2589  O    LEU A 361     -27.640 -26.444  13.252  1.00 34.31           O
ATOM   2590  CB   LEU A 361     -26.680 -25.521  15.878  1.00 31.25           C
ATOM   2591  CG   LEU A 361     -26.443 -25.624  17.386  1.00 31.39           C
ATOM   2592  CD1  LEU A 361     -27.183 -24.507  18.097  1.00 30.44           C
ATOM   2593  CD2  LEU A 361     -26.925 -26.970  17.891  1.00 31.43           C
ATOM   2594  OXT  LEU A 361     -25.515 -26.205  12.730  1.00 31.86           O
TER    2595       LEU A 361
ATOM   2596  N    ALA B  33     -27.976  11.384  49.169  1.00 53.70           N
ATOM   2597  CA   ALA B  33     -27.520  11.685  50.559  1.00 52.91           C
ATOM   2598  C    ALA B  33     -28.496  11.112  51.583  1.00 52.20           C
ATOM   2599  O    ALA B  33     -29.242  11.854  52.231  1.00 52.20           O
ATOM   2600  CB   ALA B  33     -27.381  13.202  50.750  1.00 53.09           C
ATOM   2601  N    SER B  34     -28.501   9.788  51.713  1.00 50.72           N
ATOM   2602  CA   SER B  34     -29.374   9.128  52.675  1.00 49.01           C
ATOM   2603  C    SER B  34     -28.787   9.355  54.061  1.00 47.50           C
ATOM   2604  O    SER B  34     -27.575   9.536  54.210  1.00 46.56           O
ATOM   2605  CB   SER B  34     -29.465   7.625  52.388  1.00 49.45           C
ATOM   2606  OG   SER B  34     -30.099   7.376  51.145  1.00 50.65           O
ATOM   2607  N    ALA B  35     -29.646   9.343  55.073  1.00 45.69           N
ATOM   2608  CA   ALA B  35     -29.197   9.566  56.438  1.00 44.01           C
ATOM   2609  C    ALA B  35     -28.991   8.278  57.231  1.00 42.61           C
ATOM   2610  O    ALA B  35     -28.228   8.262  58.200  1.00 43.11           O
ATOM   2611  CB   ALA B  35     -30.190  10.473  57.164  1.00 43.80           C
ATOM   2612  N    TRP B  36     -29.649   7.196  56.823  1.00 39.86           N
ATOM   2613  CA   TRP B  36     -29.518   5.950  57.566  1.00 37.23           C
ATOM   2614  C    TRP B  36     -28.087   5.428  57.783  1.00 34.81           C
ATOM   2615  O    TRP B  36     -27.815   4.775  58.783  1.00 35.04           O
ATOM   2616  CB   TRP B  36     -30.410   4.856  56.953  1.00 36.58           C
ATOM   2617  CG   TRP B  36     -30.016   4.364  55.600  1.00 35.91           C
ATOM   2618  CD1  TRP B  36     -30.525   4.762  54.400  1.00 35.58           C
ATOM   2619  CD2  TRP B  36     -29.050   3.350  55.310  1.00 35.22           C
ATOM   2620  NE1  TRP B  36     -29.939   4.053  53.378  1.00 35.17           N
ATOM   2621  CE2  TRP B  36     -29.028   3.181  53.910  1.00 35.06           C
ATOM   2622  CE3  TRP B  36     -28.200   2.566  56.100  1.00 35.29           C
ATOM   2623  CZ2  TRP B  36     -28.191   2.259  53.281  1.00 35.01           C
ATOM   2624  CZ3  TRP B  36     -27.365   1.649  55.475  1.00 35.55           C
ATOM   2625  CH2  TRP B  36     -27.369   1.504  54.076  1.00 35.39           C
ATOM   2626  N    PRO B  37     -27.154   5.703  56.860  1.00 33.37           N
ATOM   2627  CA   PRO B  37     -25.804   5.187  57.121  1.00 32.12           C
ATOM   2628  C    PRO B  37     -25.133   5.910  58.283  1.00 32.15           C
ATOM   2629  O    PRO B  37     -24.060   5.511  58.734  1.00 31.65           O
ATOM   2630  CB   PRO B  37     -25.078   5.432  55.802  1.00 31.06           C
ATOM   2631  CG   PRO B  37     -26.178   5.340  54.795  1.00 31.81           C
ATOM   2632  CD   PRO B  37     -27.280   6.132  55.456  1.00 32.40           C
ATOM   2633  N    GLU B  38     -25.769   6.974  58.766  1.00 32.47           N
ATOM   2634  CA   GLU B  38     -25.220   7.756  59.871  1.00 33.63           C
ATOM   2635  C    GLU B  38     -25.827   7.334  61.204  1.00 33.49           C
ATOM   2636  O    GLU B  38     -25.293   7.651  62.261  1.00 32.07           O
ATOM   2637  CB   GLU B  38     -25.491   9.253  59.663  1.00 34.08           C
ATOM   2638  CG   GLU B  38     -25.288   9.735  58.241  1.00 36.34           C
ATOM   2639  CD   GLU B  38     -25.586  11.214  58.070  1.00 37.13           C
ATOM   2640  OE1  GLU B  38     -26.529  11.718  58.721  1.00 37.34           O
ATOM   2641  OE2  GLU B  38     -24.884  11.866  57.269  1.00 38.57           O
ATOM   2642  N    GLU B  39     -26.950   6.625  61.148  1.00 34.83           N
ATOM   2643  CA   GLU B  39     -27.638   6.183  62.358  1.00 35.93           C
ATOM   2644  C    GLU B  39     -26.738   5.480  63.385  1.00 35.68           C
ATOM   2645  O    GLU B  39     -26.879   5.700  64.590  1.00 34.46           O
ATOM   2646  CB   GLU B  39     -28.833   5.296  61.973  1.00 36.73           C
ATOM   2647  CG   GLU B  39     -30.065   6.111  61.547  1.00 39.58           C
ATOM   2648  CD   GLU B  39     -31.155   5.283  60.869  1.00 41.56           C
```

FIGURE 4-40 (COORDINATES)

```
ATOM   2649  OE1 GLU B  39     -31.416    4.135   61.299  1.00 41.17           O
ATOM   2650  OE2 GLU B  39     -31.769    5.800   59.908  1.00 43.72           O
ATOM   2651  N   LYS B  40     -25.797    4.666   62.913  1.00 36.09           N
ATOM   2652  CA  LYS B  40     -24.897    3.950   63.814  1.00 36.31           C
ATOM   2653  C   LYS B  40     -24.096    4.846   64.766  1.00 36.24           C
ATOM   2654  O   LYS B  40     -23.790    4.433   65.886  1.00 36.40           O
ATOM   2655  CB  LYS B  40     -23.953    3.025   63.020  1.00 36.95           C
ATOM   2656  CG  LYS B  40     -23.124    3.668   61.900  1.00 37.28           C
ATOM   2657  CD  LYS B  40     -22.159    2.630   61.313  1.00 37.48           C
ATOM   2658  CE  LYS B  40     -21.372    3.145   60.101  1.00 39.56           C
ATOM   2659  NZ  LYS B  40     -22.159    3.159   58.822  1.00 38.62           N
ATOM   2660  N   ASN B  41     -23.767    6.066   64.347  1.00 36.24           N
ATOM   2661  CA  ASN B  41     -23.023    6.976   65.217  1.00 36.38           C
ATOM   2662  C   ASN B  41     -23.795    7.370   66.472  1.00 36.75           C
ATOM   2663  O   ASN B  41     -23.193    7.621   67.516  1.00 37.02           O
ATOM   2664  CB  ASN B  41     -22.651    8.273   64.493  1.00 36.45           C
ATOM   2665  CG  ASN B  41     -21.592    8.077   63.440  1.00 36.86           C
ATOM   2666  OD1 ASN B  41     -21.896    7.976   62.252  1.00 37.16           O
ATOM   2667  ND2 ASN B  41     -20.336    8.019   63.867  1.00 36.83           N
ATOM   2668  N   TYR B  42     -25.122    7.437   66.367  1.00 36.58           N
ATOM   2669  CA  TYR B  42     -25.959    7.853   67.496  1.00 36.71           C
ATOM   2670  C   TYR B  42     -26.663    6.710   68.212  1.00 36.05           C
ATOM   2671  O   TYR B  42     -27.268    6.917   69.261  1.00 36.74           O
ATOM   2672  CB  TYR B  42     -27.042    8.832   67.025  1.00 37.28           C
ATOM   2673  CG  TYR B  42     -26.623    9.775   65.930  1.00 38.51           C
ATOM   2674  CD1 TYR B  42     -25.704   10.798   66.169  1.00 39.74           C
ATOM   2675  CD2 TYR B  42     -27.165    9.660   64.648  1.00 39.27           C
ATOM   2676  CE1 TYR B  42     -25.336   11.693   65.160  1.00 40.21           C
ATOM   2677  CE2 TYR B  42     -26.805   10.546   63.634  1.00 40.69           C
ATOM   2678  CZ  TYR B  42     -25.893   11.562   63.899  1.00 40.64           C
ATOM   2679  OH  TYR B  42     -25.572   12.458   62.908  1.00 41.71           O
ATOM   2680  N   HIS B  43     -26.606    5.515   67.639  1.00 34.81           N
ATOM   2681  CA  HIS B  43     -27.276    4.369   68.230  1.00 33.72           C
ATOM   2682  C   HIS B  43     -26.838    4.104   69.660  1.00 33.57           C
ATOM   2683  O   HIS B  43     -25.652    4.127   69.978  1.00 33.72           O
ATOM   2684  CB  HIS B  43     -27.038    3.130   67.367  1.00 34.28           C
ATOM   2685  CG  HIS B  43     -27.872    1.948   67.758  1.00 34.30           C
ATOM   2686  ND1 HIS B  43     -27.361    0.872   68.453  1.00 33.52           N
ATOM   2687  CD2 HIS B  43     -29.181    1.676   67.551  1.00 32.79           C
ATOM   2688  CE1 HIS B  43     -28.320   -0.012   68.655  1.00 32.55           C
ATOM   2689  NE2 HIS B  43     -29.434    0.451   68.118  1.00 32.34           N
ATOM   2690  N   GLN B  44     -27.820    3.863   70.521  1.00 34.16           N
ATOM   2691  CA  GLN B  44     -27.584    3.582   71.930  1.00 33.54           C
ATOM   2692  C   GLN B  44     -28.200    2.228   72.254  1.00 32.67           C
ATOM   2693  O   GLN B  44     -29.185    1.828   71.642  1.00 32.66           O
ATOM   2694  CB  GLN B  44     -28.246    4.652   72.807  1.00 34.41           C
ATOM   2695  CG  GLN B  44     -27.748    6.062   72.569  1.00 36.09           C
ATOM   2696  CD  GLN B  44     -26.268    6.195   72.826  1.00 37.59           C
ATOM   2697  OE1 GLN B  44     -25.783    5.848   73.903  1.00 39.13           O
ATOM   2698  NE2 GLN B  44     -25.536    6.699   71.838  1.00 38.21           N
ATOM   2699  N   PRO B  45     -27.629    1.505   73.222  1.00 32.18           N
ATOM   2700  CA  PRO B  45     -28.181    0.199   73.579  1.00 33.02           C
ATOM   2701  C   PRO B  45     -29.360    0.346   74.537  1.00 33.84           C
ATOM   2702  O   PRO B  45     -29.483    1.359   75.225  1.00 33.72           O
ATOM   2703  CB  PRO B  45     -26.998   -0.491   74.242  1.00 32.60           C
ATOM   2704  CG  PRO B  45     -26.369    0.644   74.995  1.00 31.78           C
ATOM   2705  CD  PRO B  45     -26.375    1.758   73.954  1.00 31.82           C
ATOM   2706  N   ALA B  46     -30.226   -0.662   74.568  1.00 34.61           N
ATOM   2707  CA  ALA B  46     -31.370   -0.668   75.475  1.00 35.77           C
ATOM   2708  C   ALA B  46     -31.008   -1.698   76.536  1.00 36.95           C
ATOM   2709  O   ALA B  46     -31.290   -2.887   76.387  1.00 38.12           O
ATOM   2710  CB  ALA B  46     -32.637   -1.078   74.738  1.00 34.32           C
ATOM   2711  N   ILE B  47     -30.372   -1.229   77.603  1.00 38.66           N
ATOM   2712  CA  ILE B  47     -29.910   -2.087   78.688  1.00 40.06           C
ATOM   2713  C   ILE B  47     -30.961   -2.982   79.353  1.00 40.47           C
ATOM   2714  O   ILE B  47     -32.147   -2.653   79.403  1.00 40.60           O
ATOM   2715  CB  ILE B  47     -29.189   -1.230   79.743  1.00 40.73           C
ATOM   2716  CG1 ILE B  47     -28.106   -0.405   79.042  1.00 41.30           C
```

FIGURE 4-41 (COORDINATES)

```
ATOM   2717  CG2 ILE B  47     -28.541  -2.115  80.806  1.00 41.89           C
ATOM   2718  CD1 ILE B  47     -27.325   0.508  79.952  1.00 42.61           C
ATOM   2719  N   LEU B  48     -30.510  -4.135  79.841  1.00 40.71           N
ATOM   2720  CA  LEU B  48     -31.391  -5.094  80.500  1.00 41.30           C
ATOM   2721  C   LEU B  48     -31.318  -4.941  82.016  1.00 41.44           C
ATOM   2722  O   LEU B  48     -30.236  -4.732  82.572  1.00 41.26           O
ATOM   2723  CB  LEU B  48     -30.991  -6.528  80.124  1.00 40.59           C
ATOM   2724  CG  LEU B  48     -30.975  -6.917  78.643  1.00 41.64           C
ATOM   2725  CD1 LEU B  48     -30.558  -8.378  78.508  1.00 41.50           C
ATOM   2726  CD2 LEU B  48     -32.349  -6.707  78.031  1.00 41.94           C
ATOM   2727  N   ASN B  49     -32.463  -5.039  82.686  1.00 42.01           N
ATOM   2728  CA  ASN B  49     -32.476  -4.935  84.140  1.00 42.41           C
ATOM   2729  C   ASN B  49     -32.094  -6.290  84.723  1.00 42.84           C
ATOM   2730  O   ASN B  49     -32.012  -7.286  83.992  1.00 42.01           O
ATOM   2731  CB  ASN B  49     -33.854  -4.503  84.666  1.00 42.75           C
ATOM   2732  CG  ASN B  49     -34.974  -5.444  84.249  1.00 43.99           C
ATOM   2733  OD1 ASN B  49     -34.834  -6.667  84.295  1.00 44.25           O
ATOM   2734  ND2 ASN B  49     -36.107  -4.869  83.855  1.00 45.65           N
ATOM   2735  N   SER B  50     -31.863  -6.314  86.036  1.00 43.15           N
ATOM   2736  CA  SER B  50     -31.468  -7.524  86.756  1.00 43.70           C
ATOM   2737  C   SER B  50     -32.222  -8.785  86.357  1.00 43.59           C
ATOM   2738  O   SER B  50     -31.618  -9.810  86.040  1.00 42.81           O
ATOM   2739  CB  SER B  50     -31.627  -7.312  88.263  1.00 43.62           C
ATOM   2740  OG  SER B  50     -30.747  -6.303  88.729  1.00 45.12           O
ATOM   2741  N   SER B  51     -33.544  -8.707  86.382  1.00 43.94           N
ATOM   2742  CA  SER B  51     -34.372  -9.853  86.046  1.00 45.08           C
ATOM   2743  C   SER B  51     -34.061 -10.391  84.649  1.00 44.98           C
ATOM   2744  O   SER B  51     -33.946 -11.602  84.452  1.00 45.39           O
ATOM   2745  CB  SER B  51     -35.851  -9.470  86.150  1.00 46.07           C
ATOM   2746  OG  SER B  51     -36.679 -10.618  86.080  1.00 49.23           O
ATOM   2747  N   ALA B  52     -33.921  -9.486  83.685  1.00 44.68           N
ATOM   2748  CA  ALA B  52     -33.629  -9.879  82.310  1.00 43.86           C
ATOM   2749  C   ALA B  52     -32.248 -10.532  82.219  1.00 43.46           C
ATOM   2750  O   ALA B  52     -32.060 -11.518  81.498  1.00 42.73           O
ATOM   2751  CB  ALA B  52     -33.707  -8.660  81.390  1.00 43.26           C
ATOM   2752  N   LEU B  53     -31.285  -9.986  82.951  1.00 42.86           N
ATOM   2753  CA  LEU B  53     -29.942 -10.544  82.938  1.00 43.89           C
ATOM   2754  C   LEU B  53     -29.951 -11.991  83.434  1.00 44.42           C
ATOM   2755  O   LEU B  53     -29.245 -12.845  82.890  1.00 43.93           O
ATOM   2756  CB  LEU B  53     -28.994  -9.685  83.787  1.00 43.02           C
ATOM   2757  CG  LEU B  53     -28.601  -8.336  83.169  1.00 43.40           C
ATOM   2758  CD1 LEU B  53     -27.672  -7.566  84.100  1.00 42.74           C
ATOM   2759  CD2 LEU B  53     -27.916  -8.577  81.832  1.00 42.67           C
ATOM   2760  N   ARG B  54     -30.759 -12.274  84.455  1.00 44.96           N
ATOM   2761  CA  ARG B  54     -30.839 -13.633  84.975  1.00 45.06           C
ATOM   2762  C   ARG B  54     -31.490 -14.539  83.935  1.00 44.29           C
ATOM   2763  O   ARG B  54     -31.076 -15.683  83.756  1.00 42.84           O
ATOM   2764  CB  ARG B  54     -31.640 -13.677  86.279  1.00 47.04           C
ATOM   2765  CG  ARG B  54     -31.131 -12.717  87.338  1.00 50.32           C
ATOM   2766  CD  ARG B  54     -31.593 -13.098  88.738  1.00 52.56           C
ATOM   2767  NE  ARG B  54     -31.325 -12.018  89.684  1.00 54.10           N
ATOM   2768  CZ  ARG B  54     -32.099 -10.945  89.819  1.00 55.60           C
ATOM   2769  NH1 ARG B  54     -33.191 -10.820  89.072  1.00 55.06           N
ATOM   2770  NH2 ARG B  54     -31.773  -9.991  90.684  1.00 55.96           N
ATOM   2771  N   GLN B  55     -32.502 -14.026  83.243  1.00 43.74           N
ATOM   2772  CA  GLN B  55     -33.175 -14.814  82.218  1.00 44.62           C
ATOM   2773  C   GLN B  55     -32.154 -15.242  81.158  1.00 43.97           C
ATOM   2774  O   GLN B  55     -32.103 -16.406  80.761  1.00 43.78           O
ATOM   2775  CB  GLN B  55     -34.289 -14.002  81.554  1.00 46.50           C
ATOM   2776  CG  GLN B  55     -35.228 -14.849  80.701  1.00 49.82           C
ATOM   2777  CD  GLN B  55     -36.112 -14.022  79.778  1.00 52.36           C
ATOM   2778  OE1 GLN B  55     -35.655 -13.518  78.746  1.00 53.61           O
ATOM   2779  NE2 GLN B  55     -37.386 -13.876  80.147  1.00 52.81           N
ATOM   2780  N   ILE B  56     -31.339 -14.291  80.712  1.00 43.11           N
ATOM   2781  CA  ILE B  56     -30.319 -14.564  79.708  1.00 42.78           C
ATOM   2782  C   ILE B  56     -29.321 -15.594  80.232  1.00 42.44           C
ATOM   2783  O   ILE B  56     -29.009 -16.570  79.552  1.00 41.91           O
ATOM   2784  CB  ILE B  56     -29.552 -13.272  79.320  1.00 42.44           C
```

FIGURE 4-42 (COORDINATES)

```
ATOM   2785  CG1 ILE B  56     -30.542 -12.183  78.905  1.00 42.34           C
ATOM   2786  CG2 ILE B  56     -28.598 -13.550  78.179  1.00 42.27           C
ATOM   2787  CD1 ILE B  56     -31.529 -12.624  77.842  1.00 41.88           C
ATOM   2788  N   ALA B  57     -28.830 -15.382  81.447  1.00 42.36           N
ATOM   2789  CA  ALA B  57     -27.873 -16.305  82.039  1.00 42.46           C
ATOM   2790  C   ALA B  57     -28.436 -17.719  82.111  1.00 43.31           C
ATOM   2791  O   ALA B  57     -27.701 -18.693  81.948  1.00 43.02           O
ATOM   2792  CB  ALA B  57     -27.483 -15.832  83.420  1.00 41.75           C
ATOM   2793  N   GLU B  58     -29.741 -17.833  82.343  1.00 44.09           N
ATOM   2794  CA  GLU B  58     -30.381 -19.140  82.440  1.00 44.79           C
ATOM   2795  C   GLU B  58     -30.718 -19.730  81.074  1.00 43.46           C
ATOM   2796  O   GLU B  58     -30.769 -20.947  80.917  1.00 43.83           O
ATOM   2797  CB  GLU B  58     -31.677 -19.056  83.253  1.00 48.31           C
ATOM   2798  CG  GLU B  58     -31.567 -18.428  84.637  1.00 53.78           C
ATOM   2799  CD  GLU B  58     -30.429 -18.999  85.463  1.00 57.54           C
ATOM   2800  OE1 GLU B  58     -30.224 -20.238  85.429  1.00 59.19           O
ATOM   2801  OE2 GLU B  58     -29.746 -18.205  86.156  1.00 59.21           O
ATOM   2802  N   GLY B  59     -30.954 -18.866  80.091  1.00 41.88           N
ATOM   2803  CA  GLY B  59     -31.324 -19.327  78.762  1.00 39.74           C
ATOM   2804  C   GLY B  59     -30.273 -19.953  77.860  1.00 39.26           C
ATOM   2805  O   GLY B  59     -30.605 -20.437  76.773  1.00 38.96           O
ATOM   2806  N   THR B  60     -29.014 -19.962  78.287  1.00 38.23           N
ATOM   2807  CA  THR B  60     -27.956 -20.538  77.463  1.00 37.23           C
ATOM   2808  C   THR B  60     -27.353 -21.794  78.100  1.00 36.59           C
ATOM   2809  O   THR B  60     -27.100 -21.835  79.306  1.00 36.80           O
ATOM   2810  CB  THR B  60     -26.847 -19.493  77.201  1.00 37.35           C
ATOM   2811  OG1 THR B  60     -25.862 -20.042  76.317  1.00 36.97           O
ATOM   2812  CG2 THR B  60     -26.188 -19.084  78.502  1.00 36.75           C
ATOM   2813  N   SER B  61     -27.120 -22.815  77.283  1.00 34.72           N
ATOM   2814  CA  SER B  61     -26.568 -24.071  77.775  1.00 33.75           C
ATOM   2815  C   SER B  61     -25.201 -24.394  77.198  1.00 32.92           C
ATOM   2816  O   SER B  61     -25.087 -24.794  76.040  1.00 31.72           O
ATOM   2817  CB  SER B  61     -27.523 -25.219  77.460  1.00 33.74           C
ATOM   2818  OG  SER B  61     -26.929 -26.461  77.788  1.00 34.90           O
ATOM   2819  N   ILE B  62     -24.165 -24.245  78.015  1.00 33.21           N
ATOM   2820  CA  ILE B  62     -22.808 -24.517  77.560  1.00 33.96           C
ATOM   2821  C   ILE B  62     -22.640 -25.989  77.177  1.00 34.79           C
ATOM   2822  O   ILE B  62     -21.868 -26.325  76.272  1.00 34.44           O
ATOM   2823  CB  ILE B  62     -21.765 -24.130  78.643  1.00 33.28           C
ATOM   2824  CG1 ILE B  62     -20.350 -24.254  78.078  1.00 33.74           C
ATOM   2825  CG2 ILE B  62     -21.916 -25.016  79.860  1.00 33.17           C
ATOM   2826  CD1 ILE B  62     -20.107 -23.415  76.830  1.00 33.70           C
ATOM   2827  N   SER B  63     -23.380 -26.863  77.852  1.00 35.40           N
ATOM   2828  CA  SER B  63     -23.300 -28.291  77.575  1.00 35.35           C
ATOM   2829  C   SER B  63     -23.970 -28.618  76.248  1.00 35.11           C
ATOM   2830  O   SER B  63     -23.523 -29.507  75.527  1.00 34.60           O
ATOM   2831  CB  SER B  63     -23.951 -29.099  78.708  1.00 36.56           C
ATOM   2832  OG  SER B  63     -25.362 -28.934  78.721  1.00 37.89           O
ATOM   2833  N   GLU B  64     -25.040 -27.902  75.919  1.00 36.01           N
ATOM   2834  CA  GLU B  64     -25.737 -28.140  74.658  1.00 37.33           C
ATOM   2835  C   GLU B  64     -24.892 -27.658  73.476  1.00 36.24           C
ATOM   2836  O   GLU B  64     -24.791 -28.341  72.451  1.00 35.78           O
ATOM   2837  CB  GLU B  64     -27.092 -27.434  74.657  1.00 41.11           C
ATOM   2838  CG  GLU B  64     -28.077 -28.025  75.649  1.00 46.67           C
ATOM   2839  CD  GLU B  64     -28.205 -29.527  75.493  1.00 49.75           C
ATOM   2840  OE1 GLU B  64     -28.674 -29.980  74.422  1.00 52.32           O
ATOM   2841  OE2 GLU B  64     -27.826 -30.257  76.438  1.00 52.11           O
ATOM   2842  N   MET B  65     -24.288 -26.484  73.627  1.00 34.01           N
ATOM   2843  CA  MET B  65     -23.434 -25.923  72.586  1.00 33.46           C
ATOM   2844  C   MET B  65     -22.263 -26.867  72.334  1.00 32.87           C
ATOM   2845  O   MET B  65     -21.946 -27.203  71.193  1.00 30.80           O
ATOM   2846  CB  MET B  65     -22.880 -24.562  73.012  1.00 32.64           C
ATOM   2847  CG  MET B  65     -21.927 -23.946  71.985  1.00 31.65           C
ATOM   2848  SD  MET B  65     -20.781 -22.767  72.727  1.00 30.63           S
ATOM   2849  CE  MET B  65     -19.549 -23.878  73.359  1.00 28.44           C
ATOM   2850  N   TRP B  66     -21.627 -27.284  73.423  1.00 32.97           N
ATOM   2851  CA  TRP B  66     -20.481 -28.182  73.361  1.00 33.05           C
ATOM   2852  C   TRP B  66     -20.802 -29.446  72.560  1.00 33.94           C
```

FIGURE 4-43 (COORDINATES)

```
ATOM   2853  O    TRP B  66     -20.094  -29.810  71.621  1.00 33.79           O
ATOM   2854  CB   TRP B  66     -20.065  -28.556  74.787  1.00 31.32           C
ATOM   2855  CG   TRP B  66     -18.601  -28.812  74.946  1.00 29.68           C
ATOM   2856  CD1  TRP B  66     -17.931  -29.958  74.637  1.00 28.73           C
ATOM   2857  CD2  TRP B  66     -17.617  -27.888  75.431  1.00 28.58           C
ATOM   2858  NE1  TRP B  66     -16.590  -29.809  74.901  1.00 28.87           N
ATOM   2859  CE2  TRP B  66     -16.368  -28.549  75.389  1.00 28.77           C
ATOM   2860  CE3  TRP B  66     -17.669  -26.566  75.896  1.00 28.10           C
ATOM   2861  CZ2  TRP B  66     -15.174  -27.933  75.795  1.00 27.71           C
ATOM   2862  CZ3  TRP B  66     -16.482  -25.951  76.300  1.00 27.93           C
ATOM   2863  CH2  TRP B  66     -15.250  -26.639  76.246  1.00 28.06           C
ATOM   2864  N    GLN B  67     -21.894  -30.094  72.935  1.00 35.61           N
ATOM   2865  CA   GLN B  67     -22.339  -31.332  72.308  1.00 36.99           C
ATOM   2866  C    GLN B  67     -22.885  -31.197  70.891  1.00 36.09           C
ATOM   2867  O    GLN B  67     -22.481  -31.931  69.987  1.00 36.40           O
ATOM   2868  CB   GLN B  67     -23.403  -31.987  73.204  1.00 38.59           C
ATOM   2869  CG   GLN B  67     -24.085  -33.213  72.608  1.00 44.10           C
ATOM   2870  CD   GLN B  67     -25.130  -33.822  73.548  1.00 46.99           C
ATOM   2871  OE1  GLN B  67     -24.807  -34.256  74.658  1.00 48.07           O
ATOM   2872  NE2  GLN B  67     -26.389  -33.849  73.104  1.00 47.23           N
ATOM   2873  N    ASN B  68     -23.791  -30.251  70.691  1.00 35.64           N
ATOM   2874  CA   ASN B  68     -24.425  -30.090  69.391  1.00 35.39           C
ATOM   2875  C    ASN B  68     -23.821  -29.070  68.424  1.00 35.45           C
ATOM   2876  O    ASN B  68     -24.003  -29.190  67.206  1.00 35.39           O
ATOM   2877  CB   ASN B  68     -25.914  -29.792  69.598  1.00 36.11           C
ATOM   2878  CG   ASN B  68     -26.592  -30.801  70.534  1.00 36.34           C
ATOM   2879  OD1  ASN B  68     -26.452  -32.014  70.366  1.00 37.11           O
ATOM   2880  ND2  ASN B  68     -27.334  -30.295  71.514  1.00 34.69           N
ATOM   2881  N    ASP B  69     -23.101  -28.082  68.948  1.00 33.99           N
ATOM   2882  CA   ASP B  69     -22.500  -27.057  68.094  1.00 32.76           C
ATOM   2883  C    ASP B  69     -20.987  -27.156  67.934  1.00 31.70           C
ATOM   2884  O    ASP B  69     -20.467  -27.097  66.819  1.00 31.48           O
ATOM   2885  CB   ASP B  69     -22.841  -25.666  68.626  1.00 32.93           C
ATOM   2886  CG   ASP B  69     -24.298  -25.319  68.460  1.00 33.93           C
ATOM   2887  OD1  ASP B  69     -24.872  -24.735  69.400  1.00 36.39           O
ATOM   2888  OD2  ASP B  69     -24.868  -25.614  67.391  1.00 34.50           O
ATOM   2889  N    LEU B  70     -20.287  -27.299  69.053  1.00 29.77           N
ATOM   2890  CA   LEU B  70     -18.838  -27.362  69.049  1.00 29.04           C
ATOM   2891  C    LEU B  70     -18.205  -28.644  68.505  1.00 30.00           C
ATOM   2892  O    LEU B  70     -17.500  -28.611  67.500  1.00 29.51           O
ATOM   2893  CB   LEU B  70     -18.312  -27.100  70.462  1.00 28.25           C
ATOM   2894  CG   LEU B  70     -16.788  -27.108  70.644  1.00 28.31           C
ATOM   2895  CD1  LEU B  70     -16.123  -26.099  69.698  1.00 27.09           C
ATOM   2896  CD2  LEU B  70     -16.460  -26.796  72.098  1.00 28.54           C
ATOM   2897  N    GLN B  71     -18.456  -29.771  69.161  1.00 29.68           N
ATOM   2898  CA   GLN B  71     -17.842  -31.030  68.752  1.00 30.15           C
ATOM   2899  C    GLN B  71     -17.866  -31.356  67.267  1.00 29.91           C
ATOM   2900  O    GLN B  71     -16.862  -31.799  66.719  1.00 30.05           O
ATOM   2901  CB   GLN B  71     -18.414  -32.187  69.577  1.00 30.15           C
ATOM   2902  CG   GLN B  71     -18.052  -32.044  71.060  1.00 32.33           C
ATOM   2903  CD   GLN B  71     -18.543  -33.188  71.914  1.00 34.42           C
ATOM   2904  OE1  GLN B  71     -19.656  -33.681  71.725  1.00 37.35           O
ATOM   2905  NE2  GLN B  71     -17.724  -33.609  72.874  1.00 33.04           N
ATOM   2906  N    PRO B  72     -18.998  -31.133  66.588  1.00 29.59           N
ATOM   2907  CA   PRO B  72     -19.015  -31.447  65.156  1.00 29.59           C
ATOM   2908  C    PRO B  72     -17.964  -30.667  64.362  1.00 30.08           C
ATOM   2909  O    PRO B  72     -17.505  -31.122  63.315  1.00 30.59           O
ATOM   2910  CB   PRO B  72     -20.436  -31.075  64.741  1.00 29.38           C
ATOM   2911  CG   PRO B  72     -21.223  -31.354  65.980  1.00 29.41           C
ATOM   2912  CD   PRO B  72     -20.342  -30.753  67.054  1.00 29.96           C
ATOM   2913  N    LEU B  73     -17.581  -29.497  64.868  1.00 29.64           N
ATOM   2914  CA   LEU B  73     -16.609  -28.644  64.187  1.00 28.99           C
ATOM   2915  C    LEU B  73     -15.147  -28.948  64.509  1.00 29.17           C
ATOM   2916  O    LEU B  73     -14.244  -28.433  63.846  1.00 29.37           O
ATOM   2917  CB   LEU B  73     -16.894  -27.175  64.517  1.00 29.46           C
ATOM   2918  CG   LEU B  73     -18.202  -26.552  64.020  1.00 28.72           C
ATOM   2919  CD1  LEU B  73     -18.315  -25.150  64.586  1.00 27.59           C
ATOM   2920  CD2  LEU B  73     -18.233  -26.525  62.491  1.00 27.22           C
```

FIGURE 4-44 (COORDINATES)

```
ATOM   2921  N    LEU B  74     -14.910 -29.770  65.527  1.00 28.32           N
ATOM   2922  CA   LEU B  74     -13.549 -30.108  65.921  1.00 27.24           C
ATOM   2923  C    LEU B  74     -12.962 -31.144  64.983  1.00 27.83           C
ATOM   2924  O    LEU B  74     -12.604 -32.243  65.394  1.00 28.60           O
ATOM   2925  CB   LEU B  74     -13.537 -30.611  67.366  1.00 25.84           C
ATOM   2926  CG   LEU B  74     -13.922 -29.525  68.383  1.00 25.21           C
ATOM   2927  CD1  LEU B  74     -14.135 -30.131  69.760  1.00 24.73           C
ATOM   2928  CD2  LEU B  74     -12.834 -28.457  68.420  1.00 23.45           C
ATOM   2929  N    ILE B  75     -12.857 -30.766  63.714  1.00 28.08           N
ATOM   2930  CA   ILE B  75     -12.332 -31.634  62.671  1.00 27.92           C
ATOM   2931  C    ILE B  75     -11.422 -30.846  61.733  1.00 28.00           C
ATOM   2932  O    ILE B  75     -11.534 -29.626  61.647  1.00 26.97           O
ATOM   2933  CB   ILE B  75     -13.480 -32.223  61.831  1.00 27.59           C
ATOM   2934  CG1  ILE B  75     -14.322 -31.084  61.245  1.00 26.85           C
ATOM   2935  CG2  ILE B  75     -14.363 -33.103  62.697  1.00 27.60           C
ATOM   2936  CD1  ILE B  75     -15.384 -31.547  60.264  1.00 25.39           C
ATOM   2937  N    GLU B  76     -10.523 -31.549  61.044  1.00 28.27           N
ATOM   2938  CA   GLU B  76      -9.606 -30.926  60.086  1.00 28.80           C
ATOM   2939  C    GLU B  76     -10.486 -30.332  58.994  1.00 28.19           C
ATOM   2940  O    GLU B  76     -11.175 -31.063  58.283  1.00 28.16           O
ATOM   2941  CB   GLU B  76      -8.669 -31.980  59.502  1.00 30.24           C
ATOM   2942  CG   GLU B  76      -7.696 -31.457  58.474  1.00 33.68           C
ATOM   2943  CD   GLU B  76      -6.632 -32.480  58.116  1.00 35.94           C
ATOM   2944  OE1  GLU B  76      -6.994 -33.639  57.824  1.00 37.61           O
ATOM   2945  OE2  GLU B  76      -5.435 -32.127  58.120  1.00 37.24           O
ATOM   2946  N    ARG B  77     -10.452 -29.009  58.857  1.00 27.72           N
ATOM   2947  CA   ARG B  77     -11.317 -28.323  57.902  1.00 27.08           C
ATOM   2948  C    ARG B  77     -10.689 -27.166  57.116  1.00 27.36           C
ATOM   2949  O    ARG B  77     -11.317 -26.120  56.933  1.00 26.07           O
ATOM   2950  CB   ARG B  77     -12.552 -27.813  58.655  1.00 25.33           C
ATOM   2951  CG   ARG B  77     -12.194 -26.938  59.859  1.00 24.78           C
ATOM   2952  CD   ARG B  77     -13.400 -26.592  60.724  1.00 24.27           C
ATOM   2953  NE   ARG B  77     -13.064 -25.570  61.718  1.00 24.38           N
ATOM   2954  CZ   ARG B  77     -12.292 -25.774  62.784  1.00 23.90           C
ATOM   2955  NH1  ARG B  77     -11.770 -26.973  63.019  1.00 24.29           N
ATOM   2956  NH2  ARG B  77     -12.017 -24.769  63.602  1.00 21.66           N
ATOM   2957  N    TYR B  78      -9.460 -27.342  56.644  1.00 27.70           N
ATOM   2958  CA   TYR B  78      -8.837 -26.280  55.872  1.00 27.03           C
ATOM   2959  C    TYR B  78      -9.651 -26.122  54.582  1.00 25.75           C
ATOM   2960  O    TYR B  78     -10.408 -27.008  54.205  1.00 24.50           O
ATOM   2961  CB   TYR B  78      -7.368 -26.608  55.574  1.00 26.43           C
ATOM   2962  CG   TYR B  78      -7.142 -27.897  54.822  1.00 28.53           C
ATOM   2963  CD1  TYR B  78      -6.882 -29.093  55.500  1.00 27.97           C
ATOM   2964  CD2  TYR B  78      -7.169 -27.921  53.424  1.00 27.64           C
ATOM   2965  CE1  TYR B  78      -6.651 -30.282  54.803  1.00 27.93           C
ATOM   2966  CE2  TYR B  78      -6.942 -29.101  52.721  1.00 28.93           C
ATOM   2967  CZ   TYR B  78      -6.683 -30.276  53.414  1.00 29.46           C
ATOM   2968  OH   TYR B  78      -6.466 -31.438  52.711  1.00 30.33           O
ATOM   2969  N    PRO B  79      -9.509 -24.985  53.893  1.00 25.89           N
ATOM   2970  CA   PRO B  79     -10.265 -24.760  52.655  1.00 26.64           C
ATOM   2971  C    PRO B  79     -10.202 -25.876  51.612  1.00 27.19           C
ATOM   2972  O    PRO B  79      -9.132 -26.405  51.313  1.00 28.16           O
ATOM   2973  CB   PRO B  79      -9.679 -23.455  52.132  1.00 25.56           C
ATOM   2974  CG   PRO B  79      -9.310 -22.731  53.398  1.00 25.73           C
ATOM   2975  CD   PRO B  79      -8.644 -23.831  54.191  1.00 25.72           C
ATOM   2976  N    GLY B  80     -11.366 -26.227  51.068  1.00 27.33           N
ATOM   2977  CA   GLY B  80     -11.435 -27.242  50.031  1.00 27.44           C
ATOM   2978  C    GLY B  80     -11.378 -28.691  50.471  1.00 28.45           C
ATOM   2979  O    GLY B  80     -11.474 -29.595  49.637  1.00 28.05           O
ATOM   2980  N    SER B  81     -11.223 -28.925  51.771  1.00 28.48           N
ATOM   2981  CA   SER B  81     -11.154 -30.287  52.283  1.00 28.02           C
ATOM   2982  C    SER B  81     -12.556 -30.775  52.620  1.00 28.27           C
ATOM   2983  O    SER B  81     -13.482 -29.978  52.746  1.00 27.97           O
ATOM   2984  CB   SER B  81     -10.295 -30.334  53.546  1.00 27.87           C
ATOM   2985  OG   SER B  81     -10.971 -29.700  54.617  1.00 27.60           O
ATOM   2986  N    PRO B  82     -12.731 -32.098  52.761  1.00 28.73           N
ATOM   2987  CA   PRO B  82     -14.062 -32.616  53.096  1.00 28.35           C
ATOM   2988  C    PRO B  82     -14.566 -31.990  54.399  1.00 29.16           C
```

FIGURE 4-45 (COORDINATES)

```
ATOM   2989  O    PRO B  82     -15.750 -31.669  54.529  1.00 29.77           O
ATOM   2990  CB   PRO B  82     -13.820 -34.116  53.227  1.00 28.16           C
ATOM   2991  CG   PRO B  82     -12.728 -34.366  52.209  1.00 27.48           C
ATOM   2992  CD   PRO B  82     -11.793 -33.197  52.458  1.00 27.83           C
ATOM   2993  N    GLY B  83     -13.659 -31.814  55.359  1.00 28.91           N
ATOM   2994  CA   GLY B  83     -14.031 -31.225  56.637  1.00 28.73           C
ATOM   2995  C    GLY B  83     -14.624 -29.832  56.508  1.00 28.94           C
ATOM   2996  O    GLY B  83     -15.461 -29.422  57.315  1.00 28.93           O
ATOM   2997  N    SER B  84     -14.183 -29.097  55.492  1.00 28.91           N
ATOM   2998  CA   SER B  84     -14.680 -27.748  55.247  1.00 29.34           C
ATOM   2999  C    SER B  84     -16.159 -27.828  54.862  1.00 29.16           C
ATOM   3000  O    SER B  84     -16.995 -27.103  55.399  1.00 27.81           O
ATOM   3001  CB   SER B  84     -13.877 -27.088  54.113  1.00 28.69           C
ATOM   3002  OG   SER B  84     -14.397 -25.811  53.776  1.00 27.74           O
ATOM   3003  N    TYR B  85     -16.468 -28.719  53.926  1.00 30.16           N
ATOM   3004  CA   TYR B  85     -17.837 -28.903  53.465  1.00 31.46           C
ATOM   3005  C    TYR B  85     -18.713 -29.452  54.595  1.00 30.77           C
ATOM   3006  O    TYR B  85     -19.881 -29.083  54.721  1.00 31.05           O
ATOM   3007  CB   TYR B  85     -17.857 -29.860  52.278  1.00 33.67           C
ATOM   3008  CG   TYR B  85     -19.241 -30.185  51.781  1.00 36.52           C
ATOM   3009  CD1  TYR B  85     -20.016 -29.224  51.135  1.00 38.27           C
ATOM   3010  CD2  TYR B  85     -19.777 -31.456  51.952  1.00 38.40           C
ATOM   3011  CE1  TYR B  85     -21.295 -29.524  50.667  1.00 38.96           C
ATOM   3012  CE2  TYR B  85     -21.055 -31.766  51.491  1.00 40.42           C
ATOM   3013  CZ   TYR B  85     -21.805 -30.795  50.850  1.00 39.71           C
ATOM   3014  OH   TYR B  85     -23.065 -31.105  50.395  1.00 41.42           O
ATOM   3015  N    ALA B  86     -18.141 -30.332  55.412  1.00 29.30           N
ATOM   3016  CA   ALA B  86     -18.865 -30.917  56.533  1.00 28.07           C
ATOM   3017  C    ALA B  86     -19.219 -29.814  57.520  1.00 28.51           C
ATOM   3018  O    ALA B  86     -20.371 -29.700  57.955  1.00 28.77           O
ATOM   3019  CB   ALA B  86     -18.009 -31.973  57.209  1.00 27.08           C
ATOM   3020  N    ALA B  87     -18.220 -29.001  57.864  1.00 28.00           N
ATOM   3021  CA   ALA B  87     -18.401 -27.889  58.796  1.00 28.33           C
ATOM   3022  C    ALA B  87     -19.443 -26.905  58.271  1.00 28.30           C
ATOM   3023  O    ALA B  87     -20.314 -26.456  59.008  1.00 27.94           O
ATOM   3024  CB   ALA B  87     -17.077 -27.172  59.015  1.00 28.10           C
ATOM   3025  N    ARG B  88     -19.344 -26.582  56.988  1.00 29.34           N
ATOM   3026  CA   ARG B  88     -20.263 -25.657  56.340  1.00 30.43           C
ATOM   3027  C    ARG B  88     -21.700 -26.178  56.456  1.00 30.98           C
ATOM   3028  O    ARG B  88     -22.619 -25.430  56.793  1.00 30.93           O
ATOM   3029  CB   ARG B  88     -19.843 -25.481  54.872  1.00 30.70           C
ATOM   3030  CG   ARG B  88     -20.644 -24.447  54.100  1.00 33.50           C
ATOM   3031  CD   ARG B  88     -19.901 -23.935  52.861  1.00 33.55           C
ATOM   3032  NE   ARG B  88     -19.585 -24.979  51.886  1.00 34.18           N
ATOM   3033  CZ   ARG B  88     -18.366 -25.477  51.683  1.00 34.48           C
ATOM   3034  NH1  ARG B  88     -17.327 -25.034  52.387  1.00 33.00           N
ATOM   3035  NH2  ARG B  88     -18.184 -26.423  50.772  1.00 35.01           N
ATOM   3036  N    GLN B  89     -21.894 -27.465  56.191  1.00 32.16           N
ATOM   3037  CA   GLN B  89     -23.222 -28.061  56.290  1.00 33.03           C
ATOM   3038  C    GLN B  89     -23.740 -28.076  57.724  1.00 31.95           C
ATOM   3039  O    GLN B  89     -24.922 -27.865  57.964  1.00 31.74           O
ATOM   3040  CB   GLN B  89     -23.209 -29.488  55.764  1.00 35.79           C
ATOM   3041  CG   GLN B  89     -23.121 -29.602  54.267  1.00 40.75           C
ATOM   3042  CD   GLN B  89     -23.533 -30.979  53.805  1.00 44.69           C
ATOM   3043  OE1  GLN B  89     -22.937 -31.987  54.206  1.00 45.96           O
ATOM   3044  NE2  GLN B  89     -24.569 -31.038  52.966  1.00 45.35           N
ATOM   3045  N    HIS B  90     -22.853 -28.352  58.670  1.00 30.85           N
ATOM   3046  CA   HIS B  90     -23.221 -28.375  60.080  1.00 29.90           C
ATOM   3047  C    HIS B  90     -23.785 -27.017  60.481  1.00 30.48           C
ATOM   3048  O    HIS B  90     -24.884 -26.918  61.037  1.00 30.26           O
ATOM   3049  CB   HIS B  90     -21.992 -28.694  60.937  1.00 28.58           C
ATOM   3050  CG   HIS B  90     -22.223 -28.532  62.404  1.00 28.53           C
ATOM   3051  ND1  HIS B  90     -21.593 -27.561  63.153  1.00 29.68           N
ATOM   3052  CD2  HIS B  90     -23.048 -29.186  63.255  1.00 27.85           C
ATOM   3053  CE1  HIS B  90     -22.023 -27.621  64.400  1.00 28.00           C
ATOM   3054  NE2  HIS B  90     -22.908 -28.598  64.488  1.00 29.32           N
ATOM   3055  N    ILE B  91     -23.022 -25.970  60.184  1.00 31.39           N
ATOM   3056  CA   ILE B  91     -23.413 -24.607  60.509  1.00 31.97           C
```

FIGURE 4-46 (COORDINATES)

```
ATOM   3057  C   ILE B  91     -24.761 -24.249  59.890  1.00 32.86           C
ATOM   3058  O   ILE B  91     -25.603 -23.622  60.540  1.00 32.84           O
ATOM   3059  CB  ILE B  91     -22.324 -23.623  60.047  1.00 31.82           C
ATOM   3060  CG1 ILE B  91     -21.052 -23.880  60.860  1.00 32.24           C
ATOM   3061  CG2 ILE B  91     -22.803 -22.180  60.197  1.00 30.86           C
ATOM   3062  CD1 ILE B  91     -19.831 -23.119  60.388  1.00 32.46           C
ATOM   3063  N   MET B  92     -24.971 -24.664  58.644  1.00 33.35           N
ATOM   3064  CA  MET B  92     -26.226 -24.391  57.959  1.00 35.27           C
ATOM   3065  C   MET B  92     -27.397 -25.111  58.624  1.00 35.72           C
ATOM   3066  O   MET B  92     -28.405 -24.490  58.953  1.00 36.50           O
ATOM   3067  CB  MET B  92     -26.132 -24.799  56.480  1.00 35.72           C
ATOM   3068  CG  MET B  92     -25.220 -23.906  55.654  1.00 37.53           C
ATOM   3069  SD  MET B  92     -25.094 -24.406  53.934  1.00 39.62           S
ATOM   3070  CE  MET B  92     -26.454 -23.453  53.228  1.00 40.47           C
ATOM   3071  N   GLN B  93     -27.258 -26.417  58.826  1.00 36.31           N
ATOM   3072  CA  GLN B  93     -28.309 -27.222  59.447  1.00 37.25           C
ATOM   3073  C   GLN B  93     -28.690 -26.731  60.839  1.00 36.85           C
ATOM   3074  O   GLN B  93     -29.861 -26.742  61.198  1.00 37.31           O
ATOM   3075  CB  GLN B  93     -27.876 -28.691  59.523  1.00 38.81           C
ATOM   3076  CG  GLN B  93     -27.551 -29.298  58.162  1.00 42.93           C
ATOM   3077  CD  GLN B  93     -26.969 -30.699  58.250  1.00 45.09           C
ATOM   3078  OE1 GLN B  93     -26.083 -30.971  59.068  1.00 47.76           O
ATOM   3079  NE2 GLN B  93     -27.450 -31.592  57.394  1.00 46.05           N
ATOM   3080  N   ARG B  94     -27.711 -26.306  61.630  1.00 36.23           N
ATOM   3081  CA  ARG B  94     -28.012 -25.821  62.972  1.00 36.65           C
ATOM   3082  C   ARG B  94     -28.816 -24.527  62.932  1.00 37.09           C
ATOM   3083  O   ARG B  94     -29.653 -24.287  63.797  1.00 37.97           O
ATOM   3084  CB  ARG B  94     -26.723 -25.612  63.773  1.00 35.80           C
ATOM   3085  CG  ARG B  94     -26.021 -26.911  64.134  1.00 35.13           C
ATOM   3086  CD  ARG B  94     -26.839 -27.710  65.137  1.00 35.22           C
ATOM   3087  NE  ARG B  94     -26.798 -27.091  66.455  1.00 34.95           N
ATOM   3088  CZ  ARG B  94     -27.582 -27.427  67.472  1.00 34.77           C
ATOM   3089  NH1 ARG B  94     -28.489 -28.385  67.330  1.00 33.57           N
ATOM   3090  NH2 ARG B  94     -27.449 -26.803  68.634  1.00 34.68           N
ATOM   3091  N   ILE B  95     -28.568 -23.695  61.928  1.00 36.82           N
ATOM   3092  CA  ILE B  95     -29.292 -22.439  61.809  1.00 36.49           C
ATOM   3093  C   ILE B  95     -30.683 -22.661  61.218  1.00 37.51           C
ATOM   3094  O   ILE B  95     -31.648 -22.012  61.628  1.00 37.40           O
ATOM   3095  CB  ILE B  95     -28.518 -21.424  60.922  1.00 35.77           C
ATOM   3096  CG1 ILE B  95     -27.230 -20.991  61.629  1.00 34.99           C
ATOM   3097  CG2 ILE B  95     -29.381 -20.201  60.637  1.00 34.25           C
ATOM   3098  CD1 ILE B  95     -26.347 -20.104  60.797  1.00 33.19           C
ATOM   3099  N   GLN B  96     -30.787 -23.582  60.263  1.00 37.63           N
ATOM   3100  CA  GLN B  96     -32.064 -23.859  59.613  1.00 39.19           C
ATOM   3101  C   GLN B  96     -33.101 -24.483  60.542  1.00 39.66           C
ATOM   3102  O   GLN B  96     -34.305 -24.387  60.292  1.00 39.75           O
ATOM   3103  CB  GLN B  96     -31.855 -24.763  58.393  1.00 39.63           C
ATOM   3104  CG  GLN B  96     -31.021 -24.120  57.298  1.00 40.91           C
ATOM   3105  CD  GLN B  96     -30.784 -25.039  56.113  1.00 41.82           C
ATOM   3106  OE1 GLN B  96     -30.386 -26.195  56.275  1.00 43.35           O
ATOM   3107  NE2 GLN B  96     -31.016 -24.525  54.910  1.00 42.26           N
ATOM   3108  N   ARG B  97     -32.639 -25.113  61.615  1.00 40.06           N
ATOM   3109  CA  ARG B  97     -33.546 -25.746  62.561  1.00 40.91           C
ATOM   3110  C   ARG B  97     -34.111 -24.746  63.567  1.00 40.12           C
ATOM   3111  O   ARG B  97     -34.975 -25.092  64.376  1.00 39.94           O
ATOM   3112  CB  ARG B  97     -32.837 -26.883  63.310  1.00 43.16           C
ATOM   3113  CG  ARG B  97     -31.656 -26.441  64.159  1.00 46.15           C
ATOM   3114  CD  ARG B  97     -31.098 -27.594  64.989  1.00 48.86           C
ATOM   3115  NE  ARG B  97     -31.980 -27.961  66.097  1.00 52.03           N
ATOM   3116  CZ  ARG B  97     -32.235 -27.185  67.150  1.00 52.81           C
ATOM   3117  NH1 ARG B  97     -31.678 -25.986  67.252  1.00 52.49           N
ATOM   3118  NH2 ARG B  97     -33.049 -27.610  68.108  1.00 54.19           N
ATOM   3119  N   LEU B  98     -33.626 -23.511  63.520  1.00 38.83           N
ATOM   3120  CA  LEU B  98     -34.103 -22.483  64.437  1.00 38.39           C
ATOM   3121  C   LEU B  98     -35.401 -21.859  63.926  1.00 38.58           C
ATOM   3122  O   LEU B  98     -35.734 -21.977  62.744  1.00 38.80           O
ATOM   3123  CB  LEU B  98     -33.033 -21.403  64.626  1.00 37.07           C
ATOM   3124  CG  LEU B  98     -31.724 -21.889  65.259  1.00 36.32           C
```

FIGURE 4-47 (COORDINATES)

```
ATOM   3125  CD1 LEU B  98     -30.724 -20.756  65.298  1.00 35.38           C
ATOM   3126  CD2 LEU B  98     -31.991 -22.416  66.660  1.00 35.41           C
ATOM   3127  N   GLN B  99     -36.134 -21.201  64.816  1.00 38.43           N
ATOM   3128  CA  GLN B  99     -37.393 -20.580  64.434  1.00 39.58           C
ATOM   3129  C   GLN B  99     -37.239 -19.249  63.704  1.00 38.42           C
ATOM   3130  O   GLN B  99     -37.993 -18.963  62.776  1.00 37.34           O
ATOM   3131  CB  GLN B  99     -38.287 -20.399  65.663  1.00 41.67           C
ATOM   3132  CG  GLN B  99     -39.006 -21.670  66.088  1.00 46.14           C
ATOM   3133  CD  GLN B  99     -39.968 -21.432  67.241  1.00 50.19           C
ATOM   3134  OE1 GLN B  99     -39.550 -21.124  68.364  1.00 51.98           O
ATOM   3135  NE2 GLN B  99     -41.267 -21.564  66.967  1.00 52.03           N
ATOM   3136  N   ALA B 100     -36.269 -18.436  64.115  1.00 37.63           N
ATOM   3137  CA  ALA B 100     -36.053 -17.148  63.465  1.00 36.26           C
ATOM   3138  C   ALA B 100     -35.925 -17.345  61.957  1.00 35.84           C
ATOM   3139  O   ALA B 100     -35.486 -18.398  61.493  1.00 35.47           O
ATOM   3140  CB  ALA B 100     -34.810 -16.478  64.018  1.00 36.88           C
ATOM   3141  N   ASP B 101     -36.309 -16.321  61.204  1.00 35.20           N
ATOM   3142  CA  ASP B 101     -36.284 -16.366  59.748  1.00 35.33           C
ATOM   3143  C   ASP B 101     -34.913 -16.063  59.144  1.00 34.42           C
ATOM   3144  O   ASP B 101     -34.758 -15.119  58.370  1.00 33.17           O
ATOM   3145  CB  ASP B 101     -37.337 -15.390  59.211  1.00 37.35           C
ATOM   3146  CG  ASP B 101     -37.621 -15.585  57.742  1.00 39.23           C
ATOM   3147  OD1 ASP B 101     -37.498 -16.727  57.257  1.00 40.14           O
ATOM   3148  OD2 ASP B 101     -37.989 -14.596  57.073  1.00 42.73           O
ATOM   3149  N   TRP B 102     -33.924 -16.880  59.496  1.00 33.73           N
ATOM   3150  CA  TRP B 102     -32.567 -16.706  58.988  1.00 33.29           C
ATOM   3151  C   TRP B 102     -32.462 -17.007  57.496  1.00 33.74           C
ATOM   3152  O   TRP B 102     -32.957 -18.031  57.027  1.00 34.59           O
ATOM   3153  CB  TRP B 102     -31.589 -17.624  59.730  1.00 31.10           C
ATOM   3154  CG  TRP B 102     -31.337 -17.250  61.139  1.00 29.20           C
ATOM   3155  CD1 TRP B 102     -31.938 -17.770  62.245  1.00 29.36           C
ATOM   3156  CD2 TRP B 102     -30.406 -16.269  61.608  1.00 28.75           C
ATOM   3157  NE1 TRP B 102     -31.435 -17.176  63.382  1.00 27.95           N
ATOM   3158  CE2 TRP B 102     -30.494 -16.250  63.017  1.00 28.57           C
ATOM   3159  CE3 TRP B 102     -29.508 -15.403  60.975  1.00 28.28           C
ATOM   3160  CZ2 TRP B 102     -29.715 -15.397  63.803  1.00 28.35           C
ATOM   3161  CZ3 TRP B 102     -28.738 -14.557  61.754  1.00 28.34           C
ATOM   3162  CH2 TRP B 102     -28.847 -14.561  63.156  1.00 28.35           C
ATOM   3163  N   VAL B 103     -31.821 -16.114  56.749  1.00 33.90           N
ATOM   3164  CA  VAL B 103     -31.632 -16.340  55.323  1.00 33.92           C
ATOM   3165  C   VAL B 103     -30.168 -16.681  55.105  1.00 34.41           C
ATOM   3166  O   VAL B 103     -29.283 -15.885  55.414  1.00 33.99           O
ATOM   3167  CB  VAL B 103     -31.998 -15.104  54.484  1.00 34.23           C
ATOM   3168  CG1 VAL B 103     -31.711 -15.377  53.014  1.00 32.10           C
ATOM   3169  CG2 VAL B 103     -33.466 -14.772  54.672  1.00 33.24           C
ATOM   3170  N   LEU B 104     -29.924 -17.878  54.586  1.00 35.05           N
ATOM   3171  CA  LEU B 104     -28.572 -18.354  54.343  1.00 36.11           C
ATOM   3172  C   LEU B 104     -28.060 -18.072  52.944  1.00 36.73           C
ATOM   3173  O   LEU B 104     -28.775 -18.216  51.956  1.00 36.71           O
ATOM   3174  CB  LEU B 104     -28.493 -19.854  54.618  1.00 36.36           C
ATOM   3175  CG  LEU B 104     -28.560 -20.221  56.100  1.00 37.20           C
ATOM   3176  CD1 LEU B 104     -28.764 -21.727  56.254  1.00 37.01           C
ATOM   3177  CD2 LEU B 104     -27.282 -19.756  56.786  1.00 35.52           C
ATOM   3178  N   GLU B 105     -26.797 -17.681  52.876  1.00 37.93           N
ATOM   3179  CA  GLU B 105     -26.162 -17.364  51.613  1.00 38.90           C
ATOM   3180  C   GLU B 105     -24.742 -17.927  51.628  1.00 37.93           C
ATOM   3181  O   GLU B 105     -23.947 -17.598  52.508  1.00 37.75           O
ATOM   3182  CB  GLU B 105     -26.124 -15.845  51.440  1.00 41.83           C
ATOM   3183  CG  GLU B 105     -25.658 -15.353  50.084  1.00 47.51           C
ATOM   3184  CD  GLU B 105     -25.492 -13.838  50.051  1.00 51.04           C
ATOM   3185  OE1 GLU B 105     -26.289 -13.139  50.721  1.00 52.67           O
ATOM   3186  OE2 GLU B 105     -24.572 -13.347  49.349  1.00 53.07           O
ATOM   3187  N   ILE B 106     -24.439 -18.796  50.671  1.00 36.56           N
ATOM   3188  CA  ILE B 106     -23.108 -19.371  50.557  1.00 34.14           C
ATOM   3189  C   ILE B 106     -22.376 -18.544  49.506  1.00 33.77           C
ATOM   3190  O   ILE B 106     -22.737 -18.555  48.331  1.00 33.63           O
ATOM   3191  CB  ILE B 106     -23.147 -20.831  50.076  1.00 33.94           C
ATOM   3192  CG1 ILE B 106     -23.988 -21.678  51.030  1.00 34.55           C
```

FIGURE 4-48 (COORDINATES)

```
ATOM   3193  CG2 ILE B 106     -21.728 -21.385  49.992  1.00 32.10           C
ATOM   3194  CD1 ILE B 106     -23.419 -21.780  52.432  1.00 35.49           C
ATOM   3195  N   ASP B 107     -21.352 -17.822  49.937  1.00 32.59           N
ATOM   3196  CA  ASP B 107     -20.571 -16.984  49.042  1.00 31.31           C
ATOM   3197  C   ASP B 107     -19.334 -17.766  48.605  1.00 30.39           C
ATOM   3198  O   ASP B 107     -18.317 -17.785  49.295  1.00 29.86           O
ATOM   3199  CB  ASP B 107     -20.207 -15.687  49.777  1.00 31.54           C
ATOM   3200  CG  ASP B 107     -19.162 -14.876  49.061  1.00 32.76           C
ATOM   3201  OD1 ASP B 107     -19.221 -14.766  47.814  1.00 34.02           O
ATOM   3202  OD2 ASP B 107     -18.281 -14.333  49.761  1.00 33.52           O
ATOM   3203  N   THR B 108     -19.444 -18.427  47.455  1.00 29.28           N
ATOM   3204  CA  THR B 108     -18.361 -19.247  46.921  1.00 27.69           C
ATOM   3205  C   THR B 108     -17.577 -18.532  45.835  1.00 27.60           C
ATOM   3206  O   THR B 108     -18.139 -18.085  44.839  1.00 27.53           O
ATOM   3207  CB  THR B 108     -18.908 -20.572  46.361  1.00 26.86           C
ATOM   3208  OG1 THR B 108     -19.466 -21.335  47.434  1.00 27.60           O
ATOM   3209  CG2 THR B 108     -17.800 -21.386  45.694  1.00 26.58           C
ATOM   3210  N   PHE B 109     -16.269 -18.436  46.032  1.00 26.88           N
ATOM   3211  CA  PHE B 109     -15.411 -17.761  45.076  1.00 26.79           C
ATOM   3212  C   PHE B 109     -14.121 -18.531  44.875  1.00 26.92           C
ATOM   3213  O   PHE B 109     -13.765 -19.411  45.659  1.00 25.73           O
ATOM   3214  CB  PHE B 109     -15.070 -16.345  45.564  1.00 25.03           C
ATOM   3215  CG  PHE B 109     -14.381 -16.322  46.896  1.00 24.62           C
ATOM   3216  CD1 PHE B 109     -15.111 -16.471  48.074  1.00 24.59           C
ATOM   3217  CD2 PHE B 109     -12.994 -16.214  46.974  1.00 24.32           C
ATOM   3218  CE1 PHE B 109     -14.470 -16.514  49.319  1.00 23.67           C
ATOM   3219  CE2 PHE B 109     -12.339 -16.256  48.215  1.00 24.88           C
ATOM   3220  CZ  PHE B 109     -13.079 -16.407  49.388  1.00 23.98           C
ATOM   3221  N   LEU B 110     -13.417 -18.165  43.817  1.00 27.85           N
ATOM   3222  CA  LEU B 110     -12.156 -18.785  43.480  1.00 28.81           C
ATOM   3223  C   LEU B 110     -11.092 -17.731  43.712  1.00 29.53           C
ATOM   3224  O   LEU B 110     -11.276 -16.568  43.344  1.00 30.00           O
ATOM   3225  CB  LEU B 110     -12.158 -19.195  42.011  1.00 28.28           C
ATOM   3226  CG  LEU B 110     -11.091 -20.186  41.555  1.00 28.82           C
ATOM   3227  CD1 LEU B 110     -11.438 -21.584  42.073  1.00 25.58           C
ATOM   3228  CD2 LEU B 110     -11.022 -20.180  40.015  1.00 28.10           C
ATOM   3229  N   SER B 111      -9.989 -18.131  44.332  1.00 29.81           N
ATOM   3230  CA  SER B 111      -8.896 -17.213  44.597  1.00 30.14           C
ATOM   3231  C   SER B 111      -7.557 -17.910  44.413  1.00 30.41           C
ATOM   3232  O   SER B 111      -7.465 -19.139  44.457  1.00 29.25           O
ATOM   3233  CB  SER B 111      -9.004 -16.647  46.013  1.00 31.81           C
ATOM   3234  OG  SER B 111      -7.967 -15.712  46.268  1.00 35.57           O
ATOM   3235  N   GLN B 112      -6.525 -17.100  44.210  1.00 30.71           N
ATOM   3236  CA  GLN B 112      -5.162 -17.563  43.994  1.00 31.33           C
ATOM   3237  C   GLN B 112      -4.447 -17.830  45.315  1.00 30.42           C
ATOM   3238  O   GLN B 112      -4.547 -17.034  46.248  1.00 30.54           O
ATOM   3239  CB  GLN B 112      -4.404 -16.490  43.210  1.00 34.91           C
ATOM   3240  CG  GLN B 112      -2.922 -16.729  43.098  1.00 39.32           C
ATOM   3241  CD  GLN B 112      -2.588 -17.703  42.001  1.00 42.43           C
ATOM   3242  OE1 GLN B 112      -2.480 -17.323  40.827  1.00 43.81           O
ATOM   3243  NE2 GLN B 112      -2.436 -18.977  42.366  1.00 42.67           N
ATOM   3244  N   THR B 113      -3.721 -18.945  45.389  1.00 28.62           N
ATOM   3245  CA  THR B 113      -2.981 -19.305  46.596  1.00 27.17           C
ATOM   3246  C   THR B 113      -1.580 -19.794  46.230  1.00 27.28           C
ATOM   3247  O   THR B 113      -1.260 -19.954  45.055  1.00 27.15           O
ATOM   3248  CB  THR B 113      -3.684 -20.449  47.381  1.00 27.02           C
ATOM   3249  OG1 THR B 113      -3.329 -21.719  46.812  1.00 24.70           O
ATOM   3250  CG2 THR B 113      -5.202 -20.285  47.325  1.00 24.82           C
ATOM   3251  N   PRO B 114      -0.724 -20.033  47.240  1.00 27.93           N
ATOM   3252  CA  PRO B 114       0.640 -20.513  46.991  1.00 27.80           C
ATOM   3253  C   PRO B 114       0.637 -21.886  46.334  1.00 27.84           C
ATOM   3254  O   PRO B 114       1.687 -22.375  45.899  1.00 28.77           O
ATOM   3255  CB  PRO B 114       1.254 -20.553  48.389  1.00 27.38           C
ATOM   3256  CG  PRO B 114       0.579 -19.418  49.078  1.00 28.06           C
ATOM   3257  CD  PRO B 114      -0.868 -19.605  48.646  1.00 28.68           C
ATOM   3258  N   TYR B 115      -0.544 -22.499  46.266  1.00 27.21           N
ATOM   3259  CA  TYR B 115      -0.703 -23.820  45.664  1.00 28.06           C
ATOM   3260  C   TYR B 115      -1.661 -23.793  44.481  1.00 29.08           C
```

FIGURE 4-49 (COORDINATES)

```
ATOM   3261  O    TYR B 115      -2.208 -24.825  44.095  1.00 29.94           O
ATOM   3262  CB   TYR B 115      -1.213 -24.826  46.702  1.00 28.42           C
ATOM   3263  CG   TYR B 115      -0.293 -25.002  47.896  1.00 29.31           C
ATOM   3264  CD1  TYR B 115       1.024 -25.425  47.727  1.00 29.64           C
ATOM   3265  CD2  TYR B 115      -0.732 -24.721  49.193  1.00 29.61           C
ATOM   3266  CE1  TYR B 115       1.885 -25.560  48.819  1.00 30.88           C
ATOM   3267  CE2  TYR B 115       0.122 -24.858  50.294  1.00 30.00           C
ATOM   3268  CZ   TYR B 115       1.430 -25.276  50.094  1.00 30.59           C
ATOM   3269  OH   TYR B 115       2.286 -25.409  51.163  1.00 31.62           O
ATOM   3270  N    GLY B 116      -1.871 -22.614  43.910  1.00 29.26           N
ATOM   3271  CA   GLY B 116      -2.766 -22.503  42.774  1.00 30.18           C
ATOM   3272  C    GLY B 116      -4.152 -22.032  43.156  1.00 30.83           C
ATOM   3273  O    GLY B 116      -4.431 -21.732  44.322  1.00 30.82           O
ATOM   3274  N    TYR B 117      -5.028 -21.957  42.163  1.00 31.92           N
ATOM   3275  CA   TYR B 117      -6.396 -21.523  42.396  1.00 33.48           C
ATOM   3276  C    TYR B 117      -7.125 -22.525  43.270  1.00 32.51           C
ATOM   3277  O    TYR B 117      -6.930 -23.731  43.144  1.00 31.77           O
ATOM   3278  CB   TYR B 117      -7.152 -21.362  41.073  1.00 36.61           C
ATOM   3279  CG   TYR B 117      -6.550 -20.333  40.136  1.00 41.04           C
ATOM   3280  CD1  TYR B 117      -5.991 -19.150  40.625  1.00 43.32           C
ATOM   3281  CD2  TYR B 117      -6.561 -20.533  38.760  1.00 42.82           C
ATOM   3282  CE1  TYR B 117      -5.453 -18.193  39.761  1.00 44.96           C
ATOM   3283  CE2  TYR B 117      -6.032 -19.585  37.889  1.00 45.01           C
ATOM   3284  CZ   TYR B 117      -5.479 -18.420  38.395  1.00 45.60           C
ATOM   3285  OH   TYR B 117      -4.948 -17.494  37.522  1.00 47.19           O
ATOM   3286  N    ARG B 118      -7.961 -22.014  44.163  1.00 31.53           N
ATOM   3287  CA   ARG B 118      -8.737 -22.857  45.057  1.00 31.11           C
ATOM   3288  C    ARG B 118     -10.088 -22.223  45.343  1.00 29.93           C
ATOM   3289  O    ARG B 118     -10.244 -21.005  45.275  1.00 29.54           O
ATOM   3290  CB   ARG B 118      -7.988 -23.079  46.371  1.00 31.63           C
ATOM   3291  CG   ARG B 118      -6.675 -23.811  46.211  1.00 35.37           C
ATOM   3292  CD   ARG B 118      -6.070 -24.104  47.567  1.00 38.27           C
ATOM   3293  NE   ARG B 118      -6.856 -25.077  48.324  1.00 41.23           N
ATOM   3294  CZ   ARG B 118      -6.702 -26.395  48.239  1.00 42.11           C
ATOM   3295  NH1  ARG B 118      -5.784 -26.906  47.427  1.00 42.20           N
ATOM   3296  NH2  ARG B 118      -7.459 -27.202  48.977  1.00 42.09           N
ATOM   3297  N    SER B 119     -11.064 -23.058  45.661  1.00 28.51           N
ATOM   3298  CA   SER B 119     -12.393 -22.578  45.960  1.00 28.67           C
ATOM   3299  C    SER B 119     -12.555 -22.354  47.463  1.00 28.12           C
ATOM   3300  O    SER B 119     -12.038 -23.124  48.272  1.00 28.69           O
ATOM   3301  CB   SER B 119     -13.430 -23.586  45.465  1.00 29.76           C
ATOM   3302  OG   SER B 119     -14.742 -23.094  45.671  1.00 31.82           O
ATOM   3303  N    PHE B 120     -13.265 -21.287  47.820  1.00 26.49           N
ATOM   3304  CA   PHE B 120     -13.535 -20.931  49.212  1.00 25.82           C
ATOM   3305  C    PHE B 120     -15.036 -20.655  49.290  1.00 25.93           C
ATOM   3306  O    PHE B 120     -15.644 -20.280  48.286  1.00 25.48           O
ATOM   3307  CB   PHE B 120     -12.785 -19.652  49.599  1.00 24.89           C
ATOM   3308  CG   PHE B 120     -11.288 -19.773  49.549  1.00 23.58           C
ATOM   3309  CD1  PHE B 120     -10.557 -20.018  50.711  1.00 22.45           C
ATOM   3310  CD2  PHE B 120     -10.604 -19.627  48.344  1.00 22.29           C
ATOM   3311  CE1  PHE B 120      -9.158 -20.114  50.675  1.00 22.81           C
ATOM   3312  CE2  PHE B 120      -9.205 -19.721  48.293  1.00 21.89           C
ATOM   3313  CZ   PHE B 120      -8.482 -19.964  49.459  1.00 21.78           C
ATOM   3314  N    SER B 121     -15.635 -20.838  50.465  1.00 24.96           N
ATOM   3315  CA   SER B 121     -17.064 -20.577  50.624  1.00 25.07           C
ATOM   3316  C    SER B 121     -17.388 -19.881  51.942  1.00 26.03           C
ATOM   3317  O    SER B 121     -17.308 -20.503  53.002  1.00 25.61           O
ATOM   3318  CB   SER B 121     -17.870 -21.881  50.558  1.00 24.21           C
ATOM   3319  OG   SER B 121     -17.838 -22.464  49.266  1.00 26.35           O
ATOM   3320  N    ASN B 122     -17.737 -18.594  51.886  1.00 25.60           N
ATOM   3321  CA   ASN B 122     -18.115 -17.883  53.105  1.00 25.97           C
ATOM   3322  C    ASN B 122     -19.564 -18.246  53.418  1.00 26.09           C
ATOM   3323  O    ASN B 122     -20.353 -18.528  52.516  1.00 25.42           O
ATOM   3324  CB   ASN B 122     -18.029 -16.365  52.937  1.00 25.01           C
ATOM   3325  CG   ASN B 122     -16.607 -15.860  52.847  1.00 26.58           C
ATOM   3326  OD1  ASN B 122     -15.736 -16.254  53.633  1.00 24.71           O
ATOM   3327  ND2  ASN B 122     -16.364 -14.967  51.891  1.00 25.11           N
ATOM   3328  N    ILE B 123     -19.912 -18.240  54.697  1.00 26.61           N
```

FIGURE 4-50 (COORDINATES)

```
ATOM   3329  CA  ILE B 123     -21.276 -18.548  55.098  1.00 27.95           C
ATOM   3330  C   ILE B 123     -21.875 -17.290  55.703  1.00 28.65           C
ATOM   3331  O   ILE B 123     -21.361 -16.767  56.697  1.00 29.56           O
ATOM   3332  CB  ILE B 123     -21.328 -19.676  56.160  1.00 28.55           C
ATOM   3333  CG1 ILE B 123     -20.679 -20.948  55.611  1.00 27.86           C
ATOM   3334  CG2 ILE B 123     -22.779 -19.959  56.542  1.00 28.95           C
ATOM   3335  CD1 ILE B 123     -20.451 -22.007  56.661  1.00 28.84           C
ATOM   3336  N   ILE B 124     -22.942 -16.786  55.092  1.00 28.44           N
ATOM   3337  CA  ILE B 124     -23.604 -15.596  55.610  1.00 28.46           C
ATOM   3338  C   ILE B 124     -25.023 -15.981  56.021  1.00 28.34           C
ATOM   3339  O   ILE B 124     -25.770 -16.576  55.245  1.00 28.09           O
ATOM   3340  CB  ILE B 124     -23.667 -14.445  54.566  1.00 28.29           C
ATOM   3341  CG1 ILE B 124     -22.255 -14.031  54.132  1.00 28.79           C
ATOM   3342  CG2 ILE B 124     -24.365 -13.238  55.168  1.00 26.93           C
ATOM   3343  CD1 ILE B 124     -21.722 -14.789  52.937  1.00 28.90           C
ATOM   3344  N   SER B 125     -25.369 -15.649  57.258  1.00 28.39           N
ATOM   3345  CA  SER B 125     -26.681 -15.940  57.821  1.00 28.73           C
ATOM   3346  C   SER B 125     -27.286 -14.593  58.205  1.00 29.34           C
ATOM   3347  O   SER B 125     -26.789 -13.920  59.106  1.00 30.73           O
ATOM   3348  CB  SER B 125     -26.519 -16.827  59.059  1.00 28.11           C
ATOM   3349  OG  SER B 125     -27.773 -17.286  59.538  1.00 29.79           O
ATOM   3350  N   THR B 126     -28.357 -14.200  57.528  1.00 29.88           N
ATOM   3351  CA  THR B 126     -28.973 -12.904  57.788  1.00 30.13           C
ATOM   3352  C   THR B 126     -30.460 -12.896  58.150  1.00 31.06           C
ATOM   3353  O   THR B 126     -31.266 -13.637  57.583  1.00 30.14           O
ATOM   3354  CB  THR B 126     -28.805 -11.979  56.569  1.00 29.86           C
ATOM   3355  OG1 THR B 126     -27.432 -11.966  56.158  1.00 29.62           O
ATOM   3356  CG2 THR B 126     -29.240 -10.566  56.910  1.00 29.18           C
ATOM   3357  N   LEU B 127     -30.804 -12.044  59.111  1.00 32.00           N
ATOM   3358  CA  LEU B 127     -32.191 -11.861  59.523  1.00 33.06           C
ATOM   3359  C   LEU B 127     -32.608 -10.549  58.876  1.00 33.49           C
ATOM   3360  O   LEU B 127     -31.928  -9.534  59.038  1.00 33.41           O
ATOM   3361  CB  LEU B 127     -32.315 -11.734  61.047  1.00 32.59           C
ATOM   3362  CG  LEU B 127     -32.205 -13.019  61.878  1.00 32.63           C
ATOM   3363  CD1 LEU B 127     -32.334 -12.672  63.362  1.00 32.89           C
ATOM   3364  CD2 LEU B 127     -33.289 -14.015  61.454  1.00 31.19           C
ATOM   3365  N   ASN B 128     -33.703 -10.575  58.125  1.00 33.98           N
ATOM   3366  CA  ASN B 128     -34.197  -9.371  57.470  1.00 34.37           C
ATOM   3367  C   ASN B 128     -33.151  -8.864  56.485  1.00 35.31           C
ATOM   3368  O   ASN B 128     -32.595  -7.784  56.659  1.00 34.80           O
ATOM   3369  CB  ASN B 128     -34.494  -8.299  58.521  1.00 34.28           C
ATOM   3370  CG  ASN B 128     -35.502  -8.766  59.561  1.00 35.26           C
ATOM   3371  OD1 ASN B 128     -36.694  -8.871  59.275  1.00 37.59           O
ATOM   3372  ND2 ASN B 128     -35.026  -9.064  60.768  1.00 32.85           N
ATOM   3373  N   PRO B 129     -32.874  -9.646  55.428  1.00 36.16           N
ATOM   3374  CA  PRO B 129     -31.888  -9.290  54.402  1.00 37.09           C
ATOM   3375  C   PRO B 129     -32.031  -7.843  53.946  1.00 38.24           C
ATOM   3376  O   PRO B 129     -31.050  -7.183  53.603  1.00 38.39           O
ATOM   3377  CB  PRO B 129     -32.192 -10.275  53.279  1.00 36.37           C
ATOM   3378  CG  PRO B 129     -32.680 -11.472  54.016  1.00 36.98           C
ATOM   3379  CD  PRO B 129     -33.594 -10.874  55.052  1.00 35.64           C
ATOM   3380  N   THR B 130     -33.268  -7.363  53.955  1.00 39.46           N
ATOM   3381  CA  THR B 130     -33.585  -6.003  53.542  1.00 41.29           C
ATOM   3382  C   THR B 130     -33.398  -4.994  54.677  1.00 40.56           C
ATOM   3383  O   THR B 130     -33.467  -3.791  54.449  1.00 41.79           O
ATOM   3384  CB  THR B 130     -35.040  -5.951  52.990  1.00 42.58           C
ATOM   3385  OG1 THR B 130     -35.060  -6.537  51.684  1.00 43.57           O
ATOM   3386  CG2 THR B 130     -35.565  -4.524  52.910  1.00 44.69           C
ATOM   3387  N   ALA B 131     -33.151  -5.481  55.889  0.00 39.71           N
ATOM   3388  CA  ALA B 131     -32.943  -4.593  57.028  0.00 38.42           C
ATOM   3389  C   ALA B 131     -31.715  -3.728  56.762  0.00 37.62           C
ATOM   3390  O   ALA B 131     -30.581  -4.152  56.973  0.00 37.44           O
ATOM   3391  CB  ALA B 131     -32.750  -5.402  58.303  0.00 38.59           C
ATOM   3392  N   LYS B 132     -31.958  -2.511  56.293  1.00 36.08           N
ATOM   3393  CA  LYS B 132     -30.897  -1.561  55.968  1.00 36.34           C
ATOM   3394  C   LYS B 132     -29.655  -1.621  56.851  1.00 35.04           C
ATOM   3395  O   LYS B 132     -28.532  -1.490  56.364  1.00 34.09           O
ATOM   3396  CB  LYS B 132     -31.442  -0.129  55.981  1.00 37.35           C
```

FIGURE 4-51 (COORDINATES)

```
ATOM   3397  CG   LYS B 132     -32.477    0.144   54.902  1.00 41.04           C
ATOM   3398  CD   LYS B 132     -32.714    1.641   54.690  1.00 43.05           C
ATOM   3399  CE   LYS B 132     -33.391    2.295   55.875  1.00 44.69           C
ATOM   3400  NZ   LYS B 132     -34.793    1.813   56.056  1.00 48.08           N
ATOM   3401  N    ARG B 133     -29.863   -1.814   58.147  1.00 33.62           N
ATOM   3402  CA   ARG B 133     -28.768   -1.879   59.105  1.00 31.76           C
ATOM   3403  C    ARG B 133     -28.701   -3.227   59.805  1.00 30.72           C
ATOM   3404  O    ARG B 133     -29.730   -3.814   60.151  1.00 30.89           O
ATOM   3405  CB   ARG B 133     -28.936   -0.784   60.160  1.00 31.00           C
ATOM   3406  CG   ARG B 133     -28.810    0.618   59.624  1.00 30.41           C
ATOM   3407  CD   ARG B 133     -29.273    1.615   60.664  1.00 31.49           C
ATOM   3408  NE   ARG B 133     -28.565    1.466   61.930  1.00 30.97           N
ATOM   3409  CZ   ARG B 133     -29.055    1.874   63.094  1.00 31.93           C
ATOM   3410  NH1  ARG B 133     -30.250    2.450   63.137  1.00 33.74           N
ATOM   3411  NH2  ARG B 133     -28.362    1.707   64.209  1.00 30.06           N
ATOM   3412  N    HIS B 134     -27.487   -3.716   60.018  1.00 28.96           N
ATOM   3413  CA   HIS B 134     -27.311   -4.983   60.707  1.00 28.39           C
ATOM   3414  C    HIS B 134     -26.124   -4.969   61.652  1.00 27.60           C
ATOM   3415  O    HIS B 134     -25.092   -4.364   61.365  1.00 28.20           O
ATOM   3416  CB   HIS B 134     -27.100   -6.138   59.719  1.00 28.89           C
ATOM   3417  CG   HIS B 134     -28.341   -6.587   59.017  1.00 29.83           C
ATOM   3418  ND1  HIS B 134     -28.728   -6.088   57.790  1.00 30.92           N
ATOM   3419  CD2  HIS B 134     -29.259   -7.527   59.346  1.00 29.94           C
ATOM   3420  CE1  HIS B 134     -29.827   -6.706   57.392  1.00 29.93           C
ATOM   3421  NE2  HIS B 134     -30.170   -7.584   58.318  1.00 29.91           N
ATOM   3422  N    LEU B 135     -26.289   -5.625   62.794  1.00 26.86           N
ATOM   3423  CA   LEU B 135     -25.203   -5.780   63.753  1.00 25.58           C
ATOM   3424  C    LEU B 135     -24.569   -7.061   63.215  1.00 25.13           C
ATOM   3425  O    LEU B 135     -25.278   -8.024   62.927  1.00 23.59           O
ATOM   3426  CB   LEU B 135     -25.749   -6.022   65.166  1.00 25.26           C
ATOM   3427  CG   LEU B 135     -24.743   -6.564   66.186  1.00 24.18           C
ATOM   3428  CD1  LEU B 135     -23.624   -5.539   66.384  1.00 25.01           C
ATOM   3429  CD2  LEU B 135     -25.440   -6.876   67.509  1.00 23.27           C
ATOM   3430  N    VAL B 136     -23.254   -7.081   63.057  1.00 25.04           N
ATOM   3431  CA   VAL B 136     -22.613   -8.272   62.518  1.00 25.71           C
ATOM   3432  C    VAL B 136     -21.676   -8.992   63.480  1.00 26.29           C
ATOM   3433  O    VAL B 136     -20.778   -8.383   64.059  1.00 26.91           O
ATOM   3434  CB   VAL B 136     -21.808   -7.941   61.225  1.00 26.39           C
ATOM   3435  CG1  VAL B 136     -21.286   -9.223   60.592  1.00 24.82           C
ATOM   3436  CG2  VAL B 136     -22.681   -7.171   60.237  1.00 24.18           C
ATOM   3437  N    LEU B 137     -21.906  -10.292   63.652  1.00 27.21           N
ATOM   3438  CA   LEU B 137     -21.055  -11.126   64.495  1.00 27.40           C
ATOM   3439  C    LEU B 137     -20.357  -12.044   63.504  1.00 27.14           C
ATOM   3440  O    LEU B 137     -20.983  -12.538   62.561  1.00 26.54           O
ATOM   3441  CB   LEU B 137     -21.875  -11.959   65.490  1.00 28.51           C
ATOM   3442  CG   LEU B 137     -22.794  -11.219   66.465  1.00 30.46           C
ATOM   3443  CD1  LEU B 137     -23.275  -12.193   67.524  1.00 32.01           C
ATOM   3444  CD2  LEU B 137     -22.069  -10.055   67.121  1.00 30.60           C
ATOM   3445  N    ALA B 138     -19.061  -12.264   63.706  1.00 27.21           N
ATOM   3446  CA   ALA B 138     -18.306  -13.101   62.787  1.00 24.89           C
ATOM   3447  C    ALA B 138     -17.115  -13.818   63.403  1.00 24.43           C
ATOM   3448  O    ALA B 138     -16.683  -13.519   64.519  1.00 24.16           O
ATOM   3449  CB   ALA B 138     -17.842  -12.260   61.613  1.00 25.07           C
ATOM   3450  N    CYS B 139     -16.591  -14.773   62.645  1.00 23.95           N
ATOM   3451  CA   CYS B 139     -15.432  -15.565   63.034  1.00 23.95           C
ATOM   3452  C    CYS B 139     -15.094  -16.317   61.759  1.00 23.52           C
ATOM   3453  O    CYS B 139     -15.807  -16.179   60.760  1.00 24.00           O
ATOM   3454  CB   CYS B 139     -15.792  -16.562   64.150  1.00 24.09           C
ATOM   3455  SG   CYS B 139     -16.733  -18.029   63.605  1.00 24.75           S
ATOM   3456  N    HIS B 140     -14.011  -17.082   61.762  1.00 22.05           N
ATOM   3457  CA   HIS B 140     -13.677  -17.854   60.572  1.00 23.13           C
ATOM   3458  C    HIS B 140     -13.920  -19.329   60.911  1.00 23.59           C
ATOM   3459  O    HIS B 140     -13.697  -19.752   62.048  1.00 23.15           O
ATOM   3460  CB   HIS B 140     -12.224  -17.595   60.142  1.00 21.94           C
ATOM   3461  CG   HIS B 140     -11.196  -18.230   61.025  1.00 21.87           C
ATOM   3462  ND1  HIS B 140     -10.556  -19.403   60.692  1.00 21.47           N
ATOM   3463  CD2  HIS B 140     -10.694  -17.855   62.225  1.00 22.14           C
ATOM   3464  CE1  HIS B 140      -9.704  -19.726   61.651  1.00 22.39           C
```

FIGURE 4-52 (COORDINATES)

```
ATOM   3465  NE2 HIS B 140      -9.769 -18.803  62.593  1.00 22.31           N
ATOM   3466  N   TYR B 141     -14.411 -20.109  59.950  1.00 23.93           N
ATOM   3467  CA  TYR B 141     -14.677 -21.512  60.238  1.00 23.67           C
ATOM   3468  C   TYR B 141     -13.662 -22.493  59.667  1.00 24.08           C
ATOM   3469  O   TYR B 141     -13.768 -23.699  59.896  1.00 24.62           O
ATOM   3470  CB  TYR B 141     -16.092 -21.907  59.798  1.00 22.81           C
ATOM   3471  CG  TYR B 141     -16.281 -22.127  58.311  1.00 24.53           C
ATOM   3472  CD1 TYR B 141     -16.490 -21.056  57.437  1.00 24.22           C
ATOM   3473  CD2 TYR B 141     -16.273 -23.416  57.780  1.00 25.49           C
ATOM   3474  CE1 TYR B 141     -16.691 -21.275  56.069  1.00 24.98           C
ATOM   3475  CE2 TYR B 141     -16.470 -23.646  56.420  1.00 25.36           C
ATOM   3476  CZ  TYR B 141     -16.680 -22.576  55.569  1.00 25.84           C
ATOM   3477  OH  TYR B 141     -16.881 -22.819  54.223  1.00 27.59           O
ATOM   3478  N   ASP B 142     -12.676 -21.993  58.931  1.00 23.77           N
ATOM   3479  CA  ASP B 142     -11.658 -22.880  58.380  1.00 23.13           C
ATOM   3480  C   ASP B 142     -10.625 -23.125  59.466  1.00 22.30           C
ATOM   3481  O   ASP B 142     -10.566 -22.385  60.444  1.00 20.88           O
ATOM   3482  CB  ASP B 142     -10.969 -22.249  57.160  1.00 23.61           C
ATOM   3483  CG  ASP B 142     -10.199 -20.985  57.508  1.00 24.96           C
ATOM   3484  OD1 ASP B 142     -10.814 -20.061  58.082  1.00 25.08           O
ATOM   3485  OD2 ASP B 142      -8.984 -20.911  57.210  1.00 24.20           O
ATOM   3486  N   SER B 143      -9.830 -24.177  59.299  1.00 22.26           N
ATOM   3487  CA  SER B 143      -8.767 -24.493  60.243  1.00 22.95           C
ATOM   3488  C   SER B 143      -7.475 -24.402  59.444  1.00 23.42           C
ATOM   3489  O   SER B 143      -7.447 -24.729  58.258  1.00 22.69           O
ATOM   3490  CB  SER B 143      -8.943 -25.902  60.824  1.00 24.07           C
ATOM   3491  OG  SER B 143      -8.959 -26.898  59.814  1.00 25.78           O
ATOM   3492  N   LYS B 144      -6.409 -23.942  60.081  1.00 24.03           N
ATOM   3493  CA  LYS B 144      -5.141 -23.793  59.386  1.00 24.13           C
ATOM   3494  C   LYS B 144      -4.637 -25.114  58.827  1.00 25.69           C
ATOM   3495  O   LYS B 144      -4.661 -26.142  59.501  1.00 26.24           O
ATOM   3496  CB  LYS B 144      -4.098 -23.191  60.326  1.00 23.67           C
ATOM   3497  CG  LYS B 144      -2.774 -22.857  59.664  1.00 22.42           C
ATOM   3498  CD  LYS B 144      -1.903 -22.002  60.573  1.00 20.81           C
ATOM   3499  CE  LYS B 144      -0.571 -21.686  59.904  1.00 21.82           C
ATOM   3500  NZ  LYS B 144      -0.738 -20.897  58.647  1.00 21.52           N
ATOM   3501  N   TYR B 145      -4.180 -25.079  57.584  1.00 26.90           N
ATOM   3502  CA  TYR B 145      -3.657 -26.265  56.934  1.00 28.15           C
ATOM   3503  C   TYR B 145      -2.276 -26.632  57.481  1.00 28.90           C
ATOM   3504  O   TYR B 145      -1.335 -25.835  57.422  1.00 29.25           O
ATOM   3505  CB  TYR B 145      -3.582 -26.029  55.430  1.00 29.06           C
ATOM   3506  CG  TYR B 145      -2.948 -27.167  54.685  1.00 31.93           C
ATOM   3507  CD1 TYR B 145      -1.607 -27.118  54.311  1.00 32.91           C
ATOM   3508  CD2 TYR B 145      -3.682 -28.316  54.378  1.00 32.10           C
ATOM   3509  CE1 TYR B 145      -1.012 -28.187  53.650  1.00 34.35           C
ATOM   3510  CE2 TYR B 145      -3.100 -29.386  53.720  1.00 33.61           C
ATOM   3511  CZ  TYR B 145      -1.765 -29.318  53.359  1.00 34.93           C
ATOM   3512  OH  TYR B 145      -1.180 -30.379  52.710  1.00 36.84           O
ATOM   3513  N   PHE B 146      -2.168 -27.838  58.027  1.00 28.95           N
ATOM   3514  CA  PHE B 146      -0.915 -28.338  58.588  1.00 29.33           C
ATOM   3515  C   PHE B 146      -0.739 -29.799  58.201  1.00 29.99           C
ATOM   3516  O   PHE B 146      -1.717 -30.503  57.942  1.00 29.86           O
ATOM   3517  CB  PHE B 146      -0.925 -28.267  60.124  1.00 28.70           C
ATOM   3518  CG  PHE B 146      -0.553 -26.918  60.699  1.00 29.47           C
ATOM   3519  CD1 PHE B 146       0.647 -26.297  60.354  1.00 30.10           C
ATOM   3520  CD2 PHE B 146      -1.373 -26.301  61.642  1.00 28.48           C
ATOM   3521  CE1 PHE B 146       1.024 -25.082  60.947  1.00 29.47           C
ATOM   3522  CE2 PHE B 146      -1.008 -25.091  62.238  1.00 28.16           C
ATOM   3523  CZ  PHE B 146       0.193 -24.482  61.891  1.00 28.92           C
ATOM   3524  N   SER B 147       0.508 -30.257  58.159  1.00 31.20           N
ATOM   3525  CA  SER B 147       0.772 -31.660  57.880  1.00 32.49           C
ATOM   3526  C   SER B 147       0.412 -32.301  59.217  1.00 33.32           C
ATOM   3527  O   SER B 147       0.140 -31.588  60.184  1.00 32.70           O
ATOM   3528  CB  SER B 147       2.250 -31.883  57.562  1.00 32.50           C
ATOM   3529  OG  SER B 147       3.056 -31.510  58.666  1.00 35.59           O
ATOM   3530  N   HIS B 148       0.404 -33.625  59.296  1.00 35.44           N
ATOM   3531  CA  HIS B 148       0.043 -34.270  60.556  1.00 36.69           C
ATOM   3532  C   HIS B 148       1.214 -34.494  61.505  1.00 37.82           C
```

FIGURE 4-53 (COORDINATES)

```
ATOM   3533  O    HIS B 148       1.628 -35.627  61.760  1.00 37.41           O
ATOM   3534  CB   HIS B 148      -0.695 -35.578  60.276  1.00 36.31           C
ATOM   3535  CG   HIS B 148      -1.961 -35.384  59.504  1.00 36.91           C
ATOM   3536  ND1  HIS B 148      -2.845 -34.362  59.780  1.00 36.63           N
ATOM   3537  CD2  HIS B 148      -2.487 -36.064  58.459  1.00 36.57           C
ATOM   3538  CE1  HIS B 148      -3.860 -34.421  58.938  1.00 36.07           C
ATOM   3539  NE2  HIS B 148      -3.667 -35.445  58.126  1.00 37.05           N
ATOM   3540  N    TRP B 149       1.727 -33.384  62.026  1.00 39.48           N
ATOM   3541  CA   TRP B 149       2.844 -33.372  62.962  1.00 41.37           C
ATOM   3542  C    TRP B 149       2.578 -34.322  64.128  1.00 41.24           C
ATOM   3543  O    TRP B 149       1.502 -34.290  64.733  1.00 41.29           O
ATOM   3544  CB   TRP B 149       3.042 -31.951  63.503  1.00 43.94           C
ATOM   3545  CG   TRP B 149       4.280 -31.770  64.335  1.00 47.46           C
ATOM   3546  CD1  TRP B 149       5.561 -31.571  63.880  1.00 48.45           C
ATOM   3547  CD2  TRP B 149       4.359 -31.760  65.768  1.00 48.61           C
ATOM   3548  NE1  TRP B 149       6.427 -31.432  64.944  1.00 49.49           N
ATOM   3549  CE2  TRP B 149       5.718 -31.546  66.112  1.00 49.37           C
ATOM   3550  CE3  TRP B 149       3.414 -31.911  66.796  1.00 49.70           C
ATOM   3551  CZ2  TRP B 149       6.154 -31.479  67.443  1.00 49.82           C
ATOM   3552  CZ3  TRP B 149       3.849 -31.846  68.124  1.00 50.00           C
ATOM   3553  CH2  TRP B 149       5.209 -31.631  68.432  1.00 50.52           C
ATOM   3554  N    ASN B 150       3.557 -35.165  64.441  1.00 40.19           N
ATOM   3555  CA   ASN B 150       3.420 -36.108  65.543  1.00 39.51           C
ATOM   3556  C    ASN B 150       2.172 -36.963  65.455  1.00 38.14           C
ATOM   3557  O    ASN B 150       1.672 -37.441  66.471  1.00 38.49           O
ATOM   3558  CB   ASN B 150       3.429 -35.364  66.879  1.00 41.41           C
ATOM   3559  CG   ASN B 150       4.827 -35.193  67.434  1.00 43.25           C
ATOM   3560  OD1  ASN B 150       5.752 -34.830  66.708  1.00 43.95           O
ATOM   3561  ND2  ASN B 150       4.989 -35.455  68.729  1.00 44.63           N
ATOM   3562  N    ASN B 151       1.671 -37.153  64.241  1.00 35.70           N
ATOM   3563  CA   ASN B 151       0.486 -37.968  64.031  1.00 34.59           C
ATOM   3564  C    ASN B 151      -0.744 -37.363  64.696  1.00 33.17           C
ATOM   3565  O    ASN B 151      -1.643 -38.074  65.144  1.00 32.74           O
ATOM   3566  CB   ASN B 151       0.732 -39.390  64.551  1.00 34.40           C
ATOM   3567  CG   ASN B 151       1.988 -40.013  63.962  1.00 34.29           C
ATOM   3568  OD1  ASN B 151       2.158 -40.057  62.744  1.00 33.74           O
ATOM   3569  ND2  ASN B 151       2.872 -40.498  64.827  1.00 33.98           N
ATOM   3570  N    ARG B 152      -0.770 -36.038  64.763  1.00 32.65           N
ATOM   3571  CA   ARG B 152      -1.898 -35.331  65.345  1.00 31.48           C
ATOM   3572  C    ARG B 152      -2.504 -34.493  64.233  1.00 30.47           C
ATOM   3573  O    ARG B 152      -1.851 -34.225  63.229  1.00 31.07           O
ATOM   3574  CB   ARG B 152      -1.434 -34.449  66.507  1.00 31.80           C
ATOM   3575  CG   ARG B 152      -0.756 -35.239  67.631  1.00 33.22           C
ATOM   3576  CD   ARG B 152      -0.266 -34.336  68.758  1.00 33.12           C
ATOM   3577  NE   ARG B 152      -1.363 -33.816  69.569  1.00 34.23           N
ATOM   3578  CZ   ARG B 152      -1.221 -32.911  70.534  1.00 33.99           C
ATOM   3579  NH1  ARG B 152      -0.025 -32.413  70.816  1.00 33.31           N
ATOM   3580  NH2  ARG B 152      -2.278 -32.511  71.226  1.00 34.46           N
ATOM   3581  N    VAL B 153      -3.759 -34.098  64.400  1.00 29.62           N
ATOM   3582  CA   VAL B 153      -4.442 -33.296  63.400  1.00 29.11           C
ATOM   3583  C    VAL B 153      -4.807 -31.950  64.008  1.00 28.55           C
ATOM   3584  O    VAL B 153      -5.395 -31.896  65.088  1.00 28.27           O
ATOM   3585  CB   VAL B 153      -5.729 -33.996  62.919  1.00 29.34           C
ATOM   3586  CG1  VAL B 153      -6.482 -33.097  61.973  1.00 29.79           C
ATOM   3587  CG2  VAL B 153      -5.379 -35.316  62.229  1.00 30.46           C
ATOM   3588  N    PHE B 154      -4.456 -30.864  63.324  1.00 27.30           N
ATOM   3589  CA   PHE B 154      -4.780 -29.535  63.835  1.00 25.60           C
ATOM   3590  C    PHE B 154      -6.257 -29.261  63.602  1.00 25.76           C
ATOM   3591  O    PHE B 154      -6.740 -29.355  62.471  1.00 24.66           O
ATOM   3592  CB   PHE B 154      -3.954 -28.455  63.140  1.00 24.58           C
ATOM   3593  CG   PHE B 154      -4.208 -27.078  63.677  1.00 24.76           C
ATOM   3594  CD1  PHE B 154      -3.720 -26.707  64.926  1.00 22.92           C
ATOM   3595  CD2  PHE B 154      -4.978 -26.164  62.955  1.00 24.73           C
ATOM   3596  CE1  PHE B 154      -3.993 -25.447  65.455  1.00 23.50           C
ATOM   3597  CE2  PHE B 154      -5.260 -24.902  63.474  1.00 24.33           C
ATOM   3598  CZ   PHE B 154      -4.766 -24.542  64.731  1.00 24.40           C
ATOM   3599  N    VAL B 155      -6.970 -28.916  64.671  1.00 24.83           N
ATOM   3600  CA   VAL B 155      -8.394 -28.650  64.570  1.00 25.87           C
```

FIGURE 4-54 (COORDINATES)

```
ATOM   3601  C    VAL B 155      -8.792 -27.245  65.020  1.00 26.57           C
ATOM   3602  O    VAL B 155      -9.969 -26.900  65.000  1.00 27.60           O
ATOM   3603  CB   VAL B 155      -9.206 -29.690  65.386  1.00 25.86           C
ATOM   3604  CG1  VAL B 155      -9.007 -31.082  64.801  1.00 24.44           C
ATOM   3605  CG2  VAL B 155      -8.765 -29.670  66.833  1.00 23.90           C
ATOM   3606  N    GLY B 156      -7.813 -26.445  65.429  1.00 26.27           N
ATOM   3607  CA   GLY B 156      -8.090 -25.086  65.865  1.00 26.21           C
ATOM   3608  C    GLY B 156      -9.319 -24.923  66.736  1.00 26.16           C
ATOM   3609  O    GLY B 156     -10.282 -24.259  66.342  1.00 26.31           O
ATOM   3610  N    ALA B 157      -9.282 -25.520  67.926  1.00 25.83           N
ATOM   3611  CA   ALA B 157     -10.395 -25.460  68.870  1.00 24.47           C
ATOM   3612  C    ALA B 157     -10.790 -24.024  69.207  1.00 25.00           C
ATOM   3613  O    ALA B 157     -11.968 -23.657  69.113  1.00 24.69           O
ATOM   3614  CB   ALA B 157     -10.033 -26.217  70.147  1.00 24.05           C
ATOM   3615  N    THR B 158      -9.812 -23.217  69.615  1.00 24.14           N
ATOM   3616  CA   THR B 158     -10.068 -21.813  69.951  1.00 23.81           C
ATOM   3617  C    THR B 158      -9.980 -20.967  68.686  1.00 24.66           C
ATOM   3618  O    THR B 158     -10.433 -19.818  68.658  1.00 24.44           O
ATOM   3619  CB   THR B 158      -8.991 -21.223  70.894  1.00 23.51           C
ATOM   3620  OG1  THR B 158      -7.720 -21.235  70.221  1.00 22.43           O
ATOM   3621  CG2  THR B 158      -8.893 -22.006  72.198  1.00 21.73           C
ATOM   3622  N    ASP B 159      -9.419 -21.562  67.637  1.00 23.83           N
ATOM   3623  CA   ASP B 159      -9.143 -20.846  66.399  1.00 23.60           C
ATOM   3624  C    ASP B 159      -9.682 -21.513  65.127  1.00 23.21           C
ATOM   3625  O    ASP B 159      -8.921 -22.115  64.375  1.00 22.42           O
ATOM   3626  CB   ASP B 159      -7.611 -20.678  66.369  1.00 23.41           C
ATOM   3627  CG   ASP B 159      -7.092 -19.977  65.141  1.00 24.83           C
ATOM   3628  OD1  ASP B 159      -7.853 -19.254  64.469  1.00 24.40           O
ATOM   3629  OD2  ASP B 159      -5.879 -20.143  64.869  1.00 25.17           O
ATOM   3630  N    SER B 160     -10.986 -21.401  64.869  1.00 23.09           N
ATOM   3631  CA   SER B 160     -11.934 -20.709  65.734  1.00 23.63           C
ATOM   3632  C    SER B 160     -13.233 -21.508  65.880  1.00 23.95           C
ATOM   3633  O    SER B 160     -14.334 -20.976  65.701  1.00 23.44           O
ATOM   3634  CB   SER B 160     -12.244 -19.317  65.180  1.00 22.86           C
ATOM   3635  OG   SER B 160     -11.150 -18.447  65.406  1.00 25.50           O
ATOM   3636  N    ALA B 161     -13.101 -22.788  66.207  1.00 23.61           N
ATOM   3637  CA   ALA B 161     -14.268 -23.642  66.376  1.00 24.40           C
ATOM   3638  C    ALA B 161     -15.187 -23.101  67.474  1.00 25.11           C
ATOM   3639  O    ALA B 161     -16.401 -23.008  67.284  1.00 26.06           O
ATOM   3640  CB   ALA B 161     -13.827 -25.066  66.708  1.00 25.61           C
ATOM   3641  N    VAL B 162     -14.611 -22.746  68.619  1.00 24.47           N
ATOM   3642  CA   VAL B 162     -15.402 -22.213  69.723  1.00 24.62           C
ATOM   3643  C    VAL B 162     -16.149 -20.954  69.280  1.00 25.31           C
ATOM   3644  O    VAL B 162     -17.359 -20.837  69.496  1.00 25.67           O
ATOM   3645  CB   VAL B 162     -14.515 -21.906  70.954  1.00 25.18           C
ATOM   3646  CG1  VAL B 162     -15.306 -21.118  71.997  1.00 23.85           C
ATOM   3647  CG2  VAL B 162     -14.004 -23.220  71.558  1.00 24.48           C
ATOM   3648  N    PRO B 163     -15.438 -19.979  68.684  1.00 25.28           N
ATOM   3649  CA   PRO B 163     -16.170 -18.784  68.249  1.00 25.07           C
ATOM   3650  C    PRO B 163     -17.356 -19.180  67.350  1.00 24.48           C
ATOM   3651  O    PRO B 163     -18.422 -18.564  67.408  1.00 24.51           O
ATOM   3652  CB   PRO B 163     -15.094 -17.982  67.517  1.00 24.66           C
ATOM   3653  CG   PRO B 163     -13.887 -18.242  68.373  1.00 23.88           C
ATOM   3654  CD   PRO B 163     -13.981 -19.750  68.626  1.00 24.50           C
ATOM   3655  N    CYS B 164     -17.175 -20.218  66.535  1.00 24.38           N
ATOM   3656  CA   CYS B 164     -18.254 -20.700  65.666  1.00 24.60           C
ATOM   3657  C    CYS B 164     -19.425 -21.215  66.502  1.00 25.13           C
ATOM   3658  O    CYS B 164     -20.575 -20.850  66.263  1.00 25.65           O
ATOM   3659  CB   CYS B 164     -17.777 -21.844  64.776  1.00 24.13           C
ATOM   3660  SG   CYS B 164     -16.848 -21.366  63.325  1.00 24.64           S
ATOM   3661  N    ALA B 165     -19.126 -22.067  67.479  1.00 24.47           N
ATOM   3662  CA   ALA B 165     -20.165 -22.638  68.339  1.00 25.01           C
ATOM   3663  C    ALA B 165     -20.859 -21.565  69.167  1.00 24.13           C
ATOM   3664  O    ALA B 165     -22.062 -21.636  69.400  1.00 24.24           O
ATOM   3665  CB   ALA B 165     -19.570 -23.708  69.257  1.00 23.01           C
ATOM   3666  N    MET B 166     -20.101 -20.572  69.613  1.00 25.13           N
ATOM   3667  CA   MET B 166     -20.677 -19.490  70.401  1.00 25.89           C
ATOM   3668  C    MET B 166     -21.725 -18.738  69.584  1.00 26.23           C
```

FIGURE 4-55 (COORDINATES)

```
ATOM   3669  O    MET B 166     -22.784 -18.383  70.099  1.00 25.97           O
ATOM   3670  CB   MET B 166     -19.587 -18.528  70.855  1.00 26.21           C
ATOM   3671  CG   MET B 166     -18.648 -19.124  71.878  1.00 27.20           C
ATOM   3672  SD   MET B 166     -17.263 -18.036  72.186  1.00 27.89           S
ATOM   3673  CE   MET B 166     -18.086 -16.651  73.034  1.00 24.76           C
ATOM   3674  N    MET B 167     -21.425 -18.502  68.308  1.00 26.41           N
ATOM   3675  CA   MET B 167     -22.354 -17.805  67.429  1.00 26.85           C
ATOM   3676  C    MET B 167     -23.591 -18.674  67.237  1.00 27.01           C
ATOM   3677  O    MET B 167     -24.718 -18.184  67.245  1.00 27.18           O
ATOM   3678  CB   MET B 167     -21.675 -17.498  66.082  1.00 26.31           C
ATOM   3679  CG   MET B 167     -20.719 -16.294  66.139  1.00 25.15           C
ATOM   3680  SD   MET B 167     -19.508 -16.179  64.794  1.00 27.66           S
ATOM   3681  CE   MET B 167     -20.575 -15.764  63.392  1.00 24.17           C
ATOM   3682  N    LEU B 168     -23.378 -19.974  67.086  1.00 27.78           N
ATOM   3683  CA   LEU B 168     -24.488 -20.899  66.910  1.00 28.39           C
ATOM   3684  C    LEU B 168     -25.350 -20.956  68.169  1.00 29.25           C
ATOM   3685  O    LEU B 168     -26.586 -20.942  68.089  1.00 29.41           O
ATOM   3686  CB   LEU B 168     -23.965 -22.292  66.558  1.00 27.19           C
ATOM   3687  CG   LEU B 168     -23.391 -22.386  65.144  1.00 27.15           C
ATOM   3688  CD1  LEU B 168     -22.946 -23.812  64.861  1.00 26.46           C
ATOM   3689  CD2  LEU B 168     -24.459 -21.957  64.137  1.00 27.46           C
ATOM   3690  N    GLU B 169     -24.699 -21.008  69.329  1.00 29.11           N
ATOM   3691  CA   GLU B 169     -25.417 -21.050  70.597  1.00 29.06           C
ATOM   3692  C    GLU B 169     -26.209 -19.762  70.797  1.00 29.75           C
ATOM   3693  O    GLU B 169     -27.344 -19.792  71.276  1.00 30.52           O
ATOM   3694  CB   GLU B 169     -24.434 -21.257  71.753  1.00 29.11           C
ATOM   3695  CG   GLU B 169     -24.976 -20.974  73.163  1.00 28.74           C
ATOM   3696  CD   GLU B 169     -26.216 -21.788  73.536  1.00 29.51           C
ATOM   3697  OE1  GLU B 169     -26.547 -22.765  72.823  1.00 28.62           O
ATOM   3698  OE2  GLU B 169     -26.852 -21.445  74.561  1.00 28.33           O
ATOM   3699  N    LEU B 170     -25.618 -18.632  70.421  1.00 29.68           N
ATOM   3700  CA   LEU B 170     -26.296 -17.349  70.566  1.00 29.57           C
ATOM   3701  C    LEU B 170     -27.591 -17.333  69.749  1.00 30.72           C
ATOM   3702  O    LEU B 170     -28.627 -16.851  70.211  1.00 30.74           O
ATOM   3703  CB   LEU B 170     -25.370 -16.208  70.130  1.00 27.92           C
ATOM   3704  CG   LEU B 170     -25.940 -14.783  70.179  1.00 27.70           C
ATOM   3705  CD1  LEU B 170     -24.870 -13.809  70.643  1.00 26.08           C
ATOM   3706  CD2  LEU B 170     -26.490 -14.392  68.804  1.00 25.79           C
ATOM   3707  N    ALA B 171     -27.533 -17.879  68.539  1.00 31.46           N
ATOM   3708  CA   ALA B 171     -28.698 -17.925  67.671  1.00 31.90           C
ATOM   3709  C    ALA B 171     -29.815 -18.760  68.290  1.00 33.43           C
ATOM   3710  O    ALA B 171     -30.983 -18.363  68.268  1.00 34.03           O
ATOM   3711  CB   ALA B 171     -28.312 -18.499  66.320  1.00 31.09           C
ATOM   3712  N    ARG B 172     -29.452 -19.923  68.827  1.00 33.93           N
ATOM   3713  CA   ARG B 172     -30.419 -20.821  69.451  1.00 33.90           C
ATOM   3714  C    ARG B 172     -31.007 -20.207  70.721  1.00 34.05           C
ATOM   3715  O    ARG B 172     -32.226 -20.073  70.855  1.00 35.08           O
ATOM   3716  CB   ARG B 172     -29.752 -22.155  69.811  1.00 33.78           C
ATOM   3717  CG   ARG B 172     -30.709 -23.195  70.404  1.00 34.11           C
ATOM   3718  CD   ARG B 172     -29.971 -24.250  71.213  1.00 32.49           C
ATOM   3719  NE   ARG B 172     -29.444 -23.688  72.453  1.00 34.49           N
ATOM   3720  CZ   ARG B 172     -30.192 -23.307  73.486  1.00 35.06           C
ATOM   3721  NH1  ARG B 172     -31.515 -23.433  73.441  1.00 35.47           N
ATOM   3722  NH2  ARG B 172     -29.618 -22.782  74.563  1.00 34.12           N
ATOM   3723  N    ALA B 173     -30.132 -19.835  71.647  1.00 33.25           N
ATOM   3724  CA   ALA B 173     -30.546 -19.259  72.921  1.00 33.34           C
ATOM   3725  C    ALA B 173     -31.471 -18.060  72.782  1.00 33.30           C
ATOM   3726  O    ALA B 173     -32.452 -17.948  73.505  1.00 34.08           O
ATOM   3727  CB   ALA B 173     -29.319 -18.867  73.737  1.00 32.38           C
ATOM   3728  N    LEU B 174     -31.158 -17.163  71.855  1.00 33.35           N
ATOM   3729  CA   LEU B 174     -31.968 -15.964  71.659  1.00 33.83           C
ATOM   3730  C    LEU B 174     -33.011 -16.148  70.569  1.00 33.79           C
ATOM   3731  O    LEU B 174     -33.686 -15.194  70.189  1.00 33.75           O
ATOM   3732  CB   LEU B 174     -31.068 -14.781  71.288  1.00 32.85           C
ATOM   3733  CG   LEU B 174     -29.858 -14.551  72.194  1.00 32.98           C
ATOM   3734  CD1  LEU B 174     -29.058 -13.358  71.694  1.00 31.76           C
ATOM   3735  CD2  LEU B 174     -30.323 -14.333  73.623  1.00 31.88           C
ATOM   3736  N    ASP B 175     -33.152 -17.373  70.078  1.00 34.58           N
```

FIGURE 4-56 (COORDINATES)

```
ATOM   3737  CA   ASP B 175     -34.085 -17.654  68.993  1.00 35.64           C
ATOM   3738  C    ASP B 175     -35.474 -17.037  69.115  1.00 36.41           C
ATOM   3739  O    ASP B 175     -35.944 -16.397  68.175  1.00 36.20           O
ATOM   3740  CB   ASP B 175     -34.217 -19.164  68.769  1.00 34.72           C
ATOM   3741  CG   ASP B 175     -34.891 -19.494  67.450  1.00 34.29           C
ATOM   3742  OD1  ASP B 175     -34.625 -18.779  66.462  1.00 35.22           O
ATOM   3743  OD2  ASP B 175     -35.673 -20.464  67.386  1.00 35.50           O
ATOM   3744  N    LYS B 176     -36.128 -17.222  70.261  1.00 38.08           N
ATOM   3745  CA   LYS B 176     -37.469 -16.683  70.466  1.00 39.16           C
ATOM   3746  C    LYS B 176     -37.511 -15.164  70.343  1.00 39.23           C
ATOM   3747  O    LYS B 176     -38.416 -14.617  69.718  1.00 39.37           O
ATOM   3748  CB   LYS B 176     -38.013 -17.097  71.831  1.00 40.94           C
ATOM   3749  CG   LYS B 176     -39.441 -16.620  72.091  1.00 43.28           C
ATOM   3750  CD   LYS B 176     -39.910 -16.995  73.495  1.00 45.21           C
ATOM   3751  CE   LYS B 176     -41.388 -16.687  73.692  1.00 45.82           C
ATOM   3752  NZ   LYS B 176     -41.853 -17.097  75.049  1.00 47.35           N
ATOM   3753  N    LYS B 177     -36.541 -14.481  70.939  1.00 39.71           N
ATOM   3754  CA   LYS B 177     -36.502 -13.025  70.849  1.00 40.75           C
ATOM   3755  C    LYS B 177     -36.160 -12.568  69.429  1.00 41.07           C
ATOM   3756  O    LYS B 177     -36.739 -11.609  68.926  1.00 41.47           O
ATOM   3757  CB   LYS B 177     -35.490 -12.455  71.848  1.00 40.98           C
ATOM   3758  CG   LYS B 177     -35.997 -12.448  73.281  1.00 42.07           C
ATOM   3759  CD   LYS B 177     -34.878 -12.169  74.273  1.00 43.37           C
ATOM   3760  CE   LYS B 177     -35.415 -11.998  75.690  1.00 44.03           C
ATOM   3761  NZ   LYS B 177     -36.213 -10.739  75.831  1.00 45.32           N
ATOM   3762  N    LEU B 178     -35.227 -13.255  68.779  1.00 41.15           N
ATOM   3763  CA   LEU B 178     -34.845 -12.886  67.421  1.00 41.88           C
ATOM   3764  C    LEU B 178     -36.010 -13.103  66.457  1.00 43.09           C
ATOM   3765  O    LEU B 178     -36.081 -12.477  65.397  1.00 42.77           O
ATOM   3766  CB   LEU B 178     -33.626 -13.698  66.972  1.00 40.97           C
ATOM   3767  CG   LEU B 178     -32.304 -13.333  67.660  1.00 41.19           C
ATOM   3768  CD1  LEU B 178     -31.221 -14.331  67.287  1.00 39.31           C
ATOM   3769  CD2  LEU B 178     -31.902 -11.916  67.260  1.00 39.86           C
ATOM   3770  N    LEU B 179     -36.929 -13.985  66.840  1.00 44.51           N
ATOM   3771  CA   LEU B 179     -38.094 -14.292  66.014  1.00 45.09           C
ATOM   3772  C    LEU B 179     -39.036 -13.094  65.873  1.00 45.12           C
ATOM   3773  O    LEU B 179     -39.771 -12.990  64.892  1.00 45.11           O
ATOM   3774  CB   LEU B 179     -38.855 -15.483  66.606  1.00 45.66           C
ATOM   3775  CG   LEU B 179     -40.152 -15.908  65.909  1.00 46.50           C
ATOM   3776  CD1  LEU B 179     -39.869 -16.221  64.449  1.00 46.30           C
ATOM   3777  CD2  LEU B 179     -40.744 -17.124  66.616  1.00 46.21           C
ATOM   3778  N    SER B 180     -39.007 -12.190  66.848  1.00 45.03           N
ATOM   3779  CA   SER B 180     -39.863 -11.009  66.821  1.00 46.13           C
ATOM   3780  C    SER B 180     -39.461 -10.017  65.728  1.00 47.61           C
ATOM   3781  O    SER B 180     -40.032  -8.933  65.624  1.00 48.58           O
ATOM   3782  CB   SER B 180     -39.835 -10.303  68.176  1.00 44.90           C
ATOM   3783  OG   SER B 180     -38.564  -9.740  68.428  1.00 43.74           O
ATOM   3784  N    LEU B 181     -38.480 -10.394  64.914  1.00 48.72           N
ATOM   3785  CA   LEU B 181     -38.005  -9.539  63.830  1.00 49.17           C
ATOM   3786  C    LEU B 181     -38.555  -9.975  62.463  1.00 50.04           C
ATOM   3787  O    LEU B 181     -39.505 -10.789  62.400  1.00 50.14           O
ATOM   3788  CB   LEU B 181     -36.474  -9.548  63.791  1.00 48.32           C
ATOM   3789  CG   LEU B 181     -35.705  -9.059  65.024  1.00 47.82           C
ATOM   3790  CD1  LEU B 181     -34.240  -9.453  64.907  1.00 46.97           C
ATOM   3791  CD2  LEU B 181     -35.845  -7.557  65.162  1.00 47.46           C
ATOM   3792  N    ASP B 190     -34.733   0.349  61.797  1.00 42.95           N
ATOM   3793  CA   ASP B 190     -34.607  -0.765  60.816  1.00 42.34           C
ATOM   3794  C    ASP B 190     -33.231  -1.381  61.005  1.00 41.14           C
ATOM   3795  O    ASP B 190     -32.331  -1.204  60.181  1.00 39.84           O
ATOM   3796  CB   ASP B 190     -34.760  -0.232  59.384  1.00 44.00           C
ATOM   3797  CG   ASP B 190     -34.821  -1.344  58.351  1.00 45.17           C
ATOM   3798  OD1  ASP B 190     -35.123  -2.497  58.746  1.00 46.55           O
ATOM   3799  OD2  ASP B 190     -34.585  -1.063  57.153  1.00 44.47           O
ATOM   3800  N    LEU B 191     -33.086  -2.108  62.107  1.00 39.34           N
ATOM   3801  CA   LEU B 191     -31.824  -2.743  62.463  1.00 37.19           C
ATOM   3802  C    LEU B 191     -32.020  -4.214  62.792  1.00 35.64           C
ATOM   3803  O    LEU B 191     -32.891  -4.561  63.585  1.00 36.32           O
ATOM   3804  CB   LEU B 191     -31.224  -2.029  63.680  1.00 36.10           C
```

FIGURE 4-57 (COORDINATES)

```
ATOM   3805  CG   LEU B 191     -30.006   -2.662   64.361  1.00 35.84           C
ATOM   3806  CD1  LEU B 191     -28.777   -2.514   63.466  1.00 34.16           C
ATOM   3807  CD2  LEU B 191     -29.777   -1.990   65.714  1.00 34.24           C
ATOM   3808  N    SER B 192     -31.215   -5.081   62.189  1.00 33.71           N
ATOM   3809  CA   SER B 192     -31.332   -6.501   62.481  1.00 31.64           C
ATOM   3810  C    SER B 192     -29.982   -7.165   62.744  1.00 30.24           C
ATOM   3811  O    SER B 192     -28.985   -6.490   62.995  1.00 28.98           O
ATOM   3812  CB   SER B 192     -32.066   -7.226   61.361  1.00 31.89           C
ATOM   3813  OG   SER B 192     -32.572   -8.461   61.841  1.00 33.00           O
ATOM   3814  N    LEU B 193     -29.953   -8.492   62.680  1.00 29.09           N
ATOM   3815  CA   LEU B 193     -28.735   -9.234   62.971  1.00 28.47           C
ATOM   3816  C    LEU B 193     -28.220  -10.083   61.814  1.00 27.87           C
ATOM   3817  O    LEU B 193     -28.997  -10.602   61.012  1.00 27.43           O
ATOM   3818  CB   LEU B 193     -28.969  -10.124   64.197  1.00 28.06           C
ATOM   3819  CG   LEU B 193     -27.776  -10.915   64.733  1.00 29.10           C
ATOM   3820  CD1  LEU B 193     -26.715   -9.951   65.260  1.00 27.68           C
ATOM   3821  CD2  LEU B 193     -28.247  -11.861   65.841  1.00 28.49           C
ATOM   3822  N    GLN B 194     -26.897  -10.211   61.741  1.00 26.46           N
ATOM   3823  CA   GLN B 194     -26.251  -10.994   60.698  1.00 27.24           C
ATOM   3824  C    GLN B 194     -25.026  -11.723   61.243  1.00 26.49           C
ATOM   3825  O    GLN B 194     -24.274  -11.179   62.057  1.00 26.99           O
ATOM   3826  CB   GLN B 194     -25.840  -10.089   59.524  1.00 28.48           C
ATOM   3827  CG   GLN B 194     -25.024  -10.800   58.446  1.00 30.33           C
ATOM   3828  CD   GLN B 194     -24.764   -9.932   57.224  1.00 31.41           C
ATOM   3829  OE1  GLN B 194     -25.544   -9.931   56.269  1.00 33.77           O
ATOM   3830  NE2  GLN B 194     -23.673   -9.182   57.253  1.00 31.13           N
ATOM   3831  N    LEU B 195     -24.844  -12.963   60.798  1.00 25.65           N
ATOM   3832  CA   LEU B 195     -23.709  -13.771   61.214  1.00 25.75           C
ATOM   3833  C    LEU B 195     -22.876  -14.084   59.981  1.00 25.90           C
ATOM   3834  O    LEU B 195     -23.418  -14.464   58.943  1.00 26.02           O
ATOM   3835  CB   LEU B 195     -24.174  -15.095   61.816  1.00 25.63           C
ATOM   3836  CG   LEU B 195     -25.244  -15.085   62.903  1.00 26.45           C
ATOM   3837  CD1  LEU B 195     -25.523  -16.517   63.327  1.00 25.87           C
ATOM   3838  CD2  LEU B 195     -24.779  -14.247   64.083  1.00 26.17           C
ATOM   3839  N    ILE B 196     -21.565  -13.924   60.092  1.00 24.56           N
ATOM   3840  CA   ILE B 196     -20.685  -14.242   58.982  1.00 23.93           C
ATOM   3841  C    ILE B 196     -19.638  -15.239   59.459  1.00 23.11           C
ATOM   3842  O    ILE B 196     -18.979  -15.011   60.467  1.00 23.08           O
ATOM   3843  CB   ILE B 196     -19.939  -12.996   58.449  1.00 24.80           C
ATOM   3844  CG1  ILE B 196     -20.934  -11.982   57.875  1.00 24.05           C
ATOM   3845  CG2  ILE B 196     -18.920  -13.427   57.381  1.00 25.17           C
ATOM   3846  CD1  ILE B 196     -20.278  -10.695   57.413  1.00 22.22           C
ATOM   3847  N    PHE B 197     -19.503  -16.350   58.743  1.00 22.83           N
ATOM   3848  CA   PHE B 197     -18.508  -17.365   59.067  1.00 22.67           C
ATOM   3849  C    PHE B 197     -17.553  -17.335   57.878  1.00 22.92           C
ATOM   3850  O    PHE B 197     -17.863  -17.872   56.815  1.00 24.10           O
ATOM   3851  CB   PHE B 197     -19.158  -18.748   59.176  1.00 23.14           C
ATOM   3852  CG   PHE B 197     -20.241  -18.843   60.227  1.00 24.21           C
ATOM   3853  CD1  PHE B 197     -19.938  -19.236   61.531  1.00 24.84           C
ATOM   3854  CD2  PHE B 197     -21.568  -18.559   59.906  1.00 24.10           C
ATOM   3855  CE1  PHE B 197     -20.945  -19.350   62.501  1.00 24.14           C
ATOM   3856  CE2  PHE B 197     -22.578  -18.667   60.862  1.00 24.32           C
ATOM   3857  CZ   PHE B 197     -22.262  -19.066   62.168  1.00 24.51           C
ATOM   3858  N    PHE B 198     -16.405  -16.684   58.049  1.00 23.27           N
ATOM   3859  CA   PHE B 198     -15.418  -16.568   56.975  1.00 22.34           C
ATOM   3860  C    PHE B 198     -14.652  -17.856   56.718  1.00 22.66           C
ATOM   3861  O    PHE B 198     -14.308  -18.591   57.645  1.00 23.37           O
ATOM   3862  CB   PHE B 198     -14.375  -15.492   57.303  1.00 22.70           C
ATOM   3863  CG   PHE B 198     -14.916  -14.096   57.374  1.00 21.02           C
ATOM   3864  CD1  PHE B 198     -15.394  -13.458   56.239  1.00 20.43           C
ATOM   3865  CD2  PHE B 198     -14.898  -13.400   58.574  1.00 21.65           C
ATOM   3866  CE1  PHE B 198     -15.845  -12.140   56.300  1.00 19.42           C
ATOM   3867  CE2  PHE B 198     -15.347  -12.081   58.642  1.00 20.59           C
ATOM   3868  CZ   PHE B 198     -15.819  -11.456   57.498  1.00 19.20           C
ATOM   3869  N    ASP B 199     -14.379  -18.122   55.449  1.00 23.18           N
ATOM   3870  CA   ASP B 199     -13.584  -19.285   55.076  1.00 23.65           C
ATOM   3871  C    ASP B 199     -12.198  -18.705   54.764  1.00 23.57           C
ATOM   3872  O    ASP B 199     -12.056  -17.484   54.597  1.00 22.69           O
```

FIGURE 4-58 (COORDINATES)

```
ATOM   3873  CB  ASP B 199     -14.158 -19.962  53.828  1.00 24.10           C
ATOM   3874  CG  ASP B 199     -13.467 -21.281  53.506  1.00 25.31           C
ATOM   3875  OD1 ASP B 199     -12.592 -21.704  54.292  1.00 25.61           O
ATOM   3876  OD2 ASP B 199     -13.799 -21.899  52.471  1.00 23.68           O
ATOM   3877  N   GLY B 200     -11.187 -19.569  54.718  1.00 22.41           N
ATOM   3878  CA  GLY B 200      -9.835 -19.140  54.403  1.00 21.49           C
ATOM   3879  C   GLY B 200      -9.211 -17.976  55.157  1.00 22.26           C
ATOM   3880  O   GLY B 200      -8.539 -17.142  54.553  1.00 23.13           O
ATOM   3881  N   GLN B 201      -9.407 -17.896  56.467  1.00 22.18           N
ATOM   3882  CA  GLN B 201      -8.790 -16.812  57.212  1.00 22.27           C
ATOM   3883  C   GLN B 201      -7.285 -17.066  57.298  1.00 22.68           C
ATOM   3884  O   GLN B 201      -6.473 -16.151  57.139  1.00 22.43           O
ATOM   3885  CB  GLN B 201      -9.369 -16.725  58.626  1.00 22.06           C
ATOM   3886  CG  GLN B 201      -8.781 -15.593  59.460  1.00 23.57           C
ATOM   3887  CD  GLN B 201      -7.897 -16.081  60.595  1.00 26.78           C
ATOM   3888  OE1 GLN B 201      -7.270 -17.136  60.498  1.00 28.70           O
ATOM   3889  NE2 GLN B 201      -7.830 -15.303  61.674  1.00 26.25           N
ATOM   3890  N   GLU B 202      -6.931 -18.325  57.540  1.00 22.85           N
ATOM   3891  CA  GLU B 202      -5.544 -18.749  57.693  1.00 22.95           C
ATOM   3892  C   GLU B 202      -4.759 -18.800  56.389  1.00 23.64           C
ATOM   3893  O   GLU B 202      -5.305 -19.068  55.322  1.00 23.86           O
ATOM   3894  CB  GLU B 202      -5.503 -20.132  58.356  1.00 22.22           C
ATOM   3895  CG  GLU B 202      -6.216 -20.210  59.702  1.00 20.99           C
ATOM   3896  CD  GLU B 202      -5.362 -19.716  60.854  1.00 21.61           C
ATOM   3897  OE1 GLU B 202      -4.312 -19.094  60.593  1.00 22.03           O
ATOM   3898  OE2 GLU B 202      -5.743 -19.940  62.027  1.00 22.10           O
ATOM   3899  N   ALA B 203      -3.464 -18.544  56.491  1.00 23.76           N
ATOM   3900  CA  ALA B 203      -2.594 -18.594  55.335  1.00 24.59           C
ATOM   3901  C   ALA B 203      -2.362 -20.065  55.032  1.00 25.55           C
ATOM   3902  O   ALA B 203      -2.395 -20.901  55.936  1.00 25.50           O
ATOM   3903  CB  ALA B 203      -1.269 -17.918  55.651  1.00 23.81           C
ATOM   3904  N   PHE B 204      -2.135 -20.385  53.766  1.00 27.02           N
ATOM   3905  CA  PHE B 204      -1.876 -21.767  53.393  1.00 28.75           C
ATOM   3906  C   PHE B 204      -0.414 -22.088  53.639  1.00 30.04           C
ATOM   3907  O   PHE B 204      -0.072 -23.216  53.998  1.00 30.44           O
ATOM   3908  CB  PHE B 204      -2.188 -22.011  51.916  1.00 28.25           C
ATOM   3909  CG  PHE B 204      -3.564 -22.539  51.668  1.00 29.28           C
ATOM   3910  CD1 PHE B 204      -4.593 -21.689  51.282  1.00 28.84           C
ATOM   3911  CD2 PHE B 204      -3.843 -23.893  51.851  1.00 30.44           C
ATOM   3912  CE1 PHE B 204      -5.883 -22.179  51.082  1.00 29.48           C
ATOM   3913  CE2 PHE B 204      -5.131 -24.395  51.654  1.00 30.41           C
ATOM   3914  CZ  PHE B 204      -6.151 -23.535  51.270  1.00 29.73           C
ATOM   3915  N   LEU B 205       0.443 -21.086  53.451  1.00 30.83           N
ATOM   3916  CA  LEU B 205       1.877 -21.263  53.612  1.00 31.63           C
ATOM   3917  C   LEU B 205       2.517 -20.269  54.577  1.00 32.88           C
ATOM   3918  O   LEU B 205       3.097 -20.671  55.580  1.00 34.65           O
ATOM   3919  CB  LEU B 205       2.548 -21.183  52.239  1.00 30.59           C
ATOM   3920  CG  LEU B 205       4.061 -21.381  52.157  1.00 30.99           C
ATOM   3921  CD1 LEU B 205       4.489 -22.612  52.940  1.00 31.16           C
ATOM   3922  CD2 LEU B 205       4.450 -21.508  50.706  1.00 30.33           C
ATOM   3923  N   HIS B 206       2.424 -18.977  54.276  1.00 33.41           N
ATOM   3924  CA  HIS B 206       2.994 -17.956  55.151  1.00 33.83           C
ATOM   3925  C   HIS B 206       2.129 -16.705  55.172  1.00 32.58           C
ATOM   3926  O   HIS B 206       1.908 -16.079  54.140  1.00 32.41           O
ATOM   3927  CB  HIS B 206       4.417 -17.593  54.714  1.00 36.26           C
ATOM   3928  CG  HIS B 206       5.485 -18.239  55.543  1.00 39.47           C
ATOM   3929  ND1 HIS B 206       6.727 -17.669  55.736  1.00 40.27           N
ATOM   3930  CD2 HIS B 206       5.495 -19.405  56.236  1.00 40.19           C
ATOM   3931  CE1 HIS B 206       7.453 -18.454  56.513  1.00 41.29           C
ATOM   3932  NE2 HIS B 206       6.730 -19.514  56.830  1.00 41.45           N
ATOM   3933  N   TRP B 207       1.651 -16.344  56.358  1.00 32.01           N
ATOM   3934  CA  TRP B 207       0.788 -15.184  56.512  1.00 32.35           C
ATOM   3935  C   TRP B 207       1.355 -13.945  55.835  1.00 32.90           C
ATOM   3936  O   TRP B 207       2.435 -13.463  56.180  1.00 32.75           O
ATOM   3937  CB  TRP B 207       0.530 -14.900  57.994  1.00 31.84           C
ATOM   3938  CG  TRP B 207      -0.527 -13.859  58.217  1.00 32.85           C
ATOM   3939  CD1 TRP B 207      -0.396 -12.503  58.065  1.00 32.82           C
ATOM   3940  CD2 TRP B 207      -1.896 -14.090  58.577  1.00 32.46           C
```

FIGURE 4-59 (COORDINATES)

```
ATOM   3941  NE1 TRP B 207      -1.596 -11.881  58.305  1.00 33.29           N
ATOM   3942  CE2 TRP B 207      -2.536 -12.829  58.620  1.00 32.91           C
ATOM   3943  CE3 TRP B 207      -2.646 -15.240  58.864  1.00 32.00           C
ATOM   3944  CZ2 TRP B 207      -3.893 -12.685  58.941  1.00 32.74           C
ATOM   3945  CZ3 TRP B 207      -3.997 -15.098  59.182  1.00 31.29           C
ATOM   3946  CH2 TRP B 207      -4.606 -13.828  59.217  1.00 31.76           C
ATOM   3947  N   SER B 208       0.605 -13.441  54.862  1.00 32.56           N
ATOM   3948  CA  SER B 208       0.998 -12.263  54.108  1.00 33.10           C
ATOM   3949  C   SER B 208      -0.253 -11.716  53.420  1.00 33.55           C
ATOM   3950  O   SER B 208      -1.300 -12.362  53.427  1.00 33.99           O
ATOM   3951  CB  SER B 208       2.059 -12.642  53.070  1.00 32.77           C
ATOM   3952  OG  SER B 208       1.543 -13.570  52.137  1.00 32.47           O
ATOM   3953  N   PRO B 209      -0.163 -10.518  52.821  1.00 33.59           N
ATOM   3954  CA  PRO B 209      -1.310  -9.908  52.139  1.00 33.96           C
ATOM   3955  C   PRO B 209      -2.033 -10.802  51.129  1.00 33.37           C
ATOM   3956  O   PRO B 209      -3.265 -10.829  51.094  1.00 33.19           O
ATOM   3957  CB  PRO B 209      -0.698  -8.669  51.492  1.00 34.51           C
ATOM   3958  CG  PRO B 209       0.334  -8.260  52.513  1.00 34.34           C
ATOM   3959  CD  PRO B 209       0.982  -9.585  52.851  1.00 34.40           C
ATOM   3960  N   GLN B 210      -1.274 -11.538  50.320  1.00 33.13           N
ATOM   3961  CA  GLN B 210      -1.868 -12.412  49.311  1.00 33.05           C
ATOM   3962  C   GLN B 210      -2.114 -13.861  49.753  1.00 31.87           C
ATOM   3963  O   GLN B 210      -2.665 -14.666  48.994  1.00 31.05           O
ATOM   3964  CB  GLN B 210      -1.013 -12.385  48.042  1.00 35.94           C
ATOM   3965  CG  GLN B 210      -1.006 -11.014  47.361  1.00 41.23           C
ATOM   3966  CD  GLN B 210      -2.403 -10.553  46.924  1.00 44.29           C
ATOM   3967  OE1 GLN B 210      -2.700  -9.353  46.924  1.00 47.11           O
ATOM   3968  NE2 GLN B 210      -3.258 -11.503  46.538  1.00 44.30           N
ATOM   3969  N   ASP B 211      -1.705 -14.192  50.975  1.00 30.04           N
ATOM   3970  CA  ASP B 211      -1.917 -15.532  51.509  1.00 27.95           C
ATOM   3971  C   ASP B 211      -2.470 -15.402  52.921  1.00 27.44           C
ATOM   3972  O   ASP B 211      -1.738 -15.533  53.903  1.00 25.42           O
ATOM   3973  CB  ASP B 211      -0.609 -16.330  51.537  1.00 27.76           C
ATOM   3974  CG  ASP B 211      -0.814 -17.781  51.967  1.00 27.00           C
ATOM   3975  OD1 ASP B 211       0.187 -18.430  52.324  1.00 27.45           O
ATOM   3976  OD2 ASP B 211      -1.962 -18.279  51.940  1.00 26.11           O
ATOM   3977  N   SER B 212      -3.770 -15.121  52.996  1.00 26.84           N
ATOM   3978  CA  SER B 212      -4.495 -14.971  54.250  1.00 26.13           C
ATOM   3979  C   SER B 212      -5.734 -14.149  53.967  1.00 24.82           C
ATOM   3980  O   SER B 212      -5.814 -13.469  52.947  1.00 23.91           O
ATOM   3981  CB  SER B 212      -3.654 -14.248  55.310  1.00 26.17           C
ATOM   3982  OG  SER B 212      -3.505 -12.873  54.995  1.00 27.45           O
ATOM   3983  N   LEU B 213      -6.699 -14.223  54.876  1.00 24.09           N
ATOM   3984  CA  LEU B 213      -7.936 -13.464  54.757  1.00 23.12           C
ATOM   3985  C   LEU B 213      -8.606 -13.600  53.391  1.00 23.09           C
ATOM   3986  O   LEU B 213      -9.196 -12.648  52.881  1.00 23.80           O
ATOM   3987  CB  LEU B 213      -7.655 -11.987  55.054  1.00 22.15           C
ATOM   3988  CG  LEU B 213      -6.759 -11.772  56.276  1.00 20.73           C
ATOM   3989  CD1 LEU B 213      -6.560 -10.287  56.530  1.00 19.38           C
ATOM   3990  CD2 LEU B 213      -7.388 -12.453  57.481  1.00 20.46           C
ATOM   3991  N   TYR B 214      -8.524 -14.785  52.802  1.00 22.83           N
ATOM   3992  CA  TYR B 214      -9.145 -15.025  51.510  1.00 23.32           C
ATOM   3993  C   TYR B 214     -10.635 -14.664  51.526  1.00 23.71           C
ATOM   3994  O   TYR B 214     -11.104 -13.873  50.704  1.00 23.54           O
ATOM   3995  CB  TYR B 214      -8.981 -16.499  51.123  1.00 24.58           C
ATOM   3996  CG  TYR B 214      -7.559 -16.895  50.795  1.00 24.48           C
ATOM   3997  CD1 TYR B 214      -7.002 -16.593  49.555  1.00 25.77           C
ATOM   3998  CD2 TYR B 214      -6.767 -17.571  51.727  1.00 24.37           C
ATOM   3999  CE1 TYR B 214      -5.686 -16.959  49.248  1.00 25.95           C
ATOM   4000  CE2 TYR B 214      -5.458 -17.935  51.436  1.00 24.37           C
ATOM   4001  CZ  TYR B 214      -4.922 -17.626  50.192  1.00 26.34           C
ATOM   4002  OH  TYR B 214      -3.622 -17.977  49.891  1.00 28.18           O
ATOM   4003  N   GLY B 215     -11.366 -15.238  52.479  1.00 24.20           N
ATOM   4004  CA  GLY B 215     -12.796 -15.000  52.576  1.00 23.61           C
ATOM   4005  C   GLY B 215     -13.221 -13.577  52.880  1.00 24.51           C
ATOM   4006  O   GLY B 215     -14.120 -13.039  52.231  1.00 23.93           O
ATOM   4007  N   SER B 216     -12.577 -12.965  53.867  1.00 24.01           N
ATOM   4008  CA  SER B 216     -12.913 -11.606  54.266  1.00 24.28           C
```

FIGURE 4-60 (COORDINATES)

```
ATOM   4009  C   SER B 216     -12.545 -10.546  53.224  1.00 24.66           C
ATOM   4010  O   SER B 216     -13.323  -9.621  52.984  1.00 24.63           O
ATOM   4011  CB  SER B 216     -12.262 -11.284  55.618  1.00 23.48           C
ATOM   4012  OG  SER B 216     -10.871 -11.555  55.604  1.00 24.71           O
ATOM   4013  N   ARG B 217     -11.368 -10.673  52.614  1.00 24.81           N
ATOM   4014  CA  ARG B 217     -10.948  -9.722  51.592  1.00 25.56           C
ATOM   4015  C   ARG B 217     -11.941  -9.786  50.441  1.00 25.51           C
ATOM   4016  O   ARG B 217     -12.309  -8.767  49.862  1.00 25.48           O
ATOM   4017  CB  ARG B 217      -9.537 -10.048  51.070  1.00 26.08           C
ATOM   4018  CG  ARG B 217      -8.410  -9.652  52.010  1.00 26.50           C
ATOM   4019  CD  ARG B 217      -7.030  -9.831  51.382  1.00 29.52           C
ATOM   4020  NE  ARG B 217      -6.615 -11.227  51.246  1.00 32.11           N
ATOM   4021  CZ  ARG B 217      -6.642 -11.923  50.108  1.00 33.80           C
ATOM   4022  NH1 ARG B 217      -7.071 -11.362  48.986  1.00 34.91           N
ATOM   4023  NH2 ARG B 217      -6.219 -13.182  50.087  1.00 33.09           N
ATOM   4024  N   HIS B 218     -12.381 -10.995  50.116  1.00 25.84           N
ATOM   4025  CA  HIS B 218     -13.329 -11.163  49.028  1.00 25.95           C
ATOM   4026  C   HIS B 218     -14.730 -10.680  49.388  1.00 25.39           C
ATOM   4027  O   HIS B 218     -15.366 -10.001  48.594  1.00 25.62           O
ATOM   4028  CB  HIS B 218     -13.400 -12.624  48.580  1.00 25.71           C
ATOM   4029  CG  HIS B 218     -14.525 -12.894  47.631  1.00 26.42           C
ATOM   4030  ND1 HIS B 218     -15.811 -13.157  48.058  1.00 27.74           N
ATOM   4031  CD2 HIS B 218     -14.580 -12.852  46.279  1.00 25.43           C
ATOM   4032  CE1 HIS B 218     -16.610 -13.261  47.010  1.00 25.37           C
ATOM   4033  NE2 HIS B 218     -15.887 -13.079  45.920  1.00 26.01           N
ATOM   4034  N   LEU B 219     -15.212 -11.030  50.577  1.00 24.96           N
ATOM   4035  CA  LEU B 219     -16.553 -10.615  50.981  1.00 24.97           C
ATOM   4036  C   LEU B 219     -16.640  -9.105  51.216  1.00 24.96           C
ATOM   4037  O   LEU B 219     -17.666  -8.488  50.931  1.00 24.67           O
ATOM   4038  CB  LEU B 219     -17.009 -11.369  52.240  1.00 23.44           C
ATOM   4039  CG  LEU B 219     -18.460 -11.069  52.649  1.00 22.85           C
ATOM   4040  CD1 LEU B 219     -19.387 -11.389  51.487  1.00 21.96           C
ATOM   4041  CD2 LEU B 219     -18.851 -11.873  53.878  1.00 21.73           C
ATOM   4042  N   ALA B 220     -15.568  -8.512  51.737  1.00 26.02           N
ATOM   4043  CA  ALA B 220     -15.551  -7.072  51.983  1.00 27.02           C
ATOM   4044  C   ALA B 220     -15.658  -6.316  50.644  1.00 27.64           C
ATOM   4045  O   ALA B 220     -16.362  -5.310  50.536  1.00 28.28           O
ATOM   4046  CB  ALA B 220     -14.272  -6.680  52.719  1.00 25.91           C
ATOM   4047  N   ALA B 221     -14.967  -6.811  49.623  1.00 26.68           N
ATOM   4048  CA  ALA B 221     -15.010  -6.172  48.314  1.00 27.85           C
ATOM   4049  C   ALA B 221     -16.391  -6.359  47.688  1.00 28.90           C
ATOM   4050  O   ALA B 221     -16.943  -5.434  47.088  1.00 29.74           O
ATOM   4051  CB  ALA B 221     -13.942  -6.762  47.409  1.00 26.32           C
ATOM   4052  N   LYS B 222     -16.945  -7.559  47.835  1.00 28.45           N
ATOM   4053  CA  LYS B 222     -18.258  -7.869  47.291  1.00 28.98           C
ATOM   4054  C   LYS B 222     -19.367  -7.007  47.905  1.00 28.61           C
ATOM   4055  O   LYS B 222     -20.254  -6.533  47.198  1.00 28.56           O
ATOM   4056  CB  LYS B 222     -18.560  -9.355  47.510  1.00 30.82           C
ATOM   4057  CG  LYS B 222     -19.932  -9.811  47.047  1.00 31.66           C
ATOM   4058  CD  LYS B 222     -20.042 -11.323  47.164  1.00 33.67           C
ATOM   4059  CE  LYS B 222     -21.416 -11.827  46.735  1.00 35.61           C
ATOM   4060  NZ  LYS B 222     -22.474 -11.477  47.732  1.00 36.16           N
ATOM   4061  N   MET B 223     -19.318  -6.803  49.217  1.00 27.76           N
ATOM   4062  CA  MET B 223     -20.328  -5.996  49.890  1.00 27.82           C
ATOM   4063  C   MET B 223     -20.209  -4.504  49.569  1.00 28.16           C
ATOM   4064  O   MET B 223     -21.218  -3.815  49.438  1.00 29.35           O
ATOM   4065  CB  MET B 223     -20.251  -6.200  51.407  1.00 26.42           C
ATOM   4066  CG  MET B 223     -20.626  -7.598  51.865  1.00 26.42           C
ATOM   4067  SD  MET B 223     -20.523  -7.819  53.655  1.00 27.74           S
ATOM   4068  CE  MET B 223     -22.198  -7.393  54.145  1.00 28.03           C
ATOM   4069  N   ALA B 224     -18.983  -4.004  49.448  1.00 27.81           N
ATOM   4070  CA  ALA B 224     -18.768  -2.590  49.145  1.00 27.80           C
ATOM   4071  C   ALA B 224     -19.278  -2.196  47.763  1.00 28.04           C
ATOM   4072  O   ALA B 224     -19.612  -1.031  47.527  1.00 28.49           O
ATOM   4073  CB  ALA B 224     -17.287  -2.246  49.254  1.00 26.88           C
ATOM   4074  N   SER B 225     -19.336  -3.155  46.846  1.00 27.29           N
ATOM   4075  CA  SER B 225     -19.789  -2.849  45.500  1.00 27.61           C
ATOM   4076  C   SER B 225     -21.195  -3.359  45.249  1.00 27.29           C
```

FIGURE 4-61 (COORDINATES)

```
ATOM   4077  O    SER B 225     -21.654   -3.396   44.108  1.00 26.54           O
ATOM   4078  CB   SER B 225     -18.826   -3.445   44.471  1.00 28.04           C
ATOM   4079  OG   SER B 225     -18.797   -4.858   44.562  1.00 28.72           O
ATOM   4080  N    THR B 226     -21.873   -3.760   46.320  1.00 27.71           N
ATOM   4081  CA   THR B 226     -23.243   -4.264   46.217  1.00 27.55           C
ATOM   4082  C    THR B 226     -24.218   -3.248   46.807  1.00 27.55           C
ATOM   4083  O    THR B 226     -24.150   -2.921   47.989  1.00 28.11           O
ATOM   4084  CB   THR B 226     -23.411   -5.598   46.963  1.00 27.21           C
ATOM   4085  OG1  THR B 226     -22.521   -6.570   46.401  1.00 25.89           O
ATOM   4086  CG2  THR B 226     -24.851   -6.092   46.843  1.00 25.49           C
ATOM   4087  N    PRO B 227     -25.148   -2.744   45.989  1.00 27.79           N
ATOM   4088  CA   PRO B 227     -26.114   -1.759   46.476  1.00 28.49           C
ATOM   4089  C    PRO B 227     -26.982   -2.265   47.623  1.00 29.89           C
ATOM   4090  O    PRO B 227     -27.457   -3.406   47.608  1.00 29.69           O
ATOM   4091  CB   PRO B 227     -26.952   -1.445   45.233  1.00 27.97           C
ATOM   4092  CG   PRO B 227     -26.024   -1.763   44.093  1.00 27.42           C
ATOM   4093  CD   PRO B 227     -25.382   -3.041   44.567  1.00 27.92           C
ATOM   4094  N    HIS B 228     -27.183   -1.403   48.616  1.00 30.44           N
ATOM   4095  CA   HIS B 228     -28.030   -1.730   49.748  1.00 30.76           C
ATOM   4096  C    HIS B 228     -28.710   -0.475   50.293  1.00 31.62           C
ATOM   4097  O    HIS B 228     -28.073    0.555   50.513  1.00 30.59           O
ATOM   4098  CB   HIS B 228     -27.243   -2.401   50.870  1.00 29.88           C
ATOM   4099  CG   HIS B 228     -28.121   -3.035   51.905  1.00 30.50           C
ATOM   4100  ND1  HIS B 228     -28.878   -4.159   51.648  1.00 31.32           N
ATOM   4101  CD2  HIS B 228     -28.401   -2.678   53.182  1.00 30.03           C
ATOM   4102  CE1  HIS B 228     -29.585   -4.468   52.722  1.00 30.58           C
ATOM   4103  NE2  HIS B 228     -29.315   -3.584   53.666  1.00 31.18           N
ATOM   4104  N    PRO B 229     -30.031   -0.543   50.481  1.00 32.51           N
ATOM   4105  CA   PRO B 229     -30.820   -1.743   50.186  1.00 33.18           C
ATOM   4106  C    PRO B 229     -31.002   -1.874   48.669  1.00 34.12           C
ATOM   4107  O    PRO B 229     -30.626   -0.971   47.917  1.00 34.12           O
ATOM   4108  CB   PRO B 229     -32.129   -1.471   50.917  1.00 32.78           C
ATOM   4109  CG   PRO B 229     -32.269    0.001   50.766  1.00 33.15           C
ATOM   4110  CD   PRO B 229     -30.872    0.508   51.073  1.00 32.47           C
ATOM   4111  N    PRO B 230     -31.579   -2.996   48.200  1.00 34.00           N
ATOM   4112  CA   PRO B 230     -31.781   -3.187   46.758  1.00 34.66           C
ATOM   4113  C    PRO B 230     -32.351   -1.932   46.107  1.00 35.55           C
ATOM   4114  O    PRO B 230     -33.263   -1.309   46.649  1.00 36.34           O
ATOM   4115  CB   PRO B 230     -32.754   -4.361   46.697  1.00 34.43           C
ATOM   4116  CG   PRO B 230     -32.373   -5.168   47.908  1.00 34.55           C
ATOM   4117  CD   PRO B 230     -32.192   -4.095   48.967  1.00 34.69           C
ATOM   4118  N    GLY B 231     -31.800   -1.559   44.956  1.00 35.31           N
ATOM   4119  CA   GLY B 231     -32.273   -0.377   44.261  1.00 35.24           C
ATOM   4120  C    GLY B 231     -31.546    0.910   44.614  1.00 35.80           C
ATOM   4121  O    GLY B 231     -31.690    1.911   43.914  1.00 36.12           O
ATOM   4122  N    ALA B 232     -30.765    0.904   45.688  1.00 35.29           N
ATOM   4123  CA   ALA B 232     -30.040    2.108   46.094  1.00 36.48           C
ATOM   4124  C    ALA B 232     -29.041    2.554   45.027  1.00 36.72           C
ATOM   4125  O    ALA B 232     -28.499    1.733   44.292  1.00 36.80           O
ATOM   4126  CB   ALA B 232     -29.320    1.865   47.411  1.00 35.76           C
ATOM   4127  N    ARG B 233     -28.791    3.857   44.958  1.00 38.36           N
ATOM   4128  CA   ARG B 233     -27.870    4.419   43.974  1.00 39.45           C
ATOM   4129  C    ARG B 233     -26.453    4.666   44.491  1.00 38.60           C
ATOM   4130  O    ARG B 233     -25.486    4.565   43.726  1.00 38.63           O
ATOM   4131  CB   ARG B 233     -28.424    5.739   43.429  1.00 42.08           C
ATOM   4132  CG   ARG B 233     -29.645    5.602   42.525  1.00 47.61           C
ATOM   4133  CD   ARG B 233     -30.263    6.972   42.194  1.00 50.73           C
ATOM   4134  NE   ARG B 233     -31.293    6.871   41.159  1.00 54.90           N
ATOM   4135  CZ   ARG B 233     -31.048    6.742   39.853  1.00 56.23           C
ATOM   4136  NH1  ARG B 233     -29.800    6.706   39.401  1.00 56.28           N
ATOM   4137  NH2  ARG B 233     -32.057    6.626   38.995  1.00 56.36           N
ATOM   4138  N    GLY B 234     -26.321    4.994   45.775  1.00 36.57           N
ATOM   4139  CA   GLY B 234     -24.999    5.279   46.300  1.00 35.12           C
ATOM   4140  C    GLY B 234     -24.616    4.701   47.646  1.00 34.89           C
ATOM   4141  O    GLY B 234     -23.651    5.159   48.261  1.00 34.56           O
ATOM   4142  N    THR B 235     -25.361    3.706   48.114  1.00 34.14           N
ATOM   4143  CA   THR B 235     -25.059    3.078   49.391  1.00 33.13           C
ATOM   4144  C    THR B 235     -24.889    1.575   49.182  1.00 33.26           C
```

FIGURE 4-62 (COORDINATES)

```
ATOM   4145  O    THR B 235     -25.534   0.983  48.317  1.00 33.35           O
ATOM   4146  CB   THR B 235     -26.171   3.357  50.425  1.00 33.39           C
ATOM   4147  OG1  THR B 235     -27.442   2.973  49.890  1.00 32.88           O
ATOM   4148  CG2  THR B 235     -26.201   4.831  50.773  1.00 32.15           C
ATOM   4149  N    SER B 236     -24.011   0.961  49.965  1.00 32.32           N
ATOM   4150  CA   SER B 236     -23.750  -0.466  49.822  1.00 32.98           C
ATOM   4151  C    SER B 236     -24.061  -1.262  51.082  1.00 32.57           C
ATOM   4152  O    SER B 236     -24.475  -0.707  52.102  1.00 33.18           O
ATOM   4153  CB   SER B 236     -22.285  -0.691  49.450  1.00 33.05           C
ATOM   4154  OG   SER B 236     -21.442  -0.298  50.523  1.00 34.48           O
ATOM   4155  N    GLN B 237     -23.851  -2.570  50.998  1.00 31.80           N
ATOM   4156  CA   GLN B 237     -24.085  -3.461  52.123  1.00 31.08           C
ATOM   4157  C    GLN B 237     -23.069  -3.170  53.219  1.00 30.77           C
ATOM   4158  O    GLN B 237     -23.343  -3.339  54.405  1.00 31.73           O
ATOM   4159  CB   GLN B 237     -23.955  -4.909  51.669  1.00 30.30           C
ATOM   4160  CG   GLN B 237     -24.954  -5.290  50.615  1.00 31.11           C
ATOM   4161  CD   GLN B 237     -24.867  -6.750  50.249  1.00 33.16           C
ATOM   4162  OE1  GLN B 237     -23.772  -7.310  50.141  1.00 34.57           O
ATOM   4163  NE2  GLN B 237     -26.021  -7.379  50.036  1.00 32.34           N
ATOM   4164  N    LEU B 238     -21.893  -2.720  52.810  1.00 30.20           N
ATOM   4165  CA   LEU B 238     -20.838  -2.404  53.750  1.00 30.15           C
ATOM   4166  C    LEU B 238     -21.279  -1.221  54.602  1.00 30.30           C
ATOM   4167  O    LEU B 238     -20.987  -1.156  55.794  1.00 30.47           O
ATOM   4168  CB   LEU B 238     -19.562  -2.074  52.984  1.00 30.42           C
ATOM   4169  CG   LEU B 238     -18.294  -1.974  53.810  1.00 31.29           C
ATOM   4170  CD1  LEU B 238     -17.234  -2.858  53.172  1.00 31.68           C
ATOM   4171  CD2  LEU B 238     -17.841  -0.511  53.902  1.00 32.32           C
ATOM   4172  N    HIS B 239     -21.987  -0.282  53.988  1.00 29.79           N
ATOM   4173  CA   HIS B 239     -22.479   0.879  54.720  1.00 29.39           C
ATOM   4174  C    HIS B 239     -23.547   0.430  55.719  1.00 29.05           C
ATOM   4175  O    HIS B 239     -23.786   1.090  56.724  1.00 29.30           O
ATOM   4176  CB   HIS B 239     -23.066   1.908  53.744  1.00 29.35           C
ATOM   4177  CG   HIS B 239     -22.044   2.533  52.846  1.00 29.04           C
ATOM   4178  ND1  HIS B 239     -22.338   2.966  51.571  1.00 29.02           N
ATOM   4179  CD2  HIS B 239     -20.721   2.768  53.026  1.00 29.49           C
ATOM   4180  CE1  HIS B 239     -21.241   3.434  51.002  1.00 29.53           C
ATOM   4181  NE2  HIS B 239     -20.245   3.324  51.863  1.00 29.19           N
ATOM   4182  N    GLY B 240     -24.175  -0.708  55.443  1.00 28.73           N
ATOM   4183  CA   GLY B 240     -25.207  -1.211  56.332  1.00 28.07           C
ATOM   4184  C    GLY B 240     -24.694  -1.873  57.599  1.00 27.73           C
ATOM   4185  O    GLY B 240     -25.461  -2.098  58.534  1.00 26.96           O
ATOM   4186  N    MET B 241     -23.403  -2.195  57.636  1.00 27.25           N
ATOM   4187  CA   MET B 241     -22.817  -2.839  58.811  1.00 26.59           C
ATOM   4188  C    MET B 241     -22.630  -1.827  59.935  1.00 26.41           C
ATOM   4189  O    MET B 241     -21.737  -0.983  59.884  1.00 26.25           O
ATOM   4190  CB   MET B 241     -21.471  -3.477  58.455  1.00 27.66           C
ATOM   4191  CG   MET B 241     -21.544  -4.539  57.352  1.00 28.73           C
ATOM   4192  SD   MET B 241     -19.929  -5.256  56.954  1.00 30.83           S
ATOM   4193  CE   MET B 241     -19.541  -6.045  58.505  1.00 27.59           C
ATOM   4194  N    ASP B 242     -23.481  -1.918  60.949  1.00 26.09           N
ATOM   4195  CA   ASP B 242     -23.422  -1.016  62.092  1.00 26.85           C
ATOM   4196  C    ASP B 242     -22.124  -1.187  62.853  1.00 27.00           C
ATOM   4197  O    ASP B 242     -21.439  -0.217  63.186  1.00 26.71           O
ATOM   4198  CB   ASP B 242     -24.586  -1.306  63.042  1.00 28.62           C
ATOM   4199  CG   ASP B 242     -25.662  -0.247  62.988  1.00 29.58           C
ATOM   4200  OD1  ASP B 242     -26.159   0.061  61.878  1.00 29.94           O
ATOM   4201  OD2  ASP B 242     -26.012   0.271  64.067  1.00 29.89           O
ATOM   4202  N    LEU B 243     -21.799  -2.444  63.126  1.00 27.40           N
ATOM   4203  CA   LEU B 243     -20.606  -2.801  63.880  1.00 25.95           C
ATOM   4204  C    LEU B 243     -20.251  -4.236  63.530  1.00 25.22           C
ATOM   4205  O    LEU B 243     -21.130  -5.078  63.362  1.00 24.80           O
ATOM   4206  CB   LEU B 243     -20.897  -2.699  65.384  1.00 25.16           C
ATOM   4207  CG   LEU B 243     -19.770  -3.039  66.359  1.00 24.89           C
ATOM   4208  CD1  LEU B 243     -18.682  -1.982  66.244  1.00 23.49           C
ATOM   4209  CD2  LEU B 243     -20.313  -3.104  67.788  1.00 24.14           C
ATOM   4210  N    LEU B 244     -18.961  -4.501  63.405  1.00 23.61           N
ATOM   4211  CA   LEU B 244     -18.490  -5.841  63.099  1.00 24.15           C
ATOM   4212  C    LEU B 244     -17.841  -6.379  64.359  1.00 23.16           C
```

FIGURE 4-63 (COORDINATES)

```
ATOM   4213  O    LEU B 244     -16.799  -5.885  64.776  1.00 23.64           O
ATOM   4214  CB   LEU B 244     -17.456  -5.809  61.972  1.00 23.46           C
ATOM   4215  CG   LEU B 244     -16.729  -7.123  61.680  1.00 23.39           C
ATOM   4216  CD1  LEU B 244     -17.730  -8.189  61.235  1.00 22.61           C
ATOM   4217  CD2  LEU B 244     -15.692  -6.886  60.591  1.00 22.59           C
ATOM   4218  N    VAL B 245     -18.475  -7.368  64.978  1.00 22.84           N
ATOM   4219  CA   VAL B 245     -17.938  -7.968  66.187  1.00 22.99           C
ATOM   4220  C    VAL B 245     -17.279  -9.270  65.773  1.00 23.82           C
ATOM   4221  O    VAL B 245     -17.945 -10.267  65.493  1.00 24.93           O
ATOM   4222  CB   VAL B 245     -19.046  -8.229  67.226  1.00 23.24           C
ATOM   4223  CG1  VAL B 245     -18.434  -8.749  68.515  1.00 22.97           C
ATOM   4224  CG2  VAL B 245     -19.812  -6.935  67.504  1.00 22.55           C
ATOM   4225  N    LEU B 246     -15.955  -9.244  65.714  1.00 24.76           N
ATOM   4226  CA   LEU B 246     -15.188 -10.405  65.300  1.00 25.39           C
ATOM   4227  C    LEU B 246     -14.605 -11.178  66.468  1.00 26.22           C
ATOM   4228  O    LEU B 246     -13.842 -10.627  67.261  1.00 27.63           O
ATOM   4229  CB   LEU B 246     -14.057  -9.967  64.362  1.00 24.67           C
ATOM   4230  CG   LEU B 246     -13.110 -11.052  63.839  1.00 23.32           C
ATOM   4231  CD1  LEU B 246     -13.897 -12.040  62.982  1.00 20.57           C
ATOM   4232  CD2  LEU B 246     -11.980 -10.404  63.027  1.00 22.18           C
ATOM   4233  N    LEU B 247     -14.972 -12.457  66.554  1.00 27.09           N
ATOM   4234  CA   LEU B 247     -14.491 -13.370  67.594  1.00 27.08           C
ATOM   4235  C    LEU B 247     -13.385 -14.238  67.003  1.00 26.85           C
ATOM   4236  O    LEU B 247     -13.550 -14.829  65.937  1.00 26.23           O
ATOM   4237  CB   LEU B 247     -15.616 -14.290  68.078  1.00 27.59           C
ATOM   4238  CG   LEU B 247     -16.747 -13.727  68.940  1.00 28.45           C
ATOM   4239  CD1  LEU B 247     -17.513 -12.661  68.183  1.00 28.85           C
ATOM   4240  CD2  LEU B 247     -17.675 -14.864  69.326  1.00 28.14           C
ATOM   4241  N    ASP B 248     -12.265 -14.333  67.705  1.00 26.84           N
ATOM   4242  CA   ASP B 248     -11.154 -15.131  67.216  1.00 25.86           C
ATOM   4243  C    ASP B 248     -10.281 -15.558  68.386  1.00 25.80           C
ATOM   4244  O    ASP B 248     -10.070 -14.790  69.321  1.00 24.74           O
ATOM   4245  CB   ASP B 248     -10.344 -14.300  66.208  1.00 26.12           C
ATOM   4246  CG   ASP B 248      -9.359 -15.132  65.413  1.00 26.75           C
ATOM   4247  OD1  ASP B 248      -9.459 -16.375  65.435  1.00 27.63           O
ATOM   4248  OD2  ASP B 248      -8.488 -14.539  64.747  1.00 28.22           O
ATOM   4249  N    LEU B 249      -9.794 -16.795  68.337  1.00 25.53           N
ATOM   4250  CA   LEU B 249      -8.924 -17.327  69.379  1.00 25.45           C
ATOM   4251  C    LEU B 249      -9.566 -17.285  70.761  1.00 25.83           C
ATOM   4252  O    LEU B 249      -8.955 -16.829  71.727  1.00 26.27           O
ATOM   4253  CB   LEU B 249      -7.604 -16.550  69.401  1.00 24.41           C
ATOM   4254  CG   LEU B 249      -6.944 -16.327  68.034  1.00 24.17           C
ATOM   4255  CD1  LEU B 249      -5.600 -15.625  68.235  1.00 23.68           C
ATOM   4256  CD2  LEU B 249      -6.753 -17.658  67.314  1.00 21.49           C
ATOM   4257  N    ILE B 250     -10.797 -17.772  70.853  1.00 25.93           N
ATOM   4258  CA   ILE B 250     -11.512 -17.784  72.122  1.00 26.00           C
ATOM   4259  C    ILE B 250     -11.742 -19.212  72.602  1.00 25.63           C
ATOM   4260  O    ILE B 250     -12.048 -20.099  71.816  1.00 24.85           O
ATOM   4261  CB   ILE B 250     -12.878 -17.057  72.005  1.00 25.42           C
ATOM   4262  CG1  ILE B 250     -12.656 -15.583  71.644  1.00 25.94           C
ATOM   4263  CG2  ILE B 250     -13.640 -17.157  73.322  1.00 24.88           C
ATOM   4264  CD1  ILE B 250     -13.947 -14.782  71.476  1.00 25.17           C
ATOM   4265  N    GLY B 251     -11.588 -19.428  73.900  1.00 26.64           N
ATOM   4266  CA   GLY B 251     -11.794 -20.757  74.443  1.00 29.22           C
ATOM   4267  C    GLY B 251     -10.837 -21.078  75.568  1.00 29.99           C
ATOM   4268  O    GLY B 251     -11.151 -21.867  76.453  1.00 30.97           O
ATOM   4269  N    ALA B 252      -9.660 -20.469  75.533  1.00 30.75           N
ATOM   4270  CA   ALA B 252      -8.665 -20.696  76.565  1.00 31.35           C
ATOM   4271  C    ALA B 252      -9.079 -19.983  77.859  1.00 32.51           C
ATOM   4272  O    ALA B 252      -9.865 -19.030  77.842  1.00 32.61           O
ATOM   4273  CB   ALA B 252      -7.308 -20.194  76.094  1.00 29.93           C
ATOM   4274  N    PRO B 253      -8.565 -20.451  79.005  1.00 33.39           N
ATOM   4275  CA   PRO B 253      -8.909 -19.819  80.282  1.00 33.05           C
ATOM   4276  C    PRO B 253      -8.161 -18.503  80.492  1.00 33.21           C
ATOM   4277  O    PRO B 253      -7.095 -18.277  79.916  1.00 32.31           O
ATOM   4278  CB   PRO B 253      -8.508 -20.880  81.307  1.00 33.06           C
ATOM   4279  CG   PRO B 253      -7.311 -21.523  80.654  1.00 33.35           C
ATOM   4280  CD   PRO B 253      -7.781 -21.684  79.219  1.00 33.26           C
```

FIGURE 4-64 (COORDINATES)

```
ATOM   4281  N   ASN B 254      -8.741 -17.637  81.315  1.00 33.05           N
ATOM   4282  CA  ASN B 254      -8.140 -16.352  81.636  1.00 33.10           C
ATOM   4283  C   ASN B 254      -7.742 -15.496  80.429  1.00 32.30           C
ATOM   4284  O   ASN B 254      -6.613 -15.013  80.341  1.00 32.12           O
ATOM   4285  CB  ASN B 254      -6.922 -16.577  82.536  1.00 34.13           C
ATOM   4286  CG  ASN B 254      -7.282 -17.281  83.837  1.00 36.02           C
ATOM   4287  OD1 ASN B 254      -8.039 -16.752  84.652  1.00 36.71           O
ATOM   4288  ND2 ASN B 254      -6.743 -18.480  84.033  1.00 35.94           N
ATOM   4289  N   PRO B 255      -8.664 -15.298  79.479  1.00 30.82           N
ATOM   4290  CA  PRO B 255      -8.275 -14.472  78.339  1.00 31.11           C
ATOM   4291  C   PRO B 255      -8.299 -13.010  78.775  1.00 31.65           C
ATOM   4292  O   PRO B 255      -8.984 -12.654  79.735  1.00 30.92           O
ATOM   4293  CB  PRO B 255      -9.358 -14.781  77.314  1.00 30.21           C
ATOM   4294  CG  PRO B 255     -10.570 -14.947  78.183  1.00 28.77           C
ATOM   4295  CD  PRO B 255     -10.035 -15.811  79.311  1.00 30.19           C
ATOM   4296  N   THR B 256      -7.531 -12.173  78.087  1.00 30.98           N
ATOM   4297  CA  THR B 256      -7.510 -10.750  78.392  1.00 30.98           C
ATOM   4298  C   THR B 256      -7.694 -10.003  77.073  1.00 30.81           C
ATOM   4299  O   THR B 256      -6.806  -9.988  76.219  1.00 31.09           O
ATOM   4300  CB  THR B 256      -6.185 -10.328  79.091  1.00 31.05           C
ATOM   4301  OG1 THR B 256      -5.064 -10.693  78.279  1.00 31.70           O
ATOM   4302  CG2 THR B 256      -6.064 -11.006  80.459  1.00 29.69           C
ATOM   4303  N   PHE B 257      -8.874  -9.414  76.908  1.00 30.62           N
ATOM   4304  CA  PHE B 257      -9.229  -8.672  75.700  1.00 30.52           C
ATOM   4305  C   PHE B 257      -9.028  -7.173  75.878  1.00 30.43           C
ATOM   4306  O   PHE B 257      -9.614  -6.569  76.778  1.00 30.99           O
ATOM   4307  CB  PHE B 257     -10.708  -8.870  75.353  1.00 30.00           C
ATOM   4308  CG  PHE B 257     -11.099 -10.288  75.059  1.00 31.00           C
ATOM   4309  CD1 PHE B 257     -10.923 -10.826  73.786  1.00 30.69           C
ATOM   4310  CD2 PHE B 257     -11.694 -11.075  76.045  1.00 30.26           C
ATOM   4311  CE1 PHE B 257     -11.340 -12.127  73.500  1.00 30.98           C
ATOM   4312  CE2 PHE B 257     -12.111 -12.373  75.768  1.00 29.99           C
ATOM   4313  CZ  PHE B 257     -11.936 -12.901  74.495  1.00 29.88           C
ATOM   4314  N   PRO B 258      -8.201  -6.550  75.026  1.00 29.54           N
ATOM   4315  CA  PRO B 258      -7.990  -5.106  75.147  1.00 28.87           C
ATOM   4316  C   PRO B 258      -8.915  -4.439  74.123  1.00 28.46           C
ATOM   4317  O   PRO B 258      -9.492  -5.114  73.278  1.00 26.68           O
ATOM   4318  CB  PRO B 258      -6.529  -4.951  74.760  1.00 29.15           C
ATOM   4319  CG  PRO B 258      -6.428  -5.923  73.612  1.00 28.89           C
ATOM   4320  CD  PRO B 258      -7.193  -7.147  74.127  1.00 29.00           C
ATOM   4321  N   ASN B 259      -9.057  -3.124  74.201  1.00 29.41           N
ATOM   4322  CA  ASN B 259      -9.877  -2.395  73.235  1.00 28.80           C
ATOM   4323  C   ASN B 259      -8.943  -1.995  72.094  1.00 29.28           C
ATOM   4324  O   ASN B 259      -7.860  -1.466  72.336  1.00 29.79           O
ATOM   4325  CB  ASN B 259     -10.474  -1.148  73.883  1.00 29.13           C
ATOM   4326  CG  ASN B 259     -11.220  -0.291  72.896  1.00 28.19           C
ATOM   4327  OD1 ASN B 259     -10.673   0.652  72.338  1.00 28.88           O
ATOM   4328  ND2 ASN B 259     -12.475  -0.629  72.661  1.00 28.71           N
ATOM   4329  N   PHE B 260      -9.349  -2.240  70.855  1.00 28.75           N
ATOM   4330  CA  PHE B 260      -8.485  -1.915  69.729  1.00 28.64           C
ATOM   4331  C   PHE B 260      -8.740  -0.600  68.998  1.00 28.51           C
ATOM   4332  O   PHE B 260      -7.806  -0.008  68.451  1.00 27.55           O
ATOM   4333  CB  PHE B 260      -8.517  -3.052  68.702  1.00 28.65           C
ATOM   4334  CG  PHE B 260      -7.908  -4.331  69.194  1.00 28.78           C
ATOM   4335  CD1 PHE B 260      -8.669  -5.254  69.902  1.00 28.88           C
ATOM   4336  CD2 PHE B 260      -6.569  -4.615  68.948  1.00 28.84           C
ATOM   4337  CE1 PHE B 260      -8.102  -6.449  70.357  1.00 29.28           C
ATOM   4338  CE2 PHE B 260      -5.992  -5.807  69.399  1.00 29.18           C
ATOM   4339  CZ  PHE B 260      -6.760  -6.723  70.104  1.00 28.89           C
ATOM   4340  N   PHE B 261      -9.984  -0.132  68.992  1.00 28.37           N
ATOM   4341  CA  PHE B 261     -10.304   1.081  68.250  1.00 28.32           C
ATOM   4342  C   PHE B 261     -10.989   2.186  69.035  1.00 28.90           C
ATOM   4343  O   PHE B 261     -11.858   1.933  69.865  1.00 29.37           O
ATOM   4344  CB  PHE B 261     -11.140   0.692  67.033  1.00 28.55           C
ATOM   4345  CG  PHE B 261     -10.507  -0.383  66.204  1.00 28.16           C
ATOM   4346  CD1 PHE B 261      -9.379  -0.109  65.435  1.00 28.14           C
ATOM   4347  CD2 PHE B 261     -10.993  -1.686  66.241  1.00 27.39           C
ATOM   4348  CE1 PHE B 261      -8.742  -1.121  64.718  1.00 27.79           C
```

FIGURE 4-65 (COORDINATES)

```
ATOM   4349  CE2 PHE B 261     -10.363  -2.704  65.529  1.00 25.77           C
ATOM   4350  CZ  PHE B 261      -9.237  -2.422  64.767  1.00 27.01           C
ATOM   4351  N   PRO B 262     -10.608   3.442  68.761  1.00 29.47           N
ATOM   4352  CA  PRO B 262     -11.158   4.627  69.426  1.00 29.20           C
ATOM   4353  C   PRO B 262     -12.640   4.843  69.139  1.00 29.77           C
ATOM   4354  O   PRO B 262     -13.407   5.212  70.029  1.00 30.35           O
ATOM   4355  CB  PRO B 262     -10.317   5.779  68.861  1.00 29.29           C
ATOM   4356  CG  PRO B 262      -9.094   5.111  68.289  1.00 31.08           C
ATOM   4357  CD  PRO B 262      -9.627   3.827  67.733  1.00 29.52           C
ATOM   4358  N   ASN B 263     -13.039   4.601  67.896  1.00 29.17           N
ATOM   4359  CA  ASN B 263     -14.419   4.822  67.497  1.00 30.36           C
ATOM   4360  C   ASN B 263     -15.444   3.801  67.995  1.00 30.97           C
ATOM   4361  O   ASN B 263     -16.638   4.093  68.039  1.00 32.83           O
ATOM   4362  CB  ASN B 263     -14.495   4.971  65.966  1.00 30.40           C
ATOM   4363  CG  ASN B 263     -14.108   3.703  65.220  1.00 30.28           C
ATOM   4364  OD1 ASN B 263     -13.364   2.864  65.725  1.00 29.85           O
ATOM   4365  ND2 ASN B 263     -14.605   3.573  63.996  1.00 30.75           N
ATOM   4366  N   SER B 264     -14.996   2.616  68.383  1.00 30.06           N
ATOM   4367  CA  SER B 264     -15.923   1.611  68.877  1.00 29.27           C
ATOM   4368  C   SER B 264     -15.746   1.390  70.379  1.00 29.71           C
ATOM   4369  O   SER B 264     -16.419   0.547  70.975  1.00 29.92           O
ATOM   4370  CB  SER B 264     -15.725   0.298  68.115  1.00 28.22           C
ATOM   4371  OG  SER B 264     -14.359  -0.071  68.097  1.00 29.06           O
ATOM   4372  N   ALA B 265     -14.852   2.171  70.984  1.00 29.42           N
ATOM   4373  CA  ALA B 265     -14.562   2.070  72.415  1.00 29.24           C
ATOM   4374  C   ALA B 265     -15.796   2.027  73.300  1.00 30.03           C
ATOM   4375  O   ALA B 265     -15.819   1.282  74.282  1.00 29.63           O
ATOM   4376  CB  ALA B 265     -13.664   3.223  72.857  1.00 28.52           C
ATOM   4377  N   ARG B 266     -16.821   2.815  72.969  1.00 29.83           N
ATOM   4378  CA  ARG B 266     -18.025   2.830  73.800  1.00 30.07           C
ATOM   4379  C   ARG B 266     -18.748   1.487  73.792  1.00 29.61           C
ATOM   4380  O   ARG B 266     -19.466   1.154  74.729  1.00 29.26           O
ATOM   4381  CB  ARG B 266     -18.978   3.955  73.373  1.00 29.30           C
ATOM   4382  CG  ARG B 266     -19.622   3.787  72.014  1.00 31.25           C
ATOM   4383  CD  ARG B 266     -20.340   5.074  71.626  1.00 31.85           C
ATOM   4384  NE  ARG B 266     -21.004   4.991  70.328  1.00 33.63           N
ATOM   4385  CZ  ARG B 266     -22.253   4.576  70.148  1.00 34.06           C
ATOM   4386  NH1 ARG B 266     -22.992   4.199  71.183  1.00 34.68           N
ATOM   4387  NH2 ARG B 266     -22.770   4.548  68.929  1.00 34.32           N
ATOM   4388  N   TRP B 267     -18.555   0.709  72.738  1.00 30.00           N
ATOM   4389  CA  TRP B 267     -19.191  -0.597  72.669  1.00 30.39           C
ATOM   4390  C   TRP B 267     -18.364  -1.595  73.468  1.00 30.40           C
ATOM   4391  O   TRP B 267     -18.898  -2.562  74.013  1.00 30.86           O
ATOM   4392  CB  TRP B 267     -19.353  -1.028  71.212  1.00 29.60           C
ATOM   4393  CG  TRP B 267     -20.410  -0.211  70.536  1.00 29.69           C
ATOM   4394  CD1 TRP B 267     -20.237   0.669  69.508  1.00 28.68           C
ATOM   4395  CD2 TRP B 267     -21.801  -0.156  70.886  1.00 28.72           C
ATOM   4396  NE1 TRP B 267     -21.435   1.272  69.196  1.00 29.94           N
ATOM   4397  CE2 TRP B 267     -22.411   0.784  70.026  1.00 29.63           C
ATOM   4398  CE3 TRP B 267     -22.590  -0.809  71.846  1.00 29.66           C
ATOM   4399  CZ2 TRP B 267     -23.778   1.090  70.094  1.00 29.05           C
ATOM   4400  CZ3 TRP B 267     -23.956  -0.507  71.917  1.00 28.61           C
ATOM   4401  CH2 TRP B 267     -24.532   0.436  71.042  1.00 28.66           C
ATOM   4402  N   PHE B 268     -17.062  -1.345  73.554  1.00 30.02           N
ATOM   4403  CA  PHE B 268     -16.184  -2.205  74.332  1.00 30.49           C
ATOM   4404  C   PHE B 268     -16.528  -1.934  75.800  1.00 31.97           C
ATOM   4405  O   PHE B 268     -16.591  -2.858  76.620  1.00 32.47           O
ATOM   4406  CB  PHE B 268     -14.716  -1.849  74.074  1.00 28.56           C
ATOM   4407  CG  PHE B 268     -13.734  -2.719  74.820  1.00 27.16           C
ATOM   4408  CD1 PHE B 268     -13.249  -3.896  74.251  1.00 26.77           C
ATOM   4409  CD2 PHE B 268     -13.290  -2.358  76.090  1.00 27.04           C
ATOM   4410  CE1 PHE B 268     -12.332  -4.705  74.932  1.00 27.57           C
ATOM   4411  CE2 PHE B 268     -12.371  -3.159  76.788  1.00 28.13           C
ATOM   4412  CZ  PHE B 268     -11.889  -4.337  76.206  1.00 26.96           C
ATOM   4413  N   GLU B 269     -16.749  -0.659  76.120  1.00 32.88           N
ATOM   4414  CA  GLU B 269     -17.085  -0.251  77.479  1.00 35.00           C
ATOM   4415  C   GLU B 269     -18.364  -0.958  77.921  1.00 34.95           C
ATOM   4416  O   GLU B 269     -18.525  -1.293  79.096  1.00 34.63           O
```

FIGURE 4-66 (COORDINATES)

```
ATOM   4417  CB   GLU B 269     -17.241   1.280  77.561  1.00 37.46           C
ATOM   4418  CG   GLU B 269     -15.908   2.049  77.386  1.00 43.15           C
ATOM   4419  CD   GLU B 269     -16.037   3.588  77.457  1.00 46.35           C
ATOM   4420  OE1  GLU B 269     -16.576   4.212  76.510  1.00 46.37           O
ATOM   4421  OE2  GLU B 269     -15.585   4.177  78.469  1.00 48.60           O
ATOM   4422  N    ARG B 270     -19.271  -1.195  76.976  1.00 34.58           N
ATOM   4423  CA   ARG B 270     -20.507  -1.895  77.296  1.00 33.97           C
ATOM   4424  C    ARG B 270     -20.197  -3.347  77.679  1.00 34.46           C
ATOM   4425  O    ARG B 270     -20.864  -3.920  78.539  1.00 34.72           O
ATOM   4426  CB   ARG B 270     -21.474  -1.853  76.110  1.00 33.62           C
ATOM   4427  CG   ARG B 270     -22.145  -0.495  75.892  1.00 32.43           C
ATOM   4428  CD   ARG B 270     -22.859  -0.033  77.153  1.00 33.07           C
ATOM   4429  NE   ARG B 270     -23.758  -1.062  77.666  1.00 33.54           N
ATOM   4430  CZ   ARG B 270     -24.083  -1.202  78.949  1.00 33.60           C
ATOM   4431  NH1  ARG B 270     -23.583  -0.376  79.855  1.00 34.15           N
ATOM   4432  NH2  ARG B 270     -24.894  -2.182  79.329  1.00 33.18           N
ATOM   4433  N    LEU B 271     -19.182  -3.942  77.051  1.00 34.03           N
ATOM   4434  CA   LEU B 271     -18.811  -5.316  77.380  1.00 33.89           C
ATOM   4435  C    LEU B 271     -18.280  -5.395  78.807  1.00 33.90           C
ATOM   4436  O    LEU B 271     -18.629  -6.314  79.546  1.00 34.27           O
ATOM   4437  CB   LEU B 271     -17.762  -5.856  76.404  1.00 33.52           C
ATOM   4438  CG   LEU B 271     -18.296  -6.228  75.014  1.00 33.59           C
ATOM   4439  CD1  LEU B 271     -17.151  -6.653  74.114  1.00 32.71           C
ATOM   4440  CD2  LEU B 271     -19.318  -7.347  75.136  1.00 32.12           C
ATOM   4441  N    GLN B 272     -17.446  -4.431  79.196  1.00 33.51           N
ATOM   4442  CA   GLN B 272     -16.894  -4.400  80.550  1.00 33.92           C
ATOM   4443  C    GLN B 272     -18.028  -4.270  81.561  1.00 34.29           C
ATOM   4444  O    GLN B 272     -18.064  -4.972  82.573  1.00 34.09           O
ATOM   4445  CB   GLN B 272     -15.974  -3.197  80.744  1.00 34.50           C
ATOM   4446  CG   GLN B 272     -14.812  -3.080  79.787  1.00 35.78           C
ATOM   4447  CD   GLN B 272     -14.018  -1.816  80.041  1.00 35.78           C
ATOM   4448  OE1  GLN B 272     -13.024  -1.822  80.763  1.00 36.80           O
ATOM   4449  NE2  GLN B 272     -14.473  -0.715  79.465  1.00 36.99           N
ATOM   4450  N    ALA B 273     -18.941  -3.345  81.272  1.00 34.04           N
ATOM   4451  CA   ALA B 273     -20.086  -3.072  82.132  1.00 33.56           C
ATOM   4452  C    ALA B 273     -20.988  -4.288  82.266  1.00 33.46           C
ATOM   4453  O    ALA B 273     -21.521  -4.545  83.341  1.00 33.88           O
ATOM   4454  CB   ALA B 273     -20.885  -1.883  81.585  1.00 32.61           C
ATOM   4455  N    ILE B 274     -21.171  -5.030  81.177  1.00 33.40           N
ATOM   4456  CA   ILE B 274     -22.012  -6.217  81.228  1.00 33.19           C
ATOM   4457  C    ILE B 274     -21.302  -7.298  82.035  1.00 34.37           C
ATOM   4458  O    ILE B 274     -21.929  -7.992  82.837  1.00 34.58           O
ATOM   4459  CB   ILE B 274     -22.339  -6.747  79.814  1.00 32.36           C
ATOM   4460  CG1  ILE B 274     -23.235  -5.748  79.085  1.00 30.17           C
ATOM   4461  CG2  ILE B 274     -23.058  -8.094  79.904  1.00 32.69           C
ATOM   4462  CD1  ILE B 274     -23.532  -6.128  77.664  1.00 29.77           C
ATOM   4463  N    GLU B 275     -19.993  -7.430  81.833  1.00 34.69           N
ATOM   4464  CA   GLU B 275     -19.218  -8.423  82.566  1.00 35.57           C
ATOM   4465  C    GLU B 275     -19.286  -8.107  84.065  1.00 36.47           C
ATOM   4466  O    GLU B 275     -19.548  -8.988  84.881  1.00 36.42           O
ATOM   4467  CB   GLU B 275     -17.761  -8.429  82.086  1.00 34.81           C
ATOM   4468  CG   GLU B 275     -16.826  -9.306  82.913  1.00 35.46           C
ATOM   4469  CD   GLU B 275     -15.415  -9.388  82.336  1.00 36.71           C
ATOM   4470  OE1  GLU B 275     -14.941  -8.376  81.767  1.00 36.60           O
ATOM   4471  OE2  GLU B 275     -14.775 -10.460  82.466  1.00 35.76           O
ATOM   4472  N    HIS B 276     -19.070  -6.843  84.414  1.00 36.79           N
ATOM   4473  CA   HIS B 276     -19.102  -6.415  85.807  1.00 37.65           C
ATOM   4474  C    HIS B 276     -20.435  -6.759  86.476  1.00 37.94           C
ATOM   4475  O    HIS B 276     -20.464  -7.413  87.519  1.00 37.88           O
ATOM   4476  CB   HIS B 276     -18.864  -4.902  85.907  1.00 38.48           C
ATOM   4477  CG   HIS B 276     -18.778  -4.397  87.316  1.00 39.33           C
ATOM   4478  ND1  HIS B 276     -17.620  -4.463  88.062  1.00 40.20           N
ATOM   4479  CD2  HIS B 276     -19.721  -3.869  88.132  1.00 38.71           C
ATOM   4480  CE1  HIS B 276     -17.853  -4.000  89.278  1.00 39.09           C
ATOM   4481  NE2  HIS B 276     -19.121  -3.634  89.346  1.00 39.40           N
ATOM   4482  N    GLU B 277     -21.533  -6.320  85.866  1.00 38.03           N
ATOM   4483  CA   GLU B 277     -22.869  -6.559  86.405  1.00 37.77           C
ATOM   4484  C    GLU B 277     -23.228  -8.039  86.530  1.00 37.72           C
```

FIGURE 4-67 (COORDINATES)

```
ATOM   4485  O    GLU B 277     -23.797   -8.451  87.542  1.00 38.48           O
ATOM   4486  CB   GLU B 277     -23.916   -5.831  85.553  1.00 37.70           C
ATOM   4487  CG   GLU B 277     -25.347   -5.894  86.098  1.00 39.78           C
ATOM   4488  CD   GLU B 277     -25.524   -5.196  87.450  1.00 40.58           C
ATOM   4489  OE1  GLU B 277     -26.659   -5.188  87.970  1.00 40.52           O
ATOM   4490  OE2  GLU B 277     -24.537   -4.656  87.996  1.00 41.05           O
ATOM   4491  N    LEU B 278     -22.910   -8.841  85.515  1.00 36.78           N
ATOM   4492  CA   LEU B 278     -23.219  -10.269  85.581  1.00 36.51           C
ATOM   4493  C    LEU B 278     -22.430  -10.924  86.719  1.00 37.07           C
ATOM   4494  O    LEU B 278     -22.921  -11.839  87.388  1.00 36.59           O
ATOM   4495  CB   LEU B 278     -22.897  -10.967  84.252  1.00 35.41           C
ATOM   4496  CG   LEU B 278     -23.791  -10.684  83.036  1.00 34.78           C
ATOM   4497  CD1  LEU B 278     -23.290  -11.497  81.858  1.00 34.60           C
ATOM   4498  CD2  LEU B 278     -25.241  -11.044  83.335  1.00 34.24           C
ATOM   4499  N    HIS B 279     -21.205  -10.455  86.934  1.00 36.96           N
ATOM   4500  CA   HIS B 279     -20.382  -10.987  88.005  1.00 38.11           C
ATOM   4501  C    HIS B 279     -21.052  -10.636  89.326  1.00 39.07           C
ATOM   4502  O    HIS B 279     -21.327  -11.509  90.146  1.00 39.56           O
ATOM   4503  CB   HIS B 279     -18.981  -10.376  87.965  1.00 37.81           C
ATOM   4504  CG   HIS B 279     -18.132  -10.734  89.148  1.00 38.92           C
ATOM   4505  ND1  HIS B 279     -18.433  -10.330  90.431  1.00 39.62           N
ATOM   4506  CD2  HIS B 279     -16.995  -11.463  89.242  1.00 38.94           C
ATOM   4507  CE1  HIS B 279     -17.518  -10.794  91.264  1.00 39.46           C
ATOM   4508  NE2  HIS B 279     -16.635  -11.485  90.568  1.00 39.52           N
ATOM   4509  N    GLU B 280     -21.317   -9.346  89.511  1.00 39.50           N
ATOM   4510  CA   GLU B 280     -21.948   -8.833  90.722  1.00 40.43           C
ATOM   4511  C    GLU B 280     -23.266   -9.528  91.056  1.00 40.17           C
ATOM   4512  O    GLU B 280     -23.613   -9.682  92.226  1.00 40.96           O
ATOM   4513  CB   GLU B 280     -22.168   -7.324  90.587  1.00 41.48           C
ATOM   4514  CG   GLU B 280     -20.876   -6.518  90.562  1.00 43.82           C
ATOM   4515  CD   GLU B 280     -20.237   -6.393  91.935  1.00 45.97           C
ATOM   4516  OE1  GLU B 280     -20.806   -5.680  92.791  1.00 48.00           O
ATOM   4517  OE2  GLU B 280     -19.172   -7.006  92.163  1.00 46.67           O
ATOM   4518  N    LEU B 281     -24.002   -9.943  90.031  1.00 39.16           N
ATOM   4519  CA   LEU B 281     -25.271  -10.632  90.236  1.00 38.09           C
ATOM   4520  C    LEU B 281     -25.037  -12.132  90.423  1.00 37.44           C
ATOM   4521  O    LEU B 281     -25.982  -12.913  90.480  1.00 37.39           O
ATOM   4522  CB   LEU B 281     -26.188  -10.405  89.035  1.00 37.67           C
ATOM   4523  CG   LEU B 281     -26.771   -9.007  88.826  1.00 38.66           C
ATOM   4524  CD1  LEU B 281     -27.320   -8.892  87.401  1.00 38.76           C
ATOM   4525  CD2  LEU B 281     -27.873   -8.745  89.854  1.00 37.21           C
ATOM   4526  N    GLY B 282     -23.771  -12.525  90.513  1.00 36.96           N
ATOM   4527  CA   GLY B 282     -23.439  -13.927  90.680  1.00 36.84           C
ATOM   4528  C    GLY B 282     -23.927  -14.796  89.532  1.00 37.67           C
ATOM   4529  O    GLY B 282     -24.308  -15.948  89.740  1.00 38.24           O
ATOM   4530  N    LEU B 283     -23.912  -14.260  88.316  1.00 37.26           N
ATOM   4531  CA   LEU B 283     -24.370  -15.020  87.158  1.00 37.43           C
ATOM   4532  C    LEU B 283     -23.212  -15.526  86.297  1.00 37.72           C
ATOM   4533  O    LEU B 283     -23.403  -15.923  85.152  1.00 38.17           O
ATOM   4534  CB   LEU B 283     -25.328  -14.165  86.328  1.00 36.88           C
ATOM   4535  CG   LEU B 283     -26.597  -13.753  87.084  1.00 36.92           C
ATOM   4536  CD1  LEU B 283     -27.351  -12.685  86.313  1.00 36.34           C
ATOM   4537  CD2  LEU B 283     -27.472  -14.975  87.306  1.00 36.30           C
ATOM   4538  N    LEU B 284     -22.013  -15.517  86.873  1.00 38.61           N
ATOM   4539  CA   LEU B 284     -20.800  -15.982  86.202  1.00 38.95           C
ATOM   4540  C    LEU B 284     -20.130  -17.064  87.058  1.00 39.82           C
ATOM   4541  O    LEU B 284     -20.118  -16.967  88.286  1.00 39.83           O
ATOM   4542  CB   LEU B 284     -19.835  -14.806  86.002  1.00 38.33           C
ATOM   4543  CG   LEU B 284     -19.850  -14.037  84.673  1.00 38.43           C
ATOM   4544  CD1  LEU B 284     -21.263  -13.881  84.152  1.00 38.08           C
ATOM   4545  CD2  LEU B 284     -19.181  -12.684  84.873  1.00 37.69           C
ATOM   4546  N    LYS B 285     -19.571  -18.087  86.415  1.00 40.40           N
ATOM   4547  CA   LYS B 285     -18.910  -19.176  87.137  1.00 41.31           C
ATOM   4548  C    LYS B 285     -17.383  -19.072  87.084  1.00 41.76           C
ATOM   4549  O    LYS B 285     -16.819  -18.739  86.046  1.00 40.96           O
ATOM   4550  CB   LYS B 285     -19.347  -20.529  86.567  1.00 41.85           C
ATOM   4551  CG   LYS B 285     -20.838  -20.823  86.692  1.00 43.47           C
ATOM   4552  CD   LYS B 285     -21.154  -22.216  86.150  1.00 45.82           C
```

FIGURE 4-68 (COORDINATES)

```
ATOM   4553  CE   LYS B 285     -22.600 -22.645  86.414  1.00 47.32           C
ATOM   4554  NZ   LYS B 285     -23.609 -21.871  85.640  1.00 48.42           N
ATOM   4555  N    ASP B 286     -16.725 -19.368  88.205  1.00 42.43           N
ATOM   4556  CA   ASP B 286     -15.263 -19.306  88.304  1.00 43.68           C
ATOM   4557  C    ASP B 286     -14.753 -18.004  87.703  1.00 43.26           C
ATOM   4558  O    ASP B 286     -13.858 -18.005  86.860  1.00 43.88           O
ATOM   4559  CB   ASP B 286     -14.618 -20.483  87.563  1.00 45.26           C
ATOM   4560  CG   ASP B 286     -15.161 -21.824  88.011  1.00 47.76           C
ATOM   4561  OD1  ASP B 286     -15.223 -22.062  89.236  1.00 49.40           O
ATOM   4562  OD2  ASP B 286     -15.520 -22.646  87.142  1.00 48.84           O
ATOM   4563  N    HIS B 287     -15.316 -16.891  88.151  1.00 42.75           N
ATOM   4564  CA   HIS B 287     -14.944 -15.589  87.620  1.00 43.00           C
ATOM   4565  C    HIS B 287     -14.705 -14.567  88.726  1.00 43.19           C
ATOM   4566  O    HIS B 287     -15.480 -14.480  89.676  1.00 43.26           O
ATOM   4567  CB   HIS B 287     -16.061 -15.127  86.679  1.00 42.32           C
ATOM   4568  CG   HIS B 287     -15.833 -13.786  86.058  1.00 42.53           C
ATOM   4569  ND1  HIS B 287     -16.014 -12.606  86.747  1.00 42.15           N
ATOM   4570  CD2  HIS B 287     -15.483 -13.437  84.798  1.00 41.99           C
ATOM   4571  CE1  HIS B 287     -15.790 -11.587  85.936  1.00 42.64           C
ATOM   4572  NE2  HIS B 287     -15.467 -12.065  84.747  1.00 42.74           N
ATOM   4573  N    SER B 288     -13.626 -13.801  88.603  1.00 43.55           N
ATOM   4574  CA   SER B 288     -13.303 -12.780  89.597  1.00 44.45           C
ATOM   4575  C    SER B 288     -12.988 -11.451  88.918  1.00 44.83           C
ATOM   4576  O    SER B 288     -12.423 -11.424  87.826  1.00 44.20           O
ATOM   4577  CB   SER B 288     -12.096 -13.211  90.433  1.00 44.54           C
ATOM   4578  OG   SER B 288     -10.906 -13.129  89.673  1.00 44.89           O
ATOM   4579  N    LEU B 289     -13.353 -10.349  89.564  1.00 45.16           N
ATOM   4580  CA   LEU B 289     -13.087  -9.037  88.998  1.00 46.53           C
ATOM   4581  C    LEU B 289     -11.584  -8.815  88.862  1.00 46.95           C
ATOM   4582  O    LEU B 289     -11.138  -7.990  88.066  1.00 48.26           O
ATOM   4583  CB   LEU B 289     -13.712  -7.944  89.866  1.00 46.43           C
ATOM   4584  CG   LEU B 289     -15.239  -8.007  89.971  1.00 46.93           C
ATOM   4585  CD1  LEU B 289     -15.739  -6.839  90.801  1.00 47.18           C
ATOM   4586  CD2  LEU B 289     -15.855  -7.970  88.584  1.00 46.76           C
ATOM   4587  N    GLU B 290     -10.806  -9.564  89.633  1.00 47.18           N
ATOM   4588  CA   GLU B 290      -9.354  -9.455  89.584  1.00 47.63           C
ATOM   4589  C    GLU B 290      -8.826 -10.061  88.283  1.00 46.22           C
ATOM   4590  O    GLU B 290      -7.741  -9.715  87.819  1.00 46.28           O
ATOM   4591  CB   GLU B 290      -8.739 -10.175  90.789  1.00 50.67           C
ATOM   4592  CG   GLU B 290      -7.242 -10.434  90.686  1.00 55.38           C
ATOM   4593  CD   GLU B 290      -6.405  -9.170  90.785  1.00 58.60           C
ATOM   4594  OE1  GLU B 290      -6.645  -8.223  89.998  1.00 60.17           O
ATOM   4595  OE2  GLU B 290      -5.500  -9.129  91.652  1.00 59.68           O
ATOM   4596  N    GLY B 291      -9.602 -10.966  87.698  1.00 44.16           N
ATOM   4597  CA   GLY B 291      -9.189 -11.594  86.459  1.00 41.86           C
ATOM   4598  C    GLY B 291     -10.240 -11.445  85.379  1.00 40.76           C
ATOM   4599  O    GLY B 291     -10.473 -12.368  84.605  1.00 40.43           O
ATOM   4600  N    ARG B 292     -10.874 -10.280  85.314  1.00 39.94           N
ATOM   4601  CA   ARG B 292     -11.905 -10.063  84.314  1.00 40.05           C
ATOM   4602  C    ARG B 292     -11.351 -10.183  82.898  1.00 38.54           C
ATOM   4603  O    ARG B 292     -10.167  -9.961  82.658  1.00 37.65           O
ATOM   4604  CB   ARG B 292     -12.571  -8.701  84.515  1.00 42.20           C
ATOM   4605  CG   ARG B 292     -11.620  -7.531  84.528  1.00 45.76           C
ATOM   4606  CD   ARG B 292     -12.393  -6.235  84.364  1.00 48.54           C
ATOM   4607  NE   ARG B 292     -13.238  -5.927  85.513  1.00 50.94           N
ATOM   4608  CZ   ARG B 292     -14.317  -5.151  85.457  1.00 52.63           C
ATOM   4609  NH1  ARG B 292     -14.697  -4.608  84.305  1.00 52.67           N
ATOM   4610  NH2  ARG B 292     -15.008  -4.896  86.560  1.00 54.13           N
ATOM   4611  N    TYR B 293     -12.220 -10.531  81.960  1.00 36.65           N
ATOM   4612  CA   TYR B 293     -11.804 -10.712  80.581  1.00 35.42           C
ATOM   4613  C    TYR B 293     -11.541  -9.416  79.822  1.00 35.25           C
ATOM   4614  O    TYR B 293     -10.527  -9.282  79.143  1.00 35.18           O
ATOM   4615  CB   TYR B 293     -12.845 -11.550  79.845  1.00 33.58           C
ATOM   4616  CG   TYR B 293     -13.218 -12.812  80.591  1.00 34.16           C
ATOM   4617  CD1  TYR B 293     -12.239 -13.577  81.239  1.00 32.28           C
ATOM   4618  CD2  TYR B 293     -14.548 -13.243  80.659  1.00 32.95           C
ATOM   4619  CE1  TYR B 293     -12.574 -14.732  81.936  1.00 32.44           C
ATOM   4620  CE2  TYR B 293     -14.893 -14.401  81.354  1.00 33.04           C
```

FIGURE 4-69 (COORDINATES)

```
ATOM   4621  CZ   TYR B 293     -13.899 -15.139  81.991  1.00 32.80           C
ATOM   4622  OH   TYR B 293     -14.231 -16.277  82.685  1.00 31.97           O
ATOM   4623  N    PHE B 294     -12.445  -8.456  79.939  1.00 34.81           N
ATOM   4624  CA   PHE B 294     -12.274  -7.203  79.229  1.00 34.39           C
ATOM   4625  C    PHE B 294     -11.506  -6.177  80.031  1.00 34.92           C
ATOM   4626  O    PHE B 294     -12.002  -5.620  81.009  1.00 35.37           O
ATOM   4627  CB   PHE B 294     -13.642  -6.698  78.786  1.00 32.97           C
ATOM   4628  CG   PHE B 294     -14.344  -7.669  77.887  1.00 32.29           C
ATOM   4629  CD1  PHE B 294     -13.864  -7.905  76.600  1.00 31.18           C
ATOM   4630  CD2  PHE B 294     -15.413  -8.427  78.353  1.00 32.13           C
ATOM   4631  CE1  PHE B 294     -14.430  -8.882  75.795  1.00 30.62           C
ATOM   4632  CE2  PHE B 294     -15.990  -9.412  77.554  1.00 31.60           C
ATOM   4633  CZ   PHE B 294     -15.496  -9.640  76.273  1.00 31.75           C
ATOM   4634  N    GLN B 295     -10.268  -5.967  79.593  1.00 35.80           N
ATOM   4635  CA   GLN B 295      -9.313  -5.050  80.201  1.00 37.39           C
ATOM   4636  C    GLN B 295      -9.702  -3.585  80.070  1.00 38.21           C
ATOM   4637  O    GLN B 295     -10.502  -3.223  79.212  1.00 39.18           O
ATOM   4638  CB   GLN B 295      -7.953  -5.253  79.548  1.00 38.94           C
ATOM   4639  CG   GLN B 295      -7.462  -6.684  79.557  1.00 41.49           C
ATOM   4640  CD   GLN B 295      -7.211  -7.187  80.954  1.00 42.73           C
ATOM   4641  OE1  GLN B 295      -8.145  -7.426  81.717  1.00 44.95           O
ATOM   4642  NE2  GLN B 295      -5.940  -7.338  81.307  1.00 44.18           N
ATOM   4643  N    ASN B 296      -9.111  -2.736  80.904  1.00 38.16           N
ATOM   4644  CA   ASN B 296      -9.417  -1.311  80.858  1.00 39.26           C
ATOM   4645  C    ASN B 296      -8.307  -0.492  80.205  1.00 39.07           C
ATOM   4646  O    ASN B 296      -7.790   0.458  80.788  1.00 39.47           O
ATOM   4647  CB   ASN B 296      -9.698  -0.775  82.268  1.00 39.92           C
ATOM   4648  CG   ASN B 296     -10.429   0.559  82.241  1.00 41.14           C
ATOM   4649  OD1  ASN B 296     -11.276   0.798  81.375  1.00 41.87           O
ATOM   4650  ND2  ASN B 296     -10.118   1.426  83.193  1.00 41.29           N
ATOM   4651  N    TYR B 297      -7.948  -0.871  78.986  1.00 38.93           N
ATOM   4652  CA   TYR B 297      -6.912  -0.173  78.241  1.00 39.35           C
ATOM   4653  C    TYR B 297      -7.024  -0.573  76.780  1.00 38.96           C
ATOM   4654  O    TYR B 297      -7.628  -1.592  76.452  1.00 38.29           O
ATOM   4655  CB   TYR B 297      -5.523  -0.529  78.788  1.00 40.68           C
ATOM   4656  CG   TYR B 297      -5.089  -1.963  78.563  1.00 42.00           C
ATOM   4657  CD1  TYR B 297      -4.491  -2.357  77.362  1.00 42.64           C
ATOM   4658  CD2  TYR B 297      -5.265  -2.925  79.557  1.00 42.64           C
ATOM   4659  CE1  TYR B 297      -4.078  -3.677  77.159  1.00 44.21           C
ATOM   4660  CE2  TYR B 297      -4.858  -4.243  79.365  1.00 44.65           C
ATOM   4661  CZ   TYR B 297      -4.266  -4.613  78.167  1.00 45.30           C
ATOM   4662  OH   TYR B 297      -3.869  -5.920  77.985  1.00 48.22           O
ATOM   4663  N    SER B 298      -6.455   0.227  75.891  1.00 38.65           N
ATOM   4664  CA   SER B 298      -6.540  -0.117  74.491  1.00 38.98           C
ATOM   4665  C    SER B 298      -5.198  -0.518  73.904  1.00 38.35           C
ATOM   4666  O    SER B 298      -4.144  -0.090  74.364  1.00 38.11           O
ATOM   4667  CB   SER B 298      -7.187   1.024  73.693  1.00 39.46           C
ATOM   4668  OG   SER B 298      -6.565   2.265  73.938  1.00 42.77           O
ATOM   4669  N    TYR B 299      -5.274  -1.382  72.900  1.00 38.47           N
ATOM   4670  CA   TYR B 299      -4.129  -1.925  72.182  1.00 39.16           C
ATOM   4671  C    TYR B 299      -3.765  -0.947  71.069  1.00 40.26           C
ATOM   4672  O    TYR B 299      -4.530  -0.757  70.124  1.00 42.73           O
ATOM   4673  CB   TYR B 299      -4.534  -3.290  71.606  1.00 37.21           C
ATOM   4674  CG   TYR B 299      -3.429  -4.102  70.976  1.00 36.80           C
ATOM   4675  CD1  TYR B 299      -3.021  -3.868  69.663  1.00 36.44           C
ATOM   4676  CD2  TYR B 299      -2.820  -5.143  71.683  1.00 36.64           C
ATOM   4677  CE1  TYR B 299      -2.037  -4.659  69.067  1.00 36.79           C
ATOM   4678  CE2  TYR B 299      -1.838  -5.936  71.101  1.00 35.17           C
ATOM   4679  CZ   TYR B 299      -1.453  -5.693  69.797  1.00 36.10           C
ATOM   4680  OH   TYR B 299      -0.493  -6.487  69.220  1.00 36.77           O
ATOM   4681  N    GLY B 300      -2.600  -0.326  71.180  1.00 40.85           N
ATOM   4682  CA   GLY B 300      -2.183   0.641  70.176  1.00 40.36           C
ATOM   4683  C    GLY B 300      -2.366   0.235  68.724  1.00 40.29           C
ATOM   4684  O    GLY B 300      -3.177   0.806  67.998  1.00 40.46           O
ATOM   4685  N    GLY B 301      -1.602  -0.753  68.288  1.00 40.51           N
ATOM   4686  CA   GLY B 301      -1.707  -1.187  66.910  1.00 39.52           C
ATOM   4687  C    GLY B 301      -2.952  -1.986  66.576  1.00 38.40           C
ATOM   4688  O    GLY B 301      -4.052  -1.741  67.085  1.00 38.57           O
```

FIGURE 4-70 (COORDINATES)

```
ATOM   4689  N   VAL B 302      -2.762  -2.964  65.705  1.00 36.90           N
ATOM   4690  CA  VAL B 302      -3.847  -3.814  65.260  1.00 35.44           C
ATOM   4691  C   VAL B 302      -3.276  -5.223  65.067  1.00 33.95           C
ATOM   4692  O   VAL B 302      -2.070  -5.392  64.880  1.00 33.33           O
ATOM   4693  CB  VAL B 302      -4.420  -3.268  63.921  1.00 35.88           C
ATOM   4694  CG1 VAL B 302      -3.646  -3.839  62.743  1.00 34.82           C
ATOM   4695  CG2 VAL B 302      -5.892  -3.564  63.817  1.00 38.14           C
ATOM   4696  N   ILE B 303      -4.136  -6.233  65.135  1.00 32.41           N
ATOM   4697  CA  ILE B 303      -3.704  -7.611  64.938  1.00 30.25           C
ATOM   4698  C   ILE B 303      -4.410  -8.113  63.683  1.00 30.11           C
ATOM   4699  O   ILE B 303      -5.642  -8.170  63.637  1.00 29.14           O
ATOM   4700  CB  ILE B 303      -4.071  -8.502  66.154  1.00 29.12           C
ATOM   4701  CG1 ILE B 303      -3.316  -8.017  67.401  1.00 28.93           C
ATOM   4702  CG2 ILE B 303      -3.711  -9.948  65.868  1.00 29.06           C
ATOM   4703  CD1 ILE B 303      -3.674  -8.742  68.688  1.00 27.03           C
ATOM   4704  N   GLN B 304      -3.626  -8.446  62.659  1.00 29.91           N
ATOM   4705  CA  GLN B 304      -4.171  -8.926  61.390  1.00 30.55           C
ATOM   4706  C   GLN B 304      -5.273  -9.956  61.615  1.00 29.10           C
ATOM   4707  O   GLN B 304      -5.074 -10.924  62.334  1.00 28.00           O
ATOM   4708  CB  GLN B 304      -3.066  -9.550  60.530  1.00 32.85           C
ATOM   4709  CG  GLN B 304      -1.981  -8.580  60.097  1.00 36.98           C
ATOM   4710  CD  GLN B 304      -2.541  -7.411  59.319  1.00 39.58           C
ATOM   4711  OE1 GLN B 304      -3.091  -7.579  58.229  1.00 41.73           O
ATOM   4712  NE2 GLN B 304      -2.415  -6.214  59.882  1.00 41.43           N
ATOM   4713  N   ASP B 305      -6.428  -9.738  60.992  1.00 27.36           N
ATOM   4714  CA  ASP B 305      -7.560 -10.645  61.124  1.00 26.70           C
ATOM   4715  C   ASP B 305      -8.622 -10.277  60.083  1.00 26.21           C
ATOM   4716  O   ASP B 305      -8.466  -9.298  59.350  1.00 25.87           O
ATOM   4717  CB  ASP B 305      -8.155 -10.555  62.534  1.00 25.90           C
ATOM   4718  CG  ASP B 305      -8.732 -11.878  63.011  1.00 26.48           C
ATOM   4719  OD1 ASP B 305      -9.124 -12.708  62.159  1.00 25.44           O
ATOM   4720  OD2 ASP B 305      -8.804 -12.084  64.240  1.00 23.13           O
ATOM   4721  N   ASP B 306      -9.700 -11.057  60.032  1.00 24.66           N
ATOM   4722  CA  ASP B 306     -10.778 -10.842  59.074  1.00 24.07           C
ATOM   4723  C   ASP B 306     -11.411  -9.442  59.056  1.00 24.60           C
ATOM   4724  O   ASP B 306     -12.036  -9.054  58.067  1.00 24.87           O
ATOM   4725  CB  ASP B 306     -11.873 -11.899  59.278  1.00 23.09           C
ATOM   4726  CG  ASP B 306     -11.423 -13.303  58.864  1.00 23.72           C
ATOM   4727  OD1 ASP B 306     -10.844 -13.453  57.766  1.00 23.25           O
ATOM   4728  OD2 ASP B 306     -11.664 -14.262  59.625  1.00 22.32           O
ATOM   4729  N   HIS B 307     -11.252  -8.678  60.129  1.00 24.41           N
ATOM   4730  CA  HIS B 307     -11.828  -7.337  60.180  1.00 25.26           C
ATOM   4731  C   HIS B 307     -11.080  -6.311  59.327  1.00 25.50           C
ATOM   4732  O   HIS B 307     -11.648  -5.290  58.946  1.00 25.99           O
ATOM   4733  CB  HIS B 307     -11.850  -6.830  61.623  1.00 24.08           C
ATOM   4734  CG  HIS B 307     -10.488  -6.593  62.188  1.00 24.03           C
ATOM   4735  ND1 HIS B 307      -9.504  -7.560  62.182  1.00 22.73           N
ATOM   4736  CD2 HIS B 307      -9.938  -5.497  62.763  1.00 23.46           C
ATOM   4737  CE1 HIS B 307      -8.407  -7.068  62.731  1.00 23.16           C
ATOM   4738  NE2 HIS B 307      -8.643  -5.819  63.092  1.00 22.70           N
ATOM   4739  N   ILE B 308      -9.813  -6.572  59.031  1.00 26.05           N
ATOM   4740  CA  ILE B 308      -9.012  -5.626  58.255  1.00 27.55           C
ATOM   4741  C   ILE B 308      -9.649  -5.155  56.950  1.00 27.69           C
ATOM   4742  O   ILE B 308      -9.730  -3.956  56.695  1.00 28.19           O
ATOM   4743  CB  ILE B 308      -7.600  -6.195  57.966  1.00 28.15           C
ATOM   4744  CG1 ILE B 308      -6.844  -6.376  59.284  1.00 28.33           C
ATOM   4745  CG2 ILE B 308      -6.816  -5.248  57.052  1.00 28.70           C
ATOM   4746  CD1 ILE B 308      -6.593  -5.086  60.045  1.00 28.36           C
ATOM   4747  N   PRO B 309     -10.107  -6.086  56.099  1.00 27.91           N
ATOM   4748  CA  PRO B 309     -10.721  -5.624  54.850  1.00 27.34           C
ATOM   4749  C   PRO B 309     -11.912  -4.689  55.091  1.00 27.29           C
ATOM   4750  O   PRO B 309     -12.205  -3.829  54.260  1.00 27.61           O
ATOM   4751  CB  PRO B 309     -11.135  -6.925  54.165  1.00 28.56           C
ATOM   4752  CG  PRO B 309     -10.114  -7.920  54.681  1.00 27.34           C
ATOM   4753  CD  PRO B 309     -10.024  -7.557  56.141  1.00 27.43           C
ATOM   4754  N   PHE B 310     -12.596  -4.856  56.222  1.00 25.66           N
ATOM   4755  CA  PHE B 310     -13.748  -4.008  56.540  1.00 25.58           C
ATOM   4756  C   PHE B 310     -13.334  -2.706  57.229  1.00 26.32           C
```

FIGURE 4-71 (COORDINATES)

```
ATOM   4757  O    PHE B 310     -13.854   -1.631   56.925  1.00 27.04           O
ATOM   4758  CB   PHE B 310     -14.740   -4.775   57.415  1.00 23.63           C
ATOM   4759  CG   PHE B 310     -15.256   -6.021   56.772  1.00 24.02           C
ATOM   4760  CD1  PHE B 310     -14.513   -7.198   56.813  1.00 22.16           C
ATOM   4761  CD2  PHE B 310     -16.456   -6.006   56.061  1.00 22.76           C
ATOM   4762  CE1  PHE B 310     -14.949   -8.339   56.156  1.00 21.13           C
ATOM   4763  CE2  PHE B 310     -16.902   -7.139   55.400  1.00 22.47           C
ATOM   4764  CZ   PHE B 310     -16.146   -8.313   55.445  1.00 23.06           C
ATOM   4765  N    LEU B 311     -12.398   -2.813   58.161  1.00 26.52           N
ATOM   4766  CA   LEU B 311     -11.896   -1.656   58.874  1.00 27.79           C
ATOM   4767  C    LEU B 311     -11.362   -0.609   57.896  1.00 28.48           C
ATOM   4768  O    LEU B 311     -11.673    0.575   58.005  1.00 28.08           O
ATOM   4769  CB   LEU B 311     -10.761   -2.070   59.811  1.00 27.88           C
ATOM   4770  CG   LEU B 311     -10.126   -0.939   60.621  1.00 27.06           C
ATOM   4771  CD1  LEU B 311     -11.086   -0.533   61.730  1.00 27.05           C
ATOM   4772  CD2  LEU B 311      -8.801   -1.397   61.206  1.00 26.52           C
ATOM   4773  N    ARG B 312     -10.565   -1.047   56.932  1.00 29.33           N
ATOM   4774  CA   ARG B 312      -9.987   -0.102   56.001  1.00 31.18           C
ATOM   4775  C    ARG B 312     -11.008    0.547   55.077  1.00 31.31           C
ATOM   4776  O    ARG B 312     -10.675    1.482   54.350  1.00 31.78           O
ATOM   4777  CB   ARG B 312      -8.850   -0.755   55.201  1.00 33.10           C
ATOM   4778  CG   ARG B 312      -9.251   -1.778   54.158  1.00 37.67           C
ATOM   4779  CD   ARG B 312      -7.987   -2.374   53.528  1.00 41.38           C
ATOM   4780  NE   ARG B 312      -8.255   -3.357   52.474  1.00 44.79           N
ATOM   4781  CZ   ARG B 312      -8.774   -3.069   51.282  1.00 46.07           C
ATOM   4782  NH1  ARG B 312      -9.098   -1.818   50.969  1.00 47.43           N
ATOM   4783  NH2  ARG B 312      -8.946   -4.034   50.388  1.00 47.44           N
ATOM   4784  N    ARG B 313     -12.250    0.073   55.111  1.00 30.30           N
ATOM   4785  CA   ARG B 313     -13.285    0.664   54.274  1.00 30.52           C
ATOM   4786  C    ARG B 313     -14.250    1.489   55.120  1.00 30.37           C
ATOM   4787  O    ARG B 313     -15.265    1.979   54.629  1.00 30.44           O
ATOM   4788  CB   ARG B 313     -14.047   -0.411   53.488  1.00 30.81           C
ATOM   4789  CG   ARG B 313     -13.267   -1.025   52.318  1.00 30.04           C
ATOM   4790  CD   ARG B 313     -14.156   -1.982   51.529  1.00 30.63           C
ATOM   4791  NE   ARG B 313     -13.527   -2.537   50.330  1.00 31.41           N
ATOM   4792  CZ   ARG B 313     -12.567   -3.463   50.327  1.00 32.23           C
ATOM   4793  NH1  ARG B 313     -12.097   -3.955   51.469  1.00 31.63           N
ATOM   4794  NH2  ARG B 313     -12.086   -3.914   49.175  1.00 29.76           N
ATOM   4795  N    GLY B 314     -13.935    1.629   56.403  1.00 30.57           N
ATOM   4796  CA   GLY B 314     -14.774    2.431   57.271  1.00 29.85           C
ATOM   4797  C    GLY B 314     -15.736    1.730   58.210  1.00 29.45           C
ATOM   4798  O    GLY B 314     -16.438    2.404   58.959  1.00 29.71           O
ATOM   4799  N    VAL B 315     -15.792    0.402   58.189  1.00 28.71           N
ATOM   4800  CA   VAL B 315     -16.701   -0.312   59.091  1.00 27.54           C
ATOM   4801  C    VAL B 315     -16.214   -0.289   60.542  1.00 27.32           C
ATOM   4802  O    VAL B 315     -15.087   -0.669   60.830  1.00 27.24           O
ATOM   4803  CB   VAL B 315     -16.865   -1.790   58.683  1.00 27.32           C
ATOM   4804  CG1  VAL B 315     -17.832   -2.481   59.643  1.00 26.92           C
ATOM   4805  CG2  VAL B 315     -17.358   -1.891   57.239  1.00 26.79           C
ATOM   4806  N    PRO B 316     -17.058    0.167   61.478  1.00 28.48           N
ATOM   4807  CA   PRO B 316     -16.630    0.196   62.885  1.00 27.79           C
ATOM   4808  C    PRO B 316     -16.413   -1.247   63.353  1.00 27.83           C
ATOM   4809  O    PRO B 316     -17.249   -2.119   63.090  1.00 27.92           O
ATOM   4810  CB   PRO B 316     -17.813    0.851   63.598  1.00 27.65           C
ATOM   4811  CG   PRO B 316     -18.468    1.677   62.514  1.00 28.29           C
ATOM   4812  CD   PRO B 316     -18.393    0.773   61.317  1.00 28.32           C
ATOM   4813  N    VAL B 317     -15.314   -1.504   64.054  1.00 26.69           N
ATOM   4814  CA   VAL B 317     -15.029   -2.865   64.501  1.00 26.58           C
ATOM   4815  C    VAL B 317     -14.852   -3.041   66.002  1.00 26.16           C
ATOM   4816  O    VAL B 317     -14.350   -2.164   66.687  1.00 26.06           O
ATOM   4817  CB   VAL B 317     -13.746   -3.416   63.826  1.00 26.52           C
ATOM   4818  CG1  VAL B 317     -13.454   -4.823   64.326  1.00 25.97           C
ATOM   4819  CG2  VAL B 317     -13.903   -3.408   62.307  1.00 26.10           C
ATOM   4820  N    LEU B 318     -15.285   -4.195   66.490  1.00 25.80           N
ATOM   4821  CA   LEU B 318     -15.140   -4.574   67.887  1.00 26.35           C
ATOM   4822  C    LEU B 318     -14.413   -5.920   67.761  1.00 26.35           C
ATOM   4823  O    LEU B 318     -15.041   -6.959   67.558  1.00 26.59           O
ATOM   4824  CB   LEU B 318     -16.514   -4.755   68.535  1.00 27.34           C
```

FIGURE 4-72 (COORDINATES)

```
ATOM   4825  CG   LEU B 318     -16.552   -4.760  70.065  1.00 28.79           C
ATOM   4826  CD1  LEU B 318     -16.014   -3.427  70.588  1.00 28.63           C
ATOM   4827  CD2  LEU B 318     -17.984   -4.983  70.549  1.00 28.58           C
ATOM   4828  N    HIS B 319     -13.086   -5.883  67.844  1.00 25.91           N
ATOM   4829  CA   HIS B 319     -12.265   -7.078  67.694  1.00 25.48           C
ATOM   4830  C    HIS B 319     -12.104   -7.882  68.971  1.00 26.15           C
ATOM   4831  O    HIS B 319     -11.269   -7.558  69.809  1.00 26.39           O
ATOM   4832  CB   HIS B 319     -10.877   -6.697  67.180  1.00 24.02           C
ATOM   4833  CG   HIS B 319     -10.134   -7.833  66.552  1.00 23.21           C
ATOM   4834  ND1  HIS B 319      -8.834   -7.715  66.105  1.00 22.32           N
ATOM   4835  CD2  HIS B 319     -10.517   -9.102  66.270  1.00 20.98           C
ATOM   4836  CE1  HIS B 319      -8.450   -8.863  65.573  1.00 22.23           C
ATOM   4837  NE2  HIS B 319      -9.453   -9.720  65.661  1.00 22.27           N
ATOM   4838  N    LEU B 320     -12.887   -8.946  69.112  1.00 27.15           N
ATOM   4839  CA   LEU B 320     -12.796   -9.772  70.309  1.00 27.40           C
ATOM   4840  C    LEU B 320     -11.774  -10.903  70.128  1.00 27.45           C
ATOM   4841  O    LEU B 320     -12.128  -12.067  69.924  1.00 26.52           O
ATOM   4842  CB   LEU B 320     -14.179  -10.331  70.680  1.00 27.10           C
ATOM   4843  CG   LEU B 320     -15.320   -9.303  70.782  1.00 28.03           C
ATOM   4844  CD1  LEU B 320     -16.542   -9.949  71.420  1.00 26.15           C
ATOM   4845  CD2  LEU B 320     -14.881   -8.096  71.612  1.00 28.02           C
ATOM   4846  N    ILE B 321     -10.500  -10.526  70.177  1.00 27.13           N
ATOM   4847  CA   ILE B 321      -9.390  -11.464  70.057  1.00 27.40           C
ATOM   4848  C    ILE B 321      -8.521  -11.167  71.278  1.00 28.48           C
ATOM   4849  O    ILE B 321      -8.321  -10.008  71.640  1.00 28.53           O
ATOM   4850  CB   ILE B 321      -8.586  -11.246  68.739  1.00 26.07           C
ATOM   4851  CG1  ILE B 321      -7.541  -12.355  68.587  1.00 26.17           C
ATOM   4852  CG2  ILE B 321      -7.932   -9.860  68.732  1.00 22.91           C
ATOM   4853  CD1  ILE B 321      -6.834  -12.378  67.233  1.00 25.22           C
ATOM   4854  N    PRO B 322      -7.999  -12.208  71.938  1.00 29.34           N
ATOM   4855  CA   PRO B 322      -7.171  -11.963  73.125  1.00 29.69           C
ATOM   4856  C    PRO B 322      -5.750  -11.476  72.861  1.00 29.42           C
ATOM   4857  O    PRO B 322      -5.205  -11.653  71.775  1.00 30.14           O
ATOM   4858  CB   PRO B 322      -7.164  -13.322  73.837  1.00 29.32           C
ATOM   4859  CG   PRO B 322      -8.288  -14.099  73.188  1.00 30.55           C
ATOM   4860  CD   PRO B 322      -8.250  -13.646  71.766  1.00 28.50           C
ATOM   4861  N    SER B 323      -5.165  -10.854  73.878  1.00 29.53           N
ATOM   4862  CA   SER B 323      -3.787  -10.381  73.831  1.00 30.12           C
ATOM   4863  C    SER B 323      -3.254  -10.538  75.246  1.00 29.72           C
ATOM   4864  O    SER B 323      -3.684   -9.833  76.158  1.00 30.58           O
ATOM   4865  CB   SER B 323      -3.701   -8.913  73.417  1.00 30.94           C
ATOM   4866  OG   SER B 323      -2.340   -8.520  73.318  1.00 32.15           O
ATOM   4867  N    PRO B 324      -2.299  -11.456  75.450  1.00 29.47           N
ATOM   4868  CA   PRO B 324      -1.667  -12.353  74.473  1.00 29.03           C
ATOM   4869  C    PRO B 324      -2.570  -13.422  73.869  1.00 28.72           C
ATOM   4870  O    PRO B 324      -3.689  -13.650  74.333  1.00 28.94           O
ATOM   4871  CB   PRO B 324      -0.541  -12.977  75.280  1.00 29.34           C
ATOM   4872  CG   PRO B 324      -1.205  -13.159  76.614  1.00 29.70           C
ATOM   4873  CD   PRO B 324      -1.892  -11.820  76.820  1.00 29.43           C
ATOM   4874  N    PHE B 325      -2.065  -14.069  72.823  1.00 28.15           N
ATOM   4875  CA   PHE B 325      -2.782  -15.148  72.150  1.00 27.78           C
ATOM   4876  C    PHE B 325      -2.793  -16.343  73.103  1.00 27.45           C
ATOM   4877  O    PHE B 325      -1.939  -16.445  73.986  1.00 26.45           O
ATOM   4878  CB   PHE B 325      -2.054  -15.551  70.862  1.00 27.01           C
ATOM   4879  CG   PHE B 325      -2.302  -14.636  69.686  1.00 26.32           C
ATOM   4880  CD1  PHE B 325      -3.059  -13.479  69.816  1.00 26.76           C
ATOM   4881  CD2  PHE B 325      -1.795  -14.960  68.431  1.00 26.08           C
ATOM   4882  CE1  PHE B 325      -3.312  -12.660  68.714  1.00 25.71           C
ATOM   4883  CE2  PHE B 325      -2.044  -14.146  67.324  1.00 25.87           C
ATOM   4884  CZ   PHE B 325      -2.806  -12.996  67.469  1.00 25.47           C
ATOM   4885  N    PRO B 326      -3.756  -17.265  72.936  1.00 27.39           N
ATOM   4886  CA   PRO B 326      -3.833  -18.449  73.804  1.00 27.53           C
ATOM   4887  C    PRO B 326      -2.514  -19.217  73.745  1.00 27.75           C
ATOM   4888  O    PRO B 326      -1.897  -19.310  72.689  1.00 27.24           O
ATOM   4889  CB   PRO B 326      -4.982  -19.243  73.197  1.00 27.34           C
ATOM   4890  CG   PRO B 326      -5.861  -18.172  72.617  1.00 27.34           C
ATOM   4891  CD   PRO B 326      -4.860  -17.257  71.963  1.00 27.40           C
ATOM   4892  N    GLU B 327      -2.082  -19.773  74.870  1.00 29.22           N
```

FIGURE 4-73 (COORDINATES)

```
ATOM   4893  CA  GLU B 327      -0.821 -20.512  74.901  1.00 30.68           C
ATOM   4894  C   GLU B 327      -0.701 -21.575  73.816  1.00 29.62           C
ATOM   4895  O   GLU B 327       0.373 -21.768  73.254  1.00 28.65           O
ATOM   4896  CB  GLU B 327      -0.625 -21.166  76.267  1.00 33.75           C
ATOM   4897  CG  GLU B 327      -0.494 -20.166  77.404  1.00 40.40           C
ATOM   4898  CD  GLU B 327      -0.764 -20.789  78.769  1.00 44.23           C
ATOM   4899  OE1 GLU B 327      -0.012 -21.716  79.157  1.00 44.91           O
ATOM   4900  OE2 GLU B 327      -1.733 -20.351  79.443  1.00 45.42           O
ATOM   4901  N   VAL B 328      -1.803 -22.253  73.514  1.00 29.01           N
ATOM   4902  CA  VAL B 328      -1.801 -23.314  72.508  1.00 27.92           C
ATOM   4903  C   VAL B 328      -1.856 -22.830  71.061  1.00 28.04           C
ATOM   4904  O   VAL B 328      -1.889 -23.651  70.140  1.00 26.93           O
ATOM   4905  CB  VAL B 328      -2.986 -24.280  72.718  1.00 27.88           C
ATOM   4906  CG1 VAL B 328      -2.884 -24.942  74.079  1.00 27.80           C
ATOM   4907  CG2 VAL B 328      -4.307 -23.525  72.584  1.00 27.24           C
ATOM   4908  N   TRP B 329      -1.852 -21.512  70.862  1.00 27.10           N
ATOM   4909  CA  TRP B 329      -1.936 -20.943  69.516  1.00 27.08           C
ATOM   4910  C   TRP B 329      -1.097 -21.654  68.453  1.00 27.15           C
ATOM   4911  O   TRP B 329       0.116 -21.806  68.584  1.00 27.39           O
ATOM   4912  CB  TRP B 329      -1.555 -19.462  69.530  1.00 26.32           C
ATOM   4913  CG  TRP B 329      -1.778 -18.763  68.209  1.00 24.89           C
ATOM   4914  CD1 TRP B 329      -2.971 -18.303  67.704  1.00 24.09           C
ATOM   4915  CD2 TRP B 329      -0.779 -18.423  67.242  1.00 23.49           C
ATOM   4916  NE1 TRP B 329      -2.768 -17.694  66.488  1.00 22.63           N
ATOM   4917  CE2 TRP B 329      -1.434 -17.755  66.180  1.00 23.20           C
ATOM   4918  CE3 TRP B 329       0.606 -18.617  67.168  1.00 23.22           C
ATOM   4919  CZ2 TRP B 329      -0.749 -17.279  65.061  1.00 22.69           C
ATOM   4920  CZ3 TRP B 329       1.287 -18.145  66.054  1.00 22.91           C
ATOM   4921  CH2 TRP B 329       0.607 -17.482  65.013  1.00 23.10           C
ATOM   4922  N   HIS B 330      -1.770 -22.073  67.390  1.00 27.32           N
ATOM   4923  CA  HIS B 330      -1.130 -22.752  66.279  1.00 27.13           C
ATOM   4924  C   HIS B 330      -0.247 -23.942  66.637  1.00 28.02           C
ATOM   4925  O   HIS B 330       0.828 -24.137  66.064  1.00 28.24           O
ATOM   4926  CB  HIS B 330      -0.359 -21.739  65.427  1.00 26.27           C
ATOM   4927  CG  HIS B 330      -1.250 -20.885  64.576  1.00 25.53           C
ATOM   4928  ND1 HIS B 330      -0.786 -20.150  63.509  1.00 24.80           N
ATOM   4929  CD2 HIS B 330      -2.588 -20.677  64.621  1.00 24.55           C
ATOM   4930  CE1 HIS B 330      -1.798 -19.529  62.929  1.00 24.59           C
ATOM   4931  NE2 HIS B 330      -2.902 -19.832  63.585  1.00 24.55           N
ATOM   4932  N   THR B 331      -0.709 -24.736  67.596  1.00 27.56           N
ATOM   4933  CA  THR B 331      -0.005 -25.952  67.985  1.00 28.08           C
ATOM   4934  C   THR B 331      -1.087 -27.020  67.976  1.00 27.69           C
ATOM   4935  O   THR B 331      -2.279 -26.698  67.936  1.00 26.14           O
ATOM   4936  CB  THR B 331       0.611 -25.884  69.416  1.00 27.64           C
ATOM   4937  OG1 THR B 331      -0.432 -25.823  70.394  1.00 27.63           O
ATOM   4938  CG2 THR B 331       1.520 -24.676  69.558  1.00 28.24           C
ATOM   4939  N   MET B 332      -0.679 -28.283  68.001  1.00 28.15           N
ATOM   4940  CA  MET B 332      -1.639 -29.376  68.014  1.00 29.22           C
ATOM   4941  C   MET B 332      -2.396 -29.405  69.347  1.00 29.72           C
ATOM   4942  O   MET B 332      -3.367 -30.144  69.499  1.00 30.54           O
ATOM   4943  CB  MET B 332      -0.918 -30.704  67.791  1.00 29.30           C
ATOM   4944  CG  MET B 332      -0.375 -30.865  66.393  1.00 30.03           C
ATOM   4945  SD  MET B 332      -1.693 -30.803  65.152  1.00 32.03           S
ATOM   4946  CE  MET B 332      -0.732 -30.456  63.689  1.00 31.43           C
ATOM   4947  N   ASP B 333      -1.959 -28.592  70.306  1.00 29.33           N
ATOM   4948  CA  ASP B 333      -2.618 -28.552  71.604  1.00 30.52           C
ATOM   4949  C   ASP B 333      -3.833 -27.643  71.645  1.00 30.74           C
ATOM   4950  O   ASP B 333      -4.499 -27.549  72.681  1.00 30.15           O
ATOM   4951  CB  ASP B 333      -1.638 -28.147  72.706  1.00 31.67           C
ATOM   4952  CG  ASP B 333      -0.555 -29.190  72.928  1.00 33.24           C
ATOM   4953  OD1 ASP B 333      -0.900 -30.391  73.008  1.00 32.05           O
ATOM   4954  OD2 ASP B 333       0.634 -28.807  73.026  1.00 34.38           O
ATOM   4955  N   ASP B 334      -4.122 -26.964  70.535  1.00 30.05           N
ATOM   4956  CA  ASP B 334      -5.305 -26.109  70.489  1.00 30.02           C
ATOM   4957  C   ASP B 334      -6.454 -27.050  70.162  1.00 29.98           C
ATOM   4958  O   ASP B 334      -6.982 -27.059  69.051  1.00 29.69           O
ATOM   4959  CB  ASP B 334      -5.185 -25.024  69.410  1.00 29.33           C
ATOM   4960  CG  ASP B 334      -6.403 -24.103  69.373  1.00 28.14           C
```

FIGURE 4-74 (COORDINATES)

```
ATOM   4961  OD1 ASP B 334      -7.316 -24.278  70.205  1.00 28.62           O
ATOM   4962  OD2 ASP B 334      -6.457 -23.207  68.511  1.00 27.44           O
ATOM   4963  N   ASN B 335      -6.817 -27.852  71.158  1.00 30.98           N
ATOM   4964  CA  ASN B 335      -7.871 -28.853  71.049  1.00 30.70           C
ATOM   4965  C   ASN B 335      -8.953 -28.665  72.119  1.00 30.39           C
ATOM   4966  O   ASN B 335      -8.885 -27.760  72.946  1.00 29.04           O
ATOM   4967  CB  ASN B 335      -7.254 -30.245  71.196  1.00 30.89           C
ATOM   4968  CG  ASN B 335      -6.329 -30.339  72.405  1.00 31.33           C
ATOM   4969  OD1 ASN B 335      -6.549 -29.672  73.419  1.00 29.84           O
ATOM   4970  ND2 ASN B 335      -5.297 -31.168  72.304  1.00 31.39           N
ATOM   4971  N   GLU B 336      -9.946 -29.542  72.087  1.00 30.75           N
ATOM   4972  CA  GLU B 336     -11.061 -29.507  73.025  1.00 32.67           C
ATOM   4973  C   GLU B 336     -10.618 -29.628  74.481  1.00 33.44           C
ATOM   4974  O   GLU B 336     -11.116 -28.926  75.362  1.00 33.00           O
ATOM   4975  CB  GLU B 336     -12.038 -30.634  72.670  1.00 32.22           C
ATOM   4976  CG  GLU B 336     -13.032 -31.009  73.750  1.00 33.32           C
ATOM   4977  CD  GLU B 336     -14.066 -31.995  73.248  1.00 33.23           C
ATOM   4978  OE1 GLU B 336     -13.765 -32.715  72.278  1.00 35.16           O
ATOM   4979  OE2 GLU B 336     -15.170 -32.062  73.821  1.00 33.73           O
ATOM   4980  N   GLU B 337      -9.671 -30.521  74.719  1.00 35.05           N
ATOM   4981  CA  GLU B 337      -9.152 -30.770  76.054  1.00 37.02           C
ATOM   4982  C   GLU B 337      -8.596 -29.521  76.744  1.00 35.91           C
ATOM   4983  O   GLU B 337      -8.669 -29.399  77.968  1.00 35.27           O
ATOM   4984  CB  GLU B 337      -8.068 -31.841  75.962  1.00 40.56           C
ATOM   4985  CG  GLU B 337      -7.448 -32.237  77.271  1.00 45.63           C
ATOM   4986  CD  GLU B 337      -6.130 -32.969  77.070  1.00 49.56           C
ATOM   4987  OE1 GLU B 337      -5.567 -33.467  78.078  1.00 51.45           O
ATOM   4988  OE2 GLU B 337      -5.659 -33.038  75.905  1.00 50.28           O
ATOM   4989  N   ASN B 338      -8.047 -28.594  75.963  1.00 34.17           N
ATOM   4990  CA  ASN B 338      -7.475 -27.376  76.527  1.00 32.97           C
ATOM   4991  C   ASN B 338      -8.450 -26.198  76.607  1.00 32.10           C
ATOM   4992  O   ASN B 338      -8.070 -25.093  76.982  1.00 31.19           O
ATOM   4993  CB  ASN B 338      -6.211 -26.994  75.749  1.00 34.12           C
ATOM   4994  CG  ASN B 338      -5.018 -27.867  76.124  1.00 34.70           C
ATOM   4995  OD1 ASN B 338      -4.152 -28.150  75.304  1.00 35.96           O
ATOM   4996  ND2 ASN B 338      -4.969 -28.284  77.376  1.00 36.47           N
ATOM   4997  N   LEU B 339      -9.710 -26.438  76.261  1.00 31.15           N
ATOM   4998  CA  LEU B 339     -10.721 -25.393  76.349  1.00 30.88           C
ATOM   4999  C   LEU B 339     -11.199 -25.308  77.794  1.00 31.79           C
ATOM   5000  O   LEU B 339     -11.050 -26.257  78.564  1.00 32.24           O
ATOM   5001  CB  LEU B 339     -11.911 -25.718  75.453  1.00 29.09           C
ATOM   5002  CG  LEU B 339     -11.641 -25.697  73.951  1.00 28.82           C
ATOM   5003  CD1 LEU B 339     -12.859 -26.220  73.216  1.00 26.16           C
ATOM   5004  CD2 LEU B 339     -11.290 -24.275  73.511  1.00 28.29           C
ATOM   5005  N   ASP B 340     -11.768 -24.168  78.160  1.00 32.40           N
ATOM   5006  CA  ASP B 340     -12.273 -23.981  79.506  1.00 33.07           C
ATOM   5007  C   ASP B 340     -13.762 -23.670  79.460  1.00 33.84           C
ATOM   5008  O   ASP B 340     -14.173 -22.557  79.124  1.00 33.39           O
ATOM   5009  CB  ASP B 340     -11.527 -22.852  80.210  1.00 33.32           C
ATOM   5010  CG  ASP B 340     -11.962 -22.691  81.655  1.00 34.16           C
ATOM   5011  OD1 ASP B 340     -12.954 -21.980  81.922  1.00 34.19           O
ATOM   5012  OD2 ASP B 340     -11.318 -23.297  82.527  1.00 35.69           O
ATOM   5013  N   GLU B 341     -14.557 -24.676  79.805  1.00 34.47           N
ATOM   5014  CA  GLU B 341     -16.011 -24.592  79.818  1.00 35.27           C
ATOM   5015  C   GLU B 341     -16.566 -23.301  80.431  1.00 34.83           C
ATOM   5016  O   GLU B 341     -17.356 -22.599  79.801  1.00 33.66           O
ATOM   5017  CB  GLU B 341     -16.566 -25.804  80.569  1.00 37.88           C
ATOM   5018  CG  GLU B 341     -18.074 -25.939  80.540  1.00 43.46           C
ATOM   5019  CD  GLU B 341     -18.571 -27.036  81.470  1.00 46.41           C
ATOM   5020  OE1 GLU B 341     -18.345 -26.912  82.692  1.00 48.39           O
ATOM   5021  OE2 GLU B 341     -19.181 -28.018  80.986  1.00 47.99           O
ATOM   5022  N   SER B 342     -16.158 -22.992  81.658  1.00 34.39           N
ATOM   5023  CA  SER B 342     -16.639 -21.794  82.341  1.00 35.05           C
ATOM   5024  C   SER B 342     -16.385 -20.499  81.583  1.00 34.14           C
ATOM   5025  O   SER B 342     -17.304 -19.713  81.359  1.00 34.96           O
ATOM   5026  CB  SER B 342     -16.015 -21.680  83.732  1.00 35.23           C
ATOM   5027  OG  SER B 342     -16.588 -22.626  84.607  1.00 37.69           O
ATOM   5028  N   THR B 343     -15.134 -20.274  81.206  1.00 32.67           N
```

FIGURE 4-75 (COORDINATES)

```
ATOM   5029  CA  THR B 343     -14.770 -19.067  80.487  1.00 32.19           C
ATOM   5030  C   THR B 343     -15.721 -18.841  79.317  1.00 31.34           C
ATOM   5031  O   THR B 343     -16.314 -17.767  79.181  1.00 30.81           O
ATOM   5032  CB  THR B 343     -13.335 -19.166  79.941  1.00 32.88           C
ATOM   5033  OG1 THR B 343     -12.440 -19.531  81.001  1.00 31.58           O
ATOM   5034  CG2 THR B 343     -12.904 -17.831  79.356  1.00 32.48           C
ATOM   5035  N   ILE B 344     -15.867 -19.870  78.487  1.00 29.80           N
ATOM   5036  CA  ILE B 344     -16.730 -19.814  77.314  1.00 29.47           C
ATOM   5037  C   ILE B 344     -18.188 -19.564  77.688  1.00 29.97           C
ATOM   5038  O   ILE B 344     -18.885 -18.791  77.024  1.00 29.36           O
ATOM   5039  CB  ILE B 344     -16.634 -21.129  76.505  1.00 28.90           C
ATOM   5040  CG1 ILE B 344     -15.194 -21.339  76.026  1.00 27.87           C
ATOM   5041  CG2 ILE B 344     -17.590 -21.090  75.317  1.00 28.25           C
ATOM   5042  CD1 ILE B 344     -14.952 -22.694  75.370  1.00 26.15           C
ATOM   5043  N   ASP B 345     -18.642 -20.221  78.752  1.00 30.39           N
ATOM   5044  CA  ASP B 345     -20.016 -20.079  79.217  1.00 30.27           C
ATOM   5045  C   ASP B 345     -20.218 -18.629  79.628  1.00 30.31           C
ATOM   5046  O   ASP B 345     -21.237 -18.011  79.305  1.00 29.45           O
ATOM   5047  CB  ASP B 345     -20.265 -21.024  80.400  1.00 31.33           C
ATOM   5048  CG  ASP B 345     -21.739 -21.112  80.799  1.00 33.27           C
ATOM   5049  OD1 ASP B 345     -22.612 -21.187  79.905  1.00 32.07           O
ATOM   5050  OD2 ASP B 345     -22.020 -21.129  82.020  1.00 34.33           O
ATOM   5051  N   ASN B 346     -19.234 -18.078  80.329  1.00 29.88           N
ATOM   5052  CA  ASN B 346     -19.326 -16.693  80.762  1.00 30.59           C
ATOM   5053  C   ASN B 346     -19.369 -15.731  79.568  1.00 30.29           C
ATOM   5054  O   ASN B 346     -20.180 -14.801  79.546  1.00 30.15           O
ATOM   5055  CB  ASN B 346     -18.148 -16.331  81.671  1.00 31.87           C
ATOM   5056  CG  ASN B 346     -18.164 -17.101  82.985  1.00 32.89           C
ATOM   5057  OD1 ASN B 346     -19.229 -17.424  83.516  1.00 32.73           O
ATOM   5058  ND2 ASN B 346     -16.981 -17.383  83.520  1.00 30.74           N
ATOM   5059  N   LEU B 347     -18.500 -15.953  78.582  1.00 29.14           N
ATOM   5060  CA  LEU B 347     -18.467 -15.086  77.411  1.00 28.93           C
ATOM   5061  C   LEU B 347     -19.762 -15.187  76.629  1.00 28.81           C
ATOM   5062  O   LEU B 347     -20.239 -14.192  76.103  1.00 28.50           O
ATOM   5063  CB  LEU B 347     -17.268 -15.414  76.511  1.00 27.06           C
ATOM   5064  CG  LEU B 347     -15.887 -15.048  77.084  1.00 26.51           C
ATOM   5065  CD1 LEU B 347     -14.807 -15.490  76.124  1.00 26.25           C
ATOM   5066  CD2 LEU B 347     -15.779 -13.555  77.330  1.00 25.57           C
ATOM   5067  N   ASN B 348     -20.339 -16.384  76.561  1.00 30.12           N
ATOM   5068  CA  ASN B 348     -21.606 -16.568  75.854  1.00 29.72           C
ATOM   5069  C   ASN B 348     -22.676 -15.634  76.427  1.00 30.01           C
ATOM   5070  O   ASN B 348     -23.380 -14.946  75.687  1.00 30.90           O
ATOM   5071  CB  ASN B 348     -22.091 -18.018  75.963  1.00 29.17           C
ATOM   5072  CG  ASN B 348     -21.451 -18.934  74.929  1.00 29.93           C
ATOM   5073  OD1 ASN B 348     -20.925 -18.474  73.917  1.00 28.68           O
ATOM   5074  ND2 ASN B 348     -21.512 -20.241  75.174  1.00 29.56           N
ATOM   5075  N   LYS B 349     -22.790 -15.622  77.750  1.00 30.14           N
ATOM   5076  CA  LYS B 349     -23.758 -14.788  78.446  1.00 30.26           C
ATOM   5077  C   LYS B 349     -23.490 -13.315  78.183  1.00 29.78           C
ATOM   5078  O   LYS B 349     -24.416 -12.547  77.913  1.00 29.84           O
ATOM   5079  CB  LYS B 349     -23.701 -15.064  79.958  1.00 31.92           C
ATOM   5080  CG  LYS B 349     -24.162 -16.466  80.348  1.00 33.61           C
ATOM   5081  CD  LYS B 349     -23.952 -16.746  81.835  1.00 34.08           C
ATOM   5082  CE  LYS B 349     -24.408 -18.164  82.203  1.00 33.86           C
ATOM   5083  NZ  LYS B 349     -24.041 -18.548  83.600  1.00 32.22           N
ATOM   5084  N   ILE B 350     -22.224 -12.921  78.277  1.00 29.30           N
ATOM   5085  CA  ILE B 350     -21.848 -11.535  78.042  1.00 28.86           C
ATOM   5086  C   ILE B 350     -22.215 -11.127  76.614  1.00 29.05           C
ATOM   5087  O   ILE B 350     -22.824 -10.077  76.397  1.00 28.69           O
ATOM   5088  CB  ILE B 350     -20.328 -11.329  78.268  1.00 29.79           C
ATOM   5089  CG1 ILE B 350     -19.985 -11.555  79.749  1.00 29.71           C
ATOM   5090  CG2 ILE B 350     -19.913  -9.921  77.848  1.00 29.75           C
ATOM   5091  CD1 ILE B 350     -18.483 -11.633  80.035  1.00 27.41           C
ATOM   5092  N   LEU B 351     -21.857 -11.968  75.647  1.00 29.53           N
ATOM   5093  CA  LEU B 351     -22.139 -11.699  74.234  1.00 31.15           C
ATOM   5094  C   LEU B 351     -23.640 -11.627  73.960  1.00 31.64           C
ATOM   5095  O   LEU B 351     -24.127 -10.728  73.270  1.00 30.88           O
ATOM   5096  CB  LEU B 351     -21.526 -12.791  73.350  1.00 30.73           C
```

FIGURE 4-76 (COORDINATES)

```
ATOM   5097  CG  LEU B 351     -21.742 -12.627  71.841  1.00 30.50           C
ATOM   5098  CD1 LEU B 351     -20.947 -11.435  71.342  1.00 31.18           C
ATOM   5099  CD2 LEU B 351     -21.295 -13.873  71.118  1.00 30.98           C
ATOM   5100  N   GLN B 352     -24.366 -12.596  74.496  1.00 32.38           N
ATOM   5101  CA  GLN B 352     -25.799 -12.638  74.311  1.00 33.04           C
ATOM   5102  C   GLN B 352     -26.457 -11.382  74.872  1.00 32.49           C
ATOM   5103  O   GLN B 352     -27.379 -10.851  74.267  1.00 33.01           O
ATOM   5104  CB  GLN B 352     -26.355 -13.907  74.952  1.00 33.42           C
ATOM   5105  CG  GLN B 352     -26.018 -15.144  74.137  1.00 34.95           C
ATOM   5106  CD  GLN B 352     -26.416 -16.438  74.813  1.00 36.24           C
ATOM   5107  OE1 GLN B 352     -27.470 -16.526  75.441  1.00 37.85           O
ATOM   5108  NE2 GLN B 352     -25.579 -17.460  74.671  1.00 36.75           N
ATOM   5109  N   VAL B 353     -25.978 -10.892  76.012  1.00 33.07           N
ATOM   5110  CA  VAL B 353     -26.545  -9.673  76.586  1.00 32.95           C
ATOM   5111  C   VAL B 353     -26.219  -8.486  75.674  1.00 32.53           C
ATOM   5112  O   VAL B 353     -27.092  -7.687  75.348  1.00 33.20           O
ATOM   5113  CB  VAL B 353     -25.991  -9.383  78.007  1.00 33.55           C
ATOM   5114  CG1 VAL B 353     -26.442  -8.001  78.472  1.00 31.80           C
ATOM   5115  CG2 VAL B 353     -26.486 -10.438  78.986  1.00 33.29           C
ATOM   5116  N   PHE B 354     -24.961  -8.382  75.259  1.00 31.45           N
ATOM   5117  CA  PHE B 354     -24.539  -7.303  74.376  1.00 29.99           C
ATOM   5118  C   PHE B 354     -25.417  -7.237  73.125  1.00 30.23           C
ATOM   5119  O   PHE B 354     -25.928  -6.179  72.765  1.00 30.65           O
ATOM   5120  CB  PHE B 354     -23.083  -7.504  73.950  1.00 28.23           C
ATOM   5121  CG  PHE B 354     -22.566  -6.424  73.037  1.00 27.02           C
ATOM   5122  CD1 PHE B 354     -21.876  -5.328  73.552  1.00 26.02           C
ATOM   5123  CD2 PHE B 354     -22.790  -6.487  71.663  1.00 25.84           C
ATOM   5124  CE1 PHE B 354     -21.419  -4.311  72.712  1.00 25.14           C
ATOM   5125  CE2 PHE B 354     -22.337  -5.477  70.817  1.00 24.36           C
ATOM   5126  CZ  PHE B 354     -21.651  -4.388  71.341  1.00 25.56           C
ATOM   5127  N   VAL B 355     -25.587  -8.373  72.463  1.00 30.31           N
ATOM   5128  CA  VAL B 355     -26.383  -8.434  71.244  1.00 30.83           C
ATOM   5129  C   VAL B 355     -27.836  -8.008  71.464  1.00 32.06           C
ATOM   5130  O   VAL B 355     -28.412  -7.299  70.634  1.00 31.90           O
ATOM   5131  CB  VAL B 355     -26.338  -9.864  70.631  1.00 30.15           C
ATOM   5132  CG1 VAL B 355     -27.363 -10.005  69.515  1.00 29.30           C
ATOM   5133  CG2 VAL B 355     -24.950 -10.147  70.096  1.00 29.36           C
ATOM   5134  N   LEU B 356     -28.430  -8.437  72.576  1.00 32.64           N
ATOM   5135  CA  LEU B 356     -29.815  -8.083  72.873  1.00 33.05           C
ATOM   5136  C   LEU B 356     -29.968  -6.595  73.182  1.00 33.14           C
ATOM   5137  O   LEU B 356     -30.937  -5.958  72.765  1.00 32.48           O
ATOM   5138  CB  LEU B 356     -30.330  -8.909  74.050  1.00 33.93           C
ATOM   5139  CG  LEU B 356     -30.761 -10.336  73.722  1.00 34.06           C
ATOM   5140  CD1 LEU B 356     -31.015 -11.094  75.013  1.00 35.11           C
ATOM   5141  CD2 LEU B 356     -32.010 -10.307  72.859  1.00 33.38           C
ATOM   5142  N   GLU B 357     -29.012  -6.038  73.912  1.00 32.99           N
ATOM   5143  CA  GLU B 357     -29.079  -4.624  74.240  1.00 34.16           C
ATOM   5144  C   GLU B 357     -28.842  -3.774  72.988  1.00 35.17           C
ATOM   5145  O   GLU B 357     -29.349  -2.654  72.881  1.00 35.32           O
ATOM   5146  CB  GLU B 357     -28.056  -4.288  75.323  1.00 34.58           C
ATOM   5147  CG  GLU B 357     -28.160  -5.191  76.535  1.00 34.55           C
ATOM   5148  CD  GLU B 357     -27.372  -4.678  77.716  1.00 36.34           C
ATOM   5149  OE1 GLU B 357     -26.252  -4.160  77.509  1.00 37.03           O
ATOM   5150  OE2 GLU B 357     -27.869  -4.803  78.855  1.00 36.62           O
ATOM   5151  N   TYR B 358     -28.086  -4.313  72.031  1.00 35.24           N
ATOM   5152  CA  TYR B 358     -27.814  -3.582  70.796  1.00 34.52           C
ATOM   5153  C   TYR B 358     -29.067  -3.563  69.921  1.00 34.43           C
ATOM   5154  O   TYR B 358     -29.438  -2.528  69.381  1.00 34.24           O
ATOM   5155  CB  TYR B 358     -26.663  -4.227  70.010  1.00 32.94           C
ATOM   5156  CG  TYR B 358     -26.079  -3.309  68.955  1.00 31.72           C
ATOM   5157  CD1 TYR B 358     -24.957  -2.535  69.227  1.00 31.29           C
ATOM   5158  CD2 TYR B 358     -26.696  -3.156  67.713  1.00 31.75           C
ATOM   5159  CE1 TYR B 358     -24.464  -1.622  68.292  1.00 31.70           C
ATOM   5160  CE2 TYR B 358     -26.217  -2.246  66.769  1.00 30.80           C
ATOM   5161  CZ  TYR B 358     -25.101  -1.479  67.067  1.00 31.72           C
ATOM   5162  OH  TYR B 358     -24.639  -0.544  66.165  1.00 30.89           O
ATOM   5163  N   LEU B 359     -29.711  -4.719  69.789  1.00 34.79           N
ATOM   5164  CA  LEU B 359     -30.913  -4.854  68.972  1.00 34.95           C
```

FIGURE 4-77 (COORDINATES)

```
ATOM   5165  C    LEU B 359     -32.177   -4.393   69.684  1.00  35.83           C
ATOM   5166  O    LEU B 359     -33.251   -4.387   69.090  1.00  36.11           O
ATOM   5167  CB   LEU B 359     -31.102   -6.313   68.548  1.00  34.58           C
ATOM   5168  CG   LEU B 359     -30.050   -6.950   67.639  1.00  34.46           C
ATOM   5169  CD1  LEU B 359     -30.432   -8.398   67.347  1.00  34.20           C
ATOM   5170  CD2  LEU B 359     -29.948   -6.150   66.346  1.00  34.12           C
ATOM   5171  N    HIS B 360     -32.051   -4.012   70.952  1.00  36.54           N
ATOM   5172  CA   HIS B 360     -33.202   -3.578   71.739  1.00  37.91           C
ATOM   5173  C    HIS B 360     -34.253   -4.683   71.843  1.00  38.03           C
ATOM   5174  O    HIS B 360     -35.432   -4.462   71.565  1.00  37.76           O
ATOM   5175  CB   HIS B 360     -33.840   -2.320   71.135  1.00  38.19           C
ATOM   5176  CG   HIS B 360     -32.995   -1.093   71.264  1.00  39.53           C
ATOM   5177  ND1  HIS B 360     -33.522    0.179   71.221  1.00  40.31           N
ATOM   5178  CD2  HIS B 360     -31.661   -0.942   71.435  1.00  40.06           C
ATOM   5179  CE1  HIS B 360     -32.549    1.062   71.364  1.00  40.32           C
ATOM   5180  NE2  HIS B 360     -31.409    0.408   71.495  1.00  40.10           N
ATOM   5181  N    LEU B 361     -33.811   -5.870   72.243  1.00  38.38           N
ATOM   5182  CA   LEU B 361     -34.693   -7.018   72.398  1.00  38.73           C
ATOM   5183  C    LEU B 361     -34.651   -7.505   73.840  1.00  39.50           C
ATOM   5184  O    LEU B 361     -35.548   -8.289   74.224  1.00  40.05           O
ATOM   5185  CB   LEU B 361     -34.272   -8.148   71.456  1.00  38.25           C
ATOM   5186  CG   LEU B 361     -34.459   -7.870   69.963  1.00  39.14           C
ATOM   5187  CD1  LEU B 361     -33.922   -9.038   69.141  1.00  38.59           C
ATOM   5188  CD2  LEU B 361     -35.937   -7.646   69.674  1.00  38.47           C
ATOM   5189  OXT  LEU B 361     -33.713   -7.101   74.561  1.00  38.78           O
TER    5190       LEU B 361
```

FIGURE 4-78 (REMARKS)

```
HEADER      ----                                  xx-xxx-xx   xxxx
TITLE       ---
REMARK   3
REMARK   3 REFINEMENT.
REMARK   3   PROGRAM     : CNS 1.1
REMARK   3   AUTHORS     : BRUNGER,ADAMS,CLORE,DELANO,GROS,GROSSE-
REMARK   3               : KUNSTLEVE,JIANG,KUSZEWSKI,NILGES, PANNU,
REMARK   3               : READ,RICE,SIMONSON,WARREN
REMARK   3
REMARK   3   REFINEMENT TARGET : ENGH & HUBER
REMARK   3
REMARK   3   DATA USED IN REFINEMENT.
REMARK   3    RESOLUTION RANGE HIGH (ANGSTROMS) : 2.22
REMARK   3    RESOLUTION RANGE LOW  (ANGSTROMS) : 30.00
REMARK   3    DATA CUTOFF            (SIGMA(F)) : 0.000
REMARK   3    DATA CUTOFF HIGH         (ABS(F)) : NULL
REMARK   3    DATA CUTOFF LOW          (ABS(F)) : NULL
REMARK   3    COMPLETENESS (WORKING+TEST)   (%) : NULL
REMARK   3    NUMBER OF REFLECTIONS             : 37502
REMARK   3
REMARK   3   FIT TO DATA USED IN REFINEMENT.
REMARK   3    CROSS-VALIDATION METHOD          : NULL
REMARK   3    FREE R VALUE TEST SET SELECTION  : RANDOM
REMARK   3    R VALUE            (WORKING SET) : 0.188
REMARK   3    FREE R VALUE                     : 0.226
REMARK   3    FREE R VALUE TEST SET SIZE   (%) : NULL
REMARK   3    FREE R VALUE TEST SET COUNT      : 1978
REMARK   3    ESTIMATED ERROR OF FREE R VALUE  : NULL
REMARK   3
REMARK   3   FIT IN THE HIGHEST RESOLUTION BIN.
REMARK   3    TOTAL NUMBER OF BINS USED           : NULL
REMARK   3    BIN RESOLUTION RANGE HIGH       (A) : NULL
REMARK   3    BIN RESOLUTION RANGE LOW        (A) : NULL
REMARK   3    BIN COMPLETENESS (WORKING+TEST) (%) : NULL
REMARK   3    REFLECTIONS IN BIN    (WORKING SET) : NULL
REMARK   3    BIN R VALUE           (WORKING SET) : NULL
REMARK   3    BIN FREE R VALUE                    : NULL
REMARK   3    BIN FREE R VALUE TEST SET SIZE  (%) : NULL
REMARK   3    BIN FREE R VALUE TEST SET COUNT     : NULL
REMARK   3    ESTIMATED ERROR OF BIN FREE R VALUE : NULL
REMARK   3
REMARK   3   NUMBER OF NON-HYDROGEN ATOMS USED IN REFINEMENT.
REMARK   3    PROTEIN ATOMS            : 5188
REMARK   3    NUCLEIC ACID ATOMS       : 0
REMARK   3    HETEROGEN ATOMS          : 30
REMARK   3    SOLVENT ATOMS            : 511
REMARK   3
REMARK   3   B VALUES.
REMARK   3    FROM WILSON PLOT           (A**2) : NULL
REMARK   3    MEAN B VALUE      (OVERALL, A**2) : NULL
REMARK   3    OVERALL ANISOTROPIC B VALUE.
REMARK   3     B11 (A**2) : NULL
REMARK   3     B22 (A**2) : NULL
REMARK   3     B33 (A**2) : NULL
REMARK   3     B12 (A**2) : NULL
REMARK   3     B13 (A**2) : NULL
REMARK   3     B23 (A**2) : NULL
REMARK   3
REMARK   3   ESTIMATED COORDINATE ERROR.
REMARK   3    ESD FROM LUZZATI PLOT        (A) : NULL
REMARK   3    ESD FROM SIGMAA              (A) : NULL
REMARK   3    LOW RESOLUTION CUTOFF        (A) : NULL
REMARK   3
REMARK   3   CROSS-VALIDATED ESTIMATED COORDINATE ERROR.
REMARK   3    ESD FROM C-V LUZZATI PLOT    (A) : NULL
REMARK   3    ESD FROM C-V SIGMAA          (A) : NULL
REMARK   3
REMARK   3   RMS DEVIATIONS FROM IDEAL VALUES.
```

FIGURE 4-79 (REMARKS)

```
REMARK   3    BOND LENGTHS                  (A) : 0.006
REMARK   3    BOND ANGLES             (DEGREES) : 1.29
REMARK   3    DIHEDRAL ANGLES         (DEGREES) : NULL
REMARK   3    IMPROPER ANGLES         (DEGREES) : NULL
REMARK   3
REMARK   3  ISOTROPIC THERMAL MODEL : NULL
REMARK   3
REMARK   3  ISOTROPIC THERMAL FACTOR RESTRAINTS.    RMS      SIGMA
REMARK   3    MAIN-CHAIN BOND              (A**2) : NULL  ; NULL
REMARK   3    MAIN-CHAIN ANGLE             (A**2) : NULL  ; NULL
REMARK   3    SIDE-CHAIN BOND              (A**2) : NULL  ; NULL
REMARK   3    SIDE-CHAIN ANGLE             (A**2) : NULL  ; NULL
REMARK   3
REMARK   3  BULK SOLVENT MODELING.
REMARK   3    METHOD USED : NULL
REMARK   3    KSOL        : NULL
REMARK   3    BSOL        : NULL
REMARK   3
REMARK   3  NCS MODEL : NULL
REMARK   3
REMARK   3  NCS RESTRAINTS.                         RMS    SIGMA/WEIGHT
REMARK   3    GROUP  1  POSITIONAL         (A)    : NULL ; NULL
REMARK   3    GROUP  1  B-FACTOR           (A**2) : NULL ; NULL
REMARK   3
REMARK   3  PARAMETER FILE   1   : NULL
REMARK   3  TOPOLOGY FILE    1   : NULL
REMARK   3
REMARK   3  OTHER REFINEMENT REMARKS: NULL
CRYST1   119.137   119.137   332.612   90.00   90.00  120.00 H 3 2         36
SCALE1      0.008394   0.004846   0.000000        0.00000
SCALE2      0.000000   0.009692   0.000000        0.00000
SCALE3      0.000000   0.000000   0.003007        0.00000
```

CRYSTAL STRUCTURE OF SOLUBLE GLUTAMINYL CYCLASE

BACKGROUND OF THE INVENTION

The present invention relates to a crystal structure, and more particularly to the crystal structure of glutaminyl cyclase (QC).

The formation of N-terminal pGlu is an important post-translational or co-translational event in the processing of numerous bioactive neuropeptides, hormones, and cytokines during their maturation in the secretory pathway. The N-terminal pGlu is necessary in the formation of the proper conformation of these regulatory peptides for binding to their receptors and/or for protecting the N-termini of these peptides from exopeptidase degradation (Van Coillie et al., *Biochemistry* 37: 12672-12680 (1998); Hinke et al., *J. Biol. Chem.* 275: 3827-3834 (2000)). The N-terminal pyroglutamate (pGlu) is formed by the N-terminal cyclization of its glutaminyl precursor. And the glutaminyl cyclases (QCs) are the catalysts responsible for this posttranslational modification (Fischer et al., *Proc. Natl. Acad. Sci. USA* 84: 3628-3632 (1987); Busby et al., *J. Biol. Chem.* 262: 8532-8536 (1987)).

QCs (EC 2.3.2.5) are acyltransferases identified in both animal and plant sources (Fischer et al., *Proc. Natl. Acad. Sci. USA* 84: 3628-3632 (1987); Busby et al., *J. Biol. Chem.* 262: 8532-8536 (1987); Oberg et al., *Eur. J. Biochem.* 258: 214-222 (1998)). QCs are abundant in mammalian neuroendocrine tissues, such as hypothalamus and pituitary (Busby et al., *J. Biol. Chem.* 262: 8532-8536 (1987); Sykes et al., *FEBS Lett.* 455: 159-161 (1999)), and are highly conserved from yeast to human. Animal QCs were shown to have distinct structure and protein stability from plant QCs in spite of their similar molecular masses, i.e., 33-40 kDa (Oberg et al., *Eur. J. Biochem.* 258: 214-222 (1998); Schilling et al., *Biochemistry* 41: 10849-10857 (2002)). While no bacterial QCs have been reported thus far, the mammalian QCs had been predicted to exhibit remarkable homology to the bacterial double-zinc aminopeptidases (Schilling et al., *J. Biol. chem.* 278: 49773-49779 (2003); Booth et al., *BMC biol.* 2: 2 (2004)).

Several of human genetic diseases, e.g., osteoporosis that is a multifactorial hormonal disease characterized by reduced bone mass and microarchitectual deterioration of bone tissue (Stewart et al., *J. Endocrinol.* 166: 235-245 (2000)), appear to result from mutations of the QC gene. The gene encoding QC (QPC7) lies on chromosome 2p22.3. Within the region, thirteen single nucleotide polymorphisms (SNPs) were analyzed and shown a striking correlation with osteoporosis susceptibility in adult women (Ezura et al., *J. Bone Miner. Res.* 19: 1296-1301 (2004)). Of these SNPs, the R54W presents, statistically, the most prominent association with osteoporosis, which was proposed to affect the pathogenesis through the hypothalamus-pituitary-gonadal axis (Ezura et al., *J. Bone Miner. Res.* 19: 1296-1301 (2004)).

Interestingly, QC also catalyzes the N-terminal glutamate cyclization that leads to the formation pGlu (Schilling et al., *FEBS Lett.* 563: 191-196 (2004)). This reaction is probably related to the formation of several plaque-forming peptides, such as amyloid-β (Aβ) peptides and CLAC (collagen-like Alzheimer amyloid plaque component), which play a pivotal role in Alzheimer's disease (Morgan et al., *Prog. Neurobiol.* 74: 323-349 (2004); Hashimoto et al., *EMBO J.* 21: 1524-1534 (2002)). Peptides containing N-terminal pGlu, e.g., pGlu$^3$-Aβ peptides, are major fractions of the Aβ peptides within the core of neuritic plaques (Saido et al., *Neuron* 14: 457-466 (1995); Kuo et al., *Biochem. Biophys. Res. Commun.* 237: 188-191 (1997); Russo et al., *J. Neurochem.* 82: 1480-1489 (2002)). The N-terminal pGlu could enhance the hydrophobicity, proteolytic stability and neurotoxicity of these peptides (Russo et al., *J. Neurochem.* 82: 1480-1489 (2002); Harigaya et al., *Biochem. Biophys. Res. Commun.* 276: 422-427 (2000)), probably causing a profused accumulation of pGlu-Aβ peptides in several senile plaques, and thus accelerating the progression of neurodegenerative disorders.

To date, there remain several theories concerning the properties and structures of human and animal QCs. The present invention offers the crystal structure of QC in free form, the structures of the active sites or catalytic centers of the QC, the method for identifying an inhibitor of glutaminyl cyclase (QC), and provides a structural basis for the rational design of new inhibitors against QC-associated disorders.

BRIEF SUMMARY OF THE INVENTION

An aspect of the invention provides a crystalline structure of glutaminyl cyclase (QC).

In another example, the present invention provides crystalline compositions of a complex comprising at least one QC molecule and another molecule that ligates, interacts with, or otherwise binds to the QC molecule.

Another aspect of the invention provides a method for identifying an inhibitor of glutaminyl cyclase (QC). The method comprises the steps of: (a) preparing QC protein, preferably a polypeptide with an amino acid sequence from amino acid residues 33 to 361 of SEQ ID NO:1, wherein the polypeptide has an active site comprising one zinc ion tetrahedrally coordinated to amino acid residues 159, 202, and 330 of SEQ ID NO:1, and a water molecule; (b) contacting the polypeptide with a candidate inhibitor for forming a QC/inhibitor complex; (c) generating a three-dimensional model of the QC/candidate inhibitor complex obtained in step (b); wherein the candidate inhibitor having an imidazole nitrogen bound to the zinc ion is identified as the inhibitor of QC.

A further aspect of the invention provides a method of making a QC crystal. The method comprises the steps of: (a) expressing a QC protein; (b) purifying the QC protein; and (c) crystallizing the QC protein to form the QC crystal.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a list of X-ray coordinates of the human QC crystal structure at pH 6.5, wherein the listed RES and # correspond respectively to an amino acid and the residue number of the amino acid in SEQ ID NO:1;

FIG. 2 is a list of X-ray coordinates of the human QC crystal structure at pH 8.0, wherein the listed RES and # correspond respectively to an amino acid and the residue number of the amino acid in SEQ ID NO:1;

FIG. 3A is an overall view of the structure of human QC;

FIG. 3B is a schematic diagram illustrating a topology of the human QC structure;

FIG. 3C is a stereo view of the human QC catalytic region;

FIG. 4 is a list of X-ray coordinates of the crystal structure of human QC in complex with glutamine t-butyl ester, wherein the listed RES and # correspond respectively to an amino acid and the residue number of the amino acid in SEQ ID NO:1;

FIG. 5A depicts the active-site structure of a human QC in free form;

FIG. 5B depicts the active-site structure of a human QC bound to 1-vinylimidazole at a 1.68 Å resolution;

FIG. 5C depicts the active-site structure of a human QC bound to 1-benzylimidazole at a 1.64 Å resolution; and FIG. 5D depicts the active site structure of a human QC bound to N-ω-acetylhistamine at a 1.56 Å resolution.

DETAILED DESCRIPTION OF THE INVENTION

Figure 3A:
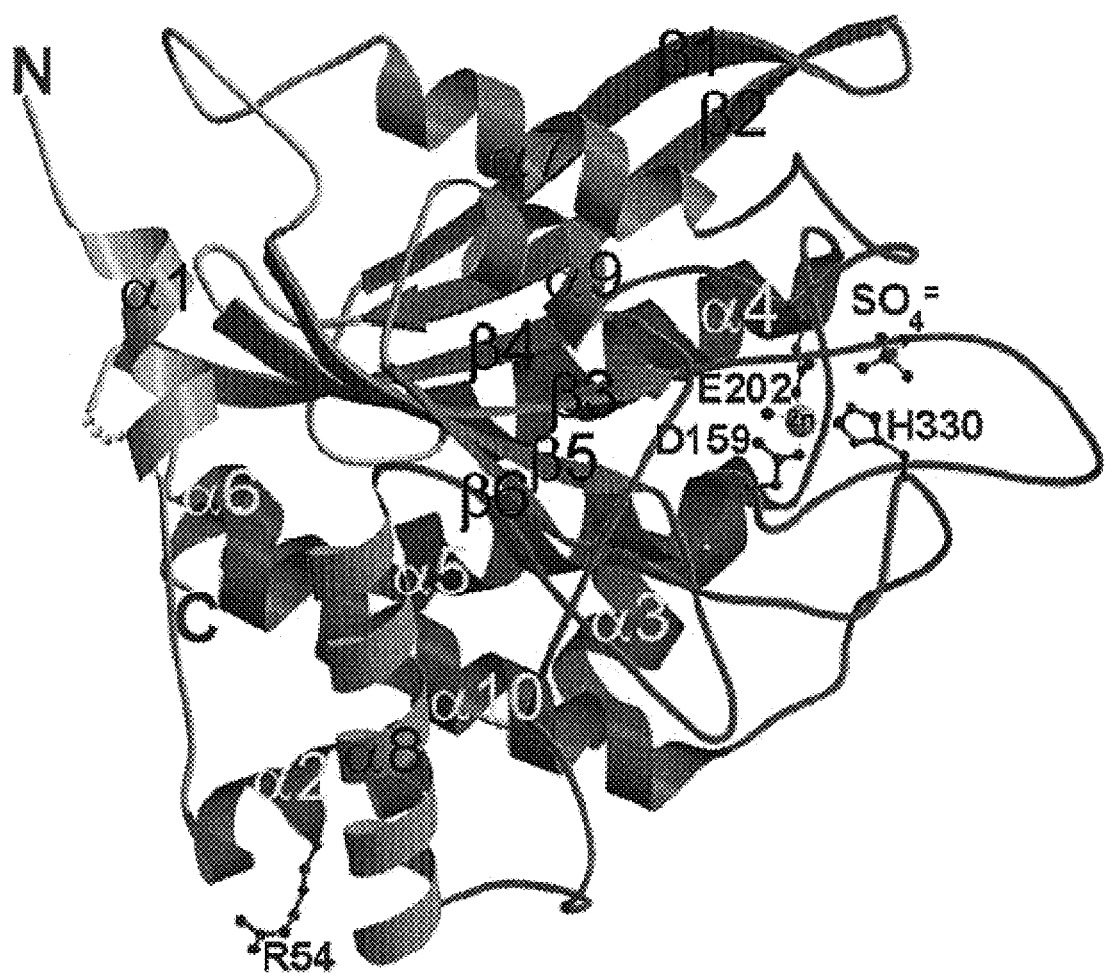

To facilitate the understanding of the invention, a number of terms are defined below.

The term "active site" refers to a specific region (or atom) in a molecular entity that is capable of entering into a stabilizing interaction with another molecular entity. In certain embodiments, the term also refers to the reactive parts of a macromolecule that directly participate in its specific combination with another molecule. In other embodiments, a binding site may be comprised or defined by the three dimensional arrangement of one or more amino acid residues within a folded polypeptide.

The term "analogue" refers to a drug or chemical compound whose structure is related in some way to that of another drug or chemical compound, but whose chemical and biological properties may be similar or different.

The term "coordinate" or "structural coordinates" refers to Cartesian coordinates derived from the mathematical equations related to the patterns obtained on diffraction of a monochromatic beam of X-ray by the atoms of a protein or protein complex in crystal form. The diffraction data are used to calculate an electron density map of the repeating units of the crystal. The electron density maps are then used to establish the positions of the individual atoms of the molecule or molecular complex.

The term "homologue" means a protein, polypeptide, oligopeptide, or portion thereof, having an amino acid sequence identity with QC as described in SEQ ID No: 1, or any active site described herein, or any functional or structural domain of binding protein. SEQ ID No:1 is a partial amino acid sequence of human QC.

The term "substrate" refers to any molecule, which is acted upon by an enzyme. According to the invention, the substrate binds with an active site of QC to form a QC-substrate-complex.

The term "mature domain" refers to a portion or segment of the QC protein or homologue that comprises an active or catalytic site; that is, the polypeptide with an amino acid sequence of amino acid residues 33 to 361 of SEQ ID NO:1.

The term "root mean square deviation" refers to the square root of the arithmetic mean of the squares of the deviations from the mean. It is a way to express the deviation or variation from a trend or object.

The term "variants" in relation to the polypeptide sequence in SEQ ID NO:1 include any substitution of, variation of, modification of, replacement of, deletion of, or addition of one or more amino acids from or to the sequence providing a resultant polypeptide sequence for a protein having QC activity.

The following amino acid abbreviations are used throughout this disclosure:

A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanin; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; H=His=Histidine.

A. Cloning, Expression and Purification

The nucleotide sequence encoding QC, or functional fragment, derivatives thereof, can be inserted into an appropriate expression vector that contains the necessary elements for the transcription and translation of the inserted protein-coding sequence. The vectors are then introduced into the desired host cells by methods known in the art.

For detailed descriptions of ways for cloning, expression, and purification of QC, please refer to U.S. patent application Ser. No. 11/331,704, the disclosure of which is hereby incorporated herein by reference.

B. Crystal Structure

X-ray structure coordinates define a unique configuration of points in space. Those skilled in the art understand that a set of structure coordinates for a protein or an enzyme/substrate complex define a set of points that, in turn, define a configuration in three dimensions. A similar or identical configuration can be defined by an entirely different set of coordinates, provided the distances and angles between atomic coordinates remain essentially the same.

Three-dimensional data generation may be provided by an instruction or set of instructions, such as a computer program or commands for generating a three-dimensional structure or graphical representation from structure. The graphical representation can be generated or displayed by commercially available software programs, such as SOLVE, RESOLVE (Terwilliger et al., *Methods Enzymol.* 374: 22-37 (2003)), O (Jones et. al., Acta Crystallogr. A47: 110-119 (1991)), PROCHECK (Laskowski et al., *J. Appl. Crystallogr.* 26: 283-291 (1993)), MOLSCRIPT (Kraulis et al., *J. appl. crystallogr.* 24: 946-950 (1991)), Raster3D (Merrit & Bacon et al., *Methods Enzymol.* 277: 505-524 (1997)) and GRASP (Nicholls et al., *Proteins* 11: 281-296 (1991)), which are incorporated herein by reference.

The present invention provides a crystalline structure of a QC polypeptide, the polypeptide comprising a QC protein, preferably a polypeptide an amino acid sequence spanning amino acid residues 33 to 361 of SEQ ID NO: 1. One embodiment of the present invention provides crystalline composition of QC that is derived from a mammal. In another embodiment, the present invention provides a crystal structure of QC that is derived from a human being.

The present invention further provides a crystal structure of human QC that comprises a three-dimensional structure characterized by the atomic structure coordinates according to FIG. 1. And in accordance with another embodiment, the present invention provides a crystal structure of human QC, that has a space group of H32 so as to form a unit cell of dimensions of a=b=119.03 Å, c=332.94 Å. In yet another embodiment, the present invention provides a crystal as characterized above, wherein the crystal diffracts x-rays for determination of atomic coordinates of the crystal to a resolution of about 1.66 Å.

The present invention further provides a crystal structure of human QC that comprises a three-dimensional structure characterized by the atomic structure coordinates of FIG. 2. In another embodiment, the present invention provides a crystal structure of human QC, that has a space group of H32 so as to form a unit cell of dimensions of a=b=118.99 Å, c=332.26 Å. In yet another embodiment, the present invention provides a crystal as characterized above, wherein the crystal diffracts x-ray for determination of atomic coordinates of the crystal to a resolution of about 2.35 Å.

In one embodiment, the present invention provides a QC crystal comprising two QC molecules. In accordance with another embodiment, the invention provides the crystal as characterized above, wherein the two QC molecules have a root mean square deviation of about 0.386 Å for all $C^\alpha$ atoms between the two QC molecules.

The mature domain (amino acid residues 33-361 of SEQ ID NO: 1) of human QC was shown to possess glutaminyl and glutamyl cyclase activities on the putative physiological substrate of human QC. The asymmetric unit of the crystals, grown at pH 6.5, contains two human QC molecules with a root mean square deviation of 0.386 Å (for all $C^\alpha$ atoms) between them. The globular structure reveals a mixed α/β fold with a size of 63×58×41 Å$^3$. There are up to 36% and 16% of the amino acid residues involved in α-helix and β-sheet, respectively, with 6% in the $3_{10}$-helix regions.

Figure 3B:
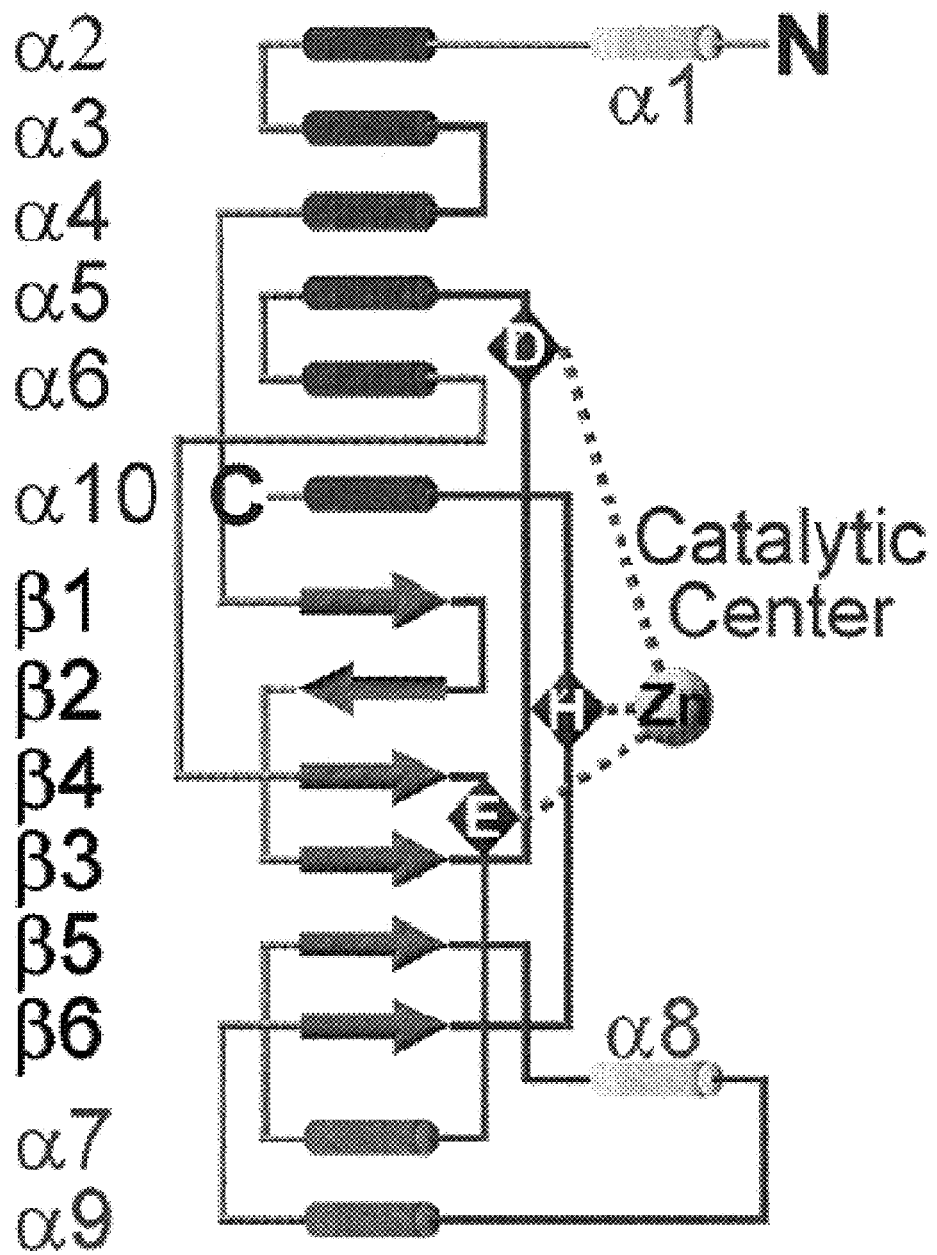

FIG. 3A is an overall view of the structure of human QC. The central six β-strands are colored orange. The α helices located on the top, bottom, and edge are colored cyan, magenta, and yellow, respectively. The zinc ion is shown as a yellow sphere. The zinc-coordinated residues, Arg54, and a sulfate ion are depicted with a ball-and-stick model. The coils and loops adjacent to the catalytic center are colored green, whereas those distant from the active site are colored gray. Gray dots further represent the disordered region of residues 183 to 188 of SEQ ID NO: 1. FIG. 3B is a schematic diagram illustrating a topology of the human QC structure. The color codes for secondary structural elements are identical to those in FIG. 3A.

Referring to both FIGS. 3A and 3B, the structure has an open-sandwich topology comprising a central six-stranded β-sheet surrounded by two α-helices (α7 and α9) and six additional (α2, α3, α4, α5, α6 and α10) α-helices on opposite sides, and flanked by two other α-helices (α1 and α8) at one edge of the β-sheet (FIG. 3A). This twisted β-sheet is formed by two antiparallel strands (β1 and β2) and four parallel strands (β3, β4, β5 and β6), constituting the hydrophobic core of the molecule. The coil and loop regions of the structure represent 42% of the total residues; about half of them are major components of the active site (FIG. 3B). The structures at pH 6.5 and pH 8.0 are essentially similar, and the structure at pH 8.0 has a root mean square deviation of 0.155 Å (for all $C^\alpha$ atoms) between the QC molecules.

C. QC/QC Substrate Complex

In another aspect, this invention provides a crystal of a complex comprising QC and a QC substrate bound to QC.

In one embodiment, the crystal of the QC/QC substrate complex comprises: (a) a polypeptide with an amino acid sequence from residues 33 to 361 of SEQ ID NO:1, or a homologue, analogue or variant thereof, and (b) a QC substrate, such that the crystal effectively diffracts X-rays for the determination of atomic coordinates of the QC/QC substrate complex to a resolution of 2.22 Å.

Another embodiment of this invention provides a QC/QC substrate complex that comprises a three-dimensional structure characterized by the atomic coordinates according to FIG. 4.

In yet another embodiment, this invention provides a QC/QC substrate complex that has a space group of H32, so as to form a unit cell of dimensions a=b=119.14 Angstroms, and c=332.61 Angstroms.

Similarly, the three-dimensional data of the crystal of the QC/QC substrate complex may be generated by an instruction or set of instructions, such as a computer program or commands for generating a three-dimensional structure or graphical representation from structure. The graphical representation can be generated or displayed by commercially available software programs, such as those described in the method for determining the QC crystal structure.

D. Identification of Inhibitor of QC

To use the structure coordinates generated for QC, homologues, thereof, or one of its active site, it is at times necessary to convert them into a three-dimensional shape or to extract three-dimensional structural information from them. One of ordinary skill in the art would know that this can be achieved through the use of commercially or publicly available software that is capable of generating a three-dimensional structure, or a three-dimensional representation, of molecules or portions thereof from a set of structure coordinates.

The present invention provides a method for identifying a inhibitor of glutaminyl cyclase (QC), comprising the steps of:

(a) preparing a polypeptide with an amino acid sequence from amino acid residues 33 to 361 of SEQ ID NO:1, wherein the polypeptide has an active site comprising one zinc ion tetrahedrally coordinated to amino acid residues 159, 202, and 330 of SEQ ID NO:1, and a water molecule;

(b) contacting the polypeptide with a candidate inhibitor for forming a QC/candidate inhibitor complex;

(c) generating a three-dimensional model of the QC/candidate inhibitor complex obtained in step (b);

wherein the candidate inhibitor having an imidazole nitrogen bound to the zinc ion is identified as the inhibitor of QC.

The active site may further comprise amino acid residues 201, 207, 248, 305, 325, and 329 of SEQ ID NO: 1.

In accordance with one embodiment, the active site of QC comprises a water molecule, a zinc ion tetrahedrally coordinated to amino acid residues 159, 202, and 330 of SEQ ID NO: 1, and the amino acid residue 160 of SEQ ID NO: 1, the amino acid residue 160 of SEQ ID NO: 1 forming a peptide bond with the amino acid residue 159 of SEQ ID NO: 1. In another embodiment, such peptide bond is stabilized by a plurality of hydrogen bonds and is cis-configured.

In yet another embodiment, the active site of QC further comprises a hydrophobic pocket lined by amino acid residues 144, 146, 154, 249, 303, 321, 325, and 329 of SEQ ID NO: 1. Additionally, the active site may further comprise a sulfate ion adjacent to the hydrophobic pocket, wherein the sulfate ion is hydrogen-bonded to the amino acid residues 144, 206, 207, and 330 of SEQ ID NO: 1, and at least two water molecules.

Similarly, the three-dimensional data of the QC/candidate inhibitor complex may be generated by an instruction or set of instructions, such as a computer program or commands for generating a three-dimensional structure or graphical representation from structure. The graphical representation can be generated or displayed by commercially available software programs, such as those described above for determining the QC crystal structure and QC/QC substrate complex crystal structure.

Figure 5A:
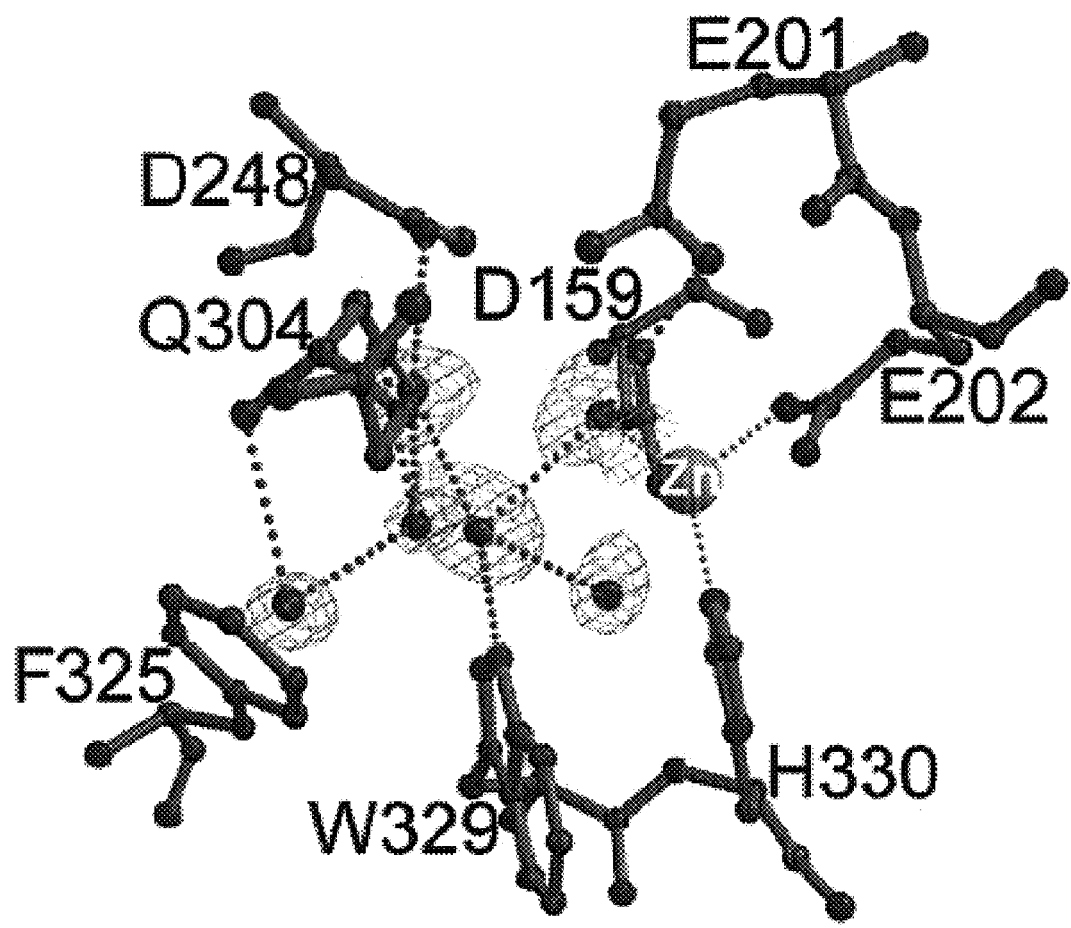
Figure 5B:
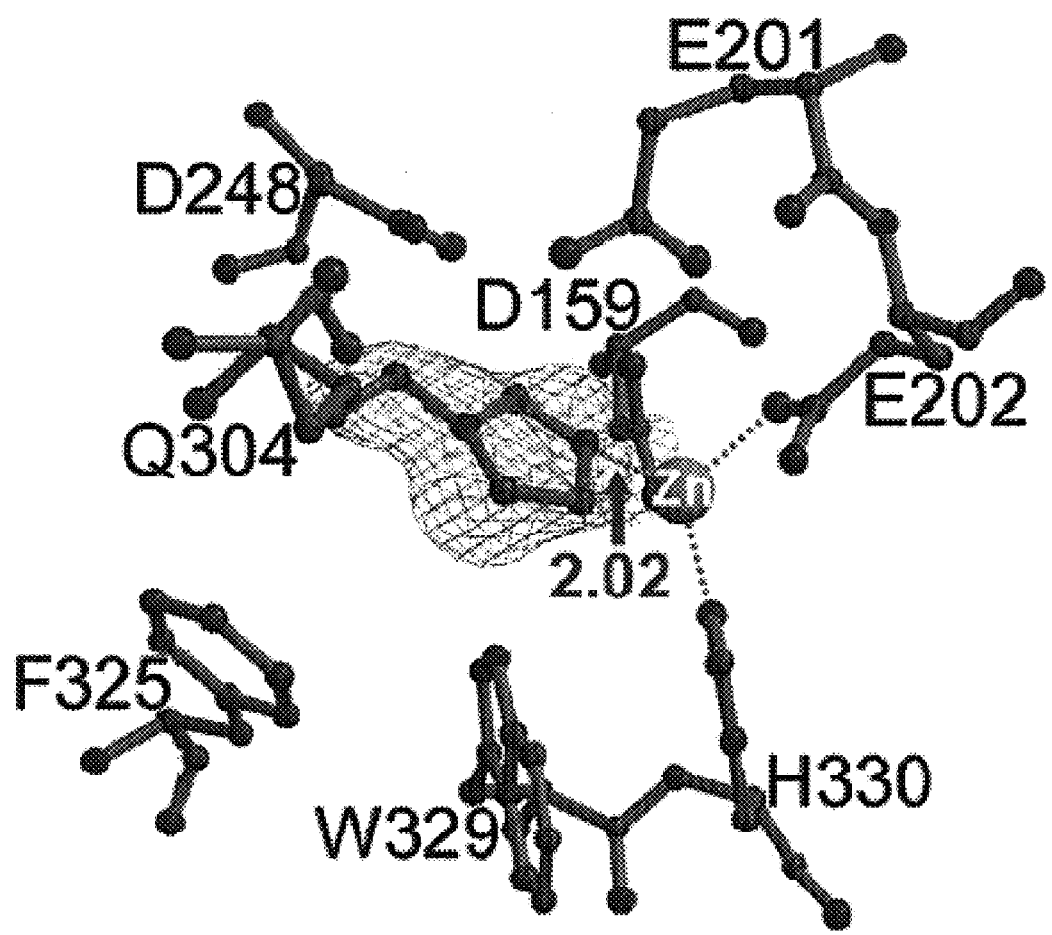

The inhibitor includes but is not limited to imidazole-derived inhibitors, such as 1-vinylimidazole, 1-benzylimidazole, N-ω-acetylhistamine. For example, an electron-rich nucleophile having a good ability to ligate to the zinc ion of human QC, and combined with bulky hydrophobic substitutents may also be the structural basis of a potent QC inhibitor. As shown in FIGS. 5B through to 5D, binding of the inhibitors results in the removal of six water molecules within the active-site pocket, including the zinc-coordinated one which is replaced by an imidazole nitrogen of the inhibitors.

The QC structure coordinates or the three-dimensional graphical representation generated from the coordinates may be used in conjunction with a computer for a variety of purposes, including identifying a inhibitor of QC. Various computational methods may also be used to determine whether a molecule or an active site thereof is "structurally equivalent" in terms of its three-dimensional structure to all or part of QC or its active site. One of ordinary skill in the art would understand that such methods may be carried out using software applications currently available.

E. Method of Making Crystal of Glutaminyl Cyclase

The present invention provides a method of making the crystal of human QC.

In one embodiment, the method of making the crystal of human QC comprises: (a) expressing the QC protein; (b) purifying the QC protein; and (c) crystallizing the QC protein to form the crystal of human QC. Preferably, the QC protein is crystallized by a hanging-drop vapor diffusion method.

F. Screening Drugs

Once a potential substrate is identified, it can be either selected from a library of chemicals as are commercially available from most large chemical companies. Alternatively, the potential substrate can be synthesized de novo.

When a suitable drug is identified, a supplemental crystal can be grown comprising a complex formed of the QC crystal and the drug. Preferably, the supplemental crystal effectively diffracts X-rays allowing the determination of the atomic coordinates of the QC/drug complex to a resolution of less than 3.0 Angstroms, and preferably less than 2.0 Angstroms.

The present invention contemplates methods for treating certain diseases in a mammal, preferably, human, by using the substrates, and preferably the inhibitors, as described herein.

The invention will now be described in further detail with reference to the following specific, non-limiting examples.

EXAMPLE 1

Expression and Purification of Human QC

The cDNA encoding human QC was amplified by PCR from a human bone marrow cDNA library (Clontech, Mountain View, Calif.); the mature enzyme (residues 33-361) was expressed in *E. coli* cells using a pET 32a expression vector (Novagen, Darmstadt, Germany) with several modifications as described previously in Taiwan Patent Application No. 094132349. SeMet-labeled protein was produced in *E. coli* using a non-auxotrophic protocol and purified in a manner similar to the native protein. In addition, the mutants of human QC were constructed using a "QuickChange site-directed mutagenesis kit" (Stratagene, La Jolla, Calif.) and were expressed and purified in the same manner as the wild-type human QC.

EXAMPLE 2

Crystallization of Human QC

Purified human QC was concentrated to 8-10 mg/ml and crystallized at 25° C. by the hanging drop vapor diffusion method. Rhombohedral crystals for wild-type, SeMet-labeled and mutant human QC were grown using equal volumes of the protein solution and the reservoir that contained 1.6-1.8 M $(NH_4)_2SO_4$, 4% dioxane and 10 mM MES, pH 6.5. In the condition of pH 8.0, the MES buffer in the reservoir was replaced by Tris-HCl.

In the case of substrate-bound form, the crystals of the mutant E201Q (grown at pH 7.0) were soaked for 1.5 hours into a solution consisting of 75% mother liquor, 25% glycerol and 1.1 M glutamine t-butyl ester. X-ray diffraction experiments were performed at various synchrotron beamlines as listed in Table 1. Prior to mounting on the X-ray machine, crystals were briefly soaked in mother liquor containing 20-25% glycerol (v/v) as cryoprotectants. All diffraction data were processed and scaled using the HKL package (Otwinowski et al., *Methods Enzymol.* 276: 307-326 (1997)). The space group of these crystals is R32, with typical unit cells of a=b=119 Å, c=333 Å, in which an asymmetric unit comprises two human QC molecules.

TABLE 1

MAD phasing statistics

| Data set* | SeMet-QC λ1 | SeMet-QC λ2 | SeMet-QC λ3 |
|---|---|---|---|
| Wavelength (Å) | 0.9792 | 0.9794 | 0.9750 |
| Space group | | R32 | |
| Resolution (Å) | | 50-1.8 (1.86-1.80)[†] | |
| Total observations | 497057 | 497051 | 497136 |
| Unique reflections | 84184 | 84209 | 84238 |
| Redundancy | | 5.9 (5.6) | |
| Completeness (%) | | 100.0 (100.0) | |
| I/σ(I) | 21.1 (4.7) | 25.2 (4.9) | 27.4 (4.9) |
| $R_{merge}$ (%) | 7.8 (36.0) | 6.4 (34.1) | 6.2 (33.2) |

Figure of merit and Z-score (SOLVE)0.65, 112.2 (at resolution range of 15-2.0 Å)
*X-ray diffraction experiment was performed at the beamline 5, KEK Photon Factory (Tsukuba, Japan).
[†]Values in parentheses correspond to highest resolution shell.

EXAMPLE 3

Structure Determination and Refinement of Crystal of Human QC

The human QC structure at pH 6.5 was solved by the Multiwavelength anomalous diffraction (MAD) phasing method using the program SOLVE (Terwilliger et al., *Methods Enzymol.* 374: 22-37 (2003)). Having the MAD data at 20 to 2.0 Å resolution range collected at the wavelengths of 0.9792 Å (peak), 0.9794 Å (edge) and 0.9750 Å (high-energy remote) (see Table 1), all 14 Se atom sites were successfully located in the asymmetric unit. Subsequently, the program RESOLVE (Terwilliger et al., *Methods Enzymol.* 374: 22-37 (2003)) was performed where the initial electron density was modified by solvent flattening, and up to 83% of the protein model was automatically built using the entire MAD data of 50 to 1.8 Å resolution. Manual building of the remaining model and further refinement were carried out using the program 0 (Jones et al., *Acta Crystallogr. A* 47: 110-119 (1991)) against a 1.66 Å resolution data set of the wild-type crystal. The isomorphous structures of the mutants, different pH values and the substrate-bound and inhibitor-bound forms were phased using the refined model. For each structure, iterative cycles of model building with the program O and computational refinement with crystallography NMR system (CNS) (Brunger et al., *Acta Crystallogr. D* 54: 905-921 (1998)) were performed. $R_{free}$ values were calculated using 5% reflections.

The stereochemical quality of the refined structures was checked using the program PROCHECK (Laskowski et al., *J. Appl. Crystallogr.* 26: 283-291 (1993)). Each of the final refined structures included 323 out of the 329 total residues in a human QC molecule, with a small disordered region of residues 183 to 188. Well-ordered water molecules were located and included in the models. The molecular figures were produced using the programs such as MOLSCRIPT (Kraulis et al., *J. appl. crystallogr.* 24: 946-950 (1991)), Raster3D (Merrit & Bacon et al., *Methods Enzymol.* 277: 505-524 (1997)) and GRASP (Nicholls et al., *Proteins* 11: 281-296 (1991)).

EXAMPLE 4

Structure of the Active Site of Human QC

The active site is mainly created by six loops between α3-α4, β3-α5, β4-7, β5-α8, α8-α9 and β6-α10 (FIG. 3B). The catalytic pocket is near the C-terminal edge of the central parallel strands β3, β4 and β5 (FIG. 3A). It is relatively narrow but accessible to the bulk solvent via a solvent channel. The single zinc ion of human QC lies at the bottom of the active-site pocket and is tetrahedrally coordinated to O delta (δ) 2 of Aspartic acid residue (D) 159 (D159 Oδ2), O epsilon (ε) 1 of Glutamic acid (E) 202 (E202 Oε1), N epsilon (ε) 2 of Histidine (H) 330 (H330 Nε2), and a water molecule. In addition, several other completely conserved residues, including E201, W207, D248, D305, F325, and W329, abut the zinc environment (see FIG. 3C), suggesting some roles in catalysis. Mutations of those amino acids decreased enzyme activity significantly as evident in Table 2. The acidic residues E201, D248 and D305 are pointing to each other at both pH 6.5 and 8.0, likely forming hydrogen bonds between them. The peptide bond between the zinc-coordinated D159 and the following S160 adopts a cis-configuration, stabilized by a network of hydrogen bonds, including D159 Oδ1-H140 Nε2 (2.70 Å), S160 Oγ-D248 Oδ1 (2.66 Å), D159 O-water (2.65 Å), and S160 N-water (2.80 Å).

TABLE 2

Kinetic parameters of wild-type and mutant human QC

|  |  | $K_m$ (mM) | $k_{cat}$ (s$^{-1}$) | $k_{cat}/K_m$ (mM$^{-1}$s$^{-1}$) |
|---|---|---|---|---|
| Wild | pH 7.0 | 0.79 ± 0.13* | 7.30 ± 0.01 | 9.459 ± 1.544 |
|  | pH 7.5 | 0.90 ± 0.09 | 9.76 ± 1.47 | 11.104 ± 2.716 |
|  | pH 8.0 | 0.63 ± 0.01 | 8.63 ± 0.48 | 13.663 ± 0.497 |
|  | pH 8.5 | 0.90 ± 0.05 | 9.93 ± 0.30 | 11.044 ± 0.331 |
|  | pH 8.8 | 2.06 ± 0.62 | 8.56 ± 1.55 | 4.319 ± 0.544 |
| Mutant† | R54W | 0.76 ± 0.04 | 7.35 ± 0.26 | 9.704 ± 0.824 |
|  | K144A | 1.47 ± 0.02 | 11.67 ± 0.34 | 7.944 ± 0.368 |
|  | F146A | 0.82 ± 0.16 | 7.91 ± 2.14 | 9.536 ± 0.769 |
|  | E201D | 12.62 ± 2.98 | 0.87 ± 0.28 | 0.068 ± 0.007 |
|  | E201Q‡ |  |  | ND |
|  | W207L | 1.77 ± 0.07 | 0.43 ± 0.01 | 0.243 ± 0.002 |
|  | W207F | 0.59 ± 0.05 | 2.32 ± 0.07 | 3.943 ± 0.189 |
|  | D248A‡ |  |  | ND |
|  | Q304L | 1.16 ± 0.09 | 9.39 ± 1.18 | 8.028 ± 0.386 |
|  | D305L‡ |  |  | ND |
|  | F325A | 4.67 ± 0.24 | 12.91 ± 0.06 | 2.772 ± 0.132 |
|  | W329A | 29.53 ± 2.29 | 1.35 ± 0.07 | 0.046 ± 0.001 |

*Values are represented as mean ±S.D. (n = 2 or 3).
†The assays for mutants were carried out under pH 8.0.
‡E201Q, D248A and D305L were shown to possess the ≈0.001%, ≈0.1% and ≈0.03% activity of the wild-type enzyme, respectively.
ND: Not detectable.

Figure 3C:
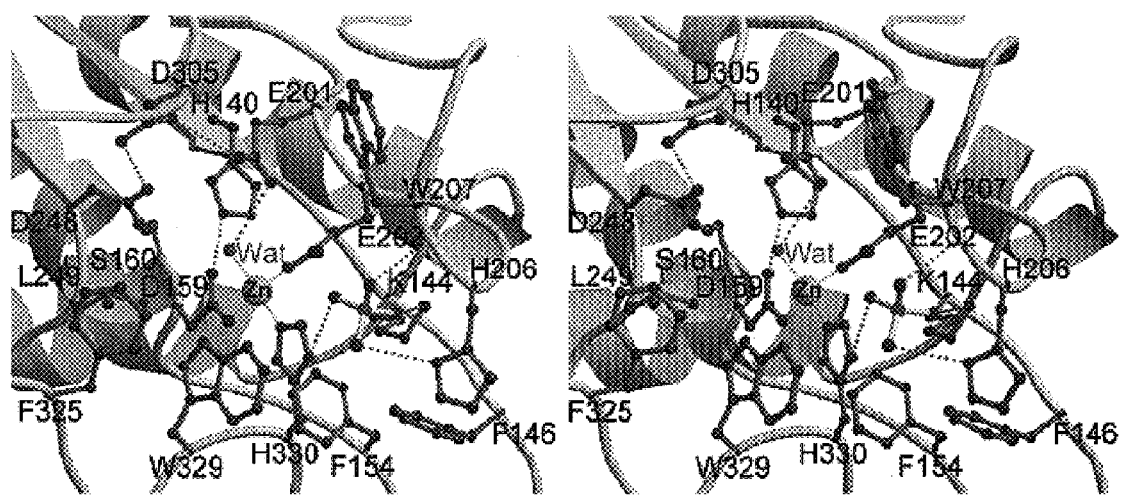

The hydrophobic active-site pocket is lined by residues $K_{144}$, F146, F154, L249, I303, I321, F325, and W329, having approximate dimensions of 13×11×7 Å$^3$. There are six water molecules located inside the pocket, including the water coordinated to the zinc ion. In addition, a sulfate ion is located near the opening of the pocket, hydrogen-bonded to $K_{144}$ Nζ, H206 Nδ1, W207 N, H330 Nδ1, and several water molecules (FIG. 3C). The active-site residues are shown and labeled. Possible hydrogen and coordination bonds are represented with dotted lines colored cyan and yellow, respectively. The green dotted lines depict the possibly unusual hydrogen bonds between D305 and E201 and between D305 and D248 of SEQ ID NO: 1

EXAMPLE 5

The Structure of Enzyme-Inhibitor Complexes

Figure 5C:
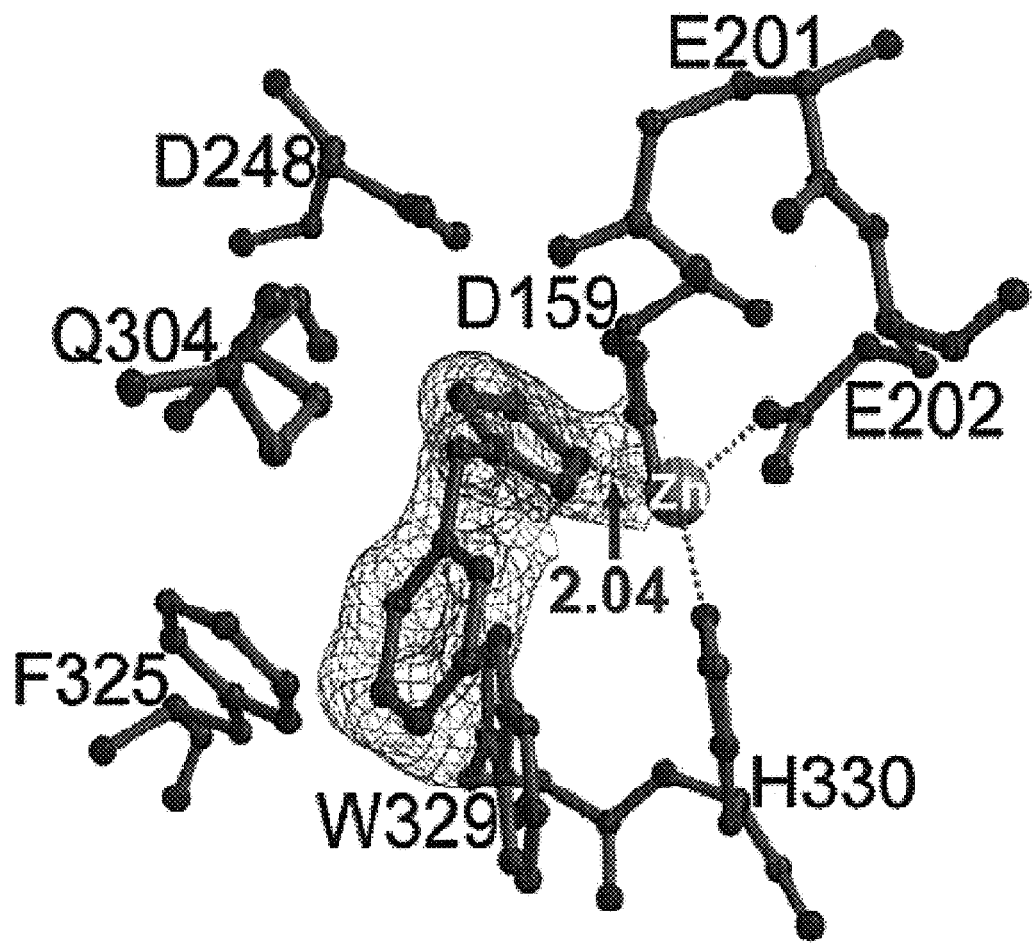
Figure 5D:
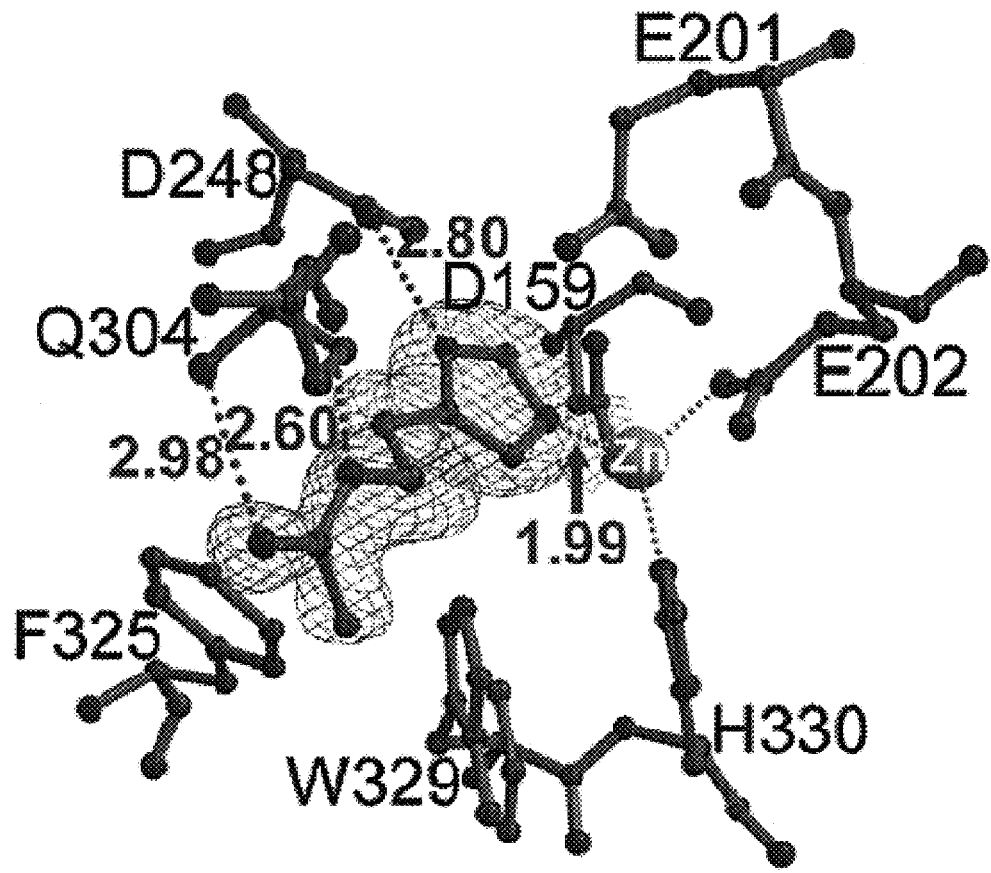

In the preparation of the inhibitor-bound crystal forms, a 1.5 μl protein solution containing human QC was mixed with 0.5 μl inhibitor solution (100 mM) in a 2 μl reservoir. The crystals formed as a result were subjected to X-ray diffraction and process as described in example 2. The crystal forms were determined and refined as described in example 3. As shown in FIGS. 5B through 5D, binding of the inhibitors results in the removal of six water molecules within the active-site pocket, including the zinc-coordinated one which is replaced by an imidazole nitrogen of the inhibitors. The inhibitors adopt different orientations, due to their different modifications on the imidazole ring. The small vinyl moiety of 1-vinylimidazole shows no interaction with the active site of human QC, leaving a large space in the catalytic pocket after its binding (FIG. 5B). However the bulky hydrophobic phenyl ring on 1-benzylimidazole is closely surrounded and stabilized by the phenyl and indole groups of F325 and W329, respectively (FIG. 5C). In contrast, the substitutent of N-ω-acetylhistamine is oriented almost parallel to the backbone of segment G301-Q304, stabilized mainly by three additional hydrogen bonds to D248 Oδ2, Q304 N and Q304 O of the enzyme (FIG. 5D). The detailed three-dimensional structures of human QC/1-vinylimidazole complex, human QC/1-benzylimidazole complex and human QC/N-ω-acetylhistamine complex are characterized by the atomic structure coordinates deposited as PDB ID codes 2AFZ, 2AFX and 2AFW, respectively in the protein data bank (www.pdb.org).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A crystal comprising a protein, wherein the protein consists of amino acid residues 33-361 of SEQ ID NO:1, wherein the crystal is characterized space group of R32 or H32 and has unit cell dimensions of a=b=119 Å, c=333 Å.

2. The crystal of claim 1, comprising a three-dimensional structure having the atomic structure coordinates of FIG. 1.

3. A crystal comprising a protein, wherein the protein consists of amino acid residues 33-361 of SEQ ID NO:1, wherein the crystal is characterized by space group R32 or H32 and has unit cell dimensions of a=b=119.03 Å, c=332.94 Å.

4. The crystal of claim 1 or 3, wherein the crystal diffracts x-rays for determination of atomic coordinates of the crystal to a resolution of about 1.66 Å.

5. A crystal comprising a protein. wherein the protein consists of amino acid residues 33-361 of SEQ ID NO:1, wherein the crystal is characterized by space group of R32 or H32 and has unit cell dimensions of a=b=118.99 Å, c=332.26 Å.

6. The crystal of claim 5, comprising a three dimensional structure characterized by the atomic structure coordinates of FIG. 2.

7. The crystal of claim 5, wherein the crystal diffracts x-rays for determination of atomic coordinates of the crystal to a resolution of about 2.35 Å.

8. The crystal of claim 1 or 3, wherein the crystal comprises two glutaminyl cyclase (QC) molecules per asymmetric unit.

9. The crystal of claim 8, wherein a root mean square deviation for all $C^{\alpha}$ atoms between the two QC molecules is about 0.386 Å.

10. A method of making the crystal of claim 1 or 3, the method comprising:
    (a) expressing the protein;
    (b) purifying the protein; and
    (c) crystallizing the protein to form the crystal of claim 1 or 3.

11. The method of claim 10, wherein the protein is crystallized by hanging-drop vapor diffusion.

* * * * *

SEQUENCE LISTING

<160> NUMBER OF SEQ ID NOS: 1

<210> SEQ ID NO 1
<211> LENGTH: 361
<212> TYPE: PRT
<213> ORGANISM: Homo sapiens

<400> SEQUENCE: 1

```
Met Ala Gly Gly Arg His Arg Val Val Gly Thr Leu His Leu Leu
  1               5                  10                  15

Leu Leu Val Ala Ala Leu Pro Trp Ala Ser Arg Gly Val Ser Pro Ser
                 20                  25                  30

Ala Ser Ala Trp Pro Glu Glu Lys Asn Tyr His Gln Pro Ala Ile Leu
             35                  40                  45

Asn Ser Ser Ala Leu Arg Gln Ile Ala Glu Gly Thr Ser Ile Ser Glu
         50                  55                  60

Met Trp Gln Asn Asp Leu Gln Pro Leu Leu Ile Glu Arg Tyr Pro Gly
 65                  70                  75                  80

Ser Pro Gly Ser Tyr Ala Ala Arg Gln His Ile Met Gln Arg Ile Gln
                 85                  90                  95

Arg Leu Gln Ala Asp Trp Val Leu Glu Ile Asp Thr Phe Leu Ser Gln
                100                 105                 110

Thr Pro Tyr Gly Tyr Arg Ser Phe Ser Asn Ile Ile Ser Thr Leu Asn
            115                 120                 125

Pro Thr Ala Lys Arg His Leu Val Leu Ala Cys His Tyr Asp Ser Lys
        130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
            180                 185                 190

Leu Gln Leu Ile Phe Phe Asp Gly Glu Glu Ala Phe Leu His Trp Ser
        195                 200                 205

Pro Gln Asp Ser Leu Tyr Gly Ser Arg His Leu Ala Ala Lys Met Ala
    210                 215                 220

Ser Thr Pro His Pro Pro Gly Ala Arg Gly Thr Ser Gln Leu His Gly
225                 230                 235                 240

Met Asp Leu Leu Val Leu Leu Asp Leu Ile Gly Ala Pro Asn Pro Thr
                245                 250                 255

Phe Pro Asn Phe Phe Pro Asn Ser Ala Arg Trp Phe Glu Arg Leu Gln
            260                 265                 270

Ala Ile Glu His Glu Leu His Glu Leu Gly Leu Leu Lys Asp His Ser
        275                 280                 285

Leu Glu Gly Arg Tyr Phe Gln Asn Tyr Ser Tyr Gly Gly Val Ile Gln
    290                 295                 300

Asp Asp His Ile Pro Phe Leu Arg Arg Gly Val Pro Val Leu His Leu
305                 310                 315                 320

Ile Pro Ser Pro Phe Pro Glu Val Trp His Thr Met Asp Asp Asn Glu
                325                 330                 335
```

```
Glu Asn Leu Asp Glu Ser Thr Ile Asp Asn Leu Asn Lys Ile Leu Gln
            340                 345                 350

Val Phe Val Leu Glu Tyr Leu His Leu
        355                 360
```